US012410160B2

(12) United States Patent
Bachman et al.

(10) Patent No.: US 12,410,160 B2
(45) Date of Patent: Sep. 9, 2025

(54) KHK INHIBITORS

(71) Applicant: Gilead Sciences, Inc., Foster City, CA (US)

(72) Inventors: James L. Bachman, Seattle, WA (US); Daniel H. Byun, Foster City, CA (US); Christopher T. Clark, Seattle, WA (US); Petr Jansa, Foster City, CA (US); Joshua A. Kaplan, Foster City, CA (US); Zachary A. Kasun, Seattle, WA (US); Jennifer R. Lo, Seattle, WA (US); Megan E. Neubig, San Diego, CA (US); Nathaniel H. Stanley, San Francisco, CA (US); Kirk L. Stevens, Bothell, WA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 17/704,440

(22) Filed: Mar. 25, 2022

(65) Prior Publication Data

US 2023/0079863 A1 Mar. 16, 2023

Related U.S. Application Data

(60) Provisional application No. 63/167,331, filed on Mar. 29, 2021.

(51) Int. Cl.
| | |
|---|---|
| *C07D 409/14* | (2006.01) |
| *A61K 45/06* | (2006.01) |
| *C07D 401/14* | (2006.01) |
| *C07D 403/04* | (2006.01) |
| *C07D 403/14* | (2006.01) |
| *C07D 405/14* | (2006.01) |
| *C07D 413/14* | (2006.01) |
| *C07D 491/107* | (2006.01) |
| *C07D 493/10* | (2006.01) |
| *C07D 495/04* | (2006.01) |
| *C07D 513/04* | (2006.01) |

(52) U.S. Cl.
CPC ............ *C07D 409/14* (2013.01); *A61K 45/06* (2013.01); *C07D 401/14* (2013.01); *C07D 403/04* (2013.01); *C07D 403/14* (2013.01); *C07D 405/14* (2013.01); *C07D 413/14* (2013.01); *C07D 491/107* (2013.01); *C07D 493/10* (2013.01); *C07D 495/04* (2013.01); *C07D 513/04* (2013.01)

(58) Field of Classification Search
CPC .. C07D 409/14; C07D 401/14; C07D 403/04; C07D 403/14; C07D 405/14; C07D 413/14; C07D 491/107; C07D 493/10; C07D 495/04; C07D 513/04; A61K 45/06
See application file for complete search history.

(56) References Cited

U.S. PATENT DOCUMENTS

| | | | |
|---|---|---|---|
| 5,137,890 A | 8/1992 | Sanfilippo et al. | |
| 7,384,949 B2* | 6/2008 | Gillespie | A61P 25/04 544/278 |
| 8,829,011 B2 | 9/2014 | Carruthers et al. | |
| 2007/0281949 A1* | 12/2007 | Bacon | A61P 25/24 544/254 |
| 2017/0183328 A1 | 6/2017 | Dowling et al. | |
| 2019/0137505 A1* | 5/2019 | Lau | A61K 31/155 |
| 2020/0392118 A1 | 12/2020 | Coates et al. | |
| 2024/0067633 A1* | 2/2024 | Li | C07D 471/04 |

FOREIGN PATENT DOCUMENTS

| | | |
|---|---|---|
| CN | 111423420 A | 7/2020 |
| CN | 111978296 A | 11/2020 |
| CN | 114181198 A | 3/2022 |
| CN | 114805312 A | 7/2022 |
| CN | 114989143 A | 9/2022 |
| EP | 0384228 A1 | 8/1990 |
| EP | 2860181 A1 | 4/2015 |
| WO | WO-2002/055524 A1 | 7/2002 |
| WO | WO-2004/081009 A1 | 9/2004 |
| WO | WO-2005/042501 A1 | 5/2005 |
| WO | WO-2007019083 A1 | 2/2007 |
| WO | WO-2009/045174 A1 | 4/2009 |
| WO | WO-2010/056320 A2 | 5/2010 |
| WO | WO-2010053825 A1 | 5/2010 |
| WO | WO-2011133750 A1 | 10/2011 |

(Continued)

OTHER PUBLICATIONS

Sharma, "Potential for combination of dipeptidyl peptidase-4 inhibitors and sodium-glucose co-transporter-2 inhibitors for the treatment of type 2 diabetes" Diabetes, Obesity and Metabolism 17: 616-621 (Year: 2015).*

Bodajla, M. et al. (1993) "Synthesis of Some Azolylquinazolines", Collection of Czechoslovak Chemical Communications, 59(6): 1463-1466.

Gillespie, R. J. et al. (2008) "Antagonists of the human adenosine A"2"A receptor, Part 2: Design and synthesis of 4-arylthieno[3,2-d]pyrimidine derivatives", Bioorganic & Medicinal Chemistry Letters, 18(9): 2920-2923.

Kumar, S. et al. (2009) "Synthesis and biological evaluation of novel 4-(hetero) aryl-2-piperazino quinazolines as anti-leishmanial and and anti-proliferative agents", Bioorganic & Medicinal Chemistry Letters, 19(9): 2542-2545.

(Continued)

*Primary Examiner* — Adam C Milligan
*Assistant Examiner* — Jed A Kucharczk

(57) ABSTRACT

Compounds of formula:

wherein the variable substituents are defined herein.

38 Claims, No Drawings

(56) References Cited

FOREIGN PATENT DOCUMENTS

| | | | |
|---|---|---|---|
| WO | WO-2018170517 A1 | 9/2018 | |
| WO | WO-2020046481 A2 | 3/2020 | |
| WO | WO-2020046481 A3 | 3/2020 | |
| WO | WO-2020051058 A1 | 3/2020 | |
| WO | WO-2020067735 A1 | 4/2020 | |
| WO | WO-2020156445 A1 | 8/2020 | |
| WO | WO-2020215022 A1 | 10/2020 | |
| WO | WO-2020/257171 A1 | 12/2020 | |
| WO | WO-2021/129817 A1 | 7/2021 | |
| WO | WO-2021129737 A1 | 7/2021 | |
| WO | WO-2021/162943 A1 | 8/2021 | |
| WO | WO-2022/135390 A1 | 6/2022 | |
| WO | WO-2022/211595 A1 | 10/2022 | |

OTHER PUBLICATIONS

Intl. Search Report-Written Opinion dated Jun. 3, 2023 for Intl. Appl. No. PCT/US2022/021912, 16 pages.
Int'l Preliminary Report on Patentability dated Oct. 13, 2023 for Intl. Appl. No. PCT/US2022/021912, 9 pages.
Aldamiz-Echevarria, L. et al. (2020) "Non-alcoholic fatty liver in hereditary fructose intolerance" Clinical Nutrition, 39(2):455-459.
Andres-Hernando, A. et al. (2017) "Protective role of fructokinase blockade in the pathogenesis of acute kidney injury in mice" Nature Communications 8, 1-12.
Asipu, A. et al. (2003) "Properties of Normal and Mutant Recombinant Human Ketohexokinases and Implications for the Pathogenesis of Essential Fructosuria" Diabetes, 52(9):2426-2432.
Bantle, J. (2009) "Dietary Fructose and Metabolic Syndrome and Diabetes 1-3" The Journal of Nutrition, 139(6):1263S-1268S.
Bonthron, D. et al. (1994) "Molecular basis of essential fructosuria: molecular cloning and mutational analysis of human ketohexokinase (fructokinase)" Human Molecular Genetics 3(9):1627-1631.
Charifson, P. et al. (2014) "Acidic and Basic Drugs in Medicinal Chemistry: A Perspective" J. Med. Chem., 57:9701-9717.
Diggle, C. et al. (2009) "Ketohexokinase: Expression and Localization of the Principal Fructose-metabolizing Enzyme" J Histochem Cytochem, 57(8):763-774.
Futatsugi, K. et al. (2020) "Discovery of PF-06835919: A Potent Inhibitor of Ketohexokinase (KHK) for the Treatment of Metabolic Disorders Driven by the Overconsumption of Fructose" J. Med. Chem., 63: 13546-13560.
Geidl-Flueck, B. et al. (2017) "Insights into the Hexose Liver Metabolism-Glucose versus Fructose" Nutrients 9(9):1-21.
Hayward, B. et al. (1998) "Structure and alternative splicing of the ketohexokinase gene" Eur. J. Biochem. 257(1):85-91.
Helsley, R. et al. (2020) "Tissue-Specific Fructose Metabolism in Obesity and Diabetes" Curr. Diab. Rep., 20(64):1-16.
Ishimoto, T. et al. (2012) "Opposing effects of fructokinase C and A isoformson fructose-induced metabolic syndrome in mice" Proc Natl Acad Sci U S A., 109(11): 4320-4325.
Jensen, T. et al. (2018) "Fructose and Sugar: A Major Mediator of Nonalcoholic Fatty Liver Disease" J Hepatol., 68(5): 1063-1075.
Johnson, R. et al. (2013) "Sugar, Uric Acid, and the Etiology of Diabetes and Obesity" Diabetes 62(10): 3307-3315.
Kalliokoski, A. et al. (2009) "Impact of OATP transporters on pharmacokinetics" British Journal of Pharmacology, 158:693-705.
Lanaspa, M. et al. (2013) "Endogenous fructose production and metabolism in the liver contributes to the development of metabolic syndrome" Nature Communications 4: 1-9.
Lassila, T. et al. (2015) "Toxicity of Carboxylic Acid-Containing Drugs: The Role of Acyl Migration and CoA Conjugation Investigated" Chem. Res. Toxicol., 28(12):2292-2303.
Maryanoff, B. et al. (2011) "Inhibitors of Ketohexokinase: Discovery of Pyrimidinopyrimidines with Specific Substitution that Complements the ATP-Binding Site" ACS Med. Chem. Lett., 2:538-543.
Maryanoff, B. et al. (2012) "Pyrimidinopyrimidine inhibitors of ketohexokinase: Exploring the ring C2 group that interacts with Asp-27B in the ligand binding pocket" Bioorganic & Medicinal Chemistry Letters, 22(16):5326-5329.
McFeely, S. et al. (2019) "Identification and Evaluation of Clinical Substrates of Organic Anion Transporting Polypeptides 1B1 and 1B3" Clin. Transl. Sci., 12:379-387.
Merino, B. et al. (2020) "Intestinal Fructose and Glucose Metabolism in Health and Disease" Nutrients 2020, 12(1):1-35.
Montrose, D. et al. (2021) "Dietary Fructose Alters the Composition, Localization, and Metabolism of Gut Microbiota in Association With Worsening Colitis" Cell Mol Gastroenterol Hepatol. 11(2): 525-550.
Schapira, F. et al. (1972) "Hereditary alterations of fructose metabolizing enzymes. Studies on essential fructosuria and on hereditary fructose intolerance" Acta Med Scand Suppl, 542, 77-83.
Sekine, T. et al. (2006) "Molecular physiology of renal organic anion transporters" Am. J. Physiol. Renal. Physiol., 290:F251-F261.
Simons, N. et al. (2019) "Patients With Aldolase B Deficiency Are Characterized by Increased Intrahepatic Triglyceride Content" J Clin Endocrinol Metab, 104(11):5056-5064.
Todoric, J. et al. (2020) "Fructose stimulated de novo lipogenesis is promoted by inflammation" Nature Metabolism, 1034-1045.
Van Vleet, et al. (2017) "Acyl glucuronide metabolites: Implications for drug safety assessment" Toxicology Letters, 272:1-7.
Yukawa, T. et al. (2020) "Utility of Physicochemical Properties for the Prediction of Toxicological Outcomes: Takeda Perspective" ACS Med. Chem. Lett., 11:203-209.
Zhang, X. et al. (2011) "Optimization of a pyrazole hit from FBDD into a novel series of indazoles as ketohexokinase inhibitors" Bioorganic & Medicinal Chemistry Letters, 21(16):4762-4767.
Office Action dated nov. 6, 2023 for Taiwanese Appl. No. 111111557, 16 pages.
Examination Report dated Feb. 16, 2024 for Australian Appl. No. 2022252182, 4 pages.
Office Action dated Sep. 4, 2024 for Japanese Appl. No. 2023-560087, 12 pages.
Examination Report dated Nov. 14, 2024 for Australian Appl. No. 2022252182, 10 pages.
Office Action dated Nov. 28, 2024 for European Appl. No. 22719399. 2, 3 pages.
Office Action dated Dec. 19, 2024 for Japanese Appl. No. 2023-560087, 5 pages.
Examination Report dated Jan. 6, 2025 for Australian Appl. No. 2022252182, 3 pages.
Office Action dated Feb. 27, 2025 for Canadian Appl. No. 3214961, 7 pages.

* cited by examiner

KHK INHIBITORS

CROSS-REFERENCE TO RELATED APPLICATIONS

This application claims the benefit under 35 U.S.C. § 119(e) of U.S. Provisional Application No. 63/167,331, filed on Mar. 29, 2021, which hereby incorporated herein by reference in its entirety for all purposes.

BACKGROUND

Excess fructose is linked with the development of insulin resistance, hyperglycemia and with several comorbidities associated with diabetes and metabolic syndrome, including: non-alcoholic fatty liver disease (NAFLD), non-alcoholic steatohepatitis (NASH), alcoholic steatohepatitis (ASH), liver disease, liver fibrosis, metabolic syndrome, obesity, hyperlipidemia, hypertriglyceridemia, hypertension, fibrosis, steatosis, cirrhosis, cardiometabolic syndrome, insulin resistance, cardiovascular disease, heart failure, type 1 and type 2 diabetes mellitus, chronic kidney disease (CKD), diabetic kidney disease (DKD), kidney disease, kidney fibrosis, kidney insufficiency, irritable bowel syndrome disease (IBD), ulcerative colitis, Crohn's disease, hyperuricemia, gout, diseases driven by inflammasome activation, arthritis, rheumatoid arthritis, osteoarthritis, osteoporosis or cancer (Bantle, 2009; Jensen et al., 2018; Johnson et al., 2013; Merino, Fernandez-Diaz, Cozar-Castellano, & Perdomo, 2019).

Although dietary consumption is a prominent source of fructose, fructose is also endogenously produced during cellular stress, injury, tissue damage or increased glucose concentrations among others. This endogenous fructose production occurs through the polyol pathway in in the liver, intestines, and kidney where it contributes to exacerbation of injury and metabolic dysfunction (Andres-Hernando et al., 2017; Lanaspa et al., 2013). In the small intestine, excess dietary fructose is linked to the accumulation of fructose-1-phosphate (F1P) leading to the loss of integrity of tight junctions and to the destruction of the mucous membrane barrier lining the intestine contributing to increased gut permeability, inflammation, dysbiosis and diarrhea (Merino et al., 2019; Montrose et al., 2020). In the liver and kidney, increased fructose metabolism causes accumulation of metabolic intermediates such as fructose-1-phosphate (F1P), glyceraldehyde, dihydroxyacetone phosphate and methylglyoxal which contribute to increased glucose production, de novo lipogenesis, insulin resistance and triglyceride synthesis (Todoric et al., 2020). Importantly, increased fructose production and/or metabolism leads to rapid adenosine triphosphate (ATP) depletion, resulting in cellular apoptosis and injury, and increased levels of the pro-inflammatory molecule uric acid (Helsley et al., 2020).

Current pharmacotherapies for the treatment of metabolic syndrome and associated comorbidities generally target modulation of insulin secretion or activity, lipid metabolism, regulation of cholesterol levels, blood pressure, glucose homeostasis and regulation of dietary consumption of high fat or high fructose diets. Currently, there are no approved therapies for reducing the metabolism of fructose, and eliminating fructose intake in the diet is not practically achievable. Ketohexokinase (GENE: KHK) is the primary and rate-limiting enzyme for both dietary and endogenous fructose metabolism, and therefore represents a promising drug target for pharmacological intervention in diseases where fructose and the polyol pathway contribute to metabolic disease and associated comorbidities.

KHK is expressed as two major mRNA splice variants. KHK mRNA variant 3C (Isoform-C, KHK-C) is preferentially expressed in the small intestine (enterocytes), liver (hepatocytes) and kidney (proximal tubule cells) (Diggle et al., 2009; Hayward & Bonthron, 1998). These organs metabolize the majority of dietary and endogenously produced fructose. An alternative splice variant of KHK (variant 3A, isoform-A, KHK-A) is expressed more ubiquitously in other organs, including, but not limited to heart, brain and skeletal muscle. KHK catalyzes the ATP-dependent conversion of fructose to F1P. Increased metabolism of fructose by KHK-C causes accumulation of F1P and uric acid, and rapid ATP depletion. KHK-C has a higher affinity for fructose than KHK-A and results in a more rapid metabolism of fructose than KHK-A. In addition, neither KHK-A or KHK-C are subject to negative feedback inhibition or allosteric regulation, therefore, fructose is immediately, and continually metabolized by KHK (Ishimoto et al., 2012). Alternative enzymes such as hexokinase, are able to metabolize fructose to fructose-6-phosphate but this does not result in rapid ATP depletion as hexokinases are subjected to negative feedback regulation (Geidl-Flueck & Gerber, 2017).

An example of the consequence of unregulated fructose metabolism via KHK is seen in subjects with Hereditary Fructose Intolerance (HFI, OMIM #229600), a severe disorder caused by defects in Aldolase B (GENE: ALDOB). ALDOB is the enzyme immediately downstream of KHK and is responsible for the conversion of F1P to dihydroxy acetone phosphate (DHAP) and Glyceraldehyde phosphate (GAP). Defects in ALDOB result in accumulation of F1P, ATP depletion and increased uric acid. HFI is a rare disorder and its prevalence is approximately 1 in 20,000 people (Simons et al., 2019). Individuals with HFI are severely intolerant to dietary fructose and demonstrate acute symptoms like vomiting, hypoglycemia, diarrhea and abdominal distress. These contribute to the development of hypoglycemia, hyperuricemia, lactic acidosis, hepatic steatosis and features reminiscent of Fanconi's Syndrome and in worst cases, death (Aldamiz-Echevarria et al., 2020; Simons et al., 2019). Currently, the only therapy for patients with HFI is strict restriction of dietary fructose. However, this is not completely sufficient to delay worsening of symptoms over time and patients often exhibit features of liver and kidney disease over their lifetimes as it does not affect endogenous fructose production and metabolism (Aldamiz-Echevarria et al., 2020).

Genetic defects in the human KHK gene leading to enzymatic loss of function or reduction in enzyme stability, results in a benign condition known as essential fructosuria (EF, OMIM #229800) and supports KHK inhibition as a therapeutic strategy. EF is a rare, benign disorder affecting approximately 1 in 100,000 people. Patients with EF appear normal and exhibit increased urinary excretion of fructose (Asipu, Hayward, O'Reilly, & Bonthron, 2003; Bonthron, Brady, Donaldson, & Steinmann, 1994; Schapira, Nordmann, & Gregori, 1972). The benign nature of EF and lack of symptoms underscore the potential safety of long term KHK inhibition. In addition, KHK-A/C homozygous knockout mice appear normal and healthy and excrete excess fructose in the urine, similar to humans with EF. Additionally, KHK-A/C null mice are protected from features of liver and kidney disease such as kidney tubular cell injury, inflammation, liver steatosis and fibrosis (Andres-Hernando et al., 2017; Lanaspa et al., 2013).

There are currently two classes of known KHK inhibitors, and both utilize the presence of a charged residue for potency and/or metabolic stability and/or acceptable pharmacokinetic properties.

One class (US2017183328, CN111978296, WO2020067735, WO2020051058, CN111423420, WO2020156445, Futatsugi et al., J. Med. Chem., 2020, 63, 13546-13560) contains negatively charged carboxylic acids which mimic the gamma phosphate residue of the natural substrate ATP. Many carboxylic acid-containing drugs are associated with idiosyncratic drug toxicity, which may be caused by reactive acyl glucuronide metabolites (Lassila et al., Chem. Res. Toxicol., 2015, 28, 12, 2292-2303). Acyl glucuronide metabolites can be chemically reactive leading to covalent binding with macromolecules and cumulative toxicity (Vleet Van et al., Toxicology Letters, 2017, 272, 1-7). Compounds containing carboxylic acids tend to be substrates for the organic anion transporter (OAT) family encoded by SLC22A, the organic anion transporting peptide (OATP) family encoded by SLC21A (SLCO), and the multidrug resistance-associated protein (MRP) family encoded by ABCC (Sekine et al., Am. J. Physiol. Renal Physiol., 2006, 290, F251-F261). This can lead to asymmetric tissue exposure (i.e. tissues accumulation via active uptake and reduced tissue exposure via active efflux). Differential tissue levels (for example toxicity due to accumulation or lack of efficacy due to active excretion) can represent a risk specific to KHK-C inhibitors where higher KHK-C inhibition in one organ may lead to higher circulating fructose concentrations in plasma which may lead to enhanced KHK-C mediated fructose metabolism (and subsequent enhanced ATP depletion and tissue damage) in an organ with reduced or lower inhibitor concentration (free drug concentration). Carboxylic acids tend to be not only substrates but also inhibitors of OATPs leading to drug-drug interactions (DDI) with some essential medications (Kalliokoski et al., Br. J. Pharmacol., 2009, 158, 693-705; McFeely et al., Clin. Transl. Sci., 2019, 12, 379-387).

The other class of known KHK inhibitors rely on the presence of a positively charged basic amine (WO18170517, WO11133750, Zhang et al., Bioorg. Med. Chem. Lett., 2011, 21, 4762-4767, Maryanoff et al., Bioorg. Med. Chem. Lett., 2012, 22, 5326-532, Maryanoff et al., ACS Med. Chem. Lett., 2011, 2, 538-543, WO2020215022, WO2020046481, US2020392118). Basic amines are well known for their higher risk of promiscuity or lack of biological selectivity or safety risks such as hERG inhibition or phospholipidosis, inter-organ variation in exposures since basic drugs tend to be stored in tissues with a pH that is lower than their pKa values e.g., lung. Basic amine containing compounds often become sequestered in acidic organelles of many different cell types and may thereby contribute to various toxicities and additionally be metabolized to form reactive iminium species (Yukawa et al., ACS Med. Chem. Lett., 2020, 11, 203-209; Charifson et al., J. Med. Chem., 2014, 57, 9701-9717). Both acids and bases are in general subjected to significantly greater renal clearance than neutral molecules (Charifson et al., J. Med. Chem., 2014, 57, 9701-9717).

There is a need for KHK inhibitors with advantageous properties, for example: equal tissue distribution, high target engagement and good pharmacokinetics properties. While progress has been made, there is still a need for more potent, novel KHK inhibitors with low tissue asymmetry, low drug-drug interaction liability, reduced off target liability and minimal toxicity.

REFERENCES

Aldamiz-Echevarria, L., de Las Heras, J., Couce, M. L., Alcalde, C., Vitoria, I., Bueno, M., . . . Vitiate, O. (2020). Non-alcoholic fatty liver in hereditary fructose intolerance. Clin Nutr, 39(2), 455-459. doi:10.1016/j.clnu.2019.02.019

Andres-Hernando, A., Li, N., Cicerchi, C., Inaba, S., Chen, W., Roncal-Jimenez, C., . . . Lanaspa, M. A. (2017). Protective role of fructokinase blockade in the pathogenesis of acute kidney injury in mice. Nat Commun, 8, 14181. doi:10.1038/ncomms14181

Asipu, A., Hayward, B. E., O'Reilly, J., & Bonthron, D. T. (2003). Properties of normal and mutant recombinant human ketohexokinases and implications for the pathogenesis of essential fructosuria. Diabetes, 52(9), 2426-2432. doi:10.2337/diabetes.52.9.2426

Bantle, J. P. (2009). Dietary fructose and metabolic syndrome and diabetes. J Nutr, 139(6), 1263S-1268S. doi: 10.3945/jn.108.098020

Bonthron, D. T., Brady, N., Donaldson, I. A., & Steinmann, B. (1994). Molecular basis of essential fructosuria: molecular cloning and mutational analysis of human ketohexokinase (fructokinase). Hum Mol Genet, 3(9), 1627-1631. doi:10.1093/hmg/3.9.1627

Diggle, C. P., Shires, M., Leitch, D., Brooke, D., Carr, I. M., Markham, A. F., . . . Bonthron, D. T. (2009). Ketohexokinase: expression and localization of the principal fructose-metabolizing enzyme. J Histochem Cytochem, 57(8), 763-774. doi:10.1369/jhc.2009.953190

Geidl-Flueck, B., & Gerber, P. A. (2017). Insights into the Hexose Liver Metabolism-Glucose versus Fructose. Nutrients, 9(9). doi:10.3390/nu9091026

Hayward, B. E., & Bonthron, D. T. (1998). Structure and alternative splicing of the ketohexokinase gene. Eur J Biochem, 257(1), 85-91. doi:10.1046/j.1432-1327.1998.2570085.x Helsley, R. N., Moreau, F., Gupta, M. K., Radulescu, A., DeBosch, B., & Softic, S. (2020). Tissue-Specific Fructose Metabolism in Obesity and Diabetes. Curr Diab Rep, 20(11), 64. doi:10.1007/s11892-020-01342-8

Ishimoto, T., Lanaspa, M. A., Le, M. T., Garcia, G. E., Diggle, C. P., Maclean, P. S., . . . Johnson, R. J. (2012). Opposing effects of fructokinase C and A isoforms on fructose-induced metabolic syndrome in mice. Proc Natl Acad Sci USA, 109(11), 4320-4325. doi:10.1073/pnas.1119908109

Jensen, T., Abdelmalek, M. F., Sullivan, S., Nadeau, K. J., Green, M., Roncal, C., . . . Johnson, R. J. (2018). Fructose and sugar: A major mediator of non-alcoholic fatty liver disease. J Hepatol, 68(5), 1063-1075. doi:10.1016/j.jhep.2018.01.019

Johnson, R. J., Nakagawa, T., Sanchez-Lozada, L. G., Shafiu, M., Sundaram, S., Le, M., . . . Lanaspa, M. A. (2013). Sugar, uric acid, and the etiology of diabetes and obesity. Diabetes, 62(10), 3307-3315. doi:10.2337/db12-1814

Lanaspa, M. A., Ishimoto, T., Li, N., Cicerchi, C., Orlicky, D. J., Ruzycki, P., . . . Johnson, R. J. (2013). Endogenous fructose production and metabolism in the liver contributes to the development of metabolic syndrome. Nat Commun, 4, 2434. doi:10.1038/ncomms3434

Merino, B., Fernandez-Diaz, C. M., Cozar-Castellano, I., & Perdomo, G. (2019). Intestinal Fructose and Glucose Metabolism in Health and Disease. Nutrients, 12(1). doi:10.3390/nu12010094

Montrose, D. C., Nishiguchi, R., Basu, S., Staab, H. A., Zhou, X. K., Wang, H., . . . Dannenberg, A. J. (2020). Dietary Fructose Alters the Composition, Localization, and Metabolism of Gut Microbiota in Association With Worsening Colitis. *Cell Mol Gastroenterol Hepatol.* doi: 10.1016/j.jcmgh.2020.09.008

Schapira, F., Nordmann, Y., & Gregori, C. (1972). Hereditary alterations of fructose metabolizing enzymes. Studies on essential fructosuria and on hereditary fructose intolerance. *Acta Med Scand Suppl,* 542, 77-83.

Simons, N., Debray, F. G., Schaper, N. C., Kooi, M. E., Feskens, E. J. M., Hollak, C. E. M., . . . Brouwers, M. (2019). Patients With Aldolase B Deficiency Are Characterized by Increased Intrahepatic Triglyceride Content. *J Clin Endocrinol Metab,* 104(11), 5056-5064. doi: 10.1210/jc.2018-02795

Todoric, J., Di Caro, G., Reibe, S., Henstridge, D. C., Green, C. R., Vrbanac, A., . . . Karin, M. (2020). Fructose stimulated de novo lipogenesis is promoted by inflammation. *Nat Metab,* 2(10), 1034-1045. doi:10.1038/s42255-020-0261-2

SUMMARY

In one embodiment, the present disclosure provides a compound of Formula I

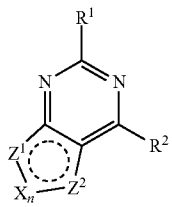

Formula I or a pharmaceutically acceptable salt or stereoisomer thereof, wherein $R^1$ is
- a 4-10 membered heterocyclic moiety, wherein the heterocycle contains 1-3 heteroatoms, and is optionally substituted with up to four $R^{1a}$; or
- $C_{3-7}$ cycloalkyl, optionally substituted with up to four substituents independently selected from $C_{1-6}$ alkyl, $C_{1-6}$ alkoxy, $C_{1-6}$ haloalkyl, halogen, CN, OH, $CH_2OH$, $CH_2OR^{11}$, $CONH_2$, $CONHR^{11}$, $NHCOR^{13}SO_2NH_2$, $SO_2NHR^{11}$, $NHSO_2R^{13}$ or oxo;

each $R^{1a}$ is independently $C_{1-6}$ alkyl, $C_{2-6}$ alkenyl, $C_{2-6}$ alkynyl, $C_{3-7}$ cycloalkyl, OH, $OR^{1b}$, $CH_2OH$, $CO_2R^{12}$, halogen, oxo, $CONH_2$, CN, $NH_2$, $NHR^{11}$, $C_{1-6}$ alkyl-$NHSO_2R^{13}$, $C_{1-6}$ alkyl-$NHCOR^{13}C_{1-6}$ alkoxy or $C_{1-6}$ haloalkyl, wherein the alkyl, alkenyl, alkynyl, cycloalkyl, alkyl-$NHSO_2R^{13}$, alkyl-$NHCOR^{13}$, alkoxy, or haloalkyl are optionally substituted with up to three $R^{1c}$; alternatively two $R^{1a}$ can be combined with the atoms to which they are attached to form a 3-6 membered spiro, fused or bridged ring;

$R^{1b}$ is H, or $C_{1-6}$ alkyl, wherein the alkyl is optionally substituted with up to three halogens, CN, or OH;

each $R^{1c}$ is independently OH, $OR^B$, halogen, oxo, $SOR^{13}$, $SO_2R^{13}$, $SR^{13}$, $SO_2NH_2$, $CONH_2$, CN, $C_{1-6}$ alkoxy, $C_{6-10}$ aryl, $C_{6-10}$ aryloxy, 5-11 membered heteroaryl, or $C_{3-7}$ cycloalkyl;

$R^2$ is $C_{6-10}$ aryl, or a 6-14 membered heteroaryl, wherein the aryl, or heteroaryl are optionally substituted with up to eight $R^{2a}$, and wherein $R^2$ is attached to the core through a carbon atom of $R^2$;

each $R^{2a}$ is independently $C_{1-6}$ alkyl, $C_{2-6}$ alkenyl, $C_{2-6}$ alkynyl, $C_{1-6}$ alkoxy, $C_{1-6}$ haloalkyl, $SO_2R^{2c}$, $SOR^{2c}$, $SO_2NH_2$, $CONHR_2$, $COR^{2c}$, $CONHR^{2e}$, $CON(R^{2c})_2$, halogen, oxo, OH, CN, $NH_2$, $NHR^{2c}$, $N(R^{2c})_2$, $NHCOR^{2c}$, $N(R^{2c})COR^{2c}$, $NHCO_2R^{2c}$, $NO_2$, $SO_2NHR^{2c}$, $SO_2N(R^{2c})_2$, $NHSO_2R^{2c}$, $N(R^{2c})SO_2R^{2c}$, $S(O)(NH)R^{2c}$, $S(O)(NH)NH_2$, $NHS(O)(NH)R^{2c}$, $NS(O)(NH_2)R^{2c}$, $NS(O)(R^{2c})_2$, $S(O)(NR^{2c})R^{2c}$, $S(O)(NR^{2c})NH_2$, $S(O)(NH)NHR^{2c}$, $S(O)(NR^{2c})NH(R^{2c})$, $OR^{2e}$, $SR^{2e}$, $C_{3-7}$ cycloalkyl, 4-7 membered heterocyclyl, $C_{6-10}$ aryl, or 5-11 membered heteroaryl, wherein the alkyl, alkenyl, alkynyl, cycloalkyl, heterocyclyl, aryl or heteroaryl are substituted with up to seven $R^{2b}$, and wherein the cycloalkyl can be fused or spiro to the heteroaryl, or the cycloalkyl can be fused to the aryl; alternatively two $R^{2c}$ can be combined with the atoms to which they are attached to form a 3-7 membered spiro, fused or bridged ring;

each $R^{2b}$ is independently $C_{1-6}$ alkyl, $C_{1-6}$ haloalkyl, $C_{1-6}$ alkoxy, OH, halogen, oxo, $CONH_2$, $CONHR^{2e}$, CON($R^{2c}$)$_2$, $NHCOR^{2c}$, $N(R^{2c})COR^{2c}$, $NHCO_2R^{2c}$, $NH_2$, $N(R^{2c})_2$, $NHR^{2c}$, $S(O)(NH)R^{2c}$, $S(O)(NH)NH_2$, $NHS(O)(NH)R^{2c}$, $NS(O)(NH_2)R^{2c}$, $NS(O)(R^{2c})_2$, $S(O)(NR^{2c})R^{2c}$, $S(O)(NR^{2c})NH_2$, $S(O)(NH)NHR^{2c}$, $S(O)(NR^{2c})NH(R^{2c})$, $OR^{2e}$, $NHSO_2R^{2c}$, $N(R^{2c})SO_2R^{2c}$, $C_{1-6}$ alkyl-$CO_2R^{12}$, $C_{1-6}$ alkyl-$CONH_2$, $C_{1-6}$ alkyl-$NHSO_2R^{2c}$, $C_{1-6}$ alkyl-$SO_2R^{2c}$ CN, $COR^{2c}$, $NHCO_2R^{2c}$, $SO_2NH_2$, $SO_2NHR^{2c}$, $SO_2R^{2c}$, $C_{3-7}$ cycloalkyl, 4-7 membered heterocyclyl, $C_{6-10}$ aryl or 5-11 membered heteroaryl, wherein the alkyl, $C_{1-6}$ alkyl-$CO_2R^{12}$, $C_{1-6}$ alkyl-$CONH_2$, $C_{1-6}$ alkyl-$NHSO_2R^{2c}$, $C_{1-6}$ alkyl-$SO_2R^{2c}$ alkoxy, haloalkyl, cycloalkyl, heterocyclyl, aryl or heteroaryl can be optionally substituted with up to four $R^{2d}$; alternatively two $R^{2b}$ can be combined with the atoms to which they are attached to form a 3-7 membered spiro, fused or bridged ring;

each $R^{2c}$ is independently $C_{1-6}$ alkyl, $C_{1-6}$ haloalkyl, $C_{1-6}$ alkoxy, $C_{3-7}$ cycloalkyl, $C_{6-10}$ aryl, $C_{1-6}$ alkyl-$C_{6-10}$ aryl, 5-11 membered heteroaryl, or 4-7 membered heterocyclyl, wherein the alkyl, haloalkyl, alkoxy, cycloalkyl, aryl, alkyl-aryl, heteroaryl or heterocyclyl are optionally substituted with up to four $R^{2d}$; alternatively two $R^{2c}$ can be combined with the atoms to which they are attached to form a 3-7 membered ring;

each $R^{2d}$ is independently OH, halogen, $NH_2$, $C_{1-6}$ alkoxy, $CONH_2$, $COR^{2e}$, $SO_2NH_2$, $NR^{11}COR^{13}$, $NCH_2OR^{11}$, $C_{1-6}$ alkyl, $C_{1-6}$ haloalkyl, $C_{3-7}$ cycloalkyl, 4-7 membered heterocyclyl, $C_{1-6}$ alkyl-$NH_2$, $C_{1-6}$ alkyl-$CO_2R^{12}$, oxo, or CN;

$R^{2e}$ is $C_{1-6}$ alkyl, $C_{3-7}$ cycloalkyl, $C_{6-10}$ aryl, $C_{1-6}$ alkyl-$C_{6-10}$ aryl, 4-7 membered heterocyclyl, or 5-11 membered heteroaryl, wherein the alkyl, cycloalkyl, aryl, alkyl-aryl, heterocyclyl or heteroaryl are optionally substituted with up to three $R^{19}$;

Each X is independently $CR^7R^8$, oxo, S, SO, $SO_2$, or O;

$Z^1$ is $CR^3R^4$, $NR^9$, S, SO, $SO_2$, C=O, or O;

$Z^2$ is $CR^5R^6$, $NR^9$, S, SO, $SO_2$, C=O, or O;

n is 0, 1, or 2;

wherein:
when n is 0, $Z^1$ is $CR^3R^4$, and $Z^2$ is $CR^5R^6$;
when n is 2, only one X can be oxo, S, SO, $SO_2$, or O;
when either $Z^1$ or $Z^2$ are O, SO, or $SO_2$, then X is $CR^7CR^8$;

when both $Z^1$ and $Z^2$ are O, SO, or $SO_2$, then X is $CR^7CR^8$;

and wherein the dashed circle represents one or more optional double bonds;

$R^3$, $R^4$, $R^5$, $R^6$, $R^7$, $R^8$ are independently absent, H, $C_{1-6}$ alkyl, halogen, or $C_{3-7}$ cycloalkyl; alternatively $R^3$, $R^4$, $R^5$, $R^6$, $R^7$ or $R^8$ can be combined with the atoms to which they are attached to form a 3-6 membered spiro, bridged or fused ring;

$R^9$ is absent, H, $C_{1-6}$ alkyl, or $C_{3-7}$ cycloalkyl;

each $R^{19}$ is independently $C_{1-6}$ alkoxy, CN, halogen, OH, $NH_2$, $NHR^{11}$, $CONH_2$, $SO_2NH_2$, or $NHCO_2$—$C_{1-6}$ alkyl;

$R^{11}$ is H, $C_{1-6}$ alkyl, or $C_{1-6}$ haloalkyl;

$R^{12}$ is $C_{1-6}$ alkyl, $C_{1-6}$ haloalkyl, 3-7 cycloalkyl, 4-7 heterocyclyl, $C_{6-10}$ aryl, or 5-11 heteroaryl; and $R^{13}$ is $C_{1-6}$ alkyl, or $C_{1-6}$ haloalkyl.

In another embodiment, the present disclosure provides a compound of Formula I,

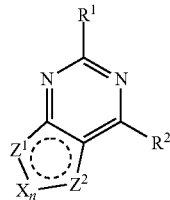

Formula I or a pharmaceutically acceptable salt or stereoisomer thereof, wherein $R^1$ is
  a 4-10 membered heterocyclic moiety, wherein the heterocycle contains 1-3 heteroatoms, and is optionally substituted with up to four $R^{1a}$; or
  $C_{3-7}$ cycloalkyl, optionally substituted with up to four substituents independently selected from $C_{1-6}$ alkyl, $C_{1-6}$ alkoxy, $C_{1-6}$ haloalkyl, halogen, CN, OH, $CH_2OH$, $CH_2OR^{11}$, $CONH_2$, $CONHR^{11}$, $NHCOR^{13}$, $SO_2NH_2$, $SO_2NHR^{11}$, $NHSO_2R^{13}$ or oxo;

each $R^{1a}$ is independently $C_{1-6}$ alkyl, $C_{2-6}$ alkenyl, $C_{2-6}$ alkynyl, OH, $OR^{1b}$, $CH_2OH$, COOH, $CO_2R^{12}$, halogen, oxo, $CONH_2$, CN, $NH_2$, $NHR^{11}$, $C_{1-6}$ alkyl-$NHSO_2R^{13}$, $C_{1-6}$ alkyl-$NHCOR^{13}$, $C_{1-6}$ alkoxy or $C_{1-6}$ haloalkyl, wherein the alkyl, alkenyl, or alkynyl are optionally substituted with up to three $R^{1c}$; alternatively two $R^{1a}$ can be combined with the atoms to which they are attached to form a 3-6 membered spiro, fused or bridged ring;

$R^{1b}$ is H, or $C_{1-6}$ alkyl, wherein the alkyl is optionally substituted with up to three halogens, CN, or OH;

each $R^{1c}$ is independently OH, $OR^{11}$, halogen, oxo, $SOR^{13}$, $SO_2R^{13}$, $SR^{13}$, $SO_2NH_2$, $CONH_2$, $C_{1-6}$ alkoxy, $C_{6-10}$ aryl, $C_{6-10}$ aryloxy, 5-11 membered heteroaryl, or $C_{3-7}$ cycloalkyl;

$R^2$ is $C_{6-10}$ aryl, or a 6-14 membered heteroaryl, wherein the aryl, or heteroaryl are optionally substituted with up to eight $R^{2a}$, and wherein $R^2$ is attached to the core through a carbon atom of $R^2$;

each $R^ea$ is independently $C_{1-6}$ alkyl, $C_{2-6}$ alkenyl, $C_{2-6}$ alkynyl, $C_{1-6}$ alkoxy, $C_{1-6}$ haloalkyl, $SO_2R^{2c}$, $SOR^{2c}$, $SO_2NH_2$, COOH, $CO_2R^{12}$, $CONH_2$, $COR^{2c}$, $CONHR^{2e}$, $CON(R^{2c})_2$, halogen, oxo, OH, CN, $NH_2$, $NHR^{2c}$, $N(R^{2c})_2$, $NHCOR^{2c}$, $N(R^{2c})COR^{2e}$, $NO_2$, $SO_2NHR^{2c}$, $SO_2N(R^{2c})_2$, $NHSO_2R^{2c}$, $N(R^{2c})SO_2R^{2c}$, $S(O)(NH)R^{2c}$, $S(O)(NH)NH_2$, $NHS(O)(NH)R^{2c}$, $NS(O)(NH_2)R^{2c}$, $NS(O)(R^{2c})^2$, $S(O)(NR^{2c})K^{2c}$, $S(O)(NR^{2c})NH_2$, $S(O)(NH)NHR^{2c}$, $S(O)(NR^{2c})NH(R^{2c})$, $OR^{2e}$, $C_{3-7}$ cycloalkyl, 4-7 membered heterocyclyl, $C_{6-10}$ aryl, or 5-11 membered heteroaryl, wherein the alkyl, alkenyl, alkynyl, cycloalkyl, heterocyclyl, aryl or heteroaryl are substituted with up to seven $R^{2b}$, and wherein the cycloalkyl can be fused or spiro to the heteroaryl, or the cycloalkyl can be fused to the aryl; alternatively two $R^ea$ can be combined with the atoms to which they are attached to form a 3-7 membered spiro, fused or bridged ring;

each $R^{2b}$ is independently $C_{1-6}$ alkyl, $C_{1-6}$ haloalkyl, $C_{1-6}$ alkoxy, OH, halogen, oxo, $CO_2H$, $CO_2R^{12}$, $CONH_2$, $NHCOR^{2c}$, $N(R^{2c})COR^{2c}$, $NHCO_2R^{2c}$, $NH_2$, $N(R^{2c})_2$, $NHR^{2c}$, $S(O)(NH)R^{2c}$, $S(O)(NH)NH_2$, $NHS(O)(NH)R^{2c}$, $NS(O)(NH_2)R^{2c}$, $NS(O)(R^{2e})_2$, $S(O)(NR^{2c})R^{2c}$, $S(O)(NR^{2c})NH_2$, $S(O)(NH)NHR^{2c}$, $S(O)(NR^{2c})NH(R^{2c})$, $OR^{2e}$, $NHSO_2R^{2c}$, $N(R^{2c})SO_2R^{2c}$, $C_{1-6}$ alkyl-$CO_2R^{12}$, $C_{1-6}$ alkyl-$CONH_2$, $C_{1-6}$ alkyl-$NHSO_2R^{2c}$, CN, $COR^{2c}$, $NHCO_2R^{2c}$, $SO_2NH_2$, $SO_2NHR^{2c}$, $SO_2R^{2c}$, $C_{3-7}$ cycloalkyl, 4-7 membered heterocyclyl, $C_{6-10}$ aryl or 5-11 membered heteroaryl, wherein the alkyl, alkoxy, haloalkyl, cycloalkyl, heterocyclyl, aryl or heteroaryl can be optionally substituted with up to four $R^{2d}$; alternatively two $R^{2b}$ can be combined with the atoms to which they are attached to form a 3-7 membered spiro, fused or bridged ring;

each $R^{2c}$ is independently $C_{1-6}$ alkyl, $C_{1-6}$ haloalkyl, $C_{1-6}$ alkoxy, $C_{6-10}$ aryl, 5-11 membered heteroaryl, or 4-7 membered heterocyclyl, wherein the alkyl, haloalkyl, alkoxy, aryl, heteroaryl or heterocyclyl are optionally substituted with up to four $R^{2d}$;

each $R^{2d}$ is independently OH, halogen, $NH_2$, $C_{1-6}$ alkoxy, $CONH_2$, $SO_2NH_2$, $CO_2H$, $CO_2R^{12}$, $NHCOR^{13}$, $C_{1-6}$ alkyl, $C_{1-6}$ haloalkyl, $C_{1-6}$ alkyl-$NH_2$, $C_{1-6}$ alkyl-$CO_2R^{12}$, oxo, or CN;

$R^{2e}$ is $C_{1-6}$ alkyl, $C_{3-7}$ cycloalkyl, $C_{6-10}$ aryl, $C_{1-6}$ alkyl-$C_{6-10}$ aryl, 4-7 membered heterocyclyl, or 5-11 membered heteroaryl, wherein the alkyl, cycloalkyl, aryl, alkyl-aryl, heterocyclyl or heteroaryl are optionally substituted with up to three $R^{10}$;

Each X is independently $CR^7R^8$, $NR^9$, oxo, S, SO, $SO_2$, or O;

$Z^1$ is $CR^3R^4$, $NR^9$, S, SO, $SO_2$, C=O, or O;

$Z^2$ is $CR^5R^6$, $NR^9$, S, SO, $SO_2$, C=O, or O;

n is 0, 1, or 2;

wherein:
  when n is 0, $Z^1$ is $CR^3R^4$, and $Z^2$ is $CR^5R^6$;
  when n is 2, only one X can be oxo, S, SO, $SO_2$, or O;
  when either $Z^1$ or $Z^2$ are O, SO, or $SO_2$, then X is $CR^7CR^8$, or $NR^9$;
  when both $Z^1$ and $Z^2$ are O, SO, or $SO_2$, then X is $CR^7CR^8$;
  and
  wherein the dashed circle represents one or more optional double bonds;

$R^3$, $R^4$, $R^5$, $R^6$, $R^7$, $R^8$ are independently absent, H, $C_{1-6}$ alkyl, halogen, or $C_{3-7}$ cycloalkyl; alternatively $R^3$, $R^4$, $R^5$, $R^6$, $R^7$ or $R^8$ can be combined with the atoms to which they are attached to form a 3-6 membered spiro, bridged or fused ring;

$R^9$ is absent, H, $C_{1-6}$ alkyl, or $C_{3-7}$ cycloalkyl;

each $R^{10}$ is independently $C_{1-6}$ alkoxy, CN, halogen, OH, $NH_2$, $NHR^{11}$, $CONH_2$, $SO_2NH_2$, COOH, $CO_2R^{12}$, or $NHCO_2$—$C_{1-6}$ alkyl;

$R^{11}$ is H, $C_{1-6}$ alkyl, or $C_{1-6}$ haloalkyl;

$R^{12}$ is H, $C_{1-6}$ alkyl, $C_{1-6}$ haloalkyl, 3-7 cycloalkyl, 4-7 heterocyclyl, $C_{6-10}$ aryl, or 5-11 heteroaryl; and $R^{13}$ is $C_{1-6}$ alkyl, or $C_{1-6}$ haloalkyl.

In another embodiment, the present disclosure provides a compound of Formula II,

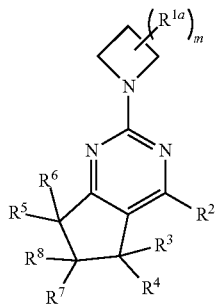

Formula II or a pharmaceutically acceptable salt or stereoisomer thereof, wherein wherein m is 0-4;

each $R^{1a}$ is independently $C_{1-6}$ alkyl, $C_{2-6}$ alkenyl, $C_{2-6}$ alkynyl, OH, $OR^{1b}$, $CH_2OH$, COOH, $CO_2R^{12}$, halogen, oxo, $CONH_2$, CN, $NH_2$, $NHR^{11}$, $C_{1-6}$ alkyl-$NHSO_2R^{13}$, $C_{1-6}$ alkyl-$NHCOR^{13}$, $C_{1-6}$ alkoxy or $C_{1-6}$ haloalkyl, wherein the alkyl, alkenyl, or alkynyl are optionally substituted with up to three $R^{1c}$, alternatively two $R^{1a}$ can be combined with the atoms to which are attached to form a 3-6 membered spiro, fused or bridged ring;

$R^{1b}$ is H, or $C_{1-6}$ alkyl, wherein the alkyl is optionally substituted with up to three halogens, CN, or OH;

each $R^{1c}$ is independently OH, $OR^{11}$, halogen, oxo, $SOR^{13}$, $SO_2R^{13}$, $SR^{13}$, $SO_2NH_2$, $CONH_2$, $C_{1-6}$ alkoxy, $C_{6-10}$ aryl, $C_{6-10}$ aryloxy, 5-11 membered heteroaryl, or $C_{3-7}$ cycloalkyl;

$R^2$ is $C_{6-10}$ aryl, or a 6-14 membered heteroaryl, wherein the aryl, or heteroaryl are optionally substituted with up to eight $R^e a$, and wherein $R^2$ is attached to the core through a carbon atom of $R^2$;

each $R^e a$ is independently $C_{1-6}$ alkyl, $C_{2-6}$ alkenyl, $C_{2-6}$ alkynyl, $C_{1-6}$ alkoxy, $C_{1-6}$ haloalkyl, $SO_2R^{2e}$, $SOR^{2e}$, $SO_2NH_2$, COOH, $CO_2R^{12}$, $CONH_2$, $COR^{2e}$, $CONHR^{2e}$, $CON(R^{2e})_2$, halogen, oxo, OH, CN, $NH_2$, $NHR^{2e}$, $N(R^{2e})_2$, $NHCOR^{2e}$, $N(R^{2e})COR^{2e}$, $NO_2$, $SO_2NHR^{2e}$, $SO_2N(R^{2e})_2$, $NHSO_2R^{2e}$, $N(R^{2e})SO_2R^{2e}$, $S(O)(NH)R^{2e}$, $S(O)(NH)NH_2$, $NHS(O)(NH)R^{2e}$, $NS(O)(NH_2)R^{2e}$, $NS(O)(R^{2e})_2$, $S(O)(NR^{2e})R^{2e}$, $S(O)(NR^{2e})NH_2$, $S(O)(NH)NHR^{2e}$, $S(O)(NR^{2e})NH(R^{2e})$, $OR^{2e}$, $C_{3-7}$ cycloalkyl, 4-7 membered heterocyclyl, $C_{6-10}$ aryl, or 5-11 membered heteroaryl, wherein the alkyl, alkenyl, alkynyl, cycloalkyl, heterocyclyl, aryl or heteroaryl are substituted with up to seven $R^{26}$, and wherein the cycloalkyl can be fused or spiro to the heteroaryl, or the cycloalkyl can be fused to the aryl; alternatively two $R^e a$ can be combined with the atoms to which they are attached to form a 3-7 membered spiro, fused or bridged ring;

each $R^{2b}$ is independently $C_{1-6}$ alkyl, $C_{1-6}$ haloalkyl, $C_{1-6}$ alkoxy, OH, halogen, oxo, COOH, $CO_2R^{12}$, $CONH_2$, $NHCOR^{2c}$, $N(R^{2c})COR^{2c}$, $NHCO_2R^{2c}$, $NH_2$, $N(R^{2c})_2$, $NHR^{2c}$, $S(O)(NH)R^{2c}$, $S(O)(NH)NH_2$, $NHS(O)(NH)$ $R^{2c}$, $NS(O)(NH_2)R^{2c}$, $NS(O)(R^{2e})_2$, $S(O)(NR^{2c})R^{2c}$, $S(O)(NR^{2c})NH_2$, $S(O)(NH)NHR^{2c}$, $S(O)(NR^{2c})NH$ $(R^{2c})$, $OR^{2e}$, $NHSO_2R^{2c}$, $N(R^{2c})SO_2R^{2c}$, $C_{1-6}$ alkyl-$CO_2R^{12}$, C alkyl-$CONH_2$, C alkyl-$NHSO_2R^{2c}$, CN, $COR^{2c}$, $NHCO_2R^{2c}$, $SO_2NH_2$, $SO_2NHR^{2c}$, $SO_2R^{2c}$, $C_{3-7}$ cycloalkyl, 4-7 membered heterocyclyl, $C_{6-10}$ aryl or 5-11 membered heteroaryl, wherein the alkyl, alkoxy, haloalkyl, cycloalkyl, heterocyclyl, aryl or heteroaryl can be optionally substituted with up to four $R^{2d}$; alternatively two $R^{26}$ can be combined with the atoms to which they are attached to form a 3-7 membered spiro, fused or bridged ring;

each $R^{2c}$ is independently $C_{1-6}$ alkyl, C haloalkyl, C alkoxy, $C_{6-10}$ aryl, 5-11 membered heteroaryl, or 4-7 membered heterocyclyl, wherein the alkyl, haloalkyl, alkoxy, aryl, heteroaryl or heterocyclyl are optionally substituted with up to four $R^{2d}$;

each $R^{2d}$ is independently OH, halogen, $NH_2$, C alkoxy, $CONH_2$, $SO_2NH_2$, COOH, $CO_2R^{12}$, $NHCOR^{13}$, $C_{1-6}$ alkyl, C haloalkyl, C alkyl-$NH_2$, $C_{1-6}$ alkyl-$CO_2R^{12}$, oxo, or CN;

$R^{2e}$ is $C_{1-6}$ alkyl, $C_{3-7}$ cycloalkyl, $C_{6-10}$ aryl, C alkyl-$C_{6-10}$ aryl, 4-7 membered heterocyclyl, or 5-11 membered heteroaryl, wherein the alkyl, cycloalkyl, aryl, alkyl-aryl, heterocyclyl or heteroaryl are optionally substituted with up to three $R^{10}$;

$R^3$, $R^4$, $R^5$, $R^6$, $R^7$, $R^8$ are independently H, $C_{1-6}$ alkyl, halogen, or $C_{3-7}$ cycloalkyl; alternatively $R^3$, $R^4$, $R^5$, $R^6$, $R^7$ or $R^8$ can be combined with the atoms to which they are attached to form a 3-6 membered spiro, bridged or fused ring;

each $R^{10}$ is independently $C_{1-6}$ alkoxy, CN, halogen, OH, $NH_2$, $NHR^{11}$, $CONH_2$, $SO_2NH_2$, COOH, $CO_2R^{12}$, or $NHCO_2$—$C_{1-6}$ alkyl;

$R^{11}$ is H, $C_{1-6}$ alkyl, or C haloalkyl;

$R^{12}$ is H, $C_{1-6}$ alkyl, $C_{1-6}$ haloalkyl, 3-7 cycloalkyl, 4-7 heterocyclyl, $C_{6-10}$ aryl, or 5-11 heteroaryl; and $R^{13}$ is $C_{1-6}$ alkyl, or $C_{1-6}$ haloalkyl.

In another embodiment, the present disclosure provides a compound of Formula V,

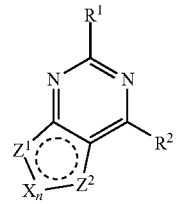

Formula V wherein $R^1$ is a 4-10 membered heterocyclic moiety, wherein the heterocycle contains 1-3 heteroatoms, and is optionally substituted with up to four $R^{1a}$; or $C_{3-7}$ cycloalkyl, optionally substituted with up to four substituents independently selected from $C_{1-6}$ alkyl, $C_{1-6}$ alkoxy, $C_{1-6}$ haloalkyl, halogen, CN, OH, $CH_2OH$, $CH_2OR^{11}$, $CONH_2$, $CONHR^{11}$, $NHCOR^{13}$, $SO_2NH_2$, $SO_2NHR^{11}$, $NHSO_2R^{13}$ or oxo;

each $R^{1a}$ is independently $C_{1-6}$ alkyl, $C_{2-6}$ alkenyl, $C_{2-6}$ alkynyl, $C_{3-7}$ cycloalkyl, OH, $OR^{1b}$, $CH_2OH$, $CO_2R^{12}$, halogen, oxo, $CONH_2$, CN, $NH_2$, $NHR^{11}$, $C_{1-6}$ alkyl-$NHSO_2R^{13}$, $C_{1-6}$ alkyl-$NHCOR^{13}$, $C_{1-6}$ alkoxy or $C_{1-6}$ haloalkyl, wherein the alkyl, alkenyl, alkynyl, cycloalkyl, alkyl-$NHSO_2R^{13}$, alkyl-$NHCOR^{13}$, alkoxy, or haloalkyl are optionally substituted with up to three $R^{1c}$; alternatively two $R^{1a}$ can be combined with the atoms to which they are attached to form a 3-6 membered spiro, fused or bridged ring;

$R^{1b}$ is H, or $C_{1-6}$ alkyl, wherein the alkyl is optionally substituted with up to three halogens, CN, or OH;

each $R^{1c}$ is independently OH, $OR^{11}$, halogen, oxo, $SOR^{13}$, $SO_2R^{13}$, $SR^{13}$, $SO_2NH_2$, $CONH_2$, CN, $C_{1-6}$ alkoxy, $C_{6-10}$ aryl, $C_{6-10}$ aryloxy, 5-11 membered heteroaryl, or $C_{3-7}$ cycloalkyl;

$R^2$ is a 5 membered heteroaryl, wherein the heteroaryl is optionally substituted with up to three $R^{2a}$, and wherein $R^2$ is attached to the core through a carbon atom of $R^2$;

each $R^{2a}$ is independently $C_{1-6}$ alkyl, $C_{2-6}$ alkenyl, $C_{2-6}$ alkynyl, $C_{1-6}$ alkoxy, $C_{1-6}$ haloalkyl, $SO_2R^{2c}$, $SOR^{2c}$, $SO_2NH_2$, $CONH_2$, $COR^{2c}$, $CONHR^{2e}$, $CON(R^{2c})_2$, halogen, oxo, OH, CN, $NH_2$, $NHR^{2c}$, $N(R^{2c})_2$, $NHCOR^{2c}$, $N(R^{2c})COR^{2c}$, $NHCO_2R^{2c}$, $NO_2$, $SO_2NHR^{2c}$, $SO_2N(R^{2c})_2$, $NHSO_2R^{2c}$, $N(R^{2c})SO_2R^{2c}$, $S(O)(NH)R^{2c}$, $S(O)(NH)NH_2$, $NHS(O)(NH)R^{2c}$, $NS(O)(NH_2)R^{2c}$, $NS(O)(R^{2c})_2$, $S(O)(NR^{2c})R^{2c}$, $S(O)(NR^{2c})NH_2$, $S(O)(NH)NHR^{2c}$, $S(O)(NR^{2c})NH(R^{2c})$, $OR^{2e}$, $SR^{2e}$, $C_{3-7}$ cycloalkyl, 4-7 membered heterocyclyl, $C_{6-10}$ aryl, or 5-11 membered heteroaryl, wherein the alkyl, alkenyl, alkynyl, cycloalkyl, heterocyclyl, aryl or heteroaryl are substituted with up to seven $R^{2b}$, and wherein the cycloalkyl can be fused or spiro to the heteroaryl, or the cycloalkyl can be fused to the aryl; alternatively two $R^{2c}$ can be combined with the atoms to which they are attached to form a 3-7 membered spiro, fused or bridged ring;

each $R^{2b}$ is independently $C_{1-6}$ alkyl, $C_{1-6}$ haloalkyl, $C_{1-6}$ alkoxy, OH, halogen, oxo, $CONH_2$, $CONHR^{2e}$, $CON(R^{2c})_2$, $NHCOR^{2c}$, $N(R^{2c})COR^{2c}$, $NHCO_2R^{2c}$, $NH_2$, $N(R^{2c})_2$, $NHR^{2c}$, $S(O)(NH)R^{2c}$, $S(O)(NH)NH_2$, $NHS(O)(NH)R^{2c}$, $NS(O)(NH_2)R^{2c}$, $NS(O)(R^{2c})_2$, $S(O)(NR^{2c})R^{2c}$, $S(O)(NR^{2c})NH_2$, $S(O)(NH)NHR^{2c}$, $S(O)(NR^{2c})NH(R^{2c})$, $OR^{2e}$, $NHSO_2R^{2c}$, $N(R^{2c})SO_2R^{2c}$, $C_{1-6}$ alkyl-$CO_2R^{12}$, $C_{1-6}$ alkyl-$CONH_2$, $C_{1-6}$ alkyl-$NHSO_2R^{2c}$, $C_{1-6}$ alkyl-$SO_2R^{2c}$, CN, $COR^{2c}$, $NHCO_2R^{2c}$, $SO_2NH_2$, $SO_2NHR^{2c}$, $SO_2R^{2c}$, $C_{3-7}$ cycloalkyl, 4-7 membered heterocyclyl, $C_{6-10}$ aryl or 5-11 membered heteroaryl, wherein the alkyl, $C_{1-6}$ alkyl-$CO_2R^{12}$, $C_{1-6}$ alkyl-$CONH_2$, $C_{1-6}$ alkyl-$NHSO_2R^{2c}$, $C_{1-6}$ alkyl-$SO_2R^{2c}$, alkoxy, haloalkyl, cycloalkyl, heterocyclyl, aryl or heteroaryl can be optionally substituted with up to four $R^{2d}$; alternatively two $R^{2b}$ can be combined with the atoms to which they are attached to form a 3-7 membered spiro, fused or bridged ring;

each $R^{2c}$ is independently $C_{1-6}$ alkyl, $C_{1-6}$ haloalkyl, $C_{1-6}$ alkoxy, $C_{3-7}$ cycloalkyl, $C_{6-10}$ aryl, alkyl-$C_{6-10}$ aryl, 5-11 membered heteroaryl, or 4-7 membered heterocyclyl, wherein the alkyl, haloalkyl, alkoxy, cycloalkyl, aryl, alkyl-aryl, heteroaryl or heterocyclyl are optionally substituted with up to four $R^{2d}$; alternatively two $R^{2c}$ can be combined with the atoms to which they are attached to form a 3-7 membered ring;

each $R^{2d}$ is independently OH, halogen, $NH_2$, $C_{1-6}$ alkoxy, $CONH_2$, $COR^{2e}$, $SO_2NH_2$, $NR^{11}COR^{13}$, $NCH_2OR^{11}$, $C_{1-6}$ alkyl, C haloalkyl, $C_{3-7}$ cycloalkyl, 4-7 membered heterocyclyl, $C_{1-6}$ alkyl-$NH_2$, $C_{1-6}$ alkyl-$CO_2R^{12}$, oxo, or CN;

$R^{2e}$ is $C_{1-6}$ alkyl, $C_{3-7}$ cycloalkyl, $C_{6-10}$ aryl, C alkyl-$C_{6-10}$ aryl, 4-7 membered heterocyclyl, or 5-11 membered heteroaryl, wherein the alkyl, cycloalkyl, aryl, alkyl-aryl, heterocyclyl or heteroaryl are optionally substituted with up to three $R^{10}$;

Each X is independently $CR^7R^8$, oxo, S, SO, $SO_2$, or O;

$Z^1$ is $CR^3R^4$, $NR^9$, S, SO, $SO_2$, C=O, or O;

$Z^2$ is $CR^5R^6$, $NR^9$, S, SO, $SO_2$, C=O, or O;

n is 0, 1, or 2;

wherein:
when n is 0, $Z^1$ is $CR^3R^4$, and $Z^2$ is $CR^5R^6$;
when n is 2, only one X can be oxo, S, SO, $SO_2$, or O;
when either $Z^1$ or $Z^2$ are O, SO, or $SO_2$, then X is $CR^7CR^8$;
when both $Z^1$ and $Z^2$ are O, SO, or $SO_2$, then X is $CR^7CR^8$;
and
wherein the dashed circle represents one or more optional double bonds;

$R^3$, $R^4$, $R^5$, $R^6$, $R^7$, $R^8$ are independently absent, H, $C_{1-6}$ alkyl, halogen, or $C_{3-7}$ cycloalkyl; alternatively $R^3$, $R^4$, $R^5$, $R^6$, $R^7$ or $R^8$ can be combined with the atoms to which they are attached to form a 3-6 membered spiro, bridged or fused ring;

$R^9$ is absent, H, $C_{1-6}$ alkyl, or $C_{3-7}$ cycloalkyl;

each $R^{10}$ is independently $C_{1-6}$ alkoxy, CN, halogen, OH, $NH_2$, $NHR^{11}$, $CONH_2$, $SO_2NH_2$, or $NHCO_2$—$C_{1-6}$ alkyl;

$R^{11}$ is H, $C_{1-6}$ alkyl, or C haloalkyl;

$R^{12}$ is $C_{1-6}$ alkyl, $C_{1-6}$ haloalkyl, 3-7 cycloalkyl, 4-7 heterocyclyl, $C_{6-10}$ aryl, or 5-11 heteroaryl; and $R^{13}$ is $C_{1-6}$ alkyl, or $C_{1-6}$ haloalkyl.

In another embodiment, the present disclosure provides a compound of Formula V,

Formula V or a pharmaceutically acceptable salt or stereoisomer thereof, wherein $R^1$ is a 4-10 membered heterocyclic moiety, wherein the heterocycle contains 1-3 heteroatoms, and is optionally substituted with up to four $R^{1a}$; or $C_{3-7}$ cycloalkyl, optionally substituted with up to four substituents independently selected from $C_{1-6}$ alkyl, $C_{1-6}$ alkoxy, $C_{1-6}$ haloalkyl, halogen, CN, OH, $CH_2OH$, $CH_2OR^{11}$, $CONH_2$, $CONHR^{11}$, $NHCOR^{13}$, $SO_2NH_2$, $SO_2NHR^{11}$, $NHSO_2R^{13}$ or oxo;

each $R^{1a}$ is independently $C_{1-6}$ alkyl, $C_{2-6}$ alkenyl, $C_{2-6}$ alkynyl, OH, $OR^{1b}$, $CH_2OH$, COOH, $CO_2R^{12}$, halogen, oxo, $CONH_2$, CN, $NH_2$, $NHR^{11}$, $C_{1-6}$ alkyl-$NHSO_2R^{13}$, $C_{1-6}$ alkyl-$NHCOR^{13}$, $C_{1-6}$ alkoxy or $C_{1-6}$ haloalkyl, wherein the alkyl, alkenyl, or alkynyl are optionally substituted with up to three $R^{1c}$; alternatively two $R^{1a}$ can be combined with the atoms to which they are attached to form a 3-6 membered spiro, fused or bridged ring;

$R^{1b}$ is H, or $C_{1-6}$ alkyl, wherein the alkyl is optionally substituted with up to three halogens, CN, or OH;

each $R^{1c}$ is independently OH, $OR^{11}$, halogen, oxo, $SOR^{13}$, $SO_2R^{13}$, $SR^{13}$, $SO_2NH_2$, $CONH_2$, $C_{1-6}$ alkoxy, $C_{6-10}$ aryl, $C_{6-10}$ aryloxy, 5-11 membered heteroaryl, or $C_{3-7}$ cycloalkyl;

$R^2$ is a 5 membered heteroaryl, wherein the heteroaryl is optionally substituted with up to three $R^{2a}$, and wherein $R^2$ is attached to the core through a carbon atom of $R^2$;

each $R^{2a}$ is independently $C_{1-6}$ alkyl, $C_{2-6}$ alkenyl, $C_{2-6}$ alkynyl, $C_{1-6}$ alkoxy, $C_{1-6}$ haloalkyl, $SO_2R^{2c}$, $SOR^{2c}$, $SO_2NH_2$, COOH, $CO_2R^{12}$, $CONH_2$, $COR^{2c}$, $CONHR^{2e}$, $CON(R^{2c})_2$, halogen, oxo, OH, CN, $NH_2$, $NHR^{2c}$, $N(R^{2c})_2$, $NHCOR^{2c}$, $N(R^{2c})COR^{2c}$, $NO_2$, $SO_2NHR^{2c}$, $SO_2N(R^{2c})_2$, $NHSO_2R^{2c}$, $N(R^{2c})SO_2R^{2c}$, $S(O)(NH)R^{2e}$, $S(O)(NH)NH_2$, $NHS(O)(NH)R^{2c}$, $NS(O)(NH_2)R^{2c}$, $NS(O)(R^{2c})_2$, $S(O)(NR^{2c})R^{2c}$, $S(O)(NR^{2c})NH_2$, $S(O)(NH)NHR^{2c}$, $S(O)(NR^{2c})NH(R^{2c})$, $OR^{2e}$, $C_{3-7}$ cycloalkyl, 4-7 membered heterocyclyl, $C_{6-10}$ aryl, or 5-11 membered heteroaryl, wherein the alkyl, alkenyl, alkynyl, cycloalkyl, heterocyclyl, aryl or heteroaryl are substituted with up to seven $R^{2b}$, and wherein the cycloalkyl can be fused or spiro to the heteroaryl; alternatively two $R^ea$ can be combined with the atoms to which they are attached to form a 3-7 membered spiro, fused or bridged ring;

each $R^{2b}$ is independently $C_{1-6}$ alkyl, $C_{1-6}$ haloalkyl, $C_{1-6}$ alkoxy, OH, halogen, oxo, $CO_2H$, $CO_2R^{12}$, $CONH_2$, $NHCOR^{2c}$, $N(R^{2c})COR^{2c}$, $NHCO_2R^{2c}$, $NH_2$, $N(R^{2c})_2$, $NHR^{2c}$, $S(O)(NH)R^{2c}$, $S(O)(NH)NH_2$, $NHS(O)(NH)R^{2c}$, $NS(O)(NH_2)R^{2c}$, $NS(O)(R^{2c})_2$, $S(O)(NR^{2c})R^{2c}$, $S(O)(NR^{2c})NH_2$, $S(O)(NH)NHR^{2c}$, $S(O)(NR^{2c})NH(R^{2c})$, $OR^{2e}$, $NHSO_2R^{2c}$, $N(R^{2c})SO_2R^{2c}$, $C_{1-6}$ alkyl-$CO_2R^{12}$, $C_{1-6}$ alkyl-$CONH_2$, $C_{1-6}$ alkyl-$NHSO_2R^{2c}$, CN, $COR^{2c}$, $NHCO_2R^{2c}$, $SO_2NH_2$, $SO_2NHR^{2c}$, $SO_2R^{2c}$, $C_{3-7}$ cycloalkyl, 4-7 membered heterocyclyl, $C_{6-10}$ aryl or 5-11 membered heteroaryl, wherein the alkyl, alkoxy, haloalkyl, cycloalkyl, heterocyclyl, aryl or heteroaryl can be optionally substituted with up to four $R^{2d}$; alternatively two $R^{2b}$ can be combined with the atoms to which they are attached to form a 3-7 membered spiro, fused or bridged ring;

each $R^{2c}$ is independently $C_{1-6}$ alkyl, $C_{1-6}$ haloalkyl, $C_{1-6}$ alkoxy, $C_{6-10}$ aryl, 5-11 membered heteroaryl, or 4-7 membered heterocyclyl, wherein the alkyl, haloalkyl, alkoxy, aryl, heteroaryl or heterocyclyl are optionally substituted with up to four $R^{2d}$;

each $R^{2d}$ is independently OH, halogen, $NH_2$, $C_{1-6}$ alkoxy, $CONH_2$, $SO_2NH_2$, $CO_2H$, $CO_2R^{12}$, $NHCOR^{13}$, $C_{1-6}$ alkyl, $C_{1-6}$ haloalkyl, $C_{1-6}$ alkyl-$NH_2$, $C_{1-6}$ alkyl-$CO_2R^{12}$, oxo, or CN;

$R^{2e}$ is $C_{1-6}$ alkyl, $C_{3-7}$ cycloalkyl, $C_{6-10}$ aryl, $C_{1-6}$ alkyl-$C_{6-10}$ aryl, 4-7 membered heterocyclyl, or 5-11 membered heteroaryl, wherein the alkyl, cycloalkyl, aryl, alkyl-aryl, heterocyclyl or heteroaryl are optionally substituted with up to three $R^{10}$;

each X is independently $CR^7R^8$, $NR^9$, oxo, S, SO, $SO_2$, or O;

$Z^1$ is $CR^3R^4$, $NR^9$, S·SO, $SO_2$, C=O, or O;

$Z^2$ is $CR^5R^6$, $NR^9$, S, SO, $SO_2$, C=O, or O;

n is 0, 1, or 2;

wherein:

when n is 0, $Z^1$ is $CR^3R^4$, and $Z^2$ is $CR^5R^6$;

when n is 2, only one X can be oxo, S, SO, $SO_2$, or O;

when either $Z^1$ or $Z^2$ are O, SO, or $SO_2$, then X is $CR^7CR^8$, or $NR^9$;

when both $Z^1$ and $Z^2$ are O, SO, or $SO_2$, then X is $CR^7CR^8$;

and wherein the dashed circle represents one or more optional double bonds;

$R^3$, $R^4$, $R^5$, $R^6$, $R^7$, $R^8$ are independently absent, H, $C_{1-6}$ alkyl, halogen, or $C_{3-7}$ cycloalkyl; alternatively $R^3$, $R^4$, $R^5$, $R^6$, $R^7$ or $R^8$ can be combined with the atoms to which they are attached to form a 3-6 membered spiro, bridged or fused ring;

$R^9$ is absent, H, $C_{1-6}$ alkyl, or $C_{3-7}$ cycloalkyl;

each $R^{10}$ is independently $C_{1-6}$ alkoxy, CN, halogen, OH, $NH_2$, $NHR^{11}$, $CONH_2$, $SO_2NH_2$, COOH, $CO_2R^{12}$, or $NHCO_2$—$C_{1-6}$ alkyl;

$R^{11}$ is H, $C_{1-6}$ alkyl, or $C_{1-6}$ haloalkyl;

$R^{12}$ is H, $C_{1-6}$ alkyl, $C_{1-6}$ haloalkyl, 3-7 cycloalkyl, 4-7 heterocyclyl, $C_{6-10}$ aryl, or 5-11 heteroaryl; and $R^{13}$ is $C_{1-6}$ alkyl, or $C_{1-6}$ haloalkyl.

DETAILED DESCRIPTION

Definitions

"Core" as used herein is represented in its broadest sense by the structure:

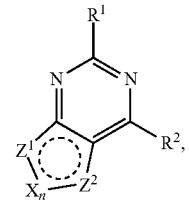

wherein $R^1$, $R^2$, $Z^1$, $Z^2$ and $X_n$ are defined herein.

"Alkyl" is a linear or branched saturated monovalent hydrocarbon. For example, an alkyl group can have 1 to 18 carbon atoms (i.e., $C_{1-18}$ alkyl) or 1 to 8 carbon atoms (i.e., $C_{1-8}$ alkyl) or 1 to 6 carbon atoms (i.e., $C_{1-6}$ alkyl) or 1 to 4 carbon atoms (i.e., $C_{1-4}$ alkyl). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), and 3,3-dimethyl-2-butyl (—$CH(CH_3)C(CH_3)_3$. Other alkyl groups include heptyl, octyl, nonyl, decyl, undecyl, dodecyl, pentadcyl, hexadecyl, heptadecyl and octadecyl.

"Alkenyl" is a monovalent or divalent linear or branched hydrocarbon radical with at least one carbon-carbon double bond. For example, an alkenyl group can have 2 to 8 carbon atoms (i.e. $C_{2-8}$ alkenyl) or 2 to 6 carbon atoms (i.e. $C_{2-6}$ alkenyl) or 2 to 4 carbon atoms (i.e. $C_{2-4}$ alkenyl). Examples of alkenyl groups include, but are not limited to, ethenyl (—CH═CH$_2$), allyl (—CH$_2$CH═CH$_2$), and —CH$_2$—CH═CH—CH$_3$. Alkenyl groups can be unsubstituted or substituted.

"Alkynyl" is a monovalent or divalent linear or branched hydrocarbon radical with at least one carbon-carbon triple bond. For example, an alkynyl group can have 2 to 8 carbon atoms (i.e. C$_{2-8}$ alkynyl) or 2 to 6 carbon atoms (i.e. C$_{2-6}$ alkynyl) or 2 to 4 carbon atoms (i.e. C$_{2-4}$ alkynyl). Examples of alkynyl groups include, but are not limited to, acetylenyl (—CCH), propargyl (—CH$_2$C≡CH), and —CH$_2$—C≡C—CH$_3$. Alkynyl groups can be unsubstituted or substituted.

"Alkoxy" refers to an alkyl group having an oxygen atom that connects the alkyl group to the point of attachment: alkyl-O—. As for alkyl group, alkoxy groups can have any suitable number of carbon atoms, such as C$_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, OCF$_3$, OCHF$_2$, etc.

"Aryl" as used herein refers to a single all carbon aromatic ring or a multiple condensed all carbon ring system wherein at least one of the rings is aromatic. For example, in some embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is also to be understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl and 1,2,3,4-tetrahydronaphthyl. Non-limiting examples of aryl groups include, but are not limited to, phenyl, indenyl, naphthyl, 1,2,3,4-tetrahydronaphthyl, anthracenyl, and the like. Specific examples of polycyclic carbocycles include, without limitation:

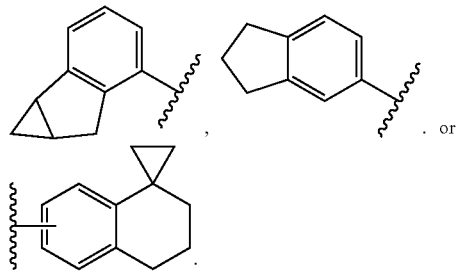

"Cycloalkyl" refers to a single saturated or partially unsaturated all carbon ring having 3 to 20 annular carbon atoms (i.e., C$_{3-20}$ cycloalkyl), for example from 3 to 12 annular atoms, for example from 3 to 10 annular atoms, or 3 to 8 annular atoms, or 3 to 6 annular atoms, or 3 to 5 annular atoms, or 3 to 4 annular atoms. The term "cycloalkyl" also includes multiple condensed, saturated and partially unsaturated all carbon ring systems (e.g., ring systems comprising 2, 3 or 4 carbocyclic rings). Accordingly, cycloalkyl includes multicyclic carbocycles such as a bicyclic carbocycles (e.g., bicyclic carbocycles having 6 to 12 annular carbon atoms such as bicyclo[3.1.0]hexane, bicyclo[2.2.1]heptane and bicyclo[2.1.1]hexane), and polycyclic carbocycles (e.g., tricyclic and tetracyclic carbocycles with up to 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

"Alkyl-cycloalkyl" refers to a radical having an alkyl component and a cycloalkyl component, where the alkyl component links the cycloalkyl component to the point of attachment. The alkyl component is as defined above, except that the alkyl component is at least divalent, an alkylene, to link to the cycloalkyl component and to the point of attachment. In some instances, the alkyl component can be absent. The alkyl component can include any number of carbons, such as C$_{1-6}$, C$_{1-2}$, C$_{1-3}$, C$_{1-4}$, C$_{1-5}$, C$_{2-3}$, C$_{2-4}$, C$_{2-5}$, C$_{2-6}$, C$_{3-4}$, C$_{3-5}$, C$_{3-6}$, C$_{4-5}$, C$_{4-6}$ and C$_{5-6}$. The cycloalkyl component is as defined within. Exemplary alkyl-cycloalkyl groups include, but are not limited to, methyl-cyclopropyl, methyl-cyclobutyl, methyl-cyclopentyl and methyl-cyclohexyl.

"Alkyl-aryl" refers to a radical having an alkyl component and an aryl component, where the alkyl component links the aryl component to the point of attachment. The alkyl component is as defined above, except that the alkyl component is at least divalent, an alkylene, to link to the aryl component and to the point of attachment. In some instances, the alkyl component can be absent. The alkyl component can include any number of carbons, such as C$_{1-6}$, C$_{1-2}$, C$_{1-3}$, C$_{1-4}$, C$_{1-5}$, C$_{2-3}$, C$_{2-4}$, C$_{2-5}$, C$_{2-6}$, C$_{3-4}$, C$_{3-5}$, C$_{3-6}$, C$_{4-5}$, C$_{4-6}$ and C$_{5-6}$. The aryl component is as defined herein. Exemplary alkyl-aryl groups include, but are not limited to, methyl-phenyl, or ethyl-phenyl.

"Heterocyclyl" or "heterocycle" or "heterocycloalkyl" or "heterocyclic" as used herein refers to a single saturated or partially unsaturated non-aromatic ring or a multiple ring system having at least one heteroatom in the ring (i.e., at least one annular heteroatom selected from oxygen, nitrogen, and sulfur) wherein the multiple ring system includes at least one non-aromatic ring containing at least one heteroatom. The multiple ring system can also include other aromatic rings and non-aromatic rings. Unless otherwise specified, a heterocyclyl group has from 3 to 20 annular atoms, for example from 3 to 12 annular atoms, for example from 3 to 10 annular atoms, or 3 to 8 annular atoms, or 3 to 6 annular atoms, or 3 to 5 annular atoms, or 4 to 6 annular atoms, or 4 to 5 annular atoms. Thus, the term includes single saturated or partially unsaturated rings (e.g., 3, 4, 5, 6 or 7-membered rings) having from 1 to 6 annular carbon atoms and from 1 to 3 annular heteroatoms selected from the group consisting of oxygen, nitrogen and sulfur in the ring. The heteroatoms can optionally be oxidized to form —N(—OH)—, —S(═O)— or —S(═O)$_2$—. The rings of the multiple condensed ring (e.g. bicyclic heterocyclyl) system can be connected to each other via fused, spiro and bridged bonds when allowed by valency requirements. Heterocycles include, but are not limited to, azetidine, aziridine, imidazolidine, morpholine, oxirane (epoxide), oxetane, thietane, piperazine, piperidine, pyrazolidine, piperidine, pyrrolidine, pyrrolidinone, tetrahydrofuran, tetrahydrothiophene, dihydropyridine, tetrahydropyridine, quinuclidine, 2-oxa-6-azaspiro[3.3]heptan-6-yl, 6-oxa-1-azaspiro[3.3]heptan-1-yl, 2-thia-6-azaspiro[3.3]heptan-6-yl, 2,6-diazaspiro[3.3]heptan-2-yl, 2-azabicyclo[3.1.0]hexan-2-yl, 3-azabicyclo[3.1.0]hexanyl, 2-azabicyclo[2.1.1]hexanyl, 2-azabicyclo[2.2.1]heptan-2-yl, 4-azaspiro[2.4]heptanyl, 5-azaspiro[2.4]heptanyl, and the like.

Examples of heterocyclyl groups include, without limitation:

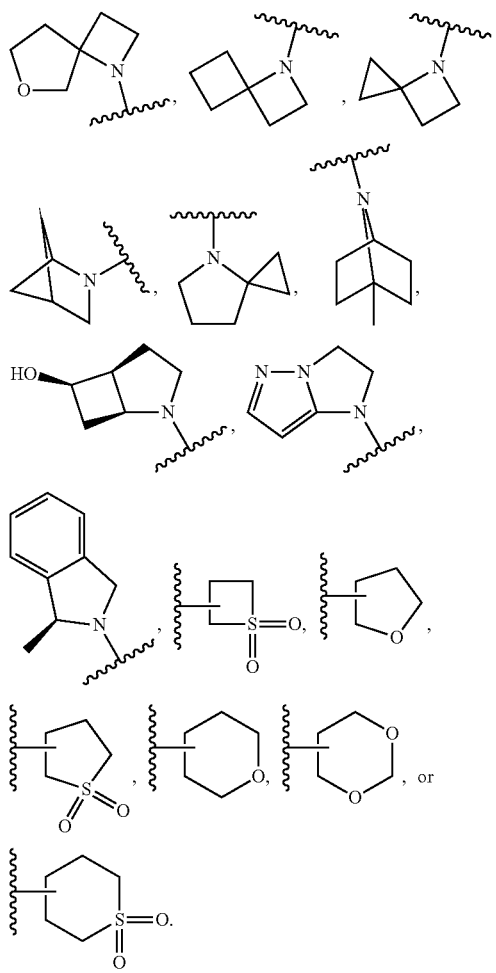

"Halo" or "halogen" as used herein refers to fluoro (—F), chloro (—Cl), bromo (—Br) and iodo (—I).

"Oxo" as used herein refers to =O, SO, SO$_2$, or SO(NH). Examples of compounds containing oxo groups include, for example but not limited to

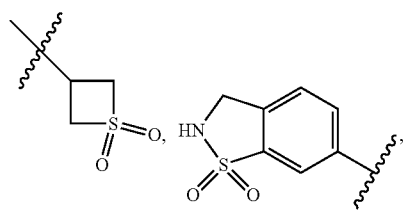

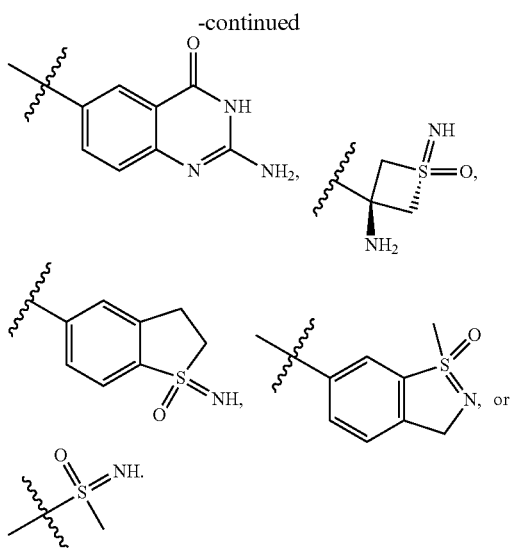

"Haloalkyl" as used herein refers to an alkyl as defined herein, wherein one or more hydrogen atoms of the alkyl are independently replaced by a halo substituent, which may be the same or different. For example, $C_{1-4}$ haloalkyl is a $C_{1-4}$ alkyl wherein one or more of the hydrogen atoms of the $C_{1-4}$ alkyl have been replaced by a halo substituent. Examples of haloalkyl groups include but are not limited to fluoromethyl, fluorochloromethyl, difluoromethyl, difluorochloromethyl, trifluoromethyl, 1,1,1-trifluoroethyl and pentafluoroethyl.

"Heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings from 1 to 6 carbon atoms and 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl.

"Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl), heterocycles, (to form for example 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has 1-20 carbon atoms and 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5 to 10 membered heteroaryl), the atom range is for the total ring atoms of the heteroaryl and includes carbon atoms and heteroatoms. For example, a 5-membered heteroaryl would include a thiazolyl and a 10-membered heteroaryl would include a quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, and triazolyl.

"Heteroaryl" rings also include 8 to 15 membered fused rings having 2, 3, or more rings wherein at least one ring is an aromatic ring and at least one ring is a non-aromatic ring containing at least one heteroatom. Representative fused bicyclic heteroaryls include, but are not limited to, indoline (dihydroindole), isoindoline (dihydroisoindole), indazoline (dihydroindazole), benzo[d]imidazole, dihydroquinoline, dihydroisoquinoline, dihydrobenzofuran, dihydroisobenzofuran, benzo[d][1,3]dioxol, dihydrobenzo[b]dioxine, dihydrobenzo[d]oxazole, dihydrobenzo[b]thiophene, dihydroisobenzo[c]thiophene, dihydrobenzo[d]thiazole, dihydrobenzo[c]isothiazole, and benzo[b][1,4]thiazine, as shown in the structures below:

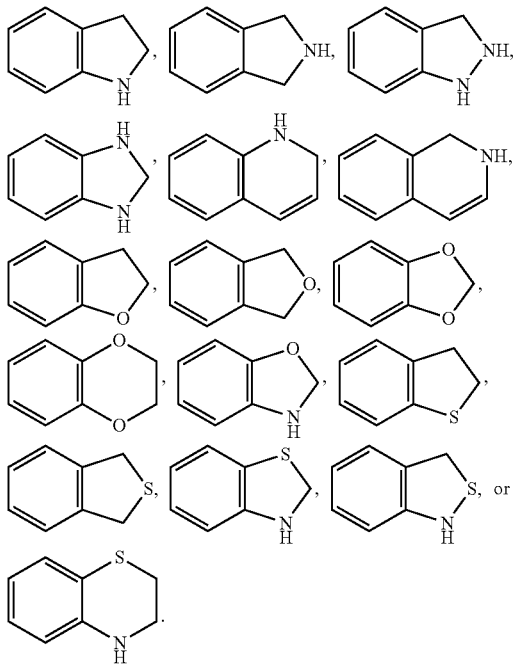

Examples of bicyclic heteroaryls can also be represented by the following structure:

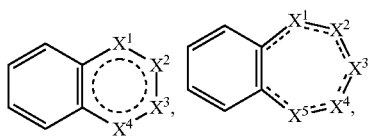

-continued

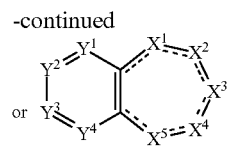

wherein $X^1$, $X^2$, $X^3$, $X^4$ and $X^5$ are each independently a bond, —CH—, —CH$_2$—, —CF$_2$—, —N—, —NH—, —CO—, —SO$_2$—, —O—, —S—, at least one of $X^1$, $X^2$, $X^3$, $X^4$ and $X^5$ is —N—, —NH—, —CO—, —O—, —SO$_2$—, or —S—, and $Y^1$, $Y^2$, $Y^3$, $Y^4$ are each independently a bond, —CH—, —O—, —CO—, —S—, —NH—, or —N—, and at least one of $Y^1$, $Y^2$, $Y^3$, $Y^4$ is —CH—, —O—, —CO—, —S—, —NH— or —N—, wherein only one of $X^1$–$X^5$ or $Y^1$-$Y^4$ can be a bond, and the dashed circle or bonds represents a saturated or partially unsaturated non-aromatic ring, wherein at least one of $Y^1$, $Y^2$, $Y^3$, $Y^4$ is carbon, and wherein the point of attachment to the core is through a carbon atom. The fused bicyclic heteroaryls are optionally substituted with up to eight $R^{2a}$, wherein each $R^{2a}$ is independently $C_{1-6}$ alkyl, $C_{2-6}$ alkenyl, $C_{2-6}$ alkynyl, $C_{1-6}$ alkoxy, $C_{1-6}$ haloalkyl, SO$_2$R$^{2c}$, SOR$^{2c}$, SO$_2$NH$_2$, COOH, CO$_2$R$^{12}$, CONH$_2$, COR$^{2c}$, CONHR$^{2e}$, CON(R$^{2c}$)$_2$, halogen, oxo, OH, CN, NH$_2$, NHR$^{2c}$, N(R$^{2c}$)$_2$, NHCOR$^{2c}$, N(R$^{2e}$)COR$^{2e}$, NO$_2$, SO$_2$NHR$^{2c}$, SO$_2$N(R$^{2c}$)$_2$, NHSO$_2$R$^{2c}$, N(R$^{2c}$)SO$_2$R$^{2c}$, S(O)(NH)R$^{2c}$, S(O)(NH)NH$_2$, NHS(O)(NH)R$^{2c}$, NS(O)(NH$_2$)R$^{2c}$, NS(O)(R$^{2c}$)$_2$, S(O)(NR$^{2c}$)R$^{2c}$, S(O)(NR$^{2c}$)NH$_2$, S(O)(NH)NHR$^{2c}$, S(O)(NR$^{2c}$)NH(R$^{2c}$), OR$^{2e}$, $C_{3-7}$ cycloalkyl, 4-7 membered heterocyclyl, $C_{6-10}$ aryl, or 5-11 membered heteroaryl, wherein the alkyl, alkenyl, alkynyl, cycloalkyl, heterocyclyl, aryl or heteroaryl are substituted with up to seven $R^{2b}$, and wherein the cycloalkyl can be fused or spiro to the heteroaryl, or the cycloalkyl can be fused to the aryl; alternatively two $R^e$a can be combined with the atoms to which they are attached to form a 3-7 membered spiro, fused or bridged ring;

each $R^{2b}$ is independently $C_{1-6}$ alkyl, $C_{1-6}$ haloalkyl, $C_{1-6}$ alkoxy, OH, halogen, oxo, CO$_2$H, CO$_2$R$^{12}$, CONH$_2$, NHCOR$^{2c}$, N(R$^{2c}$)COR$^{2c}$, NHCO$_2$R$^{2c}$, NH$_2$, N(R$^{2c}$)$_2$, NHR$^{2c}$, S(O)(NH)R$^{2c}$, S(O)(NH)NH$_2$, NHS(O)(NH) R$^{2c}$, NS(O)(NH$_2$)R$^{2c}$, NS(O)(R$^{2e}$)$_2$, S(O)(NR$^{2c}$)R$^{2c}$, S(O)(NR$^{2c}$)NH$_2$, S(O)(NH)NHR$^{2c}$, S(O)(NR$^{2c}$)NH (R$^{2c}$), OR$^{2e}$, NHSO$_2$R$^{2c}$, N(R$^{2c}$)SO$_2$R$^{2e}$, $C_{1-6}$ alkyl-CO$_2$R$^{12}$, $C_{1-6}$ alkyl-CONH$_2$, $C_{1-6}$ alkyl-NHSO$_2$R$^{2c}$, CN, COR$^{2c}$, NHCO$_2$R$^{2e}$, SO$_2$NH$_2$, SO$_2$NHR$^{2c}$, SO$_2$R$^{2c}$, $C_{3-7}$ cycloalkyl, 4-7 membered heterocyclyl, $C_{6-10}$ aryl or 5-11 membered heteroaryl, wherein the alkyl, alkoxy, haloalkyl, cycloalkyl, heterocyclyl, aryl or heteroaryl can be optionally substituted with up to four $R^{2d}$; alternatively two $R^{2b}$ can be combined with the atoms to which they are attached to form a 3-7 membered spiro, fused or bridged ring;

each $R^{2c}$ is independently $C_{1-6}$ alkyl, $C_{1-6}$ haloalkyl, $C_{1-6}$ alkoxy, $C_{6-10}$ aryl, 5-11 membered heteroaryl, or 4-7 membered heterocyclyl, wherein the alkyl, haloalkyl, alkoxy, aryl, heteroaryl or heterocyclyl are optionally substituted with up to four $R^{2d}$;

each $R^{2d}$ is independently OH, halogen, NH$_2$, $C_{1-6}$ alkoxy, CONH$_2$, SO$_2$NH$_2$, CO$_2$H, CO$_2$R$^{12}$, NHCOR$^{13}$, $C_{1-6}$ alkyl, $C_{1-6}$ haloalkyl, $C_{1-6}$ alkyl-NH$_2$, $C_{1-6}$ alkyl-CO$_2$R$^{12}$, oxo, or CN;

$R^{2e}$ is $C_{1-6}$ alkyl, $C_{3-7}$ cycloalkyl, $C_{6-10}$ aryl, $C_{1-6}$ alkyl-$C_{6-10}$ aryl, 4-7 membered heterocyclyl, or 5-11 membered heteroaryl, wherein the alkyl, cycloalkyl, aryl, alkyl-aryl, heterocyclyl or heteroaryl are optionally substituted with up to three R^m;

each $R^{10}$ is independently $C_{1-6}$ alkoxy, CN, halogen, OH, $NH_2$, $NHR^{11}$, $CONH_2$, $SO_2NH_2$, COOH, $CO_2R^{12}$, or $NHCO_2$—$C_{1-6}$ alkyl;

$R^{11}$ is H, $C_{1-6}$ alkyl, or $C_{1-6}$ haloalkyl;

$R^{12}$ is H, $C_{1-6}$ alkyl, $C_{1-6}$ haloalkyl, 3-7 cycloalkyl, 4-7 heterocyclyl, $C_{6-10}$ aryl, or 5-11 heteroaryl; and $R^{13}$ is $C_{1-6}$ alkyl, or $C_{1-6}$ haloalkyl.

Examples of heteroaryl groups include, without limitation:

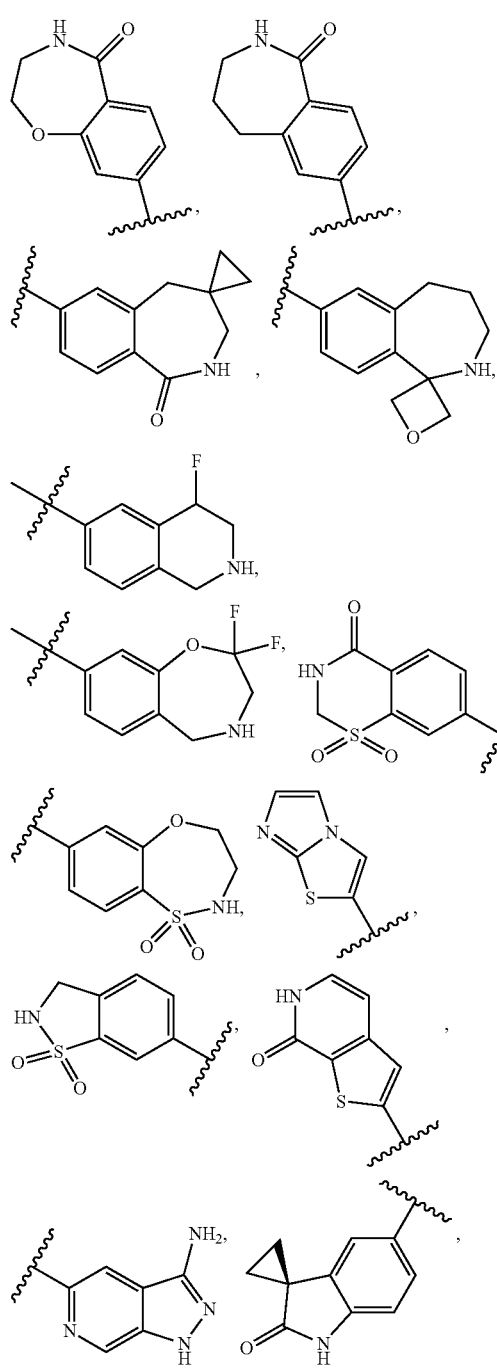

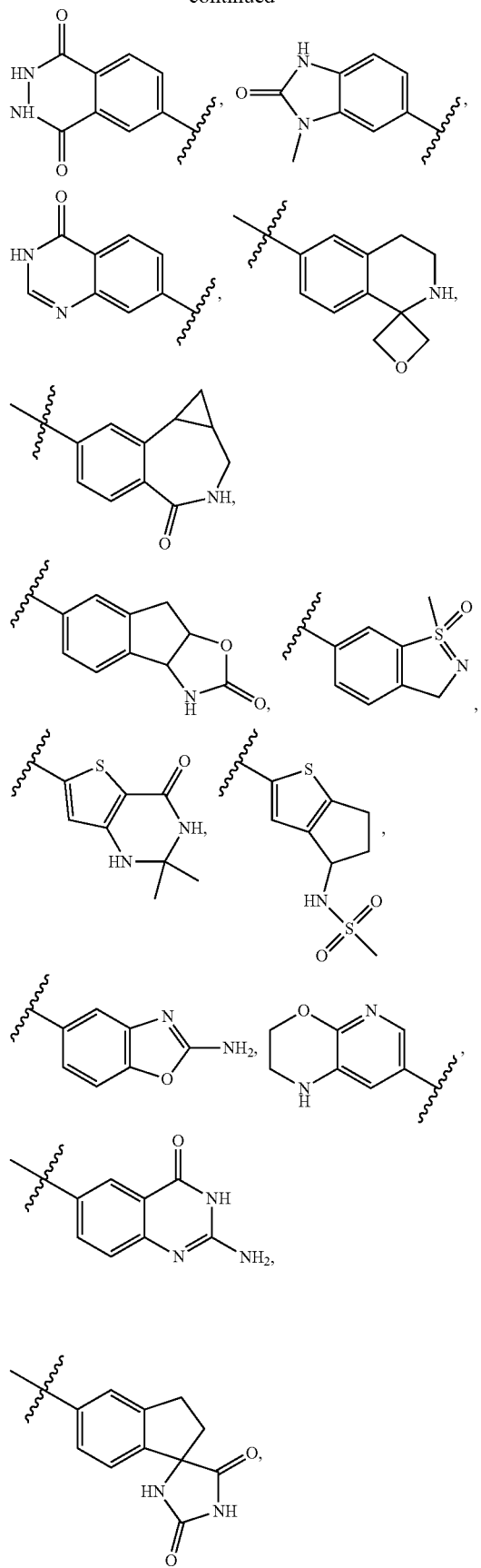

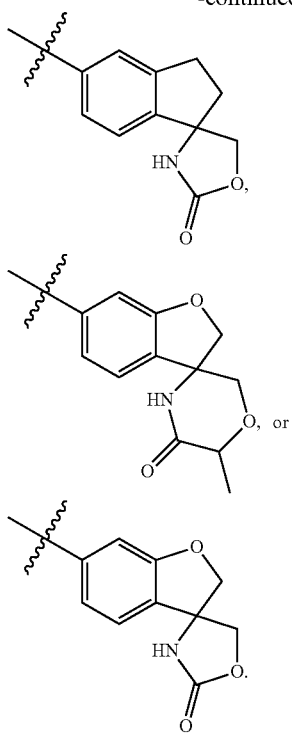

A "compound of the present disclosure" includes compounds disclosed herein, for example a compound of the present disclosure includes compounds of Formulas (I-VI).

"Composition" as used herein is intended to encompass a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation and deleterious to the recipient thereof.

"Pharmaceutically effective amount" refers to an amount of a compound of the present disclosure in a formulation or combination thereof, that provides the desired therapeutic or pharmaceutical result.

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

"Therapeutically effective amount" or "effective amount" as used herein refers to an amount that is effective to elicit the desired biological or medical response, including the amount of a compound that, when administered to a subject for treating a disease, is sufficient to effect such treatment for the disease. The effective amount can vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject. The administration can be carried out according to a schedule specifying frequency of administration, dose for administration, and other factors.

"Co-administration" as used herein refers to administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure. Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the patient.

"Subject" refers to animals such as mammals, including, but not limited to, primates (e.g., humans), cows, sheep, goats, horses, dogs, cats, rabbits, rats, mice and the like. In certain embodiments, the subject is a human.

"Disease" or "condition" refer to a state of being or health status of a patient or subject capable of being treated with a compound, pharmaceutical composition, or method provided herein.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The compounds of described herein may be prepared and/or formulated as pharmaceutically acceptable salts or when appropriate as a free base. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, 21$^{st}$ Edition, Lippincott Wiliams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and $NX_4^+$ (wherein X is $C_1$-$C_4$ alkyl). Also included are base addition salts, such as sodium or potassium salts.

Provided are also compounds described herein or pharmaceutically acceptable salts, isomers, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formulas (I-VI), can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)- isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form or a racemic or scalemic mixture of such compound(s). As used herein, "scalemic mixture" is a mixture of stereoisomers at a ratio other than 1:1.

"Racemates" refers to a mixture of enantiomers. The mixture can comprise equal or unequal amounts of each enantiomer.

"Stereoisomer" and "stereoisomers" refer to compounds that differ in the chirality of one or more stereocenters. Stereoisomers include enantiomers and diastereomers. The compounds may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see, e.g., Chapter 4 of Advanced Organic Chemistry, 4th ed., J. March, John Wiley and Sons, New York, 1992).

"Tautomer" refers to alternate forms of a compound that differ in the position of a proton, such as enol-keto and imine-enamine tautomers, or the tautomeric forms of heteroaryl groups containing a ring atom attached to both a ring —NH— and a ring=N— such as pyrazoles, imidazoles, benzimidazoles, triazoles, and tetrazoles.

Unless defined otherwise, all technical and scientific terms used herein have the same meaning as commonly understood by one of ordinary skill in the art. A dash at the front or end of a chemical group is a matter of convenience; chemical groups may be depicted with or without one or more dashes without losing their ordinary meaning. A wavy line drawn through a line in a structure indicates a point of attachment of a group. A dashed line indicates an optional bond. Unless chemically or structurally required, no directionality is indicated or implied by the order in which a chemical group is written or the point at which it is attached to the remainder of the molecule. For instance, the group "—SO$_2$CH$_2$—" is equivalent to "—CH$_2$SO$_2$—" and both may be connected in either direction. Similarly, an "arylalkyl" group, for example, may be attached to the remainder of the molecule at either an aryl or an alkyl portion of the group. A prefix such as "C$_{u-v}$" or (C$_u$-C$_v$) indicates that the following group has from u to v carbon atoms. For example, "C$_{1-6}$alkyl" and "C$_1$-C$_6$ alkyl" both indicate that the alkyl group has from 1 to 6 carbon atoms.

"Solvate" as used herein refers to the result of the interaction of a solvent and a compound. Solvates of salts of the compounds described herein are also provided. Hydrates of the compounds described herein are also provided.

Illustrative Compounds

Methods of Preparing Compounds

The compounds of the present disclosure can be prepared by any method known in the art. The following exemplary general methods illustrate routes that were used to obtain a compound of the present disclosure.

In some instances (Scheme 1), compounds of Formula 13 were prepared from commercially available or literature known compounds of Formula 1, wherein LG$^1$ or LG$^2$ are leaving groups, typically, but not limited to, halides or sulfones. Treatment of compounds of Formula 1 with an appropriate R$^2$-M (4), with or without the presence of catalyst(s), and with or without the presence of base(s) gave compounds of Formula 2 through cross coupling reaction. M groups that are suitable are, but not limited to, —B(OH)$_2$, —B(pin), —Sn(alkyl)$_3$, —ZnX, or —MgX. Functional groups on R$^2$ may require protection with appropriate protecting groups, as determined by one skilled in the art. Catalysts for this transformation were often, but not limited to Pd(PPh$_3$)$_4$, Pd(dppf)Cl$_2$, Pd(OAc)$_2$, PdCl$_2$Pd XPhos G1, G2, G3, or G4 precatalysts, Pd SPhos G1, G2, G3, or G4 precatalysts, or Pd$_2$dba$_3$ with or without phosphine ligands, selected from, but not limited to, SPhos, XPhos, RuPhos, XantPhos, PCy$_3$, PPh$_3$, or dppf. Bases for this transformation were, but not limited to, sodium carbonate, potassium carbonate, cesium carbonate, tribasic potassium phosphate, sodium hydroxide, potassium hydroxide, sodium acetate, potassium acetate, cesium fluoride, triethyl amine, diisopropylethyl amine, or pyridine.

Compounds of Formula 2 were treated with nucleophile H—R$^1$ in the presence of base in the instances where R$^1$ was an amine to give compounds of Formula 13. Alternatively, H—R$^1$ or M-R$^1$ with compounds of Formula 2 were used in the presence of a catalyst and/or base to afford compounds of Formula 13. Catalysts and bases were, but not limited to, those described above. Functional groups on R$^1$ may require protection with appropriate protecting groups, as determined by one skilled in the art.

Scheme 1

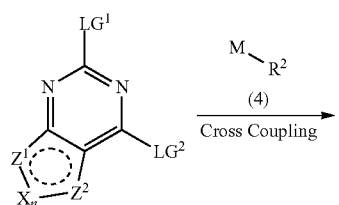

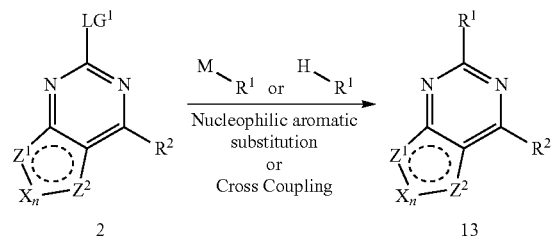

M-R$^2$ (4) compounds that were not commercially available or literature known were typically derived from the corresponding halide 3 through activation with a catalyst in the presence of a base and appropriate reagents for generating nucleophiles (Scheme 2). Catalyst and bases were, but not limited to, those listed above. Reagents to generate nucleophiles were, but not limited to, B$_2$pin$_2$ or Sn$_2$(alkyl)$_6$. Often, but not always, compounds of Formula 4 were used directly in a one-pot cross coupling with compounds of Formula 2 to give compounds of Formula 13.

Scheme 2

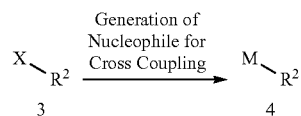

Compounds of Formula 1 not commercially available or literature known were synthesized according to the following Scheme 3. Compounds of Formula 5 were treated with a S-methylisothiourea source in the presence of base to afford compounds of Formula 6. Compounds of Formula 6 were then converted to compounds of Formula 7 through activation of the hydroxy group to LG$^2$, typically through treatment with POCl$_3$. Compounds of Formula 7 were converted to compounds of Formula 8 through cross coupling as described above and in Scheme 1. The thioether of compounds of Formula 8 was converted to LG$^1$ in compounds of Formula 9 through treatment with an oxidant, typically, but not limited to, m-chloroperbenzoic acid, peracetic acid, or Oxone®. Compounds of Formula 9 were then treated with M-R$^1$ or H—R$^1$ as described above and in Scheme 1 to give compounds of Formula 13.

Scheme 3

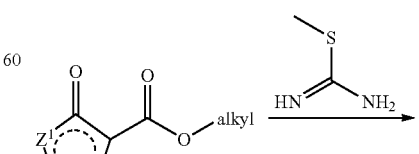

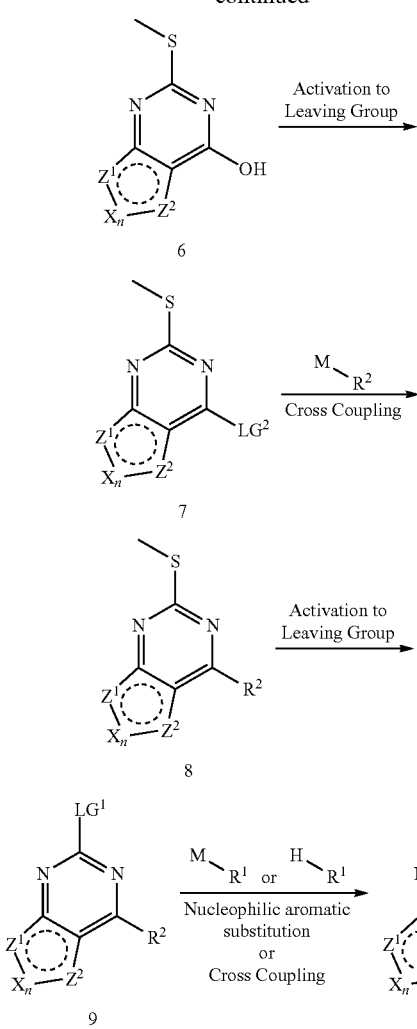

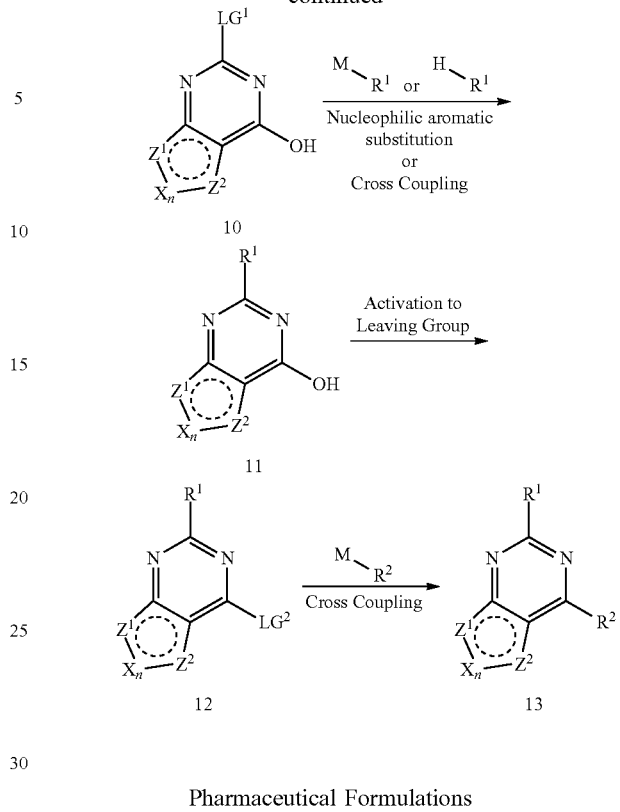

In some instances, compounds of Formula 13 were prepared by Scheme 4. Compounds of Formula 1 were treated with a hydroxide source, typically, but not limited to, sodium hydroxide to give compounds of Formula 10. Compounds of Formula 10 were then treated with M-R¹ or M-R² as described above to give compounds of Formula 11. The hydroxy group of compounds of Formula 11 was converted to LG² in compounds of Formula 12, as described above. Compounds of Formula 12 were converted to compounds of Formula 13 through cross coupling reaction with M-R² as described above.

Scheme 4

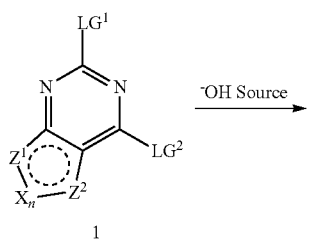

Pharmaceutical Formulations

In some embodiments, the present disclosure provides a pharmaceutical composition comprising a compound of the present disclosure (e.g. a compound of Formula I-VI), or a pharmaceutically acceptable salt or stereoisomer thereof, and a pharmaceutically acceptable excipient.

In some embodiments of the disclosure, the pharmaceutical composition comprises a compound of Formulas (I-VI), or a pharmaceutically acceptable salt or stereoisomer thereof, and one or more additional therapeutic agents, as more fully set forth below.

Pharmaceutical compositions comprising the compounds disclosed herein, or pharmaceutically acceptable salts or stereoisomers thereof, may be prepared with one or more pharmaceutically acceptable excipients which may be selected in accord with ordinary practice. Tablets may contain excipients including glidants, fillers, binders and the like. Aqueous compositions may be prepared in sterile form, and when intended for delivery by other than oral administration generally may be isotonic. In some embodiments, compositions may contain excipients such as those set forth in the Rowe et al, Handbook of Pharmaceutical Excipients, 6$^{th}$ edition, American Pharmacists Association, 2009. Excipients can include ascorbic acid and other antioxidants, chelating agents such as EDTA, carbohydrates such as dextrin, hydroxyalkylcellulose, hydroxyalkylmethylcellulose, stearic acid and the like. In some embodiments, the composition is provided as a solid dosage form, including a solid oral dosage form.

The compositions include those suitable for various administration routes, including oral administration. The compositions may be presented in unit dosage form and may be prepared by any of the methods well known in the art of pharmacy. Such methods include the step of bringing into association the active ingredient (e.g., a compound of the present disclosure or a pharmaceutical salt thereof) with one or more pharmaceutically acceptable excipients. The compositions may be prepared by uniformly and intimately bringing into association the active ingredient with liquid excipients or finely divided solid excipients or both, and then, if desired, shaping the product. Techniques and formulations generally are found in Remington: The Science and Practice of Pharmacy, 21$^{st}$ Edition, Lippincott Wiliams and Wilkins, Philadelphia, Pa., 2006.

Compositions described herein that are suitable for oral administration may be presented as discrete units (a unit dosage form) including but not limited to capsules, sachets or tablets each containing a predetermined amount of the active ingredient. In one embodiment, the pharmaceutical composition of the disclosure is a tablet.

Pharmaceutical compositions disclosed herein comprise one or more compounds disclosed herein, or a pharmaceutically acceptable salt or stereoisomer thereof, together with a pharmaceutically acceptable excipient and optionally other therapeutic agents. Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more excipients including sweetening agents, flavoring agents, coloring agents and preserving agents, in order to provide a palatable preparation. Tablets containing the active ingredient in admixture with non-toxic pharmaceutically acceptable excipients which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that may be combined with the inactive ingredients to produce a dosage form may vary depending upon the intended treatment subject and the mode of administration. For example, in some embodiments, a dosage form for oral administration to humans may contain approximately 1 to 1000 mg of active material formulated with an appropriate and convenient amount of a pharmaceutically acceptable excipient. In some embodiments, the pharmaceutically acceptable excipient varies from about 5 to about 95% of the total compositions (weight:weight).

In some embodiments, a composition comprising a compound of the present disclosure, or a pharmaceutically acceptable salt or stereoisomer thereof in one variation does not contain an agent that affects the rate at which the active ingredient is metabolized. Thus, it is understood that compositions comprising a compound of the present disclosure in one aspect do not comprise an agent that would affect (e.g., slow, hinder or retard) the metabolism of a compound of the present disclosure or any other active ingredient administered separately, sequentially or simultaneously with a compound of the present disclosure. It is also understood that any of the methods, kits, articles of manufacture and the like detailed herein in one aspect do not comprise an agent that would affect (e.g., slow, hinder or retard) the metabolism of a compound of the present disclosure or any other active ingredient administered separately, sequentially or simultaneously with a compound of the present disclosure.

In some embodiments, the pharmaceutical compositions described above are for use in a human or an animal.

The disclosure further includes a compound of the present disclosure for administration as a single active ingredient of a pharmaceutically acceptable composition which can be prepared by conventional methods known in the art, for example by binding the active ingredient to a pharmaceutically acceptable, therapeutically inert organic and/or inorganic carrier or excipient, or by mixing therewith.

In one aspect, provided herein is the use of a compound of the present disclosure as a second or other active ingredient having a synergistic effect with other active ingredients in known drugs, or administration of the compound of the present disclosure together with such drugs.

A compound of the present disclosure may also be used in the form of a prodrug or other suitably modified form which releases the active ingredient in vivo.

Routes of Administration

The compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intratumoral, intrathecal and epidural), and the like. It will be appreciated that the preferred route may vary with for example the condition of the recipient. An advantage of certain compounds disclosed herein is that they are orally bioavailable and can be dosed orally.

A compound of the present disclosure may be administered to an individual in accordance with an effective dosing regimen for a desired period of time or duration, such as at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of the present disclosure may be adjusted over the course of the treatment, based on the judgment of the administering physician.

The compound may be administered to an individual (e.g., a human) in an effective amount. In some embodiments, the compound is administered once daily.

The compound can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 mg to about 30 mg per day, or such as from about 30 mg to about 300 mg per day.

A compound of the present disclosure may be combined with one or more additional therapeutic agents in any dosage amount of the compound of the present disclosure (e.g., from 1 mg to 1000 mg of compound). Therapeutically effective amounts may include from about 1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose. Other therapeutically effective amounts of the compound of the present disclosure are about 100, 125, 150, 175, 200, 225, 250, 275, 300, 325, 350, 375, 400, 425, 450, 475, or about 500 mg per dose. Other therapeutically effective amounts of the compound of the present disclosure are about 100 mg per dose, or about 125, 150, 175, 200, 225, 250, 275, 300, 350, 400, 450, or about 500 mg per dose. A single dose can be administered hourly, daily, or weekly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In some embodiments, a single dose can be administered once every week. A single dose can also be administered once every month.

Kits that comprise a compound of the present disclosure, or a stereoisomer, or pharmaceutically acceptable salt thereof, or a pharmaceutical composition containing any of the above, are also included in the present disclosure. In one embodiment, a kit further includes instructions for use. In one aspect, a kit includes a compound of the disclosure, or a pharmaceutically acceptable salt, tautomer, stereoisomer, mixture of stereoisomers, prodrug, or deuterated analog thereof, and a label and/or instructions for use of the compounds in the treatment of the indications, such as the diseases or conditions, described herein. In one embodiment, kits comprising a compound of the present disclosure, or a pharmaceutically acceptable salt or stereoisomer thereof, in combination with one or more (e.g., one, two, three, four, one or two, or one to three, or one to four) additional therapeutic agents are provided.

Provided herein are also articles of manufacture that include a compound of the present disclosure or a pharmaceutically acceptable salt, tautomer, stereoisomer, mixture of stereoisomers, prodrug, or deuterated analog thereof in a suitable container. The container may be a vial, jar, ampoule, preloaded syringe, and intravenous bag.

Combination Therapy

NASH

In some embodiments, a compound of the present disclosure, or a pharmaceutically acceptable salt or stereoisomer thereof, can be combined with a therapeutically effective amount of one or more (e.g., one, two, three, four, one or two, one to three, or one to four) additional therapeutic agents. In some embodiments, the additional therapeutic agent comprises an apoptotic signal-regulating kinase (ASK-1) inhibitor, a farnesoid X receptor (FXR) agonist, a peroxisome proliferator-activated receptor alpha (PPARα) agonist, fish oil, an acetyl-coA carboxylase (ACC) inhibitor, a TGFβ antagonist, a LPAR antagonist, a SGLT2 inhibitor, a Tpl2 inhibitor, a VAP1 inhibitor or a GLP-1 agonist combination thereof.

The benefit of combination may be increased efficacy and/or reduced side effects for a component as the dose of that component may be adjusted down to reduce its side effects while benefiting from its efficacy augmented by the efficacy of the compound of the present disclosure.

In some embodiments, the therapeutic agent, or combination of therapeutic agents, are a(n) ACE inhibitor, 2-Acylglycerol O-acyltransferase 2 (DGAT2) inhibitor, Acetaldehyde dehydrogenase inhibitor, Acetyl CoA carboxylase inhibitor, Adrenergic receptor agonist, Alstrom syndrome protein 1 (ALMS1)/PKC alpha protein interaction inhibitor, Apelin receptor agonist, Diacylglycerol O acyltransferase 2 inhibitor, Adenosine A3 receptor agonist, Adenosine A3 receptor antagonist, Adiponectin receptor agonist, Aldehyde dehydrogenase 2 stimulator, AKT protein kinase inhibitor, AMP-activated protein kinases (AMPK), AMP kinase activator, ATP citrate lyase inhibitor, AMP activated protein kinase stimulator, Endothelial nitric oxide synthase stimulator, NAD-dependent deacetylase sirtuin-1 stimulator, Adrenergic receptor antagonist, Androgen receptor agonist, Amylin receptor agonist, Angiotensin II AT-1 receptor antagonist, Apical sodium-dependent bile acid transport inhibitor, Autophagy protein modulator, Autotaxin inhibitors, Axl tyrosine kinase receptor inhibitor, Bax protein stimulator, Beta-catenin inhibitor, Bioactive lipid, Calcitonin agonist, Cannabinoid receptor modulator, Caspase inhibitor, Caspase-3 stimulator, Cathepsin inhibitor, Caveolin 1 inhibitor, CCK receptor antagonist, CCL26 gene inhibitor, CCR2 chemokine antagonist, CCR2 chemokine antagonist, Angiotensin II AT-1 receptor antagonist, CCR3 chemokine antagonist, CCR5 chemokine antagonist, CD3 antagonist, CDGSH iron sulfur domain protein modulator, chitinase inhibitor, Chloride channel stimulator, Chitotriosidase 1 inhibitor, CNR1 inhibitor, Connective tissue growth factor ligand inhibitor, COT protein kinase inhibitor, Cyclin D1 inhibitor, Cytochrome P450 7A1 inhibitor, DGAT1/2 inhibitor, Diacylglycerol O acyltransferase 1 inhibitor (DGAT1), Cytochrome P450 2E1 inhibitor (CYP2E1), Cytochrome P450 reductase inhibitors, CXCR3 chemokine antagonist, CXCR4 chemokine antagonist, Dihydroceramide delta 4 desaturase inhibitor, Dihydroorotate dehydrogenase inhibitor, Dipeptidyl peptidase IV inhibitor, Endosialin modulator, Eotaxin ligand inhibitor, Extracellular matrix protein modulator, Farnesoid X receptor agonist, Fatty acid synthase inhibitors, FGF1 receptor agonist, Fibroblast growth factor (FGF-15, FGF-19, FGF-21) ligands, fibroblast activation protein inhibitor, Free fatty acid receptor 1 agonist, Galectin-3 inhibitor, GDNF family receptor alpha like agonist, Glucagon receptor agonist, Glucagon-like peptide 1 agonist, Glucocorticoid receptor antagonist, Glucose 6-phosphate 1-dehydrogenase inhibitor, G-protein coupled bile acid receptor 1 agonist, G-protein coupled receptor-119 agonist, G-protein coupled receptor 84 antagonist, Hedgehog (Hh) modulator, Hepatitis C virus NS3 protease inhibitor, Hepatocyte nuclear factor 4 alpha modulator (HNF4A), Hepatocyte growth factor modulator, Histone deacetylase inhibitor, STAT-3 modulator, HMG CoA reductase inhibitor, HSD17B13 gene inhibitor, 5-HT 2a receptor antagonist, Hydrolase inhibitor, Hypoxia inducible factor-2 alpha inhibitor, IL-10 agonist, IL-17 antagonist, IL-22 agonist, Ileal sodium bile acid cotransporter inhibitor, Insulin sensitizer, Insulin ligand agonist, Insulin receptor agonist, integrin modulator, Integrin Antagonist, Integrin alpha-V/beta-1 antagonist, Integrin alpha-V/beta-6 antagonist, intereukin-1 receptor-associated kinase 4 (IRAK4) inhibitor, IL-6 receptor agonist, interleukin 17 ligand inhibitor, Jak2 tyrosine kinase inhibitor, Jun N terminal kinase-1 inhibitor, Kelch like ECH associated protein 1 modulator, Ketohexokinase (KHK) inhibitor, Klotho beta stimulator, Leukotriene A4 hydrolase inhibitor, 5-Lipoxygenase inhibitor, Lipoprotein lipase inhibitor, Liver X receptor, LPL gene stimulator, Lysophosphatidic Acid Receptor (LPAR) antagonist, Lysophosphatidate-1 receptor antagonist, Lysyl oxidase homolog 2 inhibitor, LXR inverse agonists, Macrophage mannose receptor 1 modulator, Matrix metalloproteinases (MMPs) inhibitor, MEKK-5 protein kinase inhibitor, MCH receptor-1 antagonist, Membrane copper amine oxidase (VAP-1) inhibitor, Methionine aminopeptidase-2 inhibitor, Methyl CpG binding protein 2 modulator, MicroRNA-132 (miR-132) antagonist, MicroRNA-21 (miR-21) inhibitor, Mitochondrial uncoupler, Mixed lineage kinase-3 inhibitor, Motile sperm domain protein 2 inhibitor, Myelin basic protein stimulator, NACHT LRR PYD domain protein 3 (NLRP3) inhibitor, NAD-dependent deacetylase sirtuin 2 stimulator, NADPH oxidase inhibitor (NOX), NFE2L2 gene inhibitor, Nicotinic acid receptor 1 agonist, Opioid receptor mu antagonist, P2Y13 purinoceptor stimulator, Nuclear erythroid 2-related factor 2 stimulator, Nuclear receptor modulators, Nuclear transport of transcription factor modulator, P2X7 purinoceptor modulator, PACAP type I receptor agonist, PDE 3 inhibitor, PDE 4 inhibitor, PDE 5 inhibitor, PDGF receptor beta modulator, Phenylalanine hydroxylase stimulator, Phospholipase C inhibitor, Phosphoric diester hydrolase inhibitor, PPAR alpha agonist, PPAR delta agonist, PPAR gamma agonist, Peptidyl-prolyl cis-trans isomerase A inhibitor, PNPLA3 gene inhibitor, -PPAR gamma modulator, Protease-activated receptor-2 antagonist, Protein kinase modulator, Protein NOV homolog modulator, PTGS2 gene inhibitor, renin inhibitor, Resistin/CAP1 (adenylyl cyclase associated protein 1) interaction inhibitor, Rho associated protein kinase inhibitor, RNA polymerase inhibitors, S-nitrosoglutathione reductase (GSNOR) enzyme inhibitor, Sodium glucose transporter-2 inhibitor, Sphingolipid delta 4 desaturase DES1 inhibitor, SREBP transcription factor inhibitor, STAT-1 inhibitor, Stearoyl CoA desaturase-1 inhibitor, STK25 inhibitor, Suppressor of cytokine signalling-1 stimulator, Suppressor of cytokine signalling-3 stimulator, Taste receptor type 2 agonist, Telomerase stimulator, TERT gene modulator, TGF beta (TGFB1) ligand inhibitor, TNF antagonist, Transforming growth factor β (TGF-β), Transforming growth factor β activated Kinase 1 (TAK1), Thyroid hormone receptor beta agonist, TLR-4 antagonist, Transglutaminase inhibitor, Tyrosine kinase receptor modulator, GPCR modulator, nuclear hormone receptor modulator, TLR-9 antagonist, vascular adhesion protein-1 (VAP-1) inhibitor, VDR agonist, Vitamin D3 receptor modulators, WNT modulators, YAP/TAZ modulator or a Zonulin inhibitor, and combinations thereof.

Non-limiting examples of the one or more additional therapeutic agents include:

ACE inhibitors, such as enalapril;
Acetaldehyde dehydrogenase inhibitors, such as ADX-629;
Acetyl CoA carboxylase (ACC) inhibitors, such as NDI-010976 (firsocostat), DRM-01, gemcabene, GS-834356, PF-05175157, QLT-091382, PF-05221304;
Acetyl CoA carboxylase/Diacylglycerol O acyltransferase 2 inhibitors, such as PF-07055341; Adenosine 2 receptor agonists, such as namodenoson (CF-102), piclidenoson (CF-101), CF-502, CGS21680;
Adenosine A3 receptor antagonist, such as FM-101;
Adiponectin receptor agonists, such as ADP-355, ADP-399, ALY668-SR;
Adrenergic receptor antagonist, such as bromocriptine, phentermine, VI-0521;
Aldehyde dehydrogenase 2 stimulators, such as FP-045;
Amylin/calcitonin receptor agonists, such as KBP-042, KBP-089;
AMP activated protein kinase stimulators, such as C-455, PXL-770, O-304;
AMP kinase activators/ATP citrate lyase inhibitors, such as bempedoic acid (ETC-1002, ESP-55016);
AMP activated protein kinase/Endothelial nitric oxide synthase/NAD-dependent deacetylase sirtuin-1 stimulators, such as NS-0200 (leucine+metformin+sildenafil);
Androgen receptor agonists, such as LPCN-1144, LPCN-1148, testosterone prodrug;
Angiotensin II AT-1 receptor antagonists, such as irbesartan; Angiopoietin-related protein-3 inhibitors, such as vupanorsen (IONIS-ANGPTL3-LRx);
Apelin receptor agonist, such as CB-5064, MBT-2;
Apical sodium-dependent bile acid transport inhibitors, such as A-3907;
Autophagy protein modulators, such as A-2906, GM-90194;
Autotaxin (ectonucleotide pyrophosphatase/phosphodiesterase 2 (NPP2 or ENPP2)) inhibitors, such as FP10.47, PAT-505, PAT-048, GLPG-1690, X-165, PF-8380, TJC-0265, TJC-0316, AM-063, BBT-877;
Axl tyrosine kinase receptor inhibitors, such as bemcentinib (BGB-324, R-428);
Bax protein stimulators, such as CBL-514;
Bioactive lipids, such as DS-102;
Cannabinoid receptor modulators, such as namacizumab (nimacimab), GWP-42004, REV-200, CRB-4001, INV-101, SCN-002;
Caspase inhibitors, such as emricasan;
Pan cathepsin B inhibitors, such as VBY-376;
Pan cathepsin inhibitors, such as VBY-825;
CCK receptor antagonist, such as proglumide;
CCL26 gene inhibitor, such as mosedipimod, KDDF-201410-10;
CCR2/CCR5 chemokine antagonists, such as BMS-687681, cenicriviroc, maraviroc, CCX-872, leronlimab, WXSH-0213;
CCR2/CCR5 chemokine antagonists and FXR agonists, such as LJC-242 (tropifexor+cenivriviroc);
CCR2 chemokine antagonists, such as propagermanium;
CCR2 chemokine/Angiotensin II AT-1 receptor antagonists, such as DMX-200, DMX-250;
CCR3 chemokine antagonists, such as bertilimumab;
CD3 antagonists, such as NI-0401 (foralumab);
CDGSH iron sulfur domain protein modulators, such as EYP-002;
Chitinase inhibitor, such as OATD-01;
Chitotriosidase 1 inhibitors, such as OAT-2068;
Chloride channel stimulators, such as cobiprostone, and lubiprostone;
Casein kinase-1 (CK1) delta/epsilon inhibitors, such as PF-05006739;
Connective tissue growth factor ligand inhibitor, such as PBI-4050;
COT protein kinase inhibitors, such as GS-4875, GS-5290;
CXCR4 chemokine antagonists, such as AD-214;
Cytochrome P450 reductase inhibitors, such as SNP-630;

Diglyceride acyltransferase 2 (DGAT2) inhibitors, such as IONIS-DGAT2Rx, PF-06865571;

Diglyceride acyltransferase 1 (DGAT1) inhibitors, such as GSK-3008356;

Diacylglycerol O acyltransferase 1 (DGAT1)/Cytochrome P450 2E1 inhibitors (CYP2E1), such as SNP-610;

Dihydroorotate dehydrogenase inhibitor, such as vidofludimus;

Dipeptidyl peptidase IV inhibitors, such as linagliptin, evogliptin;

Eotaxin ligand inhibitors, such as bertilimumab, CM-101;

Extracellular matrix protein modulators, such as CNX-024;

Farnesoid X receptor (FXR) agonists, such as AGN-242266, AGN-242256, ASC-42, EDP-297 (EP-024297), RDX-023, BWL-200, AKN-083, EDP-305, GNF-5120, cilofexor tromethamine (GS-9674), HPG-1860, IOT-022, LMB-763, obeticholic acid, Px-102, Px-103, M790, M780, M450, M-480, MET-409, MET-642, PX20606, SYHA-1805, vonafexor (EYP-001), TERN-101, TC-100, INT-2228, TQA-3526, ZG-5266, HPD-001, alendronate;

Farnesoid X receptor (FXR)/G-protein coupled bile acid receptor 1(TGRS) agonists, such as INT-767;

Fatty acid synthase inhibitors, such as TVB-2640, FT-8225;

Fibroblast growth factor 19 (rhFGF19)/cytochrome P450 (CYP) 7A1 inhibitors, such as aldafermin (NGM-282);

Fibroblast growth factor 21 (FGF-21) ligand modulators, such as AP-025, BMS-986171, B-1654, BIO89-100, BOS-580, Pegbelfermin (BMS-986036), B-1344, NN-9499;

Fibroblast growth factor 21 (FGF-21)/glucagon like peptide 1 (GLP-1) agonists, such as YH-25723 (YH-25724; YH-22241), efruxifermin (AKR-001);

FGF receptor agonists/Klotho beta stimulators, such as BFKB-8488A (RG-7992);

Free fatty acid receptor 1 agonist, such as SCO-267;

Galectin-3 inhibitors, such as belapectin (GR-MD-02), GB-1107 (Gal-300), GB-1211 (Gal-400), IMT-001;

GDNF family receptor alpha like agonist, such as NGM-395;

Glucagon-like peptide 1 (GLP1R) agonists, such as ALT-801, AC-3174, liraglutide, cotadutide (MEDI-0382), SAR-425899, LY-3305677, HM-15211, YH-25723, YH-GLP1, RPC-8844, PB-718, PF-06882961, semaglutide;

Glucagon-like peptide 1 receptor agonist; Oxyntomodulin ligand; Glucagon receptor agonist, such as efinopegdutide;

Gastric inhibitory polypeptide/Glucagon-like peptide-1 (GIP/GLP-1) receptor co-agonist, such as tirzepatide (LY-3298176);

PEGylated long-acting glucagon-like peptide-1/glucagon (GLP-1R/GCGR) receptor dual agonist, such as DD-01;

Glucagon/GLP1-receptor agonist, such as BI-456906, NN-6177;

Glucocorticoid receptor antagonists, such as CORT-118335 (miricorilant);

Glucose 6-phosphate 1-dehydrogenase inhibitors, such as ST001;

Glucokinase stimulator, such as dorzagliatin, sinogliatin (RO-5305552);

G-protein coupled bile acid receptor 1 (TGRS) agonists, such as RDX-009, INT-777, HY-209;

G-protein coupled receptor 84 antagonist, such as PBI-4547;

G-protein coupled receptor-119 agonist, such as DA-1241;

Heat shock protein 47 (HSP47) inhibitors, such as ND-L02-s0201;

Hedgehog protein TGF beta ligand inhibitors, such as Oxy-210;

Histone deacetylase inhibitors/STAT-3 modulators, such as SFX-01;

HMG CoA reductase inhibitors, such as atorvastatin, fluvastatin, pitavastatin, pravastatin, rosuvastatin, simvastatin;

HSD17B13 gene inhibitor, such as ALN-HSD, ARO-HSD;

Hydrolase inhibitor, such as ABD-X;

Hypoxia inducible factor-2 alpha inhibitors, such as PT-2567;

IL-10 agonists, such as peg-ilodecakin;

Ileal sodium bile acid cotransporter inhibitors, such as odevixibat (A-4250), volixibat potassium ethanolate hydrate (SHP-262), GSK2330672, CJ-14199, elobixibat (A-3309);

Insulin sensitizers, such as, KBP-042, azemiglitazone potassium (MSDC-0602K), ION-224, MSDC-5514, Px-102, RG-125 (AZD4076), Tolimidone, VVP-100X, CB-4211, ETI-101; Insulin ligand/dsInsulin receptor agonists, such as ORMD-0801;

Integrin antagonists, such as IDL-2965;

IL-6 receptor agonists, such as KM-2702;

Integrin alpha-V/beta-6 and alpha-V/beta-1 dual inhibitor; such as PLN-74809;

Interleukin 17 ligand inhibitor, such as netakimab;

Jak1/2 tyrosine kinase inhibitor, such as baricitinib;

Jun N terminal kinase-1 inhibitor, such as CC-90001;

Kelch like ECH associated protein 1 modulator, such as alpha-cyclodextrin-stabilized sulforaphane;

Ketohexokinase (KHK) inhibitors, such as PF-06835919, LY-3478045, LY-3522348; beta Klotho (KLB)-FGF1c agonists, such as MK-3655 (NGM-313);

Leukotriene A4 hydrolase inhibitor, such as LYS-006;

5-Lipoxygenase inhibitors, such as tipelukast (MN-001), epeleuton (DS-102,-EAF-102);

Lipoprotein lipase inhibitors, such as CAT-2003;

LPL gene stimulators, such as alipogene tiparvovec;

Liver X receptor (LXR) inhibitors, such as PX-665, PX-L603, PX-L493, BMS-852927, T-0901317, GW-3965, SR-9238;

Lysophosphatidate-1 receptor antagonists, such as BMT-053011, UD-009 (CP-2090), AR-479, ITMN-10534, BMS-986020, KI-16198;

Lysyl oxidase homolog 2 inhibitors, such as simtuzumab, PXS-5382A (PXS-5338); Macrophage mannose receptor 1 modulators, such as tilmanocept-Cy3 (technetium Tc 99m tilmanocept);

Matrix metalloprotease inhibitors, such as ALS-L1023;

Membrane copper amine oxidase (VAP-1) inhibitors, such as TERN-201, TT-01025;

MEKK-5 protein kinase (ASK-1) inhibitors, such as CJ-16871, CS-17919, selonsertib (GS-4997), SRT-015, GS-444217, GST-HG-151, TERN-301;

MCH receptor-1 antagonists, such as CSTI-100 (ALB-127158);

Semicarbazide-Sensitive Amine Oxidase/Vascular Adhesion Protein-1 (SSAO/VAP-1) Inhibitors, such as PXS-4728A (BI-1467335);

Methionine aminopeptidase-2 inhibitors, such as ZGN-1061, ZGN-839, ZN-1345;

Methyl CpG binding protein 2 modulators, such as mercaptamine;

Mineralocorticoid receptor antagonists (MCRA), such as MT-3995 (apararenone);

Mitochondrial uncouplers, such as 2,4-dinitrophenol, HU6, Mito-99-0053;

Mixed lineage kinase-3 inhibitors, such as URMC-099-C;

Motile sperm domain protein 2 inhibitors, such as VB-601;

Myelin basic protein stimulators, such as olesoxime;

Myeloperoxidase inhibitors, such as PF-06667272, AZM-198;

NADPH oxidase inhibitors, such as GKT-831, GenKyoTex, APX-311, setanaxib;

Nicotinic acid receptor 1 agonists, such as ARI-3037MO;

NACHT LRR PYD domain protein 3 (NLRP3) inhibitors, such as KDDF-201406-03, NBC-6, IFM-514, JT-194 (JT-349);

NFE2L2 gene inhibitor, such as GeRP-amiR-144;

Nuclear transport of transcription factor modulators, such as AMTX-100;

Nuclear receptor modulators, such as DUR-928 (DV-928);

Opioid receptor mu antagonists, such as methylnaltrexone;

P2X7 purinoceptor modulators, such as SGM-1019;

P2Y13 purinoceptor stimulators, such as CER-209;

PDE 3/4 inhibitors, such as tipelukast (MN-001);

PDE 5 inhibitors, such as sildenafil, MSTM-102;

PDGF receptor beta modulators, such as BOT-191, BOT-509;

Peptidyl-prolyl cis-trans isomerase inhibitors, such as CRV-431 (CPI-432-32), NVP-018, NV-556 (NVP-025); Phenylalanine hydroxylase stimulators, such as HepaStem;

Phosphoric diester hydrolase inhibitor, such as ZSP-1601;

PNPLA3 gene inhibitor, such as AZD-2693;

PPAR agonists, such as Chiglitazar, elafibranor (GFT-505), seladelpar lysine (MBX-8025), deuterated pioglitazone R-enantiomer, pioglitazone, PXL-065 (DRX-065), saroglitazar, lanifibranor (IVA-337), CHS-131, pemafibrate (K-877), ZG-0588, ZSP-0678; ZSYM-008;

Protease-activated receptor-2 antagonists, such as PZ-235;

Protein kinase modulators, such as CNX-014;

Protein NOV homolog modulators, such as BLR-200;

PTGS2 gene inhibitors, such as STP-705, STP-707;

Renin inhibitors, such as PRO-20;

Resistin/CAP1 (adenylyl cyclase associated protein 1) interaction inhibitors, such as DWJ-211;

Rev protein modulator, such as ABX-464;

Rho associated protein kinase (ROCK) inhibitors, such as REDX-10178 (REDX-10325), KD-025, RXC-007, TDI-01;

RNA polymerase inhibitors, such as rifaximin;

S-nitrosoglutathione reductase (GSNOR) enzyme inhibitors, such as SL-891;

Sodium glucose transporter-2 (SGLT2) inhibitors, such as ipragliflozin, remogliflozin etabonate, ertugliflozin, dapagliflozin, tofogliflozin, sotagliflozin;

Sodium glucose transporter-1/2 (SGLT 1/2) inhibitors, such as licogliflozin bis(prolinate) (LIK-066);

SREBP transcription factor inhibitors, such as CAT-2003, HPN-01, MDV-4463;

Stearoyl CoA desaturase-1 inhibitors, such as aramchol;

Taste receptor type 2 agonists, such as ARD-101;

Thyroid hormone receptor beta agonists, such as ALG-009, ASC-41, CNPT-101101; CNPT-101207, CS-27186, KY-41111, resmetirom (MGL-3196), MGL-3745, TERN-501, VK-2809, HP-515;

TLR-2/TLR-4 antagonists, such as VB-201 (CI-201);

TLR-4 antagonists, such as JKB-121, JKB-122, naltrexone;

Tyrosine kinase receptor modulators, such as CNX-025, GFE-2137 (repurposed nitazoxanide);

TLR-9 antagonist, such as GNKS-356, AVO-101;

TNF antagonist, such as ALF-421;

GPCR modulators, such as CNX-023;

Nuclear hormone receptor modulators, such as Px-102;

VDR agonist, such as CK-15;

Xanthine oxidase inhibitors, such as ACQT-1127;

Xanthine oxidase/Urate anion exchanger 1 (URAT1) inhibitors, such as RLBN-1001, RLBN-1127; or Zonulin Inhibitors, such as larazotide acetate (INN-202).

In certain specific embodiments, the one or more additional therapeutic agents are selected from A-4250, AC-3174, acetylsalicylic acid, AK-20, alipogene tiparvovec, AMX-342, AN-3015, anti-TAGE antibody, aramchol, ARI-3037MO, ASP-8232, AXA-1125, bertilimumab, Betaine anhydrous, BI-1467335, BMS-986036, BMS-986171, BMT-053011, BOT-191, BTT-1023, budesonide, BX-003, CAT-2003, cenicriviroc, CBW-511, CER-209, CF-102, CGS21680, CNX-014, CNX-023, CNX-024, CNX-025, cobiprostone, colesevelam, dabigatran etexilate mesylate, dapagliflozin, DCR-LIV1, deuterated pioglitazone R-enantiomer, 2,4-dinitrophenol, DRX-065, DS-102, DUR-928, edaravone (TTYP-01), EDP-305, elafibranor (GFT-505), emricasan, enalapril, ertugliflozin, evogliptin, F-351, fluasterone (ST-002), FT-4101, GDD-3898, GH-509, GKT-831, GNF-5120, GRI-0621, GR-MD-02, GS-300, GS-4997, GS-9674, GS-4875, GS-5290, HEC-96719, HTD-1801, HS-10356, HSG-4112, HST-202, HST-201, HU-6, hydrochlorothiazide, icosabutate (PRC-4016), icosapent ethyl ester, IMM-124-E, INT-767, INV-240, ION-455, IONIS-DGAT2Rx, ipragliflozin, Irbesarta, propagermanium, IVA-337, J2H-1702, JKB-121, KB-GE-001, KBLP-004, KBLP-009, KBP-042, KD-025, M790, M780, M450, metformin, sildenafil, LB-700, LC-280126, linagliptin, liraglutide, (LJN-452) tropifexor, LM-002 (CVI-LM-002), LMB-763, LYN-100, MB-N-008, MBX-8025, MDV-4463, mercaptamine, MGL-3196, MGL-3745, MP-301, MSDC-0602K, namacizumab, NC-101, NDI-010976, ND-L02-s0201 (BMS-986263), NGM-282, NGM-313, NGM-386, NGM-395, NP-011, NP-135, NP-160 norursodeoxycholic acid, NV-422, NVP-022, O-304, obeticholic acid (OCA), 25HC3S, olesoxime, PAT-505, PAT-048, peg-ilodecakin, pioglitazone, pirfenidone, PRI-724, PX20606, Px-102, PX-L603, PX-L493, PXS-4728A, PZ-235, PZH-2109, RCYM-001, RDX-009, remogliflozin etabonate, RG-125 (AZD4076), RP-005, RPI-500, S-723595, saroglitazar, SBP-301, semaglutide, SH-2442, SHC-028, SHC-023, simtuzumab, solithromycin, sotagliflozin, statins (atorvastatin, fluvastatin, pitavastatin, pravastatin, rosuvastatin, simvastatin), TCM-606F, TEV-45478, TQA-3526, TQA-3563, tipelukast (MN-001), TLY-012, TRX-318, TVB-2640, TXR-611, TXR-612, TS-20004, UD-009, UN-03, ursodeoxycholic acid, VBY-376, VBY-825, VK-2809, vismodegib, volixibat potassium ethanolate hydrate (SHP-626), VVP-100X, WAV-301, WNT-974, WXSH-0038, WXSH-0078, XEN-103, XRx-117, XTYW-003, XW-003, XW-004, XZP-5610, ZGN-839, ZG-5216, ZSYM-008, or ZYSM-007.

In certain embodiments, examples of Acetyl CoA carboxylase (ACC) inhibitors include, but are not limited to, those described in US2013123231, US2019134041, US2017267690, US2018298025.

Examples of Acetyl CoA carboxylase (ACC) inhibitors/ Farnesoid X receptor (FXR) agonists include, but are not limited to, those described in US2018280394.

Examples of Acetyl CoA carboxylase (ACC) inhibitors/ Farnesoid X receptor (FXR) agonists/MEKK-5 protein kinase (ASK-1) inhibitors include, but are not limited to, those described in US2018021341, US2018333401.

Examples of Acetyl CoA carboxylase (ACC)/MEKK-5 protein kinase (ASK-1) inhibitors include, but are not limited to, those described in US2018311244.

Examples of Farnesoid X receptor (FXR) agonists include, but are not limited to, those described in US2014221659, US2020281911, WO2020185685.

Examples of Farnesoid X receptor (FXR) agonists/ MEKK-5 protein kinase (ASK-1) inhibitors include, but are not limited to those described in US2017273952 US201813320.

Examples of MEKK-5 protein kinase (ASK-1) inhibitors include, but are not limited to, those described in US2011009410, US2013197037, US2016244430, US2016280683.

CKD/DKD

Patients being treated for cardio-renal diseases such as chronic kidney disease may benefit from combination drug treatment.

In some embodiments, a compound of the present disclosure, or a pharmaceutically acceptable salt or stereoisomer thereof, can be combined with a therapeutically effective amount of one or more (e.g., one, two, three, four, one or two, one to three, or one to four) additional therapeutic agents. In some embodiments, the additional therapeutic agent comprises angiotensin converting enzyme (ACE) inhibitors such as enalapril, captopril, ramipril, lisinopril, and quinapril; or angiotensin II receptor blockers (ARBs) such as losartan, olmesartan, and irbesartan; or antihypertensive agents such as amlodipine, nifedipine, and felodipine; SGLT2 inhibitors such as canagliflozin, dapagliflozin, empagliflozing and luseogliflozin, mineralcorticoid receptor antagonists such as finerone, NRF2 activators such as bardoxolone methyl, LPAR antagonists, and apoptotic signal-regulating kinase (ASK-1) inhibitors such as selonsertib.

The benefit of combination may be increased efficacy and/or reduced side effects for a component as the dose of that component may be adjusted down to reduce its side effects while benefiting from its efficacy augmented by the efficacy of the compound of Formulas (I-VI) and/or other active component(s).

Patients presenting with chronic kidney disease treatable with KHK inhibitors such as a compound of Formula (I-VI), may also exhibit conditions that benefit from co-administration (as directed by a qualified caregiver) of a therapeutic agent or agents that are antibiotic, analgesic, antidepressant and/or anti-anxiety agents in combination with compound of Formula (I-VI). Combination treatments may be administered simultaneously or one after the other within intervals as directed by a qualified caregiver or via a fixed dose (all active ingredients are combined into a single dosage form e.g. tablet) combination of two or more active agents.

In some embodiments, the therapeutic agent, or combination of therapeutic agents, are ACE inhibitors, Adenosine A3 receptor antagonists, Adropin stimulators, Albumin modulators, Aldosterone antagonists, AMP activated protein kinase stimulators, Angiotensin II AT-2 receptor agonists, Angiotensin II receptor antagonists, Angiotensinogen ligand inhibitors, APOA1 gene stimulators, Apolipoprotein L1 modulators, Bone morphogenetic protein-7 ligand modulators, Bromodomain containing protein 2 inhibitors, Bromodomain containing protein 4 inhibitors, Calcium channel inhibitors, Cannabinoid CB1 receptor antagonists, CB1 inverse agonists, CCR2 chemokine antagonists, Chymase inhibitors, Complement C1s subcomponent inhibitors, CX3CR1 chemokine antagonists, Cyclooxygenase 1 inhibitors, Cyclooxygenase 2 inhibitors, Cytochrome P450 11B2 inhibitors, Ectonucleotide pyrophosphatase-PDE-2 inhibitors, Endothelin ET-A receptor antagonists, Endothelin ET-B receptor antagonists, Enteropeptidase inhibitors, Epoxide hydrolase inhibitor, Erythropoietin receptor antagonists, Farnesoid X receptor agonists, FGF receptor antagonists, Free fatty acid receptor 1 agonists, GHR gene inhibitors, Glycoprotein Ib (GPIb) antagonists, GPR40 agonists, GPR84 antagonists, G-protein beta subunit inhibitors, G-protein coupled receptor 120 agonists, G-protein coupled receptor 84 modulators, Growth hormone ligands, Growth hormone receptor agonists, Guanylate cyclase receptor agonists, Guanylate cyclase stimulators, Guanylate cyclase stimulators, Heme oxygenase 1 modulators, HIF prolyl hydroxylase inhibitors, IGF1 gene inhibitors, IgG receptor FcRn large subunit p51 modulators, IL-6 receptor antagonists, Integrin alpha-V/beta-3 antagonists, Interleukin 33 ligand inhibitors, Kelch like ECH associated protein 1 modulators, LDHA gene inhibitors, 5-Lipoxygenase activating protein inhibitors, Lysophosphatidate-1 receptor antagonists, Matrix extracell phosphoglycoprotein modulators, Membrane copper amine oxidase inhibitors, Midkine ligand inhibitors, Mineralocorticoid receptor antagonists, Myosin 2 inhibitors, NADPH oxidase 1 inhibitors, NADPH oxidase 4 inhibitors, NADPH oxidase inhibitors, NK1 receptor antagonists, Nuclear erythroid 2-related factor 2 stimulators, Nuclear factor kappa B inhibitors, Opioid receptor kappa agonist, Opioid receptor mu antagonists, p38 MAP kinase inhibitors, PDE4 inhibitors, PDGF receptor antagonists, PDGF receptor beta modulators, Phosphatonin receptor agonists, PRKAA2 gene stimulator, Proprotein convertase PC9 inhibitors, Prostacyclin (PGI2) agonists, Protein C activators, Protein NOV homolog modulators, Protein tyrosine phosphatase-1B inhibitors, Reactive oxygen species modulator inhibitors, Renin inhibitors, Rho associated protein kinase 2 inhibitors, SLC22A12 inhibitors, Sodium glucose transporter-2 inhibitors, Solute carrier family inhibitors, TGF beta ligand inhibitors, TGF beta receptor antagonists, Thromboxane A2 receptor antagonists, Thromboxane synthesis inhibitors, Tissue transglutaminase inhibitors, TRP cation channel C5 inhibitors, TRP cation channel C6 inhibitors, Tryptophanase inhibitors, Unspecified cell adhesion molecule inhibitors, Urate anion exchanger 1 inhibitors, Vasopressin V1a receptor antagonists, VEGF receptor antagonists, VIP 1 receptor agonists, VIP 2 receptor agonists, or Xanthine oxidase inhibitors, and combinations thereof.

Non-limiting examples of the one or more additional therapeutic agents include:

ACE inhibitors, such as, benazepril, imidapril;
Adenosine A3 receptor antagonists, such as FM-101;
Adropin stimulators, such as RBT-2;
Albumin modulators, such as SYNT-002;
Aldosterone/Mineralocorticoid receptor antagonists, such as MT-3995;

Allogeneic bone marrow-derived mesenchymal stromal cell therapy, such as ORBCEL-M™;
Allogenic expanded adipose-derived stem cell therapy, such as Elixcyte™;
AMP activated protein kinase stimulator/Proprotein convertase PC9 inhibitors, such as O-304;
AMP activated protein kinase stimulators, such as DZCY-01, MK-8722, PXL-770;
Angiotensin II AT-1 receptor/CCR2 chemokine antagonists, such as DMX-200;
Angiotensin II AT-2 receptor agonists, such as MOR-107, irbesartan;
Angiotensin II receptor antagonists, such as losartan;
Angiotensinogen ligand inhibitors, such as ALN-AGT;
anti-$C_1$ antibodies, such as BIVV-009 (sutimlimab);
anti-CB1 antibodies, such as GFB-024;
anti-CX3CR1 nanobodies, such as BI-655088;
anti-IL-6 antibodies, such as COR-001;
anti-VEGF-B antibodies, such as CSL-346;
APOA1 gene stimulators/Bromodomain containing protein 2/Bromodomain containing protein 4 inhibitors, such as apabetalone;
Bone morphogenetic protein-7 ligand modulators, such as BMP-7;
Calcium channel inhibitors, such as TBN (xiaotongqin);
Cannabinoid CB1 receptor antagonists, such as JNJ-2463;
CB1 inverse agonists, such as CRB-4001;
Chymase inhibitors, such as fulacimstat (BAY-1142524);
Cyclooxygenase 1 inhibitors, such as GLY-230;
Cyclooxygenase 2/Epoxide hydrolase inhibitors, such as COX-2/soluble epoxide hydrolase;
Cytochrome P450 11B2 inhibitors, such as aldosterone synthase inhibitors;
Ectonucleotide pyrophosphatase-PDE-2 inhibitors, such as BLD-0409;
Endothelin ET-A/Endothelin ET-B receptor antagonists, such as aprocitentan;
Enteropeptidase inhibitors, such as SCO-792;
Erythropoietin receptor antagonists, such as EPO-018B;
Farnesoid X receptor (FXR) agonists, such as AGN-242266, AGN-242256, ASC-42, EDP-297 (EP-024297), RDX-023, BWL-200, AKN-083, EDP-305, GNF-5120, cilofexor tromethamine (GS-9674), HPG-1860, 10T-022, LMB-763, obeticholic acid, Px-102, Px-103, M790, M780, M450, M-480, MET-409, MET-642, PX20606, SYHA-1805, vonafexor (EYP-001), TERN-101, TC-100, INT-2228, TQA-3526, ZG-5266;
FGF/PDGF/beta receptor antagonist/p38 MAP kinase inhibitors, such as pirfenidone;
GHR/IGF1 gene inhibitors, such as atesidorsen sodium;
GPR40 agonist/GPR84 antagonists, such as PBI-4050;
G-protein beta subunit inhibitors, such as galleon;
G-protein coupled receptor 84 modulators, such as PBI-4425;
Growth hormone ligand/Growth hormone receptor agonist, such as Jintropin AQ™;
Growth hormone receptor agonists, such as LAT-8881;
Guanylate cyclase receptor agonist/Guanylate cyclase stimulators, such as praliciguat;
Guanylate cyclase stimulators, such as MRL-001, runcaciguat;
Heme oxygenase 1 modulators, such as RBT-1;
HIF prolyl hydroxylase inhibitors, such as TRGX-154;
Insulin sensitizer/Kallikrein 1 modulators, such as DM-199;
Integrin alpha-V/beta-3 antagonists, such as VPI-2690B;
Interleukin 33 ligand inhibitors, such as MEDI-3506;
Kelch like ECH associated protein 1 modulator/Nuclear erythroid 2-related factor 2 stimulators, such as SFX-01;
LDHA gene inhibitors, such as nedosiran;
5-Lipoxygenase activating protein inhibitors, such as AZD-5718;
Lysophosphatidate-1 receptor antagonists, such as BMS-002, EPGN-696;
Matrix extracell phosphoglycoprotein modulator/Phosphatonin receptor agonist, such as TPX-200; MEKK-5 protein kinase inhibitors, such as selonsertib;
Membrane copper amine oxidase inhibitors, such as UD-014;
Midkine ligand inhibitors, such as CAB-101;
Mineralocorticoid receptor antagonists, such as AZD-9977, esaxerenone, finerenone, KBP-5074;
Myosin 2 inhibitor, such as DeciMab™;
NADPH oxidase 1 inhibitors/NADPH oxidase 4 inhibitors, such as setanaxib;
NADPH oxidase inhibitors, such as APX-115;
NK1 receptor antagonist/Opioid receptor kappa agonist/Opioid receptor mu antagonist, such as AV-104;
Nuclear erythroid 2-related factor 2 stimulator/TGF beta ligand inhibitors, such as CU01-1001;
Nuclear factor kappa B inhibitors, such as mefunidone, bardoxolone methyl (NSC-713200);
PDE 4 inhibitors, such as ART-648, PCS-499;
PDGF receptor beta modulators, such as BOT-191;
PDGF/VEGF receptor antagonists, such as ANG-3070;
PR84 antagonist/GPR40 (FFAR1)/GPR120 (FFAR4) agonist/and a partial activator of peroxisome proliferator-activated receptors (PPAR), such as PBI-4547;
PRKAA2 gene stimulators/AMPK activators, such as PF-06679142, PF-06685249;
Prostacyclin (PGI2) agonists, such as YS-1402;
Protein C activator/Glycoprotein Ib (GPIb) antagonist, such as AB-002;
Protein NOV homolog modulators, such as BLR-200;
Protein tyrosine phosphatase-1B inhibitors, such as MSI-1436;
Reactive oxygen species modulator inhibitors, such as SUL-121;
Renin inhibitors, such as imarikiren hydrochloride;
Rho associated protein kinase 2 inhibitors, such as ANG-4201, RXC-007;
Sodium glucose transporter-2 inhibitors, such as canagliflozin, dapagliflozin propanediol, empagliflozin;
Thromboxane A2 receptor antagonist/Thromboxane synthesis inhibitors, such as SER-150;
Tissue transglutaminase inhibitors, such as ZED-1227;
TRP cation channel $C_5$ inhibitors, such as GFB-887;
TRP cation channel C6 inhibitors, such as ALGX-2224;
Urate anion exchanger 1 (URAT1)/SLC22A12 inhibitors, such as verinurad (RDEA3170);
VIP 1/VIP 2 receptor agonists, such as LBT-3627; or
Xanthine oxidase inhibitors, such as TMX-049, TMX-049DN.

In certain specific embodiments, the one or more additional therapeutic agents are selected from A-717, ACF-TEI, alanyl-glutamine, ALLN-346, anti-SCF248 antibody, anti-TAGE monoclonal antibodies, anti-TGF beta antibodies, AST-120, BAY-2327949, BI-685509, DP-001, DZ-4001, GDT-01, LNP-1892, MEDI-8367, microRNA-targeting antisense oligonucleotide therapy, MK-2060, MPC-300-IV, NAV-003, Neo-Kidney Augment™ (NKA), NP-135, NP-160, NP-251, NRF-803, PBI-4610, PHN-033, R-HSC- 010, salvianolic acid, SGF-3, SPD-01, SZ-005, TCF-12, UMC119-06, VAR-400, veverimer, VS-105, or XRx-221.

IBD

The term "inflammatory bowel disease" or "IBD" as used herein is a collective term describing inflammatory disorders of the gastrointestinal tract, the most common forms of which are ulcerative colitis and Crohn's disease. Other forms of IBD that can be treated with the presently disclosed compounds, compositions and methods include diversion colitis, ischemic colitis, infectious colitis, chemical colitis, microscopic colitis (including collagenous colitis and lymphocytic colitis), atypical colitis, pseudomembranous colitis, fulminant colitis, autistic enterocolitis, indeterminate colitis, Behçet's disease, gastroduodenal CD, jejunoileitis, ileitis, ileocolitis, Crohn's (granulomatous) colitis, irritable bowel syndrome, mucositis, radiation induced enteritis, short bowel syndrome, celiac disease, stomach ulcers, diverticulitis, pouchitis, proctitis, chronic diarrhea, or endotoxemia due to gut barrier dysfunction.

The presently disclosed treatment methods can also be applied at any point in the course of the disease. In some embodiments, the methods are applied to a subject having IBD during a time period of remission (i.e., inactive disease). In such embodiments, the present methods provide benefit by extending the time period of remission (e.g., extending the period of inactive disease) or by preventing, reducing, or delaying the onset of active disease. In other embodiments, methods may be applied to a subject having IBD during a period of active disease. Such methods provide benefit by reducing the duration of the period of active disease, reducing or ameliorating one or more symptoms of IBD, or treating IBD.

The benefit of combination may be increased efficacy and/or reduced side effects for a component as the dose of that component may be adjusted down to reduce its side effects while benefiting from its efficacy augmented by the efficacy of the compound of the present disclosure.

In some embodiments, a compound of the present disclosure, or a pharmaceutically acceptable salt or stereoisomer thereof, can be combined with a therapeutically effective amount of one or more (e.g., one, two, three, four, one or two, one to three, or one to four) additional therapeutic agents.

Examples of agents for treatment of an inflammatory disease or condition that can be used in combination with compounds described herein, include alpha-fetoprotein modulators, adenosine A3 receptor antagonist, adrenomedullin ligands, AKT1 gene inhibitors, antibiotics; antifungals, ASK1 inhibitors, ATPase inhibitors, beta adrenoceptor antagonists, BTK inhibitors, calcineurin inhibitors, carbohydrate metabolism modulators, cathepsin S inhibitors, CCR9 chemokine antagonists, CD233 modulators, CD29 modulators, CD3 antagonists, CD40 ligand inhibitors, CD40 ligand receptor antagonists, chemokine CXC ligand inhibitors, CHST15 gene inhibitors, collagen modulators, COT protein kinase inhibitors, CSF-1 agonist, CSF-1 antagonists, CX3CR1 chemokine modulators, DYRK-1 alpha protein kinase inhibitor, eotaxin ligand inhibitors, EP4 prostanoid receptor agonists, FIFO ATP synthase modulators, farnesoid X receptor (FXR, NR1H4) agonists or modulators, fecal microbiota transplantation (FMT), fractalkine ligand inhibitors, free fatty acid receptor 2 antagonists, GATA 3 transcription factor inhibitors, glucagon-like peptide 2 agonists, glucocorticoid agonists, Glucocorticoid receptor modulators, guanylate cyclase receptor agonists HIF, prolyl hydroxylase inhibitors, histone deacetylase inhibitors, HLA class II antigen modulators, hypoxia inducible factor-1 stimulator, ICAM1 gene inhibitors, IL-1 beta ligand modulators, IL-12 antagonists, IL-13 antagonists, IL-18 antagonists, IL-18 receptor accessory protein antagonist, IL-22 agonists, IL-23 antagonists, IL-23A inhibitors, IL-6 antagonists, IL-7 receptor antagonists, IL-8 receptor antagonists, IL-36 inhibitors, integrin alpha-4/beta-1 antagonists, integrin alpha-4/beta-7 antagonists, integrin antagonists, interleukin ligand inhibitors, interleukin receptor 17A antagonists, interleukin-1 beta ligands, interleukin 1 like receptor 2 inhibitors, IL-6 receptor modulators, JAK tyrosine kinase inhibitors, Jak1 tyrosine kinase inhibitors, Jak3 tyrosine kinase inhibitors, lactoferrin stimulators, LanC like protein 2 modulators, leukocyte elastate inhibitors, leukocyte proteinase-3 inhibitors, MAdCAM inhibitors, melanin concentrating hormone (MCH-1) antagonist, melanocortin agonists, metalloprotease-9 inhibitors, microbiome-targeting therapeutics, natriuretic peptide receptor C agonists; neuregulin-4 ligand, NLRP3 inhibitors, NKG2 D activating NK receptor antagonists, NR1H4 receptor (FXR) agonists, nuclear factor kappa B inhibitors, opioid receptor antagonists, OX40 ligand inhibitors, oxidoreductase inhibitors, P2X7 purinoceptor modulators, PDE 4 inhibitors, Pellino homolog 1 inhibitors, PPAR alpha/delta agonists, PPAR gamma agonists, Protein arginine deiminase IV inhibitors, protein fimH inhibitors, P-selectin glycoprotein ligand-1 inhibitors, Ret tyrosine kinase receptor inhibitors, RIP-1 kinase inhibitors, RIP-2 kinase inhibitors, RNA polymerase inhibitors, sphingosine 1 phosphate phosphatase 1 stimulators, sphingosine-1-phosphate receptor-1 agonists, sphingosine-1-phosphate receptor-5 agonists, sphingosine-1-phosphate receptor-1 antagonists, sphingosine-1-phosphate receptor-1 modulators, stem cell antigen-1 inhibitors, superoxide dismutase modulators, SYK inhibitors, tissue transglutaminase inhibitor, TLR-3 antagonists, TLR-4 antagonists, Toll-like receptor 8 (TLR8) inhibitors, TLR-9 agonists, TNF alpha ligand inhibitors, TNF ligand inhibitors, TNF alpha ligand modulators, TNF antagonists, TPL-2 inhibitors, tumor necrosis factor 14 ligand modulators, tumor necrosis factor 15 ligand inhibitors, Tyk2 tyrosine kinase inhibitors, type I IL-1 receptor antagonists, vanilloid VR1 agonists, or zonulin inhibitors, and combinations thereof.

Included herein are methods of treatment in which a compound described herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate.

Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an $IC_{50}$ that is at least 50-fold lower than the $IC_{50}$ for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates.

The anti-inflammatory agent may also be a corticosteroid. For example, the corticosteroid may be chosen from cortisone, dexamethasone, methylprednisolone, prednisolone, prednisolone sodium phosphate, and prednisone.

In some embodiments, the anti-inflammatory compound is an anti-05 monoclonal antibody (such as eculizumab or pexelizumab), a TNF antagonist, such as etanercept, or infliximab, which is an anti-TNF alpha monoclonal antibody.

Included herein are methods of treatment in which a compound described herein, is administered in combination with an immunosuppressant. In some embodiments, the immunosuppressant is methotrexate, leflunomide, cyclosporine, tacrolimus, azathioprine, mycophenolate sodium, mercaptopurine, or mycophenolate mofetil.

Methods of Treatment

In some embodiments, compounds of Formulas (I-VI) or pharmaceutically acceptable salt or stereoisomer thereof, are useful in a method of treating and/or preventing a KHK (ketohexokinase) mediated disease or condition. In some embodiments, a method for treating and/or preventing a KHK mediated disease or condition includes administering to a subject in need thereof a pharmaceutically effective amount of a compound of the present disclosure or pharmaceutically acceptable salt or stereoisomer thereof.

In some embodiments, the disease or condition comprises chronic kidney disease (CKD), diabetic kidney disease (DKD), kidney disease, kidney fibrosis, kidney insufficiency, acute kidney injury, tubular disfunction, lupus nephritis, 2,8-dihydroxyadenine nephropathy, renal transplant rejection, renal protection against drugs inducing Fanconi's syndrome, hereditary fructose intolerance, non-alcoholic steatohepatitis (NASH), alcoholic steatohepatitis (ASH), non-alcoholic fatty liver disease (NAFLD), liver disease, liver fibrosis, metabolic syndrome, obesity, hyperlipidemia, hypertriglyceridemia, hypertension, fibrosis, steatosis, cirrhosis, cardiometabolic syndrome, insulin resistance, cardiovascular disease, heart failure, type 1 and type 2 diabetes mellitus, irritable bowel syndrome disease (IBD), ulcerative colitis, Crohn's disease, hyperuricemia, gout, arthritis, osteoporosis or cancer.

In some embodiments, a method of treating and/or preventing a non-alcoholic fatty liver disease (NAFLD), comprises administering to a subject in need thereof a compound of the present disclosure or a pharmaceutically acceptable salt or stereoisomer thereof.

In some embodiments, a method of treating and/or preventing chronic kidney disease, comprises administering to a subject in need thereof a compound of the present disclosure or a pharmaceutically acceptable salt or stereoisomer thereof.

In some embodiments, a method of treating and/or preventing irritable bowel syndrome disease (IBD), comprises administering to a subject in need thereof a compound of the present disclosure or a pharmaceutically acceptable salt or stereoisomer thereof.

Further provided herein is a pharmaceutical composition for use in treating a KHK mediated disease or condition described herein, comprising a compound of the present disclosure or a pharmaceutically acceptable salt or stereoisomer thereof.

The present disclosure also describes a use for the manufacture of a medicament in treating a KHK mediated disease or condition comprising a compound of the present disclosure or a pharmaceutically acceptable salt or stereoisomer thereof. Medicaments as referred to herein may be prepared by conventional processes, including the combination of a compound according to the present disclosure and a pharmaceutically acceptable carrier.

Also disclosed is a compound of the present disclosure or a pharmaceutically acceptable salt or stereoisomer thereof for the treatment of a KHK mediated disease or condition. Also disclosed is a compound of the present disclosure or a pharmaceutically acceptable salt or stereoisomer thereof for the prevention of a KHK mediated disease or condition.

EXAMPLES

Many general references providing commonly known chemical synthetic schemes and conditions useful for synthesizing the disclosed compounds are available (see, e.g., Smith, March's Advanced Organic Chemistry: Reactions, Mechanisms, and Structure, $7^{th}$ edition, Wiley-Interscience, 2013).

Compounds as described herein can be purified by any of the means known in the art, including chromatographic means, such as high-performance liquid chromatography (HPLC), preparative thin layer chromatography, flash column chromatography and ion exchange chromatography. Any suitable stationary phase can be used, including normal and reversed phases as well as ionic resins. For example, the disclosed compounds can be purified via silica gel and/or alumina chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

During any of the processes for preparation of the subject compounds, it may be desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4th ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the pendant groups.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure.

Other embodiments may be utilized and logical and other changes may be made without departing from the scope of the disclosure. The embodiments are also directed to processes and intermediates useful for preparing the subject compounds or pharmaceutically acceptable salts or stereoisomers thereof. The following description is, therefore, not intended to limit the scope of the present disclosure.

In some embodiments, the present disclosure generally provides a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or disatereomerically pure.

Representative syntheses of compounds of the present disclosure are described in schemes below, and the examples that follow.

The compounds detailed in the Examples were synthesized according to the general synthetic methods described below. Compounds were named using ChemDraw version 18.1.0.535 (PerkinElmer Informatics, Inc.) or BIOVIA Notebook 2020 SP2 HF1 Version 20.1.201.31 unless otherwise indicated.

Abbreviations

Certain abbreviations and acronyms are used in describing the experimental details. Although most of these would be understood by one skilled in the art, Table 1 contains a list of many of these abbreviations and acronyms.

TABLE 1

List of Abbreviations and Acronyms

| Abbreviation | Meaning |
|---|---|
| Ac | acetyl |
| ACN, MeCN | acetonitrile |
| $B_2Pin_2$ | bis(pinacolato)diboron |
| Bn | benzyl |
| Boc | tert-butyloxycarbonyl |
| $Boc_2O$ | di-tert-butyl dicarbonate |
| Bpin | (pinacolato)boron |
| Bu | butyl |
| Bz | benzoyl |
| BzCl | benzoyl chloride |
| Cbz | Carboxybenzyl |
| CSA | camphorsulfonic acid |
| Cy | cyclohexyl |
| CyBu | cyclobutyl |
| CyPr | cyclopropyl |
| DAST | Bis(2-methoxyethyl)aminosulfur trifluoride |
| dba | dibenzalacetone |
| DCE, 1,2-DCE | 1,2-dichloroethane |
| DCM | dichloromethane |
| DIPEA | diisopropylethylamine |
| DMAc | N,N-dimethylacetamide |
| DMAP | 4-dimethylaminopyridine |
| DME, 1,2-DME | dimethoxyethane |
| DMEM | Dulbecco's Modified Eagle Medium |
| DMF | N,N-dimethylformamide |
| DMSO | dimethylsulfoxide |
| dppf | 1,1'-Ferrocenediyl-bis(diphenylphosphine) |
| ES/MS | electron spray mass spectrometry |
| Et | ethyl |
| EtOAc | ethylacetate |
| EtOH | ethanol |
| FBS | fetal bovine serum |
| Ghaffar-Parkins catalyst | Hydrido(dimethylphosphinous acid-κP)[hydrogen bis(dimethylphosphinito-κP)]platinum(II) |
| HATU | 1-[Bis(dimethylamino)methylene]-1H-1,2,3-triazolo[4,5-b]pyridinium 3-oxide hexafluorophosphate |
| HPLC | high performance liquid chromatography |
| hr | hour |
| IPA, iPrOH | isopropanol |
| iPr | isopropyl |
| KOtBu | potassium tert-butoxide |
| LC | liquid chromatography |
| LCMS | liquid chromatography/mass spectrometry |
| m/z | mass to charge ratio |
| mCPBA | meta-chloroperbenzoic acid |
| Me | methyl |
| MeCN, ACN | acetonitrile |
| MeOH | methanol |
| min | minute |
| Ms | methanesulfonyl |
| MS, ms | mass spectrum |
| NaOtBu | sodium tert-butoxide |
| NMP | N-methyl-2-pyrrolidone |
| OAc | acetate |
| OATP | organic anion transporting polypeptides |

TABLE 1-continued

List of Abbreviations and Acronyms

| Abbreviation | Meaning |
|---|---|
| PCy$_3$ | tricyclohexylphosphine |
| Ph | phenyl |
| Ph$_3$P | triphenylphosphine |
| PhMe | toluene |
| pin | pinacol |
| PtBu$_3$ | tributylphosphine |
| Pyr | pyridine |
| RBF | round bottom flask |
| RT | room temperature |
| RuPhos | 2-Dicyclohexylphosphino-2',6'-diisopropoxybiphenyl |
| SFC | supercritical fluid chromatography |
| SFC | supercritical fluid chromatography |
| Sn$_2$Bu$_6$ | hexabutylditin |
| SPhos | 2-Dicyclohexylphosphino-2',6'-dimethoxybiphenyl |
| SPhos Pd G1 | (2-Dicyclohexylphosphino-2',6'-dimethoxy-1,1'-biphenyl)[2-(2-aminoethylphenyl)]palladium(II) chloride |
| SPhos Pd G2 | Chloro(2-dicyclohexylphosphino-2',6'-dimethoxy-1,1'-biphenyl)[2-(2'-amino-1,1'-biphenyl)]palladium(II) |
| SPhos Pd G3 | (2-Dicyclohexylphosphino-2',6'-dimethoxybiphenyl)[2-(2'-amino-1,1'-biphenyl)]palladium(II) methanesulfonate |
| SPhos Pd G4 | (SP-4-3)-[Dicyclohexyl(2',6'-dimethoxy[1,1'-biphenyl]-2-yl)phosphine-κP](methanesulfonato-κO)[2'-(methylamino-κN)[1,1'-biphenyl]-2-yl-κC]palladium |
| tBu | tert-butyl |
| tBuOH | tert-butanol |
| TEA, Et$_3$N | triethylamine |
| TFA | 1,1,1-trifluoroacetic acid |
| THF | tetrahydrofuran |
| THP | tetrahydropyran |
| Ts | 4-toluenesulfonyl |
| XantPhos | 4,5-Bis(diphenylphosphino)-9,9-dimethylxanthene |
| XPhos | 2-Dicyclohexylphosphino-2',4',6'-triisopropylbiphenyl |
| XPhos Pd G1 | (2-Dicyclohexylphosphino-2',4',6'-triisopropyl-1,1'-biphenyl)[2-(2-aminoethyl)phenyl)]palladium(II) chloride |
| XPhos Pd G2 | Chloro(2-dicyclohexylphosphino-2',4',6'-triisopropyl-1,1'-biphenyl)[2-(2'-amino-1,1'-biphenyl)]palladium(II) |
| XPhos Pd G3 | (2-Dicyclohexylphosphino-2',4',6'-triisopropyl-1,1'-biphenyl)[2-(2'-amino-1,1'-biphenyl)]palladium(II) methanesulfonate |
| XPhos Pd G4 | (SP-4-3)-[Dicyclohexyl[2',4',6'-tris(1-methylethyl)[1,1'-biphenyl]-2-yl]phosphine](methanesulfonato-κO)[2'-(methylamino-κN)[1,1'-biphenyl]-2-yl-κC]palladium |
| δ | parts per million referenced to residual solvent peak |

Synthesis of Intermediates and General Methods

Preparation of Intermediates

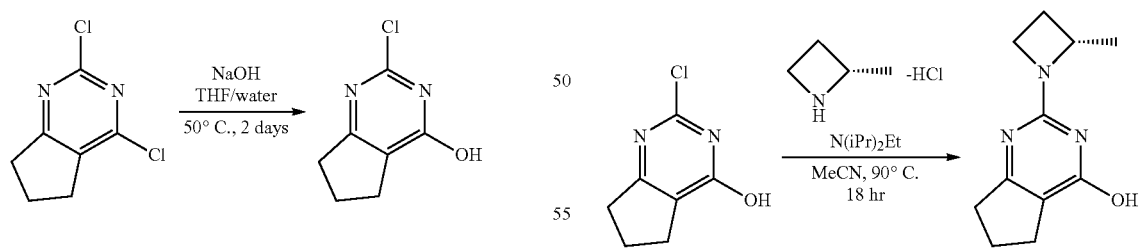

2-chloro-6,7-dihydro-5H-cyclopenta[d]pyrimidin-4-ol

A flask was charged with 2,4-dichloro-6,7-dihydro-5H-cyclopenta[d]pyrimidine (5.00 g, 26.4 mmol, 1 equiv.), and THF (26 mL) and 5N sodium hydroxide (26 mL, 130 mmol) were added. It was heated to 50° C. for two days. It was diluted with water and washed twice with dichloromethane. The aqueous layer was acidified with 10% potassium bisulfate until a pH of 5 was reached. It was extracted twice with dichloromethane, and these extracts were dried over anhydrous sodium sulfate, filtered, and concentrated in vacuo. It was purified via flash chromatography (40-100% ethyl acetate/hexanes linear gradient) to yield the title compound.

2-[(2S)-2-methylazetidin-1-yl]-6,7-dihydro-5H-cyclopenta[d]pyrimidin-4-ol

A flask was charged with 2-chloro-6,7-dihydro-5H-cyclopenta[d]pyrimidin-4-ol (776 mg, 4.55 mmol, 1 equiv.) and (2S)-2-methylazetidine hydrochloride (587 mg, 5.46 mmol), and acetonitrile (12 mL) and N,N-diisopropylethylamine (2.38 mL, 13.6 mmol) were added. It was sealed and heated to 80° C. for 16 hours. It was cooled to ambient temperature, and the solids formed were collected and washed with acetonitrile and collected to yield the title compound.

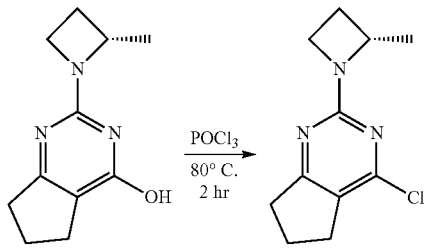

4-chloro-2-[(2S)-2-methylazetidin-1-yl]-6,7-dihydro-5H-cyclopenta[d]pyrimidine

A flask was charged with 2-[(2S)-2-methylazetidin-1-yl]-6,7-dihydro-5H-cyclopenta[d]pyrimidin-4-ol (873 mg, 4.25 mmol, 1 equiv.) and phosphoryl chloride (12 mL, 128 mmol) was added. It was heated to 80° C. for 2 hours. It was cooled to ambient temperature, poured onto ice, and neutralized with solid potassium carbonate until a pH>9 was reached. It was extracted with ethyl acetate, dried over anhydrous sodium sulfate, filtered, and concentrated to yield the title compound.

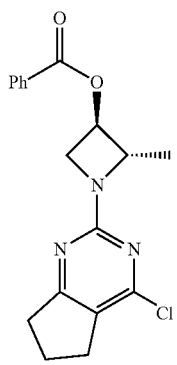

(2S,3R)-1-(4-chloro-6,7-dihydro-5H-cyclopenta[d]pyrimidin-2-yl)-2-methylazetidin-3-yl benzoate The title compound was prepared in a method analogous to 2-[(2S)-2-methylazetidin-1-yl]-6,7-dihydro-5H-cyclopenta[d]pyrimidin-4-ol using (2S,3R)-2-methylazetidin-3-yl benzoate instead of (2S)-2-methylazetidine hydrochloride.

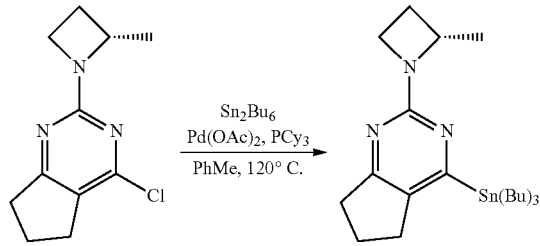

(S)-2-(2-methylazetidin-1-yl)-4-(tributylstannyl)-6,7-dihydro-5H-cyclopenta[d]pyrimidine A flask was charged with (S)-4-chloro-2-(2-methylazetidin-1-yl)-6,7-dihydro-5H-cyclopenta[d]pyrimidine (23.0 g, 102 mmol) and PhMe (58 mL), followed by Sn$_2$Bu$_6$ (48.0 g, 82.7 mmol), Pd(OAc)$_2$ (1.15 g, 5.14 mmol), and PCy$_3$ (2.88 g, 10.2 mmol). The flask was purged with nitrogen, and heated to 120° C. for 16 hrs. The reaction was cooled to ambient temperature, concentrated, and subject to flash column chromatography (Al$_2$O$_3$, petroleum ether-ethyl acetate) to give the title compound.

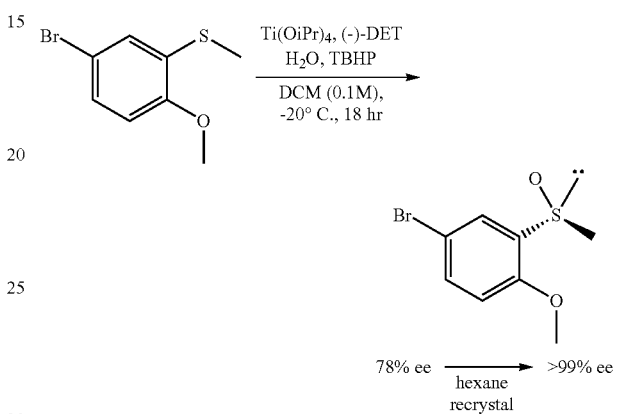

(S)-4-bromo-1-methoxy-2-(methylsulfinyl)benzene

A flask was charged with (−)-diethyl D-tartrate (15.4 g, 74.6 mmol) and DCM (400 mL), followed by Ti(OiPr)$_4$ (10.6 g, 37.3 mmol), and H$_2$O (0.67 mL, 37.3 mmol). The mixture was allowed to stir at ambient temperature for 30 min (5-bromo-2-methoxyphenyl)(methyl)sulfane (8.70 g, 37.3 mmol) was added and the mixture was stirred another 15 min at ambient temperature, after which the mixture was cooled to −20° C. (ethylene glycol-dry ice bath), and tert-butyl hydrogen peroxide (5-6 M in decane, 8.96 mL, 44.8 mmol) was added dropwise over 5 minutes. The mixture was allowed to warm to ambient temperature over 18 hours. H$_2$O (10 ml) was added, and the mixture was filtered over Celite®. The filtrate was washed with H$_2$O (200 mL) and extracted with DCM (3×100 mL). The combined organics were dried over Na$_2$SO$_4$, filtered, and concentrated. The residue was subject to flash column chromatography (hexanes-ethyl acetate) to give the title product in 78% ee. The product was recrystallized from boiling hexanes to achieve >99% ee.

General Methods

General methods represent the most commonly used methods, but slight modifications were sometimes used, including in reaction time course and temperature.

Solvents were generally selected from, but not limited to 1,2-dimethoxyethane, tetrahydrofuran, 1,4-dioxane, toluene, xylene, benzene, chlorobenzene, acetonitrile, N,N-dimethylformamide, N-methylpyrrolidone, dimethylsulfoxide, methanol, ethanol, 2-propanol or water. Palladium catalysts were generally selected from, but not limited to, Pd(PPh$_3$)$_4$, Pd(dppf)Cl$_2$, Pd(OAc)$_2$, PdCl$_2$Pd XPhos G1, G2, G3, or G4 precatalysts, Pd SPhos G1, G2, G3, or G4 precatalysts, or Pd$_2$dba$_3$ with or without phosphine ligands, selected from, but not limited to, SPhos, XPhos, RuPhos, XantPhos, PCy$_3$, PPh$_3$, or dppf. Bases were generally selected from, but not limited to, sodium carbonate, potassium carbonate, cesium carbonate, tribasic potassium phosphate, sodium hydroxide, potassium hydroxide, sodium acetate, potassium acetate, cesium fluoride, triethyl amine, diisopropylethyl amine, or pyridine.

Isomers that were separated by chiral chromatography were arbitrarily assigned stereochemistry.

General Method A

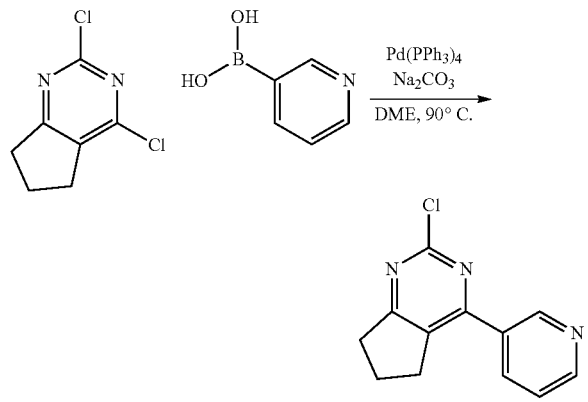

2-chloro-4-(pyridin-3-yl)-6,7-dihydro-5H-cyclopenta[d]pyrimidine

A vial was charged with 2,4-dichloro-6,7-dihydro-5H-cyclopenta[d]pyrimidine (40 mg, 0.21 mmol, 1 equiv.), 3-pyridylboronic acid (31 mg, 0.25 mmol, 1.2 equiv.) and Pd(PPh$_3$)$_4$ (25 mg, 0.021 mmol, 10 mol %), and was flushed with nitrogen. DME (10 mL) and Na$_2$CO$_3$ (2M aq, 0.53 mL, 4 equiv.) were added and the mixture was heated to 90° C. for 4 hrs. The mixture was cooled to ambient temperature, concentrated, and subject to flash column chromatography (hexanes-ethyl acetate) to give the title compound (44 mg, 0.19 mmol).

General Method B

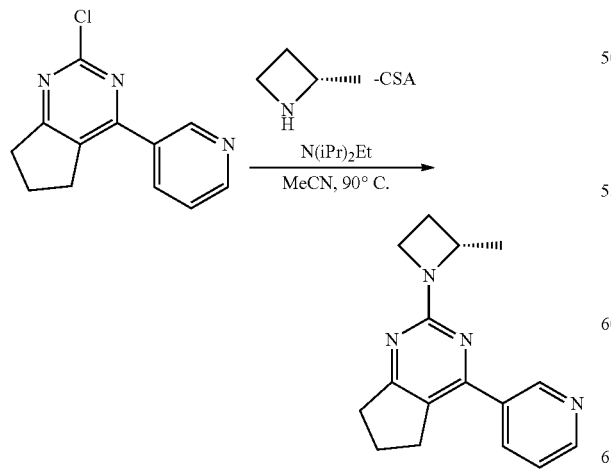

(S)-2-(2-methylazetidin-1-yl)-4-(pyridin-3-yl)-6,7-dihydro-5H-cyclopenta[d]pyrimidine A vial was charged with 2-chloro-4-(pyridin-3-yl)-6,7-dihydro-5H-cyclopenta[d]pyrimidine (44 mg, 0.19 mmol, 1.0 equiv.), (2S)-2-methylazetidine (R)-camphorsulfonic acid salt (86 mg, 0.29 mmol, 1.5 equiv.) and MeCN (1.5 mL). N(iPr)$_2$Et (0.13 mL, 98 mg, 0.76 mmol, 4.0 equiv.) was added and the mixture was heated to 90° C. for 18 hours. The mixture was concentrated and subject to HPLC (0.1% TFA in MeCN-0.1% TFA in H$_2$O) to give the title compound (36 mg, 0.14 mol).

General Method C

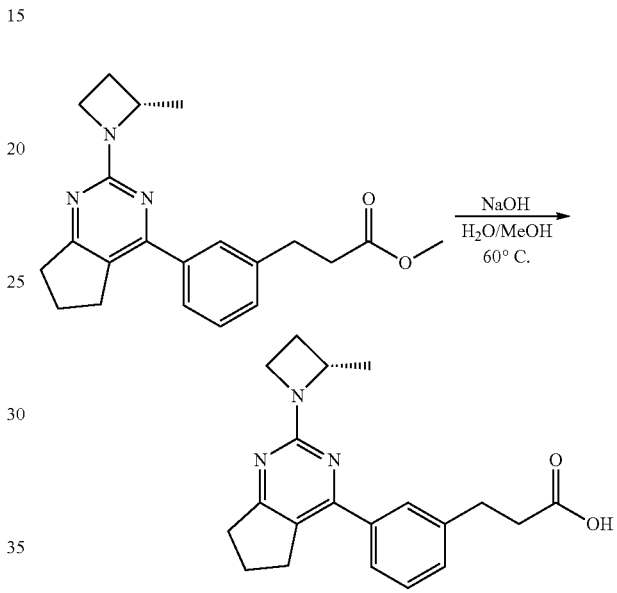

(S)-3-(3-(2-(2-methylazetidin-1-yl)-6,7-dihydro-5H-cyclopenta[d]pyrimidin-4-yl)phenyl)propanoic acid A vial was charged with methyl (S)-3-(3-(2-(2-methylazetidin-1-yl)-6,7-dihydro-5H-cyclopenta[d]pyrimidin-4-yl)phenyl)propanoate (20 mg, 0.057 mmol, 1 equiv.), MeOH (1 mL) and NaOH (2M aq., 0.6 mL). The reaction mixture was heated to 60° C. for 1 hour. The reaction mixture was cooled to room temperature, concentrated, and subjected to HPLC (0.1% TFA in MeCN-0.1% TFA in H$_2$O) to give the title compound (3.3 mg, 0.0098 mmol).

General Method D

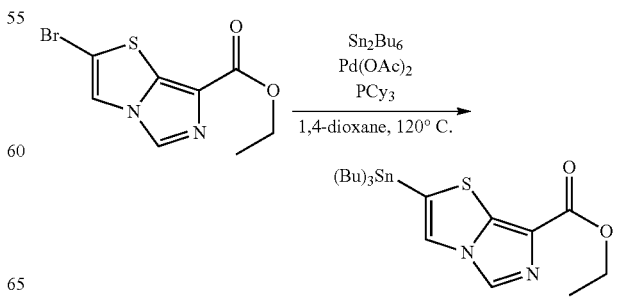

ethyl 2-tributylstannylimidazo[5,1-b]thiazole-7-carboxylate

A vial was charged with ethyl 2-bromoimidazo[5,1-b]thiazole-7-carboxylate (500 mg, 1.82 mmol, 1.0 equiv.), Pd(OAc)$_2$ (40.8 mg, 0.18 mmol, 10 mol %), PCy$_3$ (102 mg, 0.36 mmol, 20 mol %), hexa-n-butylditin (1.16 g, 2.00 mmol, 1.1 equiv.) and 1,4-dioxane (4.0 mL), and the mixture was sparged with nitrogen. The mixture was heated to 120° C. for 18 h. The mixture was concentrated and subjected to flash column chromatography (hexane-ethyl acetate) to provide the title compound (258 mg, 0.53 mmol).

General Method E

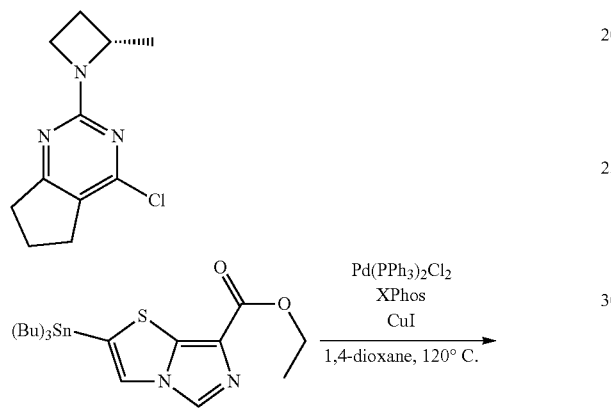

ethyl (S)-2-(2-(2-methylazetidin-1-yl)-6,7-dihydro-5H-cyclopenta[d]pyrimidin-4-yl)imidazo[5,1-b]thiazole-7-carboxylate A vial was charged with ethyl 2-tributylstannylimidazo[5,1-b]thiazole-7-carboxylate (100 mg, 0.21 mmol, 1.0 equiv.), (S)-4-chloro-2-(2-methylazetidin-1-yl)-6,7-dihydro-5H-cyclopenta[d]pyrimidine (46 mg, 0.21 mmol, 1.0 equiv.), Pd(PPh$_3$)$_2$Cl$_2$ (15 mg, 0.021 mmol, 10 mol %), XPhos (9.4 mg, 0.021 mmol, 10 mol %), CuI (3.9 mg, 0.021 mmol, 10 mol %), and 1,4-dioxane (3 mL). The mixture was heated to 120° C. for 4 hrs. The mixture was concentrated and subjected to flash column chromatography (hexanes-ethyl acetate) to give the title compound (50 mg, 0.13 mmol).

General Method F

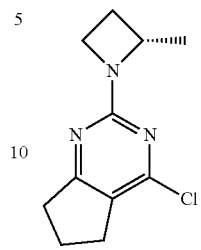

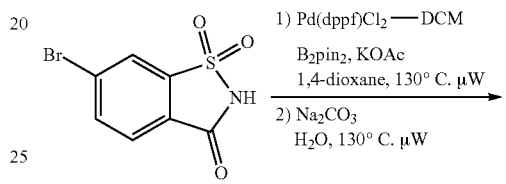

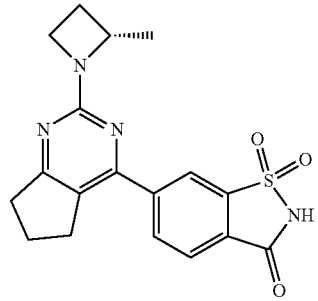

(S)-6-(2-(2-methylazetidin-1-yl)-6,7-dihydro-5H-cyclopenta[d]pyrimidin-4-yl)benzo[d]isothiazol-3(2H)-one 1,1-dioxide A microwave reaction tube was charged with 6-bromo-1,1-dioxo-1,2-benzothiazol-3-one (25.0 mg, 0.095 mmol), bis(pinacolato)diboron, (30.3 mg, 0.119 mmol), KOAc (23.4 mg, 0.238 mmol), and Pd(dppf)Cl$_2$ (7.56 mg, 0.0095 mmol, 10 mol %). 1,4-Dioxane (1 mL) was added and the mixture was sparged with nitrogen for 5 minutes before being heated to 130° C. for 1 hour in a CEM microwave reactor. The mixture was cooled to ambient temperature and filtered, washing with 1,4-dioxane (0.5 mL). A microwave reaction tube was charged with the filtrate and 4-chloro-2-[(2S)-2-methylazetidin-1-yl]-6,7-dihydro-5H-cyclopenta[d]pyrimidine (21.3 mg, 0.095 mmol). Aqueous Na$_2$CO$_3$ (2 M, 0.2 mL) was added and the reaction mixture was sparged with nitrogen for 5 minutes before being heated to 130° C. for 1 hour in a CEM microwave reactor. The mixture was cooled to ambient temperature, concentrated, and subject to HPLC (0.1% TFA in MeCN-0.1% TFA in H$_2$O) to afford the title compound (5.3 mg, 0.014 mmol).

General Method G

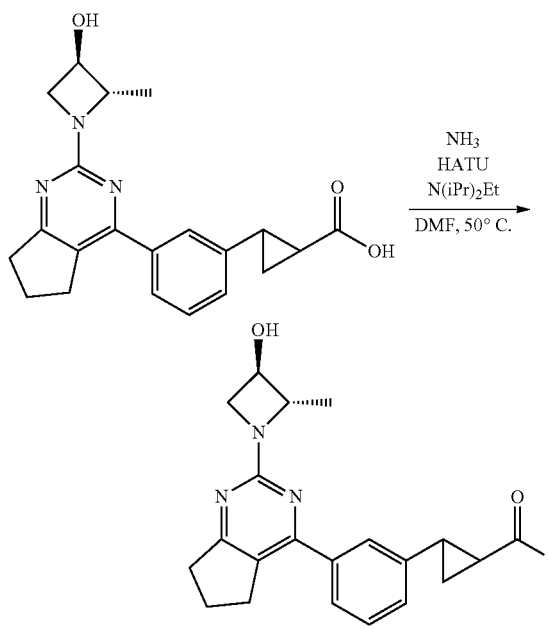

2-(3-(2-((2S,3R)-3-hydroxy-2-methylazetidin-1-yl)-6,7-dihydro-5H-cyclopenta[d]pyrimidin-4-yl)phenyl)cyclopropane-1-carboxamide A vial was charged with 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid (56 mg, 0.15 mmol, 1.0 equiv), ammonia (0.4M in 1,4-dioxane, 1.2 mL, 0.46 mmol, 3.0 equiv.), and HATU (70 mg, 0.18 mmol, 1.2 equiv.). DMF (2 mL) was added, followed by N(iPr)₂Et (0.11 mL, 0.61 mmol, 4.0 equiv.). The mixture was heated to 50° C. for 30 min, cooled to ambient temperature. H₂O (5 mL) was added, and the mixture was extract with EtOAc (3×5 mL). The combined organics were dried over Na₂SO₄, filter, and concentrated. The residue was subjected to HPLC (0.1% TFA in MeCN-0.1% TFA in H₂O) to afford the title compound (45 mg, 0.12 mmol)

General Method H

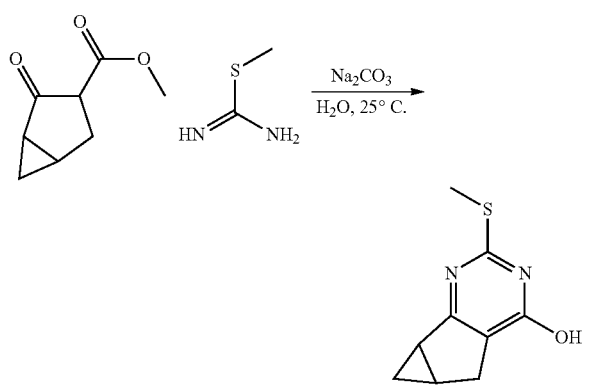

2-(methylthio)-5,5a,6,6a-tetrahydrocyclopropa[4,5]cyclopenta[1,2-d]pyrimidin-4-ol A vial was charged with methyl 2-oxobicyclo[3.1.0]hexane-3-carboxylate (300 mg, 1.95 mmol) and 2-methylisothiourea (557 mg, 3.89 mmol) followed by sodium carbonate (2M, aq., 3.89 mL, 7.78 mmol). The mixture was stirred for 18 hrs at ambient temperature. The formed solids were collected by filtration and treated with 1N HCl, then extracted with EA. The mixture was concentrated, and subject to flash column chromatography (hexanes-ethyl acetate) to give the title compound (300 mg, 1.54 mmol).

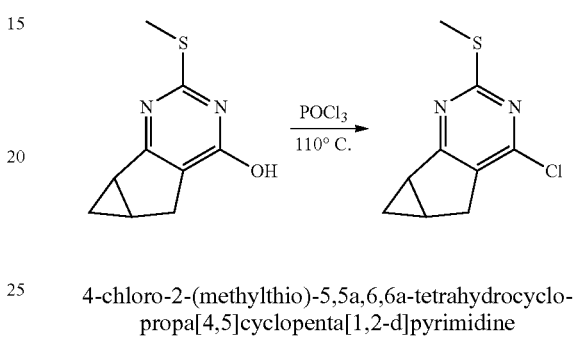

4-chloro-2-(methylthio)-5,5a,6,6a-tetrahydrocyclopropa[4,5]cyclopenta[1,2-d]pyrimidine A vial was charged with 2-(methylthio)-5,5a,6,6a-tetrahydrocyclopropa[4,5]cyclopenta[1,2-d]pyrimidin-4-ol (300 mg, 1.54 mmol) followed by addition of POCl₃ (5 mL, 46.3 mmol). The mixture was heated to 110° C. for 18 h, cooled to ambient temperature and poured over ice. The aqueous mixture was extracted twice with DCM. The combined organic layers were dried over MgSO₄, filtered and concentrated. The crude was used without further purification.

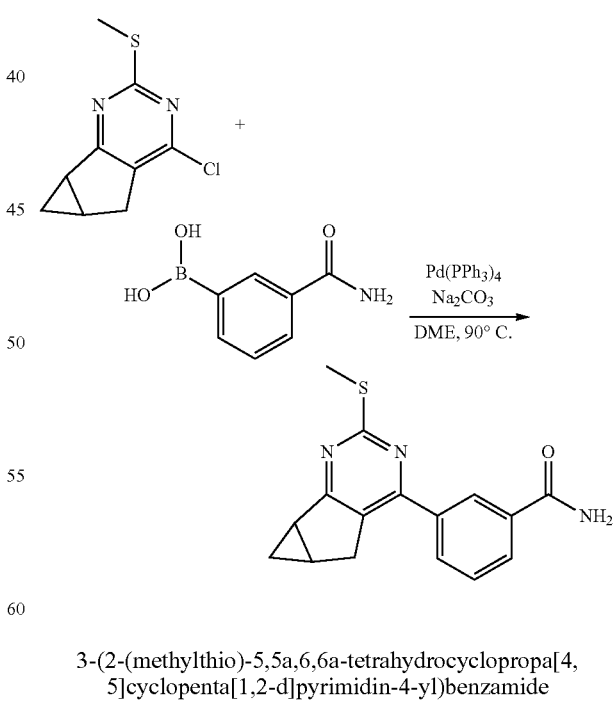

3-(2-(methylthio)-5,5a,6,6a-tetrahydrocyclopropa[4,5]cyclopenta[1,2-d]pyrimidin-4-yl)benzamide The title compound was prepared in a method analogous to General Method A using 4-chloro-2-(methylthio)-5,5a,6,6a-tetrahydrocyclopropa[4,5]cyclopenta[1,2-d]pyrimidine and (3-carbamoylphenyl)boronic acid instead of 2,4-dichloro-6,7-dihydro-5H-cyclopenta[d]pyrimidine and 3-pyridylboronic acid, respectively.

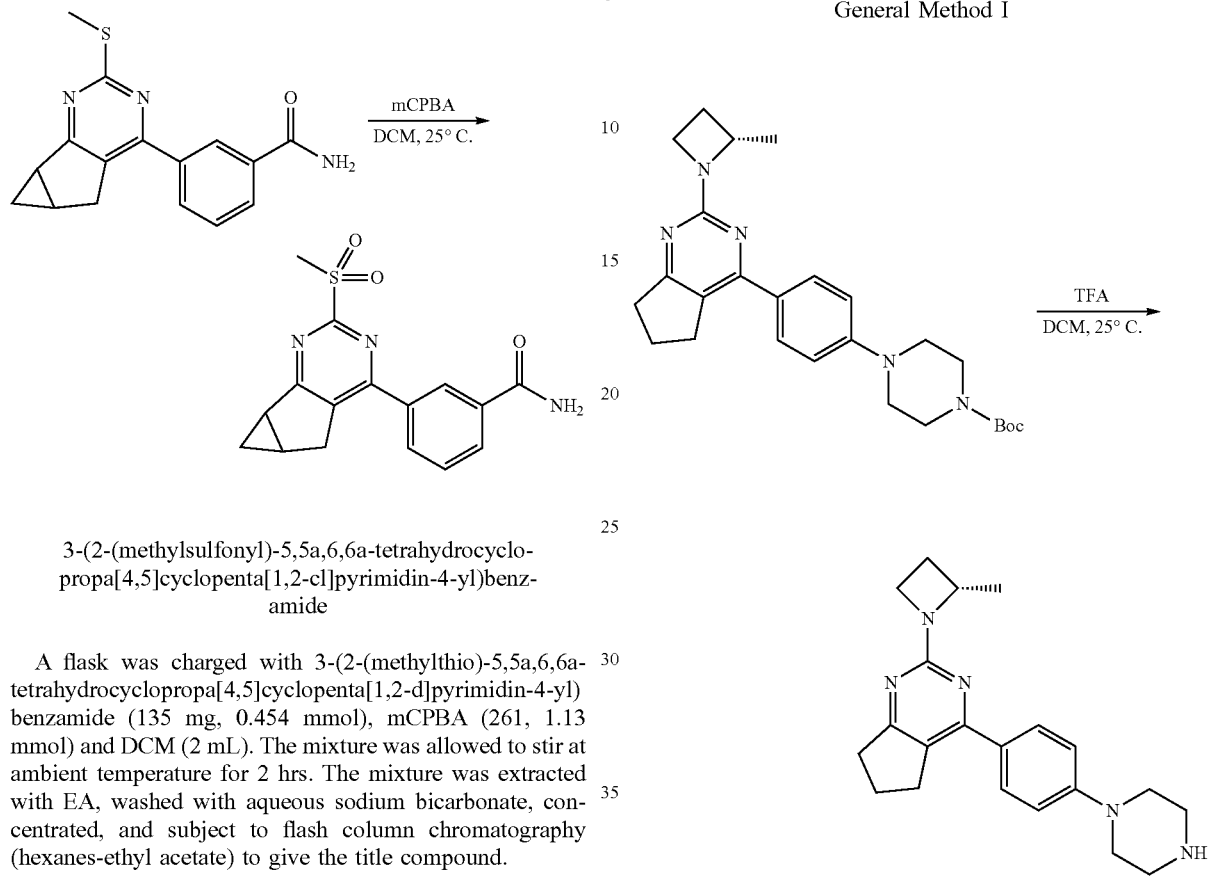

3-(2-(methylsulfonyl)-5,5a,6,6a-tetrahydrocyclopropa[4,5]cyclopenta[1,2-cl]pyrimidin-4-yl)benzamide A flask was charged with 3-(2-(methylthio)-5,5a,6,6a-tetrahydrocyclopropa[4,5]cyclopenta[1,2-d]pyrimidin-4-yl)benzamide (135 mg, 0.454 mmol), mCPBA (261, 1.13 mmol) and DCM (2 mL). The mixture was allowed to stir at ambient temperature for 2 hrs. The mixture was extracted with EA, washed with aqueous sodium bicarbonate, concentrated, and subject to flash column chromatography (hexanes-ethyl acetate) to give the title compound.

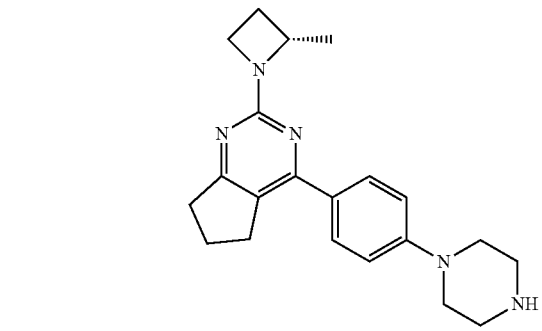

3-(2-((S)-2-methylazetidin-1-yl)-5,5a,6,6a-tetrahydrocyclopropa[4,5]cyclopenta[1,2-d]pyrimidin-4-yl)benzamide The title compound was prepared in a method analogous to General Method B using 3-(2-(methylsulfonyl)-5,5a,6,6a-tetrahydrocyclopropa[4,5]cyclopenta[1,2-d]pyrimidin-4-yl)benzamide instead of 2-chloro-4-(pyridin-3-yl)-6,7-dihydro-5H-cyclopenta[d]pyrimidine.

General Method I

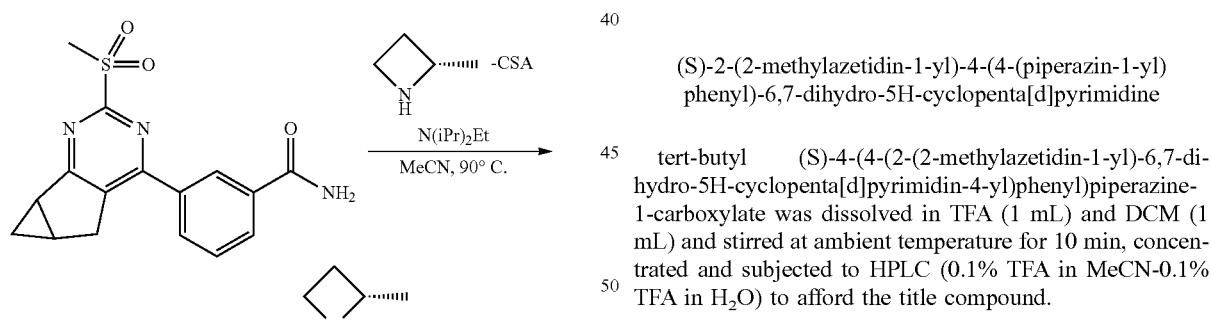

(S)-2-(2-methylazetidin-1-yl)-4-(4-(piperazin-1-yl)phenyl)-6,7-dihydro-5H-cyclopenta[d]pyrimidine tert-butyl (S)-4-(4-(2-(2-methylazetidin-1-yl)-6,7-dihydro-5H-cyclopenta[d]pyrimidin-4-yl)phenyl)piperazine-1-carboxylate was dissolved in TFA (1 mL) and DCM (1 mL) and stirred at ambient temperature for 10 min, concentrated and subjected to HPLC (0.1% TFA in MeCN-0.1% TFA in H₂O) to afford the title compound.

General Method J

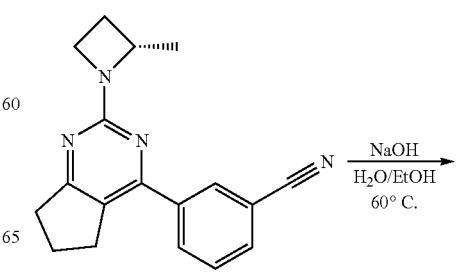

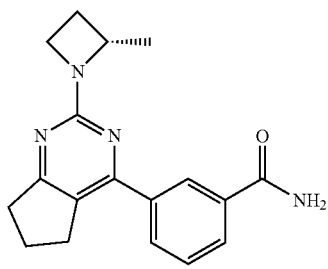

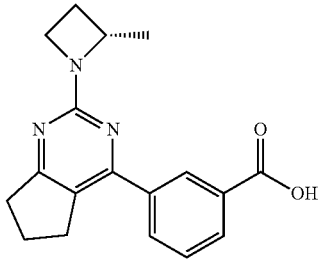

(S)-3-(2-(2-methylazetidin-1-yl)-6,7-dihydro-5H-cyclopenta[d]pyrimidin-4-yl)benzamide A vial was charged with (S)-3-(2-(2-methylazetidin-1-yl)-6,7-dihydro-5H-cyclopenta[d]pyrimidin-4-yl)benzonitrile (30 mg, 0.10 mmol, 1.0 equiv.), EtOH (1 mL), and NaOH (2M aq., 0.5 mL) and heated to 90° C. for 1 hr. The reaction mixture was concentrated and subjected to HPLC (0.1% TFA in MeCN-0.1% TFA in H₂O) to give (S)-3-(2-(2-methylazetidin-1-yl)-6,7-dihydro-5H-cyclopenta[d]pyrimidin-4-yl)benzamide and (S)-3-(2-(2-methylazetidin-1-yl)-6,7-dihydro-5H-cyclopenta[d]pyrimidin-4-yl)benzoic acid.

General Method K

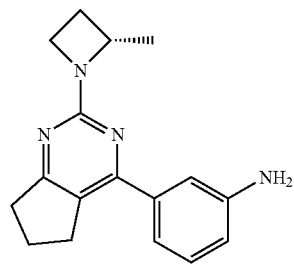

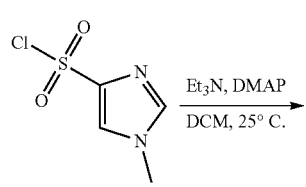

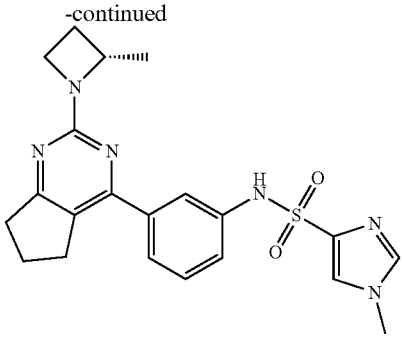

(S)-1-methyl-N-(3-(2-(2-methylazetidin-1-yl)-6,7-dihydro-5H-cyclopenta[d]pyrimidin-4-yl)phenyl)-1H-imidazole-4-sulfonamide A vial was charged with (S)-3-(2-(2-methylazetidin-1-yl)-6,7-dihydro-5H-cyclopenta[d]pyrimidin-4-yl)aniline (15 mg, 0.054 mmol, 1.0 equiv.), 4-dimethylaminopyridine (1 mg, 0.0054 mmol, 10 mol %), Et₃N (0.022 mL, 0.16 mmol, 3.0 equiv.), and DCM (1 mL). 1-methylimidazole-4-sulfonyl chloride (15 mg, 0.080 mmol, 1.5 equiv.) was then added at ambient temperature, and the mixture was allowed to stir for 4 hours. The mixture was concentrated and subjected to HPLC (0.1% TFA in MeCN-0.1% TFA in H₂O) to give the title compound.

General Method L

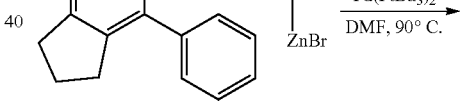

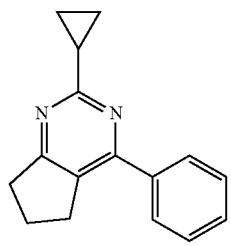

2-cyclopropyl-4-phenyl-6,7-dihydro-5H-cyclopenta[d]pyrimidine

A vial was charged with 2-chloro-4-phenyl-6,7-dihydro-5H-cyclopenta[d]pyrimidine (40 mg, 0.17 mmol, 1.0 equiv.), Pd(PtBu₃)₂ (8.9 mg, 0.017 mmol, 10 mol %), and DMF (3 mL). The vial was sparged with argon, after which cyclopropylzinc bromide (0.5 M in THF, 1.04 mL, 0.52 mmol, 3.0 equiv.) was added. The mixture was heated to 90° C. for 30 min, before being cooled to ambient temperature. NH₄Cl (5 mL, sat. aq) was added, and extracted with EtOAc (3×5 mL). The combine organic layers were dried over Na₂SO₄, filtered, and concentrated. The resulting residue was subject to flash column chromatography (hexanes-ethyl acetate) followed by HPLC (0.1% TFA in MeCN-0.1% TFA in H₂O) to give the title compound.

General Method M

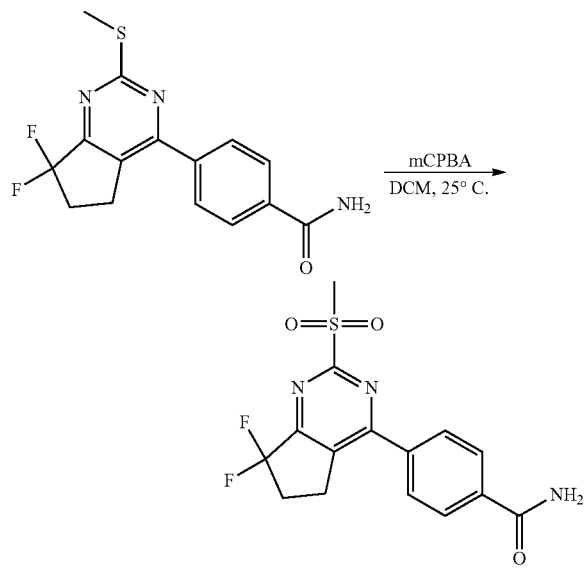

4-(7,7-difluoro-2-(methylsulfonyl)-6,7-dihydro-5H-cyclopenta[d]pyrimidin-4-yl)benzamide 4-(7,7-difluoro-2-(methylthio)-6,7-dihydro-5H-cyclopenta[d]pyrimidin-4-yl)benzamide was prepared in a method analogous to General Method A using 4-chloro-7,7-difluoro-2-(methylthio)-6,7-dihydro-5H-cyclopenta[d]pyrimidine and (4-carbamoylphenyl)boronic acid instead of 2,4-dichloro-6,7-dihydro-5H-cyclopenta[d]pyrimidine and 3-pyridylboronic acid, respectively.

To a vial containing 4-(7,7-difluoro-2-(methylthio)-6,7-dihydro-5H-cyclopenta[d]pyrimidin-4-yl)benzamide (136 mg, 0.42 mmol, 1.0 equiv.), was added 3-chloroperoxybenzoic acid (77% purity, 285 mg, 1.27 mmol, 3.0 equiv.) followed by DCM (2 mL). The mixture was stirred at ambient temperature for 2 hrs. NaHCO₃ (sat. aq., 2 mL) was added, and the mixture was extracted with DCM (3×2 mL). The combined organic extracts were dried over Na₂SO₄, filtered, and concentrated to give the title compound.

General Method N

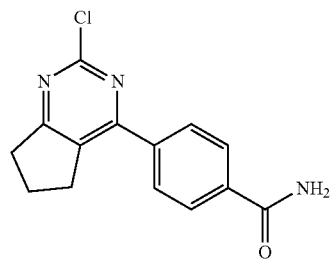

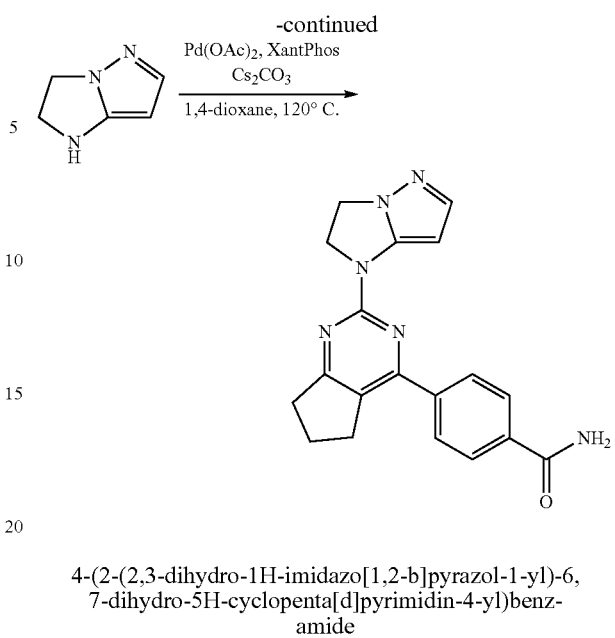

4-(2-(2,3-dihydro-1H-imidazo[1,2-b]pyrazol-1-yl)-6,7-dihydro-5H-cyclopenta[d]pyrimidin-4-yl)benzamide A vial was charged with 4-(2-chloro-6,7-dihydro-5H-cyclopenta[d]pyrimidin-4-yl)benzamide (50 mg, 0.18 mmol, 1.0 equiv.), 2,3-dihydro-1H-imidazo[1,2-b]pyrazole (50 mg, 0.46 mmol, 2.5 equiv.), Pd(OAc)₂ (4.1 mg, 0.018 mmol, 10 mol %), XantPhos (16 mg, 0.027 mmol, 15 mol %), and Cs₂CO₃ (238 mg, 0.73 mmol, 4.0 equiv.). 1,4-Dioxane (2.0 mL) was added, and the mixture was sparged with nitrogen for 2 min. The mixture was heated to 120° C. for 18 hrs, cooled to ambient temperature, and filtered over Celite®, washing with DCM. The mixture was concentrated and the residue subjected to HPLC (0.1% TFA in MeCN-0.1% TFA in H₂O) to give the title compound.

General Method O

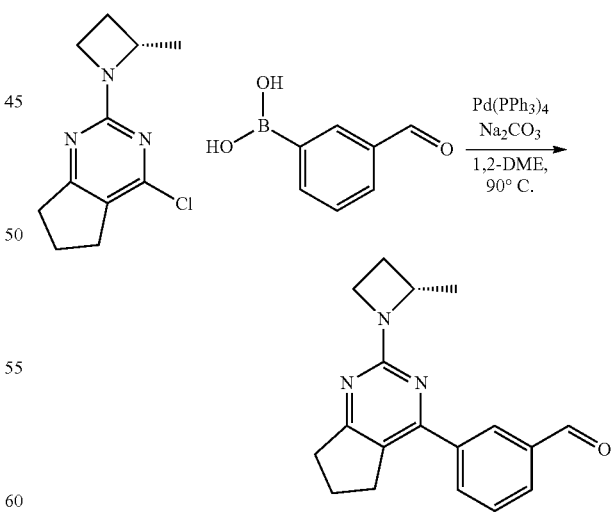

3-[2-[(2S)-2-methylazetidin-1-yl]-6,7-dihydro-5H-cyclopenta[d]pyrimidin-4-yl]benzaldehyde The title compound was prepared in a method analogous to General Method A using (3-formylphenyl)boronic acid and 4-chloro-2-[(2S)-2-methylazetidin-1-yl]-6,7-dihydro-5H-cyclopenta[d]pyrimidine instead of 3-pyridylboronic acid and 2,4-dichloro-6,7-dihydro-5H-cyclopenta[d]pyrimidine, respectively.

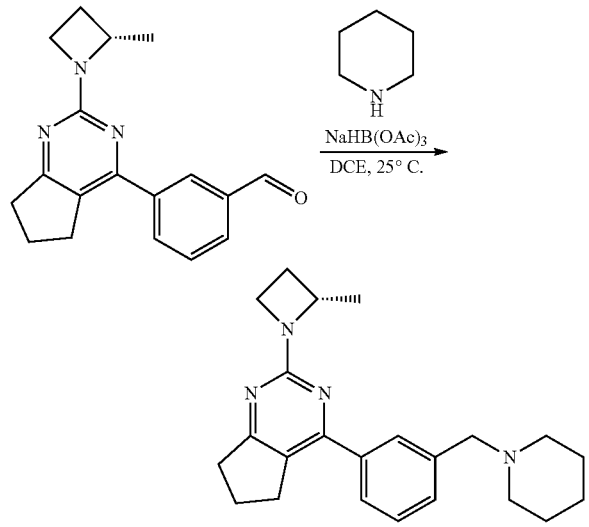

2-[(2S)-2-methylazetidin-1-yl]-4-[3-(1-piperidylmethyl)phenyl]-6,7-dihydro-5H-cyclopenta[d]pyrimidine To a solution of 3-[2-[(2S)-2-methylazetidin-1-yl]-6,7-dihydro-5H-cyclopenta[d]pyrimidin-4-yl]benzaldehyde (40 mg, 0.14 mmol) and piperidine (0.04 mL, 0.4 mmol) in 1,2-dichloroethane (0.5 mL) was added sodium triacetoxyborohydride (58 mg, 0.27 mmol), and the reaction mixture was allowed to stir for 18 hr at ambient temperature. NaHCO₃ (1 mL, sat. aq.) was added, and the mixture was extracted with DCM (3×1 mL). The combined organics were dried over Na₂SO₄, filtered, and concentrated. The residue was subjected to HPLC (0.1% TFA in MeCN-0.1% TFA in H₂O) to give the title compound General Method P

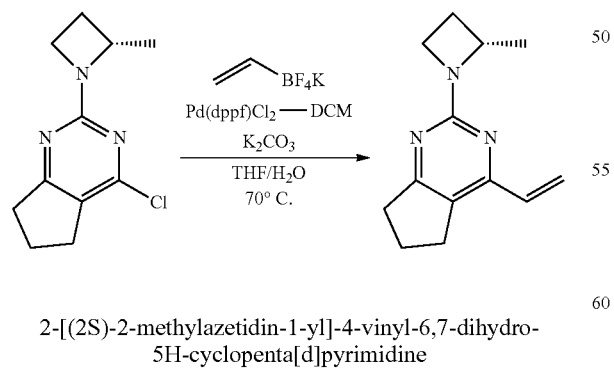

2-[(2S)-2-methylazetidin-1-yl]-4-vinyl-6,7-dihydro-5H-cyclopenta[d]pyrimidine

To a solution of 4-chloro-2-[(2S)-2-methylazetidin-1-yl]-6,7-dihydro-5H-cyclopenta[c]pyrimidine (200 mg, 0.89 mmol) in THF (5 mL) and water (1 mL) was added potassium trifluoro(vinyl)boranuide (144 mg, 1.1 mmol), potassium carbonate (272 mg, 1.97 mmol), and [1,1'-Bis(diphenylphosphino)ferrocene]dichloropalladium(II) (66 mg, 0.089 mmol), and the reaction mixture was degassed with nitrogen, sealed, and heated to 70° C. for 16 hours. It was cooled to ambient temperature, diluted with ethyl acetate, and washed with water and saturated sodium chloride. It was dried over anhydrous sodium sulfate, filtered, and concentrated. The residue was subject to flash column chromatography (ethyl acetate-hexanes) to yield the title compound.

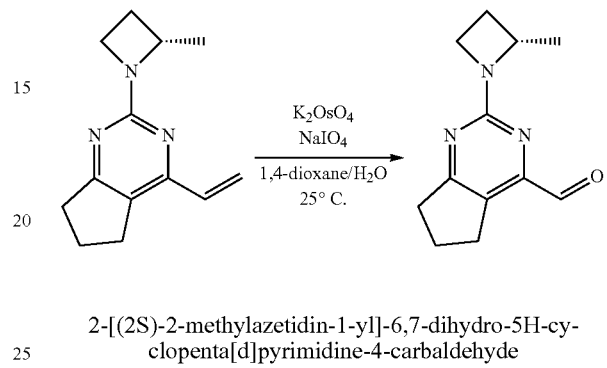

2-[(2S)-2-methylazetidin-1-yl]-6,7-dihydro-5H-cyclopenta[d]pyrimidine-4-carbaldehyde To a solution of 2-[(2S)-2-methylazetidin-1-yl]-4-vinyl-6,7-dihydro-5H-cyclopenta[d]pyrimidine (415 mg, 1.93 mmol) in dioxane (22 mL) and water (22 mL) was added potassium osmate (VI) dihydrate (28 mg, 0.077 mmol) and sodium periodate (1.24 g, 5.8 mmol), and the reaction mixture was allowed to stir at ambient temperature for 16 hours. It was filtered, diluted with EtOAc, and washed with water, saturated sodium thiosulfate, saturated sodium bicarbonate, and saturated sodium chloride. It was dried over anhydrous sodium sulfate, filtered, and concentrated. The residue was subject to flash column chromatography (ethyl acetate-hexanes) to yield the title compound.

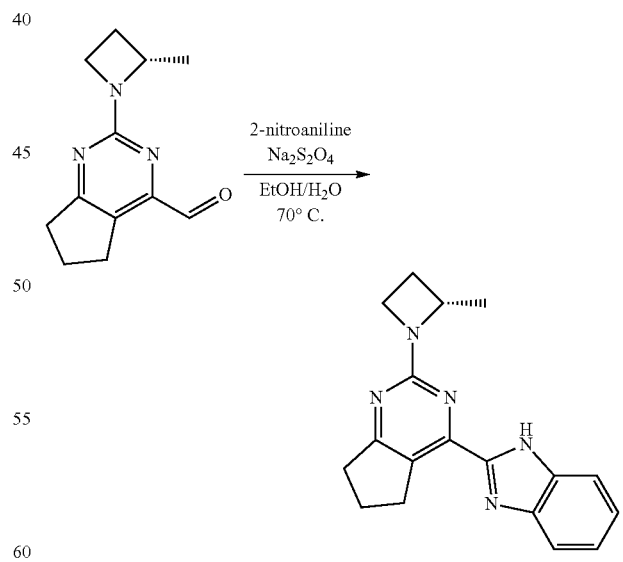

2-[2-[(2S)-2-methylazetidin-1-yl]-6,7-dihydro-5H-cyclopenta[d]pyrimidin-4-yl]-1H-benzimidazole To a solution of 2-[(2S)-2-methylazetidin-1-yl]-6,7-dihydro-5H-cyclopenta[d]pyrimidine-4-carbaldehyde (22 mg, 0.10 mmol) in ethanol (0.4 mL) was added 2-nitroaniline (14 mg, 0.10 mmol) and 1M aqueous sodium dithionite (0.3 mL, 0.3 mmol), and the reaction mixture was heated to 70° C. for 16 hours. It was cooled to ambient temperature, treated with 5N ammonium hydroxide, and the resulting solids were collected via filtration. The residue was subject to flash column chromatography (ethyl acetate-hexanes) to yield the title compound.

General Method Q

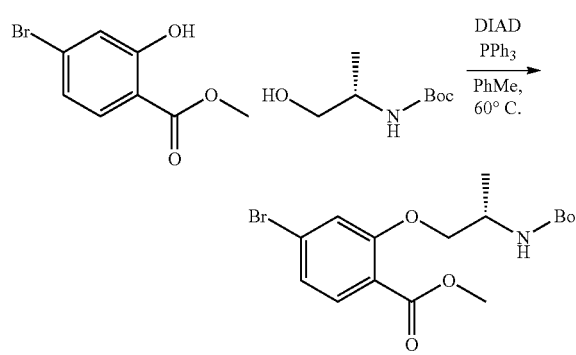

methyl (S)-4-bromo-2-(2-((tert-butoxycarbonyl)amino)propoxy)benzoate

A vial was charged with methyl 4-bromo-2-hydroxybenzoate (400 mg, 1.73 mmol), tert-butyl (S)-(1-hydroxypropan-2-yl)carbamate (303 mg, 1.73 mmol), and PhMe (4 mL). Diisopropyl azodicarboxylate (0.37 mL, 1.90 mmol) was added dropwise, followed by PPh$_3$ (499 mg, 1.90 mmoL). The mixture was heated to 90° C. for 2 hr. The mixture was concentrated and the residue subject to flash column chromatography (ethyl acetate-hexanes) to give methyl (R)-4-bromo-2-(2-((tert-butoxycarbonyl)amino)propoxy)benzoate.

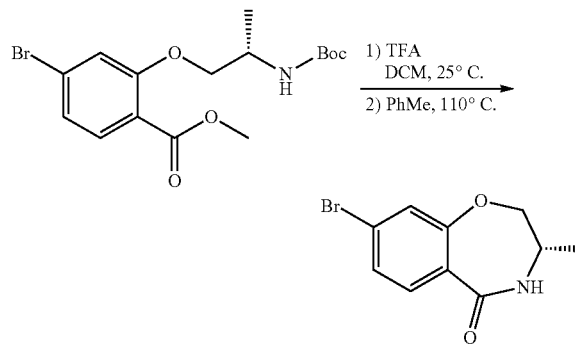

(S)-8-bromo-3-methyl-3,4-dihydrobenzo[f][1,4]oxazepin-5(2H)-one

A vial was charged with methyl (S)-4-bromo-2-(2-((tert-butoxycarbonyl)amino)propoxy)benzoate (672 mg, 1.73 mmol), TFA (2 mL), and DCM (2 mL). The mixture was stirred for 30 min at ambient temperature, before being concentrated under vacuum. The residue was dissolved in EtOAc, and washed with NaHCO$_3$ (sat, aq.). The organic layer was dried over Na$_2$SO$_4$, filtered, and concentrated. The resulting residue was dissolved in PhMe (4 mL) and heated to 110° C. for 18 hr. The mixture was concentrated and the residue subject to flash column chromatography (ethyl acetate-hexanes) to give (S)-8-bromo-3-methyl-3,4-dihydrobenzo[f][1,4]oxazepin-5(2H)-one.

General Method R

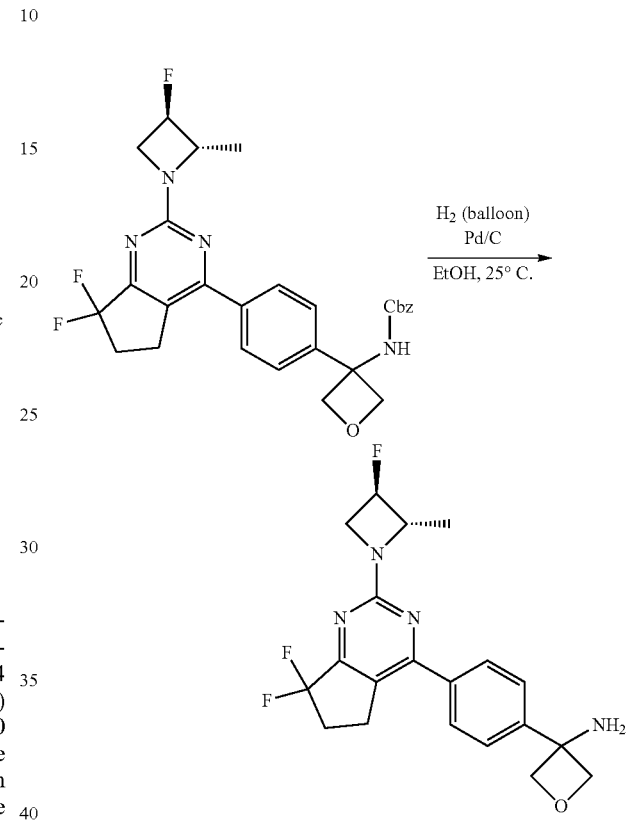

3-(4-(7,7-difluoro-24(2S,3R)-3-fluoro-2-methylazetidin-1-yl)-6,7-dihydro-5H-cyclopenta[d]pyrimidin-4-yl)phenyl)oxetan-3-amine A vial was charged with benzyl (3-(4-(7,7-difluoro-2-((2S,3R)-3-fluoro-2-methylazetidin-1-yl)-6,7-dihydro-5H-cyclopenta[d]pyrimidin-4-yl)phenyl)oxetan-3-yl)carbamate (100 mg, 0.19 mmol) and EtOH (3 mL). The vial was purged with nitrogen, and Pd/C (5% weight, 41 mg, 0.019, 10 mol %) was added. A balloon of H$_2$ gas was sparged through the solution with stirring for 2 hours. The mixture was filtered over Celite®, concentrated, and subject to reverse phase HPLC (0.1% TFA in MeCN-0.1% TFA in H$_2$O) to give the title compound.

General Method S

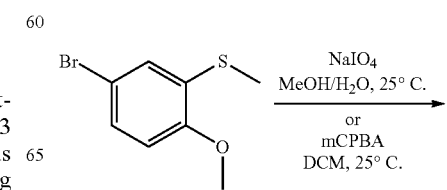

General Method T

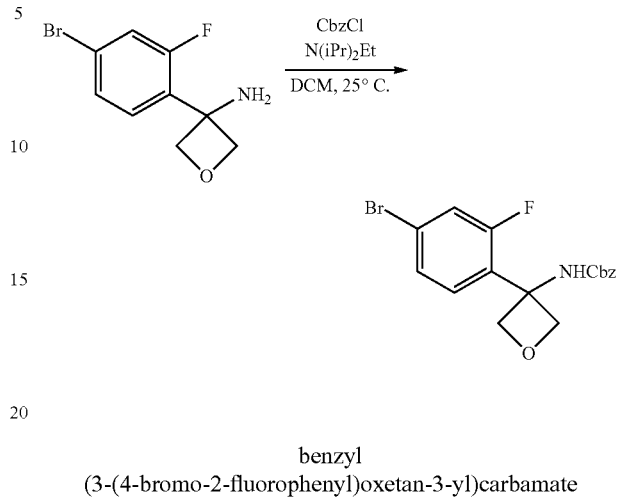

benzyl (3-(4-bromo-2-fluorophenyl)oxetan-3-yl)carbamate

A flask was charged with 3-(4-bromo-2-fluoro-phenyl)oxetan-3-amine hydrochloride (300 mg, 1.06 mmol) and DCM (5 mL), followed by N(iPr)$_2$Et (0.46 mL, 343 mg, 2.65 mmol). CbzCl (0.18 mL, 217 mg, 1.27 mmol) was added dropwise over 5 min. The mixture was allowed to stir for 4 hr at ambient temperature, before being concentrated and subject to flash column chromatography (hexanes-ethyl acetate) to provide the title compound.

General Method U

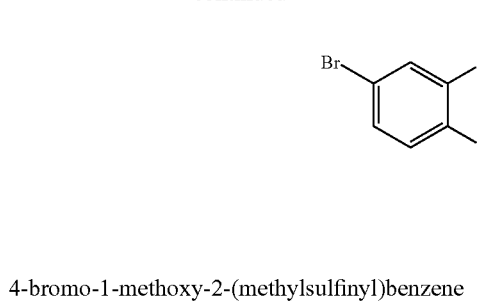

4-bromo-1-methoxy-2-(methylsulfinyl)benzene

A suspension of (5-bromo-2-methoxyphenyl)(methyl)sulfane (4.00 g, 17.2 mmol) and sodium periodate (3.97 g, 18.6 mmol) in methanol (37 mL) and water (37 mL, 0.5 M with sodium periodate) was allowed to stir overnight at ambient temperature. The mixture was filtered and the solid washed with additional methanol. The filtrate was partitioned with dichloromethane and water and the layers separated. The aqueous layer was extracted three more times with dichloromethane and the organics combined, dried over magnesium sulfate, filtered and concentrated to give the title compound.

Alternatively, the starting material was dissolved in DCM (0.3 M), and mCBPA (1.5 equiv.) was added. The mixture was allowed to stir for 30 min. K$_2$CO$_3$ (2M aq) was added and the mixture was extracted with DCM. The combined organics were dried over Na$_2$SO$_4$, filtered, and concentrated. The residue was subject to flash column chromatography (hexanes-ethyl acetate) to give the desired product.

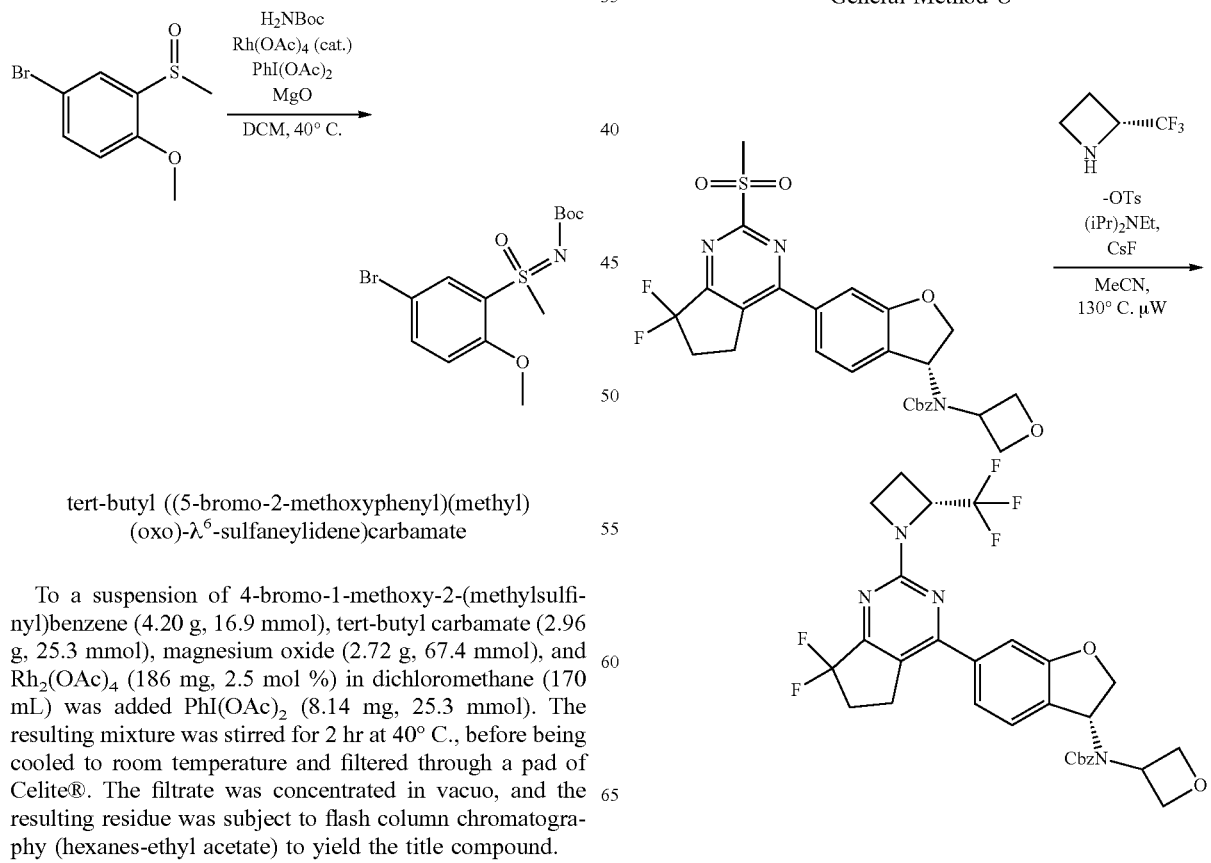

tert-butyl ((5-bromo-2-methoxyphenyl)(methyl)(oxo)-$\lambda^6$-sulfaneylidene)carbamate To a suspension of 4-bromo-1-methoxy-2-(methylsulfinyl)benzene (4.20 g, 16.9 mmol), tert-butyl carbamate (2.96 g, 25.3 mmol), magnesium oxide (2.72 g, 67.4 mmol), and Rh$_2$(OAc)$_4$ (186 mg, 2.5 mol %) in dichloromethane (170 mL) was added PhI(OAc)$_2$ (8.14 mg, 25.3 mmol). The resulting mixture was stirred for 2 hr at 40° C., before being cooled to room temperature and filtered through a pad of Celite®. The filtrate was concentrated in vacuo, and the resulting residue was subject to flash column chromatography (hexanes-ethyl acetate) to yield the title compound.

benzyl ((R)-6-(7,7-difluoro-2-((R)-2-(trifluoromethyl)azetidin-1-yl)-6,7-dihydro-5H-cyclopenta[d]pyrimidin-4-yl)-2,3-dihydrobenzofuran-3-yl)(oxetan-3-yl)carbamate A microwave reaction tube was charged with benzyl (R)-(6-(7,7-difluoro-2-(methylsulfonyl)-6,7-dihydro-5H-cyclopenta[d]pyrimidin-4-yl)-2,3-dihydrobenzofuran-3-yl)(oxetan-3-yl)carbamate (150 mg, 0.269 mmol), (2R)-2-(trifluoromethyl)azetidine (160 mg, 0.538 mmol), and CsF (81.7 mg, 0.538 mmol). CH$_3$CN (3 mL) and (iPr)$_2$EtN (139 mg, 1.08 mmol) were added to the tube and the reaction mixture was heated to 130° C. for 8 hours in a CEM microwave reactor. The mixture was cooled to ambient temperature and diluted with sat. aq. NaHCO$_3$ (10 mL). The aqueous layer was extracted with DCM (3×10 mL). The organics were combined, dried over Na$_2$SO$_4$, filtered, and concentrated. The residue was subject to flash column chromatography (hexanes-ethyl acetate) to give the title compound.

General Method V

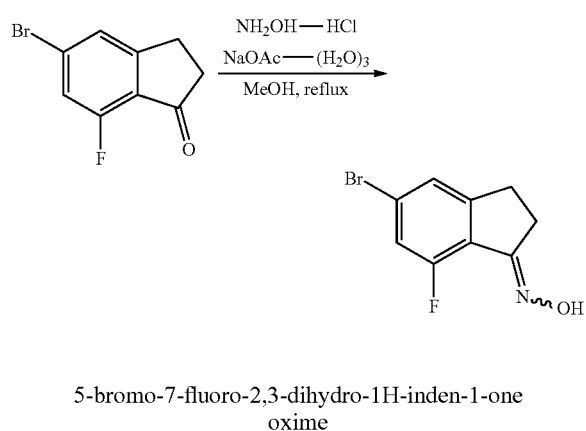

5-bromo-7-fluoro-2,3-dihydro-1H-inden-1-one oxime

A flask was charged with 5-bromo-7-fluoro-2,3-dihydro-1H-inden-1-one (1.00 g, 4.37 mmol), NaOAc—(H$_2$O)$_3$ (2.97 g, 21.8 mmol), and MeOH (20 mL). Hydroxylamine hydrochloride (1.52 g, 21.8 mmol) was added, and the mixture was equipped with a reflux condenser and heated to reflux for 1 hr. The mixture was concentrated and H$_2$O (20 mL) was added. The mixture was extracted with EtOAc (3×20 mL). The combined organics were dried over Na$_2$SO$_4$, filtered and concentrated to provide the title product.

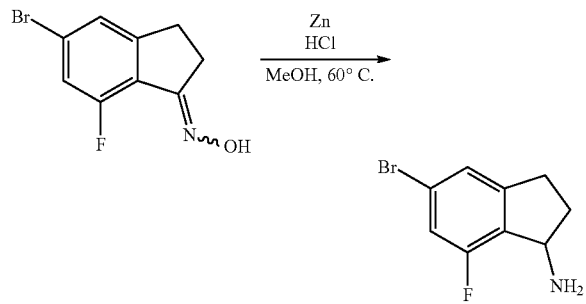

5-bromo-7-fluoro-2,3-dihydro-1H-inden-1-amine

To 5-bromo-7-fluoro-2,3-dihydro-1H-inden-1-one oxime (1.07 g, 4.37 mmol) in MeOH (10 mL), was added Zn dust (1.43 g, 21.8 mmol) and HCl (aq, 6M, 8.7 mL). The mixture was heated to 60° C. for 1 hr. Upon cooling to ambient temperature, KOH (aq, 2M) was added to adjust the pH to 12. The resulting solids were filtered off and dried under vacuum, to give the title product.

General Method W

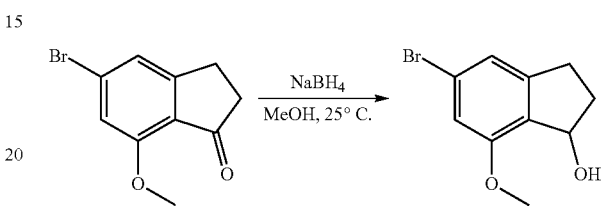

5-bromo-7-methoxy-2,3-dihydro-1H-inden-1-ol

To 5-bromo-7-methoxy-2,3-dihydro-1H-inden-1-one (498 mg, 2.07 mmol) in MeOH (10 mL), was added NaBH$_4$ (156 mg, 4.13 mmol). The mixture was stirred for 18 hours at ambient temperature, was concentrated, and subject to flash column chromatography (hexanes-ethyl acetate) to give the title compound.

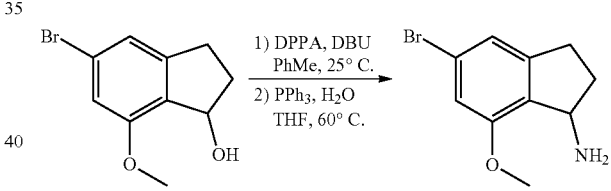

5-bromo-7-methoxy-2,3-dihydro-1H-inden-1-amine

To 5-bromo-7-methoxy-2,3-dihydro-1H-inden-1-ol (332 mg, 1.37 mmol) in PhMe (6 mL), was added diphenylphosphoryl azide (0.35 mL, 451 mg, 1.64 mmol) and DBU (0.31 mL, 312 mg, 2.05 mmol) dropwise over 5 min. The mixture was stirred overnight at ambient temperature. H$_2$O (10 mL) was added, and the mixture was extracted with EtOAc (3×10 mL). The combined organics were dried over Na$_2$SO$_4$, filtered and concentrated. The residue was dissolved in THF (10 mL) and PPh$_3$ (430 mg, 1.64 mmol) was added. The mixture was stirred for 30 minutes at ambient temperature. H$_2$O (1 mL) was added, and the mixture was heated to 50° C. for 4 hrs. Upon cooling to ambient temperature H$_2$O (10 mL) was added and the mixture was extracted with EtOAc (3×10 mL). The combined organics were dried over Na$_2$SO$_4$, filtered, concentrated, and subject to flash column chromatography (hexanes-ethyl acetate) to give the title compound.

General Method X

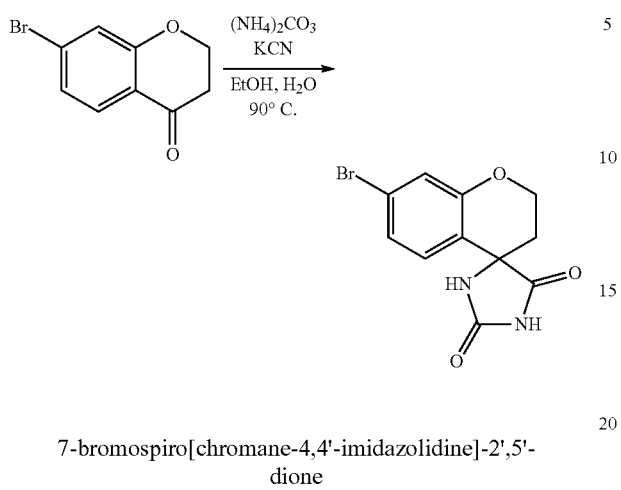

7-bromospiro[chromane-4,4'-imidazolidine]-2',5'-dione

A flask was charged with 7-bromochroman-4-one (2.00 g, 8.81 mmol), ammonium carbonate (1.69 g, 17.6 mmol), KCN (860 mg, 13.2 mmol), EtOH (10 mL), and $H_2O$ (10 mL). The flask was equipped with a reflux condenser and heated to 90° C. for 3 days. The mixture was cooled to ambient temperature and the pH was adjusted to 6 with HCl (aq, 6M). The resulting solids were collected by filtration, washed with $H_2O$, and dried under vacuum to give the title compound.

General Method Y

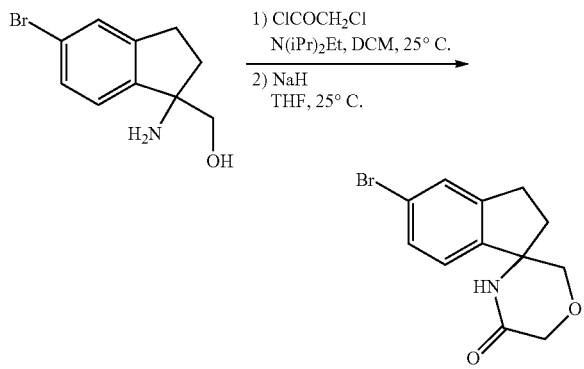

5-bromo-2,3-dihydrospiro[indene-1,3'-morpholin]-5'-one

A vial was charged with (1-amino-5-bromo-2,3-dihydro-1H-inden-1-yl)methanol (300 mg, 1.24 mmol) and DCM (12 mL), followed by $N(iPr)_2Et$ (0.86 mL, 641 mg, 4.96 mmol) and chloroacetyl chloride (0.12 mL, 168 mg, 1.49 mmol). The mixture was allowed to stir at ambient temperature for 2 hr. $H_2O$ (10 mL) was added, and the mixture was extracted with DCM (3×10 mL). The combined organics were dried over $Na_2SO_4$, filtered, and concentrated. The residue was subject to flash column chromatography (hexanes-ethyl acetate) to give N-(5-bromo-1-(hydroxymethyl)-2,3-dihydro-1H-inden-1-yl)-2-chloroacetamide.

To a solution of N-(5-bromo-1-(hydroxymethyl)-2,3-dihydro-1H-inden-1-yl)-2-chloroacetamide (278 mg, 0.87 mmol) in THF (8 mL) was added NaH (60% dispersion in mineral oil, 84 mg, 2.18 mmol). The mixture was allowed to stir for 15 min at ambient temperature. $H_2O$ (10 mL) was added, and the mixture was extracted with EtOAc (3×10 mL). The combined organics were dried over $Na_2SO_4$, filtered, and concentrated. The residue was subject to flash column chromatography (hexanes-ethyl acetate) to give the title compound.

General Method Z

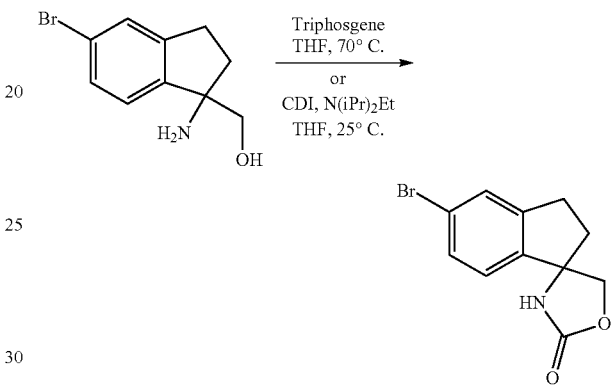

5-bromo-2,3-dihydrospiro[indene-1,4'-oxazolidin]-2'-one

A vial was charged with (1-amino-5-bromo-2,3-dihydro-1H-inden-1-yl)methanol (500 mg, 2.07 mmol) and THF (15 mL). Triphosgene (613 mg, 2.07 mmol) was added slowly. The resulting mixture was heated to 70° C. for 2 hrs. The mixture was allowed to cool to ambient temperature. $NaHCO_3$ (15 mL, sat. aq.) was added and the mixture was extracted with EtOAc (3×10 mL). The combined organic layers were dried over $Na_2SO_4$, filtered, and concentrated. The residue was subject to flash column chromatography (hexane-ethyl acetate) to give the title compound Alternatively, 1,1'-carbonyldiimidazole and $N(iPr)_2Et$ was used instead of triphosgene without heating.

General Method AA

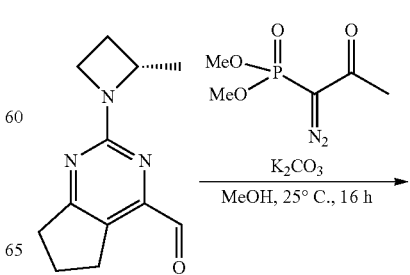

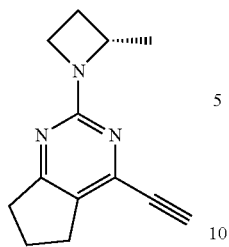

4-ethynyl-2-[(2S)-2-methylazetidin-1-yl]-6,7-di-hydro-5H-cyclopenta[d]pyrimidine A vial was charged with 2-[(2S)-2-methylazetidin-1-yl]-6,7-dihydro-5H-cyclopenta[d]pyrimidine-4-carbaldehyde (310 mg, 1.43 mmol) and methanol (12 mL). To this, potassium carbonate (197 mg, 1.43 mmol) and 1-diazo-1-dimethoxyphosphoryl-propan-2-one (0.278 mL, 1.85 mmol) were added, and the reaction mixture was stirred at ambient temperature for 16 hours. It was diluted with ethyl acetate and washed with saturated sodium bicarbonate and saturated sodium chloride. It was dried over anhydrous sodium sulfate, filtered, and concentrated. It was purified via flash chromatography (hexanes-ethyl acetate) to yield the title compound.

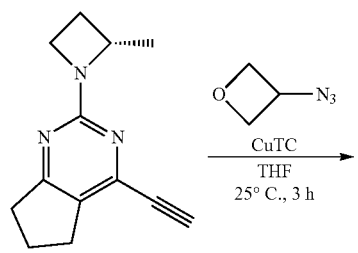

2-[(2S)-2-methylazetidin-1-yl]-4-[1-(oxetan-3-yl)triazol-4-yl]-6,7-dihydro-5H-cyclopenta[d]pyrimidine To a solution of 4-ethynyl-2-[(2S)-2-methylazetidin-1-yl]-6,7-dihydro-5H-cyclopenta[d]pyrimidine (30 mg, 0.14 mmol) and 3-azidooxetane (14 mg, 0.14 mmol) in tetrahydrofuran (0.7 mL) was added copper(I) thiophene-2-carboxylate (3 mg, 0.014 mmol), and the reaction mixture was stirred at ambient temperature for 3 hours. It was concentrated and purified via flash chromatography (hexanes-ethyl acetate) to yield the title compound.

General Method AB

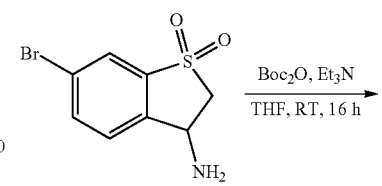

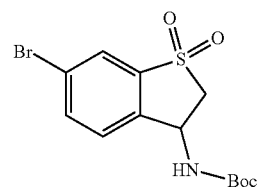

tert-butyl N-(6-bromo-1,1-dioxo-2,3-dihydrobenzothiophen-3-yl)carbamate

To a solution of 6-bromo-1,1-dioxo-2,3-dihydrobenzothiophen-3-amine (400 mg, 1.5 mmol) in tetrahydrofuran (8.3 mL) was added triethylamine (0.425 mL, 3 mmol) and tert-butoxycarbonyl tert-butyl carbonate (400 mg, 1.8 mmol), and the reaction mixture was stirred at ambient temperature for 16 hours. It was diluted with ethyl acetate and washed with 10% potassium bisulfate, saturated sodium bicarbonate, and saturated sodium chloride. It was dried over anhydrous sodium sulfate, filtered, and concentrated. It was purified via flash chromatography (hexanes-ethyl acetate) to yield the title compound.

General Method AC

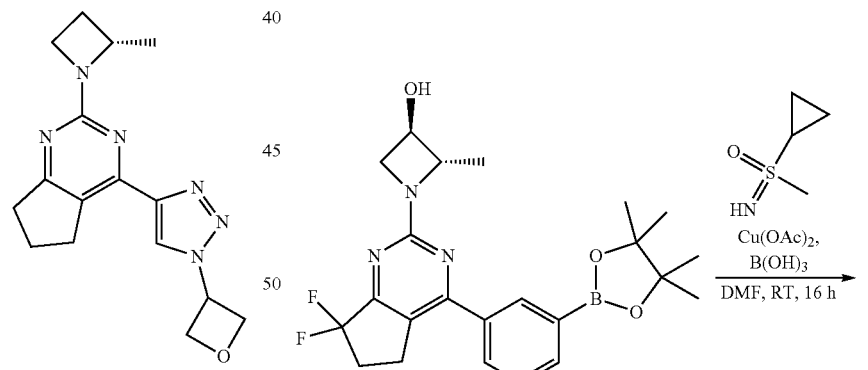

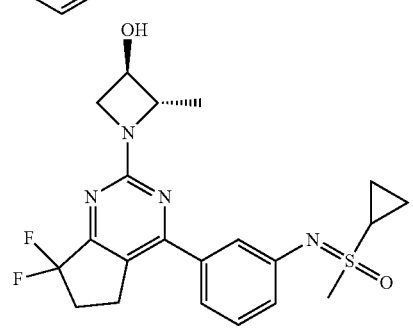

(2S,3R)-1-[4-[3-[(cyclopropyl-methyl-oxo-λ⁶-sulfanylidene)amino]phenyl]-7,7-difluoro-5,6-dihydrocyclopenta[d]pyrimidin-2-yl]-2-methyl-azetidin-3-ol To a solution of (2S,3R)-1-[7,7-difluoro-4-[3-(4,4,5,5-tetramethyl-1,3,2-dioxaborolan-2-yl)phenyl]-5,6-dihydrocyclopenta[d]pyrimidin-2-yl]-2-methyl-azetidin-3-ol (50 mg, 0.11 mmol) in dimethylformamide (1 mL) was added cyclopropyl-imino-methyl-oxo-λ⁶-sulfane (27 mg, 0.23 mmol), boric acid (14 mg, 0.23 mmol), and copper(II) acetate (10 mg, 0.056 mmol) and the reaction was stirred at ambient temperature open to the air for 16 h. It was diluted with ethyl acetate and washed with 10% ammonium hydroxide, saturated sodium bicarbonate, and saturated sodium chloride. It was dried over anhydrous sodium sulfate, filtered, and concentrated. It was purified via flash chromatography (DCM-MeOH) to yield the title compound.

General Method AD

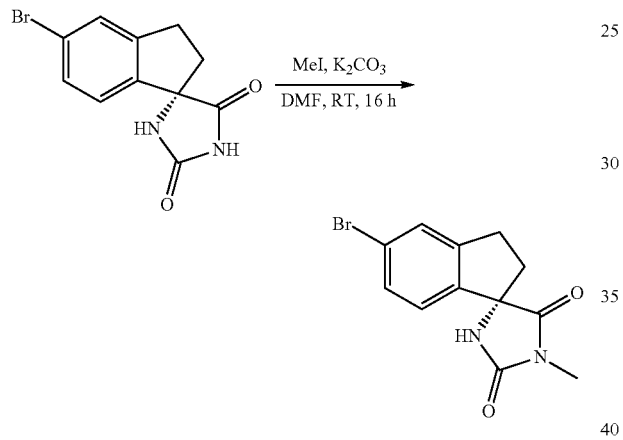

(5S)-5'-bromo-3-methyl-spiro[imidazolidine-5,1'-indane]-2,4-dione

To a suspension of (5S)-5'-bromospiro[imidazolidine-5,1'-indane]-2,4-dione (100 mg, 0.36 mmol) and potassium carbonate (49 mg, 0.36 mmol) was added methyl iodide (0.022 mL, 0.36 mmol), and the reaction mixture was stirred at ambient temperature for 16 hours. It was precipitated by the addition of water, and the solids were collected, washed with water, and dried under vacuum to yield the title compound.

General Method AE

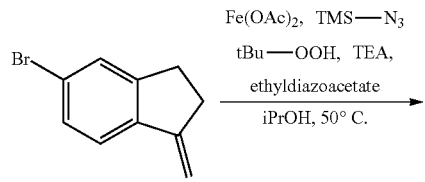

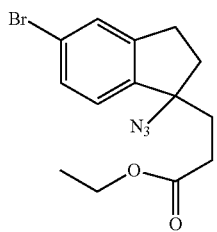

ethyl 3-(1-azido-5-bromo-2,3-dihydro-1H-inden-1-yl)propanoate

To 5-bromo-1-methylene-2,3-dihydro-1H-indene (2500 mg, 12 mmol) in iPrOH (180 mL), was added Fe(OAc)₂ (104 mg, 0.6 mmol), TMS-N₃ (3.2 mL, 24 mmol), ethyldiazoacetate (2.5 mL, 24 mmol), tBu-OOH (4.6 mL, 36 mmol), and TEA (3.3 mL, 24 mmol). The mixture was stirred for 12 hours at 50° C., was concentrated, toluene was added (20 mL) and was re-concentrated, then subjected to flash column chromatography (DCM-MeOH) to give the title compound.

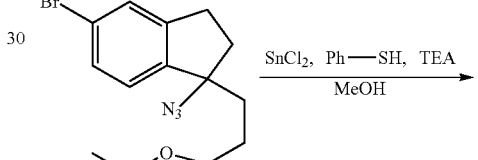

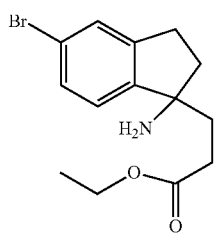

ethyl 3-(1-amino-5-bromo-2,3-dihydro-1H-inden-1-yl)propanoate

To ethyl 3-(1-azido-5-bromo-2,3-dihydro-1H-inden-1-yl)propanoate (1200 mg, 3.55 mmol) in MeOH (60 mL), was added SnCl₂ (1600 mg, 7.1 mmol), thiophenol (1.45 mL, 14.2 mmol), and TEA (2.47 mL, 17.7 mmol). The mixture was stirred for 30 minutes at ambient temperature. Ethyl Acetate was added (100 mL) and the solids were filtered off. The organic layer was washed with aq. NaHCO₃ and brine. The organics were dried over Na₂SO₄, then concentrated and subjected to flash column chromatography (DCM-MeOH) to give the title compound.

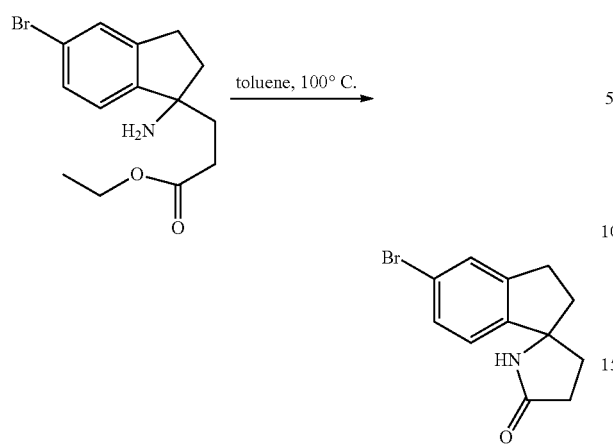

5-bromo-2,3-dihydrospiro[indene-1,2'-pyrrolidin]-5'-one

In toluene (8 mL), ethyl 3-(1-amino-5-bromo-2,3-dihydro-1H-inden-1-yl)propanoate (735 mg, 2.35 mmol) was heated to 100° C. for 12 hours. After cooling to ambient temperature, the solids were filtered off to give the title compound.

General Method AF

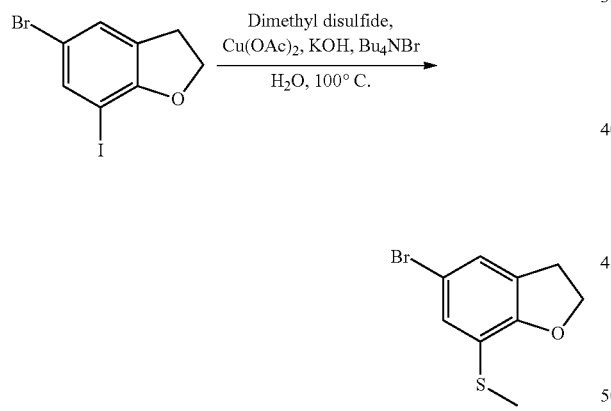

5-bromo-7-(methylthio)-2,3-dihydrobenzofuran

A vial was charged with 5-bromo-7-iodo-2,3-dihydrobenzofuran (885 mg, 2.27 mmol, 1.0 equiv.), dimethyl disulfide (0.29 mL, 3.27 mmol, 1.2 mmol), cupric acetate (49.5 mg, 0.27 mmol, 0.10 equiv.), potassium hydroxide (306 mg, 5.45 mmol, 2.0 equiv.), and tetrabutylammonium bromide (43.9 mg, 0.14 mmol, 0.05 equiv.). The vial was capped and heated to 100° C. for 12 hours. After cooling to room temperature, the mixture was partitioned between water and EtOAc. The aqueous component was extracted twice with EtOAc and the organics were dried over magnesium sulfate, filtered and concentrated to afford the title compound.

General Method AG

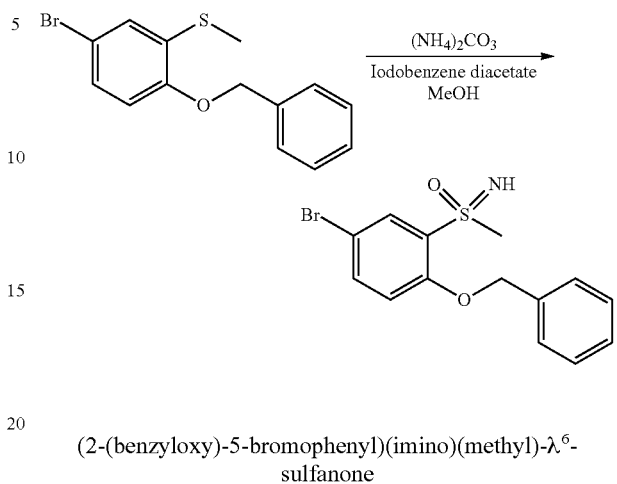

(2-(benzyloxy)-5-bromophenyl)(imino)(methyl)-$\lambda^6$-sulfanone

A vial was charged with (2-(benzyloxy)-5-bromophenyl)(methyl)sulfane (618 mg, 2.00 mmol, 1.0 equiv.) and methanol (15 mL). Ammonium carbonate (288 mg, 3.00 mmol, 1.5 equiv.) was added followed by iodobenzene diacetate (1482 mg, 4.60 mmol, 2.3 equiv.) and the vial was quickly sealed with septa and vigorously stirred at room temperature for 5 hours. After that the solvent was removed under reduced pressure and the residue was purified by silica gel flash column chromatography (0 to 5% MeOH in DCM) to afford the title compound.

General Method AH

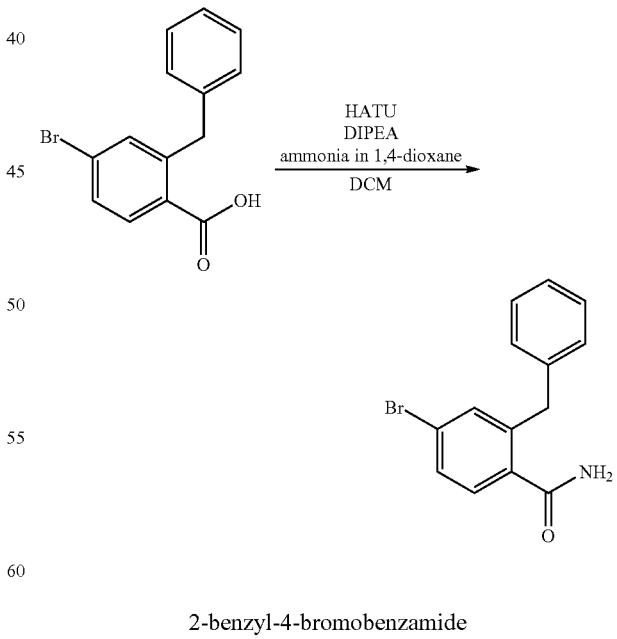

2-benzyl-4-bromobenzamide

A vial was charged with 2-benzyl-4-bromobenzoic acid (200 mg, 0.69 mmol, 1.0 equiv.) and HATU (392 mg, 1.03 mmol, 1.5 equiv.) in DCM (5 mL). DIPEA (120 µL, 0.69 mmol, 1 equiv.) was added and the reaction mixture was vigorously stirred at room temperature for 10 minutes. After that ammonia in 1,4-dioxane (6.87 mL of 0.5 M solution, 5 equiv.) was added and the reaction mixture was stirred at room temperature for 30 minutes. Solids were filtered off (washed with DCM) and the combined solutions were concentrated under reduced pressure, and the residue was purified by flash silica gel column flash chromatography (0-5% MeOH in DCM) to afford the title compound 2-benzyl-4-bromobenzamide.

General Method AI

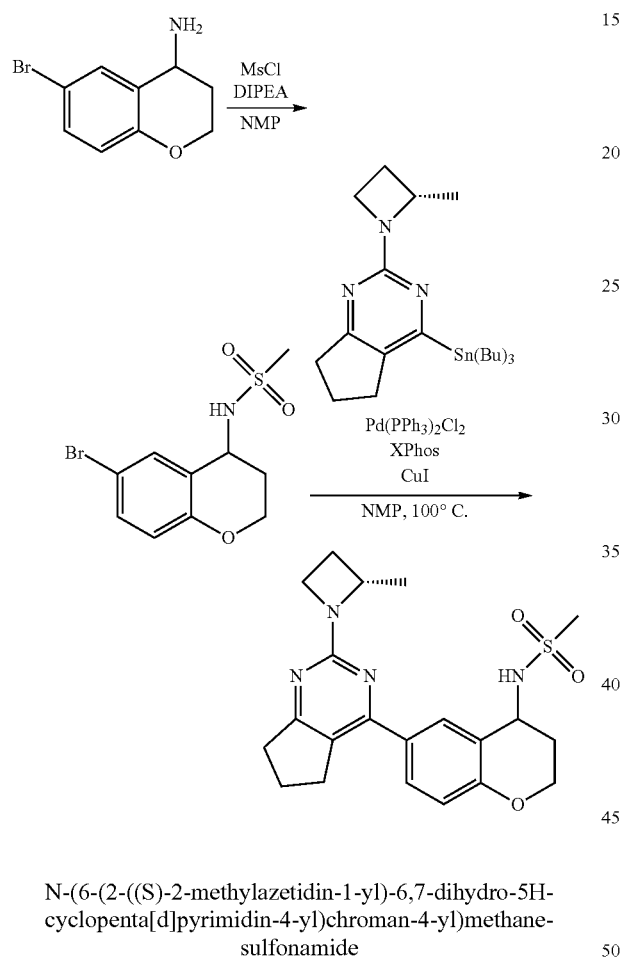

N-(6-(2-((S)-2-methylazetidin-1-yl)-6,7-dihydro-5H-cyclopenta[d]pyrimidin-4-yl)chroman-4-yl)methanesulfonamide A vial was charged with 6-bromochroman-4-amine (50 mg, 0.19 mmol, 0.91 equiv.), DIPEA (146 µL, 0.84 mmol, 4 equiv.) and dry NMP (1 mL) under argon and the reaction mixture was stirred at room temperature for 1 minute. Methanesulfonyl chloride (23 µL, 0.23 mmol, 1.1 equiv.) was then added under argon and the reaction mixture was stirred at room temperature for 20 minutes. After that (S)-2-(2-methylazetidin-1-yl)-4-(tributylstannyl)-6,7-dihydro-5H-cyclopenta[d]pyrimidine (100 mg, 0.21 mmol, 1.0 equiv.), Pd(PPh₃)₂Cl₂ (15 mg, 0.021 mmol, 10 mol %), XPhos (9.4 mg, 0.021 mmol, 10 mol %), CuI (3.9 mg, 0.021 mmol, 10 mol %) were added. The reaction mixture was purged with argon five times and heated under argon to 110° C. for 1 hour. After that the mixture was cooled down to room temperature and was diluted with DMSO (1 mL) and water (0.2 mL), and was acidified with trifluoroacetic acid (16 µL, 0.21 mmol). The solids were filtered off and the solution was purified by preparative reverse phase HPLC (0.1% TFA in MeCN-0.1% TFA in H₂O) to give the title compound.

COMPOUND EXAMPLES

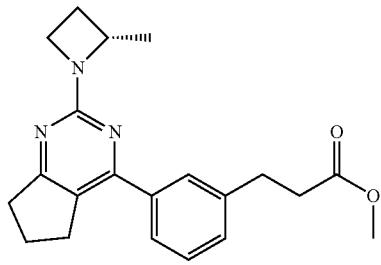 [SMILES: COC(=O)CCc1cccc(-c2nc(N3CC[C@@H]3C)nc3c2CCC3)c1]

Example 1: methyl (S)-3-(3-(2-(2-methylazetidin-1-yl)-6,7-dihydro-5H cyclopenta[d]pyrimidin-4-yl)phenyl)propanoate The title compound was prepared in a method analogous to General Method A using methyl 3-[3-(4,4,5,5-tetramethyl-1,3,2-dioxaborolan-2-yl)phenyl]propanoate instead of 3-pyridylboronic acid followed by General Method B.

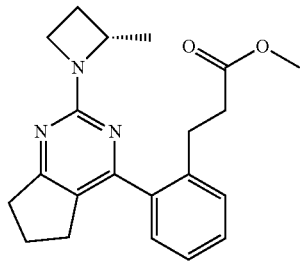 [SMILES: COC(=O)CCc1ccccc1-c1nc(N2CC[C@@H]2C)nc2c1CCC2]

Example 2: methyl (S)-3-(2-(2-(2-methylazetidin-1-yl)-6,7-dihydro-5H-cyclopenta[d]pyrimidin-4-yl)phenyl)propanoate The title compound was prepared in a method analogous to General Method A using methyl 3-[2-(4,4,5,5-tetramethyl-1,3,2-dioxaborolan-2-yl)phenyl]propanoate instead of 3-pyridylboronic acid followed by General Method B.

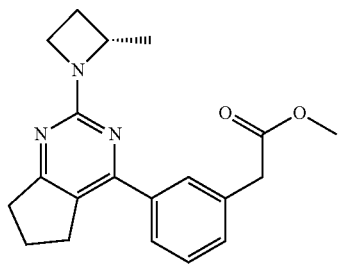 [SMILES: COC(=O)Cc1cccc(-c2nc(N3CC[C@@H]3C)nc3c2CCC3)c1]

Example 3: methyl (S)-2-(3-(2-(2-methylazetidin-1-yl)-6,7-dihydro-5H-cyclopenta[d]pyrimidin-4-yl)phenyl)acetate The title compound was prepared in a method analogous to General Method A using methyl 2-[3-(4,4,5,5-tetramethyl-1,3,2-dioxaborolan-2-yl)phenyl]acetate instead of 3-pyridylboronic acid followed by General Method B.

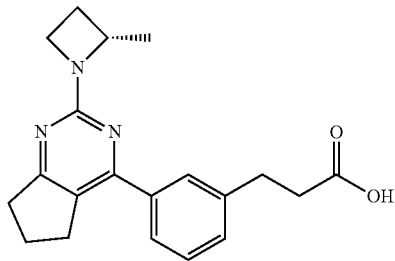 [SMILES: C[C@H]1CCN1c1nc2c(c(-c3cccc(CCC(=O)O)c3)n1)CCC2]

Example 4: (S)-3-(3-(2-(2-methylazetidin-1-yl)-6,7-dihydro-5H-cyclopenta[d]pyrimidin-4-yl)phenyl)propanoic acid The title compound was prepared according to General Method C.

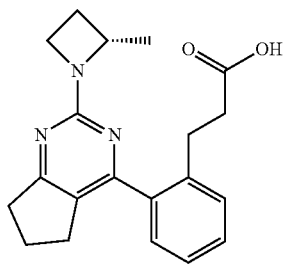 [SMILES: C[C@H]1CCN1c1nc2c(c(-c3ccccc3CCC(=O)O)n1)CCC2]

Example 5: (S)-3-(2-(2-(2-methylazetidin-1-yl)-6,7-dihydro-5H-cyclopenta[d]pyrimidin-4-yl)phenyl)propanoic acid The title compound was prepared in a method analogous to General Method C using methyl (S)-3-(2-(2-(2-methylazetidin-1-yl)-6,7-dihydro-5H-cyclopenta[d]pyrimidin-4-yl)phenyl)propanoate instead of (S)-3-(3-(2-(2-methylazetidin-1-yl)-6,7-dihydro-5H-cyclopenta[d]pyrimidin-4-yl)phenyl)propanoate.

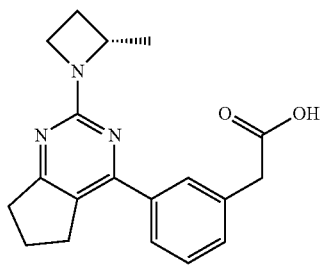 [SMILES: C[C@H]1CCN1c1nc2c(c(-c3cccc(CC(=O)O)c3)n1)CCC2]

Example 6: (S)-2-(3-(2-(2-methylazetidin-1-yl)-6,7-dihydro-5H-cyclopenta[d]pyrimidin-4-yl)phenyl)acetic acid The title compound was prepared in a method analogous to General Method C using methyl (S)-2-(3-(2-(2-methylazetidin-1-yl)-6,7-dihydro-5H-cyclopenta[d]pyrimidin-4-yl)phenyl)acetate instead of (S)-3-(3-(2-(2-methylazetidin-1-yl)-6,7-dihydro-5H-cyclopenta[d]pyrimidin-4-yl)phenyl)propanoate.

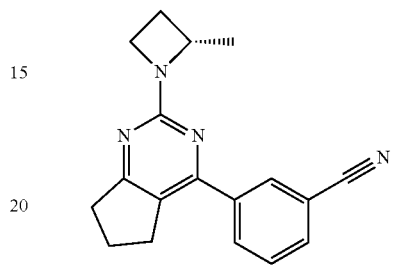

Example 7: (S)-3-(2-(2-methylazetidin-1-yl)-6,7-dihydro-5H-cyclopenta[d]pyrimidin-4-yl)benzonitrile The title compound was prepared in a method analogous to General Method A using (3-cyanophenyl)boronic acid instead of 3-pyridylboronic acid followed by General Method B.

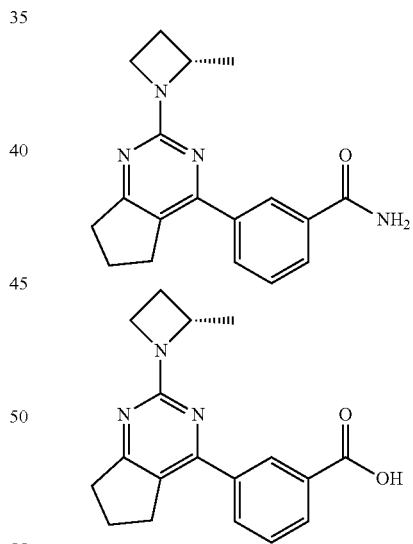

Example 8: (S)-3-(2-(2-methylazetidin-1-yl)-6,7-dihydro-5H-cyclopenta[d]pyrimidin-4-yl)benzamide

Example 9: (S)-3-(2-(2-methylazetidin-1-yl)-6,7-dihydro-5H-cyclopenta[d]pyrimidin-4-yl)benzoic acid The title compounds were prepared according to General Method J.

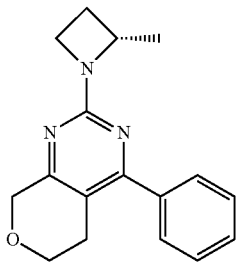 [SMILES: C[C@H]1CCN1c1nc2c(c(-c3ccccc3)n1)CCOC2]

Example 10: (S)-2-(2-methylazetidin-1-yl)-4-phenyl-5,8-dihydro-6H-pyrano[3,4-d]pyrimidine The title compound was prepared in a method analogous to General Method A using phenylboronic acid and 2,4-dichloro-5,8-dihydro-6H-pyrano[3,4-d]pyrimidine instead of 3-pyridylboronic acid and 2,4-dichloro-6,7-dihydro-5H-cyclopenta[d]pyrimidine, respectively, followed by General Method B.

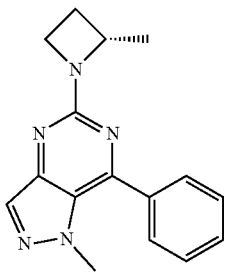 [SMILES: C[C@H]1CCN1c1nc(-c2ccccc2)c2c(cnn2C)n1]

Example 11: (S)-1-methyl-5-(2-methylazetidin-1-yl)-7-phenyl-1H-pyrazolo[4,3-d]pyrimidine The title compound was prepared in a method analogous to General Method A using phenylboronic acid and 5,7-dichloro-1-methyl-1H-pyrazolo[4,3-d]pyrimidine instead of 3-pyridylboronic acid and 2,4-dichloro-6,7-dihydro-5H-cyclopenta[d]pyrimidine, respectively, followed by General Method B.

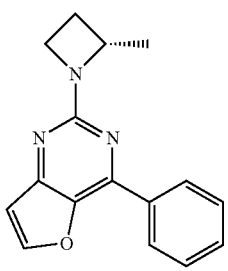 [SMILES: C[C@H]1CCN1c1nc(-c2ccccc2)c2occc2n1]

Example 12: (S)-2-(2-methylazetidin-1-yl)-4-phenylfuro[3,2-d]pyrimidine

The title compound was prepared in a method analogous to General Method A using phenylboronic acid and 2,4-dichlorofuro[3,2-d]pyrimidine instead of 3-pyridylboronic acid and 2,4-dichloro-6,7-dihydro-5H-cyclopenta[d]pyrimidine, respectively, followed by General Method B.

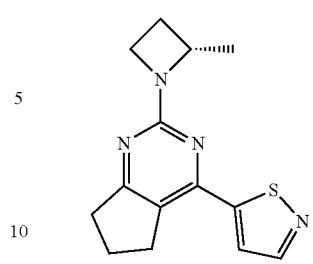

Example 13: (S)-5-(2-(2-methylazetidin-1-yl)-6,7-dihydro-5H-cyclopenta[d]pyrimidin-4-yl)isothiazole The title compound was prepared in a method analogous to General Method A using 5-(4,4,5,5-tetramethyl-1,3,2-dioxaborolan-2-yl)isothiazole instead of 3-pyridylboronic acid followed by General Method B.

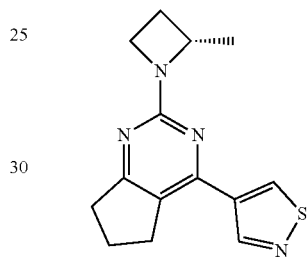

Example 14: (S)-4-(2-(2-methylazetidin-1-yl)-6,7-dihydro-5H-cyclopenta[d]pyrimidin-4-yl)isothiazole The title compound was prepared in a method analogous to General Method A using 4-(4,4,5,5-tetramethyl-1,3,2-dioxaborolan-2-yl)isothiazole instead of 3-pyridylboronic acid followed by General Method B.

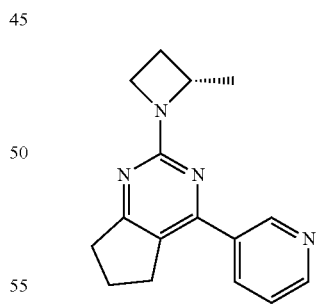

Example 15: (S)-2-(2-methylazetidin-1-yl)-4-(pyridin-3-yl)-6,7-dihydro-5H-cyclopenta[d]pyrimidine The title compound was prepared according to General Method A followed by General Method B.

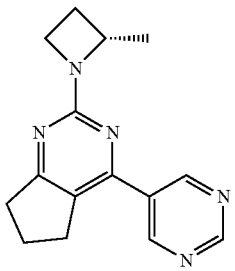 [SMILES: C[C@H]1CCN1c1nc2c(c(-c3cncnc3)n1)CCC2]

Example 16: (S)-2-(2-methylazetidin-1-yl)-4-(pyrimidin-5-yl)-6,7-dihydro-5H-cyclopenta[d]pyrimidine The title compound was prepared in a method analogous to General Method A using pyrimidin-5-ylboronic acid instead of 3-pyridylboronic acid followed by General Method B.

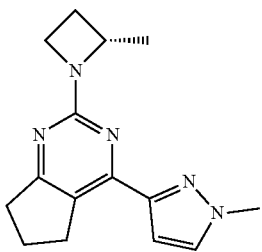 [SMILES: C[C@H]1CCN1c1nc2c(c(-c3ccn(C)n3)n1)CCC2]

Example 17: (S)-4-(1-methyl-1H-pyrazol-3-yl)-2-(2-methylazetidin-1-yl)-6,7-dihydro-5H-cyclopenta[d]pyrimidine The title compound was prepared in a method analogous to General Method A using 1-methyl-3-(4,4,5,5-tetramethyl-1,3,2-dioxaborolan-2-yl)pyrazole instead of 3-pyridylboronic acid followed by General Method B.

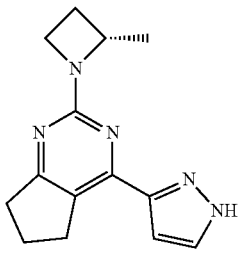 [SMILES: C[C@H]1CCN1c1nc2c(c(-c3cc[nH]n3)n1)CCC2]

Example 18: (S)-2-(2-methylazetidin-1-yl)-4-(1H-pyrazol-3-yl)-6,7-dihydro-5H-cyclopenta[d]pyrimidine The title compound was prepared in a method analogous to General Method A using tert-butyl 3-(4,4,5,5-tetramethyl-1,3,2-dioxaborolan-2-yl)pyrazole-1-carboxylate instead of 3-pyridylboronic acid followed by General Method B. In the first step, the tert-butyl carboxylate was cleaved under the reaction conditions.

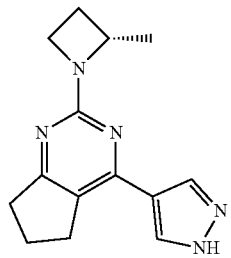 [SMILES: C[C@H]1CCN1c1nc2c(c(-c3cn[nH]c3)n1)CCC2]

Example 19: (S)-2-(2-methylazetidin-1-yl)-4-(1H-pyrazol-4-yl)-6,7-dihydro-5H-cyclopenta[d]pyrimidine The title compound was prepared in a method analogous to General Method A using tert-butyl 4-(4,4,5,5-tetramethyl-1,3,2-dioxaborolan-2-yl)-1H-pyrazole-1-carboxylate instead of 3-pyridylboronic acid followed by General Method B. In the first step, the tert-butyl carboxylate was cleaved under the reaction conditions.

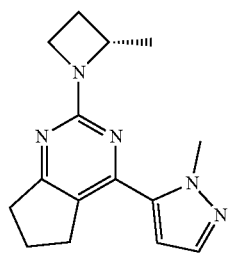 [SMILES: C[C@H]1CCN1c1nc2c(c(-c3ccnn3C)n1)CCC2]

Example 20: (S)-4-(1-methyl-1H-pyrazol-5-yl)-2-(2-methylazetidin-1-yl)-6,7-dihydro-5H-cyclopenta[d]pyrimidine The title compound was prepared in a method analogous to General Method A using 1-methyl-5-(4,4,5,5-tetramethyl-1,3,2-dioxaborolan-2-yl)pyrazole instead of 3-pyridylboronic acid followed by General Method B.

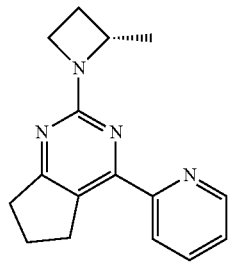

Example 21: (S)-2-(2-methylazetidin-1-yl)-4-(pyridin-2-yl)-6,7-dihydro-5H-cyclopenta[d]pyrimidine A vial was charged with 2,4-dichloro-6,7-dihydro-5H-cyclopenta[d]pyrimidine (40 mg, 0.21 mmol, 1.0 equiv.), 2-(4,4,5,5-tetramethyl-1,3,2-dioxaborolan-2-yl)pyridine (60.7 mg, 0.30 mmoL, 1.4 equiv), Pd(dppf)Cl$_2$-DCM complex (8.8 mg, 0.011 mmol, 5 mol %), CuCl (20.9 mg, 0.21 mmol, 1 equiv.), Cs₂CO₃ (138 mg, 0.42 mmol, 2.0 equiv.), and DMF (2 mL). The mixture was sparged with argon and heated to 100° C. for 24 hr. The mixture was concentrated and subject to flash column chromatography (hexanes-ethyl acetate) to give 2-chloro-4-(2-pyridyl)-6,7-dihydro-5H-cyclopenta[d]pyrimidine, followed by General Method B to give the title compound.

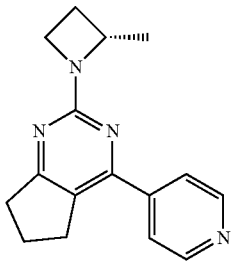 [SMILES: C[C@H]1CCN1c1nc2c(c(-c3ccncc3)n1)CCC2]

Example 22: (S)-2-(2-methylazetidin-1-yl)-4-(pyridin-4-yl)-6,7-dihydro-5H-cyclopenta[d]pyrimidine A vial was charged with 2,4-dichloro-6,7-dihydro-5H-cyclopenta[d]pyrimidine (40 mg, 0.21 mmol, 1.0 equiv.), 4-pyridylboronic acid (60.7 mg, 0.30 mmoL, 1.4 equiv), Pd(dppf)Cl₂-DCM complex (8.8 mg, 0.011 mmol, 5 mol %), CuCl (20.9 mg, 0.21 mmol, 1 equiv.), Cs₂CO₃ (138 mg, 0.42 mmol, 2.0 equiv.), and DMF (2 mL). The mixture was sparged with argon and heated to 100° C. for 24 hr. The mixture was concentrated and subject to flash column chromatography (hexanes-ethyl acetate) to give 2-chloro-4-(2-pyridyl)-6,7-dihydro-5H-cyclopenta[d]pyrimidine, followed by General Method B to give the title compound.

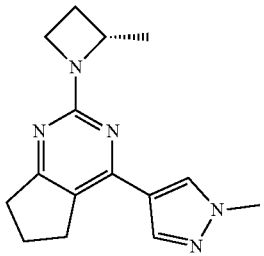 [SMILES: C[C@H]1CCN1c1nc2c(c(-c3cnn(C)c3)n1)CCC2]

Example 23: (S)-4-(1-methyl-1H-pyrazol-4-yl)-2-(2-methylazetidin-1-yl)-6,7-dihydro-5H-cyclopenta[d]pyrimidine The title compound was prepared in a method analogous to General Method A using 1-methyl-4-(4,4,5,5-tetramethyl-1,3,2-dioxaborolan-2-yl)pyrazole instead of 3-pyridylboronic acid followed by General Method B.

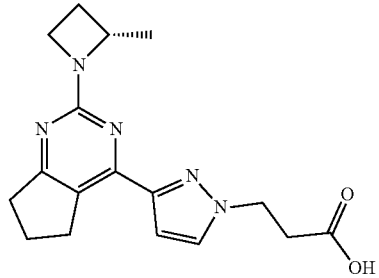 [SMILES: C[C@H]1CCN1c1nc2c(c(-c3ccn(CCC(=O)O)n3)n1)CCC2]

Example 24: (S)-3-(3-(2-(2-methylazetidin-1-yl)-6,7-dihydro-5H-cyclopenta[d]pyrimidin-4-yl)-1H-pyrazol-1-yl)propanoic acid A vial was charged with (S)-2-(2-methylazetidin-1-yl)-4-(1H-pyrazol-3-yl)-6,7-dihydro-5H-cyclopenta[d]pyrimidine (12 mg, 0.033 mmol, 1 equiv.), K₂CO₃ (9.0 mg, 0.065 mmol, 2 equiv.) and MeCN (0.5 mL), followed by methyl prop-2-enoate (84 mg, 0.975 mmol, 30 equiv.). The sealed vial was heated to 120° C. for 2 hours, and was then cooled to ambient temperature and concentrated. The resulting residue was dissolved in MeOH (0.5 mL) and NaOH (2M aq., 0.5 mL) was added. The mixture was heated to 60° C. for 20 min. The mixture was cooled to ambient temperature, concentrated, and subjected to HPLC (0.1% TFA in MeCN-0.1% TFA in H₂O) to give the title compound.

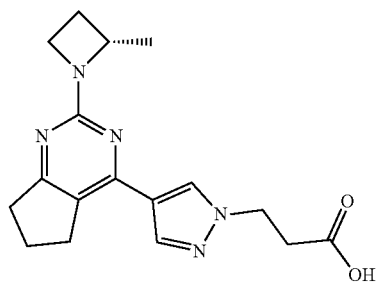 [SMILES: C[C@H]1CCN1c1nc2c(c(-c3cnn(CCC(=O)O)c3)n1)CCC2]

Example 25: (S)-3-(4-(2-(2-methylazetidin-1-yl)-6,7-dihydro-5H-cyclopenta[d]pyrimidin-4-yl)-1H-pyrazol-1-yl)propanoic acid A vial was charged with 2-[(2S)-2-methylazetidin-1-yl]-4-(1H-pyrazol-4-yl)-6,7-dihydro-5H-cyclopenta[d]pyrimidine (6 mg, 0.016 mmol, 1 equiv.), K₂CO₃ (4.5 mg, 0.033 mmol, 2 equiv.) and MeCN (0.5 mL), followed by methyl prop-2-enoate (42 mg, 0.49 mmol, 30 equiv.). The sealed vial was heated to 120° C. for 15 min, and was then cooled to ambient temperature and concentrated. The resulting residue was dissolved in MeOH (0.5 mL) and NaOH (2M aq., 0.5 mL) was added. The mixture was heated to 60° C. for 20 min. The mixture was cooled to ambient temperature, concentrated, and subjected to HPLC (0.1% TFA in MeCN-0.1% TFA in H₂O) to give the title compound.

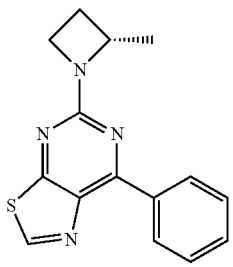 [SMILES: C[C@H]1CCN1c1nc(-c2ccccc2)c2ncsc2n1]

Example 26: (S)-5-(2-methylazetidin-1-yl)-7-phenylthiazolo[5,4-d]pyrimidine

The title compound was prepared in a method analogous to General Method A using phenylboronic acid and 5,7-dichlorothiazolo[5,4-d]pyrimidine instead of 3-pyridylboronic acid and 2,4-dichloro-6,7-dihydro-5H-cyclopenta[d]pyrimidine, respectively, followed by General Method B.

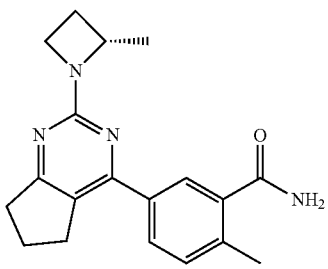 [SMILES: Cc1ccc(-c2nc(N3CC[C@@H]3C)nc3c2CCC3)cc1C(N)=O]

Example 27: (S)-2-methyl-5-(2-(2-methylazetidin-1-yl)-6,7-dihydro-5H-cyclopenta[d]pyrimidin-4-yl)benzamide The title compound was prepared in a method analogous to General Method A using 2-methyl-5-(4,4,5,5-tetramethyl-1,3,2-dioxaborolan-2-yl)benzamide instead of 3-pyridylboronic acid followed by General Method B.

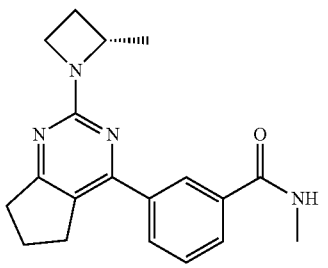 [SMILES: CNC(=O)c1cccc(-c2nc(N3CC[C@@H]3C)nc3c2CCC3)c1]

Example 28: (S)—N-methyl-3-(2-(2-methylazetidin-1-yl)-6,7-dihydro-5H-cyclopenta[d]pyrimidin-4-yl)benzamide The title compound was prepared in a method analogous to General Method A using [3-(methylcarbamoyl)phenyl]boronic acid instead of 3-pyridylboronic acid followed by General Method B.

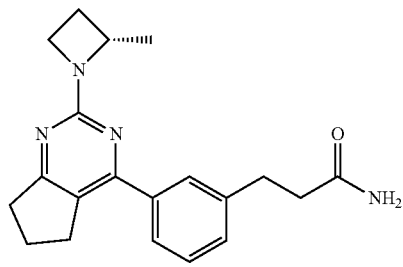 [SMILES: C[C@H]1CCN1c1nc2c(c(-c3cccc(CCC(N)=O)c3)n1)CCC2]

Example 29: (S)-3-(3-(2-(2-methylazetidin-1-yl)-6,7-dihydro-5H-cyclopenta[d]pyrimidin-4-yl)phenyl)propenamide A vial was charged with methyl 3-[3-[2-1(2S)-2-methylazetidin-1-yl]-6,7-dihydro-5H-cyclopenta[d]pyrimidin-4-yl]phenyl)propanoate (35 mg, 0.10 mmol, 1.0 equiv.), EtOH (1 mL), and $NH_4OH$ (25% aq., 2 mL) and heated to 100° C. for 18 hr. The reaction mixture was cooled to ambient temperature, concentrated, and subjected to HPLC to give the title compound.

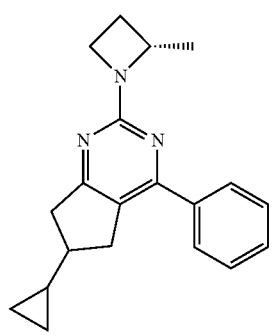 [SMILES: C[C@H]1CCN1c1nc2c(c(-c3ccccc3)n1)CC(C1CC1)C2]

Example 30: 6-cyclopropyl-2-((S)-2-methylazetidin-1-yl)-4-phenyl-6,7-dihydro-5H-cyclopenta[d]pyrimidine The title compound was prepared in a method analogous to General Method H using methyl 4-cyclopropyl-2-oxocyclopentane-1-carboxylate instead of 2-oxobicyclo[3.1.0]hexane-3-carboxylate and phenyl boronic acid instead of (3-carbamoylphenyl)boronic acid.

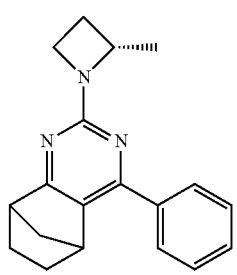 [SMILES: C[C@H]1CCN1c1nc(-c2ccccc2)c2c(n1)C1CCC2C1]

Example 31: 2-((S)-2-methylazetidin-1-yl)-4-phenyl-5,6,7,8-tetrahydro-5,8-methanoquinazoline The title compound was prepared in a method analogous to General Method H using methyl 3-oxobicyclo[2.2.1]

heptane-2-carboxylate instead of 2-oxobicyclo[3.1.0]hexane-3-carboxylate and phenyl boronic acid instead of (3-carbamoylphenyl)boronic acid.

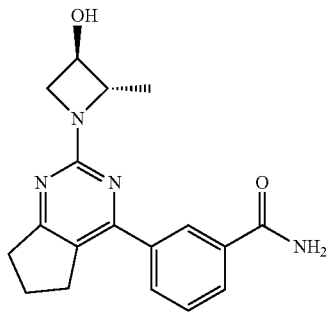 [SMILES: C[C@H]1[C@H](O)CN1c1nc2c(c(-c3cccc(C(N)=O)c3)n1)CCC2]

Example 32: 3-(24(2S,3R)-3-hydroxy-2-methylazetidin-1-yl)-6,7-dihydro-5H-cyclopenta[d]pyrimidin-4-yl)benzamide The title compound was prepared in a method analogous to General Method A using (3-carbamoylphenyl)boronic acid instead of 3-pyridylboronic acid followed by General Method B using (2S,3R)-2-methylazetidin-3-ol hydrochloride salt instead of (2S)-2-methylazetidine (R)-camphorsulfonic acid salt.

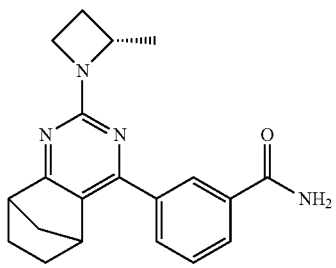 [SMILES: C[C@H]1CCN1c1nc(-c2cccc(C(N)=O)c2)c2c(n1)C1CCC2C1]

Example 33: 3-(2-((S)-2-methylazetidin-1-yl)-5,6,7,8-tetrahydro-5,8-methanoquinazolin-4-yl)benzamide The title compound was prepared in a method analogous to General Method H using methyl 3-oxobicyclo[2.2.1]heptane-2-carboxylate instead of 2-oxobicyclo[3.1.0]hexane-3-carboxylate.

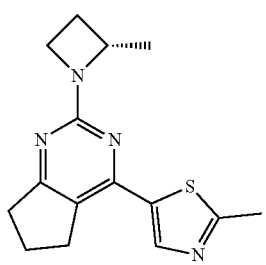

Example 34: (S)-2-methyl-5-(2-(2-methylazetidin-1-yl)-6,7-dihydro-5H-cyclopenta[d]pyrimidin-4-yl)thiazole The title compound was prepared in a method analogous to General Method A using 2-methyl-5-(4,4,5,5-tetramethyl-1,3,2-dioxaborolan-2-yl)thiazole instead of 3-pyridylboronic acid followed by General Method B.

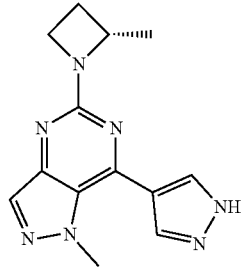 [SMILES: C[C@H]1CCN1c1nc(-c2cn[nH]c2)c2c(cnn2C)n1]

Example 35: (S)-1-methyl-5-(2-methylazetidin-1-yl)-7-(1H-pyrazol-4-yl)-1H-pyrazolo[4,3-d]pyrimidine The title compound was prepared in a method analogous to General Method A using 5,7-dichloro-1-methyl-1H-pyrazolo[4,3-d]pyrimidine and tert-butyl 4-(4,4,5,5-tetramethyl-1,3,2-dioxaborolan-2-yl)pyrazole-1-carboxylate instead of 3-pyridylboronic acid and 2,4-dichloro-6,7-dihydro-5H-cyclopenta[d]pyrimidine, respectively, followed by General Method B. In the first step, the tert-butyl carboxylate was cleaved under the reaction conditions.

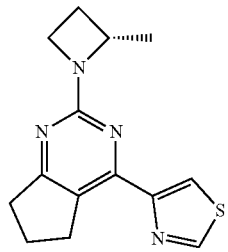 [SMILES: C[C@H]1CCN1c1nc2c(c(-c3cscn3)n1)CCC2]

Example 36: (S)-4-(2-(2-methylazetidin-1-yl)-6,7-dihydro-5H-cyclopenta[d]pyrimidin-4-yl)thiazole The title compound was prepared in a method analogous to General Method E using tributyl(thiazol-4-yl)stannane instead of ethyl 2-tributylstannylimidazo[5,1-b]thiazole-7-carboxylate.

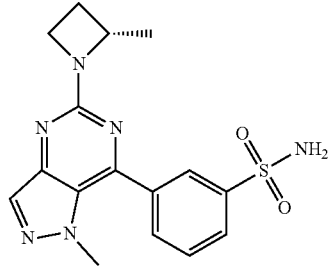 [SMILES: C[C@H]1CCN1c1nc(-c2cccc(S(N)(=O)=O)c2)c2c(cnn2C)n1]

Example 37: (S)-3-(1-methyl-5-(2-methylazetidin-1-yl)-1H-pyrazolo[4,3-d]pyrimidin-7-yl)benzenesulfonamide The title compound was prepared in a method analogous to General Method A using 5,7-dichloro-1-methyl-1H-pyrazolo[4,3-d]pyrimidine and 3-(4,4,5,5-tetramethyl-1,3,2-dioxaborolan-2-yl)benzenesulfonamide instead of 3-pyridylboronic acid and 2,4-dichloro-6,7-dihydro-5H-cyclopenta[d]pyrimidine, respectively, followed by General Method B.

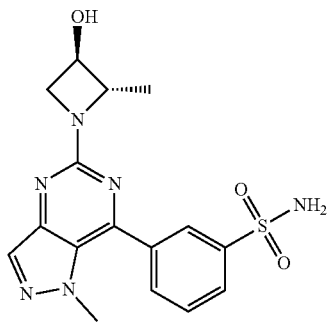 [SMILES: C[C@H]1[C@H](O)CN1c1nc(-c2cccc(S(N)(=O)=O)c2)c2c(cnn2C)n1]

Example 38: 3-(54(2S,3R)-3-hydroxy-2-methylazetidin-1-yl)-1-methyl-M-pyrazolo[4,3-d]pyrimidin-7-yl)benzenesulfonamide The title compound was prepared in a method analogous to General Method A using 5,7-dichloro-1-methyl-1H-pyrazolo[4,3-d]pyrimidine and 3-(4,4,5,5-tetramethyl-1,3,2-dioxaborolan-2-yl)benzenesulfonamide instead of 3-pyridylboronic acid and 2,4-dichloro-6,7-dihydro-5H-cyclopenta[d]pyrimidine, respectively, followed by General Method B using (2S,3R)-2-methylazetidin-3-ol hydrochloride salt instead of (2S)-2-methylazetidine.

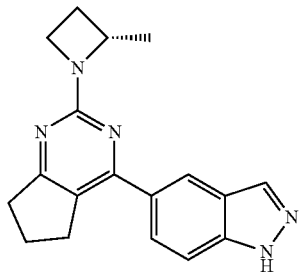 [SMILES: C[C@H]1CCN1c1nc2c(c(-c3ccc4[nH]ncc4c3)n1)CCC2]

Example 39: (S)-5-(2-(2-methylazetidin-1-yl)-6,7-dihydro-5H-cyclopenta[d]pyrimidin-4-yl)-1H-indazole The title compound was prepared in a method analogous to General Method A using 5-(4,4,5,5-tetramethyl-1,3,2-dioxaborolan-2-yl)-1H-indazole instead of 3-pyridylboronic acid followed by General Method B.

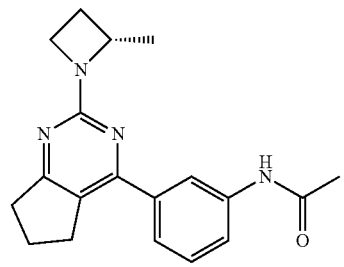 [SMILES: CC(=O)Nc1cccc(-c2nc(N3CC[C@@H]3C)nc3c2CCC3)c1]

Example 40: (S)—N-(3-(2-(2-methylazetidin-1-yl)-6,7-dihydro-5H-cyclopenta[d]pyrimidin-4-yl)phenyl)acetamide The title compound was prepared in a method analogous to General Method A using (3-acetamidophenyl)boronic acid instead of 3-pyridylboronic acid followed by General Method B.

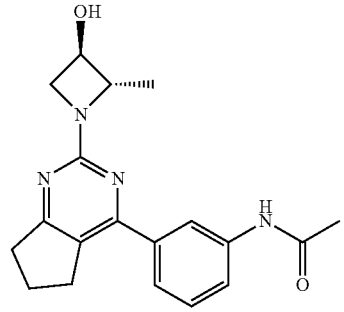 [SMILES: CC(=O)Nc1cccc(-c2nc(N3C[C@@H](O)[C@@H]3C)nc3c2CCC3)c1]

Example 41: N-(3-(24(2S,3R)-3-hydroxy-2-methylazetidin-1-yl)-6,7-dihydro-5H-cyclopenta[d]pyrimidin-4-yl)phenyl)acetamide The title compound was prepared in a method analogous to General Method A using (3-acetamidophenyl)boronic acid instead of 3-pyridylboronic acid followed by General Method B using (2S,3R)-2-methylazetidin-3-ol hydrochloride salt instead of (2S)-2-methylazetidine (R)-camphorsulfonic acid salt.

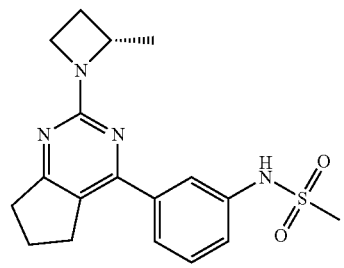 [SMILES: C[C@H]1CCN1c1nc2c(c(-c3cccc(NS(C)(=O)=O)c3)n1)CCC2]

Example 42: (S)—N-(3-(2-(2-methylazetidin-1-yl)-6,7-dihydro-5H-cyclopenta[d]pyrimidin-4-yl)phenyl)methanesulfonamide The title compound was prepared in a method analogous to General Method A using [3-(methanesulfonamido)phenyl]boronic acid instead of 3-pyridylboronic acid followed by General Method B.

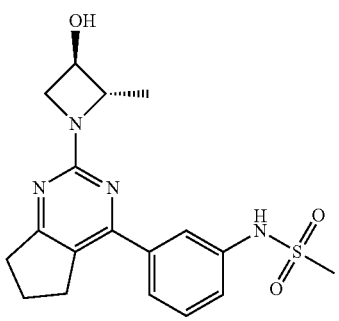 [SMILES: C[C@H]1[C@H](O)CN1c1nc2c(c(-c3cccc(NS(C)(=O)=O)c3)n1)CCC2]

Example 43: N-(3-(2-((2S,3R)-3-hydroxy-2-methylazetidin-1-yl)-6,7-dihydro-5H-cyclopenta[d]pyrimidin-4-yl)phenyl)methanesulfonamide The title compound was prepared in a method analogous to General Method A using [3-(methanesulfonamido)phenyl]boronic acid instead of 3-pyridylboronic acid followed by General Method B using (2S,3R)-2-methylazetidin-3-ol hydrochloride salt instead of (2S)-2-methylazetidine (R)-camphorsulfonic acid salt.

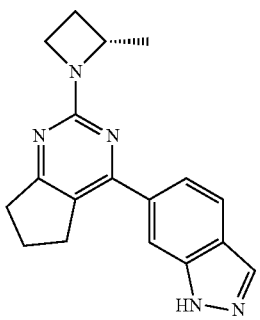 [SMILES: C[C@H]1CCN1c1nc2c(c(-c3ccc4cn[nH]c4c3)n1)CCC2]

Example 44: (S)-6-(2-(2-methylazetidin-1-yl)-6,7-dihydro-5H-cyclopenta[d]pyrimidin-4-yl)-1H-indazole The title compound was prepared in a method analogous to General Method A using 6-(4,4,5,5-tetramethyl-1,3,2-dioxaborolan-2-yl)-1H-indazole instead of 3-pyridylboronic acid followed by General Method B.

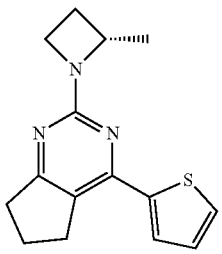 [SMILES: C[C@H]1CCN1c1nc2c(c(-c3cccs3)n1)CCC2]

Example 45: (S)-2-(2-methylazetidin-1-yl)-4-(thiophen-2-yl)-6,7-dihydro-5H-cyclopenta[d]pyrimidine The title compound was prepared in a method analogous to General Method E using 5-tributylstannylthiophene-2-carbonitrile instead of ethyl 2-tributylstannylimidazo[5,1-b]thiazole-7-carboxylate followed by General Method B using 2-chloro-4-(2-thienyl)-6,7-dihydro-5H-cyclopenta[d]pyrimidine instead of 2-chloro-4-(pyridin-3-yl)-6,7-dihydro-5H-cyclopenta[d]pyrimidine.

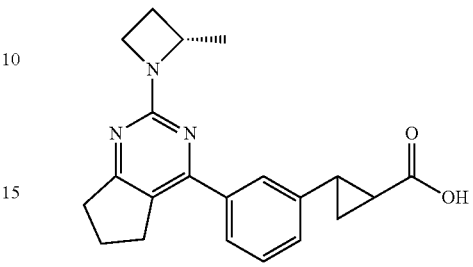

Example 46: 2-(3-(2-((S)-2-methylazetidin-1-yl)-6,7-dihydro-5H-cyclopenta[d]pyrimidin-4-yl)phenyl)cyclopropane-1-carboxylic acid A vial was charged with ethyl (trans)-2-(3-bromophenyl)cyclopropanecarboxylate (200 mg, 0.74 mmol, 1.0 equiv.), Pd(dppf)Cl$_2$-DCM complex (59 mg, 0.074 mmol, 10 mol %), B$_2$pin$_2$ (283 mg, 1.11 mmol, 1.5 equiv.), and KOAc (219 mg, 2.23 mmol, 3.0 equiv.). The vial was purged with nitrogen, and 1,4-dioxane (3.0 mL) was added. The mixture was heated to 100° C. for 1 hour, cooled to ambient temperature, and subjected to flash column chromatography (0-100% hexane/ethyl acetate) to give ethyl 2-[3-(4,4,5,5-tetramethyl-1,3,2-dioxaborolan-2-yl)phenyl]cyclopropanecarboxylate.

Ethyl 2-[3-[2-[(2S)-2-methylazetidin-1-yl]-6,7-dihydro-5H-cyclopenta[d]pyrimidin-4-yl]phenyl]cyclopropanecarboxylate was prepared in a method analogous to General Method A using 2-[3-(4,4,5,5-tetramethyl-1,3,2-dioxaborolan-2-yl)phenyl]cyclopropanecarboxylate and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

The title compound was prepared in a method analogous to General Method C using ethyl 2-[3-[2-[(2S)-2-methylazetidin-1-yl]-6,7-dihydro-5H-cyclopenta[d]pyrimidin-4-yl]phenyl]cyclopropanecarboxylate instead of methyl (S)-3-(3-(2-(2-methylazetidin-1-yl)-6,7-dihydro-5H-cyclopenta[d]pyrimidin-4-yl)phenyl)propanoate.

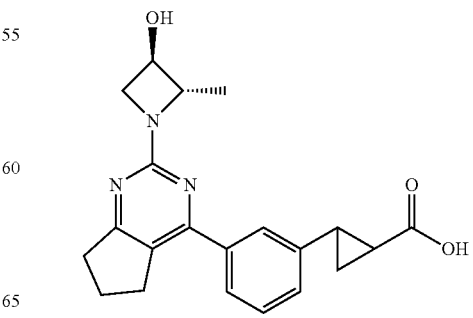

Example 47: 2-(3-(2-((2S,3R)-3-hydroxy-2-methyl-azetidin-1-yl)-6,7-dihydro-5H-cyclopenta[d]pyrimidin-4-yl)phenyl)cyclopropane-1-carboxylic acid The title compound was prepared in a method analogous to General Method A using 2-[3-(4,4,5,5-tetramethyl-1,3,2-dioxaborolan-2-yl)phenyl]cyclopropanecarboxylate instead of 3-pyridylboronic acid followed by General Method B using (2S,3R)-2-methylazetidin-3-ol hydrochloride salt instead of (2S)-2-methylazetidine.

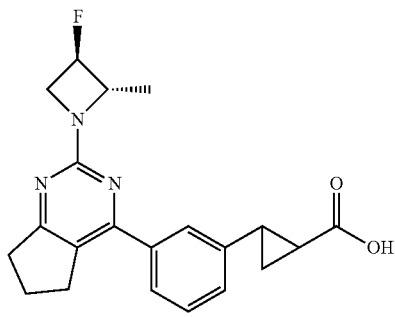 [SMILES: C[C@H]1[C@H](F)CN1c1nc2c(c(-c3cccc(C4CC4C(=O)O)c3)n1)CCC2]

Example 48: 2-(3-(24(2S,3R)-3-fluoro-2-methylaze-tidin-1-yl)-6,7-dihydro-5H-cyclopenta[d]pyrimidin-4-yl)phenyl)cyclopropane-1-carboxylic acid The title compound was prepared in a method analogous to General Method A using 2-[3-(4,4,5,5-tetramethyl-1,3,2-dioxaborolan-2-yl)phenyl]cyclopropanecarboxylate instead of 3-pyridylboronic acid followed by General Method B using (2S,3R)-3-fluoro-2-methylazetidine hydrochloride salt instead of (2S)-2-methylazetidine (R)-camphorsulfonic acid salt.

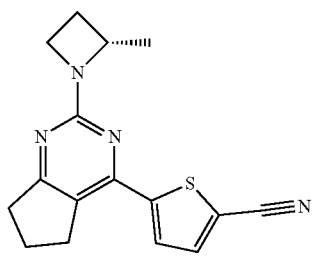 [SMILES: C[C@H]1CCN1c1nc2c(c(-c3ccc(C#N)s3)n1)CCC2]

Example 49: (S)-5-(2-(2-methylazetidin-1-yl)-6,7-dihydro-5H-cyclopenta[d]pyrimidin-4-yl)thiophene-2-carbonitrile The title compound was prepared in a method analogous to General Method E using 5-tributylstannylthiophene-2-carbonitrile instead of ethyl 2-tributylstannylimidazo[5,1-b]thiazole-7-carboxylate.

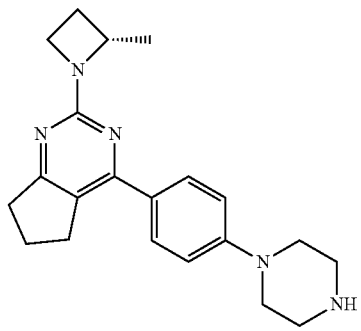 [SMILES: C[C@H]1CCN1c1nc2c(c(-c3ccc(N4CCNCC4)cc3)n1)CCC2]

Example 50: (S)-2-(2-methylazetidin-1-yl)-4-(4-(piperazin-1-yl)phenyl)-6,7-dihydro-5H-cyclopenta[d]pyrimidine tert-butyl (S)-4-(4-(2-(2-methylazetidin-1-yl)-6,7-dihydro-5H-cyclopenta[d]pyrimidin-4-yl)phenyl)piperazine-1-carboxylate was prepared in a method analogous to General Method A using (S)-4-chloro-2-(2-methylazetidin-1-yl)-6,7-dihydro-5H-cyclopenta[d]pyrimidine and tert-butyl 4-[4-(4,4,5,5-tetramethyl-1,3,2-dioxaborolan-2-yl)phenyl]piperazine-1-carboxylate instead of 2,4-dichloro-6,7-dihydro-5H-cyclopenta[d]pyrimidine and 3-pyridylboronic acid, respectively; followed by General Method I to give the title compound.

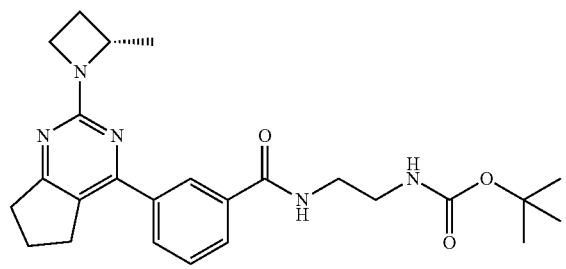 [SMILES: C[C@H]1CCN1c1nc2c(c(-c3cccc(C(=O)NCCNC(=O)OC(C)(C)C)c3)n1)CCC2]

Example 51: tert-butyl (S)-(2-(3-(2-(2-methylazetidin-1-yl)-6,7-dihydro-5H-cyclopenta[d]pyrimidin-4-yl)benzamido)ethyl)carbamate The title compound was prepared in a method analogous to General Method G using (S)-3-(2-(2-methylazetidin-1-yl)-6,7-dihydro-5H-cyclopenta[d]pyrimidin-4-yl)benzoic acid and tert-butyl (2-aminoethyl)carbamate instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid and ammonia, respectively.

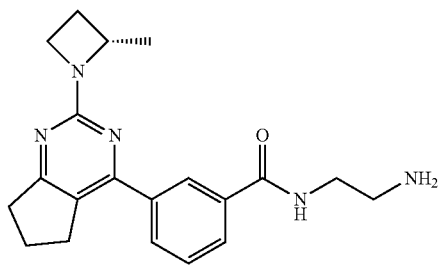 [SMILES: C[C@H]1CCN1c1nc2c(c(-c3cccc(C(=O)NCCN)c3)n1)CCC2]

Example 52: (S)—N-(2-aminoethyl)-3-(2-(2-methylazetidin-1-yl)-6,7-dihydro-5H-cyclopenta[d]pyrimidin-4-yl)benzamide The title compound was prepared in a method analogous to General Method I using tert-butyl (S)-(2-(3-(2-(2-methylazetidin-1-yl)-6,7-dihydro-5H-cyclopenta[d]pyrimidin-4-yl)benzamido) ethyl)carbamate instead of (S)-4-(4-(2-(2-methylazetidin-1-yl)-6,7-dihydro-5H-cyclopenta[d]pyrimidin-4-yl)phenyl)piperazine-1-carboxylate

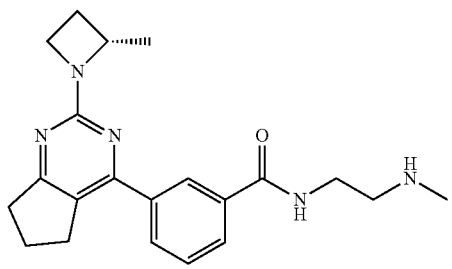 [SMILES: CNCCNC(=O)c1cccc(-c2nc(N3CC[C@@H]3C)nc3c2CCC3)c1]

Example 53: (S)—N-(2-(methylamino)ethyl)-3-(2-(2-methylazetidin-1-yl)-6,7-dihydro-5H-cyclopenta[d]pyrimidin-4-yl)benzamide The title compound was prepared in a method analogous to General Method G using (S)-3-(2-(2-methylazetidin-1-yl)-6,7-dihydro-5H-cyclopenta[d]pyrimidin-4-yl)benzoic acid and tert-butyl (2-aminoethyl)(methyl)carbamate instead of 2-(3-(2-((2S,3R)-3-hydroxy-2-methylazetidin-1-yl)-6,7-dihydro-5H-cyclopenta[d]pyrimidin-4-yl)phenyl) cyclopropane-1-carboxylic acid and ammonia, respectively, followed by Method I.

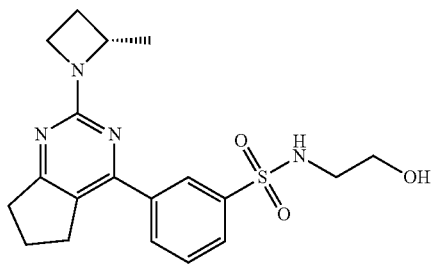 [SMILES: C[C@H]1CCN1c1nc2c(c(-c3cccc(S(=O)(=O)NCCO)c3)n1)CCC2]

Example 54: (S)—N-(2-hydroxyethyl)-3-(2-(2-methylazetidin-1-yl)-6,7-dihydro-5H-cyclopenta[d]pyrimidin-4-yl)benzenesulfonamide The title compound was prepared in a method analogous to General Method F using 3-bromo-N-(2-hydroxyethyl)benzenesulfonamide instead of 6-bromo-1,1-dioxo-1,2-benzothiazol-3-one.

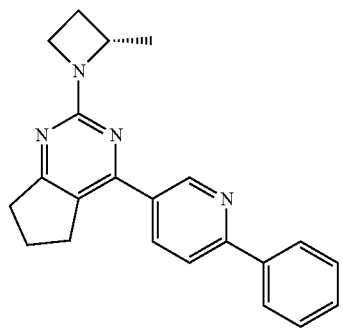 [SMILES: C[C@H]1CCN1c1nc2c(c(-c3ccc(-c4ccccc4)nc3)n1)CCC2]

Example 55: (S)-2-(2-methylazetidin-1-yl)-4-(6-phenylpyridin-3-yl)-6,7-dihydro-5H-cyclopenta[d]pyrimidine The title compound was prepared in a method analogous to General Method A using (S)-4-chloro-2-(2-methylazetidin-1-yl)-6,7-dihydro-5H-cyclopenta[d]pyrimidine and 2-phenyl-5-(4,4,5,5-tetramethyl-1,3,2-dioxaborolan-2-yl) pyridine instead of 2,4-dichloro-6,7-dihydro-5H-cyclopenta[d]pyrimidine and 3-pyridylboronic acid, respectively.

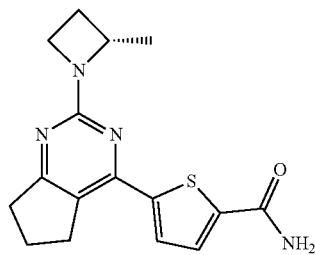 [SMILES: C[C@H]1CCN1c1nc2c(c(-c3ccc(C(N)=O)s3)n1)CCC2]

Example 56: (S)-5-(2-(2-methylazetidin-1-yl)-6,7-dihydro-5H-cyclopenta[d]pyrimidin-4-yl)thiophene-2-carboxamide The title compounds were prepared according to General Method J using (S)-5-(2-(2-methylazetidin-1-yl)-6,7-dihydro-5H-cyclopenta[d]pyrimidin-4-yl)thiophene-2-carbonitrile instead of (S)-3-(2-(2-methylazetidin-1-yl)-6,7-dihydro-5H-cyclopenta[d]pyrimidin-4-yl)benzonitrile.

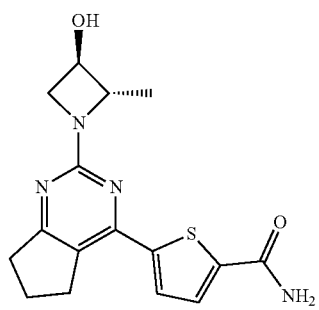 [SMILES: C[C@H]1[C@H](O)CN1c1nc2c(c(-c3ccc(C(N)=O)s3)n1)CCC2]

Example 57: 5-(2-((2S,3R)-3-hydroxy-2-methylazetidin-1-yl)-6,7-dihydro-5H-cyclopenta[d]pyrimidin-4-yl)thiophene-2-carboxamide The title compound was prepared in a method analogous to General Method E using 5-tributylstannylthiophene-2-carbonitrile and 2,4-dichloro-6,7-dihydro-5H-cyclopenta[d]pyrimidine instead of ethyl 2-tributylstannylimidazo[5,1-b]thiazole-7-carboxylate and (S)-4-chloro-2-(2-methylazetidin-1-yl)-6,7-dihydro-5H-cyclopenta[d]pyrimidine, respectively, followed by General Method B, using (2S,3R)-2-methylazetidin-3-ol instead of (2S)-2-methylazetidine and General Method J.

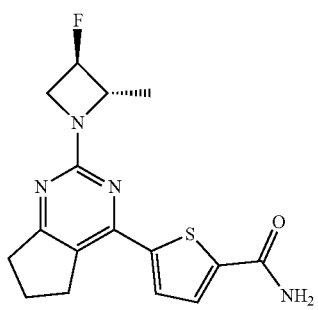 [SMILES: C[C@H]1[C@H](F)CN1c1nc2c(c(-c3ccc(C(N)=O)s3)n1)CCC2]

Example 58: 5-(2-1(2S,3R)-3-fluoro-2-methylazetidin-1-yl)-6,7-dihydro-5H-cyclopenta[d]pyrimidin-4-yl)thiophene-2-carboxamide The title compound was prepared in a method analogous to General Method E using 5-tributylstannylthiophene-2-carbonitrile and 2,4-dichloro-6,7-dihydro-5H-cyclopenta[d]pyrimidine instead of ethyl 2-tributylstannylimidazo[5,1-b]thiazole-7-carboxylate and (S)-4-chloro-2-(2-methylazetidin-1-yl)-6,7-dihydro-5H-cyclopenta[d]pyrimidine, respectively, followed by General Method B, using (2S,3R)-3-fluoro-2-methylazetidine instead of (2S)-2-methylazetidine and General Method J.

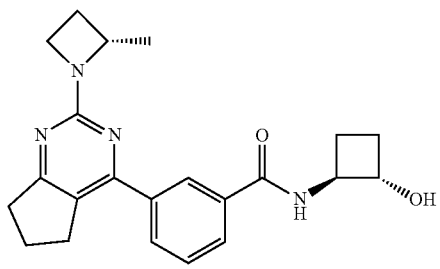 [SMILES: C[C@H]1CCN1c1nc2c(c(-c3cccc(C(=O)N[C@H]4CC[C@@H]4O)c3)n1)CCC2]

Example 59: N-((1S*,2S*)-2-hydroxycyclobutyl)-3-(2-((8)-2-methylazetidin-1-yl)-6,7-dihydro-5H-cyclopenta[d]pyrimidin-4-yl)benzamide The title compound was prepared in a method analogous to General Method G using (S)-3-(2-(2-methylazetidin-1-yl)-6,7-dihydro-5H-cyclopenta[d]pyrimidin-4-yl)benzoic acid and rac-(1S*,2S*)-2-aminocyclobutanol instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid and ammonia, respectively.

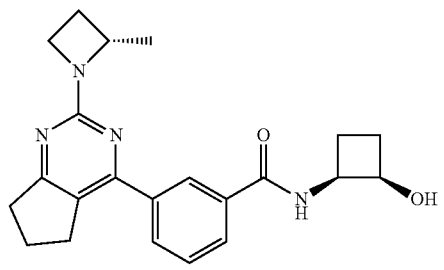 [SMILES: C[C@H]1CCN1c1nc2c(c(-c3cccc(C(=O)N[C@H]4CC[C@H]4O)c3)n1)CCC2]

Example 60: N-((1S*,2R*)-2-hydroxycyclobutyl)-3-(2-((8)-2-methylazetidin-1-yl)-6,7-dihydro-5H-cyclopenta[d]pyrimidin-4-yl)benzamide The title compound was prepared in a method analogous to General Method G using (S)-3-(2-(2-methylazetidin-1-yl)-6,7-dihydro-5H-cyclopenta[d]pyrimidin-4-yl)benzoic acid and rac-(1S*,2R*)-2-aminocyclobutanol instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid and ammonia, respectively.

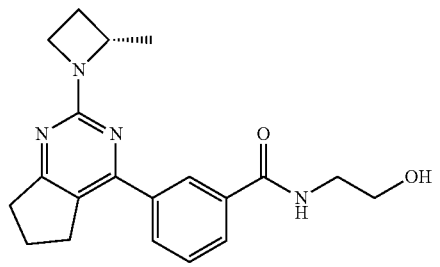 [SMILES: C[C@H]1CCN1c1nc2c(c(-c3cccc(C(=O)NCCO)c3)n1)CCC2]

Example 61: (S)—N-(2-hydroxyethyl)-3-(2-(2-methylazetidin-1-yl)-6,7-dihydro-5H-cyclopenta[d]pyrimidin-4-yl)benzamide The title compound was prepared in a method analogous to General Method G using (S)-3-(2-(2-methylazetidin-1-yl)-6,7-dihydro-5H-cyclopenta[d]pyrimidin-4-yl)benzoic acid and ethanolamine instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid and ammonia, respectively.

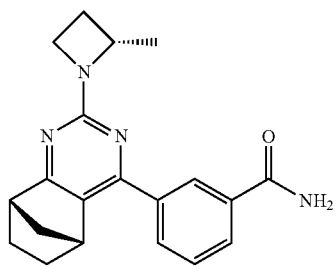

-continued

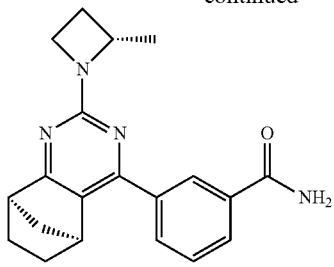

Example 62: 3-((5R,8S)-2-((S)-2-methylazetidin-1-yl)-5,6,7,8-tetrahydro-5,8-methanoquinazolin-4-yl)benzamide Example 63: 3-((5S,8R)-2-((S)-2-methylazetidin-1-yl)-5,6,7,8-tetrahydro-5,8-methanoquinazolin-4-yl)benzamide Isomers were separated by SFC (25% MeOH in $CO_2$, CHIRALPAK IG, 100×4.6 mm, 3 mL/min). (see Example 33)

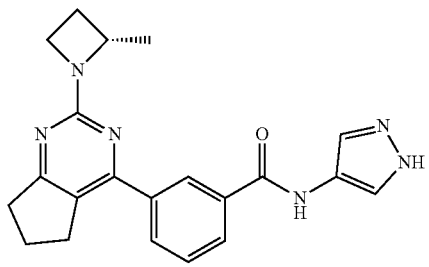 [SMILES: C[C@H]1CCN1c1nc2c(c(-c3cccc(C(=O)Nc4cn[nH]c4)c3)n1)CCC2]

Example 64: (S)-3-(2-(2-methylazetidin-1-yl)-6,7-dihydro-5H-cyclopenta[d]pyrimidin-4-yl)-N-(1H-pyrazol-4-yl)benzamide The title compound was prepared in a method analogous to General Method G using (S)-3-(2-(2-methylazetidin-1-yl)-6,7-dihydro-5H-cyclopenta[d]pyrimidin-4-yl)benzoic acid and 1H-pyrazol-4-amine instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid and ammonia, respectively.

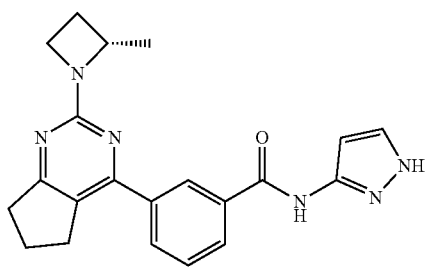 [SMILES: C[C@H]1CCN1c1nc2c(c(-c3cccc(C(=O)Nc4cc[nH]n4)c3)n1)CCC2]

Example 65: (S)-3-(2-(2-methylazetidin-1-yl)-6,7-dihydro-5H-cyclopenta[d]pyrimidin-4-yl)-N-(1H-pyrazol-3-yl)benzamide The title compound was prepared in a method analogous to General Method G using (S)-3-(2-(2-methylazetidin-1-yl)-6,7-dihydro-5H-cyclopenta[d]pyrimidin-4-yl)benzoic acid and 1H-pyrazol-3-amine instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid and ammonia, respectively.

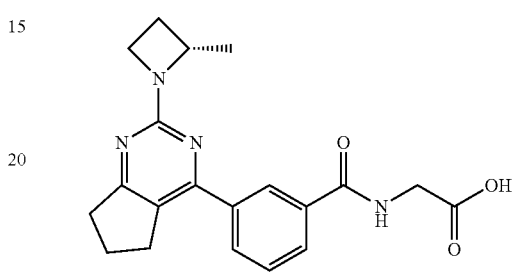

Example 66: (S)-(3-(2-(2-methylazetidin-1-yl)-6,7-dihydro-5H-cyclopenta[d]pyrimidin-4-yl)benzoyl)glycine The title compound was prepared in a method analogous to General Method G using (S)-3-(2-(2-methylazetidin-1-yl)-6,7-dihydro-5H-cyclopenta[d]pyrimidin-4-yl)benzoic acid and methyl glycinate instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid and ammonia, respectively, followed by General Method C.

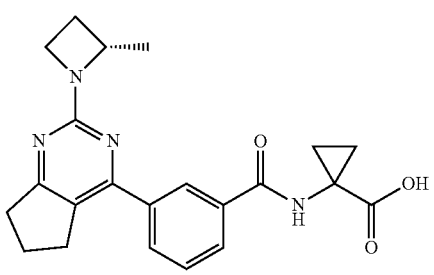 [SMILES: C[C@H]1CCN1c1nc2c(c(-c3cccc(C(=O)NC4(C(=O)O)CC4)c3)n1)CCC2]

Example 67: (S)-1-(3-(2-(2-methylazetidin-1-yl)-6,7-dihydro-5H-cyclopenta[d]pyrimidin-4-yl)benzamido)cyclopropane-1-carboxylic acid The title compound was prepared in a method analogous to General Method G using (S)-3-(2-(2-methylazetidin-1-yl)-6,7-dihydro-5H-cyclopenta[d]pyrimidin-4-yl)benzoic acid and methyl 1-aminocyclopropane-1-carboxylate hydrochloride salt instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid and ammonia, respectively, followed by General Method C.

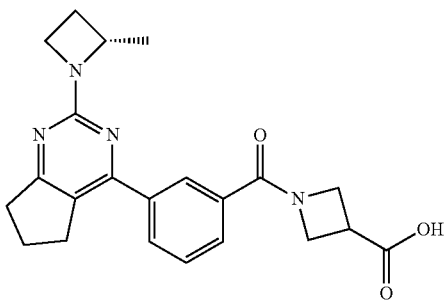 [SMILES: C[C@H]1CCN1c1nc2c(c(-c3cccc(C(=O)N4CC(C(=O)O)C4)c3)n1)CCC2]

Example 68: (S)-1-(3-(2-(2-methylazetidin-1-yl)-6,7-dihydro-5H-cyclopenta[d]pyrimidin-4-yl)benzoyl)azetidine-3-carboxylic acid The title compound was prepared in a method analogous to General Method G using (S)-3-(2-(2-methylazetidin-1-yl)-6,7-dihydro-5H-cyclopenta[d]pyrimidin-4-yl)benzoic acid and methyl azetidine-3-carboxylate hydrochloride salt instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid and ammonia, respectively, followed by General Method C.

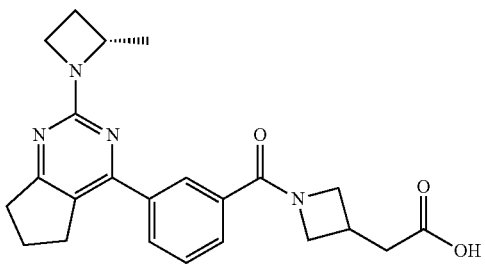 [SMILES: C[C@H]1CCN1c1nc2c(c(-c3cccc(C(=O)N4CC(CC(=O)O)C4)c3)n1)CCC2]

Example 69: (S)-2-(1-(3-(2-(2-methylazetidin-1-yl)-6,7-dihydro-5H-cyclopenta[d]pyrimidin-4-yl)benzoyl)azetidin-3-yl)acetic acid The title compound was prepared in a method analogous to General Method G using (S)-3-(2-(2-methylazetidin-1-yl)-6,7-dihydro-5H-cyclopenta[d]pyrimidin-4-yl)benzoic acid and methyl 2-(azetidin-3-yl)acetate trifluoroacetic acid salt instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid and ammonia, respectively, followed by General Method C.

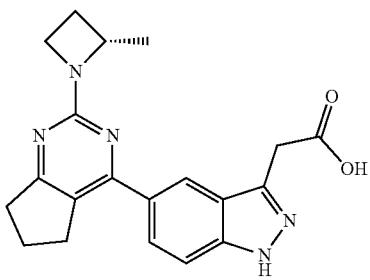 [SMILES: C[C@H]1CCN1c1nc2c(c(-c3ccc4[nH]nc(CC(=O)O)c4c3)n1)CCC2]

Example 70: (S)-2-(5-(2-(2-methylazetidin-1-yl)-6,7-dihydro-5H-cyclopenta[d]pyrimidin-4-yl)-1H-indazol-3-yl)acetic acid tert-Butyl (S)-2-(5-(2-(2-methylazetidin-1-yl)-6,7-dihydro-5H-cyclopenta[d]pyrimidin-4-yl)-1H-indazol-3-yl)acetate was prepared in a method analogous to General Method F using tert-butyl 2-(5-bromo-1H-indazol-3-yl)acetate instead of 6-bromo-1,1-dioxo-1,2-benzothiazol-3-one To a vial containing tert-butyl (S)-2-(5-(2-(2-methylazetidin-1-yl)-6,7-dihydro-5H-cyclopenta[d]pyrimidin-4-yl)-1H-indazol-3-yl)acetate was added TFA (0.5 mL) and DCM (0.5 mL). The mixture was heated to 50° C. for 30 min. The mixture was cooled to room temperature, concentrated, and subject to HPLC (0.1% TFA in MeCN-0.1% TFA in H₂O) to give the title compound.

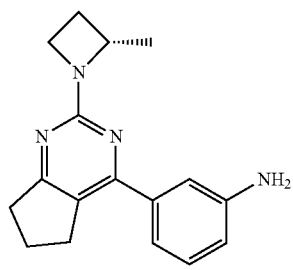 [SMILES: C[C@H]1CCN1c1nc2c(c(-c3cccc(N)c3)n1)CCC2]

Example 71: (S)-3-(2-(2-methylazetidin-1-yl)-6,7-dihydro-5H-cyclopenta[d]pyrimidin-4-yl)aniline The title compound was prepared in a method analogous to General Method A using 3-(4,4,5,5-tetramethyl-1,3,2-dioxaborolan-2-yl)aniline instead of 3-pyridylboronic acid followed by General Method B.

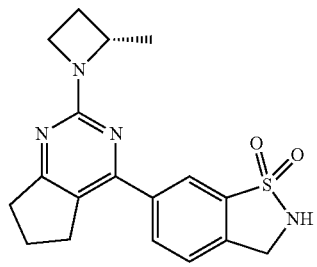 [SMILES: C[C@H]1CCN1c1nc2c(c(-c3ccc4c(c3)S(=O)(=O)NC4)n1)CCC2]

Example 72: (S)-6-(2-(2-methylazetidin-1-yl)-6,7-dihydro-5H-cyclopenta[d]pyrimidin-4-yl)-2,3-dihydrobenzo[d]isothiazole 1,1-dioxide The title compound was prepared in a method analogous to General Method F using 6-bromo-2,3-dihydrobenzo[d]isothiazole 1,1-dioxide instead of 6-bromo-1,1-dioxo-1,2-benzothiazol-3-one.

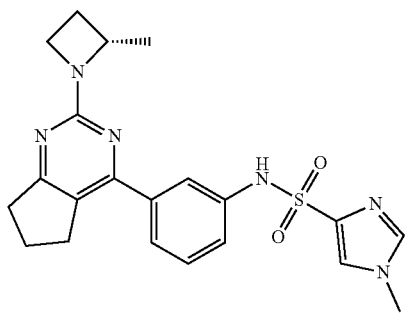 [SMILES: C[C@H]1CCN1c1nc2c(c(-c3cccc(NS(=O)(=O)c4cn(C)cn4)c3)n1)CCC2]

Example 73: (S)-1-methyl-N-(3-(2-(2-methylazetidin-1-yl)-6,7-dihydro-5H-cyclopenta[d]pyrimidin-4-yl)phenyl)-1H-imidazole-4-sulfonamide The title compound was prepared according to General Method K.

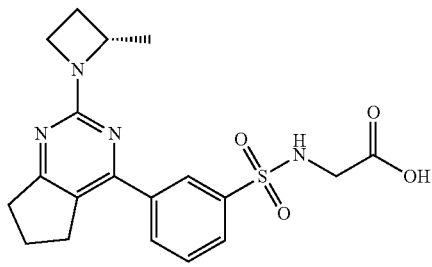 [SMILES: C[C@H]1CCN1c1nc2c(c(-c3cccc(S(=O)(=O)NCC(=O)O)c3)n1)CCC2]

Example 74: (S)-((3-(2-(2-methylazetidin-1-yl)-6,7-dihydro-5H-cyclopenta[d]pyrimidin-4-yl)phenyl)sulfonyl)glycine The title compound was prepared in a method analogous to General Method K using 3-bromobenzenesulfonyl chloride and methyl glycinate instead of 1-methylimidazole-4-sulfonyl chloride and (S)-3-(2-(2-methylazetidin-1-yl)-6,7-dihydro-5H-cyclopenta[d]pyrimidin-4-yl)aniline, respectively, followed by General Method F using methyl ((3-bromophenyl)sulfonyl)glycinate instead of 6-bromo-1,1-dioxo-1,2-benzothiazol-3-one, followed by General Method C.

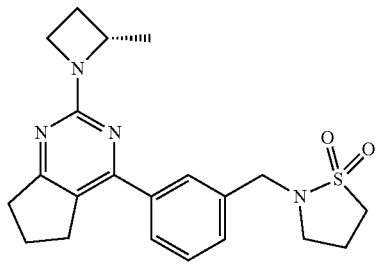 [SMILES: C[C@H]1CCN1c1nc2c(c(-c3cccc(CN4CCCS4(=O)=O)c3)n1)CCC2]

Example 75: (S)-2-(3-(2-(2-methylazetidin-1-yl)-6,7-dihydro-5H-cyclopenta[d]pyrimidin-4-yl)benzyl)isothiazolidine 1,1-dioxide The title compound was made in a method analogous to General Method D, using (S)-4-chloro-2-(2-methylazetidin-1-yl)-6,7-dihydro-5H-cyclopenta[d]pyrimidine instead of 2-bromoimidazo[5,1-b]thiazole-7-carboxylate, followed by General Method E, using 2-(3-bromobenzyl)isothiazolidine 1,1-dioxide instead of (S)-4-chloro-2-(2-methylazetidin-1-yl)-6,7-dihydro-5H-cyclopenta[d]pyrimidine.

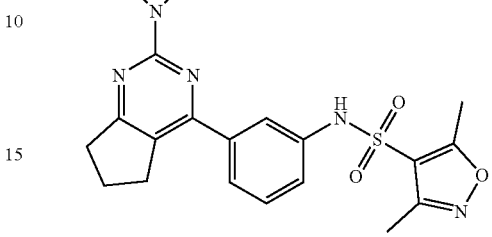

Example 76: (S)-3,5-dimethyl-N-(3-(2-(2-methylazetidin-1-yl)-6,7-dihydro-5H-cyclopenta[d]pyrimidin-4-yl)phenyl)isoxazole-4-sulfonamide The title compound was prepared in a method analogous to General Method K using 3,5-dimethylisoxazole-4-sulfonyl chloride instead of 1-methylimidazole-4-sulfonyl chloride.

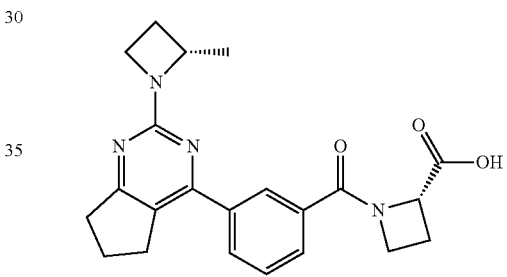

Example 77: (S)-1-(3-(2-((S)-2-methylazetidin-1-yl)-6,7-dihydro-5H-cyclopenta[d]pyrimidin-4-yl)benzoyl)azetidine-2-carboxylic acid The title compound was prepared in a method analogous to General Method G using (S)-3-(2-(2-methylazetidin-1-yl)-6,7-dihydro-5H-cyclopenta[d]pyrimidin-4-yl)benzoic acid and methyl (S)-azetidine-2-carboxylate hydrochloride salt instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid and ammonia, respectively, followed by General Method C.

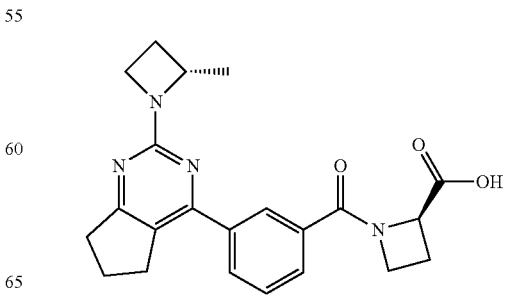

Example 78: (R)-1-(3-(2-((S)-2-methylazetidin-1-yl)-6,7-dihydro-5H-cyclopenta[d]pyrimidin-4-yl)benzoyl)azetidine-2-carboxylic acid The title compound was prepared in a method analogous to General Method G using (S)-3-(2-(2-methylazetidin-1-yl)-6,7-dihydro-5H-cyclopenta[d]pyrimidin-4-yl)benzoic acid and methyl (R)-azetidine-2-carboxylate hydrochloride salt instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid and ammonia, respectively, followed by General Method C.

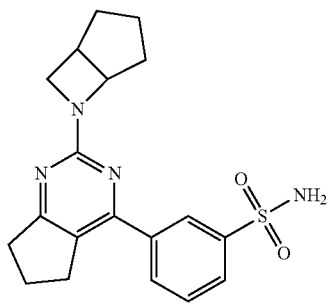 [SMILES: NS(=O)(=O)c1cccc(-c2nc(N3CC4CCCC43)nc3c2CCC3)c1]

Example 79: (rac)-3-(2-(6-azabicyclo[3.2.0]heptan-6-yl)-6,7-dihydro-5H-cyclopenta[d]pyrimidin-4-yl)benzenesulfonamide The title compound was prepared in a method analogous to General Method B using 6-azabicyclo[3.2.0]heptane and 3-(2-chloro-6,7-dihydro-5H-cyclopenta[d]pyrimidin-4-yl)benzenesulfonamide instead of (2S)-2-methylazetidine 2-chloro-4-(pyridin-3-yl)-6,7-dihydro-5H-cyclopenta[d]pyrimidine, respectively.

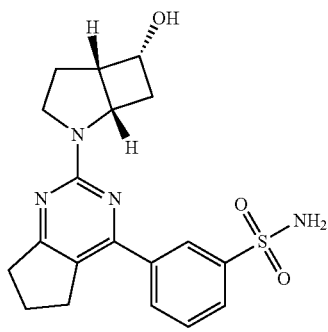 [SMILES: NS(=O)(=O)c1cccc(-c2nc(N3CC[C@@H]4[C@H](O)C[C@@H]43)nc3c2CCC3)c1]

Example 80: (rac)-3-(2-((1S*,5S*,6R*)-6-hydroxy-2-azabicyclo[3.2.0]heptan-2-yl)-6,7-dihydro-5H-cyclopenta[d]pyrimidin-4-yl)benzenesulfonamide The title compound was prepared in a method analogous to General Method B using (rac)-(1S*,5S*,6R*)-2-azabicyclo[3.2.0]heptan-6-ol hydrochloride salt and 3-(2-chloro-6,7-dihydro-5H-cyclopenta[d]pyrimidin-4-yl)benzenesulfonamide instead of (2S)-2-methylazetidine and 2-chloro-4-(pyridin-3-yl)-6,7-dihydro-5H-cyclopenta[d]pyrimidine, respectively.

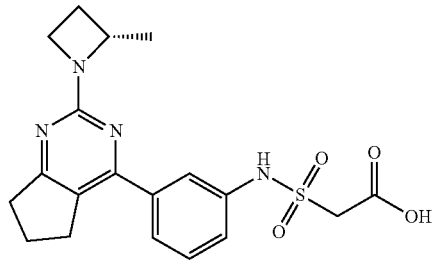 [SMILES: C[C@H]1CCN1c1nc2c(c(-c3cccc(NS(=O)(=O)CC(=O)O)c3)n1)CCC2]

Example 81: (S)-2-(N-(3-(2-(2-methylazetidin-1-yl)-6,7-dihydro-5H-cyclopenta[d]pyrimidin-4-yl)phenyl)sulfamoyl)acetic acid The title compound was prepared in a method analogous to General Method K using ethyl 2-(chlorosulfonyl)acetate instead of 1-methylimidazole-4-sulfonyl chloride, followed by General Method C.

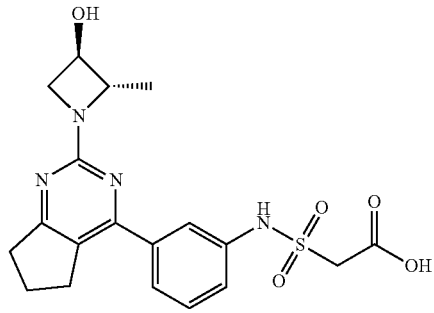 [SMILES: C[C@H]1[C@H](O)CN1c1nc2c(c(-c3cccc(NS(=O)(=O)CC(=O)O)c3)n1)CCC2]

Example 82: 2-(N-(3-(24(2S,3R)-3-hydroxy-2-methylazetidin-1-yl)-6,7-dihydro-5H-cyclopenta[d]pyrimidin-4-yl)phenyl)sulfamoyl)acetic acid The title compound was prepared in a method analogous to General Method A, using 3-(4,4,5,5-tetramethyl-1,3,2-dioxaborolan-2-yl)aniline instead of 3-pyridylboronic acid, followed by General Method K using ethyl 2-(chlorosulfonyl)acetate instead of 1-methylimidazole-4-sulfonyl chloride, followed by General Method B using (2S,3R)-2-methylazetidin-3-ol instead of (2S)-2-methylazetidine, followed by General Method C.

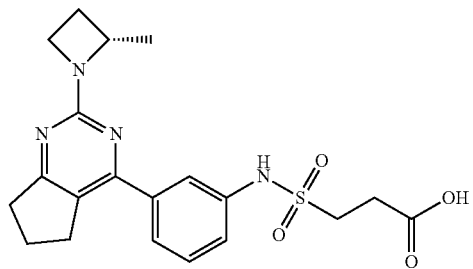 [SMILES: C[C@H]1CCN1c1nc2c(c(-c3cccc(NS(=O)(=O)CCC(=O)O)c3)n1)CCC2]

Example 83: (S)-3-(N-(3-(2-(2-methylazetidin-1-yl)-6,7-dihydro-5H-cyclopenta[d]pyrimidin-4-yl)phenyl)sulfamoyl)propanoic acid The title compound was prepared in a method analogous to General Method K using methyl 3-(chlorosulfonyl)propanoate instead of 1-methylimidazole-4-sulfonyl chloride, followed by General Method C.

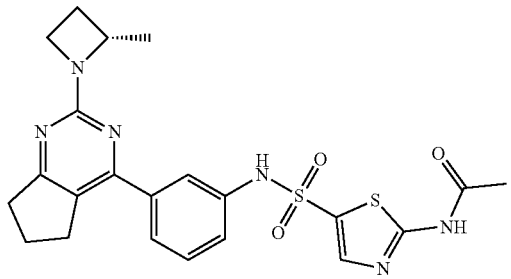 [SMILES: CC(=O)Nc1ncc(S(=O)(=O)Nc2cccc(-c3nc(N4CC[C@@H]4C)nc4c3CCC4)c2)s1]

Example 84: (S)—N-(5-(N-(3-(2-(2-methylazetidin-1-yl)-6,7-dihydro-5H-cyclopenta[d]pyrimidin-4-yl)phenyl)sulfamoyl)thiazol-2-yl)acetamide The title compound was prepared in a method analogous to General Method K using 2-acetamidothiazole-5-sulfonyl chloride instead of 1-methylimidazole-4-sulfonyl chloride.

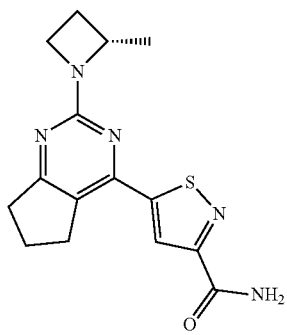 [SMILES: C[C@H]1CCN1c1nc2c(c(-c3cc(C(N)=O)ns3)n1)CCC2]

Example 85: (S)-5-(2-(2-methylazetidin-1-yl)-6,7-dihydro-5H-cyclopenta[d]pyrimidin-4-yl)isothiazole-3-carboxamide The title compound was prepared in a method analogous to General Method F using 5-bromoisothiazole-3-carboxamide instead of 6-bromo-1,1-dioxo-1,2-benzothiazol-3-one.

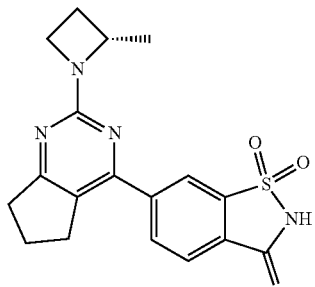

Example 86: (S)-6-(2-(2-methylazetidin-1-yl)-6,7-dihydro-5H-cyclopenta[d]pyrimidin-4-yl)benzo[d]isothiazol-3(2H)-one 1,1-dioxide The title compound was prepared according to General Method F.

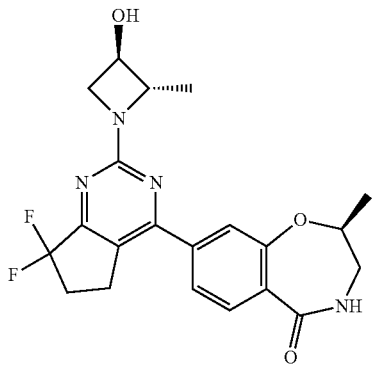 [SMILES: C[C@H]1CNC(=O)c2ccc(-c3nc(N4C[C@@H](O)[C@@H]4C)nc4c3CCC4(F)F)cc2O1]

Example 87: (S)-8-(7,7-difluoro-24(2S,3R)-3-hydroxy-2-methylazetidin-1-yl)-6,7-dihydro-5H-cyclopenta[d]pyrimidin-4-yl)-2-methyl-3,4-dihydrobenzo[f][1,4]oxazepin-5(2H)-one The title compound was prepared in a method analogous to General Method Q, using tert-butyl (R)-(2-hydroxypropyl)carbamate instead of tert-butyl (S)-(1-hydroxypropan-2-yl)carbamate, followed by General Method F, using (S)-8-bromo-2-methyl-3,4-dihydrobenzo[f][1,4]oxazepin-5(2H)-one and 4-chloro-7,7-difluoro-2-(methylthio)-6,7-dihydro-5H-cyclopenta[d]pyrimidine instead of 6-bromo-1,1-dioxo-1,2-benzothiazol-3-one and (S)-4-chloro-2-(2-methylazetidin-1-yl)-6,7-dihydro-5H-cyclopenta[d]pyrimidine, followed by General Method M, followed by General Method B using (2S,3R)-2-methylazetidin-3-ol instead of (S)-2-methylazetidine.

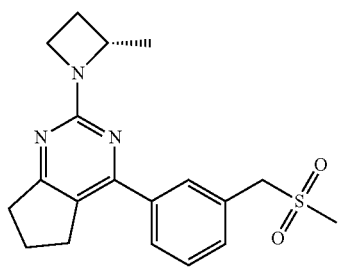 [SMILES: C[C@H]1CCN1c1nc2c(c(-c3cccc(CS(C)(=O)=O)c3)n1)CCC2]

Example 88: (S)-2-(2-methylazetidin-1-yl)-4-(3-((methylsulfonyl)methyl)phenyl)-6,7-dihydro-5H-cyclopenta[d]pyrimidine The title compound was prepared in a method analogous to General Method F using 2-[(3-bromophenyl)methylsulfonyl]acetic acid instead of 6-bromo-1,1-dioxo-1,2-benzothiazol-3-one. In situ decarboxylation was the exclusive product.

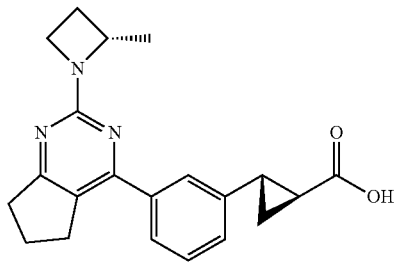

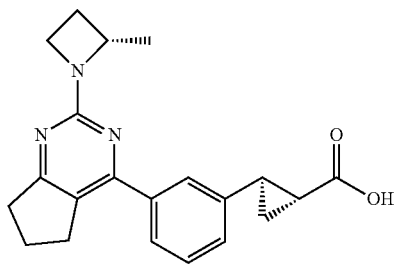

Example 89: (1S,2S)-2-(3-(2-((S)-2-methylazetidin-1-yl)-6,7-dihydro-5H-cyclopenta[d]pyrimidin-4-yl)phenyl)cyclopropane-1-carboxylic acid Example 90: (1R,2R)-2-(3-(2-((S)-2-methylazetidin-1-yl)-6,7-dihydro-5H-cyclopenta[d]pyrimidin-4-yl)phenyl)cyclopropane-1-carboxylic acid Isomers were separated by SFC (25% MeOH in CO₂, CHIRALPAK AD-H, 100×4.6 mm, 3 mL/min). (see Example 46)

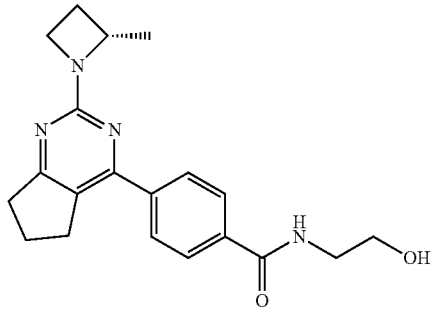 [SMILES: C[C@H]1CCN1c1nc2c(c(-c3ccc(C(=O)NCCO)cc3)n1)CCC2]

Example 91: (S)—N-(2-hydroxyethyl)-4-(2-(2-methylazetidin-1-yl)-6,7-dihydro-5H-cyclopenta[d]pyrimidin-4-yl)benzamide The title compound was prepared in a method analogous to General Method A using (S)-4-chloro-2-(2-methylazetidin-1-yl)-6,7-dihydro-5H-cyclopenta[d]pyrimidine N-(2-hydroxyethyl)-4-(4,4,5,5-tetramethyl-1,3,2-dioxaborolan-2-yl)benzamide instead of 2,4-dichloro-6,7-dihydro-5H-cyclopenta[d]pyrimidine and 3-pyridylboronic acid, respectively.

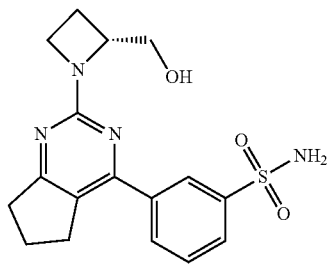 [SMILES: NS(=O)(=O)c1cccc(-c2nc(N3CC[C@@H]3CO)nc3c2CCC3)c1]

Example 92: (R)-3-(2-(2-(hydroxymethyl)azetidin-1-yl)-6,7-dihydro-5H-cyclopenta[d]pyrimidin-4-yl)benzenesulfonamide The title compound was prepared in a method analogous to General Method B using (R)-azetidin-2-ylmethanol and 3-(2-chloro-6,7-dihydro-5H-cyclopenta[d]pyrimidin-4-yl)benzenesulfonamide instead of (2S)-2-methylazetidine and 2-chloro-4-(pyridin-3-yl)-6,7-dihydro-5H-cyclopenta[d]pyrimidine, respectively.

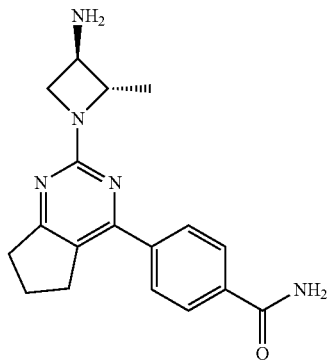 [SMILES: C[C@H]1[C@H](N)CN1c1nc2c(c(-c3ccc(C(N)=O)cc3)n1)CCC2]

Example 93: 4-(24(2S,3R)-3-amino-2-methylazetidin-1-yl)-6,7-dihydro-5H-cyclopenta[d]pyrimidin-4-yl)benzamide The title compound was prepared in a method analogous to General Method B using tert-butyl ((2S,3R)-2-methylazetidin-3-yl)carbamate hydrochloride salt and 4-(2-chloro-6,7-dihydro-5H-cyclopenta[d]pyrimidin-4-yl)benzamide instead of (2S)-2-methylazetidine and 2-chloro-4-(pyridin-3-yl)-6,7-dihydro-5H-cyclopenta[d]pyrimidine, respectively, followed by General Method I.

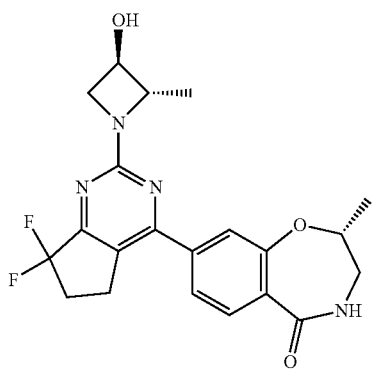 [SMILES: C[C@@H]1CNC(=O)c2ccc(-c3nc(N4C[C@@H](O)[C@@H]4C)nc4c3CCC4(F)F)cc2O1]

Example 94: (R)-8-(7,7-difluoro-24(2S,3R)-3-hydroxy-2-methylazetidin-1-yl)-6,7-dihydro-5H-cyclopenta[d]pyrimidin-4-yl)-2-methyl-3,4-dihydrobenzo[f][1,4]oxazepin-5(2H)-one The title compound was prepared in a method analogous to General Method Q, using tert-butyl (S)-(2-hydroxypropyl)carbamate instead of tert-butyl (S)-(1-hydroxypropan-2-yl)carbamate, followed by General Method F, using (R)-8-bromo-2-methyl-3,4-dihydrobenzo[f][1,4]oxazepin-5(2H)-one and 4-chloro-7,7-difluoro-2-(methylthio)-6,7-dihydro-5H-cyclopenta[d]pyrimidine instead of 6-bromo-1,1-dioxo-1,2-benzothiazol-3-one and (S)-4-chloro-2-(2-methylazetidin-1-yl)-6,7-dihydro-5H-cyclopenta[d]pyrimidine, followed by General Method M, followed by General Method B using (2S,3R)-2-methylazetidin-3-ol instead of (S)-2-methylazetidine.

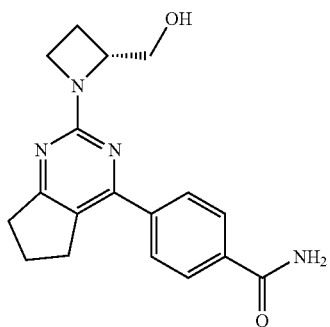 [SMILES: NC(=O)c1ccc(-c2nc(N3CC[C@@H]3CO)nc3c2CCC3)cc1]

Example 95: (R)-4-(2-(2-(hydroxymethyl)azetidin-1-yl)-6,7-dihydro-5H-cyclopenta[d]pyrimidin-4-yl)benzamide The title compound was prepared in a method analogous to General Method B using (R)-azetidin-2-ylmethanol and 4-(2-chloro-6,7-dihydro-5H-cyclopenta[d]pyrimidin-4-yl)benzamide instead of (2S)-2-methylazetidine and 2-chloro-4-(pyridin-3-yl)-6,7-dihydro-5H-cyclopenta[d]pyrimidine, respectively.

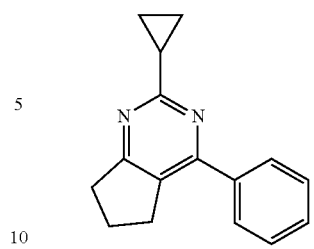

Example 96: 2-cyclopropyl-4-phenyl-6,7-dihydro-5H-cyclopenta[d]pyrimidine

The title compound was prepared according to General Method L.

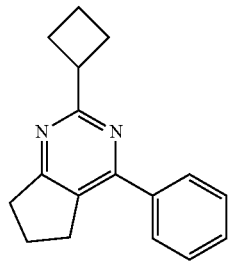 [SMILES: c1ccc(-c2nc(C3CCC3)nc3c2CCC3)cc1]

Example 97: 2-cyclobutyl-4-phenyl-6,7-dihydro-5H-cyclopenta[d]pyrimidine

The title compound was prepared in a method analogous to General Method L using cyclobutylzinc bromide instead of cyclopropylzinc bromide.

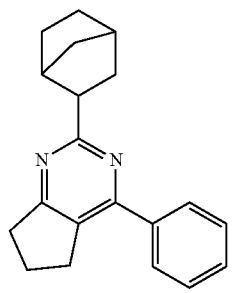 [SMILES: c1ccc(-c2nc(C3CC4CCC3C4)nc3c2CCC3)cc1]

Example 98: 2-(bicyclo[2.2.1]heptan-2-yl)-4-phenyl-6,7-dihydro-5H-cyclopenta[d]pyrimidine The title compound was prepared in a method analogous to General Method L using bicyclo[2.2.1]heptan-2-ylzinc bromide instead of cyclopropylzinc bromide.

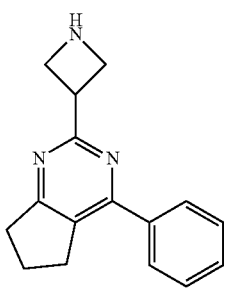 [SMILES: c1ccc(-c2nc(C3CNC3)nc3c2CCC3)cc1]

Example 99: 2-(azetidin-3-yl)-4-phenyl-6,7-dihydro-5H-cyclopenta[d]pyrimidine

The title compound was prepared in a method analogous to General Method L using (1-(tert-butoxycarbonyl)azetidin-3-yl)zinc iodide instead of cyclopropylzinc bromide, followed by General Method I.

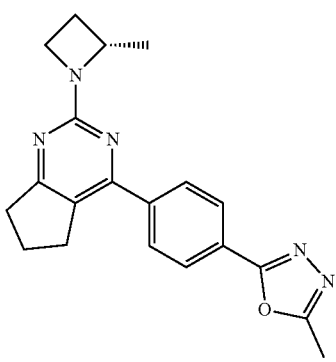 [SMILES: Cc1nnc(-c2ccc(-c3nc(N4CC[C@@H]4C)nc4c3CCC4)cc2)o1]

Example 100: (S)-2-methyl-5-(4-(2-(2-methylazetidin-1-yl)-6,7-dihydro-5H-cyclopenta[d]pyrimidin-4-yl)phenyl)-1,3,4-oxadiazole The title compound was prepared in a method analogous to General Method F using 4-(5-methyl-1,3,4-oxadiazol-2-yl)phenyl]boronic acid instead of 6-bromo-1,1-dioxo-1,2-benzothiazol-3-one.

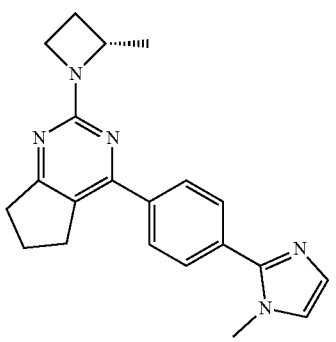 [SMILES: C[C@H]1CCN1c1nc2c(c(-c3ccc(-c4nccn4C)cc3)n1)CCC2]

Example 101: (S)-4-(4-(1-methyl-1H-imidazol-2-yl)phenyl)-2-(2-methylazetidin-1-yl)-6,7-dihydro-5H-cyclopenta[d]pyrimidine The title compound was prepared in a method analogous to General Method F using [4-(1-methylimidazol-2-yl)phenyl]boronic acid instead of 6-bromo-1,1-dioxo-1,2-benzothiazol-3-one.

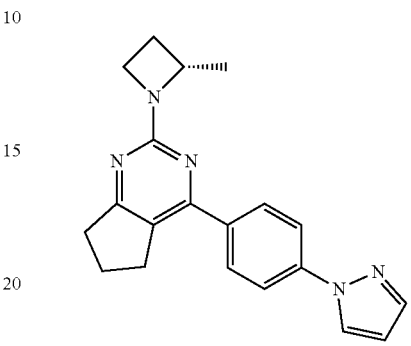

Example 102: (S)-4-(4-(1H-pyrazol-1-yl)phenyl)-2-(2-methylazetidin-1-yl)-6,7-dihydro-5H-cyclopenta[d]pyrimidine The title compound was prepared in a method analogous to General Method F using (4-pyrazol-1-ylphenyl)boronic acid instead of 6-bromo-1,1-dioxo-1,2-benzothiazol-3-one.

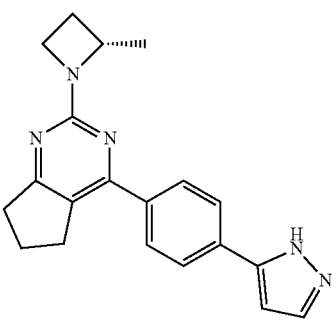 [SMILES: C[C@H]1CCN1c1nc2c(c(-c3ccc(-c4ccn[nH]4)cc3)n1)CCC2]

Example 103: (S)-4-(4-(1H-pyrazol-5-yl)phenyl)-2-(2-methylazetidin-1-yl)-6,7-dihydro-5H-cyclopenta[d]pyrimidine The title compound was prepared in a method analogous to General Method F using [4-(1H-pyrazol-5-yl)phenyl]boronic acid instead of 6-bromo-1,1-dioxo-1,2-benzothiazol-3-one.

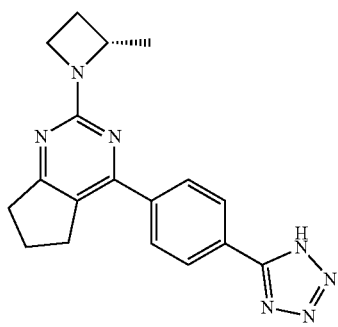 [SMILES: C[C@H]1CCN1c1nc2c(c(-c3ccc(-c4nnn[nH]4)cc3)n1)CCC2]

Example 104: (S)-4-(4-(1H-tetrazol-5-yl)phenyl)-2-(2-methylazetidin-1-yl)-6,7-dihydro-5H-cyclopenta[d]pyrimidine The title compound was prepared in a method analogous to General Method F using [4-(1H-tetrazol-5-yl)phenyl]boronic acid instead of 6-bromo-1,1-dioxo-1,2-benzothiazol-3-one.

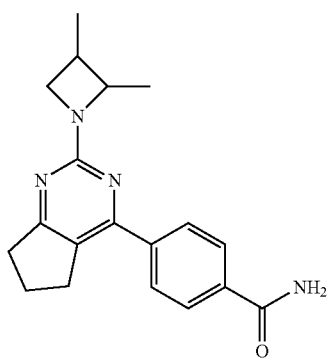 [SMILES: CC1CN(c2nc3c(c(-c4ccc(C(N)=O)cc4)n2)CCC3)C1C]

Example 105: 4-(2-(2,3-dimethylazetidin-1-yl)-6,7-dihydro-5H-cyclopenta[d]pyrimidin-4-yl)benzamide The title compound was prepared in a method analogous to General Method B 2,3-dimethylazetidine hydrochloride salt and 4-(2-chloro-6,7-dihydro-5H-cyclopenta[d]pyrimidin-4-yl)benzamide instead of (2S)-2-methylazetidine and 2-chloro-4-(pyridin-3-yl)-6,7-dihydro-5H-cyclopenta[d]pyrimidine, respectively.

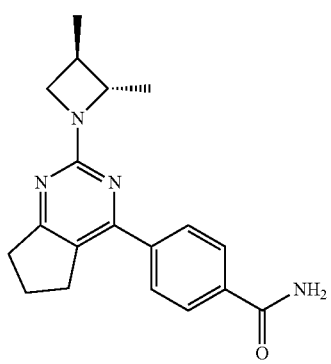

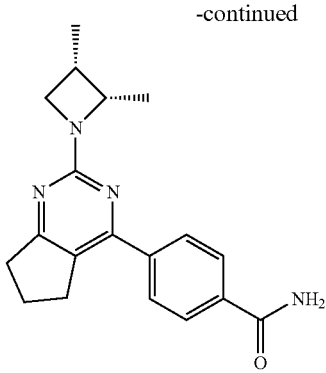

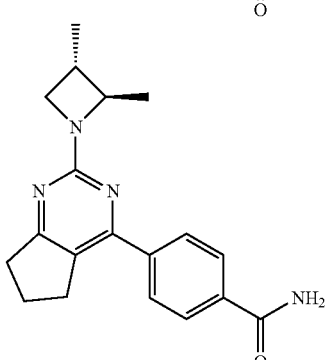

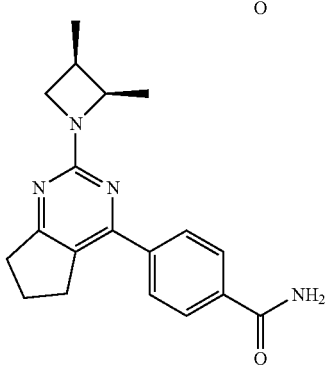

Example 106: 4-(24(2S,3R)-2,3-dimethylazetidin-1-yl)-6,7-dihydro-5H-cyclopenta[d]pyrimidin-4-yl)benzamide Example 107: 4-(2-((2S,3S)-2,3-dimethylazetidin-1-yl)-6,7-dihydro-5H-cyclopenta[d]pyrimidin-4-yl)benzamide Example 108: 4-(24(2R,3S)-2,3-dimethylazetidin-1-yl)-6,7-dihydro-5H-cyclopenta[d]pyrimidin-4-yl)benzamide Example 109: 4-(2-((2R,3R)-2,3-dimethylazetidin-1-yl)-6,7-dihydro-5H-cyclopenta[d]pyrimidin-4-yl)benzamide Isomers were separated by SFC (20% MeOH in $CO_2$, CHIRALPAK IA, 100×4.6 mm, 3 mL/min)

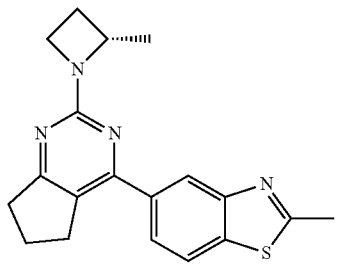 [SMILES: Cc1nc2cc(-c3nc(N4CC[C@@H]4C)nc4c3CCC4)ccc2s1]

Example 110: (S)-2-methyl-5-(2-(2-methylazetidin-1-yl)-6,7-dihydro-5H-cyclopenta[d]pyrimidin-4-yl)benzo[d]thiazole The title compound was prepared in a method analogous to General Method F using ethyl 2-(5-chlorobenzo[d]thiazol-2-yl) acetate instead of 6-bromo-1,1-dioxo-1,2-benzothiazol-3-one. In situ decarboxylation was the exclusive product.

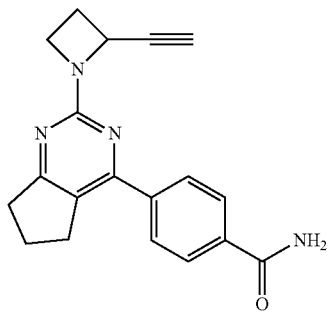 [SMILES: C#CC1CCN1c1nc2c(c(-c3ccc(C(N)=O)cc3)n1)CCC2]

Example 111: 4-(2-(2-ethynylazetidin-1-yl)-6,7-dihydro-5H-cyclopenta[d]pyrimidin-4-yl)benzamide The title compound was prepared in a method analogous to General Method B using (rac)-2-ethynylazetidine hydrochloride salt and 4-(2-chloro-6,7-dihydro-5H-cyclopenta[d]pyrimidin-4-yl)benzamide instead of (2S)-2-methylazetidine and 2-chloro-4-(pyridin-3-yl)-6,7-dihydro-5H-cyclopenta[d]pyrimidine, respectively.

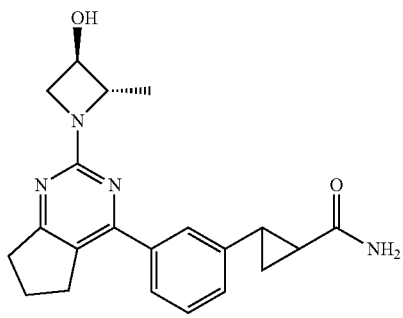 [SMILES: C[C@H]1[C@H](O)CN1c1nc2c(c(-c3cccc(C4CC4C(N)=O)c3)n1)CCC2]

Example 112: 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxamide The title compound was prepared according to General Method G.

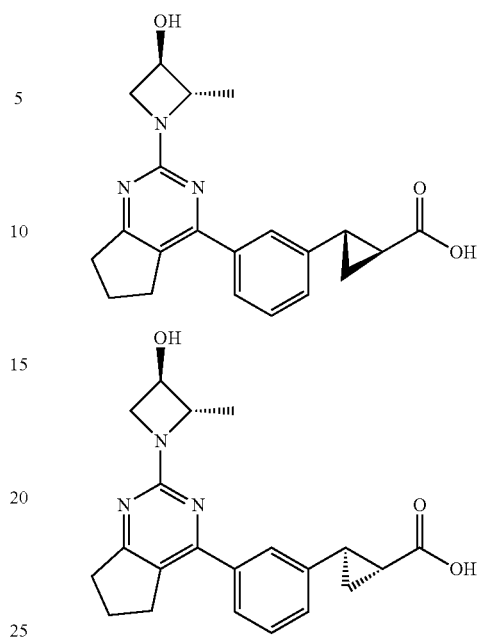

Example 113: (1S,2S)-2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid Example 114: (1R,2R)-2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid Isomers were separated by SFC (35% MeOH in $CO_2$, CHIRALPAK AD-H, 100×4.6 mm, 3 mL/min)

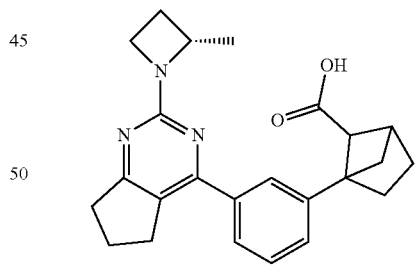

Example 115: 1-(3-(2-((S)-2-methylazetidin-1-yl)-6,7-dihydro-5H-cyclopenta[d]pyrimidin-4-yl)phenyl)bicyclo[2.1.1]hexane-5-carboxylic acid The title compound was prepared in a method analogous to General Method F using 1-(3-bromophenyl)bicyclo[2.1.1]hexane-5-carboxylic acid instead of 6-bromo-1,1-dioxo-1,2-benzothiazol-3-one. In situ decarboxylation was the exclusive product.

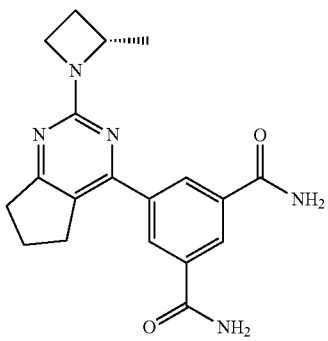 [SMILES: C[C@H]1CCN1c1nc2c(c(-c3cc(C(N)=O)cc(C(N)=O)c3)n1)CCC2]

Example 116: (S)-5-(2-(2-methylazetidin-1-yl)-6,7-dihydro-5H-cyclopenta[d]pyrimidin-4-yl)isophthalamide The title compound was prepared in a method analogous to General Method F using 5-bromoisophthalamide instead of 6-bromo-1,1-dioxo-1,2-benzothiazol-3-one

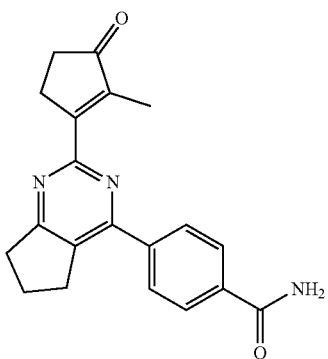 [SMILES: CC1=C(c2nc3c(c(-c4ccc(C(N)=O)cc4)n2)CCC3)CCC1=O]

Example 117: 4-(2-(2-methyl-3-oxocyclopent-1-en-1-yl)-6,7-dihydro-5H-cyclopenta[d]pyrimidin-4-yl)benzamide The title compound was prepared in a method analogous to General Method A using 2-methyl-3-(4,4,5,5-tetramethyl-1,3,2-dioxaborolan-2-yl)cyclopent-2-en-1-one and 4-(2-chloro-6,7-dihydro-5H-cyclopenta[d]pyrimidin-4-yl)benzamide instead of 3-pyridylboronic acid and 2,4-dichloro-6,7-dihydro-5H-cyclopenta[d]pyrimidine, respectively.

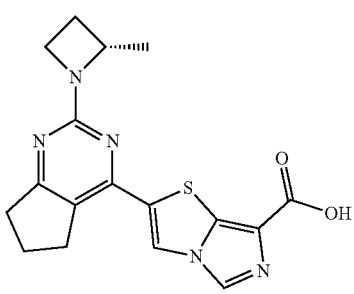 [SMILES: C[C@H]1CCN1c1nc2c(c(-c3cn4cnc(C(=O)O)c4s3)n1)CCC2]

Example 118: (S)-2-(2-(2-methylazetidin-1-yl)-6,7-dihydro-5H-cyclopenta[d]pyrimidin-4-yl)imidazo[5,1-b]thiazole-7-carboxylic acid The title compound was prepared according to General Method E, followed by General Method C.

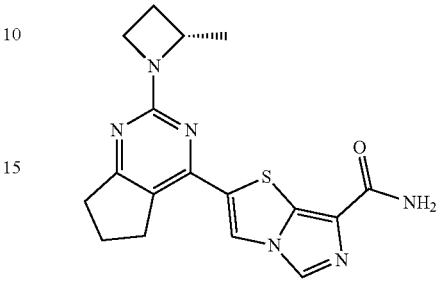

Example 119: (S)-2-(2-(2-methylazetidin-1-yl)-6,7-dihydro-5H-cyclopenta[d]pyrimidin-4-yl)imidazo[5,1-b]thiazole-7-carboxamide The title compound was prepared in a method analogous to General Method G using (S)-2-(2-(2-methylazetidin-1-yl)-6,7-dihydro-5H-cyclopenta[d]pyrimidin-4-yl)imidazo[5,1-b]thiazole-7-carboxylic acid instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid.

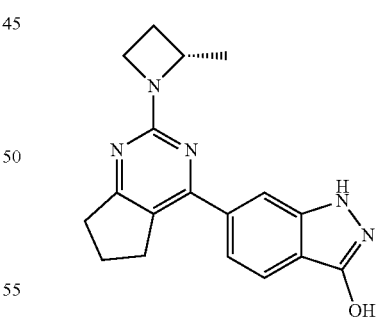

Example 120: (S)-6-(2-(2-methylazetidin-1-yl)-6,7-dihydro-5H-cyclopenta[d]pyrimidin-4-yl)-1H-indazol-3-ol The title compound was prepared in a method analogous to General Method D using 6-bromo-1H-indazol-3-ol instead of 2-bromoimidazo[5,1-b]thiazole-7-carboxylate, followed by General Method E.

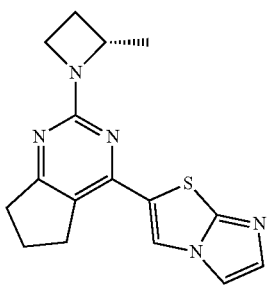 [SMILES: C[C@H]1CCN1c1nc2c(c(-c3cn4ccnc4s3)n1)CCC2]

Example 121: (S)-2-(2-(2-methylazetidin-1-yl)-6,7-dihydro-5H-cyclopenta[d]pyrimidin-4-yl)imidazo[2,1-b]thiazole The title compound was prepared in a method analogous to General Method D using 2-bromoimidazo[2,1-b]thiazole, followed by General Method E.

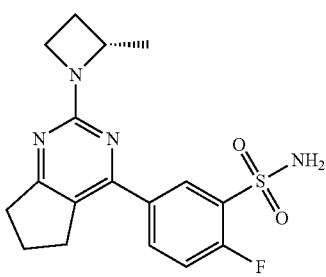

Example 122: (S)-2-fluoro-5-(2-(2-methylazetidin-1-yl)-6,7-dihydro-5H-cyclopenta[d]pyrimidin-4-yl)benzenesulfonamide The title compound was prepared in a method analogous to General Method F using 5-bromo-2-fluoro-benzenesulfonamide instead of 6-bromo-1,1-dioxo-1,2-benzothiazol-3-one

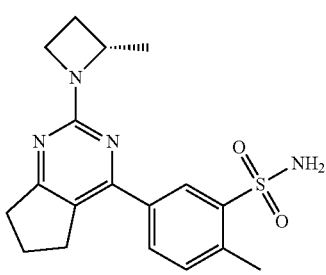 [SMILES: Cc1ccc(-c2nc(N3CC[C@@H]3C)nc3c2CCC3)cc1S(N)(=O)=O]

Example 123: (S)-2-methyl-5-(2-(2-methylazetidin-1-yl)-6,7-dihydro-5H-cyclopenta[d]pyrimidin-4-yl)benzenesulfonamide The title compound was prepared in a method analogous to General Method F using 5-bromo-2-methyl-benzenesulfonamide instead of 6-bromo-1,1-dioxo-1,2-benzothiazol-3-one

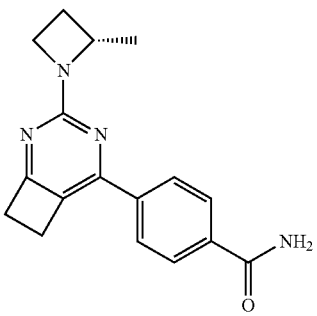 [SMILES: C[C@H]1CCN1c1nc2c(c(-c3ccc(C(N)=O)cc3)n1)CC2]

Example 124: (S)-4-(3-(2-methylazetidin-1-yl)-2,4-diazabicyclo[4.2.0]octa-1,3,5-trien-5-yl)benzamide The title compound was prepared in a method analogous to General Method A using 5-chloro-3-(methylsulfonyl)-2,4-diazabicyclo[4.2.0]octa-1,3,5-triene and (4-carbamoylphenyl)boronic acid instead of 2,4-dichloro-6,7-dihydro-5H-cyclopenta[d]pyrimidine and 3-pyridylboronic acid, followed by General Method B.

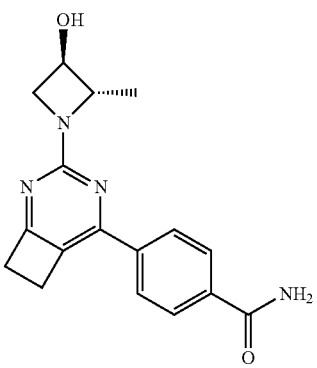 [SMILES: C[C@H]1[C@H](O)CN1c1nc2c(c(-c3ccc(C(N)=O)cc3)n1)CC2]

Example 125: 4-(3-((2S,3R)-3-hydroxy-2-methyl-azetidin-1-yl)-2,4-diazabicyclo[4.2.0]octa-1,3,5-trien-5-yl)benzamide The title compound was prepared in a method analogous to General Method A using 5-chloro-3-(methylsulfonyl)-2,4-diazabicyclo[4.2.0]octa-1,3,5-triene and (4-carbamoylphenyl)boronic acid instead of 2,4-dichloro-6,7-dihydro-5H-cyclopenta[d]pyrimidine and 3-pyridylboronic acid, followed by General Method B, using (2S,3R)-2-methyl-azetidin-3-ol instead of (2S)-2-methylazetidine.

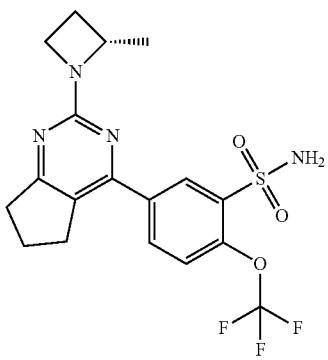 [SMILES: C[C@H]1CCN1c1nc2c(c(-c3ccc(OC(F)(F)F)c(S(N)(=O)=O)c3)n1)CCC2]

Example 126: (S)-5-(2-(2-methylazetidin-1-yl)-6,7-dihydro-5H-cyclopenta[d]pyrimidin-4-yl)-2-(trifluoromethoxy)benzenesulfonamide The title compound was prepared in a method analogous to General Method F using 5-bromo-2-(trifluoromethoxy)benzenesulfonamide instead of 6-bromo-1,1-dioxo-1,2-benzothiazol-3-one

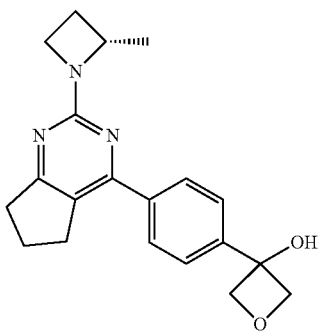 [SMILES: C[C@H]1CCN1c1nc2c(c(-c3ccc(C4(O)COC4)cc3)n1)CCC2]

Example 127: (S)-3-(4-(2-(2-methylazetidin-1-yl)-6,7-dihydro-5H-cyclopenta[d]pyrimidin-4-yl)phenyl)oxetan-3-ol The title compound was prepared in a method analogous to General Method A using 3-[4-(4,4,5,5-tetramethyl-1,3,2-dioxaborolan-2-yl)phenyl]oxetan-3-ol and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

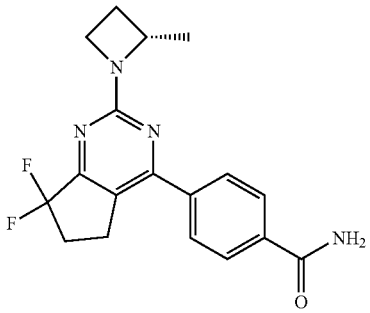 [SMILES: C[C@H]1CCN1c1nc(-c2ccc(C(N)=O)cc2)c2c(n1)C(F)(F)CC2]

Example 128: (S)-4-(7,7-difluoro-2-(2-methylazetidin-1-yl)-6,7-dihydro-5H-cyclopenta[d]pyrimidin-4-yl)benzamide The title compound was prepared in a method analogous to General Method M, followed by General Method B.

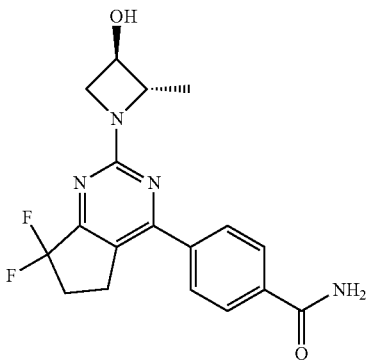 [SMILES: C[C@H]1[C@H](O)CN1c1nc(-c2ccc(C(N)=O)cc2)c2c(n1)C(F)(F)CC2]

Example 129: 4-(7,7-difluoro-2-((2S,3R)-3-hydroxy-2-methylazetidin-1-yl)-6,7-dihydro-5H-cyclopenta[d]pyrimidin-4-yl)benzamide The title compound was prepared in a method analogous to General Method M, followed by General Method B using (2S,3R)-2-methylazetidin-3-ol instead of (S)-2-methylazetidine

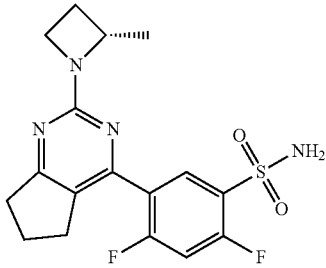 [SMILES: C[C@H]1CCN1c1nc2c(c(-c3cc(S(N)(=O)=O)c(F)cc3F)n1)CCC2]

Example 130: (S)-2,4-difluoro-5-(2-(2-methylazetidin-1-yl)-6,7-dihydro-5H-cyclopenta[d]pyrimidin-4-yl)benzenesulfonamide The title compound was prepared in a method analogous to General Method F using 5-bromo-2,4-difluoro-benzenesulfonamide instead of 6-bromo-1,1-dioxo-1,2-benzothiazol-3-one

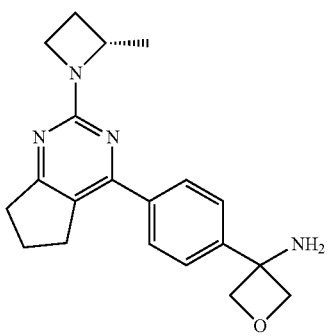 [SMILES: C[C@H]1CCN1c1nc2c(c(-c3ccc(C4(N)COC4)cc3)n1)CCC2]

Example 131: (S)-3-(4-(2-(2-methylazetidin-1-yl)-6,
7-dihydro-5H-cyclopenta[d]pyrimidin-4-yl)phenyl)
oxetan-3-amine The title compound was prepared in a method analogous to General Method A using tert-butyl N-[3-[4-(4,4,5,5-tetramethyl-1,3,2-dioxaborolan-2-yl)phenyl]oxetan-3-yl]carbamate and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively, followed by Method I.

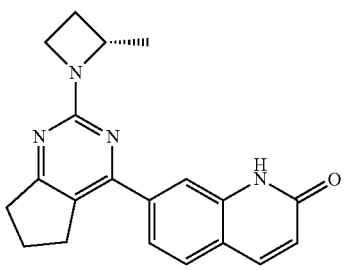 [SMILES: C[C@H]1CCN1c1nc2c(c(-c3ccc4ccc(=O)[nH]c4c3)n1)CCC2]

Example 132: (S)-7-(2-(2-methylazetidin-1-yl)-6,7-dihydro-5H-cyclopenta[d]pyrimidin-4-yl)quinolin-2
(1H)-one The title compound was prepared in a method analogous to General Method A using 7-(4,4,5,5-tetramethyl-1,3,2-dioxaborolan-2-yl)-1H-quinolin-2-one and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

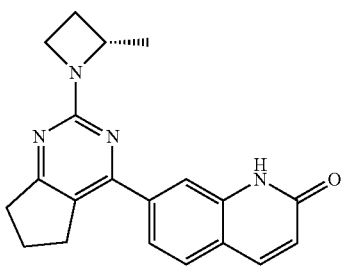 [SMILES: C[C@H]1CCN1c1nc2c(c(-c3ccc4ccc(=O)[nH]c4c3)n1)CCC2]

Example 133: (S)-3-(7-(2-(2-methylazetidin-1-yl)-6,
7-dihydro-5H-cyclopenta[d]pyrimidin-4-yl)-2-oxo-
quinolin-1(2H)-yl)propanoic acid A vial was charged with (S)-7-(2-(2-methylazetidin-1-yl)-6,7-dihydro-5H-cyclopenta[d]pyrimidin-4-yl)quinolin-2(1H)-one trifluoroacetic acid salt (20 mg, 0.045 mmol, 1 equiv.), $K_2CO_3$ (16 mg, 0.112 mmol, 2.5 equiv.) and MeCN (1 mL), followed by methyl prop-2-enoate (116 mg, 0.121 mmol, 30 equiv.). The sealed vial was heated to 120° C. for 2 hours, and was then cooled to ambient temperature and concentrated. The resulting residue was dissolved in MeOH (0.5 mL) and NaOH (2M aq., 0.5 mL) was added. The mixture was heated to 60° C. for 20 min. The mixture was cooled to ambient temperature, concentrated, and subjected to HPLC (0.1% TFA in MeCN-0.1% TFA in $H_2O$) to give the title compound.

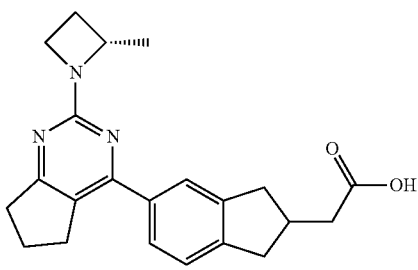 [SMILES: C[C@H]1CCN1c1nc2c(c(-c3ccc4c(c3)CC(CC(=O)O)C4)n1)CCC2]

Example 134: 2-(5-(2-((S)-2-methylazetidin-1-yl)-6,
7-dihydro-5H-cyclopenta[d]pyrimidin-4-yl)-2,3-
dihydro-1H-inden-2-yl)acetic acid The title compound was prepared in a method analogous to General Method F using 2-(5-bromoindan-2-yl)acetic acid instead of 6-bromo-1,1-dioxo-1,2-benzothiazol-3-one

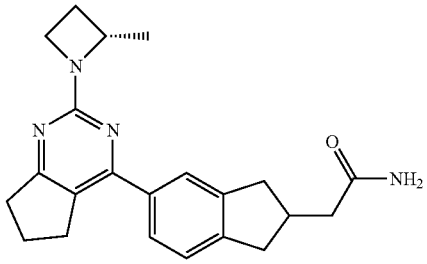 [SMILES: C[C@H]1CCN1c1nc2c(c(-c3ccc4c(c3)CC(CC(N)=O)C4)n1)CCC2]

Example 135: 2-(5-(2-((S)-2-methylazetidin-1-yl)-6,
7-dihydro-5H-cyclopenta[d]pyrimidin-4-yl)-2,3-
dihydro-1H-inden-2-yl)acetamide The title compound was prepared in a method analogous to General Method G using 2-(5-(2-((S)-2-methylazetidin-1-yl)-6,7-dihydro-5H-cyclopenta[d]pyrimidin-4-yl)-2,3-dihydro-1H-inden-2-yl)acetic acid instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid.

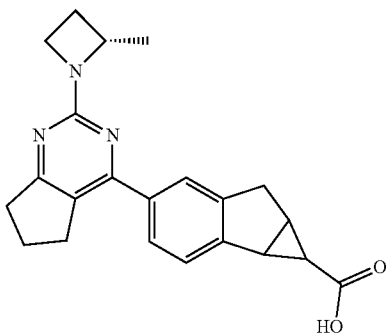 [SMILES: C[C@H]1CCN1c1nc2c(c(-c3ccc4c(c3)CC3C(C(=O)O)C43)n1)CCC2]

Example 136: 4-(2-((S)-2-methylazetidin-1-yl)-6,7-dihydro-5H-cyclopenta[d]pyrimidin-4-yl)-1,1a,6,6a-tetrahydrocyclopropa[a]indene-1-carboxylic acid The title compound was prepared in a method analogous to General Method F using 4-bromo-1,1a,6,6a-tetrahydrocyclopropa[a]indene-1-carboxylic acid instead of 6-bromo-1,1-dioxo-1,2-benzothiazol-3-one

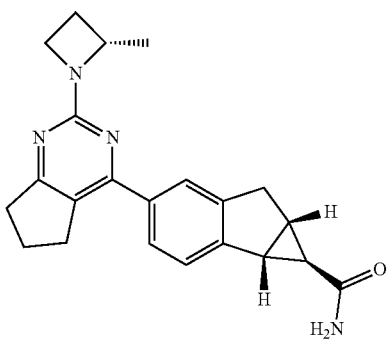

Example 137: (1R,1aR*,6aS*)-4-(2-((S)-2-methylazetidin-1-yl)-6,7-dihydro-5H-cyclopenta[d]pyrimidin-4-yl)-1,1a,6,6a-tetrahydrocyclopropa[a]indene-1-carboxamide Example 138: (1S,1aR*,6aS*)-4-(2-((S)-2-methylazetidin-1-yl)-6,7-dihydro-5H-cyclopenta[d]pyrimidin-4-yl)-1,1a,6,6a-tetrahydrocyclopropa[a]indene-1-carboxamide The title compound was prepared in a method analogous to General Method G using 4-(2-((S)-2-methylazetidin-1-yl)-6,7-dihydro-5H-cyclopenta[d]pyrimidin-4-yl)-1,1a,6,6a-tetrahydrocyclopropa[a]indene-1-carboxylic acid instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid. Isomers were separated on HPLC (0.1% TFA in MeCN-0.1% TFA in H₂O).

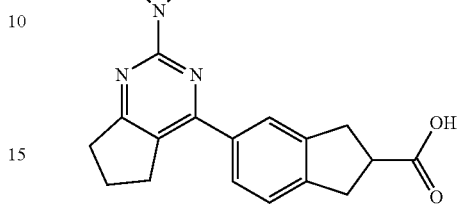

Example 139: 5-(2-((S)-2-methylazetidin-1-yl)-6,7-dihydro-5H-cyclopenta[d]pyrimidin-4-yl)-2,3-dihydro-1H-indene-2-carboxylic acid The title compound was prepared in a method analogous to General Method F using 5-bromoindane-2-carboxylic acid instead of 6-bromo-1,1-dioxo-1,2-benzothiazol-3-one

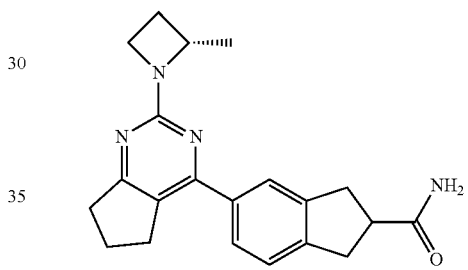

Example 140: 5-(2-((S)-2-methylazetidin-1-yl)-6,7-dihydro-5H-cyclopenta[d]pyrimidin-4-yl)-2,3-dihydro-1H-indene-2-carboxamide The title compound was prepared in a method analogous to General Method G using 5-(2-((S)-2-methylazetidin-1-yl)-6,7-dihydro-5H-cyclopenta[d]pyrimidin-4-yl)-2,3-dihydro-1H-indene-2-carboxylic acid instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid.

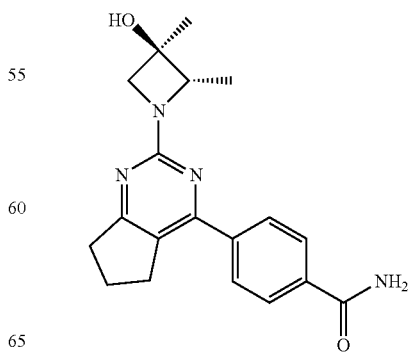

Example 141: 4-(24(2S,3R)-3-hydroxy-2,3-dimethylazetidin-1-yl)-6,7-dihydro-5H-cyclopenta[d]pyrimidin-4-yl)benzamide The title compound was prepared in a method analogous to General Method B using (2S,3R)-2,3-dimethylazetidin-3-ol (R)-camphorsulfonic acid salt and 4-(2-chloro-6,7-dihydro-5H-cyclopenta[d]pyrimidin-4-yl)benzamide instead of (S)-2-methyl azetidine and 2-chloro-4-(pyridin-3-yl)-6,7-dihydro-5H-cyclopenta[d]pyrimidine, respectively.

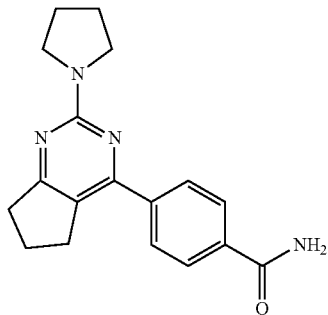 [SMILES: NC(=O)c1ccc(-c2nc(N3CCCC3)nc3c2CCC3)cc1]

Example 142: 4-(2-(pyrrolidin-1-yl)-6,7-dihydro-5H-cyclopenta[d]pyrimidin-4-yl)benzamide The title compound was prepared in a method analogous to General Method B using pyrrolidine and 4-(2-chloro-6,7-dihydro-5H-cyclopenta[d]pyrimidin-4-yl)benzamide instead of (S)-2-methyl azetidine and 2-chloro-4-(pyridin-3-yl)-6,7-dihydro-5H-cyclopenta[d]pyrimidine, respectively.

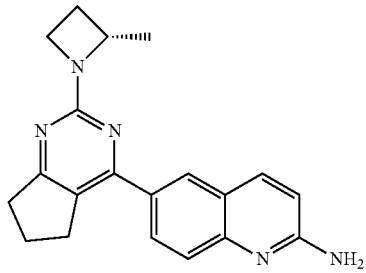 [SMILES: C[C@H]1CCN1c1nc2c(c(-c3ccc4nc(N)ccc4c3)n1)CCC2]

Example 143: (S)-6-(2-(2-methylazetidin-1-yl)-6,7-dihydro-5H-cyclopenta[d]pyrimidin-4-yl)quinolin-2-amine The title compound was prepared in a method analogous to General Method A using 6-(4,4,5,5-tetramethyl-1,3,2-dioxaborolan-2-yl)quinolin-2-amine and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

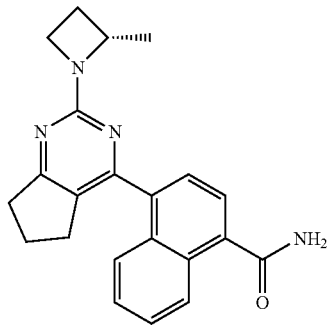 [SMILES: C[C@H]1CCN1c1nc2c(c(-c3ccc(C(N)=O)c4ccccc34)n1)CCC2]

Example 144: (S)-4-(2-(2-methylazetidin-1-yl)-6,7-dihydro-5H-cyclopenta[d]pyrimidin-4-yl)-1-naphthamide The title compound was prepared in a method analogous to General Method A using 4-(4,4,5,5-tetramethyl-1,3,2-dioxaborolan-2-yl)-1-naphthamide and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

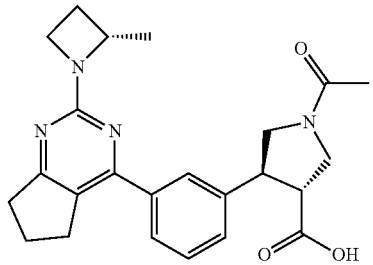 [SMILES: CC(=O)N1C[C@H](C(=O)O)[C@@H](c2cccc(-c3nc(N4CC[C@@H]4C)nc4c3CCC4)c2)C1]

Example 145: (3R,4S)-1-acetyl-4-(3-(2-((S)-2-methylazetidin-1-yl)-6,7-dihydro-5H-cyclopenta[d]pyrimidin-4-yl)phenyl)pyrrolidine-3-carboxylic acid A vial was charged with methyl (rac)-(3R*,4S*)-4-(3-bromophenyl)pyrrolidine-3-carboxylate (500 mg, 1.56 mmol, 1.0 equiv.), Et₃N (0.87 mL, 6.24 mmol, 4.0 equiv.), and DCM (10 mL). Acetic anhydride (0.30 mL, 3.12 mmol, 2.0 equiv.) was added dropwise. The mixture was allowed to stir at ambient temperature for 1 hr. The mixture was concentrated and subject to flash column chromatography (ethyl acetate-methanol) to give methyl 1-acetyl-4-(3-bromophenyl)pyrrolidine-3-carboxylate (235 mg, 0.72 mmol).

The title compound was prepared in a method analogous to General Method F, using 1-acetyl-4-(3-bromophenyl)pyrrolidine-3-carboxylate instead of 6-bromo-1,1-dioxo-1,2-benzothiazol-3-one, followed by General Method C.

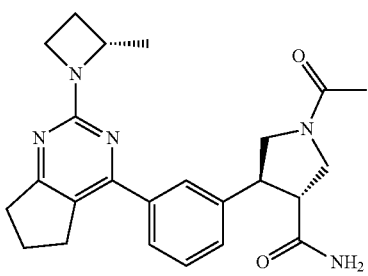 [SMILES: CC(=O)N1C[C@H](C(N)=O)[C@@H](c2cccc(-c3nc(N4CC[C@@H]4C)nc4c3CCC4)c2)C1]

Example 146: (3R*,4S*)-1-acetyl-4-(3-(2-((S)-2-methylazetidin-1-yl)-6,7-dihydro-5H-cyclopenta[d]pyrimidin-4-yl)phenyl)pyrrolidine-3-carboxamide The title compound was prepared in a method analogous to General Method G using (3R*,4S*)-1-acetyl-4-(3-(2-((S)-2-methylazetidin-1-yl)-6,7-dihydro-5H-cyclopenta[d]pyrimidin-4-yl)phenyl)pyrrolidine-3-carboxylic acid instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid.

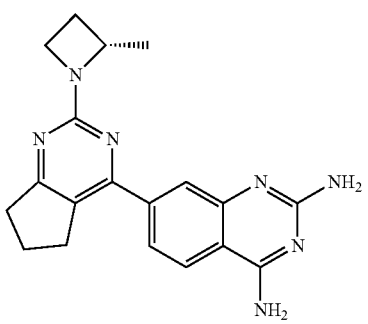 [SMILES: C[C@H]1CCN1c1nc2c(c(-c3ccc4c(N)nc(N)nc4c3)n1)CCC2]

Example 147: (S)-7-(2-(2-methylazetidin-1-yl)-6,7-dihydro-5H-cyclopenta[d]pyrimidin-4-yl)quinazoline-2,4-diamine The title compound was prepared in a method analogous to General Method F using 7-bromoquinazoline-2,4-diamine instead of 6-bromo-1,1-dioxo-1,2-benzothiazol-3-one

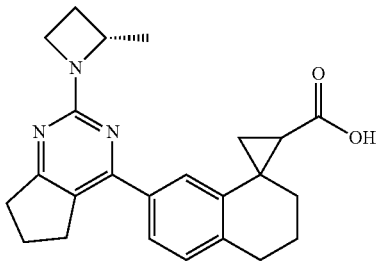 [SMILES: C[C@H]1CCN1c1nc2c(c(-c3ccc4c(c3)C3(CCC4)CC3C(=O)O)n1)CCC2]

Example 148: 7'-(2-((S)-2-methylazetidin-1-yl)-6,7-dihydro-5H-cyclopenta[d]pyrimidin-4-yl)-3',4'-dihydro-2'H-spiro[cyclopropane-1,1'-naphthalene]-2-carboxylic acid The title compound was prepared in a method analogous to General Method F using 7'-bromo-3',4'-dihydro-2'H-spiro[cyclopropane-1,1'-naphthalene]-2-carboxylic acid instead of 6-bromo-1,1-dioxo-1,2-benzothiazol-3-one

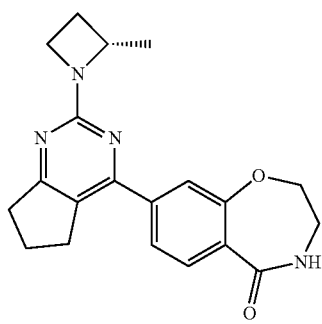 [SMILES: C[C@H]1CCN1c1nc2c(c(-c3ccc4c(c3)OCCNC4=O)n1)CCC2]

Example 149: (S)-8-(2-(2-methylazetidin-1-yl)-6,7-dihydro-5H-cyclopenta[d]pyrimidin-4-yl)-3,4-dihydrobenzo[f][1,4]oxazepin-5(2H)-one The title compound was prepared in a method analogous to General Method A using 8-(4,4,5,5-tetramethyl-1,3,2-dioxaborolan-2-yl)-3,4-dihydrobenzo[f][1,4]oxazepin-5(2H)-one and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

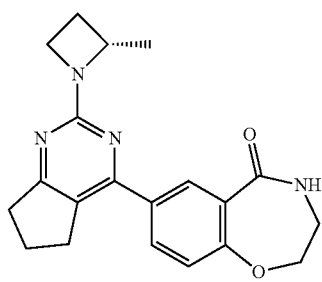 [SMILES: C[C@H]1CCN1c1nc2c(c(-c3ccc4c(c3)C(=O)NCCO4)n1)CCC2]

Example 150: (S)-7-(2-(2-methylazetidin-1-yl)-6,7-dihydro-5H-cyclopenta[d]pyrimidin-4-yl)-3,4-dihydrobenzo[f][1,4]oxazepin-5(2H)-one The title compound was prepared in a method analogous to General Method A using 7-(4,4,5,5-tetramethyl-1,3,2-dioxaborolan-2-yl)-3,4-dihydrobenzo[f][1,4]oxazepin-5(2H)-one and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

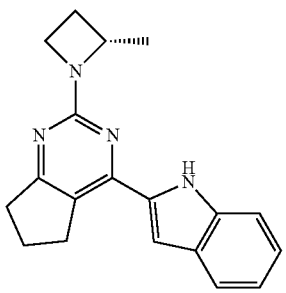

Example 151: (S)-4-(1H-indol-2-yl)-2-(2-methyl-azetidin-1-yl)-6,7-dihydro-5H-cyclopenta[d]pyrimidine The title compound was prepared in a method analogous to General Method A using (1-tert-butoxycarbonylindol-2-yl)boronic acid and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively, followed by General Method I.

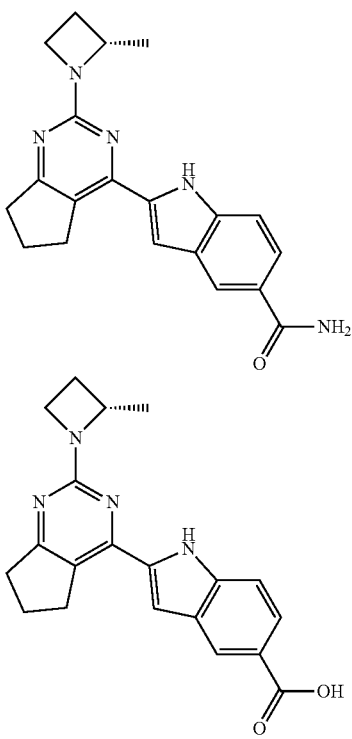

Example 152: (S)-2-(2-(2-methylazetidin-1-yl)-6,7-dihydro-5H-cyclopenta[d]pyrimidin-4-yl)-1H-indole-5-carboxamide Example 153: (S)-2-(2-(2-methylazetidin-1-yl)-6,7-dihydro-5H-cyclopenta[d]pyrimidin-4-yl)-1H-indole-5-carboxylic acid The title compounds were prepared in a method analogous to General Method A using (1-tert-butoxycarbonyl-5-cyano-indol-2-yl)boronic acid and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively, followed by General Method I and General Method J. The mixture of the two compounds was separated by HPLC (0.1% TFA in MeCN-0.1% TFA in H₂O).

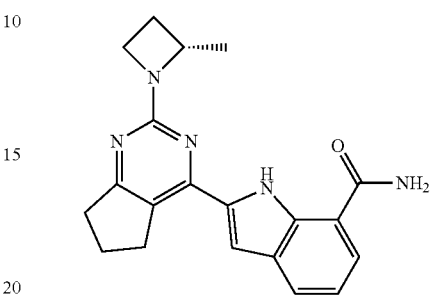

Example 154: (S)-2-(2-(2-methylazetidin-1-yl)-6,7-dihydro-5H-cyclopenta[d]pyrimidin-4-yl)-1H-indole-7-carboxamide The title compounds were prepared in a method analogous to General Method A using (1-tert-butoxycarbonyl-7-methoxycarbonyl-indol-2-yl)boronic acid and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively, followed by General Method I, General Method C, and General Method G.

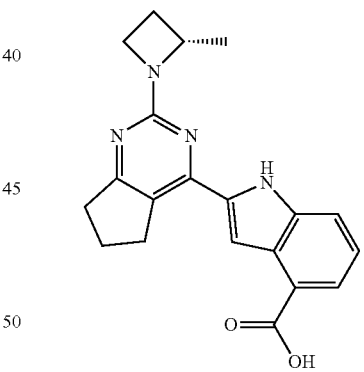

Example 155: (S)-2-(2-(2-methylazetidin-1-yl)-6,7-dihydro-5H-cyclopenta[d]pyrimidin-4-yl)-1H-indole-4-carboxylic acid The title compounds were prepared in a method analogous to General Method A using (1-tert-butoxycarbonyl-4-ethoxycarbonyl-indol-2-yl)boronic acid and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively, followed by General Method I and General Method C.

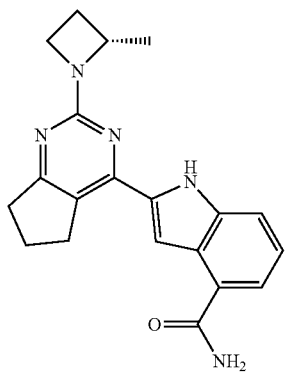 [SMILES: C[C@H]1CCN1c1nc2c(c(-c3cc4c(C(N)=O)cccc4[nH]3)n1)CCC2]

Example 156: (S)-2-(2-(2-methylazetidin-1-yl)-6,7-dihydro-5H-cyclopenta[d]pyrimidin-4-yl)-1H-indole-4-carboxamide The title compound was prepared in a method analogous to General Method G using (S)-2-(2-(2-methylazetidin-1-yl)-6,7-dihydro-5H-cyclopenta[d]pyrimidin-4-yl)-1H-indole-4-carboxylic acid instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid.

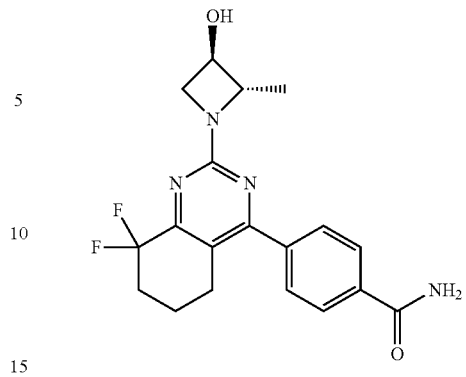

Example 158: 4-(8,8-difluoro-2-(2S,3R)-3-hydroxy-2-methylazetidin-1-yl)-5,6,7,8-tetrahydroquinazolin-4-yl)benzamide The title compound was prepared in a method analogous to General Method M using 4-chloro-8,8-difluoro-2-(methylthio)-5,6,7,8-tetrahydroquinazoline instead of 4-(7,7-difluoro-2-(methylthio)-6,7-dihydro-5H-cyclopenta[d]pyrimidin-4-yl)benzamide, followed by General Method B using (2S,3R)-2-methylazetidin-3-ol instead of (S)-2-methylazetidine.

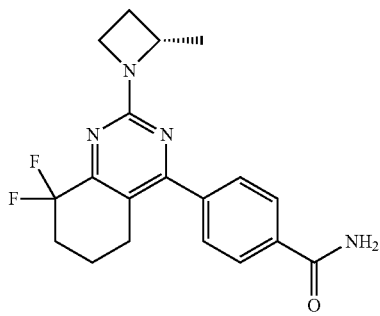 [SMILES: C[C@H]1CCN1c1nc(-c2ccc(C(N)=O)cc2)c2c(n1)C(F)(F)CCC2]

Example 157: (S)-4-(8,8-difluoro-2-(2-methylazetidin-1-yl)-5,6,7,8-tetrahydroquinazolin-4-yl)benzamide The title compound was prepared in a method analogous to General Method M using 4-chloro-8,8-difluoro-2-(methylthio)-5,6,7,8-tetrahydroquinazoline instead of 4-(7,7-difluoro-2-(methylthio)-6,7-dihydro-5H-cyclopenta[d]pyrimidin-4-yl)benzamide, followed by General Method B.

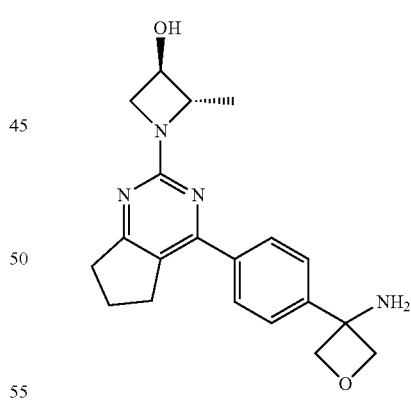

Example 159: (2S,3R)-1-(4-(4-(3-aminooxetan-3-yl)phenyl)-6,7-dihydro-5H-cyclopenta[d]pyrimidin-2-yl)-2-methylazetidin-3-ol The title compound was prepared in a method analogous to General Method A using tert-butyl (3-(4-(4,4,5,5-tetramethyl-1,3,2-dioxaborolan-2-yl)phenyl)oxetan-3-yl)carbamate instead of 3-pyridylboronic acid, followed by General Method B using (2S,3R)-2-methylazetidin-3-ol instead of (S)-2-methylazetidine and General Method I.

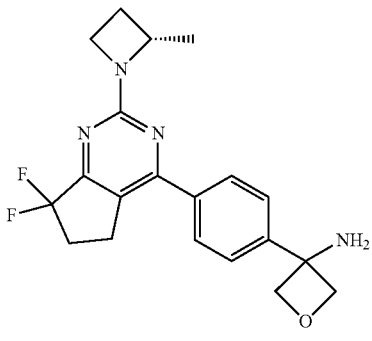 [SMILES: C[C@H]1CCN1c1nc(-c2ccc(C3(N)COC3)cc2)c2c(n1)C(F)(F)CC2]

Example 160: (S)-3-(4-(7,7-difluoro-2-(2-methyl-azetidin-1-yl)-6,7-dihydro-5H-cyclopenta[d]pyrimidin-4-yl)phenyl)oxetan-3-amine The title compound was prepared in a method analogous to General Method M using tert-butyl (3-(4-(4,4,5,5-tetramethyl-1,3,2-dioxaborolan-2-yl)phenyl)oxetan-3-yl)carbamate instead of (4-carbamoylphenyl)boronic acid, followed by General Method B and General Method I.

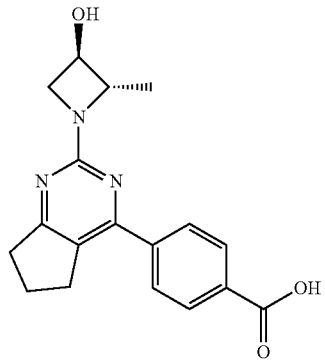

Example 162: 4-(2-((2S,3R)-3-hydroxy-2-methyl-azetidin-1-yl)-6,7-dihydro-5H-cyclopenta[d]pyrimidin-4-yl)benzoic acid The title compound was prepared in a method analogous to General Method A using 4-boronobenzoic acid instead of 3-pyridylboronic acid, followed by General Method B using (2S,3R)-2-methylazetidin-3-ol instead of (S)-2-methylazetidine

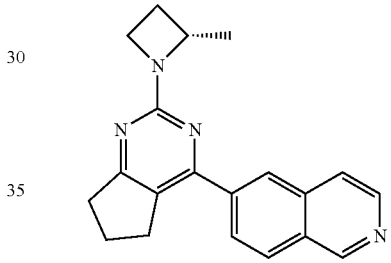

Example 163: (S)-6-(2-(2-methylazetidin-1-yl)-6,7-dihydro-5H-cyclopenta[d]pyrimidin-4-yl)isoquinoline The title compound was prepared in a method analogous to General Method A using 6-isoquinolylboronic acid and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

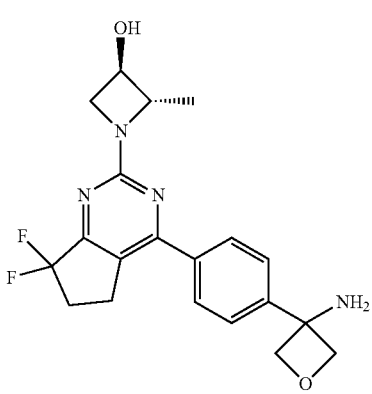 [SMILES: C[C@H]1[C@H](O)CN1c1nc(-c2ccc(C3(N)COC3)cc2)c2c(n1)C(F)(F)CC2]

Example 161: (2S,3R)-1-(4-(4-(3-aminooxetan-3-yl)phenyl)-7,7-difluoro-6,7-dihydro-5H-cyclopenta[d]pyrimidin-2-yl)-2-methylazetidin-3-ol The title compound was prepared in a method analogous to General Method M using tert-butyl (3-(4-(4,4,5,5-tetramethyl-1,3,2-dioxaborolan-2-yl)phenyl)oxetan-3-yl)carbamate instead of (4-carbamoylphenyl)boronic acid, followed by General Method B using (2S,3R)-2-methylazetidin-3-ol instead of (S)-2-methylazetidine and General Method I.

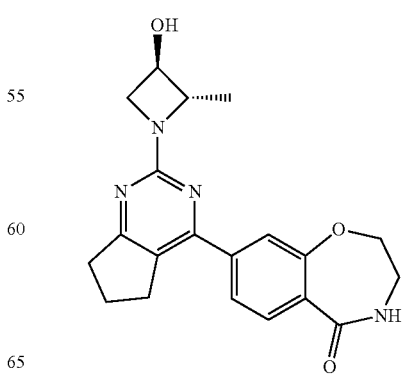

Example 164: 8-(2-((2S,3R)-3-hydroxy-2-methyl-azetidin-1-yl)-6,7-dihydro-5H-cyclopenta[d]pyrimidin-4-yl)-3,4-dihydrobenzo[f][1,4]oxazepin-5(2H)-one The title compound was prepared in a method analogous to General Method A using 8-(4,4,5,5-tetramethyl-1,3,2-dioxaborolan-2-yl)-3,4-dihydrobenzo[f][1,4]oxazepin-5 (2H)-one instead of 3-pyridylboronic acid, followed by General Method B using (2S,3R)-2-methylazetidin-3-ol instead of (S)-2-methylazetidine

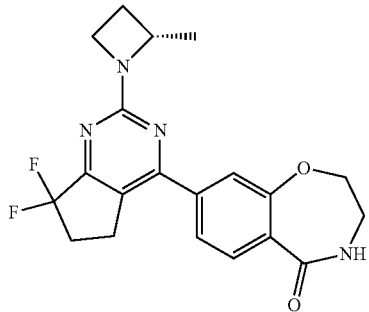 [SMILES: C[C@H]1CCN1c1nc(-c2ccc3c(c2)OCCNC3=O)c2c(n1)C(F)(F)CC2]

Example 165: (S)-8-(7,7-difluoro-2-(2-methylazetidin-1-yl)-6,7-dihydro-5H-cyclopenta[d]pyrimidin-4-yl)-3,4-dihydrobenzo[f][1,4]oxazepin-5(2H)-one The title compound was prepared in a method analogous to General Method M using 8-(4,4,5,5-tetramethyl-1,3,2-dioxaborolan-2-yl)-3,4-dihydrobenzo[f][1,4]oxazepin-5 (2H)-one instead of (4-carbamoylphenyl)boronic acid, followed by General Method B.

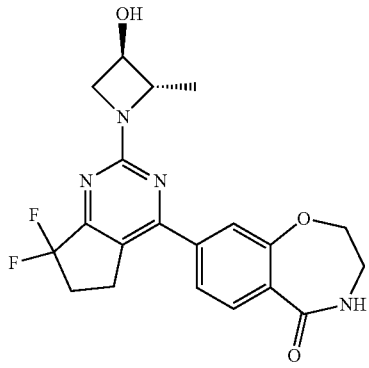

Example 166: 8-(7,7-difluoro-2-((2S,3R)-3-hydroxy-2-methylazetidin-1-yl)-6,7-dihydro-5H-cyclopenta[d]pyrimidin-4-yl)-3,4-dihydrobenzo[f][1,4]oxazepin-5(2H)-one The title compound was prepared in a method analogous to General Method M using 8-(4,4,5,5-tetramethyl-1,3,2-dioxaborolan-2-yl)-3,4-dihydrobenzo[f][1,4]oxazepin-5 (2H)-one instead of (4-carbamoylphenyl)boronic acid, followed by General Method B using (2S,3R)-2-methylazetidin-3-ol instead of (S)-2-methylazetidine

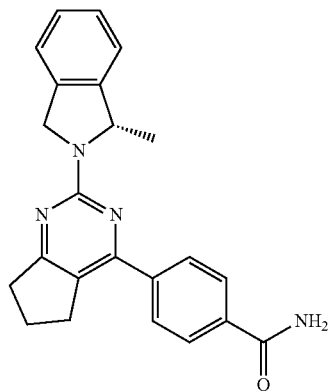 [SMILES: C[C@H]1c2ccccc2CN1c1nc2c(c(-c3ccc(C(N)=O)cc3)n1)CCC2]

Example 167: (S)-4-(2-(1-methylisoindolin-2-yl)-6,7-dihydro-5H-cyclopenta[d]pyrimidin-4-yl)benzamide The title compound was prepared in a method analogous to General Method B using (S)-1-methylisoindoline and 4-(2-chloro-6,7-dihydro-5H-cyclopenta[d]pyrimidin-4-yl) benzamide instead of (S)-2-methyl azetidine and 2-chloro-4-(pyridin-3-yl)-6,7-dihydro-5H-cyclopenta[d]pyrimidine, respectively.

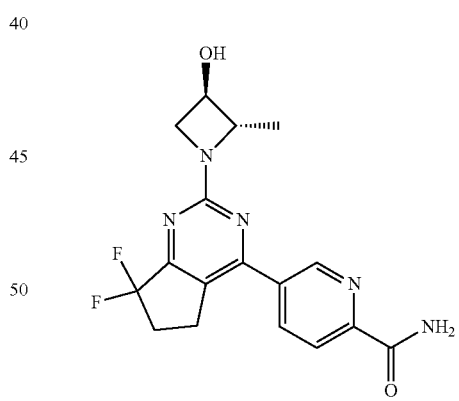

Example 168: 5-(7,7-difluoro-2-((2S,3R)-3-hydroxy-2-methylazetidin-1-yl)-6,7-dihydro-5H-cyclopenta[d]pyrimidin-4-yl)picolinamide The title compound was prepared in a method analogous to General Method M using 5-(4,4,5,5-tetramethyl-1,3,2-dioxaborolan-2-yl)picolinamide instead of (4-carbamoylphenyl)boronic acid, followed by General Method B using (2S,3R)-2-methylazetidin-3-ol instead of (S)-2-methylazetidine.

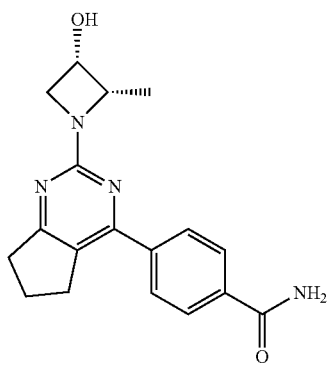 [SMILES: C[C@H]1[C@@H](O)CN1c1nc2c(c(-c3ccc(C(N)=O)cc3)n1)CCC2]

Example 169: 4-(2-((2S,3S)-3-hydroxy-2-methyl-azetidin-1-yl)-6,7-dihydro-5H-cyclopenta[d]pyrimidin-4-yl)benzamide The title compound was prepared in a method analogous to General Method A using (4-carbamoylphenyl)boronic acid instead of 3-pyridylboronic acid, followed by General Method B using (2S,3S)-2-methylazetidin-3-ol instead of (S)-2-methylazetidine

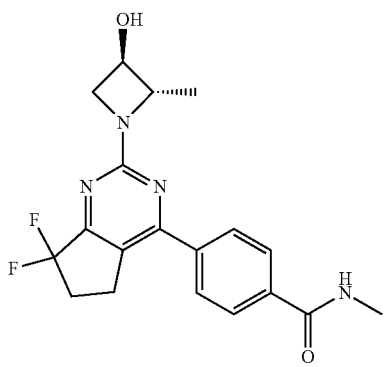

Example 171: 4-(7,7-difluoro-2-((2S,3R)-3-hydroxy-2-methylazetidin-1-yl)-6,7-dihydro-5H-cyclopenta[d]pyrimidin-4-yl)-N-methylbenzamide The title compound was prepared in a method analogous to General Method M using N-methyl-4-(4,4,5,5-tetramethyl-1,3,2-dioxaborolan-2-yl)benzamide instead of (4-carbamoylphenyl)boronic acid, followed by General Method B using (2S,3R)-2-methylazetidin-3-ol instead of (S)-2-methylazetidine

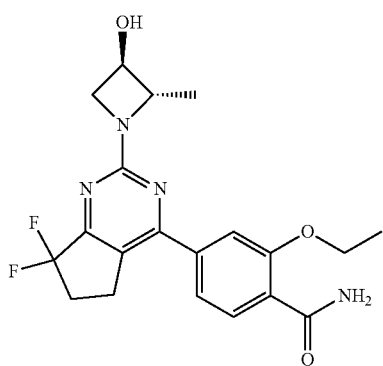 [SMILES: CCOc1cc(-c2nc(N3C[C@@H](O)[C@@H]3C)nc3c2CCC3(F)F)ccc1C(N)=O]

Example 170: 4-(7,7-difluoro-2-((2S,3R)-3-hydroxy-2-methylazetidin-1-yl)-6,7-dihydro-5H-cyclopenta[d]pyrimidin-4-yl)-2-ethoxybenzamide The title compound was prepared in a method analogous to General Method M using 2-ethoxy-4-(4,4,5,5-tetramethyl-1,3,2-dioxaborolan-2-yl)benzamide instead of (4-carbamoylphenyl)boronic acid, followed by General Method B using (2S,3R)-2-methylazetidin-3-ol instead of (S)-2-methylazetidine

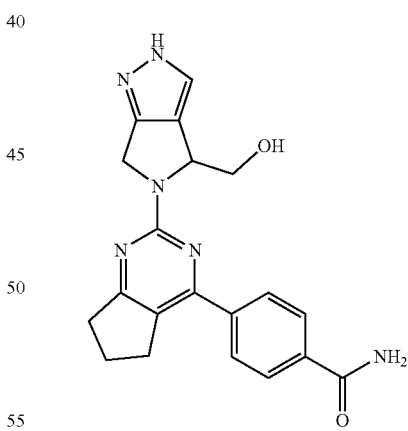

Example 172: 4-(2-(4-(hydroxymethyl)-2,6-dihydropyrrolo[3,4-c]pyrazol-5(4H)-yl)-6,7-dihydro-5H-cyclopenta[d]pyrimidin-4-yl)benzamide The title compound was prepared in a method analogous to General Method A using (4-carbamoylphenyl)boronic acid instead of 3-pyridylboronic acid, followed by General Method B using (2,4,5,6-tetrahydropyrrolo[3,4-c]pyrazol-4-yl)methanol instead of (S)-2-methylazetidine

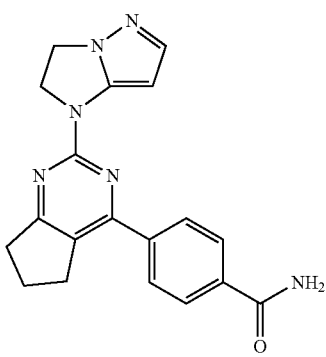 [SMILES: NC(=O)c1ccc(-c2nc(N3CCn4nccc43)nc3c2CCC3)cc1]

Example 173: 4-(2-(2,3-dihydro-1H-imidazo[1,2-b]pyrazol-1-yl)-6,7-dihydro-5H-cyclopenta[d]pyrimidin-4-yl)benzamide The title compound was prepared according to General Method N.

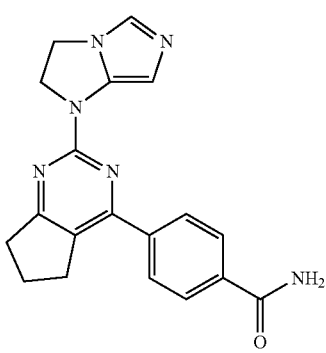 [SMILES: NC(=O)c1ccc(-c2nc(N3CCn4cncc43)nc3c2CCC3)cc1]

Example 174: 4-(2-(2,3-dihydro-1H-imidazo[1,5-a]imidazol-1-yl)-6,7-dihydro-5H-cyclopenta[d]pyrimidin-4-yl)benzamide The title compound was prepared in a method analogous to General Method N, using 2,3-dihydro-1H-imidazo[1,5-a]imidazole instead of 2,3-dihydro-1H-imidazo[1,2-b]pyrazole.

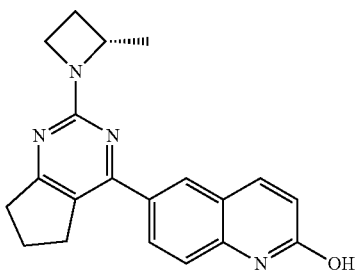 [SMILES: C[C@H]1CCN1c1nc2c(c(-c3ccc4nc(O)ccc4c3)n1)CCC2]

Example 175: (S)-6-(2-(2-methylazetidin-1-yl)-6,7-dihydro-5H-cyclopenta[d]pyrimidin-4-yl)quinolin-2-ol The title compound was prepared in a method analogous to General Method A, using 6-(4,4,5,5-tetramethyl-1,3,2-dioxaborolan-2-yl)quinolin-2-ol and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

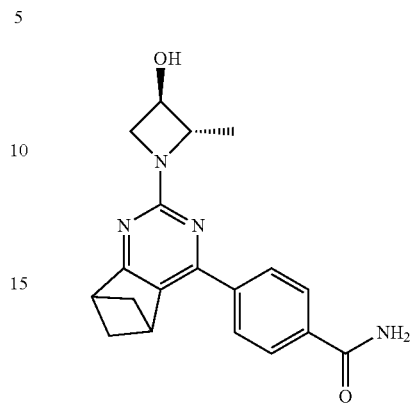

Example 176: 4-(2-((2S,3R)-3-hydroxy-2-methylazetidin-1-yl)-6,7-dihydro-5H-5,7-methanocyclopenta[d]pyrimidin-4-yl)benzamide The title compound was prepared in a method analogous to General Method H, using ethyl 3-oxobicyclo[2.1.1]hexane-2-carboxylate and (3-carbamoylphenyl)boronic acid instead of methyl 2-oxobicyclo[3.1.0]hexane-3-carboxylate and (4-carbamoylphenyl)boronic acid, respectively.

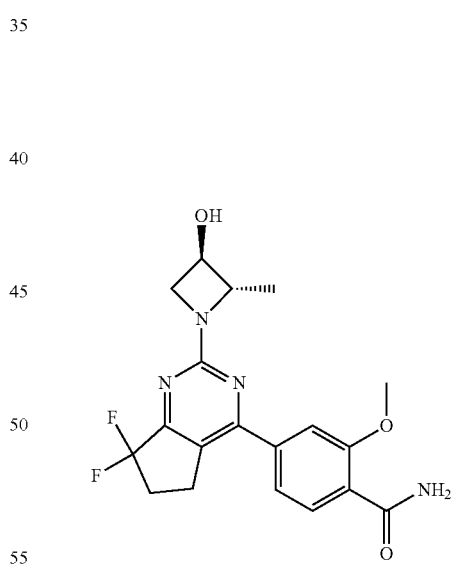

Example 177: 4-(7,7-difluoro-2-((2S,3R)-3-hydroxy-2-methylazetidin-1-yl)-6,7-dihydro-5H-cyclopenta[d]pyrimidin-4-yl)-2-methoxybenzamide The title compound was prepared in a method analogous to General Method M using 2-methoxy-4-(4,4,5,5-tetramethyl-1,3,2-dioxaborolan-2-yl)benzamide instead of (4-carbamoylphenyl)boronic acid, followed by General Method B using (2S,3R)-2-methylazetidin-3-ol instead of (S)-2-methylazetidine

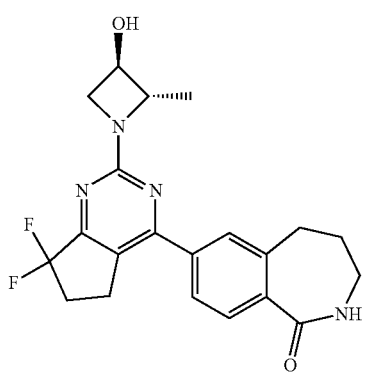 [SMILES: C[C@H]1[C@H](O)CN1c1nc(-c2ccc3c(c2)CCCNC3=O)c2c(n1)C(F)(F)CC2]

Example 178: 7-(7,7-difluoro-2-((2S,3R)-3-hydroxy-2-methylazetidin-1-yl)-6,7-dihydro-5H-cyclopenta[d]pyrimidin-4-yl)-2,3,4,5-tetrahydro-1H-benzo[c]azepin-1-one The title compound was prepared in a method analogous to General Method D, using 7-bromo-2,3,4,5-tetrahydro-1H-benzo[c]azepin-1-one instead of ethyl 2-bromoimidazo[5,1-b]thiazole-7-carboxylate, followed by General Method E using 4-chloro-7,7-difluoro-2-(methylthio)-6,7-dihydro-5H-cyclopenta[d]pyrimidine instead of (S)-4-chloro-2-(2-methylazetidin-1-yl)-6,7-dihydro-5H-cyclopenta[d]pyrimidine, followed by General Method M using 7-(7,7-difluoro-2-(methylthio)-6,7-dihydro-5H-cyclopenta[d]pyrimidin-4-yl)-2,3,4,5-tetrahydro-1H-benzo[c]azepin-1-one instead of 4-(7,7-difluoro-2-(methylthio)-6,7-dihydro-5H-cyclopenta[d]pyrimidin-4-yl)benzamide, followed by General Method B using (2S,3R)-2-methylazetidin-3-ol instead of (S)-2-methylazetidine

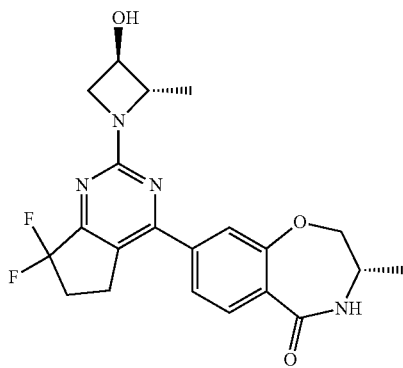 [SMILES: C[C@H]1COc2cc(-c3nc(N4C[C@@H](O)[C@@H]4C)nc4c3CCC4(F)F)ccc2C(=O)N1]

Example 179: (S)-8-(7,7-difluoro-2-((2S,3R)-3-hydroxy-2-methylazetidin-1-yl)-6,7-dihydro-5H-cyclopenta[d]pyrimidin-4-yl)-3-methyl-3,4-dihydrobenzo[f][1,4]oxazepin-5(2H)-one The title compound was prepared according to General Method Q, followed by General Method F, using (S)-8-bromo-3-methyl-3,4-dihydrobenzo[f][1,4]oxazepin-5(2H)-one and 4-chloro-7,7-difluoro-2-(methylthio)-6,7-dihydro-5H-cyclopenta[d]pyrimidine instead of 6-bromo-1,1-dioxo-1,2-benzothiazol-3-one and (S)-4-chloro-2-(2-methylazetidin-1-yl)-6,7-dihydro-5H-cyclopenta[d]pyrimidine, followed by General Method M, followed by General Method B using (2S,3R)-2-methylazetidin-3-ol instead of (S)-2-methylazetidine

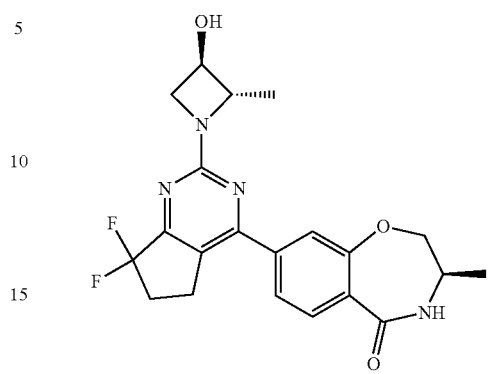

Example 180: (R)-8-(7,7-difluoro-2-((2S,3R)-3-hydroxy-2-methylazetidin-1-yl)-6,7-dihydro-5H-cyclopenta[d]pyrimidin-4-yl)-3-methyl-3,4-dihydrobenzo[f][1,4]oxazepin-5(2H)-one The title compound was prepared in a method analogous to General Method Q, using tert-butyl (R)-(1-hydroxypropan-2-yl)carbamate instead of tert-butyl (S)-(1-hydroxypropan-2-yl)carbamate, followed by General Method F, using (R)-8-bromo-3-methyl-3,4-dihydrobenzo[f][1,4]oxazepin-5(2H)-one and 4-chloro-7,7-difluoro-2-(methylthio)-6,7-dihydro-5H-cyclopenta[d]pyrimidine instead of 6-bromo-1,1-dioxo-1,2-benzothiazol-3-one and (S)-4-chloro-2-(2-methylazetidin-1-yl)-6,7-dihydro-5H-cyclopenta[d]pyrimidine, followed by General Method M, followed by General Method B using (2S,3R)-2-methylazetidin-3-ol instead of (S)-2-methylazetidine

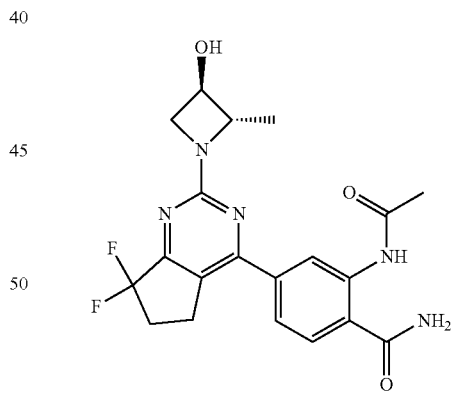

Example 181: 2-acetamido-4-(7,7-difluoro-2-((2S,3R)-3-hydroxy-2-methylazetidin-1-yl)-6,7-dihydro-5H-cyclopenta[d]pyrimidin-4-yl)benzamide The title compound was prepared in a method analogous to General Method M using 2-acetamido-4-(4,4,5,5-tetramethyl-1,3,2-dioxaborolan-2-yl)benzamide instead of (4-carbamoylphenyl)boronic acid, followed by General Method B using (2S,3R)-2-methylazetidin-3-ol instead of (S)-2-methylazetidine

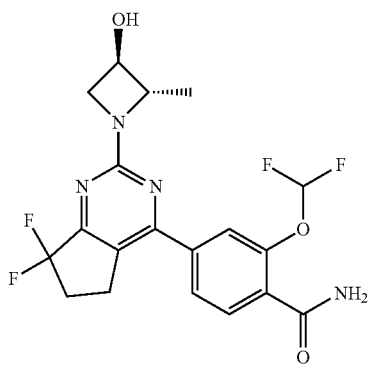 [SMILES: C[C@H]1[C@H](O)CN1c1nc(-c2ccc(C(N)=O)c(OC(F)F)c2)c2c(n1)C(F)(F)CC2]

Example 182: 4-(7,7-difluoro-2-((2S,3R)-3-hydroxy-2-methylazetidin-1-yl)-6,7-dihydro-5H-cyclopenta[d]pyrimidin-4-yl)-2-(difluoromethoxy)benzamide The title compound was prepared in a method analogous to General Method F, using methyl 4-bromo-2-(difluoromethoxy)benzoate and 4-chloro-7,7-difluoro-2-(methylthio)-6,7-dihydro-5H-cyclopenta[d]pyrimidine instead of 6-bromo-1,1-dioxo-1,2-benzothiazol-3-one and (S)-4-chloro-2-(2-methylazetidin-1-yl)-6,7-dihydro-5H-cyclopenta[d]pyrimidine, followed by General Method M using methyl 4-(7,7-difluoro-2-(methylthio)-6,7-dihydro-5H-cyclopenta[d]pyrimidin-4-yl)-2-(difluoromethoxy)benzoate instead of 4-(7,7-difluoro-2-(methylthio)-6,7-dihydro-5H-cyclopenta[d]pyrimidin-4-yl)benzamide, followed by General Method B using (2S,3R)-2-methylazetidin-3-ol instead of (S)-2-methylazetidine, followed by General Method C and General Method G.

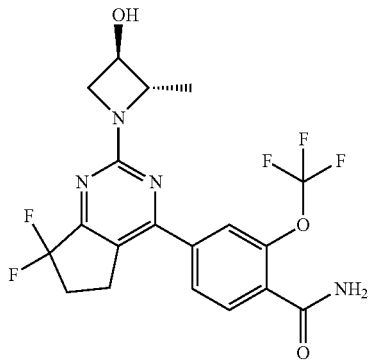 [SMILES: C[C@H]1[C@H](O)CN1c1nc(-c2ccc(C(N)=O)c(OC(F)(F)F)c2)c2c(n1)C(F)(F)CC2]

Example 183: 4-(7,7-difluoro-2-((2S,3R)-3-hydroxy-2-methylazetidin-1-yl)-6,7-dihydro-5H-cyclopenta[d]pyrimidin-4-yl)-2-(trifluoromethoxy)benzamide The title compound was prepared in a method analogous to General Method M using methyl 4-(4,4,5,5-tetramethyl-1,3,2-dioxaborolan-2-yl)-2-(trifluoromethoxy)benzoate instead of (4-carbamoylphenyl)boronic acid, followed by General Method B using (2S,3R)-2-methylazetidin-3-ol instead of (S)-2-methylazetidine, followed by General Method C and General Method G.

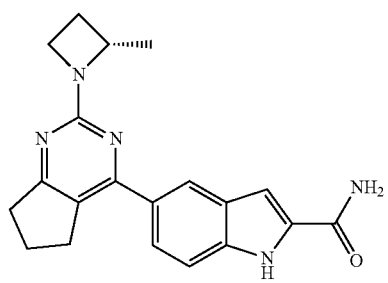 [SMILES: C[C@H]1CCN1c1nc2c(c(-c3ccc4[nH]c(C(N)=O)cc4c3)n1)CCC2]

Example 184: 5-[2-[(2S)-2-methylazetidin-1-yl]-6,7-dihydro-5H-cyclopenta[d]pyrimidin-4-yl]-1H-indole-2-carboxamide The title compound was prepared in a method analogous to General Method A using 5-(4,4,5,5-tetramethyl-1,3,2-dioxaborolan-2-yl)-1H-indole-2-carboxamide and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

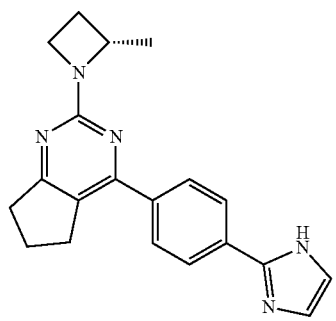 [SMILES: C[C@H]1CCN1c1nc2c(c(-c3ccc(-c4ncc[nH]4)cc3)n1)CCC2]

Example 185: 4-[4-(1H-imidazol-2-yl)phenyl]-2-[(2S)-2-methylazetidin-1-yl]-6,7-dihydro-5H-cyclopenta[d]pyrimidine The title compound was prepared in a method analogous to General Method A using 2-(4-(4,4,5,5-tetramethyl-1,3,2-dioxaborolan-2-yl)phenyl)-1H-imidazole and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

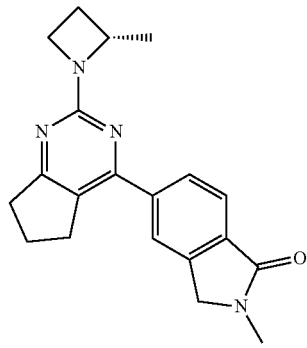 [SMILES: C[C@H]1CCN1c1nc2c(c(-c3ccc4c(c3)CN(C)C4=O)n1)CCC2]

Example 186: 2-methyl-5-[2-[(2S)-2-methylazetidin-1-yl]-6,7-dihydro-5H-cyclopenta[d]pyrimidin-4-yl]isoindolin-1-one The title compound was prepared in a method analogous to General Method A using 2-methyl-5-(4,4,5,5-tetramethyl-1,3,2-dioxaborolan-2-yl)isoindolin-1-one and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

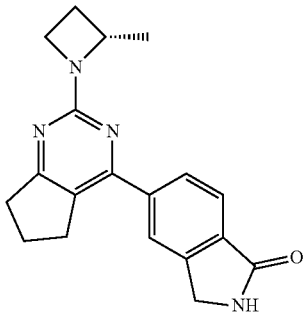 [SMILES: C[C@H]1CCN1c1nc2c(c(-c3ccc4c(c3)CNC4=O)n1)CCC2]

Example 187: 5-[2-[(2S)-2-methylazetidin-1-yl]-6,7-dihydro-5H-cyclopenta[d]pyrimidin-4-yl]isoindolin-1-one The title compound was prepared in a method analogous to General Method A using 5-(4,4,5,5-tetramethyl-1,3,2-dioxaborolan-2-yl)isoindolin-1-one and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

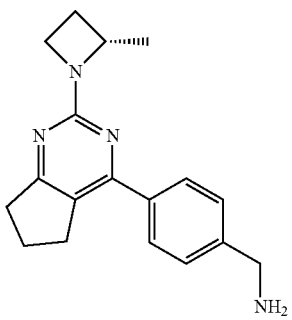 [SMILES: C[C@H]1CCN1c1nc2c(c(-c3ccc(CN)cc3)n1)CCC2]

Example 188: [4-[2-[(2S)-2-methylazetidin-1-yl]-6,7-dihydro-5H-cyclopenta[d]pyrimidin-4-yl]phenyl]methanamine The title compound was prepared in a method analogous to General Method A using (4-(4,4,5,5-tetramethyl-1,3,2-dioxaborolan-2-yl)phenyl)methanamine and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

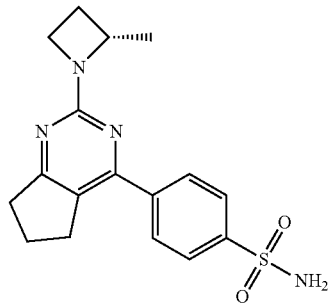 [SMILES: C[C@H]1CCN1c1nc2c(c(-c3ccc(S(N)(=O)=O)cc3)n1)CCC2]

Example 189: 4-[2-[(2S)-2-methylazetidin-1-yl]-6,7-dihydro-5H-cyclopenta[d]pyrimidin-4-yl]benzenesulfonamide The title compound was prepared in a method analogous to General Method A using 4-(4,4,5,5-tetramethyl-1,3,2-dioxaborolan-2-yl)benzenesulfonamide and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

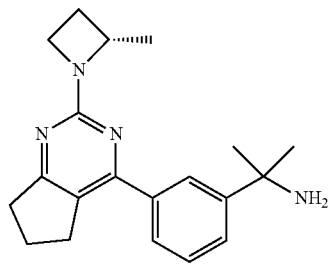 [SMILES: C[C@H]1CCN1c1nc2c(c(-c3cccc(C(C)(C)N)c3)n1)CCC2]

Example 190: 2-[3-[2-[(2S)-2-methylazetidin-1-yl]-6,7-dihydro-5H-cyclopenta[d]pyrimidin-4-yl]phenyl]propan-2-amine The title compound was prepared in a method analogous to General Method A using 2-(3-(4,4,5,5-tetramethyl-1,3,2-dioxaborolan-2-yl)phenyl)propan-2-amine and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

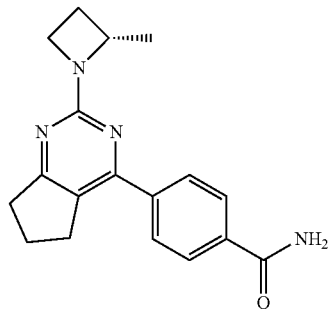

Example 191: 4-[2-[(2S)-2-methylazetidin-1-yl]-6,7-dihydro-5H-cyclopenta[d]pyrimidin-4-yl]benzamide The title compound was prepared in a method analogous to General Method A using 4-(4,4,5,5-tetramethyl-1,3,2-dioxaborolan-2-yl)benzamide and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

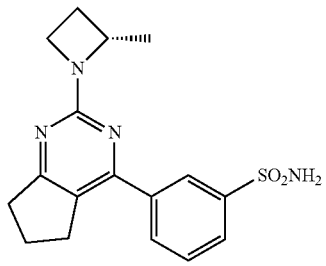 [SMILES: C[C@H]1CCN1c1nc2c(c(-c3cccc(S(N)(=O)=O)c3)n1)CCC2]

Example 192: 3-[2-[(2S)-2-methylazetidin-1-yl]-6,7-dihydro-5H-cyclopenta[d]pyrimidin-4-yl]benzenesulfonamide The title compound was prepared in a method analogous to General Method A using 3-(4,4,5,5-tetramethyl-1,3,2-dioxaborolan-2-yl)benzenesulfonamide and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

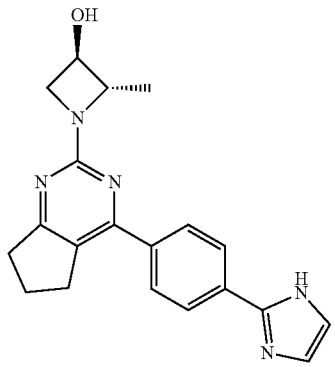 [SMILES: C[C@H]1[C@H](O)CN1c1nc2c(c(-c3ccc(-c4ncc[nH]4)cc3)n1)CCC2]

Example 193: (2S,3R)-1-[4-[4-(1H-imidazol-2-yl)phenyl]-6,7-dihydro-5H-cyclopenta[d]pyrimidin-2-yl]-2-methyl-azetidin-3-ol The title compound was prepared in a method analogous to General Method A using 2-(4-(4,4,5,5-tetramethyl-1,3,2-dioxaborolan-2-yl)phenyl)-1H-imidazole hydrochloride salt instead of 3-pyridylboronic acid, followed by General Method B using (2S,3R)-2-methylazetidin-3-ol instead of (2S)-2-methylazetidine

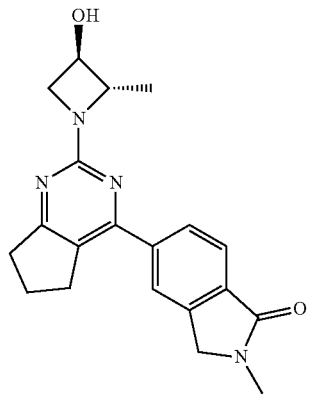 [SMILES: C[C@H]1[C@H](O)CN1c1nc2c(c(-c3ccc4c(c3)CN(C)C4=O)n1)CCC2]

Example 194: 5-[2-[(2S,3R)-3-hydroxy-2-methylazetidin-1-yl]-6,7-dihydro-5H-cyclopenta[d]pyrimidin-4-yl]-2-methyl-isoindolin-1-one The title compound was prepared in a method analogous to General Method A using 2-methyl-5-(4,4,5,5-tetramethyl-1,3,2-dioxaborolan-2-yl)isoindolin-1-one instead of 3-pyridylboronic acid, followed by General Method B using (2S,3R)-2-methylazetidin-3-ol hydrochloride salt instead of (2S)-2-methylazetidine

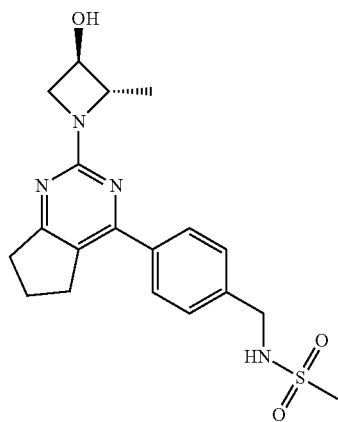 [SMILES: C[C@H]1[C@H](O)CN1c1nc2c(c(-c3ccc(CNS(C)(=O)=O)cc3)n1)CCC2]

Example 195: N-[[4-[2-[(2S,3R)-3-hydroxy-2-methyl-azetidin-1-yl]-6,7-dihydro-5H-cyclopenta[d]pyrimidin-4-yl]phenyl]methyl]methanesulfonamide The title compound was prepared in a method analogous to General Method A using (4-(methylsulfonamidomethyl)phenyl)boronic acid instead of 3-pyridylboronic acid, followed by General Method B using (2S,3R)-2-methylazetidin-3-ol hydrochloride salt instead of (2S)-2-methylazetidine.

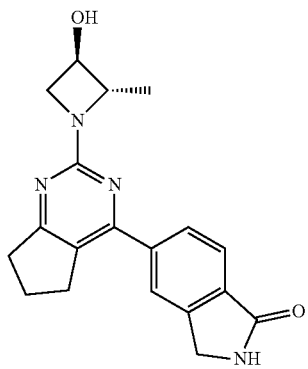 [SMILES: C[C@H]1[C@H](O)CN1c1nc2c(c(-c3ccc4c(c3)CNC4=O)n1)CCC2]

Example 196: 5-[2-[(2S,3R)-3-hydroxy-2-methyl-azetidin-1-yl]-6,7-dihydro-5H-cyclopenta[d]pyrimidin-4-yl]isoindolin-1-one The title compound was prepared in a method analogous to General Method A using 5-(4,4,5,5-tetramethyl-1,3,2-dioxaborolan-2-yl)isoindolin-1-one instead of 3-pyridylboronic acid, followed by General Method B using (2S,3R)-2-methylazetidin-3-ol hydrochloride salt instead of (2S)-2-methylazetidine

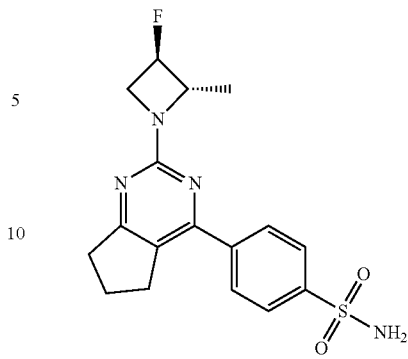

Example 198: 4-[2-[(2S,3R)-3-fluoro-2-methyl-azetidin-1-yl]-6,7-dihydro-5H-cyclopenta[d]pyrimidin-4-yl]benzenesulfonamide The title compound was prepared in a method analogous to General Method A using (4-sulfamoylphenyl)boronic acid instead of 3-pyridylboronic acid, followed by General Method B using (2S,3R)-3-fluoro-2-methylazetidine hydrochloride salt instead of (2S)-2-methylazetidine

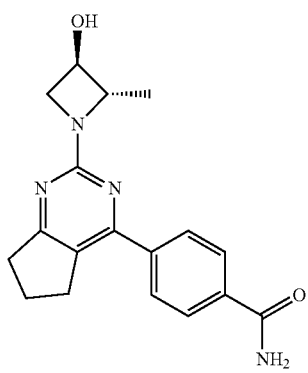

Example 197: 4-[2-[(2S,3R)-3-hydroxy-2-methyl-azetidin-1-yl]-6,7-dihydro-5H-cyclopenta[d]pyrimidin-4-yl]benzamide The title compound was prepared in a method analogous to General Method A using (4-carbamoylphenyl)boronic acid instead of 3-pyridylboronic acid, followed by General Method B using (2S,3R)-3-fluoro-2-methylazetidine hydrochloride salt instead of (2S)-2-methylazetidine

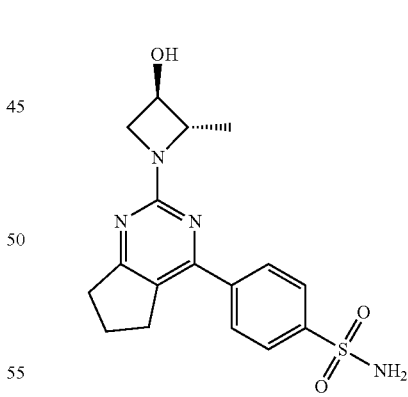

Example 199: 4-[2-[(2S,3R)-3-hydroxy-2-methyl-azetidin-1-yl]-6,7-dihydro-5H-cyclopenta[d]pyrimidin-4-yl]benzenesulfonamide The title compound was prepared in a method analogous to General Method A using (4-sulfamoylphenyl)boronic acid instead of 3-pyridylboronic acid, followed by General Method B (2S,3R)-2-methylazetidin-3-ol hydrochloride salt instead of (2S)-2-methylazetidine

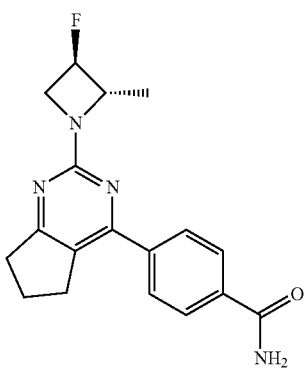 [SMILES: C[C@H]1[C@H](F)CN1c1nc2c(c(-c3ccc(C(N)=O)cc3)n1)CCC2]

Example 200: 4-[2-[(2S,3R)-3-fluoro-2-methyl-azetidin-1-yl]-6,7-dihydro-5H-cyclopenta[d]pyrimidin-4-yl]benzamide The title compound was prepared in a method analogous to General Method A using (4-carbamoylphenyl)boronic acid instead of 3-pyridylboronic acid, followed by General Method B using (2S,3R)-3-fluoro-2-methylazetidine hydrochloride salt instead of (2S)-2-methylazetidine.

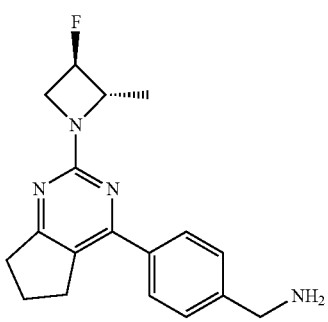 [SMILES: C[C@H]1[C@H](F)CN1c1nc2c(c(-c3ccc(CN)cc3)n1)CCC2]

Example 201: [4-[2-[(2S,3R)-3-fluoro-2-methyl-azetidin-1-yl]-6,7-dihydro-5H-cyclopenta[d]pyrimidin-4-yl]phenyl]methanamine The title compound was prepared in a method analogous to General Method A using (4-(aminomethyl)phenyl)boronic acid hydrochloride instead of 3-pyridylboronic acid, followed by General Method B using (2S,3R)-3-fluoro-2-methylazetidine hydrochloride salt instead of (2S)-2-methylazetidine

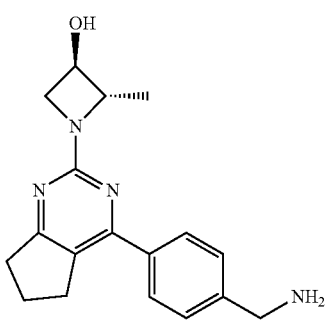 [SMILES: C[C@H]1[C@H](O)CN1c1nc2c(c(-c3ccc(CN)cc3)n1)CCC2]

Example 202: (2S,3R)-1-[4-[4-(aminomethyl)phenyl]-6,7-dihydro-5H-cyclopenta[d]pyrimidin-2-yl]-2-methyl-azetidin-3-ol The title compound was prepared in a method analogous to General Method A using (4-(aminomethyl)phenyl)boronic acid hydrochloride instead of 3-pyridylboronic acid, followed by General Method B (2S,3R)-2-methylazetidin-3-ol hydrochloride salt instead of (2S)-2-methylazetidine

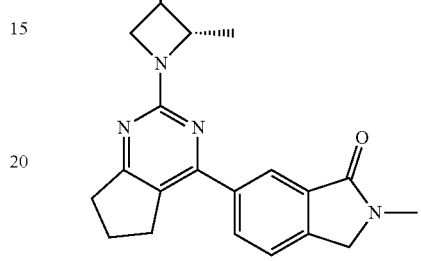

Example 203: 6-[2-[(2S,3R)-3-fluoro-2-methyl-azetidin-1-yl]-6,7-dihydro-5H-cyclopenta[d]pyrimidin-4-yl]-2-methyl-isoindolin-1-one The title compound was prepared in a method analogous to General Method A using 2-methyl-6-(4,4,5,5-tetramethyl-1,3,2-dioxaborolan-2-yl)isoindolin-1-one instead of 3-pyridylboronic acid, followed by General Method B using (2S,3R)-3-fluoro-2-methylazetidine hydrochloride salt instead of (2S)-2-methylazetidine

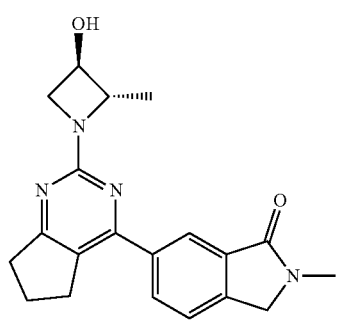 [SMILES: C[C@H]1[C@H](O)CN1c1nc2c(c(-c3ccc4c(c3)C(=O)N(C)C4)n1)CCC2]

Example 204: 6-(2-chloro-6,7-dihydro-5H-cyclopenta[d]pyrimidin-4-yl)-2-methyl-isoindolin-1-one The title compound was prepared in a method analogous to General Method A using 2-methyl-6-(4,4,5,5-tetramethyl-1,3,2-dioxaborolan-2-yl)isoindolin-1-one instead of 3-pyridylboronic acid, followed by General Method B using (2S,3R)-2-methylazetidin-3-ol hydrochloride salt instead of (2S)-2-methylazetidine

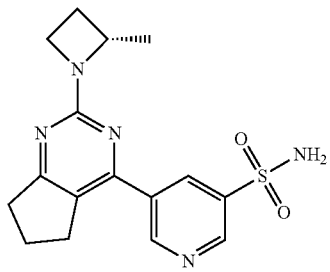 [SMILES: C[C@H]1CCN1c1nc2c(c(-c3cncc(S(N)(=O)=O)c3)n1)CCC2]

Example 205: 5-[2-[(2S)-2-methylazetidin-1-yl]-6,7-dihydro-5H-cyclopenta[d]pyrimidin-4-yl]pyridine-3-sulfonamide The title compound was prepared in a method analogous to General Method A using 5-(4,4,5,5-tetramethyl-1,3,2-dioxaborolan-2-yl)pyridine-3-sulfonamide instead of 3-pyridylboronic acid, followed by General Method B.

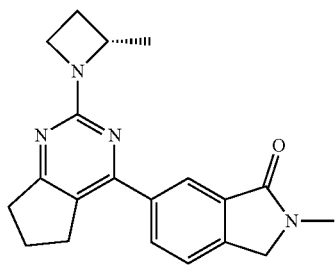 [SMILES: C[C@H]1CCN1c1nc2c(c(-c3ccc4c(c3)C(=O)N(C)C4)n1)CCC2]

Example 206: 2-methyl-6-[2-[(2S)-2-methylazetidin-1-yl]-6,7-dihydro-5H-cyclopenta[d]pyrimidin-4-yl]isoindolin-1-one The title compound was prepared in a method analogous to General Method A using 2-methyl-6-(4,4,5,5-tetramethyl-1,3,2-dioxaborolan-2-yl)isoindolin-1-one instead of 3-pyridylboronic acid, followed by General Method B.

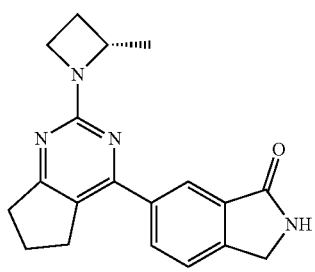 [SMILES: C[C@H]1CCN1c1nc2c(c(-c3ccc4c(c3)C(=O)NC4)n1)CCC2]

Example 207: 6-(2-chloro-6,7-dihydro-5H-cyclopenta[d]pyrimidin-4-yl)isoindolin-1-one The title compound was prepared in a method analogous to General Method A using (3-oxoisoindolin-5-yl)boronic acid instead of 3-pyridylboronic acid, followed by General Method B.

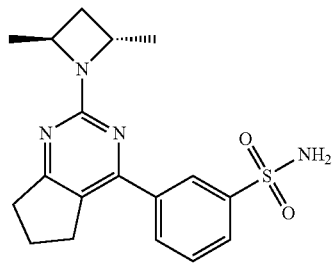 [SMILES: C[C@H]1C[C@H](C)N1c1nc2c(c(-c3cccc(S(N)(=O)=O)c3)n1)CCC2]

Example 208: 3-[2-[(2S,4S)-2,4-dimethylazetidin-1-yl]-6,7-dihydro-5H-cyclopenta[d]pyrimidin-4-yl]benzenesulfonamide The title compound was prepared in a method analogous to General Method A using 3-(4,4,5,5-tetramethyl-1,3,2-dioxaborolan-2-yl)benzenesulfonamide instead of 3-pyridylboronic acid, followed by General Method B using (2S,4S)-2,4-dimethylazetidine hydrochloride salt instead of (2S)-2-methylazetidine

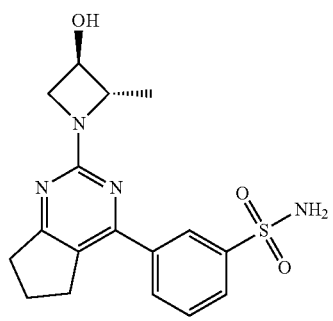 [SMILES: C[C@H]1[C@H](O)CN1c1nc2c(c(-c3cccc(S(N)(=O)=O)c3)n1)CCC2]

Example 209: 3-[2-[(2S,3R)-3-hydroxy-2-methylazetidin-1-yl]-6,7-dihydro-5H-cyclopenta[d]pyrimidin-4-yl]benzenesulfonamide The title compound was prepared in a method analogous to General Method A using 3-(4,4,5,5-tetramethyl-1,3,2-dioxaborolan-2-yl)benzenesulfonamide instead of 3-pyridylboronic acid, followed by General Method B using (2S,3R)-2-methylazetidin-3-ol hydrochloride salt instead of (2S)-2-methylazetidine.

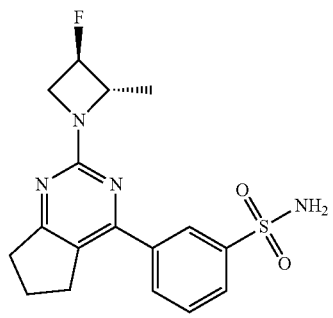 [SMILES: C[C@H]1[C@H](F)CN1c1nc2c(c(-c3cccc(S(N)(=O)=O)c3)n1)CCC2]

Example 210: 3-(2-chloro-6,7-dihydro-5H-cyclopenta[d]pyrimidin-4-yl)benzenesulfonamide The title compound was prepared in a method analogous to General Method A using 3-(4,4,5,5-tetramethyl-1,3,2-dioxaborolan-2-yl)benzenesulfonamide instead of 3-pyridylboronic acid, followed by General Method B using (2S,3R)-3-fluoro-2-methylazetidine hydrochloride salt instead of (2S)-2-methylazetidine

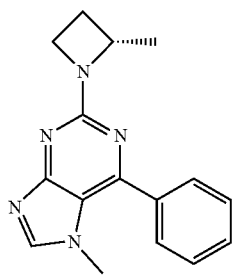 [SMILES: C[C@H]1CCN1c1nc(-c2ccccc2)c2c(ncn2C)n1]

Example 211: 7-methyl-2-[(2S)-2-methylazetidin-1-yl]-6-phenyl-purine

The title compound was prepared in a method analogous to General Method A using phenylboronic acid and 2,6-dichloro-7-methyl-7H-purine instead of 3-pyridylboronic acid and 2,4-dichloro-6,7-dihydro-5H-cyclopenta[d]pyrimidine, respectively, followed by General Method B.

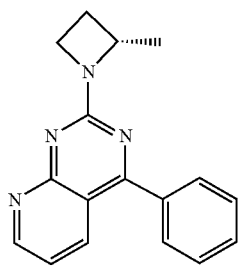 [SMILES: C[C@H]1CCN1c1nc(-c2ccccc2)c2cccnc2n1]

Example 212: 2-[(2S)-2-methylazetidin-1-yl]-4-phenyl-pyrido[2,3-d]pyrimidine The title compound was prepared in a method analogous to General Method A using phenylboronic acid and 2,4-dichloropyrido[2,3-d]pyrimidine instead of 3-pyridylboronic acid and 2,4-dichloro-6,7-dihydro-5H-cyclopenta[d]pyrimidine, respectively, followed by General Method B.

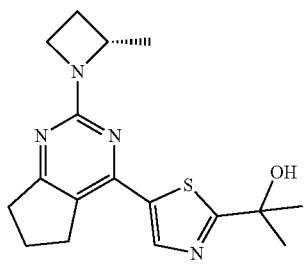 [SMILES: C[C@H]1CCN1c1nc2c(c(-c3cnc(C(C)(C)O)s3)n1)CCC2]

Example 213: 2-[5-[2-[(2S)-2-methylazetidin-1-yl]-6,7-dihydro-5H-cyclopenta[d]pyrimidin-4-yl]thiazol-2-yl]propan-2-ol The title compound was prepared in a method analogous to General Method E using 2-(5-(tributylstannyl)thiazol-2-yl)propan-2-ol instead of with ethyl 2-tributylstannylimidazo[5,1-b]thiazole-7-carboxylate.

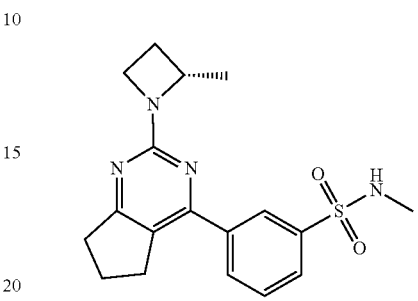

Example 214: N-methyl-3-[2-[(2S)-2-methylazetidin-1-yl]-6,7-dihydro-5H-cyclopenta[d]pyrimidin-4-yl]benzenesulfonamide 3-[2-[(2S)-2-methylazetidin-1-yl]-6,7-dihydro-5H-cyclopenta[d]pyrimidin-4-yl]benzenesulfonamide (42 mg, 0.12 mmol) was dissolved in DMF (10.5 mL) and then cooled to 0° C. over 20 mins NaH (17.1 mg, 0.43) was slowly added and the reaction mixture was allowed to run at ambient temperature for 20 mins and then methyl iodide (0.0095 mL, 0.15 mmol) was added, the reaction mixture was stirred at ambient temperature for 15 mins. The reaction mixture was cooled to 0° C., slowly quenched with water, extracted with EtOAc, dried, filtered, concentrated and purified on the HPLC (0.1% TFA in MeCN-0.1% TFA in H₂O) to provide N-methyl-3-[2-[(2S)-2-methylazetidin-1-yl]-6,7-dihydro-5H-cyclopenta[d]pyrimidin-4-yl]benzenesulfonamide

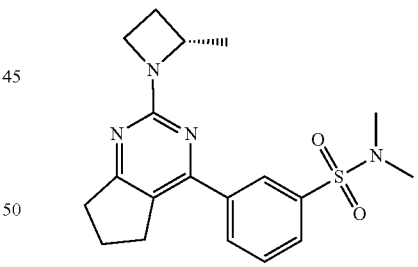

Example 215: N,N-dimethyl-3-[2-[(2S)-2-methylazetidin-1-yl]-6,7-dihydro-5H-cyclopenta[d]pyrimidin-4-yl]benzenesulfonamide 3-[2-[(2S)-2-methylazetidin-1-yl]-6,7-dihydro-5H-cyclopenta[d]pyrimidin-4-yl]benzenesulfonamide (42 mg, 0.12 mmol) was dissolved in DMF (10.5 mL) and then cooled to 0° C. over 20 mins NaH (17.1 mg, 0.43) was slowly added and the reaction mixture was allowed to run at 0° C. for 20 mins and then methyl iodide (0.0095 mL, 0.15 mmol) was added and the reaction mixture was stirred at ambient temperature for 15 mins. The reaction mixture was cooled to 0° C., slowly quenched with water, extracted with EtOAc, dried, filtered, concentrated and purified on the HPLC (0.1% TFA in MeCN-0.1% TFA in H₂O) to provide N,N-dimethyl-3-[2-[(2S)-2-methylazetidin-1-yl]-6,7-dihydro-5H-cyclopenta[d]pyrimidin-4-yl]benzenesulfonamide

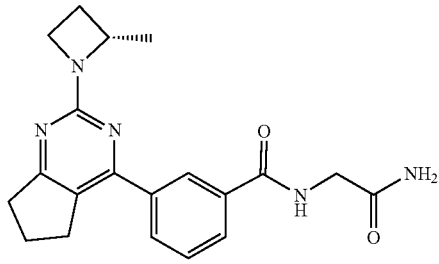 [SMILES: C[C@H]1CCN1c1nc2c(c(-c3cccc(C(=O)NCC(N)=O)c3)n1)CCC2]

Example 216: N-(2-amino-2-oxo-ethyl)-3-[2-[(2S)-2-methylazetidin-1-yl]-6,7-dihydro-5H-cyclopenta[d]pyrimidin-4-yl]benzamide The title compound was prepared in a method analogous to General Method G using 3-aminopropanoic acid and (S)-3-(2-(2-methylazetidin-1-yl)-6,7-dihydro-5H-cyclopenta[d]pyrimidin-4-yl)benzoic acid instead of ammonia and 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid, respectively.

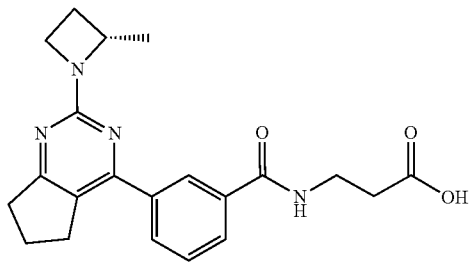 [SMILES: C[C@H]1CCN1c1nc2c(c(-c3cccc(C(=O)NCCC(=O)O)c3)n1)CCC2]

Example 217: 3-[[3-[2-[(2S)-2-methylazetidin-1-yl]-6,7-dihydro-5H-cyclopenta[d]pyrimidin-4-yl]benzoyl]amino]propanoic acid The title compound was prepared in a method analogous to General Method G using 3-aminopropanoic acid and (S)-3-(2-(2-methylazetidin-1-yl)-6,7-dihydro-5H-cyclopenta[d]pyrimidin-4-yl)benzoic acid instead of ammonia and 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid, respectively.

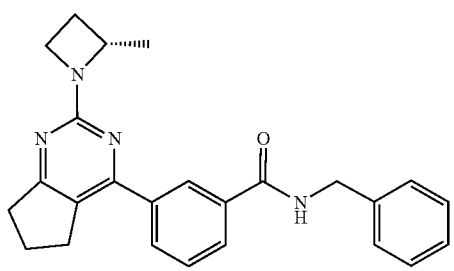 [SMILES: C[C@H]1CCN1c1nc2c(c(-c3cccc(C(=O)NCc4ccccc4)c3)n1)CCC2]

Example 218: N-benzyl-3-[2-[(2S)-2-methylazetidin-1-yl]-6,7-dihydro-5H-cyclopenta[d]pyrimidin-4-yl]benzamide The title compound was prepared in a method analogous to General Method G using benzylamine and (S)-3-(2-(2-methylazetidin-1-yl)-6,7-dihydro-5H-cyclopenta[d]pyrimidin-4-yl)benzoic acid instead of ammonia and 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid, respectively.

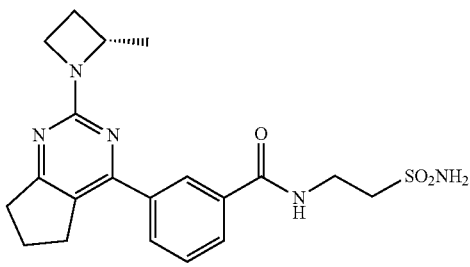 [SMILES: C[C@H]1CCN1c1nc2c(c(-c3cccc(C(=O)NCCS(N)(=O)=O)c3)n1)CCC2]

Example 219: 3-[2-[(2S)-2-methylazetidin-1-yl]-6,7-dihydro-5H-cyclopenta[d]pyrimidin-4-yl]-N-(2-sulfamoylethyl)benzamide The title compound was prepared in a method analogous to General Method G using 2-aminoethane-1-sulfonamide and (S)-3-(2-(2-methylazetidin-1-yl)-6,7-dihydro-5H-cyclopenta[d]pyrimidin-4-yl)benzoic acid instead of ammonia and 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid, respectively.

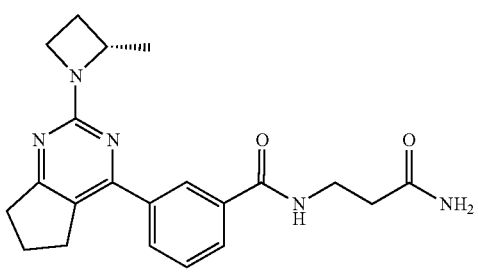 [SMILES: C[C@H]1CCN1c1nc2c(c(-c3cccc(C(=O)NCCC(N)=O)c3)n1)CCC2]

Example 220: N-(3-amino-3-oxo-propyl)-3-[2-[(2S)-2-methylazetidin-1-yl]-6,7-dihydro-5H-cyclopenta[d]pyrimidin-4-yl]benzamide The title compound was prepared in a method analogous to General Method G using 3-aminopropanamide and (S)-3-(2-(2-methylazetidin-1-yl)-6,7-dihydro-5H-cyclopenta[d]pyrimidin-4-yl)benzoic acid instead of ammonia and 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid, respectively.

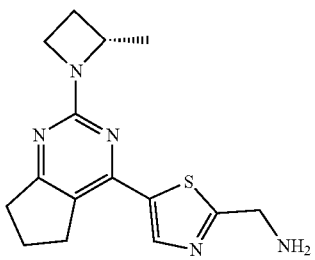 [SMILES: C[C@H]1CCN1c1nc2c(c(-c3cnc(CN)s3)n1)CCC2]

Example 221: (S)-(5-(2-(2-methylazetidin-1-yl)-6,7-dihydro-5H-cyclopenta[d]pyrimidin-4-yl)thiazol-2-yl)methanamine The title compound was prepared in a method analogous to General Method D, using (S)-4-chloro-2-(2-methylazetidin-1-yl)-6,7-dihydro-5H-cyclopenta[d]pyrimidine instead of 2-bromoimidazo[5,1-b]thiazole-7-carboxylate, followed by General Method E using tert-butyl N-[(5-bromothiazol-2-yl)methyl]carbamate instead of (S)-4-chloro-2-(2-methylazetidin-1-yl)-6,7-dihydro-5H-cyclopenta[d]pyrimidine and General Method I.

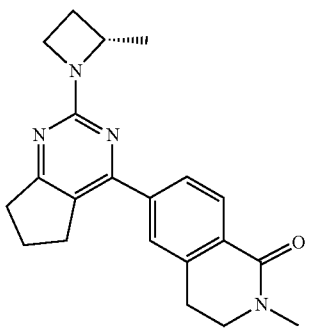 [SMILES: C[C@H]1CCN1c1nc2c(c(-c3ccc4c(c3)CCN(C)C4=O)n1)CCC2]

Example 222: (S)-2-methyl-6-(2-(2-methylazetidin-1-yl)-6,7-dihydro-5H-cyclopenta[d]pyrimidin-4-yl)-3,4-dihydroisoquinolin-1(2H)-one The title compound was prepared in a method analogous to General Method D, using (S)-4-chloro-2-(2-methylazetidin-1-yl)-6,7-dihydro-5H-cyclopenta[d]pyrimidine instead of 2-bromoimidazo[5,1-b]thiazole-7-carboxylate, followed by General Method E using 6-bromo-2-methyl-3,4-dihydroisoquinolin-1(2H)-one instead of (S)-4-chloro-2-(2-methylazetidin-1-yl)-6,7-dihydro-5H-cyclopenta[d]pyrimidine.

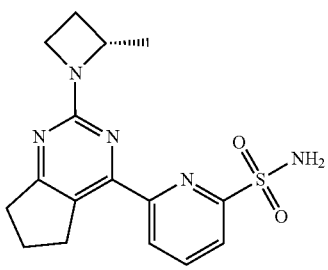 [SMILES: C[C@H]1CCN1c1nc2c(c(-c3cccc(S(N)(=O)=O)n3)n1)CCC2]

Example 223: (S)-6-(2-(2-methylazetidin-1-yl)-6,7-dihydro-5H-cyclopenta[d]pyrimidin-4-yl)pyridine-2-sulfonamide The title compound was prepared in a method analogous to General Method D, using (S)-4-chloro-2-(2-methylazetidin-1-yl)-6,7-dihydro-5H-cyclopenta[d]pyrimidine instead of 2-bromoimidazo[5,1-b]thiazole-7-carboxylate, followed by General Method E using 6-bromopyridine-2-sulfonamide instead of (S)-4-chloro-2-(2-methylazetidin-1-yl)-6,7-dihydro-5H-cyclopenta[d]pyrimidine.

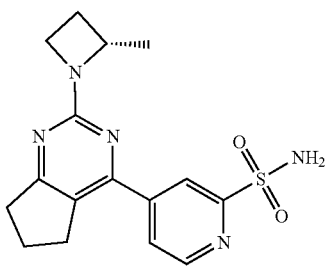 [SMILES: C[C@H]1CCN1c1nc2c(c(-c3ccnc(S(N)(=O)=O)c3)n1)CCC2]

Example 224: (S)-4-(2-(2-methylazetidin-1-yl)-6,7-dihydro-5H-cyclopenta[d]pyrimidin-4-yl)pyridine-2-sulfonamide The title compound was prepared in a method analogous to General Method D, using (S)-4-chloro-2-(2-methylazetidin-1-yl)-6,7-dihydro-5H-cyclopenta[d]pyrimidine instead of 2-bromoimidazo[5,1-b]thiazole-7-carboxylate, followed by General Method E using 4-bromopyridine-2-sulfonamide instead of (S)-4-chloro-2-(2-methylazetidin-1-yl)-6,7-dihydro-5H-cyclopenta[d]pyrimidine.

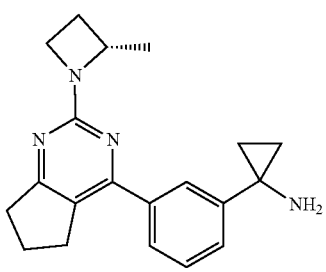 [SMILES: C[C@H]1CCN1c1nc2c(c(-c3cccc(C4(N)CC4)c3)n1)CCC2]

Example 225: (S)-1-(3-(2-(2-methylazetidin-1-yl)-6,7-dihydro-5H-cyclopenta[d]pyrimidin-4-yl)phenyl)cyclopropan-1-amine The title compound was prepared in a method analogous to General Method D, using (S)-4-chloro-2-(2-methylazetidin-1-yl)-6,7-dihydro-5H-cyclopenta[d]pyrimidine instead of 2-bromoimidazo[5,1-b]thiazole-7-carboxylate, followed by General Method E using 1-(3-bromophenyl)cyclopropan-1-amine instead of (S)-4-chloro-2-(2-methylazetidin-1-yl)-6,7-dihydro-5H-cyclopenta[d]pyrimidine.

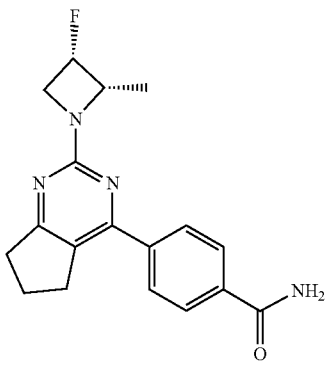 [SMILES: C[C@H]1[C@@H](F)CN1c1nc2c(c(-c3ccc(C(N)=O)cc3)n1)CCC2]

Example 226: 4-(24(2S,3S)-3-fluoro-2-methylazetidin-1-yl)-6,7-dihydro-5H-cyclopenta[d]pyrimidin-4-yl)benzamide A vial was charged with 4-(2-((2S,3R)-3-hydroxy-2-methylazetidin-1-yl)-6,7-dihydro-5H-cyclopenta[d]pyrimidin-4-yl)benzamide (23.5 mg, 0.0.72 mmols) and DCM (0.24 mL). DAST (117 mg, 0.72 mmols) was slowly added, and the reaction mixture was allowed to stir for 1 hr at ambient temperature. The reaction mixture was slowly quenched with ice chips to 0° C., extracted with 25% MeOH/DCM, washed with NaHCO₃ (aq., sat.), dried over Na₂SO₄, filterer and concentrated. The residue was subjected to HPLC HPLC (0.1% TFA in MeCN-0.1% TFA in H₂O) to give the title compound.

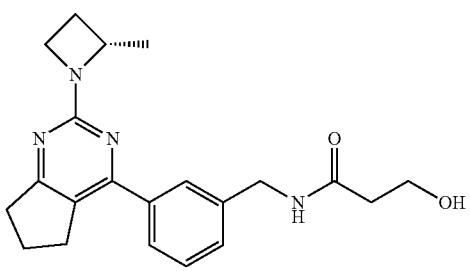 [SMILES: C[C@H]1CCN1c1nc2c(c(-c3cccc(CNC(=O)CCO)c3)n1)CCC2]

Example 227: 3-hydroxy-N-[[3-[2-[(2S)-2-methylazetidin-1-yl]-6,7-dihydro-5H-cyclopenta[d]pyrimidin-4-yl]phenyl]methyl]propanamide The title compound was prepared in a method analogous to General Method G using 3-hydroxypropanoic acid and (S)-(3-(2-(2-methylazetidin-1-yl)-6,7-dihydro-5H-cyclopenta[d]pyrimidin-4-yl)phenyl)methanamine instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid and ammonia, respectively.

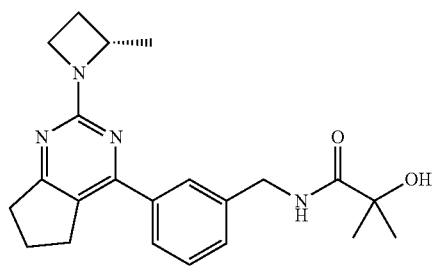 [SMILES: C[C@H]1CCN1c1nc2c(c(-c3cccc(CNC(=O)C(C)(C)O)c3)n1)CCC2]

Example 228: 2-hydroxy-2-methyl-N-[[3-[2-[(2S)-2-methylazetidin-1-yl]-6,7-dihydro-5H-cyclopenta[d]pyrimidin-4-yl]phenyl]methyl]propanamide The title compound was prepared in a method analogous to General Method G using 2-hydroxy-2-methylpropanoic acid and (S)-(3-(2-(2-methylazetidin-1-yl)-6,7-dihydro-5H-cyclopenta[d]pyrimidin-4-yl)phenyl)methanamine instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid and ammonia, respectively.

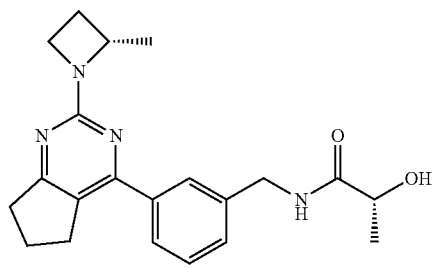 [SMILES: C[C@@H](O)C(=O)NCc1cccc(-c2nc(N3CC[C@@H]3C)nc3c2CCC3)c1]

Example 229: (2R)-2-hydroxy-N-[[3-[2-[(2S)-2-methylazetidin-1-yl]-6,7-dihydro-5H-cyclopenta[d]pyrimidin-4-yl]phenyl]methyl]propanamide The title compound was prepared in a method analogous to General Method G using (R)-2-hydroxypropanoic acid and (S)-(3-(2-(2-methylazetidin-1-yl)-6,7-dihydro-5H-cyclopenta[d]pyrimidin-4-yl)phenyl)methanamine instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid and ammonia, respectively.

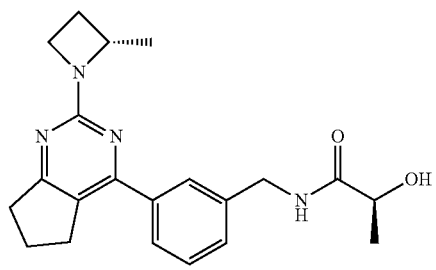 [SMILES: C[C@H](O)C(=O)NCc1cccc(-c2nc(N3CC[C@@H]3C)nc3c2CCC3)c1]

Example 230: (2S)-2-hydroxy-N-[[3-[2-[(2S)-2-methylazetidin-1-yl]-6,7-dihydro-5H-cyclopenta[d]pyrimidin-4-yl]phenyl]methyl]propanamide The title compound was prepared in a method analogous to General Method G using (S)-2-hydroxypropanoic acid and (S)-(3-(2-(2-methylazetidin-1-yl)-6,7-dihydro-5H-cyclopenta[d]pyrimidin-4-yl)phenyl)methanamine instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid and ammonia, respectively.

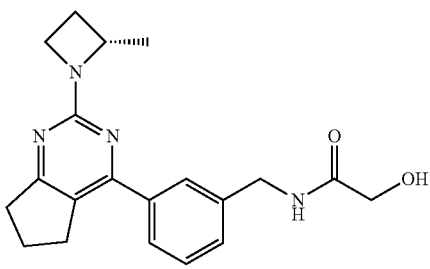 [SMILES: C[C@H]1CCN1c1nc2c(c(-c3cccc(CNC(=O)CO)c3)n1)CCC2]

Example 231: 2-hydroxy-N-[[3-[2-[(2S)-2-methylazetidin-1-yl]-6,7-dihydro-5H-cyclopenta[d]pyrimidin-4-yl]phenyl]methyl]acetamide The title compound was prepared in a method analogous to General Method G using 2-hydroxyacetic acid and (S)-(3-(2-(2-methylazetidin-1-yl)-6,7-dihydro-5H-cyclopenta[d]pyrimidin-4-yl)phenyl)methanamine instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid.

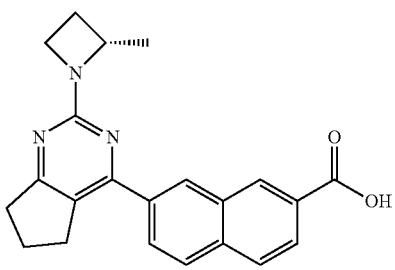 [SMILES: C[C@H]1CCN1c1nc2c(c(-c3ccc4ccc(C(=O)O)cc4c3)n1)CCC2]

Example 232: 7-[2-[(2S)-2-methylazetidin-1-yl]-6,7-dihydro-5H-cyclopenta[d]pyrimidin-4-yl]naphthalene-2-carboxylic acid The title compound was prepared in a method analogous to General Method F using 7-(4,4,5,5-tetramethyl-1,3,2-dioxaborolan-2-yl)-2-naphthoic acid instead of 6-bromo-1,1-dioxo-1,2-benzothiazol-3-one.

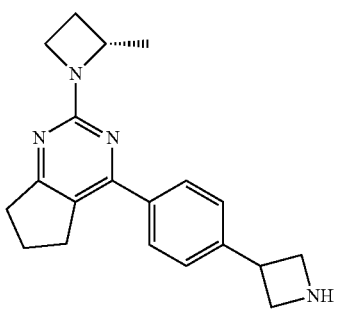 [SMILES: C[C@H]1CCN1c1nc2c(c(-c3ccc(C4CNC4)cc3)n1)CCC2]

Example 233: 4-[4-(azetidin-3-yl)phenyl]-2-[(2S)-2-methylazetidin-1-yl]-6,7-dihydro-5H-cyclopenta[d]pyrimidine The title compound was prepared in a method analogous to General Method F using tert-butyl 3-(4-(4,4,5,5-tetramethyl-1,3,2-dioxaborolan-2-yl)phenyl)azetidine-1-carboxylate instead of 6-bromo-1,1-dioxo-1,2-benzothiazol-3-one, followed by General Method I.

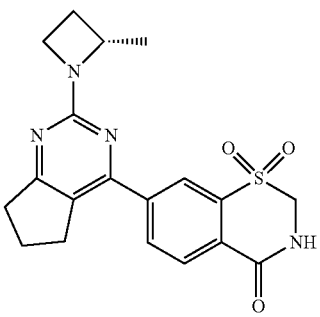 [SMILES: C[C@H]1CCN1c1nc2c(c(-c3ccc4c(c3)S(=O)(=O)CNC4=O)n1)CCC2]

Example 234: 7-[2-[(2S)-2-methylazetidin-1-yl]-6,7-dihydro-5H-cyclopenta[d]pyrimidin-4-yl]-1,1-dioxo-2,3-dihydro-1lambda6,3-benzothiazin-4-one The title compound was prepared in a method analogous to General Method D using 7-bromo-2,3-dihydro-4H-benzo[e][1,3]thiazin-4-one 1,1-dioxide instead of 2-bromoimidazo[5,1-b]thiazole-7-carboxylate, followed by General Method E.

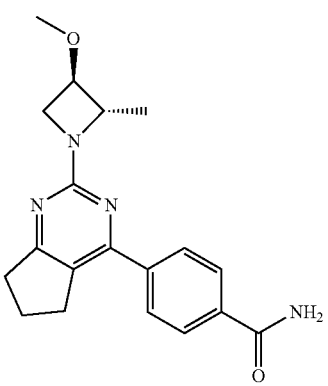 [SMILES: CO[C@@H]1CN(c2nc3c(c(-c4ccc(C(N)=O)cc4)n2)CCC3)[C@H]1C]

Example 235: 4-(2-((2S,3R)-3-methoxy-2-methylazetidin-1-yl)-6,7-dihydro-5H-cyclopenta[d]pyrimidin-4-yl)benzamide A vial was charged with (2S,3R)-1-(4-chloro-6,7-dihydro-5H-cyclopenta[d]pyrimidin-2-yl)-2-methylazetidin-3-ol (21 mg, 0.09 mmoles) and DMF (1 mL) and was cooled to 0° C. NaH (60% dispersion in mineral oil, 12.3 mg, 0.31 mmoles) was slowly added. The reaction mixture was allowed to stir at 0° C. for 20 mins and then MeI (14.9 mg, 0.11 mmoles) was slowly added and the reaction mixture was allowed to warm to ambient over 15 mins. The reaction mixture was cooled to 0° C., quenched with ice water, and extracted with DCM (3×1 mL). The combined organics were dried over Na₂SO₄, filtered, and concentrated to provide 4-(2-((2S,3R)-3-methoxy-2-methylazetidin-1-yl)-6,7-dihydro-5H-cyclopenta[d]pyrimidin-4-yl)benzamide, which was used without any further purifications.

The title compound was prepared in a method analogous to General Method A using 4-chloro-2-[(2S,3R)-3-methoxy-2-methyl-azetidin-1-yl]-6,7-dihydro-5H-cyclopenta[d]pyrimidine and (4-carbamoylphenyl)boronic acid instead of 2,4-dichloro-6,7-dihydro-5H-cyclopenta[d]pyrimidine and 3-pyridylboronic acid, respectively.

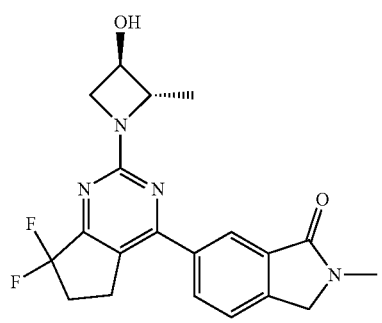 [SMILES: C[C@H]1[C@H](O)CN1c1nc(-c2ccc3c(c2)C(=O)N(C)C3)c2c(n1)C(F)(F)CC2]

Example 236: 6-(7,7-difluoro-2-((2S,3R)-3-hydroxy-2-methylazetidin-1-yl)-6,7-dihydro-5H-cyclopenta[d]pyrimidin-4-yl)-2-methylisoindolin-1-one The title compound was prepared in a method analogous to General Method A using 4-chloro-7,7-difluoro-2-(methylthio)-6,7-dihydro-5H-cyclopenta[d]pyrimidine and 2-methyl-6-(4,4,5,5-tetramethyl-1,3,2-dioxaborolan-2-yl)isoindolin-1-one instead of 2,4-dichloro-6,7-dihydro-5H-cyclopenta[d]pyrimidine and 3-pyridylboronic acid, followed by General Method M and General Method B, using (2S,3R)-2-methylazetidin-3-ol instead of (2S)-2-methylazetidine.

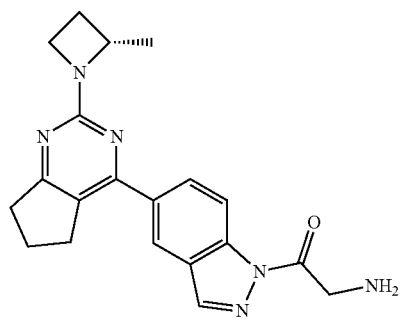

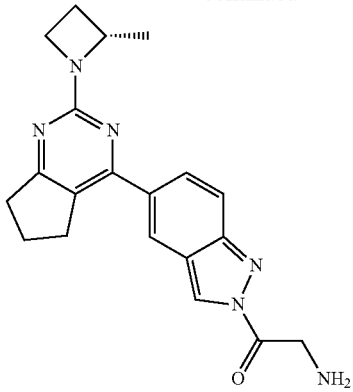

Example 237: (S)-2-amino-1-(5-(2-(2-methylazetidin-1-yl)-6,7-dihydro-5H-cyclopenta[d]pyrimidin-4-yl)-1H-indazol-1-yl)ethan-1-one Example 238: (S)-2-amino-1-(5-(2-(2-methylazetidin-1-yl)-6,7-dihydro-5H-cyclopenta[d]pyrimidin-4-yl)-2H-indazol-2-yl)ethan-1-one A vial was charged with (S)-5-(2-(2-methylazetidin-1-yl)-6,7-dihydro-5H-cyclopenta[d]pyrimidin-4-yl)-1H-indazole (28 mg, 0.092 mmoL), potassium carbonate (50.2 mg, 0.37 mmol), and MeCN (0.7 mL). The mixture was heated to 40° C. for 18 hr. NaHCO₃ (1 mL, sat. aq.) was added, and the mixture was extracted with DCM (3×1 mL). The combined organics were dried over Na₂SO₄, filtered, and concentrated. The residue was subjected to HPLC (0.1% TFA in MeCN-0.1% TFA in H₂O) to give the respective title compounds.

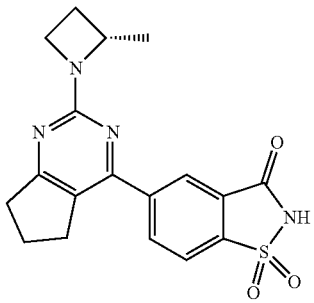 [SMILES: C[C@H]1CCN1c1nc2c(c(-c3ccc4c(c3)C(=O)NS4(=O)=O)n1)CCC2]

Example 239: (S)-5-(2-(2-methylazetidin-1-yl)-6,7-dihydro-5H-cyclopenta[d]pyrimidin-4-yl)benzo[d]isothiazol-3(2H)-one 1,1-dioxide The title compound was prepared in a method analogous to General Method F using 5-bromobenzo[d]isothiazol-3(2H)-one 1,1-dioxide instead of 6-bromo-1,1-dioxo-1,2-benzothiazol-3-one.

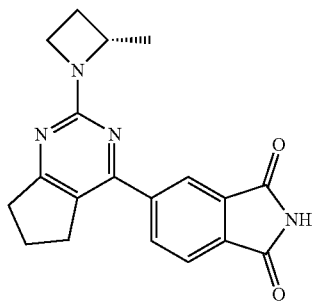 [SMILES: C[C@H]1CCN1c1nc2c(c(-c3ccc4c(c3)C(=O)NC4=O)n1)CCC2]

Example 240: 5-[2-[(2S)-2-methylazetidin-1-yl]-6,7-dihydro-5H-cyclopenta[d]pyrimidin-4-yl]isoindoline-1,3-dione The title compound was prepared in a method analogous to General Method F using 5-bromoisoindoline-1,3-dione instead of 6-bromo-1,1-dioxo-1,2-benzothiazol-3-one.

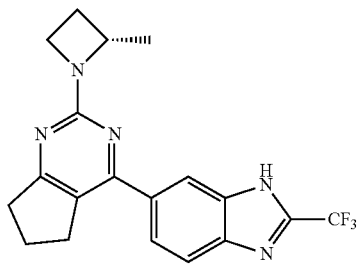 [SMILES: C[C@H]1CCN1c1nc2c(c(-c3ccc4nc(C(F)(F)F)[nH]c4c3)n1)CCC2]

Example 241: 6-[2-[(2S)-2-methylazetidin-1-yl]-6,7-dihydro-5H-cyclopenta[d]pyrimidin-4-yl]-2-(trifluoromethyl)-1H-benzimidazole The title compound was prepared in a method analogous to General Method F using 6-bromo-2-(trifluoromethyl)-1H-benzimidazole instead of 6-bromo-1,1-dioxo-1,2-benzothiazol-3-one.

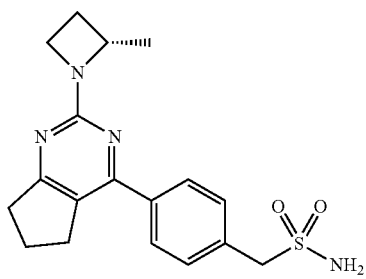 [SMILES: C[C@H]1CCN1c1nc2c(c(-c3ccc(CS(N)(=O)=O)cc3)n1)CCC2]

Example 242: [4-[2-[(2S)-2-methylazetidin-1-yl]-6,7-dihydro-5H-cyclopenta[d]pyrimidin-4-yl]phenyl]methanesulfonamide The title compound was prepared in a method analogous to General Method F using (4-bromophenyl)methanesulfonamide instead of 6-bromo-1,1-dioxo-1,2-benzothiazol-3-one.

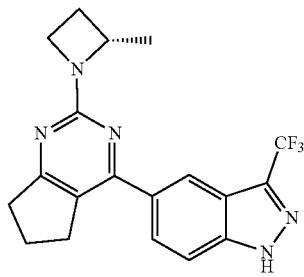 [SMILES: C[C@H]1CCN1c1nc2c(c(-c3ccc4[nH]nc(C(F)(F)F)c4c3)n1)CCC2]

Example 243: 5-[2-[(2S)-2-methylazetidin-1-yl]-6,7-dihydro-5H-cyclopenta[d]pyrimidin-4-yl]-3-(trifluoromethyl)-1H-indazole The title compound was prepared in a method analogous to General Method F using 5-bromo-3-(trifluoromethyl)-1H-indazole instead of 6-bromo-1,1-dioxo-1,2-benzothiazol-3-one.

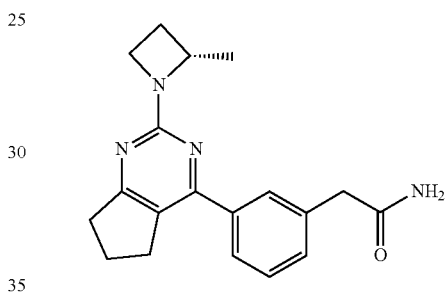

Example 244: 2-[3-[2-[(2S)-2-methylazetidin-1-yl]-6,7-dihydro-5H-cyclopenta[d]pyrimidin-4-yl]phenyl]acetamide The title compound was prepared in a method analogous to general method F using 2-(3-bromophenyl)acetamide instead of 6-bromo-1,1-dioxo-1,2-benzothiazol-3-one.

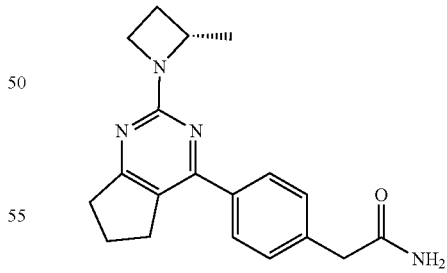

Example 245: 2-[4-[2-[(2S)-2-methylazetidin-1-yl]-6,7-dihydro-5H-cyclopenta[d]pyrimidin-4-yl]phenyl]acetamide The title compound was prepared in a method analogous to General Method F using 2-(4-bromophenyl)acetamide instead of 6-bromo-1,1-dioxo-1,2-benzothiazol-3-one.

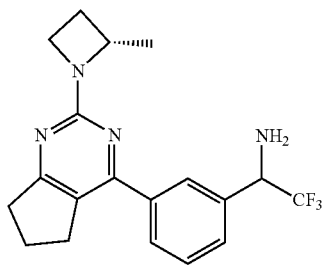 [SMILES: C[C@H]1CCN1c1nc2c(c(-c3cccc(C(N)C(F)(F)F)c3)n1)CCC2]

Example 246: 2,2,2-trifluoro-1-[3-[2-[(2S)-2-methylazetidin-1-yl]-6,7-dihydro-5H-cyclopenta[d]pyrimidin-4-yl]phenyl]ethanamine The title compound was prepared in a method analogous to General Method F using 1-(3-bromophenyl)-2,2,2-trifluoro-ethanamine instead of 6-bromo-1,1-dioxo-1,2-benzothiazol-3-one.

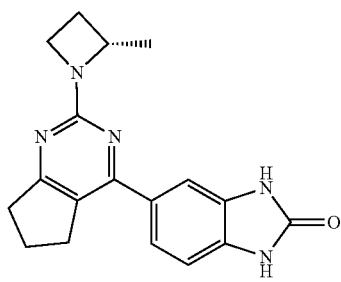 [SMILES: C[C@H]1CCN1c1nc2c(c(-c3ccc4[nH]c(=O)[nH]c4c3)n1)CCC2]

Example 247: 5-[2-[(2S)-2-methylazetidin-1-yl]-6,7-dihydro-5H-cyclopenta[d]pyrimidin-4-yl]-1,3-dihydrobenzimidazol-2-one The title compound was prepared in a method analogous to General Method F using 5-bromo-1,3-dihydrobenzimidazol-2-one instead of 6-bromo-1,1-dioxo-1,2-benzothiazol-3-one.

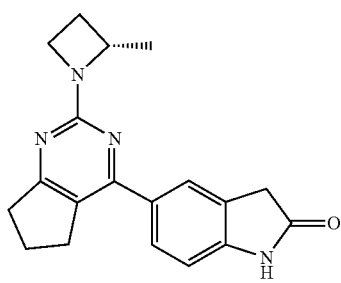 [SMILES: C[C@H]1CCN1c1nc2c(c(-c3ccc4c(c3)CC(=O)N4)n1)CCC2]

Example 248: 5-[2-[(2S)-2-methylazetidin-1-yl]-6,7-dihydro-5H-cyclopenta[d]pyrimidin-4-yl]indolin-2-one The title compound was prepared in a method analogous to General Method F using 5-bromoindolin-2-one instead of 6-bromo-1,1-dioxo-1,2-benzothiazol-3-one

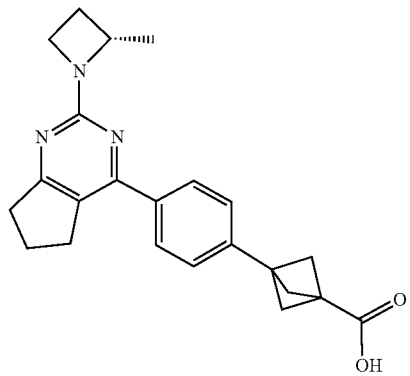 [SMILES: C[C@H]1CCN1c1nc2c(c(-c3ccc(C45CC(C(=O)O)(C4)C5)cc3)n1)CCC2]

Example 249: 3-[4-[2-[(2S)-2-methylazetidin-1-yl]-6,7-dihydro-5H-cyclopenta[d]pyrimidin-4-yl]phenyl]bicyclo[1.1.1]pentane-1-carboxylic acid The title compound was prepared in a method analogous to General Method F using 3-(4-bromophenyl)bicyclo[1.1.1]pentane-1-carboxylic acid instead of 6-bromo-1,1-dioxo-1,2-benzothiazol-3-one.

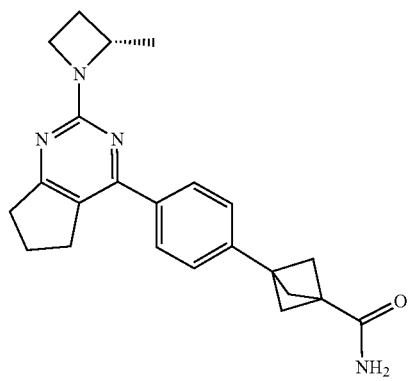 [SMILES: C[C@H]1CCN1c1nc2c(c(-c3ccc(C45CC(C(N)=O)(C4)C5)cc3)n1)CCC2]

Example 250: 3-[4-[2-[(2S)-2-methylazetidin-1-yl]-6,7-dihydro-5H-cyclopenta[d]pyrimidin-4-yl]phenyl]bicyclo[1.1.1]pentane-1-carboxamide The title compound was prepared in a method analogous to General Method F using 3-(4-bromophenyl)bicyclo[1.1.1]pentane-1-carboxamide instead of 6-bromo-1,1-dioxo-1,2-benzothiazol-3-one.

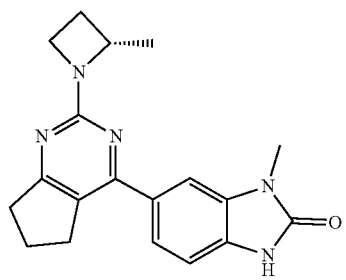 [SMILES: C[C@H]1CCN1c1nc2c(c(-c3ccc4[nH]c(=O)n(C)c4c3)n1)CCC2]

Example 251: 3-methyl-5-[2-[(2S)-2-methylazetidin-1-yl]-6,7-dihydro-5H-cyclopenta[d]pyrimidin-4-yl]-1H-benzimidazol-2-one The title compound was prepared in a method analogous to General Method F using 5-bromo-3-methyl-1H-benzimidazol-2-one instead of 6-bromo-1,1-dioxo-1,2-benzothiazol-3-one.

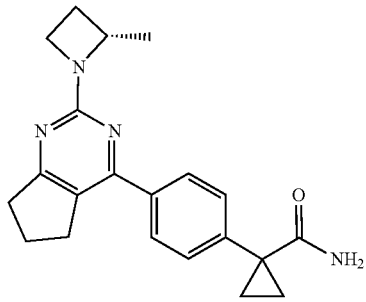 [SMILES: C[C@H]1CCN1c1nc2c(c(-c3ccc(C4(C(N)=O)CC4)cc3)n1)CCC2]

Example 252: 1-[4-[2-[(2S)-2-methylazetidin-1-yl]-6,7-dihydro-5H-cyclopenta[d]pyrimidin-4-yl]phenyl]cyclopropanecarboxamide The title compound was prepared in a method analogous to General Method F using 1-(4-bromophenyl)cyclopropanecarboxamide instead of 6-bromo-1,1-dioxo-1,2-benzothiazol-3-one.

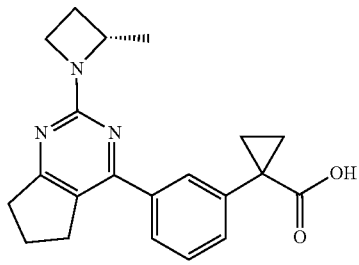 [SMILES: C[C@H]1CCN1c1nc2c(c(-c3cccc(C4(C(=O)O)CC4)c3)n1)CCC2]

Example 253: 1-[3-[2-[(2S)-2-methylazetidin-1-yl]-6,7-dihydro-5H-cyclopenta[d]pyrimidin-4-yl]phenyl]cyclopropanecarboxylic acid The title compound was prepared in a method analogous to General Method F using 1-(3-bromophenyl)cyclopropanecarboxylic acid instead of 6-bromo-1,1-dioxo-1,2-benzothiazol-3-one.

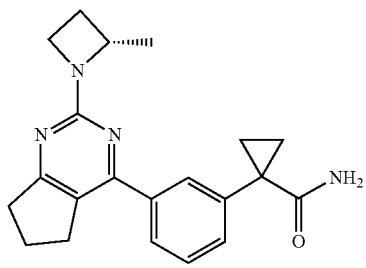 [SMILES: C[C@H]1CCN1c1nc2c(c(-c3cccc(C4(C(N)=O)CC4)c3)n1)CCC2]

Example 254: 1-[3-[2-[(2S)-2-methylazetidin-1-yl]-6,7-dihydro-5H-cyclopenta[d]pyrimidin-4-yl]phenyl]cyclopropanecarboxamide The title compound was prepared in a method analogous to General Method F using 1-(3-bromophenyl)cyclopropanecarboxamide instead of 6-bromo-1,1-dioxo-1,2-benzothiazol-3-one.

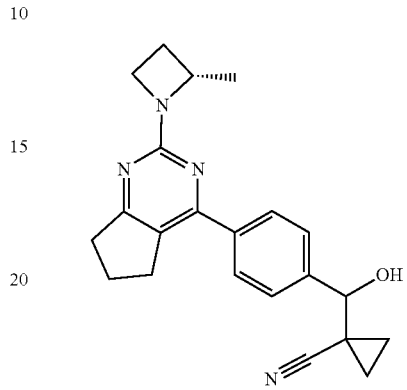

Example 255: 1-[hydroxy-[4-[2-[(2S)-2-methylazetidin-1-yl]-6,7-dihydro-5H-cyclopenta[d]pyrimidin-4-yl]phenyl]methyl]cyclopropanecarbonitrile The title compound was prepared in a method analogous to General Method A using 1-[hydroxy-[4-(4,4,5,5-tetramethyl-1,3,2-dioxaborolan-2-yl)phenyl]methyl]cyclopropanecarbonitrile and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

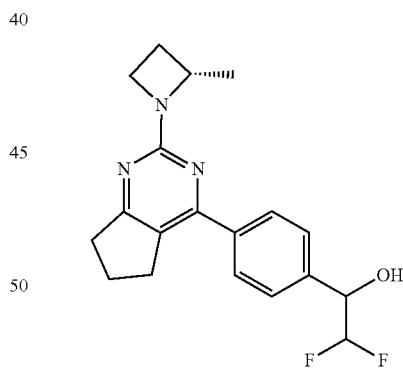

Example 256: 2,2-difluoro-1-[4-[2-[(2S)-2-methylazetidin-1-yl]-6,7-dihydro-5H-cyclopenta[d]pyrimidin-4-yl]phenyl]ethanol The title compound was prepared in a method analogous to General Method A using 2,2-difluoro-1-[4-(4,4,5,5-tetramethyl-1,3,2-dioxaborolan-2-yl)phenyl]ethanol and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

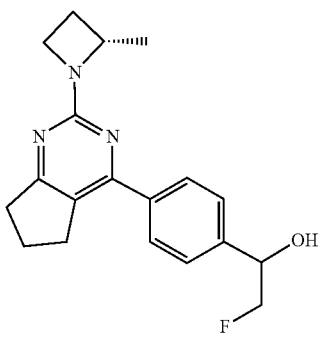 [SMILES: C[C@H]1CCN1c1nc2c(c(-c3ccc(C(O)CF)cc3)n1)CCC2]

Example 257: 2-fluoro-1-[4-[2-[(2S)-2-methylazetidin-1-yl]-6,7-dihydro-5H-cyclopenta[d]pyrimidin-4-yl]phenyl]ethanol The title compound was prepared in a method analogous to General Method A using 2-fluoro-1-[4-(4,4,5,5-tetramethyl-1,3,2-dioxaborolan-2-yl)phenyl]ethanol and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

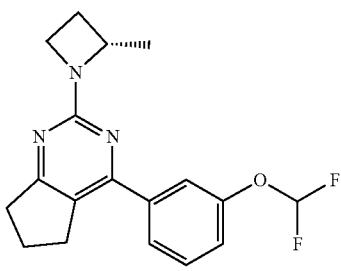 [SMILES: C[C@H]1CCN1c1nc2c(c(-c3cccc(OC(F)F)c3)n1)CCC2]

Example 258: 4-[3-(difluoromethoxy)phenyl]-2-[(2S)-2-methylazetidin-1-yl]-6,7-dihydro-5H-cyclopenta[d]pyrimidine The title compound was prepared in a method analogous to General Method A using 2-[3-(difluoromethoxy)phenyl]-4,4,5,5-tetramethyl-1,3,2-dioxaborolane and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

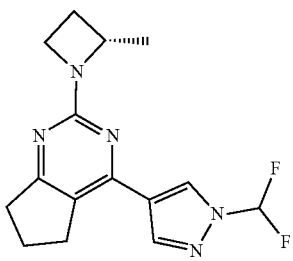 [SMILES: C[C@H]1CCN1c1nc2c(c(-c3cnn(C(F)F)c3)n1)CCC2]

Example 259: 4-[1-(difluoromethyl)pyrazol-4-yl]-2-[(2S)-2-methylazetidin-1-yl]-6,7-dihydro-5H-cyclopenta[d]pyrimidine The title compound was prepared in a method analogous to General Method A using 1-(difluoromethyl)-4-(4,4,5,5-tetramethyl-1,3,2-dioxaborolan-2-yl)pyrazole and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

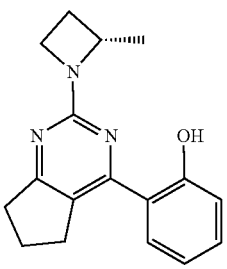 [SMILES: C[C@H]1CCN1c1nc2c(c(-c3ccccc3O)n1)CCC2]

Example 260: 2-[2-[(2S)-2-methylazetidin-1-yl]-6,7-dihydro-5H-cyclopenta[d]pyrimidin-4-yl]phenol The title compound was prepared in a method analogous to General Method A using (2-hydroxyphenyl)boronic acid and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

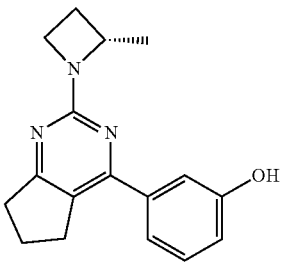 [SMILES: C[C@H]1CCN1c1nc2c(c(-c3cccc(O)c3)n1)CCC2]

Example 261: 3-[2-[(2S)-2-methylazetidin-1-yl]-6,7-dihydro-5H-cyclopenta[d]pyrimidin-4-yl]phenol The title compound was prepared in a method analogous to General Method A using (3-hydroxyphenyl)boronic acid and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

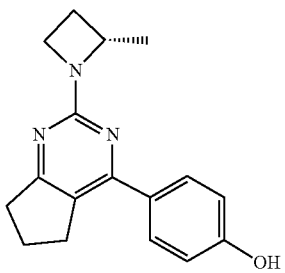 [SMILES: C[C@H]1CCN1c1nc2c(c(-c3ccc(O)cc3)n1)CCC2]

Example 262: 4-[2-[(2S)-2-methylazetidin-1-yl]-6,7-dihydro-5H-cyclopenta[d]pyrimidin-4-yl]phenol The title compound was prepared in a method analogous to General Method A using (4-hydroxyphenyl)boronic acid and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

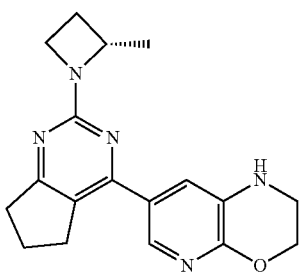 [SMILES: C[C@H]1CCN1c1nc2c(c(-c3cnc4c(c3)NCCO4)n1)CCC2]

Example 263: 7-[2-[(2S)-2-methylazetidin-1-yl]-6,7-dihydro-5H-cyclopenta[d]pyrimidin-4-yl]-2,3-dihydro-1H-pyrido[2,3-b][1,4]oxazine The title compound was prepared in a method analogous to General Method A using 7-(4,4,5,5-tetramethyl-1,3,2-dioxaborolan-2-yl)-2,3-dihydro-1H-pyrido[2,3-b][1,4]oxazine and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

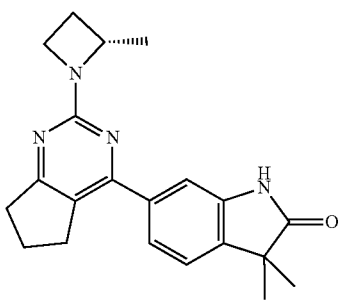 [SMILES: C[C@H]1CCN1c1nc2c(c(-c3ccc4c(c3)NC(=O)C4(C)C)n1)CCC2]

Example 264: 3,3-dimethyl-6-[2-[(2S)-2-methylazetidin-1-yl]-6,7-dihydro-5H-cyclopenta[d]pyrimidin-4-yl]indolin-2-one The title compound was prepared in a method analogous to General Method A using 3,3-dimethyl-6-(4,4,5,5-tetramethyl-1,3,2-dioxaborolan-2-yl)indolin-2-one and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

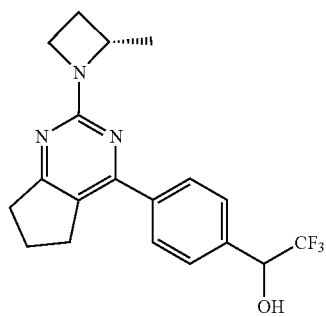 [SMILES: C[C@H]1CCN1c1nc2c(c(-c3ccc(C(O)C(F)(F)F)cc3)n1)CCC2]

Example 265: 2,2,2-trifluoro-1-[4-[2-[(2S)-2-methylazetidin-1-yl]-6,7-dihydro-5H-cyclopenta[d]pyrimidin-4-yl]phenyl]ethanol The title compound was prepared in a method analogous to General Method A using 2,2,2-trifluoro-1-[4-(4,4,5,5-tetramethyl-1,3,2-dioxaborolan-2-yl)phenyl]ethanol and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

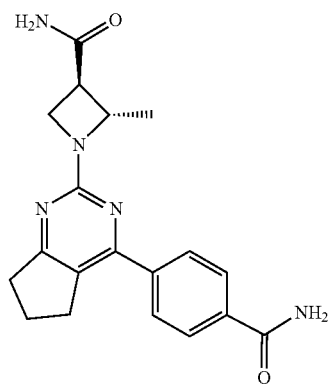 [SMILES: C[C@H]1[C@H](C(N)=O)CN1c1nc2c(c(-c3ccc(C(N)=O)cc3)n1)CCC2]

Example 266: (rac)-(2S*,3R*)-1-(4-(4-carbamoylphenyl)-6,7-dihydro-5H-cyclopenta[d]pyrimidin-2-yl)-2-methylazetidine-3-carboxamide The title compound was prepared in a method analogous to General Method B using trans-2-methylazetidine-3-carbonitrile and 4-(2-chloro-6,7-dihydro-5H-cyclopenta[d]pyrimidin-4-yl)benzamide instead of (S)-2-methyl azetidine and 2-chloro-4-(pyridin-3-yl)-6,7-dihydro-5H-cyclopenta[d]pyrimidine, respectively.

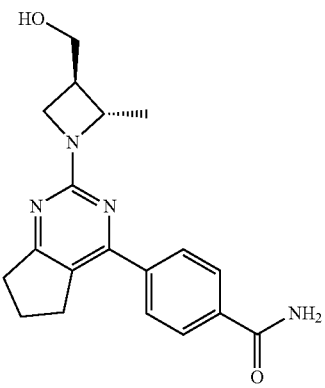 [SMILES: C[C@H]1[C@H](CO)CN1c1nc2c(c(-c3ccc(C(N)=O)cc3)n1)CCC2]

Example 267: (rac)-4-(2-((2S*,3R*)-3-(hydroxymethyl)-2-methylazetidin-1-yl)-6,7-dihydro-5H-cyclopenta[d]pyrimidin-4-yl)benzamide The title compound was prepared in a method analogous to General Method B using (trans-2-methylazetidin-3-yl)methanol and 4-(2-chloro-6,7-dihydro-5H-cyclopenta[d]pyrimidin-4-yl)benzamide instead of (S)-2-methyl azetidine and 2-chloro-4-(pyridin-3-yl)-6,7-dihydro-5H-cyclopenta[d]pyrimidine, respectively.

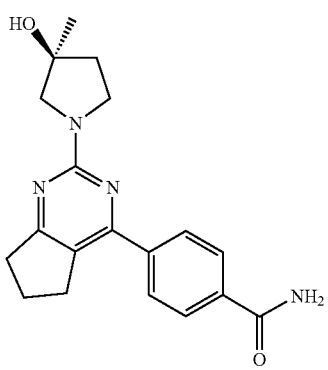 [SMILES: C[C@]1(O)CCN(c2nc3c(c(-c4ccc(C(N)=O)cc4)n2)CCC3)C1]

Example 268: 4-[2-[(3S)-3-hydroxy-3-methyl-pyrrolidin-1-yl]-6,7-dihydro-5H-cyclopenta[d]pyrimidin-4-yl]benzamide The title compound was prepared in a method analogous to General Method B using (3S)-3-methylpyrrolidin-3-ol instead of (S)-2-methyl azetidine and 2-chloro-4-(pyridin-3-yl)-6,7-dihydro-5H-cyclopenta[d]pyrimidine, respectively.

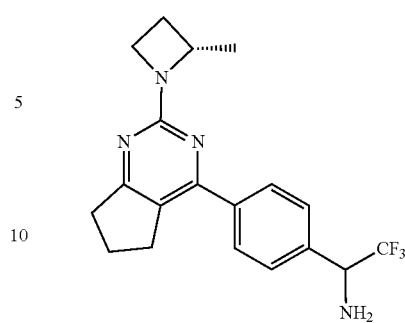

Example 269: 2,2,2-trifluoro-1-[4-[2-[(2S)-2-methylazetidin-1-yl]-6,7-dihydro-5H-cyclopenta[d]pyrimidin-4-yl]phenyl]ethanamine N-[2,2,2-trifluoro-1-[4-[2-[(2S)-2-methylazetidin-1-yl]-6,7-dihydro-5H-cyclopenta[d]pyrimidin-4-yl]phenyl]ethyl]acetamide was formed in a method analogous to General Method A using N-(2,2,2-trifluoro-1-(4-(4,4,5,5-tetramethyl-1,3,2-dioxaborolan-2-yl)phenyl)ethyl)acetamide and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

A vial was charged with N-[2,2,2-trifluoro-1-[4-[2-[(2S)-2-methylazetidin-1-yl]-6,7-dihydro-5H-cyclopenta[d]pyrimidin-4-yl]phenyl]ethyl]acetamide (140 mg, 0.35 mmol, 1.0 equiv.), HCl (2N aq., 0.43 mL, 0.87 mmol, 2.5 equiv., and MeOH (10 mL). The mixture was stirred for 1 hr, before being concentrated and subject to HPLC (0.1% TFA in MeCN-0.1% TFA in H$_2$O) to give the title compound.

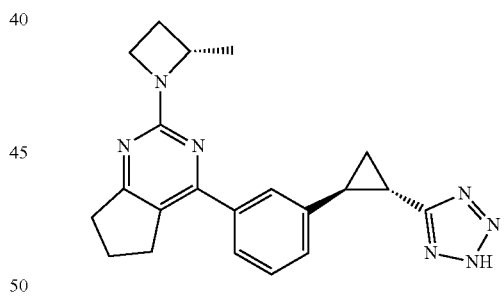

Example 270: 4-(3-((1S*,2S*)-2-(2H-tetrazol-5-yl)cyclopropyl)phenyl)-2-((S)-2-methylazetidin-1-yl)-6,7-dihydro-5H-cyclopenta[d]pyrimidine A vial was charged with trans-2-[3-[2-[rel-(2S)-2-methylazetidin-1-yl]-6,7-dihydro-5H-cyclopenta[d]pyrimidin-4-yl]phenyl]cyclopropanecarbonitrile (15.8 mg, 0.048 mmol, 1.0 equiv.), trimethyltin azide (19.9 mg, 0.096 mmol, 2.0 equiv.) and xylene (2.0 mL) The reaction mixture was stirred at 150° C. for 18 hrs before being cooled to ambient temperature and concentrated. The residue was subject to HPLC (0.1% TFA in MeCN-0.1% TFA in H$_2$O) to give the title compound (8.7 mg, 0.023 mmol, 49%).

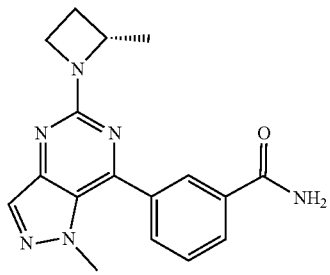 [SMILES: C[C@H]1CCN1c1nc(-c2cccc(C(N)=O)c2)c2c(cnn2C)n1]

Example 271: (S)-3-(1-methyl-5-(2-methylazetidin-1-yl)-1H-pyrazolo[4,3-d]pyrimidin-7-yl)benzamide The title compound was prepared in a method analogous to General Method A using 5,7-dichloro-1-methyl-1H-pyrazolo[4,3-d]pyrimidine and 3-(4,4,5,5-tetramethyl-1,3,2-dioxaborolan-2-yl)benzamide instead of 2,4-dichloro-6,7-dihydro-5H-cyclopenta[d]pyrimidine and 3-pyridylboronic acid, respectively, followed by General Method B.

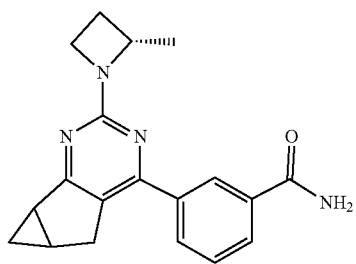 [SMILES: C[C@H]1CCN1c1nc(-c2cccc(C(N)=O)c2)c2c(n1)C1CC1C2]

Example 272: 3-(2-((S)-2-methylazetidin-1-yl)-5,5a,6,6a-tetrahydrocyclopropa[4,5]cyclopenta[1,2-d]pyrimidin-4-yl)benzamide The title compound was prepared according to General Method H.

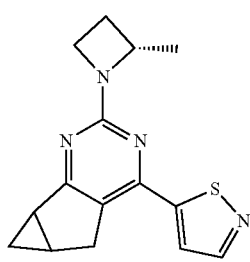 [SMILES: C[C@H]1CCN1c1nc(-c2ccns2)c2c(n1)C1CC1C2]

Example 273: 5-(2-((S)-2-methylazetidin-1-yl)-5,5a,6,6a-tetrahydrocyclopropa[4,5]cyclopenta[1,241]pyrimidin-4-yl)isothiazole The title compound was prepared in a method analogous to General Method H using 5-(4,4,5,5-tetramethyl-1,3,2-dioxaborolan-2-yl)isothiazole instead of 3-(4,4,5,5-tetramethyl-1,3,2-dioxaborolan-2-yl)benzamide

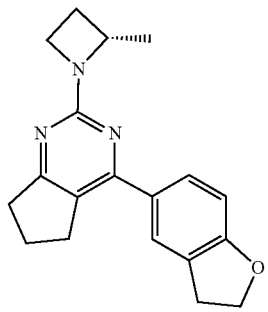 [SMILES: C[C@H]1CCN1c1nc2c(c(-c3ccc4c(c3)CCO4)n1)CCC2]

Example 274: (S)-4-(2,3-dihydrobenzofuran-5-yl)-2-(2-methylazetidin-1-yl)-6,7-dihydro-5H-cyclopenta[d]pyrimidine The title compound was prepared in a method analogous to General Method A using (S)-4-chloro-2-(2-methylazetidin-1-yl)-6,7-dihydro-5H-cyclopenta[d]pyrimidine and 2,3-dihydrobenzofuran-5-yl-boronic acid instead of 2,4-dichloro-6,7-dihydro-5H-cyclopenta[d]pyrimidine and 3-pyridylboronic acid, respectively.

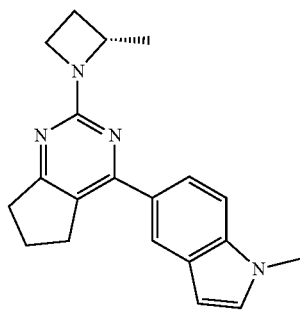 [SMILES: C[C@H]1CCN1c1nc2c(c(-c3ccc4c(ccn4C)c3)n1)CCC2]

Example 275: (S)-4-(1-methyl-1H-indol-5-yl)-2-(2-methylazetidin-1-yl)-6,7-dihydro-5H-cyclopenta[d]pyrimidine The title compound was prepared in a method analogous to General Method A using (S)-4-chloro-2-(2-methylazetidin-1-yl)-6,7-dihydro-5H-cyclopenta[d]pyrimidine and 1-methylindol-5-yl-boronic acid instead of 2,4-dichloro-6,7-dihydro-5H-cyclopenta[d]pyrimidine and 3-pyridylboronic acid, respectively.

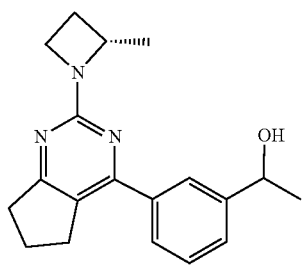 [SMILES: CC(O)c1cccc(-c2nc(N3CC[C@@H]3C)nc3c2CCC3)c1]

Example 276: 1-(3-(2-((S)-2-methylazetidin-1-yl)-6,7-dihydro-5H-cyclopenta[d]pyrimidin-4-yl)phenyl)ethan-1-ol The title compound was prepared in a method analogous to General Method A using (S)-4-chloro-2-(2-methylazetidin-1-yl)-6,7-dihydro-5H-cyclopenta[d]pyrimidine and 3-(1-hydroxyethyl)phenyl-boronic acid instead of 2,4-dichloro-6,7-dihydro-5H-cyclopenta[d]pyrimidine and 3-pyridylboronic acid, respectively.

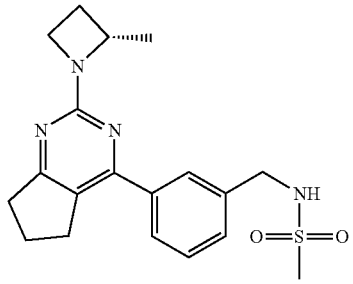 [SMILES: C[C@H]1CCN1c1nc2c(c(-c3cccc(CNS(C)(=O)=O)c3)n1)CCC2]

Example 277: (S)—N-(3-(2-(2-methylazetidin-1-yl)-6,7-dihydro-5H-cyclopenta[d]pyrimidin-4-yl)benzyl)methanesulfonamide The title compound was prepared in a method analogous to General Method A using (S)-4-chloro-2-(2-methylazetidin-1-yl)-6,7-dihydro-5H-cyclopenta[d]pyrimidine and 3-(methanesulfonamidomethyl)phenyl boronic acid instead of 2,4-dichloro-6,7-dihydro-5H-cyclopenta[d]pyrimidine and 3-pyridylboronic acid, respectively.

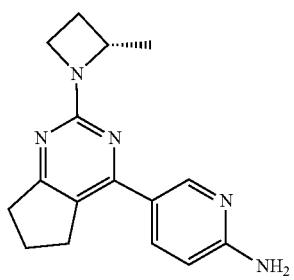 [SMILES: C[C@H]1CCN1c1nc2c(c(-c3ccc(N)nc3)n1)CCC2]

Example 278: (S)-5-(2-(2-methylazetidin-1-yl)-6,7-dihydro-5H-cyclopenta[d]pyrimidin-4-yl)pyridin-2-amine The title compound was prepared in a method analogous to General Method A using (S)-4-chloro-2-(2-methylazetidin-1-yl)-6,7-dihydro-5H-cyclopenta[d]pyrimidine and 5-(4,4,5,5-tetramethyl-1,3,2-dioxaborolan-2-yl)pyridin-2-amine instead of 2,4-dichloro-6,7-dihydro-5H-cyclopenta[d]pyrimidine and 3-pyridylboronic acid, respectively.

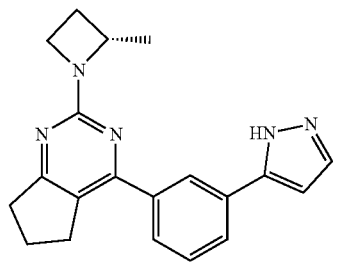 [SMILES: C[C@H]1CCN1c1nc2c(c(-c3cccc(-c4ccn[nH]4)c3)n1)CCC2]

Example 279: (S)-4-(3-(1H-pyrazol-5-yl)phenyl)-2-(2-methylazetidin-1-yl)-6,7-dihydro-5H-cyclopenta[d]pyrimidine The title compound was prepared in a method analogous to General Method A using (S)-4-chloro-2-(2-methylazetidin-1-yl)-6,7-dihydro-5H-cyclopenta[d]pyrimidine and 3-(1H-pyrazol-5-yl)phenylboronic acid instead of 2,4-dichloro-6,7-dihydro-5H-cyclopenta[d]pyrimidine and 3-pyridylboronic acid, respectively.

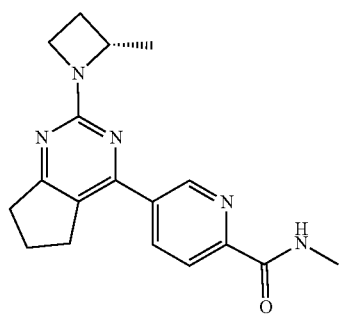 [SMILES: CNC(=O)c1ccc(-c2nc(N3CC[C@@H]3C)nc3c2CCC3)cn1]

Example 280: (S)—N-methyl-5-(2-(2-methylazetidin-1-yl)-6,7-dihydro-5H-cyclopenta[d]pyrimidin-4-yl)picolinamide The title compound was prepared in a method analogous to General Method A using (S)-4-chloro-2-(2-methylazetidin-1-yl)-6,7-dihydro-5H-cyclopenta[d]pyrimidine and N-methyl-5-(4,4,5,5-tetramethyl-1,3,2-dioxaborolan-2-yl)pyridine-2-carboxamide instead of 2,4-dichloro-6,7-dihydro-5H-cyclopenta[d]pyrimidine and 3-pyridylboronic acid, respectively.

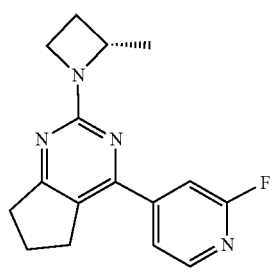 [SMILES: C[C@H]1CCN1c1nc2c(c(-c3ccnc(F)c3)n1)CCC2]

Example 281: (S)-4-(2-fluoropyridin-4-yl)-2-(2-methylazetidin-1-yl)-6,7-dihydro-5H-cyclopenta[d]pyrimidine The title compound was prepared in a method analogous to General Method A using (S)-4-chloro-2-(2-methylazetidin-1-yl)-6,7-dihydro-5H-cyclopenta[d]pyrimidine and 2-fluoro-4-(4,4,5,5-tetramethyl-1,3,2-dioxaborolan-2-yl)pyridine instead of 2,4-dichloro-6,7-dihydro-5H-cyclopenta[d]pyrimidine and 3-pyridylboronic acid, respectively.

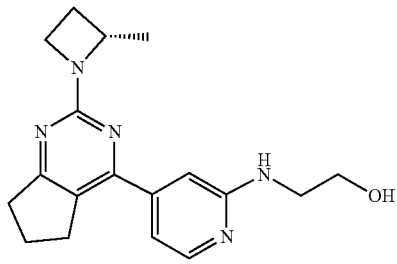 [SMILES: C[C@H]1CCN1c1nc2c(c(-c3ccnc(NCCO)c3)n1)CCC2]

Example 282: (S)-24(4-(2-(2-methylazetidin-1-yl)-6,7-dihydro-5H-cyclopenta[d]pyrimidin-4-yl)pyridin-2-yl)amino)ethan-1-ol The title compound was prepared by heating (S)-4-(2-fluoropyridin-4-yl)-2-(2-methylazetidin-1-yl)-6,7-dihydro-5H-cyclopenta[d]pyrimidine (22 mg, 0.07 mmol) in ethanolamine (2 mL) in the microwave at 150° C. for 30 minutes. The mixture was concentrated and subject to flash column chromatography (hexanes-ethyl acetate) to give the desired material.

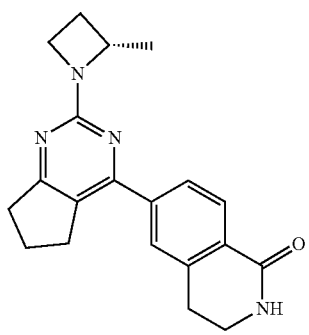 [SMILES: C[C@H]1CCN1c1nc2c(c(-c3ccc4c(c3)CCNC4=O)n1)CCC2]

Example 283: (S)-6-(2-(2-methylazetidin-1-yl)-6,7-dihydro-5H-cyclopenta[d]pyrimidin-4-yl)-3,4-dihydroisoquinolin-1(2H)-one The title compound was prepared in a method analogous to General Method A using (S)-4-chloro-2-(2-methylazetidin-1-yl)-6,7-dihydro-5H-cyclopenta[d]pyrimidine and 6-(4,4,5,5-tetramethyl-1,3,2-dioxaborolan-2-yl)-3,4-dihydro-2H-isoquinolin-1-one instead of 2,4-dichloro-6,7-dihydro-5H-cyclopenta[d]pyrimidine and 3-pyridylboronic acid, respectively.

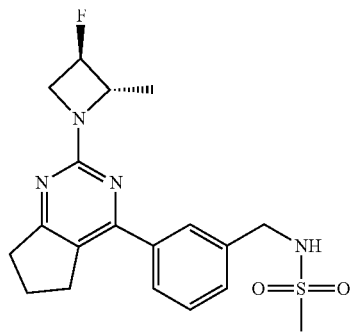 [SMILES: C[C@H]1[C@H](F)CN1c1nc2c(c(-c3cccc(CNS(C)(=O)=O)c3)n1)CCC2]

Example 284: N-(3-(24(2S,3R)-3-fluoro-2-methylazetidin-1-yl)-6,7-dihydro-5H-cyclopenta[d]pyrimidin-4-yl)benzyl)methanesulfonamide The title compound was prepared in a method analogous to General Method A using 3-(methanesulfonamidomethyl)phenylboronic acid and General Method B using (2S,3R)-3-fluoro-2-methyl-azetidine instead of 2,4-dichloro-6,7-dihydro-5H-cyclopenta[d]pyrimidine and 3-pyridylboronic acid, respectively.

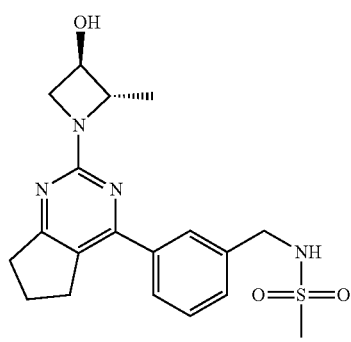 [SMILES: C[C@H]1[C@H](O)CN1c1nc2c(c(-c3cccc(CNS(C)(=O)=O)c3)n1)CCC2]

Example 285: N-(3-(24(2S,3R)-3-hydroxy-2-methylazetidin-1-yl)-6,7-dihydro-5H-cyclopenta[d]pyrimidin-4-yl)benzyl)methanesulfonamide The title compound was prepared in a method analogous to General Method A using 3-(methanesulfonamidomethyl)phenylboronic acid instead of 3-pyridylboronic acid and General Method B using (2S,3R)-2-methylazetidin-3-ol instead of (2S)-2-methylazetidine.

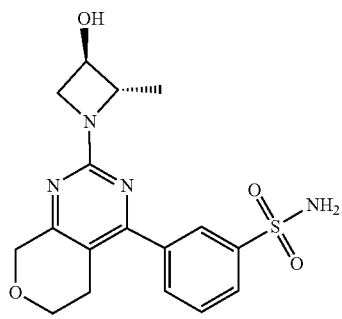 [SMILES: C[C@H]1[C@H](O)CN1c1nc2c(c(-c3cccc(S(N)(=O)=O)c3)n1)CCOC2]

Example 286: 3-(24(2S,3R)-3-hydroxy-2-methyl-azetidin-1-yl)-6,8-dihydro-5H-pyrano[3,4-d]pyrimidin-4-yl)benzenesulfonamide The title compound was prepared in a method analogous to General Method A using 2,4-dichloro-6,8-dihydro-5H-pyrano[3,4-d]pyrimidine and 3-(4,4,5,5-tetramethyl-1,3,2-dioxaborolan-2-yl)benzamide instead of 2,4-dichloro-6,7-dihydro-5H-cyclopenta[d]pyrimidine and 3-pyridylboronic acid, respectively. followed by General Method B using (2S,3R)-2-methylazetidin-3-ol instead of (2S)-2-methylazetidine.

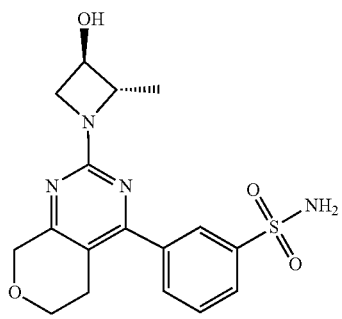 [SMILES: C[C@H]1[C@H](O)CN1c1nc2c(c(-c3cccc(S(N)(=O)=O)c3)n1)CCOC2]

Example 287: 3-(24(2S,3R)-3-fluoro-2-methylazetidin-1-yl)-6,8-dihydro-5H-pyrano[3,4-d]pyrimidin-4-yl)benzenesulfonamide The title compound was prepared in a method analogous to General Method A using 2,4-dichloro-6,8-dihydro-5H-pyrano[3,4-d]pyrimidine and 3-(4,4,5,5-tetramethyl-1,3,2-dioxaborolan-2-yl)benzamide instead of 2,4-dichloro-6,7-dihydro-5H-cyclopenta[d]pyrimidine and 3-pyridylboronic acid, respectively followed by General Method B using (2S,3R)-3-fluoro-2-methyl-azetidine instead of (2S)-2-methylazetidine.

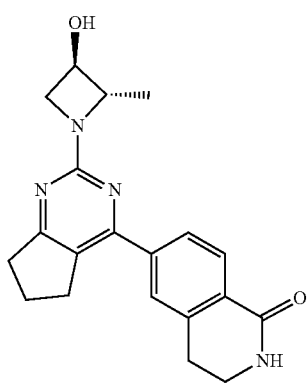 [SMILES: C[C@H]1[C@H](O)CN1c1nc2c(c(-c3ccc4c(c3)CCNC4=O)n1)CCC2]

Example 288: 6-(24(2S,3R)-3-hydroxy-2-methyl-azetidin-1-yl)-6,7-dihydro-5H-cyclopenta[d]pyrimidin-4-yl)-3,4-dihydroisoquinolin-1(2H)-one The title compound was prepared in a method analogous to General Method A using 6-(4,4,5,5-tetramethyl-1,3,2-dioxaborolan-2-yl)-3,4-dihydro-2H-isoquinolin-1-one instead of 3-pyridylboronic acid followed by General Method B using (2S,3R)-2-methylazetidin-3-ol instead of (2S)-2-methylazetidine.

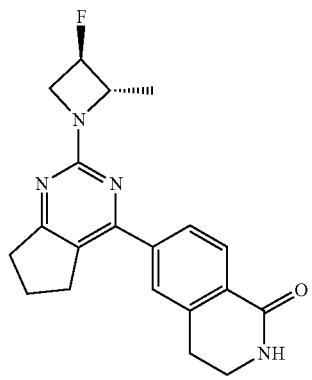 [SMILES: C[C@H]1[C@H](F)CN1c1nc2c(c(-c3ccc4c(c3)CCNC4=O)n1)CCC2]

Example 289: 6-(24(2S,3R)-3-fluoro-2-methylazetidin-1-yl)-6,7-dihydro-5H-cyclopenta[d]pyrimidin-4-yl)-3,4-dihydroisoquinolin-1(2H)-one The title compound was prepared in a method analogous to General Method A using 6-(4,4,5,5-tetramethyl-1,3,2-dioxaborolan-2-yl)-3,4-dihydro-2H-isoquinolin-1-one instead of 3-pyridylboronic acid, followed by General Method B using (2S,3R)-3-fluoro-2-methyl-azetidine instead of (2S)-2-methylazetidine.

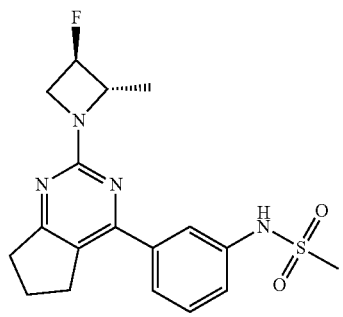 [SMILES: C[C@H]1[C@H](F)CN1c1nc2c(c(-c3cccc(NS(C)(=O)=O)c3)n1)CCC2]

Example 290: N-(3-(2-((2S,3R)-3-fluoro-2-methyl-azetidin-1-yl)-6,7-dihydro-5H-cyclopenta[d]pyrimidin-4-yl)phenyl)methanesulfonamide The title compound was prepared in a method analogous to General Method A using 3-(methanesulfonamido)phenylboronic acid instead of 3-pyridylboronic acid, followed by General Method B using (2S,3R)-3-fluoro-2-methyl-azetidine instead of (2S)-2-methylazetidine.

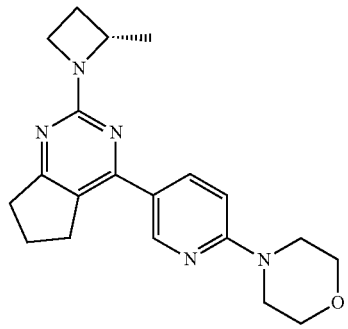 [SMILES: C[C@H]1CCN1c1nc2c(c(-c3ccc(N4CCOCC4)nc3)n1)CCC2]

Example 291: (S)-4-(5-(2-(2-methylazetidin-1-yl)-6,7-dihydro-5H-cyclopenta[d]pyrimidin-4-yl)pyridin-2-yl)morpholine The title compound was prepared in a method analogous to General Method A using (S)-4-chloro-2-(2-methylazetidin-1-yl)-6,7-dihydro-5H-cyclopenta[d]pyrimidine and 6-morpholino-3-pyridylboronic acid instead of 2,4-dichloro-6,7-dihydro-5H-cyclopenta[d]pyrimidine and 3-pyridylboronic acid, respectively.

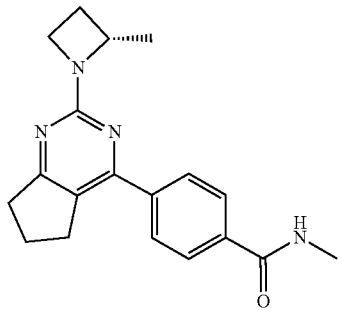 [SMILES: CNC(=O)c1ccc(-c2nc(N3CC[C@@H]3C)nc3c2CCC3)cc1]

Example 292: (S)—N-methyl-4-(2-(2-methylazetidin-1-yl)-6,7-dihydro-5H-cyclopenta[d]pyrimidin-4-yl)benzamide The title compound was prepared in a method analogous to General Method A using (S)-4-chloro-2-(2-methylazetidin-1-yl)-6,7-dihydro-5H-cyclopenta[d]pyrimidine and N-methyl-4-(4,4,5,5-tetramethyl-1,3,2-dioxaborolan-2-yl)benzamide instead of 2,4-dichloro-6,7-dihydro-5H-cyclopenta[d]pyrimidine and 3-pyridylboronic acid, respectively.

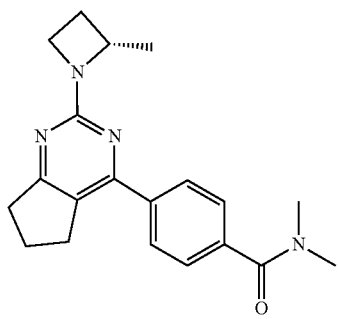 [SMILES: C[C@H]1CCN1c1nc2c(c(-c3ccc(C(=O)N(C)C)cc3)n1)CCC2]

Example 293: (S)—N,N-dimethyl-4-(2-(2-methylazetidin-1-yl)-6,7-dihydro-5H-cyclopenta[d]pyrimidin-4-yl)benzamide The title compound was prepared in a method analogous to General Method A using (S)-4-chloro-2-(2-methylazetidin-1-yl)-6,7-dihydro-5H-cyclopenta[d]pyrimidine and N,N-dimethyl-4-(4,4,5,5-tetramethyl-1,3,2-dioxaborolan-2-yl)benzamide instead of 2,4-dichloro-6,7-dihydro-5H-cyclopenta[d]pyrimidine and 3-pyridylboronic acid, respectively.

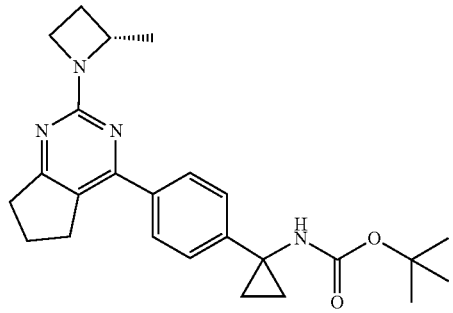 [SMILES: C[C@H]1CCN1c1nc2c(c(-c3ccc(C4(NC(=O)OC(C)(C)C)CC4)cc3)n1)CCC2]

Example 294: (S)-tert-butyl (1-(4-(2-(2-methylazetidin-1-yl)-6,7-dihydro-5H-cyclopenta[d]pyrimidin-4-yl)phenyl)cyclopropyl)carbamate The title compound was prepared in a method analogous to General Method A using (S)-4-chloro-2-(2-methylazetidin-1-yl)-6,7-dihydro-5H-cyclopenta[d]pyrimidine and 4-[1-(tert-butoxycarbonylamino)cyclopropyl]phenyl boronic acid instead of 2,4-dichloro-6,7-dihydro-5H-cyclopenta[d]pyrimidine and 3-pyridylboronic acid, respectively.

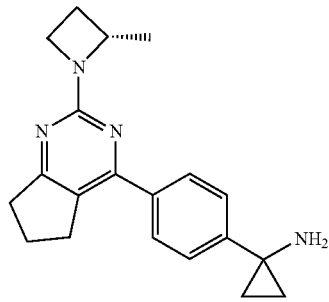 [SMILES: C[C@H]1CCN1c1nc2c(c(-c3ccc(C4(N)CC4)cc3)n1)CCC2]

Example 295: (S)-1-(4-(2-(2-methylazetidin-1-yl)-6,7-dihydro-5H-cyclopenta[d]pyrimidin-4-yl)phenyl)cyclopropan-1-amine The title compound was prepared according to General Method I using (S)-tert-butyl (1-(4-(2-(2-methylazetidin-1-yl)-6,7-dihydro-5H-cyclopenta[d]pyrimidin-4-yl)phenyl)cyclopropyl)carbamate instead of tert-butyl (S)-4-(4-(2-(2-methylazetidin-1-yl)-6,7-dihydro-5H-cyclopenta[d]pyrimidin-4-yl)phenyl)piperazine-1-carboxylate.

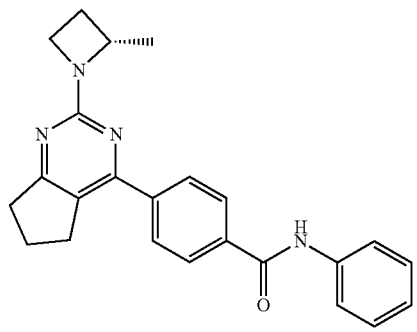 [SMILES: C[C@H]1CCN1c1nc2c(c(-c3ccc(C(=O)Nc4ccccc4)cc3)n1)CCC2]

Example 296: (S)-4-(2-(2-methylazetidin-1-yl)-6,7-dihydro-5H-cyclopenta[d]pyrimidin-4-yl)-N-phenylbenzamide The title compound was prepared in a method analogous to General Method A using (S)-4-chloro-2-(2-methylazetidin-1-yl)-6,7-dihydro-5H-cyclopenta[d]pyrimidine and 4-(4,4,5,5-tetramethyl-1,3,2-dioxaborolan-2-yl)benzoic acid instead of 2,4-dichloro-6,7-dihydro-5H-cyclopenta[d]pyrimidine and 3-pyridylboronic acid, respectively followed by General Method G using aniline instead of ammonia.

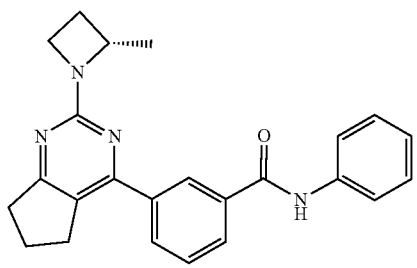 [SMILES: C[C@H]1CCN1c1nc2c(c(-c3cccc(C(=O)Nc4ccccc4)c3)n1)CCC2]

Example 297: (S)-3-(2-(2-methylazetidin-1-yl)-6,7-dihydro-5H-cyclopenta[d]pyrimidin-4-yl)-N-phenylbenzamide The title compound was prepared in a method analogous to General Method A using (S)-4-chloro-2-(2-methylazetidin-1-yl)-6,7-dihydro-5H-cyclopenta[d]pyrimidine and 3-(4,4,5,5-tetramethyl-1,3,2-dioxaborolan-2-yl)benzoic acid instead of 2,4-dichloro-6,7-dihydro-5H-cyclopenta[d]pyrimidine and 3-pyridylboronic acid, respectively followed by General Method G using aniline instead of ammonia.

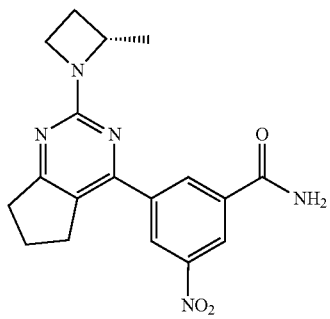 [SMILES: C[C@H]1CCN1c1nc2c(c(-c3cc(C(N)=O)cc([N+](=O)[O-])c3)n1)CCC2]

Example 298: (S)-3-(2-(2-methylazetidin-1-yl)-6,7-dihydro-5H-cyclopenta[d]pyrimidin-4-yl)-5-nitrobenzamide The title compound was prepared in a method analogous to General Method A using (S)-4-chloro-2-(2-methylazetidin-1-yl)-6,7-dihydro-5H-cyclopenta[d]pyrimidine and 3-carbamoyl-5-nitro-phenylboronic acid instead of 2,4-dichloro-6,7-dihydro-5H-cyclopenta[d]pyrimidine and 3-pyridylboronic acid, respectively.

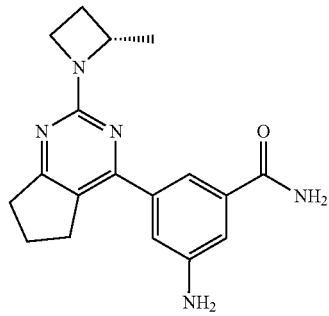 [SMILES: C[C@H]1CCN1c1nc2c(c(-c3cc(N)cc(C(N)=O)c3)n1)CCC2]

Example 299: (S)-3-amino-5-(2-(2-methylazetidin-1-yl)-6,7-dihydro-5H-cyclopenta[d]pyrimidin-4-yl)benzamide A reaction vial was charged with (S)-3-(2-(2-methylazetidin-1-yl)-6,7-dihydro-5H-cyclopenta[d]pyrimidin-4-yl)-5-nitrobenzamide (130 mg, 0.368 mmol), iron powder (101 mg, 1.84 mmol), $CaCl_2$) (61 mg, 0.55 mmol), water (1.5 mL), and EtOH (0.2 mL). The reaction mixture was heated for 18 hrs at 60° C. The mixture was concentrated and subject to flash column chromatography (hexanes-ethyl acetate) to give the title compound.

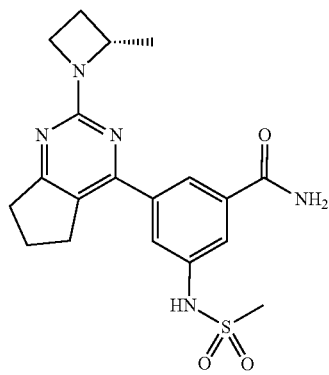 [SMILES: C[C@H]1CCN1c1nc2c(c(-c3cc(NS(C)(=O)=O)cc(C(N)=O)c3)n1)CCC2]

Example 300: (S)-3-(2-(2-methylazetidin-1-yl)-6,7-dihydro-5H-cyclopenta[d]pyrimidin-4-yl)-5-(methylsulfonamido)benzamide The title compound was prepared in a method analogous to General Method K using (S)-3-amino-5-(2-(2-methylazetidin-1-yl)-6,7-dihydro-5H-cyclopenta[d]pyrimidin-4-yl)benzamide and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively.

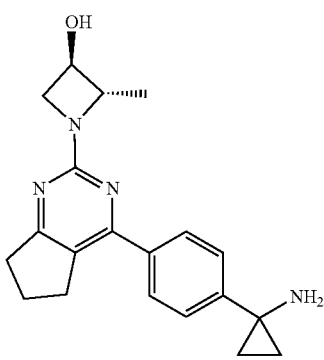 [SMILES: C[C@H]1[C@H](O)CN1c1nc2c(c(-c3ccc(C4(N)CC4)cc3)n1)CCC2]

Example 301: (2S,3R)-1-(4-(4-(1-aminocyclopropyl)phenyl)-6,7-dihydro-5H-cyclopenta[d]pyrimidin-2-yl)-2-methylazetidin-3-ol The title compound was prepared in a method analogous to General Method A using 4-[1-(tert-butoxycarbonylamino)cyclopropyl]phenyl boronic acid instead of 3-pyridylboronic acid, followed by General Method B using (2S,3R)-2-methylazetidin-3-ol instead of (2S)-2-methylazetidine then General Method I.

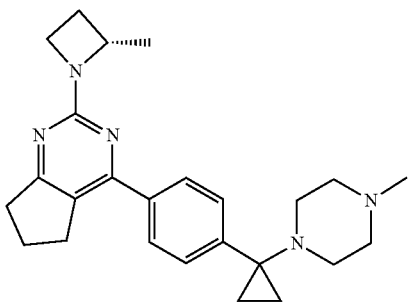 [SMILES: C[C@H]1CCN1c1nc2c(c(-c3ccc(C4(N5CCN(C)CC5)CC4)cc3)n1)CCC2]

Example 302: (S)-2-(2-methylazetidin-1-yl)-4-(4-(1-(4-methylpiperazin-1-yl)cyclopropyl)phenyl)-6,7-dihydro-5H-cyclopenta[d]pyrimidine The title compound was prepared in a method analogous to General Method A using (S)-4-chloro-2-(2-methylazetidin-1-yl)-6,7-dihydro-5H-cyclopenta[d]pyrimidine and 1-methyl-4-[1-[4-(4,4,5,5-tetramethyl-1,3,2-dioxaborolan-2-yl)phenyl]cyclopropyl]piperazine instead of 2,4-dichloro-6,7-dihydro-5H-cyclopenta[d]pyrimidine and 3-pyridylboronic acid, respectively.

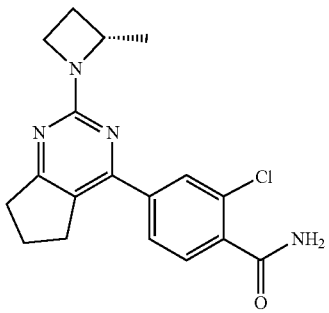 [SMILES: C[C@H]1CCN1c1nc2c(c(-c3ccc(C(N)=O)c(Cl)c3)n1)CCC2]

Example 303: (S)-2-chloro-4-(2-(2-methylazetidin-1-yl)-6,7-dihydro-5H-cyclopenta[d]pyrimidin-4-yl)benzamide The title compound was prepared in a method analogous to General Method A using (S)-4-chloro-2-(2-methylazetidin-1-yl)-6,7-dihydro-5H-cyclopenta[d]pyrimidine and 4-carbamoyl-3-chloro-phenylboronic acid instead of 2,4-dichloro-6,7-dihydro-5H-cyclopenta[d]pyrimidine and 3-pyridylboronic acid, respectively.

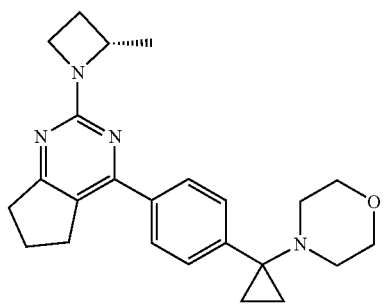 [SMILES: C[C@H]1CCN1c1nc2c(c(-c3ccc(C4(N5CCOCC5)CC4)cc3)n1)CCC2]

Example 304: (S)-4-(1-(4-(2-(2-methylazetidin-1-yl)-6,7-dihydro-5H-cyclopenta[d]pyrimidin-4-yl)phenyl)cyclopropyl)morpholine The title compound was prepared in a method analogous to General Method A using (S)-4-chloro-2-(2-methylazetidin-1-yl)-6,7-dihydro-5H-cyclopenta[d]pyrimidine and 4-[1-[4-(4,4,5,5-tetramethyl-1,3,2-dioxaborolan-2-yl)phenyl]cyclopropyl]morpholine instead of 2,4-dichloro-6,7-dihydro-5H-cyclopenta[d]pyrimidine and 3-pyridylboronic acid, respectively.

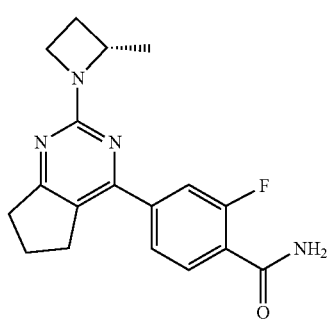 [SMILES: C[C@H]1CCN1c1nc2c(c(-c3ccc(C(N)=O)c(F)c3)n1)CCC2]

Example 305: (S)-2-fluoro-4-(2-(2-methylazetidin-1-yl)-6,7-dihydro-5H-cyclopenta[d]pyrimidin-4-yl)benzamide The title compound was prepared in a method analogous to General Method A using (S)-4-chloro-2-(2-methylazetidin-1-yl)-6,7-dihydro-5H-cyclopenta[d]pyrimidine and 4-carbamoyl-3-fluoro-phenylboronic acid instead of 2,4-dichloro-6,7-dihydro-5H-cyclopenta[d]pyrimidine and 3-pyridylboronic acid, respectively.

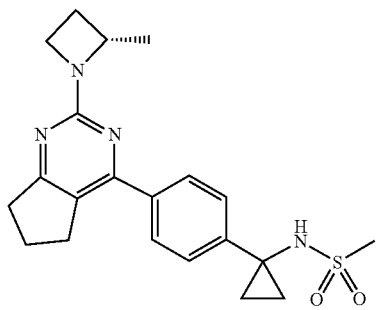 [SMILES: C[C@H]1CCN1c1nc2c(c(-c3ccc(C4(NS(C)(=O)=O)CC4)cc3)n1)CCC2]

Example 306: (S)—N-(1-(4-(2-(2-methylazetidin-1-yl)-6,7-dihydro-5H-cyclopenta[d]pyrimidin-4-yl)phenyl)cyclopropyl)methanesulfonamide The title compound was prepared in a method analogous to General Method A using (S)-4-chloro-2-(2-methylazetidin-1-yl)-6,7-dihydro-5H-cyclopenta[d]pyrimidine and N-[1-[4-(4,4,5,5-tetramethyl-1,3,2-dioxaborolan-2-yl)phenyl]cyclopropyl]methanesulfonamide instead of 2,4-dichloro-6,7-dihydro-5H-cyclopenta[d]pyrimidine and 3-pyridylboronic acid, respectively.

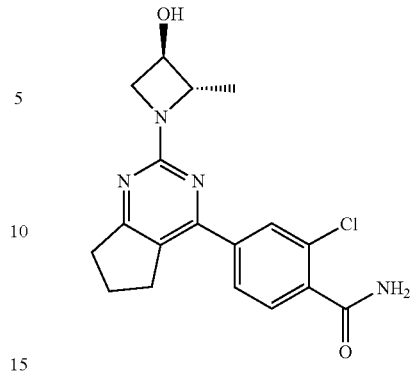

Example 308: 2-chloro-4-(24(2S,3R)-3-hydroxy-2-methylazetidin-1-yl)-6,7-dihydro-5H-cyclopenta[d]pyrimidin-4-yl)benzamide The title compound was prepared in a method analogous to General Method A using 4-carbamoyl-3-chloro-phenylboronic acid instead of 3-pyridylboronic acid followed by General Method B using (2S,3R)-2-methylazetidin-3-ol instead of (2S)-2-methylazetidine.

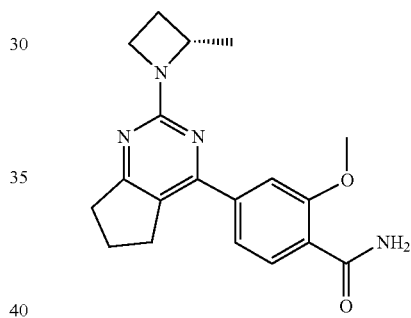

Example 309: (S)-2-methoxy-4-(2-(2-methylazetidin-1-yl)-6,7-dihydro-5H-cyclopenta[d]pyrimidin-4-yl)benzamide The title compound was prepared in a method analogous to General Method A using (S)-4-chloro-2-(2-methylazetidin-1-yl)-6,7-dihydro-5H-cyclopenta[d]pyrimidine and 4-carbamoyl-3-methoxy-phenylboronic acid instead of 2,4-dichloro-6,7-dihydro-5H-cyclopenta[d]pyrimidine and 3-pyridylboronic acid, respectively.

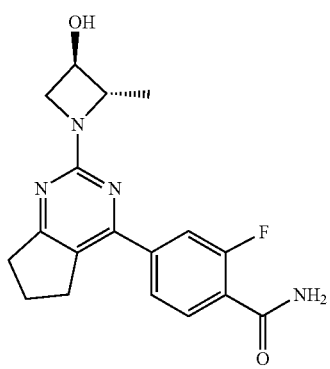 [SMILES: C[C@H]1[C@H](O)CN1c1nc2c(c(-c3ccc(C(N)=O)c(F)c3)n1)CCC2]

Example 307: 2-fluoro-4-(24(2S,3R)-3-hydroxy-2-methylazetidin-1-yl)-6,7-dihydro-5H-cyclopenta[d]pyrimidin-4-yl)benzamide The title compound was prepared in a method analogous to General Method A using 4-carbamoyl-3-fluoro-phenylboronic acid instead of 3-pyridylboronic acid followed by General Method B using (2S,3R)-2-methylazetidin-3-ol instead of (2S)-2-methylazetidine.

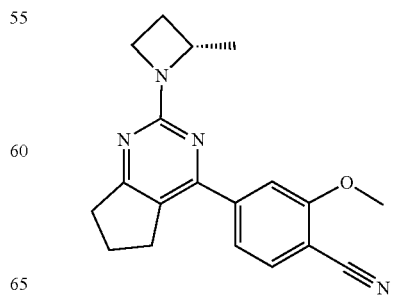

Example 310: (S)-2-methoxy-4-(2-(2-methylazetidin-1-yl)-6,7-dihydro-5H-cyclopenta[d]pyrimidin-4-yl)benzonitrile The title compound was prepared in a method analogous to General Method A using (S)-4-chloro-2-(2-methylazetidin-1-yl)-6,7-dihydro-5H-cyclopenta[d]pyrimidine and 2-methoxy-4-(4,4,5,5-tetramethyl-1,3,2-dioxaborolan-2-yl)benzonitrile instead of 2,4-dichloro-6,7-dihydro-5H-cyclopenta[d]pyrimidine and 3-pyridylboronic acid, respectively.

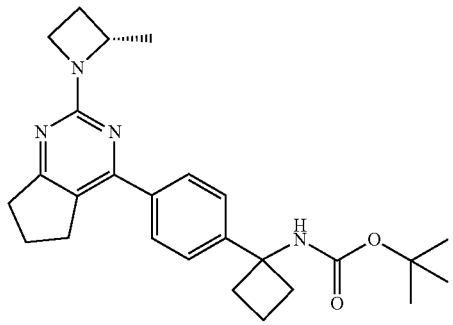 [SMILES: C[C@H]1CCN1c1nc2c(c(-c3ccc(C4(NC(=O)OC(C)(C)C)CCC4)cc3)n1)CCC2]

Example 311: (S)-tert-butyl (1-(4-(2-(2-methylazetidin-1-yl)-6,7-dihydro-5H-cyclopenta[d]pyrimidin-4-yl)phenyl)cyclobutyl)carbamate The title compound was prepared in a method analogous to General Method A using (S)-4-chloro-2-(2-methylazetidin-1-yl)-6,7-dihydro-5H-cyclopenta[d]pyrimidine and tert-butyl N-[1-[4-(4,4,5,5-tetramethyl-1,3,2-dioxaborolan-2-yl)phenyl]cyclobutyl]carbamate instead of 2,4-dichloro-6,7-dihydro-5H-cyclopenta[d]pyrimidine and 3-pyridylboronic acid, respectively.

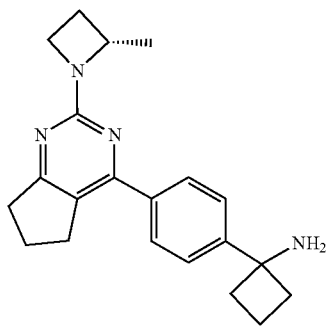 [SMILES: C[C@H]1CCN1c1nc2c(c(-c3ccc(C4(N)CCC4)cc3)n1)CCC2]

Example 312: (S)-1-(4-(2-(2-methylazetidin-1-yl)-6,7-dihydro-5H-cyclopenta[d]pyrimidin-4-yl)phenyl)cyclobutan-1-amine The title compound was prepared in a method analogous to General Method I using (S)-tert-butyl (1-(4-(2-(2-methylazetidin-1-yl)-6,7-dihydro-5H-cyclopenta[d]pyrimidin-4-yl)phenyl)cyclobutyl)carbamate instead of tert-butyl (S)-4-(4-(2-(2-methylazetidin-1-yl)-6,7-dihydro-5H-cyclopenta[d]pyrimidin-4-yl)phenyl)piperazine-1-carboxylate.

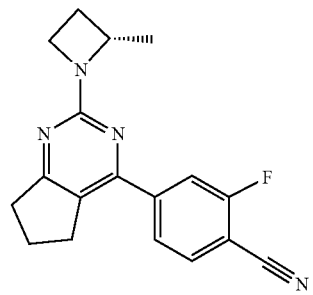 [SMILES: C[C@H]1CCN1c1nc2c(c(-c3ccc(C#N)c(F)c3)n1)CCC2]

Example 313: (S)-2-fluoro-4-(2-(2-methylazetidin-1-yl)-6,7-dihydro-5H-cyclopenta[d]pyrimidin-4-yl)benzonitrile The title compound was prepared in a method analogous to General Method A using (S)-4-chloro-2-(2-methylazetidin-1-yl)-6,7-dihydro-5H-cyclopenta[d]pyrimidine and 2-fluoro-4-(4,4,5,5-tetramethyl-1,3,2-dioxaborolan-2-yl)benzonitrile instead of 2,4-dichloro-6,7-dihydro-5H-cyclopenta[d]pyrimidine and 3-pyridylboronic acid, respectively.

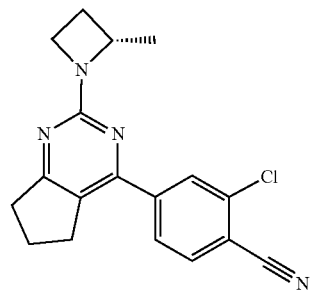 [SMILES: C[C@H]1CCN1c1nc2c(c(-c3ccc(C#N)c(Cl)c3)n1)CCC2]

Example 314: (S)-2-chloro-4-(2-(2-methylazetidin-1-yl)-6,7-dihydro-5H-cyclopenta[d]pyrimidin-4-yl)benzonitrile The title compound was prepared in a method analogous to General Method A using (S)-4-chloro-2-(2-methylazetidin-1-yl)-6,7-dihydro-5H-cyclopenta[d]pyrimidine and 2-chloro-4-(4,4,5,5-tetramethyl-1,3,2-dioxaborolan-2-yl)benzonitrile instead of 2,4-dichloro-6,7-dihydro-5H-cyclopenta[d]pyrimidine and 3-pyridylboronic acid, respectively.

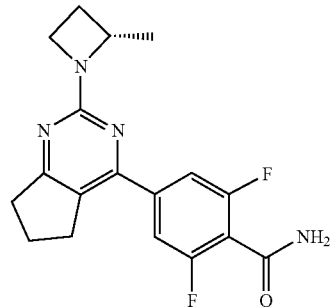 [SMILES: C[C@H]1CCN1c1nc2c(c(-c3cc(F)c(C(N)=O)c(F)c3)n1)CCC2]

Example 315: (S)-2,6-difluoro-4-(2-(2-methylazetidin-1-yl)-6,7-dihydro-5H-cyclopenta[d]pyrimidin-4-yl)benzamide The title compound was prepared in a method analogous to General Method A using (S)-4-chloro-2-(2-methylazetidin-1-yl)-6,7-dihydro-5H-cyclopenta[d]pyrimidine and 4-carbamoyl-3,5-difluoro-phenylboronic acid instead of 2,4-dichloro-6,7-dihydro-5H-cyclopenta[d]pyrimidine and 3-pyridylboronic acid, respectively.

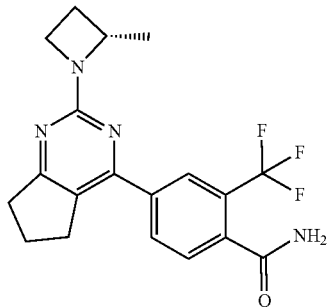 [SMILES: C[C@H]1CCN1c1nc2c(c(-c3ccc(C(N)=O)c(C(F)(F)F)c3)n1)CCC2]

Example 316: (S)-4-(2-(2-methylazetidin-1-yl)-6,7-dihydro-5H-cyclopenta[d]pyrimidin-4-yl)-2-(trifluoromethyl)benzamide The title compound was prepared in a method analogous to General Method A using (S)-4-chloro-2-(2-methylazetidin-1-yl)-6,7-dihydro-5H-cyclopenta[d]pyrimidine and 4-(4,4,5,5-tetramethyl-1,3,2-dioxaborolan-2-yl)-2-(trifluoromethyl)benzamide instead of 2,4-dichloro-6,7-dihydro-5H-cyclopenta[d]pyrimidine and 3-pyridylboronic acid, respectively.

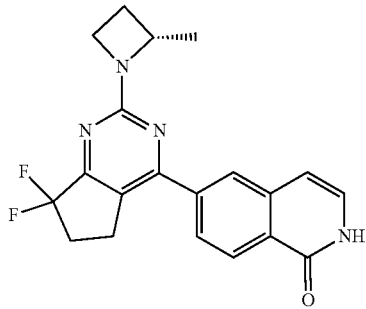 [SMILES: C[C@H]1CCN1c1nc(-c2ccc3c(=O)[nH]ccc3c2)c2c(n1)C(F)(F)CC2]

Example 317: (S)-6-(7,7-difluoro-2-(2-methylazetidin-1-yl)-6,7-dihydro-5H-cyclopenta[d]pyrimidin-4-yl)isoquinolin-1(2H)-one The title compound was prepared in a method analogous to General Method H using 4-chloro-7,7-difluoro-2-(methylthio)-6,7-dihydro-5H-cyclopenta[d]pyrimidine instead of 4-chloro-2-(methylthio)-5,5a,6,6a-tetrahydrocyclopropa[4,5]cyclopenta[1,2-d]pyrimidine and using 6-(4,4,5,5-tetramethyl-1,3,2-dioxaborolan-2-yl)isoquinolin-1(2H)-one instead of 3-carbamoylphenylboronic acid.

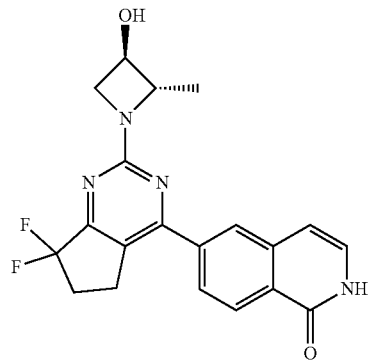 [SMILES: C[C@H]1[C@H](O)CN1c1nc(-c2ccc3c(=O)[nH]ccc3c2)c2c(n1)C(F)(F)CC2]

Example 318: 6-(7,7-difluoro-2-((2S,3R)-3-hydroxy-2-methylazetidin-1-yl)-6,7-dihydro-5H-cyclopenta[d]pyrimidin-4-yl)isoquinolin-1(2H)-one The title compound was prepared in a method analogous to General Method H using 4-chloro-7,7-difluoro-2-(methylthio)-6,7-dihydro-5H-cyclopenta[d]pyrimidine instead of 4-chloro-2-(methylthio)-5,5a,6,6a-tetrahydrocyclopropa[4,5]cyclopenta[1,2-d]pyrimidine and using 6-(4,4,5,5-tetramethyl-1,3,2-dioxaborolan-2-yl)isoquinolin-1(2H)-one instead of 3-carbamoylphenylboronic acid. Additionally, (2S,3R)-2-methylazetidin-3-ol hydrochloride salt was used instead of (2S)-2-methylazetidine (R)-camphorsulfonic acid salt.

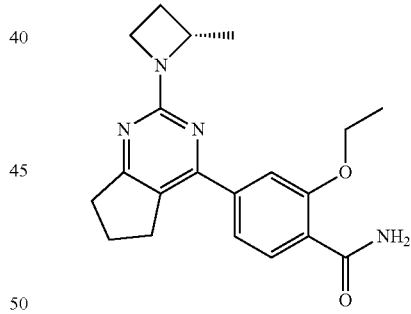

Example 319: (S)-2-ethoxy-4-(2-(2-methylazetidin-1-yl)-6,7-dihydro-5H-cyclopenta[d]pyrimidin-4-yl)benzamide The title compound was prepared in a method analogous to General Method A using (S)-4-chloro-2-(2-methylazetidin-1-yl)-6,7-dihydro-5H-cyclopenta[d]pyrimidine and 2-ethoxy-4-(4,4,5,5-tetramethyl-1,3,2-dioxaborolan-2-yl)benzamide instead of 2,4-dichloro-6,7-dihydro-5H-cyclopenta[d]pyrimidine and 3-pyridylboronic acid, respectively.

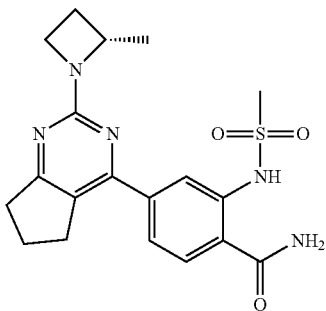 [SMILES: C[C@H]1CCN1c1nc2c(c(-c3ccc(C(N)=O)c(NS(C)(=O)=O)c3)n1)CCC2]

Example 320: (S)-4-(2-(2-methylazetidin-1-yl)-6,7-dihydro-5H-cyclopenta[d]pyrimidin-4-yl)-2-(methylsulfonamido)benzamide The title compound was prepared in a method analogous to General Method A using (S)-4-chloro-2-(2-methylazetidin-1-yl)-6,7-dihydro-5H-cyclopenta[d]pyrimidine and 3-amino-4-carbamoyl-phenylboronic acid instead of 2,4-dichloro-6,7-dihydro-5H-cyclopenta[d]pyrimidine and 3-pyridylboronic acid, respectively, followed by General Method K using methanesulfonyl chloride instead of 1-methylimidazole-4-sulfonyl chloride.

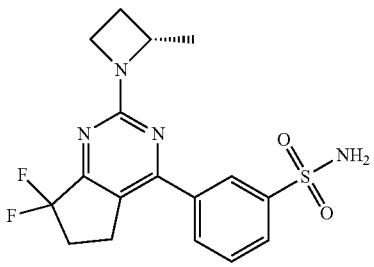 [SMILES: C[C@H]1CCN1c1nc(-c2cccc(S(N)(=O)=O)c2)c2c(n1)C(F)(F)CC2]

Example 321: (S)-3-(7,7-difluoro-2-(2-methylazetidin-1-yl)-6,7-dihydro-5H-cyclopenta[d]pyrimidin-4-yl)benzenesulfonamide The title compound was prepared in a method analogous to General Method H using 4-chloro-7,7-difluoro-2-(methylthio)-6,7-dihydro-5H-cyclopenta[d]pyrimidine instead of 4-chloro-2-(methylthio)-5,5a,6,6a-tetrahydrocyclopropa[4,5]cyclopenta[1,2-d]pyrimidine and using 3-(4,4,5,5-tetramethyl-1,3,2-dioxaborolan-2-yl)benzenesulfonamide instead of 3-carbamoylphenylboronic acid.

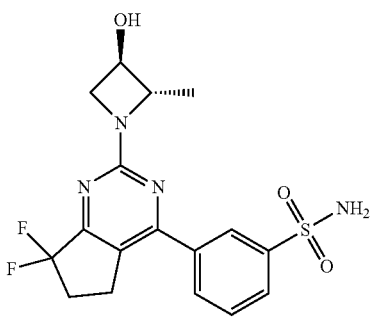 [SMILES: C[C@H]1[C@H](O)CN1c1nc(-c2cccc(S(N)(=O)=O)c2)c2c(n1)C(F)(F)CC2]

Example 322: 3-(7,7-difluoro-2-((2S,3R)-3-hydroxy-2-methylazetidin-1-yl)-6,7-dihydro-5H-cyclopenta[d]pyrimidin-4-yl)benzenesulfonamide The title compound was prepared in a method analogous to General Method H using 4-chloro-7,7-difluoro-2-(methylthio)-6,7-dihydro-5H-cyclopenta[d]pyrimidine instead of 4-chloro-2-(methylthio)-5,5a,6,6a-tetrahydrocyclopropa[4,5]cyclopenta[1,2-d]pyrimidine and using 3-(4,4,5,5-tetramethyl-1,3,2-dioxaborolan-2-yl)benzenesulfonamide instead of 3-carbamoylphenylboronic acid. Additionally, (2S,3R)-2-methylazetidin-3-ol hydrochloride salt was used instead of (2S)-2-methylazetidine (R)-camphorsulfonic acid salt.

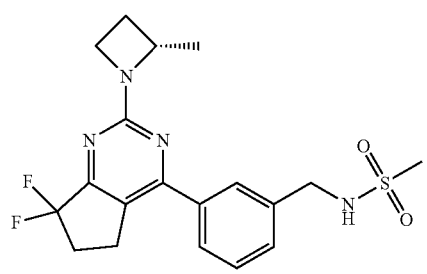 [SMILES: C[C@H]1CCN1c1nc(-c2cccc(CNS(C)(=O)=O)c2)c2c(n1)C(F)(F)CC2]

Example 323: (S)—N-(3-(7,7-difluoro-2-(2-methylazetidin-1-yl)-6,7-dihydro-5H-cyclopenta[d]pyrimidin-4-yl)benzyl)methanesulfonamide The title compound was prepared in a method analogous to General Method H using 4-chloro-7,7-difluoro-2-(methylthio)-6,7-dihydro-5H-cyclopenta[d]pyrimidine instead of 4-chloro-2-(methylthio)-5,5a,6,6a-tetrahydrocyclopropa[4,5]cyclopenta[1,2-d]pyrimidine and using 3-(methanesulfonamidomethyl)phenyl boronic acid instead of 3-carbamoylphenylboronic acid.

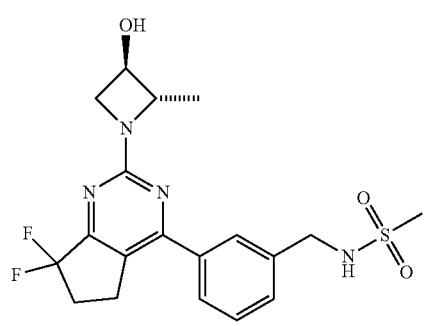 [SMILES: C[C@H]1[C@H](O)CN1c1nc(-c2cccc(CNS(C)(=O)=O)c2)c2c(n1)C(F)(F)CC2]

Example 324: N-(3-(7,7-difluoro-2-((2S,3R)-3-hydroxy-2-methylazetidin-1-yl)-6,7-dihydro-5H-cyclopenta[d]pyrimidin-4-yl)benzyl)methanesulfonamide The title compound was prepared in a method analogous to General Method H using 4-chloro-7,7-difluoro-2-(methylthio)-6,7-dihydro-5H-cyclopenta[d]pyrimidine instead of 4-chloro-2-(methylthio)-5,5a,6,6a-tetrahydrocyclopropa[4,5]cyclopenta[1,2-d]pyrimidine and using 3-(methanesulfonamidomethyl)phenyl boronic acid instead of 3-carbamoylphenylboronic acid. Additionally, (2S,3R)-2-methylazetidin-3-ol hydrochloride salt was used instead of (2S)-2-methylazetidine (R)-camphorsulfonic acid salt.

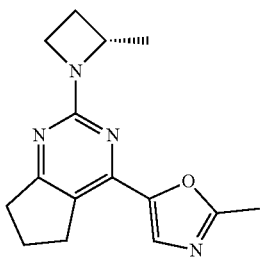 [SMILES: Cc1ncc(-c2nc(N3CC[C@@H]3C)nc3c2CCC3)o1]

Example 325: 2-methyl-5-[2-[(2S)-2-methylazetidin-1-yl]-6,7-dihydro-5H-cyclopenta[d]pyrimidin-4-yl]oxazole The title compound was prepared in a method analogous to General Method A using 2-methyl-5-(4,4,5,5-tetramethyl-1,3,2-dioxaborolan-2-yl)oxazole and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

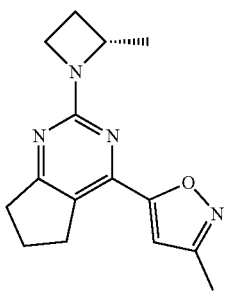

Example 326: 3-methyl-5-[2-[(2S)-2-methylazetidin-1-yl]-6,7-dihydro-5H-cyclopenta[d]pyrimidin-4-yl]isoxazole The title compound was prepared in a method analogous to General Method A using 3-methyl-5-(4,4,5,5-tetramethyl-1,3,2-dioxaborolan-2-yl)isoxazole and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

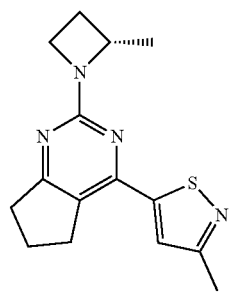 [SMILES: Cc1cc(-c2nc(N3CC[C@@H]3C)nc3c2CCC3)sn1]

Example 327: 3-methyl-5-[2-[(2S)-2-methylazetidin-1-yl]-6,7-dihydro-5H-cyclopenta[d]pyrimidin-4-yl]isothiazole The title compound was prepared in a method analogous to General Method A using 3-methyl-5-(4,4,5,5-tetramethyl-1,3,2-dioxaborolan-2-yl)isothiazole and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

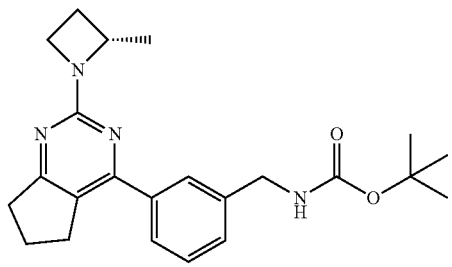 [SMILES: C[C@H]1CCN1c1nc2c(c(-c3cccc(CNC(=O)OC(C)(C)C)c3)n1)CCC2]

Example 328: tert-butyl N-[[3-[2-[(2S)-2-methylazetidin-1-yl]-6,7-dihydro-5H-cyclopenta[d]pyrimidin-4-yl]phenyl]methyl]carbamate The title compound was prepared in a method analogous to General Method A using [3-1(tert-butoxycarbonylamino)methyl)phenyl]boronic acid and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

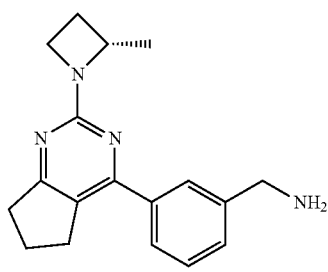 [SMILES: C[C@H]1CCN1c1nc2c(c(-c3cccc(CN)c3)n1)CCC2]

Example 329: [3-[2-[(2S)-2-methylazetidin-1-yl]-6,7-dihydro-5H-cyclopenta[d]pyrimidin-4-yl]phenyl]methanamine The title compound was prepared in a method analogous to General Method I, using tert-butyl N-[[3-[2-[(2S)-2-methylazetidin-1-yl]-6,7-dihydro-5H-cyclopenta[d]pyrimidin-4-yl]phenyl]methyl]carbamate instead of tert-butyl (S)-4-(4-(2-(2-methylazetidin-1-yl)-6,7-dihydro-5H-cyclopenta[d]pyrimidin-4-yl)phenyl)piperazine-1-carboxylate.

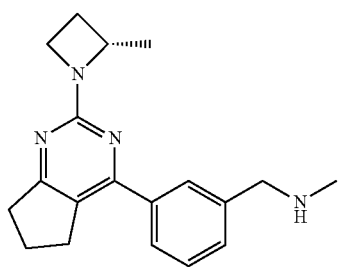 [SMILES: CNCc1cccc(-c2nc(N3CC[C@@H]3C)nc3c2CCC3)c1]

Example 330: N-methyl-1-[3-[2-[(2S)-2-methylazetidin-1-yl]-6,7-dihydro-5H-cyclopenta[d]pyrimidin-4-yl]phenyl]methanamine To a solution of tert-butyl N-[[3-[2-[(2S)-2-methylazetidin-1-yl]-6,7-dihydro-5H-cyclopenta[d]pyrimidin-4-yl]phenyl]methyl]carbamate (76 mg, 0.193 mmol) in dimethylformamide (2 mL) under a dry nitrogen atmosphere was added 60% sodium hydride in mineral oil (12 mg, 0.29 mmol), and the reaction mixture was allowed to stir at room temperature for 30 minutes. To this, methyl iodide (0.024 mL, 0.38 mmol) was added, and the reaction mixture was stirred at room temperature for 16 hours. It was diluted with ethyl acetate and washed with water and saturated sodium chloride. It was dried over anhydrous sodium sulfate, filtered, and concentrated. It was purified by flash column chromatography (ethyl acetate-hexanes) to yield tert-butyl (S)-methyl(3-(2-(2-methylazetidin-1-yl)-6,7-dihydro-5H-cyclopenta[d]pyrimidin-4-yl)benzyl)carbamate.

The title compound was prepared by General Method I using tert-butyl (S)-methyl(3-(2-(2-methylazetidin-1-yl)-6,7-dihydro-5H-cyclopenta[d]pyrimidin-4-yl)benzyl)carbamate instead of tert-butyl (S)-4-(4-(2-(2-methylazetidin-1-yl)-6,7-dihydro-5H-cyclopenta[d]pyrimidin-4-yl)phenyl)piperazine-1-carboxylate.

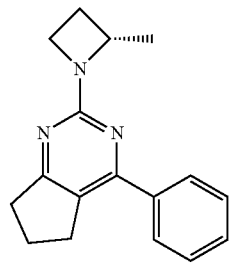 [SMILES: C[C@H]1CCN1c1nc2c(c(-c3ccccc3)n1)CCC2]

Example 331: 2-[(2S)-2-methylazetidin-1-yl]-4-phenyl-6,7-dihydro-5H-cyclopenta[d]pyrimidine The title compound was prepared in a method analogous to General Method B using 2-chloro-4-phenyl-6,7-dihydro-5H-cyclopenta[d]pyrimidine instead of 2-chloro-4-(pyridin-3-yl)-6,7-dihydro-5H-cyclopenta[d]pyrimidine.

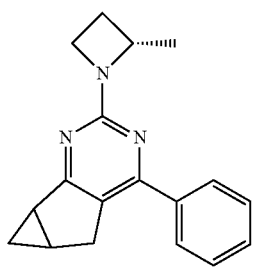 [SMILES: C[C@H]1CCN1c1nc(-c2ccccc2)c2c(n1)C1CC1C2]

Example 332: 9-[(2S)-2-methylazetidin-1-yl]-7-phenyl-8,10-diazatricyclo[4.4.0.02,4]deca-1(10),6,8-triene The title compound was prepared in a method analogous to General Method H using phenyl boronic acid instead of (3-carbamoylphenyl)boronic acid.

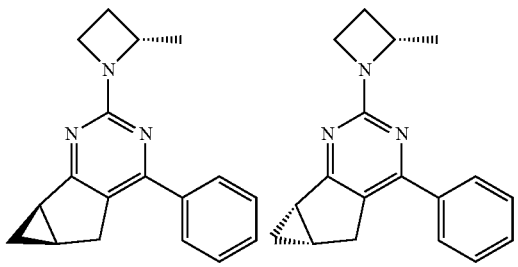

Example 333: (5aR,6aR)-2-((S)-2-methylazetidin-1-yl)-4-phenyl-5,5a,6,6a-tetrahydrocyclopropa[4,5]cyclopenta[1,2-d]pyrimidine

Example 334: (5aS,6aS)-2-((S)-2-methylazetidin-1-yl)-4-phenyl-5,5a,6,6a-tetrahydrocyclopropa[4,5]cyclopenta[1,2-d]pyrimidine Isomers were separated by SFC (35% EtOH in $CO_2$, CELL-2, 100×4 6 mm, 3 mL/min)

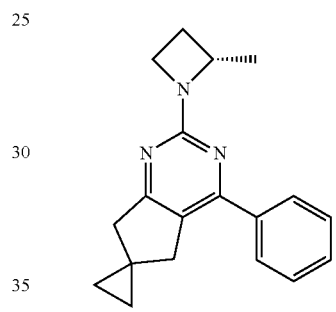

Example 335: 2-[(2S)-2-methylazetidin-1-yl]-4-phenyl-spiro[5,7-dihydrocyclopenta[d]pyrimidine-6,1'-cyclopropane]

The title compound was prepared in a method analogous to General Method H using methyl 6-oxospiro[2.4]heptane-5-carboxylate and phenyl boronic acid instead of methyl 2-oxobicyclo[3.1.0]hexane-3-carboxylate and (3-carbamoylphenyl)boronic acid, respectively.

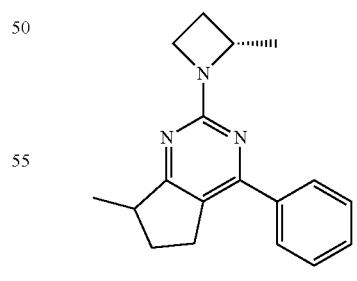

Example 336: 7-methyl-2-[(2S)-2-methylazetidin-1-yl]-4-phenyl-6,7-dihydro-5H-cyclopenta[d]pyrimidine The title compound was prepared in a method analogous to General Method H using methyl 3-methyl-2-oxocyclopentane-1-carboxylate and phenyl boronic acid instead of methyl 2-oxobicyclo[3.1.0]hexane-3-carboxylate and (3-carbamoylphenyl)boronic acid, respectively.

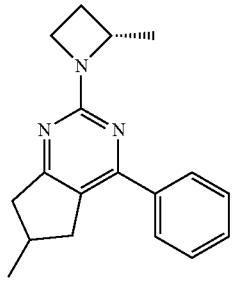 [SMILES: CC1Cc2nc(N3CC[C@@H]3C)nc(-c3ccccc3)c2C1]

Example 337: 6-methyl-2-[(2S)-2-methylazetidin-1-yl]-4-phenyl-6,7-dihydro-5H-cyclopenta[d]pyrimidine The title compound was prepared in a method analogous to General Method H using methyl 4-methyl-2-oxocyclopentane-1-carboxylate and phenyl boronic acid instead of methyl 2-oxobicyclo[3.1.0]hexane-3-carboxylate and (3-carbamoylphenyl)boronic acid, respectively.

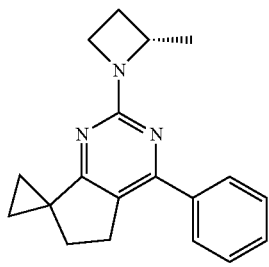 [SMILES: C[C@H]1CCN1c1nc(-c2ccccc2)c2c(n1)C1(CC2)CC1]

Example 338: 2-[(2S)-2-methylazetidin-1-yl]-4-phenyl-spiro[5,6-dihydrocyclopenta[d]pyrimidine-7,1'-cyclopropane]

The title compound was prepared in a method analogous to General Method H using methyl 4-oxospiro[2.4]heptane-5-carboxylate and phenyl boronic acid instead of methyl 2-oxobicyclo[3.1.0]hexane-3-carboxylate and (3-carbamoylphenyl)boronic acid, respectively.

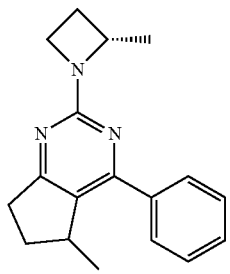 [SMILES: CC1CCc2nc(N3CC[C@@H]3C)nc(-c3ccccc3)c21]

Example 339: 5-methyl-2-[(2S)-2-methylazetidin-1-yl]-4-phenyl-6,7-dihydro-5H-cyclopenta[d]pyrimidine The title compound was prepared in a method analogous to General Method H using methyl 2-methyl-5-oxocyclopentane-1-carboxylate and phenyl boronic acid instead of methyl 2-oxobicyclo[3.1.0]hexane-3-carboxylate and (3-carbamoylphenyl)boronic acid, respectively.

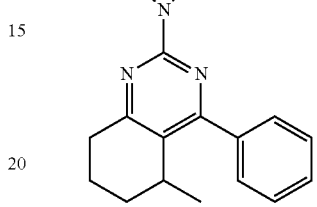

Example 340: 5-methyl-2-[(2S)-2-methylazetidin-1-yl]-4-phenyl-5,6,7,8-tetrahydroquinazoline The title compound was prepared in a method analogous to General Method H using methyl 2-methyl-6-oxocyclohexane-1-carboxylate and phenyl boronic acid instead of methyl 2-oxobicyclo[3.1.0]hexane-3-carboxylate and (3-carbamoylphenyl)boronic acid, respectively.

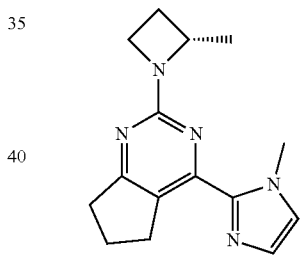

Example 341: 2-[(2S)-2-methylazetidin-1-yl]-4-(3-methylimidazol-4-yl)-6,7-dihydro-5H-cyclopenta[d]pyrimidine The title compound was prepared in a method analogous to General Method E using tributyl-(3-methylimidazol-4-yl)stannane instead of 2-tributylstannylimidazo[5,1-b]thiazole-7-carboxylate.

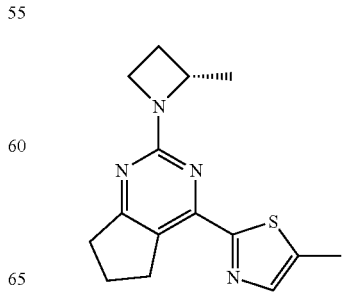

Example 342: 5-methyl-2-[2-[(2S)-2-methylazetidin-1-yl]-6,7-dihydro-5H-cyclopenta[d]pyrimidin-4-yl]thiazole The title compound was prepared in a method analogous to General Method E using tributyl-(5-methylthiazol-2-yl)stannane instead of 2-tributylstannylimidazo[5,1-b]thiazole-7-carboxylate

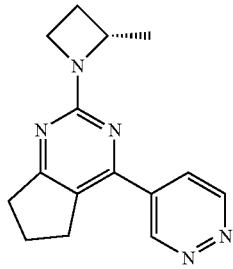 [SMILES: C[C@H]1CCN1c1nc2c(c(-c3ccnnc3)n1)CCC2]

Example 343: 2-[(2S)-2-methylazetidin-1-yl]-4-pyridazin-4-yl-6,7-dihydro-5H-cyclopenta[d]pyrimidine The title compound was prepared in a method analogous to General Method E using tributyl(pyridazin-4-yl)stannane instead of 2-tributylstannylimidazo[5,1-b]thiazole-7-carboxylate.

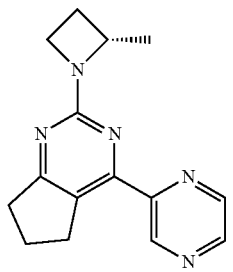 [SMILES: C[C@H]1CCN1c1nc2c(c(-c3cnccn3)n1)CCC2]

Example 344: 2-[(2S)-2-methylazetidin-1-yl]-4-pyrazin-2-yl-6,7-dihydro-5H-cyclopenta[d]pyrimidine The title compound was prepared in a method analogous to General Method E using tributyl(pyrazin-2-yl)stannane instead of 2-tributylstannylimidazo[5,1-b]thiazole-7-carboxylate.

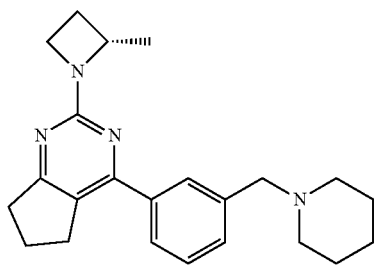 [SMILES: C[C@H]1CCN1c1nc2c(c(-c3cccc(CN4CCCCC4)c3)n1)CCC2]

Example 345: 2-[(2S)-2-methylazetidin-1-yl]-4-[3-(1-piperidylmethyl)phenyl]-6,7-dihydro-5H-cyclopenta[d]pyrimidine The title compound was prepared by General Method O.

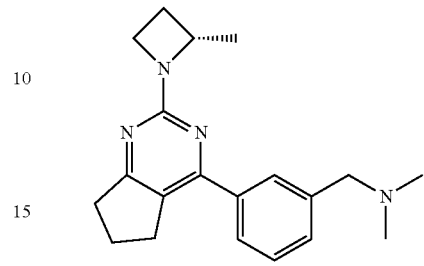

Example 346: N,N-dimethyl-1-[3-[2-[(2S)-2-methylazetidin-1-yl]-6,7-dihydro-5H-cyclopenta[d]pyrimidin-4-yl]phenyl]methanamine The title compound was prepared in a method analogous to General Method O using 2.0M dimethylamine in tetrahydrofuran instead of piperidine.

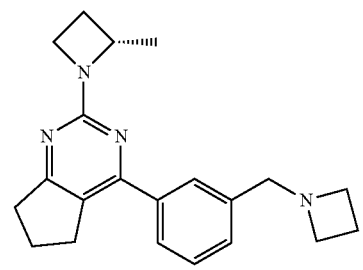 [SMILES: C[C@H]1CCN1c1nc2c(c(-c3cccc(CN4CCC4)c3)n1)CCC2]

Example 347: 4-[3-(azetidin-1-ylmethyl)phenyl]-2-[(2S)-2-methylazetidin-1-yl]-6,7-dihydro-5H-cyclopenta[d]pyrimidine The title compound was prepared in a method analogous to General Method O using equimolar azetidine hydrochloride and triethylamine instead of piperidine.

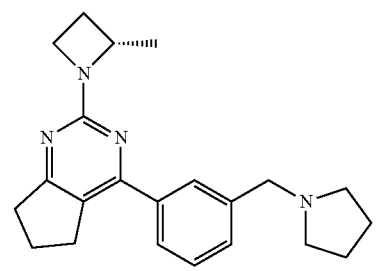 [SMILES: C[C@H]1CCN1c1nc2c(c(-c3cccc(CN4CCCC4)c3)n1)CCC2]

Example 348: 2-[(2S)-2-methylazetidin-1-yl]-4-[3-(pyrrolidin-1-ylmethyl)phenyl]-6,7-dihydro-5H-cyclopenta[d]pyrimidine The title compound was prepared in a method analogous to General Method O using pyrrolidine instead of piperidine.

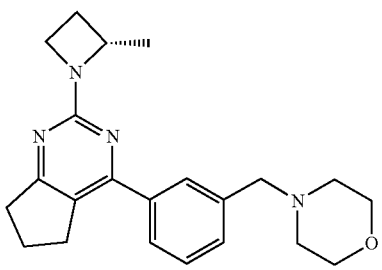 [SMILES: C[C@H]1CCN1c1nc2c(c(-c3cccc(CN4CCOCC4)c3)n1)CCC2]

Example 349: 4-[[3-[2-[(2S)-2-methylazetidin-1-yl]-6,7-dihydro-5H-cyclopenta[d]pyrimidin-4-yl]phenyl]methyl]morpholine The title compound was prepared in a method analogous to General Method O using morpholine instead of piperidine.

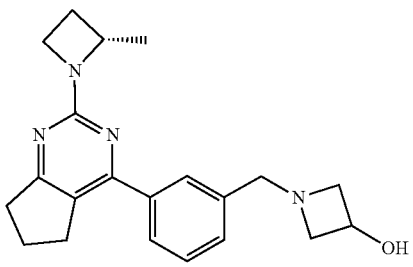 [SMILES: C[C@H]1CCN1c1nc2c(c(-c3cccc(CN4CC(O)C4)c3)n1)CCC2]

Example 350: 1-[[3-[2-[(2S)-2-methylazetidin-1-yl]-6,7-dihydro-5H-cyclopenta[d]pyrimidin-4-yl]phenyl]methyl]azetidin-3-ol The title compound was prepared in a method analogous to General Method O using equimolar 3-hydroxyazetidine hydrochloride and triethylamine instead of piperidine.

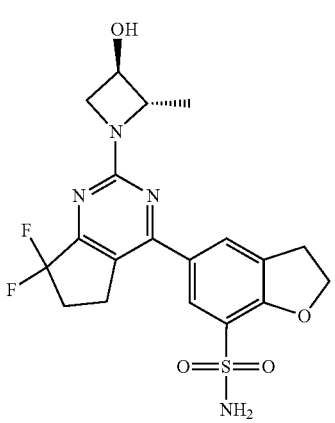 [SMILES: C[C@H]1[C@H](O)CN1c1nc(-c2cc3c(c(S(N)(=O)=O)c2)OCC3)c2c(n1)C(F)(F)CC2]

Example 351: 5-(7,7-difluoro-2-((2S,3R)-3-hydroxy-2-methylazetidin-1-yl)-6,7-dihydro-5H-cyclopenta[d]pyrimidin-4-yl)-2,3-dihydrobenzofuran-7-sulfonamide The title compound was prepared in a method analagous to General Method D using 5-bromo-2,3-dihydrobenzofuran-7-sulfonamide instead of 2-bromoimidazo[5,1-b]thiazole-7-carboxylate, followed by General Method E, using 4-chloro-7,7-difluoro-2-(methylthio)-6,7-dihydro-5H-cyclopenta[d]pyrimidine instead of (S)-4-chloro-2-(2-methylazetidin-1-yl)-6,7-dihydro-5H-cyclopenta[d]pyrimidine, followed by General Method M, followed by General Method B using (2S,3R)-2-methylazetidin-3-ol instead of (2S)-2-methylazetidine.

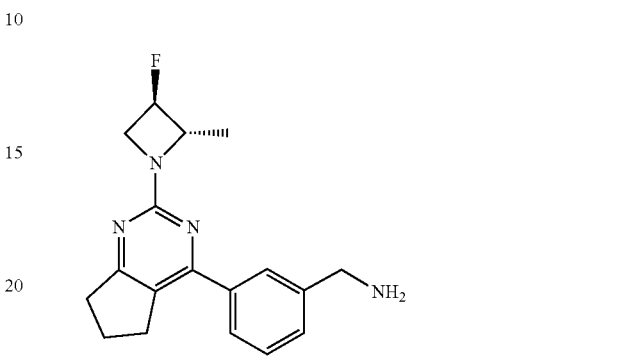

Example 352: [3-[2-[(2S,3R)-3-fluoro-2-methyl-azetidin-1-yl]-6,7-dihydro-5H-cyclopenta[d]pyrimidin-4-yl]phenyl]methanamine The title compound was prepared in a method analogous to General Method A using [3-Wert-butoxycarbonylamino)methyl)phenyl]boronic acid instead of 3-pyridylboronic acid, followed by General Method B, using (2S,3R)-3-fluoro-2-methyl-azetidine instead of (2S)-2-methylazetidine, followed by General Method I.

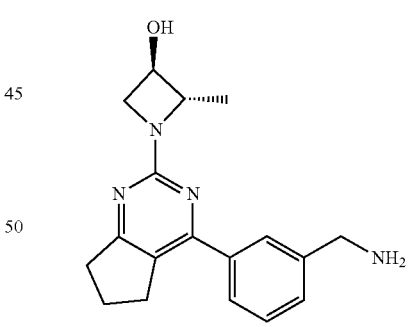

Example 353: [3-[2-[(2S,3R)-3-fluoro-2-methyl-azetidin-1-yl]-6,7-dihydro-5H-cyclopenta[d]pyrimidin-4-yl]phenyl]methanamine The title compound was prepared in a method analogous to General Method A using [3-[(tert-butoxycarbonylamino)methyl]phenyl]boronic acid instead of 3-pyridylboronic acid, followed by General Method B, using (2S,3R)-2-methylazetidin-3-ol instead of (2S)-2-methylazetidine, followed by General Method I.

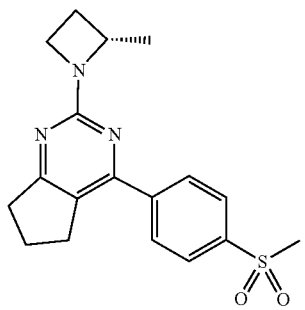 [SMILES: C[C@H]1CCN1c1nc2c(c(-c3ccc(S(C)(=O)=O)cc3)n1)CCC2]

Example 354: 2-[(2S)-2-methylazetidin-1-yl]-4-(4-methylsulfonylphenyl)-6,7-dihydro-5H-cyclopenta[d]pyrimidine The title compound was prepared in a method analogous to General Method A using 4-chloro-2-[(2S)-2-methylazetidin-1-yl]-6,7-dihydro-5H-cyclopenta[d]pyrimidine and (4-methylsulfonylphenyl)boronic acid instead of 2,4-dichloro-6,7-dihydro-5H-cyclopenta[d]pyrimidine and 3-pyridylboronic acid, respectively.

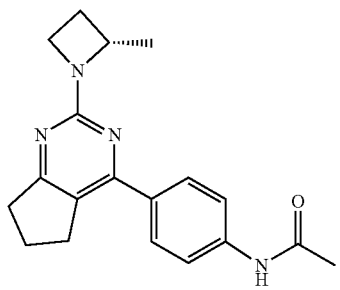 [SMILES: CC(=O)Nc1ccc(-c2nc(N3CC[C@@H]3C)nc3c2CCC3)cc1]

Example 355: N-[4-[2-[(2S)-2-methylazetidin-1-yl]-6,7-dihydro-5H-cyclopenta[d]pyrimidin-4-yl]phenyl]acetamide The title compound was prepared in a method analogous to General Method A using 4-chloro-2-[(2S)-2-methylazetidin-1-yl]-6,7-dihydro-5H-cyclopenta[d]pyrimidine and (4-acetamidophenyl)boronic acid instead of 2,4-dichloro-6,7-dihydro-5H-cyclopenta[d]pyrimidine and 3-pyridylboronic acid, respectively.

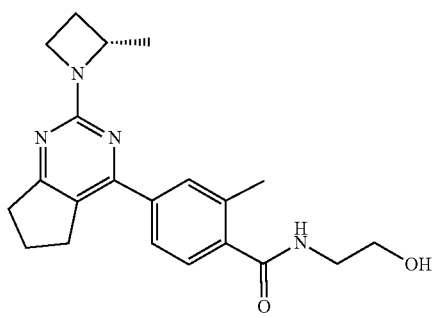 [SMILES: Cc1cc(-c2nc(N3CC[C@@H]3C)nc3c2CCC3)ccc1C(=O)NCCO]

Example 356: N-(2-hydroxyethyl)-2-methyl-4-[2-[(2S)-2-methylazetidin-1-yl]-6,7-dihydro-5H-cyclopenta[d]pyrimidin-4-yl]benzamide The title compound was prepared in a method analogous to General Method A using 4-chloro-2-[(2S)-2-methylazetidin-1-yl]-6,7-dihydro-5H-cyclopenta[d]pyrimidine and (4-methoxycarbonyl-3-methyl-phenyl)boronic acid instead of 2,4-dichloro-6,7-dihydro-5H-cyclopenta[d]pyrimidine and 3-pyridylboronic acid, respectively, followed by General Method C and General Method G using 2-aminoethanol instead of ammonia.

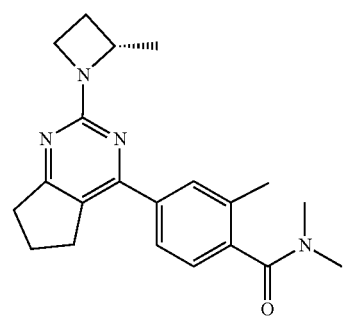 [SMILES: Cc1cc(-c2nc(N3CC[C@@H]3C)nc3c2CCC3)ccc1C(=O)N(C)C]

Example 357: N,N,2-trimethyl-4-[2-[(2S)-2-methylazetidin-1-yl]-6,7-dihydro-5H-cyclopenta[d]pyrimidin-4-yl]benzamide The title compound was prepared in a method analogous to General Method A using 4-chloro-2-[(2S)-2-methylazetidin-1-yl]-6,7-dihydro-5H-cyclopenta[d]pyrimidine and (4-methoxycarbonyl-3-methyl-phenyl)boronic acid instead of 2,4-dichloro-6,7-dihydro-5H-cyclopenta[d]pyrimidine and 3-pyridylboronic acid, respectively, followed by General Method C and General Method G using dimethylamine instead of ammonia.

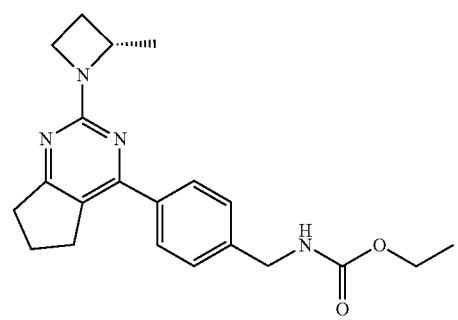 [SMILES: CCOC(=O)NCc1ccc(-c2nc(N3CC[C@@H]3C)nc3c2CCC3)cc1]

Example 358: ethyl N-[[4-[2-[(2S)-2-methylazetidin-1-yl]-6,7-dihydro-5H-cyclopenta[d]pyrimidin-4-yl]phenyl]methyl]carbamate To a solution of [4-[2-[(2S)-2-methylazetidin-1-yl]-6,7-dihydro-5H-cyclopenta[d]pyrimidin-4-yl]phenyl]methanamine (27 mg, 0.092 mmol) in dichloromethane (0.6 mL) was added triethylamine (0.026 mL, 0.18 mmol) and ethyl chloroformate (11 mg, 0.1 mmol), and the reaction mixture was allowed to stir at ambient temperature for 16 hours. It was diluted with ethyl acetate, filtered, then washed with water twice and brine once. It was dried over anhydrous sodium sulfate, filtered, and concentrated. The residue was subjected to flash column chromatography (ethyl acetate-hexanes) to yield the title compound.

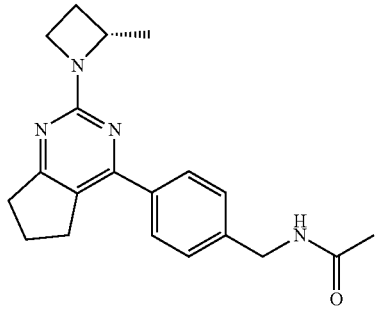 [SMILES: CC(=O)NCc1ccc(-c2nc(N3CC[C@@H]3C)nc3c2CCC3)cc1]

Example 359: ethyl N-[[4-[2-[(2S)-2-methylazetidin-1-yl]-6,7-dihydro-5H-cyclopenta[d]pyrimidin-4-yl]phenyl]methyl]carbamate To a solution of [4-[2-[(2S)-2-methylazetidin-1-yl]-6,7-dihydro-5H-cyclopenta[d]pyrimidin-4-yl]phenyl]methanamine (27 mg, 0.092 mmol) in dichloromethane (0.6 mL) was added triethylamine (0.026 mL, 0.18 mmol) and ethyl chloroformate (11 mg, 0.1 mmol), and the reaction mixture was allowed to stir at ambient temperature for 16 hours. The residue was subjected to flash column chromatography (ethyl acetate-hexanes) to yield the title compound.

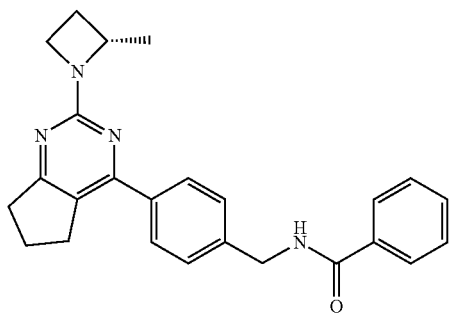 [SMILES: C[C@H]1CCN1c1nc2c(c(-c3ccc(CNC(=O)c4ccccc4)cc3)n1)CCC2]

Example 360: N-[[4-[2-[(2S)-2-methylazetidin-1-yl]-6,7-dihydro-5H-cyclopenta[d]pyrimidin-4-yl]phenyl]methyl]benzamide The title compound was made in a method analogous to ethyl N-[[4-[2-[(2S)-2-methylazetidin-1-yl]-6,7-dihydro-5H-cyclopenta[d]pyrimidin-4-yl]phenyl]methyl]carbamate using benzoic anhydride instead of acetic anhydride.

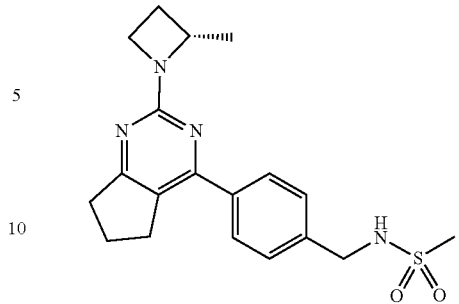

Example 361: N-[[4-[2-[(2S)-2-methylazetidin-1-yl]-6,7-dihydro-5H-cyclopenta[d]pyrimidin-4-yl]phenyl]methyl]methanesulfonamide The title compound was prepared in a method analogous to General Method K using [4-[2-[(2S)-2-methylazetidin-1-yl]-6,7-dihydro-5H-cyclopenta[d]pyrimidin-4-yl]phenyl]methanamine and mesyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively.

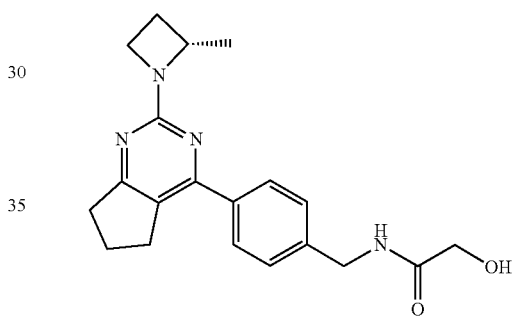

Example 362: N-(2-hydroxyethyl)-2-methyl-4-[2-[(2S)-2-methylazetidin-1-yl]-6,7-dihydro-5H-cyclopenta[d]pyrimidin-4-yl]benzamide The title compound was prepared in a method analogous to General Method G using glyoxylic acid and [4-[2-[(2S)-2-methylazetidin-1-yl]-6,7-dihydro-5H-cyclopenta[d]pyrimidin-4-yl]phenyl]methanamine instead of 2-(3-(2-((2S,3R)-3-hydroxy-2-methylazetidin-1-yl)-6,7-dihydro-5H-cyclopenta[d]pyrimidin-4-yl)phenyl)cyclopropane-1-carboxylic acid and ammonia, respectively.

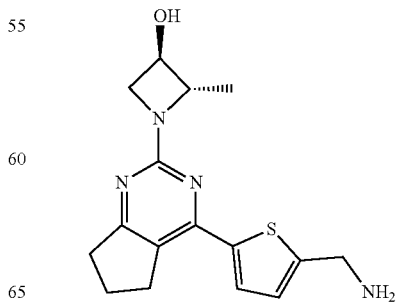

Example 363: (2S,3R)-1-[4-[5-(aminomethyl)-2-thienyl]-6,7-dihydro-5H-cyclopenta[d]pyrimidin-2-yl]-2-methyl-azetidin-3-ol The title compound was prepared in a method analogous to General Method A, using 5-[(tert-butoxycarbonylamino)methyl]-2-thienyl]boronic acid and 4-chloro-2-[(2S)-2-methylazetidin-1-yl]-6,7-dihydro-5H-cyclopenta[d]pyrimidine instead of 3-pyridylboronic acid and 2,4-dichloro-6,7-dihydro-5H-cyclopenta[d]pyrimidine, respectively, followed by General Methods B, using (2S,3R)-2-methyl-azetidin-3-ol instead of (2S)-2-methylazetidine, followed by General Method I.

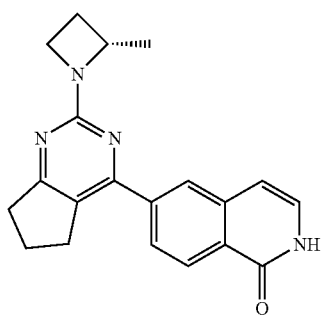 [SMILES: C[C@H]1CCN1c1nc2c(c(-c3ccc4c(=O)[nH]ccc4c3)n1)CCC2]

Example 364: 6-[2-[(2S)-2-methylazetidin-1-yl]-6,7-dihydro-5H-cyclopenta[d]pyrimidin-4-yl]-2H-isoquinolin-1-one The title compound was prepared in a method analogous to General Method A, using 6-(4,4,5,5-tetramethyl-1,3,2-dioxaborolan-2-yl)-2H-isoquinolin-1-one and 4-chloro-2-[(2S)-2-methylazetidin-1-yl]-6,7-dihydro-5H-cyclopenta[d]pyrimidine instead of 3-pyridylboronic acid and 2,4-dichloro-6,7-dihydro-5H-cyclopenta[d]pyrimidine, respectively.

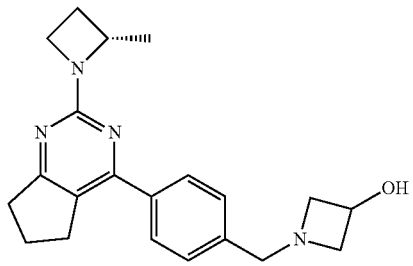 [SMILES: C[C@H]1CCN1c1nc2c(c(-c3ccc(CN4CC(O)C4)cc3)n1)CCC2]

Example 365: 1-[[4-[2-[(2S)-2-methylazetidin-1-yl]-6,7-dihydro-5H-cyclopenta[d]pyrimidin-4-yl]phenyl]methyl]azetidin-3-ol The title compound was prepared in a method analogous to General Method O using equimolar 3-hydroxyazetidine hydrochloride and triethylamine instead of piperidine and (4-formylphenyl)boronic acid instead of (3-formylphenyl)boronic acid.

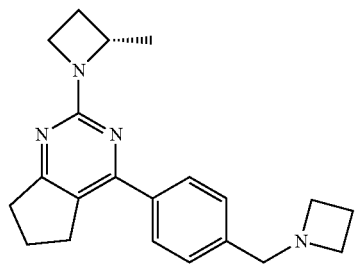 [SMILES: C[C@H]1CCN1c1nc2c(c(-c3ccc(CN4CCC4)cc3)n1)CCC2]

Example 366: 4-[4-(azetidin-1-ylmethyl)phenyl]-2-[(2S)-2-methylazetidin-1-yl]-6,7-dihydro-5H-cyclopenta[d]pyrimidine The title compound was prepared in a method analogous to General Method O using equimolar azetidine hydrochloride and triethylamine instead of piperidine and (4-formylphenyl)boronic acid instead of (3-formylphenyl)boronic acid.

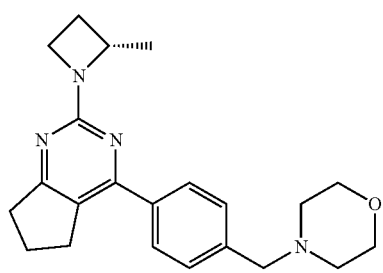 [SMILES: C[C@H]1CCN1c1nc2c(c(-c3ccc(CN4CCOCC4)cc3)n1)CCC2]

Example 367: 4-[[4-[2-[(2S)-2-methylazetidin-1-yl]-6,7-dihydro-5H-cyclopenta[d]pyrimidin-4-yl]phenyl]methyl]morpholine The title compound was prepared in a method analogous to General Method O using morpholine instead of piperidine and (4-formylphenyl)boronic acid instead of (3-formylphenyl)boronic acid.

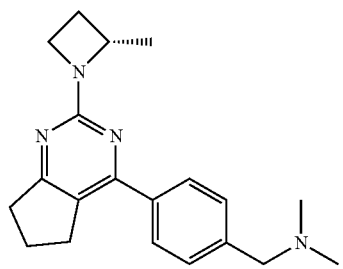 [SMILES: C[C@H]1CCN1c1nc2c(c(-c3ccc(CN(C)C)cc3)n1)CCC2]

Example 368: N,N-dimethyl-1-[4-[2-[(2S)-2-methylazetidin-1-yl]-6,7-dihydro-5H-cyclopenta[d]pyrimidin-4-yl]phenyl]methanamine The title compound was prepared in a method analogous to General Method O using dimethylamine instead of piperidine and (4-formylphenyl)boronic acid instead of (3-formylphenyl)boronic acid.

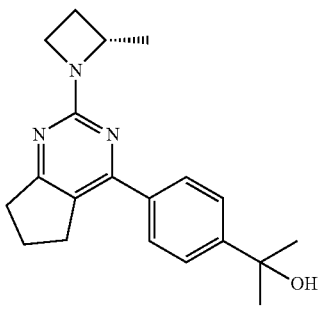 [SMILES: C[C@H]1CCN1c1nc2c(c(-c3ccc(C(C)(C)O)cc3)n1)CCC2]

Example 369: 2-[4-[2-[(2S)-2-methylazetidin-1-yl]-6,7-dihydro-5H-cyclopenta[d]pyrimidin-4-yl]phenyl]propan-2-ol The title compound was prepared in a method analogous to General Method A, using [4-(1-hydroxy-1-methyl-ethyl)phenyl]boronic acid and 4-chloro-2-[(2S)-2-methylazetidin-1-yl]-6,7-dihydro-5H-cyclopenta[d]pyrimidine instead of 3-pyridylboronic acid and 2,4-dichloro-6,7-dihydro-5H-cyclopenta[d]pyrimidine, respectively.

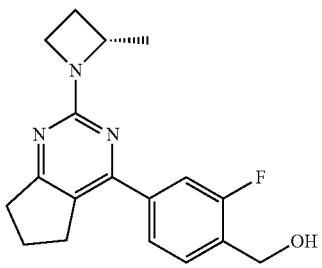 [SMILES: C[C@H]1CCN1c1nc2c(c(-c3ccc(CO)c(F)c3)n1)CCC2]

Example 370: [2-fluoro-4-[2-[(2S)-2-methylazetidin-1-yl]-6,7-dihydro-5H-cyclopenta[d]pyrimidin-4-yl]phenyl]methanol The title compound was prepared in a method analogous to General Method A, using [3-fluoro-4-(hydroxymethyl)phenyl]boronic acid and 4-chloro-2-[(2S)-2-methylazetidin-1-yl]-6,7-dihydro-5H-cyclopenta[d]pyrimidine instead of 3-pyridylboronic acid and 2,4-dichloro-6,7-dihydro-5H-cyclopenta[d]pyrimidine, respectively.

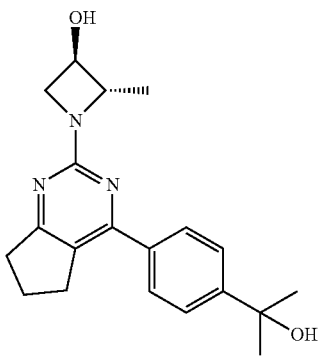 [SMILES: C[C@H]1[C@H](O)CN1c1nc2c(c(-c3ccc(C(C)(C)O)cc3)n1)CCC2]

Example 371: (2S,3R)-1-[4-[4-(1-hydroxy-1-methyl-ethyl)phenyl]-6,7-dihydro-5H-cyclopenta[d]pyrimidin-2-yl]-2-methyl-azetidin-3-ol The title compound was prepared in a method analogous to General Method A using (2S,3R)-1-(4-chloro-6,7-dihydro-5H-cyclopenta[d]pyrimidin-2-yl)-2-methylazetidin-3-yl benzoate and [4-(1-hydroxy-1-methyl-ethyl)phenyl]boronic acid instead of 2,4-dichloro-6,7-dihydro-5H-cyclopenta[d]pyrimidine and 3-pyridylboronic acid, respectively, followed by General Method C.

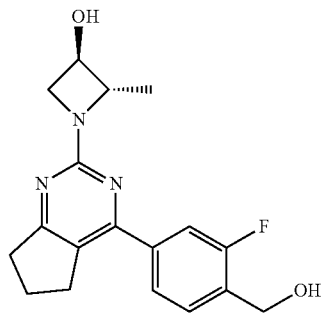 [SMILES: C[C@H]1[C@H](O)CN1c1nc2c(c(-c3ccc(CO)c(F)c3)n1)CCC2]

Example 372: (2S,3R)-1-[4-[4-(1-hydroxy-1-methyl-ethyl)phenyl]-6,7-dihydro-5H-cyclopenta[d]pyrimidin-2-yl]-2-methyl-azetidin-3-ol The title compound was prepared in a method analogous to General Method A using (2S,3R)-1-(4-chloro-6,7-dihydro-5H-cyclopenta[d]pyrimidin-2-yl)-2-methylazetidin-3-yl benzoate and [[3-fluoro-4-(hydroxymethyl)phenyl]boronic acid instead of 2,4-dichloro-6,7-dihydro-5H-cyclopenta[d]pyrimidine and 3-pyridylboronic acid, respectively, followed by General Method C.

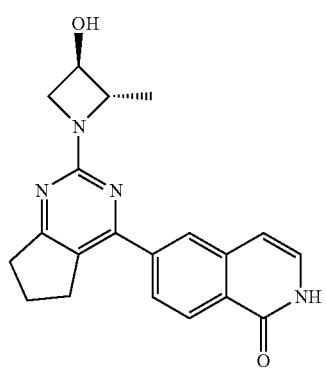 [SMILES: C[C@H]1[C@H](O)CN1c1nc2c(c(-c3ccc4c(=O)[nH]ccc4c3)n1)CCC2]

Example 373: 6-[2-[(2S,3R)-3-hydroxy-2-methyl-azetidin-1-yl]-6,7-dihydro-5H-cyclopenta[d]pyrimidin-4-yl]-2H-isoquinolin-1-one The title compound was prepared in a method analogous to General Method A using (2S,3R)-1-(4-chloro-6,7-dihydro-5H-cyclopenta[d]pyrimidin-2-yl)-2-methylazetidin-3-yl benzoate and 6-(4,4,5,5-tetramethyl-1,3,2-dioxaborolan-2-yl)-2H-isoquinolin-1-one instead of 2,4-dichloro-6,7-dihydro-5H-cyclopenta[d]pyrimidine and 3-pyridylboronic acid, respectively, followed by General Method C.

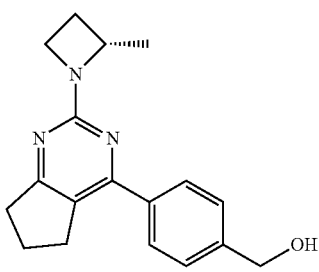 [SMILES: C[C@H]1CCN1c1nc2c(c(-c3ccc(CO)cc3)n1)CCC2]

Example 374: [4-[2-[(2S)-2-methylazetidin-1-yl]-6, 7-dihydro-5H-cyclopenta[d]pyrimidin-4-yl]phenyl] methanol The title compound was prepared in a method analogous to General Method A, using [4-(hydroxymethyl)phenyl] boronic acid and 4-chloro-2-[(2S)-2-methylazetidin-1-yl]-6, 7-dihydro-5H-cyclopenta[d]pyrimidine instead of 3-pyridylboronic acid and 2,4-dichloro-6,7-dihydro-5H-cyclopenta[d]pyrimidine, respectively.

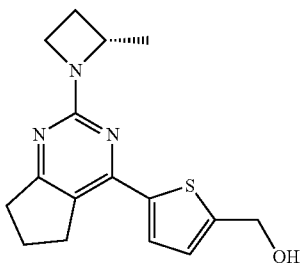 [SMILES: C[C@H]1CCN1c1nc2c(c(-c3ccc(CO)s3)n1)CCC2]

Example 375: [5-[2-[(2S)-2-methylazetidin-1-yl]-6, 7-dihydro-5H-cyclopenta[d]pyrimidin-4-yl]-2-thienyl]methanol The title compound was prepared in a method analogous to General Method A, using [5-(hydroxymethyl)-2-thienyl] boronic acid and 4-chloro-2-[(2S)-2-methylazetidin-1-yl]-6, 7-dihydro-5H-cyclopenta[d]pyrimidine instead of 3-pyridylboronic acid and 2,4-dichloro-6,7-dihydro-5H-cyclopenta[d]pyrimidine, respectively.

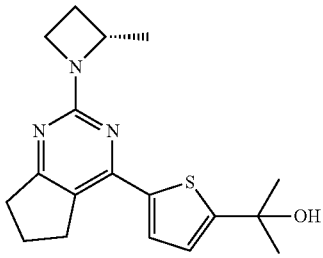 [SMILES: C[C@H]1CCN1c1nc2c(c(-c3ccc(C(C)(C)O)s3)n1)CCC2]

Example 376: 2-[5-[2-[(2S)-2-methylazetidin-1-yl]-6,7-dihydro-5H-cyclopenta[d]pyrimidin-4-yl]-2-thienyl]propan-2-ol The title compound was prepared in a method analogous to General Method A, using 2-[5-(4,4,5,5-tetramethyl-1,3,2-dioxaborolan-2-yl)-2-thienyl]propan-2-ol and 4-chloro-2-[(2S)-2-methylazetidin-1-yl]-6,7-dihydro-5H-cyclopenta[d] pyrimidine instead of 3-pyridylboronic acid and 2,4-dichloro-6,7-dihydro-5H-cyclopenta[d]pyrimidine, respectively.

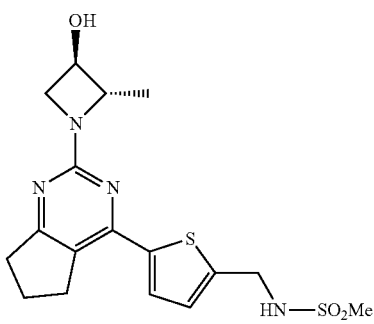 [SMILES: C[C@H]1[C@H](O)CN1c1nc2c(c(-c3ccc(CNS(C)(=O)=O)s3)n1)CCC2]

Example 377: N-[[5-[2-[(2S,3R)-3-hydroxy-2-methyl-azetidin-1-yl]-6,7-dihydro-5H-cyclopenta[d] pyrimidin-4-yl]-2-thienyl]methyl]methanesulfonamide The title compound was prepared in a method analogous to General Method K using (2S,3R)-1-[4-[5-(aminomethyl)-2-thienyl]-6,7-dihydro-5H-cyclopenta[d]pyrimidin-2-yl]-2-methyl-azetidin-3-ol and mesyl chloride instead of (S)-3-(2-(2-methylazetidin-1-yl)-6,7-dihydro-5H-cyclopenta[d] pyrimidin-4-yl)aniline and 1-methylimidazole-4-sulfonyl chloride, respectively.

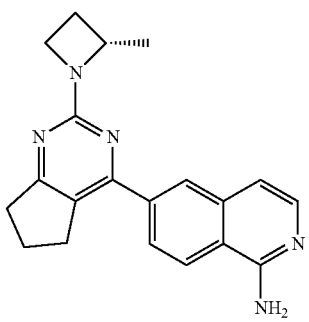 [SMILES: C[C@H]1CCN1c1nc2c(c(-c3ccc4c(N)nccc4c3)n1)CCC2]

Example 378: 6-[2-[(2S)-2-methylazetidin-1-yl]-6, 7-dihydro-5H-cyclopenta[d]pyrimidin-4-yl]isoquinolin-1-amine The title compound was prepared in a method analogous to General Method F, using 6-bromoisoquinolin-1-amine instead of 6-bromo-1,1-dioxo-1,2-benzothiazol-3-one.

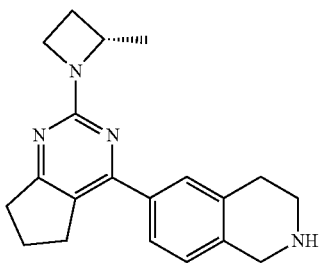 [SMILES: C[C@H]1CCN1c1nc2c(c(-c3ccc4c(c3)CCNC4)n1)CCC2]

Example 379: 6-[2-[(2S)-2-methylazetidin-1-yl]-6,7-dihydro-5H-cyclopenta[d]pyrimidin-4-yl]-1,2,3,4-tetrahydroisoquinoline The title compound was prepared in a method analogous to General Method A using tert-butyl 6-(4,4,5,5-tetramethyl-1,3,2-dioxaborolan-2-yl)-3,4-dihydro-1H-isoquinoline-2-carboxylate and 4-chloro-2-[(2S)-2-methylazetidin-1-yl]-6,7-dihydro-5H-cyclopenta[d]pyrimidine instead of 3-pyridylboronic acid and 2,4-dichloro-6,7-dihydro-5H-cyclopenta[d]pyrimidine, respectively, followed by General Method I.

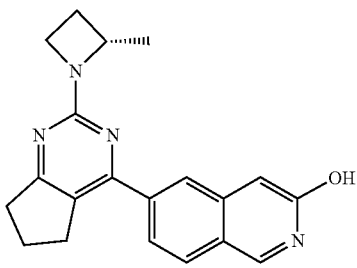 [SMILES: C[C@H]1CCN1c1nc2c(c(-c3ccc4cnc(O)cc4c3)n1)CCC2]

Example 380: 6-[2-[(2S)-2-methylazetidin-1-yl]-6,7-dihydro-5H-cyclopenta[d]pyrimidin-4-yl]isoquinolin-3-ol To a suspension of 6-bromoisoquinolin-3-ol (200 mg, 0.89 mmol) and imidazole (365 mg, 5.36 mmol) in dimethylformamide (5 mL) at 0° C. was added chloro(triisopropyl)silane (688 mg, 3.57 mmol), and the reaction mixture was allowed to warm to ambient temperature and stir for 3 days. It was diluted with EtOAc and washed with water and brine. It was dried over $Na_2SO_4$, filtered, and concentrated. The residue was subject to flash column chromatography (ethyl acetate-hexane) to give 6-bromo-3-isoquinolyl)oxy-triisopropyl-silane.

The title compound was prepared in a method analogous to General Method F using -bromo-3-isoquinolyl)oxy-triisopropyl-silane instead of 6-bromo-1,1-dioxo-1,2-benzothiazol-3-one. The triisoproylsilyl group was cleaved under reaction conditions.

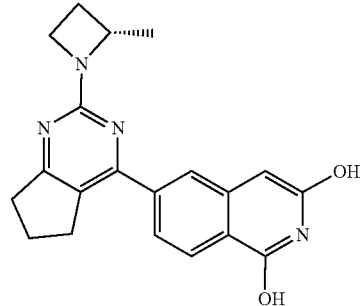 [SMILES: C[C@H]1CCN1c1nc2c(c(-c3ccc4c(O)nc(O)cc4c3)n1)CCC2]

Example 381: 6-[2-[(2S)-2-methylazetidin-1-yl]-6,7-dihydro-5H-cyclopenta[d]pyrimidin-4-yl]isoquinoline-1,3-diol The title compound was prepared in a method analogous to General Method F, using 6-bromoisoquinoline-1,3-diol instead of 6-bromo-1,1-dioxo-1,2-benzothiazol-3-one.

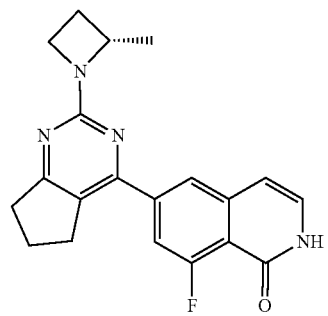 [SMILES: C[C@H]1CCN1c1nc2c(c(-c3cc(F)c4c(=O)[nH]ccc4c3)n1)CCC2]

Example 382: 8-fluoro-6-[2-[(2S)-2-methylazetidin-1-yl]-6,7-dihydro-5H-cyclopenta[d]pyrimidin-4-yl]-2H-isoquinolin-1-one The title compound was prepared in a method analogous to General Method F, using 6-bromo-8-fluoro-2H-isoquinolin-1-one instead of 6-bromo-1,1-dioxo-1,2-benzothiazol-3-one.

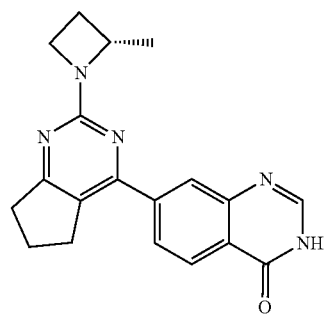 [SMILES: C[C@H]1CCN1c1nc2c(c(-c3ccc4c(=O)[nH]cnc4c3)n1)CCC2]

Example 383: 7-[2-[(2S)-2-methylazetidin-1-yl]-6,7-dihydro-5H-cyclopenta[d]pyrimidin-4-yl]-3H-quinazolin-4-one The title compound was prepared in a method analogous to General Method A using 7-(4,4,5,5-tetramethyl-1,3,2- dioxaborolan-2-yl)-3H-quinazolin-4-one and 4-chloro-2-[(2S)-2-methylazetidin-1-yl]-6,7-dihydro-5H-cyclopenta[d]pyrimidine instead of 3-pyridylboronic acid and 2,4-dichloro-6,7-dihydro-5H-cyclopenta[d]pyrimidine, respectively.

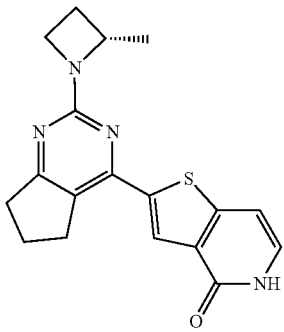 [SMILES: C[C@H]1CCN1c1nc2c(c(-c3cc4c(=O)[nH]ccc4s3)n1)CCC2]

Example 384: 2-[2-[(2S)-2-methylazetidin-1-yl]-6,7-dihydro-5H-cyclopenta[d]pyrimidin-4-yl]-5H-thieno[3,2-c]pyridin-4-one The title compound was prepared in a method analogous to General Method D using 2-bromo-5H-thieno[3,2-d]pyridin-4-one instead of ethyl 2-bromoimidazo[5,1-b]thiazole-7-carboxylate, followed by General Method E.

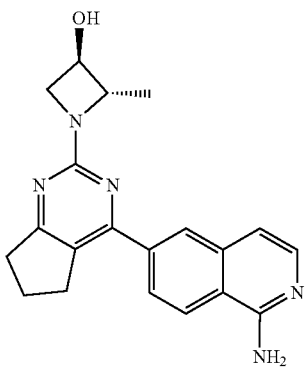 [SMILES: C[C@H]1[C@H](O)CN1c1nc2c(c(-c3ccc4c(N)nccc4c3)n1)CCC2]

Example 385: (2S,3R)-1-[4-(1-amino-6-isoquinolyl)-6,7-dihydro-5H-cyclopenta[d]pyrimidin-2-yl]-2-methyl-azetidin-3-ol The title compound was prepared in a method analogous to General Method A using 6-(4,4,5,5-tetramethyl-1,3,2-dioxaborolan-2-yl)isoquinolin-1-amine and (2S,3R)-1-(4-chloro-6,7-dihydro-5H-cyclopenta[d]pyrimidin-2-yl)-2-methylazetidin-3-yl benzoate instead of 3-pyridylboronic acid and 2,4-dichloro-6,7-dihydro-5H-cyclopenta[d]pyrimidine, respectively, followed by General Method C.

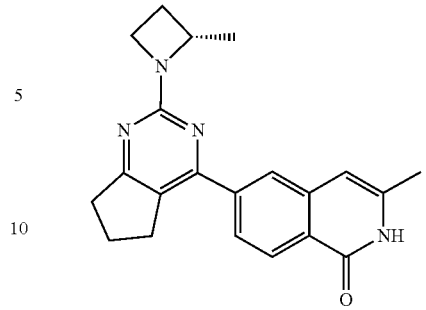

Example 386: 7-[2-[(2S)-2-methylazetidin-1-yl]-6,7-dihydro-5H-cyclopenta[d]pyrimidin-4-yl]-3H-quinazolin-4-one The title compound was prepared in a method analogous to General Method F, using 6-bromo-3-methyl-2H-isoquinolin-1-one instead of 6-bromo-1,1-dioxo-1,2-benzothiazol-3-one.

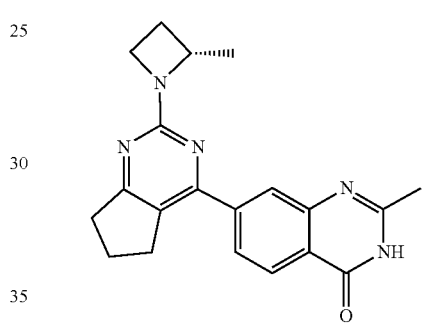

Example 387: 2-methyl-7-[2-[(2S)-2-methylazetidin-1-yl]-6,7-dihydro-5H-cyclopenta[d]pyrimidin-4-yl]-3H-quinazolin-4-one The title compound was prepared in a method analogous to General Method F, using 7-bromo-2-methyl-3H-quinazolin-4-one instead of 6-bromo-1,1-dioxo-1,2-benzothiazol-3-one.

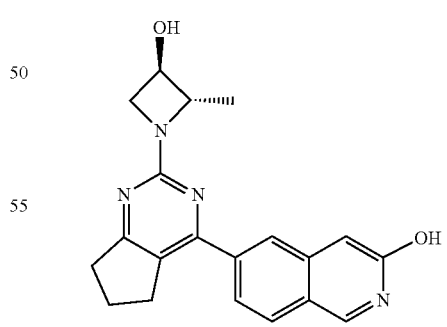

Example 388: 6-[2-[(2S,3R)-3-hydroxy-2-methyl-azetidin-1-yl]-6,7-dihydro-5H-cyclopenta[d]pyrimidin-4-yl]isoquinolin-3-ol The title compound was prepared in a method analogous to General Method A using triisopropyl-[6-(4,4,5,5-tetramethyl-1,3,2-dioxaborolan-2-yl)-3-isoquinolyl]oxyl silane instead of 3-pyridylboronic acid, followed by General Method B, using (2S,3R)-2-methylazetidin-3-ol instead of (2S)-2-methylazetidine. The triisopropylsilyl group was cleaved under reaction conditions.

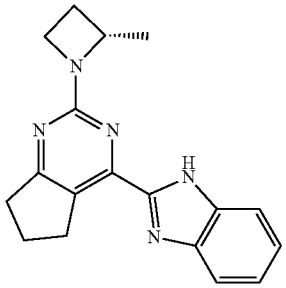 [SMILES: C[C@H]1CCN1c1nc2c(c(-c3nc4ccccc4[nH]3)n1)CCC2]

Example 389: 2-[2-[(2S)-2-methylazetidin-1-yl]-6,7-dihydro-5H-cyclopenta[d]pyrimidin-4-yl]-1H-benzimidazole The title compound was prepared according to General Method P.

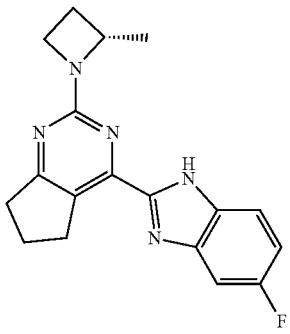 [SMILES: C[C@H]1CCN1c1nc2c(c(-c3nc4cc(F)ccc4[nH]3)n1)CCC2]

Example 390: 5-fluoro-1-methyl-2-[2-[(2S)-2-methylazetidin-1-yl]-6,7-dihydro-5H-cyclopenta[d]pyrimidin-4-yl]benzimidazole The title compound was prepared in a method analogous to General Method P using 4-fluoro-N-methyl-2-nitro-aniline instead of 2-nitroaniline.

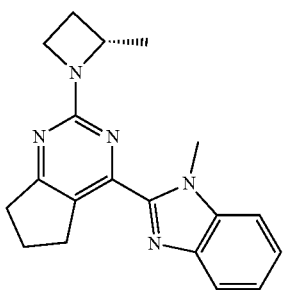 [SMILES: C[C@H]1CCN1c1nc2c(c(-c3nc4ccccc4n3C)n1)CCC2]

Example 391: 1-methyl-2-[2-[(2S)-2-methylazetidin-1-yl]-6,7-dihydro-5H-cyclopenta[d]pyrimidin-4-yl]benzimidazole The title compound was prepared in a method analogous to General Method P using N-methyl-2-nitro-aniline instead of 2-nitroaniline

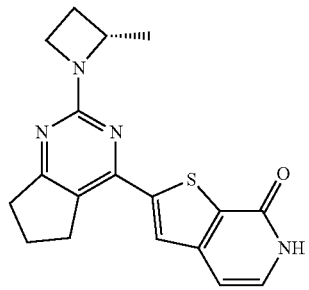 [SMILES: C[C@H]1CCN1c1nc2c(c(-c3cc4cc[nH]c(=O)c4s3)n1)CCC2]

Example 392: 2-[2-[(2S)-2-methylazetidin-1-yl]-6,7-dihydro-5H-cyclopenta[d]pyrimidin-4-yl]-6H-thieno[2,3-c]pyridin-7-one The title compound was prepared in a method analogous to General Method D using 2-bromo-6H-thieno[2,3-c]pyridin-7-one instead of ethyl 2-bromoimidazo[5,1-b]thiazole-7-carboxylate followed by General Method E.

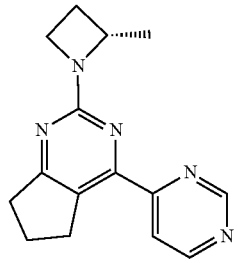 [SMILES: C[C@H]1CCN1c1nc2c(c(-c3ccncn3)n1)CCC2]

Example 393: 2-[(2S)-2-methylazetidin-1-yl]-4-pyrimidin-4-yl-6,7-dihydro-5H-cyclopenta[d]pyrimidine The title compound was prepared in a method analogous to General Method E using tributyl(pyrimidin-4-yl)stannane instead of ethyl 2-tributylstannylimidazo[5,1-b]thiazole-7-carboxylate.

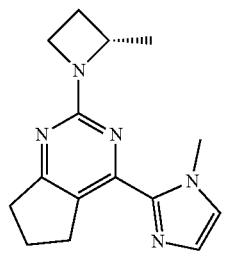 [SMILES: C[C@H]1CCN1c1nc2c(c(-c3nccn3C)n1)CCC2]

Example 394: 2-[(2S)-2-methylazetidin-1-yl]-4-(1-methylimidazol-2-yl)-6,7-dihydro-5H-cyclopenta[d]pyrimidine The title compound was prepared in a method analogous to General Method E using tributyl-(1-methylimidazol-2-yl)stannane instead of ethyl 2-tributylstannylimidazo[5,1-b]thiazole-7-carboxylate.

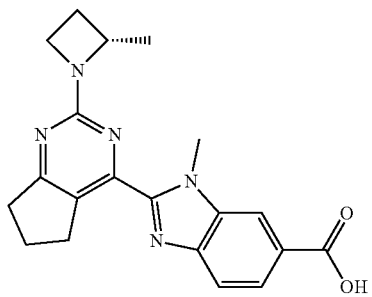 [SMILES: C[C@H]1CCN1c1nc2c(c(-c3nc4ccc(C(=O)O)cc4n3C)n1)CCC2]

Example 395: 3-methyl-2-[2-[(2S)-2-methylazetidin-1-yl]-6,7-dihydro-5H-cyclopenta[d]pyrimidin-4-yl]benzimidazole-5-carboxylic acid The title compound was prepared in a method analogous to General Method P using methyl 3-(methylamino)-4-nitrobenzoate instead of 2-nitroaniline, followed by General Method C.

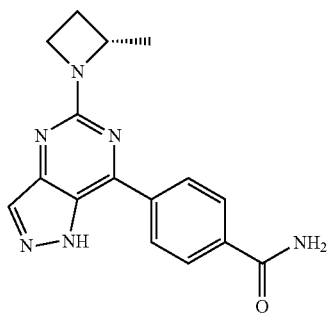 [SMILES: C[C@H]1CCN1c1nc(-c2ccc(C(N)=O)cc2)c2[nH]ncc2n1]

Example 396: (S)-4-(5-(2-methylazetidin-1-yl)-1H-pyrazolo[4,3-d]pyrimidin-7-yl)benzamide A solution of 5,7-dichloro-1H-pyrazolo[4,3-d]pyrimidine (0.94 g, 5.0 mmol) in dichloromethane/tetrahydrofuran (1:1, 20 mL) was treated successively with dihydropyran (0.91 mL, 9.9 mmol) and pyridinium p-toluenesulfonic acid (0.13 g, 0.50 mmol), and the mixture was stirred overnight at 40° C. After concentration under reduced pressure, the residue was purified by flash chromatography (silica gel) to provide 5,7-dichloro-1-tetrahydropyran-2-yl-pyrazolo[4,3-d]pyrimidine.

4-(5-((S)-2-methylazetidin-1-yl)-1-(tetrahydro-2H-pyran-2-yl)-1H-pyrazolo[4,3-d]pyrimidin-7-yl)benzamide was prepared in a method analogous to General Method A, using (4-carbamoylphenyl)boronic acid instead of 3-pyridylboronic acid, followed by General Method B.

A suspension of 4-[5-S)-2-methylazetidin-1-yl]-1-tetrahydropyran-2-yl-pyrazolo[4,3-d]pyrimidin-7-yl)benzamide (60 mg, 0.15 mmol) and pyridinium p-toluenesulfonate (38 mg, 0.15 mmol) in ethanol was heated at 60° C. for 3 days. The mixture was concentrated, and the residue was subjected to HPLC (0.1% TFA in MeCN-0.1% TFA in H$_2$O) to provide the titled compound.

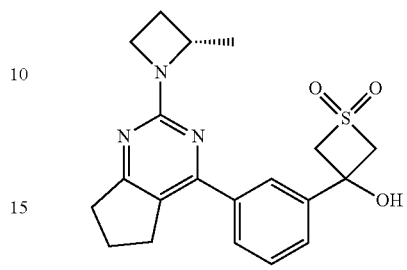

Example 397: (S)-3-hydroxy-3-(3-(2-(2-methylazetidin-1-yl)-6,7-dihydro-5H-cyclopenta[d]pyrimidin-4-yl)phenyl)thietane 1,1-dioxide The title intermediate was prepared in a method analogous to General Method F, using 3-(3-bromophenyl)-1,1-dioxo-thietan-3-ol instead of 6-bromo-1,1-dioxo-1,2-benzothiazol-3-one.

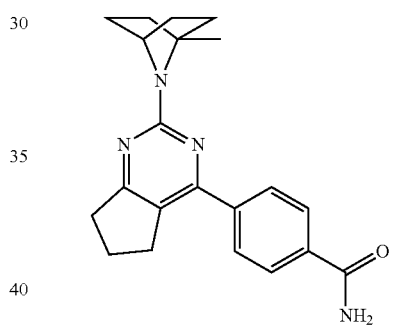

Example 398: 4-(2-(-1-methyl-7-azabicyclo[2.2.1]heptan-7-yl)-6,7-dihydro-5H-cyclopenta[d]pyrimidin-4-yl)benzamide The title compound was prepared in a method analogous to General Method B using 1-methyl-7-azabicyclo[2.2.1]heptane and 4-(2-chloro-6,7-dihydro-5H-cyclopenta[d]pyrimidin-4-yl)benzamide instead of (S)-2-methylazetidine and 2-chloro-4-(pyridin-3-yl)-6,7-dihydro-5H-cyclopenta[d]pyrimidine, respectively.

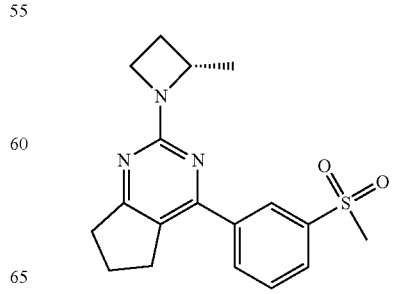

Example 399: (S)-2-(2-methylazetidin-1-yl)-4-(3-(methylsulfonyl)phenyl)-6,7-dihydro-5H-cyclopenta[d]pyrimidine The title compound was prepared in a method analogous to General Method A, using (3-methylsulfonylphenyl)boronic acid and 4-chloro-2-[(2S)-2-methylazetidin-1-yl]-6,7-dihydro-5H-cyclopenta[d]pyrimidine instead of 3-pyridylboronic acid and 2,4-dichloro-6,7-dihydro-5H-cyclopenta[d]pyrimidine, respectively.

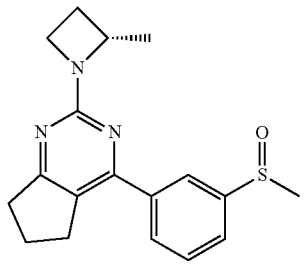 [SMILES: C[C@H]1CCN1c1nc2c(c(-c3cccc(S(C)=O)c3)n1)CCC2]

Example 400: (S)-2-(2-methylazetidin-1-yl)-4-(3-(methylsulfinyl)phenyl)-6,7-dihydro-5H-cyclopenta[d]pyrimidine The title compound was prepared in a method analogous to General Method A, using (3-methylsulfinylphenyl)boronic acid and 4-chloro-2-[(2S)-2-methylazetidin-1-yl]-6,7-dihydro-5H-cyclopenta[d]pyrimidine instead of 3-pyridylboronic acid and 2,4-dichloro-6,7-dihydro-5H-cyclopenta[d]pyrimidine, respectively.

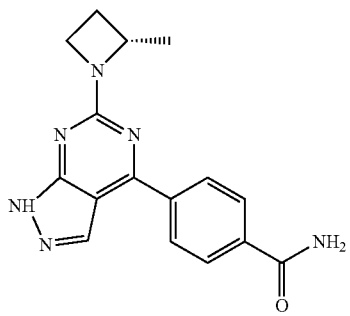

Example 401: (S)-4-(6-(2-methylazetidin-1-yl)-1H-pyrazolo[3,4-d]pyrimidin-4-yl)benzamide The title compound was prepared in a method analogous to 4-[5-[(2S)-2-methylazetidin-1-yl]-1H-pyrazolo[4,3-d]pyrimidin-7-yl]benzamide, using 4,6-dichloro-1H-pyrazolo[3,4-d]pyrimidine instead of 5,7-dichloro-1H-pyrazolo[4,3-d]pyrimidine.

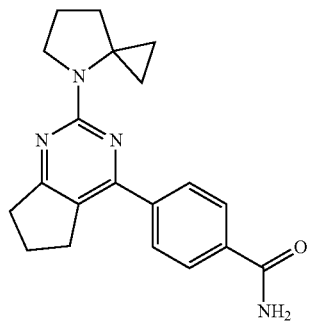 [SMILES: NC(=O)c1ccc(-c2nc(N3CCCC34CC4)nc3c2CCC3)cc1]

Example 402: 4-(2-(4-azaspiro[2.4]heptan-4-yl)-6,7-dihydro-5H-cyclopenta[d]pyrimidin-4-yl)benzamide The title compound was prepared in a method analogous to General Method B using 4-azaspiro[2.4]heptane hemioxalate and 4-(2-chloro-6,7-dihydro-5H-cyclopenta[d]pyrimidin-4-yl)benzamide instead of (S)-2-methylazetidine and 2-chloro-4-(pyridin-3-yl)-6,7-dihydro-5H-cyclopenta[d]pyrimidine, respectively.

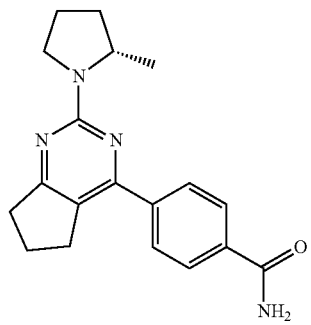 [SMILES: C[C@H]1CCCN1c1nc2c(c(-c3ccc(C(N)=O)cc3)n1)CCC2]

Example 403: (S)-4-(2-(2-methylpyrrolidin-1-yl)-6,7-dihydro-5H-cyclopenta[d]pyrimidin-4-yl)benzamide The title compound was prepared in a method analogous to General Method B using (S)-2-methylpyrrolidine and 4-(2-chloro-6,7-dihydro-5H-cyclopenta[d]pyrimidin-4-yl)benzamide instead of (S)-2-methylazetidine and 2-chloro-4-(pyridin-3-yl)-6,7-dihydro-5H-cyclopenta[d]pyrimidine, respectively.

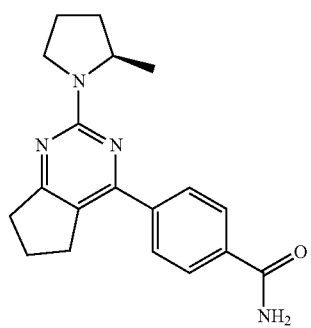 [SMILES: C[C@@H]1CCCN1c1nc2c(c(-c3ccc(C(N)=O)cc3)n1)CCC2]

Example 404: (R)-4-(2-(2-methylpyrrolidin-1-yl)-6, 7-dihydro-5H-cyclopenta[d]pyrimidin-4-yl)benzamide The title compound was prepared in a method analogous to General Method B using (R)-2-methylpyrrolidine and 4-(2-chloro-6,7-dihydro-5H-cyclopenta[d]pyrimidin-4-yl)benzamide instead of (S)-2-methylazetidine and 2-chloro-4-(pyridin-3-yl)-6,7-dihydro-5H-cyclopenta[d]pyrimidine, respectively.

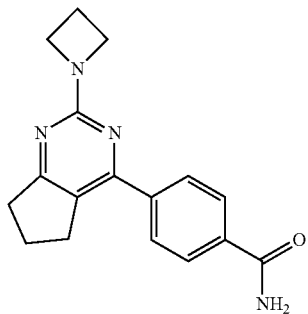 [SMILES: NC(=O)c1ccc(-c2nc(N3CCC3)nc3c2CCC3)cc1]

Example 405: 4-(2-(azetidin-1-yl)-6,7-dihydro-5H-cyclopenta[d]pyrimidin-4-yl)benzamide To a suspension of azetidine hydrochloride (85 mg, 0.91 mmol), cuprous iodide (0.17 g, 0.91 mmol), and cesium carbonate (0.44 g, 1.4 mmol) in DMF (1.5 mL) were added sequentially 4-(2-chloro-6,7-dihydro-5H-cyclopenta[d]pyrimidin-4-yl)benzamide (0.12 g, 0.45 mmol), tetramethyl-1,10-phenanthroline (0.21 g, 0.91 mmol.), and an additional volume of DMF (0.5 mL). The mixture was stirred at 50° C. for 1 hr and then at 70° C. for 16 hr. The reaction mixture was allowed to cool before being diluted with dichloromethane and filtered over Celite®. The filtrate was concentrated under reduced pressure to a residue, which was subjected to HPLC purification (0.1% TFA in MeCN-0.1% TFA in H₂O) to give the title compound.

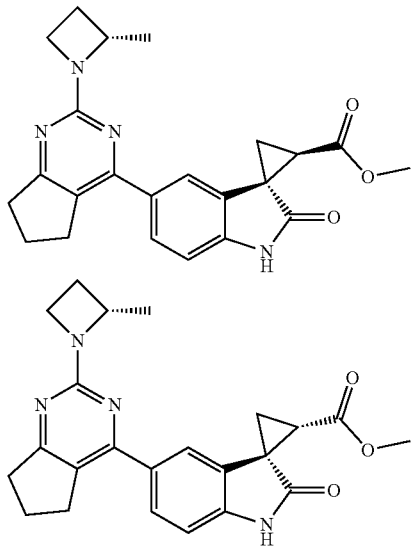

Example 406: rac-methyl (1R,2R)-5'-(2-((S)-2-methylazetidin-1-yl)-6,7-dihydro-5H-cyclopenta[d]pyrimidin-4-yl)-2'-oxospiro[cyclopropane-1,3'-indoline]-2-carboxylate (Assigned as Non-Polar Distereomer) and

Example 407: rac-methyl (1R,2S)-5'-(2-((S)-2-methylazetidin-1-yl)-6,7-dihydro-5H-cyclopenta[d]pyrimidin-4-yl)-2'-oxospiro[cyclopropane-1,3'-indoline]-2-carboxylate (Assigned as Polar Distereomer)

A mixture of 5-bromoindoline-2,3-dione (9.0 g, 40 mmol) and tosyl hydrazide (8.2 g, 44 mmol) in tetrahydrofuran (200 mL) was heated to reflux for 1 hr. After cooling to room temperature, the mixture was filtered, and the solids were then taken up as a suspension in aqueous sodium hydroxide solution (0.2 M, 200 mL) and heated for 90 min at 75 C. After cooling to room temperature, the mixture was acidified to pH 6.5. The resulting solids were collected by filtration and dried under vacuum to provide 5-bromo-3-diazoindolin-2-one.

A suspension of 5-bromo-3-diazoindolin-2-one (0.76 g, 3.2 mmol) in methyl acrylate (5.0 mL, 56 mmol) was heated at 80 C for 2 hr. The mixture was cooled to ambient temperature, concentrated under reduced pressure to provide methyl 5'-bromo-2'-oxospiro[cyclopropane-1,3'-indoline]-2-carboxylate, which was used without further purification.

The title compounds were prepared in a method analogous to General Method F, using methyl 5'-bromo-2'-oxospiro[cyclopropane-1,3'-indoline]-2-carboxylate instead of 6-bromo-1,1-dioxo-1,2-benzothiazol-3-one. The two sets of stereoisomers were separated by flash column chromatography (hexanes-ethyl acetate).

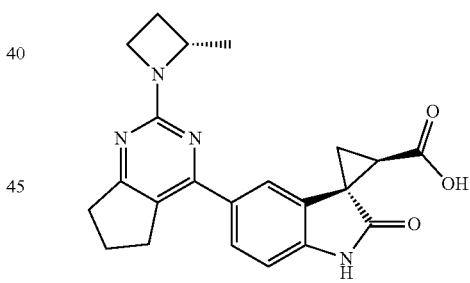

Example 408: rac-(1R,2R)-5'-(24(8)-2-methylazetidin-1-yl)-6,7-dihydro-5H-cyclopenta[d]pyrimidin-4-yl)-2'-oxospiro[cyclopropane-1,3'-indoline]-2-carboxylic acid (Assigned as Non-Polar Diastereomer)

The title compound was prepared in a method analogous to General Method C using rac-methyl (1R,2R)-5'-(2-((S)-2-methylazetidin-1-yl)-6,7-dihydro-5H-cyclopenta[d]pyrimidin-4-yl)-2'-oxospiro[cyclopropane-1,3'-indoline]-2-carboxylate instead of methyl (S)-3-(3-(2-(2-methylazetidin-1-yl)-6,7-dihydro-5H-cyclopenta[d]pyrimidin-4-yl)phenyl)propanoate.

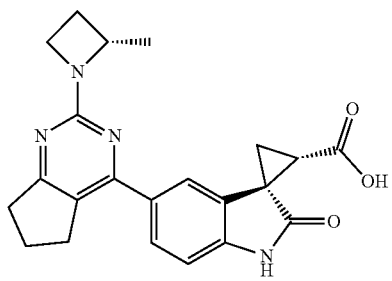 [SMILES: C[C@H]1CCN1c1nc2c(c(-c3ccc4c(c3)[C@]3(C[C@@H]3C(=O)O)C(=O)N4)n1)CCC2]

Example 409: rac-(1R,2S)-5'-(24(8)-2-methylazetidin-1-yl)-6,7-dihydro-5H-cyclopenta[d]pyrimidin-4-yl)-2'-oxospiro[cyclopropane-1,3'-indoline]-2-carboxylic acid (Assigned as Polar Diastereomer)

The title compound was prepared in a method analogous to General Method C using rac-methyl (1R,2S)-5'-(2-((S)-2-methylazetidin-1-yl)-6,7-dihydro-5H-cyclopenta[d]pyrimidin-4-yl)-2'-oxospiro[cyclopropane-1,3'-indoline]-2-carboxylate instead of methyl (S)-3-(3-(2-(2-methylazetidin-1-yl)-6,7-dihydro-5H-cyclopenta[d]pyrimidin-4-yl)phenyl)propanoate.

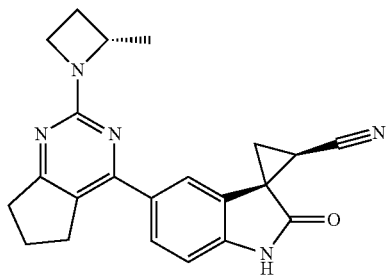

Example 410: rac-(1R,2R)-5'-(2-((S)-2-methylazetidin-1-yl)-6,7-dihydro-5H-cyclopenta[d]pyrimidin-4-yl)-2'-oxospiro[cyclopropane-1,3'-indoline]-2-carbonitrile (Assigned as Non-Polar Diastereomer)

Example 411: rac-(1R,2S)-5'-(2-((S)-2-methylazetidin-1-yl)-6,7-dihydro-5H-cyclopenta[d]pyrimidin-4-yl)-2'-oxospiro[cyclopropane-1,3'-indoline]-2-carbonitrile (Assigned as Polar Diastereomer)

A stirred mixture of palladium (II) acetate (19 mg, 85 µmol, 8.5 mol %), 1,10-phenanthroline (18 mg, 0.10 mmol, 10 mol %), and acrylonitrile (0.33 mL, 5.0 mmol) in chlorobenzene (2 mL) was heated at 80° C. for 5 min. To the reaction mixture was then added dropwise a mixture 5-bromo-3-diazoindolin-2-one (0.24 g, 1.0 mmol) in chlorobenzene (4 mL). The resulting mixture was stirred at 80° C. for 2 hr whereupon the mixture was allowed to cool before being subjected to flash column chromatography (ethyl acetate-hexanes) to provide 5'-bromo-2'-oxo-spiro[cyclopropane-2,3'-indoline]-1-carbonitrile as a mixture of diastereomers.

The title compound was prepared in a method analogous to General Method F using 5'-bromo-2'-oxo-spiro[cyclopropane-2,3'-indoline]-1-carbonitrile instead of 6-bromo-1,1-dioxo-1,2-benzothiazol-3-one.

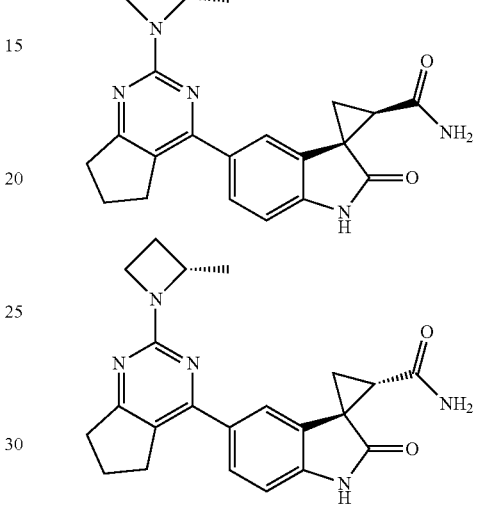

Example 412: rac-(1R,2R)-5'-(2-((S)-2-methylazetidin-1-yl)-6,7-dihydro-5H-cyclopenta[d]pyrimidin-4-yl)-2'-oxospiro[cyclopropane-1,3'-indoline]-2-carboxamide (Assigned as Non-Polar Diastereomer)

Example 413: rac-(1R,2S)-5'-(2-((S)-2-methylazetidin-1-yl)-6,7-dihydro-5H-cyclopenta[d]pyrimidin-4-yl)-2'-oxospiro[cyclopropane-1,3'-indoline]-2-carboxamide (Assigned as Non-Polar Diastereomer)

A vial was charged with 5'-[2-[(2S)-2-methylazetidin-1-yl]-6,7-dihydro-5H-cyclopenta[d]pyrimidin-4-yl]-2'-oxospiro[cyclopropane-2,3'-indoline]-1-carbonitrile (378 mg, 1.0 mmol), ethanol/water (5:3, 8 mL), and (hydrido(dimethylphosphinousacid-kP)[hydrogenbis(dimethylphosphinito-kP)]platinum(II), 22 mg, 51 µmol, 5 mol %). The vial was sealed and heated to 90° C. for 3 hr. The mixture was concentrated and subject to flash column chromatography (ethyl acetate-methanol) to provide the diastereomeric title compounds.

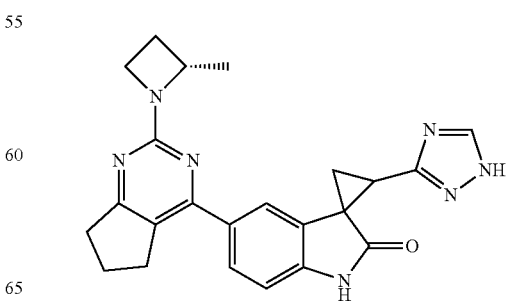

Example 414: (1R,2R)-5'-(2-((S)-2-methylazetidin-1-yl)-6,7-dihydro-5H-cyclopenta[d]pyrimidin-4-yl)-2-(1H-1,2,4-triazol-3-yl)spiro[cyclopropane-1,3'-indolin]-2'-one A mixture of rac-(1R,2R)-5'-[2-[(2S)-2-methylazetidin-1-yl]-6,7-dihydro-5H-cyclopenta[d]pyrimidin-4-yl]-2'-oxo-spiro[cyclopropane-2,3'-indoline]-1-carbonitrile (55 mg, 0.15 mmol) and azido(trimethyl)stannane (61 mg, 0.30 mmol) in o-xylene (2 mL) was heated for 16 hr at 120° C. The mixture was then concentrated under reduced pressure and subjected to HPLC (0.1% TFA in MeCN-0.1% TFA in H₂O) to give the title compound.

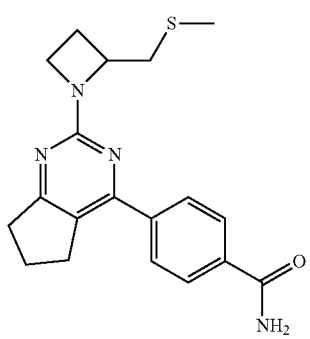 [SMILES: CSCC1CCN1c1nc2c(c(-c3ccc(C(N)=O)cc3)n1)CCC2]

Example 415: 4-(2-(2-((methylthio)methyl)azetidin-1-yl)-6,7-dihydro-5H-cyclopenta[d]pyrimidin-4-yl)benzamide The title compound was prepared in a method analogous to General Method B using 2-(methylsulfanylmethyl)azetidine and 4-(2-chloro-6,7-dihydro-5H-cyclopenta[d]pyrimidin-4-yl)benzamide instead of (2S)-2-methylazetidine and 2-chloro-4-(pyridin-3-yl)-6,7-dihydro-5H-cyclopenta[d]pyrimidine, respectively.

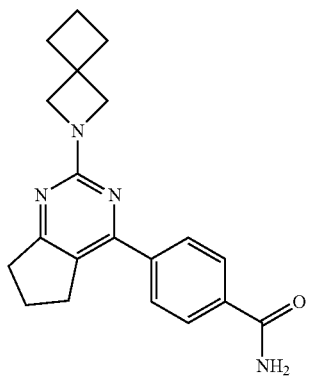 [SMILES: NC(=O)c1ccc(-c2nc(N3CC4(CCC4)C3)nc3c2CCC3)cc1]

Example 416: 4-(2-(2-azaspiro[3.3]heptan-2-yl)-6,7-dihydro-5H-cyclopenta[d]pyrimidin-4-yl)benzamide The title compound was prepared in a method analogous to General Method B using 2-azaspiro[3.3]heptane and 4-(2-chloro-6,7-dihydro-5H-cyclopenta[d]pyrimidin-4-yl)benzamide instead of (2S)-2-methylazetidine and 2-chloro-4-(pyridin-3-yl)-6,7-dihydro-5H-cyclopenta[d]pyrimidine, respectively.

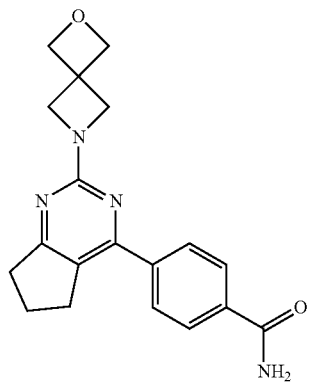 [SMILES: NC(=O)c1ccc(-c2nc(N3CC4(COC4)C3)nc3c2CCC3)cc1]

Example 417: 4-(2-(2-oxa-6-azaspiro[3.3]heptan-6-yl)-6,7-dihydro-5H-cyclopenta[d]pyrimidin-4-yl)benzamide The title compound was prepared in a method analogous to General Method B using 2-oxa-6-azaspiro[3.3]heptane and 4-(2-chloro-6,7-dihydro-5H-cyclopenta[d]pyrimidin-4-yl)benzamide instead of (2S)-2-methylazetidine and 2-chloro-4-(pyridin-3-yl)-6,7-dihydro-5H-cyclopenta[d]pyrimidine, respectively.

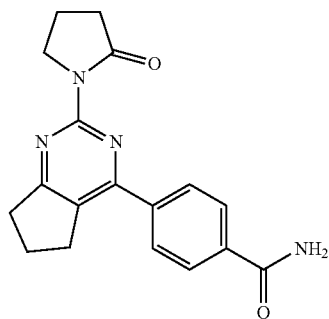 [SMILES: NC(=O)c1ccc(-c2nc(N3CCCC3=O)nc3c2CCC3)cc1]

Example 418: 4-(2-(2-oxopyrrolidin-1-yl)-6,7-dihydro-5H-cyclopenta[d]pyrimidin-4-yl)benzamide The title compound was prepared in a method analogous to General Method N using pyrrolidin-2-one instead 2,3-dihydro-1H-imidazo[1,2-b]pyrazole.

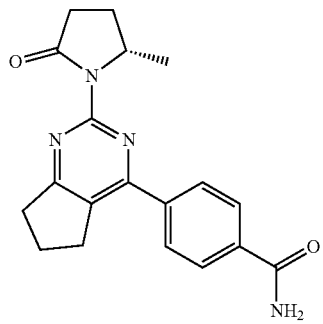 [SMILES: C[C@H]1CCC(=O)N1c1nc2c(c(-c3ccc(C(N)=O)cc3)n1)CCC2]

Example 419: (S)-4-(2-(2-methyl-5-oxopyrrolidin-1-yl)-6,7-dihydro-5H-cyclopenta[d]pyrimidin-4-yl)benzamide The title compound was prepared in a method analogous to General Method N using (5S)-5-methylpyrrolidin-2-one instead 2,3-dihydro-1H-imidazo[1,2-b]pyrazole.

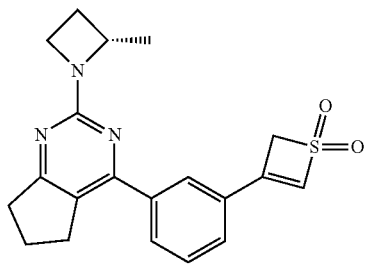 [SMILES: C[C@H]1CCN1c1nc2c(c(-c3cccc(C4=CS(=O)(=O)C4)c3)n1)CCC2]

Example 420: (S)-3-(3-(2-(2-methylazetidin-1-yl)-6,7-dihydro-5H-cyclopenta[d]pyrimidin-4-yl)phenyl)-2H-thiete 1,1-dioxide A solution of 3-(3-bromophenyl)-1,1-dioxo-thietan-3-ol (0.92 g, 3.3 mmol) in dichloromethane (15 mL) was treated successively with triethylamine (1.4 mL, 10 mmol) and then dropwise with methanesulfonyl chloride (0.77 mL, 10 mmol). After 5 minutes of stirring, water was added, and the mixture was extracted three times with ethyl acetate. The combined organic extracts were washed with saturated aqueous sodium chloride solution, dried over magnesium sulfate, filtered, and concentrated under reduced pressure to provide 3-(3-bromophenyl)-2H-thiete 1,1-dioxide.

The title compound was prepared in a method analogous to General Method F using 3-(3-bromophenyl)-2H-thiete 1,1-dioxide instead of 6-bromo-1,1-dioxo-1,2-benzothiazol-3-one.

Example 421: (S)-3-(3-(2-(2-methylazetidin-1-yl)-6,7-dihydro-5H-cyclopenta[d]pyrimidin-4-yl)phenyl)thietane 1,1-dioxide

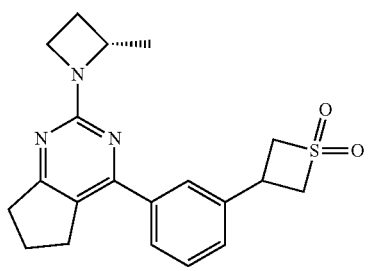 [SMILES: C[C@H]1CCN1c1nc2c(c(-c3cccc(C4CS(=O)(=O)C4)c3)n1)CCC2]

A solution of 3-(3-(4,4,5,5-tetramethyl-1,3,2-dioxaborolan-2-yl)phenyl)thietane 1,1-dioxide (prepared via the first step of General Method F on the substrate 3-(3-bromophenyl)thietane 1,1-dioxide) (0.40 g, 1.3 mmol) in ethanol (15 mL) was degassed before the introduction of 10% palladium on carbon (wetted with ca. 55% water, 0.13 g). The resulting suspension was stirred overnight under a balloon of hydrogen. The mixture was filtered through a pad of Celite®, the filtrate was concentrated under reduced pressure, and the residue was carried forward to the subsequent step without further purification.

The title compound was prepared from 3-[3-(4,4,5,5-tetramethyl-1,3,2-dioxaborolan-2-yl)phenyl]thietane 1,1-dioxide and 4-chloro-2-[(2S)-2-methylazetidin-1-yl]-6,7-dihydro-5H-cyclopenta[d]pyrimidine via the second step of General Method F.

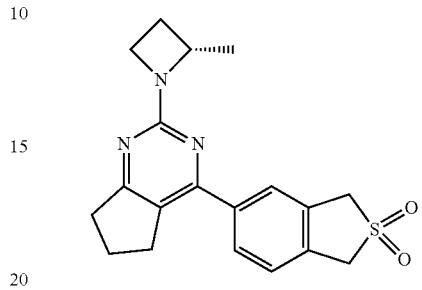

Example 422: (S)-5-(2-(2-methylazetidin-1-yl)-6,7-dihydro-5H-cyclopenta[d]pyrimidin-4-yl)-1,3-dihydrobenzo[c]thiophene 2,2-dioxide The title compound was prepared in a method analogous to General Method F using by 5-bromo-1,3-dihydro-2-benzothiophene 2,2-dioxide instead of 6-bromo-1,1-dioxo-1,2-benzothiazol-3-one.

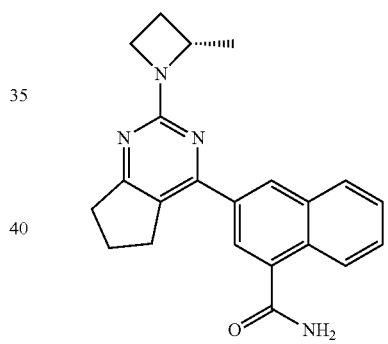

Example 423: (S)-3-(2-(2-methylazetidin-1-yl)-6,7-dihydro-5H-cyclopenta[d]pyrimidin-4-yl)-1-naphthamide The title compound was prepared in a method analogous to General Method F using 3-bromo-1-naphthamide instead of 6-bromo-1,1-dioxo-1,2-benzothiazol-3-one.

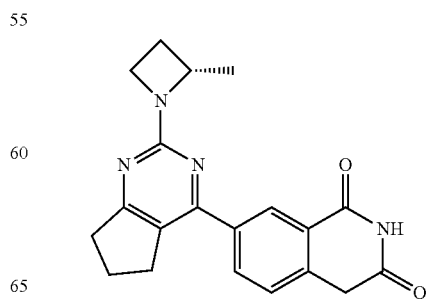

Example 424: (S)-7-(2-(2-methylazetidin-1-yl)-6,7-dihydro-5H-cyclopenta[d]pyrimidin-4-yl)isoquinoline-1,3(2H,4H)-dione The title compound was prepared in a method analogous to General Method F using 7-bromo-4H-isoquinoline-1,3-dione instead of 6-bromo-1,1-dioxo-1,2-benzothiazol-3-one.

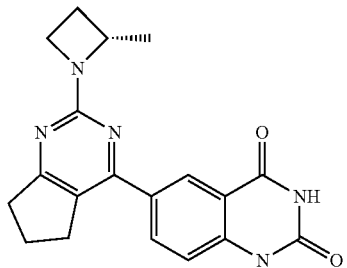 [SMILES: C[C@H]1CCN1c1nc2c(c(-c3ccc4c(c3)C(=O)NC(=O)C4)n1)CCC2]

Example 425: 6-[2-[(2S)-2-methylazetidin-1-yl]-6,7-dihydro-5H-cyclopenta[d]pyrimidin-4-yl]-1H-quinazoline-2,4-dione The title compound was prepared in a method analogous to General Method F using 6-bromo-1H-quinazoline-2,4-dione instead of 6-bromo-1,1-dioxo-1,2-benzothiazol-3-one.

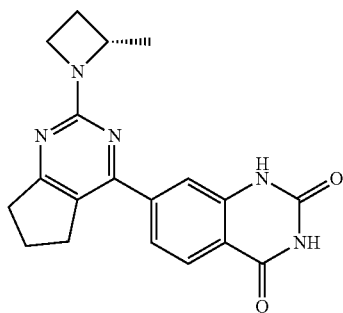 [SMILES: C[C@H]1CCN1c1nc2c(c(-c3ccc4c(=O)[nH]c(=O)[nH]c4c3)n1)CCC2]

Example 426: 7-[2-[(2S)-2-methylazetidin-1-yl]-6,7-dihydro-5H-cyclopenta[d]pyrimidin-4-yl]-1H-quinazoline-2,4-dione The title compound was prepared in a method analogous to General Method F using 7-bromo-1H-quinazoline-2,4-dione instead of 6-bromo-1,1-dioxo-1,2-benzothiazol-3-one.

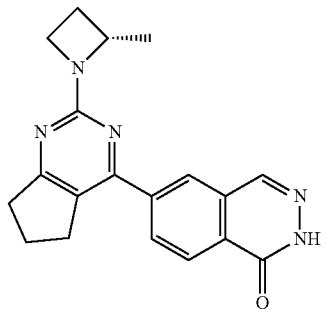 [SMILES: C[C@H]1CCN1c1nc2c(c(-c3ccc4c(=O)[nH]ncc4c3)n1)CCC2]

Example 427: 6-[2-[(2S)-2-methylazetidin-1-yl]-6,7-dihydro-5H-cyclopenta[d]pyrimidin-4-yl]-2H-phthalazin-1-one The title compound was prepared in a method analogous to General Method F using 6-bromo-2H-phthalazin-1-one instead of 6-bromo-1,1-dioxo-1,2-benzothiazol-3-one.

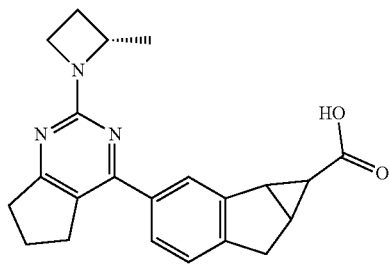 [SMILES: C[C@H]1CCN1c1nc2c(c(-c3ccc4c(c3)C3C(C4)C3C(=O)O)n1)CCC2]

Example 428: 3-[2-[(2S)-2-methylazetidin-1-yl]-6,7-dihydro-5H-cyclopenta[d]pyrimidin-4-yl]-1,1a,6,6a-tetrahydrocyclopropa[a]indene-1-carboxylic acid The title compound was prepared in a method analogous to General Method F using 3-bromo-1,1a,6,6a-tetrahydrocyclopropa[a]indene-1-carboxylic acid instead of 6-bromo-1,1-dioxo-1,2-benzothiazol-3-one.

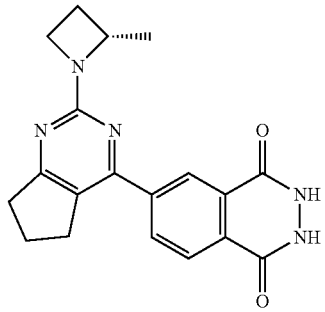 [SMILES: C[C@H]1CCN1c1nc2c(c(-c3ccc4c(=O)[nH][nH]c(=O)c4c3)n1)CCC2]

Example 429: 6-[2-[(2S)-2-methylazetidin-1-yl]-6,7-dihydro-5H-cyclopenta[d]pyrimidin-4-yl]-2,3-dihydrophthalazine-1,4-dione The title compound was prepared in a method analogous to General Method F using 6-bromo-2,3-dihydrophthalazine-1,4-dione instead of 6-bromo-1,1-dioxo-1,2-benzothiazol-3-one.

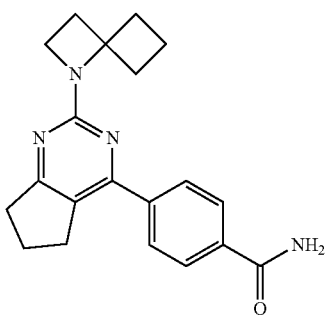 [SMILES: NC(=O)c1ccc(-c2nc(N3CCC34CCC4)nc3c2CCC3)cc1]

Example 430: 4-[2-(1-azaspiro[3.3]heptan-1-yl)-6,7-dihydro-5H-cyclopenta[d]pyrimidin-4-yl]benzamide The title compound was prepared in a method analogous to General Method B using 1-azaspiro[3.3]heptane and 4-(2-chloro-6,7-dihydro-5H-cyclopenta[d]pyrimidin-4-yl)benzamide instead of (2S)-2-methylazetidine and 2-chloro-4-(pyridin-3-yl)-6,7-dihydro-5H-cyclopenta[d]pyrimidine, respectively.

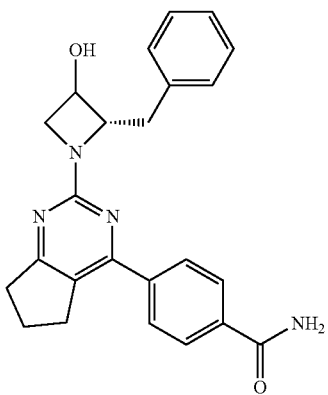 [SMILES: NC(=O)c1ccc(-c2nc(N3CC(O)[C@@H]3Cc3ccccc3)nc3c2CCC3)cc1]

Example 431: 4-[2-[(2S)-2-benzyl-3-hydroxy-azetidin-1-yl]-6,7-dihydro-5H-cyclopenta[d]pyrimidin-4-yl]benzamide The title compound was prepared in a method analogous to General Method B using (2S)-2-benzylazetidin-3-ol and 4-(2-chloro-6,7-dihydro-5H-cyclopenta[d]pyrimidin-4-yl)benzamide instead of (2S)-2-methylazetidine and 2-chloro-4-(pyridin-3-yl)-6,7-dihydro-5H-cyclopenta[d]pyrimidine, respectively.

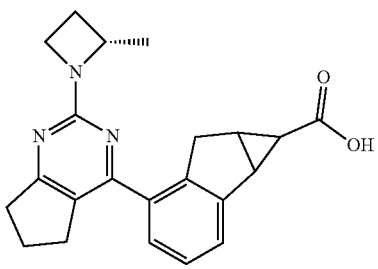 [SMILES: C[C@H]1CCN1c1nc2c(c(-c3cccc4c3CC3C(C(=O)O)C43)n1)CCC2]

Example 432: 5-[2-[(2S)-2-methylazetidin-1-yl]-6,7-dihydro-5H-cyclopenta[d]pyrimidin-4-yl]-1,1a,6,6a-tetrahydrocyclopropa[a]indene-1-carboxylic acid The title compound was prepared in a method analogous to General Method F using 5-bromo-1,1a,6,6a-tetrahydrocyclopropa[a]indene-1-carboxylic acid instead of 6-bromo-1,1-dioxo-1,2-benzothiazol-3-one.

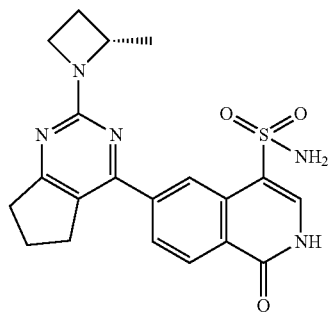 [SMILES: C[C@H]1CCN1c1nc2c(c(-c3ccc4c(=O)[nH]cc(S(N)(=O)=O)c4c3)n1)CCC2]

Example 433: 6-[2-[(2S)-2-methylazetidin-1-yl]-6,7-dihydro-5H-cyclopenta[d]pyrimidin-4-yl]-1-oxo-2H-isoquinoline-4-sulfonamide The title compound was prepared in a method analogous to General Method F using 6-bromo-1-oxo-2H-isoquinoline-4-sulfonamide instead of 6-bromo-1,1-dioxo-1,2-benzothiazol-3-one.

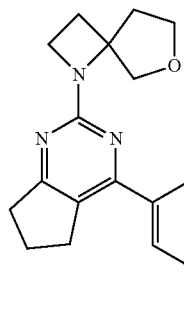

Example 434: 4-[2-(7-oxa-1-azaspiro[3.4]octan-1-yl)-6,7-dihydro-5H-cyclopenta[d]pyrimidin-4-yl]benzamide The title compound was prepared in a method analogous to General Method B using 7-oxa-1-azaspiro[3.4]octane and 4-(2-chloro-6,7-dihydro-5H-cyclopenta[d]pyrimidin-4-yl)benzamide instead of (2S)-2-methylazetidine and 2-chloro-4-(pyridin-3-yl)-6,7-dihydro-5H-cyclopenta[d]pyrimidine, respectively.

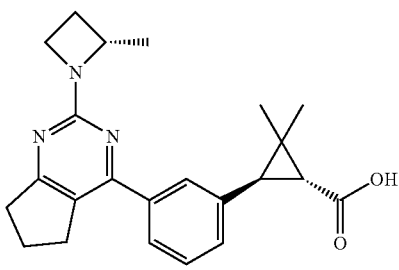 [SMILES: C[C@H]1CCN1c1nc2c(c(-c3cccc([C@@H]4[C@@H](C(=O)O)C4(C)C)c3)n1)CCC2]

Example 435: (1R,3R)-2,2-dimethyl-3-(3-(2-((S)-2-methylazetidin-1-yl)-6,7-dihydro-5H-cyclopenta[d]pyrimidin-4-yl)phenyl)cyclopropane-1-carboxylic acid The title compound was prepared in a method analogous to General Method F using (1R,3R)-3-(3-bromophenyl)-2,2-dimethyl-cyclopropanecarboxylic acid instead of 6-bromo-1,1-dioxo-1,2-benzothiazol-3-one.

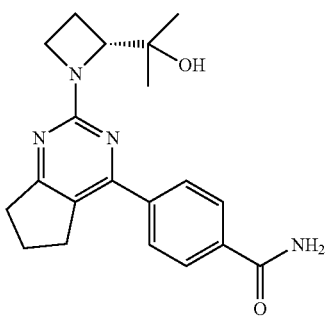 [SMILES: CC(C)(O)[C@H]1CCN1c1nc2c(c(-c3ccc(C(N)=O)cc3)n1)CCC2]

Example 436: 4-[2-[(2R)-2-(1-hydroxy-1-methyl-ethyl)azetidin-1-yl]-6,7-dihydro-5H-cyclopenta[d]pyrimidin-4-yl]benzamide The title compound was prepared in a method analogous to General Method B using 2-[(2R)-azetidin-2-yl]propan-2-ol and 4-(2-chloro-6,7-dihydro-5H-cyclopenta[d]pyrimidin-4-yl)benzamide instead of (2S)-2-methylazetidine and 2-chloro-4-(pyridin-3-yl)-6,7-dihydro-5H-cyclopenta[d]pyrimidine, respectively.

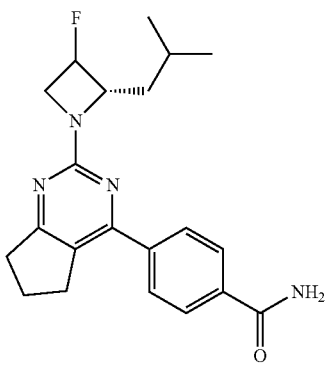 [SMILES: CC(C)C[C@H]1C(F)CN1c1nc2c(c(-c3ccc(C(N)=O)cc3)n1)CCC2]

Example 437: 4-[2-[(2S)-3-fluoro-2-isobutyl-azetidin-1-yl]-6,7-dihydro-5H-cyclopenta[d]pyrimidin-4-yl]benzamide The title compound was prepared in a method analogous to General Method B using (2S)-3-fluoro-2-isobutyl-azetidine and 4-(2-chloro-6,7-dihydro-5H-cyclopenta[d]pyrimidin-4-yl)benzamide instead of (2S)-2-methylazetidine and 2-chloro-4-(pyridin-3-yl)-6,7-dihydro-5H-cyclopenta[d]pyrimidine, respectively.

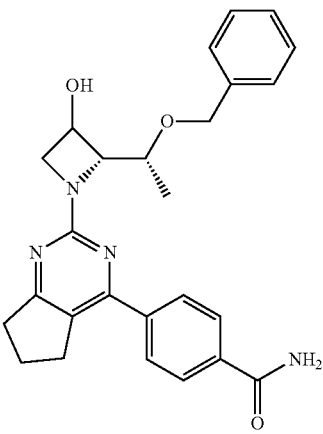

Example 438: 4-[2-[(2R)-2-[(1R)-1-benzyloxyethyl]-3-hydroxy-azetidin-1-yl]-6,7-dihydro-5H-cyclopenta[d]pyrimidin-4-yl]benzamide The title compound was prepared in a method analogous to General Method B using (2R)-2-[(1R)-1-benzyloxyethyl]azetidin-3-ol and 4-(2-chloro-6,7-dihydro-5H-cyclopenta[d]pyrimidin-4-yl)benzamide instead of (2S)-2-methylazetidine and 2-chloro-4-(pyridin-3-yl)-6,7-dihydro-5H-cyclopenta[d]pyrimidine, respectively.

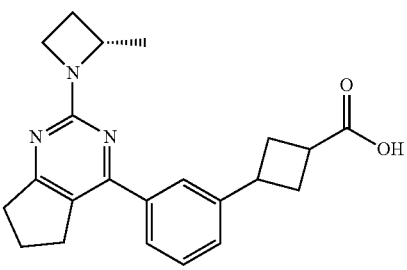 [SMILES: C[C@H]1CCN1c1nc2c(c(-c3cccc(C4CC(C(=O)O)C4)c3)n1)CCC2]

Example 439: 3-[3-[2-[(2S)-2-methylazetidin-1-yl]-6,7-dihydro-5H-cyclopenta[d]pyrimidin-4-yl]phenyl]cyclobutanecarboxylic acid The title compound was prepared in a method analogous to General Method F using 3-(3-bromophenyl)cyclobutanecarboxylic acid instead of 6-bromo-1,1-dioxo-1,2-benzothiazol-3-one.

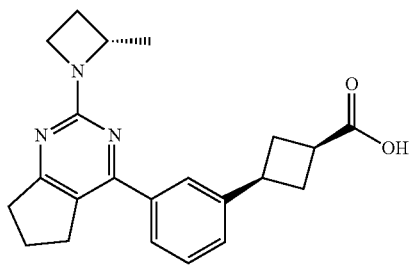

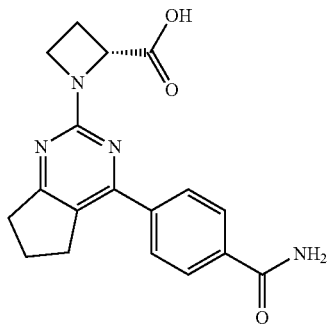 [SMILES: NC(=O)c1ccc(-c2nc(N3CC[C@@H]3C(=O)O)nc3c2CCC3)cc1]

Example 440: (1R,3s)-3-(3-(2-((S)-2-methylazetidin-1-yl)-6,7-dihydro-5H-cyclopenta[d]pyrimidin-4-yl)phenyl)cyclobutane-1-carboxylic acid Example 441: (1S,3r)-3-(3-(2-((S)-2-methylazetidin-1-yl)-6,7-dihydro-5H-cyclopenta[d]pyrimidin-4-yl)phenyl)cyclobutane-1-carboxylic acid Isomers were separated by SFC (25% EtOH in $CO_2$, CHIRALPAK AD-H, 100×4.6 mm, 3 mL/min).

Example 442: (2R)-1-[4-(4-carbamoylphenyl)-6,7-dihydro-5H-cyclopenta[d]pyrimidin-2-yl]azetidine-2-carboxylic acid The title compound was prepared in a method analogous to General Method B using (2R)-azetidine-2-carboxylic acid and 4-(2-chloro-6,7-dihydro-5H-cyclopenta[d]pyrimidin-4-yl)benzamide instead of (2S)-2-methylazetidine and 2-chloro-4-(pyridin-3-yl)-6,7-dihydro-5H-cyclopenta[d]pyrimidine, respectively.

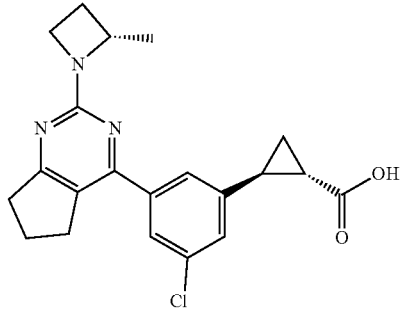 [SMILES: C[C@H]1CCN1c1nc2c(c(-c3cc(Cl)cc([C@H]4C[C@@H]4C(=O)O)c3)n1)CCC2]

Example 443: (1S,2S)-2-[3-chloro-5-[2-[(2S)-2-methylazetidin-1-yl]-6,7-dihydro-5H-cyclopenta[d]pyrimidin-4-yl]phenyl]cyclopropanecarboxylic acid The title compound was prepared in a method analogous to General Method F using (1S,2S)-2-(3-bromo-5-chlorophenyl)cyclopropanecarboxylic acid instead of 6-bromo-1,1-dioxo-1,2-benzothiazol-3-one.

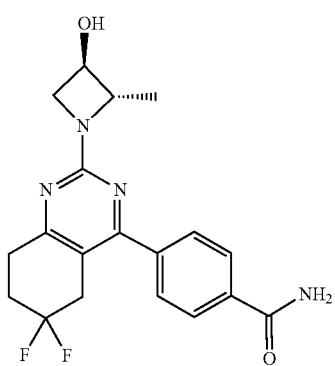 [SMILES: C[C@H]1[C@H](O)CN1c1nc2c(c(-c3ccc(C(N)=O)cc3)n1)CC(F)(F)CC2]

Example 444: 4-(6,6-difluoro-2-((2S,3R)-3-hydroxy-2-methylazetidin-1-yl)-5,6,7,8-tetrahydroquinazolin-4-yl)benzamide The title compound was prepared in a method analogous to General Method B using (2S,3R)-2-methylazetidin-3-ol and 4-(2-chloro-6,6-difluoro-5,6,7,8-tetrahydroquinazolin-4-yl)benzamide instead of (2S)-2-methylazetidine and 4-(2-chloro-6,7-dihydro-5H-cyclopenta[d]pyrimidin-4-yl)benzamide, respectively.

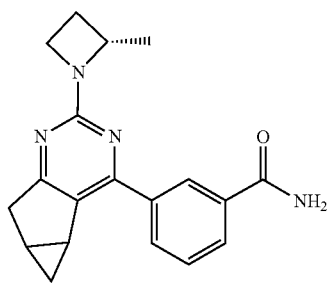 [SMILES: C[C@H]1CCN1c1nc2c(c(-c3cccc(C(N)=O)c3)n1)C1CC1C2]

Example 445: 3-(2-((S)-2-methylazetidin-1-yl)-4b,5,5a,6-tetrahydrocyclopropa[3,4]cyclopenta[1,2-d]pyrimidin-4-yl)benzamide The title compound was prepared in a method analogous to General Methods A and B, using 2,4-dichloro-4b,5,5a,6-tetrahydrocyclopropa[3,4]cyclopenta[1,2-d]pyrimidine instead of 2,4-dichloro-6,7-dihydro-5H-cyclopenta[d]pyrimidine.

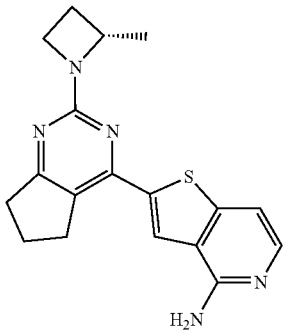 [SMILES: C[C@H]1CCN1c1nc2c(c(-c3cc4c(N)nccc4s3)n1)CCC2]

Example 446: 2-[2-[(2S)-2-methylazetidin-1-yl]-6,7-dihydro-5H-cyclopenta[d]pyrimidin-4-yl]thieno[3,2-c]pyridin-4-amine To a solution of 2-bromothieno[3,2-c]pyridin-4-amine (500 mg, 2.18 mmol), triethylamine (1.52 mL, 10.9 mmol) and N,N-dimethylpyridin-4-amine (53 mg, 0.44 mmol) in tetrahydrofuran (20 mL) was added tert-butoxycarbonyl tert-butyl carbonate (1.9 g, 8.7 mmol), and the reaction mixture was stirred at ambient temperature for 16 hours. It was diluted with ethyl acetate and washed with 10% potassium bisulfate, saturated sodium bicarbonate, and saturated sodium chloride. It was dried over anhydrous sodium sulfate, filtered, and concentrated. It was purified via flash chromatography (ethyl acetate-hexanes) to yield tert-butyl N-(2-bromothieno[3,2-c]pyridin-4-yl)-N-tert-butoxycarbonyl-carbamate.

The title compound was prepared in a method analogous to General Method D using tert-butyl N-(2-bromothieno[3,2-c]pyridin-4-yl)-N-tert-butoxycarbonyl-carbamate instead of ethyl 2-bromoimidazo[5,1-b]thiazole-7-carboxylate, followed by General Method E using tert-butyl N-tert-butoxycarbonyl-N-(2-tributylstannylthieno[3,2-c]pyridin-4-yl)carbamate instead of ethyl 2-tributylstannylimidazo[5,1-b]thiazole-7-carboxylate, followed by General Method I.

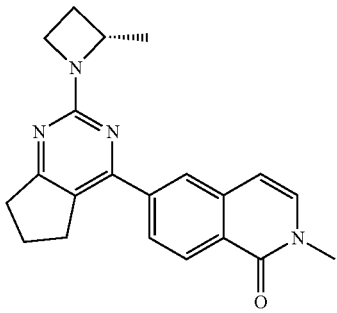 [SMILES: C[C@H]1CCN1c1nc2c(c(-c3ccc4c(=O)n(C)ccc4c3)n1)CCC2]

Example 447: 2-methyl-6-[2-[(2S)-2-methylazetidin-1-yl]-6,7-dihydro-5H-cyclopenta[d]pyrimidin-4-yl]isoquinolin-1-one The title compound was prepared in a method analogous to General Method F using 6-bromo-2-methyl-isoquinolin-1-one instead of 6-bromo-1,1-dioxo-1,2-benzothiazol-3-one.

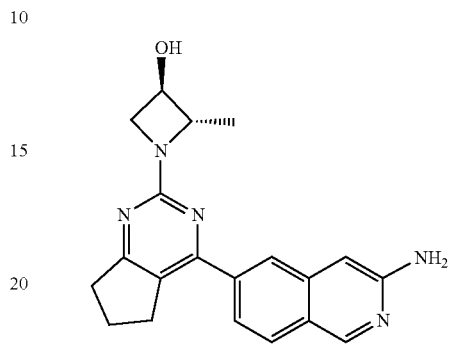

Example 448: (2S,3R)-1-[4-(3-amino-6-isoquinolyl)-6,7-dihydro-5H-cyclopenta[d]pyrimidin-2-yl]-2-methyl-azetidin-3-ol tert-butyl N-(6-bromo-3-isoquinolyl)-N-tert-butoxycarbonyl-carbamate was prepared in a method analogous to tert-butyl N-(2-bromothieno[3,2-c]pyridin-4-yl)-N-tert-butoxycarbonyl-carbamate using 6-bromo-3-aminoisoquinoline instead of 2-bromothieno[3,2-c]pyridin-4-amine.

[(2S,3R)-1-[4-[1-[bis(tert-butoxycarbonyl)amino]-6-isoquinolyl]-6,7-dihydro-5H-cyclopenta[d]pyrimidin-2-yl]-2-methyl-azetidin-3-yl] benzoate was prepared in a method analogous to General Method F using tert-butyl N-(6-bromo-3-isoquinolyl)-N-tert-butoxycarbonyl-carbamate instead of 6-bromo-1,1-dioxo-1,2-benzothiazol-3-one and [(2S,3R)-1-(4-chloro-6,7-dihydro-5H-cyclopenta[d]pyrimidin-2-yl)-2-methyl-azetidin-3-yl]benzoate instead of 4-chloro-2-[(2S)-2-methylazetidin-1-yl]-6,7-dihydro-5H-cyclopenta[d]pyrimidine.

To a solution of [(2S,3R)-1-[4-[3-[bis(tert-butoxycarbonyl)amino]-6-isoquinolyl]-6,7-dihydro-5H-cyclopenta[d]pyrimidin-2-yl]-2-methyl-azetidin-3-yl]benzoate (94 mg, 0.14 mmol) in methanol (1.6 mL) was added 1N aqueous sodium hydroxide (0.29 mL, 0.29 mmol), and the reaction mixture was stirred at ambient temperature for 16 hours. To this, trifluoroacetic acid (0.5 mL) was added, and the reaction mixture was stirred for 30 minutes. It was diluted with DMSO and purified by preparatory HPLC (0.1% TFA in MeCN-0.1% TFA in H₂O) to yield the title compound.

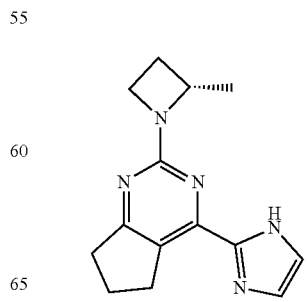

Example 449: (2S,3R)-1-[4-(3-amino-6-isoquinolyl)-6,7-dihydro-5H-cyclopenta[d]pyrimidin-2-yl]-2-methyl-azetidin-3-ol To a solution of 2-[(2S)-2-methylazetidin-1-yl]-6,7-dihydro-5H-cyclopenta[d]pyrimidine-4-carbaldehyde (82 mg, 0.38 mmol) and 8.8M glyoxal in water (0.047 mL, 0.42 mmol) in ethanol (1.2 mL) was added concentrated ammonium hydroxide (0.27 mL), and the reaction mixture was allowed to stir at ambient temperature for 16 hours. It was concentrated, taken up in DMSO, acidified with TFA, and purified by preparative HPLC to yield the title compound.

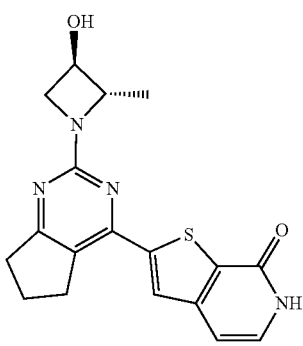 [SMILES: C[C@H]1[C@H](O)CN1c1nc2c(c(-c3cc4cc[nH]c(=O)c4s3)n1)CCC2]

Example 450: 2-[2-[(2S,3R)-3-hydroxy-2-methyl-azetidin-1-yl]-6,7-dihydro-5H-cyclopenta[d]pyrimidin-4-yl]-6H-thieno[2,3-c]pyridin-7-one The title compound was prepared in a method analogous to General Method E using 2-tributylstannyl-6H-thieno[2,3-c]pyridin-7-one and (2S,3R)-1-(4-chloro-6,7-dihydro-5H-cyclopenta[d]pyrimidin-2-yl)-2-methylazetidin-3-yl benzoate instead of ethyl 2-tributylstannylimidazo[5,1-b]thiazole-7-carboxylate and (S)-4-chloro-2-(2-methylazetidin-1-yl)-6,7-dihydro-5H-cyclopenta[d]pyrimidine, respectively, followed by General Method C.

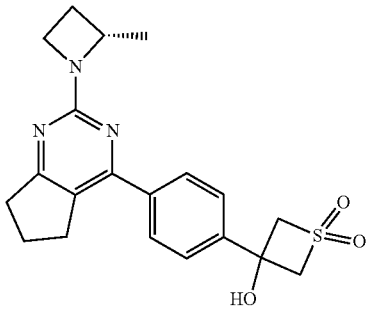 [SMILES: C[C@H]1CCN1c1nc2c(c(-c3ccc(C4(O)CS(=O)(=O)C4)cc3)n1)CCC2]

Example 451: (S)-3-hydroxy-3-(4-(2-(2-methylazetidin-1-yl)-6,7-dihydro-5H-cyclopenta[d]pyrimidin-4-yl)phenyl)thietane 1,1-dioxide The title compound was prepared in a method analogous to General Method F, using 3-(4-bromophenyl)-1,1-dioxothietan-3-ol instead of 6-bromo-1,1-dioxo-1,2-benzothiazol-3-one.

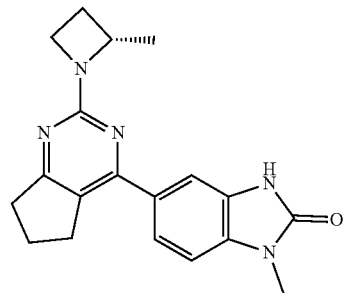 [SMILES: C[C@H]1CCN1c1nc2c(c(-c3ccc4c(c3)[nH]c(=O)n4C)n1)CCC2]

Example 452: 3-methyl-6-[2-[(2S)-2-methylazetidin-1-yl]-6,7-dihydro-5H-cyclopenta[d]pyrimidin-4-yl]-1H-benzimidazol-2-one The title compound was prepared in a method analogous to General Method A using 3-methyl-6-(4,4,5,5-tetramethyl-1,3,2-dioxaborolan-2-yl)-1H-benzimidazol-2-one 3-pyridylboronic acid.

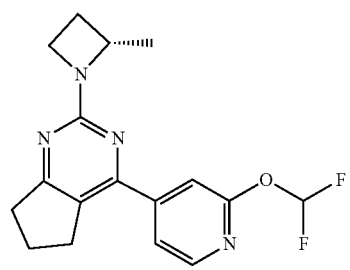 [SMILES: C[C@H]1CCN1c1nc2c(c(-c3ccnc(OC(F)F)c3)n1)CCC2]

Example 453: 4-[2-(difluoromethoxy)-4-pyridyl]-2-[(2S)-2-methylazetidin-1-yl]-6,7-dihydro-5H-cyclopenta[d]pyrimidine The title compound was prepared in a method analogous to General Method A 2-(difluoromethoxy)-4-(4,4,5,5-tetramethyl-1,3,2-dioxaborolan-2-yl)pyridine instead of 3-pyridylboronic acid.

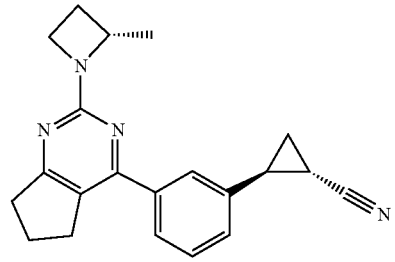 [SMILES: C[C@H]1CCN1c1nc2c(c(-c3cccc([C@H]4C[C@@H]4C#N)c3)n1)CCC2]

Example 454: trans-2-[3-[2-[(2S)-2-methylazetidin-1-yl]-6,7-dihydro-5H-cyclopenta[d]pyrimidin-4-yl]phenyl]cyclopropanecarbonitrile The title compound was prepared in a method analogous to General Method F using trans-2-(3-bromophenyl)cyclopropanecarbonitrile instead of 6-bromo-1,1-dioxo-1,2-benzothiazol-3-one.

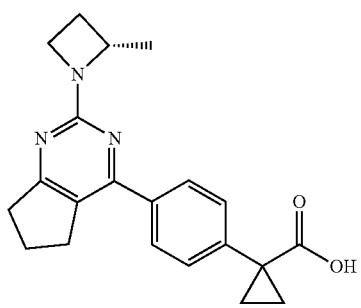 [SMILES: C[C@H]1CCN1c1nc2c(c(-c3ccc(C4(C(=O)O)CC4)cc3)n1)CCC2]

Example 455: 1-[4-[2-[(2S)-2-methylazetidin-1-yl]-6,7-dihydro-5H-cyclopenta[d]pyrimidin-4-yl]phenyl]cyclopropanecarboxylic acid The title compound was prepared in a method analogous to General Method F using 1-(4-bromophenyl)cyclopropanecarboxylic acid instead of 6-bromo-1,1-dioxo-1,2-benzothiazol-3-one.

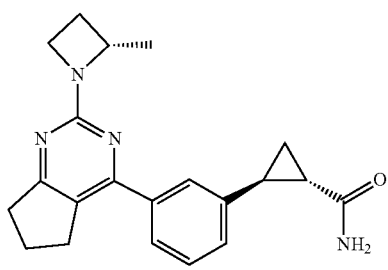 [SMILES: C[C@H]1CCN1c1nc2c(c(-c3cccc([C@H]4C[C@@H]4C(N)=O)c3)n1)CCC2]

Example 456: trans-2-[3-[2-[(2S)-2-methylazetidin-1-yl]-6,7-dihydro-5H-cyclopenta[d]pyrimidin-4-yl]phenyl]cyclopropanecarboxamide A flask was charged with trans-2-[3-[2-[rel-(2S)-2-methylazetidin-1-yl]-6,7-dihydro-5H-cyclopenta[d]pyrimidin-4-yl]phenyl]cyclopropanecarbonitrile (52.6 mg, 0.16 mmol, 1 equiv.), ethanol (2 mL), and water (1 mL). To the suspension was added Parkins-Ghaffer catalyst (hydrido(dimethylphosphinousacid-kP)[hydrogenbis(dimethylphosphinito-kP)]platinum(II), 3.4 mg, 7.9 μmol, 5 mol %). The vial was sealed and heated to 90° C. for three hours. The reaction mixture was cooled to room temperature, concentrated, and subjected to HPLC (0.1% TFA in MeCN-0.1% TFA in H$_2$O) to give the title compound.

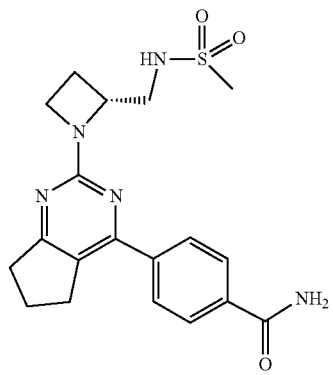 [SMILES: CS(=O)(=O)NC[C@H]1CCN1c1nc2c(c(-c3ccc(C(N)=O)cc3)n1)CCC2]

Example 457: 4-[2-[(2R)-2-(methanesulfonamidomethyl)azetidin-1-yl]-6,7-dihydro-5H-cyclopenta[d]pyrimidin-4-yl]benzamide The title compound was formed in a method analogous to General Method B using N-[[(2R)-azetidin-2-yl]methyl]methanesulfonamide and 4-(2-chloro-6,7-dihydro-5H-cyclopenta[d]pyrimidin-4-yl)benzamide instead of (2S)-2-methylazetidine and 2-chloro-4-(pyridin-3-yl)-6,7-dihydro-5H-cyclopenta[d]pyrimidine, respectively.

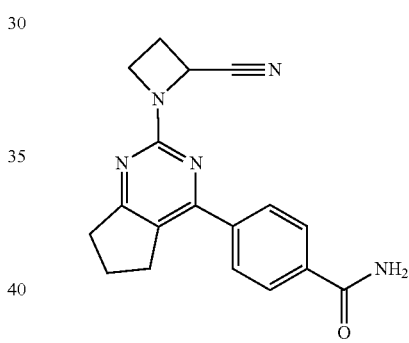

Example 458: 4-(2-(2-cyanoazetidin-1-yl)-6,7-dihydro-5H-cyclopenta[d]pyrimidin-4-yl)benzamide The title compound was formed in a method analogous to General Method B using azetidine-2-carbonitrile hemioxalate and 4-(2-chloro-6,7-dihydro-5H-cyclopenta[d]pyrimidin-4-yl)benzamide and instead of (2S)-2-methylazetidine and 2-chloro-4-(pyridin-3-yl)-6,7-dihydro-5H-cyclopenta[d]pyrimidine, respectively.

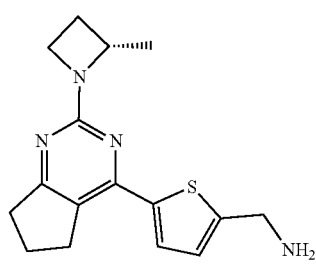 [SMILES: C[C@H]1CCN1c1nc2c(c(-c3ccc(CN)s3)n1)CCC2]

Example 459: [5-[2-[(2S)-2-methylazetidin-1-yl]-6,7-dihydro-5H-cyclopenta[d]pyrimidin-4-yl]-2-thienyl]methanamine The title compound was prepared in a method analogous to General Method A, using [5-[(tert-butoxycarbonylamino)methyl]-2-thienyl]boronic acid and 4-chloro-2-[(2S)-2-methylazetidin-1-yl]-6,7-dihydro-5H-cyclopenta[d]pyrimidine instead of 3-pyridylboronic acid and 2,4-dichloro-6,7-dihydro-5H-cyclopenta[d]pyrimidine, respectively, followed by General Methods B and I.

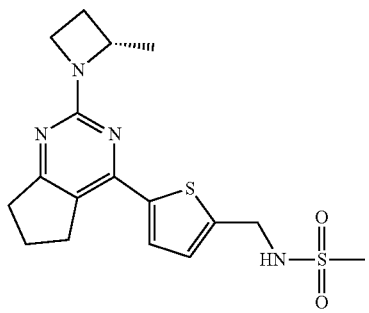 [SMILES: C[C@H]1CCN1c1nc2c(c(-c3ccc(CNS(C)(=O)=O)s3)n1)CCC2]

Example 460: N-[[5-[2-[(2S)-2-methylazetidin-1-yl]-6,7-dihydro-5H-cyclopenta[d]pyrimidin-4-yl]-2-thienyl]methyl]methanesulfonamide The title compound was prepared in a method analogous to General Method K using [5-[2-[(2S)-2-methylazetidin-1-yl]-6,7-dihydro-5H-cyclopenta[d]pyrimidin-4-yl]-2-thienyl]methanamine and mesyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively.

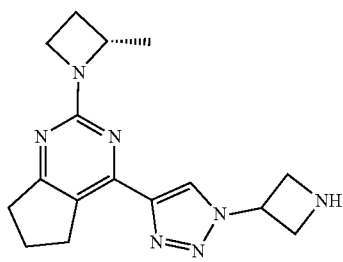 [SMILES: C[C@H]1CCN1c1nc2c(c(-c3cn(C4CNC4)nn3)n1)CCC2]

Example 461: (S)-4-(1-(azetidin-3-yl)-1H-1,2,3-triazol-4-yl)-2-(2-methylazetidin-1-yl)-6,7-dihydro-5H-cyclopenta[d]pyrimidine To a solution of 2-[(2S)-2-methylazetidin-1-yl]-4-vinyl-6,7-dihydro-5H-cyclopenta[c]pyrimidine (310 mg, 1.43 mmol) in methanol (12 mL) was added potassium carbonate (127 mg, 1.43 mmol) and 1-diazo-1-dimethoxyphosphoryl-propan-2-one (0.278 mL, 1.85 mmol), and the reaction mixture was stirred at ambient temperature for 16 hours. It was diluted with ethyl acetate, and washed with saturated sodium bicarbonate, and saturated sodium chloride. It was dried over anhydrous sodium sulfate, filtered, and concentrated. It was subject to flash chromatography (ethyl acetate-hexanes) to yield 4-ethynyl-2-[(2S)-2-methylazetidin-1-yl]-6,7-dihydro-5H-cyclopenta[d]pyrimidine.

To a solution of 4-ethynyl-2-[(2S)-2-methylazetidin-1-yl]-6,7-dihydro-5H-cyclopenta[d]pyrimidine (30 mg, 0.14 mmol) in tetrahydrofuran (0.74 mL) was added tert-butyl 3-azidoazetidine-1-carboxylate (28 mg, 0.14 mmol) and copper(I) thiophene-2-carboxylate (3 mg, 0.014 mmol), and the reaction mixture was stirred at ambient temperature for 3 hours. It was concentrated and purified by flash chromatography (1-10% methanol/dichloromethane linear gradient) to yield tert-butyl 3-[4-[2-[(2S)-2-methylazetidin-1-yl]-6,7-dihydro-5H-cyclopenta[d]pyrimidin-4-yl]triazol-1-yl]azetidine-1-carboxylate.

The title compound was prepared in a method analogous to General Method I using tert-butyl 3-[4-[2-[(2S)-2-methylazetidin-1-yl]-6,7-dihydro-5H-cyclopenta[d]pyrimidin-4-yl]triazol-1-yl]azetidine-1-carboxylate instead of tert-butyl (S)-4-(4-(2-(2-methylazetidin-1-yl)-6,7-dihydro-5H-cyclopenta[d]pyrimidin-4-yl)phenyl)piperazine-1-carboxylate.

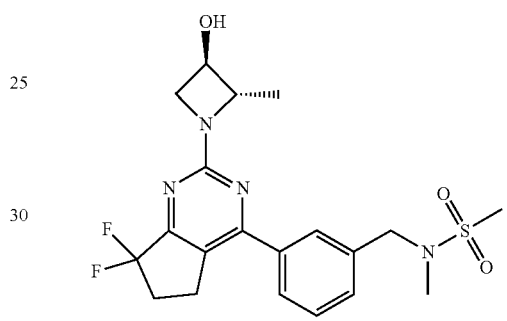

Example 462: N-(3-(7,7-difluoro-2-((2S,3R)-3-hydroxy-2-methylazetidin-1-yl)-6,7-dihydro-5H-cyclopenta[d]pyrimidin-4-yl)benzyl)-N-methylmethanesulfonamide N-(3-(7,7-difluoro-2-(methylthio)-6,7-dihydro-5H-cyclopenta[d]pyrimidin-4-yl)benzyl)methanesulfonamide was prepared in a method analogous to General Method A using 4-chloro-7,7-difluoro-2-(methylthio)-6,7-dihydro-5H-cyclopenta[d]pyrimidine and 3-(methanesulfonamidomethyl)phenyl boronic acid instead of 2,4-dichloro-6,7-dihydro-5H-cyclopenta[d]pyrimidine and 3-pyridylboronic acid, respectively.

A vial was charged with N-(3-(7,7-difluoro-2-(methylthio)-6,7-dihydro-5H-cyclopenta[d]pyrimidin-4-yl)benzyl)methanesulfonamide (130 mg, 0.337 mmol) and THF (4 mL). NaH (25 mg, 0.675 mmol, 60% dispersion in mineral oil) was added at 0° C. followed by the dropwise addition of MeI (0.042 mL, 0.675 mmol) at 0° C. The reaction mixture was allowed to warm to ambient temperature. The crude material was extracted with EA, washed with aqueous NaHCO$_3$, dried over Na$_2$SO$_4$, filtered, and concentrated. The residue was subject to flash column chromatography (ethyl aceate-hexanes) to give N-(3-(7,7-difluoro-2-(methylthio)-6,7-dihydro-5H-cyclopenta[d]pyrimidin-4-yl)benzyl)-N-methylmethanesulfonamide The title compound was prepared in a method analogous to General Method M, followed by General Method B using N-(3-(7,7-difluoro-2-(methylsulfonyl)-6,7-dihydro-5H-cyclopenta[d]pyrimidin-4-yl)benzyl)-N-methylmethanesulfonamide and (2S)-2-methylazetidin-3-ol instead of 2-chloro- 4-(pyridin-3-yl)-6,7-dihydro-5H-cyclopenta[d]pyrimidine and (2S)-2-methylazetidine, respectively.

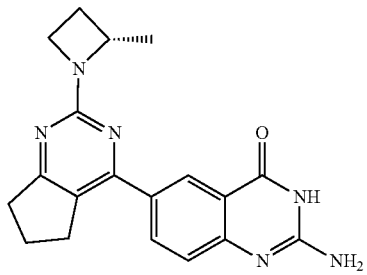 [SMILES: C[C@H]1CCN1c1nc2c(c(-c3ccc4nc(N)[nH]c(=O)c4c3)n1)CCC2]

Example 463: (S)-2-amino-6-(2-(2-methylazetidin-1-yl)-6,7-dihydro-5H-cyclopenta[d]pyrimidin-4-yl)quinazolin-4(3H)-one Ethoxycarbonyl isothiocyanate (1.4 mL, 1.2 mmol) was added to a solution of methyl 2-amino-5-bromobenzoate (2.3 g, 10 mmol) in acetonitrile (100 mL). The reaction mixture was stirred at room temperature for 90 min after which hexamethyldisilazane (21 mL, 100 mmol) and 1-ethyl-3-(3-dimethylaminopropyl)carbodiimide hydrochloride (3.8 g, 20 mmol) were added successively. The mixture was stirred for 18 hr at room temperature, and the reaction mixture was concentrated. The solids were taken up as a suspension in ethyl acetate/5% aqueous hydrochloric acid, collected by suction filtration, washed with water and ethyl acetate, and dried under vacuum to provide N-(6-bromo-4-oxo-1H-quinazolin-2-yl)carbamate.

(S)—N-(6-(2-(2-methylazetidin-1-yl)-6,7-dihydro-5H-cyclopenta[d]pyrimidin-4-yl)-4-oxo-3,4-dihydroquinazolin-2-yl)acetamide was prepared according to General Method F using N-(6-bromo-4-oxo-1H-quinazolin-2-yl)carbamate instead of 6-bromo-1,1-dioxo-1,2-benzothiazol-3-one. Note: exchange of the carbamate to acetamide occurred under reaction conditions.

(S)—N-(6-(2-(2-methylazetidin-1-yl)-6,7-dihydro-5H-cyclopenta[d]pyrimidin-4-yl)-4-oxo-3,4-dihydroquinazolin-2-yl)acetamide was suspended in methanol (50 mL) and treated with 2M aqueous sodium hydroxide solution (5 mL). The mixture was heated to reflux for 15 min and concentrated. Ethyl acetate and water was added to the residue. After acidifying to pH 1 using 1N HCl, the resulting precipitate was collected by filtration and subjected to HPLC purification (0.1% TFA in MeCN-0.1% TFA in H₂O) to give the title compound.

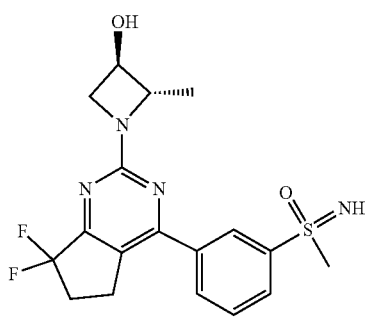 [SMILES: C[C@H]1[C@H](O)CN1c1nc(-c2cccc(S(C)(=N)=O)c2)c2c(n1)C(F)(F)CC2]

Example 464: (3-(7,7-difluoro-24(2S,3R)-3-hydroxy-2-methylazetidin-1-yl)-6,7-dihydro-5H-cyclopenta[d]pyrimidin-4-yl)phenyl)(imino)(methyl)-$\lambda^6$-sulfanone The title compound was prepared in a method analogous to General Method A using 4-chloro-7,7-difluoro-2-(methylthio)-6,7-dihydro-5H-cyclopenta[d]pyrimidine and imino (methyl)(3-(4,4,5,5-tetramethyl-1,3,2-dioxaborolan-2-yl) phenyl)-16-sulfanone instead of 2,4-dichloro-6,7-dihydro-5H-cyclopenta[d]pyrimidine and 3-pyridylboronic acid, respectively, followed by General Method M, followed by General Method B using (2S,3R)-2-methylazetidin-3-ol instead of (2S)-2-methylazetidine, respectively.

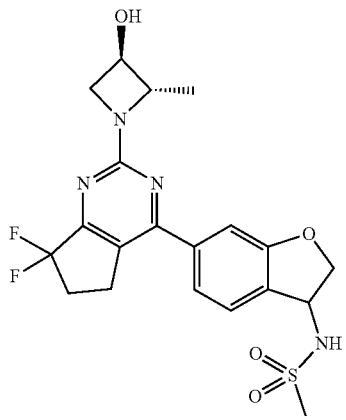

Example 465: N-(6-(7,7-difluoro-24(2S,3R)-3-hydroxy-2-methylazetidin-1-yl)-6,7-dihydro-5H-cyclopenta[d]pyrimidin-4-yl)-2,3-dihydrobenzofuran-3-yl)methanesulfonamide The title compound was prepared in a method analogous to General Method K using (rac)-6-bromo-2,3-dihydrobenzofuran-3-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-2-methylazetidin-3-ol instead of (2S)-2-methylazetidine.

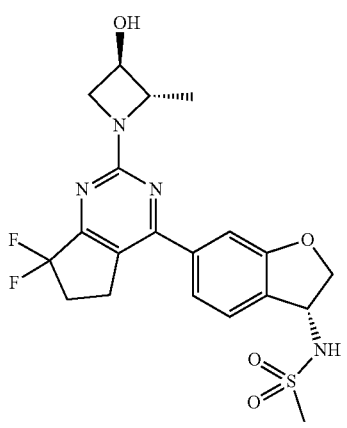

Example 466: N—((R)-6-(7,7-difluoro-2-((2S,3R)-3-hydroxy-2-methylazetidin-1-yl)-6,7-dihydro-5H-cyclopenta[d]pyrimidin-4-yl)-2,3-dihydrobenzofuran-3-yl)methanesulfonamide The title compound was prepared in a method analogous to General Method K using (R)-6-bromo-2,3-dihydrobenzofuran-3-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-2-methylazetidin-3-ol instead of (2S)-2-methylazetidine.

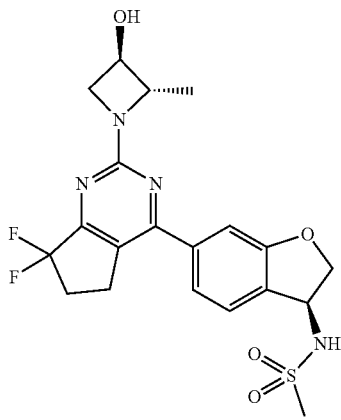 [SMILES: C[C@H]1[C@H](O)CN1c1nc(-c2ccc3c(c2)OC[C@H]3NS(C)(=O)=O)c2c(n1)C(F)(F)CC2]

Example 467: N—((S)-6-(7,7-difluoro-2-((2S,3R)-3-hydroxy-2-methylazetidin-1-yl)-6,7-dihydro-5H-cyclopenta[d]pyrimidin-4-yl)-2,3-dihydrobenzofuran-3-yl)methanesulfonamide The title compound was prepared in a method analogous to General Method K using (S)-6-bromo-2,3-dihydrobenzofuran-3-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-2-methylazetidin-3-ol instead of (2S)-2-methylazetidine.

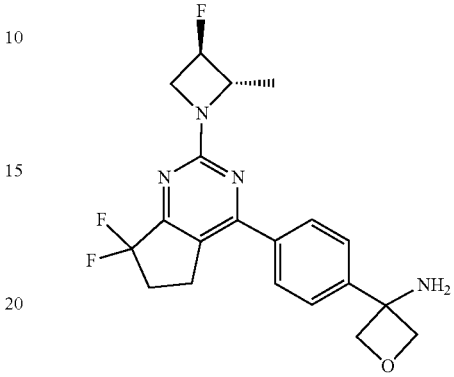

Example 468: 3-(4-(7,7-difluoro-2-((2S,3R)-3-fluoro-2-methylazetidin-1-yl)-6,7-dihydro-5H-cyclopenta[d]pyrimidin-4-yl)phenyl)oxetan-3-amine The title compound was prepared in a method analogous to General Method A using 4-chloro-7,7-difluoro-2-(methylthio)-6,7-dihydro-5H-cyclopenta[d]pyrimidine and benzyl (3-(4-(4,4,5,5-tetramethyl-1,3,2-dioxaborolan-2-yl)phenyl)oxetan-3-yl)carbamate instead of 2,4-dichloro-6,7-dihydro-5H-cyclopenta[d]pyrimidine and 3-pyridylboronic acid, respectively, followed by General Method M, followed by General Method B using (2S,3R)-3-fluoro-2-methylazetidine instead of (2S)-2-methylazetidine, followed by General Method R.

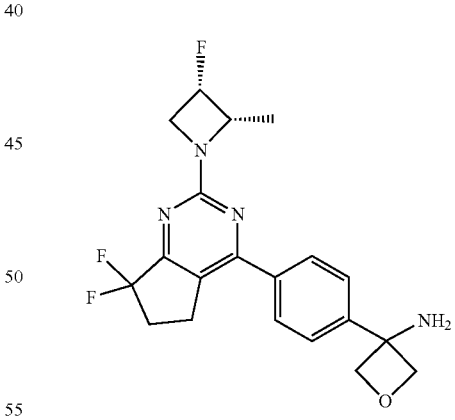

Example 469: 3-(4-(7,7-difluoro-2-((2S,3S)-3-fluoro-2-methylazetidin-1-yl)-6,7-dihydro-5H-cyclopenta[d]pyrimidin-4-yl)phenyl)oxetan-3-amine The title compound was prepared in a method analogous to General Method A using 4-chloro-7,7-difluoro-2-(methylthio)-6,7-dihydro-5H-cyclopenta[d]pyrimidine and benzyl (3-(4-(4,4,5,5-tetramethyl-1,3,2-dioxaborolan-2-yl)phenyl)oxetan-3-yl)carbamate instead of 2,4-dichloro-6,7-dihydro-5H-cyclopenta[d]pyrimidine and 3-pyridylboronic acid, respectively, followed by General Method M, followed by General Method B using (2S,3S)-3-fluoro-2-methylazetidine instead of (2S)-2-methylazetidine, followed by General Method R.

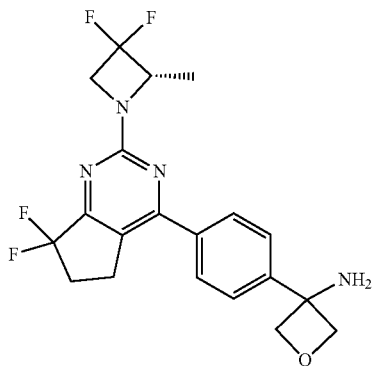 [SMILES: C[C@@H]1N(c2nc(-c3ccc(C4(N)COC4)cc3)c3c(n2)C(F)(F)CC3)CC1(F)F]

Example 470: (S)-3-(4-(2-(3,3-difluoro-2-methylazetidin-1-yl)-7,7-difluoro-6,7-dihydro-5H-cyclopenta[d]pyrimidin-4-yl)phenyl)oxetan-3-amine The title compound was prepared in a method analogous to General Method A using 4-chloro-7,7-difluoro-2-(methylthio)-6,7-dihydro-5H-cyclopenta[d]pyrimidine and benzyl (3-(4-(4,4,5,5-tetramethyl-1,3,2-dioxaborolan-2-yl)phenyl) oxetan-3-yl)carbamate instead of 2,4-dichloro-6,7-dihydro-5H-cyclopenta[d]pyrimidine and 3-pyridylboronic acid, respectively, followed by General Method M, followed by General Method B using (S)-3,3-difluoro-2-methylazetidine instead of (2S)-2-methylazetidine, followed by General Method R.

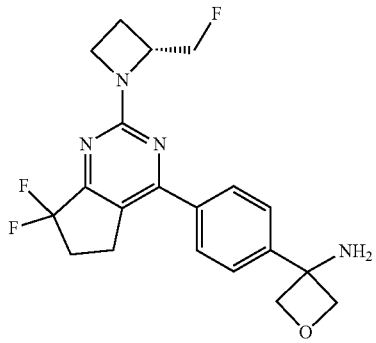 [SMILES: NC1(c2ccc(-c3nc(N4CC[C@@H]4CF)nc4c3CCC4(F)F)cc2)COC1]

Example 471: (R)-3-(4-(7,7-difluoro-2-(2-(fluoromethyl)azetidin-1-yl)-6,7-dihydro-5H-cyclopenta[d] pyrimidin-4-yl)phenyl)oxetan-3-amine The title compound was prepared in a method analogous to General Method A using 4-chloro-7,7-difluoro-2-(methylthio)-6,7-dihydro-5H-cyclopenta[d]pyrimidine and benzyl (3-(4-(4,4,5,5-tetramethyl-1,3,2-dioxaborolan-2-yl)phenyl) oxetan-3-yl)carbamate instead of 2,4-dichloro-6,7-dihydro-5H-cyclopenta[d]pyrimidine and 3-pyridylboronic acid, respectively, followed by General Method M, followed by General Method B using (R)-2-(fluoromethyl)azetidine instead of (2S)-2-methylazetidine, followed by General Method R.

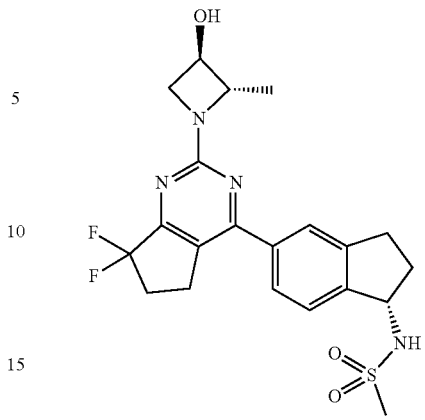

Example 472: N—((S)-5-(7,7-difluoro-2-((2S,3R)-3-hydroxy-2-methylazetidin-1-yl)-6,7-dihydro-5H-cyclopenta[d]pyrimidin-4-yl)-2,3-dihydro-1H-inden-1-yl)methanesulfonamide The title compound was prepared in a method analogous to General Method K using (S)-5-bromo-2,3-dihydro-1H-inden-1-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-2-methylazetidin-3-ol instead of (2S)-2-methylazetidine.

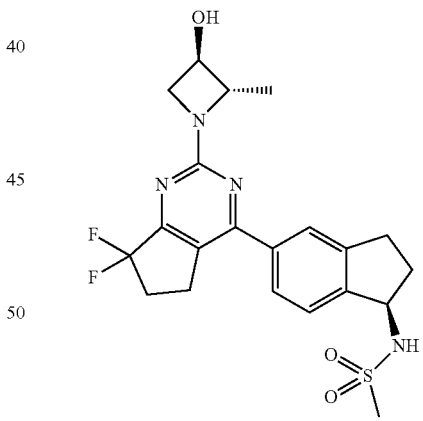

Example 473: N—((R)-5-(7,7-difluoro-2-((2S,3R)-3-hydroxy-2-methylazetidin-1-yl)-6,7-dihydro-5H-cyclopenta[d]pyrimidin-4-yl)-2,3-dihydro-1H-inden-1-yl)methanesulfonamide The title compound was prepared in a method analogous to General Method K using (R)-5-bromo-2,3-dihydro-1H-inden-1-amine and methanesulfonyl chloride instead of (S)-3-(2-(2-methylazetidin-1-yl)-6,7-dihydro-5H-cyclopenta[d] pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-2-methylazetidin-3-ol instead of (2S)-2-methylazetidine.

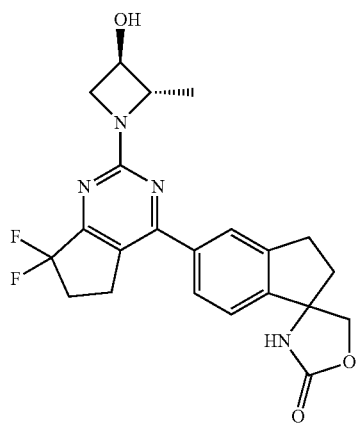 [SMILES: C[C@H]1[C@H](O)CN1c1nc(-c2ccc3c(c2)CCC32COC(=O)N2)c2c(n1)C(F)(F)CC2]

Example 474: 5-(7,7-difluoro-2-((2S,3R)-3-hydroxy-2-methylazetidin-1-yl)-6,7-dihydro-5H-cyclopenta[d]pyrimidin-4-yl)-2,3-dihydrospiro[indene-1,4'-oxazolidin]-2'-one A vial was charged with (1-amino-5-bromo-indan-1-yl)methanol (500 mg, 2.07 mmol) and THF (15 mL). Triphosgene (613 mg, 2.07 mmol) was added slowly. The resulting mixture was heated to 70° C. for 2 hrs. The mixture was allowed to cool to ambient temperature. NaHCO₃ (15 mL, sat. aq.) was added and the mixture was extracted with EtOAc (3×10 mL). The combined organic layers were dried over Na₂SO₄, filtered, and concentrated. The residue was subject to flash column chromatography (hexane-ethyl acetate) to give 5-bromo-2,3-dihydrospiro[indene-1,4'-oxazolidin]-2'-one.

The title compound was prepared in analogy to General Method F using 5-bromo-2,3-dihydrospiro[indene-1,4'-oxazolidin]-2'-one and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, and General Method B, using (2S,3R)-2-methylazetidin-3-ol instead of (2S)-2-methylazetidine.

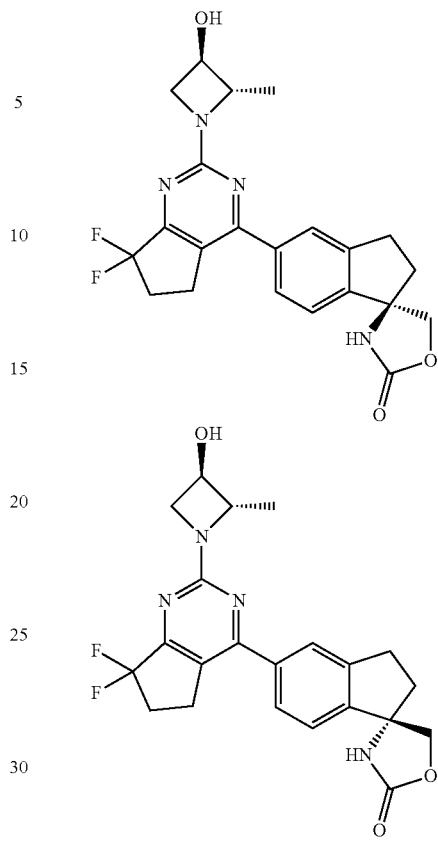

Example 475: (R)-5-(7,7-difluoro-2-((2S,3R)-3-hydroxy-2-methylazetidin-1-yl)-6,7-dihydro-5H-cyclopenta[d]pyrimidin-4-yl)-2,3-dihydrospiro[indene-1,4'-oxazolidin]-2'-one Example 476: (S)-5-(7,7-difluoro-2-((2S,3R)-3-hydroxy-2-methylazetidin-1-yl)-6,7-dihydro-5H-cyclopenta[d]pyrimidin-4-yl)-2,3-dihydrospiro[indene-1,4'-oxazolidin]-2'-one Isomers were separated by SFC (30% EtOH in CO₂, CHIRALPAK AD-H, 100×4.6 mm, 3 mL/min).

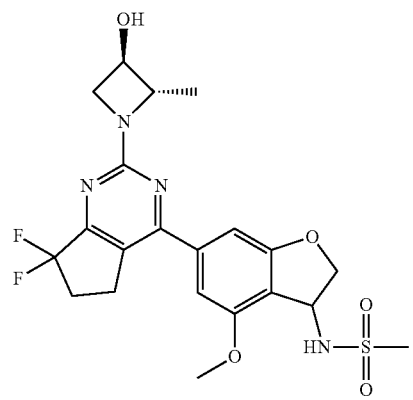 [SMILES: COc1cc(-c2nc(N3C[C@@H](O)[C@@H]3C)nc3c2CCC3(F)F)cc2c1C(NS(C)(=O)=O)CO2]

Example 477: N-(6-(7,7-difluoro-2-((2S,3R)-3-hydroxy-2-methylazetidin-1-yl)-6,7-dihydro-5H-cyclopenta[d]pyrimidin-4-yl)-4-methoxy-2,3-dihydrobenzofuran-3-yl)methanesulfonamide The title compound was prepared in a method analogous to General Method K using 6-bromo-4-methoxy-2,3-dihydrobenzofuran-3-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-2-methylazetidin-3-ol instead of (2S)-2-methylazetidine.

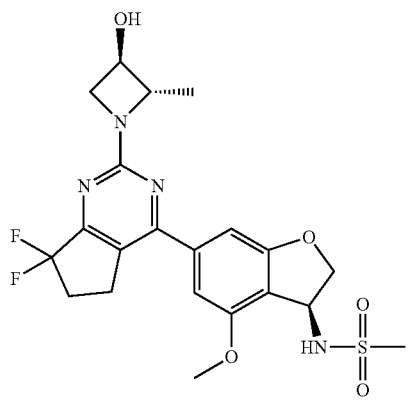

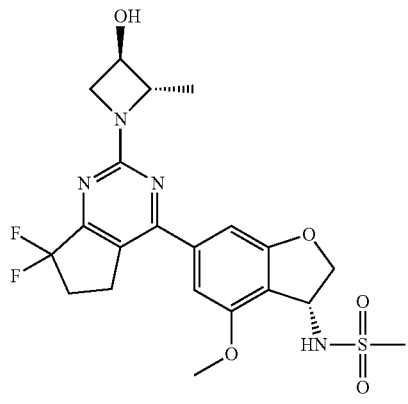

Example 478: N—((S)-6-(7,7-difluoro-2-((2S,3R)-3-hydroxy-2-methylazetidin-1-yl)-6,7-dihydro-5H-cyclopenta[d]pyrimidin-4-yl)-4-methoxy-2,3-dihydrobenzofuran-3-yl)methanesulfonamide Example 479: N—((R)-6-(7,7-difluoro-2-((2S,3R)-3-hydroxy-2-methylazetidin-1-yl)-6,7-dihydro-5H-cyclopenta[d]pyrimidin-4-yl)-4-methoxy-2,3-dihydrobenzofuran-3-yl)methanesulfonamide Isomers were separated by SFC (30% MeOH in $CO_2$, CHIRALPAK AZ-H, 100×4.6 mm, 3 mL/min).

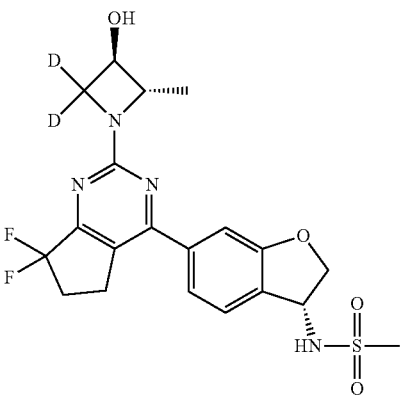 [SMILES: [2H]C1([2H])[C@@H](O)[C@H](C)N1c1nc(-c2ccc3c(c2)OC[C@@H]3NS(C)(=O)=O)c2c(n1)C(F)(F)CC2]

Example 480: N—((R)-6-(7,7-difluoro-2-((2S,3R)-3-hydroxy-2-methylazetidin-1-yl-4,4-$d_2$)-6,7-dihydro-5H-cyclopenta[d]pyrimidin-4-yl)-2,3-dihydrobenzofuran-3-yl)methanesulfonamide The title compound was prepared in a method analogous to General Method K using (R)-6-bromo-2,3-dihydrobenzofuran-3-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-2-methylazetidin-4,4-$d_2$-3-ol instead of (2S)-2-methylazetidine.

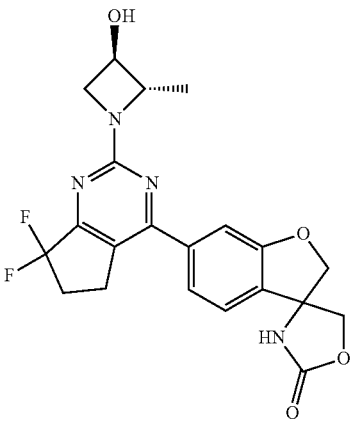 [SMILES: C[C@H]1[C@H](O)CN1c1nc(-c2ccc3c(c2)OCC32COC(=O)N2)c2c(n1)C(F)(F)CC2]

Example 481: 6-(7,7-difluoro-2-((2S,3R)-3-hydroxy-2-methylazetidin-1-yl)-6,7-dihydro-5H-cyclopenta[d]pyrimidin-4-yl)-2H-spiro[benzofuran-3,4'-oxazolidin]-2'-one A flask was charged with ethyl 6-bromobenzofuran-3-carboxylate (1.00 g, 3.72 mmol), Mg turnings (497 mg, 20.4 mmol), and MeOH (40 mL). The mixture was stirred at room temperature for 18 hours. The mixture was filtered over Celite®, washing with EtOAc. $H_2O$ (80 mL) was added and the mixture was extracted with EtOAc (3×30 mL). The combined organics were dried over $Na_2SO_4$, filtered, and concentrated. The residue was subject to flash column chromatography (hexanes-ethyl acetate) to give a 1:1 mixture of methyl 6-bromo-2,3-dihydrobenzofuran-3-carboxylate and methyl-2,3-dihydrobenzofuran-3-carboxylate (386 mg, ~1.50 mmol).

To a mixture of methyl 6-bromo-2,3-dihydrobenzofuran-3-carboxylate and methyl-2,3-dihydrobenzofuran-3-carboxylate (386 mg, ~1.50 mmol) was added paraformaldehyde (406 mg, 4.50 mmol) and DMF (5.0 mL). NaOEt (20 mg, 0.30 mmol) was then added and the reaction was allowed to stir for 36 hours. NaCl (50 mL, sat. aq.) was added and the mixture was extracted with EtOAc (3×20 mL). The combined organics were dried over Na$_2$SO$_4$, filtered, and concentrated. The residue was subject to flash column chromatography (hexanes-ethyl acetate) to give a 1:1 mixture of methyl 6-bromo-3-(hydroxymethyl)-2H-benzofuran-3-carboxylate and methyl 3-(hydroxymethyl)-2H-benzofuran-3-carboxylate (316 mg, ~1.10 mmol).

To a mixture of methyl 6-bromo-3-(hydroxymethyl)-2H-benzofuran-3-carboxylate and methyl 3-(hydroxymethyl)-2H-benzofuran-3-carboxylate (316 mg, ~1.10 mmol) was added MeOH (3 mL) and NaOH (2M aq, 3.0 mL). The mixture was stirred for 18 hours at ambient temperature. TFA (~0.5 mL) was added and the mixture was concentrated. The residue was subject to reverse phase HPLC (0.1% TFA in MeCN-0.1% TFA in H$_2$O) to give 6-bromo-3-(hydroxymethyl)-2H-benzofuran-3-carboxylic acid (150 mg, 0.55 mmol).

A vial was charged with 6-bromo-3-(hydroxymethyl)-2H-benzofuran-3-carboxylic acid (150 mg, 0.55 mmol), followed by PhMe (6 mL) and Et$_3$N (0.23 mL, 1.65 mmol). Diphenylphosphoryl azide (0.13 mL, 0.60 mmol) was added and the mixture was heated to 90° C. for 45 min NaHCO$_3$ (5 mL, sat. aq.) was added, and the mixture was extracted with EtOAc (3×5 mL). The combined organics were dried over Na$_2$SO$_4$, filtered, and concentrated. The residue was subject to flash column chromatography (hexanes-ethyl acetate) to give 6-bromospiro[2H-benzofuran-3,4'-oxazolidine]-2'-one (94 mg, 0.35 mmol).

The title compound was prepared in a method analogous to General Method F using 6-bromospiro[2H-benzofuran-3,4'-oxazolidine]-2'-one and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, and General Method B, using (2S,3R)-2-methylazetidin-3-ol instead of (2S)-2-methylazetidine.

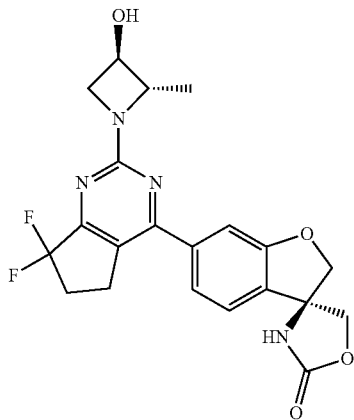

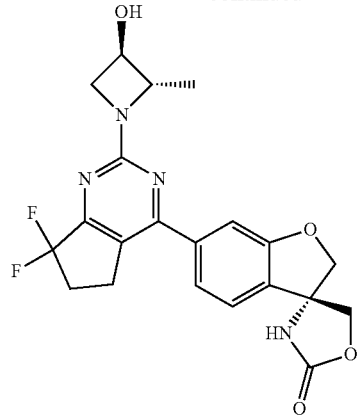

Example 482: (S)-6-(7,7-difluoro-2-((2S,3R)-3-hydroxy-2-methylazetidin-1-yl)-6,7-dihydro-5H-cyclopenta[d]pyrimidin-4-yl)-2H-spiro[benzofuran-3,4'-oxazolidin]-2'-one Example 483: (R)-6-(7,7-difluoro-2-((2S,3R)-3-hydroxy-2-methylazetidin-1-yl)-6,7-dihydro-5H-cyclopenta[d]pyrimidin-4-yl)-2H-spiro[benzofuran-3,4'-oxazolidin]-2'-one Isomers were separated by SFC (25% EtOH in CO$_2$, CHIRALPAK AD-H, 100×4.6 mm, 3 mL/min).

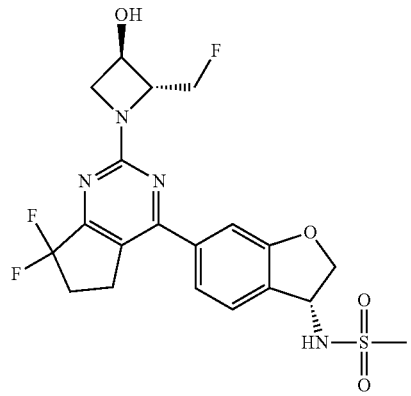 [SMILES: CS(=O)(=O)N[C@H]1COc2cc(-c3nc(N4C[C@@H](O)[C@@H]4CF)nc4c3CCC4(F)F)ccc21]

Example 484: N-((R)-6-(7,7-difluoro-2-((2R,3R)-2-(fluoromethyl)-3-hydroxyazetidin-1-yl)-6,7-dihydro-5H-cyclopenta[d]pyrimidin-4-yl)-2,3-dihydrobenzofuran-3-yl)methanesulfonamide The title compound was prepared in a method analogous to General Method K using (R)-6-bromo-2,3-dihydrobenzofuran-3-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2R,3R)-2-(fluoromethyl)azetidin-3-ol instead of (2S)-2-methylazetidine.

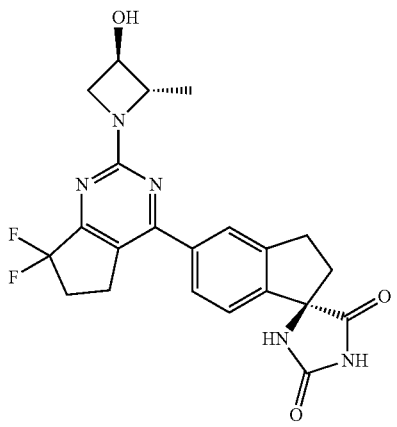 [SMILES: C[C@H]1[C@H](O)CN1c1nc(-c2ccc3c(c2)CC[C@@]32NC(=O)NC2=O)c2c(n1)C(F)(F)CC2]

Example 485: (R)-5'-(7,7-difluoro-2-((2S,3R)-3-hydroxy-2-methylazetidin-1-yl)-6,7-dihydro-5H-cyclopenta[d]pyrimidin-4-yl)-2',3'-dihydrospiro[imidazolidine-4,1'-indene]-2,5-dione The title compound was prepared in a method analogous to General Method F using 4-chloro-7,7-difluoro-2-(methylthio)-6,7-dihydro-5H-cyclopenta[d]pyrimidine and (R)-5'-bromo-2',3'-dihydrospiro[imidazolidine-4,1'-indene]-2,5-dione instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine.

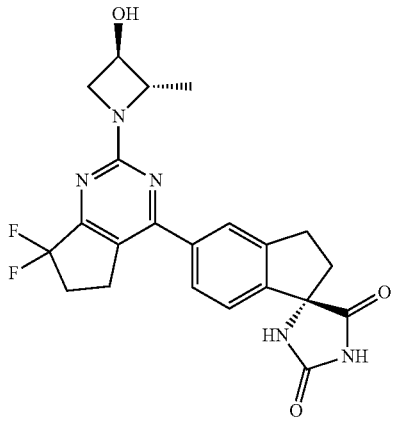 [SMILES: C[C@H]1[C@H](O)CN1c1nc(-c2ccc3c(c2)CC[C@]32NC(=O)NC2=O)c2c(n1)C(F)(F)CC2]

Example 486: (S)-5'-(7,7-difluoro-2-((2S,3R)-3-hydroxy-2-methylazetidin-1-yl)-6,7-dihydro-5H-cyclopenta[d]pyrimidin-4-yl)-2',3'-dihydrospiro[imidazolidine-4,1'-indene]-2,5-dione The title compound was prepared in a method analogous to General Method F using 4-chloro-7,7-difluoro-2-(methylthio)-6,7-dihydro-5H-cyclopenta[d]pyrimidine and (S)-5'-bromo-2',3'-dihydrospiro[imidazolidine-4,1'-indene]-2,5-dione instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine.

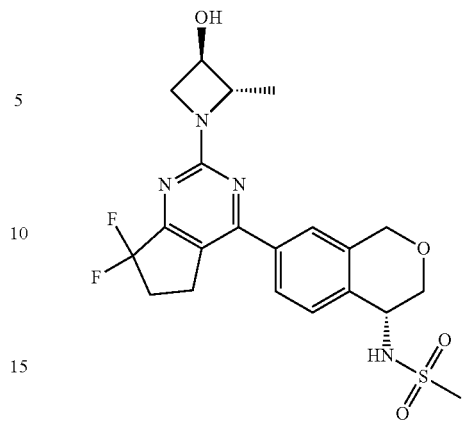

Example 487: N—((R)-7-(7,7-difluoro-2-((2S,3R)-3-hydroxy-2-methylazetidin-1-yl)-6,7-dihydro-5H-cyclopenta[d]pyrimidin-4-yl)isochroman-4-yl)methanesulfonamide The title compound was prepared in a method analogous to General Method K using (R)-7-bromoisochroman-4-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-2-methylazetidin-3-ol instead of (2S)-2-methylazetidine.

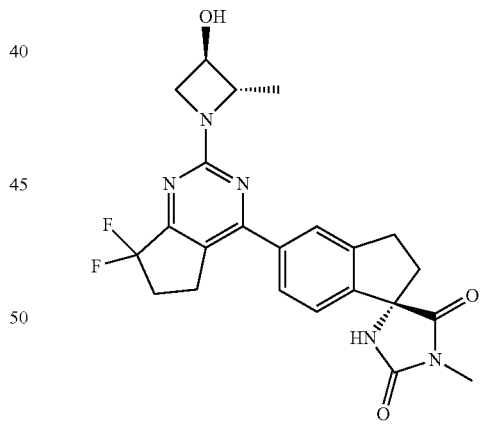

Example 488: (5S)-5'-[7,7-difluoro-2-[(2S,3R)-3-hydroxy-2-methyl-azetidin-1-yl]-5,6-dihydrocyclopenta[d]pyrimidin-4-yl]-3-methyl-spiro[imidazolidine-5,1'-indane]-2,4-dione To a suspension of (5S)-5'-bromospiro[imidazolidine-5,1'-indane]-2,4-dione (100 mg, 0.36 mmol) and potassium carbonate (50 mg, 0.36 mmol) in DMF (1.5 mL) was added iodomethane (51 mg, 0.36 mmol), and the reaction mixture was allowed to stir at ambient temperature for 2 hours. It was diluted with water, and the resulting solids were collected via filtration to yield (S)-5'-bromo-1-methyl-2',3'-dihydrospiro[imidazolidine-4,1'-indene]-2,5-dione.

The title compound was prepared in a method analogous to General Method F using 4-chloro-7,7-difluoro-2-(methylthio)-6,7-dihydro-5H-cyclopenta[d]pyrimidine and (S)-5'-bromo-1-methyl-2',3'-dihydrospiro[imidazolidine-4,1'-indene]-2,5-dione instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one, respectively, followed by General Method M, followed by General Method B using (2S,3R)-3-fluoro-2-methylazetidine instead of (2S)-2-methylazetidine.

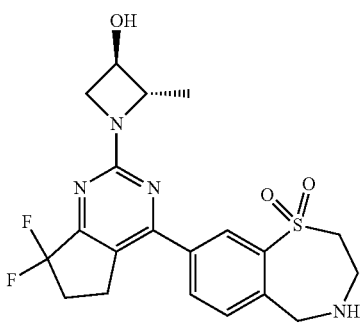 [SMILES: C[C@H]1[C@H](O)CN1c1nc(-c2ccc3c(c2)S(=O)(=O)CCNC3)c2c(n1)C(F)(F)CC2]

Example 489: 8-(7,7-difluoro-24(2S,3R)-3-hydroxy-2-methylazetidin-1-yl)-6,7-dihydro-5H-cyclopenta[d]pyrimidin-4-yl)-2,3,4,5-tetrahydrobenzo[f][1,4]thiazepine 1,1-dioxide A mixture of methyl 4-bromo-2-fluoro-benzoate (6.7 g, 29 mmol), tert-butyl N-(2-sulfanylethyl)carbamate (6.7 g, 38 mmol), and cesium carbonate (29 g, 87 mmol) in N,N-dimethylformamide (100 mL) was heated overnight at 70° C. After partitioning the mixture between water and ethyl acetate, the aqueous phase was extracted twice with ethyl acetate. The combined extracts were washed once with saturated aqueous sodium chloride solution, dried over anhydrous magnesium sulfate, filtered, and concentrated under reduced pressure to a residue which was purified by flash chromatography (hexanes-ethyl acetate) to provide methyl 4-bromo-2-[2-(tert-butoxycarbonylamino)ethylsulfanyl]benzoate.

Methyl 4-bromo-2-[2-(tert-butoxycarbonylamino)ethylsulfanyl]benzoate (7.0 g, 18 mmol) was taken up in dichloromethane (100 mL) and treated with trifluoroacetic acid (14 mL, 180 mmol). After 90 minutes, the reaction was deemed complete by LC/MS analysis. The mixture was concentrated under reduced pressure. The residue was partitioned between dichloromethane and 2M aqueous sodium carbonate solution. The aqueous phase was extracted three times with dichloromethane. The combined organic extracts were dried over anhydrous magnesium sulfate, filtered, and concentrated under reduced pressure to provide methyl 2-(2-aminoethylsulfanyl)-4-bromo-benzoate.

A stirred mixture at room temperature of methyl 2-(2-aminoethylsulfanyl)-4-bromo-benzoate (4.8 g, 17 mmol) in tetrahydrofuran (33 mL) was treated with lithium bis(trimethylsilyl)amide solution (1.5 M in THF, 22 mL, 33 mmol). The mixture was heated in a 70° C. bath for 1 hr before being allowed to cool. The mixture was concentrated under reduced pressure. The residue was treated with water (approx. 70 mL) and 1M hydrochloric acid (approx. 40 mL). The precipitate was collected on a fritted filter funnel, washed with water, and dried in a 55° C. vacuum oven to provide 8-bromo-3,4-dihydro-2H-1,4-benzothiazepin-5-one.

A stirred suspension of 8-bromo-3,4-dihydro-2H-1,4-benzothiazepin-5-one (2.0 g, 7.8 mmol) in tetrahydrofuran (25 mL) was treated with dry lithium aluminum hydride (0.39 g, 10 mmol) in five portions over 15 minutes. The mixture was warmed to 40° C. overnight. The mixture was allowed to cool to room temperature before the portion-wise addition of sodium sulfate decahydrate (0.52 g). At the end of the addition, the mixture was briefly sonicated and was then filtered through a fritted pad of Celite®. The filter cake was washed with ethyl acetate and tetrahydrofuran. The filtrate was concentrated under reduced pressure to provide 8-bromo-2,3,4,5-tetrahydro-1,4-benzothiazepine.

A mixture of 8-bromo-2,3,4,5-tetrahydro-1,4-benzothiazepine (assumed 7.8 mmol) in 2-methyltetrandyrofuran (20 mL) was treated successively with di-tert-butyl decarbonate (3.4 g, 16 mmol) and N,N-diisopropylethylamine (5.4 mL, 31 mmol). After three hours of stirring, the reaction mixture was partitioned between ethyl acetate and 5% aqueous citric acid solution. The aqueous was extracted three times with ethyl acetate. The combined organic extracts were washed successively with 10% aqueous citric acid solution, water, and saturated aqueous sodium hydrogen carbonate solution; dried over anhydrous magnesium sulfate, filtered, and concentrated to a provide a residue which was purified by flash chromatography (hexanes-ethyl acetate) to provide tert-butyl 8-bromo-3,5-dihydro-2H-1,4-benzothiazepine-4-carboxylate.

The title compound was prepared in a method analogous to General Method F using 4-chloro-7,7-difluoro-2-(methylthio)-6,7-dihydro-5H-cyclopenta[d]pyrimidine and tert-butyl 8-bromo-3,5-dihydro-2H-1,4-benzothiazepine-4-carboxylate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine, followed by General Method I.

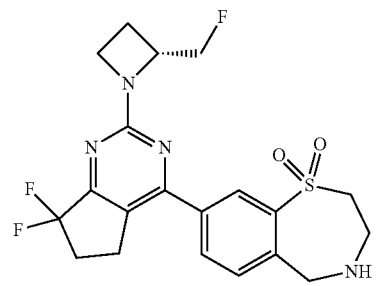 [SMILES: O=S1(=O)CCNCc2ccc(-c3nc(N4CC[C@@H]4CF)nc4c3CCC4(F)F)cc21]

Example 490: (R)-8-(7,7-difluoro-2-(2-(fluoromethyl)azetidin-1-yl)-6,7-dihydro-5H-cyclopenta[d]pyrimidin-4-yl)-2,3,4,5-tetrahydrobenzo[f][1,4]thiazepine 1,1-dioxide The title compound was prepared in a method analogous to General Method F using 4-chloro-7,7-difluoro-2-(methylthio)-6,7-dihydro-5H-cyclopenta[d]pyrimidine and tert-butyl 8-bromo-3,5-dihydro-2H-1,4-benzothiazepine-4-carboxylate instead of 4-chloro-2-[(2S)-2-methylazetidin-1-yl]-6,7-dihydro-5H-cyclopenta[d]pyrimidine and 6-bromo- 1,1-dioxo-1,2-benzothiazol-3-one respectively, followed by General Method M, and General Method B, using (R)-2-(fluoromethyl)azetidine instead of (2S)-2-methylazetidine, followed by General Method I.

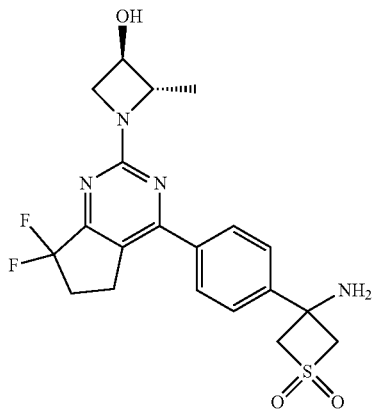 [SMILES: C[C@H]1[C@H](O)CN1c1nc(-c2ccc(C3(N)CS(=O)(=O)C3)cc2)c2c(n1)C(F)(F)CC2]

Example 491: 3-amino-3-(4-(7,7-difluoro-2-(2S,3R)-3-hydroxy-2-methylazetidin-1-yl)-6,7-dihydro-5H-cyclopenta[d]pyrimidin-4-yl)phenyl)thietane 1,1-dioxide To a solution of ethyl 2-(4-bromophenyl)acetate (49 g, 200 mmol) and paraformaldehyde (18 g, 600 mmol) in DMF (500 mL) was added sodium ethoxide (2.7 g. 40 mmol). The mixture was stirred overnight at room temperature. The reaction was quenched with water, and the mixture was extracted with diethyl ether and ethyl acetate. The combined organic extracts were washed successively with 5% aqueous lithium chloride solution and saturated aqueous sodium chloride solution; dried over anhydrous magnesium sulfate, filtered, and concentrated under reduced pressure. The residue was purified by flash chromatography (hexanes-ethyl acetate) to provide ethyl 2-(4-bromophenyl)-3-hydroxy-2-(hydroxymethyl)propanoate A solution of ethyl 2-(4-bromophenyl)-3-hydroxy-2-(hydroxymethyl)propanoate (10.7 g, 35.3 mmol) in acetonitrile (212 mL) was cooled to −15° C. and treated with triflic anhydride solution (1.0 M in dichloromethane, 74 mL, 74 mmol), followed by N,N-diisopropylethylamine (15.4 mL, 88.2 mmol). After being allowed to warm to room temperature, the mixture was quenched with water (300 mL) and extracted three times with dichloromethane. The combined extracts were dried over anhydrous magnesium sulfate and concentrated to a residue which was purified by flash chromatography (hexanes-ethyl acetate) to provide ethyl 2-(4-bromophenyl)-3-(trifluoromethylsulfonyloxy)-2-(trifluoromethylsulfonyloxymethyl)propanoate.

A solution of ethyl 2-(4-bromophenyl)-3-(trifluoromethylsulfonyloxy)-2-(trifluoromethylsulfonyloxymethyl)propanoate (5.1 g, 9.0 mmol) in N,N-dimethylformamide (40 mL) was degassed with Argon for 10 minutes before the introduction of sodium sulfide (1.1 g, 13 mmol). The resulting suspension was stirred overnight at 100-110° C. Upon cooling, the mixture was poured into ice/saturated aqueous ammonium chloride solution and extracted twice with ethyl acetate. The combined organics were washed with saturated aqueous sodium chloride solution, dried over anhydrous magnesium sulfate, filtered, and concentrated under reduced pressure. The residue was subject to flash chromatography (hexanes-ethyl acetate) to provide ethyl 3-(4-bromophenyl)thietane-3-carboxylate.

A mixture of ethyl 3-(4-bromophenyl)thietane-3-carboxylate (1.2 g, 4.1 mmol) in THF/MeOH/water (2:2:1, 20 mL), treated with lithium hydroxide monohydrate (0.43 g, 10 mmol), was heated overnight at 50° C. Upon cooling, the mixture was acidified with 10% aqueous hydrochloric acid and extracted three times with ethyl acetate. The combined extracts were washed once with saturated aqueous sodium chloride solution, dried over anhydrous magnesium sulfate, filtered, and concentrated under reduced pressure to provide 3-(4-bromophenyl)thietane-3-carboxylic acid.

To a mixture of 3-(4-bromophenyl)thietane-3-carboxylic acid (1.8 g, 6.7 mmol) in tetrahydrofuran (13 mL) were added successively azidotrimethylsilane (0.93 g, 8.1 mmol), propanephosphonic anhydride solution (w/w 50% in DMF, 5.1 g, 8.1 mmol), triethylamine (1.4 mL, 10 mmol), and benzyl alcohol (0.88 mL, 8.4 mmol). The mixture was heated overnight at 75° C. Upon cooling, the mixture was adjusted to approximately pH 8 by the addition of saturated aqueous sodium hydrogen carbonate solution. The resulting mixture was extracted three times with ethyl acetate. The combined extracts were washed once with saturated aqueous sodium chloride solution, dried over anhydrous magnesium sulfate, filtered, and concentrated under reduced pressure. A portion of the residue containing benzyl N-[3-(4-bromophenyl)thietan-3-yl]carbamate (0.31 g, 0.82 mmol) was taken up in acetonitrile (3.5 mL) and treated with peracetic acid solution (32% by wt. in dilute acetic acid, 1.7 mL, 8.2 mmol). After stirring overnight at room temperature, the mixture was neutralized with saturated aqueous sodium hydrogen carbonate solution and extracted three times with ethyl acetate. The combined organic extracts were washed once with saturated aqueous sodium thiosulfate solution, dried over anhydrous magnesium sulfate, filtered, and concentrated to provide benzyl N-[3-(4-bromophenyl)-1,1-dioxo-thietan-3-yl]carbamate.

The title compound was prepared in a method analogous to General Method F using 4-chloro-7,7-difluoro-2-(methylthio)-6,7-dihydro-5H-cyclopenta[d]pyrimidine and benzyl N-[3-(4-bromophenyl)-1,1-dioxo-thietan-3-yl]carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine, followed by General Method R.

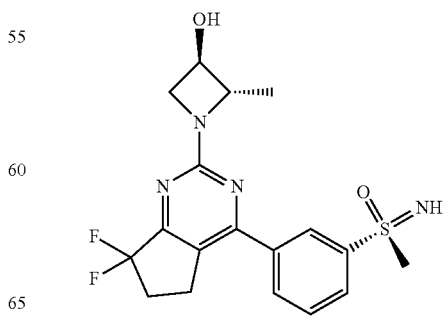

-continued

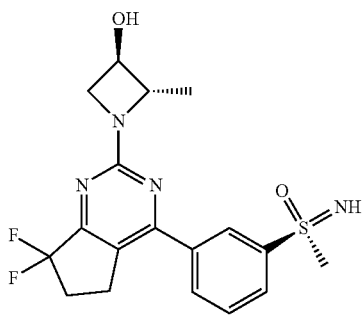

Example 492: (S)-(3-(7,7-difluoro-2-((2S,3R)-3-hydroxy-2-methylazetidin-1-yl)-6,7-dihydro-5H-cyclopenta[d]pyrimidin-4-yl)phenyl)(imino)(methyl)-$\lambda^6$-sulfanone Example 493: (R)-(3-(7,7-difluoro-2-((2S,3R)-3-hydroxy-2-methylazetidin-1-yl)-6,7-dihydro-5H-cyclopenta[d]pyrimidin-4-yl)phenyl)(imino)(methyl)-$\lambda^6$-sulfanone Isomers were separated by SFC (35% EtOH in $CO_2$, CHIRALPAK IC-5 μm, 250×21 mm, 60 mL/min). (see Example 464)

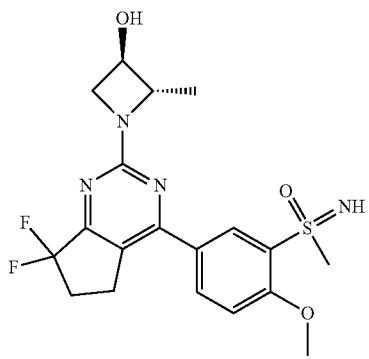 [SMILES: COc1ccc(-c2nc(N3C[C@@H](O)[C@@H]3C)nc3c2CCC3(F)F)cc1S(C)(=N)=O]

Example 494: (5-(7,7-difluoro-2-((2S,3R)-3-hydroxy-2-methylazetidin-1-yl)-6,7-dihydro-5H-cyclopenta[d]pyrimidin-4-yl)-2-methoxyphenyl)(imino)(methyl)-$\lambda^6$-sulfanone The title compound was prepared according to General Method S, followed by General Method F using 4-chloro-7,7-difluoro-2-(methylthio)-6,7-dihydro-5H-cyclopenta[d]pyrimidine and tert-butyl ((5-bromo-2-methoxyphenyl)(methyl)(oxo)-$\lambda^6$-sulfaneylidene)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine, followed by General Method I.

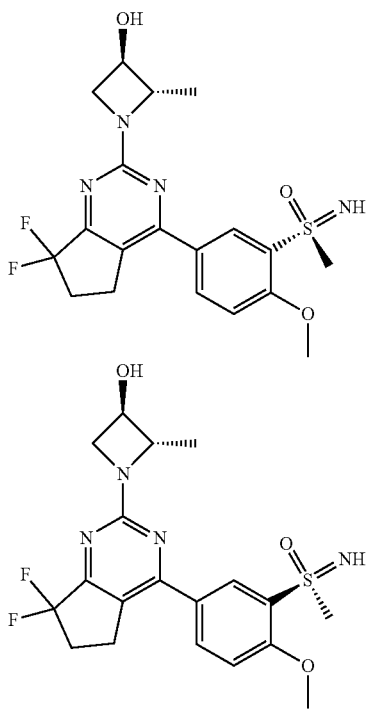

Example 495: (S)-(5-(7,7-difluoro-2-((2S,3R)-3-hydroxy-2-methylazetidin-1-yl)-6,7-dihydro-5H-cyclopenta[d]pyrimidin-4-yl)-2-methoxyphenyl)(imino)(methyl)-$\lambda^6$-sulfanone Example 496: (R)-(5-(7,7-difluoro-2-((2S,3R)-3-hydroxy-2-methylazetidin-1-yl)-6,7-dihydro-5H-cyclopenta[d]pyrimidin-4-yl)-2-methoxyphenyl)(imino)(methyl)-$\lambda^6$-sulfanone Isomers were separated by SFC (45% EtOH in $CO_2$, CHIRALPAK AD-H, 100×4.6 mm, 3 mL/min).

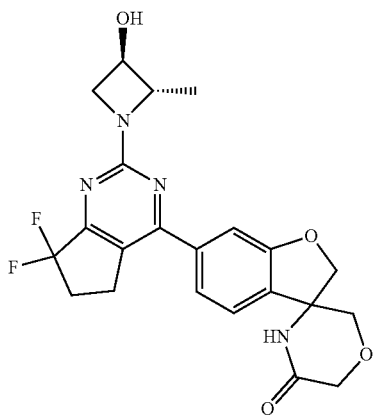 [SMILES: C[C@H]1[C@H](O)CN1c1nc(-c2ccc3c(c2)OCC32COCC(=O)N2)c2c(n1)C(F)(F)CC2]

Example 497: 6-(7,7-difluoro-2-((2S,3R)-3-hydroxy-2-methylazetidin-1-yl)-6,7-dihydro-5H-cyclopenta[d]pyrimidin-4-yl)-2H-spiro[benzofuran-3,3'-morpholin]-5'-one A flask was charged with ethyl 3-amino-6-bromo-2,3-dihydrobenzofuran-3-carboxylate (1.0 g, 3.5 mmol) and MeOH (10 mL). NaBH₄ (264 mg, 7.0 mmol) was added, and the mixture was allowed to stir for 2 hrs at ambient temperature. H₂O (40 mL) was added, and the mixture was extracted with DCM (3×20 mL), the combined organics dried over Na₂SO₄, filtered, and concentrated to provide crude (3-amino-6-bromo-2,3-dihydrobenzofuran-3-yl)methanol.

The title compound was prepared in analogy to General Method Y, using (3-amino-6-bromo-2,3-dihydrobenzofuran-3-yl)methanol instead of (1-amino-5-bromo-2,3-dihydro-1H-inden-1-yl)methanol, followed by General Method F using 6-bromo-2H-spiro[benzofuran-3,3'-morpholin]-5'-one and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, and General Method B, using (2S,3R)-2-methylazetidin-3-ol instead of (2S)-2-methylazetidine.

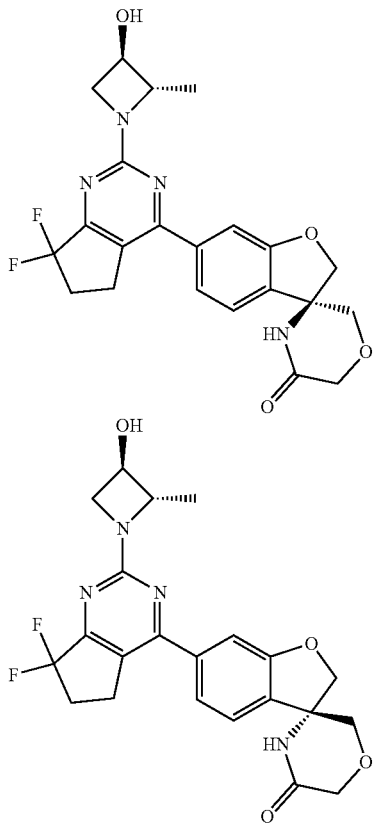

Example 498: (R)-6-(7,7-difluoro-24(2S,3R)-3-hydroxy-2-methylazetidin-1-yl)-6,7-dihydro-5H-cyclopenta[d]pyrimidin-4-yl)-2H-spiro[benzofuran-3,3'-morpholin]-5'-one Example 499: (S)-6-(7,7-difluoro-24(2S,3R)-3-hydroxy-2-methylazetidin-1-yl)-6,7-dihydro-5H-cyclopenta[d]pyrimidin-4-yl)-2H-spiro[benzofuran-3,3'-morpholin]-5'-one Isomers were separated by SFC (35% MeOH in CO₂, CHIRALPAK AD-H, 250×21 mm, 60 mL/min).

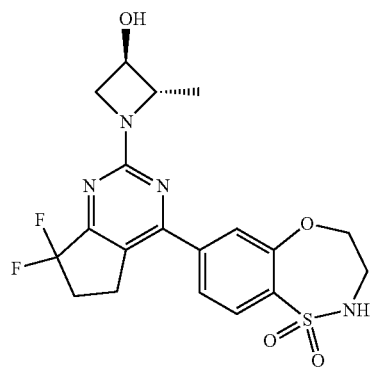 [SMILES: C[C@H]1[C@H](O)CN1c1nc(-c2ccc3c(c2)OCCNS3(=O)=O)c2c(n1)C(F)(F)CC2]

Example 500: 7-(7,7-difluoro-24(2S,3R)-3-hydroxy-2-methylazetidin-1-yl)-6,7-dihydro-5H-cyclopenta[d]pyrimidin-4-yl)-3,4-dihydro-2H-benzo[b][1,4,5]oxathiazepine 1,1-dioxide A flask was charged with 4-bromo-2-fluoro-benzenesulfonyl chloride (1.00 g, 3.66 mmol) and DCM (40 mL). N(iPr)₂Et (1.91 mL, 1.42 g, 11.0 mmoL) was added followed by ethanolamine (0.33 mL, 335 mg, 5.48 mmol). The mixture was allowed to stir at ambient temperature for 1 hr. The mixture was concentrated and subject to flash column chromatography (DCM-MeOH) to provide 4-bromo-2-fluoro-N-(2-hydroxyethyl)benzenesulfonamide.

A flask was charged with 4-bromo-2-fluoro-N-(2-hydroxyethyl)benzenesulfonamide (1.04 g, 3.49 mmol) and DMSO (10 mL), followed by KOtBu (783 mg, 6.98 mmol). The mixture was heated to 100° C. for 6 hours, and then allowed to cool to ambient temperature. 1N HCl (aq, 20 mL) was added, and the mixture extracted with EtOAc (3×10 mL). The combined organic layers were dried over Na₂SO₄, filtered, and concentrated. The residue was subject to flash chromatography (hexanes-ethyl acetate) to provide benzo[b][1,4,5]oxathiazepine 1,1-dioxide.

The title compound was prepared in analogy to General Method F using 7-bromo-3,4-dihydro-2H-benzo[b][1,4,5]oxathiazepine 1,1-dioxide and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, and General Method B, using (2S,3R)-2-methylazetidin-3-ol instead of (2S)-2-methylazetidine.

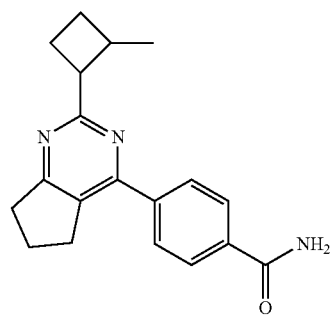 [SMILES: CC1CCC1c1nc2c(c(-c3ccc(C(N)=O)cc3)n1)CCC2]

Example 501: 4-(2-(2-methylcyclobutyl)-6,7-dihydro-5H-cyclopenta[d]pyrimidin-4-yl)benzamide A vial was charged with 4-chloro-6,7-dihydro-5H-cyclopenta[d]pyrimidine (77.3 mg, 0.5 mmol), 2-methylcyclobutanecarboxylic acid (57 mg, 0.5 mmol), AgNO$_3$ (17 mg, 0.10 mmol), K$_2$S$_2$O$_8$ (135 mg, 0.5 mmol), DCM (3 mL), and H$_2$O (3 mL). The mixture was allowed to stir at ambient temperature for 24 hr, after which another portion of 2-methylcyclobutanecarboxylic acid (57 mg, 0.5 mmol), AgNO$_3$ (17 mg, 0.10 mmol) and K$_2$S$_2$O$_8$ (135 mg, 0.5 mmol) was added. The mixture was stirred an additional 48 hr at ambient temperature. The mixture was extracted with DCM (3×5 mL). The combined organic layers were dried over Na$_2$SO$_4$, filtered, and concentrated. The residue was subject to flash chromatography (hexane-ethyl acetate) to provide 4-chloro-2-(2-methylcyclobutyl)-6,7-dihydro-5H-cyclopenta[d]pyrimidine.

The title compound was prepared in analogy to General Method A, using 4-chloro-2-(2-methylcyclobutyl)-6,7-dihydro-5H-cyclopenta[d]pyrimidine and (4-carbamoylphenyl)boronic acid instead of 2,4-dichloro-6,7-dihydro-5H-cyclopenta[d]pyrimidine and 3-pyridylboronic acid, respectively.

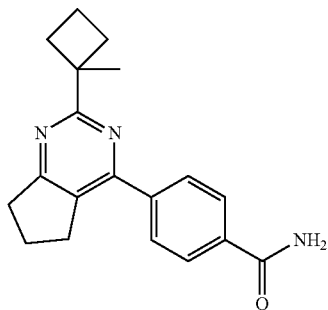 [SMILES: CC1(c2nc3c(c(-c4ccc(C(N)=O)cc4)n2)CCC3)CCC1]

Example 502: 4-(2-(1-methylcyclobutyl)-6,7-dihydro-5H-cyclopenta[d]pyrimidin-4-yl)benzamide A vial was charged with 4-chloro-6,7-dihydro-5H-cyclopenta[d]pyrimidine (77.3 mg, 0.5 mmol), 2-methylcyclobutanecarboxylic acid (114 mg, 1.0 mmol), AgNO$_3$ (34 mg, 0.20 mmol), K$_2$S$_2$O$_8$ (270 mg, 1.0 mmol), DCM (3 mL), and H$_2$O (3 mL). The mixture was allowed to stir at ambient temperature for 24 hr. The mixture was extracted with DCM (3×5 mL). The combined organic layers were dried over Na$_2$SO$_4$, filtered, and concentrated. The residue was subject to flash chromatography (hexanes-ethyl acetate) to provide 4-chloro-2-(1-methylcyclobutyl)-6,7-dihydro-5H-cyclopenta[d]pyrimidine.

The title compound was prepared in analogy to General Method A, using 4 4-chloro-2-(1-methylcyclobutyl)-6,7-dihydro-5H-cyclopenta[d]pyrimidine and (4-carbamoylphenyl)boronic acid instead of 2,4-dichloro-6,7-dihydro-5H-cyclopenta[d]pyrimidine and 3-pyridylboronic acid, respectively.

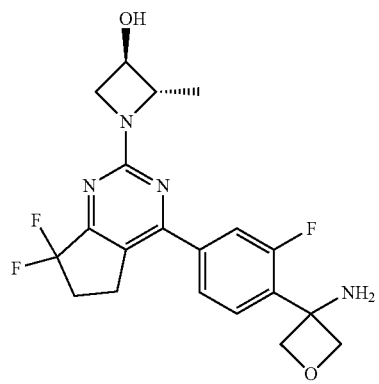 [SMILES: C[C@H]1[C@H](O)CN1c1nc(-c2ccc(C3(N)COC3)c(F)c2)c2c(n1)C(F)(F)CC2]

Example 503: (2S,3R)-1-(4-(4-(3-aminooxetan-3-yl)-3-fluorophenyl)-7,7-difluoro-6,7-dihydro-5H-cyclopenta[d]pyrimidin-2-yl)-2-methylazetidin-3-ol The title compound was prepared according to General Method T, and in analogy to General Method F using 4-chloro-7,7-difluoro-2-(methylthio)-6,7-dihydro-5H-cyclopenta[d]pyrimidine and benzyl (3-(4-bromo-2-fluorophenyl)oxetan-3-yl)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one, respectively, followed by General Method M, followed by General Method B using (2S,3R)-2-methylazetidin-3-ol instead of (2S)-2-methylazetidine, followed by General Method R.

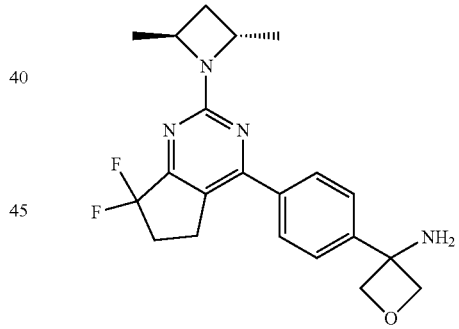

Example 504: 3-(4-(2-((2S,4S)-2,4-dimethylazetidin-1-yl)-7,7-difluoro-6,7-dihydro-5H-cyclopenta[d]pyrimidin-4-yl)phenyl)oxetan-3-amine The title compound was prepared in a method analogous to General Method A using 4-chloro-7,7-difluoro-2-(methylthio)-6,7-dihydro-5H-cyclopenta[d]pyrimidine tert-butyl (3-(4-(4,4,5,5-tetramethyl-1,3,2-dioxaborolan-2-yl)phenyl)oxetan-3-yl)carbamate instead of 2,4-dichloro-6,7-dihydro-5H-cyclopenta[d]pyrimidine and 3-pyridylboronic acid, respectively, followed by General Method M, followed by General Method B using (2S,4S)-2,4-dimethylazetidine instead of (2S)-2-methylazetidine, followed by General Method I.

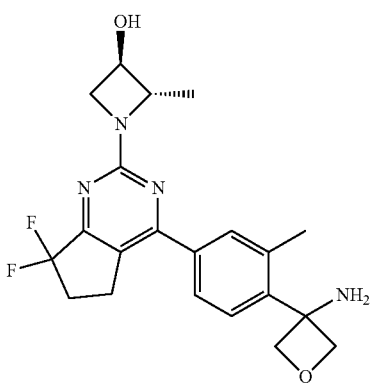 [SMILES: Cc1cc(-c2nc(N3C[C@@H](O)[C@@H]3C)nc3c2CCC3(F)F)ccc1C1(N)COC1]

Example 505: (2S,3R)-1-(4-(4-(3-aminooxetan-3-yl)-3-methylphenyl)-7,7-difluoro-6,7-dihydro-5H-cyclopenta[d]pyrimidin-2-yl)-2-methylazetidin-3-ol The title compound was prepared in analogy to General Method T, using 3-(4-bromo-2-methyl-phenyl)oxetan-3-amine instead of 3-(4-bromo-2-fluoro-phenyl)oxetan-3-amine, followed by General Method F using 4-chloro-7,7-difluoro-2-(methylthio)-6,7-dihydro-5H-cyclopenta[d]pyrimidine and benzyl (3-(4-bromo-2-methylphenyl)oxetan-3-yl)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one, respectively, followed by General Method M, followed by General Method B using (2S,3R)-2-methylazetidin-3-ol instead of (2S)-2-methylazetidine, followed by General Method R.

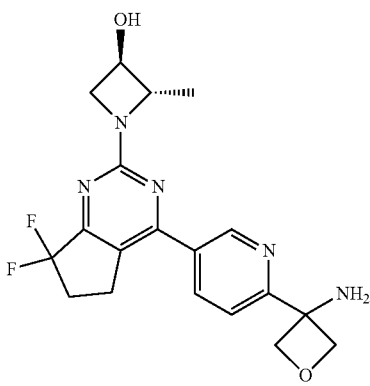 [SMILES: C[C@H]1[C@H](O)CN1c1nc(-c2ccc(C3(N)COC3)nc2)c2c(n1)C(F)(F)CC2]

Example 506: (2S,3R)-1-(4-(6-(3-aminooxetan-3-yl)pyridin-3-yl)-7,7-difluoro-6,7-dihydro-5H-cyclopenta[d]pyrimidin-2-yl)-2-methylazetidin-3-ol The title compound was prepared in analogy to General Method T, using 3-(5-bromo-2-pyridyl)oxetan-3-amine instead of 3-(4-bromo-2-fluoro-phenyl)oxetan-3-amine, followed by General Method F using 4-chloro-7,7-difluoro-2-(methylthio)-6,7-dihydro-5H-cyclopenta[d]pyrimidine and benzyl (3-(5-bromo-2-pyridyl))oxetan-3-yl)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one, respectively, followed by General Method M, followed by General Method B using (2S,3R)-2-methylazetidin-3-ol instead of (2S)-2-methylazetidine, followed by General Method R.

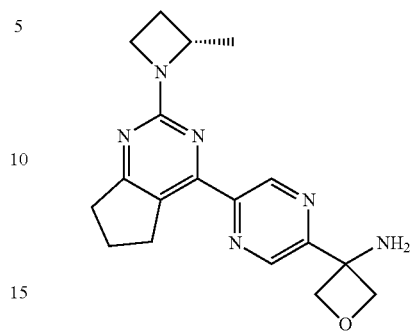

Example 507: (S)-3-(5-(2-(2-methylazetidin-1-yl)-6,7-dihydro-5H-cyclopenta[d]pyrimidin-4-yl)pyrazin-2-yl)oxetan-3-amine The title compound was prepared in analogy to General Method E, using 3-(5-bromopyrazin-2-yl)oxetan-3-amine and (S)-2-(2-methylazetidin-1-yl)-4-(tributylstannyl)-6,7-dihydro-5H-cyclopenta[d]pyrimidine instead of (S)-4-chloro-2-(2-methylazetidin-1-yl)-6,7-dihydro-5H-cyclopenta[d]pyrimidine and ethyl 2-tributylstannylimidazo[5,1-b]thiazole-7-carboxylate, respectively.

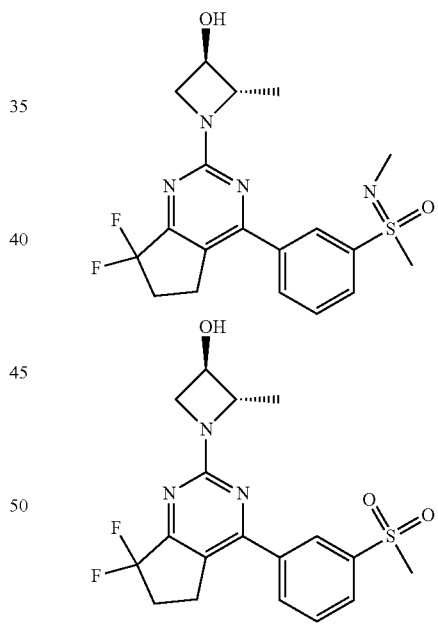

Example 508: (3-(7,7-difluoro-2-((2S,3R)-3-hydroxy-2-methylazetidin-1-yl)-6,7-dihydro-5H-cyclopenta[d]pyrimidin-4-yl)phenyl)(methyl)(methylimino)-$\lambda^6$-sulfanone Example 509: (2S,3R)-1-(7,7-difluoro-4-(3-(methylsulfonyl)phenyl)-6,7-dihydro-5H-cyclopenta[d]pyrimidin-2-yl)-2-methylazetidin-3-ol The title compounds were prepared in analogy to General Method F using (3-bromophenyl)(methyl)(methylimino)-

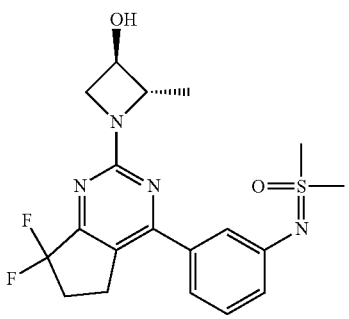 [SMILES: C[C@H]1[C@H](O)CN1c1nc(-c2cccc(N=S(C)(C)=O)c2)c2c(n1)C(F)(F)CC2]

Example 510: ((3-(7,7-difluoro-2-((2S,3R)-3-hydroxy-2-methylazetidin-1-yl)-6,7-dihydro-5H-cyclopenta[d]pyrimidin-4-yl)phenyl)imino)dimethyl-$\lambda^6$-sulfanone The title compound was prepared in analogy to General Method F using ((3-bromophenyl)imino)dimethyl-$\lambda^6$-sulfanone and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, and General Method B, using (2S,3R)-2-methylazetidin-3-ol instead of (2S)-2-methylazetidine.

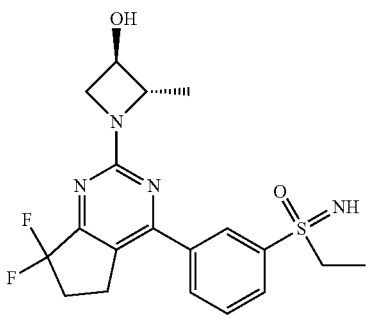 [SMILES: CCS(=N)(=O)c1cccc(-c2nc(N3C[C@@H](O)[C@@H]3C)nc3c2CCC3(F)F)c1]

Example 511: (3-(7,7-difluoro-2-((2S,3R)-3-hydroxy-2-methylazetidin-1-yl)-6,7-dihydro-5H-cyclopenta[d]pyrimidin-4-yl)phenyl)(ethyl)(imino)-$\lambda^6$-sulfanone The title compound was prepared in analogy to General Method F using (3-chlorophenyl)(ethyl)(imino)-$\lambda^6$-sulfanone and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, $\lambda^6$-sulfanone and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, and General Method B, using (2S,3R)-2-methylazetidin-3-ol instead of (2S)-2-methylazetidine. The two products were separated by HPLC in the final step.

and General Method B, using (2S,3R)-2-methylazetidin-3-ol instead of (2S)-2-methylazetidine.

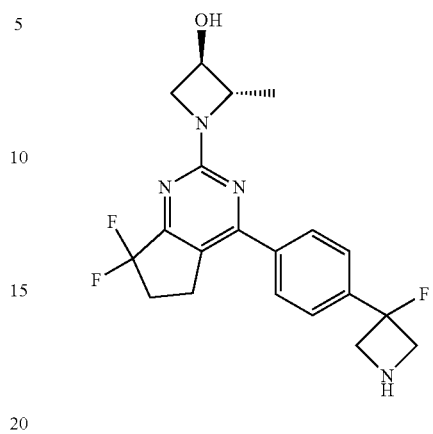

Example 512: (2S,3R)-1-(7,7-difluoro-4-(4-(3-fluoroazetidin-3-yl)phenyl)-6,7-dihydro-5H-cyclopenta[d]pyrimidin-2-yl)-2-methylazetidin-3-ol The title compound was prepared in analogy to General Method F using tert-butyl 3-(4-bromophenyl)-3-fluoro-azetidine-1-carboxylate and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, followed by General Method B, using (2S,3R)-2-methylazetidin-3-ol instead of (2S)-2-methylazetidine, followed by General Method I.

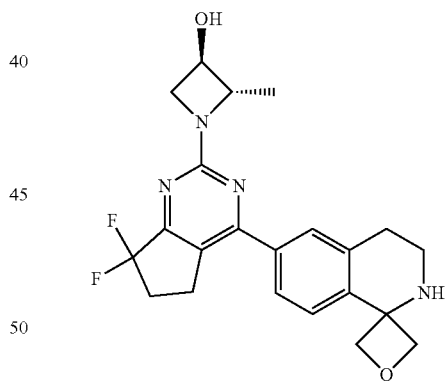

Example 513: (2S,3R)-1-(4-(3,4-dihydro-2H-spiro[isoquinoline-1,3'-oxetan]-6-yl)-7,7-difluoro-6,7-dihydro-5H-cyclopenta[d]pyrimidin-2-yl)-2-methylazetidin-3-ol The title compound was prepared in analogy to General Method T, using 6-bromo-3,4-dihydro-2H-spiro[isoquinoline-1,3'-oxetane] instead of 3-(4-bromo-2-fluoro-phenyl)oxetan-3-amine, followed by General Method F using 4-chloro-7,7-difluoro-2-(methylthio)-6,7-dihydro-5H-cyclopenta[d]pyrimidine and benzyl 6-bromo-3,4-dihydro-2H-spiro[isoquinoline-1,3'-oxetane]-2-carboxylate instead of 4-chloro-2-[(2S)-2-methylazetidin-1-yl]-6,7-dihydro-5H- cyclopenta[d]pyrimidine and 6-bromo-1,1-dioxo-1,2-benzothiazol-3-one, respectively, followed by General Method M, followed by General Method B using (2S,3R)-2-methylazetidin-3-ol instead of (2S)-2-methylazetidine, followed by General Method R.

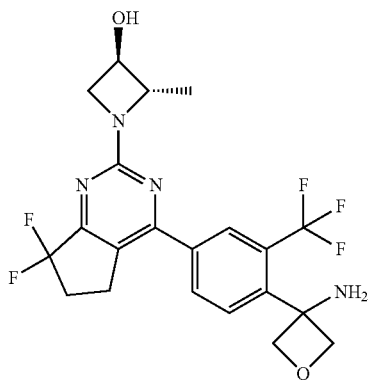 [SMILES: C[C@H]1[C@H](O)CN1c1nc(-c2ccc(C3(N)COC3)c(C(F)(F)F)c2)c2c(n1)C(F)(F)CC2]

Example 514: (2S,3R)-1-(4-(4-(3-aminooxetan-3-yl)-3-(trifluoromethyl)phenyl)-7,7-difluoro-6,7-dihydro-5H-cyclopenta[d]pyrimidin-2-yl)-2-methylazetidin-3-ol The title compound was prepared in analogy to General Method T, using 3-(4-bromo-2-(trifluoromethyl)phenyl)oxetan-3-amine instead of 3-(4-bromo-2-fluoro-phenyl)oxetan-3-amine, followed by General Method F, using 4-chloro-7,7-difluoro-2-(methylthio)-6,7-dihydro-5H-cyclopenta[d]pyrimidine and benzyl (3-(4-bromo-2-(trifluoromethyl)phenyl)oxetan-3-yl)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one, respectively, followed by General Method M, followed by General Method B using (2S,3R)-2-methylazetidin-3-ol instead of (2S)-2-methylazetidine, followed by General Method R.

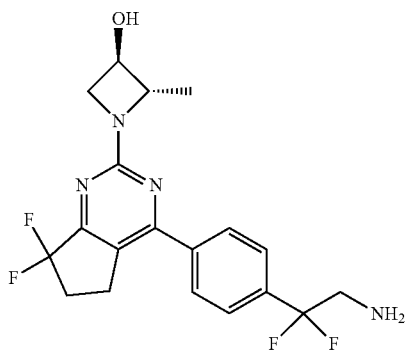 [SMILES: C[C@H]1[C@H](O)CN1c1nc(-c2ccc(C(F)(F)CN)cc2)c2c(n1)C(F)(F)CC2]

Example 515: (2S,3R)-1-(4-(4-(2-amino-1,1-difluoroethyl)phenyl)-7,7-difluoro-6,7-dihydro-5H-cyclopenta[d]pyrimidin-2-yl)-2-methylazetidin-3-ol A vial was charged with 2-(4-bromophenyl)-2,2-difluoroethanamine (250 mg, 1.06 mmol) and DCM (4 mL), followed by Et₃N (0.44 mL, 322 mg, 3.18 mmol), and Boc₂O (347 mg, 1.59 mmol). The mixture was allowed to stir at ambient temperature, was concentrated, and subject to flash column chromatography (hexanes-ethyl acetate) to provide tert-butyl N-(2-(4-bromophenyl)-2,2-difluoro-ethyl)carbamate.

The title compound was prepared in analogy to General Method F, using tert-butyl N-(2-(4-bromophenyl)-2,2-difluoro-ethyl)carbamate and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, followed by General Method B, using (2S,3R)-2-methylazetidin-3-ol instead of (2S)-2-methylazetidine, followed by General Method I.

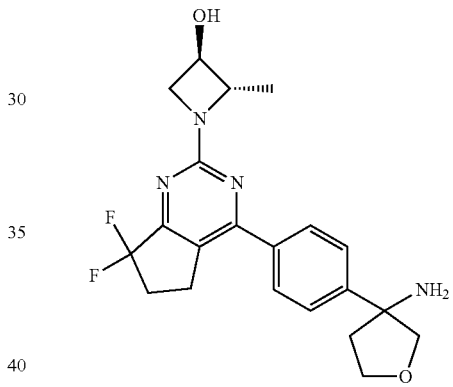

Example 516: (2S,3R)-1-(4-(4-(3-aminotetrahydrofuran-3-yl)phenyl)-7,7-difluoro-6,7-dihydro-5H-cyclopenta[d]pyrimidin-2-yl)-2-methylazetidin-3-ol A vial was charged with 3-(4-bromophenyl)tetrahydrofuran-3-amine (500 mg, 2.07 mmol) and DCM (6 mL), followed by Et₃N (0.86 mL, 627 mg, 6.2 mmol), and Boc₂O (676 mg, 3.10 mmol). The mixture was allowed to stir at ambient temperature, was concentrated, and subject to flash column chromatography (hexanes-ethyl acetate) to provide tert-butyl N-(3-(4-bromophenyl)tetrahydrofuran-3-yl)carbamate.

The title compound was prepared in analogy to General Method F using tert-butyl N-(3-(4-bromophenyl)tetrahydrofuran-3-yl)carbamate and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, followed by General Method B, using (2S,3R)-2-methylazetidin-3-ol instead of (2S)-2-methylazetidine, followed by General Method I.

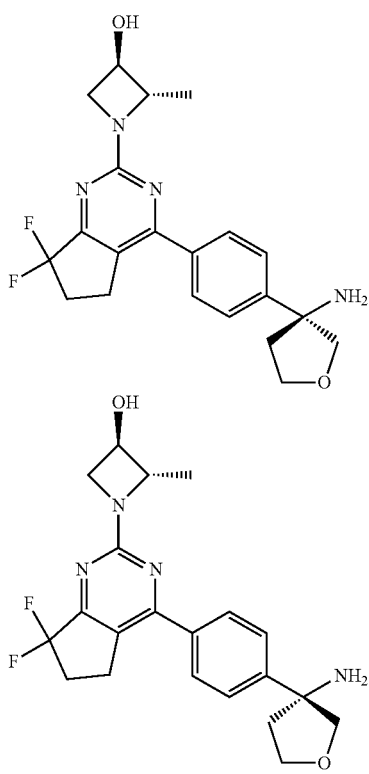

Example 517: (2S,3R)-1-(4-(4-((S)-3-aminotetrahydrofuran-3-yl)phenyl)-7,7-difluoro-6,7-dihydro-5H-cyclopenta[d]pyrimidin-2-yl)-2-methylazetidin-3-ol Example 518: (2S,3R)-1-(4-(4-((R)-3-aminotetrahydrofuran-3-yl)phenyl)-7,7-difluoro-6,7-dihydro-5H-cyclopenta[d]pyrimidin-2-yl)-2-methylazetidin-3-ol Isomers were separated by SFC (20% EtOH in CO$_2$, CHIRALPAK IG, 20×21 mm, 60 mL/min).

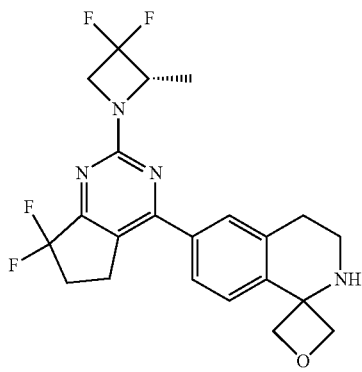 [SMILES: C[C@@H]1N(c2nc(-c3ccc4c(c3)CCNC43COC3)c3c(n2)C(F)(F)CC3)CC1(F)F]

Example 519: (S)-6-(2-(3,3-difluoro-2-methylazetidin-1-yl)-7,7-difluoro-6,7-dihydro-5H-cyclopenta[d]pyrimidin-4-yl)-3,4-dihydro-2H-spiro[isoquinoline-1,3'-oxetane]

The title compound was prepared in analogy to General Method T, using 6-bromo-3,4-dihydro-2H-spiro[isoquinoline-1,3'-oxetane] instead of 3-(4-bromo-2-fluoro-phenyl)oxetan-3-amine, followed by General Method F using 4-chloro-7,7-difluoro-2-(methylthio)-6,7-dihydro-5H-cyclopenta[d]pyrimidine and benzyl 6-bromo-3,4-dihydro-2H-spiro[isoquinoline-1,3'-oxetane]-2-carboxylate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one, respectively, followed by General Method M, followed by General Method B using (S)-3,3-difluoro-2-methylazetidine instead of (2S)-2-methylazetidine, followed by General Method R.

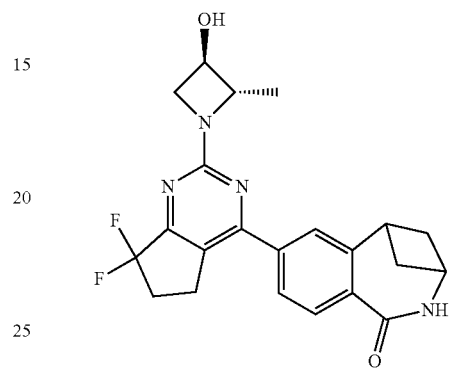

Example 520: 7-(7,7-difluoro-2-((2S,3R)-3-hydroxy-2-methylazetidin-1-yl)-6,7-dihydro-5H-cyclopenta[d]pyrimidin-4-yl)-2,3,4,5-tetrahydro-1H-3,5-methanobenzo[c]azepin-1-one The title compound was prepared in analogy to General Method F using 7-bromo-2,3,4,5-tetrahydro-1H-3,5-methanobenzo[c]azepin-1-one and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, followed by General Method B, using (2S,3R)-2-methylazetidin-3-ol instead of (2S)-2-methylazetidine.

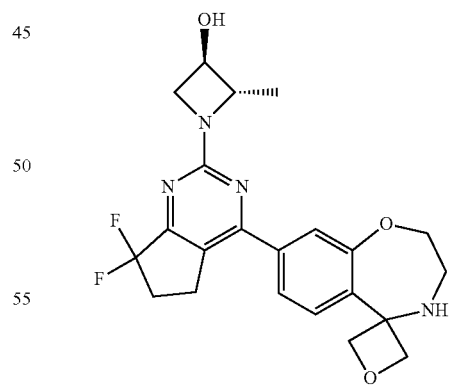

Example 521: (2S,3R)-1-(4-(3,4-dihydro-2H-spiro[benzo[f][1,4]oxazepine-5,3'-oxetan]-8-yl)-7,7-difluoro-6,7-dihydro-5H-cyclopenta[d]pyrimidin-2-yl)-2-methylazetidin-3-ol A vial was charged with 3-(4-bromo-2-fluoro-phenyl)oxetan-3-amine hydrochloride (200 mg, 0.71 mmol) and THF (5 mL), followed by Et₃N (0.40 mL, 287 mg, 2.83 mmol) and ethyl 2-bromoacetae (0.16 mL, 236 mg, 1.42 mmol). The mixture was heated to 70° C. for 24 hrs, after which an additional portion of Et₃N (0.40 mL, 287 mg, 2.83 mmol) and ethyl 2-bromoacetate (0.16 mL, 236 mg, 1.42 mmol) were added. The mixture was stirred another 24 hrs at 70° C. The mixture was cooled to ambient temperature, concentrated, and subject to flash column chromatography (hexanes-ethyl acetate) to afford ethyl 2-((3-(4-bromo-2-fluoro-phenyl)oxetan-3-yl)amino)acetate.

To ethyl 2-((3-(4-bromo-2-fluoro-phenyl)oxetan-3-yl)amino)acetate (141 mg, 0.42 mmol) in THF (5 mL) was added LiBH₄ (28 mg, 1.27 mmol). The mixture was stirred at ambient temperature for 4 hrs, concentrated and subject to flash column chromatography (hexanes-ethyl acetate) to afford 2-((3-(4-bromo-2-fluoro-phenyl)oxetan-3-yl)amino) ethanol.

To 2-((3-(4-bromo-2-fluoro-phenyl)oxetan-3-yl)amino) ethanol (40 mg, 0.14 mmol) in DMSO (2 mL), was added KOtBu (46 mg, 0.41 mmol). The mixture was heated to 60° C. for 30 min, and was allowed to cool to ambient temperature. H₂O (5 mL) was added, and the mixture was extracted with EtOAc (3×5 mL). The combined organics were dried over Na₂SO₄, filtered, and concentrated. The residue was subject to flash column chromatography (hexanes-ethyl acetate) to afford 8-bromo-3,4-dihydro-2H-spiro[benzo[f][1,4]oxazepine-5,3'-oxetane].

The title compound was prepared in analogy to General Method T, using 8-bromo-3,4-dihydro-2H-spiro[benzo[f][1,4]oxazepine-5,3'-oxetane] instead of 3-(4-bromo-2-fluoro-phenyl)oxetan-3-amine, followed by General Method F using 4-chloro-7,7-difluoro-2-(methylthio)-6,7-dihydro-5H-cyclopenta[d]pyrimidine and benzyl 8-bromo-2,3-dihydro-4H-spiro[benzo[f][1,4]oxazepine-5,3'-oxetane]-4-carboxylate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one, respectively, followed by General Method M, followed by General Method B using (S)-3,3-difluoro-2-methylazetidine instead of (2S)-2-methylazetidine, followed by General Method R.

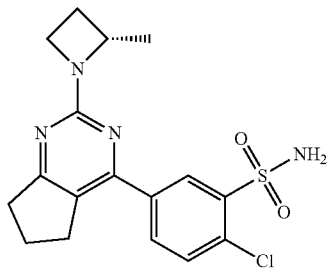 [SMILES: C[C@H]1CCN1c1nc2c(c(-c3ccc(Cl)c(S(N)(=O)=O)c3)n1)CCC2]

Example 522: (S)-2-chloro-5-(2-(2-methylazetidin-1-yl)-6,7-dihydro-5H-cyclopenta[d]pyrimidin-4-yl)benzenesulfonamide The title compound was prepared in analogy to General Method E, using 2-chloro-5-iodo-benzenesulfonamide and (S)-2-(2-methylazetidin-1-yl)-4-(tributylstannyl)-6,7-dihydro-5H-cyclopenta[d]pyrimidine instead of (S)-4-chloro-2-(2-methylazetidin-1-yl)-6,7-dihydro-5H-cyclopenta[d]pyrimidine and ethyl 2-tributylstannylimidazo[5,1-b]thiazole-7-carboxylate, respectively.

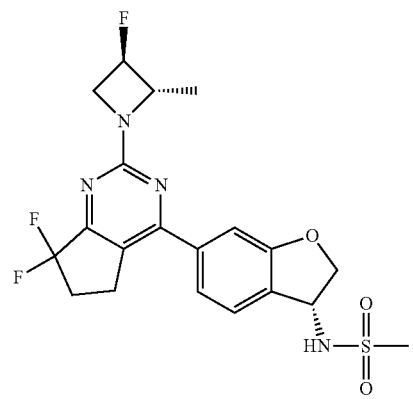 [SMILES: C[C@H]1[C@H](F)CN1c1nc(-c2ccc3c(c2)OC[C@@H]3NS(C)(=O)=O)c2c(n1)C(F)(F)CC2]

Example 523: N—((R)-6-(7,7-difluoro-2-((2S,3R)-3-fluoro-2-methylazetidin-1-yl)-6,7-dihydro-5H-cyclopenta[d]pyrimidin-4-yl)-2,3-dihydrobenzofuran-3-yl)methanesulfonamide The title compound was prepared in analogy to General Method K using (R)-6-bromo-2,3-dihydrobenzofuran-3-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-3-fluoro-2-methylazetidine instead of (2S)-2-methylazetidine.

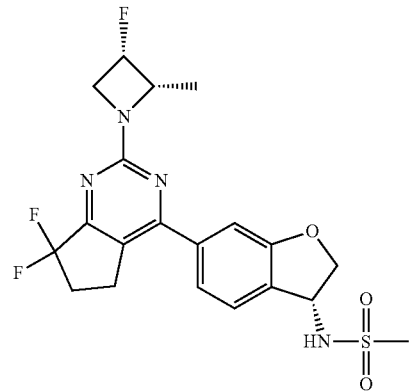 [SMILES: C[C@H]1[C@@H](F)CN1c1nc(-c2ccc3c(c2)OC[C@@H]3NS(C)(=O)=O)c2c(n1)C(F)(F)CC2]

Example 524: N—((R)-6-(7,7-difluoro-2-((2S,3S)-3-fluoro-2-methylazetidin-1-yl)-6,7-dihydro-5H-cyclopenta[d]pyrimidin-4-yl)-2,3-dihydrobenzofuran-3-yl)methanesulfonamide The title compound was prepared in analogy to General Method K using (R)-6-bromo-2,3-dihydrobenzofuran-3-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]

pyrimidine instead of 4-chloro-2-[(2S)-2-methylazetidin-1-yl]-6,7-dihydro-5H-cyclopenta[d]pyrimidine, followed by General Method M, and General Method B, using (2S,3S)-3-fluoro-2-methylazetidine instead of (2S)-2-methylazetidine.

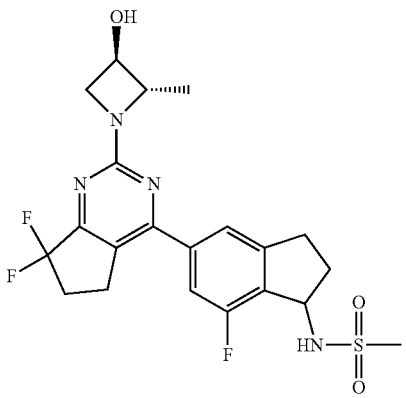 [SMILES: C[C@H]1[C@H](O)CN1c1nc(-c2cc(F)c3c(c2)CCC3NS(C)(=O)=O)c2c(n1)C(F)(F)CC2]

Example 525: N-(5-(7,7-difluoro-2-((2S,3R)-3-hydroxy-2-methylazetidin-1-yl)-6,7-dihydro-5H-cyclopenta[d]pyrimidin-4-yl)-7-fluoro-2,3-dihydro-1H-inden-1-yl)methanesulfonamide The title compound was prepared according to General Method V, and in analogy to General Method K using 5-bromo-7-fluoro-2,3-dihydro-1H-inden-1-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-2-methylazetidin-3-ol instead of (2S)-2-methylazetidine.

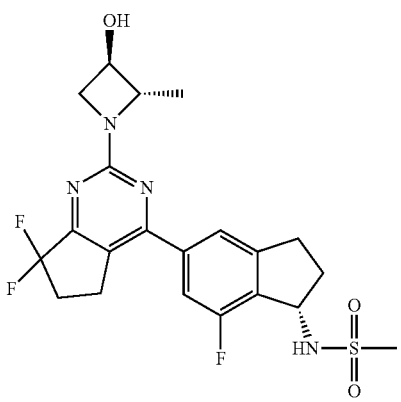

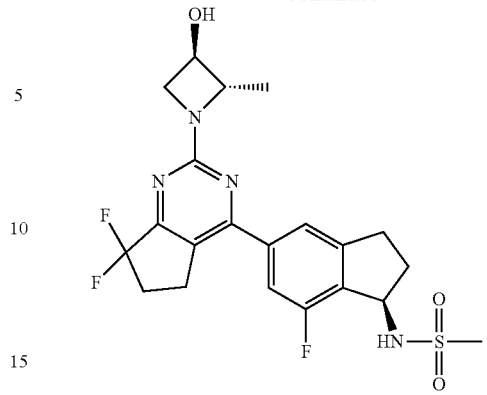

Example 526: N—((S)-5-(7,7-difluoro-2-((2S,3R)-3-hydroxy-2-methylazetidin-1-yl)-6,7-dihydro-5H-cyclopenta[d]pyrimidin-4-yl)-7-fluoro-2,3-dihydro-1H-inden-1-yl)methanesulfonamide Example 527: N—((R)-5-(7,7-difluoro-2-((2S,3R)-3-hydroxy-2-methylazetidin-1-yl)-6,7-dihydro-5H-cyclopenta[d]pyrimidin-4-yl)-7-fluoro-2,3-dihydro-1H-inden-1-yl)methanesulfonamide Isomers were separated by SFC (35% MeOH in $CO_2$, CHIRALPAK AD-H, 250×21 mm, 60 mL/min).

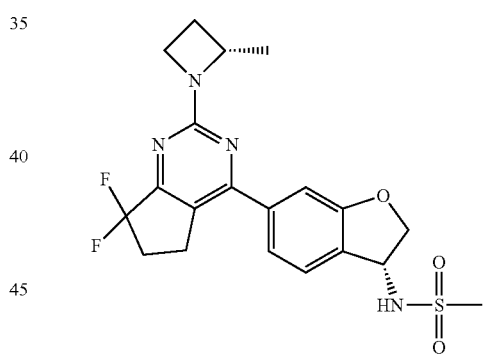

Example 528: N—((R)-6-(7,7-difluoro-2-((S)-2-methylazetidin-1-yl)-6,7-dihydro-5H-cyclopenta[d]pyrimidin-4-yl)-2,3-dihydrobenzofuran-3-yl)methanesulfonamide The title compound was prepared in analogy to General Method K using (R)-6-bromo-2,3-dihydrobenzofuran-3-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B.

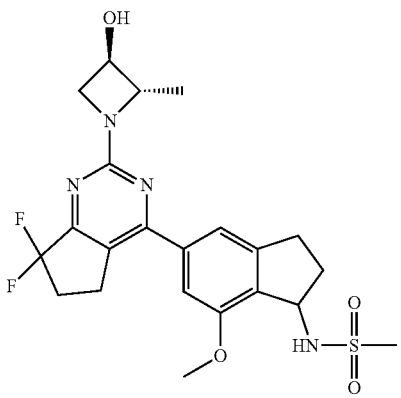 [SMILES: COc1cc(-c2nc(N3C[C@@H](O)[C@@H]3C)nc3c2CCC3(F)F)cc2c1C(NS(C)(=O)=O)CC2]

Example 529: N-(6-(7,7-difluoro-2-((2S,3R)-3-hydroxy-2-methylazetidin-1-yl)-6,7-dihydro-5H-cyclopenta[d]pyrimidin-4-yl)-4-methoxy-2,3-dihydrobenzofuran-3-yl)methanesulfonamide A flask was charged with 5-bromo-7-fluoro-indan-1-one (1.00 g, 4.37 mmol) and NaOMe (25% solution in MeOH, 5 mL). The mixture was heated to 50° C. for 1 hour. $H_2O$ (10 mL) was added, and the mixture was extracted with EtOAc (3×10 mL). The combined organics were dried over $Na_2SO_4$, filtered, and concentrated. The residue was subject to flash column chromatography (hexanes-ethyl acetate) to give 5-bromo-7-methoxy-indan-1-one.

The title compound was prepared according to General Method W, and in analogy to General Method K using 5-bromo-7-methoxy-2,3-dihydro-1H-inden-1-amine and methanesulfonyl chloride instead of (S)-3-(2-(2-methylazetidin-1-yl)-6,7-dihydro-5H-cyclopenta[d]pyrimidin-4-yl) aniline and 1-methylimidazole-4-sulfonyl chloride, respectively, followed by General Method F using 4-chloro-7,7-difluoro-2-(methylthio)-6,7-dihydro-5H-cyclopenta[d] pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-2-methylazetidin-3-ol instead of (2S)-2-methylazetidine.

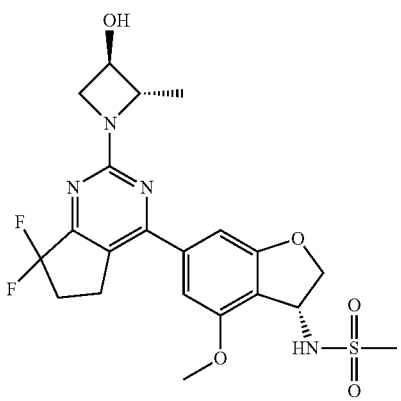

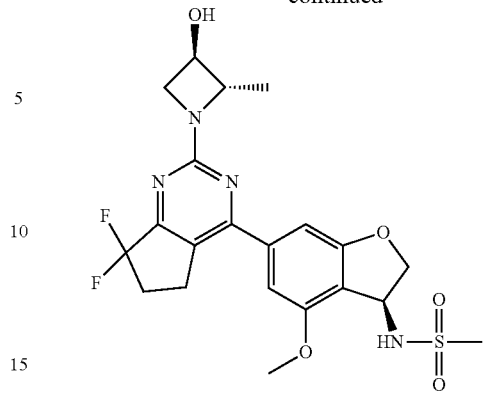

Example 530: N—((R)-6-(7,7-difluoro-2-(2S,3R)-3-hydroxy-2-methylazetidin-1-yl)-6,7-dihydro-5H-cyclopenta[d]pyrimidin-4-yl)-4-methoxy-2,3-dihydrobenzofuran-3-yl)methanesulfonamide Example 531: N—((S)-6-(7,7-difluoro-2-((2S,3R)-3-hydroxy-2-methylazetidin-1-yl)-6,7-dihydro-5H-cyclopenta[d]pyrimidin-4-yl)-4-methoxy-2,3-dihydrobenzofuran-3-yl)methanesulfonamide Isomers were separated by SFC (35% EtOH in $CO_2$, CHIRALPAK AD-H, 250×21 mm, 60 mL/min).

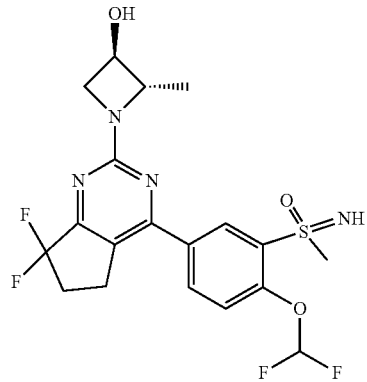 [SMILES: C[C@H]1[C@H](O)CN1c1nc(-c2ccc(OC(F)F)c(S(C)(=N)=O)c2)c2c(n1)C(F)(F)CC2]

Example 532: (5-(7,7-difluoro-24(2S,3R)-3-hydroxy-2-methylazetidin-1-yl)-6,7-dihydro-5H-cyclopenta[d]pyrimidin-4-yl)-2-(difluoromethoxy)phenyl)(imino)(methyl)-$\lambda^6$-sulfanone The title compound was prepared in analogy to General Method S using (5-bromo-2-(difluoromethoxy)phenyl)(methyl)sulfane instead of (5-bromo-2-methoxyphenyl)(methyl)sulfane, followed by General Method F using 4-chloro-7,7-difluoro-2-(methylthio)-6,7-dihydro-5H-cyclopenta[d]pyrimidine and tert-butyl ((5-bromo-2-(difluoromethoxy)phenyl)(methyl)(oxo)-$\lambda^6$-sulfaneylidene)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine, followed by General Method I.

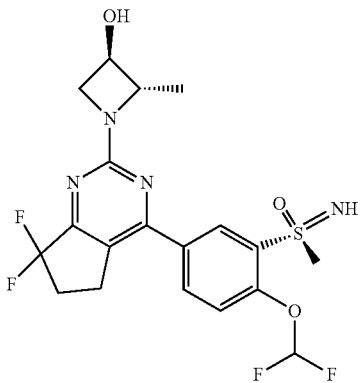

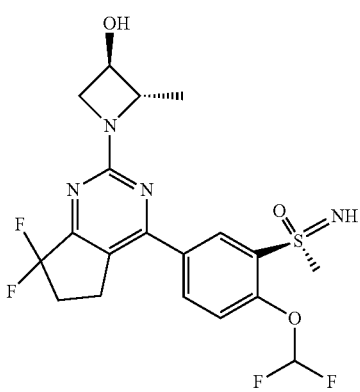

Example 533: (S)-(5-(7,7-difluoro-2-((2S,3R)-3-hydroxy-2-methylazetidin-1-yl)-6,7-dihydro-5H-cyclopenta[d]pyrimidin-4-yl)-2-(difluoromethoxy)phenyl)(imino)(methyl)-sulfanone Example 534: (R)-(5-(7,7-difluoro-2-((2S,3R)-3-hydroxy-2-methylazetidin-1-yl)-6,7-dihydro-5H-cyclopenta[d]pyrimidin-4-yl)-2-(difluoromethoxy)phenyl)(imino)(methyl)-$\lambda^6$-sulfanone Isomers were separated by SFC (25% MeOH in CO$_2$, CHIRALPAK AD-H, 250×21 mm, 60 mL/min).

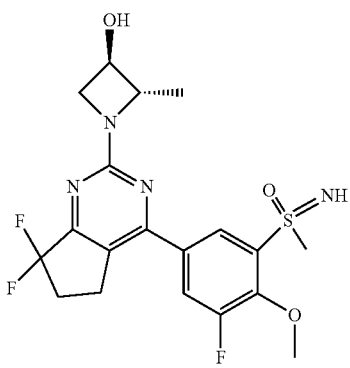 [SMILES: COc1c(F)cc(-c2nc(N3C[C@@H](O)[C@@H]3C)nc3c2CCC3(F)F)cc1S(C)(=N)=O]

Example 535: (5-(7,7-difluoro-2-((2S,3R)-3-hydroxy-2-methylazetidin-1-yl)-6,7-dihydro-5H-cyclopenta[d]pyrimidin-4-yl)-3-fluoro-2-methoxyphenyl)(imino)(methyl)-$\lambda^6$-sulfanone The title compound was prepared in analogy to General Method S using (5-bromo-3-fluoro-2-methoxyphenyl)(methyl)sulfane instead of (5-bromo-2-methoxyphenyl)(methyl)sulfane, followed by General Method F using 4-chloro-7,7-difluoro-2-(methylthio)-6,7-dihydro-5H-cyclopenta[d]pyrimidine and tert-butyl ((5-bromo-3-fluoro-2-methoxyphenyl)(methyl)(oxo)-$\lambda^6$-sulfaneylidene)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine, followed by General Method I.

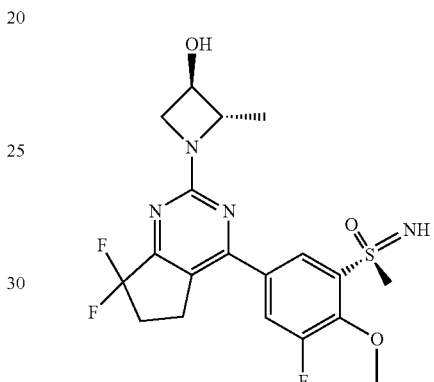

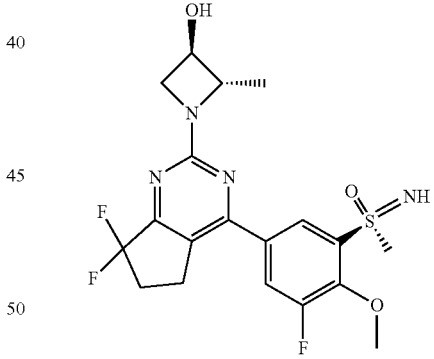

Example 536: (S)-(5-(7,7-difluoro-2-((2S,3R)-3-hydroxy-2-methylazetidin-1-yl)-6,7-dihydro-5H-cyclopenta[d]pyrimidin-4-yl)-3-fluoro-2-methoxyphenyl)(imino)(methyl)-$\lambda^6$-sulfanone Example 537: (R)-(5-(7,7-difluoro-2-((2S,3R)-3-hydroxy-2-methylazetidin-1-yl)-6,7-dihydro-5H-cyclopenta[d]pyrimidin-4-yl)-3-fluoro-2-methoxyphenyl)(imino)(methyl)-$\lambda^6$-sulfanone Isomers were separated by SFC (30% MeOH in CO$_2$, CHIRALPAK AD-H, 250×21 mm, 60 mL/min).

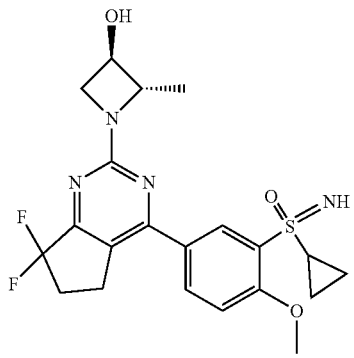

Example 538: cyclopropyl(5-(7,7-difluoro-2-((2S,3R)-3-hydroxy-2-methylazetidin-1-yl)-6,7-dihydro-5H-cyclopenta[d]pyrimidin-4-yl)-2-methoxyphenyl)(imino)-$\lambda^6$-sulfanone A vial was charged with (5-bromo-2-methoxyphenyl)(cyclopropyl)(imino)-$\lambda^6$-sulfanone (250 mg, 0.86 mmol) and THF (2 mL). KOtBu (1M in THF, 1.03 mL) was added and the mixture stirred at ambient temperature for 30 min Boc$_2$O (376 mg, 1.72 mmol) was then added and the mixture was allowed to stir for 18 hours at ambient temperature. H$_2$O (5 mL) was added, and the mixture was extracted with EtOAc (3×5 mL). The combined organics were dried over Na$_2$SO$_4$, filtered, and concentrated. The residue was subject to flash column chromatography (hexanes-ethyl acetate) to give tert-butyl ((5-bromo-2-methoxyphenyl)(cyclopropyl)(oxo)-$\lambda^6$-sulfaneylidene)carbamate.

The title compound was prepared in analogy to General Method F using 4-chloro-7,7-difluoro-2-(methylthio)-6,7-dihydro-5H-cyclopenta[d]pyrimidine and ((5-bromo-2-methoxyphenyl)(cyclopropyl)(oxo)-$\lambda^6$-sulfaneylidene)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine, followed by General Method I.

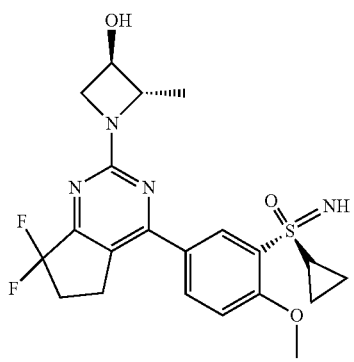 [SMILES: COc1ccc(-c2nc(N3C[C@@H](O)[C@@H]3C)nc3c2CCC3(F)F)cc1S(=N)(=O)C1CC1]

Example 539: (S)-cyclopropyl(5-(7,7-difluoro-2-((2S,3R)-3-hydroxy-2-methylazetidin-1-yl)-6,7-dihydro-5H-cyclopenta[d]pyrimidin-4-yl)-2-methoxyphenyl)(imino)$_4^6$-sulfanone Example 540: (R)-cyclopropyl(5-(7,7-difluoro-2-((2S,3R)-3-hydroxy-2-methylazetidin-1-yl)-6,7-dihydro-5H-cyclopenta[d]pyrimidin-4-yl)-2-methoxyphenyl)(imino)-$\lambda^6$-sulfanone Isomers were separated by SFC (40% EtOH in CO$_2$, CHIRALPAK AD-H, 250×21 mm, 60 mL/min).

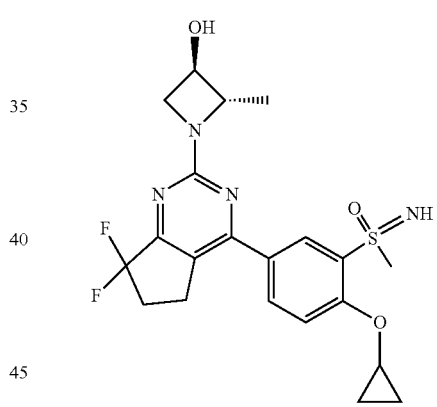

Example 541: (2-cyclopropoxy-5-(7,7-difluoro-2-((2S,3R)-3-hydroxy-2-methylazetidin-1-yl)-6,7-dihydro-5H-cyclopenta[d]pyrimidin-4-yl)phenyl)(imino)(methyl)-$\lambda^6$-sulfanone The title compound was prepared in analogy to General Method S using (5-bromo-2-cyclopropoxyphenyl)(methyl)sulfane instead of (5-bromo-2-methoxyphenyl)(methyl)sulfane, followed by General Method F using 4-chloro-7,7-difluoro-2-(methylthio)-6,7-dihydro-5H-cyclopenta[d]pyrimidine and tert-butyl ((5-bromo-2-cyclopropoxyphenyl)(methyl)(oxo)-$\lambda^6$-sulfaneylidene)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine, followed by General Method I.

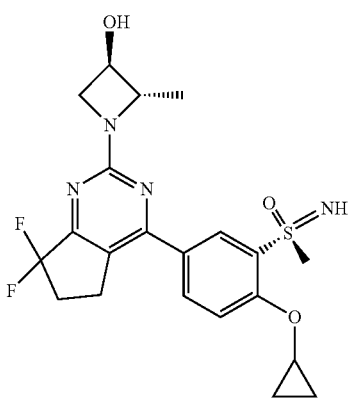

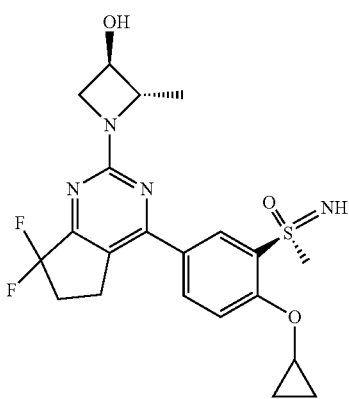 [SMILES: C[C@H]1[C@H](O)CN1c1nc(-c2ccc(OC3CC3)c(S(C)(=N)=O)c2)c2c(n1)C(F)(F)CC2]

Example 542: (S)-(2-cyclopropoxy-5-(7,7-difluoro-2-((2S,3R)-3-hydroxy-2-methylazetidin-1-yl)-6,7-dihydro-5H-cyclopenta[d]pyrimidin-4-yl)phenyl)(imino)(methyl)-λ⁶-sulfanone Example 543: (R)-(2-cyclopropoxy-5-(7,7-difluoro-2-((2S,3R)-3-hydroxy-2-methylazetidin-1-yl)-6,7-dihydro-5H-cyclopenta[d]pyrimidin-4-yl)phenyl)(imino)(methyl)-λ⁶-sulfanone Isomers were separated by SFC (30% EtOH in CO$_2$, CHIRALPAK AD-H, 250×21 mm, 60 mL/min).

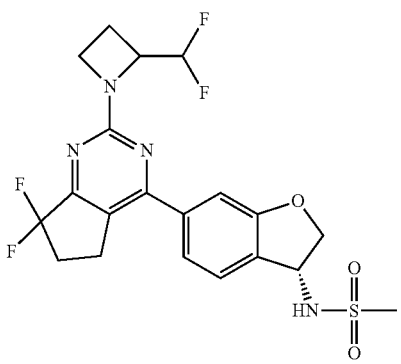 [SMILES: CS(=O)(=O)N[C@H]1COc2cc(-c3nc(N4CCC4C(F)F)nc4c3CCC4(F)F)ccc21]

Example 544: N-((3R)-6-(2-(2-(difluoromethyl)azetidin-1-yl)-7,7-difluoro-6,7-dihydro-5H-cyclopenta[d]pyrimidin-4-yl)-2,3-dihydrobenzofuran-3-yl)methanesulfonamide The title compound was prepared in analogy to General Method K using (R)-6-bromo-2,3-dihydrobenzofuran-3-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using 2-(difluoromethyl)azetidine instead of (2S)-2-methylazetidine.

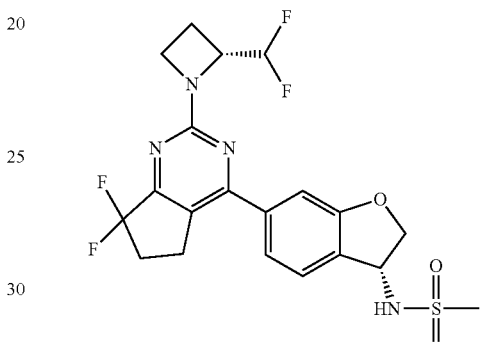

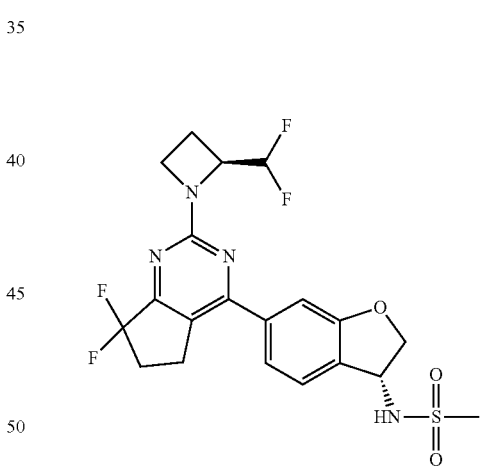

Example 545: N—((R)-6-(2-((R)-2-(difluoromethyl)azetidin-1-yl)-7,7-difluoro-6,7-dihydro-5H-cyclopenta[d]pyrimidin-4-yl)-2,3-dihydrobenzofuran-3-yl)methanesulfonamide Example 546: N—((R)-6-(2-((S)-2-(difluoromethyl)azetidin-1-yl)-7,7-difluoro-6,7-dihydro-5H-cyclopenta[d]pyrimidin-4-yl)-2,3-dihydrobenzofuran-3-yl)methanesulfonamide Isomers were separated by SFC (30% EtOH in CO$_2$, CHIRALPAK AD-H, 250×21 mm, 60 mL/min).

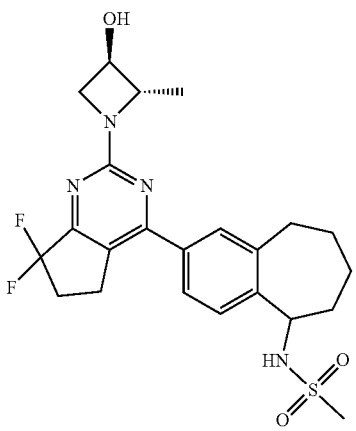 [SMILES: C[C@H]1[C@H](O)CN1c1nc(-c2ccc3c(c2)CCCCC3NS(C)(=O)=O)c2c(n1)C(F)(F)CC2]

Example 547: N-(2-(7,7-difluoro-2-((2S,3R)-3-hydroxy-2-methylazetidin-1-yl)-6,7-dihydro-5H-cyclopenta[d]pyrimidin-4-yl)-6,7,8,9-tetrahydro-5H-benzo[7]annulen-5-yl)methanesulfonamide The title compound was prepared in analogy to General Method K using 2-bromo-6,7,8,9-tetrahydro-5H-benzo[7]annulen-5-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-2-methylazetidin-3-ol instead of (2S)-2-methylazetidine.

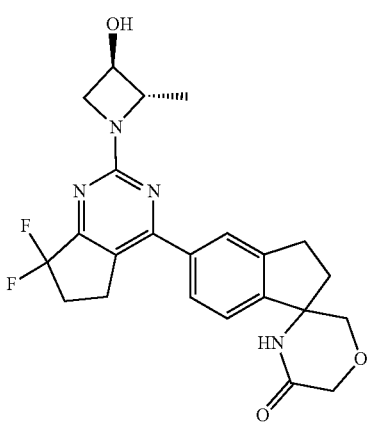 [SMILES: C[C@H]1[C@H](O)CN1c1nc(-c2ccc3c(c2)CCC32COCC(=O)N2)c2c(n1)C(F)(F)CC2]

Example 548: 5-(7,7-difluoro-2-((2S,3R)-3-hydroxy-2-methylazetidin-1-yl)-6,7-dihydro-5H-cyclopenta[d]pyrimidin-4-yl)-2,3-dihydrospiro[indene-1,3'-morpholin]-5'-one The title compound was prepared according to General Method Y and in analogy to General Method F using 4-chloro-7,7-difluoro-2-(methylthio)-6,7-dihydro-5H-cyclopenta[d]pyrimidine and 5-bromo-2,3-dihydrospiro[indene-1,3'-morpholin]-5'-one instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine.

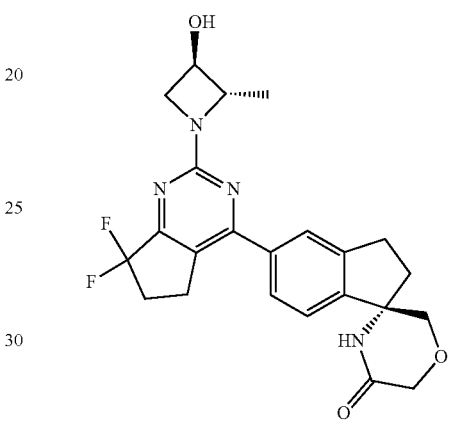

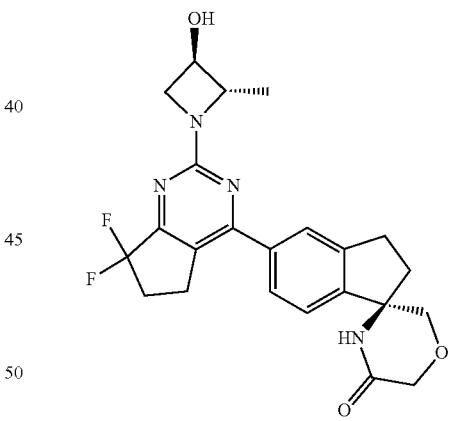

Example 549: (S)-5-(7,7-difluoro-2-((2S,3R)-3-hydroxy-2-methylazetidin-1-yl)-6,7-dihydro-5H-cyclopenta[d]pyrimidin-4-yl)-2,3-dihydrospiro[indene-1,3'-morpholin]-5'-one Example 550: (R)-5-(7,7-difluoro-2-((2S,3R)-3-hydroxy-2-methylazetidin-1-yl)-6,7-dihydro-5H-cyclopenta[d]pyrimidin-4-yl)-2,3-dihydrospiro[indene-1,3'-morpholin]-5'-one Isomers were separated by SFC (30% EtOH in $CO_2$, CHIRALPAK AD-H, 250×21 mm, 60 mL/min).

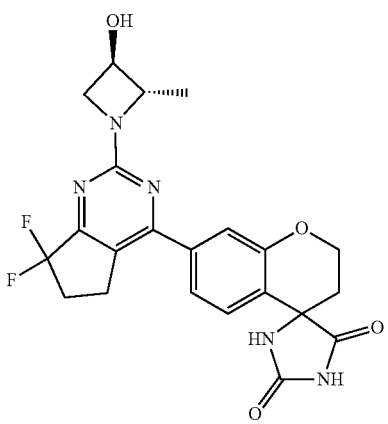 [SMILES: C[C@H]1[C@H](O)CN1c1nc(-c2ccc3c(c2)OCCC32NC(=O)NC2=O)c2c(n1)C(F)(F)CC2]

Example 551: 7-(7,7-difluoro-2-((2S,3R)-3-hydroxy-2-methylazetidin-1-yl)-6,7-dihydro-5H-cyclopenta[d]pyrimidin-4-yl)spiro[chromane-4,4'-imidazolidine]-2',5'-dione The title compound was prepared according to General Method X and in analogy to General Method F using 4-chloro-7,7-difluoro-2-(methylthio)-6,7-dihydro-5H-cyclopenta[d]pyrimidine and 7-bromospiro[chromane-4,4'-imidazolidine]-2',5'-dione instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine.

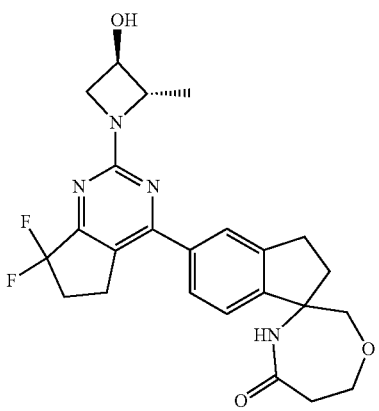 [SMILES: C[C@H]1[C@H](O)CN1c1nc(-c2ccc3c(c2)CCC32COCCC(=O)N2)c2c(n1)C(F)(F)CC2]

Example 552: 5-(7,7-difluoro-2-((2S,3R)-3-hydroxy-2-methylazetidin-1-yl)-6,7-dihydro-5H-cyclopenta[d]pyrimidin-4-yl)-2,3-dihydrospiro[indene-1,3'-[1,4]oxazepan]-5'-one The title compound was prepared in analogy to General Method Y using 3-chloropropanoyl chloride instead of 2-chloroacetyl chloride, and omitting the second step, followed by General Method F using 4-chloro-7,7-difluoro-2-(methylthio)-6,7-dihydro-5H-cyclopenta[d]pyrimidine and 5-bromo-2,3-dihydrospiro[indene-1,3'-[1,4]oxazepan]-5'-one instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine.

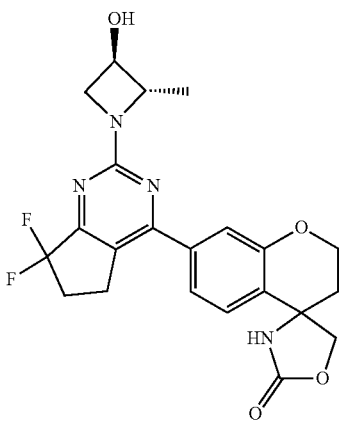 [SMILES: C[C@H]1[C@H](O)CN1c1nc(-c2ccc3c(c2)OCCC32COC(=O)N2)c2c(n1)C(F)(F)CC2]

Example 553: 7-(7,7-difluoro-2-((2S,3R)-3-hydroxy-2-methylazetidin-1-yl)-6,7-dihydro-5H-cyclopenta[d]pyrimidin-4-yl)spiro[chromane-4,4'-oxazolidin]-2'-one A vial was charged with 7-bromospiro[chromane-4,4'-imidazolidine]-2',5'-dione (400 mg, 1.35 mmol) and NaOH (2M aq., 4.7 mL, 9.42 mmol). The mixture was heated to 100° C. for 3 days. The mixture was acidified to pH=2 with 6N HCl. The precipitate was filtered off, and the filtrate was frozen and lyophilized to give crude 4-amino-7-bromo-chromane-4-carboxylic acid, which was dissolved in MeOH (10 mL). HCl (3M aq., 3.6 mL, 10.8 mmol) was added and the mixture was heated to 80° C. and allowed to stir for 4 days. The mixture was concentrated and the residue was subject to reverse phase HPLC (0.1% TFA in MeCN-0.1% TFA in H$_2$O) to give methyl 4-amino-7-bromo-chromane-4-carboxylate, which was further dissolved in MeOH (5 mL). NaBH$_4$ (250 mg, 6.61 mmol) was added and the mixture heated to 60° C. for 24 hrs. H$_2$O (10 mL) was added and the mixture was extracted with EtOAc (3×10 mL). The combined organics were dried over Na$_2$SO$_4$, filtered, and concentrated to give (4-amino-7-bromo-chroman-4-yl)methanol.

The title compound was prepared in analogy to General Method Z, using (4-amino-7-bromo-chroman-4-yl)methanol instead of (1-amino-5-bromo-indan-1-yl)methanol, followed by General Method F using 4-chloro-7,7-difluoro-2-(methylthio)-6,7-dihydro-5H-cyclopenta[d]pyrimidine and 7-bromospiro[chromane-4,4'-oxazolidin]-2'-one instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine.

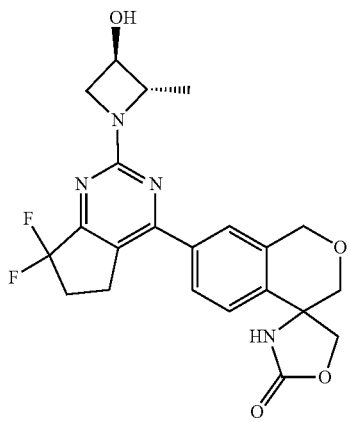 [SMILES: C[C@H]1[C@H](O)CN1c1nc(-c2ccc3c(c2)COCC32COC(=O)N2)c2c(n1)C(F)(F)CC2]

Example 554: 7-(7,7-difluoro-2-((2S,3R)-3-hydroxy-2-methylazetidin-1-yl)-6,7-dihydro-5H-cyclopenta[d]pyrimidin-4-yl)spiro[isochromane-4,4'-oxazolidin]-2'-one 7'-bromospiro[imidazolidine-4,4'-isochromane]-2,5-dione was prepared according to General Method X, using 7-bromoisochroman-4-one instead of 7-bromochroman-4-one. (4-amino-7-bromoisochroman-4-yl)methanol was prepared therefrom, in analogy to Example 553.

The title compound was prepared in analogy to General Method Z, using (4-amino-7-bromoisochroman-4-yl)methanol instead of (1-amino-5-bromo-indan-1-yl)methanol, followed by General Method F using 4-chloro-7,7-difluoro-2-(methylthio)-6,7-dihydro-5H-cyclopenta[d]pyrimidine and 7-bromospiro[chromane-4,4'-oxazolidin]-2'-one instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine.

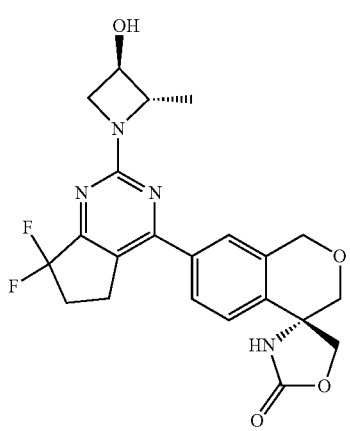

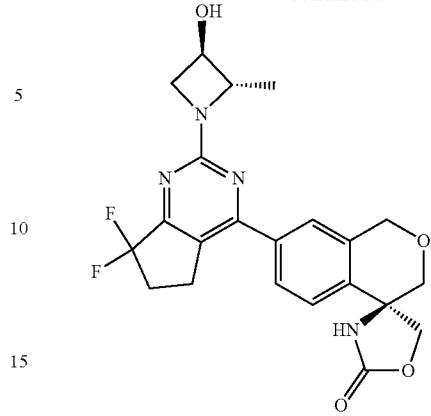

Example 555: (R)-7-(7,7-difluoro-2-(2S,3R)-3-hydroxy-2-methylazetidin-1-yl)-6,7-dihydro-5H-cyclopenta[d]pyrimidin-4-yl)spiro[isochromane-4,4'-oxazolidin]-2'-one Example 556: (S)-7-(7,7-difluoro-2-((2S,3R)-3-hydroxy-2-methylazetidin-1-yl)-6,7-dihydro-5H-cyclopenta[d]pyrimidin-4-yl)spiro[isochromane-4,4'-oxazolidin]-2'-one Isomers were separated by SFC (30% MeOH in $CO_2$, CHIRALPAK AD-H, 250×21 mm, 60 mL/min).

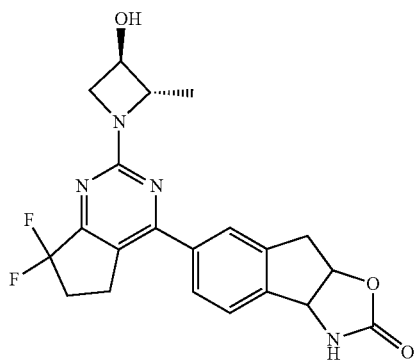 [SMILES: C[C@H]1[C@H](O)CN1c1nc(-c2ccc3c(c2)CC2OC(=O)NC32)c2c(n1)C(F)(F)CC2]

Example 557: 6-(7,7-difluoro-2-((2S,3R)-3-hydroxy-2-methylazetidin-1-yl)-6,7-dihydro-5H-cyclopenta[d]pyrimidin-4-yl)-3,3a,8,8a-tetrahydro-2H-indeno[1,2-c]oxazol-2-one The title compound was prepared in analogy to General Method Z, using 1-amino-5-bromo-2,3-dihydro-1H-inden-2-ol instead of (1-amino-5-bromo-indan-1-yl)methanol, followed by General Method F using 4-chloro-7,7-difluoro-2-(methylthio)-6,7-dihydro-5H-cyclopenta[d]pyrimidine and 6-bromo-3,3a,8,8a-tetrahydro-2H-indeno[1,2-d]oxazol-2-one instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine.

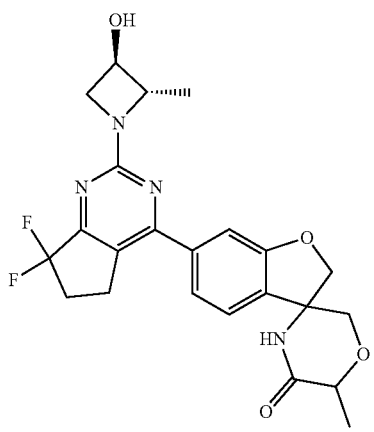 [SMILES: CC1OCC2(COc3cc(-c4nc(N5C[C@@H](O)[C@@H]5C)nc5c4CCC5(F)F)ccc32)NC1=O]

Example 558: 6-(7,7-difluoro-2-((2S,3R)-3-hydroxy-2-methylazetidin-1-yl)-6,7-dihydro-5H-cyclopenta[d]pyrimidin-4-yl)-6'-methyl-2H-spiro[benzofuran-3,3'-morpholin]-5'-one The title compound was prepared in analogy to General Method Y using 2-chloropropanoyl chloride and (3-amino-6-bromo-2,3-dihydrobenzofuran-3-yl)methanol instead of 2-chloroacetyl chloride and (1-amino-5-bromo-2,3-dihydro-1H-inden-1-yl)methanol, respectively, followed by General Method F using 4-chloro-7,7-difluoro-2-(methylthio)-6,7-dihydro-5H-cyclopenta[d]pyrimidine and 6-bromo-6'-methyl-2H-spiro[benzofuran-3,3'-morpholin]-5'-one instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine.

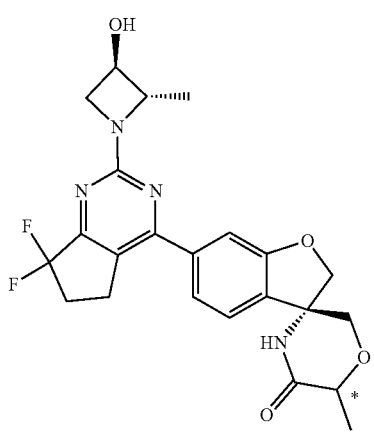

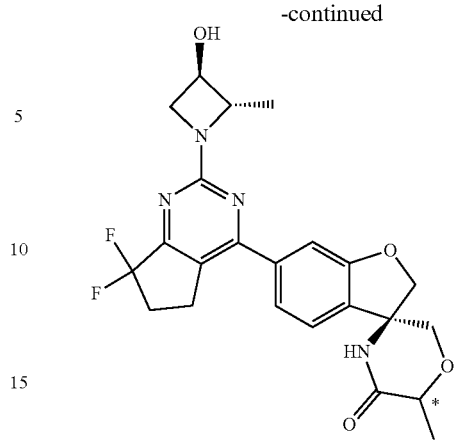

Example 559: (3S)-6-(7,7-difluoro-24(2S,3R)-3-hydroxy-2-methylazetidin-1-yl)-6,7-dihydro-5H-cyclopenta[d]pyrimidin-4-yl)-6'-methyl-2H-spiro[benzofuran-3,3'-morpholin]-5'-one Example 560: (3R)-6-(7,7-difluoro-24(2S,3R)-3-hydroxy-2-methylazetidin-1-yl)-6,7-dihydro-5H-cyclopenta[d]pyrimidin-4-yl)-6'-methyl-2H-spiro[benzofuran-3,3'-morpholin]-5'-one stereochemistry of methyl not determined
Isomers were separated by SFC (35% EtOH in $CO_2$, CHIRALPAK AD-H, 250×21 mm, 60 mL/min).

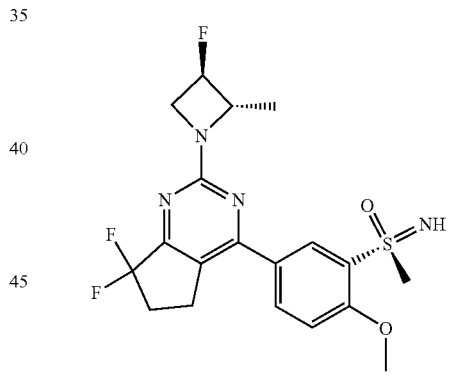

Example 561: (S)-(5-(7,7-difluoro-2-((2S,3R)-3-fluoro-2-methylazetidin-1-yl)-6,7-dihydro-5H-cyclopenta[d]pyrimidin-4-yl)-2-methoxyphenyl)(imino)(methyl)-$\lambda^6$-sulfanone The title compound was prepared according to General Method S, using (S)-4-bromo-1-methoxy-2-(methylsulfinyl)benzene instead of (rac)-4-bromo-1-methoxy-2-(methylsulfinyl)benzene, followed by General Method F using 4-chloro-7,7-difluoro-2-(methylthio)-6,7-dihydro-5H-cyclopenta[d]pyrimidine and tert-butyl (S)-((5-bromo-2-methoxyphenyl)(methyl)(oxo)-$\lambda^6$-sulfaneylidene)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-

3-fluoro-2-methylazetidine instead of (2S)-2-methylazetidine, followed by General Method I.

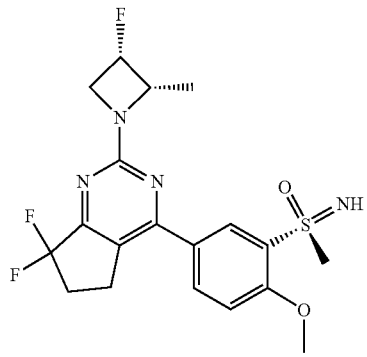 [SMILES: COc1ccc(-c2nc(N3C[C@H](F)[C@@H]3C)nc3c2CCC3(F)F)cc1[S@@](C)(=N)=O]

Example 562: (S)-(5-(7,7-difluoro-2-((2S,3S)-3-fluoro-2-methylazetidin-1-yl)-6,7-dihydro-5H-cyclopenta[d]pyrimidin-4-yl)-2-methoxyphenyl)(imino)(methyl)-λ⁶-sulfanone The title compound was prepared according to General Method S, using (S)-4-bromo-1-methoxy-2-(methylsulfinyl)benzene instead of (rac)-4-bromo-1-methoxy-2-(methylsulfinyl)benzene, followed by General Method F using 4-chloro-7,7-difluoro-2-(methylthio)-6,7-dihydro-5H-cyclopenta[d]pyrimidine and tert-butyl (S)-((5-bromo-2-methoxyphenyl)(methyl)(oxo)-λ⁶-sulfaneylidene)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3S)-3-fluoro-2-methylazetidine instead of (2S)-2-methylazetidine, followed by General Method I.

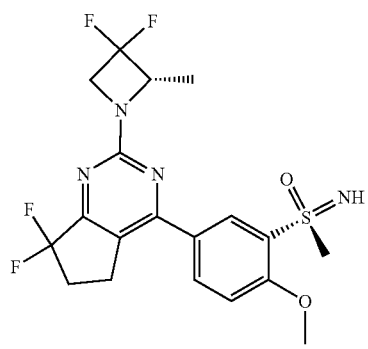 [SMILES: COc1ccc(-c2nc(N3CC(F)(F)[C@@H]3C)nc3c2CCC3(F)F)cc1[S@@](C)(=N)=O]

Example 563: (S)-(5-(2-((S)-3,3-difluoro-2-methylazetidin-1-yl)-7,7-difluoro-6,7-dihydro-5H-cyclopenta[d]pyrimidin-4-yl)-2-methoxyphenyl)(imino)(methyl)-λ⁶-sulfanone The title compound was prepared according to General Method S, using (S)-4-bromo-1-methoxy-2-(methylsulfinyl)benzene instead of (rac)-4-bromo-1-methoxy-2-(methylsulfinyl)benzene, followed by General Method F using 4-chloro-7,7-difluoro-2-(methylthio)-6,7-dihydro-5H-cyclopenta[d]pyrimidine and tert-butyl (S)-((5-bromo-2-methoxyphenyl)(methyl)(oxo)-λ⁶-sulfaneylidene)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (S)-3,3-difluoro-2-methylazetidine instead of (2S)-2-methylazetidine, followed by General Method I.

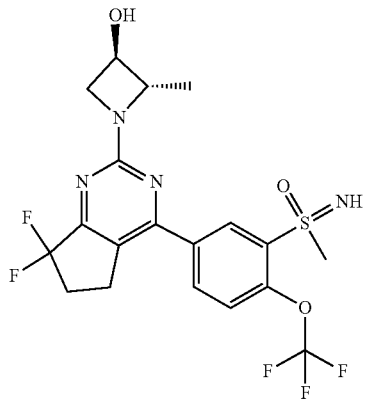 [SMILES: C[C@H]1[C@H](O)CN1c1nc(-c2ccc(OC(F)(F)F)c(S(C)(=N)=O)c2)c2c(n1)C(F)(F)CC2]

Example 564: (5-(7,7-difluoro-2-((2S,3R)-3-hydroxy-2-methylazetidin-1-yl)-6,7-dihydro-5H-cyclopenta[d]pyrimidin-4-yl)-2-(trifluoromethoxy)phenyl)(imino)(methyl)-λ⁶-sulfanone The title compound was prepared in analogy to General Method S, using (5-bromo-2-(trifluoromethoxy)phenyl)(methyl)sulfane instead of (5-bromo-2-methoxyphenyl)(methyl)sulfane, followed by General Method F using 4-chloro-7,7-difluoro-2-(methylthio)-6,7-dihydro-5H-cyclopenta[d]pyrimidine and tert-butyl ((5-bromo-2-(trifluoromethoxy)phenyl)(methyl)(oxo)-λ⁶-sulfaneylidene)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (S)-3,3-difluoro-2-methylazetidine instead of (2S)-2-methylazetidine, followed by General Method I.

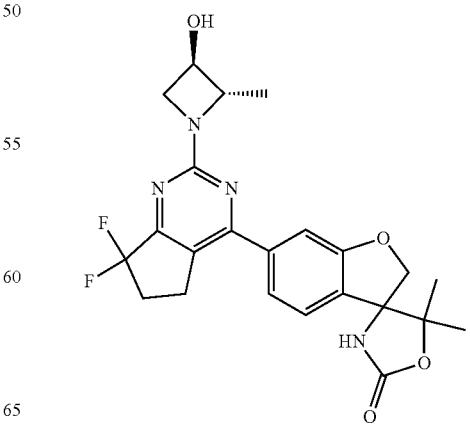

Example 565: 6-(7,7-difluoro-2-((2S,3R)-3-hydroxy-2-methylazetidin-1-yl)-6,7-dihydro-5H-cyclopenta[d]pyrimidin-4-yl)-5',5'-dimethyl-2H-spiro[benzofuran-3,4'-oxazolidin]-2'-one A vial was charged with ethyl 3-amino-6-bromo-2,3-dihydrobenzofuran-3-carboxylate (500 mg, 1.75 mmol) and THF (10 mL). The mixture was cooled to 0° C., and MeMgBr (3M in diethyl ether, 2.33 mL, 6.99 mmol) was added. The mixture was allowed to warm to ambient temperature over 18 hrs. NH$_4$Cl (sat. aq., 15 mL) was added, and the mixture was extracted with EtOAc (3×10 mL). The combined organics were dried over Na$_2$SO$_4$, filtered, and concentrated to give 2-(3-amino-6-bromo-2,3-dihydrobenzofuran-3-yl)propan-2-ol.

The title compound was prepared in analogy to General Method Z, using 2-(3-amino-6-bromo-2,3-dihydrobenzofuran-3-yl)propan-2-ol instead of (1-amino-5-bromo-indan-1-yl)methanol, followed by General Method F using 4-chloro-7,7-difluoro-2-(methylthio)-6,7-dihydro-5H-cyclopenta[d]pyrimidine and 6-bromo-5',5'-dimethyl-2H-spiro[benzofuran-3,4'-oxazolidin]-2'-one instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine.

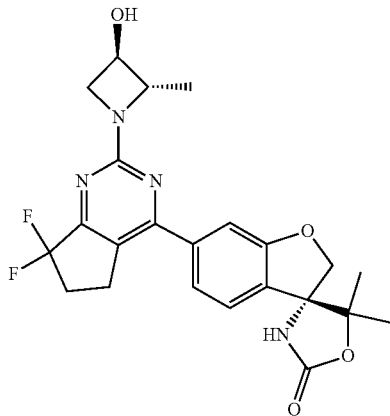

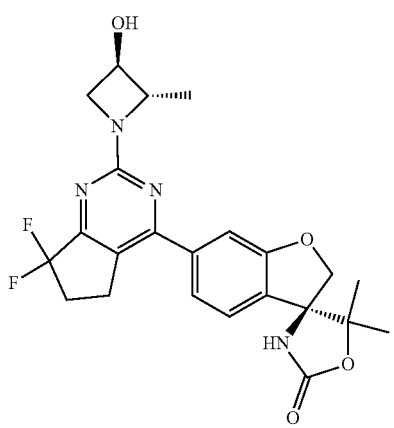 [SMILES: C[C@H]1[C@H](O)CN1c1nc(-c2ccc3c(c2)OCC32NC(=O)OC2(C)C)c2c(n1)C(F)(F)CC2]

Example 566: (R)-6-(7,7-difluoro-2-((2S,3R)-3-hydroxy-2-methylazetidin-1-yl)-6,7-dihydro-5H-cyclopenta[d]pyrimidin-4-yl)-5',5'-dimethyl-2H-spiro[benzofuran-3,4'-oxazolidin]-2'-one

Example 567: (S)-6-(7,7-difluoro-2-((2S,3R)-3-hydroxy-2-methylazetidin-1-yl)-6,7-dihydro-5H-cyclopenta[d]pyrimidin-4-yl)-5',5'-dimethyl-2H-spiro[benzofuran-3,4'-oxazolidin]-2'-one Isomers were separated by SFC (35% EtOH in CO$_2$, CHIRALPAK AD-H, 250×21 mm, 60 mL/min).

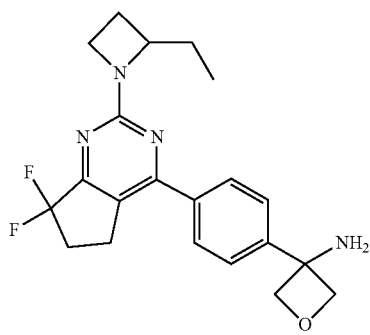 [SMILES: CCC1CCN1c1nc(-c2ccc(C3(N)COC3)cc2)c2c(n1)C(F)(F)CC2]

Example 568: 3-(4-(7,7-difluoro-2-(2-methylazetidin-1-yl)-6,7-dihydro-5H-cyclopenta[d]pyrimidin-4-yl)phenyl)oxetan-3-amine The title compound was prepared in analogy to General Method A using 4-chloro-7,7-difluoro-2-(methylthio)-6,7-dihydro-5H-cyclopenta[d]pyrimidine and benzyl (3-(4-(4,4,5,5-tetramethyl-1,3,2-dioxaborolan-2-yl)phenyl)oxetan-3-yl)carbamate instead of 2,4-dichloro-6,7-dihydro-5H-cyclopenta[d]pyrimidine and 3-pyridylboronic acid, respectively, followed by General Method M, followed by General Method B using 2-ethylazetidine instead of (2S)-2-methylazetidine, followed by General Method R.

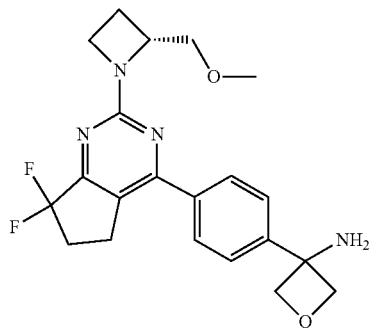 [SMILES: COC[C@H]1CCN1c1nc(-c2ccc(C3(N)COC3)cc2)c2c(n1)C(F)(F)CC2]

Example 569: (R)-3-(4-(7,7-difluoro-2-(2-(methoxymethyl)azetidin-1-yl)-6,7-dihydro-5H-cyclopenta[d]pyrimidin-4-yl)phenyl)oxetan-3-amine The title compound was prepared in analogy to General Method A using 4-chloro-7,7-difluoro-2-(methylthio)-6,7-dihydro-5H-cyclopenta[d]pyrimidine and benzyl (3-(4-(4,4,5,5-tetramethyl-1,3,2-dioxaborolan-2-yl)phenyl)oxetan-3-yl)carbamate instead of 2,4-dichloro-6,7-dihydro-5H- cyclopenta[d]pyrimidine and 3-pyridylboronic acid, respectively, followed by General Method M, followed by General Method B using (R)-2-(methoxymethyl)azetidine instead of (2S)-2-methylazetidine, followed by General Method R.

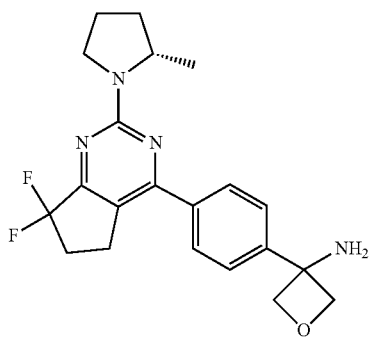 [SMILES: C[C@H]1CCCN1c1nc(-c2ccc(C3(N)COC3)cc2)c2c(n1)C(F)(F)CC2]

Example 570: (S)-3-(4-(7,7-difluoro-2-(2-methylpyrrolidin-1-yl)-6,7-dihydro-5H-cyclopenta[d]pyrimidin-4-yl)phenyl)oxetan-3-amine The title compound was prepared in analogy to General Method A using 4-chloro-7,7-difluoro-2-(methylthio)-6,7-dihydro-5H-cyclopenta[d]pyrimidine and benzyl (3-(4-(4,4,5,5-tetramethyl-1,3,2-dioxaborolan-2-yl)phenyl)oxetan-3-yl)carbamate instead of 2,4-dichloro-6,7-dihydro-5H-cyclopenta[d]pyrimidine and 3-pyridylboronic acid, respectively, followed by General Method M, followed by General Method B using (S)-2-methylpyrrolidine instead of (2S)-2-methylazetidine, followed by General Method R.

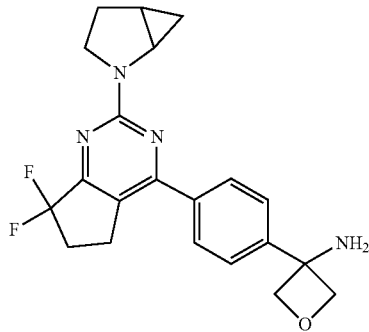 [SMILES: NC1(c2ccc(-c3nc(N4CCC5CC54)nc4c3CCC4(F)F)cc2)COC1]

Example 571: 3-(4-(2-(2-azabicyclo[3.1.0]hexan-2-yl)-7,7-difluoro-6,7-dihydro-5H-cyclopenta[d]pyrimidin-4-yl)phenyl)oxetan-3-amine The title compound was prepared in analogy to General Method A using 4-chloro-7,7-difluoro-2-(methylthio)-6,7-dihydro-5H-cyclopenta[d]pyrimidine and benzyl (3-(4-(4,4,5,5-tetramethyl-1,3,2-dioxaborolan-2-yl)phenyl)oxetan-3-yl)carbamate instead of 2,4-dichloro-6,7-dihydro-5H-cyclopenta[d]pyrimidine and 3-pyridylboronic acid, respectively, followed by General Method M, followed by General Method B using 2-azabicyclo[3.1.0]hexane instead of (2S)-2-methylazetidine, followed by General Method R.

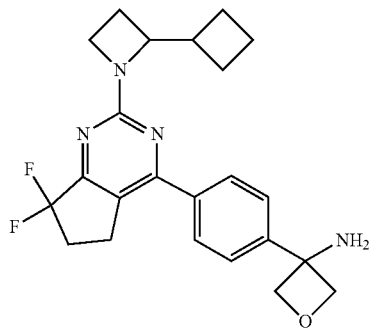 [SMILES: NC1(c2ccc(-c3nc(N4CCC4C4CCC4)nc4c3CCC4(F)F)cc2)COC1]

Example 572: 3-(4-(2-(2-cyclobutylazetidin-1-yl)-7,7-difluoro-6,7-dihydro-5H-cyclopenta[d]pyrimidin-4-yl)phenyl)oxetan-3-amine The title compound was prepared in analogy to General Method A using 4-chloro-7,7-difluoro-2-(methylthio)-6,7-dihydro-5H-cyclopenta[d]pyrimidine and benzyl (3-(4-(4,4,5,5-tetramethyl-1,3,2-dioxaborolan-2-yl)phenyl)oxetan-3-yl)carbamate instead of 2,4-dichloro-6,7-dihydro-5H-cyclopenta[d]pyrimidine and 3-pyridylboronic acid, respectively, followed by General Method M, followed by General Method B using 2-cyclobutylazetidine instead of (2S)-2-methylazetidine, followed by General Method R.

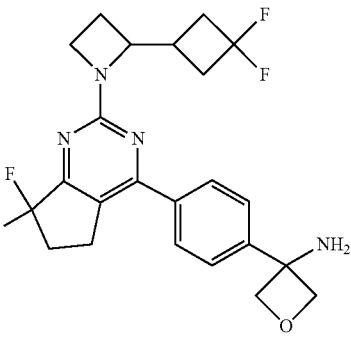

Example 573: 3-(4-(2-(2-(3,3-difluorocyclobutyl)azetidin-1-yl)-7,7-difluoro-6,7-dihydro-5H-cyclopenta[d]pyrimidin-4-yl)phenyl)oxetan-3-amine The title compound was prepared in analogy to General Method A using 4-chloro-7,7-difluoro-2-(methylthio)-6,7-dihydro-5H-cyclopenta[d]pyrimidine and benzyl (3-(4-(4,4,5,5-tetramethyl-1,3,2-dioxaborolan-2-yl)phenyl)oxetan-3-yl)carbamate instead of 2,4-dichloro-6,7-dihydro-5H-cyclopenta[d]pyrimidine and 3-pyridylboronic acid, respectively, followed by General Method M, followed by General Method B using 2-(3,3-difluorocyclobutyl)azetidine instead of (2S)-2-methylazetidine, followed by General Method R.

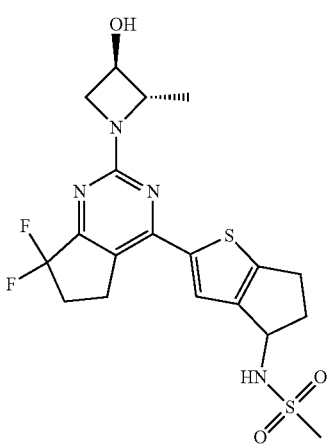 [SMILES: C[C@H]1[C@H](O)CN1c1nc(-c2cc3c(s2)CCC3NS(C)(=O)=O)c2c(n1)C(F)(F)CC2]

Example 574: N-(2-(7,7-difluoro-24(2S,3R)-3-hydroxy-2-methylazetidin-1-yl)-6,7-dihydro-5H-cyclopenta[d]pyrimidin-4-yl)-5,6-dihydro-4H-cyclopenta[b]thiophen-4-yl)methanesulfonamide The title compound was prepared in analogy to General Method W, using 2-bromo-5,6-dihydro-4H-cyclopenta[b]thiophen-4-one instead of 5-bromo-7-methoxy-2,3-dihydro-1H-inden-1-one followed by General Method K, using 2-bromo-5,6-dihydro-4H-cyclopenta[b]thiophen-4-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method D using N-(2-bromo-5,6-dihydro-4H-cyclopenta[b]thiophen-4-yl)methanesulfonamide instead of ethyl 2-bromoimidazo[5,1-b]thiazole-7-carboxylate, followed by General Method E, using 4-chloro-7,7-difluoro-2-(methylthio)-6,7-dihydro-5H-cyclopenta[d]pyrimidine and N-(2-(tributylstannyl)-5,6-dihydro-4H-cyclopenta[b]thiophen-4-yl)methanesulfonamide instead of 4-chloro-2-[(2S)-2-methylazetidin-1-yl]-6,7-dihydro-5H-cyclopenta[d]pyrimidine and ethyl 2-tributylstannylimidazo[5,1-b]thiazole-7-carboxylate respectively, followed by General Method M, and General Method B, using (2S,3R)-2-methylazetidin-3-ol instead of (2S)-2-methylazetidine.

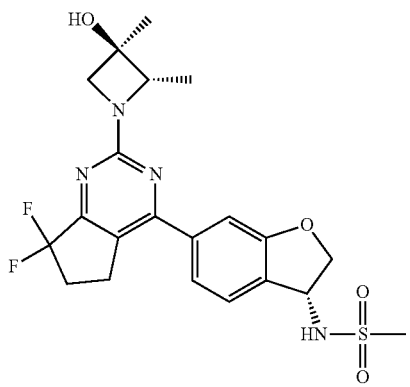 [SMILES: C[C@@H]1N(c2nc(-c3ccc4c(c3)OC[C@@H]4NS(C)(=O)=O)c3c(n2)C(F)(F)CC3)C[C@@]1(C)O]

Example 575: N—((R)-6-(7,7-difluoro-2-((2S,3R)-3-hydroxy-2,3-dimethylazetidin-1-yl)-6,7-dihydro-5H-cyclopenta[d]pyrimidin-4-yl)-2,3-dihydrobenzofuran-3-yl)methanesulfonamide The title compound was prepared in analogy to General Method K using (R)-6-bromo-2,3-dihydrobenzofuran-3-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-2,3-dimethylazetidin-3-ol instead of (2S)-2-methylazetidine.

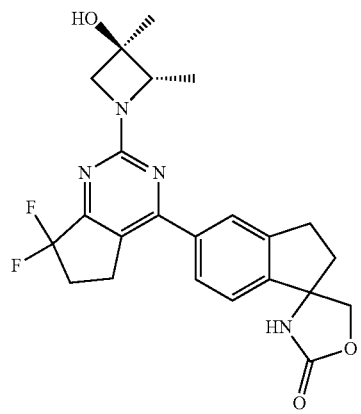 [SMILES: C[C@@H]1N(c2nc(-c3ccc4c(c3)CCC43COC(=O)N3)c3c(n2)C(F)(F)CC3)C[C@@]1(C)O]

Example 576: 5-(7,7-difluoro-2-((2S,3R)-3-hydroxy-2,3-dimethylazetidin-1-yl)-6,7-dihydro-5H-cyclopenta[d]pyrimidin-4-yl)-2,3-dihydrospiro[indene-1,4'-oxazolidin]-2'-one The title compound was prepared according to General Method Z, and in analogy to General Method F using 5-bromo-2,3-dihydrospiro[indene-1,4'-oxazolidin]-2'-one and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively followed by General Method M, and General Method B, using (2S,3R)-2,3-dimethylazetidin-3-ol instead of (2S)-2-methylazetidine.

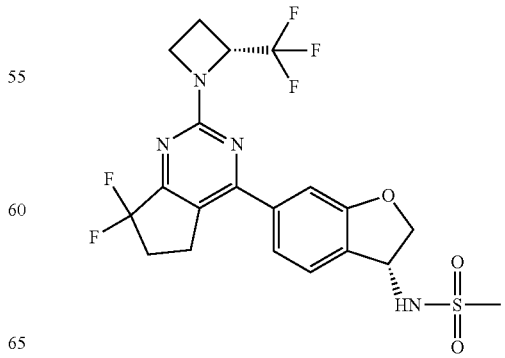

Example 577: N—((R)-6-(7,7-difluoro-2-((R)-2-(trifluoromethyl)azetidin-1-yl)-6,7-dihydro-5H-cyclopenta[d]pyrimidin-4-yl)-2,3-dihydrobenzofuran-3-yl)methanesulfonamide The title compound was prepared in analogy to General Method K using (R)-6-bromo-2,3-dihydrobenzofuran-3-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method U.

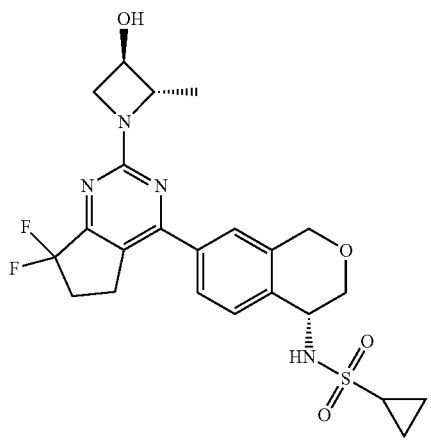

Example 579: N—((R)-7-(7,7-difluoro-2-((2S,3R)-3-hydroxy-2-methylazetidin-1-yl)-6,7-dihydro-5H-cyclopenta[d]pyrimidin-4-yl)isochroman-4-yl)cyclopropanesulfonamide The title compound was prepared in analogy to General Method K using (R)-7-bromoisochroman-4-amine and cyclopropylsulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-2-methylazetidin-3-ol instead of (2S)-2-methylazetidine.

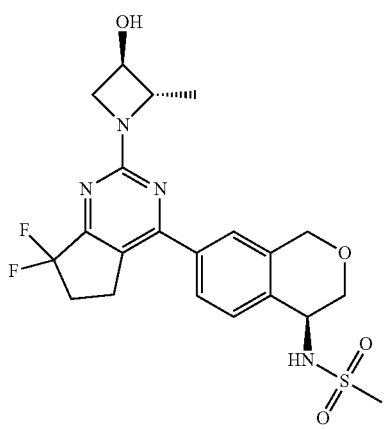 [SMILES: C[C@H]1[C@H](O)CN1c1nc(-c2ccc3c(c2)COC[C@H]3NS(C)(=O)=O)c2c(n1)C(F)(F)CC2]

Example 578: N—((S)-7-(7,7-difluoro-2-((2S,3R)-3-hydroxy-2-methylazetidin-1-yl)-6,7-dihydro-5H-cyclopenta[d]pyrimidin-4-yl)isochroman-4-yl)methanesulfonamide The title compound was prepared in analogy to General Method K using (S)-7-bromoisochroman-4-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-2-methylazetidin-3-ol instead of (2S)-2-methylazetidine.

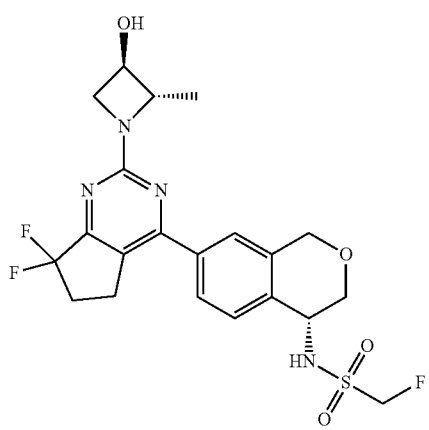 [SMILES: C[C@H]1[C@H](O)CN1c1nc(-c2ccc3c(c2)COC[C@@H]3NS(=O)(=O)CF)c2c(n1)C(F)(F)CC2]

Example 580: N—((R)-7-(7,7-difluoro-2-((2S,3R)-3-hydroxy-2-methylazetidin-1-yl)-6,7-dihydro-5H-cyclopenta[d]pyrimidin-4-yl)isochroman-4-yl)-1-fluoromethanesulfonamide The title compound was prepared in analogy to General Method K using (R)-7-bromoisochroman-4-amine and fluoromethanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro- 7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-2-methylazetidin-3-ol instead of (2S)-2-methylazetidine.

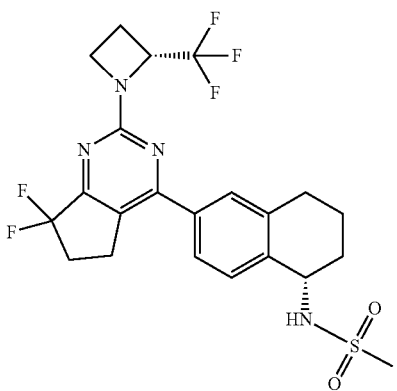 [SMILES: CS(=O)(=O)N[C@H]1CCCc2cc(-c3nc(N4CC[C@@H]4C(F)(F)F)nc4c3CCC4(F)F)ccc21]

Example 581: N—((R)-7-(7,7-difluoro-2-((R)-2-(trifluoromethyl)azetidin-1-yl)-6,7-dihydro-5H-cyclopenta[d]pyrimidin-4-yl)isochroman-4-yl)methanesulfonamide The title compound was prepared in analogy to General Method K using (R)-7-bromoisochroman-4-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method U.

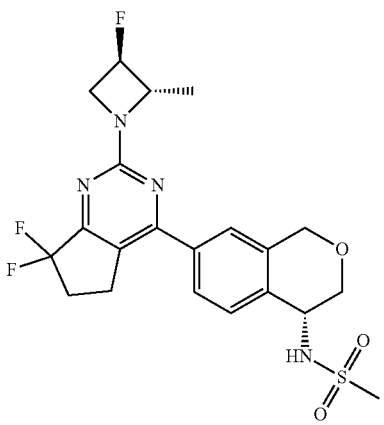 [SMILES: C[C@H]1[C@H](F)CN1c1nc(-c2ccc3c(c2)COC[C@@H]3NS(C)(=O)=O)c2c(n1)C(F)(F)CC2]

Example 582: N—((R)-7-(7,7-difluoro-2-((2S,3R)-3-fluoro-2-methylazetidin-1-yl)-6,7-dihydro-5H-cyclopenta[d]pyrimidin-4-yl)isochroman-4-yl)methanesulfonamide The title compound was prepared in analogy to General Method K using (R)-7-bromoisochroman-4-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-3-fluoro-2-methylazetidine instead of (2S)-2-methylazetidine.

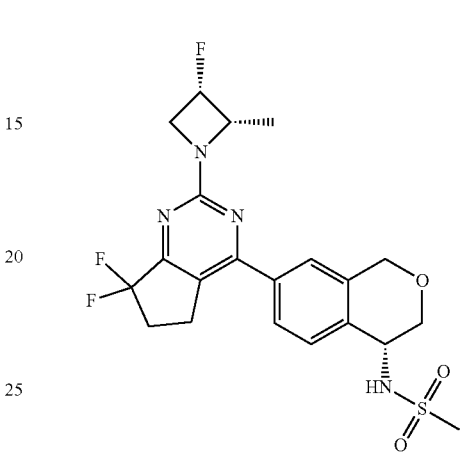

Example 583: N—((R)-7-(7,7-difluoro-2-((2S,3S)-3-fluoro-2-methylazetidin-1-yl)-6,7-dihydro-5H-cyclopenta[d]pyrimidin-4-yl)isochroman-4-yl)methanesulfonamide The title compound was prepared in analogy to General Method K using (R)-7-bromoisochroman-4-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3S)-3-fluoro-2-methylazetidine instead of (2S)-2-methylazetidine.

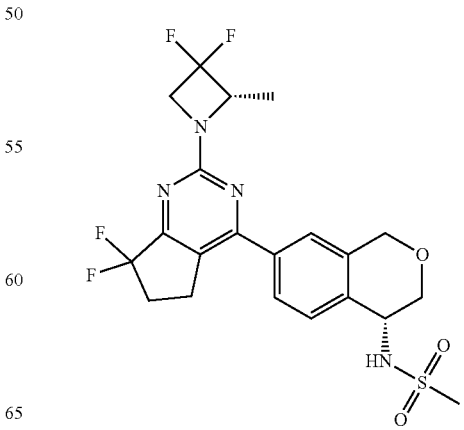

Example 584: N—((R)-7-(2-((S)-3,3-difluoro-2-methylazetidin-1-yl)-7,7-difluoro-6,7-dihydro-5H-cyclopenta[d]pyrimidin-4-yl)isochroman-4-yl)methanesulfonamide The title compound was prepared in analogy to General Method K using (R)-7-bromoisochroman-4-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method U, using (S)-3,3-difluoro-2-methylazetidine instead of (R)-2-(trifluoromethyl)azetidine.

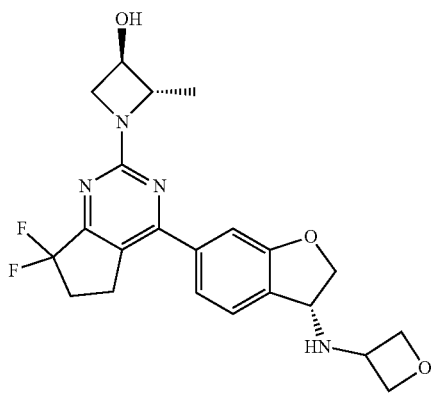 [SMILES: C[C@H]1[C@H](O)CN1c1nc(-c2ccc3c(c2)OC[C@@H]3NC2COC2)c2c(n1)C(F)(F)CC2]

Example 585: (2S,3R)-1-[7,7-difluoro-4-[(3R)-3-(oxetan-3-ylamino)-2,3-dihydrobenzofuran-6-yl]-5,6-dihydrocyclopenta[d]pyrimidin-2-yl]-2-methylazetidin-3-ol To a mixture of (3R)-6-bromo-2,3-dihydrobenzofuran-3-amine hydrochloride (1.00 g, 3.99 mmol) and ZnCl$_2$ (816 mg, 5.99 mmol) in MeOH (20 mL) was added 3-oxetanone (863 mg, 12.0 mmol) dropwise over 1-2 min. To the reaction mixture, NaCNBH$_3$ (753 mg, 12.0 mmol) was charged. The reaction mixture was placed under an atmosphere of N$_2$ and allowed to stir for 18 hours at ambient temperature. The MeOH was removed by rotary evaporation and the residue was dissolved in DCM (50 mL) and NaOH (2M, 30 mL). The layers were separated, and the aqueous layer was extracted with DCM (2×50 mL). The combined organics were washed with NaOH (2 M, 15 mL) and dried over MgSO$_4$, filtered, and concentrated. The crude was subject to flash column chromatography (hexanes-ethyl acetate-methanol) to give (3R)-6-bromo-N-(oxetan-3-yl)-2,3-dihydrobenzofuran-3-amine (542 mg, 2.01 mmol).

The title compound was prepared in analogy to General Method T, followed by General Method F using benzyl N-[(3R)-6-bromo-2,3-dihydrobenzofuran-3-yl]-N-(oxetan-3-yl)carbamate and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, followed by General method B using (2S,3R)-2-methylazetidin-3-ol instead of (2S)-2-methylazetidine, followed by General Method R.

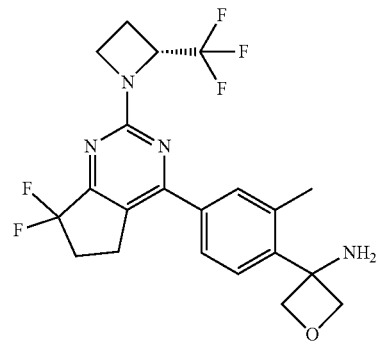 [SMILES: Cc1cc(-c2nc(N3CC[C@@H]3C(F)(F)F)nc3c2CCC3(F)F)ccc1C1(N)COC1]

Example 586: 3-[4-[7,7-difluoro-2-[(2R)-2-(trifluoromethyl)azetidin-1-yl]-5,6-dihydrocyclopenta[d]pyrimidin-4-yl]-2-methyl-phenyl]oxetan-3-amine The title compound was prepared in analogy to General Method T, using 3-(4-bromo-2-methyl-phenyl)oxetan-3-amine hydrochloride instead 3-(4-bromo-2-fluoro-phenyl)oxetan-3-amine hydrochloride, followed by General Method F using benzyl (3-(4-bromo-2-methylphenyl)oxetan-3-yl)carbamate and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, followed by General Method U, followed by General Method R.

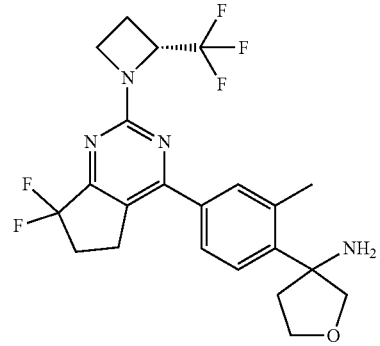 [SMILES: Cc1cc(-c2nc(N3CC[C@@H]3C(F)(F)F)nc3c2CCC3(F)F)ccc1C1(N)CCOC1]

Example 587: 3-[4-[7,7-difluoro-2-[(2R)-2-(trifluoromethyl)azetidin-1-yl]-5,6-dihydrocyclopenta[d]pyrimidin-4-yl]phenyl]tetrahydrofuran-3-amine The title compound was prepared in analogy to General Method T, using 3-(4-bromophenyl)tetrahydrofuran-3-amine instead 3-(4-bromo-2-fluoro-phenyl)oxetan-3-amine hydrochloride, followed by General Method F using benzyl (3-(4-bromophenyl)tetrahydrofuran-3-yl)carbamate and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, followed by General Method U, followed by General Method R.

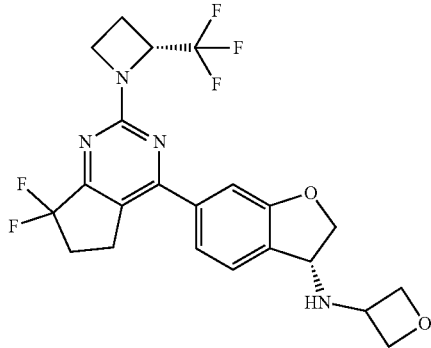 [SMILES: FC1(F)CCc2c(-c3ccc4c(c3)OC[C@@H]4NC3COC3)nc(N3CC[C@@H]3C(F)(F)F)nc21]

Example 588: (3R)-6-[7,7-difluoro-2-[(2R)-2-(trifluoromethyl)azetidin-1-yl]-5,6-dihydrocyclopenta[d]pyrimidin-4-yl]-N-(oxetan-3-yl)-2,3-dihydrobenzofuran-3-amine To a mixture of (3R)-6-bromo-2,3-dihydrobenzofuran-3-amine hydrochloride (1.00 g, 3.99 mmol) and $ZnCl_2$ (816 mg, 5.99 mmol) in MeOH (20 mL) was added 3-Oxetanone (863 mg, 12.0 mmol) dropwise over 1-2 min. To the reaction mixture, $NaCNBH_3$ (753 mg, 12.0 mmol) was charged. The reaction mixture was placed under an atmosphere of $N_2$ and allowed to stir for 18 hours at ambient temperature. The MeOH was removed by rotary evaporation and the residue was dissolved in DCM (50 mL) and NaOH (2M, 30 mL). The layers were separated, and the aqueous layer was extracted with DCM (2×50 mL). The combined organics were washed with NaOH (2 M, 15 mL) and dried over $MgSO_4$, filtered, and concentrated. The crude was subject to flash column chromatography (hexanes-ethyl acetate-methanol) to give (3R)-6-bromo-N-(oxetan-3-yl)-2,3-dihydrobenzofuran-3-amine (542 mg, 2.01 mmol).

The title compound was prepared in analogy to General Method T, followed by General Method F using benzyl N-[(3R)-6-bromo-2,3-dihydrobenzofuran-3-yl]-N-(oxetan-3-yl)carbamate and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, followed by General Method U, followed by General Method R.

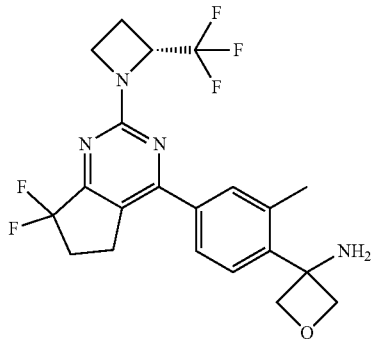 [SMILES: Cc1cc(-c2nc(N3CC[C@@H]3C(F)(F)F)nc3c2CCC3(F)F)ccc1C1(N)COC1]

Example 589: 3-[4-[7,7-difluoro-2-[(2R)-2-(trifluoromethyl)azetidin-1-yl]-5,6-dihydrocyclopenta[d]pyrimidin-4-yl]-2-fluoro-phenyl]oxetan-3-amine The title compound was prepared using General Method T, followed by General Method F using benzyl (3-(4-bromo-2-fluorophenyl)oxetan-3-yl)carbamate and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, followed by General Method U, followed by General Method R.

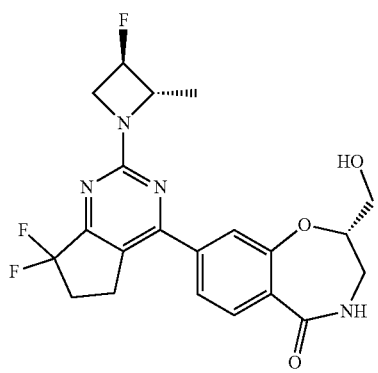 [SMILES: C[C@H]1[C@H](F)CN1c1nc(-c2ccc3c(c2)O[C@H](CO)CNC3=O)c2c(n1)C(F)(F)CC2]

Example 590: (S)-8-(7,7-difluoro-2-((2S,3R)-3-fluoro-2-methylazetidin-1-yl)-6,7-dihydro-5H-cyclopenta[d]pyrimidin-4-yl)-2-(hydroxymethyl)-3,4-dihydrobenzo[f][1,4]oxazepin-5(2H)-one To a solution of tert-butyl (R)-(2,3-dihydroxypropyl)carbamate (1.0 g, 5.23 mmol) and imidazole (570 mg, 8.37 mmol) in DCM (10 mL) at 0° C. was added tert-Butylchlorodimethylsilane (906 mg, 6.01 mmol) dropwise. Following addition, the reaction mixture was allowed to warm to ambient temperature and stirred for 2 hours. The reaction was quenched by the addition of HCl (1 M) to pH<2. The aqueous layer was extracted with DCM (3×100 mL) and the combined organics were dried with $Na_2SO_4$, filtered, and concentrated to give tert-butyl (R)-(3-((tert-butyldimethylsilyl)oxy)-2-hydroxypropyl)carbamate which was used without further purification.

The title compound was prepared in analogy to General Method Q, using tert-butyl (R)-(3-((tert-butyldimethylsilyl)oxy)-2-hydroxypropyl)carbamate instead of tert-butyl (S)-(1-hydroxypropan-2-yl)carbamate, followed by General Method F using (S)-8-bromo-2-(hydroxymethyl)-3,4-dihydrobenzo[f][1,4]oxazepin-5(2H)-one and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, General Method B using (2S,3R)-3-fluoro-2-methyl-azetidine instead of (2S)-2-methylazetidine.

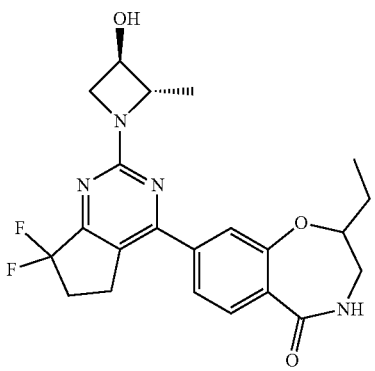 [SMILES: CCC1CNC(=O)c2ccc(-c3nc(N4C[C@@H](O)[C@@H]4C)nc4c3CCC4(F)F)cc2O1]

Example 591: 8-(7,7-difluoro-2-((2S,3R)-3-hydroxy-2-methylazetidin-1-yl)-6,7-dihydro-5H-cyclopenta[d]pyrimidin-4-yl)-2-ethyl-3,4-dihydrobenzo[f][1,4]oxazepin-5(2H)-one To a solution of 1-aminobutan-2-ol (401 mg, 4.50 mmol) in THF (22.5 mL) was charged Di-tert-butyl decarbonate (982 mg, 4.50 mmol) and the mixture was stirred for 18 hours at ambient temperature. The reaction mixture was diluted with sat. aq. NaHCO₃ (20 mL) and the layers separated. The aqueous layer was extracted with EtOAc (3×10 mL). The combined organics were dried over Na₂SO₄, filtered, and concentrated to give tert-butyl N-(2-hydroxybutyl)carbamate which was used without further purification.

The title compound was prepared in analogy to General Method Q, using tert-butyl N-(2-hydroxybutyl)carbamate instead of tert-butyl (S)-(1-hydroxypropan-2-yl)carbamate, followed by General Method F using 8-bromo-2-ethyl-3,4-dihydrobenzo[f][1,4]oxazepin-5(2H)-one and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, General Method B using (2S,3R)-2-methylazetidin-3-ol instead of (2S)-2-methylazetidine.

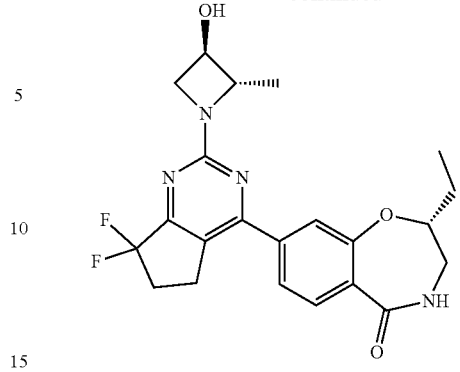

Example 592: (S)-8-(7,7-difluoro-2-((2S,3R)-3-hydroxy-2-methylazetidin-1-yl)-6,7-dihydro-5H-cyclopenta[d]pyrimidin-4-yl)-2-ethyl-3,4-dihydrobenzo[f][1,4]oxazepin-5(2H)-one Example 593: (R)-8-(7,7-difluoro-2-(2S,3R)-3-hydroxy-2-methylazetidin-1-yl)-6,7-dihydro-5H-cyclopenta[d]pyrimidin-4-yl)-2-ethyl-3,4-dihydrobenzo[f][1,4]oxazepin-5(2H)—

Isomers were separated by SFC (35% MeOH in CO₂, CHIRALPAK IG, 250×21 mm, 60 mL/min).

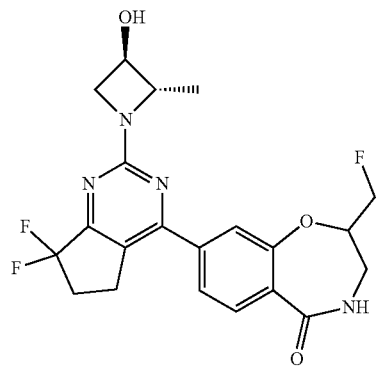 [SMILES: C[C@H]1[C@H](O)CN1c1nc(-c2ccc3c(c2)OC(CF)CNC3=O)c2c(n1)C(F)(F)CC2]

Example 594: 8-(7,7-difluoro-2-((2S,3R)-3-hydroxy-2-methylazetidin-1-yl)-6,7-dihydro-5H-cyclopenta[d]pyrimidin-4-yl)-2-(fluoromethyl)-3,4-dihydrobenzo[f][1,4]oxazepin-5(2H)-one To a solution of 1-amino-3-fluoropropan-2-ol (500 mg, 5.61 mmol) in THF (28 mL) was charged Di-tert-butyl decarbonate (1.22 g, 5.61 mmol) and the reaction mixture was stirred for 18 hours at ambient temperature. The reaction was diluted with sat. aq. NaHCO₃ (20 mL) and the layers were separated. The aqueous layer was extracted with EtOAc (3×10 mL). The combined organics were dried over Na₂SO₄, filtered, and concentrated to give tert-butyl N-(3-fluoro-2-hydroxy-propyl)carbamate which was used without further purification.

The title compound was prepared in analogy to General Method Q, using tert-butyl N-(3-fluoro-2-hydroxy-propyl) carbamate instead of tert-butyl (S)-(1-hydroxypropan-2-yl) carbamate, followed by General Method F using 8-bromo-2-(fluoromethyl)-3,4-dihydro-2H-1,4-benzoxazepin-5-one

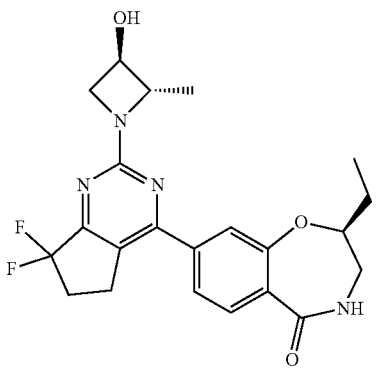

and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, General Method B using (2S,3R)-2-methylazetidin-3-ol instead of (2S)-2-methylazetidine.

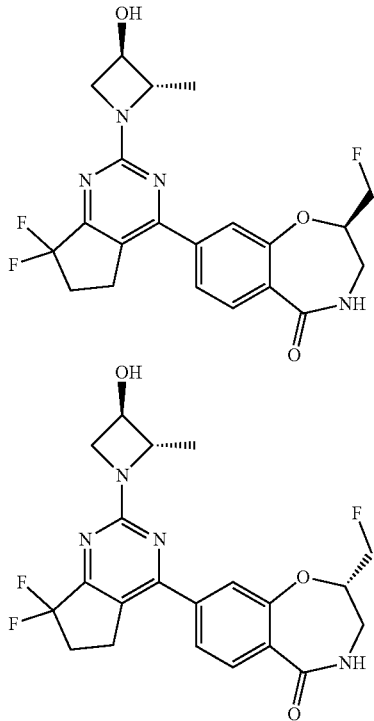 [SMILES: C[C@H]1[C@H](O)CN1c1nc(-c2ccc3c(c2)O[C@@H](CF)CNC3=O)c2c(n1)C(F)(F)CC2 ; C[C@H]1[C@H](O)CN1c1nc(-c2ccc3c(c2)O[C@H](CF)CNC3=O)c2c(n1)C(F)(F)CC2]

Example 595: (R)-8-(7,7-difluoro-2-((2S,3R)-3-hydroxy-2-methylazetidin-1-yl)-6,7-dihydro-5H-cyclopenta[d]pyrimidin-4-yl)-2-(fluoromethyl)-3,4-dihydrobenzo[f][1,4]oxazepin-5(2H)-one Example 596: (S)-8-(7,7-difluoro-2-((2S,3R)-3-hydroxy-2-methylazetidin-1-yl)-6,7-dihydro-5H-cyclopenta[d]pyrimidin-4-yl)-2-(fluoromethyl)-3,4-dihydrobenzo[f][1,4]oxazepin-5(2H)-one Isomers were separated by SFC (40% MeOH in CO₂, CHIRALPAK IG, 250×21 mm, 60 mL/min).

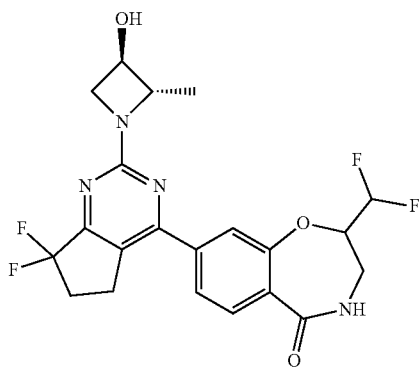 [SMILES: C[C@H]1[C@H](O)CN1c1nc(-c2ccc3c(c2)OC(C(F)F)CNC3=O)c2c(n1)C(F)(F)CC2]

Example 597: 8-(7,7-difluoro-2-((2S,3R)-3-hydroxy-2-methylazetidin-1-yl)-6,7-dihydro-5H-cyclopenta[d]pyrimidin-4-yl)-2-(difluoromethyl)-3,4-dihydrobenzo[f][1,4]oxazepin-5(2H)-one To a solution of 3-amino-1,1-difluoro-propan-2-ol (500 mg, 4.50 mmol) in THF (22.5 mL) was added di-tert-butyl decarbonate (982 mg, 4.50 mmol) and the mixture was stirred for 18 hours at ambient temperature. The reaction mixture was diluted with sat. aq. NaHCO₃ (20 mL) and the layers separated. The aqueous layer was extracted with EtOAc (3×10 mL). The combined organics were dried over Na₂SO₄, filtered, and concentrated to give tert-butyl N-(3,3-difluoro-2-hydroxy-propyl)carbamate, which was used without further purification.

The title compound was prepared in analogy to General Method Q, using tert-butyl N-(3,3-difluoro-2-hydroxy-propyl)carbamate instead of tert-butyl (S)-(1-hydroxypropan-2-yl)carbamate, followed by General Method F using 8-bromo-2-(difluoromethyl)-3,4-dihydro-2H-1,4-benzoxazepin-5-one and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, General Method B using (2S,3R)-2-methylazetidin-3-ol instead of (2S)-2-methylazetidine.

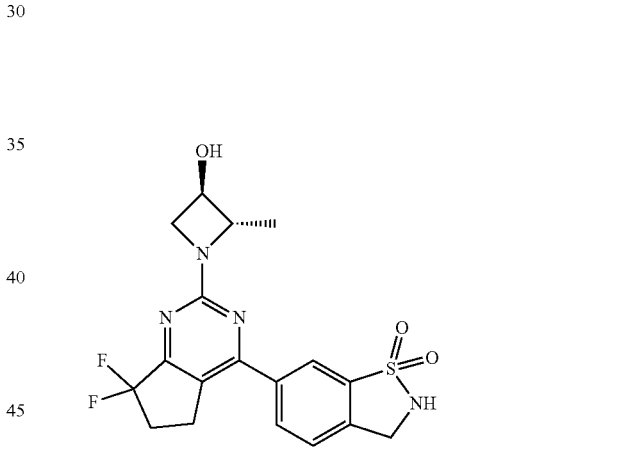

Example 598: 6-(7,7-difluoro-2((2S,3R)-3-hydroxy-2-methylazetidin-1-yl)-6,7-dihydro-5H-cyclopenta[d]pyrimidin-4-yl)-2,3-dihydrobenzo[d]isothiazole 1,1-dioxide The title compound was prepared in analogy to General Method F using 6-bromo-2,3-dihydro-1,2-benzothiazole 1,1-dioxide and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, General Method B using (2S,3R)-2-methylazetidin-3-ol instead of (2S)-2-methylazetidine.

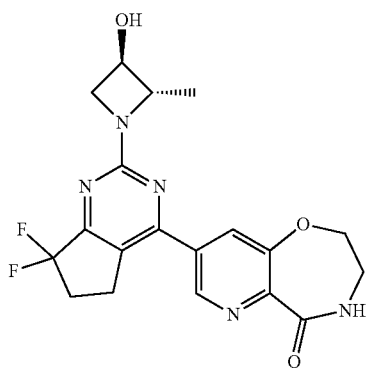 [SMILES: C[C@H]1[C@H](O)CN1c1nc(-c2cnc3c(c2)OCCNC3=O)c2c(n1)C(F)(F)CC2]

Example 599: 8-(7,7-difluoro-24(2S,3R)-3-hydroxy-2-methylazetidin-1-yl)-6,7-dihydro-5H-cyclopenta[d]pyrimidin-4-yl)-3,4-dihydropyrido[2,34][1,4]oxazepin-5(2H)-one The title compound was prepared in analogy to General Method Q, using tert-butyl N-(2-hydroxyethyl)carbamate instead of tert-butyl (S)-(1-hydroxypropan-2-yl)carbamate, followed by General Method F using 8-bromo-3,4-dihydro-2H-pyrido[2,3-f][1,4]oxazepin-5-one and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, General Method B using (2S,3R)-2-methylazetidin-3-ol instead of (2S)-2-methylazetidine.

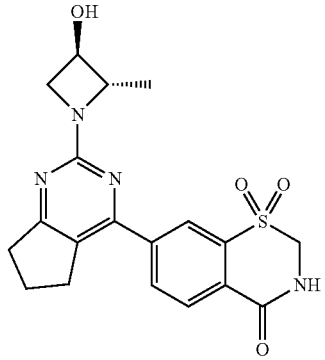

Example 601: 7-(2-((2S,3R)-3-hydroxy-2-methylazetidin-1-yl)-6,7-dihydro-5H-cyclopenta[d]pyrimidin-4-yl)-2,3-dihydro-4H-benzo[e][1,3]thiazin-4-one 1,1-dioxide The title compound was prepared in analogy to General Method F using 7-bromo-1,1-dioxo-2,3-dihydro-16,3-benzothiazin-4-one and [(2S,3R)-1-(4-chloro-6,7-dihydro-5H-cyclopenta[d]pyrimidin-2-yl)-2-methyl-azetidin-3-yl]benzoate instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method C.

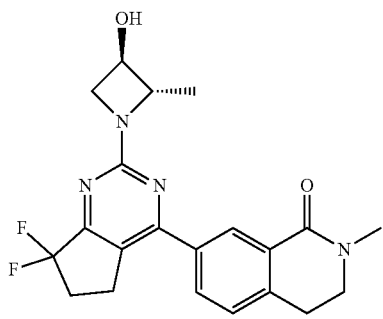 [SMILES: C[C@H]1[C@H](O)CN1c1nc(-c2ccc3c(c2)C(=O)N(C)CC3)c2c(n1)C(F)(F)CC2]

Example 600: 7-(7,7-difluoro-2-((2S,3R)-3-hydroxy-2-methylazetidin-1-yl)-6,7-dihydro-5H-cyclopenta[d]pyrimidin-4-yl)-2-methyl-3,4-dihydroisoquinolin-1(2H)-one The title compound was prepared in analogy to General Method A using 2-methyl-7-(4,4,5,5-tetramethyl-1,3,2-dioxaborolan-2-yl)-3,4-dihydroisoquinolin-1-one and 4-chloro-7,7-difluoro-2-(methylthio)-6,7-dihydro-5H-cyclopenta[d]pyrimidine instead of 3-pyridylboronic acid and 2,4-dichloro-6,7-dihydro-5H-cyclopenta[d]pyrimidine, respectively, followed by General Method M, General Method B using (2S,3R)-2-methylazetidin-3-ol instead of (2S)-2-methylazetidine

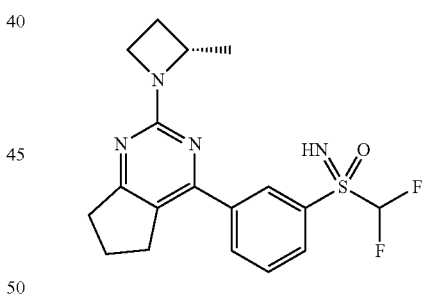

Example 602: (difluoromethyl)(imino)(3-(2-((S)-2-methylazetidin-1-yl)-6,7-dihydro-5H-cyclopenta[d]pyrimidin-4-yl)phenyl)-$\lambda^6$-sulfanone The title compound was prepared in analogy to General Method E using (S)-2-(2-methylazetidin-1-yl)-4-(tributylstannyl)-6,7-dihydro-5H-cyclopenta[d]pyrimidine instead of ethyl 2-tributylstannylimidazo[5,1-b]thiazole-7-carboxylate and (3-bromophenyl)-(difluoromethyl)-imino-oxo-$\lambda^6$-sulfane instead of (S)-4-chloro-2-(2-methylazetidin-1-yl)-6,7-dihydro-5H-cyclopenta[d]pyrimidine.

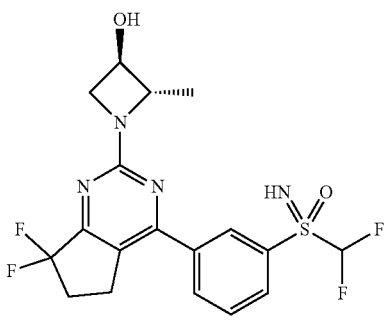 [SMILES: C[C@H]1[C@H](O)CN1c1nc(-c2cccc(S(=N)(=O)C(F)F)c2)c2c(n1)C(F)(F)CC2]

Example 603: (3-(7,7-difluoro-2-((2S,3R)-3-hydroxy-2-methylazetidin-1-yl)-6,7-dihydro-5H-cyclopenta[d]pyrimidin-4-yl)phenyl)(difluoromethyl)(imino)-$\lambda^6$-sulfanone The title compound was prepared in analogy to General Method F using (3-bromophenyl)(difluoromethyl)(imino)-$\lambda^6$-sulfanone and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, and General Method B, using (2S,3R)-2-methylazetidin-3-ol instead of (2S)-2-methylazetidine.

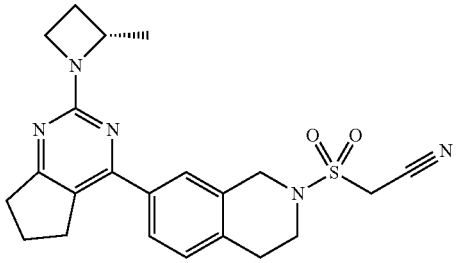 [SMILES: C[C@H]1CCN1c1nc2c(c(-c3ccc4c(c3)CN(S(=O)(=O)CC#N)CC4)n1)CCC2]

Example 604: (S)-2-((7-(2-(2-methylazetidin-1-yl)-6,7-dihydro-5H-cyclopenta[d]pyrimidin-4-yl)-3,4-dihydroisoquinolin-2(1H)-yl)sulfonyl)acetonitrile The title compound was prepared in analogy to General Method K using 7-bromo-1,2,3,4-tetrahydroisoquinoline and cyanomethanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method E using (S)-2-(2-methylazetidin-1-yl)-4-(tributylstannyl)-6,7-dihydro-5H-cyclopenta[d]pyrimidine, instead of ethyl 2-tributylstannylimidazo[5,1-b]thiazole-7-carboxylate.

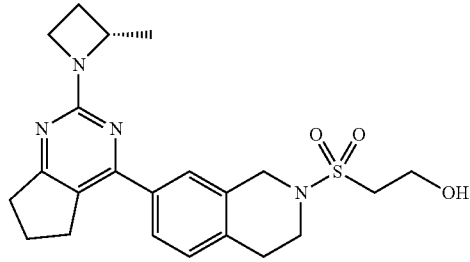 [SMILES: C[C@H]1CCN1c1nc2c(c(-c3ccc4c(c3)CN(S(=O)(=O)CCO)CC4)n1)CCC2]

Example 605: (S)-24(7-(2-(2-methylazetidin-1-yl)-6,7-dihydro-5H-cyclopenta[d]pyrimidin-4-yl)-3,4-dihydroisoquinolin-2(1H)-yl)sulfonyl)ethan-1-ol The title compound was prepared in analogy to General Method K using 7-bromo-1,2,3,4-tetrahydroisoquinoline and 2-hydroxyethane-1-sulfonyl instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method E using (S)-2-(2-methylazetidin-1-yl)-4-(tributylstannyl)-6,7-dihydro-5H-cyclopenta[d]pyrimidine, instead of ethyl 2-tributylstannylimidazo[5,1-b]thiazole-7-carboxylate.

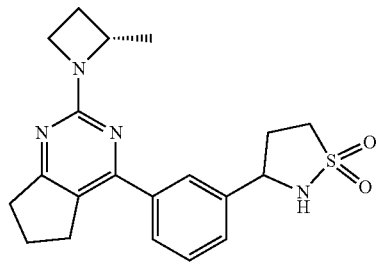 [SMILES: C[C@H]1CCN1c1nc2c(c(-c3cccc(C4CCS(=O)(=O)N4)c3)n1)CCC2]

Example 606: 3-(3-(2-((S)-2-methylazetidin-1-yl)-6,7-dihydro-5H-cyclopenta[d]pyrimidin-4-yl)phenyl)isothiazolidine 1,1-dioxide The title compound was prepared in analogy to General Method E using (S)-2-(2-methylazetidin-1-yl)-4-(tributylstannyl)-6,7-dihydro-5H-cyclopenta[d]pyrimidine and 3-(3-bromophenyl)isothiazolidine 1,1-dioxide, instead of ethyl 2-tributylstannylimidazo[5,1-b]thiazole-7-carboxylate.

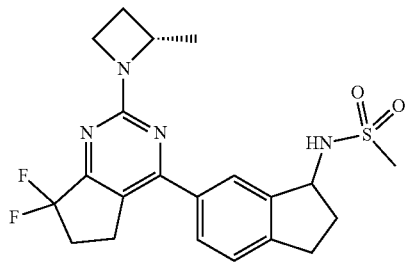 [SMILES: C[C@H]1CCN1c1nc(-c2ccc3c(c2)C(NS(C)(=O)=O)CC3)c2c(n1)C(F)(F)CC2]

Example 607: 3-(4-(7,7-difluoro-24(2S,3S)-3-fluoro-2-methylazetidin-1-yl)-6,7-dihydro-5H-cyclopenta[d]pyrimidin-4-yl)phenyl)oxetan-3-amine The title compound was prepared in a method analogous to General Method K using 6-bromo-2,3-dihydro-1H-inden- 1-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, followed by General Method B.

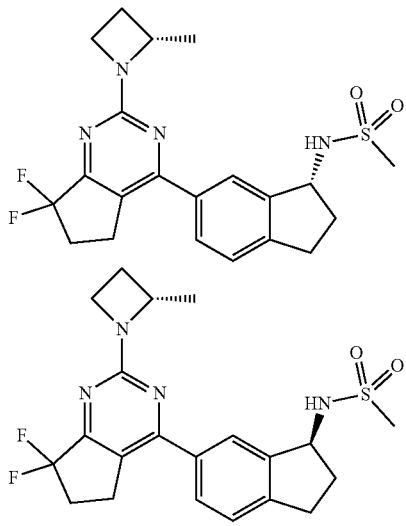

Example 608: N—((R)-6-(7,7-difluoro-2-((S)-2-methylazetidin-1-yl)-6,7-dihydro-5H-cyclopenta[d]pyrimidin-4-yl)-2,3-dihydro-1H-inden-1-yl)methanesulfonamide Example 609: N—((S)-6-(7,7-difluoro-2-((S)-2-methylazetidin-1-yl)-6,7-dihydro-5H-cyclopenta[d]pyrimidin-4-yl)-2,3-dihydro-1H-inden-1-yl)methanesulfonamide Isomers were separated by SFC (30% MeOH in $CO_2$, CHIRALPAK AD-H, 250×21 mm, 60 mL/min).

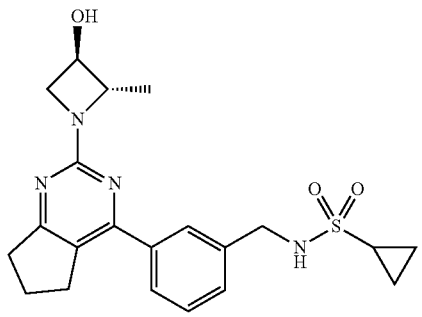 [SMILES: C[C@H]1[C@H](O)CN1c1nc2c(c(-c3cccc(CNS(=O)(=O)C4CC4)c3)n1)CCC2]

Example 610: N-(3-(2-(2S,3R)-3-hydroxy-2-methylazetidin-1-yl)-6,7-dihydro-5H-cyclopenta[d]pyrimidin-4-yl)benzyl)cyclopropanesulfonamide The title compound was prepared in analogy to General Method K using (3-(4,4,5,5-tetramethyl-1,3,2-dioxaborolan-2-yl)phenyl)methanamine and cyclopropylsulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method A using (2S,3R)-1-(4-chloro-6,7-dihydro-5H-cyclopenta[d]pyrimidin-2-yl)-2-methylazetidin-3-yl benzoate 2,4-dichloro-6,7-dihydro-5H-cyclopenta[d]pyrimidine, followed by General Method C.

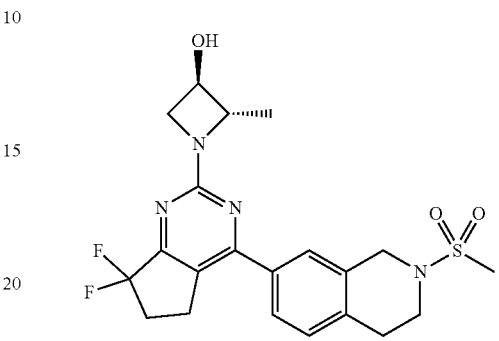

Example 611: (2S,3R)-1-(7,7-difluoro-4-(2-(methylsulfonyl)-1,2,3,4-tetrahydroisoquinolin-7-yl)-6,7-dihydro-5H-cyclopenta[d]pyrimidin-2-yl)-2-methylazetidin-3-ol The title compound was prepared in analogy to General Method A using tert-butyl 7-(4,4,5,5-tetramethyl-1,3,2-dioxaborolan-2-yl)-3,4-dihydroisoquinoline-2(1H)-carboxylate and 4-chloro-7,7-difluoro-2-(methylthio)-6,7-dihydro-5H-cyclopenta[d]pyrimidine instead of 3-pyridylboronic acid and 2,4-dichloro-6,7-dihydro-5H-cyclopenta[d]pyrimidine, respectively, followed by General Method I, followed by General Method K using methanesulfonyl chloride instead of 1-methylimidazole-4-sulfonyl chloride, followed by General Method M, followed by General Method B using (2S,3R)-2-methylazetidin-3-ol instead of (2S)-2-methylazetidine.

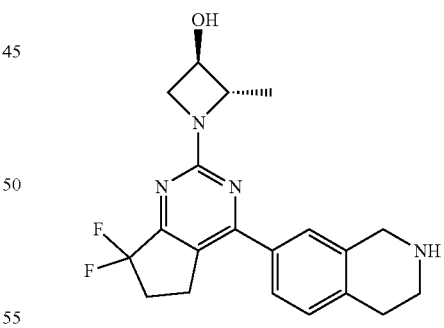

Example 612: (2S,3R)-1-(7,7-difluoro-4-(1,2,3,4-tetrahydroisoquinolin-7-yl)-6,7-dihydro-5H-cyclopenta[d]pyrimidin-2-yl)-2-methylazetidin-3-ol The title compound was prepared in analogy to General Method O using tert-butyl 7-(4,4,5,5-tetramethyl-1,3,2-dioxaborolan-2-yl)-3,4-dihydroisoquinoline-2(1H)-carboxylate and 4-chloro-7,7-difluoro-2-(methylthio)-6,7-dihydro-5H-cyclopenta[d]pyrimidine instead of 3-pyridylboronic acid and 2,4-dichloro-6,7-dihydro-5H-cyclopenta[d]pyrimidine, respectively, followed by General Method M, followed by General Method B using (2S,3R)-2-methylazetidin-3-ol instead of (2S)-2-methylazetidine, followed by General Method I.

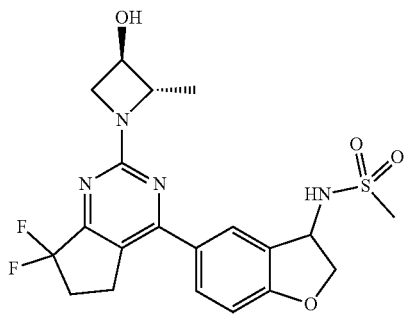 [SMILES: C[C@H]1[C@H](O)CN1c1nc(-c2ccc3c(c2)C(NS(C)(=O)=O)CO3)c2c(n1)C(F)(F)CC2]

Example 613: N-(5-(7,7-difluoro-24(2S,3R)-3-hydroxy-2-methylazetidin-1-yl)-6,7-dihydro-5H-cyclopenta[d]pyrimidin-4-yl)-2,3-dihydrobenzofuran-3-yl)methanesulfonamide The title compound was prepared in analogy to General Method K using 5-bromo-2,3-dihydrobenzofuran-3-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F, followed by General Method M, followed by General Method B using (2S,3R)-2-methylazetidin-3-ol instead of (2S)-2-methylazetidine.

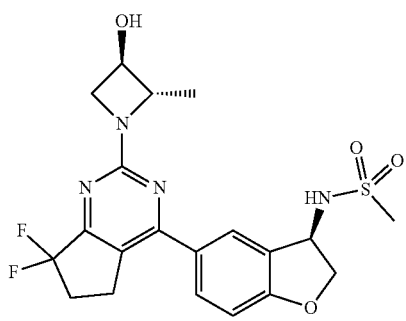

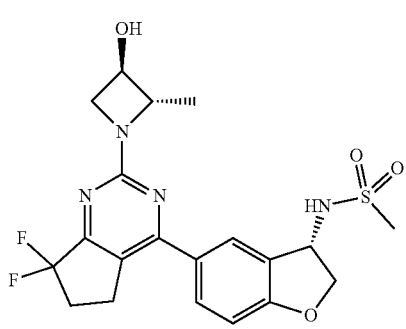

Example 614: N—((R)-5-(7,7-difluoro-24(2S,3R)-3-hydroxy-2-methylazetidin-1-yl)-6,7-dihydro-5H-cyclopenta[d]pyrimidin-4-yl)-2,3-dihydrobenzofuran-3-yl)methanesulfonamide Example 615: N—((S)-5-(7,7-difluoro-24(2S,3R)-3-hydroxy-2-methylazetidin-1-yl)-6,7-dihydro-5H-cyclopenta[d]pyrimidin-4-yl)-2,3-dihydrobenzofuran-3-yl)methanesulfonamide Isomers were separated by SFC (20% MeOH in $CO_2$, CHIRALPAK IA, 250×21 mm, 60 mL/min).

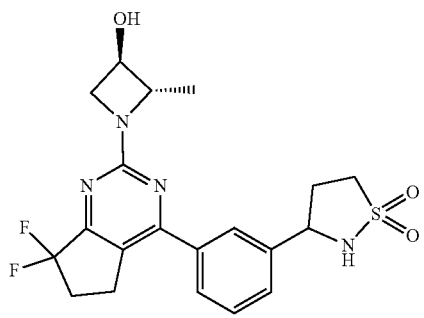 [SMILES: C[C@H]1[C@H](O)CN1c1nc(-c2cccc(C3CCS(=O)(=O)N3)c2)c2c(n1)C(F)(F)CC2]

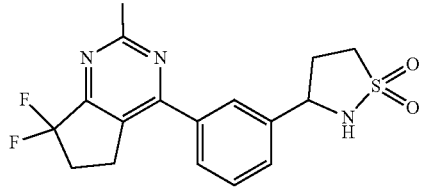

Example 616: 3-(3-(7,7-difluoro-24(2S,3R)-3-hydroxy-2-methylazetidin-1-yl)-6,7-dihydro-5H-cyclopenta[d]pyrimidin-4-yl)phenyl)isothiazolidine 1,1-dioxide The title compound was prepared in a method analogous to General Method F using 4-chloro-7,7-difluoro-2-(methylthio)-6,7-dihydro-5H-cyclopenta[d]pyrimidine and 3-(3-bromophenyl)isothiazolidine 1,1-dioxide instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one, respectively, followed by General Method M, followed by using General Method B using (2S,3R)-2-methylazetidin-3-ol instead of (2S)-2-methylazetidine.

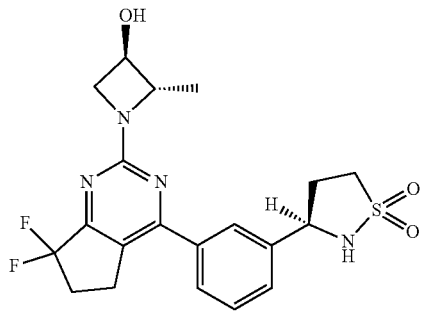

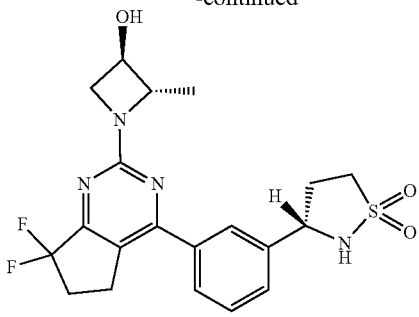

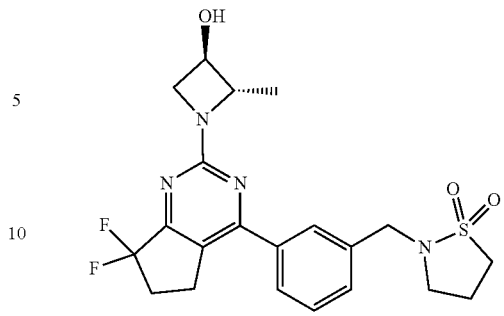

Example 617: (R)-3-(3-(7,7-difluoro-24(2S,3R)-3-hydroxy-2-methylazetidin-1-yl)-6,7-dihydro-5H-cyclopenta[d]pyrimidin-4-yl)phenyl)isothiazolidine 1,1-dioxide Example 618: (S)-3-(3-(7,7-difluoro-24(2S,3R)-3-hydroxy-2-methylazetidin-1-yl)-6,7-dihydro-5H-cyclopenta[d]pyrimidin-4-yl)phenyl)isothiazolidine 1,1-dioxide Isomers were separated by SFC (35% MeOH in $CO_2$, CHIRALPAK ADH, 250×21 mm, 60 mL/min).

Example 620: 2-(3-(7,7-difluoro-24(2S,3R)-3-hydroxy-2-methylazetidin-1-yl)-6,7-dihydro-5H-cyclopenta[d]pyrimidin-4-yl)benzyl)isothiazolidine 1,1-dioxide The title compound was prepared in a method analogous to General Method O using 4-chloro-7,7-difluoro-2-(methylthio)-6,7-dihydro-5H-cyclopenta[d]pyrimidine and 2-(3-(4,4,5,5-tetramethyl-1,3,2-dioxaborolan-2-yl)benzyl)isothiazolidine 1,1-dioxide instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one, respectively, followed by General Method M, followed by General Method B using (2S,3R)-2-methylazetidin-3-ol instead of (2S)-2-methylazetidine.

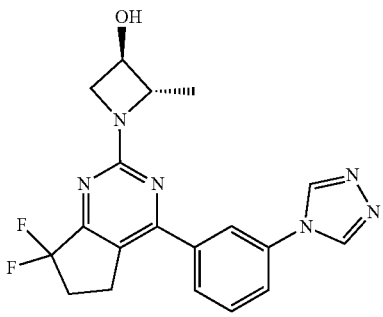 [SMILES: C[C@H]1[C@H](O)CN1c1nc(-c2cccc(-n3cnnc3)c2)c2c(n1)C(F)(F)CC2]

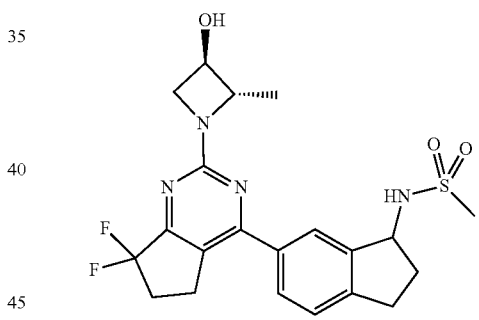

Example 621: N-(6-(7,7-difluoro-24(2S,3R)-3-hydroxy-2-methylazetidin-1-yl)-6,7-dihydro-5H-cyclopenta[d]pyrimidin-4-yl)-2,3-dihydro-1H-inden-1-yl)methanesulfonamide Example 619: (2S,3R)-1-(4-(3-(4H-1,2,4-triazol-4-yl)phenyl)-7,7-difluoro-6,7-dihydro-5H-cyclopenta[d]pyrimidin-2-yl)-2-methylazetidin-3-ol The title compound was prepared in a method analogous to General Method F using 4-chloro-7,7-difluoro-2-(methylthio)-6,7-dihydro-5H-cyclopenta[d]pyrimidine and 4-(3-bromophenyl)-4H-1,2,4-triazole instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one, respectively, followed by General Method M, followed by General Method B using (2S,3R)-2-methylazetidin-3-ol instead of (2S)-2-methylazetidine.

The title compound was prepared in a method analogous to General Method K using 6-bromo-2,3-dihydro-1H-inden-1-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one, respectively, followed by General Method M, followed by General Method B using (2S,3R)-2-methylazetidin-3-ol instead of (2S)-2-methylazetidine.

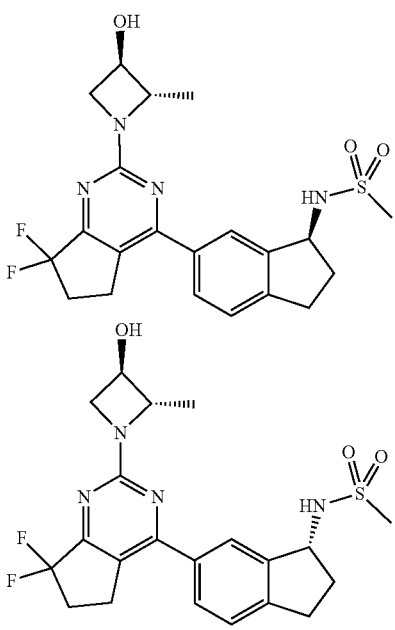

Example 622: N—((S)-6-(7,7-difluoro-2-((2S,3R)-3-hydroxy-2-methylazetidin-1-yl)-6,7-dihydro-5H-cyclopenta[d]pyrimidin-4-yl)-2,3-dihydro-1H-inden-1-yl)methanesulfonamide Example 623: N—((R)-6-(7,7-difluoro-2-((2S,3R)-3-hydroxy-2-methylazetidin-1-yl)-6,7-dihydro-5H-cyclopenta[d]pyrimidin-4-yl)-2,3-dihydro-1H-inden-1-yl)methanesulfonamide Isomers were separated by SFC (20% MeOH in $CO_2$, CHIRALPAK AD-H, 250×21 mm, 60 mL/min).

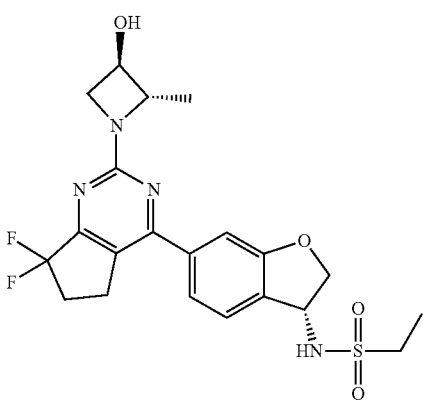 [SMILES: CCS(=O)(=O)N[C@H]1COc2cc(-c3nc(N4C[C@@H](O)[C@@H]4C)nc4c3CCC4(F)F)ccc21]

Example 624: N—((R)-6-(7,7-difluoro-2-((2S,3R)-3-hydroxy-2-methylazetidin-1-yl)-6,7-dihydro-5H-cyclopenta[d]pyrimidin-4-yl)-2,3-dihydrobenzofuran-3-yl)ethanesulfonamide The title compound was prepared in a method analogous to General Method AB using (R)-6-bromo-2,3-dihydrobenzofuran-3-amine instead of 6-bromo-1,1-dioxo-2,3-dihydrobenzothiophen-3-amine, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method I, followed by General Method K using ethanesulfonyl chloride instead of 1-methylimidazole-4-sulfonyl chloride, followed by General Method M, followed by General Method B using (2S,3R)-2-methylazetidin-3-ol instead of (2S)-2-methylazetidine.

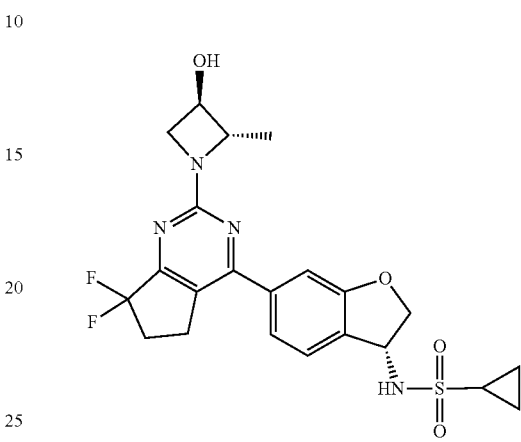

Example 625: N—((R)-6-(7,7-difluoro-2-(2S,3R)-3-hydroxy-2-methylazetidin-1-yl)-6,7-dihydro-5H-cyclopenta[d]pyrimidin-4-yl)-2,3-dihydrobenzofuran-3-yl)cyclopropanesulfonamide The title compound was prepared in a method analogous to General Method AB using (R)-6-bromo-2,3-dihydrobenzofuran-3-amine instead of 6-bromo-1,1-dioxo-2,3-dihydrobenzothiophen-3-amine, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method I, followed by General Method K using cyclopropylsulfonyl chloride instead of 1-methylimidazole-4-sulfonyl chloride, followed by General Method M, followed by General Method B using (2S,3R)-2-methylazetidin-3-ol instead of (2S)-2-methylazetidine.

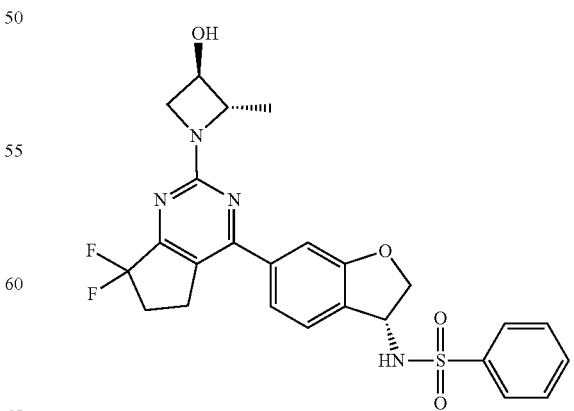

Example 626: N-((R)-6-(7,7-difluoro-2-((2S,3R)-3-hydroxy-2-methylazetidin-1-yl)-6,7-dihydro-5H-cyclopenta[d]pyrimidin-4-yl)-2,3-dihydrobenzofuran-3-yl)benzenesulfonamide The title compound was prepared in a method analogous to General Method AB using (R)-6-bromo-2,3-dihydrobenzofuran-3-amine instead of 6-bromo-1,1-dioxo-2,3-dihydrobenzothiophen-3-amine, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, followed by General Method B using (2S,3R)-2-methylazetidin-3-ol instead of (2S)-2-methylazetidine, followed by General Method I, followed by General Method K using benzenesulfonyl chloride instead of 1-methylimidazole-4-sulfonyl chloride.

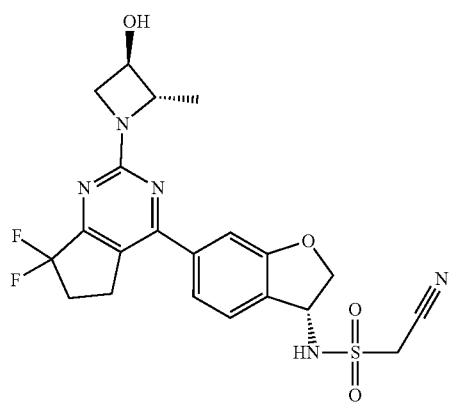 [SMILES: C[C@H]1[C@H](O)CN1c1nc(-c2ccc3c(c2)OC[C@@H]3NS(=O)(=O)CC#N)c2c(n1)C(F)(F)CC2]

Example 627: 1-cyano-N-((R)-6-(7,7-difluoro-2-((2S,3R)-3-hydroxy-2-methylazetidin-1-yl)-6,7-dihydro-5H-cyclopenta[d]pyrimidin-4-yl)-2,3-dihydrobenzofuran-3-yl)methanesulfonamide The title compound was prepared in a method analogous to General Method AB using (R)-6-bromo-2,3-dihydrobenzofuran-3-amine instead of 6-bromo-1,1-dioxo-2,3-dihydrobenzothiophen-3-amine, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, followed by General Method B using (2S,3R)-2-methylazetidin-3-ol instead of (2S)-2-methylazetidine, followed by General Method I, followed by General Method K using cyanomethylsulfonyl chloride instead of 1-methylimidazole-4-sulfonyl chloride.

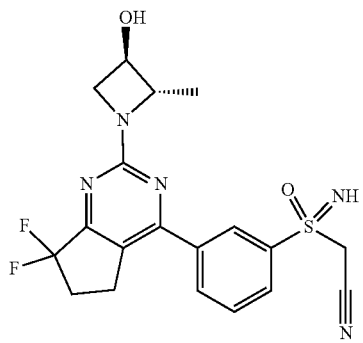 [SMILES: C[C@H]1[C@H](O)CN1c1nc(-c2cccc(S(=N)(=O)CC#N)c2)c2c(n1)C(F)(F)CC2]

Example 628: 2-(3-(7,7-difluoro-2-((2S,3R)-3-hydroxy-2-methylazetidin-1-yl)-6,7-dihydro-5H-cyclopenta[d]pyrimidin-4-yl)phenylsulfonimidoyl)acetonitrile The title compound was prepared in a method analogous to General Method F using 4-chloro-7,7-difluoro-2-(methylthio)-6,7-dihydro-5H-cyclopenta[d]pyrimidine and tert-butyl ((3-bromophenyl)(cyanomethyl)(oxo)-16-sulfaneylidene)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one, respectively, followed by General Method M, followed by General Method B using (2S,3R)-2-methylazetidin-3-ol instead of (2S)-2-methylazetidine, followed by General Method I.

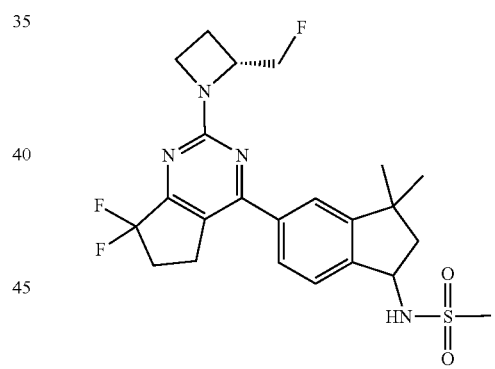

Example 629: N-(5-(7,7-difluoro-2-((R)-2-(fluoromethyl)azetidin-1-yl)-6,7-dihydro-5H-cyclopenta[d]pyrimidin-4-yl)-3,3-dimethyl-2,3-dihydro-1H-inden-1-yl)methanesulfonamide The title compound was prepared in a method analogous to General Method W using 5-bromo-3,3-dimethyl-2,3-dihydro-1H-inden-1-one instead of 5-bromo-7-methoxy-2,3-dihydro-1H-inden-1-one, followed by General Method K using methanesulfonyl chloride instead of 1-methylimidazole-4-sulfonyl chloride, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, followed by General Method B using (R)-2-(fluoromethyl)azetidine instead of (2S)-2-methylazetidine.

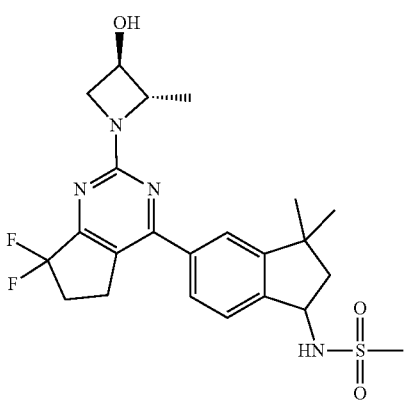 [SMILES: C[C@H]1[C@H](O)CN1c1nc(-c2ccc3c(c2)C(C)(C)CC3NS(C)(=O)=O)c2c(n1)C(F)(F)CC2]

Example 630: N-(5-(7,7-difluoro-2-((2S,3R)-3-hydroxy-2-methylazetidin-1-yl)-6,7-dihydro-5H-cyclopenta[d]pyrimidin-4-yl)-3,3-dimethyl-2,3-dihydro-1H-inden-1-yl)methanesulfonamide The title compound was prepared in a method analogous to General Method W using 5-bromo-3,3-dimethyl-2,3-dihydro-1H-inden-1-one instead of 5-bromo-7-methoxy-2,3-dihydro-1H-inden-1-one, followed by General Method K using methanesulfonyl chloride instead of 1-methylimidazole-4-sulfonyl chloride, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, followed by General Method B using (2S,3R)-2-methylazetidin-3-ol instead of (2S)-2-methylazetidine.

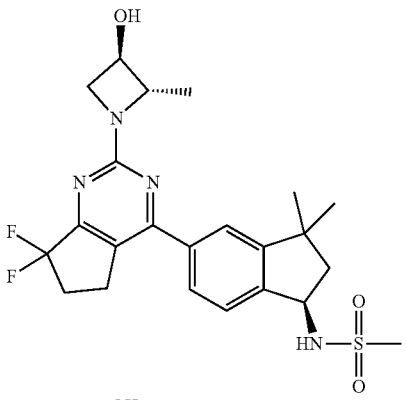

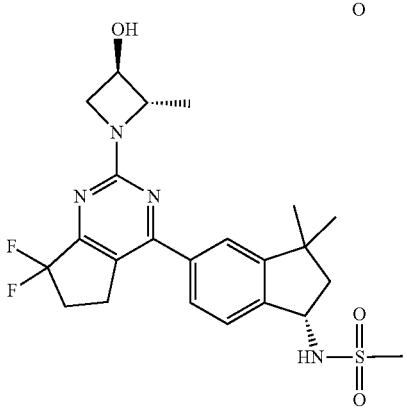

Example 631: N—((R)-5-(7,7-difluoro-2-((2S,3R)-3-hydroxy-2-methylazetidin-1-yl)-6,7-dihydro-5H-cyclopenta[d]pyrimidin-4-yl)-3,3-dimethyl-2,3-dihydro-1H-inden-1-yl)methanesulfonamide Example 632: N—((S)-5-(7,7-difluoro-2-((2S,3R)-3-hydroxy-2-methylazetidin-1-yl)-6,7-dihydro-5H-cyclopenta[d]pyrimidin-4-yl)-3,3-dimethyl-2,3-dihydro-1H-inden-1-yl)methanesulfonamide Isomers were separated by SFC (15% EtOH in $CO_2$, CHIRALPAK OJ-H, 250×21 mm, 60 mL/min).

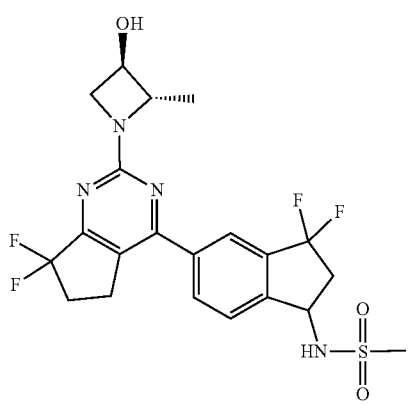 [SMILES: C[C@H]1[C@H](O)CN1c1nc(-c2ccc3c(c2)C(F)(F)CC3NS(C)(=O)=O)c2c(n1)C(F)(F)CC2]

Example 633: N-(5-(7,7-difluoro-2-((2S,3R)-3-hydroxy-2-methylazetidin-1-yl)-6,7-dihydro-5H-cyclopenta[d]pyrimidin-4-yl)-3,3-difluoro-2,3-dihydro-1H-inden-1-yl)methanesulfonamide The title compound was prepared in a method analogous to General Method W using 5-bromo-3,3-difluoro-2,3-dihydro-1H-inden-1-one instead of 5-bromo-7-methoxy-2,3-dihydro-1H-inden-1-one, followed by General Method K using methanesulfonyl chloride instead of 1-methylimidazole-4-sulfonyl chloride, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, followed by General Method B using (2S,3R)-2-methylazetidin-3-ol instead of (2S)-2-methylazetidine.

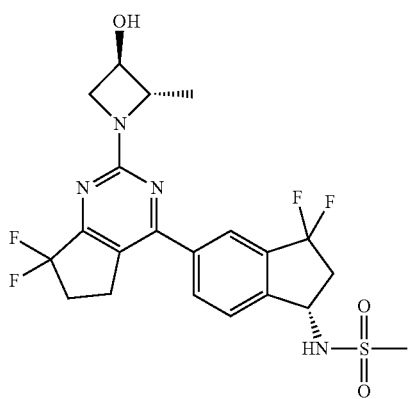

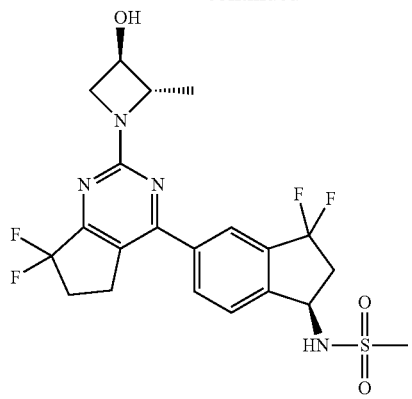

Example 634: N—((S)-5-(7,7-difluoro-2-((2S,3R)-3-hydroxy-2-methylazetidin-1-yl)-6,7-dihydro-5H-cyclopenta[d]pyrimidin-4-yl)-3,3-difluoro-2,3-dihydro-1H-inden-1-yl)methanesulfonamide Example 635: N—((R)-5-(7,7-difluoro-2-((2S,3R)-3-hydroxy-2-methylazetidin-1-yl)-6,7-dihydro-5H-cyclopenta[d]pyrimidin-4-yl)-3,3-difluoro-2,3-dihydro-1H-inden-1-yl)methanesulfonamide Isomers were separated by SFC (15% EtOH in $CO_2$, CHIRALPAK OJ-H, 250×21 mm, 60 mL/min).

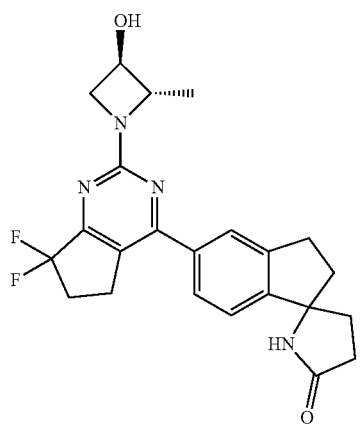 [SMILES: C[C@H]1[C@H](O)CN1c1nc(-c2ccc3c(c2)CCC32CCC(=O)N2)c2c(n1)C(F)(F)CC2]

Example 636: 5-(7,7-difluoro-2-((2S,3R)-3-hydroxy-2-methylazetidin-1-yl)-6,7-dihydro-5H-cyclopenta[d]pyrimidin-4-yl)-2,3-dihydrospiro[indene-1,2'-pyrrolidin]-5'-one The title compound was prepared according to General Method AE, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, followed by General Method B using (2S,3R)-2-methylazetidin-3-ol instead of (2S)-2-methylazetidine.

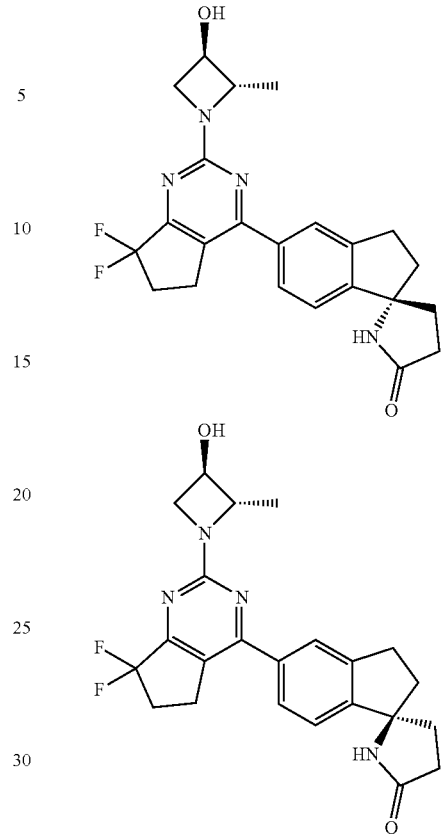

Example 637: (R)-5-(7,7-difluoro-2-((2S,3R)-3-hydroxy-2-methylazetidin-1-yl)-6,7-dihydro-5H-cyclopenta[d]pyrimidin-4-yl)-2,3-dihydrospiro[indene-1,2'-pyrrolidin]-5'-one Example 638: (S)-5-(7,7-difluoro-2-((2S,3R)-3-hydroxy-2-methylazetidin-1-yl)-6,7-dihydro-5H-cyclopenta[d]pyrimidin-4-yl)-2,3-dihydrospiro[indene-1,2'-pyrrolidin]-5'-one Isomers were separated by SFC (35% EtOH in $CO_2$, CHIRALPAK AD-H, 250×21 mm, 60 mL/min).

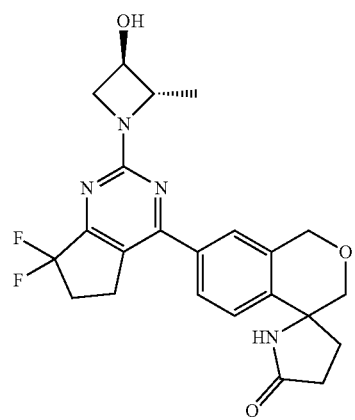 [SMILES: C[C@H]1[C@H](O)CN1c1nc(-c2ccc3c(c2)COCC32CCC(=O)N2)c2c(n1)C(F)(F)CC2]

Example 639: 7-(7,7-difluoro-24(2S,3R)-3-hydroxy-2-methylazetidin-1-yl)-6,7-dihydro-5H-cyclopenta[d]pyrimidin-4-yl)spiro[isochromane-4,2'-pyrrolidin]-5'-one To n-BuLi in hexanes (9.9 mL, 1.6M) was added dropwise a 0° C. slurry of methyltriphenylphosphonium bromide (4000 mg, 14.5 mmol) in THF (45 mL). After 1 h, a solution of 7-bromoisochroman-4-one (3000 mg, 13.2 mmol) in THF (30 mL) was added to the resulting solution and the cold bath was removed. Upon completion, the reaction mixture was quenched with water and ethyl acetate was added (400 mL). The organic layer was washed with aq. NaHCO₃ and brine. The organics were dried over Na₂SO₄, then concentrated and subjected to flash column chromatography (hexanes) to give 7-bromo-4-methyleneisochromane The title compound was prepared in analogy to General Method AE using 7-bromo-4-methyleneisochromane instead of 5-bromo-1-methylene-2,3-dihydro-1H-indene, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, followed by using General Method B using (2S,3R)-2-methylazetidin-3-ol instead of (2S)-2-methylazetidine.

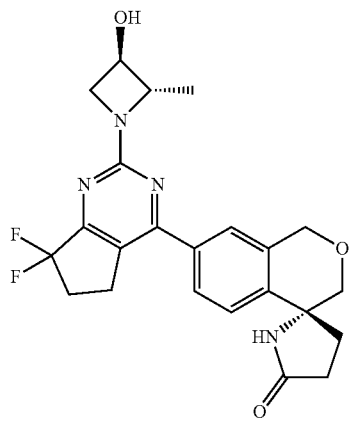

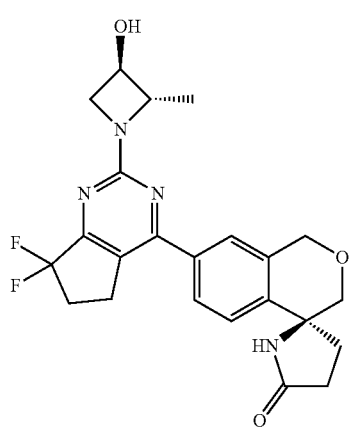

Example 640: (R)-7-(7,7-difluoro-2-((2S,3R)-3-hydroxy-2-methylazetidin-1-yl)-6,7-dihydro-5H-cyclopenta[d]pyrimidin-4-yl)spiro[isochromane-4,2'-pyrrolidin]-5'-one

Example 641: (S)-7-(7,7-difluoro-2-(2S,3R)-3-hydroxy-2-methylazetidin-1-yl)-6,7-dihydro-5H-cyclopenta[d]pyrimidin-4-yl)spiro[isochromane-4,2'-pyrrolidin]-5'-one Isomers were separated by SFC (35% EtOH in CO₂, CHIRALPAK AD-H, 250×21 mm, 60 mL/min).

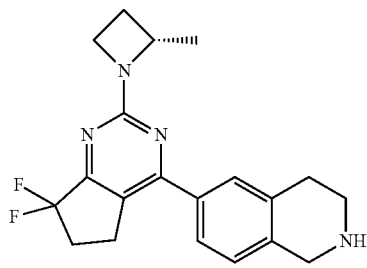 [SMILES: C[C@H]1CCN1c1nc(-c2ccc3c(c2)CCNC3)c2c(n1)C(F)(F)CC2]

Example 642: 6-[7,7-difluoro-2-[(2S)-2-methylazetidin-1-yl]-5,6-dihydrocyclopenta[d]pyrimidin-4-yl]-1,2,3,4-tetrahydroisoquinoline The title compound was prepared in a method analogous to General Method A using 4-chloro-7,7-difluoro-2-[(2S)-2-methylazetidin-1-yl]-5,6-dihydrocyclopenta[d]pyrimidine and tert-butyl 6-(4,4,5,5-tetramethyl-1,3,2-dioxaborolan-2-yl)-3,4-dihydro-1H-isoquinoline-2-carboxylate instead of 2,4-dichloro-6,7-dihydro-5H-cyclopenta[d]pyrimidine and 3-pyridylboronic acid respectively, followed by General Method I.

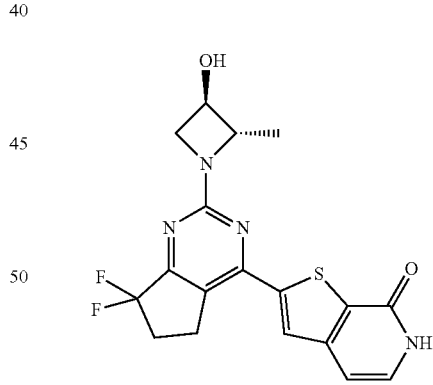

Example 643: 2-[7,7-difluoro-2-[(2S,3R)-3-hydroxy-2-methyl-azetidin-1-yl]-5,6-dihydrocyclopenta[d]pyrimidin-4-yl]-6H-thieno[2,3-c]pyridin-7-one The title compound was prepared in a method analogous to General Method D using 2-bromo-6H-thieno[2,3-c]pyridin-7-one instead of ethyl 2-bromoimidazo[5,1-b]thiazole-7-carboxylate, followed by General Method E using [(2S,3R)-1-(4-chloro-7,7-difluoro-5,6-dihydrocyclopenta[d]pyrimidin-2-yl)-2-methyl-azetidin-3-yl]benzoate instead of (S)-4-chloro-2-(2-methylazetidin-1-yl)-6,7-dihydro-5H-cyclopenta[d]pyrimidine, followed by General Method C.

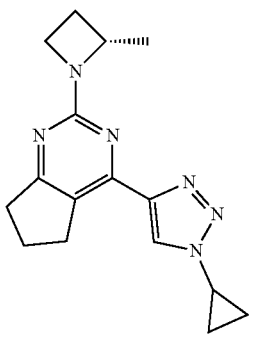 [SMILES: C[C@H]1CCN1c1nc2c(c(-c3cn(C4CC4)nn3)n1)CCC2]

Example 644: 4-(1-cyclopropyltriazol-4-yl)-2-[(2S)-2-methylazetidin-1-yl]-6,7-dihydro-5H-cyclopenta[d]pyrimidine The title compound was prepared in a method analogous to General Method AA using azidocyclopropane instead of 3-azidooxetane.

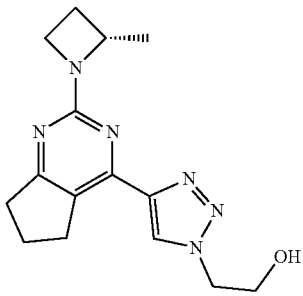 [SMILES: C[C@H]1CCN1c1nc2c(c(-c3cn(CCO)nn3)n1)CCC2]

Example 645: 2-[4-[2-[(2S)-2-methylazetidin-1-yl]-6,7-dihydro-5H-cyclopenta[d]pyrimidin-4-yl]triazol-1-yl]ethanol The title compound was prepared in a method analogous to General Method AA using 2-azidoethanol instead of 3-azidooxetane.

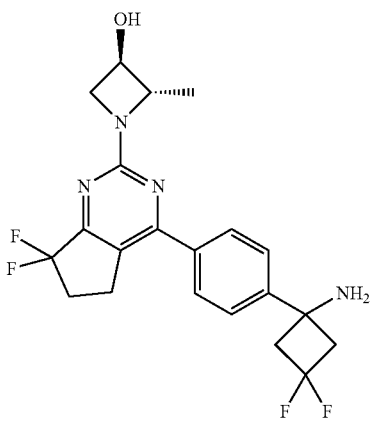 [SMILES: C[C@H]1[C@H](O)CN1c1nc(-c2ccc(C3(N)CC(F)(F)C3)cc2)c2c(n1)C(F)(F)CC2]

Example 646: (2S,3R)-1-[4-[4-(1-amino-3,3-difluoro-cyclobutyl)phenyl]-7,7-difluoro-5,6-dihydro-cyclopenta[d]pyrimidin-2-yl]-2-methyl-azetidin-3-ol The title compound was prepared in a method analogous to General Method A using [(2S,3R)-1-(4-chloro-7,7-difluoro-5,6-dihydrocyclopenta[d]pyrimidin-2-yl)-2-methyl-azetidin-3-yl]benzoate and tert-butyl N-[3,3-difluoro-1-[4-(4,4,5,5-tetramethyl-1,3,2-dioxaborolan-2-yl)phenyl]cyclobutyl]carbamate instead of 2,4-dichloro-6,7-dihydro-5H-cyclopenta[d]pyrimidine and 3-pyridylboronic acid respectively, followed by General Method I, followed by General Method C.

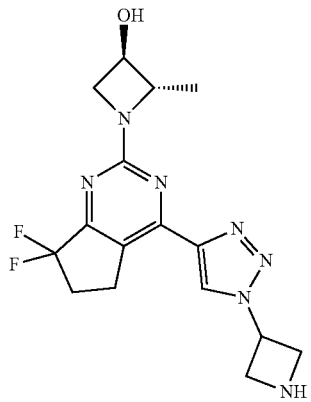 [SMILES: C[C@H]1[C@H](O)CN1c1nc(-c2cn(C3CNC3)nn2)c2c(n1)C(F)(F)CC2]

Example 647: (2S,3R)-1-[4-[1-(azetidin-3-yl)triazol-4-yl]-7,7-difluoro-5,6-dihydrocyclopenta[d]pyrimidin-2-yl]-2-methyl-azetidin-3-ol The title compound was prepared in a method analogous to General Method P using [(2S,3R)-1-(4-chloro-7,7-difluoro-5,6-dihydrocyclopenta[d]pyrimidin-2-yl)-2-methyl-azetidin-3-yl]benzoate instead of 4-chloro-2-[(2S)-2-methylazetidin-1-yl]-6,7-dihydro-5H-cyclopenta[d]pyrimidine, omitting the last step to yield [(2S,3R)-1-(7,7-difluoro-4-formyl-5,6-dihydrocyclopenta[d]pyrimidin-2-yl)-2-methyl-azetidin-3-yl]benzoate, followed by General Method AA using tert-butyl 3-azidoazetidine-1-carboxylate instead of 3-azidooxetane, followed by General Method I.

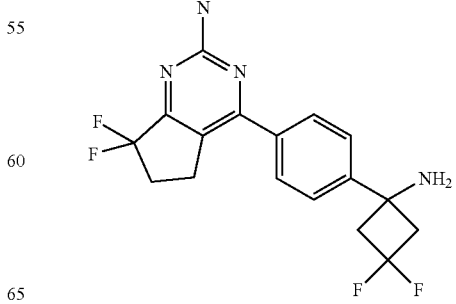

Example 648: 1-[4-[7,7-difluoro-2-[(2S)-2-methyl-azetidin-1-yl]-5,6-dihydrocyclopenta[d]pyrimidin-4-yl]phenyl]-3,3-difluoro-cyclobutanamine The title compound was prepared in a method analogous to General Method A using 4-chloro-7,7-difluoro-2-[(2S)-2-methylazetidin-1-yl]-5,6-dihydrocyclopenta[d]pyrimidine and tert-butyl N-[3,3-difluoro-1-[4-(4,4,5,5-tetramethyl-1,3,2-dioxaborolan-2-yl)phenyl]cyclobutyl]carbamate instead of 2,4-dichloro-6,7-dihydro-5H-cyclopenta[d]pyrimidine and 3-pyridylboronic acid respectively, followed by General Method I.

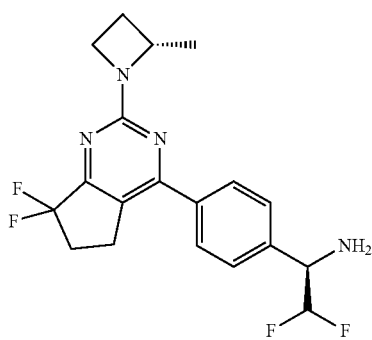 [SMILES: C[C@H]1CCN1c1nc(-c2ccc([C@@H](N)C(F)F)cc2)c2c(n1)C(F)(F)CC2]

Example 649: (1R)-1-[4-[7,7-difluoro-2-[(2S)-2-methylazetidin-1-yl]-5,6-dihydrocyclopenta[d]pyrimidin-4-yl]phenyl]-2,2-difluoro-ethanamine The title compound was prepared in a method analogous to General Method A using 4-chloro-7,7-difluoro-2-[(2S)-2-methylazetidin-1-yl]-5,6-dihydrocyclopenta[d]pyrimidine and tert-butyl N-[(1R)-2,2-difluoro-1-[4-(4,4,5,5-tetramethyl-1,3,2-dioxaborolan-2-yl)phenyl]ethyl]carbamate instead of 2,4-dichloro-6,7-dihydro-5H-cyclopenta[d]pyrimidine and 3-pyridylboronic acid respectively, followed by General Method I.

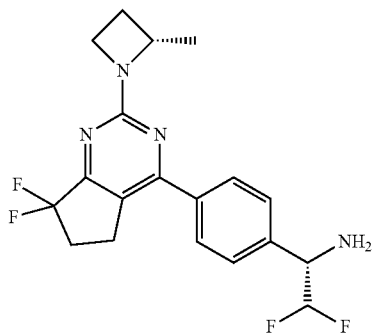 [SMILES: C[C@H]1CCN1c1nc(-c2ccc([C@H](N)C(F)F)cc2)c2c(n1)C(F)(F)CC2]

Example 650: (1S)-1-[4-[7,7-difluoro-2-[(2S)-2-methylazetidin-1-yl]-5,6-dihydrocyclopenta[d]pyrimidin-4-yl]phenyl]-2,2-difluoro-ethanamine The title compound was prepared in a method analogous to General Method A using 4-chloro-7,7-difluoro-2-[(2S)-2-methylazetidin-1-yl]-5,6-dihydrocyclopenta[d]pyrimidine and tert-butyl N-[(1S)-2,2-difluoro-1-[4-(4,4,5,5-tetramethyl-1,3,2-dioxaborolan-2-yl)phenyl]ethyl]carbamate instead of 2,4-dichloro-6,7-dihydro-5H-cyclopenta[d]pyrimidine and 3-pyridylboronic acid respectively, followed by General Method I.

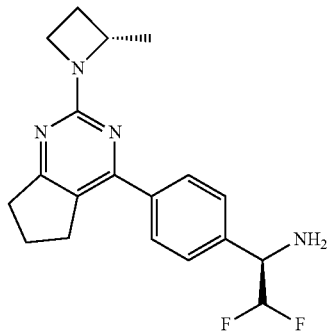 [SMILES: C[C@H]1CCN1c1nc2c(c(-c3ccc([C@@H](N)C(F)F)cc3)n1)CCC2]

Example 651: (1R)-1-[4-[7,7-difluoro-2-[(2S)-2-methylazetidin-1-yl]-5,6-dihydrocyclopenta[d]pyrimidin-4-yl]phenyl]-2,2-difluoro-ethanamine The title compound was prepared in a method analogous to General Method A using 4-chloro-2-[(2S)-2-methylazetidin-1-yl]-6,7-dihydro-5H-cyclopenta[d]pyrimidine and tert-butyl N-[(1R)-2,2-difluoro-1-[4-(4,4,5,5-tetramethyl-1,3,2-dioxaborolan-2-yl)phenyl]ethyl]carbamate instead of 2,4-dichloro-6,7-dihydro-5H-cyclopenta[d]pyrimidine and 3-pyridylboronic acid respectively, followed by General Method I.

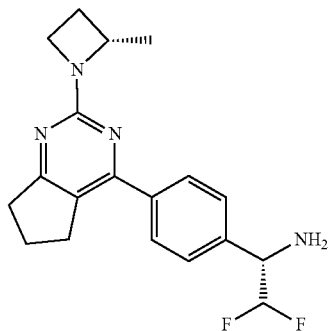 [SMILES: C[C@H]1CCN1c1nc2c(c(-c3ccc([C@H](N)C(F)F)cc3)n1)CCC2]

Example 652: (1S)-1-[4-[7,7-difluoro-2-[(2S)-2-methylazetidin-1-yl]-5,6-dihydrocyclopenta[d]pyrimidin-4-yl]phenyl]-2,2-difluoro-ethanamine The title compound was prepared in a method analogous to General Method A using 4-chloro-2-[(2S)-2-methylazetidin-1-yl]-6,7-dihydro-5H-cyclopenta[d]pyrimidine and tert-butyl N-[(1S)-2,2-difluoro-1-[4-(4,4,5,5-tetramethyl-1,3,2-dioxaborolan-2-yl)phenyl]ethyl]carbamate instead of 2,4-dichloro-6,7-dihydro-5H-cyclopenta[d]pyrimidine and 3-pyridylboronic acid respectively, followed by General Method I.

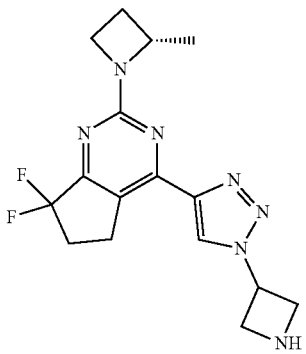 [SMILES: C[C@H]1CCN1c1nc(-c2cn(C3CNC3)nn2)c2c(n1)C(F)(F)CC2]

Example 653: 4-[1-(azetidin-3-yl)triazol-4-yl]-7,7-difluoro-2-[(2S)-2-methylazetidin-1-yl]-5,6-dihydro-cyclopenta[d]pyrimidine To a suspension of 4-chloro-7,7-difluoro-2-[(2S)-2-methylazetidin-1-yl]-5,6-dihydrocyclopenta[d]pyrimidine (100 mg, 0.39 mmol), copper(I) iodide (5.5 mg, 0.03 mmol), and bis(triphenylphosphine)palladium(II) chloride (23 mg, 0.019 mmol) in triethylamine (3 mL) was added ethynyl(trimethyl)silane (0.16 mL, 1.2 mmol), and the reaction mixture was degassed with anhydrous Na, sealed, and heated to 90° C. for 16 hours. It was cooled to ambient temperature, concentrated, and purified via flash chromatography (5-40% ethyl acetate/hexanes linear gradient) to yield 2-[7,7-difluoro-2-[(2S)-2-methylazetidin-1-yl]-5,6-dihydrocyclopenta[d]pyrimidin-4-yl]ethynyl-trimethyl-silane.

To a solution of 2-[7,7-difluoro-2-[(2S)-2-methylazetidin-1-yl]-5,6-dihydrocyclopenta[d]pyrimidin-4-yl]ethynyl-trimethyl-silane (63 mg, 0.20 mmol) in methanol (2 mL) was added potassium carbonate (54 mg, 0.39 mmol), and the reaction mixture was stirred at ambient temperature for 16 hours. It was diluted with ethyl acetate and washed with water and saturated sodium chloride, dried over anhydrous sodium sulfate, and filtered. It was purified via flash chromatography (5-50% ethyl acetate/hexanes linear gradient) to yield 4-ethynyl-7,7-difluoro-2-[(2S)-2-methylazetidin-1-yl]-5,6-dihydrocyclopenta[d]pyrimidine.

The title compound was prepared in a method analogous to General Method AA using 2-azidoethanol and 4-ethynyl-7,7-difluoro-2-[(2S)-2-methylazetidin-1-yl]-5,6-dihydrocyclopenta[d]pyrimidine instead of 3-azidooxetane and 4-ethynyl-2-[(2S)-2-methylazetidin-1-yl]-6,7-dihydro-5H-cyclopenta[d]pyrimidine respectively, followed by General Method I.

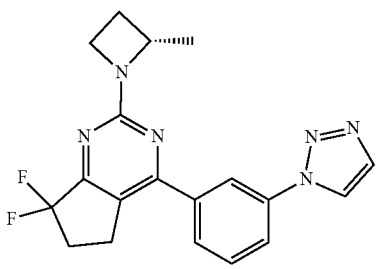 [SMILES: C[C@H]1CCN1c1nc(-c2cccc(-n3ccnn3)c2)c2c(n1)C(F)(F)CC2]

Example 654: 7,7-difluoro-2-[(2S)-2-methylazetidin-1-yl]-4-[3-(triazol-1-yl)phenyl]-5,6-dihydrocyclopenta[d]pyrimidine The title compound was prepared in a method analogous to General Method A using 4-chloro-7,7-difluoro-2-[(2S)-2-methylazetidin-1-yl]-5,6-dihydrocyclopenta[d]pyrimidine and [3-(triazol-1-yl)phenyl]boronic acid instead of 2,4-dichloro-6,7-dihydro-5H-cyclopenta[d]pyrimidine and 3-pyridylboronic acid respectively.

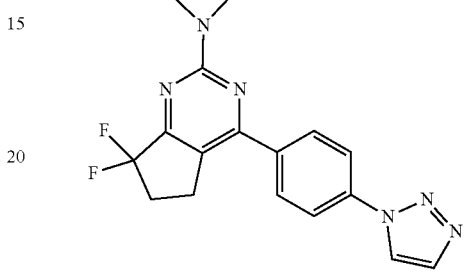

Example 655: 7,7-difluoro-2-[(2S)-2-methylazetidin-1-yl]-4-[4-(triazol-1-yl)phenyl]-5,6-dihydrocyclopenta[d]pyrimidine The title compound was prepared in a method analogous to General Method A using 4-chloro-7,7-difluoro-2-[(2S)-2-methylazetidin-1-yl]-5,6-dihydrocyclopenta[d]pyrimidine and [4-(triazol-1-yl)phenyl]boronic acid instead of 2,4-dichloro-6,7-dihydro-5H-cyclopenta[d]pyrimidine and 3-pyridylboronic acid respectively.

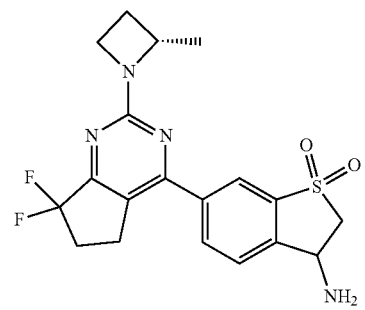 [SMILES: C[C@H]1CCN1c1nc(-c2ccc3c(c2)S(=O)(=O)CC3N)c2c(n1)C(F)(F)CC2]

Example 656: 6-[7,7-difluoro-2-[(2S)-2-methylazetidin-1-yl]-5,6-dihydrocyclopenta[d]pyrimidin-4-yl]-1,1-dioxo-2,3-dihydrobenzothiophen-3-amine The title compound was prepared in a method analogous to General Method V using 6-bromo-1,1-dioxo-benzothiophen-3-one instead of 5-bromo-7-fluoro-2,3-dihydro-1H-inden-1-one, followed by General Method F using 4-chloro-7,7-difluoro-2-[(2S)-2-methylazetidin-1-yl]-5,6-dihydrocyclopenta[d]pyrimidine and tert-butyl N-(6-bromo-1,1-dioxo-2,3-dihydrobenzothiophen-3-yl)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method I.

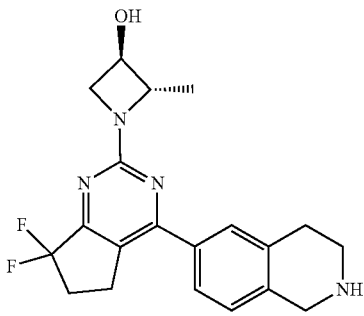 [SMILES: C[C@H]1[C@H](O)CN1c1nc(-c2ccc3c(c2)CCNC3)c2c(n1)C(F)(F)CC2]

Example 657: (2S,3R)-1-[7,7-difluoro-4-(1,2,3,4-tetrahydroisoquinolin-6-yl)-5,6-dihydrocyclopenta[d]pyrimidin-2-yl]-2-methyl-azetidin-3-ol The title compound was prepared in a method analogous to General Method A using 4-chloro-7,7-difluoro-2-methylsulfanyl-5,6-dihydrocyclopenta[d]pyrimidine and tert-butyl 6-(4,4,5,5-tetramethyl-1,3,2-dioxaborolan-2-yl)-3,4-dihydro-1H-isoquinoline-2-carboxylate instead of 2,4-dichloro-6,7-dihydro-5H-cyclopenta[d]pyrimidine and 3-pyridylboronic acid respectively, followed by General Method M, followed by General Method B using (2S,3R)-2-methylazetidin-3-ol (R)-camphorsulfonic acid salt instead of (2S)-2-methylazetidine (R)-camphorsulfonic acid salt, followed by General Method I.

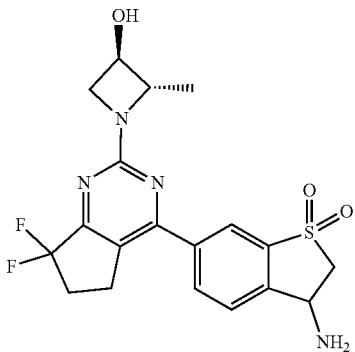

Example 658: (2S,3R)-1-[4-(3-amino-1,1-dioxo-2,3-dihydrobenzothiophen-6-yl)-7,7-difluoro-5,6-dihydrocyclopenta[d]pyrimidin-2-yl]-2-methyl-azetidin-3-ol The title compound was prepared in a method analogous to General Method V using 6-bromo-1,1-dioxo-benzothiophen-3-one instead of 5-bromo-7-fluoro-2,3-dihydro-1H-inden-1-one, followed by General Method F using 4-chloro-7,7-difluoro-2-methylsulfanyl-5,6-dihydrocyclopenta[d]pyrimidine and tert-butyl N-(6-bromo-1,1-dioxo-2,3-dihydrobenzothiophen-3-yl)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, followed by General Method B using (2S,3R)-2-methylazetidin-3-ol (R)-camphorsulfonic acid salt instead of (2S)-2-methylazetidine (R)-camphorsulfonic acid salt, followed by General Method I.

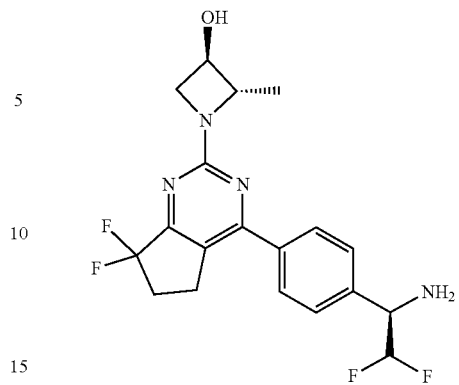

Example 659: (2S,3R)-1-[4-[4-[(1R)-1-amino-2,2-difluoro-ethyl]phenyl]-7,7-difluoro-5,6-dihydrocyclopenta[d]pyrimidin-2-yl]-2-methyl-azetidin-3-ol The title compound was prepared in a method analogous to General Method A using 4-chloro-7,7-difluoro-2-methylsulfanyl-5,6-dihydrocyclopenta[d]pyrimidine and tert-butyl N-[(1R)-2,2-difluoro-1-[4-(4,4,5,5-tetramethyl-1,3,2-dioxaborolan-2-yl)phenyl]ethyl]carbamate instead of 2,4-dichloro-6,7-dihydro-5H-cyclopenta[d]pyrimidine and 3-pyridylboronic acid respectively, followed by General Method M, followed by General Method B using (2S,3R)-2-methylazetidin-3-ol (R)-camphorsulfonic acid salt instead of (2S)-2-methylazetidine (R)-camphorsulfonic acid salt, followed by General Method I.

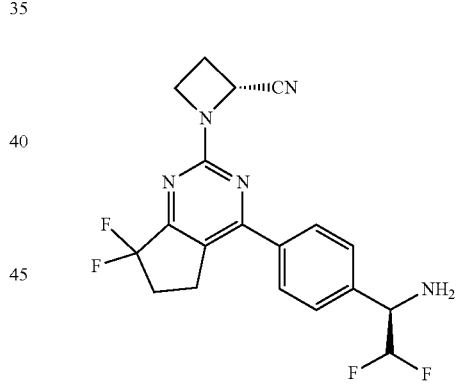

Example 660: (2R)-1-[4-[4-[(1R)-1-amino-2,2-difluoro-ethyl]phenyl]-7,7-difluoro-5,6-dihydrocyclopenta[d]pyrimidin-2-yl]azetidine-2-carbonitrile The title compound was prepared in a method analogous to General Method A using 4-chloro-7,7-difluoro-2-methylsulfanyl-5,6-dihydrocyclopenta[d]pyrimidine and tert-butyl N-[(1R)-2,2-difluoro-1-[4-(4,4,5,5-tetramethyl-1,3,2-dioxaborolan-2-yl)phenyl]ethyl]carbamate instead of 2,4-dichloro-6,7-dihydro-5H-cyclopenta[d]pyrimidine and 3-pyridylboronic acid respectively, followed by General Method M, followed by General Method B using (2R)-azetidine-2-carbonitrile hemioxalate salt instead of (2S)-2-methylazetidine (R)-camphorsulfonic acid salt, followed by General Method I.

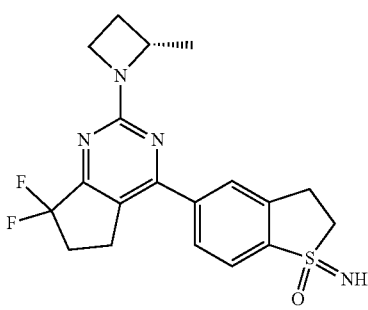 [SMILES: C[C@H]1CCN1c1nc(-c2ccc3c(c2)CCS3(=N)=O)c2c(n1)C(F)(F)CC2]

Example 661: 6-[7,7-difluoro-2-[(2S)-2-methylazetidin-1-yl]-5,6-dihydrocyclopenta[d]pyrimidin-4-yl]-1,1-dioxo-2,3-dihydrobenzothiophen-3-amine The title compound was prepared in analogy to General Method S using 5-bromo-2,3-dihydrobenzothiophene instead of (5-bromo-2-methoxyphenyl)(methyl)sulfane, followed by General Method F using 4-chloro-7,7-difluoro-2-[(2S)-2-methylazetidin-1-yl]-5,6-dihydrocyclopenta[d]pyrimidine and tert-butyl N-(6-bromo-1,1-dioxo-2,3-dihydrobenzothiophen-3-yl)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method I.

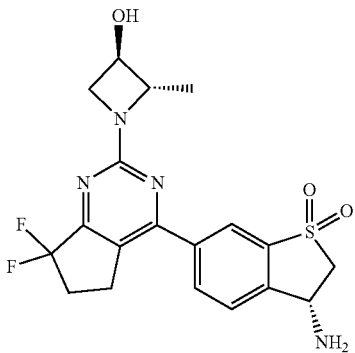

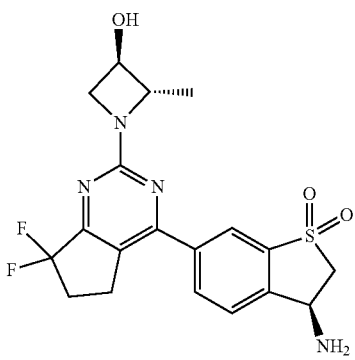

Example 662: (2S,3R)-1-[4-[(3R)-3-amino-1,1-dioxo-2,3-dihydrobenzothiophen-6-yl]-7,7-difluoro-5,6-dihydrocyclopenta[d]pyrimidin-2-yl]-2-methyl-azetidin-3-ol Example 663: (2S,3R)-1-[4-[(3S)-3-amino-1,1-dioxo-2,3-dihydrobenzothiophen-6-yl]-7,7-difluoro-5,6-dihydrocyclopenta[d]pyrimidin-2-yl]-2-methyl-azetidin-3-ol Isomers were separated by SFC (30% EtOH in $CO_2$, CHIRALPAK OJ-H, 250×21 mm, 60 mL/min). (see Example 658)

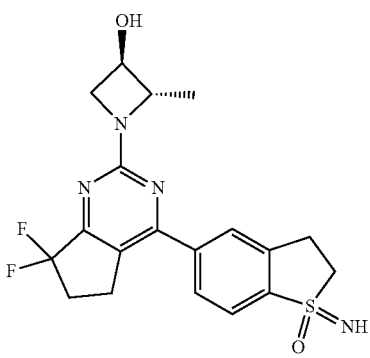 [SMILES: C[C@H]1[C@H](O)CN1c1nc(-c2ccc3c(c2)CCS3(=N)=O)c2c(n1)C(F)(F)CC2]

Example 664: (2S,3R)-1-[7,7-difluoro-4-(1-imino-1-oxo-2,3-dihydrobenzothiophen-5-yl)-5,6-dihydrocyclopenta[d]pyrimidin-2-yl]-2-methyl-azetidin-3-ol The title compound was prepared in a method analogous to General Method F using 4-chloro-7,7-difluoro-2-methylsulfanyl-5,6-dihydrocyclopenta[d]pyrimidine and tert-butyl N-(6-bromo-1,1-dioxo-2,3-dihydrobenzothiophen-3-yl)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, followed by General Method B using (2S,3R)-2-methylazetidin-3-ol (R)-camphorsulfonic acid salt instead of (2S)-2-methylazetidine (R)-camphorsulfonic acid salt, followed by General Method I.

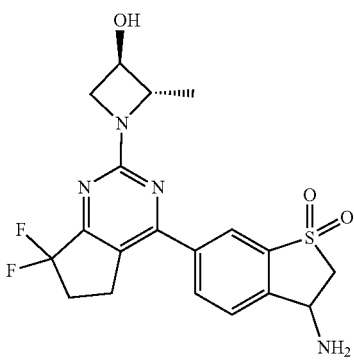 [SMILES: C[C@H]1[C@H](O)CN1c1nc(-c2ccc3c(c2)S(=O)(=O)CC3N)c2c(n1)C(F)(F)CC2]

Example 665: N-[6-[7,7-difluoro-2-[(2S,3R)-3-hydroxy-2-methyl-azetidin-1-yl]-5,6-dihydrocyclopenta[d]pyrimidin-4-yl]-1,1-dioxo-2,3-dihydrobenzothiophen-3-yl]methanesulfonamide The title compound was prepared in a method analogous to General Method F using 4-chloro-7,7-difluoro-2-methylsulfanyl-5,6-dihydrocyclopenta[d]pyrimidine and N-(6-bromo-1,1-dioxo-2,3-dihydrobenzothiophen-3-yl)methanesulfonamide instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, followed by General Method B using (2S,3R)-2-methylazetidin-3-ol (R)-camphorsulfonic acid salt instead of (2S)-2-methylazetidine (R)-camphorsulfonic acid salt to yield the title compound.

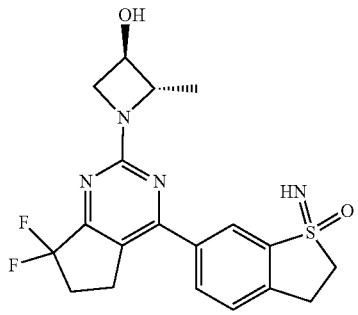 [SMILES: C[C@H]1[C@H](O)CN1c1nc(-c2ccc3c(c2)S(=N)(=O)CC3)c2c(n1)C(F)(F)CC2]

Example 666: (2S,3R)-1-[7,7-difluoro-4-(1-imino-1-oxo-2,3-dihydrobenzothiophen-6-yl)-5,6-dihydrocyclopenta[d]pyrimidin-2-yl]-2-methyl-azetidin-3-431

The title compound was prepared in analogy to General Method S using 6-bromo-2,3-dihydrobenzothiophene instead of (5-bromo-2-methoxyphenyl)(methyl)sulfane, followed by General Method F using 4-chloro-7,7-difluoro-2-methylsulfanyl-5,6-dihydrocyclopenta[d]pyrimidine and tert-butyl N-(6-bromo-1,1-dioxo-2,3-dihydrobenzothiophen-3-yl)carbamate instead of 4-chloro-2-[(2S)-2-methyl-azetidin-1-yl]-6,7-dihydro-5H-cyclopenta[d]pyrimidine and 6-bromo-1,1-dioxo-1,2-benzothiazol-3-one respectively, followed by General Method M, followed by General Method B using (2S,3R)-2-methylazetidin-3-ol (R)-camphorsulfonic acid salt instead of (2S)-2-methylazetidine (R)-camphorsulfonic acid salt, followed by General Method I.

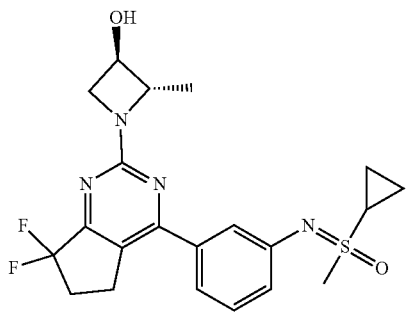 [SMILES: C[C@H]1[C@H](O)CN1c1nc(-c2cccc(N=S(C)(=O)C3CC3)c2)c2c(n1)C(F)(F)CC2]

Example 667: (2S,3R)-1-[4-[3-[(cyclopropyl-methyl-oxo-$\lambda^6$-sulfanylidene)amino]phenyl]-7,7-difluoro-5,6-dihydrocyclopenta[d]pyrimidin-2-yl]-2-methyl-azetidin-3-431

(2S,3R)-1-[4-(3-aminophenyl)-7,7-difluoro-5,6-dihydrocyclopenta[d]pyrimidin-2-yl]-2-methyl-azetidin-3-ol was prepared in a method analogous to General Method A using 4-chloro-7,7-difluoro-2-methylsulfanyl-5,6-dihydrocyclopenta[d]pyrimidine and [3-(tert-butoxycarbonylamino)phenyl]boronic acid instead of 2,4-dichloro-6,7-dihydro-5H-cyclopenta[d]pyrimidine and 3-pyridylboronic acid respectively, followed by General Method M, followed by General Method B using (2S,3R)-2-methylazetidin-3-ol (R)-camphorsulfonic acid salt instead of (2S)-2-methylazetidine (R)-camphorsulfonic acid salt, followed by General Method I.

To (2S,3R)-1-[4-(3-aminophenyl)-7,7-difluoro-5,6-dihydrocyclopenta[d]pyrimidin-2-yl]-2-methyl-azetidin-3-ol (100 mg, 0.32 mmol) in acetonitrile (1.5 mL) was added 4,4,5,5-tetramethyl-2-(4,4,5,5-tetramethyl-1,3,2-dioxaborolan-2-yl)-1,3,2-dioxaborolane (96 mg, 0.38 mmol) and tert-butyl nitrite (0.056 mL, 0.47 mmol), and the reaction mixture was stirred at ambient temperature for 16 hours. It was concentrated and purified via flash chromatography (5-100% ethyl acetate/hexanes linear gradient) to yield 7,7-difluoro-2-[(2S)-2-methylazetidin-1-yl]-4-[3-(4,4,5,5-tetramethyl-1,3,2-dioxaborolan-2-yl)phenyl]-5,6-dihydro-cyclopenta[d]pyrimidine.

The title compound was made according to General Method AC.

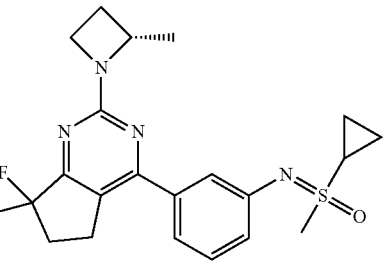

Example 668: cyclopropyl-[3-[7,7-difluoro-2-[(2S)-2-methylazetidin-1-yl]-5,6-dihydrocyclopenta[d]pyrimidin-4-yl]phenyl]imino-methyl-oxo-$\lambda^6$-sulfane To a solution of 7,7-difluoro-2-[(2S)-2-methylazetidin-1-yl]-4-[3-(4,4,5,5-tetramethyl-1,3,2-dioxaborolan-2-yl)phenyl]-5,6-dihydrocyclopenta[d]pyrimidine (60 mg, 0.14 mmol) in dimethylformamide (1.1 mL) was added cyclopropyl-imino-methyl-oxo-$\lambda^6$-sulfane (20 mg, 0.17 mmol) and copper(II) acetate (2.6 mg, 0.014 mmol) and the reaction was stirred at ambient temperature open to the air for 4 days. It was purified by preparatory HPLC (0.1% TFA in water—0.1% TFA in acetonitrile) to yield the title compound.

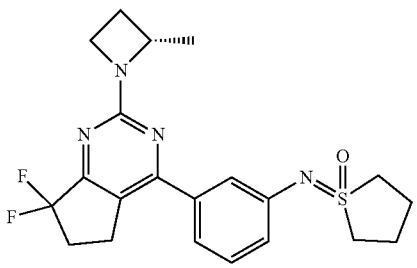 [SMILES: C[C@H]1CCN1c1nc(-c2cccc(N=S3(=O)CCCC3)c2)c2c(n1)C(F)(F)CC2]

Example 669: 1-[3-[7,7-difluoro-2-[(2S)-2-methyl-azetidin-1-yl]-5,6-dihydrocyclopenta[d]pyrimidin-4-yl]phenyl]iminothiolane 1-oxide The title compound was prepared in a method analogous to cyclopropyl-[3-[7,7-difluoro-2-[(2S)-2-methylazetidin-1-yl]-5,6-dihydrocyclopenta[d]pyrimidin-4-yl]phenyl]imino-methyl-oxo-λ⁶-sulfane (Example 668) substituting 1-iminothiolane 1-oxide, copper(I) iodide, and methanol for cyclopropyl-imino-methyl-oxo-λ⁶-sulfane, copper(II) acetate, and dimethylformamide respectively.

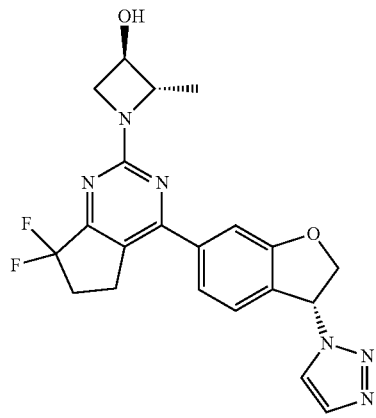 [SMILES: C[C@H]1[C@H](O)CN1c1nc(-c2ccc3c(c2)OC[C@@H]3n2ccnn2)c2c(n1)C(F)(F)CC2]

Example 670: (2S,3R)-1-[7,7-difluoro-4-(1-imino-1-oxo-2,3-dihydrobenzothiophen-6-yl)-5,6-dihydrocyclopenta[d]pyrimidin-2-yl]-2-methyl-azetidin-3-431

[1-[(3R)-6-bromo-2,3-dihydrobenzofuran-3-yl]triazol-4-yl]-trimethyl-silane was prepared in a method analogous to General Method AA using (3R)-3-azido-6-bromo-2,3-dihydrobenzofuran and ethynyl(trimethyl)silane instead of 3-azidooxetane and 4-ethynyl-2-[(2S)-2-methylazetidin-1-yl]-6,7-dihydro-5H-cyclopenta[d]pyrimidine respectively.

To a solution of [1-[(3R)-6-bromo-2,3-dihydrobenzofuran-3-yl]triazol-4-yl]-trimethyl-silane (151 mg, 0.45 mmol) in tetrahydrofuran (2 mL) was added 1.0M tetrabutylammonium fluoride (0.89 mL, 0.89 mmol), and the reaction mixture was stirred at ambient temperature for 16 hours. It was diluted with ethyl acetate and washed with 10% citric acid, saturated sodium bicarbonate, and saturated sodium chloride. It was dried over anhydrous sodium sulfate, filtered, and concentrated. It was purified via flash chromatography (hexanes-ethyl acetate) to yield 1-[(3R)-6-bromo-2,3-dihydrobenzofuran-3-yl]triazole.

The title compound was prepared in a method analogous to General Method F using 4-chloro-7,7-difluoro-2-methylsulfanyl-5,6-dihydrocyclopenta[d]pyrimidine and 1-[(3R)-6-bromo-2,3-dihydrobenzofuran-3-yl]triazole instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, followed by General Method B using (2S,3R)-2-methylazetidin-3-ol (R)-camphorsulfonic acid salt instead of (2S)-2-methylazetidine (R)-camphorsulfonic acid salt.

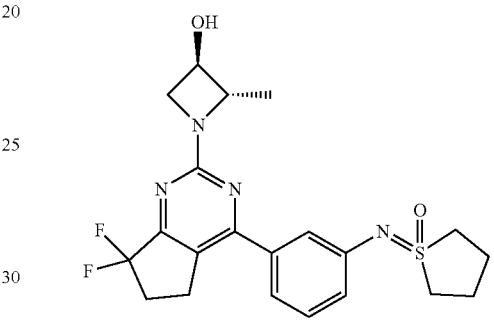

Example 671: (2S,3R)-1-[7,7-difluoro-4-[3-[(1-oxo-thiolan-1-ylidene)amino]phenyl]-5,6-dihydroeyelopenta[d]pyrimidin-2-yl]-2-methyl-azetidin-3-ol The title compound was prepared in a method analogous to General Method AC using 1-iminothiolane 1-oxide instead of cyclopropyl-imino-methyl-oxo-λ⁶-sulfane.

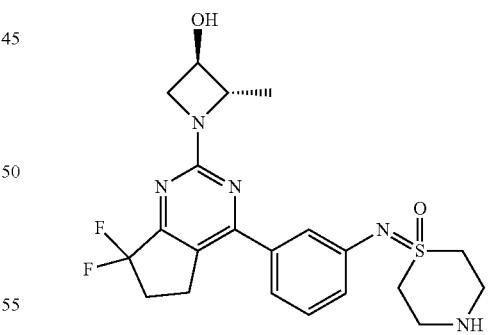

Example 672: (2S,3R)-1-[7,7-difluoro-4-[3-[(1-oxo-1,4-thiazinan-1-ylidene)amino]phenyl]-5,6-dihydroeyelopenta[d]pyrimidin-2-yl]-2-methyl-azetidin-3-ol The title compound was prepared in a method analogous to General Method AC using tert-butyl 1-imino-1-oxo-1,4-thiazinane-4-carboxylate instead of cyclopropyl-imino-methyl-oxo-λ⁶-sulfane, followed by General Method I.

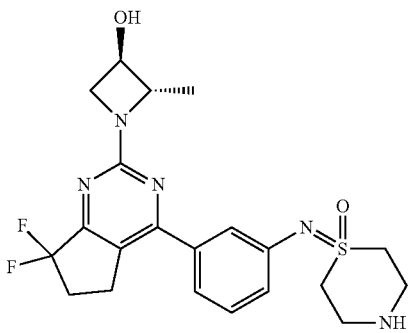 [SMILES: C[C@H]1[C@H](O)CN1c1nc(-c2cccc(N=S3(=O)CCNCC3)c2)c2c(n1)C(F)(F)CC2]

Example 673: (2S,3R)-1-[7,7-difluoro-4-[3-[(4-oxo-1,4-oxathian-4-ylidene)amino]phenyl]-5,6-dihydrocyclopenta[d]pyrimidin-2-yl]-2-methyl-azetidin-3-ol The title compound was prepared in a method analogous to General Method AC using 4-imino-1,4-oxathiane 4-oxide instead of cyclopropyl-imino-methyl-oxo-$\lambda^6$-sulfane.

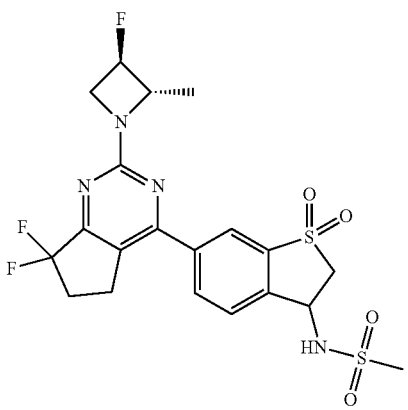 [SMILES: C[C@H]1[C@H](F)CN1c1nc(-c2ccc3c(c2)S(=O)(=O)CC3NS(C)(=O)=O)c2c(n1)C(F)(F)CC2]

Example 674: N-[6-[7,7-difluoro-2-[(2S,3R)-3-fluoro-2-methyl-azetidin-1-yl]-5,6-dihydrocyclopenta[d]pyrimidin-4-yl]-1,1-dioxo-2,3-dihydrobenzothiophen-3-yl]methanesulfonamide The title compound was prepared in a method analogous to General Method F using 4-chloro-7,7-difluoro-2-methylsulfanyl-5,6-dihydrocyclopenta[d]pyrimidine and tert-butyl N-(6-bromo-1,1-dioxo-2,3-dihydrobenzothiophen-3-yl)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, followed by General Method B using (2S,3R)-3-fluoro-2-methyl-azetidine hydrochloride instead of (2S)-2-methylazetidine (R)-camphorsulfonic acid salt, followed by General Method I, followed by General Method K, using 3-amino-6-(2-((2S,3R)-3-fluoro-2-methylazetidin-1-yl)-6,7-dihydro-5H-cyclopenta[d]pyrimidin-4-yl)-2,3-dihydrobenzo[b]thiophene 1,1-dioxide and methane sulfonyl chloride instead of (S)-3-(2-(2-methylazetidin-1-yl)-6,7-dihydro-5H-cyclopenta[d]pyrimidin-4-yl)aniline and -methylimidazole-4-sulfonyl chloride, respectively.

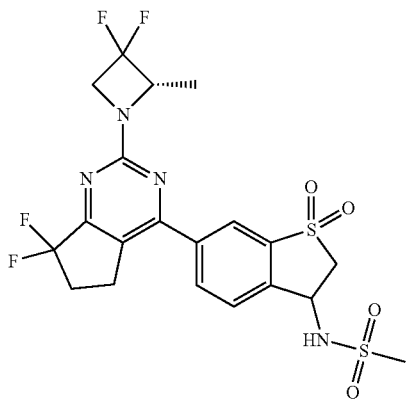 [SMILES: C[C@@H]1N(c2nc(-c3ccc4c(c3)S(=O)(=O)CC4NS(C)(=O)=O)c3c(n2)C(F)(F)CC3)CC1(F)F]

Example 675: N-[6-[7,7-difluoro-2-[(2S,3R)-3-fluoro-2-methyl-azetidin-1-yl]-5,6-dihydrocyclopenta[d]pyrimidin-4-yl]-1,1-dioxo-2,3-dihydrobenzothiophen-3-yl]methanesulfonamide The title compound was prepared in a method analogous to General Method F using 4-chloro-7,7-difluoro-2-methylsulfanyl-5,6-dihydrocyclopenta[d]pyrimidine and tert-butyl N-(6-bromo-1,1-dioxo-2,3-dihydrobenzothiophen-3-yl)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, followed by General Method B using (2S)-3,3-difluoro-2-methyl-azetidine hydrochloride instead of (2S)-2-methylazetidine (R)-camphorsulfonic acid salt, followed by General Method I, followed by General Method K, using 3-amino-6-(2-((S)-3,3-difluoro-2-methylazetidin-1-yl)-6,7-dihydro-5H-cyclopenta[d]pyrimidin-4-yl)-2,3-dihydrobenzo[b]thiophene 1,1-dioxide and methane sulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively.

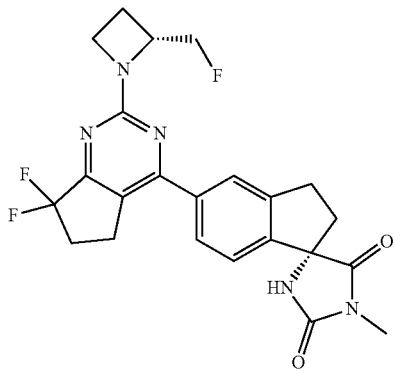 [SMILES: CN1C(=O)N[C@]2(CCc3cc(-c4nc(N5CC[C@@H]5CF)nc5c4CCC5(F)F)ccc32)C1=O]

Example 676: (5S)-5'-[7,7-difluoro-2-[(2R)-2-(fluoromethyl)azetidin-1-yl]-5,6-dihydroeyelopenta[d]pyrimidin-4-yl]-3-methyl-spiro[imidazolidine-5,1'-indane]-2,4-dione The title compound was prepared in a method analogous to General Method F using 4-chloro-7,7-difluoro-2-methylsulfanyl-5,6-dihydrocyclopenta[d]pyrimidine and (5S)-5'- bromo-3-methyl-spiro[imidazolidine-5,1'-indane]-2,4-dione instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, followed by General Method B using (2R)-2-(fluoromethyl)azetidine trifluoroacetic acid salt instead of (2S)-2-methylazetidine (R)-camphorsulfonic acid salt.

acid respectively, followed by General Method M, followed by General Method B using 2-(difluoromethyl)azetidine hydrochloride instead of (2S)-2-methylazetidine (R)-camphorsulfonic acid salt, followed by General Method R.

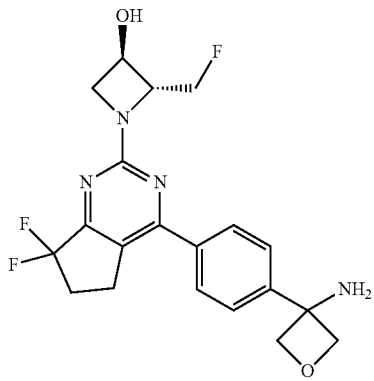 [SMILES: NC1(c2ccc(-c3nc(N4C[C@@H](O)[C@@H]4CF)nc4c3CCC4(F)F)cc2)COC1]

Example 677: (2R,3R)-1-[4-[4-(3-aminooxetan-3-yl)phenyl]-7,7-difluoro-5,6-dihydroeyelopenta[d]pyrimidin-2-yl]-2-(fluoromethyl)azetidin-3-ol The title compound was prepared in a method analogous to General Method A using 4-chloro-7,7-difluoro-2-methylsulfanyl-5,6-dihydrocyclopenta[d]pyrimidine and benzyl N-[3-[4-(4,4,5,5-tetramethyl-1,3,2-dioxaborolan-2-yl)phenyl]oxetan-3-yl]carbamate instead of 2,4-dichloro-6,7-dihydro-5H-cyclopenta[d]pyrimidine and 3-pyridylboronic acid respectively, followed by General Method M, followed by General Method B using (2R,3R)-2-(fluoromethyl)azetidin-3-ol instead of (2S)-2-methylazetidine (R)-camphorsulfonic acid salt, followed by General Method R.

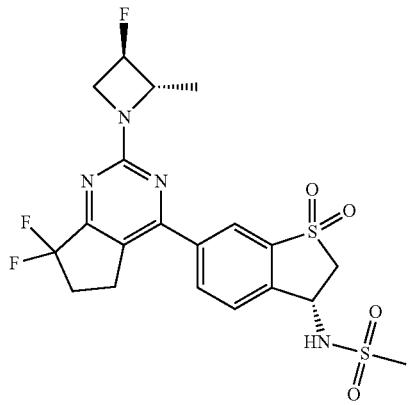

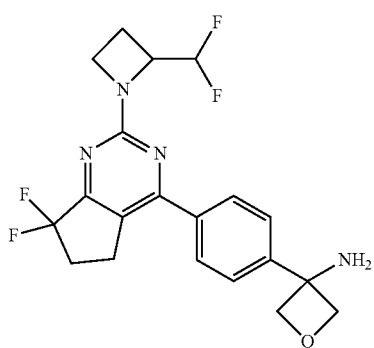 [SMILES: NC1(c2ccc(-c3nc(N4CCC4C(F)F)nc4c3CCC4(F)F)cc2)COC1]

Example 678: 3-[4-[2-[2-(difluoromethyl)azetidin-1-yl]-7,7-difluoro-5,6-dihydrocyclopenta[d]pyrimidin-4-yl]phenyl]oxetan-3-amine The title compound was prepared in a method analogous to General Method A using 4-chloro-7,7-difluoro-2-methylsulfanyl-5,6-dihydrocyclopenta[d]pyrimidine and benzyl N-[3-[4-(4,4,5,5-tetramethyl-1,3,2-dioxaborolan-2-yl)phenyl]oxetan-3-yl]carbamate instead of 2,4-dichloro-6,7-dihydro-5H-cyclopenta[d]pyrimidine and 3-pyridylboronic

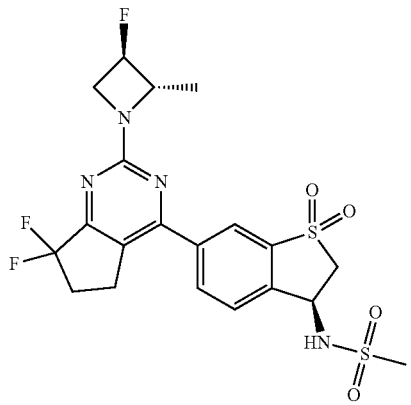

Example 679: N-[(3R)-6-[7,7-difluoro-2-[(2S,3R)-3-fluoro-2-methyl-azetidin-1-yl]-5,6-dihydrocyclopenta[d]pyrimidin-4-yl]-1,1-dioxo-2,3-dihydrobenzothiophen-3-yl]methanesulfonamide Example 680: N-[(3S)-6-[7,7-difluoro-2-[(2S,3R)-3-fluoro-2-methyl-azetidin-1-yl]-5,6-dihydrocyclopenta[d]pyrimidin-4-yl]-1,1-dioxo-2,3-dihydrobenzothiophen-3-yl]methanesulfonamide Isomers were separated by SFC (25% MeOH in $CO_2$, CHIRALPAK AD-H, 250×21 mm, 60 mL/min). (see Example 674)

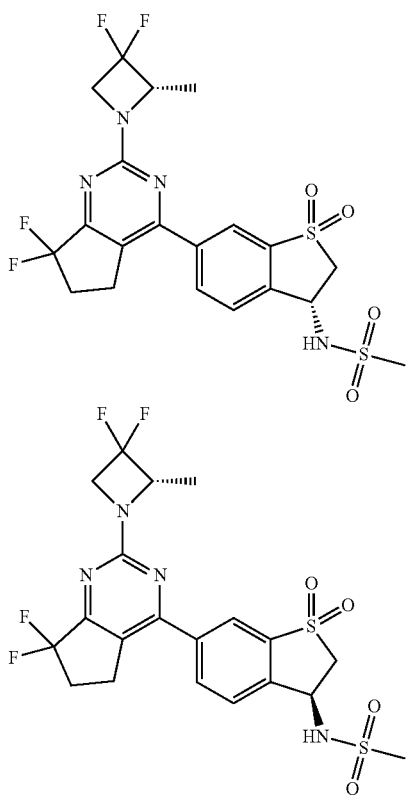

Example 681: N-[(3R)-6-[2-[(2S)-3,3-difluoro-2-methyl-azetidin-1-yl]-7,7-difluoro-5,6-dihydrocyclopenta[d]pyrimidin-4-yl]-1,1-dioxo-2,3-dihydrobenzothiophen-3-yl]methanesulfonamide Example 682: N-[(3S)-6-[2-[(2S)-3,3-difluoro-2-methyl-azetidin-1-yl]-7,7-difluoro-5,6-dihydrocyclopenta[d]pyrimidin-4-yl]-1,1-dioxo-2,3-dihydrobenzothiophen-3-yl]methanesulfonamide Isomers were separated by SFC (30% MeOH in CO$_2$, CHIRALPAK AD-H, 250×21 mm, 60 mL/min). (see Example 675)

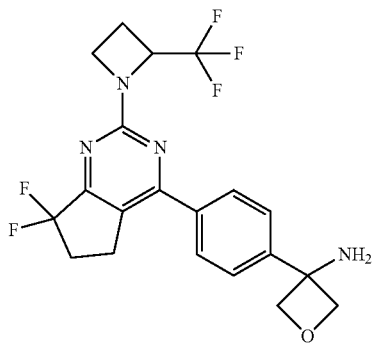 [SMILES: NC1(c2ccc(-c3nc(N4CCC4C(F)(F)F)nc4c3CCC4(F)F)cc2)COC1]

Example 683: 3-[4-[7,7-difluoro-2-[2-(trifluoromethyl)azetidin-1-yl]-5,6-dihydrocyclopenta[d]pyrimidin-4-yl]phenyl]oxetan-3-amine The title compound was prepared in a method analogous to General Method A using 4-chloro-7,7-difluoro-2-methylsulfanyl-5,6-dihydrocyclopenta[d]pyrimidine and benzyl N-[3-[4-(4,4,5,5-tetramethyl-1,3,2-dioxaborolan-2-yl)phenyl]oxetan-3-yl]carbamate instead of 2,4-dichloro-6,7-dihydro-5H-cyclopenta[d]pyrimidine and 3-pyridylboronic acid respectively, followed by General Method M, followed by General Method B using 2-(trifluoromethyl)azetidine hydrochloride instead of (2S)-2-methylazetidine (R)-camphorsulfonic acid salt and heating to 130° C. for 16 hours instead of 80° C. for 16 hours, followed by General Method R.

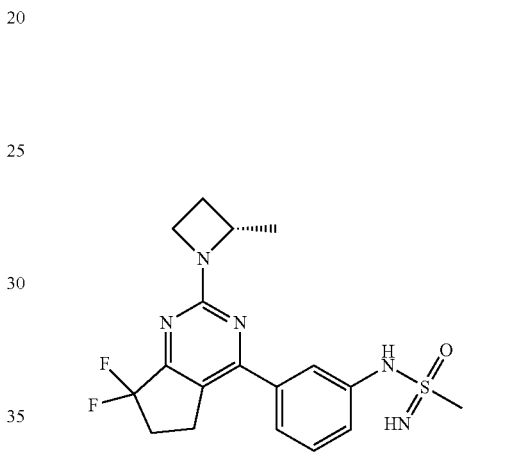

Example 684: 4-[3-[(amino-methyl-oxo-λ$^6$-sulfanylidene)amino]phenyl]-7,7-difluoro-2-[(2S)-2-methylazetidin-1-yl]-5,6-dihydrocyclopenta[d]pyrimidine To a stirred suspension of dichloro(triphenyl)-lambda5-phosphane (175 mg, 0.525 mmol) in dry chloroform (1 mL) was added triethylamine (0.1 mL, 0.72 mmol). It was stirred at ambient temperature for 10 minutes, then was cooled to 0° C. To this, N-[tert-butyl(dimethyl)silyl]methanesulfonamide (100 mg, 0.48 mmol) in dry chloroform (0.5 mL) was added and stirred for 20 minutes. Next, 3-[7,7-difluoro-2-[(2S)-2-methylazetidin-1-yl]-5,6-dihydrocyclopenta[d]pyrimidin-4-yl]aniline (181 mg, 0.57 mmol) in dry chloroform (1 mL) was added, it was stirred at 0° C. for 30 minutes, then allowed to warm to ambient temperature. It was concentrated, then was dissolved in 10 mL of acetonitrile. Next, trifluoroacetic acid (1 mL) was added, and the reaction mixture was stirred for 1 hour. It was concentrated and purified by preparatory HPLC to yield the title compound.

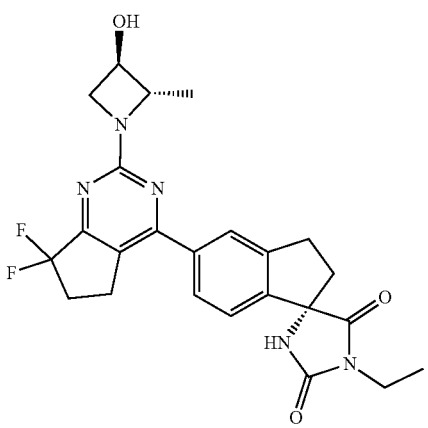 [SMILES: CCN1C(=O)N[C@]2(CCc3cc(-c4nc(N5C[C@@H](O)[C@@H]5C)nc5c4CCC5(F)F)ccc32)C1=O]

Example 685: (5S)-5'-[7,7-difluoro-2-[(2S,3R)-3-hydroxy-2-methyl-azetidin-1-yl]-5,6-dihydrocyclopenta[d]pyrimidin-4-yl]-3-ethyl-spiro[imidazolidine-5,1'-indane]-2,4-dione The title compound was prepared in a method analogous to General Method AD using ethyl iodide instead of methyl iodide, followed by General Method F using 4-chloro-7,7-difluoro-2-methylsulfanyl-5,6-dihydrocyclopenta[d]pyrimidine instead of 4-chloro-2-[(2S)-2-methylazetidin-1-yl]-6,7-dihydro-5H-cyclopenta[d]pyrimidine, followed by General Method M, followed by General Method B using (2S,3R)-2-methylazetidin-3-ol (R)-camphorsulfonic acid salt instead of (2S)-2-methylazetidine (R)-camphorsulfonic acid salt.

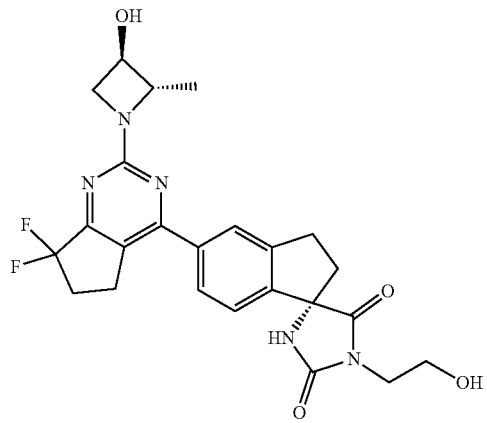 [SMILES: C[C@H]1[C@H](O)CN1c1nc(-c2ccc3c(c2)CC[C@]32NC(=O)N(CCO)C2=O)c2c(n1)C(F)(F)CC2]

Example 686: (5S)-5'-[7,7-difluoro-2-[(2S,3R)-3-hydroxy-2-methyl-azetidin-1-yl]-5,6-dihydrocyclopenta[d]pyrimidin-4-yl]-3-(2-hydroxyethyl)spiro[imidazolidine-5,1'-indane]-2,4-dione (5S)-3-[2-[tert-butyl(dimethyl)silyl]oxyethyl]-5'-[7,7-difluoro-2-[(2S,3R)-3-hydroxy-2-methyl-azetidin-1-yl]-5,6-dihydrocyclopenta[d]pyrimidin-4-yl]spiro[imidazolidine-5,1'-indane]-2,4-dione was prepared in a method analogous to General Method AD using 2-bromoethoxy-tert-butyl-dimethyl-silane instead of methyl iodide and heating at 60° C. for 4 days instead of at ambient temperature for 16 hours, followed by General Method F using 4-chloro-7,7-difluoro-2-methylsulfanyl-5,6-dihydrocyclopenta[d]pyrimidine instead of 4-chloro-2-[(2S)-2-methylazetidin-1-yl]-6,7-dihydro-5H-cyclopenta[d]pyrimidine, followed by General Method M, followed by General Method B using (2S,3R)-2-methylazetidin-3-ol (R)-camphorsulfonic acid salt instead of (2S)-2-methylazetidine (R)-camphorsulfonic acid salt.

To a solution of (5S)-3-[2-[tert-butyl(dimethyl)silyl]oxyethyl]-5'-[7,7-difluoro-2-[(2S,3R)-3-hydroxy-2-methyl-azetidin-1-yl]-5,6-dihydrocyclopenta[d]pyrimidin-4-yl]spiro[imidazolidine-5,1'-indane]-2,4-dione (79 mg, 0.13 mmol) in tetrahydrofuran (1 mL) was added 1M tetrabutylammonium fluoride in tetrahydrofuran (0.2 mL, 0.2 mmol), and the reaction mixture was stirred at ambient temperature for 16 hours. It was diluted with ethyl acetate, washed with saturated sodium bicarbonate and saturated sodium chloride, dried over anhydrous sodium sulfate, filtered, and concentrated. It was purified by flash chromatography (DCM-MeOH) to yield the title compound.

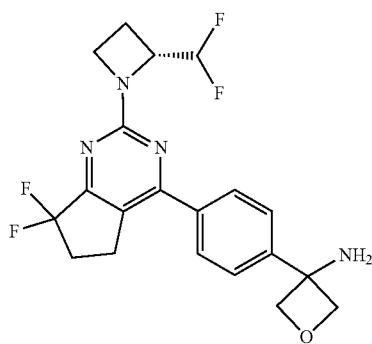

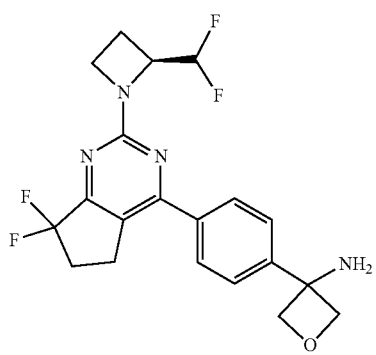

Example 687: 3-[4-[2-[(2R)-2-(difluoromethyl)azetidin-1-yl]-7,7-difluoro-5,6-dihydrocyclopenta[d]pyrimidin-4-yl]phenyl]oxetan-3-amine Example 688: 3-[4-[2-[(2S)-2-(difluoromethyl)azetidin-1-yl]-7,7-difluoro-5,6-dihydrocyclopenta[d]pyrimidin-4-yl]phenyl]oxetan-3-amine Isomers were separated by SFC (20% MeOH in $CO_2$, CHIRALPAK AD-H, 250×21 mm, 60 mL/min). (see Example 678)

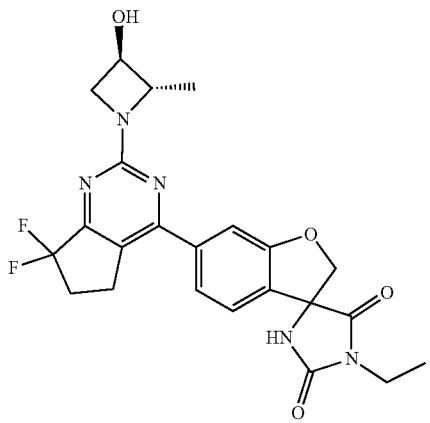 [SMILES: CCN1C(=O)NC2(COc3cc(-c4nc(N5C[C@@H](O)[C@@H]5C)nc5c4CCC5(F)F)ccc32)C1=O]

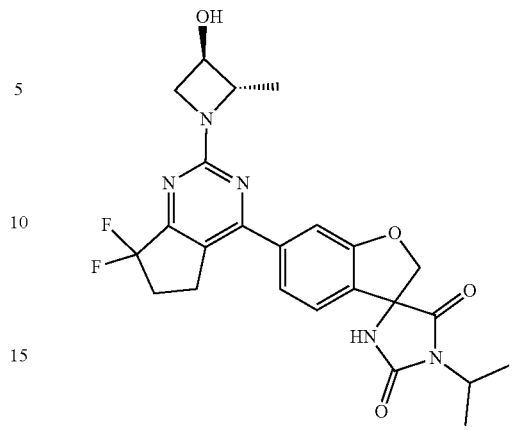

Example 689: 6-[7,7-difluoro-2-[(2S,3R)-3-hydroxy-2-methyl-azetidin-1-yl]-5,6-dihydrocyclopenta[d]pyrimidin-4-yl]-3'-ethyl-spiro[2H-benzofuran-3,5'-imidazolidine]-2',4'-dione To a solution of ethyl 3-amino-6-bromo-2H-benzofuran-3-carboxylate (1.0 g, 3.5 mmol) in acetic acid (40 mL) was added potassium cyanate (567 mg, 7.0 mmol), and the reaction mixture was stirred at ambient temperature for 16 hours. It was concentrated under reduced pressure, dissolved in ethyl acetate, and washed with saturated sodium bicarbonate and saturated sodium chloride, dried over anhydrous sodium sulfate, filtered, and concentrated. It was purified by recrystallization from ethanol and water to yield ethyl 6-bromo-3-ureido-2H-benzofuran-3-carboxylate.

To a solution of ethyl 6-bromo-3-ureido-2H-benzofuran-3-carboxylate (1.15 g, 3.5 mmol) in ethanol (15 mL) was added sodium ethoxide (21% by weight in ethanol, 1.57 mL, 4.2 mmol), and the reaction mixture was stirred at ambient temperature for 2 hours. It was quenched by the addition of saturated ammonium chloride, and it was further precipitated by the addition of water. The solids were collected via filtration and were further purified by recrystallization from ethanol/water to yield 6-bromospiro[2H-benzofuran-3,5'-imidazolidine]-2',4'-dione.

6-bromo-3'-ethyl-spiro[2H-benzofuran-3,5'-imidazolidine]-2',4'-dione was prepared in a method analogous to General Method AD using 6-bromospiro[2H-benzofuran-3,5'-imidazolidine]-2',4'-dione and ethyl iodide instead of (5S)-5'-bromospiro[imidazolidine-5,1'-indane]-2,4-dione and methyl iodide respectively.

The title compound was prepared in a method analogous to General Method F using 4-chloro-7,7-difluoro-2-methylsulfanyl-5,6-dihydrocyclopenta[d]pyrimidine and 6-bromo-3'-ethyl-spiro[2H-benzofuran-3,5'-imidazolidine]-2',4'-dione instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, followed by General Method B using (2S,3R)-2-methylazetidin-3-ol (R)-camphorsulfonic acid salt instead of (2S)-2-methylazetidine (R)-camphorsulfonic acid salt.

Example 690: 6-(7,7-difluoro-2-(2S,3R)-3-hydroxy-2-methylazetidin-1-yl)-6,7-dihydro-5H-cyclopenta[d]pyrimidin-4-yl)-1'-isopropyl-2H-spiro[benzofuran-3,4'-imidazolidine]-2',5'-dione The title compound was prepared in analogy to General Method AD using 6-bromospiro[2H-benzofuran-3,5'-imidazolidine]-2',4'-dione and 2-iodopropane instead of (5S)-5'-bromospiro[imidazolidine-5,1'-indane]-2,4-dione and methyl iodide respectively, followed by General Method F using 4-chloro-7,7-difluoro-2-methylsulfanyl-5,6-dihydrocyclopenta[d]pyrimidine and 6-bromo-3'-isopropyl-spiro[2H-benzofuran-3,5'-imidazolidine]-2',4'-dione instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, followed by General Method B using (2S,3R)-2-methylazetidin-3-ol (R)-camphorsulfonic acid salt instead of (2S)-2-methylazetidine (R)-camphorsulfonic acid salt.

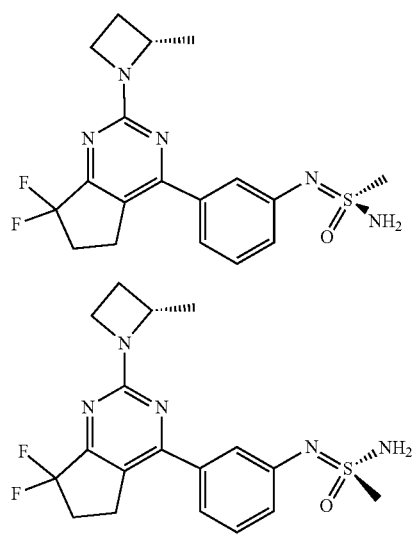

Example 691: (R)—N'-(3-(7,7-difluoro-2-((S)-2-methylazetidin-1-yl)-6,7-dihydro-5H-cyclopenta[d]pyrimidin-4-yl)phenyl)methanesulfonimidamide Example 692: (S)—N'-(3-(7,7-difluoro-2-((S)-2-methylazetidin-1-yl)-6,7-dihydro-5H-cyclopenta[d]pyrimidin-4-yl)phenyl)methanesulfonimidamide Isomers were separated by SFC (30% EtOH in $CO_2$, CHIRALPAK AD-H, 250×21 mm, 60 mL/min). (See Example 684)

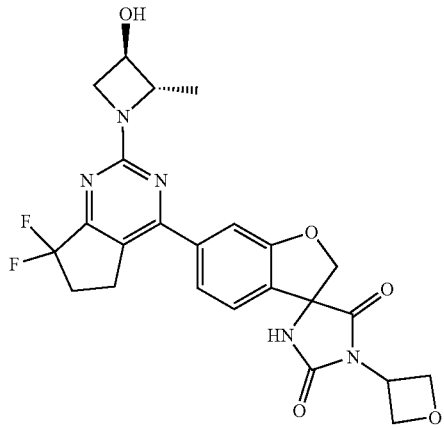

Example 694: 6-[7,7-difluoro-2-[(2S,3R)-3-hydroxy-2-methyl-azetidin-1-yl]-5,6-dihydroeyelopenta[d]pyrimidin-4-yl]-3'-(oxetan-3-yl)spiro[2H-benzofuran-3,5'-imidazolidine]-2',4'-dione The title compound was prepared in a method analogous to General Method AD using 6-bromospiro[2H-benzofuran-3,5'-imidazolidine]-2',4'-dione and 3-iodooxetane instead of (5S)-5'-bromospiro[imidazolidine-5,1'-indane]-2,4-dione and methyl iodide respectively, followed by General Method F using 4-chloro-7,7-difluoro-2-methylsulfanyl-5,6-dihydrocyclopenta[d]pyrimidine and 6-bromo-3'-(oxetan-3-yl)spiro[2H-benzofuran-3,5'-imidazolidine]-2',4'-dione instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, followed by General Method B using (2S,3R)-2-methylazetidin-3-ol (R)-camphorsulfonic acid salt instead of (2S)-2-methylazetidine (R)-camphorsulfonic acid salt.

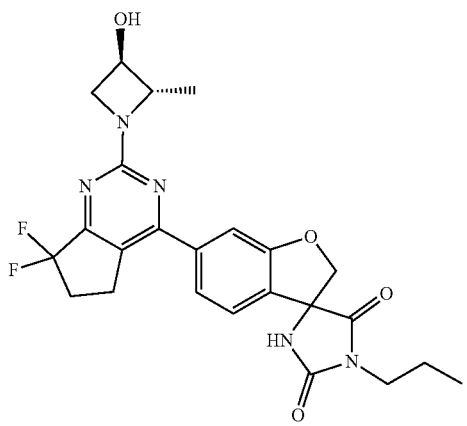 [SMILES: CCCN1C(=O)NC2(COc3cc(-c4nc(N5C[C@@H](O)[C@@H]5C)nc5c4CCC5(F)F)ccc32)C1=O]

Example 693: 6-[7,7-difluoro-2-[(2S,3R)-3-hydroxy-2-methyl-azetidin-1-yl]-5,6-dihydroeyelopenta[d]pyrimidin-4-yl]-3'-propyl-spiro[2H-benzofuran-3,5'-imidazolidine]-2',4'-dione The title compound was prepared in a method analogous to General Method AD using 6-bromospiro[2H-benzofuran-3,5'-imidazolidine]-2',4'-dione and 1-iodopropane instead of (5S)-5'-bromospiro[imidazolidine-5,1'-indane]-2,4-dione and methyl iodide respectively followed by General Method F using 4-chloro-7,7-difluoro-2-methylsulfanyl-5,6-dihydrocyclopenta[d]pyrimidine and 6-bromo-1'-propyl-2H-spiro[benzofuran-3,4'-imidazolidine]-2',5'-dione instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, followed by General Method B using (2S,3R)-2-methylazetidin-3-ol (R)-camphorsulfonic acid salt instead of (2S)-2-methylazetidine (R)-camphorsulfonic acid salt.

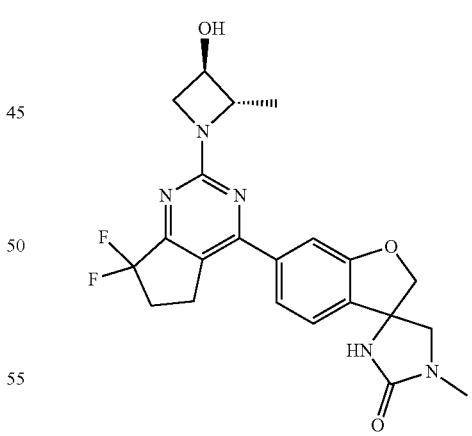

Example 695: 6-[7,7-difluoro-2-[(2S,3R)-3-hydroxy-2-methyl-azetidin-1-yl]-5,6-dihydroeyelopenta[d]pyrimidin-4-yl]-1'-methyl-spiro[2H-benzofuran-3,4'-imidazolidine]-2'-one 6-bromo-1'-methyl-2H-spiro[benzofuran-3,4'-imidazolidine]-2',5'-dione was prepared in a method analogous to General Method AD using 6-bromospiro[2H-benzofuran-3, 5'-imidazolidine]-2',4'-dione instead of (5S)-5'-bromospiro [imidazolidine-5,1'-indane]-2,4-dione.

To a suspension of sodium borohydride (64 mg, 1.7 mmol) in tetrahydrofuran (4 mL) under nitrogen at 0° C. was added boron trifluoride diethyl etherate (358 mg, 2.5 mmol) dropwise, and it was allowed to stir at this temperature for 15 minutes. To this, 6-bromo-1'-methyl-2H-spiro[benzofuran-3,4'-imidazolidine]-2',5'-dione (250 mg, 0.84 mmol) in tetrahydrofuratn (2 mL) was added, and the reaction mixture was stirred at 0° C. for 30 minutes, then was warmed to ambient temperature and stirred overnight. To this, methanol and 0.5N hydrochloric acid were added dropwise, and the mixture was stirred at ambient temperature for an additional 1 hour. The solvent was evaporated, water was added, and the mixture was extracted with ethyl acetate. The extract was washed with 1N hydrochloric acid, water, and saturated sodium chloride. It was dried over anhydrous sodium sulfate, filtered, and concentrated. It was purified by flash chromatography (hexanes-ethyl acetate) to yield 6-bromo-1'-methyl-spiro[2H-benzofuran-3,4'-imidazolidine]-2'-one.

The title compound was prepared in a method analogous to General Method F using 4-chloro-7,7-difluoro-2-methylsulfanyl-5,6-dihydrocyclopenta[d]pyrimidine and 6-bromo-1'-methyl-spiro[2H-benzofuran-3,4'-imidazolidine]-2'-one instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, followed by General Method B using (2S,3R)-2-methylazetidin-3-ol (R)-camphorsulfonic acid salt instead of (2S)-2-methylazetidine (R)-camphorsulfonic acid salt.

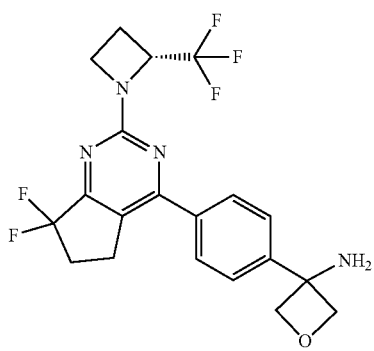 [SMILES: NC1(c2ccc(-c3nc(N4CC[C@@H]4C(F)(F)F)nc4c3CCC4(F)F)cc2)COC1]

Example 696: 3-[4-[7,7-difluoro-2-[(2R)-2-(trifluoromethyl)azetidin-1-yl]-5,6-dihydrocyclopenta[d]pyrimidin-4-yl]phenyl]oxetan-3-amine The title compound was prepared in a method analogous to General Method A using 4-chloro-7,7-difluoro-2-methylsulfanyl-5,6-dihydrocyclopenta[d]pyrimidine and benzyl N-[3-[4-(4,4,5,5-tetramethyl-1,3,2-dioxaborolan-2-yl)phenyl]oxetan-3-yl]carbamate instead of 2,4-dichloro-6,7-dihydro-5H-cyclopenta[d]pyrimidine and 3-pyridylboronic acid respectively, followed by General Method M, followed by General Method U, followed by General Method R.

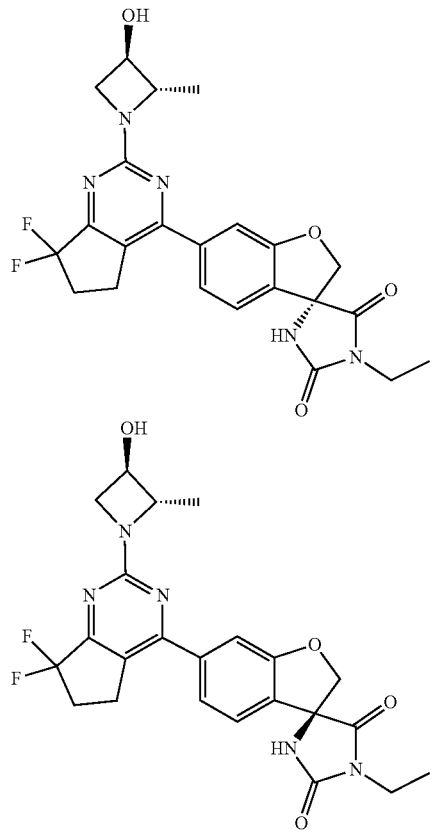

Example 697: (3R)-6-[7,7-difluoro-2-[(2S,3R)-3-hydroxy-2-methyl-azetidin-1-yl]-5,6-dihydrocyclopenta[d]pyrimidin-4-yl]-3'-ethyl-spiro[2H-benzofuran-3,5'-imidazolidine]-2',4'-dione Example 698: (3S)-6-[7,7-difluoro-2-[(2S,3R)-3-hydroxy-2-methyl-azetidin-1-yl]-5,6-dihydrocyclopenta[d]pyrimidin-4-yl]-3'-ethyl-spiro[2H-benzofuran-3,5'-imidazolidine]-2',4'-dione Isomers were separated by SFC (20% MeOH in $CO_2$, CHIRALPAK IG, 250×21 mm, 60 mL/min). (See Example 689)

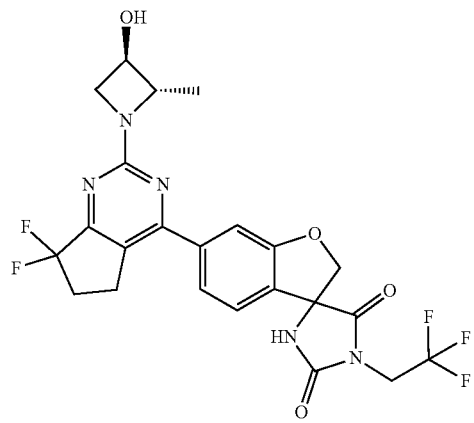 [SMILES: C[C@H]1[C@H](O)CN1c1nc(-c2ccc3c(c2)OCC32NC(=O)N(CC(F)(F)F)C2=O)c2c(n1)C(F)(F)CC2]

Example 699: 6-[7,7-difluoro-2-[(2S,3R)-3-hydroxy-2-methyl-azetidin-1-yl]-5,6-dihydrocyclopenta[d]pyrimidin-4-yl]-3'-(2,2,2-trifluoroethyl)spiro[2H-benzofuran-3,5'-imidazolidine]-2',4'-dione The title compound was prepared in a method analogous to General Method AD using 6-bromospiro[2H-benzofuran-3,5'-imidazolidine]-2',4'-dione and 1,1,1-trifluoro-2-iodo-ethane instead of (5S)-5'-bromospiro[imidazolidine-5,1'-indane]-2,4-dione and methyl iodide with heating to 60° C. for 72 hours instead of ambient temperature for 16 hours, followed by General Method F using 4-chloro-7,7-difluoro-2-methylsulfanyl-5,6-dihydrocyclopenta[d]pyrimidine and 6-bromo-3'-(2,2,2-trifluoroethyl)spiro[2H-benzofuran-3,5'-imidazolidine]-2',4'-dione instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, followed by General Method B using (2S,3R)-2-methylazetidin-3-ol (R)-camphorsulfonic acid salt instead of (2S)-2-methylazetidine (R)-camphorsulfonic acid salt.

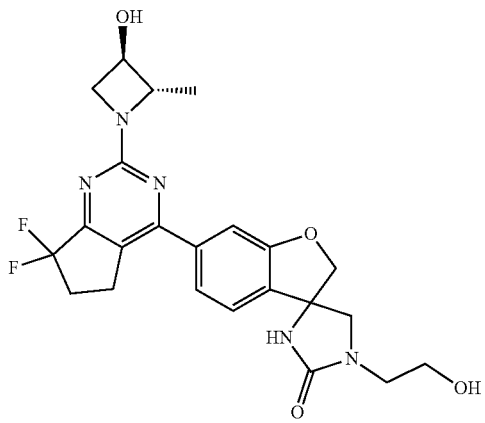 [SMILES: C[C@H]1[C@H](O)CN1c1nc(-c2ccc3c(c2)OCC32CN(CCO)C(=O)N2)c2c(n1)C(F)(F)CC2]

Example 700: 6-[7,7-difluoro-2-[(2S,3R)-3-hydroxy-2-methyl-azetidin-1-yl]-5,6-dihydrocyclopenta[d]pyrimidin-4-yl]-1'-(2-hydroxyethyl)spiro[2H-benzofuran-3,4'-imidazolidine]-2'-one 6-bromo-1'-(2-((tert-butyldimethyl silyl)oxy)ethyl)-2H-spiro[benzofuran-3,4'-imidazolidine]-2',5'-dione was prepared in a method analogous to General Method AD using 6-bromospiro[2H-benzofuran-3,5'-imidazolidine]-2',4'-dione and 2-bromoethoxy-tert-butyl-dimethyl-silane instead of (5S)-5'-bromospiro[imidazolidine-5,1'-indane]-2,4-dione and methyl iodide respectively.

6-bromo-1'-(2-((tert-butyldimethyl silyl)oxy)ethyl)-2H-spiro[benzofuran-3,4'-imidazolidin]-2'-one was prepared in a method analogous to 6-bromo-F-methyl-spiro[2H-benzofuran-3,4'-imidazolidine]-2'-one from 6-bromo-1'-(2-((tert-butyldimethylsilyl)oxy)ethyl)-2H-spiro[benzofuran-3,4'-imidazolidine]-2',5'-dione instead of 6-bromo-1'-methyl-2H-spiro[benzofuran-3,4'-imidazolidine]-2',5'-dione.

1'-(2-((tert-butyldimethylsilyl)oxy)ethyl)-6-(7,7-difluoro-2-((2S,3R)-3-hydroxy-2-methylazetidin-1-yl)-6,7-dihydro-5H-cyclopenta[d]pyrimidin-4-yl)-2H-spiro[benzofuran-3,4'-imidazolidin]-2'-one was prepared in a method analogous to General Method F using 4-chloro-7,7-difluoro-2-methyl-sulfanyl-5,6-dihydrocyclopenta[d]pyrimidine and 6-bromo-F-(2-((tert-butyldimethylsilyl)oxy)ethyl)-2H-spiro[benzofuran-3,4'-imidazolidin]-2'-one instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, followed by General Method B using (2S,3R)-2-methylazetidin-3-ol (R)-camphorsulfonic acid salt instead of (2S)-2-methylazetidine (R)-camphorsulfonic acid salt.

The title compound was prepared in a method analogous to (5S)-5'-[7,7-difluoro-2-[(2S,3R)-3-hydroxy-2-methyl-azetidin-1-yl]-5,6-dihydrocyclopenta[d]pyrimidin-4-yl]-3-(2-hydroxyethyl)spiro[imidazolidine-5,1'-indane]-2,4-dione, using 1'-[2-[tert-butyl(dimethyl)silyl]oxyethyl]-6-[7,7-difluoro-2-[(2S,3R)-3-hydroxy-2-methyl-azetidin-1-yl]-5,6-dihydrocyclopenta[d]pyrimidin-4-yl]spiro[2H-benzofuran-3,4'-imidazolidine]-2'-one instead of (5S)-3-[2-[tert-butyl(dimethyl)silyl]oxyethyl]-5'-[7,7-difluoro-2-[(2S,3R)-3-hydroxy-2-methyl-azetidin-1-yl]-5,6-dihydrocyclopenta[d]pyrimidin-4-yl]spiro[imidazolidine-5,1'-indane]-2,4-dione.

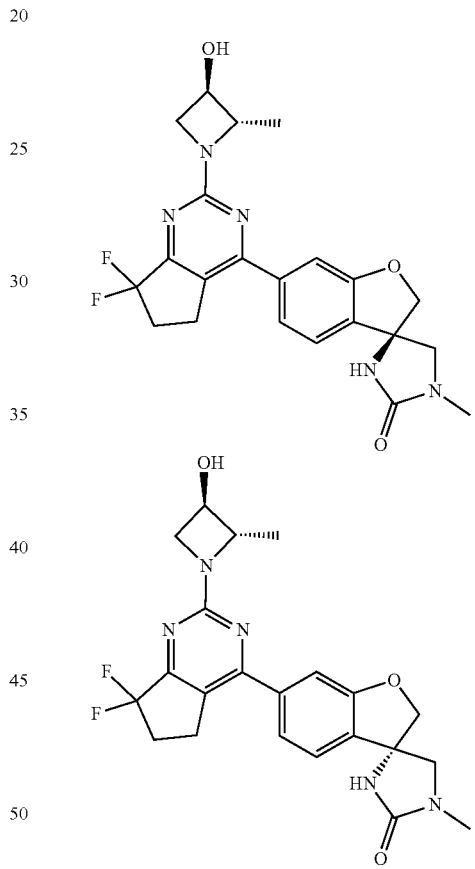

Example 701: (3R)-6-[7,7-difluoro-2-[(2S,3R)-3-hydroxy-2-methyl-azetidin-1-yl]-5,6-dihydrocyclopenta[d]pyrimidin-4-yl]-1'-methyl-spiro[2H-benzofuran-3,4'-imidazolidine]-2'-one

Example 702: (3S)-6-[7,7-difluoro-2-[(2S,3R)-3-hydroxy-2-methyl-azetidin-1-yl]-5,6-dihydrocyclopenta[d]pyrimidin-4-yl]-1'-methyl-spiro[2H-benzofuran-3,4'-imidazolidine]-2'-one Isomers were separated by SFC (35% EtOH in $CO_2$, CHIRALPAK AD-H, 250×21 mm, 60 mL/min). (See Example 695)

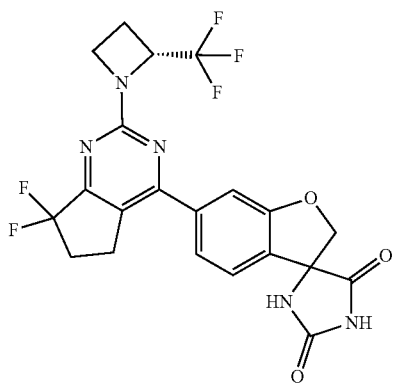 [SMILES: O=C1NC(=O)C2(COc3cc(-c4nc(N5CC[C@@H]5C(F)(F)F)nc5c4CCC5(F)F)ccc32)N1]

Example 703: 6-[7,7-difluoro-2-[(2R)-2-(trifluoromethyl)azetidin-1-yl]-5,6-dihydrocyclopenta[d]pyrimidin-4-yl]spiro[2H-benzofuran-3,5'-imidazolidine]-2',4'-dione To a solution of 6-bromospiro[2H-benzofuran-3,5'-imidazolidine]-2',4'-dione (250 mg, 0.88 mmol) and N-ethyl-N-isopropyl-propan-2-amine (0.188 mL, 1.1 mmol) in dimethylformamide (3 mL) was added 2-(chloromethoxy)ethyl-trimethyl-silane (0.195 mL, 1.1 mmol), and the reaction mixture was stirred at ambient temperature for 16 hours. It was diluted with ethyl acetate and washed with saturated ammonium chloride, saturated sodium bicarbonate, and saturated sodium chloride. It was dried over anhydrous sodium sulfate, filtered, and concentrated. It was purified via flash chromatography (5-100% ethyl acetate/hexanes linear gradient) to yield 6-bromo-3'-(2-trimethylsilylethoxymethyl)spiro[2H-benzofuran-3,5'-imidazolidine]-2',4'-dione.

6-(7,7-difluoro-2-((R)-2-(trifluoromethyl)azetidin-1-yl)-6,7-dihydro-5H-cyclopenta[d]pyrimidin-4-yl)-1'-((2-(trimethylsilyl)ethoxy)methyl)-2H-spiro[benzofuran-3,4'-imidazolidine]-2',5'-dione was prepared in a method analogous to General Method F using 4-chloro-7,7-difluoro-2-methylsulfanyl-5,6-dihydrocyclopenta[d]pyrimidine and 6-bromo-3'-(2-trimethylsilylethoxymethyl)spiro[2H-benzofuran-3,5'-imidazolidine]-2',4'-dione instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, followed by General Method B using 2-(trifluoromethyl)azetidine hydrochloride instead of (2S)-2-methylazetidine (R)-camphorsulfonic acid salt and heating to 130° C. for 16 hours instead of 80° C. for 16 hours.

To a solution of 6-[7,7-difluoro-2-[(2R)-2-(trifluoromethyl)azetidin-1-yl]-5,6-dihydrocyclopenta[d]pyrimidin-4-yl]-3'42-trimethylsilylethoxymethyl)spiro[2H-benzofuran-3,5'-imidazolidine]-2',4'-dione (38 mg, 0.062 mmol) in dichloromethane (2 mL) was added trifluoroacetic acid (70 mg), and the reaction mixture was stirred at ambient temperature for 2 hours. It was concentrated, taken up in dichloromethane, and 1N sodium hydroxide was added until a pH of >12 was reached. It was stirred for 4 hours, then was acidified with 10% potassium bisulfate and extracted twice with ethyl acetate. It was dried over anhydrous sodium sulfate, filtered, and concentrated. It was purified via flash chromatography (DCM-MeOH) to yield the title compound.

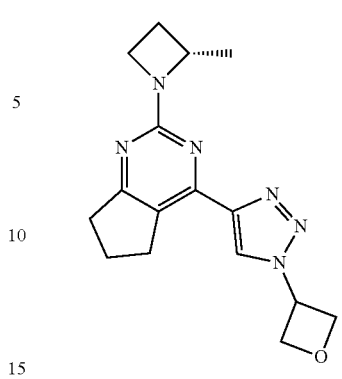

Example 704: 2-[(2S)-2-methylazetidin-1-yl]-4-[1-(oxetan-3-yl)triazol-4-yl]-6,7-dihydro-5H-cyclopenta[d]pyrimidine The title compound was made according to General Method AB.

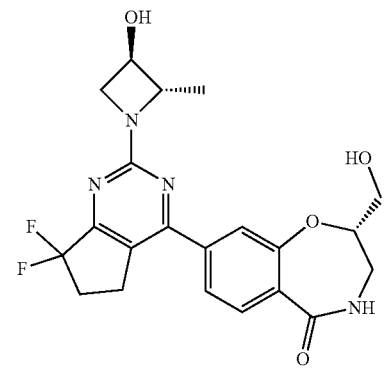 [SMILES: C[C@H]1[C@H](O)CN1c1nc(-c2ccc3c(c2)O[C@H](CO)CNC3=O)c2c(n1)C(F)(F)CC2]

Example 705: (S)-8-(7,7-difluoro-2-((2S,3R)-3-hydroxy-2-methylazetidin-1-yl)-6,7-dihydro-5H-cyclopenta[d]pyrimidin-4-yl)-2-(hydroxymethyl)-3,4-dihydrobenzo[f][1,4]oxazepin-5(2H)-one The title compound was prepared in analogy to General Method Q, using tert-butyl (R)-(3-((tert-butyldimethylsilyl)oxy)-2-hydroxypropyl)carbamate instead of tert-butyl (S)-(1-hydroxypropan-2-yl)carbamate, followed by General Method F using (S)-8-bromo-2-(hydroxymethyl)-3,4-dihydrobenzo[f][1,4]oxazepin-5(2H)-one and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, followed by General method B using (2S,3R)-2-methylazetidin-3-ol instead of (2S)-2-methylazetidine.

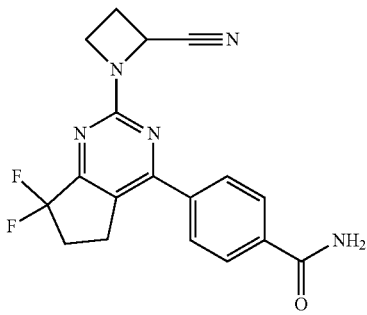 [SMILES: N#CC1CCN1c1nc(-c2ccc(C(N)=O)cc2)c2c(n1)C(F)(F)CC2]

Example 706: 4-(2-(2-cyanoazetidin-1-yl)-7,7-difluoro-6,7-dihydro-5H-cyclopenta[d]pyrimidin-4-yl)benzamide The title compound was prepared in analogy to General Method B, using 4-(7,7-difluoro-2-(methylsulfonyl)-6,7-dihydro-5H-cyclopenta[d]pyrimidin-4-yl)benzamide and azetidine-2-carbonitrileoxalic acid salt instead of with 2-chloro-4-(pyridin-3-yl)-6,7-dihydro-5H-cyclopenta[d]pyrimidine and (2S)-2-methylazetidine, respectively.

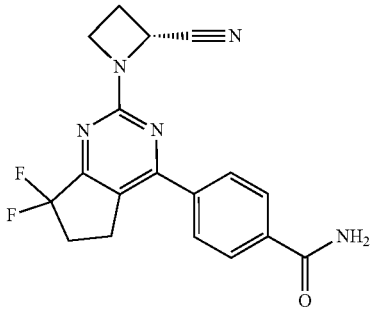 [SMILES: N#C[C@H]1CCN1c1nc(-c2ccc(C(N)=O)cc2)c2c(n1)C(F)(F)CC2]

Example 707: (R)-4-(2-(2-cyanoazetidin-1-yl)-7,7-difluoro-6,7-dihydro-5H-cyclopenta[d]pyrimidin-4-yl)benzamide The title compound was prepared in analogy to General Method B, using 4-(7,7-difluoro-2-(methylsulfonyl)-6,7-dihydro-5H-cyclopenta[d]pyrimidin-4-yl)benzamide and (2R)-azetidine-2-carbonitrile oxalic acid salt instead of with 2-chloro-4-(pyridin-3-yl)-6,7-dihydro-5H-cyclopenta[d]pyrimidine and (2S)-2-methylazetidine, respectively.

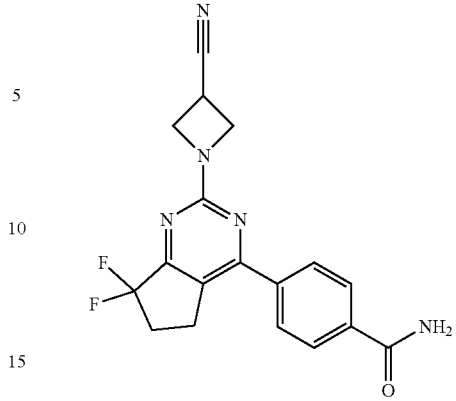

Example 708: 4-(2-(3-cyanoazetidin-1-yl)-7,7-difluoro-6,7-dihydro-5H-cyclopenta[d]pyrimidin-4-yl)benzamide The title compound was prepared in analogy to General Method B, using 4-(7,7-difluoro-2-(methylsulfonyl)-6,7-dihydro-5H-cyclopenta[d]pyrimidin-4-yl)benzamide and azetidine-3-carbonitrile HCl salt instead of 2-chloro-4-(pyridin-3-yl)-6,7-dihydro-5H-cyclopenta[d]pyrimidine and (2S)-2-methylazetidine, respectively.

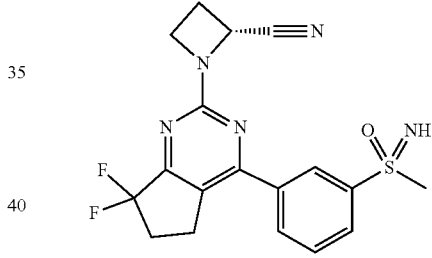

Example 709: (2R)-1-(7,7-difluoro-4-(3-(S-methylsulfonimidoyl)phenyl)-6,7-dihydro-5H-cyclopenta[d]pyrimidin-2-yl)azetidine-2-carbonitrile The title compound was prepared in analogy to General Method S using (3-bromophenyl)(methyl)sulfane instead of (5-bromo-2-methoxyphenyl)(methyl)sulfane, followed by General Method F using 4-chloro-7,7-difluoro-2-(methylthio)-6,7-dihydro-5H-cyclopenta[d]pyrimidine and tert-butyl ((3-bromophenyl)(methyl)(oxo)-$\lambda^6$-sulfaneylidene)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, followed by General Method I, followed by General Method B, using (3-(7,7-difluoro-2-(methylsulfonyl)-6,7-dihydro-5H-cyclopenta[d]pyrimidin-4-yl)phenyl)(imino)(methyl)-$\lambda^6$-sulfanone and (2R)-azetidine-2-carbonitrile instead of 2-chloro-4-(pyridin-3-yl)-6,7-dihydro-5H-cyclopenta[d]pyrimidine and (2S)-2-methylazetidine, respectively.

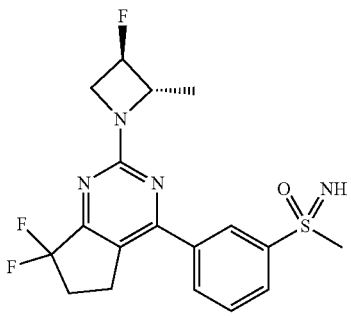 [SMILES: C[C@H]1[C@H](F)CN1c1nc(-c2cccc(S(C)(=N)=O)c2)c2c(n1)C(F)(F)CC2]

Example 710: (3-(7,7-difluoro-2-((2S,3R)-3-fluoro-2-methylazetidin-1-yl)-6,7-dihydro-5H-cyclopenta[d]pyrimidin-4-yl)phenyl)(imino)(methyl)-$\lambda^6$-sulfanone The title compound was prepared in analogy to General Method S using (3-bromophenyl)(methyl)sulfane instead of (5-bromo-2-methoxyphenyl)(methyl)sulfane, followed by General Method F using 4-chloro-7,7-difluoro-2-(methylthio)-6,7-dihydro-5H-cyclopenta[d]pyrimidine and tert-butyl ((3-bromophenyl)(methyl)(oxo)-$\lambda^6$-sulfaneylidene)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, followed by General Method I, followed by General Method B, using (3-(7,7-difluoro-2-(methylsulfonyl)-6,7-dihydro-5H-cyclopenta[d]pyrimidin-4-yl)phenyl)(imino)(methyl)-$\lambda^6$-sulfanone and (2S, 3R)-3-fluoro-2-methyl-azetidine instead of 2-chloro-4-(pyridin-3-yl)-6,7-dihydro-5H-cyclopenta[d]pyrimidine and (2S)-2-methylazetidine, respectively.

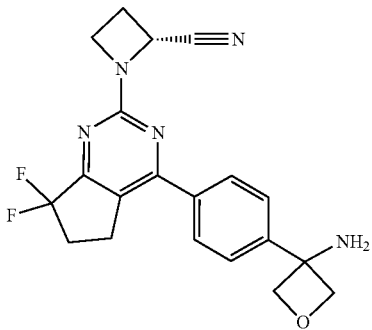 [SMILES: N#C[C@H]1CCN1c1nc(-c2ccc(C3(N)COC3)cc2)c2c(n1)C(F)(F)CC2]

Example 711: (R)-1-(4-(4-(3-aminooxetan-3-yl)phenyl)-7,7-difluoro-6,7-dihydro-5H-cyclopenta[d]pyrimidin-2-yl)azetidine-2-carbonitrile The title compound was prepared in a method analogous to General Method A using 4-chloro-7,7-difluoro-2-(methylthio)-6,7-dihydro-5H-cyclopenta[d]pyrimidine and benzyl (3-(4-(4,4,5,5-tetramethyl-1,3,2-dioxaborolan-2-yl)phenyl)oxetan-3-yl)carbamate instead of 2,4-dichloro-6,7-dihydro-5H-cyclopenta[d]pyrimidine and 3-pyridylboronic acid, respectively, followed by General Method M, followed by General Method B using (2R)-azetidine-2-carbonitrile instead of (2S)-2-methylazetidine, followed by General Method R.

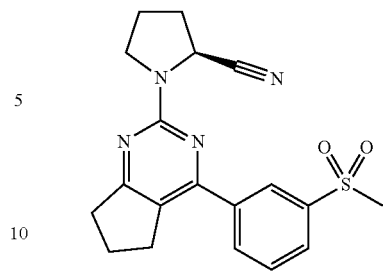

Example 712: (S)-1-(4-(3-(methylsulfonyl)phenyl)-6,7-dihydro-5H-cyclopenta[d]pyrimidin-2-yl)pyrrolidine-2-carbonitrile (S)-1-(4-(3-(methylsulfonyl)phenyl)-6,7-dihydro-5H-cyclopenta[d]pyrimidin-2-yl)pyrrolidine-2-carboxamide was prepared in analogy to General Method A using 4,4,5,5-tetramethyl-2-(3-(methylsulfonyl)phenyl)-1,3,2-dioxaborolane instead of 3-pyridylboronic acid, followed by General Method B, using 2-chloro-4-(3-(methylsulfonyl)phenyl)-6,7-dihydro-5H-cyclopenta[d]pyrimidine and (S)-pyrrolidine-2-carboxamide instead of 2-chloro-4-(pyridin-3-yl)-6,7-dihydro-5H-cyclopenta[d]pyrimidine and (2S)-2-methylazetidine, respectively.

A vial was charged with (S)-1-(4-(3-(methylsulfonyl)phenyl)-6,7-dihydro-5H-cyclopenta[d]pyrimidin-2-yl)pyrrolidine-2-carboxamide (126 mg, 0.33 mmol) and pyridine (1 mL) and cooled to 0° C. POCl$_3$ (0.15 mL, 1.62 mmol, 5.0 equiv.) was added and the mixture was stirred for 1 hour. The reaction mixture was quenched with water and extracted twice with DCM. The combined organic layers were dried over MgSO$_4$, filtered and concentrated. The residue was concentrated and subject to HPLC (0.1% TFA in MeCN-0.1% TFA in H$_2$O) to give the title compound.

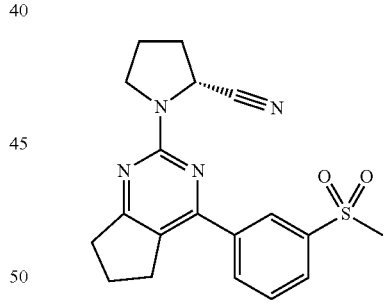

Example 713: (R)-1-(4-(3-(methylsulfonyl)phenyl)-6,7-dihydro-5H-cyclopenta[d]pyrimidin-2-yl)pyrrolidine-2-carbonitrile (R)-1-(4-(3-(methylsulfonyl)phenyl)-6,7-dihydro-5H-cyclopenta[d]pyrimidin-2-yl)pyrrolidine-2-carboxamide was prepared in analogy to General Method A using 4,4,5,5-tetramethyl-2-(3-(methylsulfonyl)phenyl)-1,3,2-dioxaborolane instead of 3-pyridylboronic acid, followed by General Method B, using 2-chloro-4-(3-(methylsulfonyl)phenyl)-6,7-dihydro-5H-cyclopenta[d]pyrimidine and (R)-pyrrolidine-2-carboxamide instead of 2-chloro-4-(pyridin-3-yl)-6,7-dihydro-5H-cyclopenta[d]pyrimidine and (2S)-2-methylazetidine, respectively.

A vial was charged with (R)-1-(4-(3-(methylsulfonyl)phenyl)-6,7-dihydro-5H-cyclopenta[d]pyrimidin-2-yl)pyrrolidine-2-carboxamide (99 mg, 0.26 mmol) and pyridine (1 mL) and cooled to 0° C. POCl₃ (0.12 mL, 1.3 mmol) was added and the mixture was stirred for 1 hour. The reaction mixture was quenched with water and extracted twice with DCM. The combined organic layers were dried over MgSO₄, filtered and concentrated. The residue was concentrated and subject to HPLC (0.1% TFA in MeCN-0.1% TFA in H₂O) to give the title compound.

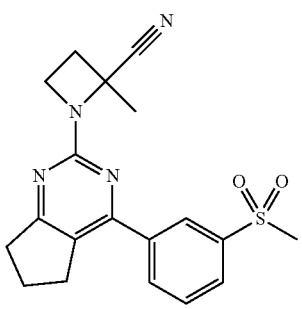 [SMILES: CC1(C#N)CCN1c1nc2c(c(-c3cccc(S(C)(=O)=O)c3)n1)CCC2]

Example 714: 2-methyl-1-(4-(3-(methylsulfonyl)phenyl)-6,7-dihydro-5H-cyclopenta[d]pyrimidin-2-yl)azetidine-2-carbonitrile 2-methyl-1-(4-(3-(methylsulfonyl)phenyl)-6,7-dihydro-5H-cyclopenta[d]pyrimidin-2-yl)azetidine-2-carboxylic acid was prepared in analogy to General Method A using 4,4,5,5-tetramethyl-2-(3-(methylsulfonyl)phenyl)-1,3,2-dioxaborolane instead of 3-pyridylboronic acid, followed by General Method B, using 2-chloro-4-(3-(methylsulfonyl)phenyl)-6,7-dihydro-5H-cyclopenta[d]pyrimidine and methyl 2-methylazetidine-2-carboxylate instead of 2-chloro-4-(pyridin-3-yl)-6,7-dihydro-5H-cyclopenta[d]pyrimidine and (2S)-2-methylazetidine, respectively, followed by General Method C.

A vial was charged with 2-methyl-1-(4-(3-(methylsulfonyl)phenyl)-6,7-dihydro-5H-cyclopenta[d]pyrimidin-2-yl)azetidine-2-carboxylic acid (79.1 mg, 0.20 mmol, 1.0 equiv.) and THF (2 mL) and cooled to 0° C. Triethyl amine (0.05 mL, 0.41 mmol, 2.0 equiv.) and isobutyl chloroformate (0.05 mL, 0.41 mmol, 2.0 equiv.) were added and the reaction mixture was allowed to stir at room temperature for 30 minutes. An aqueous solution of ammonium hydroxide (38% in water, 0.33 mL, 16 equiv.) was added and the reaction mixture was allowed to stir for an addition 30 minutes. The mixture was slowly quenched with water and extracted three times with DCM. The combined organics were dried over magnesium sulfate, filtered and concentrated to afford 2-methyl-1-(4-(3-(methylsulfonyl)phenyl)-6,7-dihydro-5H-cyclopenta[d]pyrimidin-2-yl)azetidine-2-carboxamide.

A vial was charged with 2-methyl-1-(4-(3-(methylsulfonyl)phenyl)-6,7-dihydro-5H-cyclopenta[d]pyrimidin-2-yl)azetidine-2-carboxamide (34.7 mg, 0.09 mmol, 1.0 equiv.) and pyridine (1 mL) and cooled to 0° C. POCl₃ (0.04 mL, 0.45 mmol, 5.0 equiv.) was added and the mixture was stirred for 1 hour. The reaction mixture was quenched with water and extracted twice with DCM. The combined organic layers were dried over MgSO₄, filtered and concentrated. The residue was concentrated and subject to HPLC (0.1% TFA in MeCN-0.1% TFA in H₂O) to give the title compound (1.60 mg, 0.004 mmol).

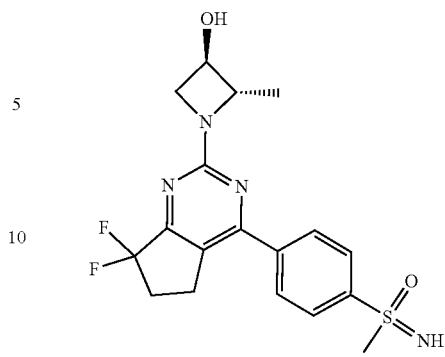

Example 715: (4-(7,7-difluoro-2-((2S,3R)-3-hydroxy-2-methylazetidin-1-yl)-6,7-dihydro-5H-cyclopenta[d]pyrimidin-4-yl)phenyl)(imino)(methyl)-λ⁶-sulfanone The title compound was prepared in analogy to General Method F using 4-chloro-7,7-difluoro-2-(methylthio)-6,7-dihydro-5H-cyclopenta[d]pyrimidine and (4-bromophenyl)(imino)(methyl)-λ⁶-sulfanone instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one, respectively, followed by General Method M, and General Method B, using (2S,3R)-2-methylazetidin-3-ol instead of (2S)-2-methylazetidine.

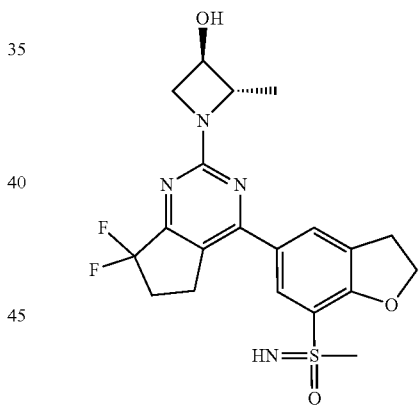

Example 716: (5-(7,7-difluoro-2-((2S,3R)-3-hydroxy-2-methylazetidin-1-yl)-6,7-dihydro-5H-cyclopenta[d]pyrimidin-4-yl)-2,3-dihydrobenzofuran-7-yl)(imino)(methyl)-λ⁶-sulfanone The title compound was prepared according to General Method AF, followed by General Method S, followed by General Method F using 4-chloro-7,7-difluoro-2-(methylthio)-6,7-dihydro-5H-cyclopenta[d]pyrimidine and tert-butyl ((5-bromo-2,3-dihydrobenzofuran-7-yl)(methyl)(oxo)-λ⁶-sulfaneylidene)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine, followed by General Method I.

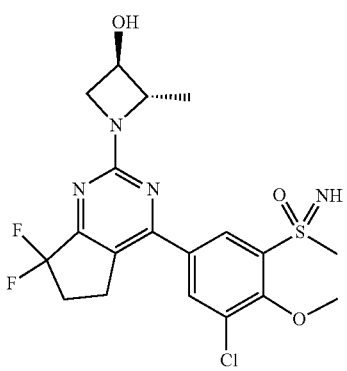 [SMILES: COc1c(Cl)cc(-c2nc(N3C[C@@H](O)[C@@H]3C)nc3c2CCC3(F)F)cc1S(C)(=N)=O]

Example 717: (3-chloro-5-(7,7-difluoro-2-((2S,3R)-3-hydroxy-2-methylazetidin-1-yl)-6,7-dihydro-5H-cyclopenta[d]pyrimidin-4-yl)-2-methoxyphenyl)(imino)(methyl)-λ⁶-sulfanone The title compound was prepared in analogy to General Method AF, using 5-bromo-1-chloro-3-iodo-2-methoxybenzene instead of 5-bromo-7-iodo-2,3-dihydrobenzofuran, followed by General Method S, followed by General Method F using 4-chloro-7,7-difluoro-2-(methylthio)-6,7-dihydro-5H-cyclopenta[d]pyrimidine and tert-butyl ((5-bromo-3-chloro-2-methoxyphenyl)(methyl)(oxo)-λ⁶-sulfaneylidene) carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine, followed by General Method I.

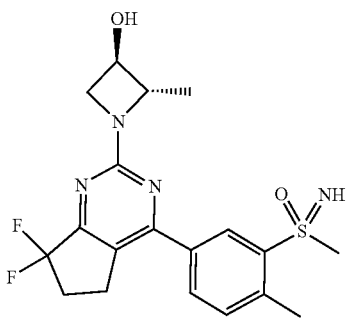 [SMILES: Cc1ccc(-c2nc(N3C[C@@H](O)[C@@H]3C)nc3c2CCC3(F)F)cc1S(C)(=N)=O]

Example 718: (5-(7,7-difluoro-2-((2S,3R)-3-hydroxy-2-methylazetidin-1-yl)-6,7-dihydro-5H-cyclopenta[d]pyrimidin-4-yl)-2-methylphenyl)(imino)(methyl)-λ⁶-sulfanone The title compound was prepared in analogy to General Method AF, using 4-bromo-2-iodo-1-methylbenzene instead of 5-bromo-7-iodo-2,3-dihydrobenzofuran, followed by General Method S, followed by General Method F using 4-chloro-7,7-difluoro-2-(methylthio)-6,7-dihydro-5H-cyclopenta[d]pyrimidine and tert-butyl ((5-bromo-2-methylphenyl)(methyl)(oxo)-λ⁶-sulfaneylidene)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine, followed by General Method I.

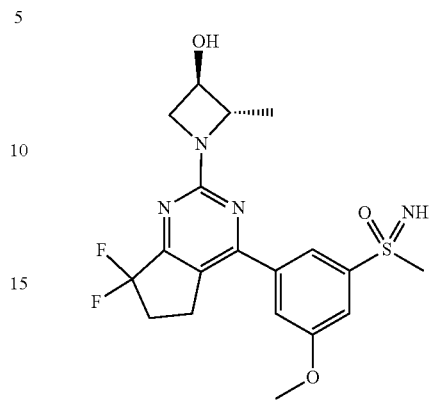

Example 719: (3-(7,7-difluoro-2-((2S,3R)-3-hydroxy-2-methylazetidin-1-yl)-6,7-dihydro-5H-cyclopenta[d]pyrimidin-4-yl)-5-methoxyphenyl)(imino)(methyl)-λ⁶-sulfanone The title compound was prepared in analogy to General Method AF, using 1-bromo-3-iodo-5-methoxybenzene instead of 5-bromo-7-iodo-2,3-dihydrobenzofuran, followed by General Method S, followed by General Method F using 4-chloro-7,7-difluoro-2-(methylthio)-6,7-dihydro-5H-cyclopenta[d]pyrimidine and tert-butyl ((3-bromo-5-methoxyphenyl)(methyl)(oxo)-λ⁶-sulfaneylidene)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine, followed by General Method I.

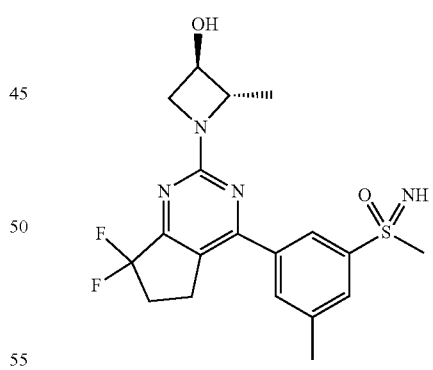

Example 720: (3-(7,7-difluoro-2-((2S,3R)-3-hydroxy-2-methylazetidin-1-yl)-6,7-dihydro-5H-cyclopenta[d]pyrimidin-4-yl)-5-methylphenyl)(imino)(methyl)-λ⁶-sulfanone The title compound was prepared in analogy to General Method AF, using 1-bromo-3-iodo-5-methylbenzene instead of 5-bromo-7-iodo-2,3-dihydrobenzofuran, followed by General Method S, followed by General Method F using 4-chloro-7,7-difluoro-2-(methylthio)-6,7-dihydro-5H-cyclopenta[d]pyrimidine and tert-butyl ((3-bromo-5-methylphenyl)(methyl)(oxo)-λ⁶-sulfaneylidene)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine, followed by General Method I.

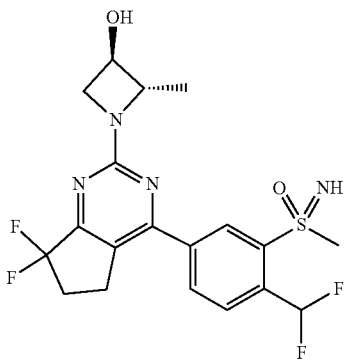 [SMILES: C[C@H]1[C@H](O)CN1c1nc(-c2ccc(C(F)F)c(S(C)(=N)=O)c2)c2c(n1)C(F)(F)CC2]

Example 721: (5-(7,7-difluoro-2-((2S,3R)-3-hydroxy-2-methylazetidin-1-yl)-6,7-dihydro-5H-cyclopenta[d]pyrimidin-4-yl)-2-(difluoromethyl)phenyl)(imino)(methyl)-λ⁶-sulfanone The title compound was prepared in analogy to General Method AF, using 4-bromo-1-(difluoromethyl)-2-iodobenzene instead of 5-bromo-7-iodo-2,3-dihydrobenzofuran, followed by General Method S, followed by General Method F using 4-chloro-7,7-difluoro-2-(methylthio)-6,7-dihydro-5H-cyclopenta[d]pyrimidine and tert-butyl ((5-bromo-2-(difluoromethyl)phenyl)(methyl)(oxo)-λ⁶-sulfaneylidene)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine, followed by General Method I.

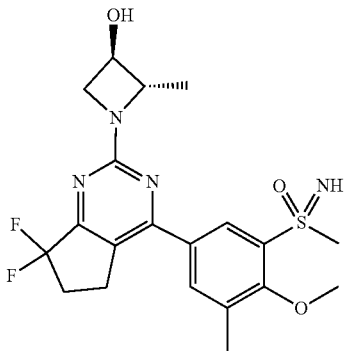 [SMILES: COc1c(C)cc(-c2nc(N3C[C@@H](O)[C@@H]3C)nc3c2CCC3(F)F)cc1S(C)(=N)=O]

Example 722: (5-(7,7-difluoro-2-((2S,3R)-3-hydroxy-2-methylazetidin-1-yl)-6,7-dihydro-5H-cyclopenta[d]pyrimidin-4-yl)-2-methoxy-3-methylphenyl)(imino)(methyl)-λ⁶-sulfanone The title compound was prepared in analogy to General Method AF, using 5-bromo-1-iodo-2-methoxy-3-methylbenzene instead of 5-bromo-7-iodo-2,3-dihydrobenzofuran, followed by General Method S, followed by General Method F using 4-chloro-7,7-difluoro-2-(methylthio)-6,7-dihydro-5H-cyclopenta[d]pyrimidine and tert-butyl ((5-bromo-2-methoxy-3-methylphenyl)(methyl)(oxo)-λ⁶-sulfaneylidene)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine, followed by General Method I.

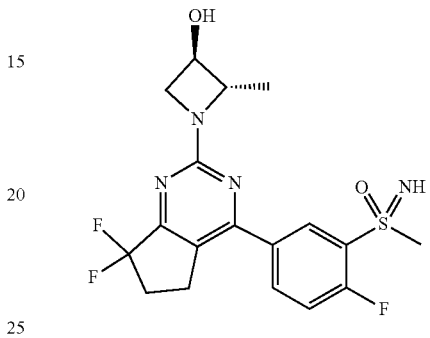

Example 723: (5-(7,7-difluoro-2-((2S,3R)-3-hydroxy-2-methylazetidin-1-yl)-6,7-dihydro-5H-cyclopenta[d]pyrimidin-4-yl)-2-fluorophenyl)(imino)(methyl)-λ⁶-sulfanone The title compound was prepared in analogy to General Method S, using (5-bromo-2-fluorophenyl)(methyl)sulfane instead of (5-bromo-2-methoxyphenyl)(methyl)sulfane, followed by General Method F using 4-chloro-7,7-difluoro-2-(methylthio)-6,7-dihydro-5H-cyclopenta[d]pyrimidine and tert-butyl ((5-bromo-2-fluorophenyl)(methyl)(oxo)-λ⁶-sulfaneylidene)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine, followed by General Method I.

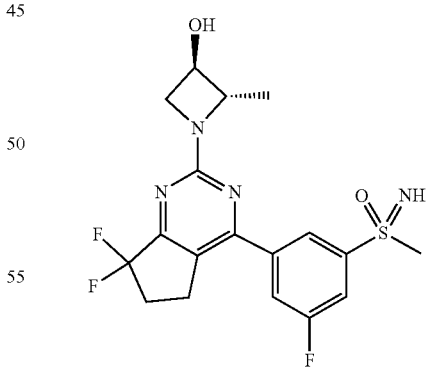

Example 724: (3-(7,7-difluoro-2((2S,3R)-3-hydroxy-2-methylazetidin-1-yl)-6,7-dihydro-5H-cyclopenta[d]pyrimidin-4-yl)-5-fluorophenyl)(imino)(methyl)-λ⁶-sulfanone The title compound was prepared in analogy to General Method S, using (3-bromo-5-fluorophenyl)(methyl)sulfane instead of (5-bromo-2-methoxyphenyl)(methyl)sulfane, followed by General Method F using 4-chloro-7,7-difluoro-2-(methylthio)-6,7-dihydro-5H-cyclopenta[d]pyrimidine and tert-butyl ((3-bromo-5-fluorophenyl)(methyl)(oxo)-λ⁶-sulfaneylidene)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine, followed by General Method I.

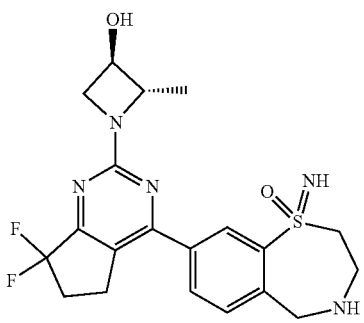 [SMILES: C[C@H]1[C@H](O)CN1c1nc(-c2ccc3c(c2)S(=N)(=O)CCNC3)c2c(n1)C(F)(F)CC2]

Example 725: 8-(7,7-difluoro-24(2S,3R)-3-hydroxy-2-methylazetidin-1-yl)-6,7-dihydro-5H-cyclopenta[d]pyrimidin-4-yl)-1-imino-2,3,4,5-tetrahydro-1H-1λ⁴-benzo[f][1,4]thiazepine 1-oxide The title compound was prepared in analogy to General Method S, using tert-butyl 8-bromo-2,3-dihydrobenzo[f][1,4]thiazepine-4(5H)-carboxylate instead of (5-bromo-2-methoxyphenyl)(methyl)sulfane, followed by General Method F using 4-chloro-7,7-difluoro-2-(methylthio)-6,7-dihydro-5H-cyclopenta[d]pyrimidine and tert-butyl 8-bromo-1-((tert-butoxycarbonyl)imino)-1,2,3,5-tetrahydro-4H-1λ⁴-benzo[f][1,4]thiazepine-4-carboxylate 1-oxide instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine, followed by General Method I.

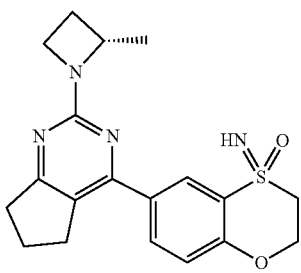 [SMILES: C[C@H]1CCN1c1nc2c(c(-c3ccc4c(c3)S(=N)(=O)CCO4)n1)CCC2]

Example 726: 4-imino-6-(24(8)-2-methylazetidin-1-yl)-6,7-dihydro-5H-cyclopenta[d]pyrimidin-4-yl)-3,4-dihydro-2H-4λ⁴-benzo[b][1,4]oxathiine 4-oxide The title compound was made in analogy to General Method E, using 6-bromo-4-imino-3,4-dihydro-2H-4λ⁴-benzo[b][1,4]oxathiine 4-oxide and (S)-2-(2-methylazetidin-1-yl)-4-(tributylstannyl)-6,7-dihydro-5H-cyclopenta[d]pyrimidine instead of (S)-4-chloro-2-(2-methylazetidin-1-yl)-6,7-dihydro-5H-cyclopenta[d]pyrimidine and ethyl 2-tributylstannylimidazo[5,1-b]thiazole-7-carboxylate, respectively.

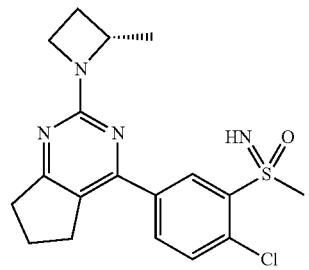 [SMILES: C[C@H]1CCN1c1nc2c(c(-c3ccc(Cl)c(S(C)(=N)=O)c3)n1)CCC2]

Example 727: (2-chloro-5-(24(8)-2-methylazetidin-1-yl)-6,7-dihydro-5H-cyclopenta[d]pyrimidin-4-yl)phenyl)(imino)(methyl)-λ⁶-sulfanone The title compound was made in analogy to General Method E, using (5-bromo-2-chlorophenyl)(imino)(methyl)-λ⁶-sulfanone and (S)-2-(2-methylazetidin-1-yl)-4-(tributylstannyl)-6,7-dihydro-5H-cyclopenta[d]pyrimidine instead of (S)-4-chloro-2-(2-methylazetidin-1-yl)-6,7-dihydro-5H-cyclopenta[d]pyrimidine and ethyl 2-tributylstannylimidazo[5,1-b]thiazole-7-carboxylate, respectively.

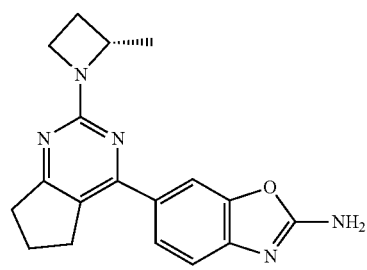 [SMILES: C[C@H]1CCN1c1nc2c(c(-c3ccc4nc(N)oc4c3)n1)CCC2]

Example 728: (S)-6-(2-(2-methylazetidin-1-yl)-6,7-dihydro-5H-cyclopenta[d]pyrimidin-4-yl)benzo[d]oxazol-2-amine The title compound was prepared in analogy to General Method A, using 6-(4,4,5,5-tetramethyl-1,3,2-dioxaborolan-2-yl)-1,3-benzoxazol-2-amine and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

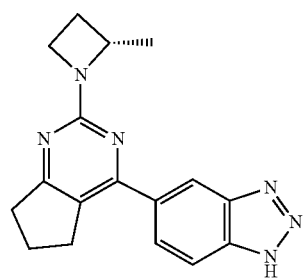 [SMILES: C[C@H]1CCN1c1nc2c(c(-c3ccc4[nH]nnc4c3)n1)CCC2]

Example 729: (S)-5-(2-(2-methylazetidin-1-yl)-6,7-dihydro-5H-cyclopenta[d]pyrimidin-4-yl)-1H-benzo[d][1,2,3]triazole The title compound was prepared in analogy to General Method A, using 1H-benzotriazol-5-ylboronic acid and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

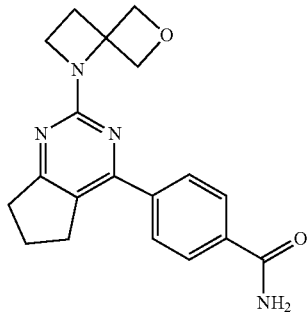 [SMILES: NC(=O)c1ccc(-c2nc(N3CCC34COC4)nc3c2CCC3)cc1]

Example 730: 4-(2-(6-oxa-1-azaspiro[3.3]heptan-1-yl)-6,7-dihydro-5H-cyclopenta[d]pyrimidin-4-yl)benzamide The title compound was prepared in analogy to General Method B using 6-oxa-1-azaspiro[3.3]heptane and 4-(2-chloro-6,7-dihydro-5H-cyclopenta[d]pyrimidin-4-yl)benzamide instead of (2S)-2-methylazetidine and 2-chloro-4-(pyridin-3-yl)-6,7-dihydro-5H-cyclopenta[d]pyrimidine, respectively.

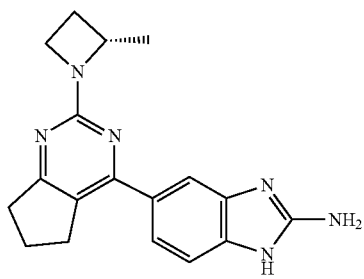 [SMILES: C[C@H]1CCN1c1nc2c(c(-c3ccc4[nH]c(N)nc4c3)n1)CCC2]

Example 731: (S)-5-(2-(2-methylazetidin-1-yl)-6,7-dihydro-5H-cyclopenta[d]pyrimidin-4-yl)-1H-benzo[d]imidazol-2-amine The title compound was prepared in analogy to General Method A using 5-(4,4,5,5-tetramethyl-1,3,2-dioxaborolan-2-yl)-1H-benzimidazol-2-amine and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

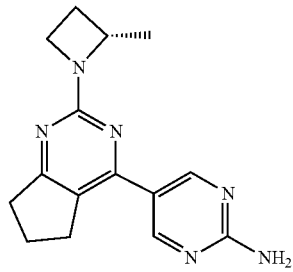 [SMILES: C[C@H]1CCN1c1nc2c(c(-c3cnc(N)nc3)n1)CCC2]

Example 732: (S)-5-(2-(2-methylazetidin-1-yl)-6,7-dihydro-5H-cyclopenta[d]pyrimidin-4-yl)pyrimidin-2-amine The title compound was prepared in analogy to General Method A using (2-aminopyrimidin-5-yl)boronic acid and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

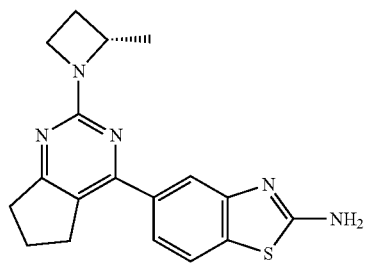 [SMILES: C[C@H]1CCN1c1nc2c(c(-c3ccc4sc(N)nc4c3)n1)CCC2]

Example 733: (S)-5-(2-(2-methylazetidin-1-yl)-6,7-dihydro-5H-cyclopenta[d]pyrimidin-4-yl)benzo[d]thiazol-2-amine The title compound was prepared in analogy to General Method F using 5-bromo-1,3-benzothiazol-2-amine instead of 6-bromo-1,1-dioxo-1,2-benzothiazol-3-one.

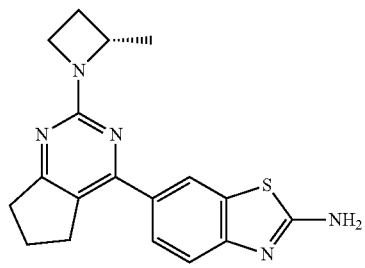 [SMILES: C[C@H]1CCN1c1nc2c(c(-c3ccc4nc(N)sc4c3)n1)CCC2]

Example 734: (S)-6-(2-(2-methylazetidin-1-yl)-6,7-dihydro-5H-cyclopenta[d]pyrimidin-4-yl)benzo[d]thiazol-2-amine The title compound was prepared in analogy to General Method F using 6-bromo-1,3-benzothiazol-2-amine instead of 6-bromo-1,1-dioxo-1,2-benzothiazol-3-one.

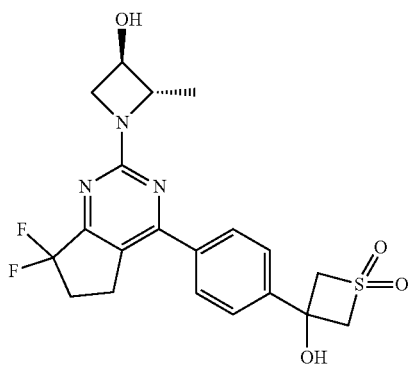 [SMILES: C[C@H]1[C@H](O)CN1c1nc(-c2ccc(C3(O)CS(=O)(=O)C3)cc2)c2c(n1)C(F)(F)CC2]

Example 735: 3-(4-(7,7-difluoro-24(2S,3R)-3-hydroxy-2-methylazetidin-1-yl)-6,7-dihydro-5H-cyclopenta[d]pyrimidin-4-yl)phenyl)-3-hydroxythietane 1,1-dioxide The title compound was prepared in analogy to General Method F using 4-chloro-7,7-difluoro-2-(methylthio)-6,7-dihydro-5H-cyclopenta[d]pyrimidine and 3-(4-bromophenyl)-3-hydroxythietane 1,1-dioxide instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one, respectively, followed by General Method M, and General Method B, using (2S,3R)-2-methylazetidin-3-ol instead of (2S)-2-methylazetidine.

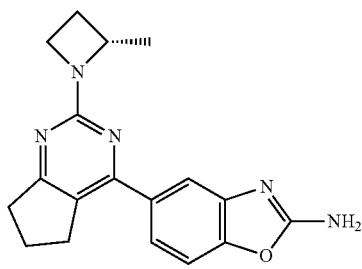 [SMILES: C[C@H]1CCN1c1nc2c(c(-c3ccc4oc(N)nc4c3)n1)CCC2]

Example 736: (S)-5-(2-(2-methylazetidin-1-yl)-6,7-dihydro-5H-cyclopenta[d]pyrimidin-4-yl)benzo[d]oxazol-2-amine The title compound was prepared in analogy to General Method A using 5-(4,4,5,5-tetramethyl-1,3,2-dioxaborolan-2-yl)-1,3-benzoxazol-2-amine and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

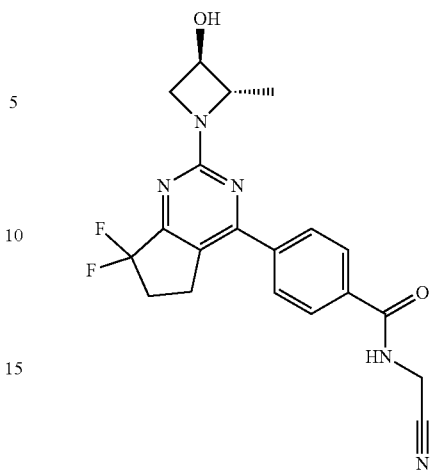

Example 737: N-(cyanomethyl)-4-(7,7-difluoro-2-((2S,3R)-3-hydroxy-2-methylazetidin-1-yl)-6,7-dihydro-5H-cyclopenta[d]pyrimidin-4-yl)benzamide 4-(7,7-difluoro-2-((2S,3R)-3-hydroxy-2-methylazetidin-1-yl)-6,7-dihydro-5H-cyclopenta[d]pyrimidin-4-yl)benzonitrile was prepared in analogy to General Method A using (4-cyanophenyl)boronic acid and 4-chloro-7,7-difluoro-2-(methylthio)-6,7-dihydro-5H-cyclopenta[d]pyrimidine instead of 3-pyridylboronic acid and 2,4-dichloro-6,7-dihydro-5H-cyclopenta[d]pyrimidine, respectively.

A suspension of 4-[7,7-difluoro-2-[(2S,3R)-3-hydroxy-2-methyl-azetidin-1-yl]-5,6-dihydrocyclopenta[d]pyrimidin-4-yl]benzonitrile (26.9 g, 78.6 mmol) and sodium perborate tetrahydrate (36 g, 240 mmol) in ethanol-water (2:1, 1200 mL) was heated at 100° C. for three hours before the addition of more sodium perborate tetrahydrate (3.6 g, 24 mmol), as well as more of the solvent mixture (200 mL). After approximately one more hour of heating, the reaction mixture was concentrated to dryness under reduced pressure. The residue was partitioned between ethyl acetate and water. The aqueous phase was extracted once with ethyl acetate. The combined organic extracts were washed once with saturated aqueous sodium chloride solution, dried over anhydrous magnesium sulfate, filtered, and concentrated to a residue which was then subjected to flash chromatography (hexanes-ethyl acetate) to provide 4-(7,7-difluoro-2-((2S,3R)-3-hydroxy-2-methylazetidin-1-yl)-6,7-dihydro-5H-cyclopenta[d]pyrimidin-4-yl)benzamide as the major product as well as 4-(7,7-difluoro-2-((2S,3R)-3-hydroxy-2-methyl-azetidin-1-yl)-6,7-dihydro-5H-cyclopenta[d]pyrimidin-4-yl)benzoic acid.

A solution of 4-[7,7-difluoro-2-S,3R)-3-hydroxy-2-methyl-azetidin-1-yl]-5,6-dihydrocyclopenta[d]pyrimidin-4-yl)benzoic acid (0.34 mmol), 2-aminoacetonitrile hydrochloride (1.7 mmol), and O-(benzotriazol-1-yl)-N,N,N',N''-tetramethyluronium tetrafluoroborate (1.4 mmol) in DMSO (4 mL) was treated with N,N-diisopropylethylamine (0.660 mL), and the mixture was stirred at room temperature overnight before being partitioned between water and ethyl acetate. The aqueous phase was extracted three times with ethyl acetate. The combined organic extracts were washed three times with water and once with saturated aqueous sodium chloride solution. The combined extracts were dried over anhydrous magnesium sulfate, filtered, and concentrated to a residue which was subjected to flash chromatography (hexanes-ethyl acetate) to provide the title compound.

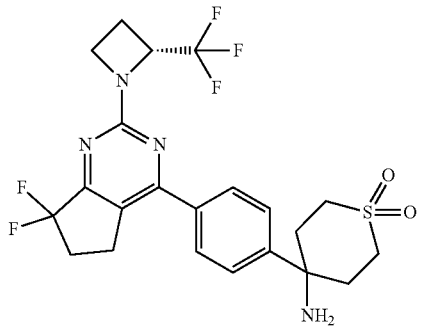 [SMILES: NC1(c2ccc(-c3nc(N4CC[C@@H]4C(F)(F)F)nc4c3CCC4(F)F)cc2)CCS(=O)(=O)CC1]

Example 738: (R)-4-amino-4-(4-(7,7-difluoro-2-(2-(trifluoromethyl)azetidin-1-yl)-6,7-dihydro-5H-cyclopenta[d]pyrimidin-4-yl)phenyl)tetrahydro-2H-thiopyran 1,1-dioxide To a solution of LDA (841 mL, 2M in THF) in THF (1.5 L) was added 2-(4-bromophenyl)acetonitrile (0.77 mol) dropwise at −30° C. under Na, and then the mixture was stirred at −30° C. for 30 min. Ethylene oxide (1.9 mol) was added dropwise, and the mixture was stirred at −30° C. for 2 h. Water (150 mL) was added, and the mixture was warmed to 25° C. and stirred for 30 min. Volatiles were removed under reduced pressure. The residue was diluted with water and extracted with dichloromethane. The organic phase was washed with saturated aqueous sodium chloride solution, dried over anhydrous sodium sulfate, and concentrated. The residue was triturated with MTBE to provide 2-(4-bromophenyl)-4-hydroxy-2-(2-hydroxyethyl)butanenitrile.

Lithium diisopropylamide solution (591 mL, 2M in THF) was added dropwise to a solution of 2-(4-bromophenyl)-4-hydroxy-2-(2-hydroxyethyl)butanenitrile (0.49 mol) in THF (5.2 L) at −30° C. under Na, and then the mixture was stirred for 30 min at −30° C. To the mixture was added dropwise methanesulfonyl chloride (1.2 mol) at −30° C. and stirred for 2 h. The mixture was poured into 10% aqueous citric acid aqueous (520 mL) and stirred. Volatiles were removed under reduced pressure, and the residue was extracted twice with ethyl acetate. The combined organic extracts were washed with saturated aqueous sodium chloride solution, dried over anhydrous sodium sulfate, and concentrated. The solids were recrystallized from ethyl acetate/heptane to provide 3-(4-bromophenyl)-3-cyanopentane-1,5-diyl dimethanesulfonate.

4-(4-bromophenyl)tetrahydro-2H-thiopyran-4-carbonitrile was prepared analogously to ethyl 3-(4-bromophenyl)thietane-3-carboxylate, using 3-(4-bromophenyl)-3-cyanopentane-1,5-diyl dimethanesulfonate instead of ethyl 2-(4-bromophenyl)-3-(trifluoromethylsulfonyloxy)-2-(trifluoromethylsulfonyloxymethyl)propanoate.

A mixture of 4-(4-bromophenyl)tetrahydro-2H-thiopyran-4-carbonitrile (7.1 mmol), sodium hydroxide (71 mmol) in ethanol/water (4:1, 64 mL) was heated at 100° C. for 5 days. An additional portion of sodium hydroxide (25 mmol) was added, and heating was continued for another two days. Upon cooling, the mixture was acidified with 10% aqueous hydrochloric acid and then filtered through a pad of Celite®. The filter cake was washed with ethyl acetate, and the aqueous phase was extracted three times with ethyl acetate. The combined organic extracts were washed once with saturated aqueous sodium chloride solution, dried over anhydrous magnesium sulfate, filtered, and concentrated under reduced pressure to provide 4-(4-bromophenyl)tetrahydro-2H-thiopyran-4-carboxylic acid.

2-(trimethylsilyl)ethyl (4-(4-bromophenyl)-1,1-dioxido-tetrahydro-2H-thiopyran-4-yl)carbamate was prepared analogously to benzyl N-[3-(4-bromophenyl)-1,1-dioxo-thietan-3-yl]carbamate, using 4-(4-bromophenyl)tetrahydro-2H-thiopyran-4-carboxylic acid and 2-(trimethylsilyl)ethanol instead of 3-(4-bromophenyl)thietane-3-carboxylic acid and benzyl alcohol, respectively.

2-(trimethylsilyl)ethyl (4-(4-(7,7-difluoro-2-(methylsulfonyl)-6,7-dihydro-5H-cyclopenta[d]pyrimidin-4-yl)phenyl)-1,1-dioxidotetrahydro-2H-thiopyran-4-yl)carbamate was prepared via General Method F using 4-chloro-7,7-difluoro-2-(methylthio)-6,7-dihydro-5H-cyclopenta[d]pyrimidine and 2-(trimethylsilyl)ethyl (4-(4-bromophenyl)-1,1-dioxidotetrahydro-2H-thiopyran-4-yl)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M.

Under the conditions used for the preparation of N-[3-[4-[7,7-difluoro-2-[(2R)-2-(trifluoromethyl)azetidin-1-yl]-5,6-dihydrocyclopenta[d]pyrimidin-4-yl]phenyl]-1,1-dioxo-thietan-3-yl]-2,2,2-trifluoro-acetamide, 2-(trimethylsilyl)ethyl (4-(4-(7,7-difluoro-2-(methylsulfonyl)-6,7-dihydro-5H-cyclopenta[d]pyrimidin-4-yl)phenyl)-1,1-dioxidotetrahydro-2H-thiopyran-4-yl)carbamate was reacted with (2R)-2-(trifluoromethyl)azetidine tosylate to provide 2-trimethylsilylethyl N-[4-[4-[7,7-difluoro-2-[(2R)-2-(trifluoromethyl)azetidin-1-yl]-5,6-dihydrocyclopenta[d]pyrimidin-4-yl]phenyl]-1,1-dioxo-thian-4-yl]carbamate The title compound was prepared from 2-trimethylsilylethyl N-[4-[4-[7,7-difluoro-2-[(2R)-2-(trifluoromethyl)azetidin-1-yl]-5,6-dihydrocyclopenta[d]pyrimidin-4-yl]phenyl]-1,1-dioxo-thian-4-yl]carbamate via General Method I.

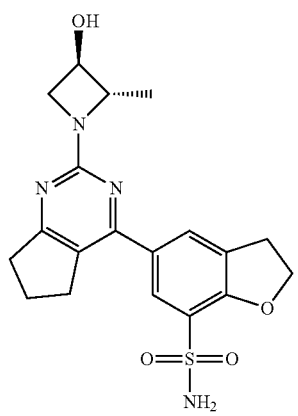 [SMILES: C[C@H]1[C@H](O)CN1c1nc2c(c(-c3cc4c(c(S(N)(=O)=O)c3)OCC4)n1)CCC2]

Example 739: 5-(2-((2S,3R)-3-hydroxy-2-methylazetidin-1-yl)-6,7-dihydro-5H-cyclopenta[d]pyrimidin-4-yl)-2,3-dihydrobenzofuran-7-sulfonamide The title compound was prepared in analogy to General Method F using 5-bromo-2,3-dihydrobenzofuran-7-sulfonamide and 2,4-dichloro-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7- dihydro-5H-cyclopenta[d]pyrimidine, respectively, followed by General Method B, using (2S,3R)-2-methyl-azetidin-3-ol instead of (2S)-2-methylazetidine.

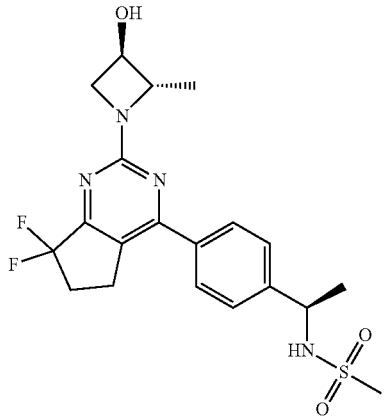 [SMILES: C[C@@H](NS(C)(=O)=O)c1ccc(-c2nc(N3C[C@@H](O)[C@@H]3C)nc3c2CCC3(F)F)cc1]

Example 740: N-[(1R)-1-[4-[7,7-difluoro-2-[(2S,3R)-3-hydroxy-2-methyl-azetidin-1-yl]-5,6-dihydro-cyclopenta[d]pyrimidin-4-yl]phenyl]ethyl]methane-sulfonamide The title compound was prepared in analogy to General Method K using (1R)-1-(4-bromophenyl)ethanamine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-2-methylazetidin-3-ol instead of (2S)-2-methylazetidine.

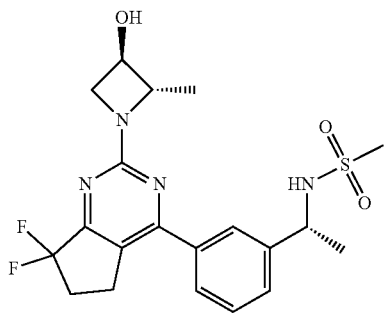 [SMILES: C[C@@H](NS(C)(=O)=O)c1cccc(-c2nc(N3C[C@@H](O)[C@@H]3C)nc3c2CCC3(F)F)c1]

Example 741: N-[(1R)-1-[3-[7,7-difluoro-2-[(2S,3R)-3-hydroxy-2-methyl-azetidin-1-yl]-5,6-dihydro-cyclopenta[d]pyrimidin-4-yl]phenyl]ethyl]methane-sulfonamide The title compound was prepared in analogy to General Method K using (1R)-1-(3-bromophenyl)ethanamine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-2-methylazetidin-3-ol instead of (2S)-2-methylazetidine.

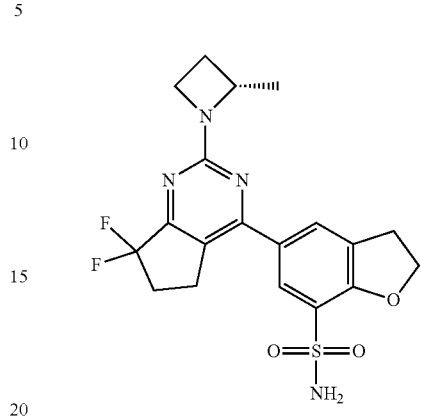

Example 742: 5-[7,7-difluoro-2-[(2S)-2-methylazetidin-1-yl]-5,6-dihydrocyclopenta[d]pyrimidin-4-yl]-2,3-dihydrobenzofuran-7-sulfonamide The title compound was prepared in analogy to General Method F using 5-bromo-2,3-dihydrobenzofuran-7-sulfonamide and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, and General Method B.

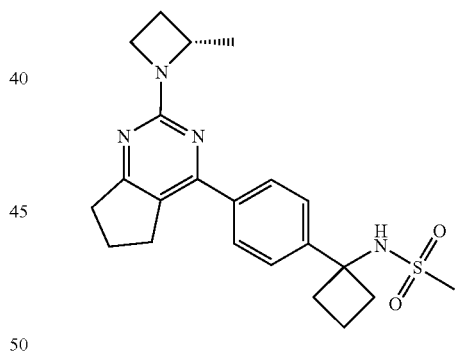

Example 743: N-[1-[4-[2-[(2S)-2-methylazetidin-1-yl]-6,7-dihydro-5H-cyclopenta[d]pyrimidin-4-yl]phenyl]cyclobutyl]methanesulfonamide The title compound was prepared in analogy to General Method K using 1-[4-[2-[(2S)-2-methylazetidin-1-yl]-6,7-dihydro-5H-cyclopenta[d]pyrimidin-4-yl]phenyl]cyclobutanamine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively.

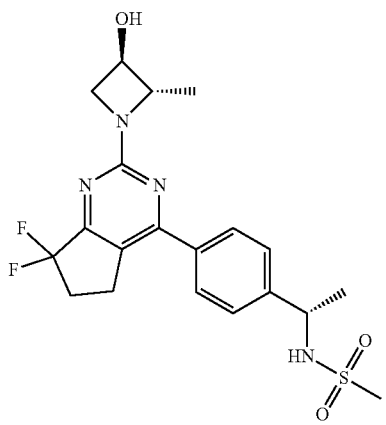 [SMILES: C[C@H](NS(C)(=O)=O)c1ccc(-c2nc(N3C[C@@H](O)[C@@H]3C)nc3c2CCC3(F)F)cc1]

Example 744: N-[(1S)-1-[4-[7,7-difluoro-2-[(2S,3R)-3-hydroxy-2-methyl-azetidin-1-yl]-5,6-dihydro-cyclopenta[d]pyrimidin-4-yl]phenyl]ethyl]methanesulfonamide The title compound was prepared in analogy to General Method K using (1S)-1-(4-bromophenyl)ethanamine and methanesulfonyl chloride instead of (S)-3-(2-(2-methylazetidin-1-yl)-6,7-dihydro-5H-cyclopenta[d]pyrimidin-4-yl) aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-2-methylazetidin-3-ol instead of (2S)-2-methylazetidine.

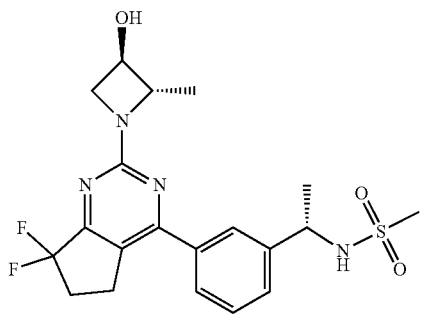 [SMILES: C[C@H](NS(C)(=O)=O)c1cccc(-c2nc(N3C[C@@H](O)[C@@H]3C)nc3c2CCC3(F)F)c1]

Example 745: N-[(1S)-1-[3-[7,7-difluoro-2-[(2S,3R)-3-hydroxy-2-methyl-azetidin-1-yl]-5,6-dihydro-cyclopenta[d]pyrimidin-4-yl]phenyl]ethyl]methanesulfonamide The title compound was prepared in analogy to General Method K using (1S)-1-(3-bromophenyl)ethanamine and methanesulfonyl chloride instead of (S)-3-(2-(2-methylazetidin-1-yl)-6,7-dihydro-5H-cyclopenta[d]pyrimidin-4-yl) aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-2-methylazetidin-3-ol instead of (2S)-2-methylazetidine.

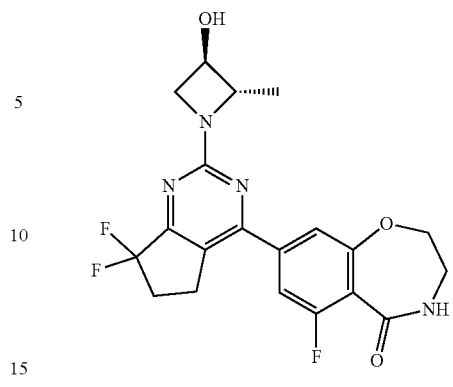

Example 746: 8-[7,7-difluoro-2-[(2S,3R)-3-hydroxy-2-methyl-azetidin-1-yl]-5,6-dihydrocyclopenta[d]pyrimidin-4-yl]-6-fluoro-3,4-dihydro-2H-1,4-benzoxazepin-5-one The title compound was prepared in analogy to General Method F using 8-bromo-6-fluoro-3,4-dihydro-2H-1,4-benzoxazepin-5-one and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, and General Method B using (2S,3R)-2-methylazetidin-3-ol instead of (2S)-2-methylazetidine.

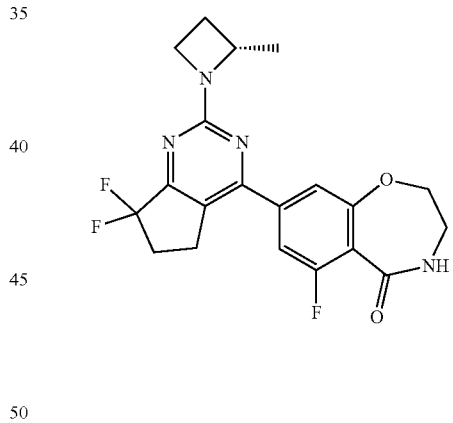

Example 747: 8-[7,7-difluoro-2-[(2S)-2-methylazetidin-1-yl]-5,6-dihydrocyclopenta[d]pyrimidin-4-yl]-6-fluoro-3,4-dihydro-2H-1,4-benzoxazepin-5-one The title compound was prepared in analogy to General Method F using 8-bromo-6-fluoro-3,4-dihydro-2H-1,4-benzoxazepin-5-one and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, and General Method B.

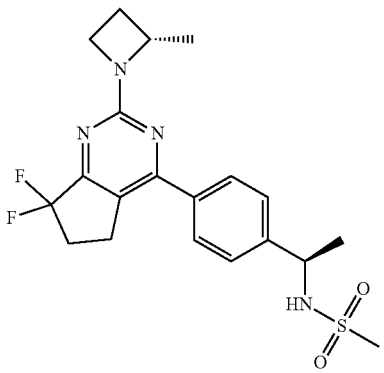 [SMILES: C[C@@H](NS(C)(=O)=O)c1ccc(-c2nc(N3CC[C@@H]3C)nc3c2CCC3(F)F)cc1]

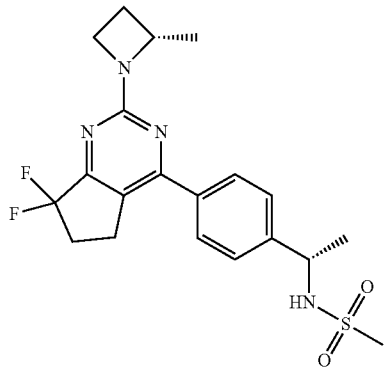

Example 748: N-[(1R)-1-[4-[7,7-difluoro-2-[(2S)-2-methylazetidin-1-yl]-5,6-dihydrocyclopenta[d]pyrimidin-4-yl]phenyl]ethyl]methanesulfonamide The title compound was prepared in analogy to General Method K using (1R)-1-(4-bromophenyl)ethanamine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B.

Example 750: N-[(1S)-1-[4-[7,7-difluoro-2-[(2S)-2-methylazetidin-1-yl]-5,6-dihydrocyclopenta[d]pyrimidin-4-yl]phenyl]ethyl]methanesulfonamide The title compound was prepared in analogy to General Method K using (1S)-1-(4-bromophenyl)ethanamine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B.

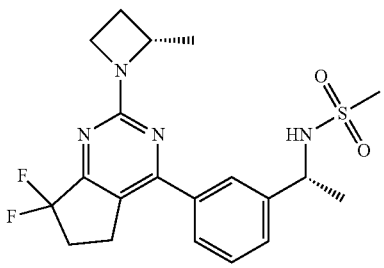 [SMILES: C[C@@H](NS(C)(=O)=O)c1cccc(-c2nc(N3CC[C@@H]3C)nc3c2CCC3(F)F)c1]

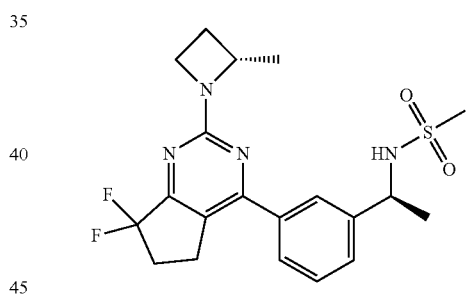

Example 749: N-[(1R)-1-[3-[7,7-difluoro-2-[(2S)-2-methylazetidin-1-yl]-5,6-dihydrocyclopenta[d]pyrimidin-4-yl]phenyl]ethyl]methanesulfonamide The title compound was prepared in analogy to General Method K using (1R)-1-(3-bromophenyl)ethanamine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B.

Example 751: N-[(1S)-1-[3-[7,7-difluoro-2-[(2S)-2-methylazetidin-1-yl]-5,6-dihydrocyclopenta[d]pyrimidin-4-yl]phenyl]ethyl]methanesulfonamide The title compound was prepared in analogy to General Method K using (1S)-1-(3-bromophenyl)ethanamine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B.

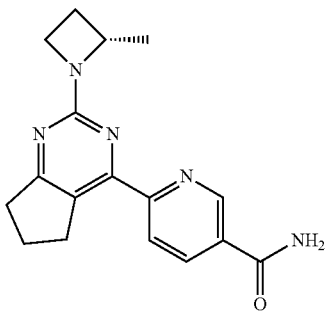 [SMILES: C[C@H]1CCN1c1nc2c(c(-c3ccc(C(N)=O)cn3)n1)CCC2]

Example 752: 6-[2-[(2S)-2-methylazetidin-1-yl]-6,
7-dihydro-5H-cyclopenta[d]pyrimidin-4-yl]pyridine-
3-carboxamide The title compound was prepared in analogy to General Method E, using 6-bromopyridine-3-carboxamide and tributyl-[2-[(2S)-2-methylazetidin-1-yl]-6,7-dihydro-5H-cyclopenta[d]pyrimidin-4-yl]stannane instead of (S)-4-chloro-2-(2-methylazetidin-1-yl)-6,7-dihydro-5H-cyclopenta[d]pyrimidine and ethyl 2-tributylstannylimidazo[5,1-b]thiazole-7-carboxylate respectively.

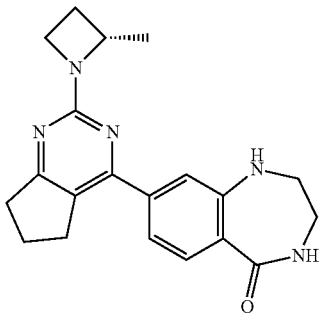 [SMILES: C[C@H]1CCN1c1nc2c(c(-c3ccc4c(c3)NCCNC4=O)n1)CCC2]

Example 753: 8-[2-[(2S)-2-methylazetidin-1-yl]-6,
7-dihydro-5H-cyclopenta[d]pyrimidin-4-yl]-1,2,3,4-
tetrahydro-1,4-benzodiazepin-5-one The title compound was prepared in analogy to General Method E, using 8-bromo-1,2,3,4-tetrahydro-1,4-benzodiazepin-5-one and tributyl-[2-[(2S)-2-methylazetidin-1-yl]-6,7-dihydro-5H-cyclopenta[d]pyrimidin-4-yl]stannane instead of (S)-4-chloro-2-(2-methylazetidin-1-yl)-6,7-dihydro-5H-cyclopenta[d]pyrimidine and ethyl 2-tributylstannylimidazo[5,1-b]thiazole-7-carboxylate respectively.

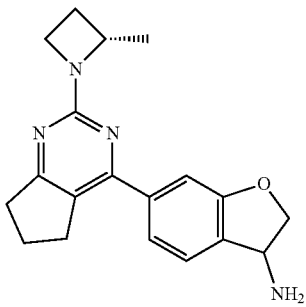 [SMILES: C[C@H]1CCN1c1nc2c(c(-c3ccc4c(c3)OCC4N)n1)CCC2]

Example 754: 6-[2-[(2S)-2-methylazetidin-1-yl]-6,
7-dihydro-5H-cyclopenta[d]pyrimidin-4-yl]-2,3-
dihydrobenzofuran-3-amine The title compound was prepared in analogy to General Method E, using 6-bromo-2,3-dihydrobenzofuran-3-amine and tributyl-[2-[(2S)-2-methylazetidin-1-yl]-6,7-dihydro-5H-cyclopenta[d]pyrimidin-4-yl]stannane instead of (S)-4-chloro-2-(2-methylazetidin-1-yl)-6,7-dihydro-5H-cyclopenta[d]pyrimidine and ethyl 2-tributylstannylimidazo[5,1-b]thiazole-7-carboxylate respectively.

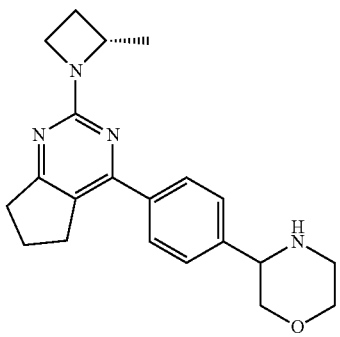 [SMILES: C[C@H]1CCN1c1nc2c(c(-c3ccc(C4COCCN4)cc3)n1)CCC2]

Example 755: 3-[4-[2-[(2S)-2-methylazetidin-1-yl]-
6,7-dihydro-5H-cyclopenta[d]pyrimidin-4-yl]phe-
nyl]morpholine The title compound was prepared in analogy to General Method E, using 3-(4-bromophenyl)morpholine and tributyl-[2-[(2S)-2-methylazetidin-1-yl]-6,7-dihydro-5H-cyclopenta[d]pyrimidin-4-yl]stannane instead of (S)-4-chloro-2-(2-methylazetidin-1-yl)-6,7-dihydro-5H-cyclopenta[d]pyrimidine and ethyl 2-tributylstannylimidazo[5,1-b]thiazole-7-carboxylate respectively.

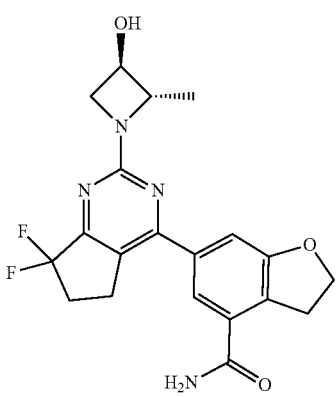 [SMILES: C[C@H]1[C@H](O)CN1c1nc(-c2cc3c(c(C(N)=O)c2)CCO3)c2c(n1)C(F)(F)CC2]

Example 756: 6-[7,7-difluoro-2-[(2S,3R)-3-hy-
droxy-2-methyl-azetidin-1-yl]-5,6-dihydrocyclo-
penta[d]pyrimidin-4-yl]-2,3-dihydrobenzofuran-4-
carboxamide The title compound was prepared in analogy to General Method F using 5-bromo-2,3-dihydrobenzofuran-7-carboxamide and 4-chloro-7,7-difluoro-2-(methylthio)-6,7-dihydro-5H-cyclopenta[d]pyrimidine instead of 6-bromo-1,1- dioxo-1,2-benzothiazol-3-one and 4-chloro-2-[(2S)-2-methylazetidin-1-yl]-6,7-dihydro-5H-cyclopenta[d]pyrimidine respectively, followed by General Method M, and General Method B using (2S,3R)-2-methylazetidin-3-ol instead of (2S)-2-methylazetidine.

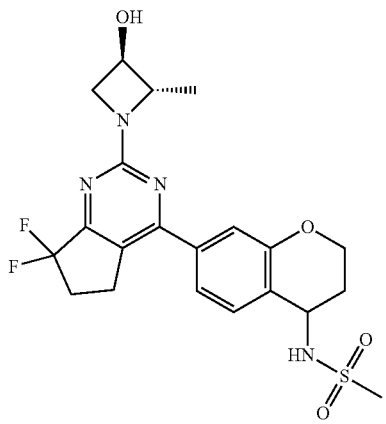 [SMILES: C[C@H]1[C@H](O)CN1c1nc(-c2ccc3c(c2)OCCC3NS(C)(=O)=O)c2c(n1)C(F)(F)CC2]

Example 757: N-[7-[7,7-difluoro-2-[(2S,3R)-3-hydroxy-2-methyl-azetidin-1-yl]-5,6-dihydrocyclopenta[d]pyrimidin-4-yl]chroman-4-yl]methanesulfonamide The title compound was prepared in analogy to General Method K using 7-bromochroman-4-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-2-methylazetidin-3-ol instead of (2S)-2-methylazetidine.

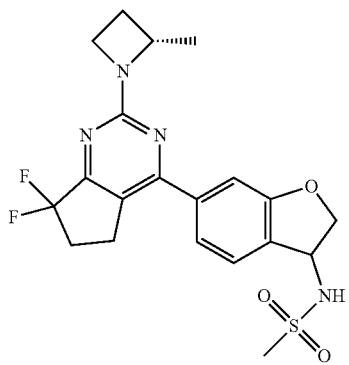 [SMILES: C[C@H]1CCN1c1nc(-c2ccc3c(c2)OCC3NS(C)(=O)=O)c2c(n1)C(F)(F)CC2]

Example 758: N-[6-[7,7-difluoro-2-[(2S)-2-methylazetidin-1-yl]-5,6-dihydrocyclopenta[d]pyrimidin-4-yl]-2,3-dihydrobenzofuran-3-yl]methanesulfonamide The title compound was prepared in analogy to General Method K using 6-bromo-2,3-dihydrobenzofuran-3-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B.

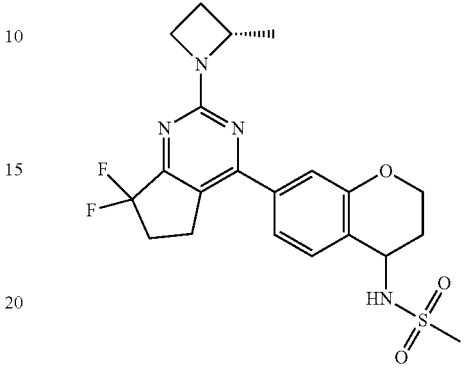

Example 759: N-[7-[7,7-difluoro-2-[(2S)-2-methyl-azetidin-1-yl]-5,6-dihydrocyclopenta[d]pyrimidin-4-yl]chroman-4-yl]methanesulfonamide The title compound was prepared in analogy to General Method K using 7-bromochroman-4-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B.

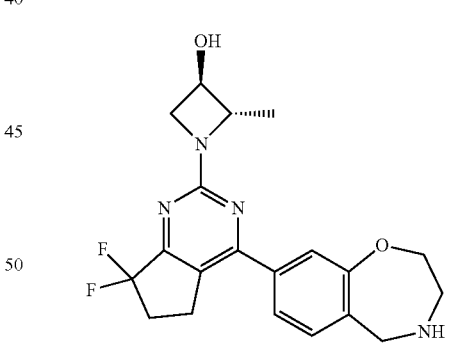

Example 760: (2S,3R)-1-[7,7-difluoro-4-(2,3,4,5-tetrahydro-1,4-benzoxazepin-8-yl)-5,6-dihydrocyclopenta[d]pyrimidin-2-yl]-2-methyl-azetidin-3-ol The title compound was prepared in analogy to General Method F using tert-butyl-8-bromo-3,5-dihydro-2H-1,4-benzoxazepine-4-carboxylate and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, followed by General Method B using (2S,3R)-

2-methylazetidin-3-ol instead of (2S)-2-methylazetidine, followed by General Method I.

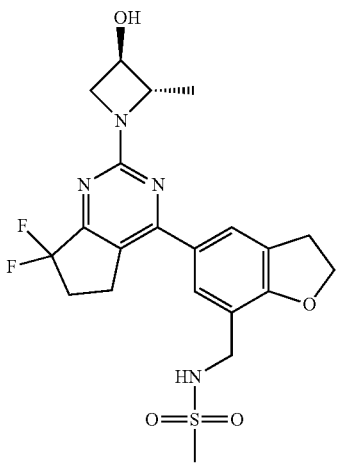 [SMILES: C[C@H]1[C@H](O)CN1c1nc(-c2cc3c(c(CNS(C)(=O)=O)c2)OCC3)c2c(n1)C(F)(F)CC2]

Example 761: N-[[5-[7,7-difluoro-2-[(2S,3R)-3-hydroxy-2-methyl-azetidin-1-yl]-5,6-dihydrocyclopenta[d]pyrimidin-4-yl]-2,3-dihydrobenzofuran-7-yl]methyl]methanesulfonamide The title compound was prepared in analogy to General Method K using (5-bromo-2,3-dihydrobenzofuran-7-yl)methanamine-hydrochloride and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using (2S,3R)-2-methylazetidin-3-ol instead of (2S)-2-methylazetidine.

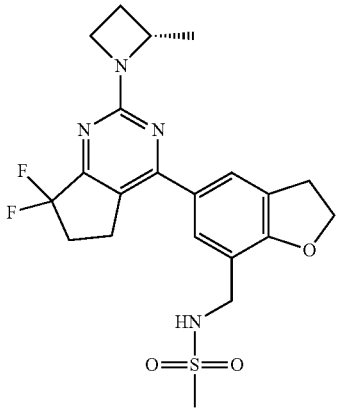 [SMILES: C[C@H]1CCN1c1nc(-c2cc3c(c(CNS(C)(=O)=O)c2)OCC3)c2c(n1)C(F)(F)CC2]

Example 762: N-[[5-[7,7-difluoro-2-[(2S)-2-methyl-azetidin-1-yl]-5,6-dihydrocyclopenta[d]pyrimidin-4-yl]-2,3-dihydrobenzofuran-7-yl]methyl]methanesulfonamide The title compound was prepared in analogy to General Method K using (5-bromo-2,3-dihydrobenzofuran-7-yl)

methanamine hydrochloride and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B.

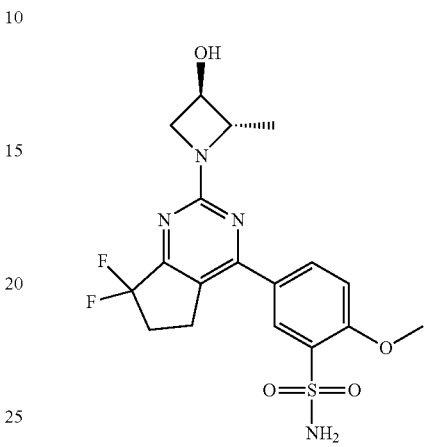

Example 763: 5-(7,7-difluoro-2-((2S,3R)-3-hydroxy-2-methylazetidin-1-yl)-6,7-dihydro-5H-cyclopenta[d]pyrimidin-4-yl)-2-methoxybenzenesulfonamide The title compound was prepared in analogy to General Method F using N-(5-bromo-2-ethoxy-phenyl)methanesulfonamide and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, and General Method B using (2S,3R)-2-methylazetidin-3-ol instead of (2S)-2-methylazetidine.

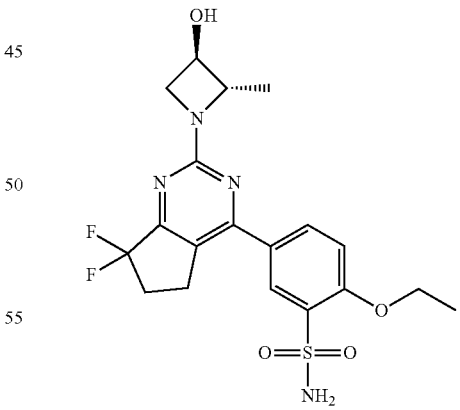

Example 764: 5-[7,7-difluoro-2-[(2S,3R)-3-hydroxy-2-methyl-azetidin-1-yl]-5,6-dihydrocyclopenta[d]pyrimidin-4-yl]-2-ethoxy-benzenesulfonamide The title compound was prepared in analogy to General Method F using N-(5-bromo-2-ethoxy-phenyl)methanesulfonamide and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, and General Method B using (2S,3R)-2-methylazetidin-3-ol instead of (2S)-2-methylazetidine.

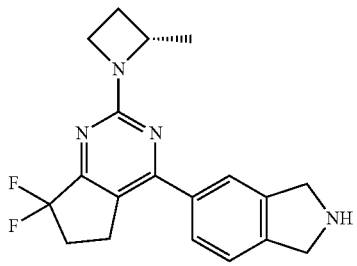 [SMILES: C[C@H]1CCN1c1nc(-c2ccc3c(c2)CNC3)c2c(n1)C(F)(F)CC2]

Example 765: 7,7-difluoro-4-isoindolin-5-yl-2-[(2S)-2-methylazetidin-1-yl]-5,6-dihydrocyclopenta[d]pyrimidine The title compound was prepared in analogy to General Method F using tert-butyl 5-bromoisoindoline-2-carboxylate and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, followed by General Method B, and General Method I.

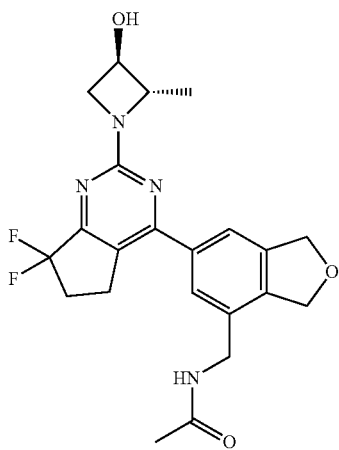 [SMILES: CC(=O)NCc1cc(-c2nc(N3C[C@@H](O)[C@@H]3C)nc3c2CCC3(F)F)cc2c1COC2]

Example 766: N-[[5-[7,7-difluoro-2-[(2S,3R)-3-hydroxy-2-methyl-azetidin-1-yl]-5,6-dihydrocyclopenta[d]pyrimidin-4-yl]-2,3-dihydrobenzofuran-7-yl]methyl]acetamide A flask was charged with (5-bromo-2,3-dihydrobenzofuran-7-yl)methanamine (200 mg, 0.88 mmol), diisopropylethylamine (0.47 mL, 2.63 mmol) and DCM (5 mL). Acetic anhydride (90 mg, 0.88 mmol) was added slowly as a solution in DCM (1 mL). The reaction mixture was stirred at room temperature for 30 minutes. The product was purified by silica gel chromatography (hexanes-ethyl acetate) to afford N-[(5-bromo-2,3-dihydrobenzofuran-7-yl)methyl]acetamide.

The title compound was prepared in analogy to General Method F using N-[(5-bromo-2,3-dihydrobenzofuran-7-yl)methyl]acetamide and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, followed by General Method B using (2S,3R)-2-methylazetidin-3-ol instead of (2S)-2-methylazetidine.

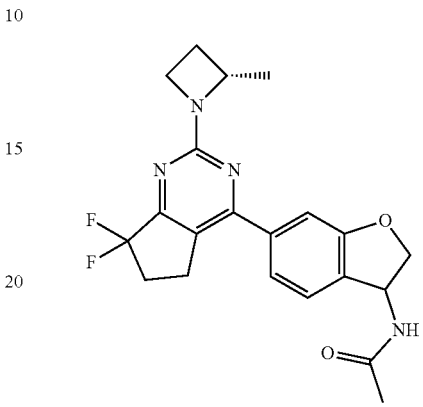

Example 767: N-[6-[7,7-difluoro-2-[(2S)-2-methyl-azetidin-1-yl]-5,6-dihydrocyclopenta[d]pyrimidin-4-yl]-2,3-dihydrobenzofuran-3-yl]acetamide A flask was charged with 6-bromo-2,3-dihydrobenzofuran-3-amine (188 mg, 0.88 mmol), diisopropylethylamine (0.47 mL, 2.63 mmol) and DCM (5 mL). Acetic anhydride (90 mg, 0.88 mmol) was added slowly as a solution in DCM (1 mL). The reaction was stirred at room temperature for 30 minutes. The product was purified by silica gel chromatography to afford N-(6-bromo-2,3-dihydrobenzofuran-3-yl)acetamide.

The title compound was prepared in analogy to General Method F using N-(6-bromo-2,3-dihydrobenzofuran-3-yl)acetamide and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, followed by General Method B.

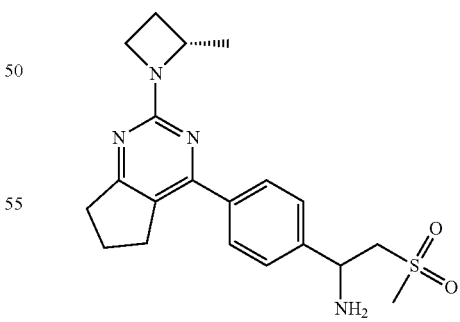

Example 768: 1-(4-(2-((S)-2-methylazetidin-1-yl)-6,7-dihydro-5H-cyclopenta[d]pyrimidin-4-yl)phenyl)-2-(methylsulfonyl)ethan-1-amine (S)-1-(4-(2-(2-methylazetidin-1-yl)-6,7-dihydro-5H-cyclopenta[d]pyrimidin-4-yl)phenyl)-2-(methylsulfonyl)

ethan-1-one was prepared as a minor component of General Method A using benzyl N-[1,1-dioxo-3-[4-(4,4,5,5-tetramethyl-1,3,2-dioxaborolan-2-yl)phenyl]thietan-3-yl]carbamate and (S)-4-chloro-2-(2-methylazetidin-1-yl)-6,7-dihydro-5H-cyclopenta[d]pyrimidine instead of 3-pyridylboronic acid and 2,4-dichloro-6,7-dihydro-5H-cyclopenta[d]pyrimidine, respectively.

1-[4-[2-[(2S)-2-methylazetidin-1-yl]-6,7-dihydro-5H-cyclopenta[d]pyrimidin-4-yl]phenyl]-2-methylsulfonyl-ethanone, (16 mg, 32 µmol) was taken up in MeOH (2 mL) and treated with ammonium acetate (5.5 mmol). After stirring for 30 min, sodium cyanoborohydride (0.48 mmol) was added. The mixture was heated overnight at 90° C. and then subjected to HPLC (0.1% TFA in MeCN-0.1% TFA in H₂O) to give the title compound.

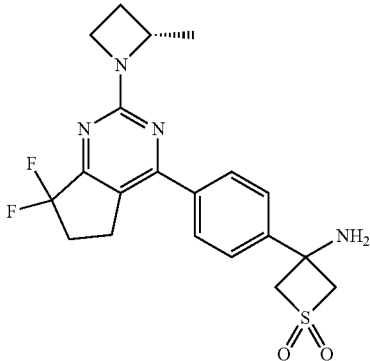 [SMILES: C[C@H]1CCN1c1nc(-c2ccc(C3(N)CS(=O)(=O)C3)cc2)c2c(n1)C(F)(F)CC2]

Example 769: (S)-3-amino-3-(4-(7,7-difluoro-2-(2-methylazetidin-1-yl)-6,7-dihydro-5H-cyclopenta[d]pyrimidin-4-yl)phenyl)thietane 1,1-dioxide The title compound was prepared in analogy to General Method B using benzyl N-[3-[4-(7,7-difluoro-2-methylsulfonyl-5,6-dihydrocyclopenta[d]pyrimidin-4-yl)phenyl]-1,1-dioxo-thietan-3-yl]carbamate instead of 2-chloro-4-(pyridin-3-yl)-6,7-dihydro-5H-cyclopenta[d]pyrimidine, followed by General Method R.

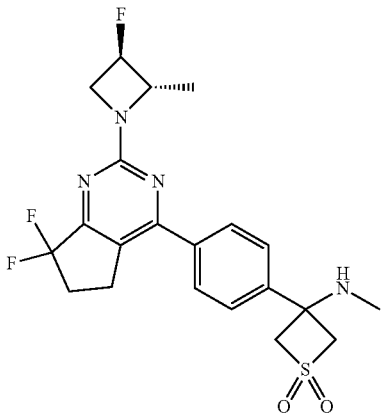 [SMILES: CNC1(c2ccc(-c3nc(N4C[C@@H](F)[C@@H]4C)nc4c3CCC4(F)F)cc2)CS(=O)(=O)C1]

Example 770: 3-(4-(7,7-difluoro-2-((2S,3R)-3-fluoro-2-methylazetidin-1-yl)-6,7-dihydro-5H-cyclopenta[d]pyrimidin-4-yl)phenyl)-3-(methylamino)thietane 1,1-dioxide The title compound was prepared in analogy to General Method B using benzyl N-[3-[4-(7,7-difluoro-2-methylsulfonyl-5,6-dihydrocyclopenta[d]pyrimidin-4-yl)phenyl]-1,1-dioxo-thietan-3-yl]carbamate and (2S,3R)-3-fluoro-2-methylazetidine instead of 2-chloro-4-(pyridin-3-yl)-6,7-dihydro-5H-cyclopenta[d]pyrimidine and (2S)-2-methylazetidine, respectively, followed by General Method R, performed in methanol at 40° C.

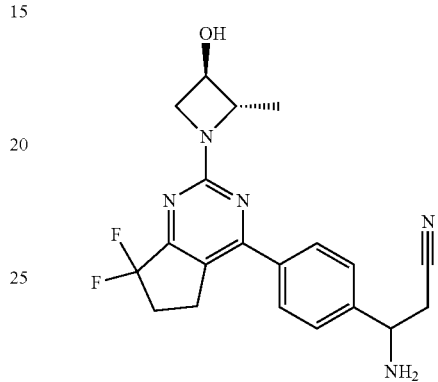

Example 771: 3-amino-3-(4-(7,7-difluoro-2-((2S,3R)-3-hydroxy-2-methylazetidin-1-yl)-6,7-dihydro-5H-cyclopenta[d]pyrimidin-4-yl)phenyl)propanenitrile A mixture of 3-(4-bromophenyl)-3-oxo-propanenitrile (32 mmol) in MeOH (50 mL) was treated with ammonium acetate (20 g, 260 mmol), and after 30 min of stirring, sodium cyanoborohydride (3.4 g, 54 mmol) was added. The mixture was heated to reflux for six hours before being allowed to cool to ambient temperature. The mixture was concentrated under reduced pressure, and the residue was partitioned between dichloromethane and 1M aqueous potassium phosphate dibasic. The mixture was extracted three times with dichloromethane before adding 3M NaOH solution to the aqueous phase (to give pH 10). After extracting three more times with dichloromethane, the combined organic extracts were washed once with saturated aqueous sodium chloride solution, dried over anhydrous magnesium sulfate, filtered, and concentrated under reduced pressure to provide 3-amino-3-(4-bromophenyl)propanenitrile, which was carried forward without further purification.

A mixture of 3-amino-3-(4-bromophenyl)propanenitrile (5.4 mmol assumed) in THF (12 mL)/water (3 mL)/MeOH (3 mL) was treated successively with sodium carbonate (16 mmol) and di-tert-butyl dicarbonate (5.9 mmol). The mixture was stirred at room temperature for 90 min before being diluted with water and extracted three times with ethyl acetate. The combined extracts were washed once with saturated aqueous sodium chloride solution, dried over anhydrous magnesium sulfate, filtered, and concentrated to a residue, which was purified by flash chromatography (hexanes-ethyl acetate) to provide tert-butyl (1-(4-bromophenyl)-2-cyanoethyl)carbamate.

The title compounds was prepared in analogy to General Method F using 4-chloro-7,7-difluoro-2-(methylthio)-6,7- dihydro-5H-cyclopenta[d]pyrimidine and tert-butyl (1-(4-bromophenyl)-2-cyanoethyl)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one, respectively, followed by General Method M, and General Method B, using (2S,3R)-2-methylazetidin-3-ol instead of (2S)-2-methylazetidine, followed by General Method I.

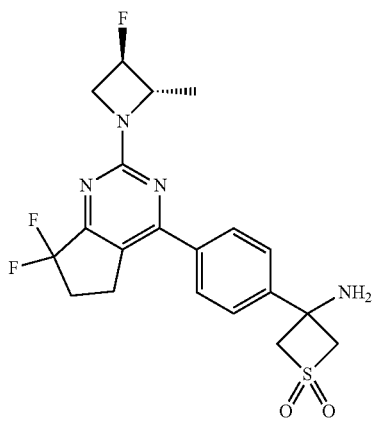 [SMILES: C[C@H]1[C@H](F)CN1c1nc(-c2ccc(C3(N)CS(=O)(=O)C3)cc2)c2c(n1)C(F)(F)CC2]

Example 772: 3-amino-3-(4-(7,7-difluoro-24(2S, 3R)-3-fluoro-2-methylazetidin-1-yl)-6,7-dihydro-5H-cyclopenta[d]pyrimidin-4-yl)phenyl)thietane 1,1-dioxide 2-(trimethylsilyl)ethyl (3-(4-(7,7-difluoro-2-(methylthio)-6,7-dihydro-5H-cyclopenta[d]pyrimidin-4-yl)phenyl)-1,1-dioxidothietan-3-yl)carbamate was prepared from 3-(4-bromophenyl)thietane-3-carboxylic acid in a manner analogous to that which provided benzyl N-[3-[4-(7,7-difluoro-2-methylsulfanyl-5,6-dihydrocyclopenta[d]pyrimidin-4-yl)phenyl]-1,1-dioxo-thietan-3-yl]carbamate, starting from 2-(trimethylsilyl)ethanol instead of benzyl alcohol (Example 491).

2-(trimethylsilyl)ethyl (3-(4-(7,7-difluoro-2-((2S,3R)-3-fluoro-2-methylazetidin-1-yl)-6,7-dihydro-5H-cyclopenta[d]pyrimidin-4-yl)phenyl)-1,1-dioxidothietan-3-yl)carbamate was prepared from 2-(trimethylsilyl)ethyl (3-(4-(7,7-difluoro-2-(methylthio)-6,7-dihydro-5H-cyclopenta[d]pyrimidin-4-yl)phenyl)-1,1-dioxidothietan-3-yl)carbamate via General Method M, followed by General Method B, substituting (2S,3R)-3-fluoro-2-methylazetidine) for (2S)-2-methylazetidine.

A mixture of 2-(trimethylsilyl)ethyl (3-(4-(7,7-difluoro-2-((2S,3R)-3-fluoro-2-methylazetidin-1-yl)-6,7-dihydro-5H-cyclopenta[d]pyrimidin-4-yl)phenyl)-1,1-dioxidothietan-3-yl)carbamate (0.41 mmol) in DMF (4 mL) was treated with tris(dimethylamino)sulfonium difluorotrimethylsilicate (4.1 mmol) and heated at 60° C. for 30 minutes. After cooling, the mixture was partitioned between saturated aqueous sodium hydrogen carbonate and ethyl acetate. The aqueous phase was extracted three times with ethyl acetate. The combined extracts were washed once with saturated aqueous sodium chloride solution, dried over anhydrous magnesium sulfate, filtered, and concentrated to dryness under reduced pressure. The residue was subjected to HPLC purification (0.1% TFA in MeCN-0.1% TFA in H₂O) to give the title compound.

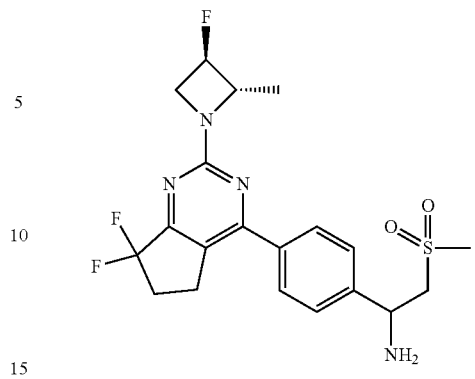

Example 773: 1-(4-(7,7-difluoro-2-((2S,3R)-3-fluoro-2-methylazetidin-1-yl)-6,7-dihydro-5H-cyclopenta[d]pyrimidin-4-yl)phenyl)-2-(methylsulfonyl)ethan-1-amine tert-Butyl (1-(4-bromophenyl)-2-(methylsulfonyl)ethyl)carbamate was prepared analogously to tert-butyl (1-(4-bromophenyl)-2-cyanoethyl)carbamate, starting from 1-(4-bromophenyl)-2-(methylsulfonyl)ethan-1-one instead of 3-(4-bromophenyl)-3-oxo-propanenitrile. (Example 771)

tert-Butyl (1-(4-(7,7-difluoro-2-((2S,3R)-3-fluoro-2-methylazetidin-1-yl)-6,7-dihydro-5H-cyclopenta[d]pyrimidin-4-yl)phenyl)-2-(methylsulfonyl)ethyl)carbamate was prepared in analogy to General Method F using 4-chloro-7,7-difluoro-2-(methylthio)-6,7-dihydro-5H-cyclopenta[d]pyrimidine and tert-butyl (1-(4-bromophenyl)-2-(methylsulfonyl)ethyl)carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one, respectively, followed by General Method M, and General Method B, using (2S,3R)-3-fluoro-2-methylazetidine instead of (2S)-2-methylazetidine, followed by General Method I.

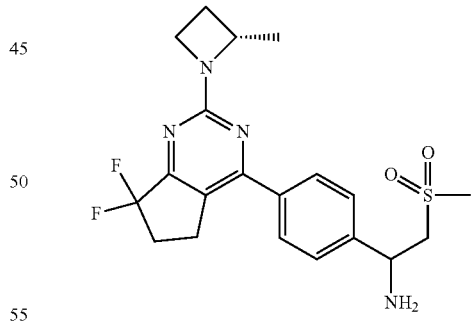

Example 774: 1-(4-(7,7-difluoro-2-((S)-2-methylazetidin-1-yl)-6,7-dihydro-5H-cyclopenta[d]pyrimidin-4-yl)phenyl)-2-(methylsulfonyl)ethan-1-amine The title compound was prepared analogously to 1-(4-(7,7-difluoro-2-((2S,3R)-3-fluoro-2-methylazetidin-1-yl)-6,7-dihydro-5H-cyclopenta[d]pyrimidin-4-yl)phenyl)-2-(methylsulfonyl)ethan-1-amine, using (2S)-2-methylazetidine instead of (2S,3R)-3-fluoro-2-methylazetidine. (Example 771)

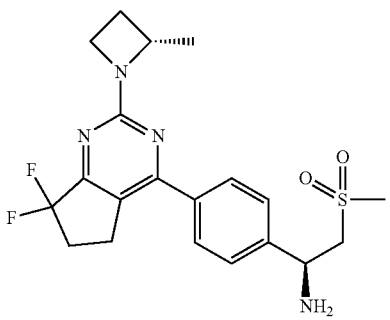

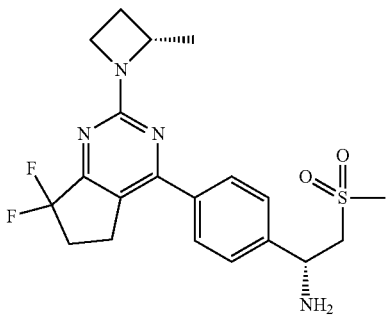 [SMILES: C[C@H]1CCN1c1nc(-c2ccc(C(N)CS(C)(=O)=O)cc2)c2c(n1)C(F)(F)CC2]

Example 775: (S)-1-(4-(7,7-difluoro-2-((S)-2-methylazetidin-1-yl)-6,7-dihydro-5H-cyclopenta[d]pyrimidin-4-yl)phenyl)-2-(methylsulfonyl)ethan-1-amine Example 776: (R)-1-(4-(7,7-difluoro-2-((S)-2-methylazetidin-1-yl)-6,7-dihydro-5H-cyclopenta[d]pyrimidin-4-yl)phenyl)-2-(methylsulfonyl)ethan-1-amine Isomers were separated by SFC (35% MeOH in $CO_2$, Lux® 5 μm Cellulose-2, 100×4.6 mm, 3 mL/min).

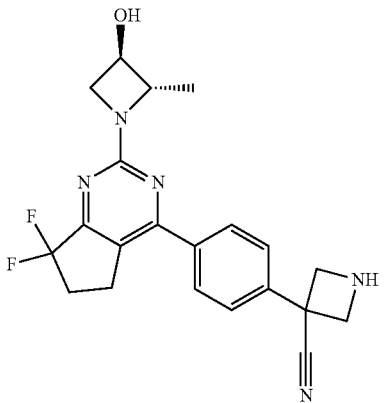 [SMILES: C[C@H]1[C@H](O)CN1c1nc(-c2ccc(C3(C#N)CNC3)cc2)c2c(n1)C(F)(F)CC2]

Example 777: 3-(4-(7,7-difluoro-2-((2S,3R)-3-hydroxy-2-methylazetidin-1-yl)-6,7-dihydro-5H-cyclopenta[d]pyrimidin-4-yl)phenyl)azetidine-3-carbonitrile To a solution of 1-bromo-4-fluorobenzene (29 mmol) in THF (60 mL) was added 1-benzhydrylazetidine-3-carbonitrile (43 mmol) and solid potassium hexamethyldisilazide (42.9 mmol). The reaction mixture was stirred overnight at room temperature and concentrated under reduced pressure. The residue was taken up in ethyl acetate, washed with water (2×50 mL), dried over anhydrous magnesium sulfate, filtered, and concentrated under reduced pressure. The residue was purified by flash chromatography (hexanes-ethyl acetate) to provide 1-benzhydryl-3-(4-bromophenyl)azetidine-3-carbonitrile.

A solution of 1-benzhydryl-3-(4-bromophenyl)azetidine-3-carbonitrile (1.0 mmol) in acetonitrile (5 mL) was treated with 1-chloroethyl chloroformate (3.0 mmol) and heated for 90 min at 90° C. An additional portion of 1-chloroethyl chloroformate (0.93 mmol) was added, and the mixture was heated overnight at the same temperature. After cooling, the mixture was concentrated under reduced pressure. The residue was taken up in methanol (5 mL), heated to reflux for 45 minutes, and then concentrated under reduced pressure to yield 3-(4-bromophenyl)azetidine-3-carbonitrile hydrochloride. 3-(4-bromophenyl)azetidine-3-carbonitrile hydrochloride (1 mmol) and di-tert-butyldicarbonate (4 mmol) were taken up in dichloromethane (4 mL) and treated with N,N-diisopropylethylamine (6 mmol). The reaction mixture was stirred at room temperature for 1 hour and was then concentrated under reduced pressure. The residue was purified by flash chromatography (hexanes-ethyl acetate) to provide tert-butyl 3-(4-bromophenyl)-3-cyanoazetidine-1-carboxylate.

The title compound was prepared in analogy to General Method F using 4-chloro-7,7-difluoro-2-(methylthio)-6,7-dihydro-5H-cyclopenta[d]pyrimidine and tert-butyl 3-(4-bromophenyl)-3-cyanoazetidine-1-carboxylate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one, respectively, followed by General Method M, and General Method B, using (2S,3R)-2-methylazetidin-3-ol instead of (2S)-2-methylazetidine, followed by General Method I.

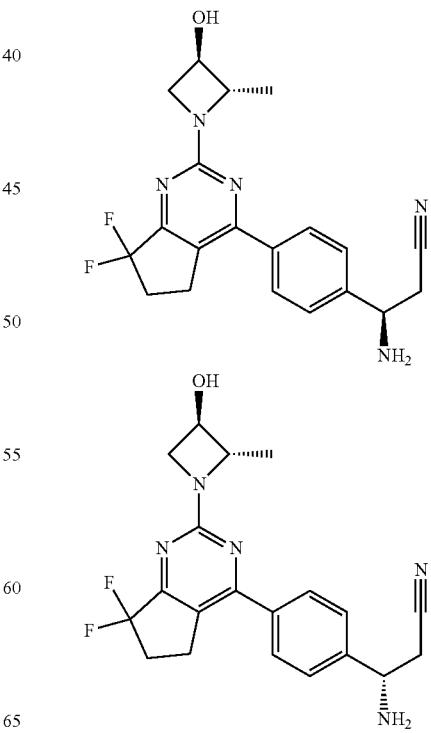

Example 778: (R)-3-amino-3-(4-(7,7-difluoro-2-((2S,3R)-3-hydroxy-2-methylazetidin-1-yl)-6,7-dihydro-5H-cyclopenta[d]pyrimidin-4-yl)phenyl)propanenitrile Example 779: (S)-3-amino-3-(4-(7,7-difluoro-2-((2S,3R)-3-hydroxy-2-methylazetidin-1-yl)-6,7-dihydro-5H-cyclopenta[d]pyrimidin-4-yl)phenyl)propanenitrile Isomers were separated by SFC (20% EtOH-TFA in CO$_2$, CHIRALPAK IC-5 µm, 250×21 mm, 60 mL/min). (see Example 771)

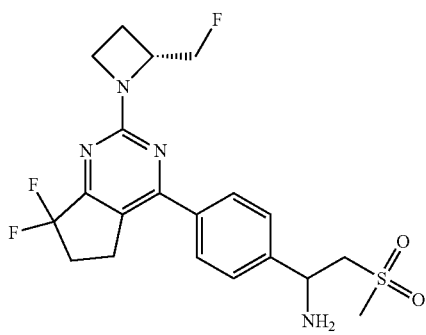 [SMILES: CS(=O)(=O)CC(N)c1ccc(-c2nc(N3CC[C@@H]3CF)nc3c2CCC3(F)F)cc1]

Example 780: 1-(4-(7,7-difluoro-2-((R)-2-(fluoromethyl)azetidin-1-yl)-6,7-dihydro-5H-cyclopenta[d]pyrimidin-4-yl)phenyl)-2-(methylsulfonyl)ethan-1-amine 2-(trimethylsilyl)ethyl (R)-(3-(4-(7,7-difluoro-2-(2-(fluoromethyl)azetidin-1-yl)-6,7-dihydro-5H-cyclopenta[d]pyrimidin-4-yl)phenyl)-1,1-dioxidothietan-3-yl)carbamate was prepared according to General Method M using 2-(trimethylsilyl)ethyl (3-(4-(7,7-difluoro-2-(methylthio)-6,7-dihydro-5H-cyclopenta[d]pyrimidin-4-yl)phenyl)-1,1-dioxidothietan-3-yl)carbamate instead of 4-(7,7-difluoro-2-(methylthio)-6,7-dihydro-5H-cyclopenta[d]pyrimidin-4-yl)benzamide, followed by General Method B, substituting (2R)-2-(fluoromethyl)azetidine for (2S)-2-methylazetidine.

A mixture of 2-(trimethylsilyl)ethyl (R)-(3-(4-(7,7-difluoro-2-(2-(fluoromethyl)azetidin-1-yl)-6,7-dihydro-5H-cyclopenta[d]pyrimidin-4-yl)phenyl)-1,1-dioxidothietan-3-yl)carbamate (0.31 mmol) in DMF (1.5 mL) was treated with tris(dimethylamino)sulfonium difluorotrimethylsilicate (TASF, 1.5 mmol) and heated at 60° C. for 20 minutes. After an additional portion of TASF (1.5 mmol) was added, heating was continued for one hour at 70° C. After cooling, the mixture was partitioned between saturated aqueous sodium hydrogen carbonate and ethyl acetate. The aqueous phase was extracted three times with ethyl acetate. The combined extracts were washed once with saturated aqueous sodium chloride solution, dried over anhydrous magnesium sulfate, filtered, and concentrated to dryness under reduced pressure. The residue was subjected to HPLC purification (0.1% TFA in MeCN-0.1% TFA in H$_2$O) to give 1-(4-(7,7-difluoro-2-(methylthio)-6,7-dihydro-5H-cyclopenta[d]pyrimidin-4-yl)phenyl)-2-(methylsulfonyl)ethan-1-one.

A mixture of 1-[4-[7,7-difluoro-2-[(2R)-2-(fluoromethyl)azetidin-1-yl]-5,6-dihydrocyclopenta[d]pyrimidin-4-yl]phenyl]-2-methylsulfonyl-ethanone, TFA salt (0.33 mmol) in MeOH (2 mL) was stirred with ammonium acetate (16 mmol). After 30 min, sodium cyanoborohydride (3.3 mmol) was added, and the mixture was heated overnight at 80° C. The mixture was concentrated and then subjected to HPLC purification (0.1% TFA in MeCN-0.1% TFA in H$_2$O) to give the title compound.

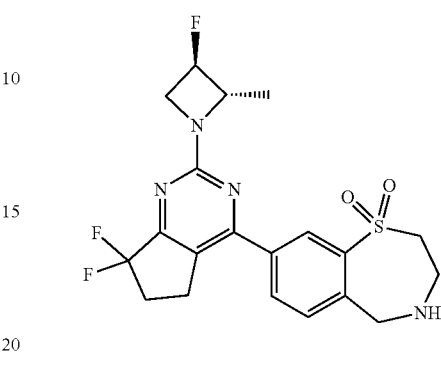

Example 781: 8-(7,7-difluoro-24(2S,3R)-3-fluoro-2-methylazetidin-1-yl)-6,7-dihydro-5H-cyclopenta[d]pyrimidin-4-yl)-2,3,4,5-tetrahydrobenzo[f][1,4]thiazepine 1,1-dioxide The title compound was prepared in analogy to General Method F using 4-chloro-7,7-difluoro-2-(methylthio)-6,7-dihydro-5H-cyclopenta[d]pyrimidine and tert-butyl 8-bromo-3,5-dihydro-2H-1,4-benzothiazepine-4-carboxylate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-3-fluoro-2-methylazetidine instead of (2S)-2-methylazetidine, followed by General Method I.

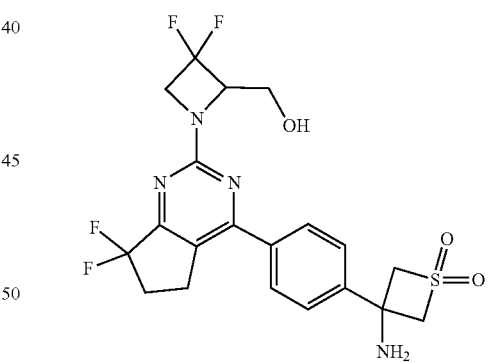

Example 782: 3-amino-3-(4-(2-(3,3-difluoro-2-(hydroxymethyl)azetidin-1-yl)-7,7-difluoro-6,7-dihydro-5H-cyclopenta[d]pyrimidin-4-yl)phenyl)thietane 1,1-dioxide 2-(trimethylsilyl)ethyl (3-(4-(2-(3,3-difluoro-2-(hydroxymethyl)azetidin-1-yl)-7,7-difluoro-6,7-dihydro-5H-cyclopenta[d]pyrimidin-4-yl)phenyl)-1,1-dioxidothietan-3-yl)carbamate was prepared from 2-(trimethylsilyl)ethyl (3-(4-(7,7-difluoro-2-(methylthio)-6,7-dihydro-5H-cyclopenta[d]pyrimidin-4-yl)phenyl)-1,1-dioxidothietan-3-yl) carbamate via General Method M, followed by General Method B, using (3,3-difluoroazetidin-2-yl)methanol instead of (2S)-2-methylazetidine.

A mixture of 2-(trimethylsilyl)ethyl (3-(4-(2-(3,3-difluoro-2-(hydroxymethyl)azetidin-1-yl)-7,7-difluoro-6,7-dihydro-5H-cyclopenta[d]pyrimidin-4-yl)phenyl)-1,1-dioxidothietan-3-yl)carbamate (0.51 mmol) in DMF (2.5 mL) was treated with tris(dimethylamino)sulfonium difluorotrimethylsilicate (TASF, 5.1 mmol) and heated at 60° C. for 5 minutes. After concentration of the mixture under reduced pressure, the residue was subjected to HPLC purification (0.1% TFA in MeCN-0.1% TFA in H₂O) to give the title compound.

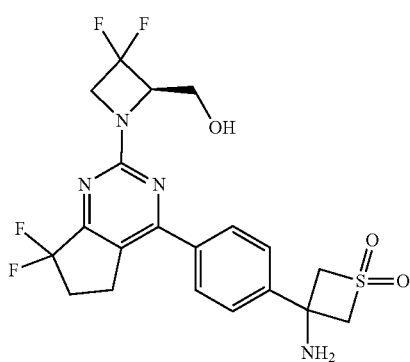

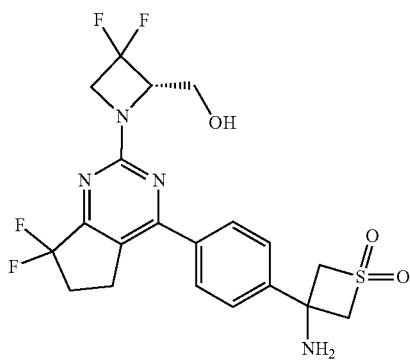 [SMILES: NC1(c2ccc(-c3nc(N4CC(F)(F)C4CO)nc4c3CCC4(F)F)cc2)CS(=O)(=O)C1]

Example 783: (R)-3-amino-3-(4-(2-(3,3-difluoro-2-(hydroxymethyl)azetidin-1-yl)-7,7-difluoro-6,7-dihydro-5H-cyclopenta[d]pyrimidin-4-yl)phenyl)thietane 1,1-dioxide Example 784: (S)-3-amino-3-(4-(2-(3,3-difluoro-2-(hydroxymethyl)azetidin-1-yl)-7,7-difluoro-6,7-dihydro-5H-cyclopenta[d]pyrimidin-4-yl)phenyl)thietane 1,1-dioxide Isomers were separated by SFC (35% EtOH in CO₂, CHIRALPAK AD-H, 100×4.6 mm, 3 mL/min).

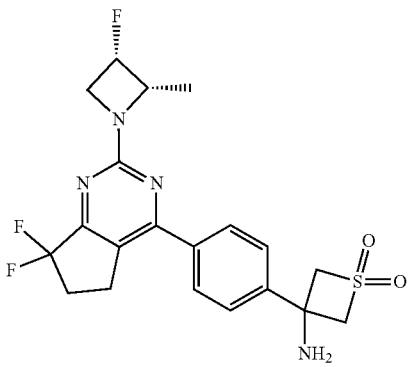 [SMILES: C[C@H]1[C@@H](F)CN1c1nc(-c2ccc(C3(N)CS(=O)(=O)C3)cc2)c2c(n1)C(F)(F)CC2]

Example 785: 3-amino-3-(4-(7,7-difluoro-24(2S,3S)-3-fluoro-2-methylazetidin-1-yl)-6,7-dihydro-5H-cyclopenta[d]pyrimidin-4-yl)phenyl)thietane 1,1-dioxide The title compound was prepared in analogy to General Method M, using 2-(trimethylsilyl)ethyl (3-(4-(7,7-difluoro-2-(methylthio)-6,7-dihydro-5H-cyclopenta[d]pyrimidin-4-yl)phenyl)-1,1-dioxidothietan-3-yl)carbamate instead of 4-(7,7-difluoro-2-(methylthio)-6,7-dihydro-5H-cyclopenta[d]pyrimidin-4-yl)benzamide, followed by General Method B using (2S,3S)-3-fluoro-2-methylazetidine instead of (2S,3R)-3-fluoro-2-methylazetidine, followed by General Method I.

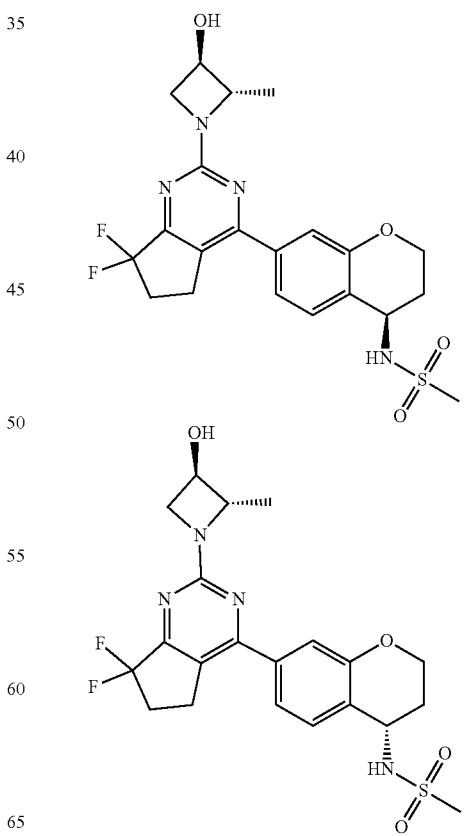

Example 786: N—((R)-(7,7-difluoro-2-((2S,3R)-3-hydroxy-2-methylazetidin-1-yl)-6,7-dihydro-5H-cyclopenta[d]pyrimidin-4-yl)chroman-4-yl)methanesulfonamide Example 787: N—((S)-7-(7,7-difluoro-2-((2S,3R)-3-hydroxy-2-methylazetidin-1-yl)-6,7-dihydro-5H-cyclopenta[d]pyrimidin-4-yl)chroman-4-yl)methanesulfonamide N-(7-(7,7-difluoro-2-((2S,3R)-3-hydroxy-2-methylazetidin-1-yl)-6,7-dihydro-5H-cyclopenta[d]pyrimidin-4-yl)chroman-4-yl)methanesulfonamide was prepared according to General Method F, using N-(7-bromochroman-4-yl)methanesulfonamide and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method B using (2S,3R)-2-methylazetidin-3-ol instead of (2S)-2-methylazetidine.

Isomers were separated by SFC (30% EtOH in $CO_2$, CHIRALPAK AD-H, 100×4.6 mm, 3 mL/min).

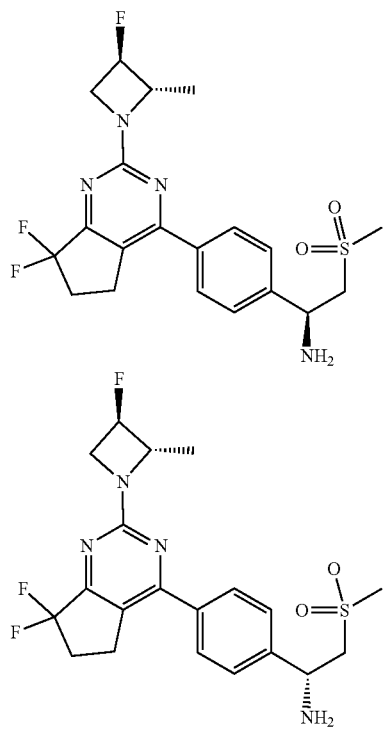

Example 788: (S)-1-(4-(7,7-difluoro-24(2S,3R)-3-fluoro-2-methylazetidin-1-yl)-6,7-dihydro-5H-cyclopenta[d]pyrimidin-4-yl)phenyl)-2-(methylsulfonyl)ethan-1-amine Example 789: (R)-1-(4-(7,7-difluoro-24(2S,3R)-3-fluoro-2-methylazetidin-1-yl)-6,7-dihydro-5H-cyclopenta[d]pyrimidin-4-yl)phenyl)-2-(methylsulfonyl)ethan-1-amine Isomers were separated by SFC (30% MeOH in $CO_2$, Lux® 5 µm Cellulose-2, 100×4.6 mm, 3 mL/min). (see Example 773)

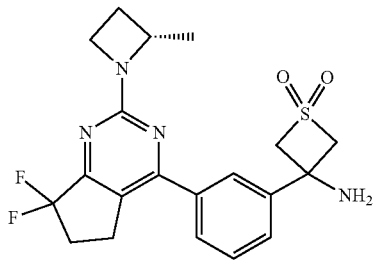 [SMILES: C[C@H]1CCN1c1nc(-c2cccc(C3(N)CS(=O)(=O)C3)c2)c2c(n1)C(F)(F)CC2]

Example 790: (S)-3-amino-3-(3-(7,7-difluoro-2-(2-methylazetidin-1-yl)-6,7-dihydro-5H-cyclopenta[d]pyrimidin-4-yl)phenyl)thietane 1,1-dioxide Benzyl N-[3-[3-(7,7-difluoro-2-methylsulfonyl-5,6-dihydrocyclopenta[d]pyrimidin-4-yl)phenyl]-1,1-dioxo-thietan-3-yl]carbamate was prepared analogously to benzyl N-[3-[4-(7,7-difluoro-2-methylsulfonyl-5,6-dihydrocyclopenta[d]pyrimidin-4-yl)phenyl]-1,1-dioxo-thietan-3-yl]carbamate, starting from ethyl 2-(3-bromophenyl)acetate instead of ethyl 2-(4-bromophenyl)acetate. (Example 491) 3-[3-(7,7-difluoro-2-methylsulfonyl-5,6-dihydrocyclopenta[d]pyrimidin-4-yl)phenyl]-1,1-dioxo-thietan-3-amine was prepared in analogy to General Procedure R, using benzyl N-[3-[3-(7,7-difluoro-2-methylsulfonyl-5,6-dihydrocyclopenta[d]pyrimidin-4-yl)phenyl]-1,1-dioxo-thietan-3-yl]carbamate instead of benzyl (3-(4-(7,7-difluoro-2-((2S,3R)-3-fluoro-2-methylazetidin-1-yl)-6,7-dihydro-5H-cyclopenta[d]pyrimidin-4-yl)phenyl)oxetan-3-yl)carbamate and ethyl acetate instead of ethanol.

The title compound was prepared according to General Method B using 3-[3-(7,7-difluoro-2-methylsulfonyl-5,6-dihydrocyclopenta[d]pyrimidin-4-yl)phenyl]-1,1-dioxo-thietan-3-amine instead of 2-chloro-4-(pyridin-3-yl)-6,7-dihydro-5H-cyclopenta[d]pyrimidine.

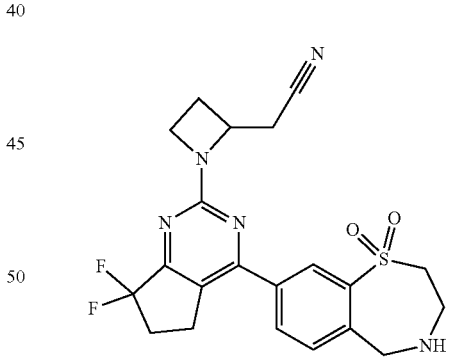

Example 791: 2-(1-(4-(1,1-dioxido-2,3,4,5-tetrahydrobenzo[f][1,4]thiazepin-8-yl)-7,7-difluoro-6,7-dihydro-5H-cyclopenta[d]pyrimidin-2-yl)azetidin-2-yl)acetonitrile A mixture of 2-(1-tert-butoxycarbonylazetidin-2-yl)acetic acid (4.6 mmol) and 4-methylmorpholine (5.1 mmol) in tetrahydrofuran (12 mL) was cooled to −14° C. before isobutylchloroformate (5.1 mmol) was added dropwise. After 20 minutes of stirring, ammonium hydroxide solution (28-30%, 3.1 mL, 23 mmol) was added. After 10 minutes, the bath was removed, and the mixture was allowed to warm to room temperature. After volatiles were removed under reduced pressure, the mixture was treated with 10% aqueous citric acid solution and then extracted three times with ethyl acetate. The combined extracts were washed successively once each with water and saturated aqueous sodium hydrogen carbonate solution, dried over anhydrous magnesium sulfate, filtered, and concentrated to provide tert-butyl 2-(2-amino-2-oxo-ethyl)azetidine-1-carboxylate, which was carried forward without further purification.

tert-butyl 2-(2-amino-2-oxo-ethyl)azetidine-1-carboxylate (0.54 mmol) was dissolved in dichloromethane (1 mL), treated with trifluoroacetic acid (5.4 mmol), and heated for 30 minutes at 50° C. After cooling, the mixture was concentrated under reduced pressure to provide 2-(azetidin-2-yl)acetamide, which was carried forward without further purification. tert-butyl 8-(2-(2-(2-amino-2-oxoethyl)azetidin-1-yl)-7,7-difluoro-6,7-dihydro-5H-cyclopenta[d]pyrimidin-4-yl)-2,3-dihydrobenzo[f][1,4]thiazepine-4(5H)-carboxylate 1,1-dioxide was prepared according to General Method B, using tert-butyl 8-(7,7-difluoro-2-(methylsulfonyl)-6,7-dihydro-5H-cyclopenta[d]pyrimidin-4-yl)-2,3-dihydrobenzo[f][1,4]thiazepine-4(5H)-carboxylate 1,1-dioxide and 2-(azetidin-2-yl)acetamide instead of 2-chloro-4-(pyridin-3-yl)-6,7-dihydro-5H-cyclopenta[d]pyrimidine and (2S)-2-methylazetidine, respectively.

A mixture of tert-butyl 8-(2-(2-(2-amino-2-oxoethyl)azetidin-1-yl)-7,7-difluoro-6,7-dihydro-5H-cyclopenta[d]pyrimidin-4-yl)-2,3-dihydrobenzo[f][1,4]thiazepine-4(5H)-carboxylate 1,1-dioxide (0.22 mmol) in tetrahydrofuran (2 mL) was treated with triethylamine (0.48 mmol) and cooled in an ice-water bath. Trifluoroacetic anhydride (0.24 mmol) was added dropwise, and the mixture was stirred for 5 minutes before it was allowed to warm to room temperature. The mixture was quenched with water (0.1 mL) and concentrated under reduced pressure to provide 8-(2-(2-(cyanomethyl)azetidin-1-yl)-7,7-difluoro-6,7-dihydro-5H-cyclopenta[d]pyrimidin-4-yl)-2,3-dihydrobenzo[f][1,4]thiazepine-4(5H)-carboxylate 1,1-dioxide.

Treatment of a solution of tert-butyl 8-(2-(2-(cyanomethyl)azetidin-1-yl)-7,7-difluoro-6,7-dihydro-5H-cyclopenta[d]pyrimidin-4-yl)-2,3-dihydrobenzo[f][1,4]thiazepine-4(5H)-carboxylate 1,1-dioxide (0.2 mmol) in dichloromethane (2 mL) with trifluoroacetic acid (1.0 mL), followed by concentration and HPLC purification (0.1% TFA in MeCN-0.1% TFA in H₂O), provided the title compound.

Example 792: N-((3R)-6-(2-(3,3-difluoro-2-(hydroxymethyl)azetidin-1-yl)-7,7-difluoro-6,7-dihydro-5H-cyclopenta[d]pyrimidin-4-yl)-2,3-dihydrobenzofuran-3-yl)methanesulfonamide A solution of tert-butyl 3,3-difluoro-2-(hydroxymethyl)azetidine-1-carboxylate (4.5 mmol) in dichloromethane (5 mL) was treated with hydrogen chloride solution (4N in dioxane, 140 mmol), and the mixture was stirred at 45° C. overnight. The mixture was concentrated under reduced pressure to provide (3,3-difluoroazetidin-2-yl)methanol hydrochloride.

The title compound was prepared in analogy to General Method K using (R)-6-bromo-2,3-dihydrobenzofuran-3-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B, using of (3,3-difluoroazetidin-2-yl)methanol of (2S)-2-methylazetidine.

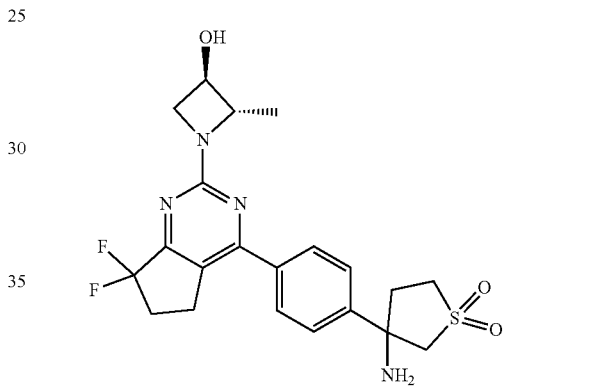

Example 793: 3-amino-3-(4-(7,7-difluoro-24(2S, 3R)-3-hydroxy-2-methylazetidin-1-yl)-6,7-dihydro-5H-cyclopenta[d]pyrimidin-4-yl)phenyl)tetrahydrothiophene 1,1-dioxide Copper iodide (11 mmol), cesium carbonate (110 mmol), and picolinic acid (23 mmol) were added to a round-bottom flask under a nitrogen atmosphere. A solution of 1-bromo-4-iodo-benzene (57 mmol) in dioxane (66 mL) was added, followed by tert-butyl ethyl malonate (57 mmol). The flask was placed under vacuum and back filled with argon; this process was repeated a total of three times. The reaction mixture, under a balloon of Argon, was then heated overnight with stirring at 85° C. After cooling, the mixture was filtered, and the filtrate was concentrated under reduced pressure. The residue was purified by flash chromatography (hexanes-ethyl acetate) to provide 1-(tert-butyl) 3-ethyl 2-(4-bromophenyl)malonate.

A solution of 1-(tert-butyl) 3-ethyl 2-(4-bromophenyl) malonate (assumed 55 mmol) in N,N-dimethylformamide (165 mL) was treated with potassium carbonate (170 mmol) and potassium iodide (0.92 g, 5.5 mmol). To the stirred suspension was added allyl bromide (110 mmol), and the resulting suspension was stirred at room temperature. The reaction mixture was diluted with water and extracted three times (3×200 mL) with 1:1 hexane/ethyl acetate. The com-

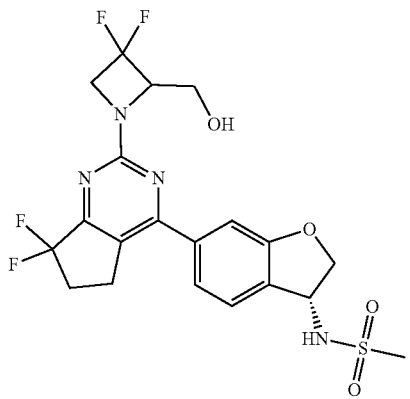 [SMILES: CS(=O)(=O)N[C@H]1COc2cc(-c3nc(N4CC(F)(F)C4CO)nc4c3CCC4(F)F)ccc21]

bined organic extracts were then washed once with saturated aqueous sodium chloride solution, dried over anhydrous magnesium sulfate, filtered, and concentrated under reduced pressure. The residue was purified by flash chromatography (hexanes-ethyl acetate) to provide 1-(tert-butyl) 3-ethyl 2-allyl-2-(4-bromophenyl)malonate.

Ozone was bubbled into a −78° C. solution of 1-(tert-butyl) 3-ethyl 2-allyl-2-(4-bromophenyl)malonate (17 mmol) in EtOAc (150 mL) until the solution was saturated. After purging with argon for 30 minutes, dimethyl sulfide (170 mmol) was added slowly at −78° C. The stirred mixture was allowed to warm to room temperature overnight. Saturated aqueous sodium thiosulfate solution (40 mL) was then added. After stirring for 15 min at RT, the layers were separated. The organic phase was washed successively with water and saturated aqueous sodium chloride solution before being dried over anhydrous magnesium sulfate, filtered, and concentrated. The residue was purified by flash chromatography (hexanes-ethyl acetate) to provide 1-(tert-butyl) 3-ethyl 2-(4-bromophenyl)-2-(2-oxoethyl)malonate.

Sodium borohydride (40 mmol) was added to a stirred solution of 1-(tert-butyl) 3-ethyl 2-(4-bromophenyl)-2-(2-oxoethyl)malonate (33 mmol) in ethanol (200 mL) at −20° C. Tetrahydrofuran (50 mL) was then added, followed by the portionwise addition of cerium(III) trichloride heptahydrate (66 mmol). After stirring the reaction mixture for 20 min at 0° C., sodium borohydride (170 mmol) was added portionwise. After 30 min of stirring at 0° C., glacial acetic acid was added until the cessation of effervescence (approximately 10 mL). The mixture was concentrated under reduced pressure. The residue was taken up as a mixture in ethyl acetate and water and filtered through a pad of Celite®. The aqueous phase was extracted three times with ethyl acetate. The combined extracts were washed once each with saturated aqueous sodium hydrogen carbonate solution and saturated aqueous sodium chloride solution, dried over anhydrous magnesium sulfate, filtered, and concentrated under reduced pressure to provide tert-butyl 2-(4-bromophenyl)-4-hydroxy-2-(hydroxymethyl)butanoate.

tert-butyl 2-(4-bromophenyl)-4-methylsulfonyloxy-2-(methylsulfonyloxymethyl)butanoate was prepared analogously to ethyl 2-(4-bromophenyl)-3-(trifluoromethylsulfonyloxy)-2-(trifluoromethylsulfonyloxymethyl)propanoate, using tert-butyl 2-(4-bromophenyl)-4-hydroxy-2-(hydroxymethyl)butanoate and methanesulfonyl chloride instead of ethyl 2-(4-bromophenyl)-3-hydroxy-2-(hydroxymethyl)propanoate and triflic anhydride, respectively.

tert-butyl 3-(4-bromophenyl)tetrahydrothiophene-3-carboxylate was prepared analogously to ethyl 3-(4-bromophenyl)thietane-3-carboxylate, using tert-butyl 2-(4-bromophenyl)-4-methylsulfonyloxy-2-(methylsulfonyloxymethyl) butanoate instead of ethyl 2-(4-bromophenyl)-3-(trifluoromethylsulfonyloxy)-2-(trifluoromethylsulfonyloxymethyl)propanoate.

A mixture of tert-butyl 3-(4-bromophenyl)tetrahydrothiophene-3-carboxylate (5.1 mmol) in dichloromethane (14 mL) was treated with trifluoroacetic acid (78 mmol) and heated for 15 minutes at 50° C. The mixture was then concentrated under reduced pressure. The residue was co-evaporated twice from 4N hydrogen chloride in dioxane solution and then triturated with acetone. The solids were collected by filtration and dried (vacuum oven, 50° C.) to provide 3-(4-bromophenyl)tetrahydrothiophene-3-carboxylic acid.

2-trimethylsilylethyl N-[3-(4-bromophenyl)tetrahydrothiophen-3-yl]carbamate was prepared analogously to benzyl N-[3-(4-bromophenyl)-1,1-dioxo-thietan-3-yl]carbamate, using 3-(4-bromophenyl)tetrahydrothiophene-3-carboxylic acid and 2-(trimethylsilyl)ethanol instead of 3-(4-bromophenyl)thietane-3-carboxylic acid and benzyl alcohol, respectively.

The title compound was prepared in analogy to General Method F using 4-chloro-7,7-difluoro-2-(methylthio)-6,7-dihydro-5H-cyclopenta[d]pyrimidine and 2-trimethylsilylethyl N-[3-(4-bromophenyl)tetrahydrothiophen-3-yl]carbamate instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one respectively, followed by General Method M, and General Method B, using (2S,3R)-2-methylazetidin-3-ol instead of (2S)-2-methylazetidine, followed by General Method I.

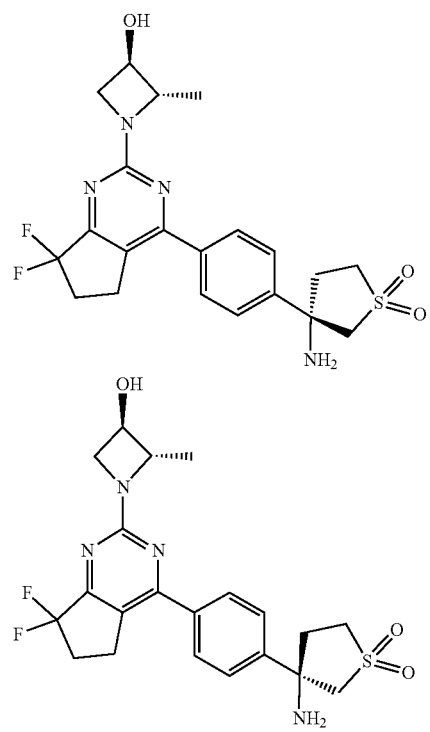

Example 794: (S)-3-amino-3-(4-(7,7-difluoro-24(2S,3R)-3-hydroxy-2-methylazetidin-1-yl)-6,7-dihydro-5H-cyclopenta[d]pyrimidin-4-yl)phenyl)tetrahydrothiophene 1,1-dioxide Example 795: (R)-3-amino-3-(4-(7,7-difluoro-2-((2S,3R)-3-hydroxy-2-methylazetidin-1-yl)-6,7-dihydro-5H-cyclopenta[d]pyrimidin-4-yl)phenyl)tetrahydrothiophene 1,1-dioxide Isomers were separated by SFC (25% EtOH in $CO_2$, CHIRALPAK AD-H, 100×4.6 mm, 3 mL/min).

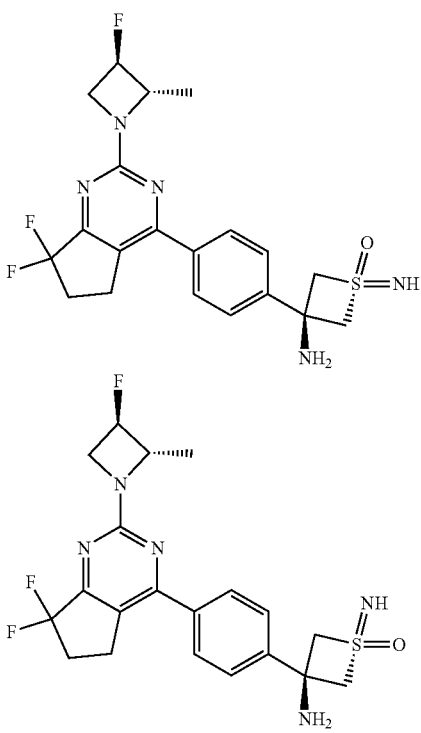

Example 796: (1S,3r)-3-amino-3-(4-(7,7-difluoro-24 (2S,3R)-3-fluoro-2-methylazetidin-1-yl)-6,7-dihydro-5H-cyclopenta[d]pyrimidin-4-yl)phenyl)-1-imino-1λ$^6$-thietane 1-oxide Example 797: (1R,3s)-3-amino-3-(4-(7,7-difluoro-2-((2S,3R)-3-fluoro-2-methylazetidin-1-yl)-6,7-dihydro-5H-cyclopenta[d]pyrimidin-4-yl)phenyl)-1-imino-1λ$^6$-thietane 1-oxide 2-trimethylsilylethyl N-[3-[4-(7,7-difluoro-2-methylsulfanyl-5,6-dihydrocyclopenta[d]pyrimidin-4-yl)phenyl]thietan-3-yl]carbamate was prepared in analogy to General Method F using 4-chloro-7,7-difluoro-2-(methylthio)-6,7-dihydro-5H-cyclopenta[d]pyrimidine and 2-trimethylsilylethyl N-[3-(4-bromophenyl)thietan-3-yl]carbamate, instead of 4-chloro-2-[(2S)-2-methylazetidin-1-yl]-6,7-dihydro-5H-cyclopenta[d]pyrimidine and 6-bromo-1,1-dioxo-1,2-benzothiazol-3-one, respectively.

3-[4-(7,7-difluoro-2-methylsulfanyl-5,6-dihydrocyclopenta[d]pyrimidin-4-yl)phenyl]thietan-3-amine was prepared from 2-trimethylsilylethyl N-[3-[4-(7,7-difluoro-2-methylsulfanyl-5,6-dihydrocyclopenta[d]pyrimidin-4-yl)phenyl]thietan-3-yl]carbamate was prepared in analogy to General Method I. At the end of the reaction, volatiles were removed under reduced pressure and the residue was carried forward without further purification.

A mixture of 3-[4-(7,7-difluoro-2-methylsulfanyl-5,6-dihydrocyclopenta[d]pyrimidin-4-yl)phenyl]thietan-3-amine; 2,2,2-trifluoroacetate salt (2.5 mmol) and N,N-diisopropylethylamine (15 mmol) in tetrahydrofuran (15 mL) was cooled to −12° C. while stirring under a balloon of nitrogen. Trifluoroacetic anhydride (2.9 mmol) was added dropwise via syringe. After 10 min of stirring, the mixture was quenched with water and extracted three times with ethyl acetate. The combined extracts were washed once with saturated aqueous sodium chloride solution, dried over anhydrous magnesium sulfate, filtered, and concentrated under reduced pressure to provide N-[3-[4-(7,7-difluoro-2-methylsulfanyl-5,6-dihydrocyclopenta[d]pyrimidin-4-yl)phenyl]thietan-3-yl]-2,2,2-trifluoro-acetamide.

A mixture of N-[3-[4-(7,7-difluoro-2-methylsulfanyl-5,6-dihydrocyclopenta[d]pyrimidin-4-yl)phenyl]thietan-3-yl]-2,2,2-trifluoro-acetamide (2.5 mmol) in acetic acid (10 mL) was treated with sodium perborate monohydrate (5.0 mmol). The mixture was heated in a 60° C. until the perborate had dissolved (— 5 min) and then an additional portion of sodium perborate monohydrate (3.0 mmol) was added. After another 5-10 minutes of stirring, the final addition of sodium perborate monohydrate was made (0.74 mmol). The mixture was heated for another 5-10 min and was then cooled. To the cooled mixture 2M aqueous sodium carbonate solution was added slowly to pH 8. The mixture was extracted three times with dichloromethane. The combined extracts were dried over anhydrous magnesium sulfate, filtered, and concentrated under reduced pressure to provide N-[3-[4-(7,7-difluoro-2-methylsulfinyl-5,6-dihydrocyclopenta[d]pyrimidin-4-yl)phenyl]-1-oxo-thietan-3-yl]-2,2,2-trifluoro-acetamide.

N-[3-[4-[7,7-difluoro-2-[(2S,3R)-3-fluoro-2-methyl-azetidin-1-yl]-5,6-dihydrocyclopenta[d]pyrimidin-4-yl]phenyl]-1-oxo-thietan-3-yl]-2,2,2-trifluoro-acetamide was prepared from N-[3-[4-(7,7-difluoro-2-methylsulfinyl-5,6-dihydrocyclopenta[d]pyrimidin-4-yl)phenyl]-1-oxo-thietan-3-yl]-2,2,2-trifluoro-acetamide via General Method B, substituting (2S,3R)-3-fluoro-2-methylazetidine for (2S)-2-methylazetidine.

Methanol (1.6 mL) was added to a mixture of N-[3-[4-[7,7-difluoro-2-[(2S,3R)-3-fluoro-2-methyl-azetidin-1-yl]-5,6-dihydrocyclopenta[d]pyrimidin-4-yl]phenyl]-1-oxo-thietan-3-yl]-2,2,2-trifluoro-acetamide (0.80 mmol), iodobenzene diacetate (2.4 mmol) and ammonium carbamate (3.2 mmol). After 30 min of stirring, additions were made of iodobenzene diacetate (2.4 mmol) and ammonium carbamate (3.2 mmol). After another 10 minutes of stirring, the mixture was concentrated under reduced pressure. The residue was co-evaporated twice from toluene to give N-[3-[4-[7,7-difluoro-2-[(2S,3R)-3-fluoro-2-methyl-azetidin-1-yl]-5,6-dihydrocyclopenta[d]pyrimidin-4-yl]phenyl]-1-imino-1-oxo-thietan-3-yl]-2,2,2-trifluoro-acetamide, which was carried forward without further purification.

N-[3-[4-[7,7-difluoro-2-[(2S,3R)-3-fluoro-2-methyl-azetidin-1-yl]-5,6-dihydrocyclopenta[d]pyrimidin-4-yl]phenyl]-1-imino-1-oxo-thietan-3-yl]-2,2,2-trifluoro-acetamide (0.80 mmol) was taken up in methanol (10 mL) and treated with sodium borohydride (4.0 mmol). Over the course of the next hour, additional sodium borohydride (12 mmol) was added portionwise. The mixture was then concentrated under reduced pressure. The residue was subjected to HPLC purification (0.1% TFA in MeCN-0.1% TFA in H$_2$O), which separated the mixture into its component diastereomers. The eluate containing the respective title compound was neutralized with saturated aqueous sodium bicarbonate solution and extracted into dichloromethane (three times). The combined extracts were dried over anhydrous magnesium sulfate, filtered, and concentrated to dryness under reduced pressure. The residues were purified by flash chromatography (hexanes-ethyl acetate) to give the title compounds.

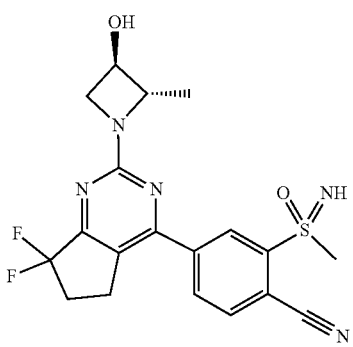 [SMILES: C[C@H]1[C@H](O)CN1c1nc(-c2ccc(C#N)c(S(C)(=N)=O)c2)c2c(n1)C(F)(F)CC2]

Example 798: 4-(7,7-difluoro-2-((S)-2-methylazetidin-1-yl)-6,7-dihydro-5H-cyclopenta[d]pyrimidin-4-yl)-2-(S-methylsulfonimidoyl)benzonitrile 4-(7,7-difluoro-2-methylsulfanyl-5,6-dihydrocyclopenta[d]pyrimidin-4-yl)-2-methylsulfanyl-benzonitrile was prepared according to General Method F, using 4-bromo-2-methylsulfanyl-benzonitrile and 4-chloro-7,7-difluoro-2-methylsulfanyl-5,6-dihydrocyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively.

A mixture of 4-(7,7-difluoro-2-methylsulfanyl-5,6-dihydrocyclopenta[d]pyrimidin-4-yl)-2-methylsulfanyl-benzonitrile (1.8 mmol) in acetic acid (10 mL) was treated with sodium perborate monohydrate (5.0 mmol). The mixture was heated to 60° C. for five minutes, then an additional portion of sodium perborate monohydrate (3.0 mmol) was added. The mixture was allowed to cool to room temperature after another 30 min of stirring. After cooling, the mixture was added slowly to saturated aqueous sodium carbonate solution (50 mL). The aqueous phase was extracted three times with ethyl acetate. The combined extracts were washed once with a 1:1 mixture of saturated aqueous sodium chloride solution and saturated aqueous sodium hydrogen carbonate solution, dried over anhydrous magnesium sulfate, filtered, and concentrated under reduced pressure to provide 4-(7,7-difluoro-2-methylsulfinyl-5,6-dihydrocyclopenta[d]pyrimidin-4-yl)-2-methylsulfinyl-benzonitrile.

4-[7,7-difluoro-2-[(2S,3R)-3-hydroxy-2-methyl-azetidin-1-yl]-5,6-dihydrocyclopenta[d]pyrimidin-4-yl]-2-methylsulfinyl-benzonitrile was prepared from 4-(7,7-difluoro-2-methylsulfinyl-5,6-dihydrocyclopenta[d]pyrimidin-4-yl)-2-methylsulfinyl-benzonitrile via General Method B, substituting (2S,3R)-2-methylazetidin-3-ol for (2S)-2-methylazetidine.

Methanol (3.4 mL) was added to a mixture of 4-[7,7-difluoro-2-[(2S,3R)-3-hydroxy-2-methyl-azetidin-1-yl]-5,6-dihydrocyclopenta[d]pyrimidin-4-yl]-2-methylsulfinyl-benzonitrile (1.7 mmol), iodobenzene diacetate (5.0 mmol) and ammonium carbamate (6.6 mmol). After 30 min, additional portions of iodobenzene diacetate (5.0 mmol) and ammonium carbamate (6.6 mmol) were added. After another 30 min of stirring at room temperature, the final portions of iodobenzene diacetate (5.0 mmol) and ammonium carbamate (6.6 mmol) were added. After 30 minutes of stirring, the mixture was concentrated under reduced pressure. The residue was partitioned into a biphasic mixture of saturated aqueous sodium hydrogen carbonate solution and dichloromethane. The aqueous phase was extracted three times with dichloromethane. The combined extracts were dried over anhydrous magnesium sulfate, filtered, and concentrated under reduced pressure. The residue was subjected to HPLC purification (0.1% TFA in MeCN-0.1% TFA in H$_2$O) to provide the title compound.

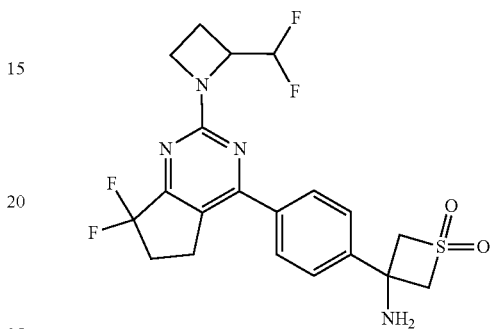

Example 799: 3-amino-3-(4-(2-(2-(difluoromethyl)azetidin-1-yl)-7,7-difluoro-6,7-dihydro-5H-cyclopenta[d]pyrimidin-4-yl)phenyl)thietane 1,1-dioxide A solution of N-[3-[4-(7,7-difluoro-2-methylsulfanyl-5,6-dihydrocyclopenta[d]pyrimidin-4-yl)phenyl]thietan-3-yl]-2,2,2-trifluoro-acetamide (2.6 mmol) in acetonitrile (10 mL) was treated with peracetic acid solution (32% by weight in dilute acetic acid, 13 mmol). The mixture was stirred overnight at room temperature. The pH was then adjusted to 8 by the addition of 2M aqueous sodium carbonate solution. The mixture was partitioned between ethyl acetate and saturated aqueous sodium chloride solution. The aqueous phase was extracted three times with ethyl acetate. The combined extracts were washed once with saturated aqueous sodium thiosulfate solution, dried over anhydrous magnesium sulfate, filtered, and concentrated under reduced pressure to give N-[3-[4-(7,7-difluoro-2-methylsulfonyl-5,6-dihydrocyclopenta[d]pyrimidin-4-yl)phenyl]-1,1-dioxo-thietan-3-yl]-2,2,2-trifluoro-acetamide.

N-[3-[4-[2-[2-(difluoromethyl)azetidin-1-yl]-7,7-difluoro-5,6-dihydrocyclopenta[d]pyrimidin-4-yl]phenyl]-1,1-dioxo-thietan-3-yl]-2,2,2-trifluoro-acetamide was prepared according to General Method B, using 2-(difluoromethyl)azetidine instead of (2S)-2-methylazetidine.

To a solution of N-[3-[4-[2-[2-(difluoromethyl)azetidin-1-yl]-7,7-difluoro-5,6-dihydrocyclopenta[d]pyrimidin-4-yl]phenyl]-1,1-dioxo-thietan-3-yl]-2,2,2-trifluoro-acetamide (0.35 mmol) in methanol (10 mL) was added sodium borohydride (7.9 mmol) portionwise at room temperature. The mixture was stirred overnight before being concentrated under reduced pressure and subjected to HPLC purification (0.1% TFA in MeCN-0.1% TFA in H$_2$O) to provide the title compound.

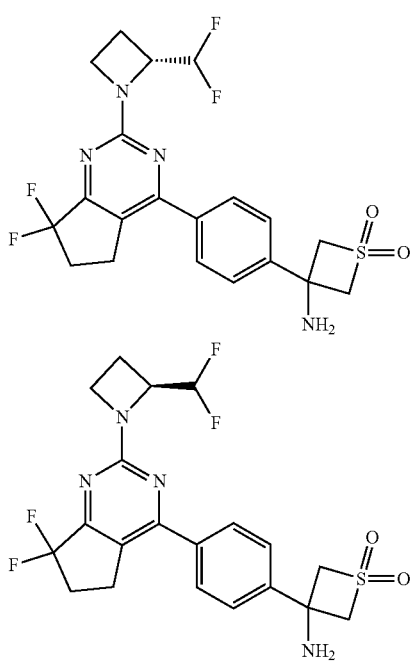

Example 800: (R)-3-amino-3-(4-(2-(2-(difluoromethyl)azetidin-1-yl)-7,7-difluoro-6,7-dihydro-5H-cyclopenta[d]pyrimidin-4-yl)phenyl)thietane 1,1-dioxide Example 801: (S)-3-amino-3-(4-(2-(2-(difluoromethyl)azetidin-1-yl)-7,7-difluoro-6,7-dihydro-5H-cyclopenta[d]pyrimidin-4-yl)phenyl)thietane 1,1-dioxide Isomers were separated by SFC (35% MeOH in $CO_2$, CHIRALPAK AD-H, 100×4.6 mm, 3 mL/min).

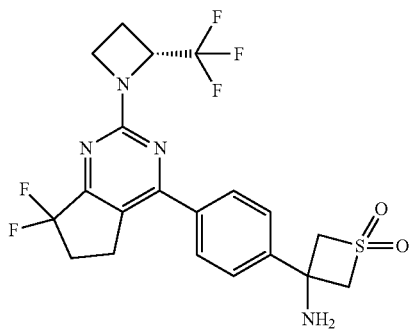 [SMILES: NC1(c2ccc(-c3nc(N4CC[C@@H]4C(F)(F)F)nc4c3CCC4(F)F)cc2)CS(=O)(=O)C1]

Example 802: (R)-3-amino-3-(4-(7,7-difluoro-2-(2-(trifluoromethyl)azetidin-1-yl)-6,7-dihydro-5H-cyclopenta[d]pyrimidin-4-yl)phenyl)thietane 1,1-dioxide In a microwave vial, N-[3-[4-(7,7-difluoro-2-methylsulfonyl-5,6-dihydrocyclopenta[d]pyrimidin-4-yl)phenyl]-1,1-dioxo-thietan-3-yl]-2,2,2-trifluoro-acetamide (0.39 mmol) was dissolved in acetonitrile (3 mL) and treated successively with (2R)-2-(trifluoromethyl)azetidine tosylate (1.2 mmol) and N,N-diisopropylethylamine (2.3 mmol). The mixture was irradiated in an Anton Paar Monowave 450 reactor for 18 hours at 130° C. After cooling, additional portions were added of (2R)-2-(trifluoromethyl)azetidine tosylate (0.58 mmol) and N,N-diisopropylethylamine (1.2 mmol). The mixture was irradiated again in the microwave reactor for 18 hours at 130° C. After cooling, the mixture was partitioned between ethyl acetate and 10% aqueous citric acid solution. The aqueous phase was extracted three times with ethyl acetate. The combined extracts were washed once with saturated aqueous sodium chloride solution, dried over anhydrous magnesium sulfate, filtered, and concentrated to provide N-[3-[4-[7,7-difluoro-2-[(2R)-2-(trifluoromethyl)azetidin-1-yl]-5,6-dihydrocyclopenta[d]pyrimidin-4-yl]phenyl]-1,1-dioxo-thietan-3-yl]-2,2,2-trifluoro-acetamide.

To a solution of N-[3-[4-[7,7-difluoro-2-[(2R)-2-(trifluoromethyl)azetidin-1-yl]-5,6-dihydrocyclopenta[d]pyrimidin-4-yl]phenyl]-1,1-dioxo-thietan-3-yl]-2,2,2-trifluoro-acetamide (0.39 mmol) in methanol (15 mL) was added sodium borohydride (7.9 mmol) portionwise at room temperature. After 15 minutes of stirring, a second portion of sodium borohydride (5.3 mmol) was added, and the mixture was stirred overnight before being concentrated under reduced pressure and subjected to HPLC purification (0.1% TFA in MeCN-0.1% TFA in $H_2O$) to provide the title compound.

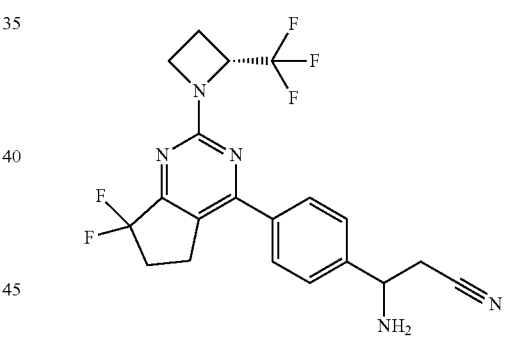

Example 803: 3-amino-3-(4-(7,7-difluoro-2-((R)-2-(trifluoromethyl)azetidin-1-yl)-6,7-dihydro-5H-cyclopenta[d]pyrimidin-4-yl)phenyl)propanenitrile The title compound was prepared analogously to N-[3-[4-[7,7-difluoro-2-[(2R)-2-(trifluoromethyl)azetidin-1-yl]-5,6-dihydrocyclopenta[d]pyrimidin-4-yl]phenyl]-1,1-dioxo-thietan-3-yl]-2,2,2-trifluoro-acetamide, using tert-butyl N-[2-cyano-1-[4-(7,7-difluoro-2-methylsulfonyl-5,6-dihydrocyclopenta[d]pyrimidin-4-yl)phenyl]ethyl]carbamate instead of N-[3-[4-(7,7-difluoro-2-methylsulfonyl-5,6-dihydrocyclopenta[d]pyrimidin-4-yl)phenyl]-1,1-dioxo-thietan-3-yl]-2,2,2-trifluoro-acetamide, and then followed by General Method I.

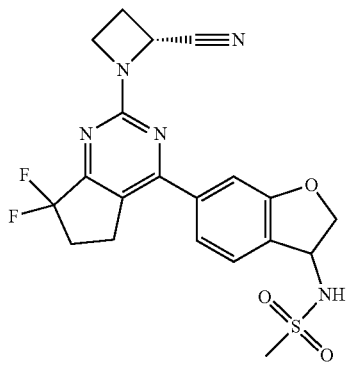 [SMILES: CS(=O)(=O)NC1COc2cc(-c3nc(N4CC[C@@H]4C#N)nc4c3CCC4(F)F)ccc21]

Example 804: N-[6-[2-[(2R)-2-cyanoazetidin-1-yl]-7,7-difluoro-5,6-dihydrocyclopenta[d]pyrimidin-4-yl]-2,3-dihydrobenzofuran-3-yl]methanesulfonamide The title compound was prepared in analogy to General Method K using 6-bromo-2,3-dihydrobenzofuran-3-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B using (2R)-azetidine-2-carbonitrile oxalic acid instead of (2S)-2-methylazetidine.

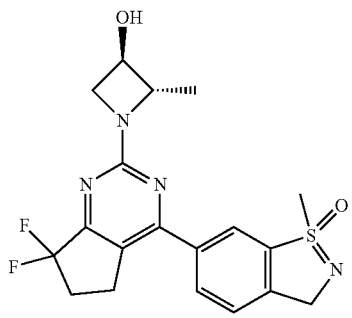 [SMILES: C[C@H]1[C@H](O)CN1c1nc(-c2ccc3c(c2)S(C)(=O)=NC3)c2c(n1)C(F)(F)CC2]

Example 805: (2S,3R)-1-[7,7-difluoro-4-(1-methyl-1-oxo-3H-1,2-benzothiazol-6-yl)-5,6-dihydrocyclopenta[d]pyrimidin-2-yl]-2-methyl-azetidin-3-ol The title compound was prepared in analogy to General Method F using 6-bromo-1-methyl-3H-1,2-benzothiazole 1-oxide and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, and General Method B using (2S,3R)-2-methylazetidin-3-ol instead of (2S)-2-methylazetidine.

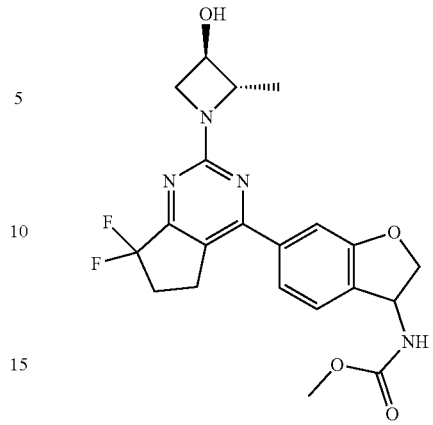

Example 806: methyl N-[6-[7,7-difluoro-2-[(2S,3R)-3-hydroxy-2-methyl-azetidin-1-yl]-5,6-dihydro-cyclopenta[d]pyrimidin-4-yl]-2,3-dihydrobenzo-furan-3-yl]carbamate A flask was charged with 6-bromo-2,3-dihydrobenzofuran-3-amine (200 mg, 0.93 mmol), diisopropylethylamine (0.50 mL, 2.80 mmol) and DCM (5 mL). Methyl carbonochloridate (88.3 mg, 0.94 mmol) was added slowly as a solution in DCM (1 mL). The reaction mixture was stirred at room temperature for 30 minutes. The mixture was purified by silica gel chromatography to afford methyl N-(6-bromo-2,3-dihydrobenzofuran-3-yl)carbamate.

The title compound was prepared in analogy to General Method F using methyl N-(6-bromo-2,3-dihydrobenzofuran-3-yl)carbamate and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, followed by General Method B using (2S,3R)-2-methylazetidin-3-ol instead of (2S)-2-methylazetidine.

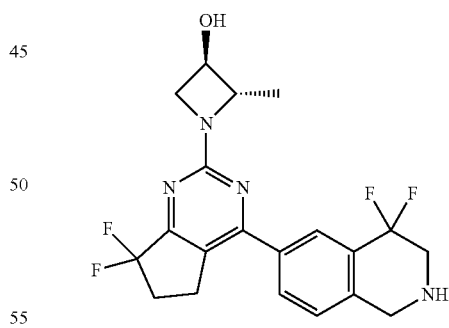

Example 807: (2S,3R)-1-[4-(4,4-difluoro-2,3-dihydro-1H-isoquinolin-6-yl)-7,7-difluoro-5,6-dihydrocyclopenta[d]pyrimidin-2-yl]-2-methyl-azetidin-3-ol The title compound was prepared in analogy to General Method F using tert-butyl 6-bromo-4,4-difluoro-1,3-dihydroisoquinoline-2-carboxylate and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, followed by General Method B using (2S,3R)-2-methylazetidin-3-ol instead of (2S)-2-methylazetidine, and then General Method I.

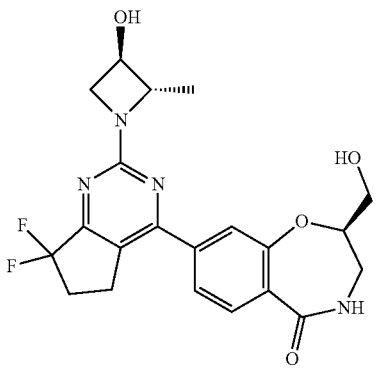 [SMILES: C[C@H]1[C@H](O)CN1c1nc(-c2ccc3c(c2)O[C@@H](CO)CNC3=O)c2c(n1)C(F)(F)CC2]

Example 808: (R)-8-(7,7-difluoro-2-((2S,3R)-3-hydroxy-2-methylazetidin-1-yl)-6,7-dihydro-5H-cyclopenta[d]pyrimidin-4-yl)-2-(hydroxymethyl)-3,4-dihydrobenzo[f][1,4]oxazepin-5(2H)-one The title compound was prepared in analogy to General Method Q, using tert-butyl S)-(3-((tert-butyldimethylsilyl)oxy)-2-hydroxypropyl)carbamate instead of tert-butyl (R)-(1-hydroxypropan-2-yl)carbamate, followed by General Method F using (S)-8-bromo-2-(hydroxymethyl)-3,4-dihydrobenzo[f][1,4]oxazepin-5(2H)-one and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine, respectively, followed by General Method M, followed by General method B using (2S,3R)-2-methylazetidin-3-ol instead of (2S)-2-methylazetidine.

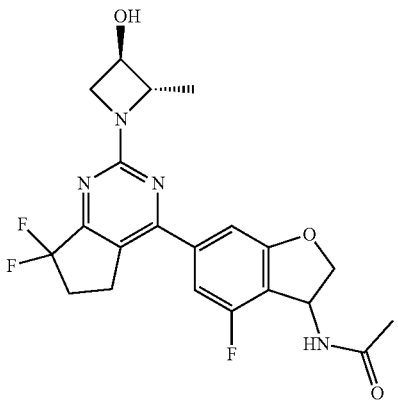 [SMILES: CC(=O)NC1COc2cc(-c3nc(N4C[C@@H](O)[C@@H]4C)nc4c3CCC4(F)F)cc(F)c21]

Example 809: N-[6-[7,7-difluoro-2-[(2S,3R)-3-hydroxy-2-methyl-azetidin-1-yl]-5,6-dihydrocyclopenta[d]pyrimidin-4-yl]-4-fluoro-2,3-dihydrobenzofuran-3-yl]methanesulfonamide A flask was charged with 6-bromo-4-fluoro-2,3-dihydrobenzofuran-3-amine (204 mg, 0.88 mmol), diisopropylethylamine (0.47 mL, 2.63 mmol) and DCM (5 mL). Acetic anhydride (90 mg, 0.88 mmol) was added slowly as a solution in DCM (1 mL). The reaction mixture was stirred at room temperature for 30 minutes. The mixture was purified by silica gel chromatography to afford N-(6-bromo-4-fluoro-2,3-dihydrobenzofuran-3-yl)acetamide.

The title compound was prepared in analogy to General Method F using N-(6-bromo-4-fluoro-2,3-dihydrobenzofuran-3-yl)acetamide and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, and General Method B using (2S,3R)-2-methylazetidin-3-ol instead of (2S)-2-methylazetidine.

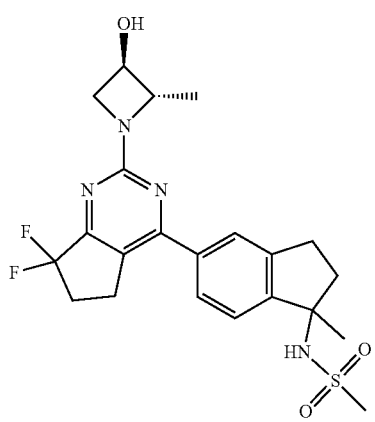 [SMILES: C[C@H]1[C@H](O)CN1c1nc(-c2ccc3c(c2)CCC3(C)NS(C)(=O)=O)c2c(n1)C(F)(F)CC2]

Example 810: N-[5-[7,7-difluoro-2-[(2S,3R)-3-hydroxy-2-methyl-azetidin-1-yl]-5,6-dihydrocyclopenta[d]pyrimidin-4-yl]-1-methyl-indan-1-yl]methanesulfonamide The title compound was prepared in analogy to General Method K using 5-bromo-1-methyl-indan-1-amine hydrochloride and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B using (2S,3R)-2-methylazetidin-3-ol instead of (2S)-2-methylazetidine.

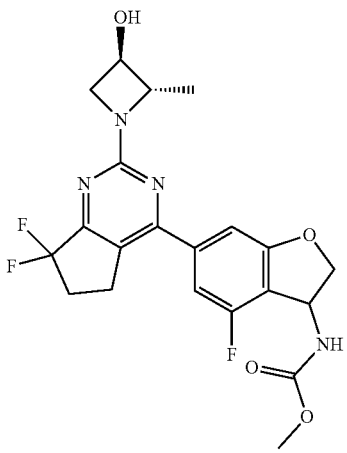 [SMILES: COC(=O)NC1COc2cc(-c3nc(N4C[C@@H](O)[C@@H]4C)nc4c3CCC4(F)F)cc(F)c21]

Example 811: methyl (6-(7,7-difluoro-2-((2S,3R)-3-hydroxy-2-methylazetidin-1-yl)-6,7-dihydro-5H-cyclopenta[d]pyrimidin-4-yl)-4-fluoro-2,3-dihydrobenzofuran-3-yl)carbamate A flask was charged with 6-bromo-4-fluoro-2,3-dihydrobenzofuran-3-amine (204 mg, 0.88 mmol), diisopropylethylamine (0.47 mL, 2.63 mmol) and DCM (5 mL). Methyl carbonochloridate (83 mg, 0.88 mmol) was added slowly as a solution in DCM (1 mL). The reaction mixture was stirred at room temperature for 30 minutes. The mixture was purified by silica gel chromatography (hexanes-ethyl acetate) to afford methyl N-(6-bromo-4-fluoro-2,3-dihydrobenzofuran-3-yl)carbamate.

The title compound was prepared in analogy to General Method F using methyl N-(6-bromo-4-fluoro-2,3-dihydrobenzofuran-3-yl)carbamate and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, and General Method B using (2S,3R)-2-methylazetidin-3-ol instead of (2S)-2-methylazetidine.

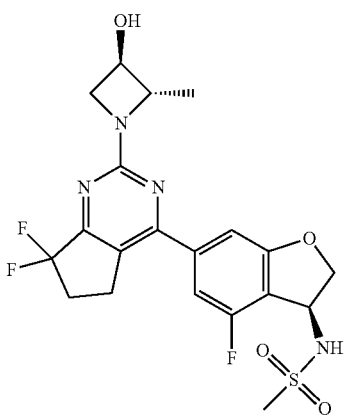

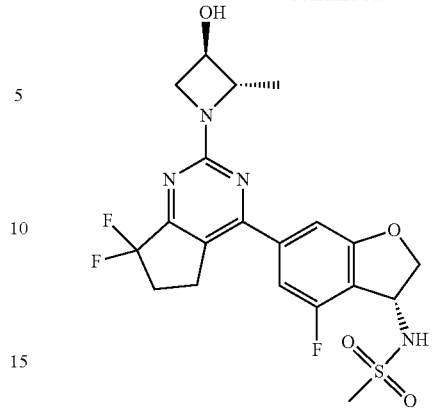

Example 812: N-[(3S)-6-[7,7-difluoro-2-[(2S,3R)-3-hydroxy-2-methyl-azetidin-1-yl]-5,6-dihydrocyclopenta[d]pyrimidin-4-yl]-4-fluoro-2,3-dihydrobenzofuran-3-yl]methanesulfonamide Example 813: N-[(3R)-6-[7,7-difluoro-2-[(2S,3R)-3-hydroxy-2-methyl-azetidin-1-yl]-5,6-dihydrocyclopenta[d]pyrimidin-4-yl]-4-fluoro-2,3-dihydrobenzofuran-3-yl]methanesulfonamide N-[6-[7,7-difluoro-2-[(2 S,3R)-3-hydroxy-2-methyl-azetidin-1-yl]-5,6-dihydrocyclopenta[d]pyrimidin-4-yl]-4-fluoro-2,3-dihydrobenzofuran-3-yl]methanesulfonamide was prepared according to General Method V using 6-bromo-4-fluorobenzofuran-3(2H)-one instead of 5-bromo-7-fluoro-2,3-dihydro-1H-inden-1-one, followed by General Method K, using methanesulfonyl chloride instead of 1-methylimidazole-4-sulfonyl chloride, followed by General Method F using N-(6-bromo-4-fluoro-2,3-dihydrobenzofuran-3-yl)methanesulfonamide and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, and General Method B using (2S,3R)-2-methylazetidin-3-ol instead of (2S)-2-methylazetidine.

Isomers were separated by SFC (30% EtOH in $CO_2$, CHIRALPAK IG 4.6×100 mm 5mic, 3 mL/min).

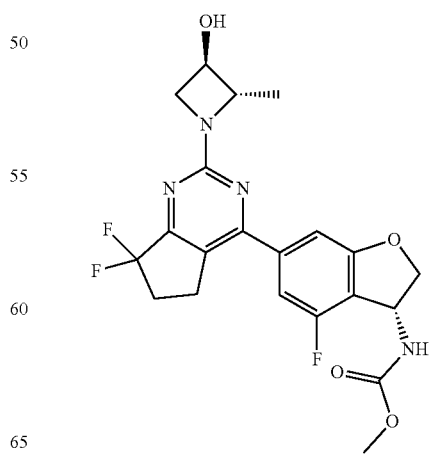

Example 814: Methyl N-[(3R)-6-[7,7-difluoro-2-[(2S,3R)-3-hydroxy-2-methyl-azetidin-1-yl]-5,6-dihydrocyclopenta[d]pyrimidin-4-yl]-2,3-dihydrobenzofuran-3-yl]carbamate A flask was charged with (3R)-6-bromo-2,3-dihydrobenzofuran-3-amine (200 mg, 0.93 mmol), diisopropylethylamine (0.50 mL, 2.80 mmol) and DCM (5 mL). Methyl carbonochloridate (88.3 mg, 0.94 mmol) was added slowly as a solution in DCM (1 mL). The reaction mixture was stirred at room temperature for 30 minutes. The mixture was purified by silica gel chromatography to afford methyl N-[(3R)-6-bromo-2,3-dihydrobenzofuran-3-yl]carbamate.

The title compound was prepared in analogy to General Method F using methyl N-[(3R)-6-bromo-2,3-dihydrobenzofuran-3-yl)carbamate and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-1(2S)-2-methylazetidin-1-yl]-6,7-dihydro-5H-cyclopenta[d]pyrimidine respectively, followed by General Method M, followed by General Method B using (2S,3R)-2-methylazetidin-3-ol instead of (2S)-2-methylazetidine.

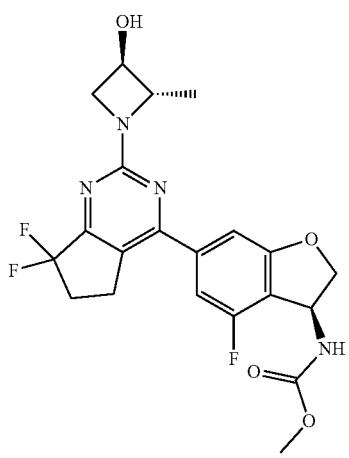 [SMILES: COC(=O)N[C@@H]1COc2cc(-c3nc(N4C[C@@H](O)[C@@H]4C)nc4c3CCC4(F)F)cc(F)c21]

Example 815: Methyl N-[(3S)-6-[7,7-difluoro-2-[(2S,3R)-3-hydroxy-2-methyl-azetidin-1-yl]-5,6-dihydrocyclopenta[d]pyrimidin-4-yl]-2,3-dihydrobenzofuran-3-yl]carbamate A flask was charged with (3S)-6-bromo-2,3-dihydrobenzofuran-3-amine (200 mg, 0.93 mmol), diisopropylethylamine (0.50 mL, 2.80 mmol) and DCM (5 mL). Methyl carbonochloridate (88.3 mg, 0.94 mmol) was added slowly as a solution in DCM (1 mL). The reaction mixture was stirred at room temperature for 30 minutes. The mixture was purified by silica gel chromatography to afford methyl N-[(3S)-6-bromo-2,3-dihydrobenzofuran-3-yl]carbamate.

The title compound was prepared in analogy to General Method F using methyl N-[(3S)-6-bromo-2,3-dihydrobenzofuran-3-yl]carbamate and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, followed by General Method B using (2S,3R)-2-methylazetidin-3-ol instead of (2S)-2-methylazetidine.

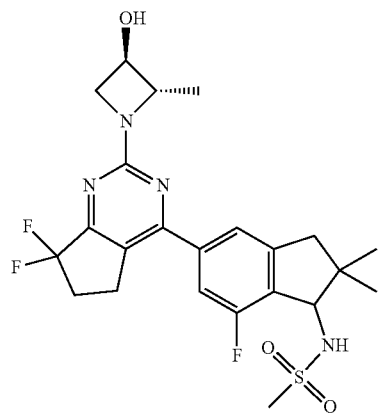 [SMILES: C[C@H]1[C@H](O)CN1c1nc(-c2cc(F)c3c(c2)CC(C)(C)C3NS(C)(=O)=O)c2c(n1)C(F)(F)CC2]

Example 816: N-[5-[7,7-difluoro-2-[(2S,3R)-3-hydroxy-2-methyl-azetidin-1-yl]-5,6-dihydrocyclopenta[d]pyrimidin-4-yl]-2,2-dimethyl-indan-1-yl]methanesulfonamide The title compound was prepared in analogy to General Method K using N-(5-bromo-2,2-dimethyl-indan-1-yl)methanesulfonamide and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B using (2S,3R)-2-methylazetidin-3-ol instead of (2S)-2-methylazetidine.

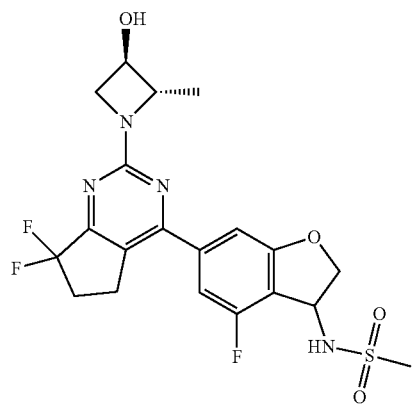 [SMILES: C[C@H]1[C@H](O)CN1c1nc(-c2cc(F)c3c(c2)OCC3NS(C)(=O)=O)c2c(n1)C(F)(F)CC2]

Example 817: N-(6-(7,7-difluoro-2-((2S,3R)-3-hydroxy-2-methylazetidin-1-yl)-6,7-dihydro-5H-cyclopenta[d]pyrimidin-4-yl)-4-fluoro-2,3-dihydrobenzofuran-3-yl)methanesulfonamide The title compound was prepared in analogy to General Method K using 6-bromo-4-fluoro-2,3-dihydrobenzofuran-3-amine and methanesulfonyl chloride instead of (S)-3-(2-(2-methylazetidin-1-yl)-6,7-dihydro-5H-cyclopenta[d]pyrimidin-4-yl)aniline and 1-methylimidazole-4-sulfonyl chloride, respectively, followed by General Method F using 4-chloro-7,7-difluoro-2-(methylthio)-6,7-dihydro-5H-cyclopenta[d]pyrimidine instead of 4-chloro-2-[(2S)-2-methylazetidin-1-yl]-6,7-dihydro-5H-cyclopenta[d]pyrimidine, followed by General Method M, and General Method B using (2S,3R)-2-methylazetidin-3-ol instead of (2S)-2-methylazetidine.

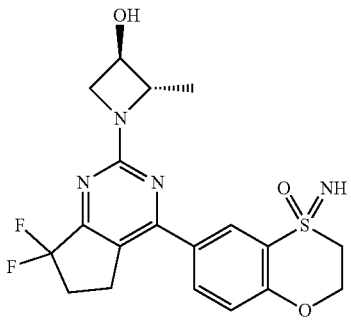 [SMILES: C[C@H]1[C@H](O)CN1c1nc(-c2ccc3c(c2)S(=N)(=O)CCO3)c2c(n1)C(F)(F)CC2]

Example 818: (2S,3R)-1-[7,7-difluoro-4-(4-imino-4-oxo-2,3-dihydro-1,4λ$^6$-benzoxathiin-6-yl)-5,6-dihydrocyclopenta[d]pyrimidin-2-yl]-2-methyl-azetidin-3-ol A flask was charged with 6-bromo-4-imino-2,3-dihydro-1,4-λ$^6$-benzoxathiine 4-oxide (200 mg, 0.763 mmol), tert-butylchlorodimethylsilane, (138 mg, 0.916 mmol) and DCM (10 mL). 2,6-Lutidine (0.258 mL, 2.29 mmol) was added. After 4 h, the reaction mixture was purified by silica gel chromatography to afford[(6-bromo-4-oxo-2,3-dihydro-1,4λ$^6$-benzoxathiin-4-ylidene)amino]-tert-butyl-dimethyl-silane.

The title compound was prepared in analogy to General Method F using [(6-bromo-4-oxo-2,3-dihydro-1,4λ$^6$-benzoxathiin-4-ylidene)amino]-tert-butyl-dimethyl-silane and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, followed by General Method B using (2S,3R)-2-methylazetidin-3-ol instead of (2S)-2-methylazetidine.

The residue was taken up in DCM (3 mL). TBAF (1M in THF, 0.559 mL, 0.559 mmol) was added. After 6 h, the reaction mixture was concentrated. The product was purified by HPLC (0.1% TFA in MeCN—0.1% TFA in H$_2$O) to afford the title compound.

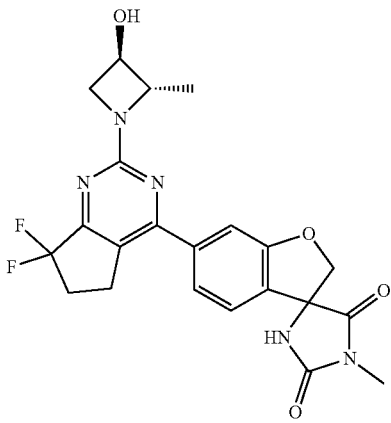 [SMILES: C[C@H]1[C@H](O)CN1c1nc(-c2ccc3c(c2)OCC32NC(=O)N(C)C2=O)c2c(n1)C(F)(F)CC2]

Example 819: 6-[7,7-difluoro-2-[(2S,3R)-3-hydroxy-2-methyl-azetidin-1-yl]-5,6-dihydrocyclopenta[d]pyrimidin-4-yl]-3'-methyl-spiro[2H-benzofuran-3,5'-imidazolidine]-2',4'-dione A flask was charged with ethyl 3-amino-6-bromo-2H-benzofuran-3-carboxylate (535 mg, 1.87 mmol), methylamine (9800 mmol/L, 3.82 mL, 37.4 mmol) and THF (100 mL). The reaction mixture was heated to 100° C. in a sealed flask for 2 hours. The mixture was concentrated to afford 3-amino-6-bromo-N-methyl-2H-benzofuran-3-carboxamide A flask was charged with 3-amino-6-bromo-N-methyl-2H-benzofuran-3-carboxamide (150 mg, 0.553 mmol), triethylamine (0.377 mL, 2.77 mmol) and 1,1'-carbonyldiimidazole (108 mg, 0.664 mmol) and DCM (3 mL). The reaction mixture was stirred for 16 h at rt. The reaction was washed with water. The organics were dried over sodium sulfate, filtered and concentrated. The residue was purified by silica gel to afford 6-bromo-3'-methyl-spiro[2H-benzofuran-3,5'-imidazolidine]-2',4'-dione.

The title compound was prepared in analogy to General Method F using 6-bromo-3'-methyl-spiro[2H-benzofuran-3,5'-imidazolidine]-2',4'-dione and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, followed by General Method B using (2S,3R)-2-methylazetidin-3-ol instead of (2S)-2-methylazetidine.

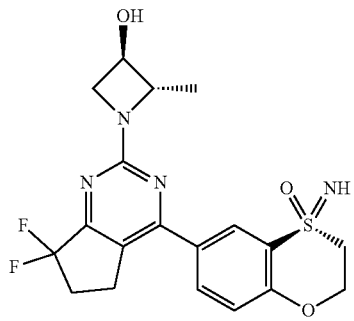

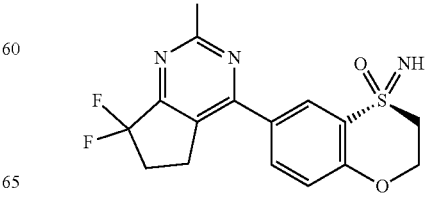

Example 820: (R)-6-(7,7-difluoro-24(2S,3R)-3-hydroxy-2-methylazetidin-1-yl)-6,7-dihydro-5H-cyclopenta[d]pyrimidin-4-yl)-4-imino-3,4-dihydro-2H-4λ⁴-benzo[b][1,4]oxathiine 4-oxide Example 821: (S)-6-(7,7-difluoro-24(2S,3R)-3-hydroxy-2-methylazetidin-1-yl)-6,7-dihydro-5H-cyclopenta[d]pyrimidin-4-yl)-4-imino-3,4-dihydro-2H-4λ⁴-benzo[b][1,4]oxathiine 4-oxide Isomers were separated by SFC (40% EtOH in $CO_2$, CHIRALPAK IG 4.6×100 mm 5mic, 3 mL/min). (see Example 818)

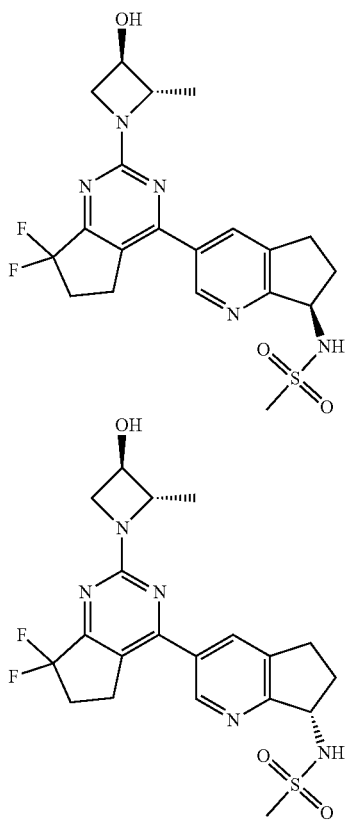

Example 822: N—((S)-6-(7,7-difluoro-2-((2S,3R)-3-hydroxy-2-methylazetidin-1-yl)-6,7-dihydro-5H-cyclopenta[d]pyrimidin-4-yl)-2,3-dihydrofuro[3,2-b]pyridin-3-yl)methanesulfonamide Example 823: N—((R)-6-(7,7-difluoro-24(2S,3R)-3-hydroxy-2-methylazetidin-1-yl)-6,7-dihydro-5H-cyclopenta[d]pyrimidin-4-yl)-2,3-dihydrofuro[3,2-b]pyridin-3-yl)methanesulfonamide The title compounds were prepared in analogy to General Method F, using N-(3-bromo-6,7-dihydro-5H-cyclopenta[b]pyridin-7-yl)methanesulfonamide and 4-chloro-7,7-difluoro-2-(methylthio)-6,7-dihydro-5H-cyclopenta[d]pyrimidine instead of 6-bromo-1,1-dioxo-1,2-benzothiazol-3-one 4-chloro-2-[(2S)-2-methylazetidin-1-yl]-6,7-dihydro-5H-cyclopenta[d]pyrimidine, respectively, followed by General Method M, and General Method B using (2S,3R)-2-methylazetidin-3-ol instead of (2S)-2-methylazetidine.

Isomers were separated by SFC (35% EtOH in $CO_2$, AD-H 4.6×100 mm 5 mic, 3 mL/min).

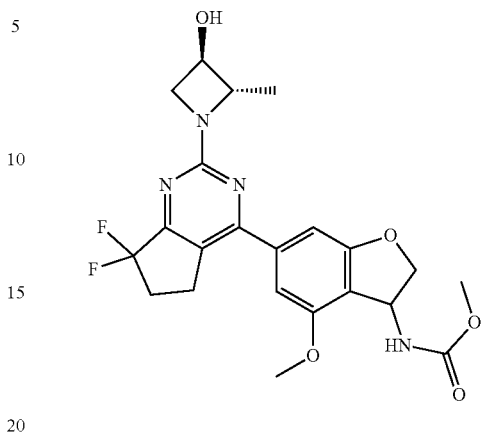

Example 824: Methyl N-[6-[7,7-difluoro-2-[(2S,3R)-3-hydroxy-2-methyl-azetidin-1-yl]-5,6-dihydrocyclopenta[d]pyrimidin-4-yl]-4-methoxy-2,3-dihydrobenzofuran-3-yl]carbamate A flask was charged with 6-bromo-4-methoxy-2,3-dihydrobenzofuran-3-amine (215 mg, 0.93 mmol), diisopropylethylamine (0.50 mL, 2.80 mmol) and DCM (5 mL). Methyl carbonochloridate (88.3 mg, 0.94 mmol) was added slowly as a solution in DCM (1 mL). The reaction mixture was stirred at room temperature for 30 minutes. The mixture was purified by silica gel chromatography to afford methyl N-(6-bromo-4-methoxy-2,3-dihydrobenzofuran-3-yl)carbamate.

The title compound was prepared in analogy to General Method F using methyl N-(6-bromo-4-methoxy-2,3-dihydrobenzofuran-3-yl)carbamate and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, followed by General Method B using (2S,3R)-2-methylazetidin-3-ol instead of (2S)-2-methylazetidine.

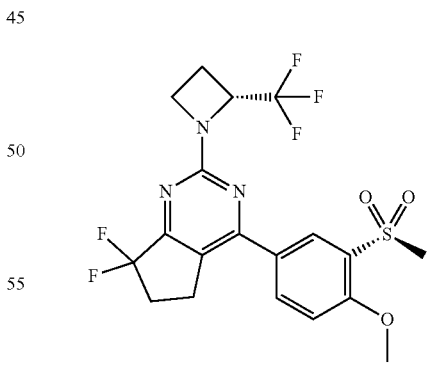

Example 825: (S)-(5-(7,7-difluoro-2-((R)-2-(trifluoromethyl)azetidin-1-yl)-6,7-dihydro-5H-cyclopenta[d]pyrimidin-4-yl)-2-methoxyphenyl)(imino)(methyl)-λ⁶-sulfanone The title compound was prepared in analogy to General Method F using tert-butyl (S)-((5-bromo-2-methoxyphenyl)

(methyl)(oxo)-λ⁶-sulfaneylidene)carbamate and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, followed by General Method B using (2R)-2-(trifluoromethyl)azetidine instead of (2S)-2-methylazetidine, followed by General Method I.

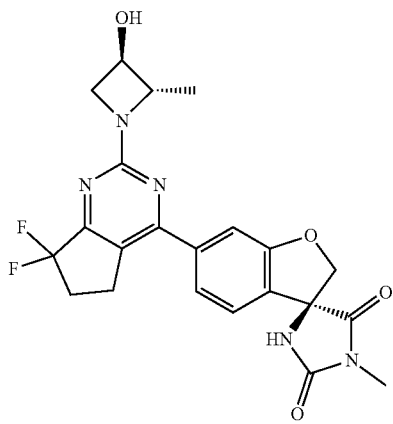

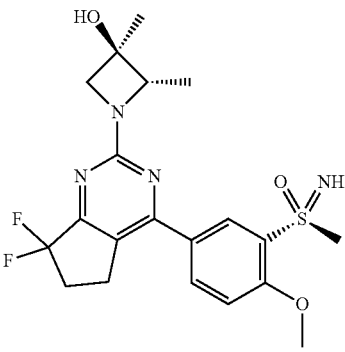 [SMILES: COc1ccc(-c2nc(N3C[C@@](C)(O)[C@@H]3C)nc3c2CCC3(F)F)cc1[S@@](C)(=N)=O]

Example 828: (S)-(5-(7,7-difluoro-2-((2S,3R)-3-hydroxy-2,3-dimethylazetidin-1-yl)-6,7-dihydro-5H-cyclopenta[d]pyrimidin-4-yl)-2-methoxyphenyl)(imino)(methyl)-l6-sulfanone The title compound was prepared in analogy to General Method F using tert-butyl N-[(5-bromo-2-methoxy-phenyl)-methyl-oxo-λ⁶-sulfanylidene]carbamate and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, followed by General Method B using (2S,3R)-2,3-dimethylazetidin-3-ol instead of (2S)-2-methylazetidine, followed by General Method I.

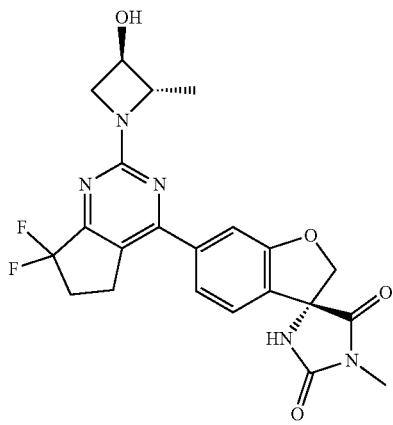

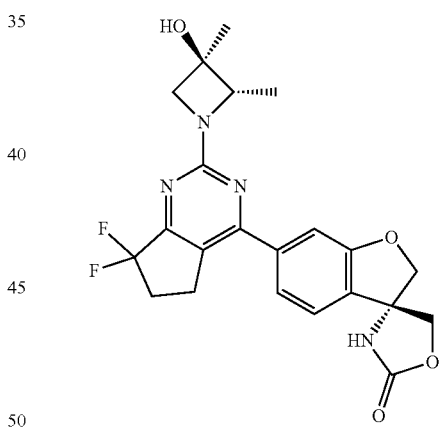

Example 826: (S)-6-(7,7-difluoro-2-((2S,3R)-3-hydroxy-2-methylazetidin-1-yl)-6,7-dihydro-5H-cyclopenta[d]pyrimidin-4-yl)-1'-methyl-2H-spiro[benzofuran-3,4'-imidazolidine]-2',5'-dione Example 827: (R)-6-(7,7-difluoro-2-((2S,3R)-3-hydroxy-2-methylazetidin-1-yl)-6,7-dihydro-5H-cyclopenta[d]pyrimidin-4-yl)-1'-methyl-2H-spiro[benzofuran-3,4'-imidazolidine]-2',5'-dione Isomers were separated by SFC (35% MeOH in CO₂, CHIRALPAK IG 4.6×100 mm 5 mic, 3 mL/min). (see Example 819)

Example 829: (3R)-6-[7,7-difluoro-2-[(2S,3R)-3-hydroxy-2,3-dimethyl-azetidin-1-yl]-5,6-dihydrocyclopenta[d]pyrimidin-4-yl]spiro[2H-benzofuran-3,4'-oxazolidine]-2'-one The title compound was prepared in analogy to General Method F using (3R)-6-bromospiro[2H-benzofuran-3,4'-oxazolidine]-2'-one and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, followed by General Method B using (2S,3R)-2,3-dimethylazetidin-3-ol instead of (2S)-2-methylazetidine.

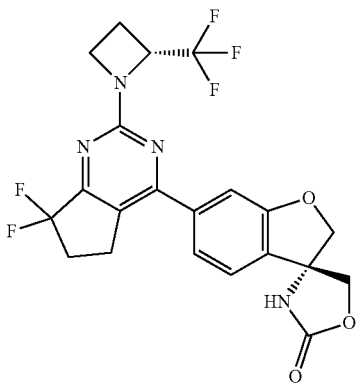 [SMILES: O=C1N[C@@]2(CO1)COc1cc(-c3nc(N4CC[C@@H]4C(F)(F)F)nc4c3CCC4(F)F)ccc12]

Example 830: (R)-6-(7,7-difluoro-2-((R)-2-(trifluoromethyl)azetidin-1-yl)-6,7-dihydro-5H-cyclopenta[d]pyrimidin-4-yl)-2H-spiro[benzofuran-3,4'-oxazolidin]-2'-one The title compound was prepared in analogy to General Method F using (3R)-6-bromospiro[2H-benzofuran-3,4'-oxazolidine]-2'-one and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, followed by General Method B using (2R)-2-(trifluoromethyl)azetidine instead of (2S)-2-methylazetidine.

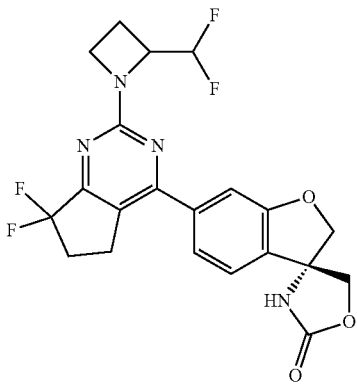 [SMILES: O=C1N[C@@]2(CO1)COc1cc(-c3nc(N4CCC4C(F)F)nc4c3CCC4(F)F)ccc12]

Example 831: (3R)-6-(2-(2-(difluoromethyl)azetidin-1-yl)-7,7-difluoro-6,7-dihydro-5H-cyclopenta[d]pyrimidin-4-yl)-2H-spiro[benzofuran-3,4'-oxazolidin]-2'-one The title compound was prepared in analogy to General Method F using (3R)-6-bromospiro[2H-benzofuran-3,4'-oxazolidine]-2'-one and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, followed by General Method B using 2-(difluoromethyl)azetidine instead of (2S)-2-methylazetidine.

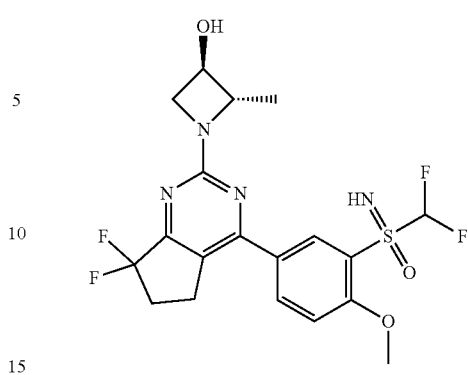

Example 832: (2S,3R)-1-[4-[3-(difluoromethylsulfonimidoyl)-4-methoxy-phenyl]-7,7-difluoro-5,6-dihydrocyclopenta[d]pyrimidin-2-yl]-2-methyl-azetidin-3-ol A flask was charged with (5-bromo-2-methoxy-phenyl)-(difluoromethyl)-imino-oxo-$\lambda^6$-sulfane (200 mg, 0.763 mmol), tert-butylchlorodimethylsilane, (138 mg, 0.916 mmol) and DCM (10 mL). 2,6-Lutidine (0.258 mL, 2.29 mmol) was added. After 4 h, the reaction mixture was purified by silica gel chromatography (hexanes-ethyl acetate) to afford [[(5-bromo-2-methoxy-phenyl)-(difluoromethyl)-oxo-$\lambda^6$-sulfanylidene]amino]-tert-butyl-dimethyl-silane.

The title compound was prepared in analogy to General Method F using [[(5-bromo-2-methoxy-phenyl)-(difluoromethyl)-oxo-$\lambda^6$-sulfanylidene]amino]-tert-butyl-dimethyl-silane and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, followed by General Method B using (2S,3R)-2-methylazetidin-3-ol instead of (2S)-2-methylazetidine.

The residue was taken up in DCM (3 mL). TBAF (1 M in THF, 0.559 mL, 0.559 mmol) was added. After 6 h, the reaction mixture was concentrated. The mixture was purified by HPLC to afford the title compound.

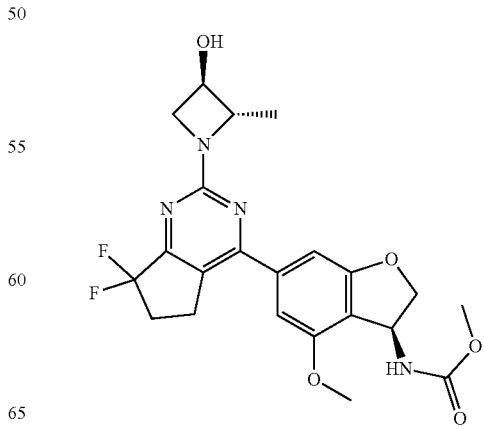

-continued

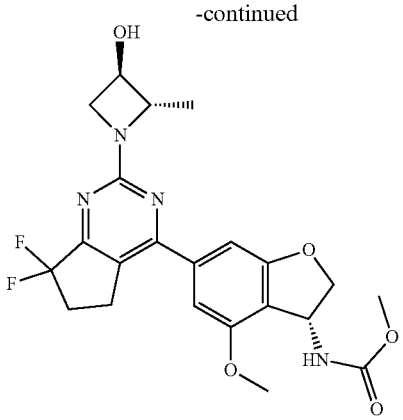

Example 833: methyl ((S)-6-(7,7-difluoro-2-((2S,3R)-3-hydroxy-2-methylazetidin-1-yl)-6,7-dihydro-5H-cyclopenta[d]pyrimidin-4-yl)-4-methoxy-2,3-dihydrobenzofuran-3-yl)carbamate Example 834: methyl ((R)-6-(7,7-difluoro-24(2S,3R)-3-hydroxy-2-methylazetidin-1-yl)-6,7-dihydro-5H-cyclopenta[d]pyrimidin-4-yl)-4-methoxy-2,3-dihydrobenzofuran-3-yl)carbamate The title compounds were prepared in analogy to General Method F, using methyl (5-bromo-7-methoxy-2,3-dihydro-1H-inden-1-yl)carbamate and 4-chloro-7,7-difluoro-2-(methylthio)-6,7-dihydro-5H-cyclopenta[d]pyrimidine instead of 6-bromo-1,1-dioxo-1,2-benzothiazol-3-one 4-chloro-2-[(2S)-2-methylazetidin-1-yl]-6,7-dihydro-5H-cyclopenta[d]pyrimidine, respectively, followed by General Method M, and General Method B using (2S,3R)-2-methylazetidin-3-ol instead of (2S)-2-methylazetidine.

Isomers were separated by SFC (35% MeOH in CO$_2$, Cell-2 4.6×100 mm 5 mic, 3 mL/min).

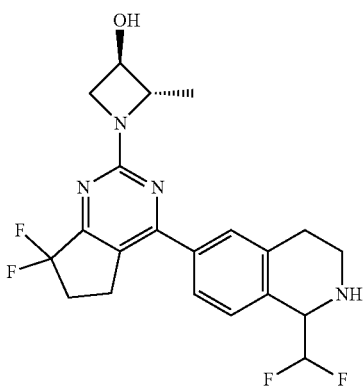 [SMILES: C[C@H]1[C@H](O)CN1c1nc(-c2ccc3c(c2)CCNC3C(F)F)c2c(n1)C(F)(F)CC2]

Example 835: (2S,3R)-1-(4-(1-(difluoromethyl)-1,2,3,4-tetrahydroisoquinolin-6-yl)-7,7-difluoro-6,7-dihydro-5H-cyclopenta[d]pyrimidin-2-yl)-2-methyl-azetidin-3-ol The title compound was prepared in analogy to General Method F using tert-butyl 6-bromo-1-(difluoromethyl)-3,4-dihydro-1H-isoquinoline-2-carboxylate and 4-chloro-7,7-difluoro-2-(methylthio)-6,7-dihydro-5H-cyclopenta[d]py-rimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, followed by General Method B using (2S,3R)-2-methylazetidin-3-ol instead of (2S)-2-methylazetidine, followed by General Method I.

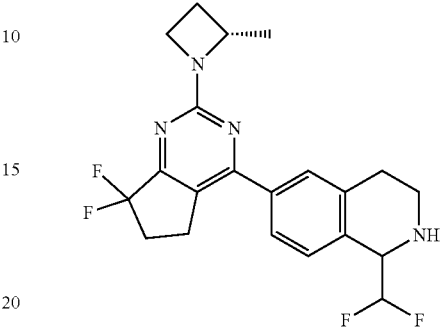

Example 836: 6-(7,7-difluoro-2-((S)-2-methylazetidin-1-yl)-6,7-dihydro-5H-cyclopenta[d]pyrimidin-4-yl)-1-(difluoromethyl)-1,2,3,4-tetrahydroisoquinoline The title compound was prepared in analogy to General Method F using tert-butyl 6-bromo-1-(difluoromethyl)-3,4-dihydro-1H-isoquinoline-2-carboxylate and 4-chloro-7,7-difluoro-2-(methylthio)-6,7-dihydro-5H-cyclopenta[d]py-rimidine instead of 6-bromo-1,1-dioxo-1,2-benzothiazol-3-one and 4-chloro-2-[(2S)-2-methylazetidin-1-yl]-6,7-dihydro-5H-cyclopenta[d]pyrimidine respectively, followed by General Method M, followed by General Method B, and General Method I.

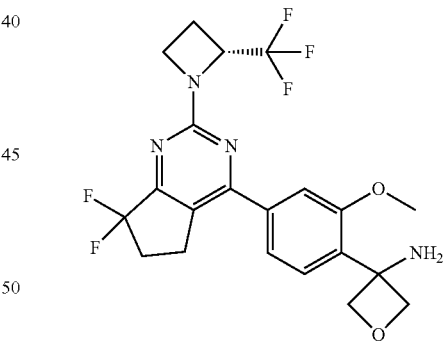

Example 837: (R)-3-(4-(7,7-difluoro-2-(2-(trifluoromethyl)azetidin-1-yl)-6,7-dihydro-5H-cyclopenta[d]pyrimidin-4-yl)-2-methoxyphenyl)oxetan-3-amine To a flame-dried 50 mL flask equipped with a magnetic stir bar, 4-bromo-1-iodo-2-methoxy-benzene (3.92 g, 12.5 mmol) was charged and dissolved in anhydrous THF (25 mL). To this solution, 3-oxetanone (1.35 g, 18.8 mmol) was added and the mixture was placed under a flow of N$_2$ and cooled to −78° C. After stirring for 10 mins, n-butyllithium in hexanes (5.3 mL, 13.1 mmol) was added dropwise over 15 mins, and the reaction mixture was allowed to stir at this temperature for 2 hours. The reaction mixture was quenched by the addition of sat. aq. $NH_4C_1$ (10 mL). The reaction mixture was diluted with $H_2O$ (15 mL) and the layers were separated. The aqueous layer was extracted with DCM (3×15 mL). The combined organics were dried over $MgSO_4$, filtered, and concentrated. The crude was subject to flash column chromatography (hexanes-ethyl acetate) to give 3-(4-bromo-2-methoxy-phenyl)oxetan-3-ol.

To a 100 mL RBF equipped with a magnetic stir bar, 3-(4-bromo-2-methoxy-phenyl)oxetan-3-ol (2.15 g, 8.30 mmol) was charged and dissolved in DCM (35 mL). The reaction mixture was placed under a flow of $N_2$ and N,N-diisopropylamine (2.89 mL, 16.6 mmol) was added and the mixture was cooled to 0° C. After stirring for 10 mins, methanesulfonyl chloride (0.963 mL, 12.4 mmol) was added dropwise over 1-2 mins and the mixture was stirred at 0° C. for 1 hr. The reaction mixture was quenched by the addition of 1 N HCl (15 mL). The layers were separated and the aqueous layer was extracted with DCM (3×15 mL). The combined organics were dried over $MgSO_4$, filtered, and concentrated. The crude was subject to flash column chromatography (hexanes-ethyl acetate) to give 3-(4-bromo-2-methoxy-phenyl)-3-chloro-oxetane.

To a 40 mL vial equipped with a magnetic stir bar, 3-(4-bromo-2-methoxy-phenyl)-3-chloro-oxetane (1.47 g, 5.28 mmol) was charged and dissolved in DMSO (6 mL). To the vial, $NaN_3$ (858 mg, 13.2 mmol) was charged and the reaction was heated to 70° C. and stirred for 2 hours. Upon cooling to ambient temperature, the reaction was diluted with EtOAc (10 mL) and brine (10 mL). The layers were separated and the aqueous layer was extracted with EtOAc (3×15 mL). The combined organics were dried over $Na_2SO_4$, filtered, and concentrated. The crude was subject to flash column chromatography (hexanes-ethyl acetate) to give 3-azido-3-(4-bromo-2-methoxy-phenyl)oxetane.

To a 40 mL vial equipped with a magnetic stir bar, 3-azido-3-(4-bromo-2-methoxy-phenyl)oxetane (833 mg, 2.93 mmol) was charged, dissolved in EtOAc (15 mL) and placed under a flow of $N_2$. Trimethylphosphine (1 M in THF, 4.46 mL, 4.46 mmol) was added dropwise over 1-2 mins. After stirring for 20 mins at ambient temperature, water (1.5 mL) was added to the reaction mixture, which was heated to 70° C. and stirred for 1 hr. Upon cooling to ambient temperature, the reaction mixture was diluted with brine (10 mL). The layers were separated and the aqueous layer was extracted with EtOAc (3×15 mL). The combined organics were dried over $Na_2SO_4$, filtered, and concentrated to give 3-(4-bromo-2-methoxy-phenyl)oxetan-3-amine, which was used without further purification.

To a 40 mL vial equipped with a magnetic stir bar, 3-(4-bromo-2-methoxy-phenyl)oxetan-3-amine (804 mg, 3.12 mmol) was charged and dissolved in THF (12 mL) and placed under a flow of $N_2$. To the solution, aq. $K_2CO_3$ (12 mL) was added followed by benzyl chloroformate (1.10 mL, 7.79 mmol). The reaction mixture was stirred at ambient temperature for 18 hours. The layers were separated and the aqueous layer was extracted with EtOAc (3×10 mL). The combined organics were dried over $Na_2SO_4$, filtered, and concentrated. The crude was subject to flash column chromatography (hexanes-ethyl acetate) to give benzyl N-[3-(4-bromo-2-methoxy-phenyl)oxetan-3-yl]carbamate The title compound was prepared in analogy to General Method F using benzyl N-[3-(4-bromo-2-methoxy-phenyl)oxetan-3-yl]carbamate and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d] pyrimidine, respectively, followed by General Method M, followed by General Method U, followed by General Method R.

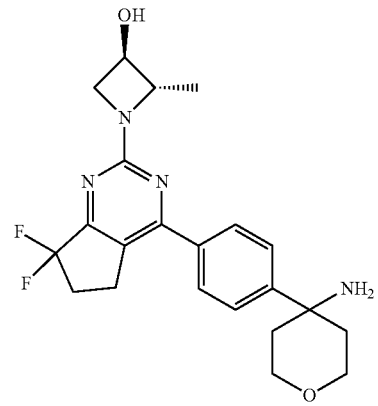 [SMILES: C[C@H]1[C@H](O)CN1c1nc(-c2ccc(C3(N)CCOCC3)cc2)c2c(n1)C(F)(F)CC2]

Example 838: (2S,3R)-1-(4-(4-(4-aminotetrahydro-2H-pyran-4-yl)phenyl)-7,7-difluoro-6,7-dihydro-5H-cyclopenta[d]pyrimidin-2-yl)-2-methylazetidin-3-ol The title compound was prepared in analogy to General Method F using tert-butyl N-[4-(4-bromophenyl)tetrahydropyran-4-yl]carbamate and 4-chloro-7,7-difluoro-2-(methylthio)-6,7-dihydro-5H-cyclopenta[d]pyrimidine instead of 6-bromo-1,1-dioxo-1,2-benzothiazol-3-one and 4-chloro-2-[(2S)-2-methylazetidin-1-yl]-6,7-dihydro-5H-cyclopenta[d] pyrimidine, respectively, followed by General Method M, followed by General method B using (2S,3R)-2-methylazetidin-3-ol instead of (2S)-2-methylazetidine, followed by General Method I.

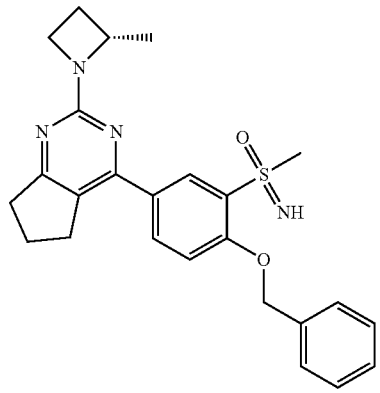 [SMILES: C[C@H]1CCN1c1nc2c(c(-c3ccc(OCc4ccccc4)c(S(C)(=N)=O)c3)n1)CCC2]

Example 839: (2-(benzyloxy)-5-(2-((S)-2-methylazetidin-1-yl)-6,7-dihydro-5H-cyclopenta[d]pyrimidin-4-yl)phenyl)(imino)(methyl)$_4^6$-sulfanone (2-(Benzyloxy)-5-bromophenyl)(imino)(methyl)-$\lambda^6$-sulfanone was prepared according to General Method AG.

(2-(Benzyloxy)-5-(2-((S)-2-methylazetidin-1-yl)-6,7-dihydro-5H-cyclopenta[d]pyrimidin-4-yl)phenyl)(imino)(methyl)-λ6-sulfanone was prepared according to General Method AE using (2-(benzyloxy)-5-bromophenyl)(imino)(methyl)-$\lambda^6$-sulfanone instead of 3-(4-iodophenyl)-1,2,4-oxadiazol-5(4H)-one.

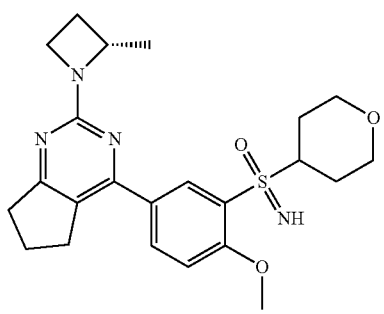 [SMILES: COc1ccc(-c2nc(N3CC[C@@H]3C)nc3c2CCC3)cc1S(=N)(=O)C1CCOCC1]

Example 840: imino(2-methoxy-5-(2-((S)-2-methyl-azetidin-1-yl)-6,7-dihydro-5H-cyclopenta[d]pyrimidin-4-yl)phenyl)(tetrahydro-2H-pyran-4-yl)-$\lambda^6$-sulfanone (5-Bromo-2-methoxyphenyl)(imino)(tetrahydro-2H-pyran-4-yl)-$\lambda^6$-sulfanone was prepared according to General Method AG using 4-((5-bromo-2-methoxyphenyl)thio)tetrahydro-2H-pyran instead of (2-(benzyloxy)-5-bromophenyl)(methyl)sulfane.

Imino (2-methoxy-5-(2-((S)-2-methylazetidin-1-yl)-6,7-dihydro-5H-cyclopenta[d]pyrimidin-4-yl)phenyl)(tetrahydro-2H-pyran-4-yl)-$\lambda$6-sulfanone was prepared according to General Method AE using (5-bromo-2-methoxyphenyl)(imino)(tetrahydro-2H-pyran-4-yl)-$\lambda^6$-sulfanone instead of 3-(4-iodophenyl)-1,2,4-oxadiazol-5 (4H)-one.

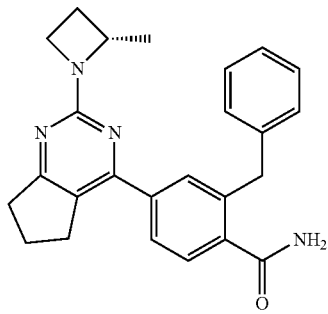 [SMILES: C[C@H]1CCN1c1nc2c(c(-c3ccc(C(N)=O)c(Cc4ccccc4)c3)n1)CCC2]

Example 841: (S)-2-benzyl-4-(2-(2-methylazetidin-1-yl)-6,7-dihydro-5H-cyclopenta[d]pyrimidin-4-yl)benzamide 2-Benzyl-4-bromobenzamide was prepared according to General Method AH.

(S)-2-Benzyl-4-(2-(2-methylazetidin-1-yl)-6,7-dihydro-5H-cyclopenta[d]pyrimidin-4-yl)benzamide was prepared according to General Method AE using 2-benzyl-4-bromobenzamide instead of 3-(4-iodophenyl)-1,2,4-oxadiazol-5(4H)-one.

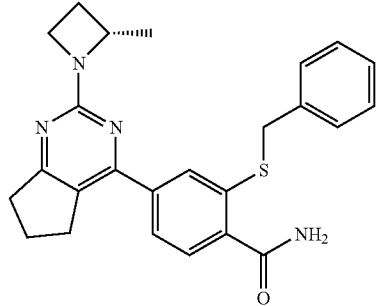 [SMILES: C[C@H]1CCN1c1nc2c(c(-c3ccc(C(N)=O)c(SCc4ccccc4)c3)n1)CCC2]

Example 842: (S)-2-(benzylthio)-4-(2-(2-methylazetidin-1-yl)-6,7-dihydro-5H-cyclopenta[d]pyrimidin-4-yl)benzamide 2-(Benzylthio)-4-bromobenzamide was prepared according to General Method AH using 2-(benzylthio)-4-bromobenzoic acid instead of 2-benzyl-4-bromobenzoic acid.

(S)-2-(Benzylthio)-4-(2-(2-methylazetidin-1-yl)-6,7-dihydro-5H-cyclopenta[d]pyrimidin-4-yl)benzamide was prepared according to General Method AE using 2-(benzylthio)-4-bromobenzamide instead of 3-(4-iodophenyl)-1,2,4-oxadiazol-5(4H)-one.

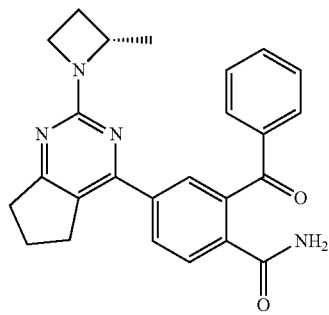 [SMILES: C[C@H]1CCN1c1nc2c(c(-c3ccc(C(N)=O)c(C(=O)c4ccccc4)c3)n1)CCC2]

Example 843: (S)-2-benzoyl-4-(2-(2-methylazetidin-1-yl)-6,7-dihydro-5H-cyclopenta[d]pyrimidin-4-yl)benzamide 2-Benzoyl-4-bromobenzamide was prepared according to General Method AH using 2-benzoyl-4-bromobenzoic acid instead of 2-benzyl-4-bromobenzoic acid.

(S)-2-Benzoyl-4-(2-(2-methylazetidin-1-yl)-6,7-dihydro-5H-cyclopenta[d]pyrimidin-4-yl)benzamide was prepared according to General Method AE using 2-benzoyl-4-bromobenzamide instead of 3-(4-iodophenyl)-1,2,4-oxadiazol-5(4H)-one.

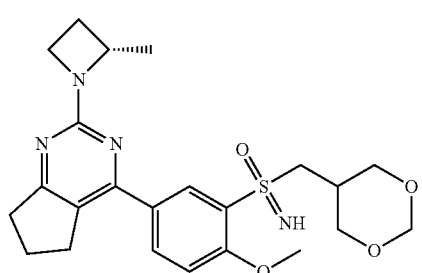

Example 844: ((1,3-dioxan-5-yl)methyl)(imino)(2-methoxy-5-(2-((S)-2-methylazetidin-1-yl)-6,7-dihydro-5H-cyclopenta[d]pyrimidin-4-yl)phenyl)-λ⁶-sulfanone ((1,3-Dioxan-5-yl)methyl)(5-bromo-2-methoxyphenyl)(imino)-λ⁶-sulfanone was prepared according to General Method AG using 5-(((5-bromo-2-methoxyphenyl)thio)methyl)-1,3-dioxane instead of (2-(benzyloxy)-5-bromophenyl)(methyl)sulfane.

((1,3-Dioxan-5-yl)methyl)(imino)(2-methoxy-5-(2-((S)-2-methylazetidin-1-yl)-6,7-dihydro-5H-cyclopenta[d]pyrimidin-4-yl)phenyl)-λ⁶-sulfanone was prepared according to General Method AE using ((1,3-dioxan-5-yl)methyl)(5-bromo-2-methoxyphenyl)(imino)-λ⁶-sulfanone instead of 3-(4-iodophenyl)-1,2,4-oxadiazol-5 (4H)-one.

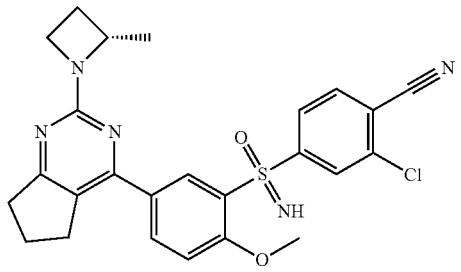 [SMILES: COc1ccc(-c2nc(N3CC[C@@H]3C)nc3c2CCC3)cc1S(=N)(=O)c1ccc(C#N)c(Cl)c1]

Example 845: 2-chloro-4-(2-methoxy-5-(2-((S)-2-methylazetidin-1-yl)-6,7-dihydro-5H-cyclopenta[d]pyrimidin-4-yl)phenylsulfonimidoyl)benzonitrile 4-(5-Bromo-2-methoxyphenylsulfonimidoyl)-2-chlorobenzonitrile was prepared according to General Method AG using 4-((5-bromo-2-methoxyphenyl)thio)-2-chlorobenzonitrile instead of (2-(benzyloxy)-5-bromophenyl)(methyl)sulfane.

2-Chloro-4-(2-methoxy-5-(2-((S)-2-methylazetidin-1-yl)-6,7-dihydro-5H-cyclopenta[d]pyrimidin-4-yl)phenylsulfonimidoyl)benzonitrile was prepared according to General Method AE using 4-(5-bromo-2-methoxyphenylsulfonimidoyl)-2-chlorobenzonitrile instead of 3-(4-iodophenyl)-1,2,4-oxadiazol-5(4H)-one.

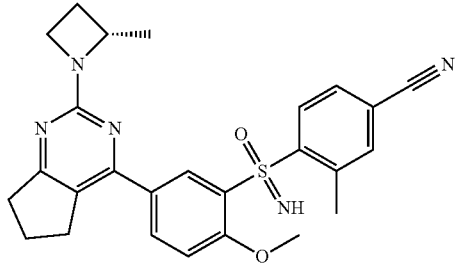 [SMILES: COc1ccc(-c2nc(N3CC[C@@H]3C)nc3c2CCC3)cc1S(=N)(=O)c1ccc(C#N)cc1C]

Example 846: 4-(2-methoxy-5-(2-((S)-2-methylazetidin-1-yl)-6,7-dihydro-5H-cyclopenta[d]pyrimidin-4-yl)phenylsulfonimidoyl)-3-methylbenzonitrile 4-(5-Bromo-2-methoxyphenylsulfonimidoyl)-3-methylbenzonitrile was prepared according to General Method AG using 4-((5-bromo-2-methoxyphenyl)thio)-3-methylbenzonitrile instead of (2-(benzyloxy)-5-bromophenyl)(methyl)sulfane.

4-(2-Methoxy-5-(2-((S)-2-methylazetidin-1-yl)-6,7-dihydro-5H-cyclopenta[d]pyrimidin-4-yl)phenylsulfonimidoyl)-3-methylbenzonitrile was prepared according to General Method AE using 4-(5-bromo-2-methoxyphenylsulfonimidoyl)-3-methylbenzonitrile instead of 3-(4-iodophenyl)-1,2,4-oxadiazol-5(4H)-one.

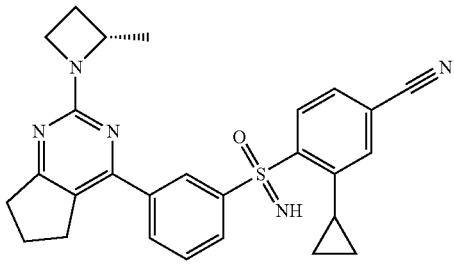 [SMILES: C[C@H]1CCN1c1nc2c(c(-c3cccc(S(=N)(=O)c4ccc(C#N)cc4C4CC4)c3)n1)CCC2]

Example 847: 3-cyclopropyl-4-(3-(2(S)-2-methylazetidin-1-yl)-6,7-dihydro-5H-cyclopenta[d]pyrimidin-4-yl)phenylsulfonimidoyl)benzonitrile 4-(3-Bromophenylsulfonimidoyl)-3-cyclopropylbenzonitrile was prepared according to General Method AG using 4-((3-bromophenyl)thio)-3-cyclopropylbenzonitrile instead of (2-(benzyloxy)-5-bromophenyl)(methyl)sulfane.

3-Cyclopropyl-4-(3-(2-((S)-2-methylazetidin-1-yl)-6,7-dihydro-5H-cyclopenta[d]pyrimidin-4-yl)phenylsulfonimidoyl)benzonitrile was prepared according to General Method AE using 4-(3-bromophenylsulfonimidoyl)-3-cyclopropylbenzonitrile instead of 3-(4-iodophenyl)-1,2,4-oxadiazol-5(4H)-one.

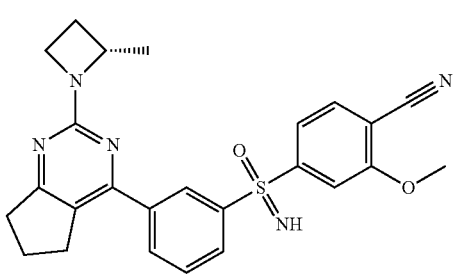 [SMILES: COc1cc(S(=N)(=O)c2cccc(-c3nc(N4CC[C@@H]4C)nc4c3CCC4)c2)ccc1C#N]

Example 848: 2-methoxy-4-(3-(2-((S)-2-methylazetidin-1-yl)-6,7-dihydro-5H-cyclopenta[d]pyrimidin-4-yl)phenylsulfonimidoyl)benzonitrile 4-(3-Bromophenylsulfonimidoyl)-2-methoxybenzonitrile was prepared according to General Method AG using 4-((3-bromophenyl)thio)-2-methoxybenzonitrile instead of (2-(benzyloxy)-5-bromophenyl)(methyl)sulfane.

2-Methoxy-4-(3-(2-((S)-2-methylazetidin-1-yl)-6,7-dihydro-5H-cyclopenta[d]pyrimidin-4-yl)phenylsulfonimidoyl)benzonitrile was prepared according to General Method AE using 4-(3-bromophenylsulfonimidoyl)-2-methoxybenzonitrile instead of 3-(4-iodophenyl)-1,2,4-oxadiazol-5(4H)-one.

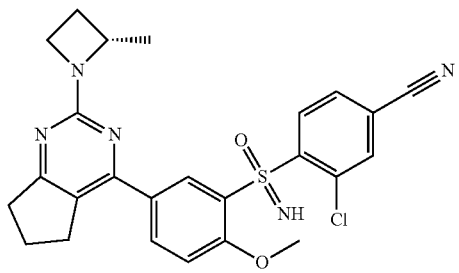 [SMILES: COc1ccc(-c2nc(N3CC[C@@H]3C)nc3c2CCC3)cc1S(=N)(=O)c1ccc(C#N)cc1Cl]

Example 849: 3-chloro-4-(2-methoxy-5-(2-((S)-2-methylazetidin-1-yl)-6,7-dihydro-5H-cyclopenta[d]pyrimidin-4-yl)phenylsulfonimidoyl)benzonitrile 4-(5-Bromo-2-methoxyphenylsulfonimidoyl)-3-chlorobenzonitrile was prepared according to General Method AG using 4-((5-bromo-2-methoxyphenyl)thio)-3-chlorobenzonitrile instead of (2-(benzyloxy)-5-bromophenyl)(methyl)sulfane.

3-Chloro-4-(2-methoxy-5-(2-((S)-2-methylazetidin-1-yl)-6,7-dihydro-5H-cyclopenta[d]pyrimidin-4-yl)phenylsulfonimidoyl)benzonitrile was prepared according to General Method AE using 4-(5-bromo-2-methoxyphenylsulfonimidoyl)-3-chlorobenzonitrile instead of 3-(4-iodophenyl)-1,2,4-oxadiazol-5(4H)-one.

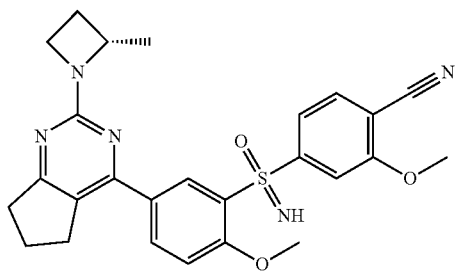 [SMILES: COc1cc(S(=N)(=O)c2cc(-c3nc(N4CC[C@@H]4C)nc4c3CCC4)ccc2OC)ccc1C#N]

Example 850: 2-methoxy-4-(2-methoxy-5-(2-((S)-2-methylazetidin-1-yl)-6,7-dihydro-5H-cyclopenta[d]pyrimidin-4-yl)phenylsulfonimidoyl)benzonitrile 4-(5-Bromo-2-methoxyphenylsulfonimidoyl)-2-methoxybenzonitrile was prepared according to General Method AG using 4-((5-bromo-2-methoxyphenyl)thio)-2-methoxybenzonitrile instead of (2-(benzyloxy)-5-bromophenyl)(methyl)sulfane.

2-Methoxy-4-(2-methoxy-5-(2-((S)-2-methylazetidin-1-yl)-6,7-dihydro-5H-cyclopenta[d]pyrimidin-4-yl)phenylsulfonimidoyl)benzonitrile was prepared according to General Method AE using 4-(5-bromo-2-methoxyphenylsulfonimidoyl)-2-methoxybenzonitrile instead of 3-(4-iodophenyl)-1,2,4-oxadiazol-5(4H)-one.

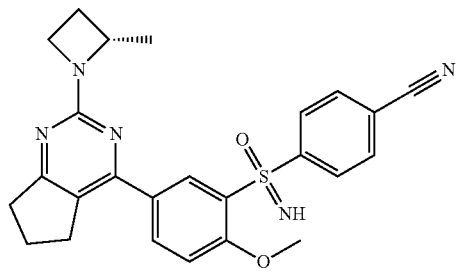 [SMILES: COc1ccc(-c2nc(N3CC[C@@H]3C)nc3c2CCC3)cc1S(=N)(=O)c1ccc(C#N)cc1]

Example 851: 4-(2-methoxy-5-(2-((S)-2-methylazetidin-1-yl)-6,7-dihydro-5H-cyclopenta[d]pyrimidin-4-yl)phenylsulfonimidoyl)benzonitrile 4-(5-Bromo-2-methoxyphenylsulfonimidoyl)benzonitrile was prepared according to General Method AG using 4-((5-bromo-2-methoxyphenyl)thio)benzonitrile instead of (2-(benzyloxy)-5-bromophenyl)(methyl)sulfane.

4-(2-Methoxy-5-(2-((S)-2-methylazetidin-1-yl)-6,7-dihydro-5H-cyclopenta[d]pyrimidin-4-yl)phenylsulfonimidoyl)benzonitrile was prepared according to General Method AE using 4-(5-bromo-2-methoxyphenylsulfonimidoyl)benzonitrile instead of 3-(4-iodophenyl)-1,2,4-oxadiazol-5(4H)-one.

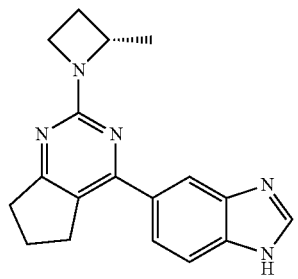 [SMILES: C[C@H]1CCN1c1nc2c(c(-c3ccc4[nH]cnc4c3)n1)CCC2]

Example 852: (S)-5-(2-(2-methylazetidin-1-yl)-6,7-dihydro-5H-cyclopenta[d]pyrimidin-4-yl)-1H-benzo[d]imidazole The title compound was prepared according to General Method AE using 5-bromo-1H-benzo[d]imidazole instead of 3-(4-iodophenyl)-1,2,4-oxadiazol-5(4H)-one.

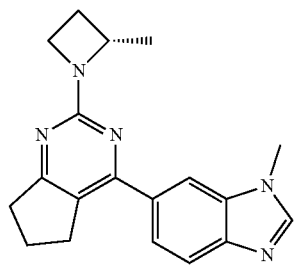 [SMILES: C[C@H]1CCN1c1nc2c(c(-c3ccc4ncn(C)c4c3)n1)CCC2]

Example 853: (S)-1-methyl-6-(2-(2-methylazetidin-1-yl)-6,7-dihydro-5H-cyclopenta[d]pyrimidin-4-yl)-1H-benzo[d]imidazole The title compound was prepared according to General Method AE using 6-bromo-1-methyl-1H-benzo[d]imidazole instead of 3-(4-iodophenyl)-1,2,4-oxadiazol-5(4H)-one.

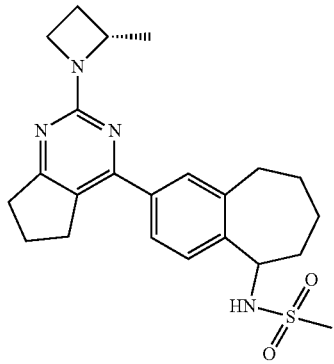 [SMILES: C[C@H]1CCN1c1nc2c(c(-c3ccc4c(c3)CCCCC4NS(C)(=O)=O)n1)CCC2]

Example 854: N-(2-(2-((S)-2-methylazetidin-1-yl)-6,7-dihydro-5H-cyclopenta[d]pyrimidin-4-yl)-6,7,8,9-tetrahydro-5H-benzo[7]annulen-5-yl)methanesulfonamide The title compound was prepared according to General Method AI using 2-bromo-6,7,8,9-tetrahydro-5H-benzo[7]annulen-5-amine instead of 6-bromochroman-4-amine

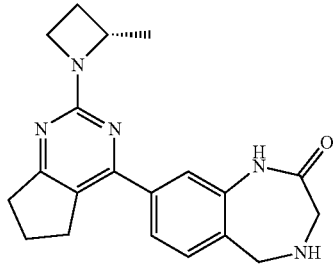 [SMILES: C[C@H]1CCN1c1nc2c(c(-c3ccc4c(c3)NC(=O)CNC4)n1)CCC2]

Example 855: (S)-8-(2-(2-methylazetidin-1-yl)-6,7-dihydro-5H-cyclopenta[d]pyrimidin-4-yl)-1,3,4,5-tetrahydro-2H-benzo[e][1,4]diazepin-2-one The title compound was prepared according to General Method AE using 8-bromo-1,3,4,5-tetrahydro-2H-benzo[e][1,4]diazepin-2-one instead of 3-(4-iodophenyl)-1,2,4-oxadiazol-5(4H)-one.

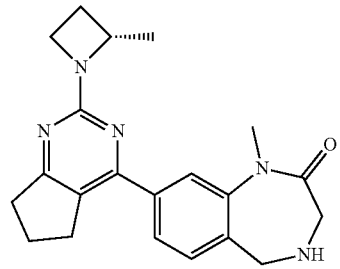 [SMILES: C[C@H]1CCN1c1nc2c(c(-c3ccc4c(c3)N(C)C(=O)CNC4)n1)CCC2]

Example 856: (S)-1-methyl-8-(2-(2-methylazetidin-1-yl)-6,7-dihydro-5H-cyclopenta[d]pyrimidin-4-yl)-1,3,4,5-tetrahydro-2H-benzo[e][1,4]diazepin-2-one The title compound was prepared according to General Method AE using 8-bromo-1-methyl-1,3,4,5-tetrahydro-2H-benzo[e][1,4]diazepin-2-one instead of 3-(4-iodophenyl)-1,2,4-oxadiazol-5(4H)-one.

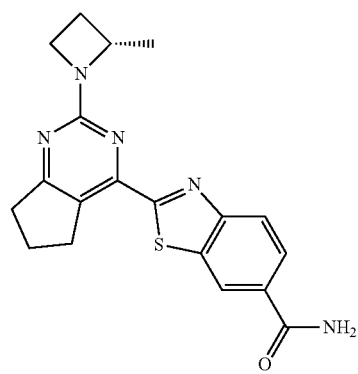 [SMILES: C[C@H]1CCN1c1nc2c(c(-c3nc4ccc(C(N)=O)cc4s3)n1)CCC2]

Example 857: (S)-2-(2-(2-methylazetidin-1-yl)-6,7-dihydro-5H-cyclopenta[d]pyrimidin-4-yl)benzo[d]thiazole-6-carboxamide The title compound was prepared according to General Method AE using 2-bromobenzo[d]thiazole-6-carboxamide instead of 3-(4-iodophenyl)-1,2,4-oxadiazol-5 (4H)-one.

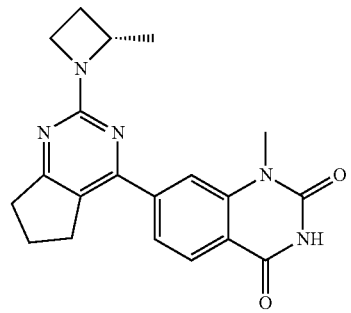 [SMILES: C[C@H]1CCN1c1nc2c(c(-c3ccc4c(=O)[nH]c(=O)n(C)c4c3)n1)CCC2]

Example 858: (S)-1-methyl-7-(2-(2-methylazetidin-1-yl)-6,7-dihydro-5H-cyclopenta[d]pyrimidin-4-yl)quinazoline-2,4(1H,3H)-dione The title compound was prepared according to General Method AE using 7-bromo-1-methylquinazoline-2,4(1H,3H)-dione instead of 3-(4-iodophenyl)-1,2,4-oxadiazol-5(4H)-one.

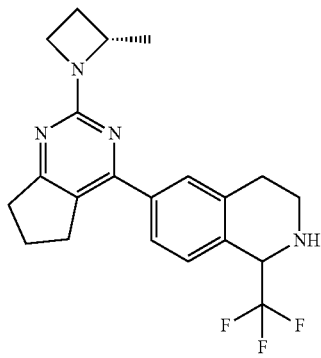 [SMILES: C[C@H]1CCN1c1nc2c(c(-c3ccc4c(c3)CCNC4C(F)(F)F)n1)CCC2]

Example 859: 6-(2-((S)-2-methylazetidin-1-yl)-6,7-dihydro-5H-cyclopenta[d]pyrimidin-4-yl)-1-(trifluoromethyl)-1,2,3,4-tetrahydroisoquinoline The title compound was prepared according to General Method AE using 6-bromo-1-(trifluoromethyl)-1,2,3,4-tetrahydroisoquinoline instead of 3-(4-iodophenyl)-1,2,4-oxadiazol-5 (4H)-one.

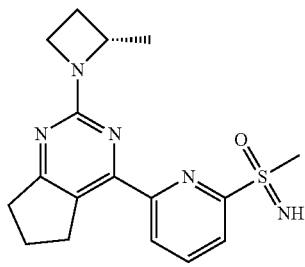 [SMILES: C[C@H]1CCN1c1nc2c(c(-c3cccc(S(C)(=N)=O)n3)n1)CCC2]

Example 860: imino(methyl)(6-(2-((S)-2-methylazetidin-1-yl)-6,7-dihydro-5H-cyclopenta[d]pyrimidin-4-yl)pyridin-2-yl)-$\lambda^6$-sulfanone The title compound was prepared according to General Method AE using (6-bromopyridin-2-yl)(imino)(methyl)-$\lambda^6$-sulfanone instead of 3-(4-iodophenyl)-1,2,4-oxadiazol-5 (4H)-one.

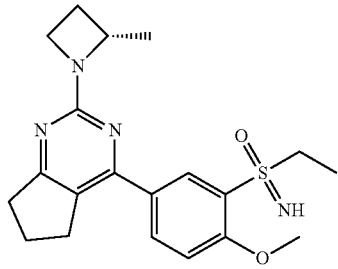 [SMILES: CCS(=N)(=O)c1cc(-c2nc(N3CC[C@@H]3C)nc3c2CCC3)ccc1OC]

Example 861: ethyl(imino)(2-methoxy-5-(2-((S)-2-methylazetidin-1-yl)-6,7-dihydro-5H-cyclopenta[d]pyrimidin-4-yl)phenyl)-$\lambda^6$-sulfanone The title compound was prepared according to General Method AE using (5-bromo-2-methoxyphenyl)(ethyl)(imino)-$\lambda^6$-sulfanone instead of 3-(4-iodophenyl)-1,2,4-oxadiazol-5(4H)-one.

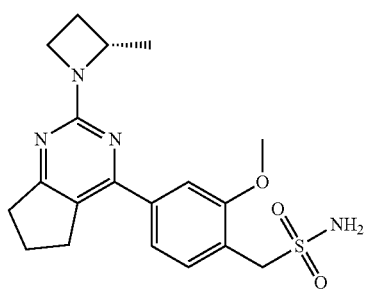 [SMILES: COc1cc(-c2nc(N3CC[C@@H]3C)nc3c2CCC3)ccc1CS(N)(=O)=O]

Example 862: (S)-(2-methoxy-4-(2-(2-methylazetidin-1-yl)-6,7-dihydro-5H-cyclopenta[d]pyrimidin-4-yl)phenyl)methanesulfonamide The title compound was prepared according to General Method AE using (4-bromo-2-methoxyphenyl)methanesulfonamide instead of 3-(4-iodophenyl)-1,2,4-oxadiazol-5(4H)-one.

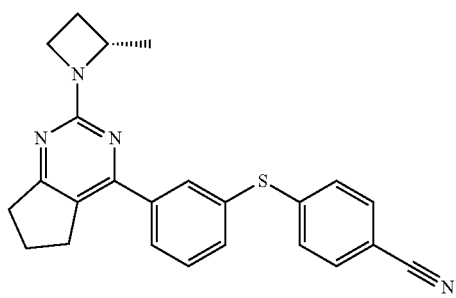 [SMILES: C[C@H]1CCN1c1nc2c(c(-c3cccc(Sc4ccc(C#N)cc4)c3)n1)CCC2]

Example 863: (S)-4-((3-(2-(2-methylazetidin-1-yl)-6,7-dihydro-5H-cyclopenta[d]pyrimidin-4-yl)phenyl)thio)benzonitrile The title compound was prepared according to General Method AE using 4-((3-bromophenyl)thio)benzonitrile instead of 3-(4-iodophenyl)-1,2,4-oxadiazol-5(4H)-one.

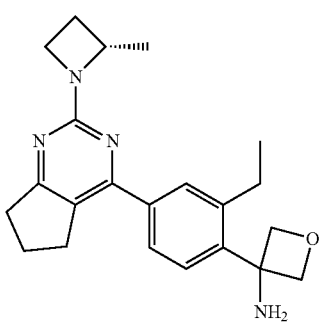 [SMILES: CCc1cc(-c2nc(N3CC[C@@H]3C)nc3c2CCC3)ccc1C1(N)COC1]

Example 864: (S)-3-(2-ethyl-4-(2-(2-methylazetidin-1-yl)-6,7-dihydro-5H-cyclopenta[d]pyrimidin-4-yl)phenyl)oxetan-3-amine The title compound was prepared according to General Method AE using 3-(4-bromo-2-ethylphenyl)oxetan-3-amine instead of 3-(4-iodophenyl)-1,2,4-oxadiazol-5(4H)-one.

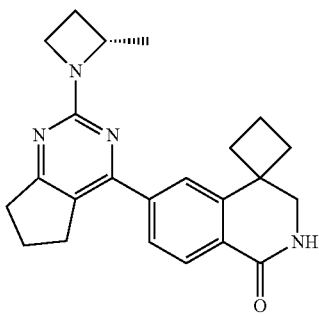 [SMILES: C[C@H]1CCN1c1nc2c(c(-c3ccc4c(c3)C3(CCC3)CNC4=O)n1)CCC2]

Example 865: (S)-6'-(2-(2-methylazetidin-1-yl)-6,7-dihydro-5H-cyclopenta[d]pyrimidin-4-yl)-2',3'-dihydro-1'H-spiro[cyclobutane-1,4'-isoquinolin]-1'-one The title compound was prepared according to General Method AE using 6'-bromo-2',3'-dihydro-1'H-spiro[cyclobutane-1,4'-isoquinolin]-1'-one instead of 3-(4-iodophenyl)-1,2,4-oxadiazol-5(4H)-one.

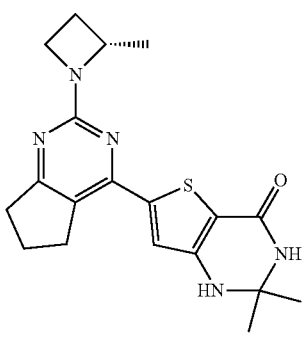 [SMILES: C[C@H]1CCN1c1nc2c(c(-c3cc4c(s3)C(=O)NC(C)(C)N4)n1)CCC2]

Example 866: (S)-2,2-dimethyl-6-(2-(2-methylazetidin-1-yl)-6,7-dihydro-5H-cyclopenta[d]pyrimidin-4-yl)-2,3-dihydrothieno[3,2-d]pyrimidin-4(1H)-one The title compound was prepared according to General Method AE using 6-bromo-2,2-dimethyl-2,3-dihydrothieno[3,2-d]pyrimidin-4(1H)-one instead of 3-(4-iodophenyl)-1,2,4-oxadiazol-5(4H)-one.

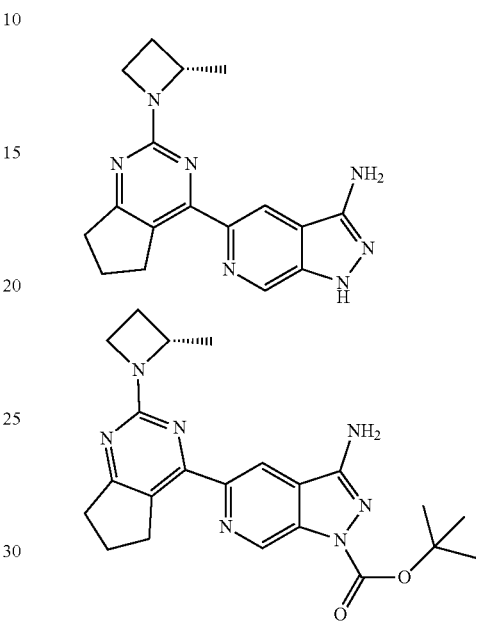

Example 867: (S)-5-(2-(2-methylazetidin-1-yl)-6,7-dihydro-5H-cyclopenta[d]pyrimidin-4-yl)-1H-pyrazolo[3,4-c]pyridin-3-amine Example 868: tert-butyl (S)-3-amino-5-(2-(2-methylazetidin-1-yl)-6,7-dihydro-5H-cyclopenta[d]pyrimidin-4-yl)-1H-pyrazolo[3,4-c]pyridine-1-carboxylate Both title compounds were prepared according to General Method AE using tert-butyl 3-amino-5-bromo-1H-pyrazolo[3,4-c]pyridine-1-carboxylate instead of 3-(4-iodophenyl)-1,2,4-oxadiazol-5(4H)-one. Example 867 was isolated as the earlier eluting product during the preparative HPLC. Example 868 was isolated as the later eluting product during the preparative HPLC.

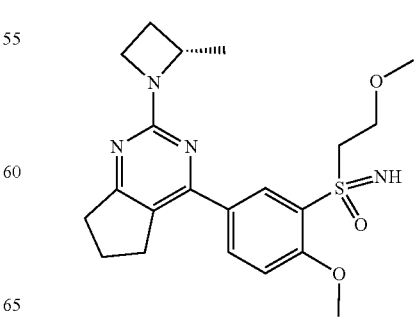

Example 869: imino(2-methoxy-5-(2-((S)-2-methyl-azetidin-1-yl)-6,7-dihydro-5H-cyclopenta[d]pyrimidin-4-yl)phenyl)(2-methoxyethyl)-λ⁶-sulfanone The title compound was prepared according to General Method AE using (5-bromo-2-methoxyphenyl)(imino)(2-methoxyethyl)-λ⁶-sulfanone instead of 3-(4-iodophenyl)-1,2,4-oxadiazol-5(4H)-one.

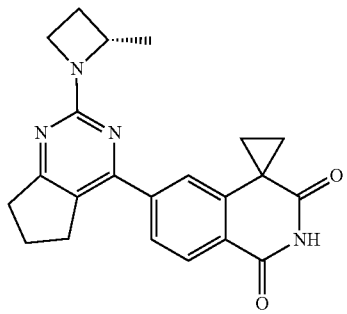 [SMILES: C[C@H]1CCN1c1nc2c(c(-c3ccc4c(c3)C3(CC3)C(=O)NC4=O)n1)CCC2]

Example 870: (S)-6'-(2-(2-methylazetidin-1-yl)-6,7-dihydro-5H-cyclopenta[d]pyrimidin-4-yl)-1'H-spiro[cyclopropane-1,4'-isoquinoline]-1',3'(2'H)-dione The title compound was prepared according to General Method AE using 6'-bromo-1'H-spiro[cyclopropane-1,4'-isoquinoline]-1',3'(2'H)-dione instead of 3-(4-iodophenyl)-1,2,4-oxadiazol-5 (4H)-one.

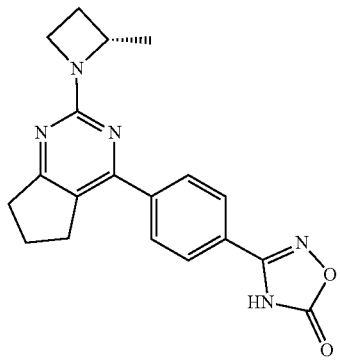 [SMILES: C[C@H]1CCN1c1nc2c(c(-c3ccc(-c4noc(=O)[nH]4)cc3)n1)CCC2]

Example 871: (S)-3-(4-(2-(2-methylazetidin-1-yl)-6,7-dihydro-5H-cyclopenta[d]pyrimidin-4-yl)phenyl)-1,2,4-oxadiazol-5(4H)-one The title compound was prepared according to General Method AE.

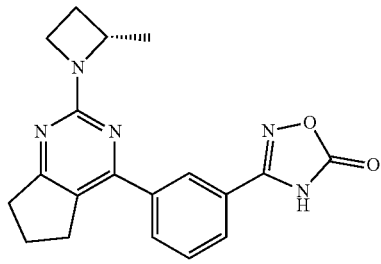 [SMILES: C[C@H]1CCN1c1nc2c(c(-c3cccc(-c4noc(=O)[nH]4)c3)n1)CCC2]

Example 872: (S)-3-(3-(2-(2-methylazetidin-1-yl)-6,7-dihydro-5H-cyclopenta[d]pyrimidin-4-yl)phenyl)-1,2,4-oxadiazol-5(4H)-one The title compound was prepared according to General Method AE using 3-(3-iodophenyl)-1,2,4-oxadiazol-5(4H)-one instead of 3-(4-iodophenyl)-1,2,4-oxadiazol-5(4H)-one.

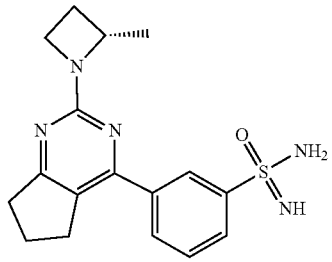 [SMILES: C[C@H]1CCN1c1nc2c(c(-c3cccc(S(=N)(N)=O)c3)n1)CCC2]

Example 873: 3-(2-((S)-2-methylazetidin-1-yl)-6,7-dihydro-5H-cyclopenta[d]pyrimidin-4-yl)benzenesulfonimidamide The title compound was prepared according to General Method AE using 3-bromobenzenesulfonimidamide instead of 3-(4-iodophenyl)-1,2,4-oxadiazol-5(4H)-one.

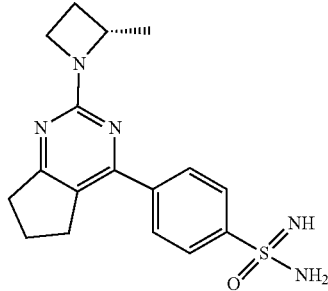 [SMILES: C[C@H]1CCN1c1nc2c(c(-c3ccc(S(=N)(N)=O)cc3)n1)CCC2]

Example 874: 4-(2-((S)-2-methylazetidin-1-yl)-6,7-dihydro-5H-cyclopenta[d]pyrimidin-4-yl)benzenesulfonimidamide The title compound was prepared according to General Method AE using 4-bromobenzenesulfonimidamide instead of 3-(4-iodophenyl)-1,2,4-oxadiazol-5(4H)-one.

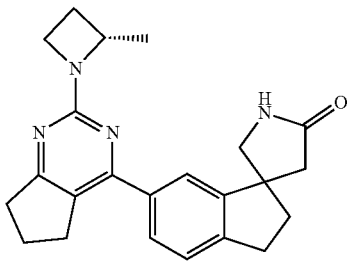 [SMILES: C[C@H]1CCN1c1nc2c(c(-c3ccc4c(c3)C3(CC4)CNC(=O)C3)n1)CCC2]

Example 875: 6-(2-((S)-2-methylazetidin-1-yl)-6,7-dihydro-5H-cyclopenta[d]pyrimidin-4-yl)-2,3-dihydrospiro[indene-1,3'-pyrrolidin]-5'-one The title compound was prepared according to General Method AE using 6-bromo-2,3-dihydrospiro[indene-1,3'-pyrrolidin]-5'-one instead of 3-(4-iodophenyl)-1,2,4-oxadiazol-5(4H)-one.

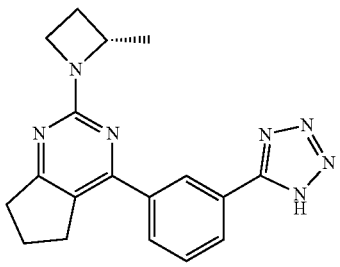 [SMILES: C[C@H]1CCN1c1nc2c(c(-c3cccc(-c4nnn[nH]4)c3)n1)CCC2]

Example 876: (S)-4-(3-(1H-tetrazol-5-yl)phenyl)-2-(2-methylazetidin-1-yl)-6,7-dihydro-5H-cyclopenta[d]pyrimidine The title compound was prepared according to General Method AE using 5-(3-iodophenyl)-1H-tetrazole instead of 3-(4-iodophenyl)-1,2,4-oxadiazol-5(4H)-one.

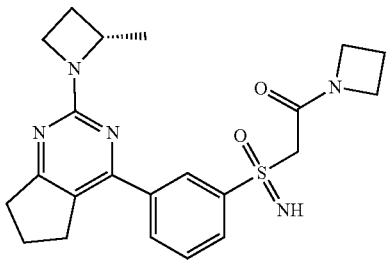 [SMILES: C[C@H]1CCN1c1nc2c(c(-c3cccc(S(=N)(=O)CC(=O)N4CCC4)c3)n1)CCC2]

Example 877: (2-(azetidin-1-yl)-2-oxoethyl)(imino)(3-(2-((S)-2-methylazetidin-1-yl)-6,7-dihydro-5H-cyclopenta[d]pyrimidin-4-yl)phenyl)-$\lambda^6$-sulfanone The title compound was prepared according to General Method AE using (2-(azetidin-1-yl)-2-oxoethyl)(3-bromophenyl)(imino)-$\lambda^6$-sulfanone instead of 3-(4-iodophenyl)-1,2,4-oxadiazol-(4H)-one.

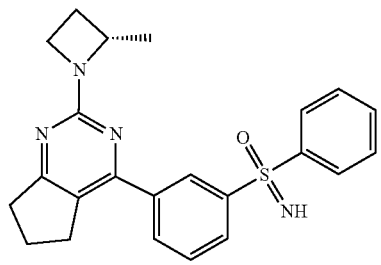 [SMILES: C[C@H]1CCN1c1nc2c(c(-c3cccc(S(=N)(=O)c4ccccc4)c3)n1)CCC2]

Example 878: imino(3-(2-((S)-2-methylazetidin-1-yl)-6,7-dihydro-5H-cyclopenta[d]pyrimidin-4-yl)phenyl)(phenyl)-$\lambda^6$-sulfanone (3-Bromophenyl)(imino)(phenyl)-$\lambda^6$-sulfanone was prepared according to General Method AG using (3-bromophenyl)(phenyl)sulfane instead of (2-(benzyloxy)-5-bromophenyl)(methyl)sulfane.

Imino(3-(2-((S)-2-methylazetidin-1-yl)-6,7-dihydro-5H-cyclopenta[d]pyrimidin-4-yl)phenyl)(phenyl)-$\lambda^6$-sulfanone was prepared according to General Method AE using (3-bromophenyl)(imino)(phenyl)-$\lambda^6$-sulfanone instead of 3-(4-iodophenyl)-1,2,4-oxadiazol-5(4H)-one.

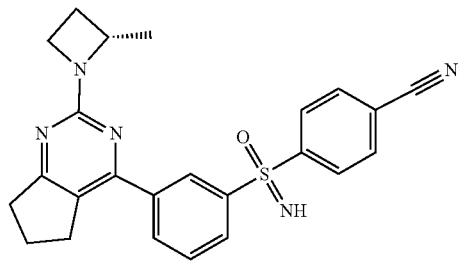 [SMILES: C[C@H]1CCN1c1nc2c(c(-c3cccc(S(=N)(=O)c4ccc(C#N)cc4)c3)n1)CCC2]

Example 879: 4-(3-(2-((S)-2-methylazetidin-1-yl)-6,7-dihydro-5H-cyclopenta[d]pyrimidin-4-yl)phenylsulfonimidoyl)benzonitrile 4-(3-Bromophenylsulfonimidoyl)benzonitrile was prepared according to General Method AG using 4-((3-bromophenyl)thio)benzonitrile instead of (2-(benzyloxy)-5-bromophenyl)(methyl)sulfane.

4-(3-(2-((S)-2-Methylazetidin-1-yl)-6,7-dihydro-5H-cyclopenta[d]pyrimidin-4-yl)phenylsulfonimidoyl)benzonitrile was prepared according to General Method AE using 4-(3-bromophenylsulfonimidoyl)benzonitrile instead of 3-(4-iodophenyl)-1,2,4-oxadiazol-5(4H)-one.

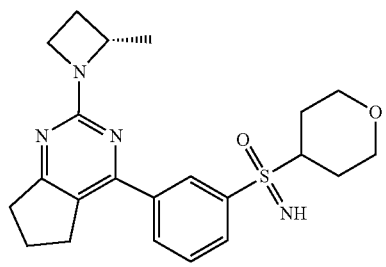 [SMILES: C[C@H]1CCN1c1nc2c(c(-c3cccc(S(=N)(=O)C4CCOCC4)c3)n1)CCC2]

481

Example 880: imino(3-(2-((S)-2-methylazetidin-1-yl)-6,7-dihydro-5H-cyclopenta[d]pyrimidin-4-yl)phenyl)(tetrahydro-2H-pyran-4-yl)-λ⁶-sulfanone The title compound was prepared according to General Method AE using (3-bromophenyl)(imino)(tetrahydro-2H-pyran-4-ye-λ⁶-sulfanone instead of 3-(4-iodophenyl)-1,2,4-oxadiazol-5 (4H)-one.

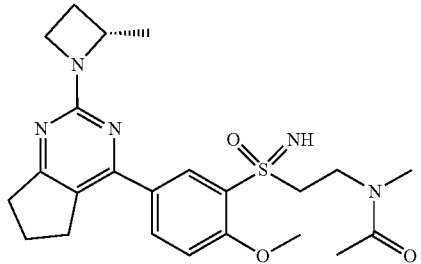 [SMILES: COc1ccc(-c2nc(N3CC[C@@H]3C)nc3c2CCC3)cc1S(=N)(=O)CCN(C)C(C)=O]

Example 881: N-(2-(2-methoxy-5-(2-((S)-2-methyl-azetidin-1-yl)-6,7-dihydro-5H-cyclopenta[d]pyrimidin-4-yl)phenylsulfonimidoyl)ethyl)-N-methylacetamide A vial was charged with 2-((5-bromo-2-methoxyphenyl)thio)-N-methylethan-1-amine (500 mg, 1.81 mmol, 1 equiv.), triethylamine (0.30 mL, 2.17 mmol, 1.2 equiv.) and DCM (15 mL) under argon. The reaction mixture was cooled to 0° C. and acetic acid anhydride was added dropwise under argon. The reaction mixture was allowed to warm to room temperature and was stirred at room temperature for 30 minutes, transferred into a separatory funnel and washed with water and brine. The organic phase was dried over sodium sulfate and concentrated under reduced pressure to afford N-(2-((5-bromo-2-methoxyphenyl)thio)ethyl)-N-methylacetamide, which was used in the next step without further purification.

(2-(Benzyloxy)-5-bromophenyl)(methyl)sulfane was prepared according to General Method AG using N-(2-((5-bromo-2-methoxyphenyl)thio)ethyl)-N-methylacetamide instead of (2-(benzyloxy)-5-bromophenyl)(methyl)sulfane.

N-(2-(2-Methoxy-5-(2-((S)-2-methylazetidin-1-yl)-6,7-dihydro-5H-cyclopenta[d]pyrimidin-4-yl)phenylsulfonimidoyl)ethyl)-N-methylacetamide was made according to General Method AF using (2-(benzyloxy)-5-bromophenyl)(methyl)sulfane. Final purification was done using flash chromatography (0 to 10% MeOH in DCM) to afford the title compound.

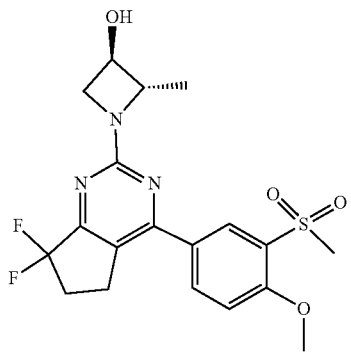 [SMILES: COc1ccc(-c2nc(N3C[C@@H](O)[C@@H]3C)nc3c2CCC3(F)F)cc1S(C)(=O)=O]

482

Example 882: (2S,3R)-1-(7,7-difluoro-4-(4-methoxy-3-(methylsulfonyl)phenyl)-6,7-dihydro-5H-cyclopenta[d]pyrimidin-2-yl)-2-methylazetidin-3-ol A vial was charged with (R)-(5-(7,7-difluoro-2-((2S,3R)-3-hydroxy-2-methylazetidin-1-yl)-6,7-dihydro-5H-cyclopenta[d]pyrimidin-4-yl)-2-methoxyphenyl)(imino)(methyl)-λ⁶-sulfanone (50 mg, 0.12 mmol, 1 equiv.), 3-chloroperoxybenzoic acid (186 mg, 0.72 mmol, 6 equiv.), 1M aqueous HCl (1 uL, 0.001 mmol, 0.01 equiv.) and THF (2 mL). The reaction mixture was heated at 75° C. for 3 hours, cooled down to room temperature, diluted with DCM (30 mL) and washed with 1M NaOH (20 mL). The organic layer was separated, washed with brine, dried over sodium sulfate, filtered, concentrated under reduced pressure and purified by preparative reverse phase HPLC (10% to 80% MeCN+0.1% TFA in H₂O+0.1% TFA) to give the title compound.

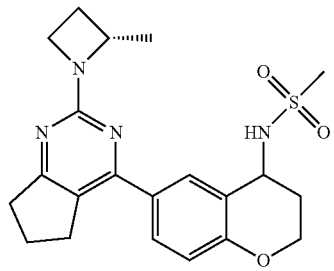 [SMILES: C[C@H]1CCN1c1nc2c(c(-c3ccc4c(c3)C(NS(C)(=O)=O)CCO4)n1)CCC2]

Example 883: N-(6-(2-((S)-2-methylazetidin-1-yl)-6,7-dihydro-5H-cyclopenta[d]pyrimidin-4-yl)chroman-4-yl)methanesulfonamide The title compound was prepared according to General Method AI.

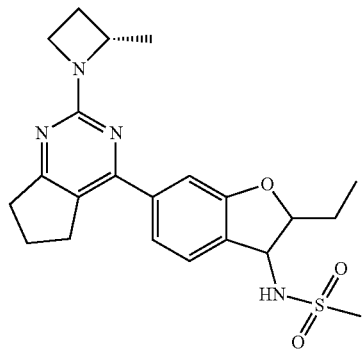 [SMILES: CCC1Oc2cc(-c3nc(N4CC[C@@H]4C)nc4c3CCC4)ccc2C1NS(C)(=O)=O]

Example 884: N-(2-ethyl-6-(2-((S)-2-methylazetidin-1-yl)-6,7-dihydro-5H-cyclopenta[d]pyrimidin-4-yl)-2,3-dihydrobenzofuran-3-yl)methanesulfonamide The title compound was prepared according to General Method AI using 6-bromo-2-ethyl-2,3-dihydrobenzofuran-3-amine instead of 6-bromochroman-4-amine

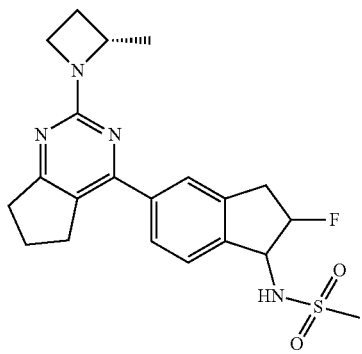 [SMILES: C[C@H]1CCN1c1nc2c(c(-c3ccc4c(c3)CC(F)C4NS(C)(=O)=O)n1)CCC2]

Example 885: N-(2-fluoro-5-(2-((S)-2-methylazetidin-1-yl)-6,7-dihydro-5H-cyclopenta[d]pyrimidin-4-yl)-2,3-dihydro-1H-inden-1-yl)methanesulfonamide The title compound was prepared according to General Method AI using 5-bromo-2-fluoro-2,3-dihydro-1H-inden-1-amine instead of 6-bromochroman-4-amine

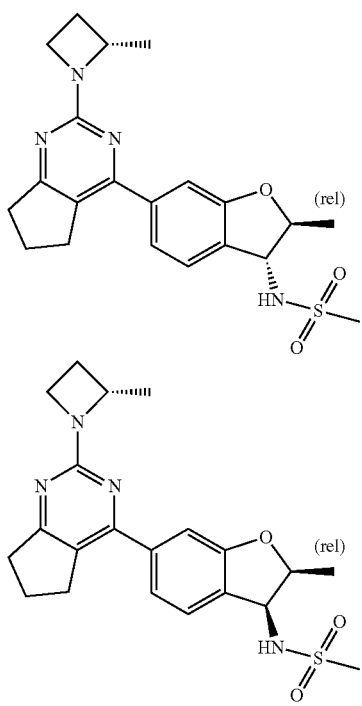

Example 886: N-((2s,3r)-2-methyl-6-(2-((S)-2-methylazetidin-1-yl)-6,7-dihydro-5H-cyclopenta[d]pyrimidin-4-yl)-2,3-dihydrobenzofuran-3-yl)methanesulfonamide Example 887: N-((2s,3s)-2-methyl-6-(2-((S)-2-methylazetidin-1-yl)-6,7-dihydro-5H-cyclopenta[d]pyrimidin-4-yl)-2,3-dihydrobenzofuran-3-yl)methanesulfonamide The title compounds were prepared according to General Method AI using 6-bromo-2-methyl-2,3-dihydrobenzofuran-3-amine instead of 6-bromochroman-4-amine Isomers were separated by reverse phase HPLC.

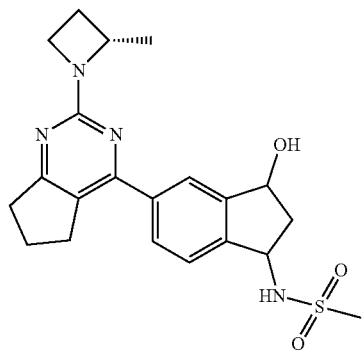 [SMILES: C[C@H]1CCN1c1nc2c(c(-c3ccc4c(c3)C(O)CC4NS(C)(=O)=O)n1)CCC2]

Example 888: N-(3-hydroxy-5-(2-((S)-2-methylazetidin-1-yl)-6,7-dihydro-5H-cyclopenta[d]pyrimidin-4-yl)-2,3-dihydro-1H-inden-1-yl)methanesulfonamide The title compound was prepared according to General Method AI using 3-amino-6-bromo-2,3-dihydro-1H-inden-1-ol instead of 6-bromochroman-4-amine

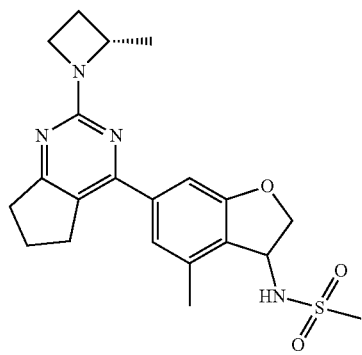 [SMILES: Cc1cc(-c2nc(N3CC[C@@H]3C)nc3c2CCC3)cc2c1C(NS(C)(=O)=O)CO2]

Example 889: N-(4-methyl-6-(2-((S)-2-methylazetidin-1-yl)-6,7-dihydro-5H-cyclopenta[d]pyrimidin-4-yl)-2,3-dihydrobenzofuran-3-yl)methanesulfonamide The title compound was prepared according to General Method AI using 6-bromo-4-methyl-2,3-dihydrobenzofuran-3-amine instead of 6-bromochroman-4-amine

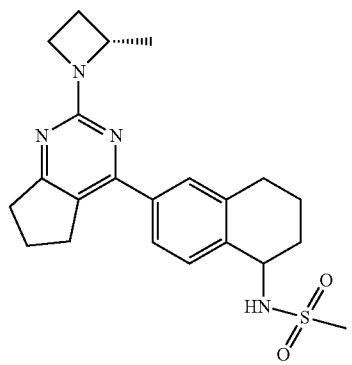 [SMILES: C[C@H]1CCN1c1nc2c(c(-c3ccc4c(c3)CCCC4NS(C)(=O)=O)n1)CCC2]

Example 890: N-(6-(2-((S)-2-methylazetidin-1-yl)-6,7-dihydro-5H-cyclopenta[d]pyrimidin-4-yl)-1,2,3,4-tetrahydronaphthalen-1-yl)methanesulfonamide The title compound was prepared according to General Method AI using 6-bromo-1,2,3,4-tetrahydronaphthalen-1-amine instead of 6-bromochroman-4-amine

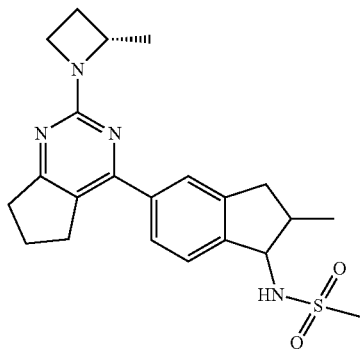 [SMILES: CC1Cc2cc(-c3nc(N4CC[C@@H]4C)nc4c3CCC4)ccc2C1NS(C)(=O)=O]

Example 891: N-(2-methyl-5-(2-((S)-2-methylazetidin-1-yl)-6,7-dihydro-5H-cyclopenta[d]pyrimidin-4-yl)-2,3-dihydro-1H-inden-1-yl)methanesulfonamide The title compound was prepared according to General Method AI using 5-bromo-2-methyl-2,3-dihydro-1H-inden-1-amine instead of 6-bromochroman-4-amine

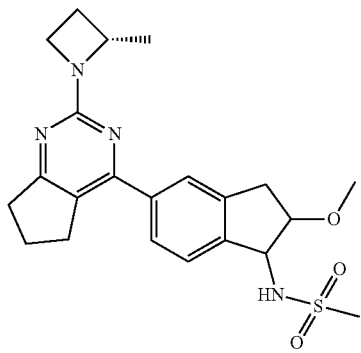 [SMILES: COC1Cc2cc(-c3nc(N4CC[C@@H]4C)nc4c3CCC4)ccc2C1NS(C)(=O)=O]

Example 892: N-(2-methoxy-5-(2-((S)-2-methylazetidin-1-yl)-6,7-dihydro-5H-cyclopenta[d]pyrimidin-4-yl)-2,3-dihydro-1H-inden-1-yl)methanesulfonamide The title compound was prepared according to General Method AI using 5-bromo-2-methoxy-2,3-dihydro-1H-inden-1-amine instead of 6-bromochroman-4-amine

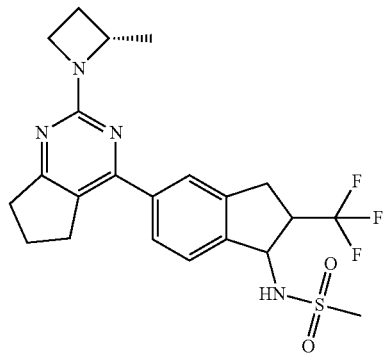 [SMILES: C[C@H]1CCN1c1nc2c(c(-c3ccc4c(c3)CC(C(F)(F)F)C4NS(C)(=O)=O)n1)CCC2]

Example 893: N-(5-(2-((S)-2-methylazetidin-1-yl)-6,7-dihydro-5H-cyclopenta[d]pyrimidin-4-yl)-2-(trifluoromethyl)-2,3-dihydro-1H-inden-1-yl)methanesulfonamide The title compound was prepared according to General Method AI using 5-bromo-2-(trifluoromethyl)-2,3-dihydro-1H-inden-1-amine instead of 6-bromochroman-4-amine

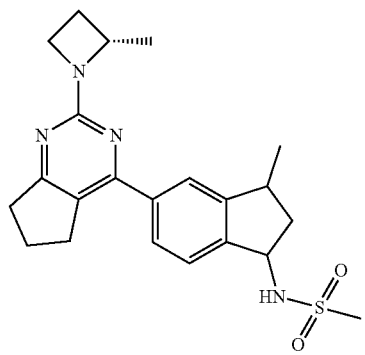 [SMILES: CC1CC(NS(C)(=O)=O)c2ccc(-c3nc(N4CC[C@@H]4C)nc4c3CCC4)cc21]

Example 894: N-(3-methyl-5-(2-((S)-2-methylazetidin-1-yl)-6,7-dihydro-5H-cyclopenta[d]pyrimidin-4-yl)-2,3-dihydro-1H-inden-1-yl)methanesulfonamide The title compound was prepared according to General Method AI using 5-bromo-3-methyl-2,3-dihydro-1H-inden-1-amine instead of 6-bromochroman-4-amine

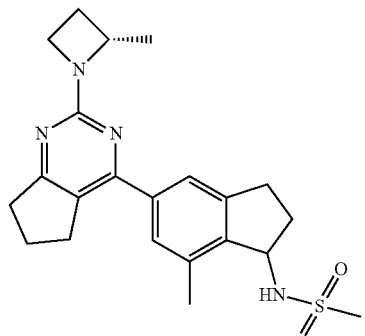

487

Example 895: N-(7-methyl-5-(2-((S)-2-methylazetidin-1-yl)-6,7-dihydro-5H-cyclopenta[d]pyrimidin-4-yl)-2,3-dihydro-1H-inden-1-yl)methanesulfonamide The title compound was prepared according to General Method AI using 5-bromo-7-methyl-2,3-dihydro-1H-inden-1-amine instead of 6-bromochroman-4-amine

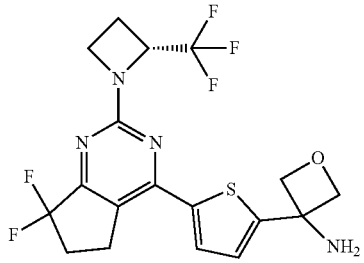 [SMILES: NC1(c2ccc(-c3nc(N4CC[C@@H]4C(F)(F)F)nc4c3CCC4(F)F)s2)COC1]

Example 896: (R)-3-(5-(7,7-difluoro-2-(2-(trifluoromethyl)azetidin-1-yl)-6,7-dihydro-5H-cyclopenta[d]pyrimidin-4-yl)thiophen-2-yl)oxetan-3-amine A flask was charged with 2,5-dibromothiophene (3.00 g, 12.4 mmol), 3-oxetanone (1.34 g, 18.6 mmol), and THF (25 mL). The mixture was cooled to −78° C. under a stream of N$_2$. n-BuLi (2.5 M in hexane, 5.3 mL, 13.1 mmol) was added dropwise over 10 min. The mixture was allowed to stir for 2 hrs at −78° C., at which point NH$_4$Cl was added (aq. sat., 15 mL). The mixture was allowed to warm to ambient temperature and extracted with EtOAc (3×15 mL). The combined organic layers were dried over Na$_2$SO$_4$, filtered, and concentrated. The residue was subject to flash column chromatography (hexanes-ethyl acetate) to give 3-(5-bromothiophen-2-yl)oxetan-3-ol.

The title compound was prepared in analogy to General Method W, using 3-(5-bromothiophen-2-yl)oxetan-3-ol instead of 5-bromo-7-methoxy-2,3-dihydro-1H-inden-1-ol, followed by General Method T, followed by General Method D, followed by General Method AF, using 4-chloro-7,7-difluoro-2-(methylthio)-6,7-dihydro-5H-cyclopenta[d]pyrimidine instead of N-(2-(5-bromo-2-methoxyphenylsulfonimidoyl)ethyl)-N-methylacetamide and Pd(PPh$_3$)$_4$ instead of P(t-Bu)3 Pd G4, followed by General Method M, followed by General Method U.

(2S,3R)-1-(4-(4,4-difluoro-1,2,3,4-tetrahydroisoquinolin-6-yl)-7,7-difluoro-6,7-dihydro-5H-cyclopenta[d]pyrimidin-2-yl)-2-methylazetidin-3-ol The title compound can be made according to the general scheme below.

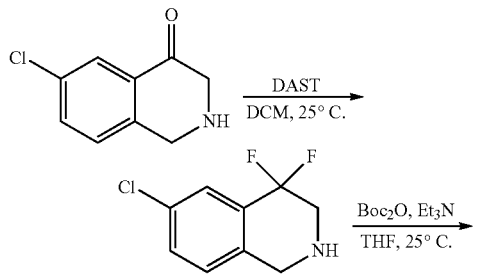

488

-continued

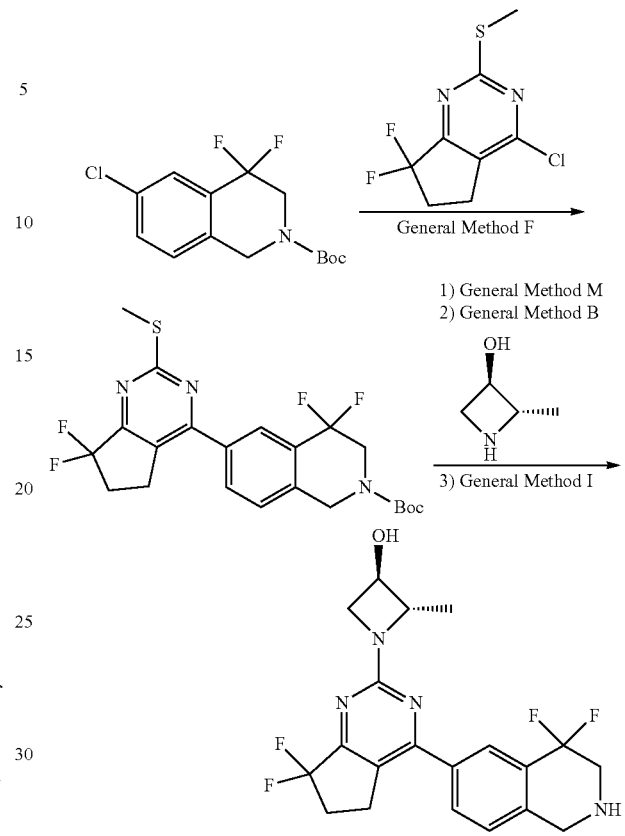

(2S,3R)-1-(7,7-difluoro-4-(4-fluoro-1,2,3,4-tetrahydroisoquinolin-6-yl)-6,7-dihydro-5H-cyclopenta[d]pyrimidin-2-yl)-2-methylazetidin-3-ol The title compound can be made according to the general scheme below.

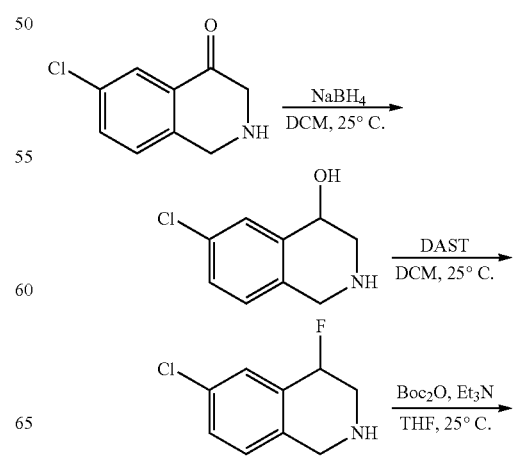

489

-continued

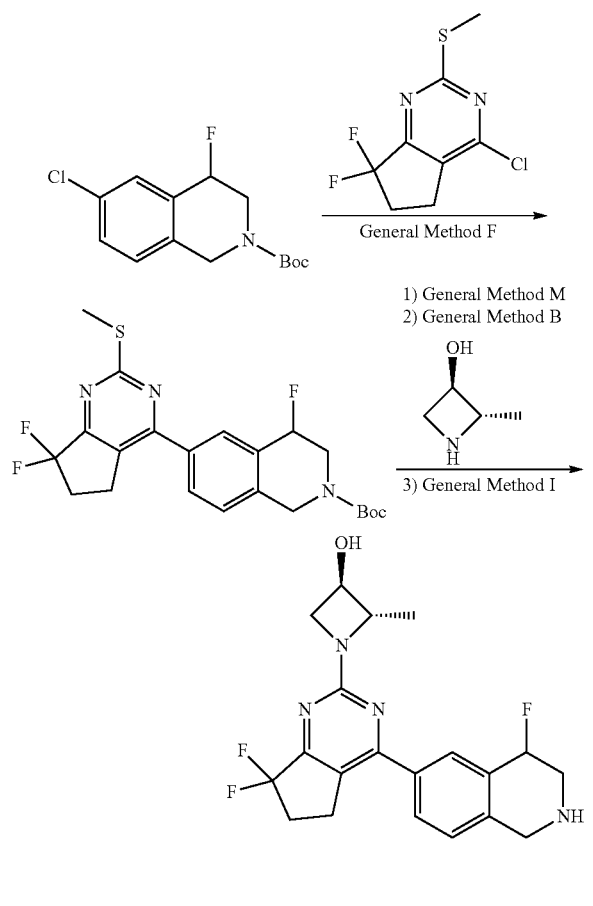

(2S,3R)-1-(4-(5,5-difluoro-2,3,4,5-tetrahydro-1H-benzo[c]azepin-7-yl)-7,7-difluoro-6,7-dihydro-5H-cyclopenta[d]pyrimidin-2-yl)-2-methylazetidin-3-ol- The title compound can be made according to the general scheme below.

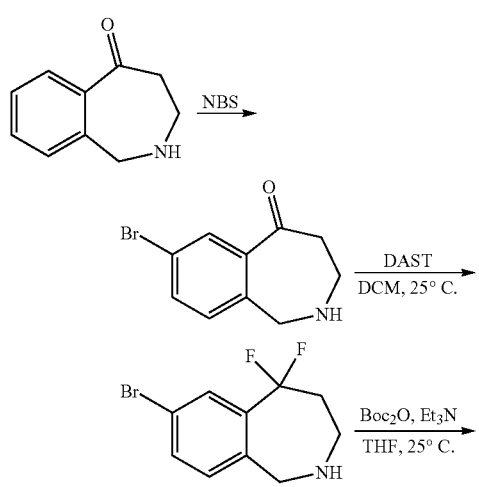

490

-continued

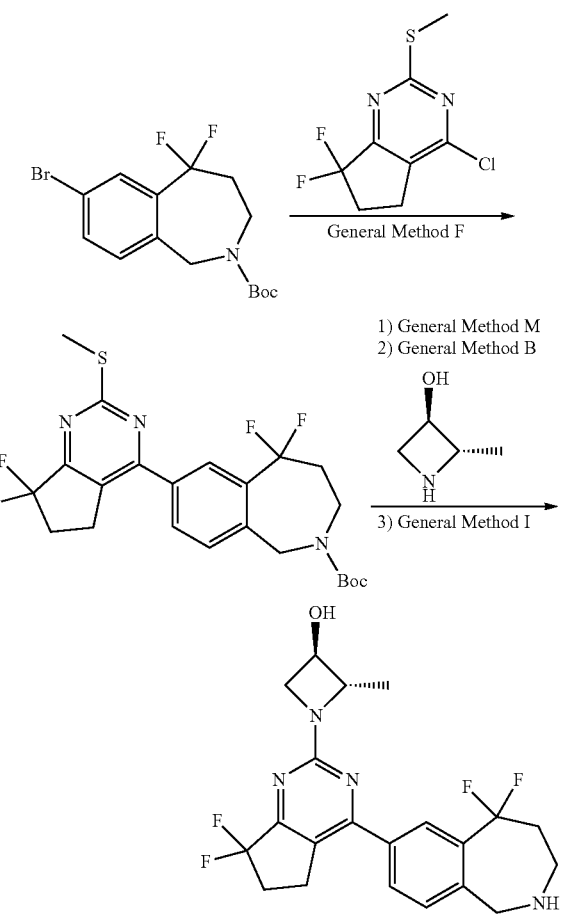

4-(7,7-difluoro-2-((2S,3R)-3-hydroxy-2-methylazetidin-1-yl)-6,7-dihydro-5H-cyclopenta[d]pyrimidin-4-yl)-2-(phenylethynyl)benzamide The title compound can be made according to the general scheme below.

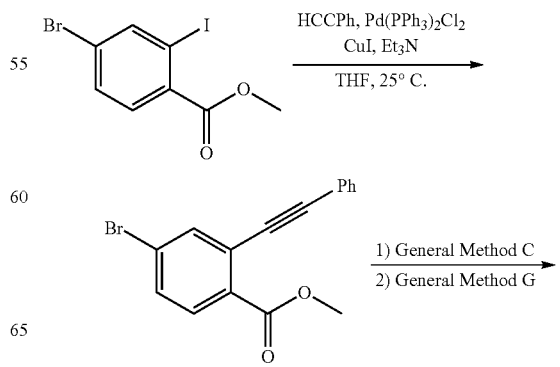

491
-continued

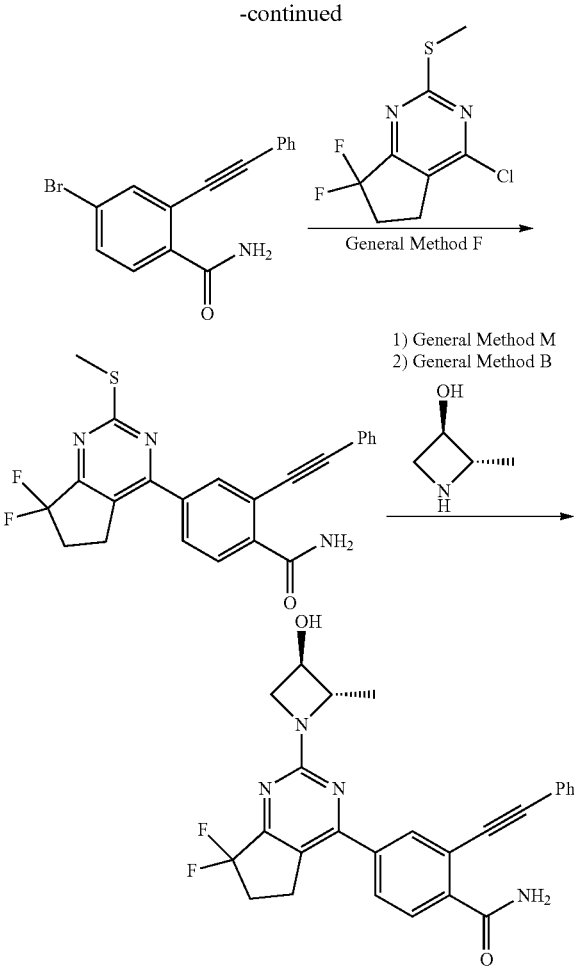

(2S,3R)-1-(4-(3,4-dihydro-2H-spiro[isoquinoline-1,
3'-oxetan]-6-yl)-7,7-difluoro-6,7-dihydro-5H-cyclo-
penta[d]pyrimidin-2-yl)-2-methylazetidin-3-ol- The title compound can be made according to the general scheme below.

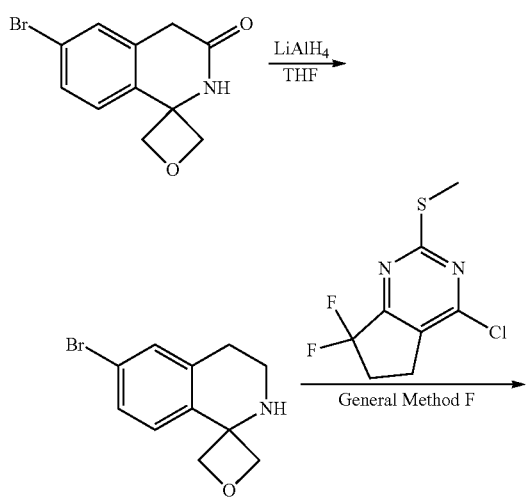

492
-continued

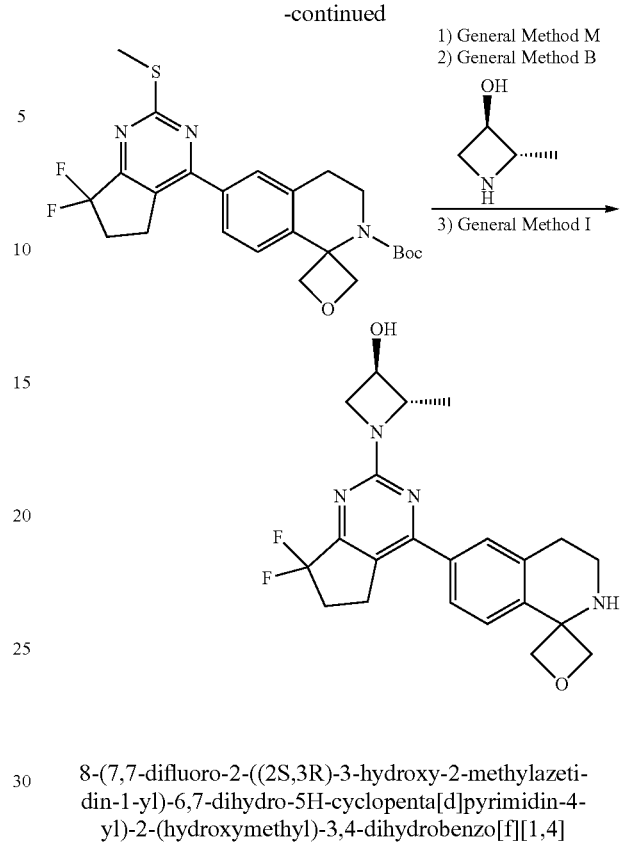

8-(7,7-difluoro-2-((2S,3R)-3-hydroxy-2-methylazeti-
din-1-yl)-6,7-dihydro-5H-cyclopenta[d]pyrimidin-4-
yl)-2-(hydroxymethyl)-3,4-dihydrobenzo[f][1,4]
oxazepin-5(2H)-one The title compound can be made according to the general scheme below.

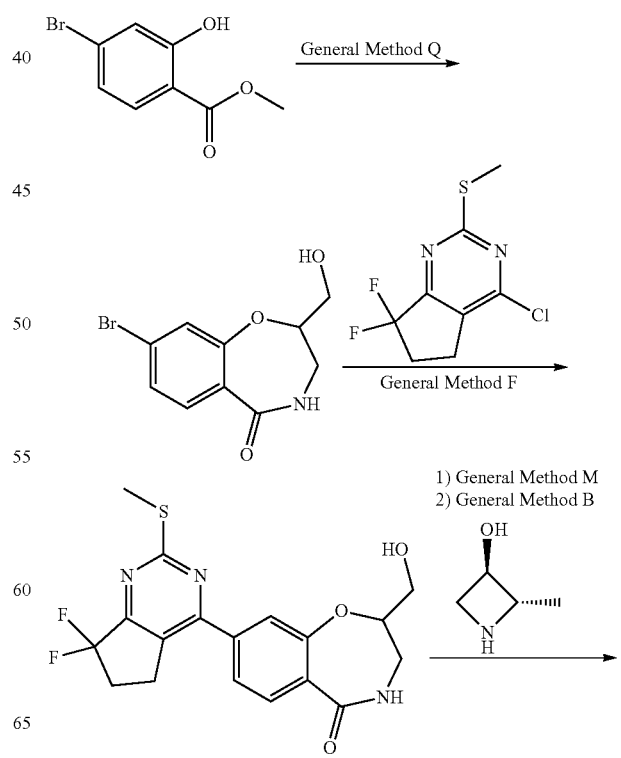

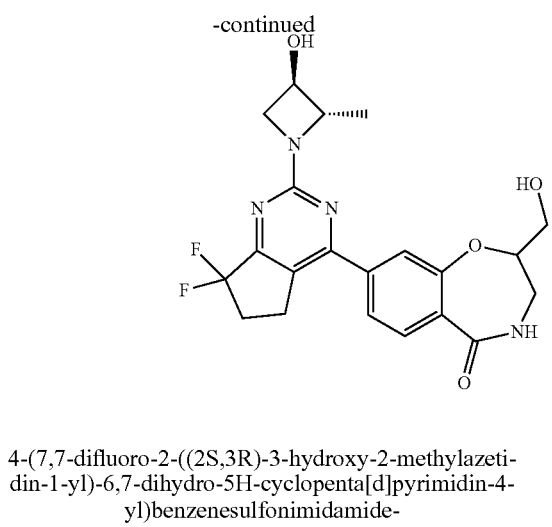

4-(7,7-difluoro-2-((2S,3R)-3-hydroxy-2-methylazetidin-1-yl)-6,7-dihydro-5H-cyclopenta[d]pyrimidin-4-yl)benzenesulfonimidamide- The title compound can be made according to the general scheme below.

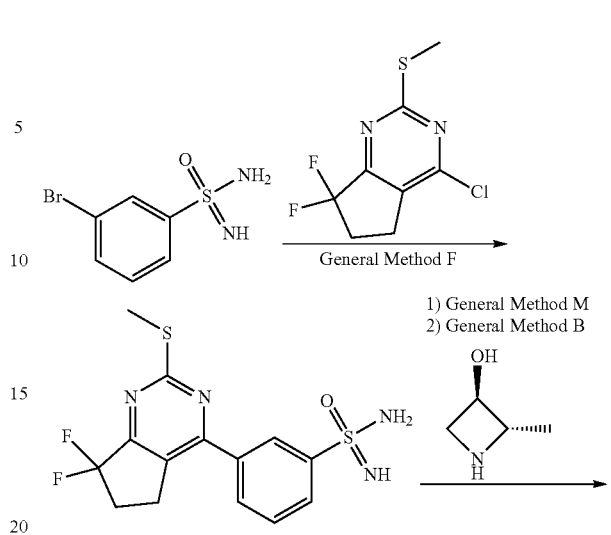

3-(7,7-difluoro-2-((2S,3R)-3-hydroxy-2-methylazetidin-1-yl)-6,7-dihydro-5H-cyclopenta[d]pyrimidin-4-yl)benzenesulfonimidamide The title compound can be made according to the general scheme below.

8-(7,7-difluoro-2-((2S,3R)-3-hydroxy-2-methylazetidin-1-yl)-6,7-dihydro-5H-cyclopenta[d]pyrimidin-4-yl)-2,2-difluoro-3,4-dihydrobenzo[f][1,4]oxazepin-5(2H)-one The title compound can be made according to the general scheme below.

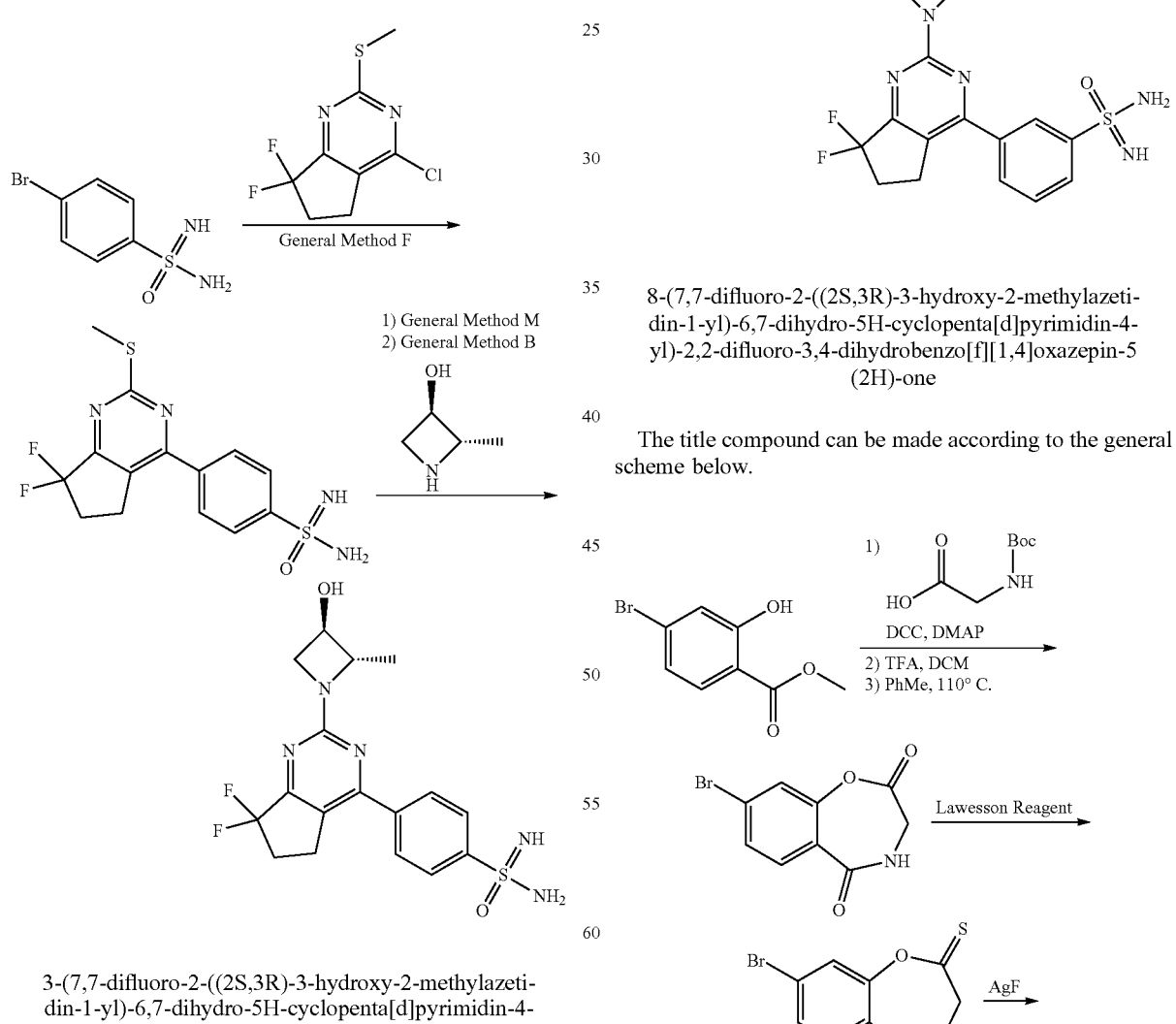

495

-continued

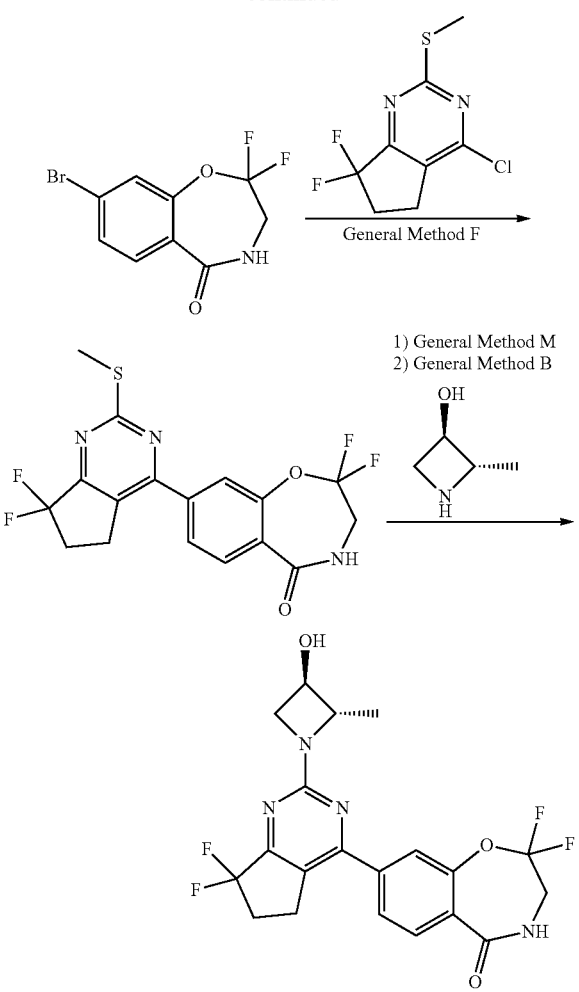

(2S,3R)-1-(4-(4-(1-amino-3,3-difluorocyclobutyl)
phenyl)-7,7-difluoro-6,7-dihydro-5H-cyclopenta[d]
pyrimidin-2-yl)-2-methylazetidin-3-ol- The title compound can be made according to the general scheme below.

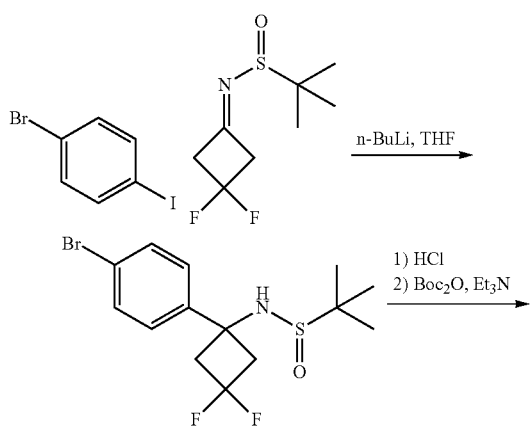

496

-continued

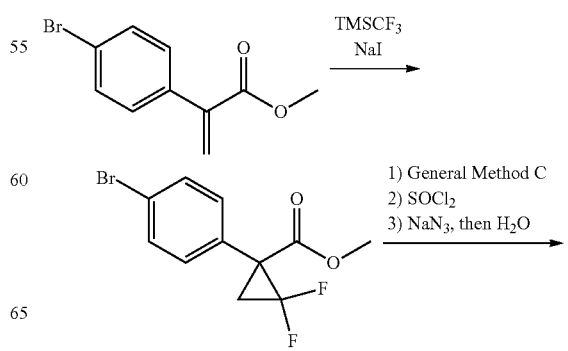

(2S,3R)-1-(4-(4-(1-amino-2,2-difluorocyclopropyl)
phenyl)-7,7-difluoro-6,7-dihydro-5H-cyclopenta[d]
pyrimidin-2-yl)-2-methylazetidin-3-ol The title compound can be made according to the general scheme below.

497
-continued
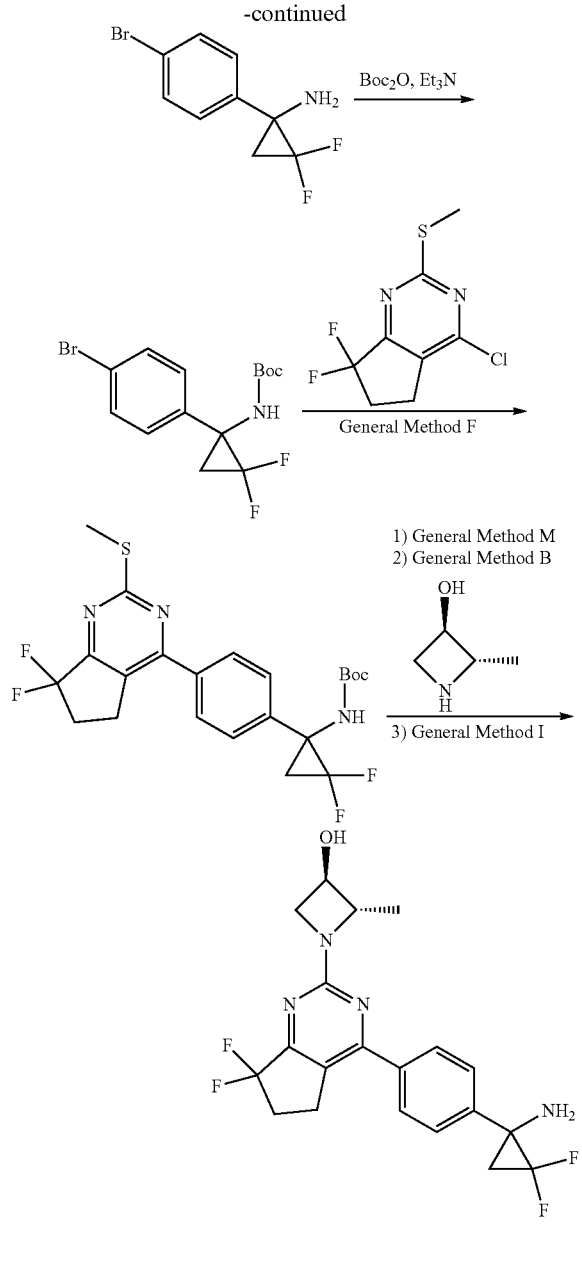
8-(7,7-difluoro-2-((2S,3R)-3-hydroxy-2-methylazetidin-1-yl)-6,7-dihydro-5H-cyclopenta[d]pyrimidin-4-yl)-3,4-dihydro-5H-spiro[benzo[f][1,4]oxazepine-2,1'-cyclopropan]-5-one
The title compound can be made according to the general scheme below.
498
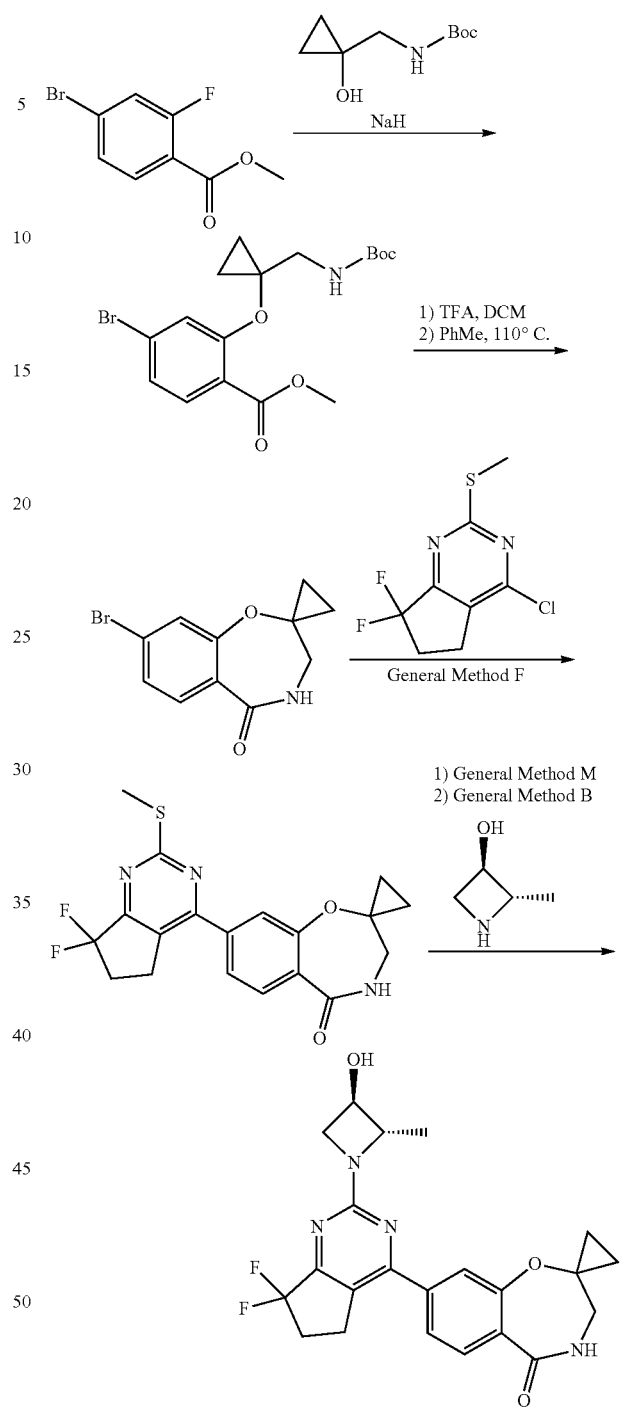
TABLE 1
MS and NMR DATA
| Example No | ES/MS m/z (M + H)+ | 1H NMR |
|---|---|---|
| 1 | 352.2 | 1H NMR (400 MHz, Chloroform-d) δ 7.76-7.67 (m, 2H), 7.37 (t, J = 8.0 Hz, 1H), 7.27-7.24 (m, 1H), 4.58-4.47 (m, 1H), 4.19-4.05 (m, 1H), 4.05-3.94 (m, 1H), 3.68 (s, 3H), 3.11-2.94 (m, 4H), 2.88 (d, J = 7.7 Hz, 2H), 2.73-2.59 (m, 2H), 2.49-2.35 (m, 1H), 2.12-1.96 (m, 3H), 1.59-1.57 (m, 3H). |

TABLE 1-continued

| | MS and NMR DATA | |
|---|---|---|
| Example No | ES/MS m/z (M + H)+ | 1H NMR |
| 2 | 352.2 | 1H NMR (400 MHz, Chloroform-d) δ 7.34-7.19 (m, 4H), 4.53-4.41 (m, 1H), 4.14-4.05 (m, 1H), 4.03-3.93 (m, 1H), 3.63 (s, 3H), 3.07-2.83 (m, 4H), 2.70-2.52 (m, 4H), 2.47-2.35 (m, 1H), 2.06-1.90 (m, 3H), 1.50 (d, J = 6.1 Hz, 3H). |
| 3 | 338.1 | 1H NMR (400 MHz, Chloroform-d) δ 7.87-7.77 (m, 2H), 7.41 (t, J = 7.6 Hz, 1H), 7.36-7.31 (m, 1H), 4.56-4.44 (m, 1H), 4.19-4.04 (m, 1H), 4.05-3.97 (m, 1H), 3.78-3.66 (m, 5H), 3.12-2.94 (m, 2H), 2.89 (t, J = 7.7 Hz, 2H), 2.48-2.37 (m, 1H), 2.12-1.94 (m, 3H), 1.59-1.56 (m, 3H). |
| 4 | 338.1 | 1H NMR (400 MHz, DMSO-d6) δ 7.75-7.69 (m, 2H), 7.47-7.35 (m, 2H), 4.52-4.41 (m, 1H), 4.08-3.89 (m, 2H), 3.09-2.94 (m, 2H), 2.91 (t, J = 7.5 Hz, 2H), 2.87-2.82 (m, 2H), 2.58 (t, J = 7.5 Hz, 2H), 2.48-2.37 (m, 1H), 2.07-1.93 (m, 3H), 1.51 (d, J = 6.2 Hz, 3H). |
| 5 | 338.1 | 1H NMR (400 MHz, DMSO-d6) δ 7.43-7.36 (m, 2H), 7.35-7.26 (m, 2H), 4.51-4.40 (m, 1H), 4.05-3.86 (m, 2H), 2.88 (t, J = 7.7 Hz, 2H), 2.84-2.73 (m, 2H), 2.61 (t, J = 7.4 Hz, 2H), 2.49-2.36 (m, 3H), 2.03-1.91 (m, 3H), 1.45 (d, J = 6.2 Hz, 3H). |
| 6 | 324.1 | 1H NMR (400 MHz, DMSO-d6) δ 7.81-7.75 (m, 2H), 7.47 (t, J = 7.6 Hz, 1H), 7.44-7.38 (m, 1H), 4.56-4.42 (m, 1H), 4.08-3.92 (m, 2H), 3.68 (s, 2H), 3.09-2.92 (m, 2H), 2.91-2.81 (m, 2H), 2.49-2.37 (m, 1H), 2.11-1.92 (m, 3H), 1.51 (d, J = 6.2 Hz, 3H). |
| 7 | 291.1 | 1H NMR (400 MHz, Chloroform-d) δ 8.18 (d, J = 1.7 Hz, 1H), 8.15-8.09 (m, 1H), 7.86-7.82 (m, 1H), 7.66 (t, J = 7.9 Hz, 1H), 4.88-4.74 (m, 1H), 4.45-4.37 (m, 1H), 4.36-4.25 (m, 1H), 3.17 (t, J = 7.8 Hz, 2H), 3.13-3.01 (m, 2H), 2.75-2.59 (m, 1H), 2.24 (p, J = 7.5 Hz, 2H), 2.18-2.05 (m, 1H), 1.62 (d, J = 6.3 Hz, 3H). |
| 8 | 309.1 | 1H NMR (400 MHz, DMSO-d6) δ 8.34-8.31 (m, 1H), 8.06 (s, 1H), 8.01 (d, J = 7.7 Hz, 1H), 7.96 (d, J = 8.0 Hz, 1H), 7.58 (t, J = 7.7 Hz, 1H), 7.45 (s, 1H), 4.47-4.37 (m, 1H), 4.04-3.85 (m, 2H), 3.08-2.95 (m, 2H), 2.82 (t, J = 7.7 Hz, 2H), 2.45-2.30 (m, 1H), 2.07-1.90 (m, 3H), 1.50 (d, J = 6.2 Hz, 3H). |
| 9 | 310.1 | 1H NMR (400 MHz, DMSO-d6) δ 8.49-8.46 (m, 1H), 8.13 (d, J = 7.8 Hz, 1H), 8.04 (d, J = 7.8 Hz, 1H), 7.65 (t, J = 7.8 Hz, 1H), 4.50-4.36 (m, 1H), 4.02-3.88 (m, 2H), 3.12-2.93 (m, 2H), 2.83 (t, J = 7.7 Hz, 2H), 2.43-2.30 (m, 1H), 2.10-1.90 (m, 3H), 1.51 (d, J = 6.2 Hz, 3H). |
| 10 | 282.1 | 1H NMR (400 MHz, Chloroform-d) δ 7.61-7.56 (m, 2H), 7.53-7.46 (m, 3H), 4.78 (s, 2H), 4.74-4.65 (m, 1H), 4.38-4.27 (m, 1H), 4.26-4.17 (m, 1H), 3.92-3.85 (m, 1H), 3.84-3.76 (m, 1H), 2.72-2.50 (m, 3H), 2.12-1.99 (m, 1H), 1.57 (d, J = 6.3 Hz, 3H). |
| 11 | 280.1 | 1H NMR (400 MHz, Chloroform-d) δ 8.06 (s, 1H), 7.69-7.57 (m, 5H), 4.85-4.75 (m, 1H), 4.48-4.37 (m, 1H), 4.36-4.27 (m, 1H), 3.79 (s, 3H), 2.68-2.57 (m, 1H), 2.16-2.04 (m, 1H), 1.61 (d, J = 6.3 Hz, 3H). |
| 12 | 266.1 | 1H NMR (400 MHz, Chloroform-d) δ 8.49-8.41 (m, 2H), 7.95 (d, J = 2.1 Hz, 1H), 7.66-7.56 (m, 3H), 7.14 (d, J = 2.1 Hz, 1H), 4.93-4.81 (m, 1H), 4.49-4.41 (m, 1H), 4.39-4.27 (m, 1H), 2.71-2.61 (m, 1H), 2.20-2.08 (m, 1H), 1.69 (d, J = 6.3 Hz, 3H). |
| 13 | 273.1 | 1H NMR (400 MHz, Chloroform-d) δ 8.63 (d, J = 1.8 Hz, 1H), 7.73 (d, J = 1.9 Hz, 1H), 4.80-4.71 (m, 1H), 4.39-4.21 (m, 2H), 3.17 (t, J = 7.9 Hz, 2H), 3.09 (t, J = 7.5 Hz, 2H), 2.69-2.56 (m, 1H), 2.29 (p, J = 7.8 Hz, 2H), 2.15-2.05 (m, 1H), 1.62 (d, J = 6.3 Hz, 3H). |
| 14 | 273.1 | 1H NMR (400 MHz, Chloroform-d) δ 9.31 (s, 1H), 9.12 (s, 1H), 4.86-4.76 (m, 1H), 4.45-4.37 (m, 1H), 4.34-4.26 (m, 1H), 3.19 (t, J = 7.9 Hz, 2H), 3.13-3.06 (m, 2H), 2.70-2.60 (m, 1H), 2.29 (p, J = 7.8 Hz, 2H), 2.17-2.06 (m, 1H), 1.63 (d, J = 6.3 Hz, 3H). |
| 15 | 267.1 | 1H NMR (400 MHz, Chloroform-d) δ 9.42-9.31 (m, 1H), 8.91 (dd, J = 5.3, 1.4 Hz, 1H), 8.66 (d, J = 8.2 Hz, 1H), 7.83 (dd, J = 8.2, 5.3 Hz, 1H), 4.82-4.74 (m, 1H), 4.43-4.32 (m, 1H), 4.31-4.20 (m, 1H), 3.17-3.09 (m, 4H), 2.65 (ddd, J = 14.7, 11.9, 8.0 Hz, 1H), 2.26 (p, J = 7.6 Hz, 2H), 2.16-2.03 (m, 1H), 1.62 (d, J = 6.3 Hz, 3H). |
| 16 | 268.1 | 1H NMR (400 MHz, Chloroform-d) δ 9.37 (s, 1H), 9.31 (s, 2H), 4.82-4.72 (m, 1H), 4.41-4.34 (m, 1H), 4.32-4.23 (m, 1H), 3.20-3.07 (m, 4H), 2.70-2.59 (m, 1H), 2.26 (p, J = 7.5 Hz, 2H), 2.16-2.06 (m, 1H), 1.62 (d, J = 6.3 Hz, 3H). |
| 17 | 270.1 | 1H NMR (400 MHz, Chloroform-d) δ 7.43 (d, J = 2.4 Hz, 1H), 7.01 (d, J = 2.4 Hz, 1H), 4.88-4.72 (m, 1H), 4.47-4.36 (m, 1H), 4.36-4.26 (m, 1H), 4.01 (s, 3H), 3.22 (t, J = 7.5 Hz, 2H), 3.14 (t, J = 7.9 Hz, 2H), 2.69-2.53 (m, 1H), 2.18 (p, J = 7.7 Hz, 2H), 2.12-2.02 (m, 1H), 1.61 (d, J = 6.3 Hz, 3H). |
| 18 | 256.1 | 1H NMR (400 MHz, Chloroform-d) δ 7.70 (d, J = 2.3 Hz, 1H), 6.89 (d, J = 2.2 Hz, 1H), 4.79-4.69 (m, 1H), 4.40-4.30 (m, 1H), 4.29-4.19 (m, 1H), 3.11-2.98 (m, 4H), 2.67-2.54 (m, 1H), 2.20-2.04 (m, 3H), 1.61 (d, J = 6.3 Hz, 3H). |

TABLE 1-continued

MS and NMR DATA

| Example No | ES/MS m/z (M + H)+ | 1H NMR |
|---|---|---|
| 19 | 256.1 | 1H NMR (400 MHz, Chloroform-d) δ 8.17-7.94 (m, 2H), 4.85-4.66 (m, 1H), 4.41-4.20 (m, 2H), 3.12-2.99 (m, 2H), 2.93-2.82 (m, 2H), 2.72-2.56 (m, 1H), 2.28-2.14 (m, 2H), 2.12-2.01 (m, 1H), 1.62 (d, J = 6.3 Hz, 3H). |
| 20 | 270.1 | 1H NMR (400 MHz, Chloroform-d) δ 7.59 (d, J = 2.1 Hz, 1H), 6.76 (d, J = 2.1 Hz, 1H), 4.80-4.68 (m, 1H), 4.41-4.32 (m, 1H), 4.27 (s, 4H), 3.14 (t, J = 7.8 Hz, 2H), 2.99 (t, J = 7.4 Hz, 2H), 2.72-2.58 (m, 1H), 2.21 (p, J = 7.6 Hz, 2H), 2.13-2.03 (m, 1H), 1.60 (d, J = 6.3 Hz, 3H). |
| 21 | 267.1 | 1H NMR (400 MHz, Chloroform-d) δ 8.75 (d, J = 4.8 Hz, 1H), 8.32 (d, J = 8.0 Hz, 1H), 7.87 (td, J = 7.8, 1.8 Hz, 1H), 7.42 (dd, J = 7.3, 4.9 Hz, 1H), 4.87-4.73 (m, 1H), 4.45-4.35 (m, 1H), 4.35-4.24 (m, 1H), 3.43-3.31 (m, 2H), 3.13 (t, J = 7.9 Hz, 2H), 2.67-2.57 (m, 1H), 2.22-2.04 (m, 3H), 1.64 (d, J = 6.3 Hz, 3H). |
| 22 | 267.1 | 1H NMR (400 MHz, Chloroform-d) δ 8.93 (d, J = 6.6 Hz, 2H), 8.22 (d, J = 6.6 Hz, 2H), 4.72-4.60 (m, 1H), 4.31-4.22 (m, 1H), 4.19-4.10 (m, 1H), 3.15-3.01 (m, 4H), 2.63-2.51 (m, 1H), 2.21 (p, J = 7.6 Hz, 2H), 2.14-2.01 (m, 1H), 1.59 (d, J = 6.2 Hz, 3H). |
| 23 | 270.1 | 1H NMR (400 MHz, Chloroform-d) δ 8.06 (s, 1H), 8.05 (s, 1H), 4.85-4.71 (m, 1H), 4.43-4.33 (m, 1H), 4.32-4.22 (m, 1H), 4.02 (s, 3H), 3.13 (t, J = 7.9 Hz, 2H), 3.05-2.93 (m, 2H), 2.70-2.58 (m, 1H), 2.26 (p, J = 7.8 Hz, 2H), 2.14-2.00 (m, 1H), 1.61 (d, J = 6.3 Hz, 3H). |
| 24 | 328.1 | 1H NMR (400 MHz, DMSO-d6) δ 7.83 (d, J = 2.3 Hz, 1H), 6.83 (d, J = 2.3 Hz, 1H), 4.47-4.35 (m, 3H), 4.04-3.85 (m, 2H), 3.11-3.05 (m, 2H), 2.88-2.78 (m, 4H), 2.43-2.31 (m, 1H), 2.06-1.90 (m, 3H), 1.49 (d, J = 6.2 Hz, 3H). |
| 25 | 328.1 | 1H NMR (400 MHz, DMSO-d6) δ 8.27 (s, 1H), 7.96 (s, 1H), 4.44-4.35 (m, 3H), 3.98-3.84 (m, 2H), 2.91 (t, J = 7.5 Hz, 2H), 2.83 (t, J = 6.7 Hz, 2H), 2.78 (t, J = 7.7 Hz, 2H), 2.41-2.32 (m, 1H), 2.09-1.91 (m, 3H), 1.49 (d, J = 6.2 Hz, 3H). |
| 26 | 283.1 | 1H NMR (400 MHz, Chloroform-d) δ 8.67 (s, 1H), 8.61-8.54 (m, 2H), 7.55-7.50 (m, 3H), 4.74-4.60 (m, 1H), 4.28-4.20 (m, 1H), 4.20-4.11 (m, 1H), 2.60-2.46 (m, 1H), 2.13-2.02 (m, 1H), 1.65 (d, J = 6.2 Hz, 3H). |
| 27 | 323.2 | 1H NMR (400 MHz, Chloroform-d) δ 7.89-7.86 (m, 1H), 7.63 (d, J = 7.5 Hz, 1H), 7.38 (d, J = 8.0 Hz, 1H), 6.19 (s, 1H), 4.92-4.77 (m, 1H), 4.50-4.39 (m, 1H), 4.39-4.27 (m, 1H), 3.12-3.04 (m, 2H), 3.03-2.92 (m, 2H), 2.73-2.60 (m, 1H), 2.57 (s, 3H), 2.28-2.02 (m, 3H), 1.63 (d, J = 6.3 Hz, 3H). |
| 28 | 323.1 | 1H NMR (400 MHz, Chloroform-d) δ 8.23 (s, 1H), 7.96 (d, J = 7.9 Hz, 1H), 7.85 (d, J = 7.8 Hz, 1H), 7.56 (t, J = 7.8 Hz, 1H), 7.10 (s, 1H), 4.89-4.77 (m, 1H), 4.48-4.38 (m, 1H), 4.37-4.29 (m, 1H), 3.13-2.97 (m, 7H), 2.71-2.60 (m, 1H), 2.26-2.04 (m, 3H), 1.63 (d, J = 6.3 Hz, 3H). |
| 29 | 337.2 | 1H NMR (400 MHz, Chloroform-d) δ 7.72-7.69 (m, 1H), 7.65-7.61 (m, 1H), 7.45-7.39 (m, 2H), 4.86-4.76 (m, 1H), 4.48-4.39 (m, 1H), 4.39-4.23 (m, 1H), 3.15-2.98 (m, 7H), 2.68-2.54 (m, 3H), 2.12-2.02 (m, 2H), 1.63 (d, J = 6.3 Hz, 3H). |
| 30 | 306.2 | 1H NMR (400 MHz, Chloroform-d) δ 7.93-7.84 (m, 2H), 7.59-7.46 (m, 3H), 4.85-4.75 (m, 1H), 4.48-4.38 (m, 1H), 4.38-4.27 (m, 1H), 3.35-3.15 (m, 2H), 3.06-2.89 (m, 2H), 2.70-2.55 (m, 1H), 2.13-2.04 (m, 1H), 1.98-1.82 (m, 1H), 1.63 (dd, J = 6.3, 4.4 Hz, 3H), 0.91-0.75 (m, 1H), 0.59-0.44 (m, 2H), 0.28-0.10 (m, 2H). |
| 31 | 292.1 | 1H NMR (400 MHz, Chloroform-d) δ 7.91-7.77 (m, 2H), 7.50-7.37 (m, 3H), 4.59-4.42 (m, 1H), 4.17-4.08 (m, 1H), 4.06-3.95 (m, 1H), 3.64 (d, J = 20.2 Hz, 1H), 3.30 (s, 1H), 2.50-2.33 (m, 1H), 2.13-1.95 (m, 3H), 1.81-1.70 (m, 1H), 1.61-1.56 (m, 3H), 1.52-1.38 (m, 2H), 1.27-1.24 (m, 1H). |
| 32 | 325.1 | 1H NMR (400 MHz, DMSO-d6) δ 8.37-8.30 (m, 1H), 8.07 (s, 1H), 8.02 (d, J = 7.8 Hz, 1H), 7.96 (d, J = 7.8 Hz, 1H), 7.59 (t, J = 7.7 Hz, 1H), 7.45 (s, 1H), 5.59 (s, 1H), 4.20-4.12 (m, 1H), 4.11-3.99 (m, 2H), 3.62 (dd, J = 8.6, 5.0 Hz, 1H), 3.12-2.93 (m, 2H), 2.82 (t, J = 7.7 Hz, 2H), 2.08-1.92 (m, 2H), 1.48 (d, J = 6.1 Hz, 3H). |
| 33 | 335.1 | 1H NMR (400 MHz, Chloroform-d) δ 8.31 (d, J = 11.1 Hz, 1H), 8.05-7.96 (m, 1H), 7.88 (d, J = 7.9 Hz, 1H), 7.55 (t, J = 7.8 Hz, 1H), 4.60-4.47 (m, 1H), 4.12 (q, J = 7.1 Hz, 2H), 4.07-3.97 (m, 1H), 3.64 (d, J = 17.9 Hz, 1H), 3.37-3.30 (m, 1H), 2.49-2.36 (m, 1H), 2.07-1.99 (m, 1H), 1.84-1.72 (m, 1H), 1.61-1.53 (m, 3H), 1.50-1.37 (m, 2H), 1.30-1.22 (m, 2H). |
| 34 | 287.1 | 1H NMR (400 MHz, Chloroform-d) δ 8.25 (s, 1H), 4.79-4.69 (m, 1H), 4.41-4.33 (m, 1H), 4.31-4.22 (m, 1H), 3.16 (t, J = 7.9 Hz, 2H), 3.07 (t, J = 7.5 Hz, 2H), 2.81 (s, 3H), 2.67-2.57 (m, 1H), 2.28 (p, J = 7.8 Hz, 2H), 2.15-2.04 (m, 1H), 1.61 (d, J = 6.3 Hz, 3H). |

TABLE 1-continued

MS and NMR DATA

| Example No | ES/MS m/z (M + H)+ | 1H NMR |
|---|---|---|
| 35 | 270.1 | 1H NMR (400 MHz, Chloroform-d) δ 8.11 (s, 2H), 8.00 (s, 1H), 4.88-4.75 (m, 1H), 4.46-4.27 (m, 2H), 4.10 (s, 3H), 2.73-2.61 (m, 1H), 2.16-2.04 (m, 1H), 1.61 (d, J = 6.3 Hz, 3H). |
| 36 | 273.1 | 1H NMR (400 MHz, Chloroform-d) δ 8.93 (d, J = 2.1 Hz, 1H), 8.45 (d, J = 2.1 Hz, 1H), 4.84-4.75 (m, 1H), 4.46-4.37 (m, 1H), 4.35-4.27 (m, 1H), 3.36-3.27 (m, 2H), 3.16 (t, J = 7.9 Hz, 2H), 2.69-2.58 (m, 1H), 2.25-2.15 (m, 3H), 2.15-2.02 (m, 1H), 1.63 (d, J = 6.3 Hz, 3H). |
| 37 | 359.1 | 1H NMR (400 MHz, Chloroform-d) δ 8.23-8.22 (m, 1H), 8.20 (d, J = 8.1 Hz, 1H), 8.04 (s, 1H), 7.90 (d, J = 7.8 Hz, 1H), 7.79 (t, J = 7.8 Hz, 1H), 5.14-5.03 (m, 2H), 4.90-4.75 (m, 1H), 4.46-4.37 (m, 1H), 4.37-4.28 (m, 1H), 3.81 (s, 3H), 2.71-2.61 (m, 1H), 2.18-2.06 (m, 1H), 1.61 (d, J = 6.2 Hz, 3H). |
| 38 | 375.1 | 1H NMR (400 MHz, Chloroform-d) δ 8.23 (s, 1H), 8.19 (d, J = 8.1 Hz, 1H), 8.04 (s, 1H), 7.91 (d, J = 7.8 Hz, 1H), 7.79 (t, J = 7.8 Hz, 1H), 5.00-4.93 (m, 2H), 4.63-4.55 (m, 1H), 4.54-4.47 (m, 1H), 4.37-4.31 (m, 1H), 4.13-4.00 (m, 1H), 3.82 (s, 3H), 1.61 (d, J = 6.5 Hz, 3H). |
| 39 | 306.1 | 1H NMR (400 MHz, Chloroform-d) δ 8.34-8.30 (m, 1H), 8.22 (s, 1H), 8.02-7.96 (m, 1H), 7.57 (d, J = 8.9 Hz, 1H), 4.89-4.76 (m, 1H), 4.47-4.37 (m, 1H), 4.36-4.25 (m, 1H), 3.21-3.05 (m, 4H), 2.69-2.59 (m, 1H), 2.23-2.05 (m, 3H), 1.65 (d, J = 6.3 Hz, 3H). |
| 40 | 323.1 | 1H NMR (400 MHz, Chloroform-d) δ 9.04 (s, 1H), 7.78 (d, J = 7.8 Hz, 1H), 7.69 (s, 1H), 7.45 (t, J = 7.9 Hz, 1H), 7.38-7.31 (m, 1H), 4.88-4.77 (m, 1H), 4.37 (t, J = 7.8 Hz, 2H), 2.99-2.92 (m, 5H), 2.87-2.81 (m, 2H), 2.70 (d, J = 17.9 Hz, 1H), 2.12-1.98 (m, 3H), 1.63 (d, J = 6.3 Hz, 3H). |
| 41 | 339.2 | 1H NMR (400 MHz, Chloroform-d) δ 8.36 (s, 1H), 8.30 (s, 1H), 7.60 (d, J = 8.1 Hz, 1H), 7.53 (d, J = 7.6 Hz, 1H), 7.41 (t, J = 7.9 Hz, 1H), 4.64-4.54 (m, 2H), 4.35-4.26 (m, 1H), 4.09 (dd, J = 10.7, 4.2 Hz, 1H), 3.11-2.99 (m, 4H), 2.23 (s, 3H), 2.20-2.06 (m, 2H), 1.63 (d, J = 6.5 Hz, 3H). |
| 42 | 359.1 | 1H NMR (400 MHz, Chloroform-d) δ 8.25-8.20 (m, 2H), 7.64 (d, J = 8.0 Hz, 1H), 7.55 (d, J = 7.8 Hz, 1H), 7.43 (t, J = 7.9 Hz, 1H), 4.87-4.77 (m, 1H), 4.46-4.38 (m, 1H), 4.35-4.26 (m, 1H), 3.14-3.00 (m, 4H), 2.69-2.59 (m, 1H), 2.23 (s, 3H), 2.20-2.06 (m, 3H), 1.63 (d, J = 6.3 Hz, 3H). |
| 43 | 375.1 | 1H NMR (400 MHz, Chloroform-d) δ 9.70 (s, 1H), 7.95 (d, J = 7.9 Hz, 1H), 7.59 (s, 1H), 7.47 (t, J = 7.9 Hz, 1H), 7.33-7.28 (m, 1H), 4.84-4.75 (m, 1H), 4.61 (dd, J = 10.4, 7.3 Hz, 1H), 4.39 (dd, J = 10.8, 4.5 Hz, 1H), 4.32-4.25 (m, 1H), 2.93 (s, 3H), 2.86 (t, J = 7.9 Hz, 2H), 2.71-2.59 (m, 2H), 2.03-1.89 (m, 2H), 1.66 (d, J = 6.5 Hz, 3H). |
| 44 | 306.1 | 1H NMR (400 MHz, DMSO-d6) δ 8.14 (s, 1H), 8.05 (s, 1H), 7.87 (d, J = 8.5 Hz, 1H), 7.73-7.63 (m, 1H), 4.53-4.39 (m, 1H), 4.05-3.91 (m, 2H), 3.16-2.99 (m, 2H), 2.85 (t, J = 7.7 Hz, 2H), 2.46-2.36 (m, 1H), 2.10-1.93 (m, 3H), 1.53 (d, J = 6.2 Hz, 3H). |
| 45 | 272.1 | 1H NMR (400 MHz, Chloroform-d) δ 7.72 (d, J = 3.9 Hz, 1H), 7.61 (d, J = 5.1 Hz, 1H), 7.20 (t, J = 4.4 Hz, 1H), 4.74-4.65 (m, 1H), 4.38-4.27 (m, 1H), 4.27-4.16 (m, 1H), 3.15-3.05 (m, 4H), 2.61-2.48 (m, 1H), 2.22 (p, J = 7.7 Hz, 2H), 2.10-1.99 (m, 1H), 1.62 (d, J = 6.3 Hz, 3H). |
| 46 | 350.2 | 1H NMR (400 MHz, DMSO-d6) δ 7.70 (d, J = 7.8 Hz, 1H), 7.64 (s, 1H), 7.44 (t, J = 7.7 Hz, 1H), 7.32 (d, J = 7.7 Hz, 1H), 4.55-4.43 (m, 1H), 4.11-3.89 (m, 2H), 3.11-2.94 (m, 2H), 2.90-2.83 (m, 2H), 2.56-2.35 (m, 3H), 2.10-1.93 (m, 3H), 1.89-1.82 (m, 1H), 1.55-1.44 (m, 3H), 1.42-1.32 (m, 1H). |
| 47 | 366.1 | 1H NMR (400 MHz, DMSO-d6) δ 7.73-7.68 (m, 1H), 7.65-7.61 (m, 1H), 7.42 (t, J = 7.7 Hz, 1H), 7.33-7.27 (m, 1H), 4.20 (dd, J = 8.8, 5.8 Hz, 1H), 4.13-4.03 (m, 2H), 3.64 (dd, J = 8.8, 4.7 Hz, 1H), 3.09-2.92 (m, 2H), 2.87-2.77 (m, 2H), 2.49-2.46 (m, 1H), 2.08-1.93 (m, 2H), 1.90-1.81 (m, 1H), 1.51-1.45 (m, 4H), 1.41-1.34 (m, 1H). |
| 48 | 368.1 | 1H NMR (400 MHz, DMSO-d6) δ 7.70 (d, J = 7.8 Hz, 1H), 7.65-7.63 (m, 1H), 7.42 (t, J = 7.7 Hz, 1H), 7.32-7.25 (m, 1H), 5.12 (ddt, J = 57.1, 5.8, 3.9 Hz, 1H), 4.49-3.83 (m, 3H), 3.08-2.95 (m, 2H), 2.87-2.79 (m, 2H), 2.49-2.44 (m, 1H), 2.07-1.96 (m, 2H), 1.90-1.83 (m, 1H), 1.53 (d, J = 6.4 Hz, 3H), 1.51-1.45 (m, 1H), 1.42-1.35 (m, 1H). |
| 49 | 297.1 | 1H NMR (400 MHz, Chloroform-d) δ 7.66 (d, J = 4.1 Hz, 1H), 7.62 (d, J = 4.1 Hz, 1H), 4.75-4.65 (m, 1H), 4.36-4.27 (m, 1H), 4.25-4.17 (m, 1H), 3.14-3.06 (m, 4H), 2.64-2.52 (m, 1H), 2.26 (p, J = 7.7 Hz, 2H), 2.15-2.04 (m, 1H), 1.61 (d, J = 6.2 Hz, 3H). |
| 50 | 350.2 | 1H NMR (400 MHz, DMSO-d6) δ 8.83-8.72 (m, 2H), 7.88 (d, J = 8.6 Hz, 2H), 7.10 (d, J = 8.7 Hz, 2H), 4.46-4.36 (m, 1H), 4.01-3.87 (m, 2H), 3.51-3.45 (m, 4H), 3.30-3.22 (m, 4H), 3.09-2.95 (m, |

TABLE 1-continued

MS and NMR DATA

| Example No | ES/MS m/z (M + H)+ | 1H NMR |
|---|---|---|
| | | 2H), 2.81 (t, J = 7.8 Hz, 2H), 2.45-2.34 (m, 1H), 2.05-1.92 (m, 3H), 1.50 (d, J = 6.1 Hz, 3H). |
| 51 | 452.2 | 1H NMR (400 MHz, DMSO-d6) δ 8.54 (t, J = 5.6 Hz, 1H), 8.31 (s, 1H), 8.01 (d, J = 7.8 Hz, 1H), 7.93 (d, J = 7.8 Hz, 1H), 7.60 (t, J = 7.8 Hz, 1H), 6.91 (t, J = 5.7 Hz, 1H), 4.49-4.39 (m, 1H), 4.03-3.89 (m, 2H), 3.35-3.28 (m, 2H), 3.16-3.08 (m, 2H), 3.07-2.95 (m, 2H), 2.83 (t, J = 7.7 Hz, 2H), 2.45-2.36 (m, 1H), 2.07-1.92 (m, 3H), 1.50 (d, J = 6.2 Hz, 3H), 1.37 (s, 9H). |
| 52 | 352.2 | 1H NMR (400 MHz, DMSO-d6) δ 8.69 (t, J = 5.6 Hz, 1H), 8.34 (s, 1H), 8.03 (d, J = 7.7 Hz, 1H), 7.96 (d, J = 7.7 Hz, 1H), 7.82-7.76 (m, 3H), 7.62 (t, J = 7.8 Hz, 1H), 4.46-4.36 (m, 1H), 4.00-3.89 (m, 2H), 3.56-3.50 (m, 2H), 3.09-2.95 (m, 4H), 2.82 (t, J = 7.7 Hz, 2H), 2.45-2.36 (m, 1H), 2.08-1.94 (m, 3H), 1.50 (d, J = 6.1 Hz, 3H). |
| 53 | 366.2 | 1H NMR (400 MHz, DMSO-d6) δ 8.74 (t, J = 5.7 Hz, 1H), 8.45-8.36 (m, 2H), 8.36-8.34 (m, 1H), 8.04 (d, J = 7.7 Hz, 1H), 7.96 (d, J = 7.8 Hz, 1H), 7.63 (t, J = 7.7 Hz, 1H), 4.45-4.34 (m, 1H), 4.01-3.86 (m, 2H), 3.58-3.54 (m, 2H), 3.14-3.08 (m, 2H), 3.06-2.97 (m, 2H), 2.82 (t, J = 7.7 Hz, 2H), 2.61 (t, J = 5.4 Hz, 3H), 2.45-2.34 (m, 1H), 2.10-1.90 (m, 3H), 1.50 (d, J = 6.1 Hz, 3H). |
| 54 | 389.1 | 1H NMR (400 MHz, DMSO-d6) δ 8.30 (s, 1H), 8.16-8.10 (m, 1H), 7.90 (d, J = 7.8 Hz, 1H), 7.77-7.71 (m, 2H), 4.49-4.35 (m, 1H), 4.04-3.88 (m, 2H), 3.38 (t, J = 6.3 Hz, 2H), 3.10-2.97 (m, 2H), 2.87-2.80 (m, 4H), 2.41 (dt, J = 11.6, 4.1 Hz, 1H), 2.10-1.91 (m, 3H), 1.50 (d, J = 6.1 Hz, 3H). |
| 55 | 343.1 | 1H NMR (400 MHz, DMSO-d6) δ 9.19-9.15 (m, 1H), 8.36 (dd, J = 8.4, 2.3 Hz, 1H), 8.18-8.11 (m, 3H), 7.58-7.46 (m, 3H), 4.54-4.40 (m, 1H), 4.05-3.89 (m, 2H), 3.14-3.03 (m, 2H), 2.84 (t, J = 7.7 Hz, 2H), 2.47-2.35 (m, 1H), 2.17-1.94 (m, 3H), 1.52 (d, J = 6.1 Hz, 3H). |
| 56 | 315.1 | 1H NMR (400 MHz, DMSO-d6) δ 8.08 (s, 1H), 7.78 (d, J = 3.9 Hz, 1H), 7.61 (d, J = 4.0 Hz, 1H), 7.50 (s, 1H), 4.44-4.33 (m, 1H), 3.99-3.84 (m, 2H), 3.02 (t, J = 7.3 Hz, 2H), 2.80 (t, J = 7.9 Hz, 2H), 2.41-2.31 (m, 1H), 2.13-1.92 (m, 3H), 1.50 (d, J = 6.2 Hz, 3H). |
| 57 | 331.1 | 1H NMR (400 MHz, DMSO-d6) δ 8.09 (s, 1H), 7.79 (d, J = 4.0 Hz, 1H), 7.62 (d, J = 4.1 Hz, 1H), 7.52 (s, 1H), 4.19-4.12 (m, 1H), 4.10-3.98 (m, 2H), 3.59 (dd, J = 8.6, 5.0 Hz, 2H), 3.03 (t, J = 7.4 Hz, 2H), 2.81 (t, J = 7.8 Hz, 2H), 2.11-2.03 (m, 2H), 1.49 (d, J = 6.3 Hz, 3H). |
| 58 | 333.1 | 1H NMR (400 MHz, DMSO-d6) δ 8.10 (s, 1H), 7.79 (d, J = 4.0 Hz, 1H), 7.64 (d, J = 4.1 Hz, 1H), 7.52 (s, 1H), 5.24-5.00 (m, 1H), 4.42-4.25 (m, 2H), 3.90 (ddd, J = 25.7, 10.1, 4.1 Hz, 1H), 3.09-3.02 (m, 2H), 2.83 (t, J = 7.9 Hz, 2H), 2.08 (p, J = 7.8 Hz, 2H), 1.55 (d, J = 6.5 Hz, 3H). |
| 59 | 379.2 | 1H NMR (400 MHz, DMSO-d6) δ 8.71 (d, J = 8.3 Hz, 1H), 8.32 (s, 1H), 8.01 (d, J = 7.8 Hz, 1H), 7.95 (d, J = 7.8 Hz, 1H), 7.60 (t, J = 7.8 Hz, 1H), 4.49-4.38 (m, 1H), 4.24-3.92 (m, 4H), 3.07-2.96 (m, 2H), 2.83 (t, J = 7.7 Hz, 2H), 2.45-2.36 (m, 1H), 2.11-1.88 (m, 5H), 1.50 (d, J = 6.2 Hz, 3H), 1.48-1.29 (m, 2H). |
| 60 | 379.2 | 1H NMR (400 MHz, DMSO-d6) δ 8.37-8.33 (m, 1H), 8.28-8.23 (m, 1H), 8.05-7.97 (m, 2H), 7.61 (t, J = 7.7 Hz, 1H), 4.48-4.39 (m, 1H), 4.34-4.23 (m, 2H), 4.05-3.89 (m, 2H), 3.11-2.94 (m, 2H), 2.84 (t, J = 7.7 Hz, 2H), 2.45-2.36 (m, 1H), 2.12-1.91 (m, 6H), 1.82 (dt, J = 6.5, 3.4 Hz, 1H), 1.51 (d, J = 6.2 Hz, 3H). |
| 61 | 353.2 | 1H NMR (400 MHz, DMSO-d6) δ 8.33 (d, J = 2.0 Hz, 1H), 8.01 (d, J = 8.0 Hz, 1H), 7.95 (d, J = 7.8 Hz, 1H), 7.65-7.55 (m, 2H), 4.60 (t, J = 5.7 Hz, 2H), 4.47-4.40 (m, 1H), 4.04-3.88 (m, 2H), 3.53 (t, J = 6.2 Hz, 2H), 3.06-2.94 (m, 2H), 2.86-2.81 (m, 2H), 2.44-2.34 (m, 1H), 2.10-1.92 (m, 3H), 1.50 (d, J = 6.2 Hz, 3H). |
| 62 | 335.1 | 1H NMR (400 MHz, Chloroform-d) δ 8.17 (s, 1H), 8.08 (d, J = 7.6 Hz, 1H), 7.87-7.71 (m, 1H), 7.67 (d, J = 7.8 Hz, 1H), 7.61 (t, J = 7.7 Hz, 1H), 6.40-6.26 (m, 1H), 4.91-4.78 (m, 1H), 4.49-4.33 (m, 2H), 3.53-3.49 (m, 1H), 3.46-3.43 (m, 1H), 2.73-2.61 (m, 1H), 2.24-2.02 (m, 3H), 1.93 (d, J = 9.9 Hz, 1H), 1.72 (d, J = 9.8 Hz, 1H), 1.64 (d, J = 6.3 Hz, 3H), 1.54-1.46 (m, 1H), 1.46-1.35 (m, 1H). |
| 63 | 335.1 | 1H NMR (400 MHz, Chloroform-d) δ 8.17 (s, 1H), 8.09 (d, J = 7.2 Hz, 1H), 7.96-7.81 (m, 1H), 7.68-7.58 (m, 2H), 6.38-6.25 (m, 1H), 4.91-4.81 (m, 1H), 4.52-4.41 (m, 1H), 4.39-4.30 (m, 1H), 3.49-3.46 (m, 1H), 3.46-3.39 (m, 1H), 2.75-2.61 (m, 1H), 2.25-2.02 (m, 3H), 1.88 (d, J = 9.9 Hz, 1H), 1.72 (d, J = 9.8 Hz, 1H), 1.64 (d, J = 6.3 Hz, 3H), 1.56-1.48 (m, 2H). |
| 64 | 375.1 | 1H NMR (400 MHz, DMSO-d6) δ 10.53 (s, 1H), 8.41 (s, 1H), 8.05 (d, J = 8.0 Hz, 2H), 7.89-7.84 (m, 2H), 7.66 (t, J = 7.8 Hz, 1H), 4.48-4.41 (m, 1H), 4.03-3.90 (m, 2H), 3.11-2.97 (m, 2H), 2.84 (t, J = 7.7 Hz, 2H), 2.46-2.33 (m, 1H), 2.08-1.92 (m, 3H), 1.51 (d, J = 6.1 Hz, 3H). |

TABLE 1-continued

MS and NMR DATA

| Example No | ES/MS m/z (M + H)+ | 1H NMR |
|---|---|---|
| 65 | 375.2 | 1H NMR (400 MHz, DMSO-d6) δ 8.49 (s, 1H), 8.22 (d, J = 3.1 Hz, 1H), 8.12 (d, J = 7.9 Hz, 1H), 8.08 (d, J = 7.7 Hz, 1H), 7.65 (t, J = 7.8 Hz, 1H), 6.05 (d, J = 3.0 Hz, 1H), 4.49-4.37 (m, 1H), 4.03-3.87 (m, 2H), 3.10-2.98 (m, 2H), 2.83 (t, J = 7.7 Hz, 2H), 2.44-2.35 (m, 1H), 2.09-1.91 (m, 3H), 1.50 (d, J = 6.2 Hz, 3H). |
| 66 | 367.1 | 1H NMR (400 MHz, DMSO-d6) δ 8.94 (t, J = 5.9 Hz, 1H), 8.36 (s, 1H), 8.04 (d, J = 7.8 Hz, 1H), 7.97 (d, J = 7.8 Hz, 1H), 7.63 (t, J = 7.8 Hz, 1H), 4.47-4.38 (m, 1H), 4.04-3.88 (m, 4H), 3.09-2.97 (m, 2H), 2.83 (t, J = 7.7 Hz, 2H), 2.44-2.33 (m, 1H), 2.06-1.92 (m, 3H), 1.50 (d, J = 6.1 Hz, 3H). |
| 67 | 393.2 | 1H NMR (400 MHz, DMSO-d6) δ 9.08 (s, 1H), 8.34 (s, 1H), 8.03 (d, J = 7.8 Hz, 1H), 7.96 (d, J = 7.8 Hz, 1H), 7.60 (t, J = 7.8 Hz, 1H), 4.51-4.37 (m, 1H), 4.03-3.89 (m, 2H), 3.11-2.93 (m, 2H), 2.83 (t, J = 7.7 Hz, 2H), 2.47-2.33 (m, 1H), 2.11-1.92 (m, 3H), 1.50 (d, J = 6.1 Hz, 3H), 1.45-1.39 (m, 2H), 1.19-1.09 (m, 2H). |
| 68 | 393.1 | 1H NMR (400 MHz, DMSO-d6) δ 8.14 (s, 1H), 8.06-7.97 (m, 1H), 7.80-7.71 (m, 1H), 7.61 (t, J = 7.7 Hz, 1H), 4.55-4.35 (m, 3H), 4.31-4.23 (m, 1H), 4.14-4.06 (m, 1H), 4.02-3.90 (m, 3H), 3.49 (tt, J = 9.1, 5.8 Hz, 1H), 3.09-2.97 (m, 2H), 2.83 (t, J = 7.8 Hz, 2H), 2.46-2.36 (m, 1H), 2.11-1.92 (m, 3H), 1.50 (d, J = 6.2 Hz, 3H). |
| 69 | 407.2 | 1H NMR (400 MHz, DMSO-d6) δ 8.15-8.11 (m, 1H), 8.06-7.98 (m, 1H), 7.79-7.72 (m, 1H), 7.59 (t, J = 7.7 Hz, 1H), 4.50-4.38 (m, 2H), 4.21-4.15 (m, 1H), 4.07-3.70 (m, 4H), 3.06-2.97 (m, 2H), 2.95-2.87 (m, 1H), 2.83 (t, J = 7.7 Hz, 2H), 2.64 (d, J = 7.7 Hz, 2H), 2.45-2.35 (m, 1H), 2.09-1.91 (m, 3H), 1.50 (d, J = 6.2 Hz, 3H). |
| 70 | 364.1 | 1H NMR (400 MHz, DMSO-d6) δ 8.26 (s, 1H), 7.99 (dd, J = 8.8, 1.6 Hz, 1H), 7.60 (d, J = 8.7 Hz, 1H), 4.50-4.41 (m, 1H), 4.04-3.89 (m, 4H), 3.16-3.01 (m, 2H), 2.84 (t, J = 7.8 Hz, 2H), 2.45-2.35 (m, 1H), 2.11-1.92 (m, 3H), 1.52 (d, J = 6.2 Hz, 3H). |
| 71 | 281.1 | 1H NMR (400 MHz, DMSO-d6) δ 7.61-7.54 (m, 2H), 7.45 (t, J = 7.8 Hz, 1H), 7.19-7.13 (m, 1H), 4.51-4.34 (m, 1H), 4.05-3.87 (m, 2H), 3.10-2.91 (m, 2H), 2.86-2.78 (m, 2H), 2.46-2.35 (m, 1H), 2.08-1.91 (m, 3H), 1.51 (d, J = 6.2 Hz, 3H). |
| 72 | 357.1 | 1H NMR (400 MHz, DMSO-d6) δ 8.19-8.17 (m, 1H), 8.17-8.13 (m, 1H), 7.96-7.91 (m, 1H), 7.70 (d, J = 8.0 Hz, 1H), 4.53-4.36 (m, 3H), 4.02-3.89 (m, 2H), 3.13-2.96 (m, 2H), 2.83 (t, J = 7.8 Hz, 2H), 2.47-2.35 (m, 1H), 2.10-1.91 (m, 3H), 1.50 (d, J = 6.2 Hz, 3H). |
| 73 | 425.1 | 1H NMR (400 MHz, DMSO-d6) δ 10.40 (s, 1H), 7.83-7.82 (m, 1H), 7.77-7.73 (m, 1H), 7.72-7.68 (m, 1H), 7.53-7.48 (m, 1H), 7.35 (t, J = 7.9 Hz, 1H), 7.28-7.22 (m, 1H), 4.47-4.34 (m, 1H), 4.01-3.85 (m, 2H), 3.64 (s, 3H), 3.00-2.77 (m, 4H), 2.46-2.34 (m, 1H), 2.07-1.91 (m, 3H), 1.50 (d, J = 6.2 Hz, 3H). |
| 74 | 403.1 | 1H NMR (400 MHz, DMSO-d6) δ 8.31-8.28 (m, 1H), 8.19 (t, J = 6.1 Hz, 1H), 8.14-8.10 (m, 1H), 7.92-7.88 (m, 1H), 7.72 (t, J = 7.8 Hz, 1H), 4.49-4.40 (m, 1H), 4.05-3.88 (m, 2H), 3.63 (d, J = 6.1 Hz, 2H), 3.12-2.95 (m, 2H), 2.88-2.79 (m, 2H), 2.46-2.35 (m, 1H), 2.10-1.91 (m, 3H), 1.51 (d, J = 6.2 Hz, 3H). |
| 75 | 433.2 | 1H NMR (400 MHz, Chloroform-d) δ 7.89 (d, J = 1.9 Hz, 1H), 7.81 (dt, J = 7.5, 1.7 Hz, 1H), 7.59-7.46 (m, 2H), 5.46 (s, 5H), 4.83 (h, J = 6.2 Hz, 1H), 4.41 (dd, J = 9.5, 6.0 Hz, 1H), 4.34 (dd, J = 9.6, 6.4 Hz, 1H), 4.28 (s, 2H), 3.30-2.94 (m, 9H), 2.74-2.55 (m, 1H), 2.41-2.29 (m, 2H), 2.27-2.03 (m, 2H), 1.63 (d, J = 6.3 Hz, 3H). |
| 76 | 440.1 | F1H NMR (400 MHz, DMSO-d6) δ 10.61 (s, 1H), 7.73-7.69 (m, 1H), 7.68-7.62 (m, 1H), 7.45 (t, J = 7.9 Hz, 1H), 7.28-7.19 (m, 1H), 4.44-4.33 (m, 1H), 4.01-3.84 (m, 2H), 2.97-2.86 (m, 2H), 2.84-2.77 (m, 2H), 2.45 (s, 3H), 2.43-2.37 (m, 1H), 2.24 (s, 3H), 2.05-1.90 (m, 3H), 1.49 (d, J = 6.2 Hz, 3H). |
| 77 | 393.1 | 1H NMR (400 MHz, DMSO-d6) δ 8.25-7.50 (m, 4H), 5.14-4.70 (m, 1H), 4.43 (q, J = 6.6 Hz, 1H), 4.19 (d, J = 67.1 Hz, 1H), 4.04-3.87 (m, 2H), 3.09-2.95 (m, 2H), 2.82 (t, J = 7.7 Hz, 2H), 2.72-2.57 (m, 1H), 2.46-2.34 (m, 1H), 2.29-2.13 (m, 1H), 2.07-1.90 (m, 3H), 1.50 (d, J = 6.2 Hz, 3H). |
| 78 | 393.1 | 1H NMR (400 MHz, DMSO-d6) δ 8.25-7.50 (m, 4H), 5.14-4.70 (m, 1H), 4.43 (q, J = 6.6 Hz, 1H), 4.19 (d, J = 67.1 Hz, 1H), 4.04-3.87 (m, 2H), 3.09-2.95 (m, 2H), 2.82 (t, J = 7.7 Hz, 2H), 2.72-2.57 (m, 1H), 2.46-2.34 (m, 1H), 2.29-2.13 (m, 1H), 2.07-1.90 (m, 3H), 1.50 (d, J = 6.2 Hz, 3H). |
| 79 | 371.1 | 1H NMR (400 MHz, DMSO-d6) δ 8.35-8.22 (m, 1H), 8.07 (d, J = 7.7 Hz, 1H), 7.93 (d, J = 7.7 Hz, 1H), 7.71 (t, J = 7.7 Hz, 1H), 7.48 (s, 2H), 5.07-4.69 (m, 3H), 3.65-3.47 (m, 1H), 3.08-2.92 (m, 3H), 2.87-2.76 (m, 2H), 2.25-1.65 (m, 5H), 1.58-1.32 (m, 2H). |

TABLE 1-continued

MS and NMR DATA

| Example No | ES/MS m/z (M + H)+ | 1H NMR |
|---|---|---|
| 80 | 387.1 | 1H NMR (400 MHz, DMSO-d6) δ 8.38 (s, 1H), 8.10 (d, J = 7.7 Hz, 1H), 7.93 (d, J = 7.7 Hz, 1H), 7.71 (t, J = 7.8 Hz, 1H), 7.48 (s, 2H), 4.37-3.59 (m, 4H), 3.24-3.11 (m, 1H), 3.11-2.93 (m, 2H), 2.90-2.70 (m, 3H), 2.38-2.23 (m, 1H), 2.14-1.80 (m, 3H), 1.62-1.46 (m, 1H). |
| 81 | 403.1 | 1H NMR (400 MHz, DMSO-d6) δ 10.26 (s, 1H), 7.91-7.77 (m, 1H), 7.66 (d, J = 7.7 Hz, 1H), 7.47 (t, J = 7.8 Hz, 1H), 7.37-7.29 (m, 1H), 4.47-4.34 (m, 1H), 4.12 (s, 2H), 4.02-3.88 (m, 2H), 3.08-2.92 (m, 2H), 2.87-2.76 (m, 2H), 2.43-2.34 (m, 1H), 2.11-1.91 (m, 3H), 1.50 (d, J = 6.0 Hz, 3H). |
| 82 | 419.1 | 1H NMR (400 MHz, DMSO-d6) δ 10.26 (s, 1H), 7.87-7.81 (m, 1H), 7.66 (d, J = 7.8 Hz, 1H), 7.47 (t, J = 7.9 Hz, 1H), 7.38-7.30 (m, 1H), 4.24-3.98 (m, 5H), 3.66-3.58 (m, 1H), 3.09-2.93 (m, 2H), 2.82 (t, J = 7.7 Hz, 2H), 2.07-1.97 (m, 2H), 1.48 (d, J = 6.1 Hz, 3H). |
| 83 | 417.1 | 1H NMR (400 MHz, DMSO-d6) δ 10.16-10.00 (m, 1H), 7.90-7.75 (m, 1H), 7.70-7.55 (m, 1H), 7.50-7.41 (m, 1H), 7.35-7.23 (m, 1H), 4.49-4.33 (m, 1H), 4.07-3.91 (m, 2H), 3.41-3.27 (m, 2H), 3.10-2.91 (m, 2H), 2.90-2.75 (m, 2H), 2.73-2.59 (m, 2H), 2.45-2.36 (m, 1H), 2.17-1.86 (m, 3H), 1.57-1.39 (m, 3H). |
| 84 | 485.1 | 1H NMR (400 MHz, DMSO-d6) δ 12.65 (s, 1H), 10.61 (s, 1H), 7.86 (s, 1H), 7.75-7.68 (m, 1H), 7.62 (d, J = 7.7 Hz, 1H), 7.42 (t, J = 7.9 Hz, 1H), 7.25 (dd, J = 7.9, 2.2 Hz, 1H), 4.44-4.31 (m, 1H), 3.99-3.83 (m, 2H), 2.98-2.75 (m, 4H), 2.42-2.34 (m, 1H), 2.15 (s, 3H), 2.03-1.86 (m, 3H), 1.48 (d, J = 6.2 Hz, 3H). |
| 85 | 316.1 | 1H NMR (400 MHz, DMSO-d6) δ 10.33 (s, 1H), 9.22 (d, J = 4.7 Hz, 1H), 7.88 (d, J = 4.7 Hz, 1H), 4.41-4.31 (m, 1H), 3.98-3.82 (m, 2H), 2.85-2.69 (m, 4H), 2.45-2.35 (m, 1H), 2.03-1.89 (m, 3H), 1.45 (d, J = 6.2 Hz, 3H). |
| 86 | 371.1 | 1H NMR (400 MHz, DMSO-d6) δ 8.39 (d, J = 1.3 Hz, 1H), 8.29 (dd, J = 8.0, 1.5 Hz, 1H), 8.04 (d, J = 8.0 Hz, 1H), 4.51-4.39 (m, 1H), 4.03-3.91 (m, 2H), 3.11-2.95 (m, 2H), 2.84 (t, J = 7.7 Hz, 2H), 2.47-2.34 (m, 1H), 2.08-1.92 (m, 3H), 1.50 (d, J = 6.2 Hz, 3H). |
| 87 | 417.1 | $^1$H NMR (400 MHz,) δ 7.83 (d, J = 8.1 Hz, 1H), 7.75 (dd, J = 8.1, 1.7 Hz, 1H), 7.60 (d, J = 1.6 Hz, 1H), 4.69-4.55 (m, 1H), 4.46-4.33 (m, 1H), 4.27-4.19 (m, 2H), 3.81 (dd, J = 9.3, 4.7 Hz, 1H), 3.47-3.36 (m, 1H), 3.22-3.05 (m, 3H), 2.71-2.50 (m, 2H), 1.58 (d, J = 6.1 Hz, 3H), 1.37 (d, J = 6.4 Hz, 3H). |
| 88 | 358.1 | 1H NMR (400 MHz, DMSO-d6) δ 7.93-7.87 (m, 2H), 7.59-7.50 (m, 2H), 4.59 (s, 2H), 4.48-4.37 (m, 1H), 4.00-3.89 (m, 2H), 3.10-2.96 (m, 2H), 2.94 (s, 3H), 2.85-2.79 (m, 2H), 2.45-2.36 (m, 1H), 2.11-1.87 (m, 3H), 1.50 (d, J = 6.2 Hz, 3H). |
| 89 | 350.2 | 1H NMR (400 MHz, DMSO-d6) δ 7.69 (d, J = 7.8 Hz, 1H), 7.63-7.61 (m, 1H), 7.42 (t, J = 7.7 Hz, 1H), 7.31-7.26 (m, 1H), 4.48-4.37 (m, 1H), 4.03-3.89 (m, 2H), 3.08-2.93 (m, 2H), 2.82 (t, J = 7.8 Hz, 2H), 2.49-2.45 (m, 1H), 2.44-2.35 (m, 1H), 2.07-1.90 (m, 3H), 1.87-1.80 (m, 1H), 1.48 (dd, J = 11.2, 5.4 Hz, 4H), 1.38 (ddd, J = 8.4, 6.4, 4.4 Hz, 1H). |
| 90 | 350.1 | 1H NMR (400 MHz, DMSO-d6) δ 7.71-7.67 (m, 1H), 7.64-7.61 (m, 1H), 7.42 (t, J = 7.7 Hz, 1H), 7.33-7.25 (m, 1H), 4.49-4.36 (m, 1H), 4.02-3.89 (m, 2H), 3.06-2.93 (m, 2H), 2.87-2.75 (m, 2H), 2.49-2.44 (m, 1H), 2.43-2.36 (m, 1H), 2.06-1.91 (m, 3H), 1.88-1.81 (m, 1H), 1.53-1.44 (m, 4H), 1.41-1.35 (m, 1H). |
| 91 | 353.2 | 1H NMR (400 MHz, DMSO-d6) δ 8.53 (t, J = 5.6 Hz, 1H), 8.00-7.92 (m, 4H), 4.48-4.38 (m, 1H), 4.01-3.92 (m, 2H), 3.53 (t, J = 6.2 Hz, 2H), 3.35 (q, J = 6.0 Hz, 2H), 3.09-2.94 (m, 2H), 2.83 (t, J = 7.7 Hz, 2H), 2.46-2.35 (m, 1H), 2.07-1.92 (m, 3H), 1.50 (d, J = 6.2 Hz, 3H). |
| 92 | 361.2 | 1H NMR (400 MHz, DMSO-d6) δ 8.30-8.27 (m, 1H), 8.06 (d, J = 7.8 Hz, 1H), 7.93 (d, J = 7.7 Hz, 1H), 7.72 (t, J = 7.8 Hz, 1H), 7.48 (s, 2H), 4.46-4.34 (m, 1H), 3.98-3.89 (m, 2H), 3.86-3.70 (m, 2H), 3.07-2.96 (m, 2H), 2.83 (t, J = 7.7 Hz, 2H), 2.33-2.20 (m, 2H), 2.07-1.98 (m, 2H). |
| 93 | 324.2 | 1H NMR (400 MHz, DMSO-d6) δ 8.24 (s, 2H), 8.07 (s, 1H), 8.02-7.92 (m, 4H), 7.44 (d, J = 30.5 Hz, 2H), 4.40-4.30 (m, 1H), 4.23 (dd, J = 9.4, 7.4 Hz, 1H), 3.96-3.88 (m, 1H), 3.79-3.68 (m, 1H), 3.11-3.01 (m, 2H), 2.84 (t, J = 7.8 Hz, 2H), 2.07-1.99 (m, 2H), 1.54 (d, J = 6.3 Hz, 3H). |
| 94 | 417.1 | $^1$H NMR (400 MHz,) δ 7.87-7.81 (m, 1H), 7.78-7.74 (m, 1H), 7.62-7.60 (m, 1H), 4.67-4.54 (m, 1H), 4.42-4.31 (m, 1H), 4.30-4.15 (m, 2H), 3.84-3.75 (m, 1H), 3.50-3.34 (m, 1H), 3.22-3.08 (m, 3H), 2.68-2.50 (m, 2H), 1.58 (d, J = 6.2 Hz, 3H), 1.37 (d, J = 6.4 Hz, 3H). |

TABLE 1-continued

MS and NMR DATA

| Example No | ES/MS m/z (M + H)+ | 1H NMR |
|---|---|---|
| 95 | 325.2 | 1H NMR (400 MHz, DMSO-d6) δ 8.07 (s, 1H), 7.98 (d, J = 8.5 Hz, 2H), 7.91 (d, J = 8.4 Hz, 2H), 7.48 (s, 1H), 4.48-4.38 (m, 1H), 4.00-3.90 (m, 2H), 3.82-3.71 (m, 2H), 3.05-2.97 (m, 2H), 2.83 (t, J = 7.7 Hz, 2H), 2.38-2.16 (m, 2H), 2.06-1.97 (m, 2H). |
| 96 | 237.2 | 1H NMR (400 MHz, Chloroform-d) δ 7.94-7.87 (m, 2H), 7.52-7.43 (m, 3H), 3.14 (t, J = 7.3 Hz, 2H), 3.00 (t, J = 7.7 Hz, 2H), 2.33-2.24 (m, 1H), 2.12 (p, J = 7.6 Hz, 2H), 1.23-1.14 (m, 2H), 1.07-1.00 (m, 2H). |
| 97 | 251.2 | 1H NMR (400 MHz, Chloroform-d) δ 7.99-7.92 (m, 2H), 7.54-7.41 (m, 3H), 3.85 (p, J = 8.5 Hz, 1H), 3.17 (t, J = 7.4 Hz, 2H), 3.05 (t, J = 7.7 Hz, 2H), 2.61-2.48 (m, 2H), 2.44-2.34 (m, 2H), 2.20-1.89 (m, 4H). |
| 98 | 291.2 | 1:1 mixture of diastereomers: 1H NMR (400 MHz, Chloroform-d) δ 8.11-7.99 (m, 2H), 7.63-7.52 (m, 3H), 3.76-3.64 (m, 0.5H), 3.42-3.24 (m, 4.5H), 2.85-2.78 (m, 0.5H), 2.64-2.56 (m, 0.5H), 2.46-2.40 (m, 1H), 2.34-2.13 (m, 3H), 2.04-1.91 (m, 0.5H), 1.82-1.41 (m, 4.5H), 1.40-1.30 (m, 1H), 1.25-1.10 (m, 1H). |
| 99 | 252.1 | 1H NMR (400 MHz, DMSO-d6) δ 9.25-8.62 (m, 2H), 8.09-7.89 (m, 2H), 7.65-7.47 (m, 3H), 4.51-3.95 (m, 5H), 3.27-3.12 (m, 2H), 3.04-2.94 (m, 2H), 2.14-2.05 (m, 2H). |
| 100 | 348.2 | 1H NMR (400 MHz, DMSO-d6) δ 8.12-8.07 (m, 4H), 4.52-4.37 (m, 1H), 4.04-3.86 (m, 2H), 3.13-2.97 (m, 2H), 2.84 (t, J = 7.7 Hz, 2H), 2.61 (s, 3H), 2.46-2.36 (m, 1H), 2.10-1.90 (m, J = 7.7 Hz, 3H), 1.51 (d, J = 6.1 Hz, 3H). |
| 101 | 346.1 | 1H NMR (400 MHz, DMSO-d6) δ 8.17-8.11 (m, 2H), 7.97-7.91 (m, 2H), 7.90-7.84 (m, 2H), 4.43 (q, J = 6.7 Hz, 1H), 4.03-3.83 (m, 5H), 3.15-2.95 (m, 2H), 2.84 (t, J = 7.8 Hz, 2H), 2.45-2.33 (m, 1H), 2.08-1.89 (m, 3H), 1.51 (d, J = 6.2 Hz, 3H). |
| 102 | 332.2 | 1H NMR (400 MHz, DMSO-d6) δ 8.63-8.57 (m, 1H), 8.08-7.96 (m, 4H), 7.83-7.78 (m, 1H), 6.61-6.56 (m, 1H), 4.55-4.38 (m, 1H), 4.07-3.90 (m, 2H), 3.14-2.96 (m, 2H), 2.85 (t, J = 7.8 Hz, 2H), 2.49-2.32 (m, 1H), 2.09-1.93 (m, 3H), 1.52 (d, J = 6.2 Hz, 3H). |
| 103 | 332.1 | 1H NMR (400 MHz, DMSO-d6) δ 7.97-7.92 (m, 4H), 7.77 (d, J = 2.2 Hz, 1H), 6.80 (d, J = 2.2 Hz, 1H), 4.50-4.40 (m, 1H), 4.05-3.90 (m, 2H), 3.15-2.96 (m, 2H), 2.84 (t, J = 7.8 Hz, 2H), 2.47-2.36 (m, 1H), 2.10-1.93 (m, 3H), 1.52 (d, J = 6.2 Hz, 3H)." |
| 104 | 334.1 | 1H NMR (400 MHz, DMSO-d6) δ 8.17 (d, J = 8.5 Hz, 2H), 8.11 (d, J = 8.4 Hz, 2H), 4.50-4.37 (m, 1H), 4.04-3.88 (m, 2H), 3.09-3.01 (m, 2H), 2.84 (t, J = 7.7 Hz, 2H), 2.45-2.35 (m, 1H), 2.09-1.90 (m, 3H), 1.51 (d, J = 6.2 Hz, 3H). |
| 105 | 323.1 | 1H NMR (400 MHz, DMSO-d6) δ 8.10-8.04 (m, 1H), 8.03-7.89 (m, 4H), 7.50-7.37 (m, 1H), 4.14-4.05 (m, 1H), 3.99-3.89 (m, 1H), 3.54-3.44 (m, 1H), 3.09-2.94 (m, 2H), 2.86-2.78 (m, 2H), 2.40-2.28 (m, 1H), 2.08-1.89 (m, 2H), 1.51-1.34 (m, 3H), 1.22-1.11 (m, 3H). |
| 106 | 323.1 | 1H NMR (400 MHz, DMSO-d6) δ 8.07 (s, 1H), 8.00-7.88 (m, 4H), 7.47 (s, 1H), 4.17-4.08 (m, 1H), 3.99-3.90 (m, 1H), 3.54-3.48 (m, 1H), 3.11-2.94 (m, 2H), 2.84 (t, J = 7.8 Hz, 2H), 2.38-2.28 (m, 1H), 2.08-1.94 (m, 2H), 1.49 (d, J = 6.2 Hz, 3H), 1.17 (d, J = 6.8 Hz, 3H). |
| 107 | 323.1 | 1H NMR (400 MHz, DMSO-d6) δ 8.07 (s, 1H), 8.00-7.88 (m, 4H), 7.47 (s, 1H), 4.17-4.08 (m, 1H), 3.99-3.90 (m, 1H), 3.54-3.48 (m, 1H), 3.11-2.94 (m, 2H), 2.84 (t, J = 7.8 Hz, 2H), 2.38-2.28 (m, 1H), 2.08-1.94 (m, 2H), 1.49 (d, J = 6.2 Hz, 3H), 1.17 (d, J = 6.8 Hz, 3H). |
| 108 | 323.1 | 1H NMR (400 MHz, DMSO-d6) δ 8.06 (s, 1H), 8.03-7.92 (m, 4H), 7.46 (s, 1H), 4.55-4.39 (m, 1H), 4.15-4.02 (m, 1H), 3.12-2.92 (m, 2H), 2.88-2.61 (m, 3H), 2.41-2.25 (m, 1H), 2.10-1.89 (m, 2H), 1.39 (d, J = 6.5 Hz, 3H), 1.18 (d, J = 7.3 Hz, 3H). |
| 109 | 323.1 | 1H NMR (400 MHz, DMSO-d6) δ 8.06 (s, 1H), 8.03-7.92 (m, 4H), 7.46 (s, 1H), 4.55-4.39 (m, 1H), 4.15-4.02 (m, 1H), 3.12-2.92 (m, 2H), 2.88-2.61 (m, 3H), 2.41-2.25 (m, 1H), 2.10-1.89 (m, 2H), 1.39 (d, J = 6.5 Hz, 3H), 1.18 (d, J = 7.3 Hz, 3H). |
| 110 | 337.1 | 1H NMR (400 MHz, DMSO-d6) δ 8.38 (d, J = 1.6 Hz, 1H), 8.16 (d, J = 8.4 Hz, 1H), 7.94 (dd, J = 8.4, 1.7 Hz, 1H), 4.51-4.41 (m, 1H), 4.06-3.90 (m, 2H), 3.17-3.00 (m, 2H), 2.88-2.78 (m, 5H), 2.47-2.36 (m, 1H), 2.11-1.93 (m, 3H), 1.52 (d, J = 6.2 Hz, 3H)." |
| 111 | 319.1 | 1H NMR (400 MHz, DMSO-d6) δ 8.09-8.02 (m, 1H), 8.01-7.94 (m, 4H), 7.50-7.42 (m, 1H), 4.93-4.82 (m, 1H), 4.07-3.99 (m, 1H), 3.99-3.91 (m, 1H), 3.44 (d, J = 2.0 Hz, 1H), 3.14-2.97 (m, J = 7.2 Hz, 2H), 2.85 (t, J = 7.7 Hz, 2H), 2.68-2.58 (m, 1H), 2.42-2.30 (m, 1H), 2.09-1.97 (m, 2H). |

TABLE 1-continued

MS and NMR DATA

| Example No | ES/MS m/z (M + H)+ | 1H NMR |
|---|---|---|
| 112 | 365.2 | 1H NMR (400 MHz, DMSO-d6) δ 7.68 (d, J = 7.7 Hz, 1H), 7.62-7.56 (m, 2H), 7.42 (t, J = 7.7 Hz, 1H), 7.26 (d, J = 7.7 Hz, 1H), 6.93 (s, 1H), 4.26-4.16 (m, 1H), 4.14-4.00 (m, 2H), 3.73-3.58 (m, 1H), 3.09-2.93 (m, 2H), 2.83 (t, J = 7.8 Hz, 2H), 2.35-2.26 (m, 1H), 2.09-1.95 (m, 2H), 1.91-1.84 (m, 1H), 1.48 (d, J = 5.9 Hz, 3H), 1.41-1.33 (m, 1H), 1.25-1.17 (m, 1H). |
| 113 | 366.1 | 1H NMR (400 MHz, DMSO-d6) δ 7.72-7.67 (m, 1H), 7.63-7.60 (m, 1H), 7.42 (t, J = 7.7 Hz, 1H), 7.32-7.26 (m, 1H), 4.22-4.14 (m, 1H), 4.10-3.97 (m, 2H), 3.66-3.57 (m, 1H), 3.08-2.94 (m, 2H), 2.81 (t, J = 7.8 Hz, 2H), 2.48-2.45 (m, 1H), 2.06-1.93 (m, 2H), 1.89-1.81 (m, 1H), 1.51-1.44 (m, 4H), 1.40-1.32 (m, 1H). |
| 114 | 366.1 | 1H NMR (400 MHz, DMSO-d6) δ 7.72-7.67 (m, 1H), 7.63-7.60 (m, 1H), 7.42 (t, J = 7.7 Hz, 1H), 7.32-7.26 (m, 1H), 4.22-4.14 (m, 1H), 4.10-3.97 (m, 2H), 3.66-3.57 (m, 1H), 3.08-2.94 (m, 2H), 2.81 (t, J = 7.8 Hz, 2H), 2.48-2.45 (m, 1H), 2.06-1.93 (m, 2H), 1.89-1.81 (m, 1H), 1.51-1.44 (m, 4H), 1.40-1.32 (m, 1H). |
| 115 | 390.2 | 1H NMR (400 MHz, DMSO-d6) δ 7.95-7.92 (m, 1H), 7.77-7.71 (m, 1H), 7.53-7.42 (m, 2H), 4.49-4.39 (m, 1H), 4.06-3.89 (m, 2H), 3.12-2.91 (m, 2H), 2.84 (t, J = 7.8 Hz, 2H), 2.76-2.73 (m, 1H), 2.73-2.67 (m, 1H), 2.46-2.33 (m, 1H), 2.13-1.93 (m, 4H), 1.90-1.72 (m, 3H), 1.71-1.65 (m, 1H), 1.51 (d, J = 6.2 Hz, 3H), 1.34 (d, J = 6.3 Hz, 1H). |
| 116 | 352.2 | 1H NMR (400 MHz, DMSO-d6) δ 8.46-8.39 (m, 3H), 8.10 (s, 2H), 7.54 (s, 2H), 4.49-4.35 (m, 1H), 4.07-3.88 (m, 2H), 3.09-2.96 (m, 2H), 2.82 (t, J = 7.8 Hz, 2H), 2.44-2.32 (m, 1H), 2.08-1.90 (m, 3H), 1.50 (d, J = 6.2 Hz, 3H). |
| 117 | 334.1 | 1H NMR (400 MHz, DMSO-d6) δ 8.15-8.02 (m, 5H), 7.51 (s, 1H), 3.27 (t, J = 7.3 Hz, 2H), 3.11-3.04 (m, 4H), 2.50-2.47 (m, 2H), 2.22-2.17 (m, 3H), 2.17-2.09 (m, 2H). |
| 118 | 356.0 | 1H NMR (400 MHz, DMSO-d6) δ 8.60 (s, 1H), 8.30 (s, 1H), 4.46-4.34 (m, 1H), 4.03-3.85 (m, 2H), 3.01 (t, J = 7.4 Hz, 2H), 2.84 (t, J = 7.8 Hz, 2H), 2.45-2.35 (m, 1H), 2.18-2.06 (m, 2H), 2.02-1.91 (m, 1H), 1.51 (d, J = 6.2 Hz, 3H). |
| 119 | 731.2 (2M + Na)+ | 1H NMR (400 MHz, DMSO-d6) δ 8.56 (s, 1H), 8.26 (s, 1H), 7.41 (s, 1H), 7.24 (s, 1H), 4.47-4.37 (m, 1H), 4.04-3.85 (m, 2H), 3.01 (t, J = 7.4 Hz, 2H), 2.84 (t, J = 7.8 Hz, 2H), 2.45-2.36 (m, 1H), 2.18-2.05 (m, 2H), 2.03-1.92 (m, 1H), 1.52 (d, J = 6.2 Hz, 3H). |
| 120 | 322.1 | 1H NMR (400 MHz, DMSO-d6) δ 7.78 (s, 1H), 7.71 (d, J = 8.4 Hz, 1H), 7.56-7.50 (m, 1H), 4.48-4.36 (m, 1H), 4.03-3.85 (m, 2H), 3.12-2.95 (m, 2H), 2.82 (t, J = 7.8 Hz, 2H), 2.45-2.35 (m, 1H), 2.08-1.92 (m, 3H), 1.51 (d, J = 6.2 Hz, 3H). |
| 121 | 312.1 | 1H NMR (400 MHz, DMSO-d6) δ 8.64 (s, 1H), 7.93 (d, J = 1.7 Hz, 1H), 7.56 (d, J = 1.7 Hz, 1H), 4.48-4.34 (m, 1H), 4.05-3.82 (m, 2H), 3.01 (t, J = 7.4 Hz, 2H), 2.84 (t, J = 7.8 Hz, 2H), 2.47-2.36 (m, 1H), 2.12 (p, J = 7.5 Hz, 2H), 2.04-1.91 (m, 1H), 1.51 (d, J = 6.2 Hz, 3H). |
| 122 | 363.0 | 1H NMR (400 MHz, DMSO-d6) δ 8.38 (dd, J = 7.2, 2.3 Hz, 1H), 8.20-8.11 (m, 1H), 7.79 (s, 2H), 7.61-7.52 (m, 1H), 4.49-4.36 (m, 1H), 4.03-3.86 (m, 2H), 3.10-2.97 (m, 2H), 2.90-2.78 (m, 2H), 2.46-2.35 (m, 1H), 2.13-1.94 (m, 3H), 1.50 (d, J = 6.2 Hz, 3H). |
| 123 | 359.1 | 1H NMR (400 MHz, DMSO-d6) δ 8.45 (d, J = 1.8 Hz, 1H), 8.00 (dd, J = 7.9, 1.9 Hz, 1H), 7.52-7.45 (m, 3H), 4.48-4.38 (m, 1H), 4.03-3.86 (m, 2H), 3.12-2.94 (m, 2H), 2.82 (t, J = 7.8 Hz, 2H), 2.65 (s, 3H), 2.46-2.35 (m, 1H), 2.07-1.93 (m, 3H), 1.50 (d, J = 6.2 Hz, 3H). |
| 124 | 295.1 | 1H NMR (400 MHz, DMSO-d6) δ 8.12-7.96 (m, 5H), 7.48 (s, 1H), 4.50-4.36 (m, 1H), 4.03-3.87 (m, 2H), 3.41-3.31 (m, 4H), 2.46-2.36 (m, 1H), 2.04-1.94 (m, 1H), 1.51 (d, J = 6.2 Hz, 3H). |
| 125 | 311.1 | 1H NMR (400 MHz, DMSO-d6) δ 8.09-7.95 (m, 5H), 7.49 (s, 1H), 4.23-4.15 (m, 1H), 4.11-4.00 (m, 2H), 3.68-3.58 (m, 1H), 3.35 (s, 4H), 1.50 (d, J = 6.1 Hz, 3H). |
| 126 | 429.1 | 1H NMR (400 MHz, DMSO-d6) δ 8.50 (d, J = 2.2 Hz, 1H), 8.22 (dd, J = 8.6, 2.3 Hz, 1H), 7.77 (s, 2H), 7.69 (dd, J = 8.7, 1.9 Hz, 1H), 4.49-4.37 (m, 1H), 4.05-3.88 (m, 2H), 3.12-2.98 (m, 2H), 2.84 (t, J = 7.8 Hz, 2H), 2.47-2.36 (m, 1H), 2.12-1.90 (m, 3H), 1.50 (d, J = 6.1 Hz, 3H). |
| 127 | 338.1 | 1H NMR (400 MHz, DMSO-d6) δ 7.93 (d, J = 8.4 Hz, 2H), 7.74 (d, J = 8.4 Hz, 2H), 4.80 (d, J = 6.5 Hz, 2H), 4.72 (d, J = 6.4 Hz, 2H), 4.50-4.40 (m, 1H), 4.04-3.88 (m, 2H), 3.07-2.97 (m, 2H), 2.83 (t, J = 7.7 Hz, 2H), 2.45-2.34 (m, 1H), 2.07-1.93 (m, 3H), 1.50 (d, J = 6.2 Hz, 3H). |
| 128 | 345.1 | 1H NMR (400 MHz, DMSO-d6) δ 8.10 (s, 1H), 8.04-7.95 (m, 4H), 7.51 (s, 1H), 4.57-4.44 (m, 1H), 4.11-3.94 (m, 2H), 3.22-3.04 (m, 2H), 2.65-2.54 (m, 2H), 2.49-2.38 (m, 1H), 2.05-1.92 (m, 1H), 1.52 (d, J = 6.2 Hz, 3H). |

TABLE 1-continued

MS and NMR DATA

| Example No | ES/MS m/z (M + H)+ | 1H NMR |
|---|---|---|
| 129 | 361.1 | 1H NMR (400 MHz, DMSO-d6) δ 8.10 (s, 1H), 8.06-7.96 (m, 4H), 7.51 (s, 1H), 4.29-4.23 (m, 1H), 4.19-4.09 (m, 2H), 3.75-3.65 (m, 1H), 3.23-3.07 (m, 2H), 2.66-2.53 (m, 2H), 1.50 (d, J = 5.8 Hz, 3H). |
| 130 | 381.1 | 1H NMR (400 MHz, DMSO-d6) δ 8.00-7.87 (m, 1H), 7.45-7.30 (m, 1H), 7.30-7.17 (m, 1H), 4.09-3.57 (m, 3H), 2.74 (t, J = 7.6 Hz, 2H), 2.59 (t, J = 7.4 Hz, 2H), 2.44-2.30 (m, 1H), 1.98 (p, J = 7.6 Hz, 2H), 1.90-1.76 (m, 1H), 1.31 (d, J = 6.2 Hz, 3H). |
| 131 | 337.1 | 1H NMR (400 MHz, DMSO-d6) δ 9.03 (s, 3H), 7.99 (d, J = 8.4 Hz, 2H), 7.65 (d, J = 8.4 Hz, 2H), 5.00-4.92 (m, 4H), 4.46-4.36 (m, 1H), 4.00-3.86 (m, 2H), 3.08-2.95 (m, 2H), 2.82 (t, J = 7.7 Hz, 2H), 2.44-2.33 (m, 1H), 2.09-1.92 (m, 3H), 1.49 (d, J = 6.2 Hz, 3H). |
| 132 | 333.1 | 1H NMR (400 MHz, DMSO-d6) δ 11.89 (s, 1H), 7.95 (d, J = 9.5 Hz, 1H), 7.91-7.89 (m, 1H), 7.76 (d, J = 8.2 Hz, 1H), 7.70 (dd, J = 8.2, 1.5 Hz, 1H), 6.56 (d, J = 9.5 Hz, 1H), 4.49-4.38 (m, 1H), 4.07-3.87 (m, 2H), 3.12-2.97 (m, 2H), 2.84 (t, J = 7.8 Hz, 2H), 2.46-2.34 (m, 1H), 2.11-1.88 (m, 3H), 1.52 (d, J = 6.2 Hz, 3H). |
| 133 | 405.2 | 1H NMR (400 MHz, DMSO-d6) δ 8.04 (s, 1H), 7.99 (d, J = 9.5 Hz, 1H), 7.86 (d, J = 8.1 Hz, 1H), 7.77 (d, J = 8.1 Hz, 1H), 6.68 (d, J = 9.5 Hz, 1H), 4.56-4.39 (m, 3H), 4.07-3.91 (m, 2H), 3.23-3.01 (m, 2H), 2.85 (t, J = 7.7 Hz, 2H), 2.69-2.56 (m, 2H), 2.46-2.36 (m, 1H), 2.12-1.92 (m, 3H), 1.51 (d, 3H). |
| 134 | 364.2 | 1H NMR (400 MHz, DMSO-d6) δ 7.71 (s, 1H), 7.68-7.62 (m, 1H), 7.33 (d, J = 7.9 Hz, 1H), 4.51-4.36 (m, 1H), 4.04-3.88 (m, 2H), 3.19-3.06 (m, 2H), 3.05-2.89 (m, 2H), 2.86-2.72 (m, 3H), 2.65 (dt, J = 15.9, 6.1 Hz, 2H), 2.46-2.36 (m, 3H), 2.05-1.89 (m, 3H), 1.50 (d, J = 6.2 Hz, 3H). |
| 135 | 363.2 | 1H NMR (400 MHz, DMSO-d6) δ 7.71 (s, 1H), 7.68-7.61 (m, 1H), 7.36-7.29 (m, 2H), 6.79 (s, 1H), 4.50-4.38 (m, 1H), 4.05-3.87 (m, 2H), 3.15-2.91 (m, 4H), 2.88-2.72 (m, 3H), 2.68-2.57 (m, 2H), 2.46-2.35 (m, 1H), 2.23 (d, J = 7.4 Hz, 2H), 2.07-1.89 (m, 3H), 1.50 (d, J = 6.2 Hz, 3H). |
| 136 | 362.1 | 1H NMR (400 MHz, DMSO-d6) δ 7.73-7.60 (m, 2H), 7.52 (d, J = 7.9 Hz, 0.5H), 7.41 (d, J = 8.3 Hz, 0.5H), 4.56-4.38 (m, 1H), 4.11-3.86 (m, 2H), 3.41-2.89 (m, 5H), 2.89-2.76 (m, 2H), 2.46-2.25 (m, 3H), 2.14-1.90 (m, 4H), 1.59-1.42 (m, 3H). |
| 137 | 361.2 | 1H NMR (400 MHz, DMSO-d6) δ 7.64-7.56 (m, 2H), 7.38 (d, J = 7.8 Hz, 1H), 7.10 (s, 1H), 6.47 (s, 1H), 4.47-4.34 (m, 1H), 4.02-3.86 (m, 2H), 3.42-3.33 (m, 1H), 3.14-3.04 (m, 1H), 3.03-2.88 (m, 2H), 2.85-2.73 (m, 3H), 2.45-2.28 (m, 1H), 2.23-2.14 (m, 1H), 2.07-1.90 (m, 4H), 1.49 (d, J = 6.2 Hz, 3H). |
| 138 | 361.2 | 1H NMR (400 MHz, DMSO-d6) δ 7.70 (s, 1H), 7.69-7.63 (m, 1H), 7.50-7.42 (m, 2H), 6.92-6.83 (m, 1H), 4.48-4.34 (m, 1H), 4.01-3.88 (m, 2H), 3.33-3.20 (m, 1H), 3.09-2.89 (m, 3H), 2.84-2.77 (m, 2H), 2.77-2.71 (m, 1H), 2.44-2.34 (m, 1H), 2.30-2.21 (m, 1H), 2.07-1.91 (m, 4H), 1.49 (d, J = 6.1 Hz, 3H). |
| 139 | 350.1 | 1H NMR (400 MHz, DMSO-d6) δ 7.72 (s, 1H), 7.70-7.65 (m, 1H), 7.35 (d, J = 7.9 Hz, 1H), 4.51-4.39 (m, 1H), 4.09-3.87 (m, 2H), 3.39-3.27 (m, 1H), 3.26-3.12 (m, 4H), 3.07-2.91 (m, 2H), 2.83 (t, J = 7.7 Hz, 2H), 2.45-2.37 (m, 1H), 2.08-1.92 (m, 3H), 1.50 (d, J = 6.2 Hz, 3H). |
| 140 | 349.2 | 1H NMR (400 MHz, DMSO-d6) δ 7.70 (s, 1H), 7.68-7.61 (m, 1H), 7.43 (s, 1H), 7.33 (d, J = 7.9 Hz, 1H), 6.89 (s, 1H), 4.52-4.38 (m, 1H), 4.08-3.88 (m, 2H), 3.26-3.16 (m, 1H), 3.15-3.05 (m, 4H), 3.05-2.92 (m, 2H), 2.83 (t, J = 7.7 Hz, 2H), 2.47-2.36 (m, 1H), 2.06-1.93 (m, 3H), 1.50 (d, J = 6.2 Hz, 3H). |
| 141 | 339.1 | 1H NMR (400 MHz, DMSO-d6) δ 8.06 (s, 1H), 8.00-7.92 (m, 4H), 7.46 (s, 1H), 4.14 (q, J = 6.4 Hz, 1H), 3.89-3.71 (m, 2H), 3.11-2.97 (m, 2H), 2.83 (t, J = 7.7 Hz, 2H), 2.06-1.93 (m, 2H), 1.39 (d, J = 6.5 Hz, 3H), 1.32 (s, 3H). |
| 142 | 309.1 | 1H NMR (400 MHz, DMSO-d6) δ 8.07 (s, 1H), 8.00-7.96 (m, 4H), 7.46 (s, 1H), 3.62-3.50 (m, 4H), 3.03 (t, J = 7.2 Hz, 2H), 2.84 (t, J = 7.7 Hz, 2H), 2.02 (p, J = 7.6 Hz, 2H), 1.97-1.92 (m, 4H). |
| 143 | 332.1 | 1H NMR (400 MHz, DMSO-d6) δ 8.51 (d, J = 9.3 Hz, 1H), 8.42-8.36 (m, 1H), 8.34-8.29 (m, 1H), 7.78 (d, J = 8.7 Hz, 1H), 7.11 (d, J = 9.3 Hz, 1H), 4.50-4.36 (m, 1H), 4.05-3.86 (m, 2H), 3.18-2.97 (m, 2H), 2.83 (t, J = 7.7 Hz, 2H), 2.47-2.35 (m, 1H), 2.11-1.91 (m, 3H), 1.51 (d, J = 6.1 Hz, 3H). |
| 144 | 359.2 | 1H NMR (400 MHz, DMSO-d6) δ 8.34 (d, J = 8.3 Hz, 1H), 8.09 (s, 1H), 7.82 (d, J = 8.4 Hz, 1H), 7.73-7.65 (m, 2H), 7.64-7.59 (m, 1H), 7.58-7.51 (m, 2H), 4.49-4.34 (m, 1H), 4.05-3.84 (m, 2H), 2.90 (t, J = 7.7 Hz, 2H), 2.63-2.53 (m, 2H), 2.45-2.34 (m, 1H), 2.04-1.88 (m, 3H), 1.43 (d, J = 6.2 Hz, 3H). |
| 145 | 421.2 | 1H NMR (400 MHz, DMSO-d6) δ 7.84-7.72 (m, 2H), 7.53-7.43 (m, 2H), 4.51-4.42 (m, 1H), 4.07-3.80 (m, 4H), 3.77-3.20 (m, |

TABLE 1-continued

| Example No | ES/MS m/z (M + H)+ | 1H NMR |
|---|---|---|
| | | 4H), 3.10-2.91 (m, 2H), 2.84 (t, J = 7.7 Hz, 2H), 2.45-2.35 (m, 1H), 2.05-1.92 (m, 6H), 1.50 (d, J = 6.1 Hz, 3H). |
| 146 | 420.2 | 1H NMR (400 MHz, DMSO-d6) δ 7.83-7.70 (m, 2H), 7.51-7.41 (m, 3H), 7.05-6.93 (m, 2H), 4.45-4.39 (m, 1H), 4.05-3.45 (m, 6H), 3.35-2.93 (m, 4H), 2.82 (t, J = 7.7 Hz, 2H), 2.47-2.35 (m, 1H), 2.08-1.93 (m, 6H), 1.50 (d, J = 6.1 Hz, 3H). |
| 147 | 348.1 | 1H NMR (400 MHz, DMSO-d6) δ 12.44 (s, 1H), 9.04 (s, 1H), 8.88 (s, 1H), 8.29 (d, J = 8.6 Hz, 1H), 8.07-7.81 (m, 3H), 4.53-4.34 (m, 1H), 4.05-3.86 (m, 2H), 3.15-2.96 (m, 2H), 2.84 (t, J = 7.7 Hz, 2H), 2.46-2.30 (m, 1H), 2.13-1.91 (m, 3H), 1.51 (d, J = 6.2 Hz, 3H). |
| 148 | 390.2 | 1H NMR (400 MHz, DMSO-d6) δ 7.74-7.57 (m, 2H), 7.26-7.15 (m, 1H), 4.54-4.38 (m, 1H), 4.06-3.90 (m, 2H), 3.22-2.76 (m, 6H), 2.46-2.30 (m, 1H), 2.13-1.75 (m, 8H), 1.60-1.44 (m, 3H), 1.41-1.22 (m, 2H). |
| 149 | 351.2 | 1H NMR (400 MHz, DMSO-d6) δ 8.42 (t, J = 5.4 Hz, 1H), 7.90 (d, J = 8.2 Hz, 1H), 7.64-7.58 (m, 1H), 7.53-7.47 (m, 1H), 4.48-4.38 (m, 1H), 4.34 (t, J = 4.7 Hz, 2H), 4.06-3.86 (m, 2H), 3.36 (q, J = 5.1 Hz, 2H), 3.10-2.92 (m, 2H), 2.82 (t, J = 7.7 Hz, 2H), 2.45-2.35 (m, 1H), 2.08-1.90 (m, 3H), 1.50 (d, J = 6.1 Hz, 3H). |
| 150 | 351.2 | 1H NMR (400 MHz, DMSO-d6) δ 8.50-8.37 (m, 2H), 8.03 (dd, J = 8.6, 2.4 Hz, 1H), 7.14 (d, J = 8.6 Hz, 1H), 4.52-4.41 (m, 1H), 4.41-4.36 (m, 2H), 4.07-3.88 (m, 2H), 3.44-3.36 (m, 2H), 3.13-2.93 (m, 2H), 2.91-2.78 (m, 2H), 2.48-2.36 (m, 1H), 2.12-1.89 (m, 3H), 1.51 (d, J = 6.2 Hz, 3H). |
| 151 | 305.2 | 1H NMR (400 MHz, DMSO-d6) δ 11.28 (s, 1H), 7.66 (d, J = 8.0 Hz, 1H), 7.60 (d, J = 8.3 Hz, 1H), 7.23 (t, J = 7.6 Hz, 1H), 7.10 (s, 1H), 7.06 (t, J = 7.5 Hz, 1H), 4.62-4.47 (m, 1H), 4.17-3.98 (m, 2H), 3.08 (t, J = 7.4 Hz, 2H), 2.87 (t, J = 7.8 Hz, 2H), 2.51-2.43 (m, 1H), 2.13 (p, J = 7.7 Hz, 2H), 2.06-1.92 (m, 1H), 1.56 (d, J = 6.2 Hz, 3H). |
| 152 | 348.2 | 1H NMR (400 MHz, DMSO-d6) δ 11.42 (s, 1H), 8.23 (s, 1H), 7.86 (s, 1H), 7.79-7.73 (m, 1H), 7.62-7.56 (m, 1H), 7.15 (s, 1H), 7.10 (s, 1H), 4.55-4.43 (m, 1H), 4.13-3.93 (m, 2H), 3.08 (t, J = 7.4 Hz, 2H), 2.84 (t, J = 7.8 Hz, 2H), 2.46-2.41 (m, 1H), 2.17-2.04 (m, 2H), 2.03-1.93 (m, 1H), 1.54 (d, J = 6.1 Hz, 3H). |
| 153 | 349.2 | 1H NMR (400 MHz, DMSO-d6) δ 11.49 (s, 1H), 7.86 (d, J = 8.1 Hz, 1H), 7.76 (d, J = 7.3 Hz, 1H), 7.52 (s, 1H), 7.30 (t, J = 7.8 Hz, 1H), 4.57-4.43 (m, 1H), 4.12-3.94 (m, 2H), 3.07 (t, J = 7.4 Hz, 2H), 2.83 (t, J = 7.9 Hz, 2H), 2.50-2.35 (m, 1H), 2.19-2.08 (m, 2H), 2.05-1.90 (m, 1H), 1.54 (d, J = 6.1 Hz, 3H). |
| 154 | 348.2 | 1H NMR (400 MHz, DMSO-d6) δ 11.38 (s, 1H), 8.21 (s, 1H), 7.93-7.85 (m, 2H), 7.56 (s, 1H), 7.21-7.11 (m, 2H), 4.55-4.43 (m, 1H), 4.08-3.91 (m, 2H), 3.08 (t, J = 7.5 Hz, 2H), 2.86 (t, J = 7.8 Hz, 2H), 2.49-2.35 (m, 1H), 2.22-2.08 (m, 2H), 2.07-1.96 (m, 1H), 1.60 (d, J = 6.2 Hz, 3H). |
| 155 | 349.2 | 1H NMR (400 MHz, DMSO-d6) δ 11.49 (s, 1H), 7.86 (d, J = 8.1 Hz, 1H), 7.76 (d, J = 7.3 Hz, 1H), 7.52 (s, 1H), 7.30 (t, J = 7.8 Hz, 1H), 4.57-4.43 (m, 1H), 4.12-3.94 (m, 2H), 3.07 (t, J = 7.4 Hz, 2H), 2.83 (t, J = 7.9 Hz, 2H), 2.50-2.35 (m, 1H), 2.19-2.08 (m, 2H), 2.05-1.90 (m, 1H), 1.54 (d, J = 6.1 Hz, 3H). |
| 156 | 348.1 | 1H NMR (400 MHz, DMSO-d6) δ 11.42 (s, 1H), 7.86 (s, 1H), 7.75 (d, J = 8.2 Hz, 1H), 7.57-7.49 (m, 2H), 7.32-7.22 (m, 2H), 4.60-4.48 (m, 1H), 4.17-3.98 (m, 2H), 3.08 (t, J = 7.4 Hz, 2H), 2.87 (t, J = 7.8 Hz, 2H), 2.49-2.40 (m, 1H), 2.20-2.05 (m, 2H), 2.06-1.92 (m, 1H), 1.56 (d, J = 6.1 Hz, 3H). |
| 157 | 359.1 | 1H NMR (400 MHz, DMSO-d6) δ 8.07 (s, 1H), 7.97 (d, J = 8.1 Hz, 2H), 7.64 (d, J = 8.1 Hz, 2H), 7.47 (s, 1H), 4.52-4.36 (m, 1H), 4.02-3.86 (m, 2H), 2.72-2.54 (m, 2H), 2.47-2.24 (m, 3H), 2.04-1.90 (m, 1H), 1.83-1.69 (m, 2H), 1.46 (d, J = 6.2 Hz, 3H)." |
| 158 | 375.1 | 1H NMR (400 MHz, DMSO-d6) δ 8.07 (s, 1H), 7.97 (d, J = 8.0 Hz, 2H), 7.65 (d, J = 8.1 Hz, 2H), 7.47 (s, 1H), 4.22-4.16 (m, 1H), 4.13-4.02 (m, 2H), 3.69-3.58 (m, 1H), 2.76-2.56 (m, 2H), 2.41-2.22 (m, 2H), 1.85-1.69 (m, 2H), 1.44 (d, J = 5.9 Hz, 3H). |
| 159 | 353.1 | 1H NMR (400 MHz, DMSO-d6) δ 9.03 (s, 3H), 7.99 (d, J = 8.2 Hz, 2H), 7.66 (d, J = 8.2 Hz, 2H), 4.99-4.90 (m, 4H), 4.21-4.14 (m, 1H), 4.12-3.98 (m, 2H), 3.68-3.55 (m, 1H), 3.11-2.94 (m, 2H), 2.83 (t, J = 7.7 Hz, 2H), 2.09-1.94 (m, 2H), 1.47 (d, J = 6.2 Hz, 3H). |
| 160 | 373.2 | 1H NMR (400 MHz, DMSO-d6) δ 9.07 (s, 3H), 8.05 (d, J = 8.2 Hz, 2H), 7.70 (d, J = 8.2 Hz, 2H), 5.02-4.89 (m, 4H), 4.54-4.43 (m, 1H), 4.09-3.91 (m, 2H), 3.21-3.04 (m, 2H), 2.67-2.52 (m, 2H), 2.48-2.42 (m, 1H), 2.08-1.93 (m, 1H), 1.52 (d, J = 6.2 Hz, 3H). |
| 161 | 389.1 | 1H NMR (400 MHz, DMSO-d6) δ 9.06 (s, 3H), 8.05 (d, J = 8.3 Hz, 2H), 7.71 (d, J = 8.1 Hz, 2H), 5.01-4.90 (m, 4H), 4.30-4.22 (m, 1H), 4.17-4.07 (m, 2H), 3.74-3.65 (m, 1H), 3.22-3.04 (m, 2H), 2.68-2.52 (m, 2H), 1.50 (d, J = 5.7 Hz, 3H). |

TABLE 1-continued

| | | MS and NMR DATA |
|---|---|---|
| Example No | ES/MS m/z (M + H)+ | 1H NMR |
| 162 | 326.1 | 1H NMR (400 MHz, DMSO-d6) δ 8.06 (d, J = 8.2 Hz, 2H), 7.99 (d, J = 8.2 Hz, 2H), 4.23-4.14 (m, 1H), 4.11-3.99 (m, 2H), 3.65-3.59 (m, 1H), 3.09-2.94 (m, 2H), 2.83 (t, J = 7.7 Hz, 2H), 2.06-1.95 (m, 2H), 1.48 (d, J = 6.1 Hz, 3H). |
| 163 | 317.1 | 1H NMR (400 MHz, DMSO-d6) δ 9.68 (s, 1H), 8.67 (d, J = 6.1 Hz, 1H), 8.58 (s, 1H), 8.46 (d, J = 8.6 Hz, 1H), 8.39-8.30 (m, 2H), 4.52-4.38 (m, 1H), 4.08-3.90 (m, 2H), 3.21-3.04 (m, 2H), 2.87 (t, J = 7.7 Hz, 2H), 2.48-2.36 (m, 1H), 2.10-1.91 (m, 3H), 1.53 (d, J = 6.1 Hz, 3H). |
| 164 | 367.1 | 1H NMR (400 MHz, DMSO-d6) δ 8.42 (t, J = 5.4 Hz, 1H), 7.90 (d, J = 8.2 Hz, 1H), 7.65-7.59 (m, 1H), 7.51-7.49 (m, 1H), 4.34 (t, J = 4.7 Hz, 2H), 4.23-4.14 (m, 1H), 4.11-3.99 (m, 2H), 3.66-3.58 (m, 1H), 3.36 (q, J = 5.0 Hz, 2H), 3.09-2.94 (m, 2H), 2.82 (t, J = 7.7 Hz, 2H), 2.06-1.93 (m, 2H), 1.48 (d, J = 6.1 Hz, 3H). |
| 165 | 387.1 | 1H NMR (400 MHz, DMSO-d6) δ 8.46 (t, J = 5.5 Hz, 1H), 7.93 (d, J = 8.2 Hz, 1H), 7.70-7.63 (m, 1H), 7.57-7.52 (m, 1H), 4.55-4.43 (m, 1H), 4.36 (t, J = 4.7 Hz, 2H), 4.11-3.93 (m, 2H), 3.37 (q, J = 5.0 Hz, 2H), 3.19-3.06 (m, 2H), 2.66-2.53 (m, 2H), 2.49-2.39 (m, 1H), 2.07-1.92 (m, 1H), 1.51 (d, J = 6.2 Hz, 3H). |
| 166 | 403.1 | 1H NMR (400 MHz, DMSO-d6) δ 8.46 (t, J = 5.2 Hz, 1H), 7.93 (d, J = 8.3 Hz, 1H), 7.73-7.64 (m, 1H), 7.57-7.51 (m, 1H), 4.36 (t, J = 4.7 Hz, 2H), 4.29-4.22 (m, 1H), 4.17-4.07 (m, 2H), 3.73-3.64 (m, 1H), 3.37 (q, J = 5.1 Hz, 2H), 3.21-3.06 (m, 2H), 2.69-2.53 (m, 2H), 1.50 (d, J = 5.7 Hz, 3H). |
| 167 | 371.2 | 1H NMR (400 MHz, DMSO-d6) δ 8.12-7.94 (m, 5H), 7.48 (s, 1H), 7.43-7.36 (m, 2H), 7.35-7.29 (m, 2H), 5.44-5.32 (m, 1H), 5.00-4.80 (m, 2H), 3.17-2.99 (m, 2H), 2.89 (t, J = 7.7 Hz, 2H), 2.11-2.01 (m, 2H), 1.59 (d, J = 6.2 Hz, 3H). |
| 168 | 362.1 | 1H NMR (400 MHz, DMSO-d6) δ 9.18-9.09 (m, 1H), 8.52-8.44 (m, 1H), 8.23 (s, 1H), 8.19 (d, J = 8.2 Hz, 1H), 7.79 (s, 1H), 4.32-4.24 (m, 1H), 4.19-4.10 (m, 2H), 3.76-3.68 (m, 1H), 3.25-3.13 (m, 2H), 2.69-2.53 (m, 2H), 1.50 (d, J = 5.9 Hz, 3H). |
| 169 | 325.1 | 1H NMR (400 MHz, DMSO-d6) δ 8.06 (s, 1H), 7.98 (d, J = 8.3 Hz, 2H), 7.93 (d, J = 8.2 Hz, 2H), 7.47 (s, 1H), 4.59-4.44 (m, 2H), 4.27-4.19 (m, 1H), 3.82-3.73 (m, 1H), 3.08-2.95 (m, 2H), 2.82 (t, J = 7.7 Hz, 2H), 2.08-1.94 (m, 2H), 1.38 (d, J = 6.0 Hz, 3H). |
| 170 | 405.1 | 1H NMR (400 MHz, DMSO-d6) δ 7.91 (d, J = 8.0 Hz, 1H), 7.68-7.61 (m, 3H), 7.59-7.53 (m, 1H), 4.33-4.21 (m, 3H), 4.15-4.09 (m, 2H), 3.74-3.64 (m, 1H), 3.22-3.10 (m, 2H), 2.65-2.53 (m, 2H), 1.50 (d, J = 5.7 Hz, 3H), 1.43 (t, J = 6.9 Hz, 3H). |
| 171 | 375.2 | 1H NMR (400 MHz, DMSO-d6) δ 8.58 (q, J = 4.6 Hz, 1H), 8.05-7.93 (m, 4H), 4.30-4.22 (m, 1H), 4.19-4.07 (m, 2H), 3.72-3.65 (m, 1H), 3.22-3.07 (m, 2H), 2.82 (d, J = 4.4 Hz, 3H), 2.65-2.53 (m, 2H), 1.50 (d, J = 5.7 Hz, 3H). |
| 172 | 377.1 | 1H NMR (400 MHz, DMSO-d6) δ 8.08 (s, 1H), 8.05-7.95 (m, 4H), 7.53 (s, 1H), 7.47 (s, 1H), 5.29-5.01 (m, 1H), 4.86-4.64 (m, 1H), 4.65-4.48 (m, 1H), 4.16-3.98 (m, 1H), 3.14-2.96 (m, 2H), 2.87 (t, J = 7.8 Hz, 2H), 2.12-1.98 (m, 2H), 1.31-1.16 (m, 1H). |
| 173 | 347.1 | 1H NMR (400 MHz, DMSO-d6) δ 8.09 (s, 1H), 8.04 (d, J = 1.4 Hz, 4H), 7.49 (s, 1H), 7.40 (d, J = 1.5 Hz, 1H), 6.11-6.04 (m, 1H), 4.63 (t, J = 8.1 Hz, 2H), 4.44-4.36 (m, 2H), 3.13 (t, J = 7.2 Hz, 2H), 2.95 (t, J = 7.7 Hz, 2H), 2.14-2.03 (m, 2H). |
| 174 | 347.1 | 1H NMR (400 MHz, DMSO-d6) δ 8.13 (s, 1H), 8.09-7.98 (m, 4H), 7.53 (s, 1H), 7.46 (d, J = 2.2 Hz, 1H), 7.25 (d, J = 2.2 Hz, 1H), 4.79 (t, J = 8.5 Hz, 2H), 4.51-4.40 (m, 2H), 3.18 (t, J = 7.3 Hz, 2H), 3.06 (t, J = 7.7 Hz, 2H), 2.14 (p, J = 7.6 Hz, 2H). |
| 175 | 333.1 | 1H NMR (400 MHz, DMSO-d6) δ 11.93 (s, 1H), 8.19 (d, J = 1.9 Hz, 1H), 8.09 (dd, J = 8.7, 2.0 Hz, 1H), 8.04 (d, J = 9.6 Hz, 1H), 7.41 (d, J = 8.7 Hz, 1H), 6.59-6.50 (m, 1H), 4.51-4.41 (m, 1H), 4.06-3.90 (m, 2H), 3.15-3.01 (m, 2H), 2.84 (t, J = 7.8 Hz, 2H), 2.47-2.37 (m, 1H), 2.12-1.93 (m, 3H), 1.52 (d, J = 6.2 Hz, 3H). |
| 176 | 418.1 | 1H NMR (400 MHz, DMSO-d6) δ 11.59 (s, 1H), 9.10 (s, 1H), 8.37 (s, 1H), 7.92 (d, J = 8.3 Hz, 1H), 7.85 (s, 1H), 7.69 (dd, J = 8.3, 1.8 Hz, 1H), 4.29-4.22 (m, 1H), 4.17-4.07 (m, 2H), 3.72-3.65 (m, 1H), 3.20-3.05 (m, 2H), 2.68-2.52 (m, 2H), 2.13 (s, 3H), 1.51 (d, J = 5.8 Hz, 3H). |
| 177 | 401.1 | 1H NMR (400 MHz, DMSO-d6) δ 8.16 (t, J = 5.9 Hz, 1H), 7.89 (dd, J = 7.9, 1.8 Hz, 1H), 7.81 (d, J = 1.7 Hz, 1H), 7.66 (d, J = 8.0 Hz, 1H), 4.29-4.23 (m, 1H), 4.18-4.07 (m, 2H), 3.70 (dd, J = 8.9, 4.3 Hz, 1H), 3.22-3.10 (m, 2H), 3.00-2.91 (m, 2H), 2.84 (t, J = 7.1 Hz, 2H), 2.64-2.52 (m, 2H), 1.99-1.86 (m, 2H), 1.50 (d, J = 5.8 Hz, 3H). |

TABLE 1-continued

MS and NMR DATA

| Example No | ES/MS m/z (M + H)+ | 1H NMR |
|---|---|---|
| 178 | 391.1 | 1H NMR (400 MHz, DMSO-d6) δ 7.90 (d, J = 8.0 Hz, 1H), 7.74-7.69 (m, 1H), 7.65 (d, J = 1.5 Hz, 2H), 7.60-7.56 (m, 1H), 4.29-4.23 (m, 1H), 4.16-4.08 (m, 2H), 3.96 (s, 3H), 3.70 (dd, J = 9.0, 4.4 Hz, 1H), 3.25-3.10 (m, 2H), 2.67-2.54 (m, 2H), 1.51 (d, J = 5.8 Hz, 3H). |
| 179 | 375.1 | 1H NMR (400 MHz, DMSO-d6) δ 8.07 (s, 1H), 8.00-7.96 (m, 2H), 7.65-7.60 (m, 2H), 7.47 (s, 1H), 4.20-4.13 (m, 1H), 4.11-4.01 (m, 2H), 3.64-3.59 (m, 1H), 3.24-3.03 (m, 2H), 2.98-2.91 (m, 2H), 2.40-2.26 (m, 2H), 1.43 (d, J = 6.1 Hz, 3H). |
| 180 | 370.2 | 1H NMR (400 MHz, DMSO-d6) δ 7.91 (d, J = 1.9 Hz, 1H), 7.80 (dt, J = 6.9, 1.9 Hz, 1H), 7.56-7.48 (m, 2H), 4.70-4.60 (m, 2H), 4.42 (dt, J = 7.8, 6.1 Hz, 1H), 4.37-4.27 (m, 2H), 3.98 (m, 1H), 3.93 (m, 1H), 3.02 (m, 2H), 2.82 (m, 2H), 2.40 (dtd, J = 10.7, 8.5, 4.7 Hz, 1H), 2.11-1.89 (m, 3H), 1.50 (d, J = 6.2 Hz, 3H). |
| 181 | 337.1 | 1H NMR (400 MHz, DMSO-d6) δ 8.05 (s, 1H), 7.97 (d, J = 8.5 Hz, 2H), 7.91 (d, J = 8.5 Hz, 2H), 7.44 (s, 1H), 4.26-4.18 (m, 1H), 4.12-4.05 (m, 2H), 3.70-3.59 (m, 2H), 3.21-3.14 (m, 1H), 2.92-2.81 (m, 2H), 2.40-2.24 (m, 2H), 1.49 (d, J = 5.8 Hz, 3H). |
| 182 | 356.1 | 1H NMR (400 MHz, DMSO-d6) δ 7.88 (s, 1H), 7.87 (d, J = 8.1 Hz, 1H), 7.52 (d, J = 8.0 Hz, 1H), 4.59 (s, 2H), 4.57 (s, 2H), 4.44 (p, J = 6.7 Hz, 1H), 4.00 (tt, J = 8.5, 4.2 Hz, 1H), 3.94 (d, J = 8.1 Hz, 1H), 3.10-2.90 (m, 2H), 2.84 (t, J = 7.7 Hz, 2H), 2.42 (qd, J = 8.9, 4.8 Hz, 1H), 2.11-1.89 (m, 3H), 1.50 (d, J = 6.2 Hz, 3H). |
| 183 | 338.1 | 1H NMR (400 MHz, DMSO-d6) δ 8.45 (s, 1H), 7.80 (d, J = 6.9 Hz, 1H), 7.60 (d, J = 6.9 Hz, 1H), 4.42 (q, J = 6.6 Hz, 1H), 4.03-3.84 (m, 2H), 3.12 (t, J = 7.4 Hz, 2H), 2.86 (t, J = 7.8 Hz, 2H), 2.42 (s, 2H), 2.14 (m, 1H), 1.99 (p, J = 8.1 Hz, 1H), 1.52 (d, J = 6.1 Hz, 3H) |
| 184 | 348.1 | 1H NMR (400 MHz, DMSO-d6) δ 11.73 (s, 1H), 8.15 (s, 1H), 7.99 (s, 1H), 7.89-7.77 (m, 1H), 7.52 (s, 1H), 7.41 (s, 1H), 7.22 (d, J = 2.1 Hz, 1H), 4.52-4.31 (m, 1H), 3.95 (dd, J = 18.0, 9.2 Hz, 2H), 3.07 (h, J = 7.9 Hz, 2H), 2.81 (t, J = 7.7 Hz, 2H), 2.45-2.26 (m, 1H), 2.10-1.86 (m, 3H), 1.52 (d, J = 6.2 Hz, 3H). |
| 185 | 332.2 | 1H NMR (400 MHz, DMSO-d6) δ 8.23-8.04 (m, 4H), 7.96-7.82 (m, 2H), 4.43 (dt, J = 7.8, 6.2 Hz, 1H), 4.03-3.83 (m, 2H), 3.05 (hept, J = 7.6, 6.9 Hz, 2H), 2.83 (t, J = 7.7 Hz, 2H), 2.45-2.34 (m, 1H), 2.07-1.84 (m, 3H), 1.51 (d, J = 6.2 Hz, 3H). |
| 186 | 335.2 | 1H NMR (400 MHz, DMSO-d6) δ 8.04 (s, 1H), 7.97 (d, J = 7.9 Hz, 1H), 7.78 (d, J = 7.9 Hz, 1H), 4.54 (s, 2H), 4.50-4.38 (m, 1H), 4.03-3.97 (m, 2H), 3.10 (s, 3H), 3.08-2.92 (m, 2H), 2.84 (t, J = 7.7 Hz, 2H), 2.45-2.32 (m, 1H), 2.13-1.93 (m, 3H), 1.51 (d, J = 6.2 Hz, 3H). |
| 187 | 320.9 | 1H NMR (400 MHz, DMSO-d6) δ 8.67 (s, 1H), 8.04 (s, 1H), 8.00-7.93 (m, 1H), 7.78 (d, J = 7.9 Hz, 1H), 4.54-4.33 (m, 3H), 4.05-3.85 (m, 2H), 3.13-2.94 (m, 2H), 2.83 (t, J = 7.8 Hz, 2H), 2.45-2.33 (m, 1H), 2.08-1.87 (m, 3H), 1.50 (d, J = 6.2 Hz, 3H). |
| 188 | 295.1 | 1H NMR (400 MHz, DMSO-d6) δ 8.21 (s, 2H), 7.98-7.81 (m, 2H), 7.64-7.49 (m, 2H), 4.46-4.33 (m, 1H), 4.20-4.04 (m, 2H), 4.02-3.85 (m, 2H), 3.09-2.89 (m, 2H), 2.81 (t, J = 7.7 Hz, 2H), 2.44-2.32 (m, 1H), 2.11-1.93 (m, 3H), 1.49 (d, J = 6.2 Hz, 3H). |
| 189 | 345.1 | 1H NMR (400 MHz, DMSO-d6) δ 8.09-7.98 (m, 2H), 7.98-7.88 (m, 2H), 7.45 (s, 2H), 4.42 (dt, J = 7.9, 6.2 Hz, 1H), 4.05-3.80 (m, 2H), 3.08-2.92 (m, 2H), 2.82 (t, J = 7.7 Hz, 2H), 2.45-2.29 (m, 1H), 2.09-1.88 (m, 2H), 1.49 (d, J = 6.1 Hz, 3H). |
| 190 | 323.2 | 1H NMR (400 MHz, DMSO-d6) δ 8.45 (s, 2H), 7.99 (t, J = 1.8 Hz, 1H), 7.85 (dt, J = 7.5, 1.4 Hz, 1H), 7.68-7.57 (m, 2H), 4.55-4.33 (m, 1H), 4.09-3.83 (m, 2H), 3.17-2.87 (m, 2H), 2.87-2.73 (m, 2H), 2.44-2.32 (m, 1H), 2.09-1.87 (m, 3H), 1.68 (s, 6H), 1.50 (d, J = 6.2 Hz, 3H). |
| 191 | 309.1 | 1H NMR (400 MHz, DMSO-d6) δ 8.07-7.89 (m, 5H), 7.46 (s, 1H), 4.42 (q, J = 6.6 Hz, 1H), 4.04-3.85 (m, 2H), 3.12-2.95 (m, 2H), 2.81 (t, J = 7.7 Hz, 2H), 2.44-2.31 (m, 1H), 2.14-1.87 (m, 3H), 1.49 (d, J = 6.2 Hz, 3H). |
| 192 | 345.1 | 1H NMR (400 MHz, DMSO-d6) δ 8.33 (d, J = 1.8 Hz, 1H), 8.08 (d, J = 7.8 Hz, 1H), 7.98-7.89 (m, 1H), 7.71 (t, J = 7.8 Hz, 1H), 7.46 (s, 2H), 4.42 (q, J = 6.6 Hz, 1H), 4.04-3.85 (m, 2H), 3.11-2.94 (m, 2H), 2.82 (t, J = 7.7 Hz, 2H), 2.44-2.28 (m, 1H), 2.13-1.88 (m, 3H), 1.50 (d, J = 6.2 Hz, 3H). |
| 193 | 348.2 | 1H NMR (400 MHz, Methanol-d4) δ 8.17-8.05 (m, 2H), 8.03-7.92 (m, 2H), 7.62 (s, 2H), 4.29 (dd, J = 9.2, 6.1 Hz, 1H), 4.23-4.11 (m, 2H), 3.72 (dd, J = 9.1, 4.6 Hz, 1H), 3.11-2.96 (m, 2H), 2.88 (t, J = 7.8 Hz, 2H), 2.15-1.98 (m, 2H), 1.49 (d, J = 6.1 Hz, 3H). |

TABLE 1-continued

MS and NMR DATA

| Example No | ES/MS m/z (M + H)+ | 1H NMR |
|---|---|---|
| 194 | 351.1 | 1H NMR (400 MHz, DMSO-d6) δ 8.05 (s, 1H), 7.97 (dd, J = 8.0, 1.4 Hz, 1H), 7.78 (d, J = 7.9 Hz, 1H), 4.54 (s, 2H), 4.20 (dd, J = 8.8, 5.9 Hz, 1H), 4.12-4.01 (m, 2H), 3.64 (dd, J = 8.7, 4.8 Hz, 1H), 3.06-2.95 (m, 2H), 2.88-2.80 (m, 2H), 2.10-1.95 (m, 2H), 1.49 (d, J = 6.0 Hz, 4H). |
| 195 | 389.1 | 1H NMR (400 MHz, DMSO-d6) δ 7.89 (d, J = 8.1 Hz, 2H), 7.64 (t, J = 6.3 Hz, 1H), 7.49 (d, J = 8.0 Hz, 2H), 4.27-4.17 (m, 3H), 4.15-4.02 (m, 2H), 3.65 (dd, J = 8.8, 4.6 Hz, 1H), 3.03 (s, 2H), 2.91 (s, 3H), 2.84 (t, J = 7.8 Hz, 2H), 2.10-1.92 (m, 2H), 1.49 (d, J = 5.8 Hz, 3H). |
| 196 | 337.1 | 1H NMR (400 MHz, DMSO-d6) δ 8.66 (s, 1H), 8.04 (s, 1H), 7.97 (dd, J = 8.0, 1.4 Hz, 1H), 7.78 (d, J = 7.9 Hz, 1H), 4.46 (s, 2H), 4.25-4.13 (m, 1H), 4.13-3.98 (m, 2H), 3.08-2.97 (m, 2H), 2.83 (dd, J = 8.6, 6.9 Hz, 2H), 2.09 (s, 2H), 2.06-1.91 (m, 2H), 1.48 (d, J = 6.1 Hz, 3H). |
| 197 | 325.1 | 1H NMR (400 MHz, DMSO-d6) δ 8.06 (s, 1H), 7.96 (q, J = 8.5 Hz, 4H), 7.45 (d, J = 5.3 Hz, 1H), 4.18 (dd, J = 8.6, 6.3 Hz, 1H), 4.10-3.97 (m, 2H), 3.62 (dd, J = 8.7, 5.0 Hz, 1H), 3.03 (h, J = 8.4 Hz, 2H), 2.82 (t, J = 7.8 Hz, 2H), 2.05-1.90 (m, 2H), 1.48 (d, J = 6.2 Hz, 3H). |
| 198 | 363.0 | 1H NMR (400 MHz, DMSO-d6) δ 8.17-7.86 (m, 4H), 7.46 (s, 2H), 5.28-5.01 (m, 1H), 4.50-4.20 (m, 2H), 4.08-3.78 (m, 1H), 3.18-2.91 (m, 2H), 2.85 (t, J = 7.8 Hz, 2H), 2.14-1.87 (m, 2H), 1.53 (d, J = 6.5 Hz, 3H). |
| 199 | 361.5 | 1H NMR (400 MHz, DMSO-d6) δ 8.12-7.77 (m, 4H), 7.46 (s, 2H), 4.22-4.09 (m, 1H), 4.09-3.96 (m, 2H), 3.62 (dd, J = 8.7, 5.0 Hz, 1H), 3.02 (h, J = 8.4 Hz, 2H), 2.83 (t, J = 7.8 Hz, 2H), 2.12-1.91 (m, 2H), 1.48 (d, J = 6.2 Hz, 3H). |
| 200 | 326.9 | 1H NMR (400 MHz, DMSO-d6) δ 8.07 (s, 1H), 8.04-7.88 (m, 4H), 7.47 (s, 1H), 5.23-5.00 (m, 1H), 4.51-4.19 (m, 2H), 4.03-3.83 (m, 1H), 3.14-2.93 (m, 2H), 2.84 (t, J = 7.8 Hz, 2H), 2.12-1.97 (m, 2H), 1.53 (d, J = 6.5 Hz, 3H). |
| 201 | 312.9 | 1H NMR (400 MHz, DMSO-d6) δ 8.24 (s, 2H), 8.01-7.92 (m, 2H), 7.65-7.50 (m, 2H), 5.13 (ddt, J = 57.0, 5.9, 3.9 Hz, 1H), 4.43-4.23 (m, 2H), 4.15-4.05 (m, 2H), 3.97-3.92 (m, 1H), 3.11-2.93 (m, 2H), 2.84 (t, J = 7.7 Hz, 2H), 2.11-1.95 (m, 2H), 1.53 (d, J = 6.5 Hz, 3H). |
| 202 | 310.9 | 1H NMR (400 MHz, DMSO-d6) δ 8.19 (s, 2H), 7.97-7.88 (m, 2H), 7.63-7.51 (m, 2H), 4.19-4.05 (m, 4H), 4.05-3.95 (m, 1H), 3.65-3.56 (m, 1H), 3.10-2.91 (m, 2H), 2.82 (t, J = 7.7 Hz, 2H), 2.10-1.93 (m, 2H), 1.47 (d, J = 6.3 Hz, 3H). |
| 203 | 353.1 | 1H NMR (400 MHz, DMSO-d6) δ 8.14-8.08 (m, 2H), 7.78-7.67 (m, 1H), 5.25-4.97 (m, 1H), 4.54 (s, 2H), 4.46-4.26 (m, 2H), 4.02-3.86 (m, 1H), 3.10 (s, 3H), 3.05 (q, J = 6.9 Hz, 2H), 2.91-2.78 (m, 2H), 2.13-1.96 (m, 2H), 1.54 (d, J = 6.5 Hz, 3H). |
| 204 | 351.1 | 1H NMR (400 MHz, Chloroform-d) δ 8.29 (s, 1H), 8.14 (dd, J = 8.0, 1.6 Hz, 1H), 7.58 (d, J = 8.0 Hz, 1H), 4.66-4.57 (m, 1H), 4.54-4.45 (m, 3H), 4.33 (dt, J = 6.5, 4.1 Hz, 1H), 4.07 (dd, J = 10.2, 4.4 Hz, 1H), 3.25 (s, 3H), 3.16-3.05 (m, 4H), 2.25-2.12 (m, 2H), 1.62 (d, J = 6.5 Hz, 3H). |
| 205 | 346.1 | 1H NMR (400 MHz, DMSO-d6) δ 9.23 (d, J = 1.9 Hz, 1H), 9.05 (d, J = 2.3 Hz, 1H), 8.60 (t, 1H), 7.74 (s, 2H), 4.52-4.31 (m, 1H), 4.02-3.88 (m, 2H), 3.14-2.96 (m, 2H), 2.84 (t, J = 7.7 Hz, 2H), 2.46-2.35 (m, 1H), 2.11-1.91 (m, 3H), 1.50 (d, J = 6.2 Hz, 3H). |
| 206 | 335.1 | 1H NMR (400 MHz, DMSO-d6) δ 8.15-8.07 (m, 2H), 7.71 (d, J = 8.4 Hz, 1H), 4.53 (s, 2H), 4.44-4.35 (m, 1H), 4.03-3.87 (m, 2H), 3.10 (s, 3H), 3.01 (dd, J = 15.0, 7.9 Hz, 2H), 2.81 (t, J = 7.7 Hz, 2H), 2.39 (s, 1H), 2.08-1.92 (m, 3H), 1.50 (d, J = 6.1 Hz, 3H). |
| 207 | 321.1 | 1H NMR (400 MHz, DMSO-d6) δ 8.68 (s, 1H), 8.19-8.04 (m, 2H), 7.71 (d, J = 7.9 Hz, 1H), 4.45 (s, 3H), 4.06-3.85 (m, 2H), 3.11-2.97 (m, 2H), 2.83 (t, J = 7.7 Hz, 2H), 2.46-2.36 (m, 1H), 2.08-1.95 (m, 3H), 1.51 (d, J = 6.1 Hz, 3H). |
| 208 | 359.1 | 1H NMR (400 MHz, DMSO-d6) δ 8.32 (s, 1H), 8.07 (d, J = 7.7 Hz, 1H), 7.92 (d, J = 8.0 Hz, 1H), 7.71 (t, J = 7.8 Hz, 1H), 7.46 (s, 2H), 4.60-4.26 (m, 2H), 3.13-2.87 (m, 2H), 2.81 (t, J = 7.7 Hz, 2H), 2.11-1.93 (m, 4H), 1.50-1.35 (m, 6H). |
| 209 | 361.1 | 1H NMR (400 MHz, DMSO-d6) δ 8.34 (s, 1H), 8.08 (d, J = 7.9 Hz, 1H), 7.98-7.86 (m, 1H), 7.72 (t, J = 7.8 Hz, 1H), 7.47 (s, 2H), 4.23-4.11 (m, 1H), 4.11-3.99 (m, 2H), 3.73-3.57 (m, 1H), 3.11-2.96 (m, 2H), 2.83 (t, J = 7.8 Hz, 2H), 2.09-1.89 (m, 2H), 1.48 (d, J = 6.1 Hz, 3H). |
| 210 | 363.1 | 1H NMR (400 MHz, DMSO-d6) δ 8.34 (d, J = 1.9 Hz, 1H), 8.09 (d, J = 7.9 Hz, 1H), 7.93 (d, J = 7.9 Hz, 1H), 7.72 (t, J = 7.8 Hz, 1H), 7.48 (s, 2H), 5.24-5.02 (m, 1H), 4.46-4.24 (m, 2H), 4.03-3.85 (m, 1H), 3.12-2.98 (m, 2H), 2.85 (t, J = 7.7 Hz, 2H), 2.09-2.00 (m, 2H), 1.54 (d, J = 6.5 Hz, 3H). |

TABLE 1-continued

MS and NMR DATA

| Example No | ES/MS m/z (M + H)+ | 1H NMR |
|---|---|---|
| 211 | 280.1 | 1H NMR (400 MHz, DMSO-d6) δ 8.47 (s, 1H), 7.66 (dd, J = 6.7, 3.0 Hz, 2H), 7.62-7.50 (m, 3H), 4.50-4.30 (m, 1H), 4.00-3.81 (m, 2H), 3.48 (s, 3H), 2.43-2.35 (m, 1H), 2.07-1.88 (m, 1H), 1.48 (d, J = 6.1 Hz, 3H). |
| 212 | 277.1 | 1H NMR (400 MHz, DMSO-d6) δ 8.92 (s, 1H), 8.39 (d, J = 8.1 Hz, 1H), 7.80-7.72 (m, 2H), 7.70-7.58 (m, 3H), 7.37 (dd, J = 8.2, 4.8 Hz, 1H), 4.69 (d, J = 7.2 Hz, 1H), 4.18 (ddd, J = 18.7, 13.6, 7.5 Hz, 2H), 2.59-2.53 (m, 1H), 2.13-1.95 (m, 1H), 1.58 (d, J = 6.2 Hz, 3H). |
| 213 | 331.1 | 1H NMR (400 MHz, Chloroform-d) δ 8.24 (s, 1H), 4.76-4.65 (m, 1H), 4.41-4.18 (m, 2H), 3.13 (t, J = 7.9 Hz, 2H), 3.06 (t, J = 7.4 Hz, 2H), 2.65-2.47 (m, 1H), 2.33-2.18 (m, 2H), 2.18-2.04 (m, 1H), 1.72 (s, 6H), 1.60 (d, J = 6.2 Hz, 3H). |
| 214 | 359.1 | 1H NMR (400 MHz, DMSO-d6) δ 8.28 (d, J = 1.8 Hz, 1H), 8.14 (d, J = 7.8 Hz, 1H), 7.87 (d, J = 7.8 Hz, 1H), 7.75 (t, J = 7.8 Hz, 1H), 7.57 (q, J = 5.0 Hz, 1H), 4.51-4.25 (m, 1H), 4.08-3.95 (m, 1H), 3.95-3.84 (m, 1H), 3.11-2.94 (m, 1H), 2.82 (t, J = 7.7 Hz, 5H), 2.48-2.29 (m, 3H), 2.14-1.80 (m, 2H), 1.50 (d, J = 6.2 Hz, 3H). |
| 215 | 374.4 | 1H NMR (400 MHz, DMSO-d6) δ 8.29-8.11 (m, 2H), 7.91-7.69 (m, 2H), 4.41 (p, J = 6.5 Hz, 1H), 4.06-3.79 (m, 2H), 3.03 (p, J = 8.3, 7.9 Hz, 2H), 2.82 (t, J = 7.7 Hz, 2H), 2.65 (s, 6H), 2.45-2.32 (m, 1H), 2.09-1.90 (m, 3H), 1.49 (d, J = 6.2 Hz, 3H). |
| 216 | 365.9 | 1H NMR (400 MHz, DMSO-d6) δ 8.75 (t, J = 5.9 Hz, 1H), 8.35 (d, J = 1.9 Hz, 1H), 8.09-7.92 (m, 2H), 7.61 (t, J = 7.7 Hz, 1H), 7.39 (s, 1H), 7.04 (s, 1H), 4.52-4.36 (m, 1H), 4.07-3.91 (m, 1H), 3.98-3.75 (m, 3H), 3.09-2.95 (m, 2H), 2.83 (t, J = 7.7 Hz, 2H), 2.45-2.30 (m, 1H), 2.13-1.86 (m, 2H), 1.50 (d, J = 6.1 Hz, 3H), 1.31-1.19 (m, 1H). |
| 217 | 381.1 | 1H NMR (400 MHz, DMSO-d6) δ 8.62 (t, J = 5.5 Hz, 1H), 8.30 (t, J = 1.8 Hz, 1H), 8.01 (dt, J = 7.8, 1.5 Hz, 1H), 7.92 (dt, 1H), 7.59 (t, J = 7.8 Hz, 1H), 4.48-4.37 (m, 1H), 4.06-3.96 (m, 1H), 3.96-3.86 (m, 1H), 3.11-2.96 (m, 2H), 2.82 (t, J = 7.8 Hz, 2H), 2.56-2.51 (m, 2H), 2.45-2.34 (m, 1H), 2.11-1.94 (m, 3H), 1.50 (d, J = 6.2 Hz, 3H). |
| 218 | 399.2 | 1H NMR (400 MHz, DMSO-d6) δ 9.15 (t, J = 6.0 Hz, 1H), 8.38 (d, J = 1.9 Hz, 1H), 8.07-7.95 (m, 2H), 7.61 (t, J = 7.8 Hz, 1H), 7.33 (t, J = 4.3 Hz, 4H), 7.29-7.19 (m, 1H), 4.49 (d, J = 9.7 Hz, 1H), 4.47-4.36 (m, 1H), 4.01-3.84 (m, 2H), 3.12-2.93 (m, 2H), 2.83 (t, J = 7.8 Hz, 2H), 2.45-2.32 (m, 1H), 2.15-1.91 (m, 3H), 1.50 (d, J = 6.2 Hz, 3H). |
| 219 | 416.1 | 1H NMR (400 MHz, DMSO-d6) δ 8.70 (t, J = 5.7 Hz, 1H), 8.31 (t, J = 1.8 Hz, 1H), 8.03 (dt, J = 7.7, 1.4 Hz, 1H), 7.92 (dt, J = 7.7, 1.4 Hz, 1H), 7.61 (t, J = 7.8 Hz, 1H), 6.95 (s, 2H), 4.42 (q, J = 6.7 Hz, 1H), 4.07-3.95 (m, 1H), 3.95-3.85 (m, 1H), 3.71-3.64 (m, 2H), 3.30-3.24 (m, 1H), 3.17 (s, 1H), 3.10-2.96 (m, 2H), 2.82 (t, J = 7.7 Hz, 2H), 2.47-2.34 (m, 1H), 2.10-1.92 (m, 3H), 1.50 (d, J = 6.2 Hz, 3H). |
| 220 | 380.2 | 1H NMR (400 MHz, Chloroform-d) δ 8.25 (t, J = 1.7 Hz, 1H), 7.98 (dt, J = 7.8, 1.4 Hz, 1H), 7.88 (d, J = 7.8 Hz, 1H), 7.68 (s, 1H), 7.58 (t, J = 7.8 Hz, 1H), 6.31 (s, 1H), 5.91 (s, 1H), 4.84 (h, J = 6.2 Hz, 1H), 4.39 (dtd, J = 41.4, 9.8, 6.1 Hz, 2H), 3.77 (t, J = 5.7 Hz, 2H), 3.14-3.05 (m, 3H), 3.05-2.97 (m, 1H), 2.71-2.55 (m, 3H), 2.28-2.15 (m, 2H), 2.15-2.00 (m, 1H), 1.63 (d, J = 6.3 Hz, 3H). |
| 221 | 302.1 | 1H NMR (400 MHz, Methanol-d4) δ 8.29 (s, 1H), 4.58-4.49 (m, 1H), 4.47 (s, 2H), 4.16-4.03 (m, 1H), 4.03-3.94 (m, 1H), 3.22 (p, J = 1.7 Hz, 2H), 3.02 (t, J = 7.5 Hz, 2H), 2.91 (t, J = 7.8 Hz, 2H), 2.56-2.40 (m, 1H), 2.17 (p, J = 7.8 Hz, 2H), 2.07-1.94 (m, 1H), 1.49 (d, J = 6.3 Hz, 3H). |
| 222 | 349.1 | 1H NMR (400 MHz, Methanol-d4) δ 8.16-7.99 (m, 1H), 7.90 (dd, J = 8.1, 1.7 Hz, 1H), 7.88-7.76 (m, 1H), 4.81-4.69 (m, 1H), 4.36-4.08 (m, 2H), 3.70 (t, J = 6.7 Hz, 2H), 3.20-2.99 (m, 9H), 2.71-2.57 (m, 1H), 2.29-2.07 (m, 3H), 1.63 (d, J = 6.3 Hz, 3H). |
| 223 | 346.1 | 1H NMR (400 MHz, Chloroform-d) δ 8.86 (d, J = 5.0 Hz, 1H), 8.45 (s, 1H), 7.96 (d, J = 4.6 Hz, 1H), 5.14 (s, 2H), 4.82-4.69 (m, 1H), 4.42-4.13 (m, 2H), 3.16-3.00 (m, 4H), 2.68-2.55 (m, 1H), 2.27-2.17 (m, 2H), 2.14-2.01 (m, 1H), 1.61 (d, J = 6.3 Hz, 3H). |
| 224 | 346.1 | 1H NMR (400 MHz, DMSO-d6) δ 8.47 (dd, J = 7.9, 1.0 Hz, 1H), 8.23 (t, J = 7.8 Hz, 1H), 7.99 (dd, J = 7.8, 1.0 Hz, 1H), 7.49 (s, 2H), 4.51-4.34 (m, 1H), 4.11-3.85 (m, 2H), 3.40-3.23 (m, 2H), 2.82 (t, J = 7.8 Hz, 2H), 2.46-2.33 (m, 1H), 2.10-1.93 (m, 3H), 1.52 (d, J = 6.2 Hz, 3H). |
| 225 | 322.1 | 1H NMR (400 MHz, Chloroform-d) δ 8.51 (d, J = 1.8 Hz, 1H), 8.19-8.06 (m, 2H), 7.62 (t, J = 7.8 Hz, 1H), 4.85-4.71 (m, 1H), 4.47-4.27 (m, 2H), 3.22-2.98 (m, 6H), 2.69-2.57 (m, 1H), 2.30-2.16 (m, 1H), 2.16-2.05 (m, 1H), 1.64 (d, J = 6.2 Hz, 3H), 1.39-1.30 (m, 2H), 1.27 (t, J = 7.2 Hz, 3H). |

TABLE 1-continued

| MS and NMR DATA | | |
|---|---|---|
| Example No | ES/MS m/z (M + H)+ | 1H NMR |
| 226 | 327.1 | 1H NMR (400 MHz, DMSO-d6) δ 8.06 (s, 1H), 8.02-7.91 (m, 4H), 7.46 (s, 1H), 5.25-4.98 (m, 1H), 4.45-4.27 (m, 2H), 4.01-3.79 (m, 1H), 3.15-2.96 (m, 2H), 2.84 (t, J = 7.8 Hz, 2H), 2.09-1.97 (m, 2H), 1.53 (d, J = 6.5 Hz, 2H). |
| 227 | 367.2 | 1H NMR (400 MHz, Chloroform-d) δ 7.73 (s, 1H), 7.51 (t, J = 4.7 Hz, 1H), 7.49-7.30 (m, 3H), 4.82 (h, J = 6.1 Hz, 1H), 4.66-4.29 (m, 4H), 3.97 (s, 2H), 3.05 (t, J = 7.8 Hz, 2H), 3.02-2.85 (m, 2H), 2.69-2.62 (m, 2H), 2.58 (s, 2H), 2.28-1.95 (m, 2H), 1.62 (d, J = 6.3 Hz, 3H). |
| 228 | 381.2 | 1H NMR (400 MHz, Chloroform-d) δ 7.70 (s, 1H), 7.66-7.49 (m, 2H), 7.49-7.43 (m, 2H), 4.87-4.75 (m, 1H), 4.66-4.27 (m, 4H), 3.09 (t, J = 7.8 Hz, 2H), 3.06-2.91 (m, 2H), 2.71-2.57 (m, 1H), 2.27-2.02 (m, 2H), 1.65-1.59 (m, 3H), 1.59-1.54 (m, 3H), 1.50 (d, J = 2.6 Hz, 3H), 1.45 (d, J = 2.2 Hz, 2H). |
| 229 | 367.2 | 1H NMR (400 MHz, Chloroform-d) δ 7.68 (s, 1H), 7.55 (d, J = 5.1 Hz, 1H), 7.52-7.40 (m, 3H), 4.92-4.71 (m, 1H), 4.65-4.29 (m, 4H), 3.14-3.02 (m, 2H), 3.02-2.90 (m, 2H), 2.70-2.58 (m, 1H), 2.27-2.00 (m, 2H), 1.67-1.58 (m, 4H), 1.58-1.40 (m, 4H). |
| 230 | 367.2 | 1H NMR (400 MHz, Chloroform-d) δ 7.69 (s, 1H), 7.59-7.55 (m, 1H), 7.55-7.40 (m, 3H), 4.89-4.78 (m, 1H), 4.66 (dd, J = 15.2, 6.6 Hz, 1H), 4.45-4.27 (m, 4H), 3.12-2.87 (m, 4H), 2.71-2.58 (m, 1H), 2.27-2.03 (m, 2H), 1.62 (d, J = 6.3 Hz, 3H), 1.57 (t, J = 6.9 Hz, 1H), 1.54-1.41 (m, 4H). |
| 231 | 353.2 | 1H NMR (400 MHz, Chloroform-d) δ 7.67 (s, 1H), 7.52 (d, J = 4.9 Hz, 1H), 7.44 (d, J = 4.7 Hz, 2H), 4.93-4.76 (m, 1H), 4.63 (dd, J = 15.1, 6.4 Hz, 2H), 4.57-4.27 (m, 4H), 4.21 (s, 2H), 3.06 (t, J = 7.8 Hz, 2H), 3.02-2.87 (m, 2H), 2.70-2.58 (m, 1H), 2.23-2.00 (m, 3H), 1.62 (d, J = 6.3 Hz, 3H). |
| 232 | 360.1 | 1H NMR (400 MHz, DMSO-d6) δ 8.77 (s, 1H), 8.58 (d, J = 1.6 Hz, 1H), 8.30-8.11 (m, 2H), 8.11-8.02 (m, 2H), 4.46 (q, J = 6.6 Hz, 1H), 4.13-3.88 (m, 2H), 3.24-3.04 (m, 2H), 2.85 (t, J = 7.8 Hz, 2H), 2.45-2.35 (m, 1H), 2.16-1.90 (m, 3H), 1.53 (d, J = 6.2 Hz, 3H). |
| 233 | 321.2 | 1H NMR (400 MHz, Methanol-d4) δ 8.10-7.95 (m, 2H), 7.70-7.54 (m, 2H), 4.88-4.78 (m, 1H), 4.55-4.15 (m, 8H), 3.22-3.05 (m, 4H), 2.76-2.64 (m, 1H), 2.34-2.10 (m, 3H), 1.65 (d, J = 6.3 Hz, 3H). |
| 234 | 385.1 | 1H NMR (400 MHz, DMSO-d6) δ 9.34 (t, J = 4.2 Hz, 1H), 8.34 (d, J = 1.6 Hz, 1H), 8.31 (dd, J = 8.0, 1.8 Hz, 1H), 8.17 (d, J = 8.1 Hz, 1H), 5.09 (d, J = 4.2 Hz, 2H), 4.43 (q, J = 6.7 Hz, 1H), 4.09-3.86 (m, 2H), 3.13-2.92 (m, J = 6.9 Hz, 2H), 2.83 (t, J = 7.8 Hz, 2H), 2.43-2.36 (m, 1H), 2.06 (s, 1H), 2.05-1.90 (m, 2H), 1.50 (d, J = 6.2 Hz, 3H). |
| 235 | 339.1 | 1H NMR (400 MHz, DMSO-d6) δ 8.06 (s, 1H), 8.03-7.87 (m, 4H), 7.46 (s, 1H), 4.27-4.10 (m, 2H), 3.91 (dt, J = 6.2, 4.5 Hz, 1H), 3.43 (s, 1H), 3.25 (d, J = 8.7 Hz, 3H), 3.16-2.98 (m, 2H), 2.82 (t, J = 7.7 Hz, 2H), 2.08-1.89 (m, 2H), 1.53 (d, J = 6.4 Hz, 3H). |
| 236 | 387.1 | 1H NMR (400 MHz, Methanol-d4) δ 8.24 (s, 1H), 8.14 (dd, J = 8.0, 1.6 Hz, 1H), 7.63 (d, J = 7.9 Hz, 1H), 4.49 (s, 2H), 4.36-4.22 (m, 1H), 4.22-4.10 (m, 2H), 3.81-3.66 (m, 1H), 3.18-3.04 (m, 5H), 2.57-2.41 (m, 2H), 1.49 (d, J = 6.2 Hz, 3H). |
| 237 | 320.2 | 1H NMR (400 MHz, DMSO-d6) δ 8.00 (d, J = 2.1 Hz, 4H), 5.38-4.77 (m, 1H), 4.28-3.90 (m, 3H), 3.09 (q, J = 8.3, 7.8 Hz, 1H), 2.99-2.79 (m, 1H), 2.77-2.63 (m, 1H), 2.06 (t, J = 7.9 Hz, 2H), 1.35-1.09 (m, 2H). |
| 238 | 337.3 | 1H NMR (400 MHz, DMSO-d6) δ 8.10 (s, 1H), 8.08-7.98 (m, 4H), 7.49 (s, 1H), 4.65 (m, 1H), 3.18 (m, 2H), 2.98 (m, 2H), 2.65 (m, 1H), 2.44 (m, 1H), 2.28 (m, 1H), 2.11 (m, 2H), 1.79-1.62 (m, 1H), 1.30 (d, J = 6.2 Hz, 3H). |
| 239 | 371.1 | 1H NMR (400 MHz, CD3CN) δ 8.50-8.39 (m, 2H), 8.08 (d, J = 8.6 Hz, 1H), 4.52 (dt, J = 8.1, 6.2 Hz, 1H), 4.14-3.84 (m, 2H), 3.09 (td, J = 7.1, 5.3 Hz, 2H), 2.88 (t, J = 7.8 Hz, 2H), 2.15-2.02 (m, 4H), 1.56 (d, J = 6.2 Hz, 3H). |
| 240 | 335.1 | 1H NMR (400 MHz, CD3CN) δ 8.39-8.14 (m, 2H), 7.94 (dd, J = 7.8, 0.8 Hz, 1H), 4.75-4.36 (m, 1H), 4.19-3.94 (m, 2H), 3.09 (q, J = 7.1 Hz, 2H), 2.93 (t, J = 7.8 Hz, 2H), 2.20-2.05 (m, 4H), 1.58 (d, J = 6.2 Hz, 3H). |
| 241 | 374.1 | 1H NMR (400 MHz, CD3CN) δ 8.34 (s, 1H), 8.09-7.98 (m, 1H), 7.85 (d, J = 8.7 Hz, 1H), 4.67 (q, J = 6.6 Hz, 1H), 4.34-3.95 (m, 2H), 3.15 (dp, J = 15.3, 7.5 Hz, 2H), 2.99 (t, J = 7.8 Hz, 2H), 2.67-2.52 (m, 4H), 1.61 (d, J = 6.3 Hz, 3H). |
| 242 | 359.1 | 1H NMR (400 MHz, CD3CN) δ 7.99 (d, J = 8.3 Hz, 2H), 7.59 (d, J = 8.4 Hz, 2H), 5.36 (bs, 1H), 4.74-4.56 (m, 1H), 4.43 (s, 2H), 4.22 (td, J = 9.2, 5.4 Hz, 1H), 4.14 (td, J = 9.2, 6.7 Hz, 1H), 3.29-3.04 (m, 2H), 3.00 (t, J = 7.8 Hz, 2H), 2.32-2.02 (m, 4H), 1.60 (d, J = 6.3 Hz, 3H). |

TABLE 1-continued

MS and NMR DATA

| Example No | ES/MS m/z (M + H)+ | 1H NMR |
|---|---|---|
| 243 | 374.1 | 1H NMR (400 MHz, CD3CN) δ 8.40 (s, 1H), 8.16 (dd, J = 8.9, 1.7 Hz, 1H), 7.96-7.67 (m, 1H), 4.62 (q, J = 6.5 Hz, 1H), 4.22-3.88 (m, 2H), 3.12 (dp, J = 15.2, 7.6 Hz, 2H), 2.95 (t, J = 7.8 Hz, 2H), 2.18-2.06 (m, 4H), 1.60 (d, J = 6.3 Hz, 3H). |
| 244 | 323.1 | 1H NMR (400 MHz, CD3CN) δ 7.90-7.75 (m, 2H), 7.64-7.37 (m, 2H), 4.65 (dt, J = 8.0, 6.1 Hz, 1H), 4.32-4.01 (m, 2H), 3.59 (s, 2H), 3.21-2.99 (m, 3H), 2.96 (t, J = 7.7 Hz, 2H), 2.24-2.06 (m, 3H), 1.59 (d, J = 6.2 Hz, 3H). |
| 245 | 323 | 1H NMR (400 MHz, CD3CN) δ 7.92 (d, J = 8.2 Hz, 2H), 7.44 (d, J = 8.2 Hz, 2H), 4.57 (q, J = 6.8 Hz, 1H), 4.20-3.90 (m, 4H), 3.57 (s, 2H), 3.10-3.01 (m, 3H), 2.91 (t, J = 7.8 Hz, 3H), 1.57 (d, J = 6.2 Hz, 3H). |
| 246 | 363 | 1H NMR (400 MHz, CD3CN) δ 8.05 (s, 1H), 7.96 (d, J = 7.8 Hz, 1H), 7.67 (t, J = 6.7 Hz, 1H), 7.60 (t, J = 7.7 Hz, 1H), 4.74-4.60 (m, 2H), 4.24-4.07 (m, 1H), 3.18-2.93 (m, 4H), 2.17-2.09 (m, 4H), 1.59 (dd, J = 6.4, 1.0 Hz, 3H). |
| 247 | 322.1 | 1H NMR (400 MHz, CD3CN) δ 7.92 (d, J = 8.7 Hz, 1H), 6.96 (d, J = 8.8 Hz, 2H), 4.73-4.49 (m, 1H), 4.28-3.81 (m, 2H), 3.08 (q, J = 7.2 Hz, 3H), 2.93 (t, J = 7.8 Hz, 5H), 1.58 (d, J = 6.3 Hz, 3H). |
| 248 | 321.1 | 1H NMR (400 MHz, CD3CN) δ 7.22 (q, J = 7.5 Hz, 1H), 7.06-6.95 (m, 1H), 6.89 (d, J = 7.7 Hz, 1H), 4.79-4.65 (m, 1H), 4.28 (td, J = 9.2, 5.5 Hz, 1H), 4.18 (td, J = 9.3, 6.5 Hz, 2H), 3.55 (s, 2H), 3.10 (q, J = 7.6 Hz, 2H), 3.02 (t, J = 7.8 Hz, 2H), 2.23-2.13 (m, 3H), 1.61 (d, J = 6.3 Hz, 3H). |
| 249 | 376.2 | 1H NMR (400 MHz, CD3CN) δ 7.94 (d, J = 8.3 Hz, 2H), 7.58-7.36 (m, 2H), 4.76 (dt, J = 8.3, 6.1 Hz, 1H), 4.38-4.25 (m, 1H), 4.25-4.14 (m, 1H), 3.18-3.00 (m, 8H), 2.69-2.55 (m, 2H), 2.23-2.06 (m, 4H), 1.61 (d, J = 6.3 Hz, 3H). |
| 250 | 375.1 | 1H NMR (400 MHz, CD3CN) δ 7.93 (d, J = 8.4 Hz, 2H), 7.44 (d, J = 8.4 Hz, 2H), 4.77-4.65 (m, 1H), 4.25 (td, J = 9.2, 5.5 Hz, 1H), 4.16 (td, J = 9.3, 6.6 Hz, 1H), 3.20-2.92 (m, 7H), 2.67-2.52 (m, 2H), 2.23-2.06 (m, 6H), 1.60 (d, J = 6.3 Hz, 3H). |
| 251 | 336.1 | 1H NMR (400 MHz, CD3CN) δ 7.70 (dd, J = 8.3, 1.7 Hz, 1H), 7.65 (d, J = 1.7 Hz, 1H), 7.17 (d, J = 8.2 Hz, 1H), 4.77-4.57 (m, 1H), 4.38-4.17 (m, 1H), 4.17-3.83 (m, 1H), 3.38 (s, 3H), 3.14 (h, J = 8.2 Hz, 4H), 2.97 (t, J = 7.8 Hz, 4H), 1.61 (d, J = 6.3 Hz, 3H). |
| 252 | 349.1 | 1H NMR (400 MHz, CD3CN) δ 7.96 (d, J = 8.4 Hz, 2H), 7.61 (d, J = 8.4 Hz, 2H), 4.73 (dt, J = 8.2, 6.0 Hz, 1H), 4.28 (td, J = 9.3, 5.6 Hz, 1H), 4.18 (td, J = 9.3, 6.6 Hz, 1H), 3.38-2.91 (m, 5H), 2.71-2.49 (m, 2H), 2.29-2.03 (m, 5H), 1.61 (d, J = 6.3 Hz, 3H). |
| 253 | 350.1 | 1H NMR (400 MHz, CD3CN) δ 7.93 (s, 1H), 7.83 (dt, J = 7.8, 1.5 Hz, 1H), 7.59 (dt, J = 7.7, 1.5 Hz, 1H), 7.50 (t, J = 7.7 Hz, 1H), 4.70 (dt, J = 8.1, 6.1 Hz, 1H), 4.24 (td, J = 9.2, 5.4 Hz, 1H), 4.15 (td, J = 9.2, 6.7 Hz, 1H), 3.28-2.88 (m, 8H), 2.59 (dtd, J = 10.9, 8.7, 5.2 Hz, 1H), 2.29-2.04 (m, 3H), 1.60 (d, J = 6.3 Hz, 3H). |
| 254 | 349.1 | 1H NMR (400 MHz, CD3CN) δ 7.96 (t, J = 1.9 Hz, 1H), 7.88 (dt, J = 7.7, 1.5 Hz, 1H), 7.68 (dt, J = 7.7, 1.5 Hz, 1H), 7.58 (t, J = 7.7 Hz, 1H), 4.80 (dt, J = 8.3, 6.1 Hz, 1H), 4.33 (td, J = 9.4, 5.8 Hz, 1H), 4.23 (td, J = 9.4, 6.4 Hz, 1H), 3.18-3.00 (m, 4H), 2.79-2.52 (m, 1H), 2.30-2.01 (m, 3H), 1.62 (d, J = 6.3 Hz, 3H), 1.52 (q, J = 3.5 Hz, 2H), 1.13 (q, J = 3.5 Hz, 2H). |
| 255 | 361.1 | 1H NMR (400 MHz, CD3CN) δ 8.00 (d, J = 8.4 Hz, 2H), 7.67 (d, J = 8.4 Hz, 2H), 4.85-4.64 (m, 1H), 4.36 (s, 1H), 4.35-4.26 (m, 1H), 4.21 (td, J = 9.4, 6.5 Hz, 1H), 4.01 (bs, 1H), 3.23-2.94 (m, 3H), 2.74-2.58 (m, 1H), 2.26-2.08 (m, 3H), 1.62 (d, J = 6.3 Hz, 3H), 1.48-1.20 (m, 4H). |
| 256 | 346 | 1H NMR (400 MHz, CD3CN) δ 7.99 (d, J = 8.4 Hz, 2H), 7.61 (d, J = 8.1 Hz, 2H), 6.12-5.71 (m, 1H), 4.94 (td, J = 11.6, 4.0 Hz, 1H), 4.68 (dt, J = 8.1, 6.1 Hz, 1H), 4.34-3.97 (m, 1H), 3.09 (q, J = 7.7 Hz, 2H), 2.99 (t, J = 7.8 Hz, 2H), 2.64-2.51 (m, 2H), 2.28-2.02 (m, 3H), 1.60 (d, J = 6.3 Hz, 3H). |
| 257 | 328.1 | 1H NMR (400 MHz, CD3CN) δ 7.97 (d, J = 8.4 Hz, 2H), 7.58 (d, J = 8.3 Hz, 2H), 5.04 (ddd, J = 16.9, 6.9, 3.7 Hz, 1H), 4.79-4.63 (m, 1H), 4.61 (dd, J = 9.6, 3.7 Hz, 1H), 4.56-4.45 (m, 1H), 4.40 (dd, J = 9.6, 7.0 Hz, 1H), 4.30-4.01 (m, 2H), 3.13-3.04 (m, 1H), 2.99 (t, J = 7.8 Hz, 2H), 2.65-2.43 (m, 1H), 2.29-2.03 (m, 3H), 1.60 (d, J = 6.3 Hz, 3H). |
| 258 | 332.1 | 1H NMR (400 MHz, CD3CN) δ 7.85-7.78 (m, 1H), 7.75 (s, 1H), 7.60 (t, J = 8.0 Hz, 1H), 7.36 (dd, J = 8.2, 2.5 Hz, 1H), 7.08-6.57 (m, 1H), 4.70 (dp, J = 8.5, 6.2 Hz, 1H), 4.24 (td, J = 9.2, 5.4 Hz, 1H), 4.15 (td, J = 9.2, 6.7 Hz, 1H), 3.17-2.97 (m, 4H), 2.67-2.52 (m, 1H), 2.26-2.00 (m, 3H), 1.59 (d, J = 6.3 Hz, 3H). |

TABLE 1-continued

| | | MS and NMR DATA |
|---|---|---|
| Example No | ES/MS m/z (M + H)+ | 1H NMR |
| 259 | 306.1 | 1H NMR (400 MHz, CD3CN) δ 8.63 (s, 1H), 8.35 (s, 1H), 7.67-7.06 (m, 1H), 4.74 (dt, J = 8.1, 6.1 Hz, 1H), 4.36-4.12 (m, 2H), 3.05 (m, 3.12-2.96, 4H), 2.70-2.47 (m, 1H), 2.24 (p, J = 7.8 Hz, 2H), 2.10 (ddt, J = 11.2, 9.2, 6.2 Hz, 1H), 1.61 (d, J = 6.3 Hz, 3H). |
| 260 | 282 | 1H NMR (400 MHz, CD3CN) δ 14.34 (s, 1H), 7.88-7.78 (m, 1H), 7.36 (td, J = 7.7, 1.7 Hz, 1H), 6.99-6.86 (m, 2H), 4.57-4.44 (m, 1H), 4.16-3.88 (m, 3H), 3.30-3.11 (m, 2H), 2.85 (t, J = 7.8 Hz, 2H), 2.56-2.43 (m, 3H), 1.54 (d, J = 6.2 Hz, 3H). |
| 261 | 282.1 | 1H NMR (400 MHz, CD3CN) δ 7.49-7.32 (m, 3H), 7.01 (ddd, J = 7.9, 2.5, 1.2 Hz, 1H), 4.66 (dt, J = 8.2, 6.1 Hz, 1H), 4.21 (td, J = 9.1, 5.3 Hz, 1H), 4.12 (td, J = 9.1, 6.8 Hz, 1H), 3.17-3.01 (m, 2H), 2.97 (t, J = 7.8 Hz, 2H), 2.19-2.02 (m, 4H), 1.59 (d, J = 6.2 Hz, 3H). |
| 262 | 282.1 | 1H NMR (400 MHz, CD3CN) δ 7.92 (d, J = 8.7 Hz, 2H), 6.96 (d, J = 8.8 Hz, 2H), 4.67-4.57 (m, 2H), 4.22-4.03 (m, 3H), 3.08 (q, J = 7.2 Hz, 3H), 2.93 (t, J = 7.8 Hz, 3H), 1.58 (d, J = 6.3 Hz, 3H). |
| 263 | 324.1 | 1H NMR (400 MHz, CD3CN) δ 8.12 (d, J = 2.0 Hz, 1H), 7.60 (d, J = 2.0 Hz, 1H), 4.65 (q, J = 6.8 Hz, 1H), 4.44 (t, J = 4.4 Hz, 2H), 4.24-4.15 (m, 1H), 4.11 (q, J = 8.5 Hz, 1H), 3.41 (t, J = 4.4 Hz, 2H), 3.08 (q, J = 6.7 Hz, 2H), 2.96 (t, J = 7.8 Hz, 2H), 2.36-2.02 (m, 5H), 1.59 (d, J = 6.3 Hz, 3H). |
| 264 | 349.1 | 1H NMR (400 MHz, CD3CN) δ 7.62 (dd, J = 7.8, 1.6 Hz, 1H), 7.51 (d, J = 1.5 Hz, 1H), 7.43 (d, J = 7.7 Hz, 1H), 4.76 (dt, J = 8.2, 6.0 Hz, 1H), 4.29 (dd, J = 9.3, 5.7 Hz, 1H), 4.20 (td, J = 9.3, 6.4 Hz, 1H), 3.28-2.95 (m, 4H), 2.24-2.05 (m, 4H), 1.62 (d, J = 6.3 Hz, 3H), 1.38 (s, 6H). |
| 265 | 364 | 1H NMR (400 MHz, CD3CN) δ 8.00 (d, J = 8.4 Hz, 2H), 7.66 (d, J = 8.1 Hz, 2H), 5.23 (q, J = 7.1 Hz, 1H), 4.71-4.45 (m, 1H), 4.19-3.98 (m, 2H), 3.07 (hept, J = 7.8 Hz, 2H), 2.95 (t, J = 7.8 Hz, 2H), 2.61-2.48 (m, 2H), 2.19-2.04 (m, 2H), 1.58 (d, J = 6.3 Hz, 3H). |
| 266 | 352.2 | 1H NMR (400 MHz, CD3CN) δ 8.03 (d, J = 8.3 Hz, 2H), 7.95 (d, J = 8.5 Hz, 2H), 4.54 (t, J = 6.1 Hz, 1H), 4.23 (t, J = 8.6 Hz, 1H), 4.17-4.07 (m, 1H), 3.21-3.02 (m, 4H), 2.94 (t, J = 7.8 Hz, 2H), 1.80 (p, J = 2.5 Hz, 1H), 1.64 (d, J = 6.3 Hz, 3H). |
| 267 | 339.1 | 1H NMR (400 MHz, CD3CN) δ 8.03 (d, J = 8.4 Hz, 2H), 7.97 (d, J = 8.4 Hz, 2H), 4.39 (p, J = 6.2 Hz, 1H), 4.23 (t, J = 8.7 Hz, 1H), 3.89 (dd, J = 9.1, 6.1 Hz, 1H), 3.68 (d, J = 5.8 Hz, 2H), 3.09 (q, J = 7.5 Hz, 2H), 2.98 (t, J = 7.8 Hz, 2H), 2.21-2.07 (m, 3H), 1.59 (d, J = 6.3 Hz, 3H). |
| 268 | 339.1 | 1H NMR (400 MHz, CD3CN) δ 8.07 (d, J = 8.5 Hz, 2H), 7.97 (d, J = 8.5 Hz, 2H), 3.92-3.61 (m, 2H), 3.52 (d, J = 11.6 Hz, 2H), 3.10 (dd, J = 8.0, 6.6 Hz, 2H), 3.00 (t, J = 7.8 Hz, 2H), 2.17 (p, J = 7.5 Hz, 2H), 2.08-2.02 (m, 2H), 1.47 (s, 3H). |
| 269 | 363.1 | 1H NMR (400 MHz, CD3CN) δ 8.03 (d, J = 8.9 Hz, 2H), 7.69 (d, J = 8.1 Hz, 2H), 4.85-4.69 (m, 1H), 4.66 (q, J = 7.8 Hz, 1H), 4.26 (dt, J = 13.9, 5.0 Hz, 1H), 4.21-4.07 (m, 1H), 3.87 (s, 1H), 3.69-3.61 (m, 2H), 3.27-3.09 (m, 2H), 2.28 (q, J = 8.4 Hz, 1H), 2.13 (dd, J = 6.6, 3.7 Hz, 1H), 1.39 (d, J = 6.5 Hz, 3H). |
| 270 | 374.1 | 1H NMR (400 MHz, CD3CN) δ 7.82-7.72 (m, 1H), 7.43 (d, J = 7.7 Hz, 1H), 7.39-7.33 (m, 1H), 7.19 (q, J = 3.6 Hz, 1H), 4.75 (q, J = 6.5 Hz, 1H), 4.29 (q, J = 8.9 Hz, 1H), 4.19 (q, J = 8.5 Hz, 1H), 3.17-2.88 (m, 2H), 2.71 (ddd, J = 9.1, 6.2, 4.3 Hz, 2H), 2.65-2.50 (m, 2H), 2.22-2.05 (m, 2H), 1.83 (ddt, J = 6.8, 5.5, 2.8 Hz, 2H), 1.72 (dp, J = 8.7, 3.1 Hz, 2H), 1.60 (d, J = 6.3 Hz, 3H). |
| 271 | 323.1 | 1H NMR (400 MHz, DMSO-d6) δ 8.47 (s, 1H), 7.66 (dd, J = 6.7, 3.0 Hz, 2H), 7.62-7.50 (m, 3H), 4.50-4.30 (m, 1H), 4.00-3.81 (m, 2H), 2.67 (p, J = 1.9 Hz, 1H), 2.43-2.35 (m, 1H), 2.07-1.88 (m, 1H), 1.48 (d, J = 6.1 Hz, 3H). |
| 272 | 321.1 | 1H NMR (400 MHz, DMSO-d6) δ 8.30 (s, 1H), 8.07-7.96 (m, 2H), 7.97-7.87 (m, 1H), 7.55 (t, J = 7.7 Hz, 1H), 7.44 (s, 1H), 4.41 (q, J = 6.4 Hz, 1H), 4.08-3.86 (m, 2H), 3.32-3.15 (m, 1H), 3.06 (dd, J = 22.5, 16.4 Hz, 1H), 2.39 (ddd, J = 14.8, 11.3, 6.7 Hz, 1H), 2.32 (s, 1H), 2.06-1.89 (m, 2H), 1.50 (dd, J = 6.2, 1.8 Hz, 3H), 1.29-1.13 (m, 1H), 0.21 (dq, J = 15.7, 3.9 Hz, 1H). |
| 273 | 285.1 | 1H NMR (400 MHz, DMSO-d6) δ 8.66 (d, J = 1.8 Hz, 1H), 7.54 (t, J = 8.1 Hz, 1H), 4.39 (hept, J = 6.5 Hz, 1H), 3.93 (dtd, J = 17.2, 8.2, 7.8, 4.5 Hz, 2H), 3.22-3.02 (m, 2H), 2.36 (dt, J = 8.4, 4.5 Hz, 2H), 2.11-2.09 (m, 1H), 2.03-1.87 (m, 1H), 1.49 (d, J = 6.2 Hz, 3H), 1.37-1.21 (m, 1H), 0.30 (p, J = 3.9 Hz, 1H). |
| 274 | 308.2 | 1H NMR (400 MHz, DMSO-d6) δ 7.80 (d, J = 1.9 Hz, 1H), 7.68 (dd, J = 8.4, 1.9 Hz, 1H), 6.86 (d, J = 8.3 Hz, 2H), 4.59 (t, J = 8.7 Hz, 2H), 4.36 (p, J = 6.4 Hz, 1H), 4.08-3.81 (m, 2H), 3.30-3.20 (m, 2H), 2.98 (hept, J = 7.4, 6.8 Hz, 2H), 2.76 (t, J = 7.7 Hz, 2H), 2.43-2.30 (m, 1H), 2.04-1.88 (m, 3H), 1.48 (d, J = 6.1 Hz, 3H). |
| 275 | 319.2 | 1H NMR (400 MHz, DMSO-d6) δ 8.11 (d, J = 1.6 Hz, 1H), 7.79 (dd, J = 8.6, 1.6 Hz, 1H), 7.52 (d, J = 8.6 Hz, 1H), 7.39 (d, J = 3.1 Hz, 1H), |

TABLE 1-continued

MS and NMR DATA

| Example No | ES/MS m/z (M + H)+ | 1H NMR |
|---|---|---|
| | | 6.54 (d, J = 3.1 Hz, 1H), 4.39 (p, J = 6.6 Hz, 1H), 4.01-3.86 (m, 2H), 3.82 (d, J = 1.1 Hz, 3H), 3.06 (m, 2H), 2.78 (t, J = 7.7 Hz, 2H), 2.44-2.31 (m, 1H), 1.99 (m, 3H), 1.51 (d, J = 6.2 Hz, 3H). |
| 276 | 310.2 | 1H NMR (400 MHz, Chloroform-d) δ 7.90 (s, 1H), 7.80 (m, 1H), 7.48-7.38 (m, 2H), 4.96 (m, 1H), 4.52 (m, 1H), 4.22-4.07 (m, 1H), 4.07-3.96 (m, 1H), 3.14-2.94 (m, 2H), 2.88 (t, J = 7.7 Hz, 2H), 2.42 (m, 1H), 2.15-1.94 (m, 4H), 1.58 (d, J = 6.2 Hz, 3H), 1.53 (d, J = 6.4 Hz, 3H). |
| 277 | 373.2 | 1H NMR (400 MHz, DMSO-d6) δ 7.86 (s, 1H), 7.79 (d, J = 7.5 Hz, 1H), 7.63 (d, J = 6.2 Hz, 1H), 7.46 (dt, J = 14.2, 7.6 Hz, 2H), 4.39 (h, J = 6.4 Hz, 1H), 4.24 (d, J = 5.3 Hz, 2H), 4.12-3.82 (m, 3H), 3.10-2.93 (m, 2H), 2.89 (s, 3H), 2.80 (t, J = 7.7 Hz, 2H), 2.45-2.32 (m, 1H), 2.08-1.89 (m, 2H), 1.49 (d, J = 6.1 Hz, 3H). |
| 278 | 282.2 | 1H NMR (400 MHz, Chloroform-d) δ 8.57 (d, J = 8.5 Hz, 1H), 8.26-8.20 (m, 1H), 7.64 (ddd, J = 8.9, 7.3, 2.0 Hz, 1H), 7.01-6.87 (m, 2H), 4.50 (dt, J = 8.0, 6.1 Hz, 1H), 4.12 (td, J = 8.8, 5.4 Hz, 1H), 4.05-3.94 (m, 1H), 2.84 (dd, J = 8.5, 6.9 Hz, 2H), 2.77-2.68 (m, 2H), 2.50-2.37 (m, 1H), 2.16-1.93 (m, 3H), 1.57 (d, J = 6.2 Hz, 3H). |
| 279 | 332.1 | 1H NMR (400 MHz, Chloroform-d) δ 8.29 (s, 1H), 7.97-7.78 (m, 2H), 7.64 (d, J = 2.3 Hz, 1H), 7.50 (t, J = 7.7 Hz, 1H), 7.26 (s, 1H), 6.66 (d, J = 2.2 Hz, 1H), 4.53 (dt, J = 13.2, 6.6 Hz, 1H), 4.20-3.98 (m, 3H), 3.21-3.00 (m, 2H), 2.90 (t, J = 7.7 Hz, 2H), 2.50-2.39 (m, 1H), 2.17-1.95 (m, 2H), 1.65-1.55 (m, 3H). |
| 280 | 324.2 | 1H NMR (400 MHz, Chloroform-d) δ 9.08 (d, J = 2.1 Hz, 1H), 8.35 (dd, J = 8.2, 2.1 Hz, 1H), 8.27 (d, J = 8.1 Hz, 1H), 8.05 (s, 1H), 4.53 (dt, J = 8.1, 6.2 Hz, 1H), 4.14 (td, J = 8.7, 4.8 Hz, 1H), 4.08-3.97 (m, 1H), 3.15-2.97 (m, 5H), 2.91 (t, J = 7.7 Hz, 2H), 2.52-2.39 (m, 1H), 2.20-2.04 (m, 2H), 2.09-1.94 (m, 1H), 1.58 (d, J = 6.2 Hz, 3H). |
| 281 | 285.2 | 1H NMR (400 MHz, Chloroform-d) δ 8.31 (d, J = 5.2 Hz, 1H), 7.68 (dt, J = 5.2, 1.5 Hz, 1H), 7.45 (s, 1H), 4.53 (dt, J = 8.1, 6.2 Hz, 1H), 4.13 (td, J = 8.8, 4.8 Hz, 1H), 4.08-3.97 (m, 1H), 3.14-2.97 (m, 2H), 2.91 (t, J = 7.7 Hz, 2H), 2.46 (dtd, J = 11.0, 8.6, 4.8 Hz, 1H), 2.18-2.05 (m, 2H), 2.09-1.92 (m, 1H), 1.57 (d, J = 6.2 Hz, 3H). |
| 282 | 326.2 | 1H NMR (400 MHz, Chloroform-d) δ 8.12 (d, J = 5.4 Hz, 1H), 7.04 (dd, J = 5.3, 1.4 Hz, 1H), 6.96 (s, 1H), 4.98 (t, J = 5.6 Hz, 1H), 4.56-4.46 (m, 1H), 4.12 (td, J = 8.7, 4.8 Hz, 1H), 4.06-3.95 (m, 1H), 3.87-3.80 (m, 2H), 3.56 (q, J = 4.9 Hz, 2H), 3.01 (hept, J = 8.5, 7.9 Hz, 2H), 2.88 (t, J = 7.7 Hz, 2H), 2.50-2.37 (m, 1H), 2.14-1.95 (m, 3H), 1.56 (d, J = 6.3 Hz, 3H). |
| 283 | 335.2 | 1H NMR (400 MHz, DMSO-d6) δ 8.01 (s, 1H), 7.94 (d, J = 8.0 Hz, 1H), 7.85-7.74 (m, 2H), 4.40 (h, J = 6.4 Hz, 1H), 4.08-3.84 (m, 2H), 3.41 (td, J = 6.5, 2.7 Hz, 2H), 3.01 (dh, J = 14.7, 7.6 Hz, 4H), 2.80 (t, J = 7.7 Hz, 2H), 2.45-2.32 (m, 1H), 1.99 (dp, J = 15.2, 9.8, 8.0 Hz, 3H), 1.49 (d, J = 6.4 Hz, 2H). |
| 284 | 391.1 | 1H NMR (400 MHz, DMSO-d6) δ 7.88 (d, J = 1.8 Hz, 1H), 7.80 (dt, J = 7.5, 1.7 Hz, 1H), 7.65 (s, 1H), 7.56-7.41 (m, 2H), 5.12 (ddd, J = 57.0, 3.7, 1.9 Hz, 1H), 4.44-4.33 (m, 1H), 4.37-4.26 (m, 1H), 4.26 (dd, J = 14.7, 4.8 Hz, 2H), 3.91 (ddd, J = 26.0, 10.1, 4.1 Hz, 1H), 3.12-2.94 (m, 2H), 2.93-2.79 (m, 5H), 2.02 (td, J = 7.2, 2.4 Hz, 1H), 1.53 (d, J = 6.5 Hz, 3H). |
| 285 | 389.1 | 1H NMR (400 MHz, DMSO-d6) δ 7.88 (d, J = 2.0 Hz, 1H), 7.79 (dt, J = 7.5, 1.6 Hz, 1H), 7.64 (s, 1H), 7.53-7.40 (m, 2H), 5.56 (d, J = 6.5 Hz, 1H), 4.24 (s, 2H), 4.16 (dd, J = 8.4, 6.5 Hz, 1H), 4.12-3.96 (m, 2H), 3.61 (dd, J = 8.6, 5.1 Hz, 1H), 3.01 (hept, J = 7.6, 7.0 Hz, 2H), 2.89 (s, 3H), 2.81 (dd, J = 8.5, 7.0 Hz, 2H), 2.06-1.94 (m, 2H), 1.48 (d, J = 6.2 Hz, 3H). |
| 286 | 377.1 | 1H NMR (400 MHz, DMSO-d6) δ 8.06 (t, J = 1.8 Hz, 1H), 7.96-7.82 (m, 2H), 7.69 (t, J = 7.8 Hz, 1H), 7.47 (s, 2H), 5.60 (d, J = 6.3 Hz, 1H), 4.55 (s, 2H), 4.14 (dd, J = 8.6, 6.3 Hz, 1H), 4.04 (m, 2H), 3.88-3.73 (m, 2H), 3.60 (dd, J = 8.7, 4.8 Hz, 1H), 2.67 (qt, J = 16.0, 5.4 Hz, 2H), 1.43 (d, J = 6.2 Hz, 3H). |
| 287 | 379.1 | 1H NMR (400 MHz, Chloroform-d) δ 8.17 (t, J = 1.7 Hz, 1H), 7.99 (ddd, J = 7.9, 1.9, 1.1 Hz, 1H), 7.82 (dt, J = 7.8, 1.3 Hz, 1H), 7.61 (t, J = 7.8 Hz, 1H), 5.06 (s, 2H), 4.95 (ddt, J = 56.9, 6.0, 3.9 Hz, 1H), 4.64 (d, J = 1.0 Hz, 2H), 4.58-4.36 (m, 1H), 4.40-4.28 (m, 1H), 4.17-3.96 (m, 2H), 3.95-3.77 (m, 2H), 2.85-2.64 (m, 1H), 1.56 (d, J = 6.5 Hz, 3H) |
| 288 | 351.1 | 1H NMR (400 MHz, DMSO-d6) δ 8.01 (s, 1H), 7.94 (d, J = 8.0 Hz, 1H), 7.86-7.75 (m, 2H), 5.57 (d, J = 6.4 Hz, 1H), 4.17 (dd, J = 8.5, 6.4 Hz, 1H), 4.13-3.97 (m, 2H), 3.61 (dd, J = 8.7, 5.1 Hz, 1H), 3.41 (td, J = 6.5, 2.7 Hz, 2H), 3.11-2.93 (m, 4H), 2.81 (dd, J = 8.4, 7.1 Hz, 2H), 2.00 (pt, J = 7.9, 3.4 Hz, 2H), 1.48 (d, J = 6.2 Hz, 3H). |
| 289 | 353.2 | 1H NMR (400 MHz, DMSO-d6) δ 8.02 (s, 1H), 7.95 (d, J = 8.0 Hz, 1H), 7.87-7.76 (m, 2H), 5.24-5.00 (m, 1H), 4.44-4.26 (m, 2H), 3.92 (ddd, J = 26.0, 10.2, 4.0 Hz, 1H), 3.41 (tt, J = 6.8, 2.8 Hz, 2H), |

TABLE 1-continued

MS and NMR DATA

| Example No | ES/MS m/z (M + H)+ | 1H NMR |
|---|---|---|
| | | 3.03 (dq, J = 21.9, 7.5, 6.6 Hz, 4H), 2.84 (t, J = 7.7 Hz, 2H), 2.08-1.96 (m, 2H), 1.53 (d, J = 6.5 Hz, 3H). |
| 290 | 377.1 | 1H NMR (400 MHz, Chloroform-d) δ 7.83 (t, J = 1.9 Hz, 1H), 7.73 (dt, J = 7.8, 1.3 Hz, 1H), 7.45 (t, J = 7.9 Hz, 1H), 7.29 (ddd, J = 8.0, 2.4, 1.0 Hz, 1H), 4.98 (ddt, J = 56.9, 6.0, 4.0 Hz, 1H), 4.59-4.42 (m, 1H), 4.46-4.34 (m, 1H), 4.16-4.01 (m, 2H), 3.16-2.98 (m, 5H), 2.91 (dd, J = 8.5, 7.0 Hz, 2H), 2.09 (ddt, J = 10.4, 5.5, 2.5 Hz, 2H), 1.62 (d, J = 6.5 Hz, 3H). |
| 291 | 352.1 | 1H NMR (400 MHz, Chloroform-d) δ 8.80 (d, J = 2.3 Hz, 1H), 8.18 (dd, J = 9.0, 2.4 Hz, 1H), 6.73-6.66 (m, 1H), 4.50 (m, 1H), 4.16-4.06 (m, 1H), 3.99 (td, J = 8.7, 7.2 Hz, 1H), 3.83 (dd, J = 5.8, 4.0 Hz, 4H), 3.61 (dd, J = 5.7, 4.1 Hz, 4H), 3.13-2.96 (m, 2H), 2.87 (t, J = 7.8 Hz, 2H), 2.41 (m, 1H), 2.15-1.94 (m, 3H), 1.57 (d, J = 6.2 Hz, 3H). |
| 292 | 323.2 | 1H NMR (400 MHz, DMSO-d6) δ 8.55-8.48 (m, 1H), 7.93 (d, J = 1.3 Hz, 4H), 4.40 (dt, J = 7.8, 6.2 Hz, 1H), 4.03-3.84 (m, 2H), 3.02 (h, J = 8.3 Hz, 2H), 2.85-2.71 (m, 5H), 2.39 (dtd, J = 10.6, 8.6, 4.7 Hz, 1H), 2.02 (dd, J = 7.3, 5.6 Hz, 1H), 2.02-1.90 (m, 2H), 1.49 (d, J = 6.2 Hz, 3H). |
| 293 | 337.2 | 1H NMR (400 MHz, Chloroform-d) δ 7.98-7.90 (m, 2H), 7.54-7.46 (m, 2H), 4.53 (dp, J = 8.0, 6.2 Hz, 1H), 4.19-4.08 (m, 1H), 4.02 (td, J = 8.7, 7.1 Hz, 1H), 3.14 (s, 3H), 3.12-2.94 (m, 5H), 2.90 (t, J = 7.7 Hz, 2H), 2.44 (m, 2H), 2.17-1.95 (m, 2H), 1.58 (d, J = 6.2 Hz, 3H). |
| 294 | 421.3 | 1H NMR (400 MHz, DMSO-d6) δ 7.80 (d, J = 8.1 Hz, 2H), 7.74 (s, 1H), 7.22 (d, J = 8.2 Hz, 2H), 4.38 (h, J = 6.3 Hz, 1H), 3.99-3.82 (m, 2H), 2.99 (m, 2H), 2.78 (t, J = 7.7 Hz, 2H), 2.44-2.31 (m, 1H), 2.04-1.88 (m, 3H), 1.48 (d, J = 6.2 Hz, 3H), 1.39 (s, 9H), 1.32-1.22 (m, 2H), 1.21-1.12 (m, 2H). |
| 295 | 321.2 | 1H NMR (400 MHz, DMSO-d6) δ 8.68 (m, 2H), 7.95-7.88 (m, 2H), 7.55-7.48 (m, 2H), 4.40 (m, 1H), 4.01-3.86 (m, 2H), 3.00 (h, J = 8.3 Hz, 2H), 2.85-2.71 (m, 2H), 2.45-2.33 (m, 1H), 1.98 (m, 3H), 1.48 (d, J = 6.1 Hz, 3H), 1.41-1.25 (m, 4H). |
| 296 | 385.3 | 1H NMR (400 MHz, DMSO-d6) δ 10.33 (s, 1H), 8.10-7.98 (m, 4H), 7.83-7.76 (m, 2H), 7.41-7.32 (m, 2H), 7.16-7.07 (m, 1H), 4.43 (p, J = 6.5 Hz, 1H), 4.04-3.87 (m, 2H), 3.05 (h, J = 8.4 Hz, 2H), 2.83 (t, J = 7.7 Hz, 2H), 2.40 (ddd, J = 13.0, 6.5, 3.5 Hz, 1H), 2.10-1.91 (m, 3H), 1.51 (d, J = 6.2 Hz, 3H). |
| 297 | 385.2 | 1H NMR (400 MHz, DMSO-d6) δ 10.35 (s, 1H), 8.41 (t, J = 1.8 Hz, 1H), 8.12-8.01 (m, 2H), 7.82-7.75 (m, 2H), 7.67 (t, J = 7.8 Hz, 1H), 7.41-7.32 (m, 2H), 7.11 (t, J = 7.4 Hz, 1H), 4.42 (dt, J = 12.9, 6.4 Hz, 1H), 4.04-3.87 (m, 2H), 3.8-3.7 (m, 2H, under water peak), 3.05 (h, J = 8.3 Hz, 2H), 2.83 (t, J = 7.8 Hz, 2H), 2.46-2.34 (m, 1H), 2.08-1.91 (m, 1H), 1.51 (d, J = 6.2 Hz, 3H). |
| 298 | 354.2 | 1H NMR (400 MHz, DMSO-d6) δ 8.82-8.78 (m, 2H), 8.74 (t, J = 1.6 Hz, 1H), 8.45 (s, 1H), 7.80 (s, 1H), 4.44 (h, J = 6.3 Hz, 1H), 4.08-3.88 (m, 2H), 3.18-2.99 (m, 2H), 2.84 (t, J = 7.8 Hz, 2H), 2.47-2.35 (m, 1H), 2.05 (tt, J = 7.8, 4.1 Hz, 1H), 1.52 (d, J = 6.1 Hz, 3H). |
| 299 | 324.2 | 1H NMR (400 MHz, DMSO-d6) δ 7.79 (s, 1H), 7.40 (d, J = 1.6 Hz, 1H), 7.20 (t, J = 2.0 Hz, 1H), 7.11 (t, J = 1.9 Hz, 1H), 5.37 (s, 1H), 4.39 (p, J = 6.5 Hz, 1H), 4.03-3.83 (m, 2H), 2.97 (h, J = 8.4 Hz, 2H), 2.78 (t, J = 7.7 Hz, 2H), 2.44-2.34 (m, 1H), 2.02-1.88 (m, 1H), 1.49 (d, J = 6.1 Hz, 3H). |
| 300 | 402.1 | 1H NMR (400 MHz, Chloroform-d) δ 8.12 (d, J = 1.5 Hz, 1H), 8.05 (t, J = 1.8 Hz, 1H), 7.77 (t, J = 1.9 Hz, 1H), 7.33 (s, 1H), 6.31 (s, 1H), 5.84 (s, 1H), 4.52 (dt, J = 12.8, 6.3 Hz, 1H), 4.19-3.97 (m, 2H), 3.15-2.97 (m, 2H), 3.06 (s, 3H), 2.90 (t, J = 7.7 Hz, 2H), 2.52-2.38 (m, 1H), 2.15-1.98 (m, 1H), 1.58 (d, J = 6.2 Hz, 3H). |
| 301 | 337.2 | 1H NMR (400 MHz, DMSO-d6) δ 8.68 (s, 2H), 7.95-7.88 (m, 2H), 7.55-7.48 (m, 2H), 4.16 (dd, J = 8.6, 6.4 Hz, 1H), 4.12-3.96 (m, 2H), 3.60 (dd, J = 8.6, 5.1 Hz, 1H), 3.00 (hept, J = 7.6, 6.9 Hz, 2H), 2.81 (t, J = 7.8 Hz, 2H), 2.01 (p, J = 7.5 Hz, 2H), 1.47 (d, J = 6.2 Hz, 3H), 1.42-1.25 (m, 4H). |
| 302 | 404.3 | 1H NMR (400 MHz, Chloroform-d) δ 7.83 (d, J = 8.1 Hz, 2H), 7.43-7.36 (m, 2H), 4.82 (dt, J = 8.2, 6.0 Hz, 1H), 4.42 (td, J = 9.6, 5.9 Hz, 1H), 4.32 (td, J = 9.7, 6.3 Hz, 1H), 3.52 (s, 2H), 3.13 (t, J = 7.8 Hz, 2H), 3.13-3.05 (m, 4H), 3.06-2.98 (m, 4H), 2.79-2.78 (m, 1H), 2.76 (s, 3H), 2.73-2.59 (m, 1H), 2.21-2.19 (m, 2H), 2.10 (m, 1H), 1.63 (d, J = 6.3 Hz, 3H), 1.21-1.09 (m, 2H), 1.08-0.96 (m, 2H). |
| 303 | 343.2 | 1H NMR (400 MHz, DMSO-d6) δ 7.97-7.89 (m, 2H), 7.84 (dd, J = 8.0, 1.5 Hz, 1H), 7.67 (s, 1H), 7.56 (d, J = 7.8 Hz, 2H), 4.40 (q, J = 6.8 Hz, 1H), 4.08-3.84 (m, 2H), 3.00 (hept, J = 7.6, 7.0 Hz, 2H), 2.80 (t, J = 7.7 Hz, 2H), 2.44-2.31 (m, 1H), 2.00 (dq, J = 18.6, 10.0, 8.7 Hz, 3H), 1.49 (d, J = 6.1 Hz, 3H). |
| 304 | 391.2 | 1H NMR (400 MHz, DMSO-d6) δ 7.94 (dd, J = 8.6, 1.9 Hz, 2H), 7.62 (d, J = 7.9 Hz, 2H), 4.42 (dt, J = 7.6, 6.1 Hz, 1H), 4.03-3.86 (m, 2H), |

TABLE 1-continued

MS and NMR DATA

| Example No | ES/MS m/z (M + H)+ | 1H NMR |
|---|---|---|
| | | 3.75-3.70 (m, 3H) 3.11-2.93 (m, 3H), 2.82 (t, J = 7.7 Hz, 2H), 2.40 (dtd, J = 10.8, 8.7, 4.8 Hz, 1H), 2.07-1.88 (m, 3H), 1.50 (d, J = 6.1 Hz, 3H), 1.43 (s, 2H), 1.12 (s, 2H). |
| 305 | 327.2 | 1H NMR (400 MHz, DMSO-d6) δ 7.82-7.68 (m, 5H), 4.42 (p, J = 6.3 Hz, 1H), 4.04-3.86 (m, 2H), 3.03 (h, J = 8.3 Hz, 2H), 2.82 (t, J = 7.7 Hz, 2H), 2.40 (ddt, J = 13.4, 8.5, 4.7 Hz, 1H), 2.08-1.88 (m, 3H), 1.49 (d, J = 6.1 Hz, 3H). |
| 306 | 399.2 | 1H NMR (400 MHz, DMSO-d6) δ 8.27 (s, 1H), 7.85 (d, J = 8.4 Hz, 2H), 7.49 (d, J = 8.3 Hz, 2H), 4.43 (m, 1H), 4.04-3.87 (m, 1H), 3.00 (m, 2H), 2.82 (t, J = 7.8 Hz, 2H), 2.67 (s, 3H), 2.45-2.34 (m, 1H), 1.98 (m, 3H), 1.50 (d, J = 6.2 Hz, 3H), 1.41-1.26 (m, 2H), 1.20 (t, J = 3.6 Hz, 2H). |
| 307 | 343.2 | 1H NMR (400 MHz, DMSO-d6) δ 7.82-7.68 (m, 5H), 4.18 (dd, J = 8.7, 6.3 Hz, 1H), 4.07 (m, 2H), 3.62 (dd, J = 8.7, 5.0 Hz, 1H), 3.03 (m, 2H), 2.83 (t, J = 7.7 Hz, 2H), 2.02 (p, J = 7.5 Hz, 2H), 1.48 (d, J = 6.1 Hz, 3H). |
| 308 | 359.2 | 1H NMR (400 MHz, DMSO-d6) δ 7.98-7.89 (m, 2H), 7.85 (dd, J = 8.0, 1.6 Hz, 1H), 7.68 (s, 1H), 7.57 (d, J = 7.9 Hz, 1H), 4.18 (dd, J = 8.7, 6.3 Hz, 1H), 4.06 (m, 2H), 3.62 (dd, J = 8.7, 5.0 Hz, 1H), 3.03 (m, 2H), 2.82 (t, J = 7.8 Hz, 2H), 2.02 (m, 2H), 1.47 (d, J = 6.2 Hz, 3H). |
| 309 | 339.2 | 1H NMR (400 MHz, DMSO-d6) δ 7.88 (d, J = 8.0 Hz, 1H), 7.71-7.66 (m, 1H), 7.60 (t, J = 2.3 Hz, 2H), 7.52 (dd, J = 7.9, 1.5 Hz, 1H), 4.43 (h, J = 6.3 Hz, 1H), 4.03-3.87 (m, 2H), 3.94 (s, 3H), 3.14-2.95 (m, 2H), 2.82 (t, J = 7.8 Hz, 2H), 2.47-2.33 (m, 1H), 2.00 (m, 3H), 1.51 (d, J = 6.1 Hz, 3H). |
| 310 | 321.2 | 1H NMR (400 MHz, DMSO-d6) δ 7.86 (d, J = 8.0 Hz, 1H), 7.64 (d, J = 1.3 Hz, 1H), 7.56 (dd, J = 8.0, 1.3 Hz, 1H), 4.43 (q, J = 6.6 Hz, 1H), 3.98 (s, 3H), 4.04-3.87 (m, 2H), 3.13-2.94 (m, 2H), 2.83 (t, J = 7.7 Hz, 2H), 2.47-2.34 (m, 1H), 2.10-1.91 (m, 3H), 1.50 (d, J = 6.1 Hz, 3H). |
| 311 | 435.3 | 1H NMR (400 MHz, Chloroform-d) δ 7.94-7.87 (m, 2H), 7.51 (d, J = 8.1 Hz, 2H), 5.09 (s, 1H), 4.52 (m, 1H), 4.13 (m, 1H), 4.07-3.96 (m, 1H), 3.15-2.96 (m, 2H), 2.89 (t, J = 7.7 Hz, 2H), 2.60-2.51 (m, 3H), 2.42 (m, 1H), 2.19-2.05 (m, 1H), 2.09-1.88 (m, 3H), 1.87 (m, 1H), 1.59 (t, J = 6.4 Hz, 3H), 1.37-1.22 (m, 9H), 1.00-0.86 (m, 2H), 0.90-0.80 (m, 2H). |
| 312 | 335.2 | 1H NMR (400 MHz, DMSO-d6) δ 8.50 (s, 3H), 7.96 (d, J = 8.1 Hz, 2H), 7.64 (d, J = 8.3 Hz, 2H), 4.41 (p, J = 6.5 Hz, 1H), 4.01-3.86 (m, 2H), 3.00 (m, 2H), 2.81 (t, J = 7.7 Hz, 2H), 2.72-2.52 (m, 2H), 2.46-2.34 (m, 1H), 2.24-1.76 (m, 5H), 1.49 (d, J = 6.2 Hz, 3H). |
| 313 | 309.2 | 1H NMR (400 MHz, DMSO-d6) δ 8.11-8.03 (m, 1H), 7.96-7.84 (m, 2H), 4.42 (q, J = 6.6 Hz, 1H), 4.03-3.86 (m, 2H), 3.03 (h, J = 8.4 Hz, 2H), 2.82 (t, J = 7.8 Hz, 2H), 2.47-2.34 (m, 1H), 2.07-1.90 (m, 3H), 1.49 (d, J = 6.2 Hz, 3H). |
| 314 | 325.2 | 1H NMR (400 MHz, DMSO-d6) δ 8.15-8.08 (m, 2H), 7.98 (dd, J = 8.1, 1.5 Hz, 1H), 4.43 (m, 1H), 4.04-3.86 (m, 2H), 3.01 (m, 2H), 2.82 (t, J = 7.8 Hz, 2H), 2.41 (m, 1H), 2.10-1.91 (m, 3H), 1.49 (d, J = 6.2 Hz, 3H). |
| 315 | 345.2 | 1H NMR (400 MHz, DMSO-d6) δ 8.19 (s, 1H), 7.93 (s, 1H), 7.58 (d, J = 8.4 Hz, 2H), 4.41 (m, 1H), 4.03-3.85 (m, 2H), 3.03 (m, 2H), 2.81 (t, J = 7.8 Hz, 2H), 2.40 (m, 1H), 2.08-1.90 (m, 3H), 1.48 (d, J = 6.2 Hz, 3H). |
| 316 | 377.2 | 1H NMR (400 MHz, DMSO-d6) δ 8.23 (d, J = 1.6 Hz, 1H), 8.16 (dd, J = 7.9, 1.6 Hz, 1H), 8.02 (s, 1H), 7.72-7.64 (m, 2H), 4.42 (h, J = 6.4 Hz, 1H), 4.03-3.86 (m, 2H), 3.03 (h, J = 8.2 Hz, 2H), 2.83 (t, J = 7.8 Hz, 2H), 2.47-2.34 (m, 1H), 2.09-1.88 (m, 3H), 1.49 (d, J = 6.2 Hz, 3H). |
| 317 | 369.2 | 1H NMR (400 MHz, DMSO-d6) δ 11.37 (d, J = 5.8 Hz, 1H), 8.30 (d, J = 8.4 Hz, 1H), 8.16 (d, J = 1.6 Hz, 1H), 7.99 (dd, J = 8.3, 1.6 Hz, 1H), 7.29-7.20 (m, 1H), 6.69 (d, J = 7.1 Hz, 1H), 4.52 (q, J = 6.7 Hz, 1H), 4.12-3.95 (m, 2H), 3.17 (ddq, J = 9.2, 6.1, 3.4, 2.9 Hz, 2H), 2.67-2.52 (m, 3H), 2.01 (ddt, J = 10.9, 9.0, 6.6 Hz, 1H), 1.53 (d, J = 6.2 Hz, 3H). |
| 318 | 385.2 | 1H NMR (400 MHz, DMSO-d6) δ 11.38 (d, J = 5.7 Hz, 1H), 8.31 (d, J = 8.4 Hz, 1H), 8.17 (d, J = 1.6 Hz, 1H), 8.00 (dd, J = 8.5, 1.7 Hz, 1H), 7.29-7.21 (m, 1H), 6.69 (d, J = 7.1 Hz, 1H), 4.28 (dd, J = 9.1, 5.9 Hz, 1H), 4.21-4.09 (m, 1H), 3.72 (dd, J = 9.1, 4.5 Hz, 1H), 3.19 (tq, J = 6.4, 3.7, 2.7 Hz, 2H), 2.60 (ddd, J = 23.6, 15.8, 7.3 Hz, 2H), 1.51 (d, J = 5.9 Hz, 3H). |
| 319 | 353.2 | 1H NMR (400 MHz, DMSO-d6) δ 7.89 (d, J = 8.0 Hz, 1H), 7.61 (d, J = 16.1 Hz, 3H), 7.51 (d, J = 8.1 Hz, 1H), 4.43 (q, J = 6.7 Hz, 1H), 4.24 (q, J = 6.9 Hz, 2H), 4.04-3.87 (m, 2H), 3.13-2.95 (m, 2H), 2.83 (t, J = 7.7 Hz, 2H), 2.50 (p, J = 1.8 Hz, 3H), 2.46-2.34 (m, 1H), 2.10-1.91 (m, 3H), 1.50 (d, J = 6.1 Hz, 3H), 1.42 (t, J = 6.9 Hz, 3H). |

TABLE 1-continued

MS and NMR DATA

| Example No | ES/MS m/z (M + H)+ | 1H NMR |
|---|---|---|
| 320 | 402.1 | 1H NMR (400 MHz, Chloroform-d) δ 8.99-8.94 (m, 1H), 8.47 (s, 1H), 7.91 (dt, J = 8.2, 1.1 Hz, 1H), 7.82 (d, J = 8.1 Hz, 1H), 7.26 (s, 3H), 4.77 (h, J = 6.3 Hz, 1H), 4.38 (td, J = 9.5, 5.7 Hz, 1H), 4.27 (td, J = 9.5, 6.4 Hz, 1H), 3.13 (dt, J = 10.8, 7.3 Hz, 4H), 2.71-2.56 (m, 1H), 2.29-2.15 (m, 2H), 2.10 (dq, J = 16.2, 6.0 Hz, 1H), 1.62 (d, J = 6.2 Hz, 3H). |
| 321 | 381.1 | 1H NMR (400 MHz, DMSO-d6) δ 8.37 (d, J = 1.9 Hz, 1H), 8.14 (d, J = 7.8 Hz, 1H), 7.99 (d, J = 7.8 Hz, 1H), 7.76 (t, J = 7.8 Hz, 1H), 7.51 (s, 2H), 4.50 (td, J = 12.7, 11.8, 6.0 Hz, 1H), 4.11-3.94 (m, 2H), 3.13 (d, J = 8.4 Hz, 3H), 2.60 (tt, J = 16.1, 7.1 Hz, 2H), 2.49-2.40 (m, 1H), 2.06-1.96 (m, 1H), 1.52 (d, J = 6.2 Hz, 3H). |
| 322 | 397.1 | 1H NMR (400 MHz, Chloroform-d) δ 8.45 (d, J = 1.8 Hz, 1H), 8.12 (dt, J = 7.9, 1.4 Hz, 1H), 8.04 (ddd, J = 7.9, 2.0, 1.0 Hz, 1H), 7.66 (t, J = 7.9 Hz, 1H), 4.97 (s, 2H), 4.45 (dd, J = 9.7, 5.8 Hz, 1H), 4.33 (p, J = 4.7 Hz, 2H), 3.91 (dd, J = 9.7, 4.3 Hz, 1H), 3.20-3.00 (m, 2H), 2.57 (tt, J = 13.5, 6.3 Hz, 2H), 2.16 (d, J = 6.0 Hz, 1H), 1.61 (d, J = 6.0 Hz, 3H). |
| 323 | 409.1 | 1H NMR (400 MHz, DMSO-d6) δ 7.92 (s, 1H), 7.85 (dd, J = 6.3, 2.5 Hz, 1H), 7.66 (t, J = 6.4 Hz, 1H), 7.53 (d, J = 6.4 Hz, 2H), 4.49 (q, J = 6.7 Hz, 1H), 4.26 (d, J = 6.2 Hz, 2H), 4.10-3.92 (m, 2H), 3.12 (dd, J = 6.8, 3.0 Hz, 1H), 2.89 (s, 3H), 2.58 (dt, J = 15.5, 8.4 Hz, 2H), 2.49 (s, 1H), 2.00 (t, J = 9.4 Hz, 1H), 1.52 (d, J = 6.2 Hz, 3H). |
| 324 | 425.2 | 1H NMR (400 MHz, DMSO-d6) δ 7.94 (s, 1H), 7.93-7.82 (m, 2H), 7.74-7.63 (m, 1H), 7.59-7.50 (m, 2H), 4.26 (d, J = 6.3 Hz, 3H), 4.13 (m, 2H), 3.69 (m, 1H), 3.14 (d, J = 8.7 Hz, 2H), 2.90 (s, 3H), 2.59 (m, 2H), 1.50 (d, J = 5.7 Hz, 3H). |
| 325 | 271.1 | 1H NMR (400 MHz, Chloroform-d) δ 7.53 (s, 1H), 4.50 (h, J = 6.4 Hz, 1H), 4.11 (td, J = 8.7, 4.7 Hz, 1H), 4.00 (q, J = 8.2 Hz, 1H), 3.01 (t, J = 7.4 Hz, 2H), 2.87 (t, J = 7.8 Hz, 2H), 2.56 (s, 3H), 2.43 (dtd, J = 16.3, 8.6, 4.7 Hz, 1H), 2.17-1.93 (m, 3H), 1.55 (d, J = 6.2 Hz, 3H). |
| 326 | 271.1 | 1H NMR (400 MHz, Chloroform-d) δ 6.89 (s, 1H), 4.72 (dt, J = 8.2, 6.1 Hz, 1H), 4.34 (td, J = 9.4, 5.6 Hz, 1H), 4.23 (td, J = 9.4, 6.5 Hz, 1H), 3.22 (t, J = 7.5 Hz, 2H), 3.11 (t, J = 7.9 Hz, 2H), 2.60 (dtd, J = 11.3, 8.9, 5.6 Hz, 1H), 2.41 (s, 3H), 2.22 (p, J = 7.7 Hz, 2H), 2.08 (ddt, J = 11.7, 9.3, 6.2 Hz, 1H), 1.59 (d, J = 6.2 Hz, 3H). |
| 327 | 287.1 | 1H NMR (400 MHz, Chloroform-d) δ 7.48 (s, 1H), 4.73 (dt, J = 8.2, 6.2 Hz, 1H), 4.34 (td, J = 9.4, 5.6 Hz, 1H), 4.23 (td, J = 9.4, 6.5 Hz, 1H), 3.14 (t, J = 7.9 Hz, 2H), 3.06 (t, J = 7.4 Hz, 2H), 2.58 (m, 4H), 2.26 (p, J = 7.8 Hz, 2H), 2.09 (ddt, J = 11.7, 9.3, 6.2 Hz, 1H), 1.61 (d, J = 6.3 Hz, 3H). |
| 328 | 395.2 | 1H NMR (400 MHz, Chloroform-d) δ 7.83 (s, 1H), 7.80 (dd, J = 7.7, 1.5 Hz, 1H), 7.41 (t, J = 7.6 Hz, 1H), 7.34 (d, J = 7.6 Hz, 1H), 4.87 (s, 1H), 4.51 (dt, J = 14.1, 6.4 Hz, 1H), 4.38 (d, J = 6.0 Hz, 2H), 4.13 (td, J = 8.6, 4.6 Hz, 1H), 4.07-3.94 (m, 1H), 3.15-2.94 (m, 2H), 2.89 (t, J = 7.7 Hz, 2H), 2.43 (dtd, J = 10.7, 8.5, 4.7 Hz, 1H), 2.15-1.95 (m, 3H), 1.58 (d, J = 6.2 Hz, 3H), 1.47 (s, 9H). |
| 329 | 295.1 | 1H NMR (400 MHz, DMSO-d6) δ 8.17 (s, 3H), 7.96-7.83 (m, 2H), 7.57 (d, J = 5.3 Hz, 2H), 4.41 (p, J = 6.5 Hz, 1H), 4.13 (q, J = 5.8 Hz, 2H), 4.04-3.83 (m, 2H), 3.00 (hept, J = 7.6, 7.0 Hz, 2H), 2.81 (t, J = 7.7 Hz, 2H), 2.41 (q, J = 8.4 Hz, 1H), 1.99 (ddt, J = 19.2, 10.5, 4.7 Hz, 3H), 1.50 (d, J = 6.1 Hz, 3H). |
| 330 | 309.2 | 1H NMR (400 MHz, DMSO-d6) δ 8.78 (s, 2H), 7.99-7.84 (m, 2H), 7.59 (d, J = 6.0 Hz, 2H), 4.40 (h, J = 6.4 Hz, 1H), 4.22 (t, J = 6.0 Hz, 2H), 4.05-3.78 (m, 2H), 3.01 (hept, J = 7.5, 6.9 Hz, 2H), 2.82 (t, J = 7.7 Hz, 2H), 2.61 (t, J = 5.4 Hz, 3H), 2.40 (dp, J = 11.2, 4.3 Hz, 1H), 2.06-1.90 (m, 3H), 1.50 (d, J = 6.1 Hz, 3H). |
| 331 | 266.1 | 1H NMR (400 MHz, DMSO-d6) δ 7.99-7.79 (m, 2H), 7.58-7.41 (m, 3H), 4.42 (q, J = 6.7 Hz, 1H), 4.05-3.83 (m, 2H), 3.13-2.92 (m, 2H), 2.81 (t, J = 7.7 Hz, 2H), 2.40 (m, 1H), 2.11-1.84 (m, 3H), 1.50 (d, J = 6.2 Hz, 3H). |
| 332 | 278.1 | 1H NMR (400 MHz, Chloroform-d) δ 7.89 (dt, J = 7.7, 1.7 Hz, 2H), 7.50-7.36 (m, 3H), 4.65-4.40 (m, 1H), 4.21-4.10 (m, 1H), 4.10-3.90 (m, 1H), 3.47-2.99 (m, 1H), 2.55-2.32 (m, 2H), 2.09-1.81 (m, 2H), 1.59 (dd, J = 6.2, 2.3 Hz, 4H), 1.36-1.10 (m, 1H), 0.27 (dq, J = 20.7, 4.1 Hz, 1H). |
| 333 | 278.1 | 1H NMR (400 MHz, DMSO-d6) δ 7.91-7.84 (m, 2H), 7.54-7.39 (m, 3H), 4.40 (dt, J = 13.7, 6.5 Hz, 1H), 3.99-3.83 (m, 2H), 3.20 (dd, J = 16.3, 6.5 Hz, 1H), 3.07 (d, J = 16.4 Hz, 1H), 2.44-2.25 (m, 2H), 2.09-1.86 (m, 2H), 1.49 (d, J = 6.2 Hz, 3H), 1.22 (dq, J = 8.1, 4.2 Hz, 1H), 0.21 (q, J = 3.9 Hz, 1H). |
| 334 | 278.1 | 1H NMR (400 MHz, DMSO-d6) δ 7.92-7.83 (m, 2H), 7.52-7.41 (m, 3H), 4.39 (h, J = 6.3 Hz, 1H), 3.99-3.82 (m, 2H), 3.30-3.19 (m, 1H), 3.07-2.92 (m, 1H), 2.38 (dtd, J = 10.7, 8.5, 4.7 Hz, 1H), 2.33-2.25 (m, 1H), 2.09-1.90 (m, 2H), 1.50 (d, J = 6.2 Hz, 3H), 1.21 (td, J = 8.1, 4.3 Hz, 1H), 0.18 (td, J = 4.2, 3.1 Hz, 1H). |

TABLE 1-continued

| | | MS and NMR DATA |
|---|---|---|
| Example No | ES/MS m/z (M + H)+ | 1H NMR |
| 335 | 292.1 | 1H NMR (400 MHz, Chloroform-d) δ 7.92-7.80 (m, 2H), 7.49-7.37 (m, 3H), 4.53 (h, J = 6.3 Hz, 1H), 4.13 (td, J = 8.7, 4.7 Hz, 1H), 4.02 (q, J = 8.2 Hz, 1H), 3.19-2.76 (m, 4H), 2.52-2.35 (m, 1H), 2.02 (ddt, J = 10.9, 8.9, 6.7 Hz, 1H), 1.59 (d, J = 6.2 Hz, 3H), 0.75-0.51 (m, 4H). |
| 336 | 280.1 | 1H NMR (400 MHz, Chloroform-d) δ 7.97-7.84 (m, 2H), 7.49-7.36 (m, 3H), 4.52 (q, J = 6.7, 6.3 Hz, 1H), 4.12 (td, J = 8.7, 4.7 Hz, 1H), 4.02 (dt, J = 14.2, 8.0 Hz, 1H), 3.00 (dtt, J = 26.5, 15.4, 7.5 Hz, 3H), 2.50-2.23 (m, 2H), 2.10-1.94 (m, 1H), 1.59 (dd, J = 6.3, 2.6 Hz, 4H), 1.31 (dd, J = 7.0, 0.9 Hz, 3H). |
| 337 | 280.2 | 1H NMR (400 MHz, Chloroform-d) δ 7.98-7.80 (m, 2H), 7.50-7.34 (m, 3H), 4.61-4.42 (m, 1H), 4.20-4.06 (m, 1H), 4.02 (q, J = 8.2 Hz, 1H), 3.33-3.11 (m, 1H), 3.11-2.91 (m, 1H), 2.74-2.35 (m, 4H), 2.13-1.91 (m, 1H), 1.58 (dd, J = 6.2, 1.5 Hz, 3H), 1.15 (dd, J = 17.9, 6.4 Hz, 3H). |
| 338 | 292.1 | 1H NMR (400 MHz, Chloroform-d) δ 7.99-7.88 (m, 2H), 7.51-7.38 (m, 3H), 4.44 (h, J = 6.5 Hz, 1H), 4.05 (td, J = 8.7, 4.5 Hz, 1H), 3.95 (q, J = 8.3 Hz, 1H), 3.15 (dq, J = 18.7, 8.0 Hz, 2H), 2.41-2.31 (m, 1H), 2.15 (t, J = 7.5 Hz, 2H), 2.06-1.91 (m, 1H), 1.53 (m, 3H), 1.32-1.17 (m, 2H), 0.96-0.85 (m, 2H),. |
| 339 | 280.1 | 1H NMR (400 MHz, Chloroform-d) δ 7.82 (m, 2H), 7.50-7.37 (m, 3H), 4.60-4.47 (m, 1H), 4.13 (m, 1H), 4.09-3.94 (m, 1H), 3.63 (m, 1H), 2.94 (m, 1H), 2.82 (m, 1H), 2.42 (m, 1H), 2.36-2.23 (m, 1H), 2.06-1.94 (m, 1H), 1.66 (m, 1H), 1.58 (m, 3H), 0.95 (m, 3H). |
| 340 | 294.2 | 1H NMR (400 MHz, Chloroform-d) δ 7.50-7.31 (m, 5H), 4.56-4.39 (m, 1H), 4.05 (mz, 1H), 4.00-3.90 (m, 1H), 3.34-3.08 (m, 1H), 2.89-2.61 (m, 2H), 2.38 (m, 1H), 2.05-1.71 (m, 3H), 1.59 (m, 2H), 1.51 (m, 3H), 0.75 (m, 3H). |
| 341 | 270.1 | 1H NMR (400 MHz, Chloroform-d) δ 7.52 (s, 1H), 7.47 (s, 1H), 4.54-4.41 (m, 1H), 4.11 (dt, J = 8.8, 4.4 Hz, 1H), 4.06 (s, 3H), 3.98 (q, J = 8.2 Hz, 1H), 2.95 (t, J = 7.3 Hz, 2H), 2.88 (t, J = 7.8 Hz, 2H), 2.44 (dtd, J = 16.5, 8.7, 4.7 Hz, 1H), 2.09 (p, J = 7.6 Hz, 2H), 2.01 (dq, J = 11.0, 6.9 Hz, 1H), 1.53 (d, J = 6.1 Hz, 3H). |
| 342 | 287.1 | 1H NMR (400 MHz, Chloroform-d) δ 7.73 (d, J = 1.3 Hz, 1H), 4.73 (h, J = 6.3 Hz, 1H), 4.36 (td, J = 9.4, 5.5 Hz, 1H), 4.26 (td, J = 9.4, 6.5 Hz, 1H), 3.27 (t, J = 7.5 Hz, 2H), 3.11 (t, J = 7.8 Hz, 2H), 2.57 (d, J = 1.1 Hz, 4H), 2.19 (p, J = 7.7 Hz, 2H), 2.09 (ddt, J = 11.7, 9.5, 6.3 Hz, 1H), 1.62 (d, J = 6.2 Hz, 3H). |
| 343 | 268.1 | 1H NMR (400 MHz, DMSO-d6) δ 9.67 (dd, J = 2.4, 1.3 Hz, 1H), 9.39 (dd, J = 5.4, 1.3 Hz, 1H), 8.06 (dd, J = 5.4, 2.4 Hz, 1H), 4.44 (h, J = 6.3 Hz, 1H), 4.05-3.88 (m, 2H), 3.08 (h, J = 8.5 Hz, 2H), 2.83 (t, J = 7.8 Hz, 2H), 2.42 (dtd, J = 10.8, 8.6, 4.8 Hz, 1H), 2.12-1.86 (m, 3H), 1.50 (d, J = 6.2 Hz, 3H). |
| 344 | 268.1 | 1H NMR (400 MHz, Chloroform-d) δ 9.56 (d, J = 1.4 Hz, 1H), 8.75-8.65 (m, 2H), 4.81 (dt, J = 8.2, 6.1 Hz, 1H), 4.47-4.36 (m, 1H), 4.31 (td, J = 9.5, 6.5 Hz, 1H), 3.34 (td, J = 7.3, 3.0 Hz, 2H), 3.14 (t, J = 7.9 Hz, 2H), 2.73-2.58 (m, 1H), 2.26-2.06 (m, 3H), 1.65 (d, J = 6.3 Hz, 3H). |
| 345 | 363.3 | 1H NMR (400 MHz, Chloroform-d) δ 7.98 (d, J = 1.8 Hz, 1H), 7.89 (dt, J = 6.9, 1.9 Hz, 1H), 7.63-7.54 (m, 2H), 4.81 (h, J = 6.2 Hz, 1H), 4.42 (td, J = 9.7, 6.1 Hz, 1H), 4.35-4.21 (m, 3H), 3.72 (br s, 2H), 3.58 (d, J = 11.8 Hz, 2H), 3.11 (t, J = 7.8 Hz, 2H), 3.04 (td, J = 7.1, 4.4 Hz, 2H), 2.74-2.55 (m, 2H), 2.26-2.14 (m, 2H), 2.09 (ddt, J = 11.6, 9.3, 6.1 Hz, 1H), 2.04-1.76 (m, 4H), 1.61 (d, J = 6.3 Hz, 3H), 1.49-1.32 (m, 1H). |
| 346 | 323.2 | 1H NMR (400 MHz, Chloroform-d) δ 8.00 (d, J = 1.9 Hz, 1H), 7.91 (dt, J = 6.5, 2.0 Hz, 1H), 7.66-7.57 (m, 2H), 4.82 (dt, J = 8.3, 6.0 Hz, 1H), 4.47-4.37 (m, 1H), 4.37-4.25 (m, 3H), 3.12 (t, J = 7.8 Hz, 2H), 3.05 (td, J = 7.1, 4.8 Hz, 2H), 2.84 (s, 6H), 2.74-2.58 (m, 1H), 2.26-2.15 (m, 2H), 2.09 (ddt, J = 11.6, 9.3, 6.0 Hz, 1H), 1.61 (d, J = 6.3 Hz, 3H). |
| 347 | 335.2 | 1H NMR (400 MHz, Chloroform-d) δ 7.93 (d, J = 2.1 Hz, 1H), 7.88-7.82 (m, 1H), 7.58 (dd, J = 5.0, 2.0 Hz, 2H), 4.83 (dt, J = 8.3, 6.0 Hz, 1H), 4.43 (td, J = 9.6, 5.9 Hz, 1H), 4.38-4.24 (m, 5H), 3.91 (d, J = 9.8 Hz, 2H), 3.11 (t, J = 7.8 Hz, 2H), 3.04 (q, J = 6.9 Hz, 2H), 2.82-2.69 (m, 1H), 2.69-2.57 (m, 1H), 2.41 (s, 1H), 2.27-2.15 (m, 2H), 2.09 (ddt, J = 11.5, 9.3, 6.0 Hz, 1H), 1.62 (d, J = 6.3 Hz, 3H). |
| 348 | 349.2 | 1H NMR (400 MHz, Chloroform-d) δ 8.00 (d, J = 1.8 Hz, 1H), 7.86 (dt, J = 7.8, 1.5 Hz, 1H), 7.64 (dt, J = 7.7, 1.5 Hz, 1H), 7.58 (t, J = 7.7 Hz, 1H), 4.83 (dt, J = 8.3, 6.0 Hz, 1H), 4.48-4.38 (m, 1H), 4.36 (d, J = 3.5 Hz, 2H), 4.34-4.27 (m, 1H), 3.70 (s, 2H), 3.11 (t, J = 7.8 Hz, 2H), 3.04 (td, J = 7.1, 4.7 Hz, 2H), 2.97 (d, J = 21.6 Hz, 2H), 2.72-2.59 (m, 1H), 2.25-2.17 (m, 2H), 2.17-2.06 (m, 6H), 1.61 (d, J = 6.3 Hz, 3H). |

TABLE 1-continued

MS and NMR DATA

| Example No | ES/MS m/z (M + H)+ | 1H NMR |
|---|---|---|
| 349 | 365.2 | 1H NMR (400 MHz, Chloroform-d) δ 7.99 (q, J = 1.4 Hz, 1H), 7.89 (ddd, J = 5.8, 3.1, 1.8 Hz, 1H), 7.64-7.52 (m, 2H), 4.81 (dt, J = 8.2, 6.0 Hz, 1H), 4.42 (td, J = 9.6, 6.1 Hz, 1H), 4.37-4.25 (m, 3H), 3.97 (t, J = 4.9 Hz, 4H), 3.47 (br s, 4H), 3.11 (t, J = 7.8 Hz, 2H), 3.03 (td, J = 7.1, 3.9 Hz, 2H), 2.73-2.55 (m, 1H), 2.26-2.14 (m, 2H), 2.09 (m, 1H), 1.61 (d, J = 6.3 Hz, 3H). |
| 350 | 351.2 | 1H NMR (400 MHz, Chloroform-d) δ 7.92 (s, 1H), 7.85 (s, 1H), 7.67-7.52 (m, 2H), 4.82 (h, J = 6.3 Hz, 1H), 4.66 (q, J = 6.5 Hz, 1H), 4.52-4.35 (m, 4H), 4.30 (td, J = 9.7, 6.3 Hz, 1H), 3.87 (s, 1H), 3.07 (m, 3H), 2.96 (s, 5H), 2.75-2.58 (m, 1H), 2.30-2.15 (m, 2H), 2.10 (m, 1H), 1.62 (d, J = 6.3 Hz, 3H). |
| 351 | 439.0 | 1H NMR (400 MHz, DMSO-d6) δ 8.17 (s, 1H), 8.07 (s, 1H), 7.38 (d, J = 9.2 Hz, 2H), 4.81 (t, J = 8.8 Hz, 2H), 4.28-4.21 (m, 1H), 4.14-4.09 (m, 1H), 3.72-3.64 (m, 1H), 3.36 (t, J = 8.8 Hz, 2H), 3.21-3.05 (m, 3H), 2.70-2.53 (m, 2H), 1.51 (d, J = 5.8 Hz, 3H). |
| 352 | 313.2 | 1H NMR (400 MHz, DMSO-d6) δ 8.32 (s, 3H), 7.96 (d, J = 1.9 Hz, 1H), 7.94-7.86 (m, 1H), 7.58 (d, J = 5.7 Hz, 2H), 5.13 (ddt, J = 57.0, 5.9, 3.9 Hz, 1H), 4.50-4.38 (m, 2H), 4.15 (q, J = 5.8 Hz, 2H), 3.94 (ddd, J = 26.1, 10.2, 4.0 Hz, 1H), 3.05 (h, J = 8.7 Hz, 2H), 2.85 (t, J = 7.7 Hz, 2H), 2.04 (m, 2H), 1.54 (d, J = 6.5 Hz, 3H). |
| 353 | 311.1 | 1H NMR (400 MHz, DMSO-d6) δ 8.26 (s, 3H), 7.94 (s, 1H), 7.89 (td, J = 4.6, 1.7 Hz, 1H), 7.57 (d, J = 4.8 Hz, 2H), 4.25-4.00 (m, 5H), 3.63 (dd, J = 8.7, 5.0 Hz, 1H), 3.03 (h, J = 8.4 Hz, 2H), 2.83 (t, J = 7.7 Hz, 2H), 2.01 (pt, J = 7.7, 3.3 Hz, 2H), 1.48 (d, J = 6.2 Hz, 3H). |
| 354 | 344.2 | 1H NMR (400 MHz, DMSO-d6) δ 8.10 (d, J = 8.5 Hz, 2H), 8.08-7.98 (m, 2H), 4.41 (h, J = 6.3 Hz, 1H), 4.00-3.79 (m, 2H), 3.27 (s, 3H), 3.02 (h, J = 8.4 Hz, 2H), 2.82 (t, J = 7.7 Hz, 2H), 2.46-2.35 (m, 1H), 2.11-1.91 (m, 3H), 1.49 (d, J = 6.1 Hz, 3H). |
| 355 | 323.2 | 1H NMR (400 MHz, DMSO-d6) δ 10.13 (s, 1H), 7.86 (d, J = 8.7 Hz, 2H), 7.69 (d, J = 8.7 Hz, 2H), 4.38 (q, J = 6.7 Hz, 1H), 3.99-3.81 (m, 2H), 3.01 (h, J = 8.3 Hz, 2H), 2.77 (t, J = 7.8 Hz, 2H), 2.44-2.30 (m, 1H), 2.07 (s, 3H), 1.97 (tt, J = 17.4, 7.7 Hz, 3H), 1.49 (d, J = 6.2 Hz, 3H). |
| 356 | 367.2 | 1H NMR (400 MHz, DMSO-d6) δ 8.24 (t, J = 5.7 Hz, 1H), 7.70 (d, J = 6.7 Hz, 2H), 7.47-7.38 (m, 1H), 4.70 (t, J = 5.6 Hz, 1H), 4.39 (h, J = 6.4 Hz, 1H), 3.99-3.84 (m, 2H), 3.51 (q, J = 6.1 Hz, 2H), 3.30 (d, J = 2.7 Hz, 2H), 2.99 (hept, J = 7.6, 7.0 Hz, 2H), 2.80 (t, J = 7.7 Hz, 2H), 2.39 (s, 4H), 2.09-1.89 (m, 3H), 1.49 (d, J = 6.2 Hz, 3H). |
| 357 | 351.2 | 1H NMR (400 MHz, DMSO-d6) δ 7.73 (dd, J = 10.5, 2.7 Hz, 2H), 7.27 (d, J = 7.8 Hz, 1H), 4.39 (h, J = 6.3 Hz, 1H), 4.03-3.81 (m, 2H), 3.11-2.93 (m, 5H), 2.79 (d, J = 4.4 Hz, 5H), 2.45-2.31 (m, 1H), 2.26 (s, 3H), 2.06-1.91 (m, 3H), 1.49 (d, J = 6.2 Hz, 3H). |
| 358 | 367.2 | 1H NMR (400 MHz, Ethanol-d6) δ 7.83 (d, J = 8.1 Hz, 2H), 7.70 (t, J = 6.2 Hz, 1H), 7.36 (d, J = 8.1 Hz, 2H), 4.38 (h, J = 6.2 Hz, 1H), 4.23 (d, J = 6.2 Hz, 2H), 4.01 (q, J = 7.1 Hz, 2H), 3.98-3.78 (m, 2H), 2.98 (hept, J = 7.6, 7.0 Hz, 2H), 2.78 (t, J = 7.7 Hz, 2H), 2.45-2.29 (m, 1H), 2.09-1.84 (m, 3H), 1.48 (d, J = 6.1 Hz, 3H), 1.17 (t, J = 7.1 Hz, 3H). |
| 359 | 337.2 | 1H NMR (400 MHz, DMSO-d6) δ 8.39 (t, J = 5.9 Hz, 1H), 7.90-7.77 (m, 2H), 7.36 (d, J = 8.2 Hz, 2H), 4.38 (h, J = 6.2 Hz, 1H), 4.30 (d, J = 5.9 Hz, 2H), 3.99-3.80 (m, 2H), 2.98 (hept, J = 7.6, 7.0 Hz, 2H), 2.78 (t, J = 7.7 Hz, 2H), 2.37 (dtd, J = 10.9, 8.6, 4.7 Hz, 1H), 1.98 (dq, J = 15.3, 8.3, 7.9 Hz, 3H), 1.89 (s, 3H), 1.48 (d, J = 6.1 Hz, 3H). |
| 360 | 399.2 | 1H NMR (400 MHz, DMSO-d6) δ 9.10 (t, J = 6.0 Hz, 1H), 7.94-7.89 (m, 2H), 7.85 (d, J = 8.3 Hz, 2H), 7.57-7.46 (m, 3H), 7.44 (d, J = 8.2 Hz, 2H), 4.54 (d, J = 5.9 Hz, 2H), 4.38 (h, J = 6.3 Hz, 1H), 4.00-3.79 (m, 2H), 2.98 (hept, J = 7.6, 7.0 Hz, 2H), 2.78 (t, J = 7.7 Hz, 2H), 2.37 (dtd, J = 10.9, 8.7, 4.7 Hz, 1H), 1.97 (ddt, J = 15.5, 10.7, 7.7 Hz, 3H), 1.48 (d, J = 6.1 Hz, 3H). |
| 361 | 373.1 | 1H NMR (400 MHz, DMSO-d6) δ 7.87 (d, J = 8.3 Hz, 2H), 7.62 (t, J = 6.3 Hz, 1H), 7.46 (d, J = 8.1 Hz, 2H), 4.46-4.32 (m, 1H), 4.22 (d, J = 6.3 Hz, 2H), 3.99-3.84 (m, 2H), 3.00 (h, J = 8.3 Hz, 2H), 2.90 (s, 3H), 2.79 (t, J = 7.7 Hz, 2H), 2.44-2.30 (m, 1H), 2.08-1.89 (m, 2H), 1.49 (d, J = 6.2 Hz, 3H). |
| 362 | 353.2 | 1H NMR (400 MHz, DMSO-d6) δ 8.35 (t, J = 6.3 Hz, 1H), 7.83 (d, J = 8.1 Hz, 2H), 7.39 (d, J = 8.1 Hz, 2H), 4.38 (dd, J = 19.0, 6.5 Hz, 3H), 4.01-3.85 (m, 4H), 2.99 (hept, J = 7.7, 7.3 Hz, 2H), 2.80 (t, J = 7.8 Hz, 2H), 1.99 (dq, J = 15.6, 8.0 Hz, 3H), 1.49 (d, J = 6.2 Hz, 3H). |
| 363 | 317.1 | 1H NMR (400 MHz, DMSO-d6) δ 8.22 (s, 3H), 7.57 (d, J = 3.8 Hz, 1H), 7.29 (d, J = 3.8 Hz, 1H), 4.30 (d, J = 5.7 Hz, 2H), 4.19-4.11 (m, 1H), 4.09-4.04 (m, 1H), 4.04-3.94 (m, 1H), 3.58 (dd, J = 8.5, 5.0 Hz, 1H), 3.01 (t, J = 7.4 Hz, 2H), 2.81 (t, J = 7.8 Hz, 2H), 2.08 (p, J = 7.6 Hz, 2H), 1.49 (d, J = 6.3 Hz, 3H). |
| 364 | 333.1 | 1H NMR (400 MHz, Chloroform-d) δ 9.79 (s, 1H), 8.50 (d, J = 8.4 Hz, 1H), 8.04 (d, J = 1.6 Hz, 1H), 7.98 (dd, J = 8.4, 1.7 Hz, 1H), 7.22- |

TABLE 1-continued

| | | MS and NMR DATA |
|---|---|---|
| Example No | ES/MS m/z (M + H)+ | 1H NMR |
| | | 7.11 (m, 1H), 6.66 (d, J = 7.2 Hz, 1H), 4.75 (h, J = 6.3 Hz, 1H), 4.36 (td, J = 9.3, 5.5 Hz, 1H), 4.26 (td, J = 9.3, 6.6 Hz, 1H), 3.24-3.00 (m, 4H), 2.60 (tdd, J = 14.2, 7.2, 4.1 Hz, 1H), 2.26-2.13 (m, 2H), 2.13-2.02 (m, 1H), 1.63 (d, J = 6.3 Hz, 3H). |
| 365 | 351.2 | 1H NMR (400 MHz, Chloroform-d) δ 7.90 (d, J = 8.0 Hz, 2H), 7.58 (d, J = 8.3 Hz, 2H), 4.81 (dt, J = 8.3, 6.0 Hz, 1H), 4.68 (p, J = 6.4 Hz, 1H), 4.46-4.32 (m, 4H), 4.30-4.22 (m, 1H), 3.82 (s, 1H), 3.57 (s, 3H), 3.21-2.91 (m, 4H), 2.76-2.58 (m, 1H), 2.21 (pd, J = 7.7, 3.1 Hz, 2H), 2.11 (ddt, J = 11.6, 9.2, 6.1 Hz, 1H), 1.63 (d, J = 6.3 Hz, 3H). |
| 366 | 335.2 | 1H NMR (400 MHz, Chloroform-d) δ 8.02-7.82 (m, 2H), 7.57 (d, J = 8.3 Hz, 2H), 4.78 (dt, J = 8.3, 6.1 Hz, 1H), 4.41-4.35 (m, 1H), 4.33 (s, 2H), 4.26 (td, J = 9.5, 6.3 Hz, 1H), 3.93 (s, 2H), 3.33 (m, 3H), 3.08 (dt, J = 19.1, 7.4 Hz, 4H), 2.64 (dtd, J = 11.3, 9.0, 5.7 Hz, 1H), 2.41 (s, 1H), 2.26-2.15 (m, 2H), 2.10 (ddt, J = 11.7, 9.3, 6.2 Hz, 1H), 1.62 (d, J = 6.2 Hz, 3H). |
| 367 | 365.2 | 1H NMR (400 MHz, Chloroform-d) δ 8.01-7.85 (m, 2H), 7.68-7.52 (m, 2H), 4.77 (dt, J = 8.2, 6.0 Hz, 1H), 4.37 (td, J = 9.5, 5.7 Hz, 1H), 4.30 (s, 2H), 4.30-4.21 (m, 1H), 3.97 (t, J = 4.8 Hz, 4H), 3.18-2.99 (m, 8H), 2.71-2.56 (m, 1H), 2.20 (dtt, J = 12.3, 7.7, 3.4 Hz, 2H), 2.09 (ddt, J = 11.7, 9.2, 6.2 Hz, 1H), 1.62 (d, J = 6.3 Hz, 3H). |
| 368 | 323.2 | 1H NMR (400 MHz, Chloroform-d) δ 8.00-7.90 (m, 2H), 7.66-7.55 (m, 2H), 4.82 (h, J = 6.3 Hz, 1H), 4.42 (td, J = 9.6, 5.9 Hz, 1H), 4.32 (td, J = 9.7, 6.3 Hz, 1H), 4.27 (s, 2H), 3.15 (t, J = 7.8 Hz, 2H), 3.06 (td, J = 7.1, 4.8 Hz, 2H), 2.84 (s, 6H), 2.73-2.58 (m, 1H), 2.28-2.16 (m, 2H), 2.11 (ddt, J = 11.6, 9.2, 6.0 Hz, 1H), 1.63 (d, J = 6.3 Hz, 3H). |
| 369 | 324.2 | 1H NMR (400 MHz, DMSO-d6) δ 7.85-7.76 (m, 2H), 7.58 (d, J = 8.4 Hz, 2H), 4.38 (h, J = 6.4 Hz, 1H), 3.99-3.79 (m, 2H), 2.99 (hept, J = 7.5, 6.9 Hz, 2H), 2.78 (t, J = 7.7 Hz, 2H), 2.44-2.30 (m, 1H), 2.07-1.88 (m, 3H), 1.49 (d, J = 6.2 Hz, 3H), 1.45 (s, 6H). |
| 370 | 314.1 | 1H NMR (400 MHz, DMSO-d6) δ 7.71 (dd, J = 7.9, 1.6 Hz, 1H), 7.66-7.55 (m, 2H), 5.35 (t, J = 5.7 Hz, 1H), 4.60 (d, J = 5.7 Hz, 2H), 4.39 (dt, J = 7.7, 6.1 Hz, 1H), 4.00-3.84 (m, 2H), 3.01 (hept, J = 7.6, 6.9 Hz, 2H), 2.79 (t, J = 7.7 Hz, 2H), 2.38 (dtd, J = 10.7, 8.6, 4.6 Hz, 1H), 2.13-1.85 (m, 3H), 1.49 (d, J = 6.2 Hz, 3H). |
| 371 | 340.2 | 1H NMR (400 MHz, DMSO-d6) δ 7.89-7.76 (m, 2H), 7.66-7.53 (m, 2H), 4.18 (dd, J = 8.7, 6.2 Hz, 1H), 4.13-3.93 (m, 2H), 3.62 (dd, J = 8.7, 5.0 Hz, 1H), 3.01 (hept, J = 7.6, 7.0 Hz, 2H), 2.82 (t, J = 7.7 Hz, 2H), 2.01 (p, J = 7.3 Hz, 2H), 1.48 (d, J = 6.1 Hz, 3H), 1.46 (s, 6H). |
| 372 | 330.1 | 1H NMR (400 MHz, DMSO-d6) δ 7.72 (dd, J = 7.9, 1.6 Hz, 1H), 7.67-7.56 (m, 2H), 4.61 (s, 2H), 4.18 (dd, J = 8.7, 6.3 Hz, 1H), 4.12-3.99 (m, 2H), 3.62 (dd, J = 8.7, 5.0 Hz, 1H), 3.02 (hept, J = 7.6, 6.9 Hz, 2H), 2.81 (t, J = 7.7 Hz, 2H), 2.01 (p, J = 6.9, 6.3 Hz, 2H), 1.48 (d, J = 6.2 Hz, 3H). |
| 373 | 349.1 | 1H NMR (400 MHz, DMSO-d6) δ 11.31 (d, J = 5.4 Hz, 1H), 8.27 (d, J = 8.4 Hz, 1H), 8.09 (d, J = 1.6 Hz, 1H), 7.96 (dd, J = 8.4, 1.7 Hz, 1H), 7.22 (dd, J = 7.1, 5.7 Hz, 1H), 6.67 (d, J = 7.1 Hz, 1H), 5.58 (d, J = 6.4 Hz, 1H), 4.19 (dd, J = 8.7, 6.1 Hz, 1H), 4.07 (tq, J = 11.1, 5.6 Hz, 2H), 3.64 (dd, J = 8.7, 4.9 Hz, 1H), 3.06 (hept, J = 7.6, 6.9 Hz, 2H), 2.84 (t, J = 7.7 Hz, 2H), 2.14-1.93 (m, 2H), 1.49 (d, J = 6.1 Hz, 3H). |
| 374 | 296.1 | 1H NMR (400 MHz, DMSO-d6) δ 7.86 (d, J = 8.1 Hz, 2H), 7.44 (d, J = 8.0 Hz, 2H), 4.56 (s, 2H), 4.42 (q, J = 6.7 Hz, 1H), 4.05-3.86 (m, 2H), 3.01 (h, J = 8.2 Hz, 2H), 2.81 (t, J = 7.7 Hz, 2H), 2.45-2.36 (m, 1H), 2.00 (m, 3H), 1.50 (d, J = 6.2 Hz, 3H). |
| 375 | 302.2 | 1H NMR (400 MHz, DMSO-d6) δ 7.47 (d, J = 3.8 Hz, 1H), 7.03 (d, J = 3.7 Hz, 1H), 5.57 (t, J = 5.7 Hz, 1H), 4.66 (d, J = 5.6 Hz, 2H), 4.44-4.28 (m, 1H), 3.98-3.78 (m, 2H), 2.98 (dd, J = 8.2, 6.6 Hz, 2H), 2.77 (t, J = 7.8 Hz, 2H), 2.37 (m, 1H), 2.06 (q, J = 7.6 Hz, 2H), 2.02-1.89 (m, 1H), 1.49 (d, J = 6.2 Hz, 3H). |
| 376 | 330.1 | 1H NMR (400 MHz, DMSO-d6) δ 7.49 (d, J = 3.9 Hz, 1H), 7.01 (d, J = 3.8 Hz, 1H), 4.41 (q, J = 6.7 Hz, 1H), 4.06-3.74 (m, 2H), 2.99 (t, J = 7.4 Hz, 2H), 2.81 (t, J = 7.8 Hz, 2H), 2.40 (td, J = 13.4, 8.6 Hz, 1H), 2.07 (p, J = 7.9 Hz, 2H), 2.02-1.91 (m, 1H), 1.51 (d, J = 6.0 Hz, 9H). |
| 377 | 395.1 | 1H NMR (400 MHz, DMSO-d6) δ 7.77 (t, J = 6.3 Hz, 1H), 7.53 (d, J = 3.8 Hz, 1H), 7.13 (d, J = 3.8 Hz, 1H), 4.38 (d, J = 6.1 Hz, 2H), 4.25-4.12 (m, 1H), 4.12-3.94 (m, 2H), 3.60 (dd, J = 8.7, 5.0 Hz, 1H), 3.00 (t, J = 7.4 Hz, 2H), 2.90 (s, 3H), 2.81 (t, J = 7.8 Hz, 2H), 2.08 (p, J = 7.7 Hz, 2H), 1.49 (d, J = 6.2 Hz, 3H). |
| 378 | 332.1 | 1H NMR (400 MHz, DMSO-d6) δ 9.04 (s, 2H), 8.64 (d, J = 8.7 Hz, 1H), 8.36 (d, J = 1.6 Hz, 1H), 8.21 (dd, J = 8.7, 1.7 Hz, 1H), 7.72 (d, J = 7.0 Hz, 1H), 7.39 (d, J = 7.0 Hz, 1H), 4.44 (q, J = 6.8 Hz, 1H), 4.05-3.86 (m, 2H), 3.09 (h, J = 8.4 Hz, 2H), 2.85 (t, J = 7.7 Hz, 2H), 2.46-2.32 (m, 2H), 2.14-1.92 (m, 3H), 1.51 (d, J = 6.1 Hz, 3H). |

TABLE 1-continued

MS and NMR DATA

| Example No | ES/MS m/z (M + H)+ | 1H NMR |
|---|---|---|
| 379 | 321.2 | 1H NMR (400 MHz, DMSO-d6) δ 7.75 (d, J = 8.1 Hz, 1H), 7.71 (s, 1H), 7.34 (d, J = 8.1 Hz, 1H), 4.46-4.26 (m, 3H), 4.02-3.83 (m, 2H), 3.43 (s, 2H), 3.07 (t, J = 6.4 Hz, 2H), 2.99 (q, J = 7.4 Hz, 2H), 2.78 (dt, J = 13.9, 7.6 Hz, 2H), 2.44-2.35 (m, 1H), 1.97 (m, 3H), 1.48 (d, J = 6.1 Hz, 3H). |
| 380 | 333.1 | 1H NMR (400 MHz, DMSO-d6) δ 8.99 (s, 1H), 8.15 (d, J = 1.5 Hz, 1H), 8.06 (d, J = 8.6 Hz, 1H), 7.83 (dd, J = 8.6, 1.6 Hz, 1H), 7.06 (s, 1H), 4.44 (h, J = 6.4 Hz, 1H), 4.07-3.88 (m, 2H), 3.09 (m, 2H), 2.85 (t, J = 7.7 Hz, 2H), 2.46-2.38 (m, 1H), 2.15-1.84 (m, 3H), 1.51 (d, J = 6.2 Hz, 3H). |
| 381 | 349.2 | 1H NMR (400 MHz, DMSO-d6) δ 11.36 (s, 1H), 8.12 (d, J = 8.2 Hz, 1H), 7.92 (dd, J = 8.2, 1.6 Hz, 1H), 7.84-7.76 (m, 1H), 4.42 (h, J = 6.2 Hz, 1H), 4.12 (s, 2H), 4.04-3.84 (m, 2H), 3.01 (h, J = 8.2 Hz, 2H), 2.82 (t, J = 7.7 Hz, 2H), 2.40 (m, 1H), 2.10-1.88 (m, 3H), 1.49 (d, J = 6.1 Hz, 3H). |
| 382 | 351.1 | 1H NMR (400 MHz, DMSO-d6) δ 11.33 (d, J = 5.8 Hz, 1H), 7.89 (d, J = 1.5 Hz, 1H), 7.62 (dd, J = 13.0, 1.5 Hz, 1H), 7.29-7.17 (m, 1H), 6.73-6.59 (m, 1H), 4.44 (h, J = 6.4 Hz, 1H), 4.04-3.87 (m, 2H), 3.07 (hept, J = 7.6, 6.9 Hz, 2H), 2.83 (t, J = 7.7 Hz, 2H), 2.46-2.34 (m, 1H), 2.11-1.90 (m, 3H), 1.50 (d, J = 6.2 Hz, 3H). |
| 383 | 334.1 | 1H NMR (400 MHz, DMSO-d6) δ 8.23 (d, J = 8.3 Hz, 1H), 8.20 (s, 1H), 8.10 (d, J = 1.6 Hz, 1H), 8.02 (dd, J = 8.2, 1.6 Hz, 1H), 4.44 (h, J = 6.3 Hz, 1H), 4.08-3.85 (m, 2H), 3.19-2.93 (m, 2H), 2.84 (t, J = 7.7 Hz, 2H), 2.41 (dp, J = 13.1, 4.4 Hz, 1H), 2.15-1.92 (m, 3H), 1.51 (d, J = 6.2 Hz, 3H). |
| 384 | 339.1 | 1H NMR (400 MHz, DMSO-d6) δ 11.55 (d, J = 5.9 Hz, 1H), 7.85 (s, 1H), 7.33 (t, J = 6.4 Hz, 1H), 6.90 (d, J = 7.0 Hz, 1H), 4.40 (p, J = 6.5 Hz, 1H), 4.04-3.82 (m, 2H), 3.08 (t, J = 7.4 Hz, 2H), 2.83 (t, J = 7.8 Hz, 2H), 2.44-2.31 (m, 1H), 2.11 (p, J = 7.7 Hz, 2H), 1.97 (dq, J = 18.5, 10.6, 9.1 Hz, 1H), 1.52 (d, J = 6.2 Hz, 3H). |
| 385 | 348.2 | 1H NMR (400 MHz, DMSO-d6) δ 8.65 (d, J = 8.7 Hz, 1H), 8.37 (d, J = 1.6 Hz, 1H), 8.26-8.16 (m, 1H), 7.72 (d, J = 7.0 Hz, 1H), 7.40 (d, J = 7.0 Hz, 1H), 4.20 (dd, J = 8.7, 6.3 Hz, 1H), 4.16-4.00 (m, 2H), 3.65 (dd, J = 8.8, 4.9 Hz, 1H), 3.10 (q, J = 7.3 Hz, 2H), 2.86 (t, J = 7.7 Hz, 2H), 2.05 (q, J = 7.5 Hz, 2H), 1.49 (d, J = 6.1 Hz, 3H). |
| 386 | 347.2 | 1H NMR (400 MHz, DMSO-d6) δ 11.35 (s, 1H), 8.21 (d, J = 8.4 Hz, 1H), 7.96 (d, J = 1.5 Hz, 1H), 7.87 (dd, J = 8.3, 1.6 Hz, 1H), 6.44 (s, 1H), 4.44 (h, J = 6.3 Hz, 1H), 4.06-3.86 (m, 2H), 3.16-2.92 (m, 2H), 2.84 (t, J = 7.7 Hz, 2H), 2.46-2.36 (m, 1H), 2.23 (s, 3H), 2.00 (tdd, J = 17.3, 8.1, 4.3 Hz, 3H), 1.51 (d, J = 6.2 Hz, 3H). |
| 387 | 348.2 | 1H NMR (400 MHz, DMSO-d6) δ 12.27 (s, 1H), 8.16 (d, J = 8.2 Hz, 1H), 7.99 (d, J = 1.5 Hz, 1H), 7.93 (dd, J = 8.3, 1.6 Hz, 1H), 4.42 (h, J = 6.3 Hz, 1H), 4.02-3.81 (m, 2H), 3.05 (h, J = 8.2 Hz, 2H), 2.82 (t, J = 7.7 Hz, 2H), 2.37 (m, 4H), 2.01 (tdd, J = 16.3, 9.1, 5.0 Hz, 3H), 1.51 (d, J = 6.1 Hz, 3H). |
| 388 | 349.2 | 1H NMR (400 MHz, DMSO-d6) δ 8.86 (s, 1H), 7.98 (s, 1H), 7.92 (d, J = 8.7 Hz, 1H), 7.67 (d, J = 8.5 Hz, 1H), 6.78 (s, 1H), 4.18 (dd, J = 8.6, 6.2 Hz, 1H), 4.06 (dq, J = 13.7, 5.1 Hz, 2H), 3.63 (dd, J = 8.7, 5.0 Hz, 1H), 3.07 (hept, J = 7.6, 6.9 Hz, 2H), 2.83 (t, J = 7.7 Hz, 2H), 2.13-1.93 (m, 2H), 1.49 (d, J = 6.1 Hz, 3H). |
| 389 | 306.1 | 1H NMR (400 MHz, Chloroform-d) δ 10.32 (s, 1H), 7.88 (d, J = 7.8 Hz, 1H), 7.55 (d, J = 7.8 Hz, 1H), 7.37-7.28 (m, 2H), 4.57 (h, J = 6.3 Hz, 1H), 4.17 (td, J = 8.7, 4.8 Hz, 1H), 4.06 (q, J = 8.3 Hz, 1H), 3.44 (t, J = 7.4 Hz, 2H), 2.92 (t, J = 7.8 Hz, 2H), 2.57-2.41 (m, 1H), 2.16 (p, J = 7.6 Hz, 2H), 2.11-1.99 (m, 1H), 1.62 (d, J = 6.2 Hz, 3H). |
| 390 | 338.1 | 1H NMR (400 MHz, DMSO-d6) δ 7.70 (dd, J = 8.9, 4.7 Hz, 1H), 7.54 (dd, J = 9.7, 2.5 Hz, 1H), 7.25 (td, J = 9.3, 2.5 Hz, 1H), 4.45 (h, J = 6.4 Hz, 1H), 4.20 (s, 3H), 4.06-3.87 (m, 2H), 3.18 (t, J = 7.4 Hz, 2H), 2.85 (t, J = 7.7 Hz, 2H), 2.43 (dp, J = 13.2, 4.4 Hz, 1H), 2.02 (p, J = 7.6 Hz, 3H), 1.50 (d, J = 6.2 Hz, 3H). |
| 391 | 320.1 | 1H NMR (400 MHz, Chloroform-d) δ 7.83 (d, J = 7.9 Hz, 1H), 7.43 (d, J = 8.0 Hz, 1H), 7.39-7.28 (m, 2H), 4.51 (h, J = 6.3 Hz, 1H), 4.21 (d, J = 0.7 Hz, 3H), 4.14 (td, J = 8.7, 4.7 Hz, 1H), 4.03 (q, J = 8.3 Hz, 1H), 3.31 (td, J = 7.4, 5.5 Hz, 2H), 2.93 (t, J = 7.8 Hz, 2H), 2.46 (ddd, J = 13.1, 10.9, 6.8 Hz, 1H), 2.07 (dp, J = 17.2, 7.3 Hz, 3H), 1.57 (d, J = 6.2 Hz, 3H). |
| 392 | 339.1 | 1H NMR (400 MHz, DMSO-d6) δ 11.55 (d, J = 5.9 Hz, 1H), 7.85 (s, 1H), 7.33 (t, J = 6.4 Hz, 1H), 6.90 (d, J = 7.0 Hz, 1H), 4.40 (p, J = 6.5 Hz, 1H), 4.04-3.82 (m, 2H), 3.08 (t, J = 7.4 Hz, 2H), 2.83 (t, J = 7.8 Hz, 2H), 2.44-2.31 (m, 1H), 2.11 (p, J = 7.7 Hz, 2H), 1.97 (dq, J = 18.5, 10.6, 9.1 Hz, 1H), 1.52 (d, J = 6.2 Hz, 3H). |

TABLE 1-continued

MS and NMR DATA

| Example No | ES/MS m/z (M + H)+ | 1H NMR |
|---|---|---|
| 393 | 268.1 | 1H NMR (400 MHz, Chloroform-d) δ 9.29 (d, J = 1.3 Hz, 1H), 8.86 (d, J = 5.2 Hz, 1H), 8.31 (dt, J = 5.2, 1.1 Hz, 1H), 4.53 (h, J = 6.4 Hz, 1H), 4.14 (td, J = 8.7, 4.7 Hz, 1H), 4.03 (q, J = 8.3 Hz, 1H), 3.35 (q, J = 7.6 Hz, 2H), 2.90 (t, J = 7.8 Hz, 2H), 2.46 (ddt, J = 16.4, 8.6, 4.7 Hz, 1H), 2.14-1.98 (m, 3H), 1.59 (d, J = 6.2 Hz, 3H). |
| 394 | 270.1 | 1H NMR (400 MHz, Chloroform-d) δ 7.56 (t, J = 1.2 Hz, 1H), 7.16 (d, J = 1.5 Hz, 1H), 4.69-4.54 (m, 1H), 4.23 (td, J = 9.2, 5.5 Hz, 1H), 4.17-4.11 (m, 1H), 4.09 (d, J = 0.9 Hz, 3H), 3.15 (td, J = 7.4, 4.9 Hz, 2H), 3.02 (t, J = 7.8 Hz, 2H), 2.57 (ddd, J = 14.3, 11.9, 7.2 Hz, 1H), 2.14 (p, J = 7.9 Hz, 2H), 2.10-2.01 (m, 1H), 1.55 (d, J = 6.2 Hz, 3H). |
| 395 | 364.1 | 1H NMR (400 MHz, Chloroform-d) δ 8.03 (d, J = 8.7 Hz, 1H), 7.99 (s, 1H), 7.87 (d, J = 8.5 Hz, 1H), 4.72 (m, 1H), 4.39-4.21 (m, 2H), 3.93 (s, 3H), 3.40 (t, J = 7.4 Hz, 2H), 3.15 (t, J = 7.8 Hz, 2H), 2.70 (t, J = 8.1 Hz, 1H), 2.24 (p, J = 7.7 Hz, 2H), 2.12 (d, J = 4.7 Hz, 1H), 1.61 (d, J = 6.3 Hz, 3H). |
| 396 | 309.2 | 1H NMR (400 MHz, DMSO-d6) δ 8.74-8.26 (m, 3H), 8.18 (m, 2H), 8.09 (d, J = 8.0 Hz, 2H), 7.57 (s, 1H), 4.29-3.83 (m, 4H), 2.04 (p, J = 8.2 Hz, 1H), 1.57 (d, J = 6.2 Hz, 3H). |
| 397 | 386.2 | 1H NMR (400 MHz, DMSO-d6) δ 8.47 (d, J = 1.8 Hz, 1H), 8.20 (dt, J = 7.7, 1.4 Hz, 1H), 8.17 (dt, J = 7.9, 1.4 Hz, 1H), 7.72 (t, J = 7.8 Hz, 1H), 5.17 (s, 2H), 4.44 (dt, J = 7.8, 6.1 Hz, 1H), 4.00 (dt, J = 8.7, 4.3 Hz, 1H), 3.97-3.88 (m, 1H), 3.17 (s, 2H), 3.14-2.96 (m, 2H), 2.84 (dd, J = 8.5, 7.0 Hz, 2H), 2.41 (dtd, J = 10.8, 8.6, 4.8 Hz, 1H), 2.11-1.91 (m, 3H), 1.51 (d, J = 6.2 Hz, 3H). |
| 398 | 349.2 | 1H NMR (400 MHz, DMSO-d6) δ 8.06 (s, 1H), 7.98 (d, J = 8.5 Hz, 2H), 7.94 (d, J = 8.5 Hz, 2H), 7.46 (s, 1H), 4.76 (t, J = 4.8 Hz, 1H), 3.04 (t, J = 7.3 Hz, 2H), 2.83 (t, J = 7.8 Hz, 2H), 2.01 (p, J = 7.6 Hz, 2H), 1.87 (s, 3H), 1.75 (dddt, J = 12.0, 9.2, 6.9, 3.4 Hz, 2H), 1.69-1.58 (m, 4H), 1.46 (dt, J = 11.3, 5.7 Hz, 2H). |
| 399 | 344.2 | 1H NMR (400 MHz, DMSO-d6) δ 8.40 (t, J = 1.8 Hz, 1H), 8.21 (dt, J = 8.0, 1.3 Hz, 1H), 8.06 (ddd, J = 7.8, 2.0, 1.1 Hz, 1H), 7.80 (t, J = 7.8 Hz, 1H), 4.45 (dt, J = 7.8, 6.1 Hz, 1H), 4.01 (tt, J = 7.7, 3.8 Hz, 1H), 3.97-3.83 (m, 1H), 3.27 (s, 4H), 3.14-2.94 (m, 2H), 2.85 (dd, J = 8.5, 7.0 Hz, 2H), 2.45-2.33 (m, 1H), 2.09-1.88 (m, 2H), 1.50 (d, J = 6.2 Hz, 3H). |
| 400 | 328.1 | 1H NMR (400 MHz, DMSO-d6) δ 8.17 (q, J = 2.0 Hz, 1H), 8.02 (tt, J = 6.4, 1.7 Hz, 1H), 7.79 (dq, J = 7.8, 1.3 Hz, 1H), 7.72 (t, J = 7.7 Hz, 1H), 4.44 (dt, J = 7.8, 6.1 Hz, 1H), 3.99 (td, J = 9.5, 9.1, 5.1 Hz, 1H), 3.95-3.84 (m, 1H), 3.11-2.93 (m, 2H), 2.88-2.79 (m, 3H), 2.78 (d, J = 0.8 Hz, 3H), 2.41 (dtd, J = 10.8, 8.7, 4.8 Hz, 1H), 2.07-1.91 (m, 2H), 1.50 (d, J = 6.2 Hz, 3H). |
| 401 | 309.1 | 1H NMR (400 MHz, DMSO-d6) δ 13.28 (bs, 1H), 8.35 (s, 1H), 8.25 (d, J = 8.3 Hz, 2H), 8.13 (s, 1H), 8.05 (d, J = 8.4 Hz, 2H), 7.52 (s, 1H), 4.52 (p, J = 6.4 Hz, 1H), 4.04 (m, 2H), 2.00 (m, 1H), 1.56 (d, J = 6.2 Hz, 3H). |
| 402 | 335.3 | 1H NMR (400 MHz, DMSO-d6) δ 8.04 (bs, 1H), 7.97 (d, J = 8.1 Hz, 2H), 7.89 (d, J = 8.4 Hz, 2H), 7.45 (bs, 1H), 3.72 (t, J = 6.6 Hz, 2H), 3.00 (t, J = 7.2 Hz, 2H), 2.78 (t, J = 7.7 Hz, 2H), 2.08 (q, J = 4.0 Hz, 2H), 2.04-1.88 (m, 6H), 0.49 (q, J = 4.1 Hz, 2H). |
| 403 | 323.3 | 1H NMR (400 MHz, DMSO-d6) δ 8.08 (s, 1H), 7.98 (s, 4H), 7.48 (s, 1H), 4.30 (p, J = 6.6 Hz, 1H), 3.63 (dq, J = 11.0, 3.5 Hz, 1H), 3.58-3.46 (m, 1H), 3.02 (hept, J = 7.5, 6.9 Hz, 2H), 2.87 (t, J = 7.7 Hz, 2H), 2.11-1.98 (m, 4H), 1.92 (td, J = 8.0, 4.3 Hz, 1H), 1.74-1.63 (m, 1H), 1.24 (d, J = 6.3 Hz, 3H). |
| 404 | 323.3 | 1H NMR (400 MHz, DMSO-d6) δ 8.08 (s, 1H), 7.98 (s, 4H), 7.48 (s, 1H), 4.30 (h, J = 6.1, 5.6 Hz, 1H), 3.63 (ddd, J = 10.7, 7.2, 3.4 Hz, 1H), 3.52 (dt, J = 11.3, 7.7 Hz, 1H), 3.02 (hept, J = 7.5, 6.9 Hz, 2H), 2.87 (t, J = 7.7 Hz, 2H), 2.16-1.96 (m, 4H), 1.96-1.82 (m, 1H), 1.78-1.55 (m, 1H), 1.24 (d, J = 6.2 Hz, 3H). |
| 405 | 295.2 | 1H NMR (400 MHz, DMSO-d6) δ 8.06 (s, 1H), 7.98 (d, J = 8.4 Hz, 2H), 7.93 (d, J = 8.3 Hz, 2H), 7.46 (s, 1H), 4.08 (t, J = 7.5 Hz, 4H), 3.01 (t, J = 7.3 Hz, 2H), 2.83 (t, J = 7.7 Hz, 2H), 2.32 (t, J = 7.5 Hz, 2H), 2.01 (p, J = 7.6 Hz, 2H). |
| 406 | 405.3 | 1H NMR (400 MHz, Acetonitrile-d3) δ 8.94 (s, 1H), 7.93 (m, 2H), 7.10 (d, J = 8.8 Hz, 1H), 4.66 (dt, J = 12.4, 6.2 Hz, 1H), 4.20 (td, J = 9.2, 5.4 Hz, 1H), 4.11 (dt, J = 10.2, 8.0 Hz, 1H), 3.65 (s, 1H), 3.65 (s, 2H), 3.22-2.99 (m, 2H), 2.97 (t, J = 7.8 Hz, 2H), 2.60 (ddd, J = 9.0, 7.5, 2.1 Hz, 1H), 2.57-2.49 (m, 1H), 2.18-2.12 (m, 2H), 2.12-2.03 (m, 1H), 1.95 (m, 2H), 1.59 (m, 3H). |
| 407 | 405.3 | 1H NMR (400 MHz, Acetonitrile-d3) δ 8.97 (s, 1H), 7.87 (dt, J = 8.3, 1.7 Hz, 1H), 7.52 (d, J = 1.8 Hz, 1H), 7.09 (d, J = 8.3 Hz, 1H), 4.71 (dt, J = 8.4, 6.2 Hz, 1H), 4.25 (tdd, J = 9.3, 5.6, 0.9 Hz, 1H), 4.15 (td, J = 9.3, 6.5 Hz, 1H), 3.65 (d, J = 1.0 Hz, 3H), 3.06 (q, J = 7.3 Hz, 2H), 2.99 (t, J = 7.8 Hz, 2H), 2.84 (td, J = 8.4, 4.4 Hz, 1H), 2.58 (dddd, J = 11.2, 9.4, 8.4, 5.6 Hz, 1H), 2.22-2.12 (m, 1H), 2.14 (q, J = 1.7, 1.1 |

TABLE 1-continued

MS and NMR DATA

| Example No | ES/MS m/z (M + H)+ | 1H NMR |
|---|---|---|
| | | Hz, 1H), 2.15-2.01 (m, 2H), 1.95 (partially obscured by MeCN, 1H), 1.57 (d, J = 6.3 Hz, 3H). |
| 408 | 391.3 | 1H NMR (400 MHz, Acetonitrile-d3) δ 9.11 (d, J = 9.6 Hz, 1H), 7.97-7.89 (m, 2H), 7.10 (dd, J = 8.2, 3.8 Hz, 1H), 4.80-4.62 (m, 1H), 4.25 (tdd, J = 8.9, 5.6, 2.7 Hz, 1H), 4.15 (tdd, J = 9.4, 6.5, 3.2 Hz, 1H), 3.17-3.08 (m, 1H), 3.08-3.02 (m, 1H), 2.98 (t, J = 8.0 Hz, 3H), 2.65-2.53 (m, 2H), 2.23-2.02 (m, 3H), 1.91 (partially obscured by MeCN, m, 1H), 1.59 (dd, J = 6.3, 2.9 Hz, 3H). |
| 409 | 391.2 | 1H NMR (400 MHz, Acetonitrile-d3) δ 9.41 (m, 1H), 7.86 (dt, J = 8.3, 2.2 Hz, 1H), 7.50 (d, J = 1.8 Hz, 1H), 7.13 (d, J = 8.3 Hz, 1H), 4.74 (dtt, J = 12.2, 8.5, 4.3 Hz, 1H), 4.28 (td, J = 9.3, 5.7 Hz, 1H), 4.18 (td, J = 9.4, 6.4 Hz, 1H), 3.14-2.95 (m, 4H), 2.88 (dt, J = 10.2, 8.6 Hz, 1H), 2.61 (dtd, J = 11.1, 8.9, 5.7 Hz, 1H), 2.21-2.12 (m, 3H), 2.12-2.04 (m, 2H), 1.57 (d, J = 6.3 Hz, 3H). |
| 410 | 372.2 | 1H NMR (400 MHz, Acetonitrile-d3) δ 9.12 (s, 1H), 8.01 (td, J = 8.1, 1.8 Hz, 1H), 7.82 (dd, J = 6.2, 1.7 Hz, 1H), 7.17 (d, J = 8.3 Hz, 1H), 4.70 (ddt, J = 12.6, 8.1, 6.1 Hz, 1H), 4.24 (td, J = 9.3, 5.6 Hz, 1H), 4.14 (td, J = 9.3, 6.5 Hz, 1H), 3.22-3.03 (m, 2H), 3.00 (t, J = 7.8 Hz, 2H), 2.59 (dtq, J = 14.0, 5.8, 2.7 Hz, 1H), 2.51 (dd, J = 9.5, 7.1 Hz, 1H), 2.25-2.00 (m, 5H), 1.57 (dd, J = 9.1, 6.3 Hz, 3H). 1H NMR (400 MHz, Acetonitrile-d3) δ 9.08 (s, 1H), 7.90 (dd, J = 8.3, 1.8 Hz, 1H), 7.52 (d, J = 1.7 Hz, 1H), 7.13 (d, J = 8.3 Hz, 1H), 4.71 (dt, J = 8.3, 6.1 Hz, 1H), 4.24 (td, J = 9.3, 5.5 Hz, 1H), 4.15 (td, J = 9.3, 6.5 Hz, 1H), 3.12-2.94 (m, 4H), 2.67 (q, J = 8.5 Hz, 1H), 2.58 (m, 1H), 2.22-2.10 (m, 3H), 2.13-2.02 (m, 1H), 2.06-1.97 (m, 1H), 1.57 (d, J = 6.3 Hz, 3H). |
| 411 | 372.2 | 1H NMR (400 MHz, Acetonitrile-d3) δ 9.08 (s, 1H), 7.90 (dd, J = 8.3, 1.8 Hz, 1H), 7.52 (d, J = 1.7 Hz, 1H), 7.13 (d, J = 8.3 Hz, 1H), 4.71 (dt, J = 8.3, 6.1 Hz, 1H), 4.24 (td, J = 9.3, 5.5 Hz, 1H), 4.15 (td, J = 9.3, 6.5 Hz, 1H), 3.12-2.94 (m, 4H), 2.67 (q, J = 8.5 Hz, 1H), 2.58 (m, 1H), 2.22-2.10 (m, 3H), 2.13-2.02 (m, 1H), 2.06-1.97 (m, 1H), 1.57 (d, J = 6.3 Hz, 3H). |
| 412 | 390.3 | 1H NMR (400 MHz, Acetonitrile-d3) δ 8.95 (s, 1H), 7.94 (m, 2H), 7.09 (d, J = 8.2 Hz, 1H), 6.45 (s, 1H), 5.84 (d, J = 11.9 Hz, 1H), 4.66 (dtd, J = 8.7, 6.1, 2.6 Hz, 1H), 4.20 (td, J = 9.1, 5.4 Hz, 1H), 4.11 (tdd, J = 9.0, 6.7, 1.7 Hz, 1H), 3.11-3.04 (m, 1H), 2.95 (t, J = 7.8 Hz, 2H), 2.63 (ddd, J = 8.7, 7.4, 1.3 Hz, 1H), 2.50 (presumably obscured by broad singlet, m, 3H), 2.18-2.03 (m, 3H), 1.83 (ddd, J = 8.5, 4.2, 1.4 Hz, 1H), 1.59 (dd, J = 6.3, 1.0 Hz, 3H). |
| 413 | 390.3 | 1H NMR (400 MHz, DMSO-d6) δ 10.78 (s, 1H), 7.77 (dt, J = 8.2, 2.2 Hz, 1H), 7.52 (s, 1H), 7.47 (t, J = 2.1 Hz, 1H), 7.00 (d, J = 8.2 Hz, 2H), 4.41 (p, J = 6.5 Hz, 1H), 4.04-3.86 (m, 2H), 3.10-2.86 (m, 2H), 2.81 (t, J = 7.8 Hz, 2H), 2.67 (td, J = 8.7, 3.9 Hz, 1H), 2.39 (dtd, J = 10.6, 8.5, 4.7 Hz, 1H), 2.14-2.00 (m, 1H), 2.04-1.88 (m, 3H), 1.85 (ddd, J = 9.1, 4.3, 2.8 Hz, 1H), 1.49 (d, J = 6.2 Hz, 3H). |
| 414 | 415.2 | 1H NMR (400 MHz, DMSO-d6) δ 11.05 (d, J = 2.0 Hz, 1H), 7.81 (ddd, J = 11.2, 8.2, 1.8 Hz, 1H), 7.09-6.99 (m, 2H), 4.40 (q, J = 6.7 Hz, 1H), 3.98 (tt, J = 8.8, 4.3 Hz, 1H), 3.94-3.80 (m, 1H), 3.19 (dd, J = 9.1, 7.6 Hz, 1H), 2.94-2.80 (m, 1H), 2.82-2.72 (m, 2H), 2.41 (ddt, J = 8.5, 5.8, 2.8 Hz, 2H), 2.21 (dd, J = 9.2, 4.8 Hz, 1H), 2.05-1.87 (m, 3H), 1.48 (dd, J = 8.5, 6.1 Hz, 3H). |
| 415 | 402.2 | 1H NMR (400 MHz, DMSO-d6) δ 8.08 (s, 1H), 8.05-7.88 (m, 4H), 7.47 (s, 1H), 4.45 (p, J = 6.0 Hz, 1H), 4.11-3.83 (m, 2H), 3.65-3.32 (m, 2H), 3.04 (h, J = 8.4 Hz, 2H), 2.92 (m, 3H), 2.84 (t, J = 7.7 Hz, 2H), 2.42-2.16 (m, 2H), 2.13-1.97 (m, 2H) |
| 416 | 347.1 | 1H NMR (400 MHz, DMSO-d6) δ 8.31 (d, J = 8.4 Hz, 1H), 8.09 (d, J = 1.6 Hz, 1H), 7.98 (dd, J = 8.4, 1.7 Hz, 1H), 7.53 (d, J = 7.3 Hz, 1H), 6.74 (d, J = 7.3 Hz, 1H), 4.44 (h, J = 6.3 Hz, 1H), 4.06-3.87 (m, 2H), 3.53 (s, 3H), 3.06 (m, 2H), 2.84 (t, J = 7.7 Hz, 2H), 2.46-2.34 (m, 1H), 2.09-1.92 (m, 3H), 1.51 (d, J = 6.2 Hz, 3H) |
| 417 | 348.1 | 1H NMR (400 MHz, DMSO-d6) δ 9.04 (s, 1H), 8.07 (d, J = 1.5 Hz, 1H), 8.03 (d, J = 8.8 Hz, 1H), 7.76 (dd, J = 8.7, 1.5 Hz, 1H), 7.09 (s, 1H), 4.19 (dd, J = 8.7, 6.2 Hz, 1H), 4.14-4.01 (m, 2H), 3.64 (dd, J = 8.7, 5.0 Hz, 1H), 3.09 (h, J = 8.5 Hz, 2H), 2.85 (t, J = 7.7 Hz, 2H), 2.04 (q, J = 7.6 Hz, 2H), 1.49 (d, J = 6.2 Hz, 3H) |
| 418 | 355.1 | 1H NMR (400 MHz, DMSO-d6) δ 11.55 (d, J = 5.8 Hz, 1H), 7.87 (s, 1H), 7.30 (dd, J = 6.9, 5.8 Hz, 1H), 6.76 (dd, J = 6.9, 1.1 Hz, 1H), 4.24-4.14 (m, 1H), 4.07 (m, 2H), 3.69-3.58 (m, 1H), 3.11 (t, J = 7.4 Hz, 2H), 2.85 (t, J = 7.8 Hz, 2H), 2.11 (p, J = 7.8 Hz, 2H), 1.52 (d, J = 6.2 Hz, 3H) |
| 419 | 363.1 | 1H NMR (400 MHz, Methanol-d4) δ 8.41 (s, 1H), 8.24 (s, 1H), 8.10 (d, J = 9.3 Hz, 1H), 7.67 (d, J = 8.9 Hz, 1H), 5.19 (s, 2H), 4.77-4.65 (m, 1H), 4.32-4.22 (m, 1H), 4.22-4.07 (m, 1H), 3.26-3.11 (m, 2H), 3.02 (t, J = 7.8 Hz, 2H), 2.63-2.51 (m, 1H), 2.28-2.03 (m, 3H), 1.63 (d, J = 6.2 Hz, 3H). |

TABLE 1-continued

MS and NMR DATA

| Example No | ES/MS m/z (M + H)+ | 1H NMR |
|---|---|---|
| 420 | 256.2 | 1H NMR (400 MHz, DMSO-d6) δ 7.63 (s, 2H), 4.47 (dt, J = 7.9, 6.1 Hz, 1H), 3.99 (m, 2H), 3.17-3.03 (m, 2H), 2.84 (dd, J = 8.3, 7.3 Hz, 2H), 2.48-2.39 (m, 1H), 2.05 (p, J = 7.7 Hz, 2H), 2.01-1.89 (m, 1H), 1.50 (d, J = 6.2 Hz, 3H) |
| 421 | 417.1 | 1H NMR (400 MHz, DMSO-d6) δ 8.41 (d, J = 4.5 Hz, 1H), 7.99 (d, J = 8.3 Hz, 1H), 7.68 (dd, J = 8.3, 1.8 Hz, 1H), 7.56 (d, J = 1.7 Hz, 1H), 4.29-4.22 (m, 2H), 4.19-4.09 (m, 3H), 3.73-3.61 (m, 2H), 3.22-3.05 (m, 2H), 2.71-2.53 (m, 2H), 1.50 (d, J = 6.0 Hz, 3H), 1.14 (d, J = 6.8 Hz, 3H). |
| 422 | 427.1 | 1H NMR (400 MHz, DMSO-d6) δ 7.86 (dd, J = 8.0, 1.6 Hz, 1H), 7.83-7.79 (m, 2H), 7.74-7.66 (m, 2H), 7.25 (t, J = 73.8 Hz, 1H), 4.30-4.21 (m, 1H), 4.15-4.10 (m, 2H), 3.73-3.65 (m, 1H), 3.22-3.07 (m, 2H), 2.68-2.52 (m, 2H), 1.50 (d, J = 6.0 Hz, 3H). |
| 423 | 359.1 | 1H NMR (400 MHz, DMSO-d6) δ 8.49-8.48 (m, 1H), 8.32-8.27 (m, 1H), 8.19-8.17 (m, 1H), 8.16-8.08 (m, 2H), 7.71-7.60 (m, 3H), 4.48 (dt, J = 7.7, 6.1 Hz, 1H), 4.08-3.93 (m, 2H), 3.26-3.08 (m, 2H), 2.91-2.84 (m, 2H), 2.48-2.39 (m, 1H), 2.12-1.95 (m, 3H), 1.54 (d, J = 6.1 Hz, 3H). |
| 424 | 349.1 | 1H NMR (400 MHz, DMSO-d6) δ 12.05 (s, 1H), 8.63-8.52 (m, 1H), 8.39-8.30 (m, 1H), 8.21-8.14 (m, 1H), 4.44 (p, J = 6.8 Hz, 1H), 4.05-3.86 (m, 3H), 3.12-2.98 (m, 2H), 2.91-2.76 (m, 2H), 2.46-2.36 (m, 1H), 2.13-1.94 (m, 4H), 1.58-1.46 (m, 3H). |
| 425 | 350.1 | 1H NMR (400 MHz, DMSO-d6) δ 11.42 (s, 1H), 11.36 (s, 1H), 8.44 (d, J = 2.0 Hz, 1H), 8.22 (dd, J = 8.6, 2.1 Hz, 1H), 7.29 (d, J = 8.6 Hz, 1H), 4.49-4.38 (m, 1H), 4.04-3.88 (m, 2H), 3.11-2.98 (m, 2H), 2.82 (t, J = 7.8 Hz, 2H), 2.46-2.36 (m, 1H), 2.12-1.92 (m, 3H), 1.51 (d, J = 6.2 Hz, 3H). |
| 426 | 350.1 | 1H NMR (400 MHz, DMSO-d6) δ 11.35 (s, 1H), 11.27 (s, 1H), 8.01-7.96 (m, 1H), 7.75-7.73 (m, 1H), 7.69-7.65 (m, 1H), 4.47-4.38 (m, 1H), 4.03-3.88 (m, 2H), 3.10-2.94 (m, 2H), 2.83 (t, J = 7.7 Hz, 2H), 2.46-2.37 (m, 1H), 2.09-1.93 (m, 3H), 1.52 (d, J = 6.1 Hz, 3H). |
| 427 | 334.1 | 1H NMR (400 MHz, DMSO-d6) δ 12.73 (s, 1H), 8.51 (s, 1H), 8.40-8.29 (m, 3H), 4.51-4.35 (m, 1H), 4.05-3.92 (m, 2H), 3.16-3.01 (m, 2H), 2.86 (t, J = 7.7 Hz, 2H), 2.47-2.38 (m, 1H), 2.11-1.94 (m, 3H), 1.52 (d, J = 6.1 Hz, 3H). |
| 428 | 362.2 | 1H NMR (400 MHz, DMSO-d6) δ 7.96-7.79 (m, 1H), 7.71-7.59 (m, 1H), 7.37-7.21 (m, 1H), 4.47-4.38 (m, 1H), 4.03-3.89 (m, 2H), 3.35-2.94 (m, 7H), 2.81 (t, J = 7.7 Hz, 2H), 2.44-2.36 (m, 1H), 2.10-1.93 (m, 3H), 1.55-1.45 (m, 3H). |
| 429 | 350.1 | 1H NMR (400 MHz, DMSO-d6) δ 11.95-11.41 (m, 2H), 8.86-7.97 (m, 3H), 4.52-4.37 (m, 1H), 4.06-3.90 (m, 2H), 3.15-3.01 (m, 2H), 2.88-2.80 (m, 2H), 2.46-2.38 (m, 1H), 2.10-1.97 (m, 3H), 1.52 (d, J = 6.2 Hz, 3H). |
| 430 | 335.1 | 1H NMR (400 MHz, DMSO-d6) δ 8.06 (s, 1H), 8.02-7.94 (m, 4H), 7.46 (s, 1H), 3.89 (t, J = 7.2 Hz, 2H), 3.10-2.98 (m, 4H), 2.82 (t, J = 7.8 Hz, 2H), 2.42 (t, J = 7.2 Hz, 3H), 2.07-1.96 (m, 5H). |
| 431 | 401.1 | 1H NMR (400 MHz, DMSO-d6) δ 8.07 (s, 1H), 8.03-7.95 (m, 4H), 7.47 (s, 1H), 7.37-7.27 (m, 4H), 7.26-7.20 (m, 1H), 4.31-4.20 (m, 2H), 4.07 (dd, J = 8.8, 5.9 Hz, 1H), 3.66-3.60 (m, 1H), 3.39 (dd, J = 13.9, 3.4 Hz, 1H), 3.16-2.99 (m, 3H), 2.85 (t, J = 8.5, 7.0 Hz, 2H), 2.11-1.98 (m, 2H). |
| 432 | 362.2 | 1H NMR (400 MHz, DMSO-d6) δ 12.00 (s, 1H), 7.53-7.47 (m, 1H), 7.36-7.18 (m, 2H), 4.47-4.36 (m, 1H), 4.00-3.88 (m, 1H), 3.51-3.31 (m, 2H), 3.17 (dd, J = 18.6, 8.8 Hz, 1H), 3.04-2.93 (m, 1H), 2.91-2.64 (m, 4H), 2.46-2.33 (m, 2H), 2.07-1.88 (m, 4H), 1.53-1.42 (m, 3H). |
| 433 | 412.1 | 1H NMR (400 MHz, DMSO-d6) δ 11.23 (s, 1H), 8.33-8.15 (m, 2H), 7.97-7.77 (m, 1H), 7.74-7.61 (m, 1H), 7.59-7.43 (m, 1H), 6.60-6.47 (m, 1H), 4.28-4.17 (m, 1H), 4.04-3.88 (m, 2H), 3.16-2.99 (m, 1H), 2.71-2.57 (m, 3H), 2.48-2.37 (m, 1H), 2.07-1.85 (m, 3H), 1.56-1.39 (m, 3H). |
| 434 | 351.1 | 1H NMR (400 MHz, DMSO-d6) δ 8.06 (s, 1H), 8.01-7.90 (m, 4H), 7.46 (s, 1H), 4.22-4.17 (m, 1H), 4.09-4.01 (m, 1H), 3.99-3.88 (m, 2H), 3.86-3.78 (m, 2H), 3.13-2.95 (m, 2H), 2.88-2.80 (m, 2H), 2.76-2.63 (m, 1H), 2.46-2.30 (m, 2H), 2.08-1.93 (m, 3H). |
| 435 | 378.1 | 1H NMR (400 MHz, DMSO-d6) δ 7.75-7.67 (m, 2H), 7.45 (t, J = 7.7 Hz, 1H), 7.38-7.33 (m, 1H), 4.47-4.41 (m, 1H), 4.04-3.89 (m, 2H), 3.12-2.94 (m, 2H), 2.83 (t, J = 7.7 Hz, 2H), 2.57 (d, J = 5.9 Hz, 1H), 2.47-2.37 (m, 1H), 2.09-1.93 (m, 4H), 1.51 (d, J = 6.2, 1.1 Hz, 3H), 1.34 (s, 3H), 0.91 (s, 3H). |

TABLE 1-continued

MS and NMR DATA

| Example No | ES/MS m/z (M + H)+ | 1H NMR |
|---|---|---|
| 436 | 353.1 | 1H NMR (400 MHz, DMSO-d6) δ 8.08 (s, 1H), 8.03-7.97 (m, 2H), 7.92-7.84 (m, 2H), 7.49 (s, 1H), 4.71 (s, 1H), 4.32 (t, J = 7.8 Hz, 1H), 4.04-3.97 (m, 1H), 3.93-3.85 (m, 1H), 3.08-2.96 (m, 2H), 2.91-2.79 (m, 2H), 2.32-2.22 (m, 1H), 2.18-2.10 (m, 1H), 2.09-1.99 (m, 2H), 1.21 (s, 3H), 1.06 (s, 3H). |
| 437 | 369.1 | 1H NMR (400 MHz, DMSO-d6) δ 8.07 (s, 1H), 8.02-7.94 (m, 4H), 7.47 (s, 1H), 5.57-5.31 (m, 1H), 4.67-4.53 (m, 1H), 4.36-4.24 (m, 1H), 4.10-3.99 (m, 1H), 3.11-2.99 (m, 2H), 2.83 (t, J = 7.7 Hz, 2H), 2.09-1.91 (m, 3H), 1.87-1.72 (m, 2H), 1.01-0.94 (m, 6H). |
| 438 | 445.1 | 1H NMR (400 MHz, DMSO-d6) δ 8.07 (s, 1H), 7.99-7.90 (m, 4H), 7.48 (s, 1H), 7.39-7.19 (m, 5H), 4.74-4.62 (m, 2H), 4.56-4.48 (m, 2H), 4.41-4.34 (m, 1H), 4.19-4.14 (m, 1H), 4.01-3.95 (m, 1H), 3.12-2.96 (m, 2H), 2.91-2.66 (m, 2H), 2.08-1.96 (m, 2H), 1.35 (d, J = 6.2 Hz, 3H). |
| 439 | 364.1 | 1H NMR (400 MHz, DMSO-d6) δ 7.80-7.69 (m, 2H), 7.51-7.35 (m, 2H), 4.52-4.43 (m, 1H), 4.07-3.93 (m, 2H), 3.77-3.67 (m, 0.5H), 3.57-3.47 (m, 0.5H), 3.14-2.94 (m, 3H), 2.85 (t, J = 7.8 Hz, 2H), 2.64-2.55 (m, 2H), 2.47-2.33 (m, 2H), 2.30-2.21 (m, 1H), 2.09-1.94 (m, 3H), 1.52 (d, J = 6.2 Hz, 3H). |
| 440 | 364.2 | 1H NMR (400 MHz, DMSO-d6) δ 7.78 (s, 1H), 7.71 (d, J = 7.7 Hz, 1H), 7.44 (t, J = 7.6 Hz, 1H), 7.34 (d, J = 7.7 Hz, 1H), 4.47-4.38 (m, 1H), 4.02-3.88 (m, 2H), 3.60-3.50 (m, 1H), 3.16-2.94 (m, 3H), 2.81 (t, J = 7.7 Hz, 2H), 2.64-2.55 (m, 2H), 2.45-2.35 (m, 1H), 2.30-2.19 (m, 3H), 2.07-1.94 (m, 3H), 1.51 (d, J = 6.2 Hz, 3H). |
| 441 | 364.2 | 1H NMR (400 MHz, DMSO-d6) δ 7.76 (s, 1H), 7.68 (d, J = 7.7 Hz, 1H), 7.43 (t, J = 7.6 Hz, 1H), 7.35 (d, J = 7.9 Hz, 1H), 4.44-4.36 (m, 1H), 4.03-3.85 (m, 2H), 3.71-3.58 (m, 1H), 3.11-2.94 (m, 2H), 2.91-2.76 (m, 2H), 2.59-2.53 (m, 2H), 2.45-2.32 (m, 1H), 2.29-2.16 (m, 3H), 2.07-1.89 (m, 3H), 1.50 (d, J = 6.2 Hz, 3H). |
| 442 | 339.1 | 1H NMR (400 MHz, DMSO-d6) δ 8.10-8.04 (m, 1H), 8.00-7.92 (m, 4H), 7.46 (s, 1H), 4.07 (t, J = 7.4 Hz, 4H), 3.02 (t, J = 7.3 Hz, 2H), 2.82 (t, J = 7.7 Hz, 2H), 2.36-2.27 (m, 1H), 2.07-1.97 (m, 2H). |
| 443 | 384.9 | 1H NMR (400 MHz, DMSO-d6) δ 7.69 (s, 1H), 7.57 (s, 1H), 7.39 (s, 1H), 4.52-4.37 (m, 1H), 4.05-3.87 (m, 2H), 3.10-2.93 (m, 2H), 2.81 (t, J = 7.7 Hz, 2H), 2.59-2.54 (m, 1H), 2.45-2.36 (m, 1H), 2.06-1.90 (m, 4H), 1.57-1.39 (m, 5H). |
| 444 | 417.1 | 1H NMR (400 MHz, DMSO-d6) δ 8.41 (d, J = 4.5 Hz, 1H), 7.98 (d, J = 8.2 Hz, 1H), 7.68 (dd, J = 8.2, 1.7 Hz, 1H), 7.56 (d, J = 1.7 Hz, 1H), 4.30-4.22 (m, 2H), 4.18-4.03 (m, 3H), 3.74-3.60 (m, 2H), 3.20-3.08 (m, 2H), 2.67-2.53 (m, 2H), 1.50 (d, J = 5.8 Hz, 3H), 1.14 (d, J = 6.8 Hz, 3H). |
| 445 | 321.2 | 1H NMR (400 MHz, DMSO-d6) δ 8.51-8.40 (m, 1H), 8.16-8.11 (m, 1H), 8.06 (s, 1H), 7.96 (d, J = 7.8 Hz, 1H), 7.63-7.56 (m, 1H), 7.44 (s, 1H), 4.48-4.25 (m, 1H), 4.00-3.81 (m, 2H), 3.17-3.06 (m, 1H), 2.81 (d, J = 18.6 Hz, 1H), 2.02-1.93 (m, 1H), 1.87-1.77 (m, 1H), 1.52-1.36 (m, 3H), 1.33-1.11 (m, 2H), 0.93-0.76 (m, 1H), 0.27-0.16 (m, 1H). |
| 446 | 445.1 | 1H NMR (400 MHz, DMSO-d6) δ 8.02-7.94 (m, 3H), 7.79-7.71 (m, 2H), 4.30-4.22 (m, 1H), 4.17-4.07 (m, 2H), 3.72-3.66 (m, 1H), 3.24-3.06 (m, 2H), 2.69-2.54 (m, 2H), 1.50 (d, J = 5.8 Hz, 3H). |
| 447 | 335.2 | 1H NMR (400 MHz, DMSO-d6) δ 8.06 (s, 1H), 7.97 (d, J = 8.4 Hz, 2H), 7.93 (d, J = 8.3 Hz, 2H), 7.45 (s, 1H), 4.02 (s, 4H), 3.01 (t, J = 7.2 Hz, 2H), 2.80 (t, J = 7.7 Hz, 2H), 2.18 (t, J = 7.6 Hz, 4H), 2.01 (d, J = 7.4 Hz, 1H), 1.82 (t, J = 7.6 Hz, 2H). |
| 448 | 337.2 | 1H NMR (400 MHz, DMSO-d6) δ 8.06 (s, 1H), 7.98 (d, J = 8.2 Hz, 2H), 7.93 (d, J = 8.2 Hz, 2H), 7.46 (s, 1H), 4.73 (s, 4H), 4.22 (s, 4H), 3.01 (t, J = 7.3 Hz, 2H), 2.81 (t, J = 7.7 Hz, 2H), 2.00 (p, J = 7.5 Hz, 2H). |
| 449 | 368.1 | 1H NMR (400 MHz, DMSO-d6) δ 8.04 (dt, J = 7.8, 1.5 Hz, 1H), 8.02 (t, J = 1.7 Hz, 1H), 7.76 (dt, J = 7.8, 1.5 Hz, 1H), 7.71-7.65 (m, 2H), 5.09 (s, 2H), 4.45 (dt, J = 7.9, 6.1 Hz, 1H), 3.97 (m, 2H), 3.04 (m, 2H), 2.84 (t, J = 7.7 Hz, 2H), 2.41 (m, 1H), 2.12-1.91 (m, 2H), 1.50 (d, J = 6.2 Hz, 3H). |
| 450 | 323.2 | 1H NMR (400 MHz, DMSO-d6) δ 8.10 (s, 1H), 8.07 (d, J = 8.3 Hz, 2H), 8.01 (d, J = 8.2 Hz, 2H), 7.49 (s, 1H), 4.03 (t, J = 7.0 Hz, 2H), 3.18 (t, J = 7.3 Hz, 2H), 2.98 (q, J = 7.3 Hz, 2H), 2.54 (t, J = 8.4 Hz, 2H), 2.17-1.96 (m, 4H). |
| 451 | 386.2 | 1H NMR (400 MHz, DMSO-d6) δ 8.16 (d, J = 8.5 Hz, 2H), 8.04 (d, J = 8.5 Hz, 2H), 5.16 (s, 2H), 4.45 (dt, J = 7.9, 6.1 Hz, 1H), 4.01 (dt, J = 8.7, 4.3 Hz, 1H), 3.94 (m, 1H), 3.17 (s, 3H), 3.03 (h, J = 8.3 Hz, 2H), 2.84 (t, J = 7.7 Hz, 2H), 2.41 (m, 1H), 2.02 (m, 2H), 1.50 (d, J = 6.2 Hz, 3H). |
| 452 | 336.1 | 1H NMR (400 MHz, DMSO-d6) δ 10.99 (s, 1H), 7.72-7.63 (m, 1H), 7.60 (s, 1H), 7.21 (d, J = 8.2 Hz, 1H), 4.46 (q, J = 6.7 Hz, 1H), 4.13- |

TABLE 1-continued

MS and NMR DATA

| Example No | ES/MS m/z (M + H)+ | 1H NMR |
|---|---|---|
| | | 3.85 (m, 2H), 3.33 (s, 3H), 3.16-2.94 (m, 2H), 2.84 (t, J = 7.8 Hz, 2H), 2.42 (ddt, J = 10.3, 8.5, 4.3 Hz, 2H), 2.25-1.90 (m, 2H), 1.52 (d, J = 6.2 Hz, 3H). |
| 453 | 333 | 1H NMR (400 MHz, DMSO-d6) δ 8.41 (d, J = 5.3 Hz, 1H), 7.86 (t, J = 72.8 Hz, 1H), 7.71 (dd, J = 5.3, 1.4 Hz, 1H), 7.44 (d, J = 1.3 Hz, 1H), 4.43 (p, J = 7.9, 6.1 Hz, 6.1 Hz, 1H), 4.05-3.87 (m, 2H), 3.04 (h, J = 8.4 Hz, 2H), 2.83 (t, J = 7.8 Hz, 2H), 2.46-2.36 (m, 2H), 2.10-1.87 (m, 2H), 1.50 (d, J = 6.2 Hz, 3H). |
| 454 | 331.2 | 1H NMR (400 MHz, DMSO-d6) δ 7.68 (d, J = 7.7 Hz, 1H), 7.60 (t, J = 4.6 Hz, 2H), 7.42 (t, J = 7.7 Hz, 1H), 7.25 (d, J = 7.7 Hz, 1H), 4.43 (p, J = 6.5 Hz, 1H), 4.06-3.90 (m, 2H), 3.17-2.90 (m, 2H), 2.83 (t, J = 7.7 Hz, 2H), 2.43-2.38 (m, 1H), 2.40 (d, J = 9.2 Hz, 2H), 2.18-1.93 (m, 3H), 1.89 (m, 2H), 1.51 (d, J = 6.2 Hz, 3H), 1.55-1.24 (m, 1H), 1.41-1.22 (m, 2H). |
| 455 | 350.2 | 1H NMR (400 MHz, DMSO-d6) δ 7.82 (d, J = 8.3 Hz, 2H), 7.46 (d, J = 8.3 Hz, 2H), 4.42 (q, J = 6.7 Hz, 1H), 4.04-3.82 (m, 2H), 3.02 (q, J = 7.2 Hz, 2H), 2.82 (t, J = 7.7 Hz, 2H), 2.46-2.35 (m, 2H), 2.06-1.87 (m, 2H), 1.50 (d, J = 5.8 Hz, 3H). |
| 456 | 349 | δ 7.68 (d, J = 7.7 Hz, 1H), 7.60 (t, J = 4.6 Hz, 2H), 7.42 (t, J = 7.7 Hz, 1H), 7.25 (d, J = 7.7 Hz, 1H), 6.93 (s, 1H), 4.43 (p, J = 6.5 Hz, 1H), 4.06-3.90 (m, 2H), 3.17-2.90 (m, 2H), 2.83 (t, J = 7.7 Hz, 2H), 2.40 (d, J = 9.2 Hz, 2H), 2.35-2.26 (m, 1H), 2.18-1.93 (m, 3H), 1.89 (dt, J = 9.1, 4.8 Hz, 2H), 1.51 (d, J = 6.2 Hz, 3H), 1.43-1.33 (m, 1H), 1.30-1.13 (m, 2H). |
| 457 | 355.2 | 1H NMR (400 MHz, DMSO-d6) δ 8.06 (s, 1H), 7.97 (s, 4H), 7.45 (s, 1H), 3.97-3.86 (m, 1H), 3.69 (dt, J = 13.0, 7.0 Hz, 1H), 3.65-3.54 (m, 1H), 3.54-3.40 (m, 1H), 3.29 (partially obscured by water peak, m, 1H), 3.02 (t, J = 7.2 Hz, 2H), 2.82 (t, J = 7.7 Hz, 2H), 2.30 (dq, J = 12.8, 6.4 Hz, 1H), 2.14 (s, 3H), 2.10-1.95 (m, 2H), 1.99-1.87 (m, 1H). |
| 458 | 363.2 | 1H NMR (400 MHz, Methanol-d4) δ 8.49 (s, 1H), 8.41 (s, 1H), 7.97 (d, J = 9.0 Hz, 1H), 7.73 (d, J = 9.2 Hz, 1H), 5.24 (s, 2H), 4.75 (q, J = 6.7 Hz, 1H), 4.33-4.09 (m, 2H), 3.24-3.10 (m, 2H), 3.03 (t, J = 7.8 Hz, 2H), 2.69-2.58 (m, 1H), 2.27-2.04 (m, 3H), 1.63 (d, J = 6.3 Hz, 3H). |
| 459 | 301.1 | 1H NMR (400 MHz, DMSO-d6) δ 8.28 (s, 3H), 7.56 (d, J = 3.9 Hz, 1H), 7.29 (d, J = 3.8 Hz, 1H), 4.38 (h, J = 6.4 Hz, 1H), 4.29 (q, J = 5.7 Hz, 2H), 4.00-3.83 (m, 2H), 3.00 (dd, J = 8.3, 6.5 Hz, 2H), 2.80 (t, J = 7.9 Hz, 2H), 2.45-2.33 (m, 1H), 2.07 (p, J = 7.7 Hz, 2H), 1.97 (ddt, J = 10.8, 8.8, 7.0 Hz, 1H), 1.50 (d, J = 6.2 Hz, 3H). |
| 460 | 379.1 | 1H NMR (400 MHz, DMSO-d6) δ 7.77 (t, J = 6.3 Hz, 1H), 7.54 (d, J = 3.9 Hz, 1H), 7.13 (d, J = 3.8 Hz, 1H), 4.49-4.33 (m, 3H), 4.07-3.81 (m, 2H), 3.00 (dd, J = 8.2, 6.6 Hz, 2H), 2.90 (s, 3H), 2.82 (t, J = 7.8 Hz, 2H), 2.40 (dtd, J = 10.7, 8.6, 4.7 Hz, 1H), 2.08 (p, J = 7.2, 6.7 Hz, 2H), 2.04-1.89 (m, 1H), 1.51 (d, J = 6.2 Hz, 3H). |
| 461 | 312.2 | 1H NMR (400 MHz, DMSO-d6) δ 8.77 (s, 1H), 5.74 (p, J = 7.5 Hz, 1H), 4.52 (d, J = 6.5 Hz, 2H), 4.49 (d, J = 6.6 Hz, 2H), 4.38 (h, J = 6.4 Hz, 1H), 4.01-3.83 (m, 2H), 3.16 (td, J = 7.2, 2.1 Hz, 2H), 2.80 (t, J = 7.8 Hz, 2H), 2.39 (m, 1H), 2.04 (p, J = 7.5 Hz, 2H), 2.00-1.88 (m, 1H), 1.50 (d, J = 6.2 Hz, 3H). |
| 462 | 439.1 | 1H NMR (400 MHz, DMSO-d6) δ 7.95 (d, J = 1.8 Hz, 1H), 7.89 (dt, J = 7.7, 1.5 Hz, 1H), 7.61-7.48 (m, 2H), 4.35 (s, 2H), 4.25 (m, 1H), 4.17-4.06 (m, 2H), 3.68 (m, 1H), 3.14 (m, 2H), 2.98 (s, 3H), 2.72 (s, 3H), 2.60 (m, 2H), 1.50 (d, J = 6.0 Hz, 3H). |
| 463 | 349.0 | 1H NMR (400 MHz, DMSO-$d_6$) δ 8.50 (d, J = 2.1 Hz, 1H), 8.49 (bs, 1H), 8.33 (dd, J = 8.6, 2.1 Hz, 1H), 7.53 (d, J = 8.6 Hz, 1H), 4.42 (dt, J = 7.9, 6.1 Hz, 1H), 4.30 (bs, 2H), 3.98 (m, 1H), 3.92 (q, J = 8.5 Hz, 1H), 3.04 (h, J = 8.2 Hz, 2H), 2.82 (t, J = 7.8 Hz, 2H), 2.41 (dtd, J = 10.8, 8.5, 4.7 Hz, 1H), 2.10-1.90 (m, 3H), 1.51 (d, J = 6.1 Hz, 3H). |
| 464 | 395.2 | 1H NMR (400 MHz, DMSO-d6) δ 8.54 (s, 1H), 8.32 (d, J = 7.8, 1.2 Hz, 1H), 8.19 (d, J = 8.0, 1.3 Hz, 1H), 7.89 (t, J = 7.9 Hz, 1H), 4.28 (dd, J = 9.0, 5.6 Hz, 1H), 4.24-3.96 (m, 2H), 3.81-3.63 (m, 1H), 3.50 (s, 3H), 3.28-3.02 (m, 2H), 2.74-2.55 (m, 2H), 1.52 (d, J = 5.8 Hz, 3H). |
| 465 | 453.1 | 1H NMR (400 MHz, DMSO-d6) δ 7.91 (d, J = 7.9 Hz, 1H), 7.57-7.46 (m, 2H), 7.36 (s, 1H), 5.65 (d, J = 6.2 Hz, 1H), 5.27 (td, J = 8.2, 5.2 Hz, 1H), 4.78 (t, J = 9.1 Hz, 1H), 4.38 (dd, J = 9.8, 5.2 Hz, 1H), 4.24 (dd, J = 9.0, 5.7 Hz, 1H), 4.12 (t, J = 5.7 Hz, 2H), 3.67 (dd, J = 9.0, 4.4 Hz, 1H), 3.14-3.08 (m, 2H), 3.07 (s, 3H), 2.58 (td, J = 15.3, 7.5 Hz, 2H), 1.49 (d, J = 5.8 Hz, 3H). |
| 466 | 453.1 | 1H NMR (400 MHz, DMSO-d6) δ 7.91 (d, J = 7.9 Hz, 1H), 7.57-7.46 (m, 2H), 7.36 (s, 1H), 5.65 (d, J = 6.2 Hz, 1H), 5.27 (td, J = 8.2, 5.2 Hz, 1H), 4.78 (t, J = 9.1 Hz, 1H), 4.38 (dd, J = 9.8, 5.2 Hz, 1H), 4.24 |

TABLE 1-continued

MS and NMR DATA

| Example No | ES/MS m/z (M + H)+ | 1H NMR |
|---|---|---|
| | | (dd, J = 9.0, 5.7 Hz, 1H), 4.12 (t, J = 5.7 Hz, 2H), 3.67 (dd, J = 9.0, 4.4 Hz, 1H), 3.14-3.08 (m, 2H), 3.07 (s, 3H), 2.58 (td, J = 15.3, 7.5 Hz, 2H), 1.49 (d, J = 5.8 Hz, 3H). |
| 467 | 453.1 | 1H NMR (400 MHz, DMSO-d6) δ 7.91 (d, J = 7.9 Hz, 1H), 7.57-7.46 (m, 2H), 7.36 (s, 1H), 5.65 (d, J = 6.2 Hz, 1H), 5.27 (td, J = 8.2, 5.2 Hz, 1H), 4.78 (t, J = 9.1 Hz, 1H), 4.38 (dd, J = 9.8, 5.2 Hz, 1H), 4.24 (dd, J = 9.0, 5.7 Hz, 1H), 4.12 (t, J = 5.7 Hz, 2H), 3.67 (dd, J = 9.0, 4.4 Hz, 1H), 3.14-3.08 (m, 2H), 3.07 (s, 3H), 2.58 (td, J = 15.3, 7.5 Hz, 2H), 1.49 (d, J = 5.8 Hz, 3H). |
| 468 | 391.1 | 1H NMR (400 MHz, DMSO-d6) δ 9.07 (s, 3H), 8.07 (d, J = 8.5 Hz, 2H), 7.71 (d, J = 8.5 Hz, 2H), 5.18 (ddt, J = 56.9, 6.0, 3.7 Hz, 1H), 5.01-4.93 (m, 4H), 4.58-4.34 (m, 2H), 4.02 (ddd, J = 25.6, 10.4, 3.8 Hz, 1H), 3.22-3.05 (m, 2H), 2.70-2.55 (m, 2H), 1.55 (d, J = 6.5 Hz, 3H). |
| 469 | 391.1 | 1H NMR (400 MHz, DMSO-d6) δ 9.05 (s, 3H), 8.06 (d, J = 8.5 Hz, 2H), 7.71 (d, J = 8.5 Hz, 2H), 5.44 (dtd, J = 58.0, 6.0, 2.6 Hz, 1H), 5.06-4.92 (m, 4H), 4.79-4.63 (m, 1H), 4.47-4.30 (m, 1H), 4.21-4.05 (m, 1H), 3.23-3.06 (m, 2H), 2.61 (ddd, J = 22.2, 15.1, 6.6 Hz, 2H), 1.54-1.41 (m, 3H). |
| 470 | 409.1 | 1H NMR (400 MHz, DMSO-d6) δ 9.06 (s, 3H), 8.09 (d, J = 8.5 Hz, 2H), 7.72 (d, J = 8.5 Hz, 2H), 5.03-4.92 (m, 4H), 4.88-4.78 (m, 1H), 4.50 (t, J = 12.3 Hz, 2H), 3.24-3.13 (m, 2H), 2.70-2.56 (m, 2H), 1.53 (d, J = 6.5 Hz, 3H). |
| 471 | 391.1 | 1H NMR (400 MHz, DMSO-d6) δ 9.03 (s, 3H), 8.06 (d, J = 8.5 Hz, 2H), 7.70 (d, J = 8.5 Hz, 2H), 5.02-4.85 (m, 5H), 4.76-4.57 (m, 2H), 4.09-3.96 (m, 2H), 3.20-3.05 (m, 2H), 2.73-2.53 (m, 2H), 2.47-2.31 (m, 2H). |
| 472 | 451.1 | 1H NMR (400 MHz, DMSO-d6) δ 7.86-7.76 (m, 2H), 7.61 (d, J = 8.7 Hz, 1H), 7.50 (d, J = 7.8 Hz, 1H), 4.88 (q, J = 8.2 Hz, 1H), 4.24 (dd, J = 9.0, 5.5 Hz, 1H), 4.15-4.05 (m, 2H), 3.68 (dd, J = 9.0, 4.4 Hz, 1H), 3.21-2.94 (m, 6H), 2.65-2.53 (m, 3H), 2.01-1.84 (m, 1H), 1.49 (d, J = 5.8 Hz, 3H). |
| 473 | 451.1 | 1H NMR (400 MHz, DMSO-d6) δ 7.84-7.77 (m, 2H), 7.61 (d, J = 8.7 Hz, 1H), 7.50 (d, J = 7.8 Hz, 1H), 4.88 (q, J = 8.2 Hz, 1H), 4.24 (dd, J = 8.9, 5.6 Hz, 1H), 4.15-4.08 (m, 2H), 3.68 (dd, J = 9.0, 4.4 Hz, 1H), 3.16-3.08 (m, 2H), 3.06 (s, 3H), 3.03-2.94 (m, 1H), 2.91-2.79 (m, 1H), 2.63-2.53 (m, 3H), 2.01-1.84 (m, 1H), 1.49 (d, J = 5.9 Hz, 3H). |
| 474 | 429.1 | 1H NMR (400 MHz, DMSO-d6) δ 8.26 (s, 1H), 7.85 (d, J = 8.0 Hz, 1H), 7.80 (s, 1H), 7.52 (d, J = 8.0 Hz, 1H), 4.47 (d, J = 8.7 Hz, 1H), 4.31-4.16 (m, 2H), 4.18-4.03 (m, 2H), 3.68 (dd, J = 9.0, 4.3 Hz, 1H), 3.18-3.04 (m, 2H), 3.01-2.89 (m, 2H), 2.63-2.53 (m, 2H), 2.47-2.36 (m, 1H), 2.26-2.13 (m, 1H), 1.49 (d, J = 5.7 Hz, 3H). |
| 475 | 429.1 | 1H NMR (400 MHz, DMSO-d6) δ 8.26 (s, 1H), 7.85 (d, J = 8.1 Hz, 1H), 7.80 (s, 1H), 7.52 (d, J = 7.9 Hz, 1H), 4.47 (d, J = 8.7 Hz, 1H), 4.29-4.18 (m, 2H), 4.14-4.05 (m, 2H), 3.68 (dd, J = 8.9, 4.3 Hz, 1H), 3.18-2.87 (m, 4H), 2.63-2.52 (m, 2H), 2.48-2.35 (m, 1H), 2.25-2.11 (m, 1H), 1.49 (d, J = 5.7 Hz, 3H). |
| 476 | 429.1 | 1H NMR (400 MHz, DMSO-d6) δ 8.26 (s, 1H), 7.85 (d, J = 8.1 Hz, 1H), 7.80 (s, 1H), 7.52 (d, J = 7.9 Hz, 1H), 4.47 (d, J = 8.7 Hz, 1H), 4.29-4.18 (m, 2H), 4.14-4.05 (m, 2H), 3.68 (dd, J = 8.9, 4.3 Hz, 1H), 3.18-2.87 (m, 4H), 2.63-2.52 (m, 2H), 2.48-2.35 (m, 1H), 2.25-2.11 (m, 1H), 1.49 (d, J = 5.7 Hz, 3H). |
| 477 | 483.1 | 1H NMR (400 MHz, DMSO-d6) δ 7.80-7.74 (m, 1H), 7.09 (s, 1H), 6.99 (s, 1H), 5.23-5.08 (m, 1H), 4.73-4.59 (m, 1H), 4.42 (dd, J = 9.9, 3.1 Hz, 1H), 4.24 (dd, J = 9.0, 5.5 Hz, 1H), 4.17-4.06 (m, 2H), 3.89 (s, 3H), 3.67 (dd, J = 9.0, 4.4 Hz, 1H), 3.21-3.04 (m, 2H), 3.01 (s, 3H), 2.65-2.53 (m, 2H), 1.49 (d, J = 5.7 Hz, 3H). |
| 478 | 483.1 | 1H NMR (400 MHz, DMSO-d6) δ 7.77 (d, J = 7.3 Hz, 1H), 7.09 (s, 1H), 6.99 (s, 1H), 5.18 (td, J = 7.6, 2.9 Hz, 1H), 4.66 (dd, J = 9.9, 7.8 Hz, 1H), 4.42 (dd, J = 9.9, 3.0 Hz, 1H), 4.25 (dd, J = 9.0, 5.5 Hz, 1H), 4.18-4.07 (m, 2H), 3.89 (s, 3H), 3.67 (dd, J = 9.0, 4.3 Hz, 1H), 3.22-3.07 (m, 2H), 3.00 (s, 3H), 2.65-2.52 (m, 2H), 1.49 (d, J = 5.7 Hz, 3H). |
| 479 | 483.1 | 1H NMR (400 MHz, DMSO-d6) δ 7.77 (d, J = 7.3 Hz, 1H), 7.09 (s, 1H), 6.99 (s, 1H), 5.18 (td, J = 7.6, 2.9 Hz, 1H), 4.66 (dd, J = 9.9, 7.8 Hz, 1H), 4.42 (dd, J = 9.9, 3.0 Hz, 1H), 4.25 (dd, J = 9.0, 5.5 Hz, 1H), 4.18-4.07 (m, 2H), 3.89 (s, 3H), 3.67 (dd, J = 9.0, 4.3 Hz, 1H), 3.22-3.07 (m, 2H), 3.00 (s, 3H), 2.65-2.52 (m, 2H), 1.49 (d, J = 5.7 Hz, 3H). |
| 480 | 455.1 | 1H NMR (400 MHz, DMSO-d6) δ 7.91 (d, J = 7.9 Hz, 1H), 7.56-7.47 (m, 2H), 7.36 (s, 1H), 5.32-5.22 (m, 1H), 4.78 (t, J = 9.1 Hz, 1H), 4.38 (dd, J = 9.8, 5.2 Hz, 1H), 4.16-4.05 (m, 2H), 3.18-2.99 (m, 5H), 2.65-2.52 (m, 2H), 1.49 (d, J = 5.6 Hz, 3H). |

TABLE 1-continued

MS and NMR DATA

| Example No | ES/MS m/z (M + H)+ | 1H NMR |
|---|---|---|
| 481 | 431.1 | 1H NMR (400 MHz, DMSO-d6) δ 8.58 (s, 1H), 7.66-7.51 (m, 2H), 7.38 (s, 1H), 4.71 (d, J = 10.3 Hz, 1H), 4.61 (d, J = 9.2 Hz, 1H), 4.58-4.49 (m, 2H), 4.24 (dd, J = 9.1, 5.5 Hz, 1H), 4.16-4.08 (m, 2H), 3.67 (dd, J = 9.0, 4.3 Hz, 1H), 3.16-3.03 (m, 2H), 2.65-2.52 (m, 2H), 1.48 (d, J = 5.7 Hz, 3H). |
| 482 | 431.1 | 1H NMR (400 MHz, DMSO-d6) δ 8.58 (s, 1H), 7.66-7.51 (m, 2H), 7.38 (s, 1H), 4.71 (d, J = 10.3 Hz, 1H), 4.61 (d, J = 9.2 Hz, 1H), 4.58-4.49 (m, 2H), 4.24 (dd, J = 9.1, 5.5 Hz, 1H), 4.16-4.08 (m, 2H), 3.67 (dd, J = 9.0, 4.3 Hz, 1H), 3.16-3.03 (m, 2H), 2.65-2.52 (m, 2H), 1.48 (d, J = 5.7 Hz, 3H). |
| 483 | 431.2 | 1H NMR (400 MHz, DMSO-d6) δ 8.58 (s, 1H), 7.66-7.51 (m, 2H), 7.38 (s, 1H), 4.71 (d, J = 10.3 Hz, 1H), 4.61 (d, J = 9.2 Hz, 1H), 4.58-4.49 (m, 2H), 4.24 (dd, J = 9.1, 5.5 Hz, 1H), 4.16-4.08 (m, 2H), 3.67 (dd, J = 9.0, 4.3 Hz, 1H), 3.16-3.03 (m, 2H), 2.65-2.52 (m, 2H), 1.48 (d, J = 5.7 Hz, 3H). |
| 484 | 471.1 | 1H NMR (400 MHz, DMSO-d6) δ 7.92 (d, J = 7.9 Hz, 1H), 7.56-7.48 (m, 2H), 7.39-7.34 (m, 1H), 5.33-5.17 (m, 1H), 5.02-4.65 (m, 3H), 4.58-4.49 (m, 1H), 4.38 (dd, J = 9.8, 5.2 Hz, 1H), 4.34-4.16 (m, 2H), 3.75 (dd, J = 9.0, 4.9 Hz, 1H), 3.19-2.99 (m, 5H), 2.67-2.53 (m, 2H). |
| 485 | 442.1 | 1H NMR (400 MHz, Chloroform-d) δ 7.83-7.73 (m, 2H), 7.72 (s, 1H), 7.34 (d, J = 8.0 Hz, 1H), 5.72 (s, 1H), 4.45 (dd, J = 9.6, 5.5 Hz, 1H), 4.37-4.20 (m, 2H), 3.89 (dd, J = 9.6, 4.3 Hz, 1H), 3.18-2.96 (m, 3H), 2.90-2.77 (m, 1H), 2.71-2.43 (m, 3H), 2.33 (dtd, J = 12.5, 8.6, 3.9 Hz, 1H), 1.60 (dd, J = 6.3, 1.7 Hz, 3H). |
| 486 | 442.1 | 1H NMR (400 MHz, Chloroform-d) δ 7.83-7.74 (m, 1H), 7.61 (s, 1H), 7.34 (d, J = 8.0 Hz, 1H), 5.66 (s, 1H), 4.44 (dd, J = 9.6, 5.6 Hz, 1H), 4.31 (d, J = 5.5 Hz, 2H), 3.89 (dd, J = 9.7, 4.2 Hz, 1H), 3.32 (d, J = 6.7 Hz, 1H), 3.08 (s, 2H), 2.84 (m, 1H), 2.56 (m, 2H), 2.45-2.28 (m, 1H), 2.20-2.07 (m, 1H), 1.60 (d, J = 5.8 Hz, 3H). |
| 487 | 467.1 | 1H NMR (400 MHz, DMSO-d6) δ 7.91 (d, J = 7.9 Hz, 1H), 7.57-7.46 (m, 2H), 7.36 (s, 1H), 5.65 (d, J = 6.2 Hz, 1H), 5.27 (td, J = 8.2, 5.2 Hz, 1H), 4.78 (t, J = 9.1 Hz, 1H), 4.38 (dd, J = 9.8, 5.2 Hz, 1H), 4.24 (dd, J = 9.0, 5.7 Hz, 1H), 4.12 (t, J = 5.7 Hz, 2H), 3.67 (dd, J = 9.0, 4.4 Hz, 1H), 3.14-3.08 (m, 2H), 3.07 (s, 3H), 2.58 (td, J = 15.3, 7.5 Hz, 2H), 1.49 (d, J = 5.8 Hz, 3H). |
| 488 | 456.2 | 1H NMR (400 MHz, DMSO) δ 8.77 (s, 1H), 7.86 (d, J = 1.4 Hz, 1H), 7.79 (dd, J = 8.0, 1.6 Hz, 1H), 7.31 (d, J = 8.0 Hz, 1H), 4.25 (dd, J = 9.0, 5.6 Hz, 1H), 4.12 (d, J = 4.4 Hz, 2H), 3.68 (dd, J = 8.9, 4.4 Hz, 1H), 3.11 (d, J = 8.2 Hz, 4H), 2.91 (s, 3H), 2.66-2.51 (m, 4H), 2.24 (dt, J = 13.3, 8.3 Hz, 1H), 1.49 (d, J = 6.0 Hz, 3H). |
| 489 | 437.2 | 1H NMR (400 MHz, DMSO-d6) δ 9.37 (bs, 2H), 8.58 (d, J = 1.8 Hz, 1H), 8.32 (dd, J = 7.9, 1.9 Hz, 1H), 7.92 (d, J = 7.9 Hz, 1H), 5.70 (bs, 1H), 4.68 (s, 2H), 4.27 (dd, J = 9.1, 5.5 Hz, 1H), 4.14 (q, J = 4.6 Hz, 2H), 3.85 (d, J = 6.5 Hz, 2H), 3.75 (t, J = 5.1 Hz, 2H), 3.70 (dd, J = 9.0, 4.3 Hz, 1H), 3.27-3.01 (m, 2H), 2.62 (tt, J = 15.2, 6.5 Hz, 2H), 1.51 (d, J = 5.7 Hz, 3H). |
| 490 | 439.2 | 1H NMR (400 MHz, DMSO-d6) 9.52 (bs, 2H), 8.54 (d, J = 1.9 Hz, 1H), 8.33 (d, J = 7.9, 1.9 Hz, 1H), 7.93 (d, J = 7.9 Hz, 1H), 4.95 (ddd, J = 48.5, 10.3, 3.3 Hz, 1H), 4.76-4.66 (m, 3H), 4.61 (m, 1H), 4.02 (m, 2H), 3.86 (m, 2H), 3.75 (t, J = 5.2 Hz, 2H), 3.17 (m, 2H), 2.63 (tt, J = 15.3, 6.7 Hz, 2H), 2.42 (m, 2H). |
| 491 | 436.9 | 1H NMR (400 MHz, DMSO-d6) δ 7.96 (d, J = 8.5 Hz, 2H), 7.72 (d, J = 8.5 Hz, 2H), 5.66 (d, J = 5.8 Hz, 1H), 4.65 (d, J = 14.5 Hz, 2H), 4.31 (d, J = 14.5 Hz, 2H), 4.25 (dd, J = 9.0, 5.4 Hz, 1H), 4.12 (q, J = 4.8 Hz, 2H), 3.68 (dd, J = 8.9, 4.4 Hz, 1H), 3.14 (m, 2H), 2.85 (s, 2H), 2.58 (tt, J = 15.6, 6.6 Hz, 2H), 1.50 (d, J = 5.7 Hz, 3H). |
| 492 | 395.2 | 1H NMR (400 MHz, DMSO-d6) δ 8.49 (s, 1H), 8.22 (d, J = 7.8, 1.4 Hz, 1H), 8.11 (d, J = 7.9, 1.3 Hz, 1H), 7.80 (t, J = 7.8 Hz, 1H), 5.70 (d, J = 6.2 Hz, 1H), 4.28 (dd, J = 9.0, 5.7 Hz, 1H), 4.20-4.10 (m, 2H), 3.71 (dd, J = 9.0, 4.4 Hz, 1H), 3.24-3.14 (m, 2H), 3.13 (s, 3H), 2.74-2.54 (m, 2H), 1.52 (d, J = 5.8 Hz, 3H). |
| 493 | 395.2 | 1H NMR (400 MHz, DMSO-d6) δ 8.55 (s, 1H), 8.34 (d, J = 7.9, 1.3 Hz, 1H), 8.21 (d, J = 8.0, 1.3 Hz, 1H), 7.91 (t, J = 7.9 Hz, 1H), 4.28 (dd, J = 9.0, 5.5 Hz, 1H), 4.15 (dd, J = 6.1, 3.0 Hz, 2H), 3.71 (ddd, J = 9.0, 4.6, 1.7 Hz, 1H), 3.56 (s, 3H), 3.26-3.04 (m, 2H), 2.71-2.55 (m, 2H), 1.52 (d, J = 5.8 Hz, 3H). |
| 494 | 425.1 | 1H NMR (400 MHz, DMSO-d6) δ 8.55 (s, 1H), 8.25 (d, J = 8.7, 2.3 Hz, 1H), 7.42 (d, J = 8.8 Hz, 1H), 5.67 (d, J = 6.3 Hz, 1H), 4.39 (s, 1H), 4.26 (dd, J = 9.0, 5.7 Hz, 1H), 4.16-4.08 (m, 1H), 4.02 (s, 3H), 3.68 (dd, J = 9.0, 4.4 Hz, 1H), 3.20 (s, 3H), 2.84-2.55 (m, 1H), 1.69-1.27 (m, 3H). |
| 495 | 425.3 | 1H NMR (400 MHz, DMSO-d6) δ 8.56 (s, 1H), 8.25 (d, J = 8.7, 2.3 Hz, 1H), 7.42 (d, J = 8.8 Hz, 1H), 5.69 (d, J = 6.2 Hz, 1H), 4.39 (s, 1H), 4.26 (dd, J = 9.0, 5.7 Hz, 1H), 4.20-4.06 (m, 1H), 4.02 (s, 3H), |

TABLE 1-continued

MS and NMR DATA

| Example No | ES/MS m/z (M + H)+ | 1H NMR |
|---|---|---|
| | | 3.69 (dd, J = 8.9, 4.4 Hz, 1H), 3.20 (s, 3H), 2.73-2.55 (m, 1H), 1.51 (d, J = 5.8 Hz, 3H). |
| 496 | 425.1 | 1H NMR (400 MHz, DMSO-d6) δ 8.55 (s, 1H), 8.25 (d, J = 8.7, 2.4 Hz, 1H), 7.42 (d, J = 8.8 Hz, 1H), 5.68 (d, J = 6.2 Hz, 1H), 4.40 (s, 1H), 4.26 (dd, J = 9.0, 5.8 Hz, 1H), 4.20-4.08 (m, 1H), 4.02 (s, 3H), 3.69 (dd, J = 8.9, 4.4 Hz, 1H), 3.20 (s, 3H), 2.73-2.55 (m, 1H), 1.52 (d, J = 5.7 Hz, 3H). |
| 497 | 445.2 | 1H NMR (400 MHz, DMSO-d6) δ 8.77 (s, 1H), 7.63-7.45 (m, 2H), 7.37 (s, 1H), 4.67 (d, J = 9.7 Hz, 1H), 4.37 (d, J = 9.7 Hz, 1H), 4.28-4.21 (m, 1H), 4.19-4.06 (m, 4H), 3.90 (d, J = 11.7 Hz, 1H), 3.82 (d, J = 11.7 Hz, 1H), 3.67 (dd, J = 9.0, 4.3 Hz, 1H), 3.19-2.96 (m, 2H), 2.66-2.53 (m, 2H), 1.49 (d, J = 5.7 Hz, 3H). |
| 498 | 445.1 | 1H NMR (400 MHz, DMSO-d6) δ 8.77 (s, 1H), 7.63-7.45 (m, 2H), 7.37 (s, 1H), 4.67 (d, J = 9.7 Hz, 1H), 4.37 (d, J = 9.7 Hz, 1H), 4.28-4.21 (m, 1H), 4.19-4.06 (m, 4H), 3.90 (d, J = 11.7 Hz, 1H), 3.82 (d, J = 11.7 Hz, 1H), 3.67 (dd, J = 9.0, 4.3 Hz, 1H), 3.19-2.96 (m, 2H), 2.66-2.53 (m, 2H), 1.49 (d, J = 5.7 Hz, 3H). |
| 499 | 445.1 | 1H NMR (400 MHz, DMSO-d6) δ 8.77 (s, 1H), 7.63-7.45 (m, 2H), 7.37 (s, 1H), 4.67 (d, J = 9.7 Hz, 1H), 4.37 (d, J = 9.7 Hz, 1H), 4.28-4.21 (m, 1H), 4.19-4.06 (m, 4H), 3.90 (d, J = 11.7 Hz, 1H), 3.82 (d, J = 11.7 Hz, 1H), 3.67 (dd, J = 9.0, 4.3 Hz, 1H), 3.19-2.96 (m, 2H), 2.66-2.53 (m, 2H), 1.49 (d, J = 5.7 Hz, 3H). |
| 500 | 439.0 | f1H NMR (400 MHz, DMSO-d6) δ 7.96-7.87 (m, 2H), 7.82 (dd, J = 8.2, 1.7 Hz, 1H), 7.72 (d, J = 1.6 Hz, 1H), 4.30-4.22 (m, 1H), 4.20-4.08 (m, 4H), 3.69 (dd, J = 9.0, 4.4 Hz, 1H), 3.52-3.43 (m, 2H), 3.21-3.07 (m, 2H), 2.68-2.53 (m, 2H), 1.49 (d, J = 5.9 Hz, 3H). |
| 501 | 308.1 | 1H NMR (400 MHz, DMSO-d6) δ 7.96 (s, 1H), 7.85-7.82 (m, 1H), 7.79-7.76 (m, 1H), 7.58-7.53 (m, 2H), 4.64-4.58 (m, 1H), 4.28-4.22 (m, 1H), 4.17-4.10 (m, 2H), 3.74-3.67 (m, 1H), 3.18-3.12 (m, 2H), 2.72 (s, 3H), 2.67-2.57 (m, 2H), 1.51 (d, J = 5.9 Hz, 3H), 1.45 (d, J = 6.9 Hz, 3H). |
| 502 | 308.1 | 1H NMR (400 MHz, DMSO-d6) δ 8.09 (s, 1H), 8.04-7.95 (m, 4H), 7.49 (s, 1H), 3.17 (t, J = 7.3 Hz, 2H), 2.98 (t, J = 7.7 Hz, 2H), 2.70-2.60 (m, 2H), 2.12-1.94 (m, 5H), 1.88-1.76 (m, 1H), 1.56 (s, 3H). |
| 503 | 407.1 | 1H NMR (400 MHz, DMSO-d6) δ 9.20 (s, 3H), 7.96-7.76 (m, 2H), 7.60 (t, J = 8.0 Hz, 1H), 5.16 (d, J = 7.9 Hz, 2H), 4.92 (d, J = 7.9 Hz, 2H), 4.26 (dd, J = 9.0, 5.5 Hz, 1H), 4.17-4.09 (m, 2H), 3.69 (dd, J = 9.0, 4.3 Hz, 1H), 3.20-3.08 (m, 2H), 2.69-2.52 (m, 2H), 1.49 (d, J = 5.8 Hz, 3H). |
| 504 | 387.1 | 1H NMR (400 MHz, DMSO-d6) δ 9.03 (s, 3H), 8.03 (d, J = 8.5 Hz, 2H), 7.70 (d, J = 8.5 Hz, 2H), 5.03-4.92 (m, 4H), 4.57-4.48 (m, 2H), 3.21-3.03 (m, 2H), 2.65-2.54 (m, 2H), 2.18-2.05 (m, 2H), 1.47 (d, J = 11.1 Hz, 6H). |
| 505 | 403.1 | 1H NMR (400 MHz, DMSO-d6) δ 9.07 (s, 3H), 7.87-7.75 (m, 2H), 7.30 (d, J = 8.0 Hz, 1H), 5.23 (d, J = 7.9 Hz, 2H), 4.88 (d, J = 8.1 Hz, 2H), 4.25 (dd, J = 9.0, 5.7 Hz, 1H), 4.17-4.05 (m, 2H), 3.68 (dd, J = 9.0, 4.5 Hz, 1H), 3.19-3.02 (m, 2H), 2.71-2.52 (m, 2H), 2.27 (s, 3H), 1.49 (d, J = 5.9 Hz, 3H). |
| 506 | 390.1 | 1H NMR (400 MHz, DMSO-d6) δ 9.22-9.07 (m, 4H), 8.52 (dd, J = 8.3, 2.3 Hz, 1H), 8.10 (d, J = 8.4 Hz, 1H), 5.02-4.87 (m, 4H), 4.33-4.22 (m, 1H), 4.17-4.09 (m, 2H), 3.71 (dd, J = 9.1, 4.3 Hz, 1H), 3.28-3.07 (m, 2H), 2.70-2.55 (m, 2H), 1.50 (d, J = 5.8 Hz, 3H). |
| 507 | 339.1 | 1H NMR (400 MHz, DMSO-d6) δ 9.49 (s, 1H), 9.34-9.09 (m, 3H), 8.17 (s, 1H), 5.13-4.82 (m, 4H), 4.51-4.35 (m, 1H), 4.10-3.84 (m, 2H), 3.32-3.10 (m, 2H), 2.93-2.69 (m, 2H), 2.48-2.34 (m, 1H), 2.16-1.87 (m, 3H), 1.52 (d, J = 6.2 Hz, 3H). |
| 508 | 409.1 | 1H NMR (400 MHz, DMSO-d6) δ 8.47-8.41 (m, 1H), 8.34-8.30 (m, 1H), 8.13-8.07 (m, 1H), 7.91 (t, J = 7.8 Hz, 1H), 4.33-4.22 (m, 1H), 4.19-4.07 (m, 2H), 3.73-3.65 (m, 1H), 3.58-3.49 (m, 3H), 3.26-3.08 (m, 2H), 2.69-2.55 (m, 5H), 1.55-1.45 (m, 3H). |
| 509 | 396.1 | 1H NMR (400 MHz, DMSO-d6) δ 8.47-8.43 (m, 1H), 8.30-8.26 (m, 1H), 8.14-8.09 (m, 1H), 7.85 (t, J = 7.8 Hz, 1H), 4.27 (dd, J = 9.0, 5.5 Hz, 1H), 4.18-4.10 (m, 2H), 3.70 (dd, J = 9.0, 4.4 Hz, 1H), 3.29 (s, 3H), 3.21-3.11 (m, 2H), 2.68-2.55 (m, 2H), 1.51 (d, J = 5.8 Hz, 3H). |
| 510 | 409.1 | 1H NMR (400 MHz, DMSO-d6) δ 7.58-7.55 (m, 1H), 7.48-7.43 (m, 1H), 7.35 (t, J = 7.8 Hz, 1H), 7.12-7.05 (m, 1H), 4.24 (dd, J = 8.9, 5.5 Hz, 1H), 4.17-4.09 (m, 2H), 3.67 (dd, J = 8.9, 4.4 Hz, 1H), 3.26 (s, 6H), 3.17-3.03 (m, 2H), 2.64-2.52 (m, 2H), 1.50 (d, J = 5.8 Hz, 3H). |
| 511 | 409.1 | 1H NMR (400 MHz, DMSO-d6) δ 8.49-8.45 (m, 1H), 8.33-8.26 (m, 1H), 8.14-8.07 (m, 1H), 7.86 (t, J = 7.8 Hz, 1H), 4.27 (dd, J = 9.0, 5.6 Hz, 1H), 4.17-4.09 (m, 2H), 3.70 (dd, J = 9.1, 4.4 Hz, 1H), 3.43 (q, J = 7.2 Hz, 2H), 3.24-3.04 (m, 2H), 2.71-2.54 (m, 2H), 1.51 (d, J = 5.8 Hz, 3H), 1.14 (t, J = 7.3 Hz, 3H). |

TABLE 1-continued

| | | MS and NMR DATA |
|---|---|---|
| Example No | ES/MS m/z (M + H)+ | 1H NMR |
| 512 | 391.1 | 1H NMR (400 MHz, DMSO-d6) δ 9.56 (s, 1H), 8.99 (s, 1H), 8.05 (d, J = 8.1 Hz, 2H), 7.75 (d, J = 8.1 Hz, 2H), 4.72-4.45 (m, 4H), 4.26 (dd, J = 9.0, 5.5 Hz, 1H), 4.16-4.09 (m, 2H), 3.69 (dd, J = 9.0, 4.4 Hz, 1H), 3.21-3.04 (m, 2H), 2.70-2.53 (m, 2H), 1.50 (d, J = 5.8 Hz, 3H). |
| 513 | 415.1 | 1H NMR (400 MHz, DMSO-d6) δ 9.98 (s, 2H), 8.07 (d, J = 8.3 Hz, 1H), 7.99 (dd, J = 8.4, 1.8 Hz, 1H), 7.79 (d, J = 1.7 Hz, 1H), 4.97 (d, J = 7.9 Hz, 2H), 4.90-4.79 (m, 2H), 4.26 (dd, J = 9.0, 5.5 Hz, 1H), 4.17-4.08 (m, 2H), 3.68 (dd, J = 9.0, 4.4 Hz, 1H), 3.50-3.41 (m, 2H), 3.18-3.04 (m, 4H), 2.68-2.55 (m, 2H), 1.49 (d, J = 5.8 Hz, 3H). |
| 514 | 457.1 | 1H NMR (400 MHz, DMSO-d6) δ 9.36-9.15 (m, 3H), 8.32 (s, 1H), 8.30 (d, J = 8.2 Hz, 1H), 7.57 (d, J = 8.1 Hz, 1H), 5.26-5.17 (m, 2H), 4.92 (d, J = 7.8 Hz, 2H), 4.27 (dd, J = 9.1, 5.6 Hz, 1H), 4.20-4.08 (m, 2H), 3.69 (dd, J = 9.0, 4.4 Hz, 1H), 3.22-3.04 (m, 2H), 2.69-2.55 (m, 2H), 1.49 (d, J = 5.8 Hz, 3H). |
| 515 | 397.1 | 1H NMR (400 MHz, DMSO-d6) δ 8.60 (s, 3H), 8.09 (d, J = 8.2 Hz, 2H), 7.80 (d, J = 8.2 Hz, 2H), 4.30-4.21 (m, 1H), 4.17-4.09 (m, 2H), 3.85 (t, J = 16.2 Hz, 2H), 3.69 (dd, J = 9.0, 4.3 Hz, 1H), 3.21-3.06 (m, 2H), 2.69-2.53 (m, 2H), 1.50 (d, J = 5.8 Hz, 3H). |
| 516 | 403.1 | 1H NMR (400 MHz, DMSO-d6) δ 8.65 (s, 3H), 8.02 (d, J = 8.0 Hz, 2H), 7.66 (d, J = 8.1 Hz, 2H), 4.30-4.21 (m, 2H), 4.19-4.06 (m, 3H), 4.04-3.96 (m, 1H), 3.93-3.85 (m, 1H), 3.75-3.59 (m, 1H), 3.21-3.00 (m, 2H), 2.68-2.52 (m, 4H), 1.49 (d, J = 5.7 Hz, 3H). |
| 517 | 403.1 | 1H NMR (400 MHz, DMSO-d6) δ 8.59 (s, 3H), 8.02 (d, J = 8.2 Hz, 2H), 7.66 (d, J = 8.2 Hz, 2H), 4.29-4.21 (m, 2H), 4.19-4.08 (m, 3H), 4.06-3.95 (m, 1H), 3.93-3.85 (m, 1H), 3.68 (dd, J = 9.0, 4.4 Hz, 1H), 3.43-3.39 (m, 2H), 3.20-3.02 (m, 2H), 2.73-2.53 (m, 2H), 1.49 (d, J = 5.8 Hz, 3H). |
| 518 | 403.1 | 1H NMR (400 MHz, DMSO-d6) δ 8.59 (s, 3H), 8.02 (d, J = 8.2 Hz, 2H), 7.66 (d, J = 8.2 Hz, 2H), 4.29-4.21 (m, 2H), 4.19-4.08 (m, 3H), 4.06-3.95 (m, 1H), 3.93-3.85 (m, 1H), 3.68 (dd, J = 9.0, 4.4 Hz, 1H), 3.43-3.39 (m, 2H), 3.20-3.02 (m, 2H), 2.73-2.53 (m, 2H), 1.49 (d, J = 5.8 Hz, 3H). |
| 519 | 435.1 | 1H NMR (400 MHz, DMSO-d6) δ 10.01 (s, 2H), 8.09 (d, J = 8.3 Hz, 1H), 8.02 (dd, J = 8.3, 1.8 Hz, 1H), 7.82 (d, J = 1.8 Hz, 1H), 4.97 (d, J = 7.9 Hz, 2H), 4.88-4.72 (m, 3H), 4.49 (t, J = 12.3 Hz, 2H), 3.47 (t, J = 6.1 Hz, 2H), 3.24-3.00 (m, 4H), 2.72-2.55 (m, 2H), 1.52 (d, J = 6.5 Hz, 3H). |
| 520 | 413.1 | 1H NMR (400 MHz, DMSO-d6) δ 8.65 (d, J = 7.2 Hz, 1H), 8.51 (d, J = 8.2 Hz, 1H), 7.86 (dd, J = 8.3, 1.9 Hz, 1H), 7.81 (s, 1H), 4.30-4.20 (m, 1H), 4.17-4.08 (m, 2H), 3.87-3.77 (m, 1H), 3.71-3.58 (m, 2H), 3.22-3.08 (m, 2H), 2.96-2.82 (m, 2H), 2.64-2.52 (m, 2H), 1.67-1.56 (m, 2H), 1.50 (d, J = 5.7 Hz, 3H). |
| 521 | 431.1 | 1H NMR (400 MHz, DMSO-d6) δ 10.21-9.75 (m, 2H), 7.91-7.80 (m, 2H), 7.66 (d, J = 1.6 Hz, 1H), 5.13 (d, J = 8.2 Hz, 2H), 4.99 (d, J = 8.1 Hz, 2H), 4.26 (dd, J = 9.0, 5.5 Hz, 1H), 4.21-4.06 (m, 4H), 3.73-3.60 (m, 3H), 3.14 (d, J = 6.8 Hz, 2H), 2.70-2.52 (m, 2H), 1.50 (d, J = 5.8 Hz, 3H). |
| 522 | 379.1 | 1H NMR (400 MHz, DMSO-d6) δ 8.57 (d, J = 2.1 Hz, 1H), 8.09 (dd, J = 8.3, 2.2 Hz, 1H), 7.78 (d, J = 8.3 Hz, 1H), 7.73 (s, 2H), 4.48-4.38 (m, 1H), 4.03-3.86 (m, 2H), 3.09-2.95 (m, 2H), 2.83 (t, J = 7.8 Hz, 2H), 2.45-2.34 (m, 1H), 2.10-1.90 (m, 3H), 1.50 (d, J = 6.2 Hz, 3H). |
| 523 | 455.1 | 1H NMR (400 MHz, DMSO-d6) δ 7.91 (d, J = 7.9 Hz, 1H), 7.55-7.48 (m, 2H), 7.38 (s, 1H), 5.34-5.05 (m, 2H), 4.78 (t, J = 9.1 Hz, 2H), 4.57-4.32 (m, 3H), 4.07-3.94 (m, 1H), 3.22-2.99 (m, 5H), 2.68-2.51 (m, 2H), 1.54 (d, J = 6.5 Hz, 3H). |
| 524 | 455.1 | 1H NMR (400 MHz, DMSO-d6) δ 7.91 (d, J = 7.9 Hz, 1H), 7.60-7.48 (m, 2H), 7.37 (s, 1H), 5.56-5.31 (m, 1H), 5.30-5.23 (m, 1H), 4.82-4.64 (m, 2H), 4.42-4.28 (m, 2H), 4.10 (dd, J = 22.7, 11.0 Hz, 1H), 3.19-2.98 (m, 5H), 2.65-2.52 (m, 2H), 1.47 (d, J = 6.6 Hz, 3H). |
| 525 | 469.1 | 1H NMR (400 MHz, DMSO-d6) δ 7.69 (d, J = 8.5 Hz, 1H), 7.63 (s, 1H), 7.54 (d, J = 10.5 Hz, 1H), 5.15-5.02 (m, 1H), 4.25 (dd, J = 9.1, 5.6 Hz, 1H), 4.16-4.07 (m, 2H), 3.68 (dd, J = 9.0, 4.2 Hz, 1H), 3.21-3.05 (m, 3H), 3.00 (s, 3H), 2.94-2.82 (m, 1H), 2.58 (ddd, J = 21.2, 14.6, 6.9 Hz, 3H), 2.10-1.96 (m, 1H), 1.49 (d, J = 5.7 Hz, 3H). |
| 526 | 469.1 | 1H NMR (400 MHz, DMSO-d6) δ 7.69 (d, J = 8.5 Hz, 1H), 7.63 (s, 1H), 7.54 (d, J = 10.5 Hz, 1H), 5.15-5.02 (m, 1H), 4.25 (dd, J = 9.1, 5.6 Hz, 1H), 4.16-4.07 (m, 2H), 3.68 (dd, J = 9.0, 4.2 Hz, 1H), 3.21-3.05 (m, 3H), 3.00 (s, 3H), 2.94-2.82 (m, 1H), 2.58 (2.65-2.45, 3H), 2.10-1.96 (m, 1H), 1.49 (d, J = 5.7 Hz, 3H). |
| 527 | 469.1 | 1H NMR (400 MHz, DMSO-d6) δ 7.69 (d, J = 8.5 Hz, 1H), 7.63 (s, 1H), 7.54 (d, J = 10.5 Hz, 1H), 5.15-5.02 (m, 1H), 4.25 (dd, J = 9.1, 5.6 Hz, 1H), 4.16-4.07 (m, 2H), 3.68 (dd, J = 9.0, 4.2 Hz, 1H), 3.21-3.05 (m, 3H), 3.00 (s, 3H), 2.94-2.82 (m, 1H), 2.58 (2.65-2.45, 3H), 2.10-1.96 (m, 1H), 1.49 (d, J = 5.7 Hz, 3H). |

TABLE 1-continued

| | | MS and NMR DATA |
|---|---|---|
| Example No | ES/MS m/z (M + H)+ | 1H NMR |
| 528 | 437.1 | 1H NMR (400 MHz, DMSO-d6) δ 7.91 (d, J = 7.9 Hz, 1H), 7.58-7.46 (m, 2H), 7.36 (s, 1H), 5.33-5.18 (m, 1H), 4.77 (t, J = 9.1 Hz, 1H), 4.54-4.43 (m, 1H), 4.41-4.30 (m, 1H), 4.09-3.88 (m, 2H), 3.18-2.97 (m, 5H), 2.65-2.51 (m, 2H), 2.48-2.40 (m, 1H), 2.04-1.88 (m, 1H), 1.50 (d, J = 6.2 Hz, 3H). |
| 529 | 481.1 | 1H NMR (400 MHz, DMSO-d6) δ 7.66-6.87 (m, 3H), 4.90 (td, J = 7.4, 2.4 Hz, 1H), 4.25 (dd, J = 9.0, 5.5 Hz, 1H), 4.15-4.07 (m, 2H), 3.87 (s, 3H), 3.68 (dd, J = 9.0, 4.3 Hz, 1H), 3.23-3.04 (m, 3H), 2.98 (s, 3H), 2.88-2.74 (m, 1H), 2.66-2.53 (m, 2H), 2.41-2.28 (m, 1H), 2.10-1.98 (m, 1H), 1.50 (d, J = 5.7 Hz, 3H). |
| 530 | 481.1 | 1H NMR (400 MHz, DMSO-d6) δ 7.43-7.27 (m, 3H), 4.90 (td, J = 7.5, 2.3 Hz, 1H), 4.25 (dd, J = 9.1, 5.5 Hz, 1H), 4.16-4.04 (m, 2H), 3.87 (s, 3H), 3.68 (dd, J = 9.0, 4.3 Hz, 1H), 3.22-3.05 (m, 3H), 2.98 (s, 3H), 2.87-2.75 (m, 1H), 2.67-2.52 (m, 2H), 2.40-2.27 (m, 1H), 2.11-1.96 (m, 1H), 1.50 (d, J = 5.7 Hz, 3H). |
| 531 | 481.1 | 1H NMR (400 MHz, DMSO-d6) δ 7.43-7.27 (m, 3H), 4.90 (td, J = 7.5, 2.3 Hz, 1H), 4.25 (dd, J = 9.1, 5.5 Hz, 1H), 4.16-4.04 (m, 2H), 3.87 (s, 3H), 3.68 (dd, J = 9.0, 4.3 Hz, 1H), 3.22-3.05 (m, 3H), 2.98 (s, 3H), 2.87-2.75 (m, 1H), 2.67-2.52 (m, 2H), 2.40-2.27 (m, 1H), 2.11-1.96 (m, 1H), 1.50 (d, J = 5.7 Hz, 3H). |
| 532 | 461.1 | 1H NMR (400 MHz, DMSO-d6) δ 8.60 (d, J = 2.5 Hz, 1H), 8.37-8.23 (m, 1H), 7.63-7.20 (m, 2H), 5.69 (d, J = 6.0 Hz, 1H), 4.72 (s, 1H), 4.31-4.21 (m, 1H), 4.18-4.07 (m, 2H), 3.76-3.61 (m, 1H), 3.27-2.98 (m, 5H), 2.67-2.53 (m, 2H), 1.59-1.38 (m, 3H). |
| 533 | 461.1 | 1H NMR (400 MHz, DMSO-d6) δ 8.60 (d, J = 2.5 Hz, 1H), 8.37-8.23 (m, 1H), 7.63-7.20 (m, 2H), 5.69 (d, J = 6.0 Hz, 1H), 4.72 (s, 1H), 4.31-4.21 (m, 1H), 4.18-4.07 (m, 2H), 3.76-3.61 (m, 1H), 3.27-2.98 (m, 5H), 2.67-2.53 (m, 2H), 1.59-1.38 (m, 3H). |
| 534 | 461.1 | 1H NMR (400 MHz, DMSO-d6) δ 8.60 (d, J = 2.5 Hz, 1H), 8.37-8.23 (m, 1H), 7.63-7.20 (m, 2H), 5.69 (d, J = 6.0 Hz, 1H), 4.72 (s, 1H), 4.31-4.21 (m, 1H), 4.18-4.07 (m, 2H), 3.76-3.61 (m, 1H), 3.27-2.98 (m, 5H), 2.67-2.53 (m, 2H), 1.59-1.38 (m, 3H). |
| 535 | 443.1 | 1H NMR (400 MHz, DMSO-d6) δ 8.32 (s, 1H), 8.13 (d, J = 12.5 Hz, 1H), 4.32-3.99 (m, 6H), 3.71-3.63 (m, 1H), 3.34-3.03 (m, 5H), 2.72-2.53 (m, 2H), 1.50 (d, J = 5.7 Hz, 3H). |
| 536 | 443.2 | 1H NMR (400 MHz, DMSO-d6) δ 8.32 (s, 1H), 8.13 (d, J = 12.5 Hz, 1H), 4.32-3.99 (m, 6H), 3.71-3.63 (m, 1H), 3.34-3.03 (m, 5H), 2.72-2.53 (m, 2H), 1.50 (d, J = 5.7 Hz, 3H). |
| 537 | 443.2 | 1H NMR (400 MHz, DMSO-d6) δ 8.32 (s, 1H), 8.13 (d, J = 12.5 Hz, 1H), 4.32-3.99 (m, 6H), 3.71-3.63 (m, 1H), 3.34-3.03 (m, 5H), 2.72-2.53 (m, 2H), 1.50 (d, J = 5.7 Hz, 3H). |
| 538 | 451.2 | 1H NMR (400 MHz, DMSO-d6) δ 8.49 (s, 1H), 8.34 (d, J = 8.8 Hz, 1H), 7.53 (d, J = 8.9 Hz, 1H), 4.29-4.21 (m, 1H), 4.17-4.01 (m, 5H), 3.69-3.65 (m, 1H), 3.34-3.02 (m, 3H), 2.69-2.53 (m, 2H), 1.50 (dd, J = 6.1, 2.9 Hz, 3H), 1.29-1.02 (m, 4H). |
| 539 | 451.1 | 1H NMR (400 MHz, DMSO-d6) δ 8.49 (s, 1H), 8.34 (d, J = 8.8 Hz, 1H), 7.53 (d, J = 8.9 Hz, 1H), 4.29-4.21 (m, 1H), 4.17-4.01 (m, 5H), 3.69-3.65 (m, 1H), 3.34-3.02 (m, 3H), 2.69-2.53 (m, 2H), 1.50 (dd, J = 6.1, 2.9 Hz, 3H), 1.29-1.02 (m, 4H). |
| 540 | 451.1 | 1H NMR (400 MHz, DMSO-d6) δ 8.49 (s, 1H), 8.34 (d, J = 8.8 Hz, 1H), 7.53 (d, J = 8.9 Hz, 1H), 4.29-4.21 (m, 1H), 4.17-4.01 (m, 5H), 3.69-3.65 (m, 1H), 3.34-3.02 (m, 3H), 2.69-2.53 (m, 2H), 1.50 (dd, J = 6.1, 2.9 Hz, 3H), 1.29-1.02 (m, 4H). |
| 541 | 451.2 | 1H NMR (400 MHz, DMSO-d6) δ 8.54 (s, 1H), 8.43-8.34 (m, 1H), 7.78 (d, J = 8.8 Hz, 1H), 4.29-4.21 (m, 2H), 4.18-4.07 (m, 2H), 3.68-3.64 (m, 1H), 3.53 (s, 3H), 3.25-3.04 (m, 2H), 2.72-2.54 (m, 2H), 1.56-1.43 (m, 3H), 0.99-0.74 (m, 4H). |
| 542 | 451.1 | 1H NMR (400 MHz, DMSO-d6) δ 8.54 (s, 1H), 8.43-8.34 (m, 1H), 7.78 (d, J = 8.8 Hz, 1H), 4.29-4.21 (m, 2H), 4.18-4.07 (m, 2H), 3.68-3.64 (m, 1H), 3.53 (s, 3H), 3.25-3.04 (m, 2H), 2.72-2.54 (m, 2H), 1.56-1.43 (m, 3H), 0.99-0.74 (m, 4H). |
| 543 | 451.1 | 1H NMR (400 MHz, DMSO-d6) δ 8.54 (s, 1H), 8.43-8.34 (m, 1H), 7.78 (d, J = 8.8 Hz, 1H), 4.29-4.21 (m, 2H), 4.18-4.07 (m, 2H), 3.68-3.64 (m, 1H), 3.53 (s, 3H), 3.25-3.04 (m, 2H), 2.72-2.54 (m, 2H), 1.56-1.43 (m, 3H), 0.99-0.74 (m, 4H). |
| 544 | 473.2 | 1H NMR (400 MHz, DMSO-d6) δ 7.91 (d, J = 7.9 Hz, 1H), 7.56-7.51 (m, 2H), 7.41 (s, 1H), 6.58-6.25 (m, 1H), 5.31-5.20 (m, 1H), 4.83-4.64 (m, 2H), 4.38 (dd, J = 9.8, 5.2 Hz, 1H), 4.16-3.97 (m, 2H), 3.22-3.01 (m, 5H), 2.66-2.53 (m, 2H), 2.47-2.39 (m, 2H). |
| 545 | 473.2 | 1H NMR (400 MHz, DMSO-d6) δ 7.91 (d, J = 7.9 Hz, 1H), 7.56-7.51 (m, 2H), 7.41 (s, 1H), 6.58-6.25 (m, 1H), 5.31-5.20 (m, 1H), 4.83-4.64 (m, 2H), 4.38 (dd, J = 9.8, 5.2 Hz, 1H), 4.16-3.97 (m, 2H), 3.22-3.01 (m, 5H), 2.66-2.53 (m, 2H), 2.47-2.39 (m, 2H). |
| 546 | 473.2 | 1H NMR (400 MHz, DMSO-d6) δ 7.91 (d, J = 7.9 Hz, 1H), 7.56-7.51 (m, 2H), 7.41 (s, 1H), 6.58-6.25 (m, 1H), 5.31-5.20 (m, 1H), 4.83- |

TABLE 1-continued

MS and NMR DATA

| Example No | ES/MS m/z (M + H)+ | 1H NMR |
|---|---|---|
| | | 4.64 (m, 2H), 4.38 (dd, J = 9.8, 5.2 Hz, 1H), 4.16-3.97 (m, 2H), 3.22-3.01 (m, 5H), 2.66-2.53 (m, 2H), 2.47-2.39 (m, 2H). |
| 547 | 479.1 | 1H NMR (400 MHz, DMSO-d6) δ 7.80-7.67 (m, 3H), 7.57 (d, J = 8.0 Hz, 1H), 4.66 (t, J = 8.3 Hz, 1H), 4.25 (dd, J = 9.0, 5.6 Hz, 1H), 4.18-4.02 (m, 2H), 3.68 (dd, J = 9.0, 4.3 Hz, 1H), 3.21-3.05 (m, 2H), 3.02-2.81 (m, 5H), 2.63-2.53 (m, 2H), 2.00-1.35 (m, 5H), 1.56-1.33 (m, 4H). |
| 548 | 443.2 | 1H NMR (400 MHz, DMSO-d6) δ 8.52 (s, 1H), 7.85-7.75 (m, 2H), 7.45 (d, J = 7.8 Hz, 1H), 4.28-4.19 (m, 1H), 4.17-4.07 (m, 4H), 3.75 (d, J = 11.6 Hz, 1H), 3.68 (dd, J = 9.0, 4.4 Hz, 1H), 3.61 (d, J = 11.6 Hz, 1H), 3.21-2.87 (m, 4H), 2.65-2.52 (m, 2H), 2.45-2.32 (m, 1H), 2.19-2.03 (m, 1H), 1.49 (d, J = 5.7 Hz, 3H). |
| 549 | 443.1 | 1H NMR (400 MHz, DMSO-d6) δ 8.52 (s, 1H), 7.85-7.75 (m, 2H), 7.45 (d, J = 7.8 Hz, 1H), 4.28-4.19 (m, 1H), 4.17-4.07 (m, 4H), 3.75 (d, J = 11.6 Hz, 1H), 3.68 (dd, J = 9.0, 4.4 Hz, 1H), 3.61 (d, J = 11.6 Hz, 1H), 3.21-2.87 (m, 4H), 2.65-2.52 (m, 2H), 2.45-2.32 (m, 1H), 2.19-2.03 (m, 1H), 1.49 (d, J = 5.7 Hz, 3H). |
| 550 | 443.1 | 1H NMR (400 MHz, DMSO-d6) δ 8.52 (s, 1H), 7.85-7.75 (m, 2H), 7.45 (d, J = 7.8 Hz, 1H), 4.28-4.19 (m, 1H), 4.17-4.07 (m, 4H), 3.75 (d, J = 11.6 Hz, 1H), 3.68 (dd, J = 9.0, 4.4 Hz, 1H), 3.61 (d, J = 11.6 Hz, 1H), 3.21-2.87 (m, 4H), 2.65-2.52 (m, 2H), 2.45-2.32 (m, 1H), 2.19-2.03 (m, 1H), 1.49 (d, J = 5.7 Hz, 3H). |
| 551 | 458.2 | 1H NMR (400 MHz, DMSO-d6) δ 11.06 (s, 1H), 8.64 (s, 1H), 7.50 (dd, J = 8.2, 1.8 Hz, 1H), 7.39 (d, J = 1.8 Hz, 1H), 7.25 (d, J = 8.1 Hz, 1H), 4.61-4.52 (m, 1H), 4.32-4.19 (m, 2H), 4.15-4.06 (m, 2H), 3.67 (dd, J = 9.0, 4.3 Hz, 1H), 3.18-3.00 (m, 2H), 2.69-2.54 (m, 2H), 2.39-2.27 (m, 1H), 2.21-2.08 (m, 1H), 1.48 (d, J = 5.8 Hz, 3H). |
| 552 | 457.3 | 1H NMR (400 MHz, DMSO-d6) δ 8.10 (s, 1H), 7.75 (d, 1H), 7.72 (d, J = 8.0 Hz, 1H), 7.40 (d, J = 7.9 Hz, 1H), 6.38 (dd, J = 17.0, 10.1 Hz, 1H), 6.00 (dd, J = 17.0, 2.3 Hz, 1H), 5.53 (dd, J = 10.2, 2.3 Hz, 1H), 4.24 (dd, J = 8.9, 5.6 Hz, 1H), 4.15-4.07 (m, 2H), 3.73-3.57 (m, 4H), 3.17-2.84 (m, 4H), 2.64-2.53 (m, 2H), 2.47-2.38 (m, 1H), 2.36-2.27 (m, 1H), 1.49 (d, J = 5.7 Hz, 3H). |
| 553 | 445.2 | 1H NMR (400 MHz, DMSO-d6) δ 8.31 (s, 1H), 7.60-7.50 (m, 2H), 7.34 (d, J = 1.6 Hz, 1H), 4.45 (d, J = 9.0 Hz, 1H), 4.36-4.30 (m, 2H), 4.27-4.17 (m, 2H), 4.14-4.05 (m, 2H), 3.66 (dd, J = 9.0, 4.4 Hz, 1H), 3.14-2.99 (m, 2H), 2.63-2.52 (m, 2H), 2.25-2.07 (m, 2H), 1.48 (d, J = 5.8 Hz, 3H). |
| 554 | 445.2 | 1H NMR (400 MHz, DMSO-d6) δ 8.31 (s, 1H), 7.94-7.87 (m, 1H), 7.71 (d, J = 8.2 Hz, 1H), 7.67-7.62 (m, 1H), 4.99-4.74 (m, 2H), 4.48 (d, J = 8.9 Hz, 1H), 4.27-4.17 (m, 2H), 4.15-4.06 (m, 2H), 4.01 (d, J = 11.3 Hz, 1H), 3.73-3.61 (m, 2H), 3.18-3.02 (m, 2H), 2.67-2.53 (m, 2H), 1.49 (d, J = 5.8 Hz, 3H). |
| 555 | 445.1 | 1H NMR (400 MHz, DMSO-d6) δ 8.31 (s, 1H), 7.94-7.87 (m, 1H), 7.71 (d, J = 8.2 Hz, 1H), 7.67-7.62 (m, 1H), 4.99-4.74 (m, 2H), 4.48 (d, J = 8.9 Hz, 1H), 4.27-4.17 (m, 2H), 4.15-4.06 (m, 2H), 4.01 (d, J = 11.3 Hz, 1H), 3.73-3.61 (m, 2H), 3.18-3.02 (m, 2H), 2.67-2.53 (m, 2H), 1.49 (d, J = 5.8 Hz, 3H). |
| 556 | 445.1 | 1H NMR (400 MHz, DMSO-d6) δ 8.31 (s, 1H), 7.94-7.87 (m, 1H), 7.71 (d, J = 8.2 Hz, 1H), 7.67-7.62 (m, 1H), 4.99-4.74 (m, 2H), 4.48 (d, J = 8.9 Hz, 1H), 4.27-4.17 (m, 2H), 4.15-4.06 (m, 2H), 4.01 (d, J = 11.3 Hz, 1H), 3.73-3.61 (m, 2H), 3.18-3.02 (m, 2H), 2.67-2.53 (m, 2H), 1.49 (d, J = 5.8 Hz, 3H). |
| 557 | 415.2 | 1H NMR (400 MHz, DMSO-d6) δ 8.37 (s, 1H), 7.91-7.83 (m, 2H), 7.50 (d, J = 8.0 Hz, 1H), 5.40-5.31 (m, 1H), 5.18 (d, J = 7.0 Hz, 1H), 4.25 (dd, J = 9.0, 5.6 Hz, 1H), 4.18-4.07 (m, 2H), 3.68 (dd, J = 8.9, 4.4 Hz, 1H), 3.44 (dd, J = 18.1, 6.3 Hz, 1H), 3.23 (d, J = 18.0 Hz, 1H), 3.17-3.04 (m, 2H), 2.63-2.51 (m, 2H), 1.49 (d, J = 6.0 Hz, 3H). |
| 558 | 459.3 | 1H NMR (400 MHz, DMSO-d6) δ 8.65 (s, 1H), 7.57-7.45 (m, 2H), 7.40-7.33 (m, 1H), 4.52 (d, J = 10.0 Hz, 1H), 4.39 (d, J = 10.0 Hz, 1H), 4.28-4.18 (m, 2H), 4.15-4.05 (m, 2H), 3.98-3.85 (m, 2H), 3.67 (dd, J = 9.0, 4.3 Hz, 1H), 3.14-3.03 (m, 2H), 2.63-2.52 (m, 2H), 1.49 (d, J = 5.7 Hz, 3H), 1.45 (d, J = 6.9 Hz, 3H). |
| 559 | 459.1 | 1H NMR (400 MHz, DMSO-d6) δ 8.65 (s, 1H), 7.57-7.45 (m, 2H), 7.40-7.33 (m, 1H), 4.52 (d, J = 10.0 Hz, 1H), 4.39 (d, J = 10.0 Hz, 1H), 4.28-4.18 (m, 2H), 4.15-4.05 (m, 2H), 3.98-3.85 (m, 2H), 3.67 (dd, J = 9.0, 4.3 Hz, 1H), 3.14-3.03 (m, 2H), 2.63-2.52 (m, 2H), 1.49 (d, J = 5.7 Hz, 3H), 1.45 (d, J = 6.9 Hz, 3H). |
| 560 | 459.1 | 1H NMR (400 MHz, DMSO-d6) δ 8.65 (s, 1H), 7.57-7.45 (m, 2H), 7.40-7.33 (m, 1H), 4.52 (d, J = 10.0 Hz, 1H), 4.39 (d, J = 10.0 Hz, 1H), 4.28-4.18 (m, 2H), 4.15-4.05 (m, 2H), 3.98-3.85 (m, 2H), 3.67 (dd, J = 9.0, 4.3 Hz, 1H), 3.14-3.03 (m, 2H), 2.63-2.52 (m, 2H), 1.49 (d, J = 5.7 Hz, 3H), 1.45 (d, J = 6.9 Hz, 3H). |
| 561 | 427.2 | 1H NMR (400 MHz, DMSO-d6) δ 8.56 (d, J = 2.3 Hz, 1H), 8.38 (dd, J = 8.8, 2.4 Hz, 1H), 7.53 (d, J = 8.8 Hz, 1H), 5.28-5.05 (m, 1H), 4.57- |

TABLE 1-continued

MS and NMR DATA

| Example No | ES/MS m/z (M + H)+ | 1H NMR |
|---|---|---|
| | | 4.33 (m, 2H), 4.10-3.92 (m, 4H), 3.59 (s, 3H), 3.26-3.07 (m, 2H), 2.74-2.53 (m, 2H), 1.56 (d, J = 6.5 Hz, 3H). |
| 562 | 427.2 | 1H NMR (400 MHz, DMSO-d6) δ 8.56 (d, J = 2.3 Hz, 1H), 8.38 (dd, J = 8.8, 2.3 Hz, 1H), 7.54 (d, J = 8.9 Hz, 1H), 5.44 (dtd, J = 58.0, 6.0, 2.6 Hz, 1H), 4.80-4.62 (m, 1H), 4.46-4.28 (m, 1H), 4.17-4.02 (m, 4H), 3.62 (s, 3H), 3.24-3.10 (m, 2H), 2.71-2.56 (m, 2H), 1.49 (dd, J = 6.7, 1.9 Hz, 3H). |
| 563 | 445.2 | 1H NMR (400 MHz, DMSO-d6) δ 8.56 (d, J = 2.3 Hz, 1H), 8.41 (dd, J = 8.8, 2.3 Hz, 1H), 7.55 (d, J = 8.9 Hz, 1H), 4.92-4.76 (m, 1H), 4.49 (t, J = 11.7 Hz, 2H), 4.08 (s, 3H), 3.62 (s, 3H), 3.29-3.13 (m, 2H), 2.75-2.55 (m, 2H), 1.54 (d, J = 6.5 Hz, 3H). |
| 564 | 479.2 | 1H NMR (400 MHz, DMSO-d6) δ 8.64 (d, J = 2.5 Hz, 1H), 8.35 (ddd, J = 8.7, 2.4, 0.9 Hz, 1H), 7.76 (dd, J = 8.7, 1.8 Hz, 1H), 4.27 (dd, J = 9.0, 5.6 Hz, 1H), 4.17-4.09 (m, 2H), 3.72-3.65 (m, 1H), 3.26 (s, 5H), 2.72-2.54 (m, 2H), 1.56-1.44 (m, 3H). |
| 565 | 459.3 | 1H NMR (400 MHz, DMSO-d6) δ 8.40 (s, 1H), 7.55 (dd, J = 7.9, 1.5 Hz, 1H), 7.49 (d, J = 7.9 Hz, 1H), 7.42-7.39 (m, 1H), 4.83 (d, J = 10.7 Hz, 1H), 4.38 (d, J = 10.7 Hz, 1H), 4.24 (dd, J = 9.0, 5.5 Hz, 1H), 4.15-4.06 (m, 2H), 3.67 (dd, J = 9.0, 4.4 Hz, 1H), 3.18-3.00 (m, 2H), 2.64-2.52 (m, 2H), 1.49 (d, J = 5.9 Hz, 3H), 1.46 (s, 3H), 1.30 (s, 3H). |
| 566 | 459.3 | 1H NMR (400 MHz, DMSO-d6) δ 8.40 (s, 1H), 7.55 (dd, J = 7.9, 1.5 Hz, 1H), 7.49 (d, J = 7.9 Hz, 1H), 7.42-7.39 (m, 1H), 4.83 (d, J = 10.7 Hz, 1H), 4.38 (d, J = 10.7 Hz, 1H), 4.24 (dd, J = 9.0, 5.5 Hz, 1H), 4.15-4.06 (m, 2H), 3.67 (dd, J = 9.0, 4.4 Hz, 1H), 3.18-3.00 (m, 2H), 2.64-2.52 (m, 2H), 1.49 (d, J = 5.9 Hz, 3H), 1.46 (s, 3H), 1.30 (s, 3H). |
| 567 | 459.3 | 1H NMR (400 MHz, DMSO-d6) δ 8.40 (s, 1H), 7.55 (dd, J = 7.9, 1.5 Hz, 1H), 7.49 (d, J = 7.9 Hz, 1H), 7.42-7.39 (m, 1H), 4.83 (d, J = 10.7 Hz, 1H), 4.38 (d, J = 10.7 Hz, 1H), 4.24 (dd, J = 9.0, 5.5 Hz, 1H), 4.15-4.06 (m, 2H), 3.67 (dd, J = 9.0, 4.4 Hz, 1H), 3.18-3.00 (m, 2H), 2.64-2.52 (m, 2H), 1.49 (d, J = 5.9 Hz, 3H), 1.46 (s, 3H), 1.30 (s, 3H). |
| 568 | 387.3 | 1H NMR (400 MHz, DMSO-d6) δ 9.15 (s, 3H), 8.04 (d, J = 8.3 Hz, 2H), 7.71 (d, J = 8.1 Hz, 2H), 5.08-4.88 (m, 4H), 4.42-4.33 (m, 1H), 4.05-3.92 (m, 2H), 3.22-3.00 (m, 2H), 2.67-2.51 (m, 2H), 2.44-2.31 (m, 1H), 2.13-1.98 (m, 2H), 1.86-1.66 (m, 1H), 0.93 (t, J = 7.4 Hz, 3H). |
| 569 | 403.3 | 1H NMR (400 MHz, DMSO-d6) δ 9.13 (s, 3H), 8.05 (d, J = 8.5 Hz, 2H), 7.71 (d, J = 8.5 Hz, 2H), 5.00-4.89 (m, 4H), 4.60-4.48 (m, 1H), 4.00 (t, J = 7.5 Hz, 2H), 3.83 (dd, J = 10.1, 5.2 Hz, 1H), 3.70 (dd, J = 10.1, 3.0 Hz, 1H), 3.32 (s, 3H), 3.18-3.04 (m, 2H), 2.69-2.52 (m, 2H), 2.44-2.24 (m, 2H). |
| 570 | 387.3 | 1H NMR (400 MHz, DMSO-d6) δ 9.12 (s, 3H), 8.18-7.92 (m, 2H), 7.71 (d, J = 8.3 Hz, 2H), 5.06-4.80 (m, 4H), 4.43-4.17 (m, 1H), 3.72-3.40 (m, 2H), 3.25-3.02 (m, 2H), 2.66-2.52 (m, 2H), 2.19-1.98 (m, 2H), 1.98-1.85 (m, 1H), 1.77-1.62 (m, 1H), 1.26 (d, J = 6.3 Hz, 3H). |
| 571 | 385.3 | 1H NMR (400 MHz, DMSO-d6) δ 9.11 (s, 3H), 8.09 (d, J = 8.3 Hz, 2H), 7.75-7.57 (m, 2H), 5.08-4.86 (m, 4H), 4.02-3.76 (m, 2H), 3.21-3.04 (m, 3H), 2.66-2.53 (m, 2H), 2.30-2.14 (m, 1H), 2.08-1.99 (m, 1H), 1.77-1.62 (m, 1H), 0.85-0.77 (m, 1H), 0.64-0.54 (m, 1H). |
| 572 | 413.3 | 1H NMR (400 MHz, DMSO-d6) δ 9.06 (s, 3H), 8.05 (d, J = 8.2 Hz, 2H), 7.70 (d, J = 8.2 Hz, 2H), 5.04-4.88 (m, 4H), 4.53-4.38 (m, 1H), 4.05-3.92 (m, 2H), 3.17-3.05 (m, 2H), 2.95-2.78 (m, 1H), 2.66-2.53 (m, 2H), 2.43-2.31 (m, 1H), 2.14-1.68 (m, 7H). |
| 573 | 449.3 | 1H NMR (400 MHz, DMSO-d6) δ 9.06 (s, 3H), 8.04 (d, J = 8.5 Hz, 2H), 7.71 (d, J = 8.5 Hz, 2H), 5.04-4.93 (m, 4H), 4.67-4.45 (m, 1H), 4.08-3.97 (m, 2H), 3.17-3.09 (m, 2H), 2.87-2.53 (m, 7H), 2.48-2.34 (m, 1H), 2.11-1.96 (m, 1H). |
| 574 | 457.2 | 1H NMR (400 MHz, DMSO-d6) δ 7.59-7.52 (m, 2H), 4.84-4.73 (m, 1H), 4.20 (dd, J = 8.9, 6.0 Hz, 1H), 4.14-4.01 (m, 2H), 3.64 (dd, J = 8.9, 4.7 Hz, 1H), 3.17-2.96 (m, 6H), 2.92-2.73 (m, 2H), 2.71-2.57 (m, 2H), 2.37-2.16 (m, 1H), 1.49 (d, J = 6.0 Hz, 3H). |
| 575 | 467.2 | 1H NMR (400 MHz, DMSO-d6) δ 7.91 (d, J = 7.9 Hz, 1H), 7.57-7.48 (m, 2H), 7.38-7.34 (m, 1H), 5.27 (td, J = 8.2, 5.1 Hz, 1H), 4.78 (dd, J = 9.8, 8.5 Hz, 1H), 4.38 (dd, J = 9.8, 5.2 Hz, 1H), 4.20 (q, J = 6.5 Hz, 1H), 3.92-3.76 (m, 2H), 3.16-3.03 (m, 5H), 2.66-2.53 (m, 2H), 1.40 (d, J = 6.6 Hz, 3H), 1.33 (s, 3H). |
| 576 | 443.3 | 1H NMR (400 MHz, DMSO-d6) δ 8.26 (s, 1H), 7.85 (d, J = 8.1 Hz, 1H), 7.80 (s, 1H), 7.53 (d, J = 7.9 Hz, 1H), 4.47 (d, J = 8.7 Hz, 1H), 4.26 (d, J = 8.7 Hz, 1H), 4.20 (q, J = 6.5 Hz, 1H), 3.95-3.75 (m, 2H), 3.16-3.06 (m, 2H), 3.03-2.85 (m, 2H), 2.67-2.51 (m, 2H), 2.48-2.34 (m, 1H), 2.26-2.09 (m, 1H), 1.41 (d, J = 6.5 Hz, 3H), 1.33 (s, 3H). |
| 577 | 491.2 | 1H NMR (400 MHz, DMSO-d6) δ 7.92 (d, J = 7.9 Hz, 1H), 7.57-7.49 (m, 2H), 7.47-7.37 (m, 1H), 5.31-5.22 (m, 1H), 5.13-5.01 (m, 1H), |

TABLE 1-continued

MS and NMR DATA

| Example No | ES/MS m/z (M + H)+ | 1H NMR |
|---|---|---|
| | | 4.78 (dd, J = 9.8, 8.5 Hz, 1H), 4.38 (dd, J = 9.8, 5.2 Hz, 1H), 4.20-4.04 (m, 2H), 3.25-3.10 (m, 2H), 3.07 (s, 3H), 2.72-2.51 (m, 3H), 2.48-2.36 (m, 1H). |
| 578 | 467.2 | 1H NMR (400 MHz, DMSO-d6) δ 7.85 (dd, J = 8.2, 1.7 Hz, 1H), 7.71 (d, J = 8.6 Hz, 1H), 7.65-7.60 (m, 2H), 4.84-4.72 (m, 2H), 4.62-4.50 (m, 1H), 4.24 (dd, J = 9.0, 5.6 Hz, 1H), 4.17-4.09 (m, 2H), 4.05 (dd, J = 11.4, 4.8 Hz, 1H), 3.75 (dd, J = 11.4, 6.5 Hz, 1H), 3.68 (dd, J = 8.9, 4.4 Hz, 1H), 3.18-3.03 (m, 5H), 2.64-2.50 (m, 2H), 1.49 (d, J = 5.8 Hz, 3H). |
| 579 | 493.3 | 1H NMR (400 MHz, DMSO-d6) δ 7.86 (dd, J = 8.1, 1.8 Hz, 1H), 7.77 (d, J = 8.8 Hz, 1H), 7.70-7.61 (m, 2H), 4.79 (d, J = 2.7 Hz, 2H), 4.56 (q, J = 6.6 Hz, 1H), 4.24 (dd, J = 9.0, 5.5 Hz, 1H), 4.16-4.02 (m, 3H), 3.77 (dd, J = 11.4, 6.7 Hz, 1H), 3.68 (dd, J = 9.0, 4.3 Hz, 1H), 3.12 (d, J = 7.8 Hz, 2H), 2.87-2.71 (m, 1H), 2.63-2.52 (m, 2H), 1.49 (d, J = 5.9 Hz, 3H), 1.05-0.89 (m, 4H). |
| 580 | 485.2 | 1H NMR (400 MHz, DMSO-d6) δ 8.45 (d, J = 8.8 Hz, 1H), 7.87 (dd, J = 8.1, 1.8 Hz, 1H), 7.65-7.63 (m, 1H), 7.60 (d, J = 8.2 Hz, 1H), 5.66-5.56 (m, 1H), 5.55-5.45 (m, 1H), 4.86-4.72 (m, 2H), 4.63-4.54 (m, 1H), 4.25 (dd, J = 9.0, 5.5 Hz, 1H), 4.15-4.07 (m, 2H), 4.03 (dd, J = 11.4, 4.7 Hz, 1H), 3.75 (dd, J = 11.4, 6.5 Hz, 1H), 3.68 (dd, J = 9.0, 4.4 Hz, 1H), 3.20-3.02 (m, 2H), 2.67-2.52 (m, 2H), 1.49 (d, J = 5.8 Hz, 3H). |
| 581 | 505.3 | 1H NMR (400 MHz, DMSO-d6) δ 7.90 (dd, J = 8.1, 1.8 Hz, 1H), 7.78-7.58 (m, 3H), 5.14-5.01 (m, 1H), 4.84-4.72 (m, 2H), 4.64-4.53 (m, 1H), 4.20-4.08 (m, 2H), 4.05 (dd, J = 11.4, 4.8 Hz, 1H), 3.76 (dd, J = 11.4, 6.5 Hz, 1H), 3.29-3.00 (m, 5H), 2.72-2.53 (m, 3H), 2.48-2.38 (m, 1H). |
| 582 | 469.3 | 1H NMR (400 MHz, DMSO-d6) δ 7.86 (dd, J = 8.1, 1.8 Hz, 1H), 7.71 (d, J = 8.6 Hz, 1H), 7.66-7.59 (m, 2H), 5.16 (ddt, J = 56.9, 6.0, 3.7 Hz, 1H), 4.85-4.73 (m, 2H), 4.62-4.34 (m, 3H), 4.12-3.94 (m, 2H), 3.76 (dd, J = 11.4, 6.5 Hz, 1H), 3.21-3.03 (m, 5H), 2.68-2.52 (m, 2H), 1.55 (d, J = 6.5 Hz, 3H). |
| 583 | 469.3 | 1H NMR (400 MHz, DMSO-d6) δ 7.86 (dd, J = 8.1, 1.8 Hz, 1H), 7.71 (d, J = 8.6 Hz, 1H), 7.66-7.59 (m, 2H), 5.43 (dtd, J = 58.0, 6.0, 2.6 Hz, 1H), 4.86-4.61 (m, 3H), 4.61-4.49 (m, 1H), 4.36 (ddd, J = 22.4, 11.0, 6.0 Hz, 1H), 4.16-3.99 (m, 2H), 3.76 (dd, J = 11.4, 6.5 Hz, 1H), 3.19-3.06 (m, 5H), 2.68-2.52 (m, 2H), 1.47 (dd, J = 6.6, 1.9 Hz, 3H). |
| 584 | 487.3 | 1H NMR (400 MHz, DMSO-d6) δ 7.88 (dd, J = 8.2, 1.8 Hz, 1H), 7.72 (d, J = 8.6 Hz, 1H), 7.68-7.61 (m, 2H), 4.88-4.69 (m, 3H), 4.62-4.53 (m, 1H), 4.48 (t, J = 12.3 Hz, 2H), 4.05 (dd, J = 11.4, 4.8 Hz, 1H), 3.76 (dd, J = 11.4, 6.5 Hz, 1H), 3.23-3.04 (m, 5H), 2.68-2.52 (m, 2H), 1.52 (d, J = 6.5 Hz, 3H). |
| 585 | 431.3 | 1H NMR (400 MHz, DMSO-d6) δ 7.73 (d, J = 7.9 Hz, 1H), 7.59-7.52 (m, 1H), 7.48 (d, J = 1.4 Hz, 1H), 5.19-5.11 (m, 1H), 4.81-4.53 (m, 7H), 4.31-4.20 (m, 1H), 4.17-4.05 (m, 2H), 3.73-3.63 (m, 1H), 3.18-3.01 (m, 2H), 2.67-2.52 (m, 2H), 1.49 (d, J = 5.8 Hz, 3H). |
| 586 | 441.3 | 1H NMR (400 MHz, DMSO-d6) δ 9.07 (s, 3H), 7.90-7.83 (m, 2H), 7.32 (d, J = 8.0 Hz, 1H), 5.23 (d, J = 7.8 Hz, 2H), 5.13-5.00 (m, 1H), 4.88 (d, J = 7.8 Hz, 2H), 4.23-4.04 (m, 2H), 3.27-3.09 (m, 3H), 2.74-2.55 (m, 3H), 2.49-2.39 (m, 1H), 2.27 (s, 3H). |
| 587 | 441.3 | 1H NMR (400 MHz, DMSO-d6) δ 8.60 (s, 3H), 8.09-8.03 (m, 2H), 7.72-7.62 (m, 2H), 5.19-4.83 (m, 1H), 4.25 (d, J = 9.9 Hz, 1H), 4.20-4.07 (m, 3H), 4.07-3.96 (m, 1H), 3.91 (d, J = 9.9 Hz, 1H), 3.30-3.09 (m, 2H), 2.75-2.52 (m, 3H), 2.49-2.36 (m, 3H). |
| 588 | 469.2 | 1H NMR (400 MHz, DMSO-d6) δ 7.74 (d, J = 7.9 Hz, 1H), 7.64-7.56 (m, 1H), 7.55 (d, J = 1.4 Hz, 1H), 5.18-5.02 (m, 2H), 4.82-4.62 (m, 4H), 4.64-4.55 (m, 3H), 4.21-4.04 (m, 2H), 3.26-3.08 (m, 2H), 2.73-2.54 (m, 3H), 2.50-2.38 (m, 1H). |
| 589 | 445.2 | 1H NMR (400 MHz, DMSO-d6) δ 9.23 (s, 3H), 7.95-7.83 (m, 2H), 7.62 (t, J = 8.0 Hz, 1H), 5.20-5.04 (m, 3H), 4.92 (d, J = 7.9 Hz, 2H), 4.21-4.05 (m, 2H), 3.31-3.08 (m, 2H), 2.73-2.56 (m, 3H), 2.48-2.38 (m, 1H). |
| 590 | 435.3 | 1H NMR (400 MHz, DMSO-d6) δ 8.42 (t, J = 5.7 Hz, 1H), 7.79 (d, J = 8.1 Hz, 1H), 7.72 (dd, J = 8.1, 1.7 Hz, 1H), 7.59 (d, J = 1.6 Hz, 1H), 5.17 (ddt, J = 56.8, 6.4, 3.6 Hz, 1H), 4.63-4.22 (m, 3H), 4.02 (ddd, J = 25.5, 10.4, 3.8 Hz, 1H), 3.63 (dd, J = 11.3, 5.4 Hz, 1H), 3.52 (dd, J = 11.4, 6.2 Hz, 1H), 3.40-3.28 (m, 1H), 3.23-3.01 (m, 3H), 2.73-2.52 (m, 2H), 1.55 (d, J = 6.5 Hz, 3H). |
| 591 | 431.1 | 1H NMR (400 MHz, DMSO-d6) δ 8.44 (t, J = 5.6 Hz, 1H), 7.82-7.77 (m, 1H), 7.76-7.70 (m, 1H), 7.58-7.51 (m, 1H), 4.38-4.20 (m, 2H), 4.15-4.06 (m, 2H), 3.71-3.67 (m, 1H), 3.37-3.24 (m, 1H), 3.21-2.95 (m, 3H), 2.68-2.52 (m, 2H), 1.68-1.40 (m, 5H), 1.03 (t, J = 7.4 Hz, 3H). |

TABLE 1-continued

| | MS and NMR DATA | |
|---|---|---|
| Example No | ES/MS m/z (M + H)+ | 1H NMR |
| 592 | 431.1 | 1H NMR (400 MHz, DMSO-d6) δ 8.44 (t, J = 5.6 Hz, 1H), 7.82-7.77 (m, 1H), 7.76-7.70 (m, 1H), 7.58-7.51 (m, 1H), 4.38-4.20 (m, 2H), 4.15-4.06 (m, 2H), 3.71-3.67 (m, 1H), 3.37-3.24 (m, 1H), 3.21-2.95 (m, 3H), 2.68-2.52 (m, 2H), 1.68-1.40 (m, 5H), 1.03 (t, J = 7.4 Hz, 3H). |
| 593 | 431.1 | 1H NMR (400 MHz, DMSO-d6) δ 8.44 (t, J = 5.6 Hz, 1H), 7.82-7.77 (m, 1H), 7.76-7.70 (m, 1H), 7.58-7.51 (m, 1H), 4.38-4.20 (m, 2H), 4.15-4.06 (m, 2H), 3.71-3.67 (m, 1H), 3.37-3.24 (m, 1H), 3.21-2.95 (m, 3H), 2.68-2.52 (m, 2H), 1.68-1.40 (m, 5H), 1.03 (t, J = 7.4 Hz, 3H). |
| 594 | 435.2 | 1H NMR (400 MHz, DMSO-d6) δ 8.48 (t, J = 5.8 Hz, 1H), 7.82-7.72 (m, 2H), 7.59 (d, J = 1.4 Hz, 1H), 4.76-4.62 (m, 2H), 4.66-4.51 (m, 1H), 4.26 (dd, J = 9.0, 5.6 Hz, 1H), 4.13 (qd, J = 5.7, 3.6 Hz, 2H), 3.69 (dd, J = 9.1, 4.4 Hz, 1H), 3.40 (m, 1H), 3.26 (m, 1H), 3.14 (d, J = 6.9 Hz, 2H), 2.60 (td, J = 15.3, 7.4 Hz, 2H), 1.50 (d, J = 5.8 Hz, 3H). |
| 595 | 435.2 | 1H NMR (400 MHz, DMSO-d6) δ 8.48 (t, J = 5.7 Hz, 1H), 7.82-7.72 (m, 2H), 7.60 (d, J = 1.4 Hz, 1H), 4.76-4.50 (m, 3H), 4.26 (dd, J = 9.0, 5.6 Hz, 1H), 4.13 (q, J = 4.3 Hz, 2H), 3.69 (dd, J = 9.1, 4.3 Hz, 1H), 3.40 (m, 1H), 3.25 (m, 1H), 3.14 (d, J = 6.9 Hz, 2H), 2.60 (m, 2H), 1.50 (d, J = 5.7 Hz, 3H). |
| 596 | 435.2 | 1H NMR (400 MHz, DMSO-d6) δ 8.48 (t, J = 5.8 Hz, 1H), 7.82-7.72 (m, 2H), 7.59 (d, J = 1.4 Hz, 1H), 4.76-4.62 (m, 2H), 4.66-4.51 (m, 1H), 4.26 (dd, J = 9.0, 5.6 Hz, 1H), 4.13 (qd, J = 5.7, 3.6 Hz, 2H), 3.69 (dd, J = 9.1, 4.4 Hz, 1H), 3.40 (m, 1H), 3.26 (m, 1H), 3.14 (d, J = 6.9 Hz, 2H), 2.60 (td, J = 15.3, 7.4 Hz, 2H), 1.50 (d, J = 5.8 Hz, 3H). |
| 597 | 453.5 | 1H NMR (400 MHz, DMSO-d6) δ 8.54 (t, J = 5.9 Hz, 1H), 7.79 (s, 2H), 7.62 (d, J = 5.9 Hz, 1H), 6.29 (t, J = 54.2 Hz, 1H), 4.80-4.64 (m, 1H), 4.31-4.21 (m, 1H), 4.17-4.06 (m, 2H), 3.74-3.65 (m, 1H), 3.55-3.44 (m, 1H), 3.17-3.06 (m, 2H), 2.69-2.54 (m, 2H), 1.50 (d, J = 5.8 Hz, 3H). |
| 598 | 409.1 | 1H NMR (400 MHz, DMSO-d6) δ 8.25 (d, J = 1.5 Hz, 1H), 8.20 (dd, J = 8.1, 1.6 Hz, 1H), 7.97 (t, J = 4.9 Hz, 1H), 7.75 (d, J = 8.0 Hz, 1H), 4.50 (d, J = 4.8 Hz, 2H), 4.28 (dd, J = 9.1, 5.8 Hz, 1H), 4.21-4.10 (m, 2H), 3.72-3.69 (m, 1H), 3.16 (d, J = 8.0 Hz, 2H), 2.69-2.54 (m, 2H), 1.50 (d, J = 6.0 Hz, 3H). |
| 599 | 404.1 | 1H NMR (400 MHz, DMSO-d6) δ 8.94 (s, 1H), 8.66 (s, 1H), 7.99 (s, 1H), 4.36 (t, J = 5.0 Hz, 2H), 4.27 (dd, J = 9.1, 5.6 Hz, 1H), 4.15 (q, J = 5.0 Hz, 2H), 3.70 (dd, J = 9.1, 4.3 Hz, 1H), 3.37 (q, J = 5.4 Hz, 2H), 3.18 (d, J = 7.1 Hz, 2H), 2.70-2.54 (m, 2H), 1.50 (d, J = 5.8 Hz, 3H). |
| 600 | 401.1 | 1H NMR (400 MHz, DMSO-d6) δ 8.46 (d, J = 2.0 Hz, 1H), 8.05 (dd, J = 7.9, 2.0 Hz, 1H), 7.48 (d, J = 8.0 Hz, 1H), 4.25 (dd, J = 9.0, 5.6 Hz, 1H), 4.19-4.09 (m, 2H), 3.68 (dd, J = 9.0, 4.5 Hz, 1H), 3.59 (t, J = 6.7 Hz, 2H), 3.23-3.11 (m, 3H), 3.06 (d, J = 3.5 Hz, 5H), 2.71-2.54 (m, 1H), 1.50 (d, J = 6.1 Hz, 3H). |
| 601 | 401.1 | 1H NMR (400 MHz, Methanol-d4) δ 8.48 (d, J = 1.7 Hz, 1H), 8.37 (dd, J = 8.2, 1.8 Hz, 1H), 8.25 (dd, J = 8.2, 0.5 Hz, 1H), 4.91 (s, 2H), 4.36 (dd, J = 9.1, 5.8 Hz, 1H), 4.28-4.18 (m, 2H), 3.80-3.72 (m, 1H), 3.21-3.06 (m, 2H), 2.95 (t, J = 7.8 Hz, 2H), 2.23-2.05 (m, 2H), 1.58 (d, J = 6.1 Hz, 3H). |
| 602 | 379.1 | 1H NMR (400 MHz, DMSO-d6) δ 8.48 (d, J = 1.8 Hz, 1H), 8.30 (d, J = 7.8 Hz, 1H), 8.06 (d, J = 8.1 Hz, 1H), 7.85 (t, J = 7.8 Hz, 1H), 6.94 (t, J = 53.5 Hz, 1H), 4.42 (q, J = 6.7 Hz, 1H), 4.03-3.88 (m, 2H), 3.01 (m, 2H), 2.83 (t, J = 7.7 Hz, 2H), 2.39 (m, 1H), 2.01 (m, 3H), 1.50 (d, J = 6.1 Hz, 3H). |
| 603 | 431.0 | 1H NMR (400 MHz, DMSO-d6) δ 8.54 (s, 1H), 8.36 (d, J = 8.0 Hz, 1H), 8.13 (d, J = 8.1 Hz, 1H), 7.94-7.85 (m, 2H), 7.56 (td, J = 8.7, 8.1, 5.6 Hz, 1H), 6.96 (t, J = 53.4 Hz, 1H), 4.27 (dd, J = 9.1, 5.5 Hz, 1H), 4.14 (q, J = 4.7 Hz, 2H), 3.99 (s, 0H), 3.70 (dd, J = 9.0, 4.4 Hz, 1H), 3.15 (s, 3H), 2.68-2.52 (m, 2H), 1.51 (d, J = 5.7 Hz, 3H). |
| 604 | 424.1 | 1H NMR (400 MHz, DMSO-d6) δ 7.77-7.67 (m, 2H), 7.34 (d, J = 8.1 Hz, 1H), 4.97 (s, 2H), 4.63 (s, 2H), 4.41 (m, 1H), 3.94 (m, 2H), 3.64 (d, J = 11.8 Hz, 2H), 3.11-2.93 (m, 4H), 2.81 (t, J = 7.8 Hz, 2H), 2.39 (s, 1H), 2.06-1.90 (m, 3H), 1.49 (d, J = 6.2 Hz, 3H). |
| 605 | 429.2 | 1H NMR (400 MHz, Chloroform-d) δ 7.77-7.65 (m, 2H), 7.24 (d, J = 8.0 Hz, 1H), 4.59 (s, 2H), 4.52 (q, J = 6.7 Hz, 1H), 4.11 (dd, J = 22.7, 4.9 Hz, 3H), 4.02 (d, J = 8.0 Hz, 1H), 3.65 (t, J = 6.0 Hz, 2H), 3.26-3.19 (m, 2H), 3.14-2.93 (m, 4H), 2.89 (t, J = 7.7 Hz, 2H), 2.63 (s, 1H), 2.44 (dtd, J = 10.8, 8.7, 4.7 Hz, 1H), 2.14-1.95 (m, 3H), 1.58 (d, J = 6.2 Hz, 3H). |
| 606 | 385.1 | 1H NMR (400 MHz, Chloroform-d) δ 7.99-7.93 (m, 1H), 7.85 (m, 1H), 7.52-7.42 (m, 2H), 4.80 (dt, J = 8.8, 6.1 Hz, 1H), 4.58 (s, 1H), 4.58-4.46 (m, 1H), 4.14 (m, 1H), 4.02 (m, 1H), 3.37 (m, 1H), 3.22 (m, 1H), 3.13-2.95 (m, 2H), 2.89 (t, J = 7.7 Hz, 2H), 2.81 (m, 1H), 2.52-2.36 (m, 2H), 2.16-1.95 (m, 3H), 1.60-1.54 (m, 3H). |

TABLE 1-continued

MS and NMR DATA

| Example No | ES/MS m/z (M + H)+ | 1H NMR |
|---|---|---|
| 607 | 435.2 | 1H NMR (400 MHz, DMSO-d6) δ 7.95 (s, 1H), 7.87-7.79 (m, 1H), 7.64 (dd, J = 8.6, 5.8 Hz, 1H), 7.41 (d, J = 7.9 Hz, 1H), 4.89 (q, J = 8.0 Hz, 1H), 4.49 (m, 1H), 4.08-3.90 (m, 2H), 3.32 (s, 3H), 3.05 (s, 3H), 2.98 (m, 1H), 2.83 (dt, J = 16.5, 8.4 Hz, 1H), 2.66-2.56 (m, 1H), 2.59-2.51 (m, 1H), 2.49-2.38 (m, 1H), 1.92 (m, 1H), 1.51 (d, J = 6.2 Hz, 3H). |
| 608 | 435.2 | 1H NMR (400 MHz, DMSO-d6) δ 7.95 (s, 1H), 7.86-7.79 (m, 1H), 7.65 (d, J = 8.6 Hz, 1H), 7.41 (d, J = 7.9 Hz, 1H), 4.89 (q, J = 8.0 Hz, 1H), 4.47 (p, J = 6.4 Hz, 1H), 4.08-3.91 (m, 2H), 3.14-3.07 (m, 2H), 3.05 (s, 3H), 2.98 (m, 1H), 2.83 (dt, J = 16.5, 8.4 Hz, 1H), 2.66-2.50 (m, 3H), 2.44 (ddd, J = 13.2, 6.7, 3.5 Hz, 1H), 2.00 (m, 1H), 1.91 (dt, J = 12.6, 8.7 Hz, 1H), 1.51 (d, J = 6.2 Hz, 3H). |
| 609 | 435.2 | 1H NMR (400 MHz, DMSO-d6) δ 7.95 (s, 1H), 7.83 (dd, J = 7.9, 1.6 Hz, 1H), 7.63 (d, J = 8.5 Hz, 1H), 7.41 (d, J = 7.9 Hz, 1H), 4.89 (q, J = 8.0 Hz, 1H), 4.48 (q, J = 6.6 Hz, 1H), 4.08-3.91 (m, 2H), 3.12 (d, J = 35.0 Hz, 1H), 3.05 (s, 3H), 2.98 (m, 1H), 2.83 (dt, J = 16.4, 8.4 Hz, 1H), 2.60-2.52 (m, 2H), 2.49-2.38 (m, 1H), 2.06-1.85 (m, 2H), 1.52 (d, J = 6.2 Hz, 3H). |
| 610 | 415.2 | 1H NMR (400 MHz, DMSO-d6) δ 7.90 (d, J = 1.8 Hz, 1H), 7.79 (dt, J = 6.7, 2.1 Hz, 1H), 7.73 (t, J = 6.4 Hz, 1H), 7.51-7.45 (m, 2H), 4.27 (d, J = 6.2 Hz, 2H), 4.19 (dd, J = 8.8, 5.9 Hz, 1H), 4.13-4.00 (m, 2H), 3.64 (dd, J = 8.8, 4.8 Hz, 1H), 3.12-2.93 (m, 2H), 2.84 (dd, J = 8.5, 6.9 Hz, 2H), 2.57-2.44 (m, 1H), 2.02 (dtt, J = 12.5, 8.0, 3.5 Hz, 2H), 1.48 (d, J = 6.0 Hz, 3H), 0.96-0.83 (m, 4H). |
| 611 | 451.1 | 1H NMR (400 MHz, DMSO-d6) δ 7.85-7.75 (m, 2H), 7.37 (d, J = 8.0 Hz, 1H), 4.47 (s, 2H), 4.25 (dd, J = 9.0, 5.6 Hz, 1H), 4.12 (dt, J = 6.7, 3.5 Hz, 2H), 3.68 (dd, J = 9.0, 4.4 Hz, 1H), 3.47 (t, J = 5.9 Hz, 2H), 3.14 (d, J = 7.6 Hz, 3H), 2.98 (d, J = 7.4 Hz, 5H), 2.65-2.51 (m, 2H), 1.50 (d, J = 5.8 Hz, 3H). |
| 612 | 373.2 | 1H NMR (400 MHz, DMSO-d6) δ 7.69-7.56 (m, 2H), 7.22 (d, J = 8.0 Hz, 1H), 4.46 (s, 2H), 4.24 (m, 1H), 4.11 (t, J = 4.8 Hz, 2H), 3.68 (m, 1H), 3.47 (t, J = 5.7 Hz, 2H), 3.13 (s, 3H), 2.71-2.54 (m, 3H), 1.50 (d, J = 5.9 Hz, 3H). |
| 613 | 453.2 | 1H NMR (400 MHz, DMSO-d6) δ 8.10-8.03 (m, 1H), 7.93 (m, 2H), 7.02 (d, J = 8.5 Hz, 1H), 5.64 (d, J = 6.1 Hz, 1H), 5.28 (t, J = 4.7 Hz, 1H), 4.80 (m, 1H), 4.42 (m, 1H), 4.23 (m, 1H), 4.15-3.98 (m, 2H), 3.67 (m, 1H), 3.13 (s, 2H), 3.07 (s, 3H), 2.59 (m, 2H), 1.50 (d, J = 5.8 Hz, 3H). |
| 614 | 453.2 | 1H NMR (400 MHz, Chloroform-d) δ 8.05-7.99 (m, 1H), 7.88 (dd, J = 8.5, 1.9 Hz, 1H), 6.95 (d, J = 8.5 Hz, 1H), 5.27 (td, J = 8.2, 4.0 Hz, 1H), 4.87 (d, J = 8.6 Hz, 1H), 4.77 (dd, J = 10.4, 8.0 Hz, 1H), 4.55 (dd, J = 10.4, 4.1 Hz, 1H), 4.44 (dd, J = 9.5, 5.5 Hz, 1H), 4.30 (q, J = 5.0 Hz, 2H), 3.86 (dd, J = 9.6, 4.2 Hz, 1H), 3.09 (s, 3H), 2.57 (tt, J = 14.3, 6.6 Hz, 2H), 2.06 (d, J = 17.0 Hz, 1H), 1.60 (d, J = 6.0 Hz, 3H). |
| 615 | 453.2 | 1H NMR (400 MHz, Chloroform-d) δ 8.06 (d, J = 1.9 Hz, 1H), 7.89 (dd, J = 8.6, 2.0 Hz, 1H), 6.96 (d, J = 8.5 Hz, 1H), 5.29 (td, J = 8.4, 4.2 Hz, 1H), 4.78 (dd, J = 10.4, 8.0 Hz, 1H), 4.69 (d, J = 8.8 Hz, 1H), 4.54 (dd, J = 10.4, 4.1 Hz, 1H), 4.45 (dd, J = 9.5, 5.4 Hz, 1H), 4.31 (q, J = 5.0 Hz, 2H), 3.89 (dd, J = 9.6, 4.3 Hz, 1H), 3.11 (d, J = 5.7 Hz, 2H), 3.09 (s, 3H), 2.57 (m, 2H), 2.03 (d, J = 14.6 Hz, 1H), 1.61 (d, J = 6.0 Hz, 3H). |
| 616 | 437.2 | 1H NMR (400 MHz, DMSO-d6) δ 7.99 (s, 1H), 7.91-7.83 (m, 1H), 7.61 (d, J = 6.1 Hz, 1H), 7.55 (m, 2H), 4.76 (m, 1H), 4.25 (m, 1H), 4.12 (d, J = 4.4 Hz, 2H), 3.69 (m, 1H), 3.34 (m, 1H), 3.14 (m, 2H), 2.84 (m, 1H), 2.60 (m, 2H), 2.18-2.02 (m, 1H), 1.51 (d, J = 5.9 Hz, 3H). |
| 617 | 437.2 | 1H NMR (400 MHz, DMSO-d6) δ 7.99 (s, 1H), 7.91-7.83 (m, 1H), 7.61 (d, J = 6.1 Hz, 1H), 7.55 (m, 2H), 4.76 (m, 1H), 4.25 (m, 1H), 4.12 (d, J = 4.4 Hz, 2H), 3.69 (m, 1H), 3.34 (m, 1H), 3.14 (m, 2H), 2.84 (m, 1H), 2.60 (m, 2H), 2.18-2.02 (m, 1H), 1.51 (d, J = 5.9 Hz, 3H). |
| 618 | 437.2 | 1H NMR (400 MHz, DMSO-d6) δ 8.00 (m, 1H), 7.92-7.83 (m, 1H), 7.62 (m, 1H), 7.55 (m, 2H), 4.76 (s, 1H), 4.25 (m, 1H), 4.13 (m, 2H), 3.69 (m, 1H), 3.34 (m, 1H), 3.14 (m, 2H), 2.83 (m, 1H), 2.59 (m, 2H), 2.10 (m, 1H), 1.50 (d, J = 5.8 Hz, 3H). |
| 619 | 385.3 | 1H NMR (400 MHz, DMSO-d6) δ 9.19 (s, 2H), 8.13 (t, J = 1.9 Hz, 1H), 8.02-7.95 (m, 1H), 7.89 (dd, J = 7.6, 2.1 Hz, 1H), 7.76 (t, J = 7.9 Hz, 1H), 5.72 (s, 1H), 4.27 (dd, J = 9.1, 5.9 Hz, 1H), 4.14 (m, 2H), 3.71 (dd, J = 9.2, 4.6 Hz, 1H), 3.19 (d, J = 6.7 Hz, 2H), 2.60 (m, 2H), 1.50 (d, J = 6.0 Hz, 3H). |
| 620 | 451.2 | 1H NMR (400 MHz, DMSO-d6) δ 7.93 (s, 1H), 7.88 (dt, J = 7.4, 1.8 Hz, 1H), 7.60-7.48 (m, 2H), 4.25 (dd, J = 9.0, 5.5 Hz, 1H), 4.21 (s, 2H), 4.13 (q, J = 4.2, 3.7 Hz, 2H), 3.69 (dd, J = 9.0, 4.4 Hz, 1H), 3.31-3.22 (m, 2H), 3.14 (t, J = 6.7 Hz, 3H), 2.59 (td, J = 15.3, 7.5 Hz, 2H), 2.29-2.17 (m, 2H), 1.50 (d, J = 5.8 Hz, 3H). |
| 621 | 451.2 | 1H NMR (400 MHz, DMSO-d6) δ 7.97 (s, 1H), 7.87-7.80 (m, 1H), 7.64 (dd, J = 8.6, 5.8 Hz, 1H), 7.41 (d, J = 7.9 Hz, 1H), 5.65 (d, J = 5.9 |

TABLE 1-continued

MS and NMR DATA

| Example No | ES/MS m/z (M + H)+ | 1H NMR |
|---|---|---|
| | | Hz, 1H), 4.89 (q, J = 8.1 Hz, 1H), 4.24 (dd, J = 9.0, 5.6 Hz, 1H), 4.12 (t, J = 5.3 Hz, 2H), 3.67 (dd, J = 8.9, 4.4 Hz, 1H), 3.32 (s, 3H), 3.05 (s, 3H), 3.04-2.92 (m, 1H), 2.83 (dt, J = 16.4, 8.4 Hz, 1H), 2.67-2.51 (m, 2H), 1.97-1.86 (m, 1H), 1.50 (d, J = 5.8 Hz, 3H). |
| 622 | 451.2 | 1H NMR (400 MHz, DMSO-d6) δ 7.97 (s, 1H), 7.87-7.80 (m, 1H), 7.63 (d, J = 8.5 Hz, 1H), 7.41 (d, J = 7.9 Hz, 1H), 5.65 (d, J = 6.3 Hz, 1H), 4.90 (q, J = 8.0 Hz, 1H), 4.24 (dd, J = 9.0, 5.7 Hz, 1H), 4.11 (d, J = 5.6 Hz, 2H), 3.67 (dd, J = 9.0, 4.4 Hz, 1H), 3.12 (d, J = 14.7 Hz, 2H), 3.05 (s, 3H), 2.98 (m, 1H), 2.83 (dt, J = 16.6, 8.5 Hz, 1H), 2.67-2.51 (m, 2H), 1.94 (dt, J = 12.5, 8.6 Hz, 1H), 1.50 (d, J = 5.9 Hz, 3H). |
| 623 | 451.2 | 1H NMR (400 MHz, DMSO-d6) δ 7.97 (s, 1H), 7.83 (dd, J = 7.9, 1.6 Hz, 1H), 7.65 (d, J = 8.5 Hz, 1H), 7.41 (d, J = 7.9 Hz, 1H), 5.65 (s, 1H), 4.89 (q, J = 8.0 Hz, 1H), 4.24 (dd, J = 9.0, 5.6 Hz, 1H), 4.11 (q, J = 5.0 Hz, 2H), 3.67 (dd, J = 9.0, 4.4 Hz, 1H), 3.11 (d, J = 6.6 Hz, 2H), 3.05 (s, 3H), 2.98 (m, 1H), 2.83 (dt, J = 16.5, 8.5 Hz, 1H), 2.67-2.51 (m, 2H), 1.98-1.86 (m, 1H), 1.50 (d, J = 5.8 Hz, 3H). |
| 624 | 431.1 | 1H NMR (400 MHz, DMSO-d6) δ 7.93 (d, J = 8.2 Hz, 1H), 7.51 (s, 2H), 7.36 (s, 1H), 5.23 (td, J = 8.3, 5.2 Hz, 1H), 4.77 (t, J = 9.2 Hz, 1H), 4.35 (dd, J = 9.7, 5.2 Hz, 1H), 4.24 (dd, J = 9.0, 5.5 Hz, 1H), 4.12 (t, J = 4.6 Hz, 2H), 3.67 (dd, J = 9.0, 4.3 Hz, 1H), 3.13 (m, 4H), 2.58 (d, J = 7.0 Hz, 1H), 1.49 (d, J = 5.8 Hz, 3H), 1.25 (t, J = 7.3 Hz, 4H). |
| 625 | 479.2 | 1H NMR (400 MHz, DMSO-d6) δ 7.96 (d, J = 8.6 Hz, 1H), 7.59-7.47 (m, 3H), 7.36 (s, 1H), 5.32-5.22 (m, 1H), 4.80 (t, J = 9.2 Hz, 1H), 4.41 (dd, J = 9.7, 5.4 Hz, 1H), 4.24 (dd, J = 9.0, 5.5 Hz, 1H), 4.12 (t, J = 4.5 Hz, 2H), 3.10 (m, 2H), 2.77-2.67 (m, 1H), 2.63-2.52 (m, 1H), 1.49 (d, J = 5.7 Hz, 3H), 1.08-0.97 (m, 5H). |
| 626 | 515.1 | 1H NMR (400 MHz, DMSO-d6) δ 8.54 (d, J = 8.2 Hz, 1H), 7.90 (d, J = 7.7 Hz, 2H), 7.71 (d, J = 7.1 Hz, 1H), 7.66 (t, J = 7.5 Hz, 2H), 7.37 (d, J = 7.9 Hz, 1H), 7.32 (s, 1H), 7.01 (d, J = 7.8 Hz, 1H), 5.19-5.09 (m, 1H), 4.53 (t, J = 9.1 Hz, 1H), 4.23 (dd, J = 9.0, 5.8 Hz, 1H), 4.16-4.06 (m, 3H), 3.65 (dd, J = 9.1, 4.3 Hz, 1H), 3.06 (s, 2H), 2.63-2.52 (m, 2H), 1.47 (d, J = 5.8 Hz, 3H). |
| 627 | 478.1 | 1H NMR (400 MHz, DMSO-d6) δ 8.41 (s, H), 7.68 (d, J = 7.9 Hz, 1H), 7.57 (d, J = 8.3 Hz, 1H), 7.47 (s, 1H), 5.46 (s, 2H), 5.29 (q, J = 4.6 Hz, 1H), 5.13 (s, 1H), 4.78 (dd, J = 10.9, 8.3 Hz, 1H), 4.56 (dt, J = 11.0, 5.5 Hz, 2H), 4.50 (dd, J = 10.2, 6.5 Hz, 1H), 4.10 (dd, J = 10.4, 4.5 Hz, 1H), 3.13 (s, 2H), 2.67-2.58 (m, 1H), 1.59 (d, J = 6.4 Hz, 3H). |
| 628 | 419.1 | 1H NMR (400 MHz, DMSO-d6) δ 8.42-8.36 (m, 1H), 8.15 (dt, J = 7.9, 1.4 Hz, 1H), 7.99 (ddd, J = 7.9, 1.9, 1.1 Hz, 1H), 7.76 (t, J = 7.8 Hz, 1H), 7.51 (s, 2H), 4.27 (dd, J = 9.0, 5.5 Hz, 1H), 4.13 (dq, J = 9.0, 4.5 Hz, 2H), 3.70 (dd, J = 9.0, 4.3 Hz, 1H), 3.14 (d, J = 7.7 Hz, 2H), 2.67-2.52 (m, 2H), 1.51 (d, J = 5.8 Hz, 3H). |
| 629 | 481.1 | 1H NMR (400 MHz, Chloroform-d) δ 7.75 (dt, J = 8.0, 1.7 Hz, 1H), 7.68 (t, J = 2.0 Hz, 1H), 7.51 (d, J = 7.9 Hz, 1H), 5.15-5.06 (m, 1H), 5.09-4.94 (m, 1H), 4.75-4.48 (m, 3H), 4.25-4.05 (m, 3H), 3.12 (s, 3H), 3.08 (td, J = 6.2, 3.2 Hz, 2H), 2.64-2.39 (m, 4H), 1.85 (dd, J = 12.6, 8.5 Hz, 1H), 1.44 (d, J = 2.5 Hz, 3H), 1.30-1.21 (m, 6H). |
| 630 | 479.1 | 1H NMR (400 MHz, Chloroform-d) δ 7.76 (dd, J = 7.9, 1.6 Hz, 1H), 7.70 (t, J = 2.0 Hz, 1H), 7.51 (d, J = 7.9 Hz, 1H), 5.08 (q, J = 8.4 Hz, 1H), 4.59 (t, J = 9.4 Hz, 1H), 4.44 (dd, J = 9.5, 5.7 Hz, 1H), 4.31 (tt, J = 5.9, 3.3 Hz, 2H), 3.89 (dd, J = 9.6, 4.2 Hz, 1H), 3.11 (s, 3H), 3.12-3.03 (m, 1H), 2.64-2.48 (m, 3H), 2.25 (d, J = 6.0 Hz, 1H), 1.86 (dd, J = 12.6, 8.5 Hz, 1H), 1.61 (d, J = 5.8 Hz, 3H), 1.44 (d, J = 3.8 Hz, 3H). |
| 631 | 479.1 | 1H NMR (400 MHz, DMSO-d6) δ 7.80 (d, J = 7.9 Hz, 1H), 7.75 (s, 1H), 7.56 (d, J = 8.7 Hz, 1H), 7.47 (d, J = 7.9 Hz, 1H), 5.65 (d, J = 6.3 Hz, 1H), 4.94 (q, J = 8.4 Hz, 1H), 4.24 (dd, J = 8.9, 5.7 Hz, 1H), 4.11 (q, J = 6.6, 4.7 Hz, 2H), 3.68 (dd, J = 9.1, 4.4 Hz, 1H), 3.16 (s, 1H), 3.07 (s, 3H), 2.57 (s, 1H), 2.49-2.41 (m, 1H), 1.85 (dd, J = 12.3, 9.2 Hz, 1H), 1.50 (d, J = 5.8 Hz, 3H), 1.39 (s, 3H), 1.20 (s, 3H). |
| 632 | 479.1 | 1H NMR (400 MHz, DMSO-d6) δ 7.80 (d, J = 7.9 Hz, 1H), 7.76 (s, 1H), 7.56 (d, J = 8.6 Hz, 1H), 7.48 (d, J = 7.9 Hz, 1H), 5.65 (d, J = 6.1 Hz, 1H), 4.94 (q, J = 8.3 Hz, 1H), 4.24 (dd, J = 9.0, 5.5 Hz, 1H), 4.12 (q, J = 5.0 Hz, 2H), 3.68 (dd, J = 9.0, 4.3 Hz, 1H), 3.13 (s, 2H), 3.07 (s, 3H), 2.58 (dq, J = 14.8, 7.7, 7.1 Hz, 2H), 2.49-2.41 (m, 1H), 1.85 (dd, J = 12.4, 9.1 Hz, 1H), 1.50 (d, J = 5.6 Hz, 3H), 1.39 (s, 3H), 1.20 (s, 3H). |
| 633 | 487.1 | 1H NMR (400 MHz, DMSO-d6) δ 8.22-8.15 (m, 1H), 8.08 (s, 1H), 7.90 (dd, J = 8.8, 1.1 Hz, 1H), 7.72 (d, J = 8.1 Hz, 1H), 5.67 (d, J = 6.3 Hz, 1H), 5.14-5.05 (m, 1H), 4.26 (dd, J = 9.0, 5.6 Hz, 1H), 4.13 (qd, J = 7.1, 6.0, 4.1 Hz, 2H), 3.69 (dd, J = 9.0, 4.4 Hz, 1H), 3.29 (s, 1H), 3.13 (s, 3H), 2.59 (tt, J = 14.1, 6.3 Hz, 2H), 1.50 (d, J = 5.8 Hz, 3H). |

TABLE 1-continued

| Example No | ES/MS m/z (M + H)+ | 1H NMR |
|---|---|---|
| 634 | 487.0 | 1H NMR (400 MHz, DMSO-d6) δ 8.19 (d, J = 8.1 Hz, 1H), 8.09 (s, 1H), 7.90 (d, J = 8.8 Hz, 1H), 7.73 (d, J = 8.1 Hz, 1H), 5.09 (dt, J = 12.7, 6.2 Hz, 1H), 4.27 (dd, J = 9.0, 5.5 Hz, 1H), 4.14 (q, J = 4.3 Hz, 2H), 3.70 (dd, J = 9.0, 4.4 Hz, 1H), 3.36-3.21 (m, 1H), 3.14 (s, 3H), 2.68-2.51 (m, 2H), 1.50 (d, J = 5.8 Hz, 3H). |
| 635 | 487 | 1H NMR (400 MHz, DMSO-d6) δ 8.19 (d, J = 8.1 Hz, 1H), 8.08 (s, 2H), 7.90 (d, J = 8.8 Hz, 1H), 7.73 (d, J = 8.2 Hz, 1H), 5.09 (dt, J = 12.9, 6.2 Hz, 1H), 4.27 (dt, J = 9.3, 4.8 Hz, 1H), 4.14 (dq, J = 5.6, 3.3, 2.1 Hz, 2H), 3.70 (dd, J = 9.0, 4.4 Hz, 1H), 3.14 (s, 3H), 2.72-2.54 (m, 2H), 1.50 (d, J = 5.8 Hz, 3H). |
| 636 | 427.2 | 1H NMR (400 MHz, DMSO-d6) δ 8.14 (s, 1H), 7.84-7.75 (m, 2H), 7.41 (d, J = 7.9 Hz, 1H), 5.65 (d, J = 6.4 Hz, 1H), 4.24 (dd, J = 9.0, 5.6 Hz, 1H), 4.12 (t, J = 5.7 Hz, 2H), 3.67 (dd, J = 9.0, 4.4 Hz, 1H), 3.14-3.08 (m, 2H), 3.03-2.92 (m, 1H), 2.96-2.85 (m, 1H), 2.58 (dq, J = 15.5, 8.4, 7.5 Hz, 2H), 2.44-2.19 (m, 3H), 2.15-1.95 (m, 2H), 1.49 (d, J = 5.9 Hz, 3H). |
| 637 | 427.2 | 1H NMR (400 MHz,) δ 8.15 (tt, J = 8.4, 4.9 Hz, 1H), 7.86-7.75 (m, 2H), 7.42 (tt, J = 8.4, 5.0 Hz, 1H), 5.71-5.61 (m, 1H), 4.30-4.20 (m, 1H), 4.13 (dd, J = 11.1, 5.7 Hz, 2H), 3.68 (td, J = 9.2, 4.5 Hz, 1H), 3.11 (s, 2H), 3.03-2.86 (m, 2H), 2.66-2.47 (m, 3H), 2.43-2.25 (m, 3H), 2.24 (s, 1H), 2.06 (m, 2H), 1.54-1.46 (m, 3H). |
| 638 | 427.2 | 1H NMR (400 MHz, DMSO-d6) δ 8.14 (s, 1H), 7.84-7.75 (m, 2H), 7.41 (d, J = 7.9 Hz, 1H), 5.65 (d, J = 6.3 Hz, 1H), 4.24 (dd, J = 9.0, 5.6 Hz, 1H), 4.12 (dq, J = 7.2, 4.3, 3.0 Hz, 2H), 3.67 (dd, J = 8.9, 4.5 Hz, 1H), 3.11 (d, J = 6.8 Hz, 2H), 3.04-2.85 (m, 2H), 2.58 (td, J = 15.3, 7.5 Hz, 2H), 2.47-2.19 (m, 3H), 2.15-1.95 (m, 2H), 1.49 (d, J = 5.9 Hz, 3H). |
| 639 | 443.2 | 1H NMR (400 MHz, DMSO-d6) δ 8.07 (s, 1H), 7.86 (dd, J = 7.8, 1.6 Hz, 1H), 7.64-7.55 (m, 2H), 5.65 (d, J = 6.3 Hz, 1H), 4.87 (d, J = 15.5 Hz, 1H), 4.78 (d, J = 15.5 Hz, 1H), 4.24 (dd, J = 9.0, 5.6 Hz, 1H), 4.17-4.08 (m, 2H), 3.90 (d, J = 11.2 Hz, 1H), 3.67 (dd, J = 8.7, 4.1 Hz, 1H), 3.60-3.50 (m, 1H), 3.29 (s, 0H), 3.11 (s, 2H), 2.58 (dq, J = 15.3, 8.4, 7.5 Hz, 2H), 2.51-2.40 (m, 1H), 2.42-2.26 (m, 2H), 2.10-1.93 (m, 1H), 1.49 (d, J = 5.9 Hz, 3H). |
| 640 | 443.3 | 1H NMR (400 MHz, DMSO-d6) δ 8.07 (s, 1H), 7.86 (dd, J = 8.3, 1.8 Hz, 1H), 7.64-7.55 (m, 2H), 5.66 (d, J = 6.3 Hz, 1H), 4.87 (d, J = 15.5 Hz, 1H), 4.78 (d, J = 15.4 Hz, 1H), 4.24 (dd, J = 9.0, 5.6 Hz, 1H), 4.12 (m, 2H), 3.90 (d, J = 11.1 Hz, 1H), 3.68 (dd, J = 9.0, 4.4 Hz, 1H), 3.54 (dd, J = 11.1, 1.4 Hz, 1H), 3.10 (m, 2H), 2.58 (m, 2H), 2.51-2.40 (m, 1H), 2.42-2.26 (m, 2H), 2.05-1.94 (m, 1H), 1.49 (d, J = 5.9 Hz, 3H). |
| 641 | 443.3 | 1H NMR (400 MHz, DMSO-d6) δ 8.07 (s, 1H), 7.86 (dd, J = 8.3, 1.8 Hz, 1H), 7.64-7.55 (m, 2H), 5.66 (d, J = 6.3 Hz, 1H), 4.87 (d, J = 15.5 Hz, 1H), 4.78 (d, J = 15.5 Hz, 1H), 4.24 (dd, J = 9.0, 5.6 Hz, 1H), 4.12 (m, 2H), 3.90 (d, J = 11.2 Hz, 1H), 3.67 (dd, J = 9.0, 4.4 Hz, 1H), 3.54 (dd, J = 11.2, 1.4 Hz, 1H), 3.11 (m, 2H), 2.58 (td, J = 15.3, 7.5 Hz, 1H), 2.51-2.40 (m, 1H), 2.42-2.26 (m, 2H), 2.10-1.88 (m, 1H), 1.49 (d, J = 6.0 Hz, 3H). |
| 642 | 357.1 | 1H NMR (400 MHz, DMSO) δ 9.07 (s, 2H), 7.89-7.71 (m, 2H), 7.39 (d, J = 8.1 Hz, 1H), 4.49 (dt, J = 7.9, 6.1 Hz, 1H), 4.40-4.33 (m, 2H), 4.09-3.92 (m, 2H), 3.43 (d, J = 7.8 Hz, 2H), 3.09 (m, 4H), 2.65-2.51 (m, 2H), 2.45 (m, 1H), 2.06-1.93 (m, 1H), 1.51 (d, J = 6.2 Hz, 3H). |
| 643 | 391.1 | 1H NMR (400 MHz, DMSO) δ 11.64 (d, J = 5.7 Hz, 1H), 8.02 (s, 1H), 7.33 (dd, J = 6.9, 5.8 Hz, 1H), 6.78 (dd, J = 6.9, 1.1 Hz, 1H), 4.26 (dd, J = 9.0, 5.6 Hz, 1H), 4.14 (d, J = 4.3 Hz, 2H), 3.69 (dd, J = 9.0, 4.4 Hz, 1H), 3.23 (s, 2H), 2.69 (td, J = 15.1, 7.8 Hz, 3H), 1.54 (d, J = 5.7 Hz, 3H). |
| 644 | 297.1 | 1H NMR (400 MHz, CDCl3) δ 8.36 (s, 1H), 4.79 (dt, J = 8.3, 6.0 Hz, 1H), 4.41 (td, J = 9.6, 6.1 Hz, 1H), 4.30 (td, J = 9.6, 6.3 Hz, 1H), 3.88 (tt, J = 7.4, 3.9 Hz, 1H), 3.36 (dd, J = 8.2, 6.8 Hz, 2H), 3.13 (t, J = 7.9 Hz, 2H), 2.71-2.58 (m, 1H), 2.23 (p, J = 7.7 Hz, 2H), 2.09 (ddt, J = 11.6, 9.3, 6.0 Hz, 1H), 1.61 (d, J = 6.3 Hz, 3H), 1.42-1.20 (m, 4H). |
| 645 | 301.1 | 1H NMR (400 MHz, CDCl3) δ 8.57 (s, 1H), 4.90-4.71 (m, 1H), 4.68-4.56 (m, 2H), 4.42 (td, J = 9.7, 6.1 Hz, 1H), 4.29 (td, J = 9.7, 6.3 Hz, 1H), 4.13 (t, J = 4.9 Hz, 2H), 3.35 (td, J = 7.3, 3.0 Hz, 2H), 3.10 (t, J = 7.9 Hz, 2H), 2.70-2.57 (m, 1H), 2.22 (p, J = 7.7 Hz, 2H), 2.08 (ddt, J = 11.6, 9.3, 6.0 Hz, 1H), 1.60 (d, J = 6.3 Hz, 3H). |
| 646 | 423.1 | 1H NMR (400 MHz, DMSO) δ 8.83 (s, 3H), 8.08-8.01 (m, 2H), 7.81-7.74 (m, 2H), 4.26 (dd, J = 9.0, 5.4 Hz, 1H), 4.13 (q, J = 4.5 Hz, 2H), 3.69 (dd, J = 9.0, 4.3 Hz, 1H), 3.55-3.31 (m, 4H), 3.14 (m, 2H), 2.67-2.52 (m, 2H), 1.50 (d, J = 5.8 Hz, 3H). |

TABLE 1-continued

| Example No | ES/MS m/z (M + H)+ | 1H NMR |
|---|---|---|
| 647 | 364.1 | 1H NMR (400 MHz, DMSO) δ 8.93 (s, 1H), 5.76 (t, J = 7.5 Hz, 1H), 4.52 (d, J = 6.8 Hz, 5H), 4.24 (dd, J = 9.0, 5.7 Hz, 1H), 4.11 (m, 2H), 3.68 (dd, J = 9.0, 4.5 Hz, 1H), 3.25 (s, 2H), 2.74-2.57 (m, 2H), 1.51 (d, J = 5.9 Hz, 3H). |
| 648 | 407.2 | 1H NMR (400 MHz, DMSO) δ 8.78 (s, 3H), 8.03 (d, J = 8.5 Hz, 2H), 7.77 (d, J = 8.5 Hz, 2H), 4.50 (q, J = 6.6 Hz, 1H), 4.10-3.93 (m, 2H), 3.55-3.30 (m, 3H), 3.22-2.98 (m, 2H), 2.79-2.54 (m, 2H), 2.48-2.37 (m, 1H), 2.02 (td, J = 16.4, 8.6 Hz, 1H), 1.51 (d, J = 6.2 Hz, 3H). |
| 649 | 381.1 | 1H NMR (400 MHz, DMSO) δ 9.03 (s, 3H), 8.04 (d, J = 8.3 Hz, 2H), 7.70 (d, J = 8.2 Hz, 2H), 6.74-6.30 (m, 1H), 5.07 (s, 1H), 4.50 (q, J = 6.7 Hz, 1H), 4.10-3.93 (m, 2H), 3.11 (s, 2H), 2.66-2.52 (m, 2H), 2.02 (d, J = 9.5 Hz, 1H), 1.51 (d, J = 6.2 Hz, 3H). |
| 650 | 381.1 | 1H NMR (400 MHz, DMSO) δ 9.04 (s, 3H), 8.04 (d, J = 8.3 Hz, 2H), 7.70 (d, J = 8.3 Hz, 2H), 6.52 (td, J = 53.7, 3.5 Hz, 1H), 5.07 (s, 1H), 4.50 (q, J = 6.7 Hz, 1H), 4.14-3.90 (m, 2H), 3.12 (s, 2H), 2.68-2.53 (m, 2H), 2.02 (td, J = 17.0, 9.2 Hz, 1H), 1.51 (d, J = 6.2 Hz, 3H). |
| 651 | 345.2 | 1H NMR (400 MHz, DMSO) δ 9.02 (s, 3H), 7.97 (d, J = 8.2 Hz, 2H), 7.65 (d, J = 8.3 Hz, 2H), 6.51 (td, J = 53.7, 3.4 Hz, 1H), 5.03 (s, 1H), 4.40 (q, J = 6.7 Hz, 1H), 4.05-3.73 (m, 2H), 3.00 (td, J = 7.0, 3.4 Hz, 2H), 2.81 (t, J = 7.7 Hz, 2H), 2.47-2.20 (m, 1H), 1.99 (dp, J = 16.9, 7.9 Hz, 3H), 1.49 (d, J = 6.2 Hz, 3H). |
| 652 | 345.1 | 1H NMR (400 MHz, DMSO) δ 9.02 (s, 3H), 7.97 (d, J = 8.4 Hz, 2H), 7.66 (d, J = 8.2 Hz, 2H), 6.51 (td, J = 53.7, 3.4 Hz, 1H), 5.04 (s, 1H), 4.40 (h, J = 6.4 Hz, 1H), 4.08-3.83 (m, 2H), 3.12-2.87 (m, 2H), 2.81 (t, J = 7.7 Hz, 2H), 2.44-2.24 (m, 1H), 1.99 (ddd, J = 16.1, 8.7, 6.3 Hz, 3H), 1.49 (d, J = 6.2 Hz, 3H). |
| 653 | 348.1 | 1H NMR (400 MHz, DMSO) δ 8.91 (s, 1H), 5.85-5.66 (m, 1H), 4.51 (m, 6H), 4.06-3.94 (m, 2H), 3.24 (s, 2H), 2.63 (dd, J = 16.0, 9.0 Hz, 2H), 2.00 (s, 1H), 1.53 (d, J = 6.2 Hz, 3H). |
| 654 | 369.1 | 1H NMR (400 MHz, DMSO) δ 8.92 (d, J = 1.2 Hz, 1H), 8.42 (d, J = 2.0 Hz, 1H), 8.12-8.07 (m, 1H), 8.07-7.97 (m, 2H), 7.79 (t, J = 8.0 Hz, 1H), 4.57-4.42 (m, 1H), 4.12-3.89 (m, 2H), 3.19 (d, J = 7.9 Hz, 2H), 2.83 (d, J = 6.9 Hz, 1H), 2.61 (qd, J = 14.0, 6.6 Hz, 2H), 2.01 (dt, J = 16.9, 7.3 Hz, 1H), 1.53 (d, J = 6.2 Hz, 3H). |
| 655 | 369.1 | 1H NMR (400 MHz, CDCl3) δ 8.14-8.04 (m, 3H), 7.95-7.86 (m, 3H), 4.62 (dt, J = 8.0, 6.1 Hz, 1H), 4.26-4.06 (m, 2H), 3.14 (tt, J = 6.0, 3.3 Hz, 2H), 2.67-2.44 (m, 3H), 2.11-1.99 (m, 1H), 1.61 (d, J = 6.2 Hz, 3H). |
| 656 | 407.2 | 1H NMR (400 MHz, DMSO) δ 8.82 (s, 3H), 8.39-8.30 (m, 2H), 8.02 (d, J = 8.2 Hz, 1H), 5.39 (s, 1H), 4.57-4.49 (m, 1H), 4.21 (dd, J = 14.1, 8.0 Hz, 1H), 4.10-3.97 (m, 2H), 3.71 (dd, J = 14.0, 5.7 Hz, 1H), 3.13 (s, 2H), 2.75-2.51 (m, 3H), 2.00 (d, J = 9.4 Hz, 1H), 1.51 (d, J = 6.2 Hz, 3H). |
| 657 | 373.1 | 1H NMR (400 MHz, DMSO-d6) δ 9.06 (s, 2H), 7.86-7.74 (m, 2H), 7.40 (d, J = 8.1 Hz, 1H), 4.36 (d, J = 4.9 Hz, 2H), 4.25 (dd, J = 9.0, 5.5 Hz, 1H), 4.12 (q, J = 4.7 Hz, 2H), 3.68 (dd, J = 9.0, 4.3 Hz, 1H), 3.44 (d, J = 6.6 Hz, 2H), 3.10 (q, J = 7.4, 6.4 Hz, 4H), 2.67-2.53 (m, 2H), 1.49 (d, J = 5.8 Hz, 3H). |
| 658 | 423.1 | 1H NMR (400 MHz, DMSO-d6) δ 8.84 (s, 3H), 8.36 (d, J = 8.0 Hz, 1H), 8.32 (d, J = 1.5 Hz, 1H), 8.03 (d, J = 8.2 Hz, 1H), 5.40 (t, J = 7.0 Hz, 1H), 4.34-4.06 (m, 4H), 3.75-3.67 (m, 2H), 3.13 (s, 2H), 2.69-2.54 (m, 2H), 1.49 (d, J = 5.8 Hz, 3H). |
| 659 | 397.1 | 1H NMR (400 MHz, DMSO-d6) δ 9.06 (s, 3H), 8.05 (d, J = 8.3 Hz, 2H), 7.71 (d, J = 8.2 Hz, 2H), 6.53 (td, J = 53.7, 3.5 Hz, 1H), 5.07 (t, J = 12.9 Hz, 1H), 4.26 (dd, J = 9.0, 5.5 Hz, 1H), 4.13 (q, J = 4.3 Hz, 2H), 3.69 (dd, J = 9.0, 4.3 Hz, 1H), 3.13 (s, 2H), 2.70-2.53 (m, 2H), 1.49 (d, J = 5.8 Hz, 3H). |
| 660 | 392.1 | 1H NMR (400 MHz, DMSO-d6) δ 9.05 (s, 3H), 8.14-8.02 (m, 2H), 7.73 (d, J = 8.1 Hz, 2H), 6.53 (td, J = 53.8, 3.4 Hz, 1H), 5.25 (dd, J = 8.4, 6.7 Hz, 1H), 5.08 (t, J = 12.9 Hz, 1H), 4.24-4.05 (m, 2H), 3.20 (s, 2H), 2.80-2.57 (m, 4H). |
| 661 | 391.1 | 1H NMR (400 MHz, DMSO) δ 8.07-7.99 (m, 2H), 7.90 (d, J = 8.1 Hz, 1H), 4.51 (h, J = 6.3 Hz, 1H), 4.11-3.94 (m, 2H), 3.76 (dd, J = 7.8, 6.0 Hz, 2H), 3.55-3.36 (m, 2H), 3.12 (tq, J = 6.0, 3.2 Hz, 2H), 2.66-2.51 (m, 2H), 2.45 (dq, J = 8.8, 4.0 Hz, 1H), 2.10-1.94 (m, 1H), 1.51 (d, J = 6.2 Hz, 3H). |
| 662 | 423.1 | 1H NMR (400 MHz, DMSO) δ 8.84 (s, 3H), 8.40-8.30 (m, 2H), 8.03 (d, J = 8.2 Hz, 1H), 5.40 (t, J = 7.0 Hz, 1H), 4.32-4.13 (m, 2H), 4.14 (s, 2H), 3.86 (s, 4H), 3.76-3.66 (m, 2H), 3.13 (s, 2H), 2.67-2.52 (m, 2H), 1.49 (d, J = 5.7 Hz, 3H). |
| 663 | 423.1 | 1H NMR (400 MHz, DMSO) δ 8.84 (s, 3H), 8.40-8.30 (m, 2H), 8.03 (d, J = 8.2 Hz, 1H), 5.70 (s, 1H), 5.40 (t, J = 6.9 Hz, 1H), 4.32-4.12 (m, 4H), 3.76-3.66 (m, 2H), 3.13 (s, 2H), 2.60 (m, 2H), 1.49 (d, J = 5.8 Hz, 3H). |

TABLE 1-continued

| Example No | ES/MS m/z (M + H)+ | 1H NMR |
|---|---|---|
| 664 | 407.1 | 1H NMR (400 MHz, DMSO) δ 8.05-7.96 (m, 2H), 7.84 (d, J = 8.1 Hz, 1H), 4.26 (dd, J = 9.0, 5.5 Hz, 1H), 4.13 (q, J = 4.5 Hz, 2H), 3.69 (dd, J = 9.1, 4.3 Hz, 1H), 3.63 (t, J = 6.9 Hz, 2H), 3.41 (q, J = 6.6 Hz, 2H), 3.13 (m, 2H), 2.60 (m, 2H), 1.49 (d, J = 5.7 Hz, 3H). |
| 665 | 501 | 1H NMR (400 MHz, DMSO) δ 8.30 (d, J = 8.2 Hz, 1H), 8.24 (d, J = 1.4 Hz, 1H), 8.12-8.05 (m, 1H), 7.88 (d, J = 8.2 Hz, 1H), 5.40 (q, J = 7.7 Hz, 1H), 4.29 (dt, J = 15.3, 7.9 Hz, 2H), 4.14 (t, J = 5.1 Hz, 2H), 3.70 (dd, J = 9.0, 4.3 Hz, 1H), 3.52 (d, J = 13.4, 7.2 Hz, 1H), 3.19 (s, 3H), 3.14 (s, 2H), 2.61 (ddt, J = 22.6, 15.4, 7.2 Hz, 2H), 1.50 (d, J = 5.8 Hz, 3H). |
| 666 | 407.1 | 1H NMR (400 MHz, DMSO) δ 8.20 (s, 1H), 8.14 (dd, J = 8.1, 1.7 Hz, 1H), 7.67 (d, J = 8.1 Hz, 1H), 4.27 (dd, J = 9.0, 5.5 Hz, 1H), 4.13 (t, J = 4.9 Hz, 2H), 3.70 (dd, J = 9.0, 4.3 Hz, 1H), 3.65 (t, J = 6.9 Hz, 2H), 3.41 (q, J = 6.5 Hz, 2H), 3.14 (s, 2H), 2.62 (tt, J = 15.4, 6.6 Hz, 2H), 1.56-1.46 (m, 3H). |
| 667 | 435.1 | 1H NMR (400 MHz, DMSO) δ 7.58 (d, J = 8.5 Hz, 1H), 7.44 (d, J = 7.7 Hz, 1H), 7.33 (t, J = 7.8 Hz, 1H), 7.08 (dd, J = 8.3, 2.0 Hz, 1H), 5.65 (d, J = 6.2 Hz, 1H), 4.24 (dd, J = 8.9, 5.5 Hz, 1H), 4.14-4.07 (m, 2H), 3.67 (dd, J = 9.0, 4.3 Hz, 1H), 3.22 (s, 3H), 3.09 (s, 2H), 2.85 (qd, J = 9.1, 5.2 Hz, 1H), 2.58 (td, J = 15.2, 7.4 Hz, 1H), 1.49 (d, J = 5.7 Hz, 3H), 1.26-0.95 (m, 4H). |
| 668 | 419.1 | 1H NMR (400 MHz, DMSO) δ 7.56 (d, J = 7.7 Hz, 1H), 7.43 (d, J = 7.8 Hz, 1H), 7.33 (t, J = 7.9 Hz, 1H), 7.08 (d, J = 8.3 Hz, 1H), 4.48 (q, J = 6.5 Hz, 1H), 4.06-3.93 (m, 2H), 3.21 (s, 3H), 3.08 (s, 2H), 2.88-2.81 (m, 1H), 2.57 (q, J = 8.4 Hz, 1H), 1.45 (m, 1H), 1.98 (d, J = 8.8 Hz, 1H), 1.54-1.48 (m, 4H), 1.41-1.13 (m, 1H), 1.13-0.99 (m, 3H). |
| 669 | 419.1 | 1H NMR (400 MHz, DMSO) δ 7.52 (s, 1H), 7.45 (d, J = 7.8 Hz, 1H), 7.36 (t, J = 7.8 Hz, 1H), 7.06 (d, J = 7.8 Hz, 1H), 4.48 (q, J = 6.7 Hz, 1H), 4.12-3.91 (m, 2H), 3.32 (m, 4H), 3.09 (s, 2H), 2.56 (m, 2H), 2.22 (m, 1H), 2.17-2.05 (m, 2H), 1.97 (m, 2H), 1.51 (d, J = 6.2 Hz, 3H). |
| 670 | 427.1 | 1H NMR (400 MHz, DMSO) δ 8.17 (s, 1H), 7.77 (s, 1H), 7.50 (m, 3H), 6.62 (dd, J = 8.4, 3.5 Hz, 1H), 5.01 (dd, J = 10.7, 8.4 Hz, 1H), 4.91 (dd, J = 10.8, 3.5 Hz, 1H), 4.25 (dd, J = 9.0, 5.6 Hz, 1H), 4.12 (d, J = 5.0 Hz, 2H), 3.68 (dd, J = 9.0, 4.3 Hz, 1H), 3.12 (s, 2H), 2.68-2.54 (m, 2H), 1.49 (d, J = 5.7 Hz, 3H). |
| 671 | 435.1 | 1H NMR (400 MHz, DMSO) δ 7.54 (d, J = 2.3 Hz, 1H), 7.46 (d, J = 7.7 Hz, 1H), 7.37 (t, J = 7.8 Hz, 1H), 7.10-7.03 (m, 1H), 5.65 (d, J = 6.2 Hz, 1H), 4.24 (dd, J = 9.0, 5.5 Hz, 1H), 4.12 (p, J = 4.7 Hz, 2H), 3.67 (dd, J = 8.9, 4.4 Hz, 1H), 3.40 (dt, J = 13.1, 6.7 Hz, 2H), 3.32-3.21 (m, 2H), 3.13-3.07 (m, 2H), 2.58 (dq, J = 15.6, 7.5 Hz, 2H), 2.16 (ddd, J = 49.0, 14.7, 8.3 Hz, 4H), 1.50 (d, J = 5.7 Hz, 3H). |
| 672 | 450.1 | 1H NMR (400 MHz, DMSO) δ 8.98 (s, 2H), 7.61 (d, J = 2.3 Hz, 1H), 7.54 (d, J = 7.8 Hz, 1H), 7.42 (t, J = 7.8 Hz, 1H), 7.17 (dd, J = 7.9, 2.2 Hz, 1H), 5.66 (s, 1H), 4.24 (dd, J = 9.0, 5.7 Hz, 1H), 4.11 (q, J = 5.2 Hz, 2H), 3.77-3.46 (m, 9H), 3.11 (d, J = 7.8 Hz, 2H), 2.59 (td, J = 15.1, 7.2 Hz, 2H), 1.50 (d, J = 5.8 Hz, 3H). |
| 673 | 451.0 | 1H NMR (400 MHz, DMSO) δ 7.61 (s, 1H), 7.48 (d, J = 7.7 Hz, 1H), 7.37 (t, J = 7.8 Hz, 1H), 7.15 (d, J = 7.9 Hz, 1H), 5.65 (d, J = 6.3 Hz, 1H), 4.24 (dd, J = 8.7, 5.9 Hz, 1H), 4.14-4.04 (m, 4H), 3.94 (t, J = 10.5 Hz, 2H), 3.67 (dd, J = 9.0, 4.3 Hz, 1H), 3.50 (m, 2H), 3.41 (dd, J = 11.9, 7.8 Hz, 2H), 3.11 (s, 2H), 2.64-2.53 (m, 1H), 1.50 (d, J = 5.7 Hz, 3H). |
| 674 | 503.0 | m1H NMR (400 MHz, DMSO) δ 8.31 (d, J = 8.1 Hz, 1H), 8.26 (s, 1H), 8.09 (d, J = 8.8 Hz, 1H), 7.88 (d, J = 8.2 Hz, 1H), 5.40 (q, J = 7.7 Hz, 1H), 5.17 (m, 1H), 4.63-4.37 (m, 2H), 4.30 (dd, J = 13.4, 7.5 Hz, 1H), 4.13-3.97 (m, 1H), 3.52 (m, 1H), 3.19 (s, 3H), 3.15 (s, 2H), 2.61 (m, 2H), 1.55 (d, J = 6.5 Hz, 3H). |
| 675 | 521.0 | 1H NMR (400 MHz, DMSO) δ 8.36-8.27 (m, 2H), 8.09 (d, J = 8.9 Hz, 1H), 7.88 (d, J = 8.1 Hz, 1H), 5.41 (q, J = 7.7 Hz, 1H), 4.86 (dt, J = 14.5, 7.2 Hz, 1H), 4.52 (t, J = 12.3 Hz, 2H), 4.30 (dd, J = 13.5, 7.4 Hz, 1H), 3.50 (m, 3H), 3.20 (s, 3H), 2.71-2.52 (m, 2H), 1.52 (d, J = 6.5 Hz, 3H). |
| 676 | 458.2 | 1H NMR (400 MHz, DMSO) δ 8.77 (s, 1H), 7.86 (d, J = 1.5 Hz, 1H), 7.79 (dd, J = 8.0, 1.6 Hz, 1H), 7.31 (d, J = 8.0 Hz, 1H), 4.94 (ddd, J = 48.5, 10.3, 3.3 Hz, 1H), 4.73-4.66 (m, 1H), 4.63-4.54 (m, 1H), 4.07-3.94 (m, 2H), 3.11 (dd, J = 8.3, 4.7 Hz, 4H), 2.91 (s, 3H), 2.67-2.53 (m, 3H), 2.46-2.30 (m, 2H), 2.24 (dt, J = 13.2, 8.2 Hz, 1H). |
| 677 | 407.2 | 1H NMR (400 MHz, DMSO) δ 8.01-7.94 (m, 2H), 7.80-7.73 (m, 2H), 5.83 (d, J = 7.0 Hz, 1H), 5.03-4.79 (m, 2H), 4.73 (d, J = 6.1 Hz, 2H), 4.69 (d, J = 6.1 Hz, 2H), 4.53 (q, J = 5.8 Hz, 1H), 4.37-4.18 (m, 2H), 3.76 (dd, J = 8.9, 4.9 Hz, 1H), 3.17 (s, 2H), 2.71-2.54 (m, 4H). |

TABLE 1-continued

| | | MS and NMR DATA |
|---|---|---|
| Example No | ES/MS m/z (M + H)+ | 1H NMR |
| 678 | 409.2 | 1H NMR (400 MHz, DMSO) δ 8.04-7.93 (m, 2H), 7.80-7.73 (m, 2H), 6.45 (t, J = 57.0 Hz, 1H), 4.84-4.74 (m, 1H), 4.73 (d, J = 6.0 Hz, 2H), 4.69 (d, J = 6.0 Hz, 2H), 4.07 (h, J = 8.1 Hz, 2H), 3.26-3.04 (m, 2H), 2.62 (dq, J = 15.7, 7.5 Hz, 4H), 2.48-2.39 (m, 2H). |
| 679 | 503.1 | 1H NMR (400 MHz, DMSO) δ 8.31 (dd, J = 8.2, 1.7 Hz, 1H), 8.26 (d, J = 1.6 Hz, 1H), 8.09 (d, J = 8.9 Hz, 1H), 7.88 (d, J = 8.1 Hz, 1H), 5.40 (q, J = 7.7 Hz, 1H), 5.17 (ddt, J = 56.9, 6.7, 3.7 Hz, 1H), 4.58-4.37 (m, 2H), 4.30 (dd, J = 13.4, 7.5 Hz, 1H), 4.04 (ddd, J = 25.7, 10.5, 3.8 Hz, 1H), 3.52 (dd, J = 13.4, 7.2 Hz, 1H), 3.19 (s, 3H), 3.18-3.05 (m, 2H), 2.61 (ddd, J = 22.2, 15.1, 6.6 Hz, 2H), 1.55 (d, J = 6.5 Hz, 3H). |
| 680 | 503.1 | 1H NMR (400 MHz, DMSO) δ 8.31 (dd, J = 8.2, 1.7 Hz, 1H), 8.26 (d, J = 1.6 Hz, 1H), 8.11-8.06 (m, 1H), 7.88 (d, J = 8.2 Hz, 1H), 5.40 (t, J = 7.3 Hz, 1H), 5.27-5.03 (m, 1H), 4.60-4.36 (m, 2H), 4.30 (dd, J = 13.4, 7.5 Hz, 1H), 4.04 (ddd, J = 25.6, 10.5, 3.9 Hz, 1H), 3.52 (dd, J = 13.4, 7.2 Hz, 1H), 3.19 (s, 3H), 3.18-3.05 (m, 2H), 2.62 (td, J = 15.3, 7.3 Hz, 2H), 1.55 (d, J = 6.5 Hz, 3H). |
| 681 | 521.1 | 1H NMR (400 MHz, DMSO) δ 8.36-8.27 (m, 2H), 8.09 (s, 1H), 7.88 (d, J = 8.2 Hz, 1H), 5.40 (s, 1H), 4.86 (dt, J = 14.9, 7.3 Hz, 1H), 4.52 (t, J = 12.3 Hz, 2H), 4.31 (dd, J = 13.4, 7.5 Hz, 1H), 3.58-3.46 (m, 2H), 3.20 (m, 5H), 2.62 (m, 2H), 1.52 (d, J = 6.5 Hz, 3H). |
| 682 | 521.1 | 1H NMR (400 MHz, DMSO) δ 8.36-8.27 (m, 2H), 8.09 (d, J = 8.7 Hz, 1H), 7.88 (d, J = 8.1 Hz, 1H), 5.41 (q, J = 7.7 Hz, 1H), 4.86 (dt, J = 14.7, 7.2 Hz, 1H), 4.52 (t, J = 12.3 Hz, 2H), 4.30 (dd, J = 13.4, 7.5 Hz, 1H), 3.57-3.48 (m, 1H), 3.20 (m, 5H), 2.62 (td, J = 15.3, 7.7 Hz, 2H), 1.52 (d, J = 6.5 Hz, 3H). |
| 683 | 427.2 | 1H NMR (400 MHz, DMSO) δ 8.06-7.98 (m, 2H), 7.80-7.74 (m, 2H), 5.08 (q, J = 7.1 Hz, 1H), 4.74 (d, J = 6.1 Hz, 2H), 4.69 (d, J = 6.0 Hz, 2H), 4.21-4.07 (m, 2H), 3.25-3.10 (m, 1H), 2.73-2.54 (m, 3H), 2.47-2.34 (m, 2H). |
| 684 | 394.2 | 1H NMR (400 MHz, DMSO) δ 7.63 (q, J = 2.0 Hz, 1H), 7.45 (ddt, J = 7.8, 2.0, 1.1 Hz, 1H), 7.34 (t, J = 7.8 Hz, 1H), 7.16 (ddt, J = 7.9, 2.0, 1.0 Hz, 1H), 4.48 (dt, J = 7.9, 6.1 Hz, 1H), 4.08-3.91 (m, 2H), 3.19 (s, 3H), 3.13-3.03 (m, 2H), 2.57 (dq, J = 15.5, 7.4 Hz, 2H), 2.44 (dtd, J = 10.7, 8.7, 4.9 Hz, 1H), 1.99 (ddt, J = 10.8, 8.9, 6.8 Hz, 1H), 1.52 (d, J = 6.2 Hz, 3H). |
| 685 | 470.3 | 1H NMR (400 MHz, DMSO) δ 8.78 (s, 1H), 7.86 (s, 1H), 7.81 (dd, J = 8.0, 1.6 Hz, 1H), 7.27 (d, J = 8.0 Hz, 1H), 5.65 (d, J = 6.0 Hz, 1H), 4.25 (dd, J = 9.0, 5.5 Hz, 1H), 4.12 (q, J = 4.9 Hz, 2H), 3.68 (dd, J = 9.0, 4.4 Hz, 1H), 3.45 (q, J = 7.2 Hz, 2H), 3.11 (d, J = 7.9 Hz, 4H), 2.65-2.51 (m, 2H), 2.24 (dt, J = 13.2, 8.3 Hz, 1H), 1.49 (d, J = 5.8 Hz, 3H), 1.13 (t, J = 7.2 Hz, 3H). |
| 686 | 486.3 | 1H NMR (400 MHz, DMSO) δ 8.76 (s, 1H), 7.86 (s, 1H), 7.83-7.77 (m, 1H), 7.31 (d, J = 8.0 Hz, 1H), 5.65 (d, J = 6.2 Hz, 1H), 4.85 (t, J = 5.6 Hz, 1H), 4.25 (dd, J = 9.0, 5.5 Hz, 1H), 4.12 (q, J = 4.8 Hz, 2H), 3.68 (dd, J = 9.0, 4.4 Hz, 1H), 3.60-3.42 (m, 4H), 3.12 (t, J = 7.1 Hz, 4H), 2.66-2.51 (m, 3H), 2.24 (m, 1H), 1.49 (d, J = 5.8 Hz, 3H). |
| 687 | 409.1 | 41H NMR (400 MHz, DMSO) δ 9.13 (s, 2H), 8.15-8.04 (m, 2H), 7.77-7.62 (m, 2H), 6.45 (m, 1H), 4.98 (s, 4H), 4.87-4.64 (m, 1H), 4.08 (m, 2H), 3.17 (m, 2H), 2.80-2.55 (m, 2H), 2.48-2.29 (m, 2H). |
| 688 | 409.2 | 1H NMR (400 MHz, DMSO) δ 9.13 (s, 2H), 8.15-8.04 (m, 2H), 7.77-7.62 (m, 2H), 6.45 (m, 1H), 4.98 (s, 4H), 4.87-4.64 (m, 1H), 4.08 (m, 2H), 3.17 (m, 2H), 2.80-2.55 (m, 2H), 2.48-2.29 (m, 2H). |
| 689 | 472.3 | 1H NMR (400 MHz, DMSO) δ 9.04 (s, 1H), 7.51 (dt, J = 8.0, 1.3 Hz, 1H), 7.44 (d, J = 1.4 Hz, 1H), 7.38 (d, J = 7.9 Hz, 1H), 5.66 (d, J = 5.5 Hz, 1H), 4.78 (d, J = 10.5 Hz, 1H), 4.58 (d, J = 10.5 Hz, 1H), 4.24 (dd, J = 9.0, 5.6 Hz, 1H), 4.11 (d, J = 5.6 Hz, 2H), 3.67 (dd, J = 8.9, 4.4 Hz, 1H), 3.48 (q, J = 7.1 Hz, 2H), 3.10 (s, 2H), 2.58 (dq, J = 15.4, 7.5 Hz, 2H), 1.48 (d, J = 5.7 Hz, 3H), 1.17 (t, J = 7.2 Hz, 3H). |
| 690 | 486.3 | 1H NMR (400 MHz, DMSO) δ 9.01 (s, 1H), 7.51 (dt, J = 7.9, 1.3 Hz, 1H), 7.43 (d, J = 1.5 Hz, 1H), 7.37 (d, J = 7.9 Hz, 1H), 5.66 (d, J = 6.2 Hz, 1H), 4.77 (d, J = 10.5 Hz, 1H), 4.58 (d, J = 10.5 Hz, 1H), 4.23 (p, J = 7.0 Hz, 2H), 4.12 (t, J = 5.3 Hz, 2H), 3.67 (dd, J = 9.0, 4.4 Hz, 1H), 3.10 (s, 2H), 2.58 (dq, J = 15.4, 7.4 Hz, 2H), 1.51-1.45 (m, 3H), 1.38 (d, J = 6.9 Hz, 6H). |
| 691 | 394.1 | 1H NMR (400 MHz, DMSO) δ 7.63 (d, J = 2.0 Hz, 1H), 7.44 (dt, J = 7.7, 1.4 Hz, 1H), 7.33 (t, J = 7.8 Hz, 1H), 7.19-7.11 (m, 1H), 4.48 (dt, J = 7.8, 6.0 Hz, 1H), 4.08-3.91 (m, 3H), 3.18 (s, 3H), 3.08 (tt, J = 8.8, 2.9 Hz, 1H), 2.67-2.53 (m, 2H), 2.46-2.38 (m, 1H), 2.00 (ddt, J = 10.8, 8.9, 6.8 Hz, 1H), 1.52 (d, J = 6.2 Hz, 3H). |
| 692 | 394.1 | 1H NMR (400 MHz, DMSO) δ 7.62 (d, J = 2.0 Hz, 1H), 7.43 (d, J = 8.1 Hz, 1H), 7.32 (t, J = 7.8 Hz, 1H), 7.15 (dd, J = 7.9, 2.2 Hz, 1H), 4.48 (q, J = 6.6 Hz, 1H), 4.08-3.91 (m, 2H), 3.17 (s, 3H), 3.12-2.94 (m, 1H), 2.74-2.52 (m, 2H), 2.45-2.21 (m, 1H), 2.05-1.89 (m, 2H), 1.52 (d, J = 6.2 Hz, 3H). |

TABLE 1-continued

MS and NMR DATA

| Example No | ES/MS m/z (M + H)+ | 1H NMR |
|---|---|---|
| 693 | 486.3 | 1H NMR (400 MHz, DMSO) δ 9.05 (s, 1H), 7.52 (d, J = 8.0 Hz, 1H), 7.44 (d, J = 1.4 Hz, 1H), 7.35 (d, J = 7.9 Hz, 1H), 5.66 (d, J = 6.1 Hz, 1H), 4.78 (d, J = 10.5 Hz, 1H), 4.59 (d, J = 10.5 Hz, 1H), 4.24 (dd, J = 9.0, 5.5 Hz, 1H), 4.12 (d, J = 5.4 Hz, 2H), 3.67 (dd, J = 9.0, 4.4 Hz, 1H), 3.41 (t, J = 7.0 Hz, 2H), 3.10 (s, 2H), 2.58 (m, 1H), 1.61 (h, J = 7.3 Hz, 2H), 1.48 (d, J = 5.7 Hz, 3H), 0.89 (t, J = 7.4 Hz, 3H). |
| 694 | 500.3 | 1H NMR (400 MHz, DMSO) δ 9.13 (s, 1H), 7.57-7.46 (m, 2H), 7.43 (s, 1H), 5.66 (d, J = 6.3 Hz, 1H), 5.18-5.04 (m, 3H), 4.79 (d, J = 10.6 Hz, 1H), 4.69 (td, J = 6.6, 4.1 Hz, 2H), 4.56 (d, J = 10.6 Hz, 1H), 4.24 (dd, J = 9.0, 5.5 Hz, 1H), 4.12 (d, J = 5.4 Hz, 2H), 3.67 (dd, J = 9.0, 4.4 Hz, 1H), 3.10 (s, 2H), 2.59 (m, 2H), 1.48 (d, J = 5.7 Hz, 3H). |
| 695 | 444.3 | 1H NMR (400 MHz, DMSO) δ 7.56-7.47 (m, 2H), 7.38-7.32 (m, 2H), 5.65 (d, J = 6.3 Hz, 1H), 4.63 (d, J = 9.8 Hz, 1H), 4.43 (d, J = 9.8 Hz, 1H), 4.24 (dd, J = 9.0, 5.6 Hz, 1H), 4.11 (d, J = 5.6 Hz, 2H), 3.71-3.60 (m, 2H), 3.57 (d, J = 9.3 Hz, 1H), 3.10 (s, 2H), 2.70 (s, 3H), 2.57 (m, 2H), 1.48 (d, J = 5.9 Hz, 3H). |
| 696 | 427.2 | 1H NMR (400 MHz, DMSO) δ 8.05-7.98 (m, 2H), 7.81-7.73 (m, 2H), 5.08 (dt, J = 9.1, 6.3 Hz, 1H), 4.79-4.65 (m, 4H), 4.14 (m, 2H), 3.26-3.13 (m, 2H), 2.63 (m, 4H), 2.43 (m, 2H). |
| 697 | 472.1 | 1H NMR (400 MHz, DMSO) δ 9.04 (s, 1H), 7.52 (dd, J = 7.9, 1.5 Hz, 1H), 7.44 (d, J = 1.4 Hz, 1H), 7.38 (d, J = 7.9 Hz, 1H), 4.79 (d, J = 10.5 Hz, 1H), 4.59 (d, J = 10.5 Hz, 1H), 4.25 (dd, J = 9.0, 5.6 Hz, 1H), 4.13 (h, J = 3.2 Hz, 2H), 3.68 (dd, J = 9.0, 4.4 Hz, 1H), 3.49 (q, J = 7.1 Hz, 2H), 3.11 (h, J = 3.3 Hz, 2H), 2.65-2.51 (m, 2H), 1.49 (d, J = 5.8 Hz, 3H), 1.17 (t, J = 7.2 Hz, 3H). |
| 698 | 472.1 | 1H NMR (400 MHz, DMSO) δ 9.04 (s, 1H), 7.51 (dd, J = 7.9, 1.5 Hz, 1H), 7.44 (d, J = 1.4 Hz, 1H), 7.38 (d, J = 7.9 Hz, 1H), 4.79 (d, J = 10.5 Hz, 1H), 4.59 (d, J = 10.5 Hz, 1H), 4.25 (dd, J = 9.0, 5.5 Hz, 1H), 4.12 (q, J = 4.2 Hz, 2H), 3.68 (m, 1H), 3.49 (q, J = 7.1 Hz, 2H), 3.16-3.05 (m, 2H), 2.68-2.52 (m, 2H), 1.49 (d, J = 5.8 Hz, 3H), 1.17 (t, J = 7.2 Hz, 3H). |
| 699 | 526.3 | 1H NMR (400 MHz, DMSO) δ 9.37 (s, 1H), 7.55 (dt, J = 7.9, 1.4 Hz, 1H), 7.46 (d, J = 1.4 Hz, 1H), 7.32 (d, J = 7.9 Hz, 1H), 5.66 (d, J = 6.2 Hz, 1H), 4.81 (d, J = 10.7 Hz, 1H), 4.63 (d, J = 10.7 Hz, 1H), 4.35-4.20 (m, 2H), 4.12 (q, J = 4.8 Hz, 2H), 3.68 (dd, J = 9.0, 4.4 Hz, 1H), 3.10 (s, 2H), 2.58 (m, 2H), 1.48 (d, J = 5.7 Hz, 3H). |
| 700 | 474.3 | 1H NMR (400 MHz, DMSO) δ 7.52 (d, J = 0.9 Hz, 2H), 7.38-7.30 (m, 2H), 5.65 (d, J = 6.4 Hz, 1H), 4.73 (t, J = 5.4 Hz, 1H), 4.62 (d, J = 9.8 Hz, 1H), 4.44 (d, J = 9.8 Hz, 1H), 4.24 (dd, J = 9.0, 5.7 Hz, 1H), 4.11 (q, J = 6.2 Hz, 2H), 3.76-3.63 (m, 3H), 3.53 (q, J = 5.7 Hz, 2H), 3.19 (td, J = 5.7, 1.2 Hz, 2H), 3.10 (s, 2H), 2.58 (m, 2H), 1.48 (d, J = 5.8 Hz, 3H). |
| 701 | 444.3 | 1H NMR (400 MHz, DMSO) δ 7.51 (d, J = 1.6 Hz, 2H), 7.35 (d, J = 3.9 Hz, 2H), 4.63 (d, J = 9.8 Hz, 1H), 4.43 (d, J = 9.8 Hz, 1H), 4.24 (dd, J = 8.9, 5.4 Hz, 1H), 4.11 (t, J = 4.7 Hz, 2H), 3.66 (dd, J = 14.0, 9.1 Hz, 2H), 3.57 (d, J = 9.3 Hz, 1H), 3.09 (m, 2H), 2.70 (s, 3H), 2.63-2.52 (m, 2H), 1.48 (d, J = 5.8 Hz, 3H). |
| 702 | 444.3 | 1H NMR (400 MHz, DMSO) δ 7.51 (m, 2H), 7.35 (m, 2H), 4.63 (d, J = 9.8 Hz, 1H), 4.43 (d, J = 9.8 Hz, 1H), 4.24 (dd, J = 8.9, 5.5 Hz, 1H), 4.11 (t, J = 4.6 Hz, 2H), 3.71-3.60 (m, 2H), 3.58 (m, 2H), 3.10 (s, 2H), 2.70 (s, 3H), 2.63-2.52 (m, 2H), 1.48 (d, J = 5.9 Hz, 3H). |
| 703 | 482.2 | 1H NMR (400 MHz, DMSO) δ 11.09 (s, 1H), 8.75 (s, 1H), 7.55 (dd, J = 7.9, 1.5 Hz, 1H), 7.51-7.42 (m, 2H), 5.08 (m, 1H), 4.78 (d, J = 10.4 Hz, 1H), 4.57 (d, J = 10.4 Hz, 1H), 4.12 (m, 2H), 3.16 (m, 1H), 2.71-2.53 (m, 3H), 2.42 (m, 2H). |
| 704 | 313.1 | 1H NMR (400 MHz, DMSO) δ 8.78 (s, 1H), 5.99-5.88 (m, 1H), 5.01 (m, 4H), 4.40 (s, 1H), 4.11-3.84 (m, 3H), 3.23-3.09 (m, 2H), 2.81 (t, J = 7.8 Hz, 2H), 2.18-1.87 (m, 3H), 1.50 (d, J = 6.2 Hz, 3H). |
| 705 | 433.1 | 1H NMR (400 MHz, DMSO-d6) δ 8.42 (t, J = 5.7 Hz, 1H), 7.78 (d, J = 8.1 Hz, 1H), 7.71 (dd, J = 8.1, 1.7 Hz, 1H), 7.58 (d, J = 1.7 Hz, 1H), 4.42-4.32 (m, 1H), 4.30-4.21 (m, 1H), 4.17-4.05 (m, 2H), 3.69 (dd, J = 9.0, 4.3 Hz, 1H), 3.63 (dd, J = 11.3, 5.4 Hz, 1H), 3.52 (dd, J = 11.4, 6.2 Hz, 1H), 3.38-3.30 (m, 1H), 3.26-3.05 (m, 3H), 2.65-2.53 (m, 2H), 1.50 (d, J = 5.8 Hz, 3H). |
| 706 | 356.1 | 1H NMR (400 MHz, DMSO-d6) δ 8.03 (s, 4H), 5.12 (dd, J = 8.3, 6.8 Hz, 1H), 4.21-3.91 (m, 2H), 3.18-2.98 (m, 2H), 2.89 (dd, J = 8.5, 7.0 Hz, 1H), 2.74-2.64 (m, 1H), 2.15-1.92 (m, 2H). |
| 707 | 320.1 | 1H NMR (400 MHz, DMSO-d6) δ 8.00 (s, 4H), 5.14 (dd, J = 8.3, 6.8 Hz, 1H), 4.21-3.91 (m, 2H), 3.18-2.98 (m, 2H), 2.89 (dd, J = 8.5, 7.0 Hz, 1H), 2.76-2.64 (m, 1H), 2.13-1.93 (m, 2H). |
| 708 | 320.2 | 1H NMR (400 MHz, DMSO-d6) δ 8.04-7.87 (m, 4H), 4.37 (t, J = 8.7 Hz, 2H), 4.21 (dd, J = 8.5, 5.8 Hz, 2H), 3.88 (tt, J = 8.8, 5.8 Hz, 1H), 3.05 (t, J = 7.3 Hz, 2H), 2.85 (t, J = 7.8 Hz, 2H), 2.06-1.97 (m, 2H). |
| 709 | 390.1 | 1H NMR (400 MHz, DMSO-d6) δ 8.54 (d, J = 2.3 Hz, 1H), 8.33 (d, J = 7.6 Hz, 1H), 8.26-8.11 (m, 1H), 7.89 (t, J = 7.8 Hz, 1H), 5.27 (t, |

TABLE 1-continued

MS and NMR DATA

| Example No | ES/MS m/z (M + H)+ | 1H NMR |
|---|---|---|
| | | J = 7.6 Hz, 1H), 4.28-4.09 (m, 4H), 3.38 (s, 3H), 2.70 (dtd, J = 29.0, 15.1, 14.6, 10.4 Hz, 5H). |
| 710 | 397.2 | 1H NMR (400 MHz, DMSO-d6) δ 8.57 (s, 1H), 8.47-8.30 (m, 1H), 8.24 (ddd, J = 7.9, 2.1, 1.0 Hz, 1H), 7.94 (t, J = 7.9 Hz, 1H), 5.19 (ddt, J = 56.9, 6.1, 3.7 Hz, 1H), 4.71-4.29 (m, 2H), 4.05 (ddt, J = 25.5, 10.5, 3.5 Hz, 1H), 3.65 (d, J = 1.0 Hz, 3H), 3.33-2.92 (m, 2H), 2.64 (ddt, J = 22.3, 15.1, 6.5 Hz, 2H), 1.57 (dd, J = 6.5, 1.0 Hz, 3H). |
| 711 | 383.9 | 1H NMR (400 MHz, DMSO-d6) δ 8.12 (d, J = 8.5 Hz, 2H), 7.74 (d, J = 8.5 Hz, 2H), 5.25 (dd, J = 8.4, 6.7 Hz, 1H), 5.05-4.85 (m, 4H), 4.36-3.96 (m, 2H), 3.21 (dt, J = 6.6, 3.0 Hz, 2H), 2.81-2.58 (m, 4H). |
| 712 | 369.2 | 1H NMR (400 MHz, DMSO-d6) δ 8.48 (s, 1H), 8.33 (d, J = 7.9 Hz, 1H), 8.07 (dt, J = 7.9, 1.4 Hz, 1H), 7.84 (t, J = 7.8 Hz, 1H), 5.02 (dd, J = 7.4, 3.3 Hz, 1H), 3.72 (d, J = 6.1 Hz, 1H), 3.59 (dt, J = 10.4, 7.8 Hz, 1H), 3.29 (s, 3H), 3.11 (q, J = 7.5 Hz, 2H), 2.91 (dd, J = 8.6, 6.9 Hz, 2H), 2.33 (ddd, J = 10.1, 6.8, 3.2 Hz, 2H), 2.10 (dddd, J = 17.2, 10.3, 7.3, 3.5 Hz, 4H). |
| 713 | 369.2 | 1H NMR (400 MHz, DMSO-d6) δ 8.48 (s, 1H), 8.33 (d, J = 7.8 Hz, 1H), 8.07 (ddd, J = 7.8, 1.9, 1.1 Hz, 1H), 7.84 (t, J = 7.8 Hz, 1H), 5.02 (dd, J = 7.4, 3.3 Hz, 1H), 3.72 (d, J = 7.1 Hz, 1H), 3.67-3.44 (m, 1H), 3.29 (s, 3H), 3.10 (p, J = 8.5, 8.1 Hz, 2H), 2.96-2.81 (m, 2H), 2.36-2.25 (m, 2H), 2.15-1.93 (m, 4H). |
| 714 | 369.1 | 1H NMR (400 MHz, DMSO-d6) δ 8.45 (s, 1H), 8.28 (d, J = 7.9 Hz, 1H), 8.08 (dt, J = 7.8, 1.3 Hz, 1H), 7.84 (t, J = 7.8 Hz, 1H), 4.20-3.92 (m, 2H), 3.28 (s, 3H), 3.11 (q, J = 6.9 Hz, 2H), 2.90 (t, J = 7.8 Hz, 2H), 2.76 (ddd, J = 11.3, 8.4, 4.8 Hz, 1H), 2.65-2.55 (m, 1H), 2.07 (t, J = 7.5 Hz, 2H), 1.88 (s, 3H). |
| 715 | 395.2 | 1H NMR (400 MHz, DMSO-d6) δ 8.32-8.11 (m, 4H), 4.28 (dd, J = 9.0, 5.5 Hz, 1H), 4.15 (dq, J = 5.5, 3.2, 2.1 Hz, 2H), 3.71 (dd, J = 9.1, 4.3 Hz, 1H), 3.48 (s, 3H), 3.15 (tq, J = 8.6, 5.3, 4.1 Hz, 2H), 2.73-2.55 (m, 2H), 1.50 (d, J = 5.7 Hz, 3H). |
| 716 | 437.3 | 1H NMR (400 MHz, DMSO-d6) δ 8.25 (d, J = 2.0 Hz, 2H), 8.18-7.97 (m, 2H), 4.65 (td, J = 6.5, 2.5 Hz, 1H), 4.54-4.37 (m, 2H), 4.25 (dd, J = 9.0, 5.6 Hz, 2H), 4.12 (dd, J = 5.6, 2.8 Hz, 2H), 3.91-3.77 (m, 1H), 3.69 (ddd, J = 9.0, 4.5, 2.2 Hz, 2H), 3.57 (s, 3H), 2.60 (tq, J = 13.2, 6.5 Hz, 2H), 1.51 (d, J = 6.0, 2.0 Hz, 3H). |
| 717 | 459.2 | 1H NMR (400 MHz, DMSO-d6) δ 7.78 (d, J = 2.4 Hz, 1H), 7.69 (s, 1H), 5.69 (d, J = 6.2 Hz, 1H), 4.52 (d, J = 5.2 Hz, 1H), 4.26 (dd, J = 9.1, 5.8 Hz, 1H), 4.22-4.00 (m, 2H), 3.92 (s, 3H), 3.70 (dd, J = 8.6, 4.0 Hz, 2H), 3.58 (s, 3H), 2.80-2.54 (m, 2H), 1.41 (d, J = 6.0, 2.8 Hz, 3H). |
| 718 | 409.2 | 1H NMR (400 MHz, DMSO-d6) δ 8.64 (s, 1H), 8.13 (dd, J = 7.9, 1.9 Hz, 1H), 7.60 (d, J = 7.9 Hz, 1H), 5.67 (d, J = 6.1 Hz, 1H), 4.42 (s, 1H), 4.26 (dd, J = 9.0, 5.7 Hz, 1H), 4.13 (d, J = 4.8 Hz, 2H), 3.69 (dd, J = 9.1, 4.3 Hz, 1H), 3.17 (s, 1H), 3.14 (s, 3H), 2.77 (s, 3H), 2.62 (td, J = 15.7, 8.1 Hz, 2H), 1.52 (dd, J = 6.1, 2.4 Hz, 3H). |
| 719 | 425.3 | 1H NMR (400 MHz, DMSO-d6) δ 8.04 (s, 1H), 7.72 (s, 1H), 7.62 (s, 1H), 5.69 (d, J = 5.9 Hz, 1H), 4.36 (s, 1H), 4.27 (dd, J = 9.1, 5.6 Hz, 1H), 4.14 (q, J = 5.0 Hz, 2H), 3.93 (s, 3H), 3.70 (dd, J = 9.1, 4.3 Hz, 1H), 3.16 (s, 1H), 3.13 (s, 3H), 2.61 (tt, J = 14.8, 6.5 Hz, 2H), 1.51 (d, J = 5.7 Hz, 3H). |
| 720 | 409.2 | 1H NMR (400 MHz, DMSO-d6) δ 8.27 (s, 1H), 8.00 (s, 1H), 7.94 (d, J = 1.9 Hz, 1H), 5.68 (d, J = 6.1 Hz, 1H), 4.31 (s, 1H), 4.27 (dd, J = 9.0, 5.6 Hz, 1H), 4.14 (q, J = 5.1 Hz, 2H), 3.70 (dd, J = 9.0, 4.4 Hz, 1H), 3.32 (s, 3H), 3.16 (s, 1H), 3.11 (s, 3H), 2.61 (dt, J = 15.6, 8.4 Hz, 2H), 1.51 (d, J = 5.6 Hz, 3H). |
| 721 | 445.3 | 1H NMR (400 MHz, DMSO-d6) δ 8.69 (s, 1H), 8.39 (dd, J = 8.1, 1.8 Hz, 1H), 8.07 (d, J = 8.2 Hz, 1H), 7.91 (t, 1H), 5.70 (d, J = 6.0 Hz, 1H), 4.84 (s, 1H), 4.28 (dd, J = 9.1, 5.7 Hz, 2H), 4.15 (d, J = 5.4 Hz, 2H), 3.71 (dd, J = 9.1, 4.4 Hz, 2H), 3.20 (s, 3H), 2.76-2.57 (m, 2H), 1.52 (d, J = 5.7 Hz, 3H). |
| 722 | 439.3 | 1H NMR (400 MHz, DMSO-d6) δ 8.35 (d, J = 2.4 Hz, 1H), 8.09 (s, 1H), 5.67 (d, J = 6.2 Hz, 1H), 4.52 (d, J = 5.2 Hz, 1H), 4.26 (dd, J = 9.1, 5.8 Hz, 1H), 4.22-4.00 (m, 2H), 3.92 (s, 3H), 3.70 (dd, J = 8.6, 4.0 Hz, 2H), 3.58 (s, 3H), 2.80-2.54 (m, 2H), 2.43 (s, 3H), 1.51 (d, J = 6.0, 2.8 Hz, 3H). |
| 723 | 413.3 | 1H NMR (400 MHz, DMSO-d6) δ 8.50 (d, J = 6.9 Hz, 1H), 8.29 (s, 1H), 7.63 (t, J = 9.1 Hz, 1H), 5.72 (d, J = 6.1 Hz, 1H), 4.89 (s, 1H), 4.27 (dd, J = 9.0, 5.7 Hz, 1H), 4.14 (s, 3H), 3.81-3.64 (m, 1H), 3.57 (s, 3H), 2.65-2.56 (m, 2H), 1.51 (d, J = 3.9 Hz, 3H). |
| 724 | 413.2 | 1H NMR (400 MHz, DMSO-d6) δ 8.31 (s, 1H), 8.08-7.98 (m, 1H), 7.96-7.84 (m, 1H), 5.72 (d, J = 6.1 Hz, 1H), 4.54 (s, 1H), 4.28 (dd, J = 9.1, 5.7 Hz, 1H), 4.15 (p, J = 4.8, 4.3 Hz, 2H), 3.71 (dd, J = 9.2, 4.4 Hz, 2H), 2.61 (tt, J = 15.2, 6.7 Hz, 2H), 2.51 (s, 3H), 1.51 (d, J = 5.5 Hz, 3H). |

TABLE 1-continued

MS and NMR DATA

| Example No | ES/MS m/z (M + H)+ | 1H NMR |
|---|---|---|
| 725 | 436.2 | 1H NMR (400 MHz, DMSO-d6) δ 8.59 (s, 1H), 8.09 (d, 1H), 7.55 (d, J = 7.9 Hz, 1H), 5.71 (d, J = 6.1 Hz, 1H), 4.56 (s, 1H), 4.26 (d, J = 8.2 Hz, 2H), 4.13 (s, 1H), 3.76-3.66 (m, 3H), 3.57 (s, 3H), 3.16 (s, 3H), 2.73-2.55 (m, 4H), 1.52 (d, J = 5.4 Hz, 3H). |
| 726 | 371.2 | 1H NMR (400 MHz, DMSO-d6) δ 8.32 (s, 1H), 8.01 (d, J = 8.8, 2.1 Hz, 1H), 7.17 (d, J = 8.7 Hz, 1H), 4.81 (dd, J = 7.4, 3.2 Hz, 2H), 4.57-4.33 (m, 1H), 3.99 (ddd, J = 19.1, 14.9, 8.5 Hz, 3H), 3.74 (dd, J = 6.8, 3.6 Hz, 2H), 3.04 (ddt, J = 26.4, 15.2, 7.5 Hz, 2H), 2.84 (t, J = 7.8 Hz, 2H), 2.20-1.89 (m, 3H), 1.51 (d, J = 6.0, 3.9 Hz, 3H). |
| 727 | 377.3 | 1H NMR (400 MHz, DMSO-d6) δ 7.81-7.73 (m, 1H), 7.70-7.62 (m, 1H), 7.59-7.56 (m, 1H), 4.41 (h, J = 6.0 Hz, 1H), 4.01-3.84 (m, 2H), 3.01 (dq, J = 22.4, 7.6 Hz, 2H), 2.81 (td, J = 8.4, 7.9, 2.9 Hz, 2H), 2.51 (s, 3H), 2.45-2.34 (m, 1H), 2.06-1.90 (m, 3H), 1.50 (d, J = 6.2 Hz, 3H). |
| 728 | 322.2 | 1H NMR (400 MHz, DMSO-d6) δ7.97 (bs, 2H), 7.90 (d, J = 1.6 Hz, 1H), 7.78 (dd, J = 8.3, 1.7 Hz, 1H), 7.33 (d, J = 8.3 Hz, 1H), 4.54 (m, 1H), 4.05 (m, 2H), 3.20-2.98 (m, 2H), 2.88 (t, J = 7.8 Hz, 2H), 2.45 (partially obscured by DMSO, m, 1H), 2.16-1.92 (m, 3H), 1.53 (d, J = 6.2 Hz, 3H). |
| 729 | 307.2 | 1H NMR (400 MHz, DMSO-d6) δ8.39 (s, 1H), 8.03 (d, J = 9.1 Hz, 1H), 8.00 (d, J = 8.9 Hz, 1H), 4.48 (dt, J = 8.0, 6.1 Hz, 1H), 4.03 (m, 1H), 3.98 (m, 1H), 3.09 (m, 2H), 2.86 (m, 2H), 2.43 (m, 1H), 2.02 (m, 3H), 1.52 (d, J = 6.2 Hz, 3H). |
| 730 | 337.2 | 1H NMR (400 MHz, DMSO-d6)δ 8.06 (s, 1H), 8.03 (d, J = 8.2 Hz, 2H), 7.98 (d, J = 8.3 Hz, 2H), 7.46 (s, 1H), 5.41 (d, J = 6.5 Hz, 2H), 4.56 (d, J = 6.4 Hz, 2H), 3.87 (t, J = 7.1 Hz, 2H), 3.06 (t, J = 7.3 Hz, 2H), 2.84 (t, J = 7.7 Hz, 2H), 2.60 (t, J = 7.1 Hz, 2H), 2.02 (p, J = 7.6 Hz, 2H). |
| 731 | 321.2 | 1H NMR (400 MHz, DMSO-d6) δ12.81 (m, 2H), 8.68 (s, 2H), 7.91 (s, 1H), 7.79 (dd, J = 8.4, 1.5 Hz, 1H), 7.46 (d, J = 8.4 Hz, 1H), 4.43 (h, J = 5.9 Hz, 1H), 4.43 (m, 2H), 3.95 (m, 1H), 2.82 (t, J = 7.7 Hz, 2H), 2.41 (m, 1H), 2.01 (m, 3H), 1.51 (d, J = 6.2 Hz, 3H). |
| 732 | 283.2 | 1H NMR (400 MHz, DMSO-d6) δ8.82 (s, 2H), 7.34 (bs, 2H), 4.48 (dq, J = 12.5, 6.4 Hz, 1H), 4.03 (td, J = 8.8, 5.0 Hz, 1H), 3.95 (td, J = 8.8, 7.0 Hz, 1H), 3.01 (td, J = 7.1, 4.4 Hz, 2H), 2.83 (t, J = 7.8 Hz, 2H), 2.43 (m, 1H), 2.10-1.92 (m, 3H), 1.49 (d, J = 6.2 Hz, 3H). |
| 733 | 338.2 | 1H NMR (400 MHz, DMSO-d6) δ8.41 (bs, 2H), 7.90 (d, J = 1.6 Hz, 1H), 7.87 (d, J = 8.3 Hz, 1H), 7.66 (dd, J = 8.3, 1.7 Hz, 1H), 4.46 (dt, J = 8.0, 6.1 Hz, 1H), 4.06-3.89 (m, 2H), 3.13-2.94 (m, 2H), 2.84 (dd, J = 8.5, 6.9 Hz, 2H), 2.42 (m, 1H), 2.10-1.92 (m, 3H), 1.51 (d, J = 6.2 Hz, 3H). |
| 734 | 338.2 | 1H NMR (400 MHz, DMSO-d6) δ8.29 (d, J = 1.8 Hz, 1H), 8.20 (s, 2H), 7.87 (dd, J = 8.5, 1.8 Hz, 1H), 7.46 (d, J = 8.5 Hz, 1H), 4.48 (q, J = 6.7 Hz, 1H), 4.03 (td, J = 8.8, 5.0 Hz, 1H), 3.96 (q, J = 8.5 Hz, 1H), 3.05 (m, 2H), 2.84 (t, J = 7.7 Hz, 2H), 2.44 (m, 1H), 2.01 (m, 3H), 1.51 (d, J = 6.2 Hz, 3H). |
| 735 | 438.2 | 1H NMR (400 MHz, DMSO-d6) δ8.20 (d, J = 8.5 Hz, 2H), 8.13 (s, 1H), 8.10 (d, J = 8.6 Hz, 2H), 5.18 (s, 4H), 4.67-4.45 (m, 1H), 4.27 (dd, J = 9.1, 5.7 Hz, 1H), 4.14 (dq, J = 9.6, 4.6 Hz, 2H), 3.70 (dd, J = 9.0, 4.4 Hz, 1H), 3.16 (partially obscured by singlet, m, 2H), 2.59 (m, 2H), 1.50 (d, J = 5.9 Hz, 3H). |
| 736 | 322.2 | 1H NMR (400 MHz, DMSO-d6) δ7.86 (s, 2H), 7.73 (d, J = 1.7 Hz, 1H), 7.58 (dd, J = 8.4, 1.7 Hz, 1H), 7.49 (d, J = 8.4 Hz, 1H), 4.50 (p, J = 6.5 Hz, 1H), 4.04 (td, J = 8.9, 5.0 Hz, 1H), 4.01-3.89 (m, 1H), 3.03 (m, 2H), 2.86 (t, J = 7.7 Hz, 2H), 2.43 (m, 1H), 2.13-1.92 (m, 3H), 1.51 (d, J = 6.2 Hz, 3H). |
| 737 | 400.22 | 1H NMR (400 MHz, DMSO-d6) δ 9.35 (t, J = 5.4 Hz, 1H), 8.06 (d, J = 8.3 Hz, 2H), 8.01 (d, J = 8.4 Hz, 2H), 5.67 (d, J = 6.2 Hz, 1H), 4.35 (d, J = 5.2 Hz, 2H), 4.27 (dd, J = 9.0, 5.8 Hz, 1H), 4.13 (m, 2H), 3.70 (dd, J = 9.0, 4.4 Hz, 1H), 3.16 (m, 2H), 2.60 (m, 2H), 1.50 (d, J = 5.9 Hz, 3H). |
| 738 | 502.9 | 1H NMR (400 MHz, DMSO-d6) δ 8.74 (bs, 3H), 8.12 (d, J = 8.2 Hz, 2H), 7.86 (d, J = 8.3 Hz, 2H), 5.09 (dt, J = 9.0, 6.1 Hz, 1H), 4.15 (dq, J = 15.1, 8.1, 6.9 Hz, 2H), 3.42 (dd, J = 15.3, 6.8 Hz, 2H), 3.21 (m, 2H), 2.98 (m, 4H), 2.75-2.55 (m, 5H), 2.45 (m, 1H). |
| 739 | 403.1 | 1H NMR (400 MHz, DMSO-d6) δ 8.12 (s, 1H), 8.01 (s, 1H), 7.33 (s, 2H), 5.11-4.48 (m, 3H), 4.22-4.14 (m, 1H), 4.12-4.00 (m, 2H), 3.67-3.59 (m, 1H), 3.40-3.29 (m, 2H), 3.11-2.95 (m, 2H), 2.86-2.77 (m, 2H), 2.09-1.97 (m, 3H), 1.49 (d, J = 6.1 Hz, 3H). |
| 740 | 439.0 | 1H NMR (400 MHz, DMSO-d6) δ 7.94 (d, J = 8.4 Hz, 2H), 7.77 (d, J = 8.1 Hz, 1H), 7.56 (d, J = 8.4 Hz, 2H), 4.64-4.55 (m, 1H), 4.29-4.22 (m, 1H), 4.17-4.09 (m, 2H), 3.73-3.65 (m, 1H), 3.22-3.09 (m, 2H), 2.75 (s, 3H), 2.66-2.53 (m, 2H), 1.51 (d, J = 6.0 Hz, 3H), 1.44 (d, J = 6.9 Hz, 3H). |

TABLE 1-continued

MS and NMR DATA

| Example No | ES/MS m/z (M + H)+ | 1H NMR |
|---|---|---|
| 741 | 439.1 | 1H NMR (400 MHz, DMSO-d6) δ 7.96 (s, 1H), 7.85-7.82 (m, 1H), 7.79-7.76 (m, 1H), 7.58-7.53 (m, 2H), 4.64-4.58 (m, 1H), 4.28-4.22 (m, 1H), 4.17-4.10 (m, 2H), 3.74-3.67 (m, 1H), 3.18-3.12 (m, 2H), 2.72 (s, 3H), 2.67-2.57 (m, 2H), 1.51 (d, J = 5.9 Hz, 3H), 1.45 (d, J = 6.9 Hz, 3H). |
| 742 | 423.0 | 1H NMR (400 MHz, DMSO-d6) δ 8.16 (s, 1H), 8.07 (s, 1H), 7.37 (s, 2H), 4.81 (t, J = 8.8 Hz, 2H), 4.54-4.43 (m, 1H), 4.09-3.93 (m, 2H), 3.36 (t, J = 8 Hz, 2H), 3.20-3.06 (m, 2H), 2.70-2.55 (m, 4H), 1.53 (d, J = 6.2 Hz, 3H). |
| 743 | 414.0 | 1H NMR (400 MHz, DMSO-d6) δ 8.04-7.83 (m, 3H), 7.63-7.55 (m, 2H), 4.06-3.83 (m, 1H), 3.18-3.08 (m, 2H), 2.84-2.74 (m, 2H), 2.61-2.53 (m, 2H), 2.34-2.24 (m, 5H), 2.12-1.92 (m, 4H), 1.78-1.62 (m, 2H), 1.54-1.46 (m, 2H), 1.24-1.12 (m, 3H). |
| 744 | 439.0 | 1H NMR (400 MHz, DMSO-d6) δ 7.94 (d, J = 8.4 Hz, 2H), 7.77 (d, J = 8.1 Hz, 1H), 7.56 (d, J = 8.4 Hz, 2H), 4.62-4.54 (m, 1H), 4.28-4.23 (m, 1H), 4.14-4.09 (m, 2H), 3.70-3.66 (m, 1H), 3.19-3.10 (m, 2H), 2.75 (s, 3H), 2.65-2.53 (m, 2H), 1.50 (d, J = 6.1, 2.9 Hz, 3H), 1.44 (d, J = 7.0 Hz, 3H). |
| 745 | 439.0 | 1H NMR (400 MHz, DMSO-d6) δ 7.96 (s, 1H), 7.86-7.82 (m, 1H), 7.78 (d, J = 8.2 Hz, 1H), 7.58-7.51 (m, 2H), 4.64-4.57 (m, 1H), 4.29-4.23 (m, 1H), 4.16-4.11 (m, 2H), 3.72-3.67 (m, 1H), 3.21-3.09 (m, 2H), 2.72 (s, 3H), 2.65-2.54 (m, 2H), 1.51 (d, J = 5.7 Hz, 3H), 1.45 (d, J = 6.9 Hz, 3H). |
| 746 | 421.0 | 1H NMR (400 MHz, DMSO-d6) δ 8.61 (t, J = 6.0 Hz, 1H), 7.71-7.68 (m, 1H), 7.47-7.45 (m, 1H), 4.29-4.24 (m, 2H), 4.16-4.10 (m, 2H), 3.74-3.66 (m, 1H), 3.36-3.27 (m, 2H), 3.21-3.10 (m, 2H), 2.64-2.42 (m, 4H), 1.50 (d, J = 5.9 Hz, 3H). |
| 747 | 405.0 | 1H NMR (400 MHz, DMSO-d6) δ 8.63-8.57 (m, 1H), 7.60-7.56 (m, 1H), 7.47-7.43 (m, 1H), 6.51 (s, 1H), 4.55-4.47 (m, 1H), 4.28-4.22 (m, 2H), 4.10-3.96 (m, 2H), 3.20-3.09 (m, 2H), 2.63-2.30 (m, 6H), 1.52 (d, J = 6.2 Hz, 3H). |
| 748 | 423.1 | 1H NMR (400 MHz, DMSO-d6) δ 7.99-7.89 (m, 2H), 7.77 (d, J = 8.1 Hz, 1H), 7.60-7.51 (m, 2H), 4.66-4.54 (m, 2H), 4.31-4.22 (m, 1H), 4.17-4.05 (m, 2H), 3.75-3.63 (m, 1H), 3.23-3.07 (m, 2H), 2.75 (s, 3H), 2.65-2.53 (m, 2H), 1.51 (d, J = 6.0 Hz, 3H), 1.44 (d, J = 6.9 Hz, 3H). |
| 749 | 423.0 | 1H NMR (400 MHz, DMSO-d6) δ 7.94 (s, 1H), 7.85-7.76 (m, 2H), 7.59-7.50 (m, 2H), 4.66-4.55 (m, 2H), 4.54-4.43 (m, 1H), 4.10-3.94 (m, 2H), 3.78-3.69 (m, 1H), 3.18-3.07 (m, 2H), 2.71 (s, 3H), 2.64-2.54 (m, 2H), 1.53 (d, J = 6.2 Hz, 3H), 1.45 (d, J = 6.9 Hz, 3H). |
| 750 | 423.1 | 1H NMR (400 MHz, DMSO-d6) δ 7.94 (d, J = 8.2 Hz, 2H), 7.77 (d, J = 8.1 Hz, 1H), 7.55 (d, J = 8.3 Hz, 2H), 4.64-4.55 (m, 2H), 4.54-4.45 (m, 1H), 4.09-3.94 (m, 2H), 3.19-3.08 (m, 2H), 2.73 (d, J = 7.1 Hz, 4H), 2.63-2.41 (m, 2H), 1.52 (d, J = 6.2 Hz, 3H), 1.44 (d, J = 6.8 Hz, 3H). |
| 751 | 423.1 | 1H NMR (400 MHz, DMSO-d6) δ 7.94 (d, J = 8.2 Hz, 2H), 7.77 (d, J = 8.1 Hz, 1H), 7.55 (d, J = 8.3 Hz, 2H), 4.64-4.55 (m, 2H), 4.54-4.45 (m, 1H), 4.09-3.94 (m, 2H), 3.19-3.08 (m, 2H), 2.73 (d, J = 7.1 Hz, 4H), 2.63-2.41 (m, 2H), 1.52 (d, J = 6.2 Hz, 3H), 1.44 (d, J = 6.8 Hz, 3H). |
| 752 | 310.0 | 1H NMR (400 MHz, DMSO-d6) δ 9.13 (s, 1H), 8.40-8.20 (m, 3H), 7.68 (s, 1H), 4.51-4.39 (m, 1H), 4.06-3.91 (m, 2H), 3.31-3.20 (m, 2H), 2.85-2.76 (m, 2H), 2.07-1.93 (m, 4H), 1.52 (d, J = 6.2 Hz, 3H). |
| 753 | 350.2 | 1H NMR (400 MHz, DMSO-d6) δ 8.04 (t, J = 5.6 Hz, 1H), 7.82 (d, J = 8.4 Hz, 1H), 7.23 (s, 1H), 7.05 (d, J = 8.4, 1.7 Hz, 1H), 4.47-4.38 (m, 1H), 4.02-3.87 (m, 2H), 3.48-3.25 (m, 4H), 3.09-2.90 (m, 2H), 2.87-2.78 (m, 2H), 2.44-2.29 (m, 2H), 2.08-1.91 (m, 2H), 1.50 (d, J = 6.2 Hz, 3H). |
| 754 | 323.1 | 1H NMR (400 MHz, DMSO-d6) δ 7.63 (d, J = 7.9 Hz, 1H), 7.52-7.43 (m, 1H), 7.26-7.16 (m, 1H), 5.16-4.99 (m, 2H), 4.79-4.71 (m, 2H), 4.58-4.49 (m, 2H), 4.43-4.35 (m, 1H), 3.98-3.85 (m, 2H), 3.03-2.92 (m, 2H), 2.83-2.78 (m, 1H), 2.05-1.92 (m, 2H), 1.48 (d, J = 6.1 Hz, 3H). |
| 755 | 351.1 | 1H NMR (400 MHz, DMSO-d6) δ 7.71 (d, J = 8.5 Hz, 2H), 7.49 (d, J = 8.5 Hz, 2H), 4.60-4.45 (m, 2H), 4.44-4.34 (m, 1H), 4.11-3.91 (m, 6H), 3.87-3.69 (m, 6H), 3.07-2.94 (m, 1H), 2.06-1.92 (m, 2H), 1.49 (d, J = 6.2 Hz, 3H). |
| 756 | 403.0 | 1H NMR (400 MHz, DMSO-d6) δ 8.32-8.29 (m, 1H), 8.06-8.04 (m, 1H), 7.74-7.69 (m, 2H), 7.31 (s, 1H), 4.81 (t, J = 8.7 Hz, 2H), 4.28-4.22 (m, 1H), 4.15-4.08 (m, 2H), 3.72-3.65 (m, 1H), 3.39-3.31 (m, 23H), 3.18-3.08 (m, 2H), 2.68-2.54 (m, 2H), 1.51 (d, J = 6.0 Hz, 3H). |
| 757 | 467.1 | 1H NMR (400 MHz, DMSO-d6) δ 7.71 (d, J = 8.3 Hz, 1H), 7.55-7.46 (m, 2H), 7.32 (s, 1H), 4.69-4.61 (m, 1H), 4.36-4.19 (m, 3H), |

TABLE 1-continued

| | | MS and NMR DATA |
|---|---|---|
| Example No | ES/MS m/z (M + H)+ | 1H NMR |
| | | 4.16-4.07 (m, 2H), 3.70-3.63 (m, 1H), 3.13-3.03 (m, 5H), 2.64-2.53 (m, 2H), 2.26-2.15 (m, 1H), 2.11-1.98 (m, 1H), 1.49 (d, J = 5.7 Hz, 3H). |
| 758 | 437.0 | 1H NMR (400 MHz, DMSO-d6) δ 7.96-7.87 (m, 1H), 7.56-7.48 (m, 2H), 7.36 (d, J = 1.2 Hz, 1H), 5.33-5.22 (m, 1H), 4.78 (t, J = 9.1 Hz, 2H), 4.53-4.43 (m, 1H), 4.41-4.34 (m, 2H), 4.07-3.92 (m, 2H), 3.15-3.02 (m, 3H), 2.60-2.41 (m, 3H), 2.05-1.93 (m, 1H), 1.51 (d, J = 6.2 Hz, 3H). |
| 759 | 451.0 | 1H NMR (400 MHz, DMSO-d6) δ 7.71 (d, J = 8.3 Hz, 1H), 7.55-7.45 (m, 2H), 7.32 (s, 1H), 4.69-4.60 (m, 1H), 4.52-4.44 (m, 1H), 4.30-4.25 (m, 2H), 4.06-3.93 (m, 2H), 3.12-3.05 (m, 5H), 2.62-2.54 (m, 2H), 2.26-2.15 (m, 1H), 2.08-1.94 (m, 3H), 1.51 (d, J = 6.2 Hz, 3H). |
| 760 | 389.1 | 1H NMR (400 MHz, DMSO-d6) δ 9.26-9.17 (m, 1H), 7.75-7.58 (m, 3H), 4.48-4.41 (m, 2H), 4.32-4.21 (m, 3H), 4.15-4.06 (m, 2H), 3.71-3.66 (m, 1H), 3.57-3.52 (m, 2H), 3.19-3.06 (m, 2H), 2.68-2.54 (m, 2H), 1.50 (d, J = 5.9 Hz, 3H). |
| 761 | 467.1 | 1H NMR (400 MHz, DMSO-d6) δ 7.86-7.80 (m, 2H), 7.57-7.51 (m, 1H), 4.67 (t, J = 8.7 Hz, 2H), 4.28-4.07 (m, 5H), 3.70-3.65 (m, 1H), 3.19-3.09 (m, 2H), 2.92 (s, 2H), 2.66-2.56 (m, 2H), 2.55 (s, 3H), 1.51 (d, J = 5.9 Hz, 3H). |
| 762 | 451.1 | 1H NMR (400 MHz, DMSO-d6) δ 7.87-7.80 (m, 2H), 7.53 (t, J = 6.2 Hz, 1H), 4.67 (t, J = 8.7 Hz, 2H), 4.52-4.43 (m, 1H), 4.16 (d, J = 6.1 Hz, 2H), 4.08-3.92 (m, 2H), 3.29 (t, J = 8.7 Hz, 2H), 3.19-3.08 (m, 2H), 2.91 (s, 3H), 2.65-2.39 (m, 3H), 2.06-1.93 (m, 1H), 1.52 (d, J = 6.2 Hz, 3H). |
| 763 | 427.0 | 1H NMR (400 MHz, DMSO-d6) δ 8.50-8.45 (m, 1H), 8.23-8.18 (m, 1H), 7.39 (d, J = 8.8 Hz, 1H), 7.24 (s, 2H), 4.28-4.22 (m, 1H), 4.16-4.09 (m, 2H), 4.00 (s, 3H), 3.72-3.66 (m, 1H), 3.22-3.08 (m, 2H), 2.73-2.55 (m, 2H), 1.51 (d, J = 5.7 Hz, 3H). |
| 764 | 441.1 | 1H NMR (400 MHz, DMSO-d6) δ 8.50-8.46 (m, 1H), 8.20-8.15 (m, 1H), 7.39 (d, J = 8.7 Hz, 1H), 7.12 (s, 2H), 4.33 (q, J = 7.0 Hz, 2H), 4.27-4.23 (m, 1H), 4.16-4.09 (m, 2H), 3.71-3.66 (m, 1H), 3.22-3.09 (m, 2H), 2.70-2.55 (m, 2H), 1.51 (d, J = 5.7 Hz, 3H), 1.42 (t, J = 6.9 Hz, 3H). |
| 765 | 343.1 | 1H NMR (400 MHz, DMSO-d6) δ 8.73 (s, 1H), 8.19 (s, 1H), 7.85-7.74 (m, 1H), 7.65-7.59 (m, 1H), 4.58-4.43 (m, 4H), 4.10-3.95 (m, 2H), 3.26-3.07 (m, 2H), 2.70-2.54 (m, 4H), 2.08-1.95 (m, 1H), 1.53 (d, J = 6.2, 1.7 Hz, 3H). |
| 766 | 431.0 | 1H NMR (400 MHz, DMSO-d6) δ 7.93-7.88 (m, 1H), 7.72-7.69 (m, 1H), 5.64 (s, 1H), 4.70-4.64 (m, 1H), 4.27-4.06 (m, 4H), 3.75-3.64 (m, 1H), 3.30-3.03 (m, 2H), 2.65-2.37 (m, 6H), 1.89 (s, 3H), 1.57-1.42 (m, 3H). |
| 767 | 401.1 | 1H NMR (400 MHz, DMSO-d6) δ 8.55 (d, J = 7.2 Hz, 1H), 7.49-7.45 (m, 2H), 7.37 (s, 1H), 5.57-5.47 (m, 1H), 4.73 (t, J = 9.1 Hz, 1H), 4.52-4.45 (m, 1H), 4.32-4.24 (m, 1H), 4.06-3.88 (m, 2H), 3.15-3.02 (m, 2H), 2.63-2.39 (m, 4H), 1.86 (s, 3H), 1.51 (d, J = 6.2 Hz, 3H). |
| 768 | 387.06 | 1H NMR (400 MHz, DMSO-d6)δ 8.56 (bs, 3H), 7.95 (d, J = 8.3 Hz, 2H), 7.67 (d, J = 8.5 Hz, 2H), 4.93 (bs, 1H), 4.40 (dt, J = 7.8, 6.1 Hz, 1H), 4.06-3.85 (m, 3H), 3.73 (dd, J = 14.7, 6.9 Hz, 1H), 3.00 (partially obscured by s, m, 2H), 2.99 (s, 3H), 2.81 (t, J = 7.7 Hz, 2H), 2.38 (partially obscured by DMSO, m, 1H), 2.05-1.91 (m, 3H), 1.49 (d, J = 6.2 Hz, 3H). |
| 769 | 421.0 | 1H NMR (400 MHz, DMSO-d6)δ 7.95 (d, J = 8.5 Hz, 2H), 7.71 (d, J = 8.4 Hz, 2H), 4.64 (d, J = 14.4 Hz, 2H), 4.49 (dt, J = 8.1, 6.1 Hz, 1H), 4.31 (d, J = 14.5 Hz, 2H), 4.04 (dt, J = 8.8, 4.3 Hz, 1H), 4.01 (s, 1H), 3.12 (m, 2H), 2.83 (bs, 2H), 2.58 (td, J = 15.5, 7.7 Hz, 2H), 2.43 (partially obscured by DMSO peak, m, 2H), 2.00 (m, 1H), 1.51 (d, J = 6.2 Hz, 3H). |
| 770 | 453.0 | 1H NMR (400 MHz, DMSO-d6) δ 8.07 (d, J = 8.5 Hz, 2H), 7.79 (d, J = 8.1 Hz, 2H), 5.18 (ddt, J = 56.8, 5.9, 3.7 Hz, 1H), 5.00 (d, J = 14.2 Hz, 2H), 4.91 (d, J = 14.9 Hz, 2H), 4.58-4.35 (m, 2H), 4.02 (ddd, J = 25.6, 10.5, 3.8 Hz, 1H), 3.17 (m, 2H), 2.60 (partially obscured by DMSO, m, 2H), 2.30 (s, 3H), 1.55 (d, J = 6.6 Hz, 3H). |
| 771 | 385.9 | 1H NMR (400 MHz, DMSO-d6)δ 8.73 (s, 3H), 8.04 (d, J = 8.3 Hz, 2H), 7.72 (d, J = 8.4 Hz, 2H), 4.85 (s, 1H), 4.26 (dd, J = 9.0, 5.7 Hz, 1H), 4.17-4.10 (m, 2H), 3.69 (dd, J = 9.0, 4.4 Hz, 1H), 3.30 (d, J = 7.1 Hz, 2H), 3.13 (dtd, J = 9.4, 5.9, 2.7 Hz, 2H), 2.59 (tt, J = 15.5, 6.6 Hz, 2H), 1.50 (d, J = 5.8 Hz, 3H). |
| 772 | 438.9 | 1H NMR (400 MHz, DMSO-d6) δ 9.14 (bs, 3H), 8.07 (d, J = 8.4 Hz, 2H), 7.85 (d, J = 8.5 Hz, 2H), 5.25 (dt, J = 6.3, 3.7 Hz, 1H), 5.09 (d, J = 15.7 Hz, 2H), 4.94 (d, J = 15.5 Hz, 2H), 4.57-4.35 (m, 2H), 4.02 (ddd, J = 25.6, 10.5, 3.8 Hz, 1H), 3.16 (dp, J = 9.1, 2.9 Hz, 2H), 2.62 (td, J = 15.4, 7.7 Hz, 2H), 1.55 (d, J = 6.5 Hz, 3H). |

TABLE 1-continued

| | | MS and NMR DATA |
|---|---|---|
| Example No | ES/MS m/z (M + H)+ | 1H NMR |
| 773 | 441.2 | 1H NMR (400 MHz, DMSO-d6) δ8.66 (s, 3H), 8.04 (d, J = 8.4 Hz, 2H), 7.74 (d, J = 8.4 Hz, 2H), 5.18 (ddt, J = 56.9, 5.9, 3.7 Hz, 1H), 4.96 (d, J = 6.9 Hz, 1H), 4.59-4.35 (m, 2H), 4.10-3.95 (m, 2H), 3.79 (dd, J = 14.6, 6.6 Hz, 1H), 3.24-3.07 (m, 3H), 3.01 (s, 3H), 2.61 (tt, J = 15.6, 6.6 Hz, 2H), 1.56 (d, J = 6.5 Hz, 3H). |
| 774 | 423.2 | 1H NMR (400 MHz, DMSO-d6) δ 8.66 (s, 3H), 8.01 (d, J = 8.4 Hz, 2H), 7.72 (d, J = 8.4 Hz, 2H), 4.94 (m, 1H), 4.50 (partially obscured by bs, m, 1H), 4.15-3.89 (m, 3H), 3.78 (dd, J = 14.6, 6.6 Hz, 1H), 3.11 (m, 2H), 2.99 (s, 3H), 2.59 (m, 2H), 2.50 (partially obscured by DMSO, m, 1H), 2.00 (ddt, J = 10.8, 8.8, 6.7 Hz, 1H), 1.51 (d, J = 6.2 Hz, 3H). |
| 775 | 423.0 | 1H NMR (400 MHz, DMSO-d6) δ 8.66 (s, 3H), 8.01 (d, J = 8.4 Hz, 2H), 7.72 (d, J = 8.4 Hz, 2H), 4.94 (m, 1H), 4.50 (partially obscured by bs, m, 1H), 4.15-3.89 (m, 3H), 3.78 (dd, J = 14.6, 6.6 Hz, 1H), 3.11 (m, 2H), 2.99 (s, 3H), 2.59 (m, 2H), 2.50 (partially obscured by DMSO, m, 1H), 2.00 (ddt, J = 10.8, 8.8, 6.7 Hz, 1H), 1.51 (d, J = 6.2 Hz, 3H). |
| 776 | 423.0 | 1H NMR (400 MHz, DMSO-d6) δ 8.62 (s, 3H), 8.01 (d, J = 8.4 Hz, 2H), 7.72 (d, J = 8.4 Hz, 2H), 4.94 (m, 1H), 4.50 (dt, J = 8.0, 6.0 Hz, 1H), 4.01 (partially obscured by bs, m, 3H), 3.11 (m, 2H), 3.00 (s, 3H), 2.59 (td, J = 15.5, 7.7 Hz, 2H), 2.44 (partially obscured by DMSO, m, 1H), 2.00 (ddt, J = 10.8, 8.9, 6.7 Hz, 1H), 1.51 (d, J = 6.2 Hz, 3H). |
| 777 | 398.2 | 1H NMR (400 MHz, DMSO-d6)δ 9.48 (broad d, 2H), 8.07 (d, J = 8.2 Hz, 2H), 7.80 (d, J = 8.2 Hz, 2H), 4.75 (d, J = 11.6 Hz, 2H), 4.53 (d, J = 11.5 Hz, 2H), 4.26 (dd, J = 9.0, 5.5 Hz, 1H), 4.13 (q, J = 4.3 Hz, 2H), 3.69 (dd, J = 9.0, 4.3 Hz, 1H), 3.14 (m, 2H), 2.59 (m, 2H), 1.50 (d, J = 5.7 Hz, 3H). |
| 778 | 385.9 | 1H NMR (400 MHz, DMSO-d6) δ 8.70 (bs, 3H), 8.04 (d, J = 8.2 Hz, 2H), 7.71 (d, J = 8.2 Hz, 2H), 4.85 (m, 2H), 4.26 (dd, J = 9.0, 5.6 Hz, 1H), 4.13 (q, J = 5.2 Hz, 2H), 3.69 (dd, J = 9.0, 4.3 Hz, 1H), 3.29 (d, J = 7.0 Hz, 2H), 3.13 (m, 2H), 2.60 (m, 1H), 1.50 (d, J = 5.8 Hz, 3H). |
| 779 | 385.9 | 1H NMR (400 MHz, DMSO-d6) δ 8.70 (bs, 3H), 8.04 (d, J = 8.2 Hz, 2H), 7.71 (d, J = 8.2 Hz, 2H), 4.85 (m, 2H), 4.26 (dd, J = 9.0, 5.6 Hz, 1H), 4.13 (q, J = 5.2 Hz, 2H), 3.69 (dd, J = 9.0, 4.3 Hz, 1H), 3.29 (d, J = 7.0 Hz, 2H), 3.13 (m, 2H), 2.60 (m, 1H), 1.50 (d, J = 5.8 Hz, 3H). |
| 780 | 441.0 | 1H NMR (400 MHz, DMSO-d6) δ 8.58 (bs, 3H), 8.02 (d, J = 8.1 Hz, 2H), 7.72 (d, J = 8.2 Hz, 2H), 4.96 (bs, 1H), 4.94 (ddd, J = 48.1, 10.3, 3.3 Hz, 1H), 4.75-4.66 (m, 1H), 4.66-4.55 (m, 1H), 4.01 (m, 2H), 3.73 (partially obscured by water peak, m, 2H), 3.12 (m, 2H), 3.01 (s, 3H), 2.71-2.53 (m, 2H), 2.47-2.30 (m, 2H). |
| 781 | 439.2 | 1H NMR (400 MHz, DMSO-d6)δ 9.32 (bs, 2H), 8.56 (d, J = 1.8 Hz, 1H), 8.33 (dd, J = 7.9, 1.9 Hz, 1H), 7.92 (d, J = 7.9 Hz, 1H), 5.45-4.88 (m, 1H), 4.67 (s, 2H), 4.59-4.36 (m, 2H), 4.03 (ddd, J = 25.4, 10.4, 3.8 Hz, 1H), 3.88-3.81 (m, 2H), 3.74 (t, J = 5.1 Hz, 2H), 3.16 (m, 2H), 2.64 (tt, J = 15.2, 6.8 Hz, 2H), 1.57 (d, J = 6.5 Hz, 3H). |
| 782 | 473.2 | 1H NMR (400 MHz, DMSO-d6) δδ 8.90 (bs, 3H), 8.08 (d, J = 8.3 Hz, 2H), 7.84 (d, J = 8.3 Hz, 2H), 5.07 (d, J = 15.5 Hz, 2H), 4.91 (d, J = 14.9 Hz, 2H), 4.72 (m, 1H), 4.47 (m, 2H), 4.01 (dd, J = 11.4, 3.6 Hz, 1H), 3.86 (dd, J = 11.3, 8.3 Hz, 1H), 3.18 (m, 2H), 2.63 (tt, J = 15.0, 6.7 Hz, 2H). |
| 783 | 473.2 | 1H NMR (400 MHz, DMSO-d6) δ 8.69 (bs, 3H), 8.08 (d, J = 8.5 Hz, 2H), 7.85 (d, J = 8.5 Hz, 2H), 5.07 (d, J = 15.6 Hz, 2H), 4.91 (d, J = 15.2 Hz, 2H), 4.72 (m, 1H), 4.47 (m, 2H), 4.01 (dd, J = 11.4, 3.7 Hz, 1H), 3.86 (dd, J = 11.3, 8.3 Hz, 1H), 3.18 (m, 2H), 2.64 (tt, J = 15.6, 6.3 Hz, 2H). |
| 784 | 473.2 | 1H NMR (400 MHz, DMSO-d6) δ 8.69 (bs, 3H), 8.08 (d, J = 8.5 Hz, 2H), 7.85 (d, J = 8.5 Hz, 2H), 5.07 (d, J = 15.6 Hz, 2H), 4.91 (d, J = 15.2 Hz, 2H), 4.72 (m, 1H), 4.47 (m, 2H), 4.01 (dd, J = 11.4, 3.7 Hz, 1H), 3.86 (dd, J = 11.3, 8.3 Hz, 1H), 3.18 (m, 2H), 2.64 (tt, J = 15.6, 6.3 Hz, 2H). |
| 785 | 439.1 | 1H NMR (400 MHz, DMSO-d6) δ9.23 (bs, 3H), 8.06 (d, J = 8.3 Hz, 2H), 7.85 (d, J = 8.5 Hz, 2H), 5.44 (dtd, J = 58.0, 5.9, 2.6 Hz, 1H), 5.08 (d, J = 15.6 Hz, 2H), 4.96 (d, J = 15.4 Hz, 2H), 4.71 (dq, J = 19.2, 6.4 Hz, 1H), 4.38 (ddd, J = 22.4, 11.1, 6.0 Hz, 1H), 4.12 (ddt, J = 22.9, 11.2, 2.1 Hz, 1H), 3.15 (m, 2H), 2.59 (m, 2H), 1.48 (dd, J = 6.6, 1.9 Hz, 3H). |
| 786 | 467.3 | 1H NMR (400 MHz, DMSO-d6) δ 7.72 (d, J = 8.3 Hz, 1H), 7.57-7.45 (m, 2H), 7.32 (d, J = 1.6 Hz, 1H), 5.66 (d, J = 6.1 Hz, 1H), 4.65 (q, J = 6.5 Hz, 1H), 4.26 (m, 3H), 4.12 (m, 2H), 3.67 (dd, J = 9.0, 4.4 Hz, 1H), 3.11 (s, 3H), 3.11 (partially obscured by singlet, m, 1H), 2.58 (m, 2H), 2.21 (m, 1H), 2.05 (m, 1H), 1.49 (d, J = 5.8 Hz, 3H). |
| 787 | 467.3 | 1H NMR (400 MHz, DMSO-d6) δ 7.72 (d, J = 8.3 Hz, 1H), 7.58-7.43 (m, 2H), 7.33 (d, J = 1.7 Hz, 1H), 5.66 (d, J = 6.1 Hz, 1H), 4.65 |

TABLE 1-continued

MS and NMR DATA

| Example No | ES/MS m/z (M + H)+ | 1H NMR |
|---|---|---|
| | | (m, 1H), 4.26 (m, 2H), 4.11 (m, 2H), 3.68 (dd, J = 8.9, 4.4 Hz, 1H), 3.11 (s, 3H), 3.11 (partially obscured by singlet, m, 1H), 2.56 (m, 2H), 2.21 (m, 1H), 2.06 (m, 1H), 1.50 (d, J = 5.9 Hz, 3H). |
| 788 | 441.0 | 1H NMR (400 MHz, DMSO-d6) δ 8.62 (s, 3H), 8.03 (d, J = 8.0 Hz, 2H), 7.73 (d, J = 8.0 Hz, 2H), 5.17 (ddt, J = 56.9, 6.6, 3.7 Hz, 1H), 4.96 (s, 1H), 4.56-4.35 (m, 2H), 4.11-3.93 (m, 2H). 3.76 (dd, J = 14.7, 6.8 Hz, 1H), 3.14 (tdd, J = 10.7, 6.8, 3.8 Hz, 2H), 3.00 (s, 3H), 2.60 (tt, J = 15.1, 6.7 Hz, 2H), 1.55 (d, J = 6.5 Hz, 3H). |
| 789 | 441.0 | 1H NMR (400 MHz, DMSO-d6) δ 8.63 (s, 3H), 8.03 (d, J = 8.2 Hz, 2H), 7.73 (d, J = 8.3 Hz, 2H), 5.17 (ddt, J = 56.9, 6.3, 3.7 Hz, 1H), 4.96 (s, 1H), 4.58-4.35 (m, 2H), 4.07-3.93 (m, 2H), 3.77 (dd, J = 14.7, 6.7 Hz, 1H), 3.14 (m, 2H), 3.00 (s, 3H), 2.60 (tt, J = 15.6, 6.6 Hz, 2H), 1.55 (d, J = 6.5 Hz, 3H). |
| 790 | 421.2 | 1H NMR (400 MHz, DMSO-d6)δ 9.16 (bs, 3H), 8.13 (t, J = 1.9 Hz, 1H), 8.03 (dt, J = 7.7, 1.3 Hz, 1H), 7.84 (dt, J = 8.2, 1.2 Hz, 1H), 7.72 (t, J = 7.9 Hz, 1H), 5.06 (d, J = 15.0 Hz, 2H), 4.95 (d, J = 15.0 Hz, 2H), 4.51 (dt, J = 7.8, 6.0 Hz, 1H), 4.04 (m, 2H), 3.16 (tq, J = 6.0, 3.1 Hz, 2H), 2.60 (m, 2H), 2.01 (m, 1H), 1.52 (d, J = 6.2 Hz, 3H). |
| 791 | 446.3 | 1H NMR (400 MHz, DMSO-d6)δ 9.44 (bs, 2H), 8.53 (d, J = 1.8 Hz, 1H), 8.36 (dd, J = 7.9, 1.9 Hz, 1H), 7.92 (d, J = 7.9 Hz, 1H), 4.68 (s, 2H) 4.68 (partially obscured by s, m, 1H), 4.07 (td, J = 8.3, 3.3 Hz, 2H), 3.91-3.80 (m, 2H), 3.74 (t, J = 5.2 Hz, 2H), 3.24 (m, 1H), 3.20-3.04 (m, 3H), 2.65 (m, 2H), 2.59-2.51 (m, 1H), 2.32 (m, 1H). |
| 792 | 489.3 | 1H NMR (400 MHz, DMSO-d6) δ 7.92 (d, J = 7.9 Hz, 1H), 7.67-7.53 (m, 1H), 7.57-7.48 (m, 2H), 7.42 (m, 1H), 5.28 (td, J = 8.1, 5.2 Hz, 1H), 5.16 (bs, 1H), 5.03-4.86 (m, 1H), 4.78 (t, J = 9.2 Hz, 1H), 4.75-4.64 (m, 1H), 4.62-4.34 (m, 2H), 4.04-3.96 (m, 1H), 3.84 (dd, J = 11.3, 8.4 Hz, 1H), 3.24-3.10 (m, 2H), 3.07 (s, 3H), 2.62 (m, 2H). |
| 793 | 451.1 | 1H NMR (400 MHz, DMSO-d6) δ 8.02 (d, J = 8.1 Hz, 2H), 7.78 (d, J = 8.1 Hz, 2H), 5.69 (s, 1H), 4.25 (m, 1H), 4.13 (m, 2H), 3.97 (d, J = 14.4 Hz, 1H), 3.80-3.52 (m, 3H), 3.32-3.23 (partially obscured by water, m, 1H), 3.13 (m, 2H), 2.85 (m, 1H), 2.74 (m, 1H), 2.68-2.45 (m, 2H), 1.49 (d, J = 5.7 Hz, 3H). |
| 794 | 451.1 | 1H NMR (400 MHz, DMSO-d6) δ 8.95 (s, 3H), 8.05 (d, J = 8.3 Hz, 2H), 7.80 (d, J = 8.3 Hz, 2H), 4.25 (dd, J = 9.0, 5.5 Hz, 1H), 4.19-4.08 (m, 3H), 3.77 (obscured by large bs, d, J = 14.6 Hz, 1H), 3.73-3.59 (obscured by large bs, m, 3H), 3.30 (dt, J = 14.1, 7.3 Hz, 1H), 3.13 (qq, J = 9.5, 6.5, 4.6 Hz, 2H), 2.95 (dt, J = 14.8, 7.5 Hz, 1H), 2.82 (dt, J = 14.6, 7.4 Hz, 1H), 2.67-2.48 (m, 2H), 1.49 (d, J = 5.7 Hz, 3H). |
| 795 | 451.1 | 1H NMR (400 MHz, DMSO-d6) δ 8.94 (s, 3H), 8.05 (d, J = 8.4 Hz, 2H), 7.80 (d, J = 8.5 Hz, 2H), 4.25 (m, 1H), 4.20-4.07 (m, 3H), 3.77 (obscured by large bs, d, J = 13.8 Hz, 1H), 3.66 (obscured by large bs, m, 3H), 3.30 (dt, J = 14.1, 7.3 Hz, 1H), 3.19-3.05 (m, 2H), 2.95 (dt, J = 14.9, 7.5 Hz, 1H), 2.82 (dt, J = 14.4, 7.4 Hz, 1H), 2.59 (m, 2H), 1.48 (d, J = 5.2 Hz, 3H). |
| 796 | 438.1 | 1H NMR (400 MHz, DMSO-d6) δ 7.97 (d, J = 8.5 Hz, 2H), 7.77 (d, J = 8.5 Hz, 2H), 5.17 (ddt, J = 56.9, 6.0, 3.7 Hz, 1H), 4.57 (bs, 1H), 4.56-4.32 (m, 1H), 4.44 (d, J = 14.0 Hz, 2H), 4.16 (d, J = 15.0 Hz, 2H), 4.01 (m, 1H), 3.16 (m, 2H), 2.78 (bs, 2H), 2.59 (m, 2H), 1.56 (d, J = 6.5 Hz, 3H). |
| 797 | 438.1 | 1H NMR (400 MHz, DMSO-d6) δ 7.96 (d, J = 8.5 Hz, 2H), 7.71 (d, J = 8.5 Hz, 2H), 5.28-5.04 (m, 1H), 4.56-4.35 (m, 1H), 4.54 (m, 1H), 4.49 (d, J = 13.7 Hz, 2H), 4.07 (d, J = 14.0 Hz, 2H), 4.04-3.89 (m, 1H), 3.16 (m, 2H), 2.86 (bs, 2H), 2.60 (m, 2H), 1.55 (d, J = 6.5 Hz, 3H). |
| 798 | 420.3 | 1H NMR (400 MHz, DMSO-d6) δ10.85 (d, J = 11.9 Hz, 2H), 9.09 (s, 1H), 8.64 (d, J = 8.2 Hz, 1H), 8.58 (d, J = 8.1 Hz, 1H), 5.73 (bs, 1H), 4.31 (m, 1H), 4.23 (s, 3H), 4.18 (m, 1H), 3.76 (obscured by bs, m, 1H), 3.22 (m, 1H), 3.15 (m, 2H), 2.65 (m, 2H), 1.51 (d, J = 6.4 Hz, 3H). |
| 799 | 457.1 | 1H NMR (400 MHz, DMSO-d6)δ 9.09 (bs, 3H), 8.10 (d, J = 8.5 Hz, 2H), 7.85 (d, J = 8.6 Hz, 2H), 6.46 (ddd, J = 57.3, 54.8, 2.4 Hz, 1H), 5.09 (d, J = 15.6 Hz, 2H), 4.94 (d, J = 15.4 Hz, 2H), 4.83-4.70 (m, 1H), 4.08 (m, 1H), 3.25 (m, 2H), 2.62 (m, 2H), 2.52-2.41 (partially obscured by DMSO, m, 3H). |
| 800 | 457.2 | 1H NMR (400 MHz, DMSO-d6) δ 9.06 (bs, 3H), 8.10 (d, J = 8.6 Hz, 2H), 7.85 (d, J = 8.6 Hz, 2H), 6.46 (ddd, J = 57.3, 54.9, 2.4 Hz, 1H), 5.09 (d, J = 15.5 Hz, 2H), 4.94 (d, J = 15.3 Hz, 2H), 4.76 (m, 1H), 4.08 (m, 2H), 3.25-3.11 (m, 2H), 2.62 (m, 2H), 2.47 (partially obscured by DMSO, m, 2H). |
| 801 | 457.2 | 1H NMR (400 MHz, DMSO-d6) δ 9.11 (bs, 3H), 8.10 (d, J = 8.5 Hz, 2H), 7.85 (d, J = 8.6 Hz, 2H), 6.46 (ddd, J = 57.4, 54.9, 2.4 Hz, 1H), 5.09 (d, J = 15.5 Hz, 2H), 4.95 (d, J = 15.3 Hz, 2H), 4.76 (m, 1H), 4.09 (m, 2H), 3.27-3.08 (m, 2H), 2.62 (m, 2H), 2.52-2.41 (partially obscured by DMSO, m, 2H). |

TABLE 1-continued

MS and NMR DATA

| Example No | ES/MS m/z (M + H)+ | 1H NMR |
|---|---|---|
| 802 | 475.1 | 1H NMR (400 MHz, DMSO-d6) δ 9.11 (bs, 3H), 8.11 (d, J = 8.2 Hz, 2H), 7.87 (d, J = 8.2 Hz, 2H), 5.10 (m, 1H), 5.09 (d, J = 14.8 Hz, 2H), 4.95 (d, J = 14.6 Hz, 2H), 4.16 (m, 2H), 3.21 (m, 2H), 2.65 (m, 3H), 2.44 (m, 1H). |
| 803 | 423.9 | 1H NMR (400 MHz, DMSO-d6)δ 8.72 (s, 3H), 8.08 (d, J = 8.1 Hz, 2H), 7.73 (d, J = 8.3 Hz, 2H), 5.09 (m, 1H), 4.85 (t, J = 7.1 Hz, 1H), 4.15 (dtd, J = 14.8, 8.4, 6.2 Hz, 2H), 3.30 (d, J = 7.0 Hz, 2H), 3.19 (m, 2H), 2.72-2.55 (m, 3H), 2.44 (partially obscured by DMSO, m, 1H). |
| 804 | 448.0 | 1H NMR (400 MHz, DMSO-d6) δ 7.98-7.87 (m, 1H), 7.58-7.47 (m, 2H), 7.40-7.33 (m, 1H), 5.36-5.21 (m, 1H), 4.84-4.74 (m, 1H), 4.57-4.37 (m, 2H), 4.10-3.94 (m, 2H), 3.19-3.02 (m, 5H), 2.63-2.39 (m, 3H), 2.09-1.93 (m, 1H). |
| 805 | 407.0 | 1H NMR (400 MHz, DMSO-d6) δ 8.62 (s, 1H), 8.30-8.23 (m, 1H), 7.86 (d, J = 8.1 Hz, 1H), 4.93-4.68 (m, 1H), 4.35-4.25 (m, 1H), 4.21-4.12 (m, 2H), 3.78-3.66 (m, 2H), 3.28-3.06 (m, 2H), 2.72-2.58 (m, 2H), 2.55 (s, 3H), 1.57-1.47 (m, 3H). |
| 806 | 433.1 | 1H NMR (400 MHz, DMSO-d6) δ 7.91 (d, J = 7.8 Hz, 1H), 7.52-7.39 (m, 2H), 7.35 (s, 1H), 5.42-5.34 (m, 1H), 4.74 (t, J = 9.2 Hz, 1H), 4.35-4.21 (m, 2H), 4.16-4.09 (m, 2H), 3.72-3.65 (m, 1H), 3.59 (s, 3H), 3.15-3.07 (m, 2H), 2.65-2.54 (m, 2H), 1.49 (d, J = 5.8 Hz, 3H). |
| 807 | 409.1 | 1H NMR (400 MHz, DMSO-d6) δ 8.24 (s, 1H), 8.12 (d, J = 8.3 Hz, 1H), 7.58 (d, J = 8.2 Hz, 1H), 5.68 (s, 1H), 4.37 (s, 2H), 4.31-4.24 (m, 1H), 4.18-4.10 (m, 2H), 3.99-3.87 (m, 2H), 3.73-3.67 (m, 1H), 3.20-3.04 (m, 2H), 2.70-2.55 (m, 2H), 1.51 (d, J = 5.9 Hz, 3H). |
| 808 | 433.1 | 1H NMR (400 MHz, DMSO-d6) δ 8.42 (t, J = 5.7 Hz, 1H), 7.78 (d, J = 8.1 Hz, 1H), 7.71 (dd, J = 8.1, 1.7 Hz, 1H), 7.58 (d, J = 1.7 Hz, 1H), 4.42-4.32 (m, 1H), 4.30-4.21 (m, 1H), 4.17-4.05 (m, 2H), 3.69 (dd, J = 9.0, 4.3 Hz, 1H), 3.63 (dd, J = 11.3, 5.4 Hz, 1H), 3.52 (dd, J = 11.4, 6.2 Hz, 1H), 3.38-3.30 (m, 1H), 3.26-3.05 (m, 3H), 2.65-2.53 (m, 2H), 1.50 (d, J = 5.8 Hz, 3H). |
| 809 | 435.0 | 1H NMR (400 MHz, DMSO-d6) δ 8.67 (d, J = 7.6 Hz, 1H), 7.29-7.23 (m, 2H), 5.73-5.66 (m, 1H), 4.78 (t, J = 9.7, 8.3 Hz, 1H), 4.38-4.32 (m, 1H), 4.29-4.22 (m, 1H), 4.17-4.09 (m, 2H), 3.72-3.65 (m, 1H), 3.17-3.08 (m, 2H), 2.66-2.53 (m, 2H), 1.85 (s, 3H), 1.49 (d, J = 5.8 Hz, 3H). |
| 810 | 465.1 | 1H NMR (400 MHz, Chloroform-d) δ 8.28 (d, J = 8.1, 1.8 Hz, 1H), 8.23-8.17 (m, 1H), 7.66 (d, J = 8.1 Hz, 1H), 6.00 (s, 1H), 4.52-4.45 (m, 1H), 4.40-4.32 (m, 2H), 3.98-3.91 (m, 1H), 3.44 (d, J = 18.5 Hz, 1H), 3.25-3.13 (m, 2H), 2.94-2.74 (m, 3H), 2.67-2.54 (m, 2H), 2.02 (s, 3H), 1.74 (s, 3H), 1.64 (d, J = 6.1 Hz, 3H). |
| 811 | 451.0 | 1H NMR (400 MHz, DMSO-d6) δ 8.00 (d, J = 8.3 Hz, 1H), 7.27-7.19 (m, 2H), 5.60-5.51 (m, 1H), 4.85-4.75 (m, 1H), 4.42-4.32 (m, 1H), 4.30-4.22 (m, 1H), 4.18-4.07 (m, 2H), 3.72-3.65 (m, 1H), 3.58 (s, 3H), 3.18-3.03 (m, 2H), 2.65-2.55 (m, 2H), 1.49 (d, J = 5.8 Hz, 3H). |
| 812 | 471.1 | 1H NMR (400 MHz, DMSO-d6) δ 8.07 (d, J = 8.2 Hz, 1H), 7.36-7.19 (m, 2H), 5.48-5.40 (m, 1H), 4.87-4.74 (m, 1H), 4.53-4.47 (m, 1H), 4.30-4.21 (m, 1H), 4.17-4.09 (m, 2H), 3.75-3.64 (m, 1H), 3.17-3.06 (m, 2H), 3.04 (s, 3H), 2.67-2.54 (m, 2H), 1.49 (d, J = 5.9 Hz, 3H). |
| 813 | 470.0 | 1H NMR (400 MHz, DMSO-d6) δ 8.07 (d, J = 8.2 Hz, 1H), 7.32-7.20 (m, 2H), 5.51-5.38 (m, 1H), 4.85-4.77 (m, 1H), 4.54-4.47 (m, 1H), 4.30-4.22 (m, 1H), 4.16-4.08 (m, 2H), 3.72-3.66 (m, 1H), 3.16-3.07 (m, 2H), 3.04 (s, 3H), 2.68-2.54 (m, 2H), 1.49 (d, J = 6.0 Hz, 3H). |
| 814 | 433.1 | 1H NMR (400 MHz, DMSO-d6) δ 7.94-7.88 (m, 1H), 7.67-7.53 (m, 1H), 7.46 (s, 1H), 7.35 (s, 1H), 5.44-5.32 (m, 1H), 4.74 (t, J = 9.2 Hz, 1H), 4.36-4.22 (m, 2H), 4.16-4.09 (m, 2H), 3.72-3.64 (m, 1H), 3.59 (s, 3H), 3.16-3.05 (m, 2H), 2.64-2.54 (m, 2H), 1.49 (d, J = 5.8 Hz, 3H). |
| 815 | 433.1 | 1H NMR (400 MHz, DMSO-d6) δ 7.95-7.88 (m, 1H), 7.68-7.55 (m, 1H), 7.46 (s, 1H), 7.35 (s, 1H), 5.44-5.33 (m, 1H), 4.74 (t, J = 9.2 Hz, 1H), 4.35-4.20 (m, 2H), 4.15-4.08 (m, 2H), 3.71-3.65 (m, 1H), 3.59 (s, 3H), 3.15-3.02 (m, 2H), 2.62-2.53 (m, 2H), 1.49 (d, J = 5.8 Hz, 3H). |
| 816 | 479.0 | 1H NMR (400 MHz, DMSO-d6) δ 7.80 (d, J = 7.9, 1.7 Hz, 1H), 7.75 (s, 1H), 7.63 (d, J = 9.4 Hz, 1H), 7.47 (d, J = 7.9 Hz, 1H), 4.54 (d, J = 9.3 Hz, 1H), 4.29-4.22 (m, 1H), 4.15-4.09 (m, 2H), 3.71-3.65 (m, 1H), 3.11 (s, 3H), 2.77 (s, 2H), 2.62-2.47 (m, 4H), 1.50 (d, J = 5.8 Hz, 3H), 1.22 (s, 3H), 0.89 (s, 3H). |
| 817 | 471.0 | 1H NMR (400 MHz, DMSO-d6) δ 8.07 (d, J = 8.2 Hz, 1H), 7.30-7.22 (m, 2H), 5.51-5.41 (m, 1H), 4.80 (t, J = 9.9, 8.1 Hz, 1H), 4.54-4.47 (m, 1H), 4.29-4.22 (m, 1H), 4.17-4.09 (m, 2H), 3.73-3.66 |

TABLE 1-continued

| | | MS and NMR DATA |
|---|---|---|
| Example No | ES/MS m/z (M + H)+ | 1H NMR |
| | | (m, 1H), 3.18-3.09 (m, 2H), 3.04 (s, 3H), 2.65-2.53 (m, 2H), 1.49 (d, J = 5.8 Hz, 3H). |
| 818 | 423.1 | 1H NMR (400 MHz, DMSO-d6) δ 8.36 (s, 1H), 8.09-7.99 (m, 1H), 7.18 (d, J = 8.8 Hz, 1H), 5.66 (d, J = 6.2 Hz, 1H), 4.86-4.72 (m, 2H), 4.31-4.22 (m, 1H), 4.18-4.07 (m, 2H), 3.75-3.58 (m, 2H), 3.24-3.00 (m, 2H), 2.69-2.56 (m, 2H), 1.55-1.48 (m, 3H). |
| 819 | 458.1 | 1H NMR (400 MHz, DMSO-d6) δ 9.02 (s, 1H), 7.54-7.40 (m, 3H), 4.82-4.54 (m, 2H), 4.31-4.22 (m, 1H), 4.16-4.08 (m, 2H), 3.72-3.65 (m, 1H), 3.15-3.07 (m, 2H), 2.94 (s, 3H), 2.63-2.53 (m, 2H), 1.49 (d, J = 5.9 Hz, 3H). |
| 820 | 423.0 | 1H NMR (400 MHz, DMSO-d6) δ 8.38-8.35 (m, 1H), 8.06-8.02 (m, 1H), 7.22-7.17 (m, 1H), 4.87-4.77 (m, 2H), 4.31-4.24 (m, 1H), 4.16-4.10 (m, 2H), 3.74-3.68 (m, 3H), 3.27-3.03 (m, 2H), 2.71-2.56 (m, 2H), 1.51 (d, J = 5.7 Hz, 3H). |
| 821 | 423.1 | 1H NMR (400 MHz, DMSO-d6) δ 8.38-8.34 (m, 1H), 8.07-8.01 (m, 1H), 7.25-7.17 (m, 1H), 4.85-4.78 (m, 2H), 4.30-4.23 (m, 1H), 4.18-4.10 (m, 2H), 3.74-3.69 (m, 2H), 3.35-3.30 (m, 1H), 3.20-3.11 (m, 2H), 2.72-2.54 (m, 2H), 1.50 (d, J = 5.7 Hz, 3H). |
| 822 | 452.0 | 1H NMR (400 MHz, DMSO-d6) δ 8.94 (s, 1H), 8.16 (s, 1H), 7.67 (d, J = 8.9 Hz, 1H), 4.95-4.83 (m, 1H), 4.32-4.21 (m, 1H), 4.18-4.10 (m, 3H), 3.76-3.66 (m, 1H), 3.21-3.10 (m, 5H), 3.07-2.82 (m, 2H), 2.68-2.57 (m, 2H), 2.01-1.90 (m, 1H), 1.50 (d, J = 5.9 Hz, 3H). |
| 823 | 452.0 | 1H NMR (400 MHz, DMSO-d6) δ 8.94 (s, 1H), 8.16 (s, 1H), 7.67 (d, J = 8.9 Hz, 1H), 4.96-4.86 (m, 1H), 4.30-4.23 (m, 1H), 4.18-4.08 (m, 3H), 3.75-3.64 (m, 1H), 3.21-3.07 (m, 5H), 3.07-2.80 (m, 2H), 2.67-2.54 (m, 2H), 2.02-1.91 (m, 1H), 1.50 (d, J = 5.9 Hz, 3H). |
| 824 | 463.1 | 1H NMR (400 MHz, DMSO-d6) δ 7.79-7.69 (m, 1H), 7.07 (s, 1H), 6.98 (s, 1H), 5.38-5.27 (m, 1H), 4.68 (t, J = 8.9 Hz, 1H), 4.37-4.21 (m, 2H), 4.16-4.09 (m, 2H), 3.85 (s, 3H), 3.73-3.64 (m, 1H), 3.56 (s, 3H), 3.20-3.06 (m, 2H), 2.67-2.54 (m, 2H), 1.50 (d, J = 5.7 Hz, 3H). |
| 825 | 463.1 | 1H NMR (400 MHz, DMSO-d6) δ 8.60-8.58 (m, 1H), 8.44-8.37 (m, 1H), 7.58-7.50 (m, 1H), 5.14-5.02 (m, 1H), 4.21-4.10 (m, 2H), 4.07 (s, 3H), 3.49 (s, 3H), 3.26-3.19 (m, 2H), 2.74-2.59 (m, 2H), 2.48-2.39 (m, 2H). |
| 826 | 458.1 | 1H NMR (400 MHz, DMSO-d6) δ 9.02 (s, 1H), 7.54-7.40 (m, 3H), 4.82-4.54 (m, 2H), 4.31-4.22 (m, 1H), 4.16-4.08 (m, 2H), 3.72-3.65 (m, 1H), 3.15-3.07 (m, 2H), 2.94 (s, 3H), 2.63-2.53 (m, 2H), 1.49 (d, J = 5.9 Hz, 3H). |
| 827 | 458.0 | 1H NMR (400 MHz, DMSO-d6) δ 9.02 (s, 1H), 7.54-7.40 (m, 3H), 4.82-4.54 (m, 2H), 4.31-4.22 (m, 1H), 4.16-4.08 (m, 2H), 3.72-3.65 (m, 1H), 3.15-3.07 (m, 2H), 2.94 (s, 3H), 2.63-2.53 (m, 2H), 1.49 (d, J = 5.9 Hz, 3H). |
| 828 | 439.0 | 1H NMR (400 MHz, DMSO-d6) δ 8.58 (s, 1H), 8.36 (d, J = 8.7, 2.3 Hz, 1H), 7.53 (d, J = 8.8 Hz, 1H), 4.28-4.20 (m, 1H), 4.07 (s, 3H), 3.93-3.78 (m, 2H), 3.57 (s, 3H), 3.22-3.12 (m, 2H), 2.70-2.56 (m, 2H), 1.43 (d, J = 6.6 Hz, 3H), 1.35 (s, 3H). |
| 829 | 445.0 | 1H NMR (400 MHz, DMSO-d6) δ 8.58 (s, 1H), 7.66-7.53 (m, 2H), 7.38 (s, 1H), 4.77-4.49 (m, 4H), 4.25-4.15 (m, 1H), 3.90-3.77 (m, 2H), 3.14-3.04 (m, 2H), 2.64-2.53 (m, 2H), 1.41 (d, J = 6.6 Hz, 3H), 1.34 (s, 3H). |
| 830 | 469.1 | 1H NMR (400 MHz, DMSO-d6) δ 8.58 (s, 1H), 7.69-7.57 (m, 2H), 7.45 (s, 1H), 5.15-5.03 (m, 1H), 4.76-4.53 (m, 4H), 4.20-4.07 (m, 2H), 3.24-3.13 (m, 2H), 2.74-2.39 (m, 4H). |
| 831 | 451.0 | 1H NMR (400 MHz, DMSO-d6) δ 8.58 (s, 1H), 7.68-7.56 (m, 2H), 7.43 (s, 1H), 6.62-6.25 (m, 1H), 4.83-4.49 (m, 5H), 4.12-4.01 (m, 2H), 3.25-3.04 (m, 2H), 2.70-2.35 (m, 4H). |
| 832 | 461.0 | 1H NMR (400 MHz, DMSO-d6) δ 8.69 (s, 1H), 8.38-8.30 (m, 1H), 7.48 (d, J = 8.8 Hz, 1H), 7.25-6.93 (m, 2H), 4.30-4.22 (m, 1H), 4.17-4.10 (m, 2H), 4.03 (s, 3H), 3.73-3.69 (m, 1H), 3.21-3.06 (m, 2H), 2.70-2.55 (m, 2H), 1.52 (d, J = 5.9 Hz, 3H). |
| 833 | 463.1 | 1H NMR (400 MHz, DMSO-d6) δ 7.86 (dd, J = 8.2, 1.7 Hz, 1H), 7.71 (d, J = 8.6 Hz, 1H), 7.67-7.60 (m, 2H), 4.82-4.75 (m, 2H), 4.65-4.53 (m, 1H), 4.28-4.21 (m, 1H), 4.17-4.03 (m, 3H), 3.80-3.74 (m, 1H), 3.71-3.65 (m, 1H), 3.12 (s, 5H), 2.64-2.54 (m, 2H), 1.50 (d, J = 5.7 Hz, 3H). |
| 834 | 463.1 | 1H NMR (400 MHz, DMSO-d6) δ 7.86 (dd, J = 8.2, 1.7 Hz, 1H), 7.71 (d, J = 8.6 Hz, 1H), 7.67-7.60 (m, 2H), 4.82-4.75 (m, 2H), 4.65-4.53 (m, 1H), 4.28-4.21 (m, 1H), 4.17-4.03 (m, 3H), 3.80-3.74 (m, 1H), 3.71-3.65 (m, 1H), 3.12 (s, 5H), 2.64-2.54 (m, 2H), 1.50 (d, J = 5.7 Hz, 3H). |
| 835 | 423.1 | 1H NMR (400 MHz, DMSO-d6) δ 7.92-7.84 (m, 2H), 7.61 (d, J = 8.2 Hz, 1H), 6.84 (t, J = 53.0, 2.9 Hz, 1H), 5.34-5.24 (m, 1H), 4.29- |

TABLE 1-continued

MS and NMR DATA

| Example No | ES/MS m/z (M + H)+ | 1H NMR |
|---|---|---|
| | | 4.24 (m, 1H), 4.17-4.11 (m, 2H), 3.72-3.68 (m, 1H), 3.56-3.41 (m, 2H), 3.21-3.08 (m, 4H), 2.67-2.54 (m, 2H), 1.50 (d, J = 5.8 Hz, 3H). |
| 836 | 407.1 | 1H NMR (400 MHz, DMSO-d6) δ 7.92-7.83 (m, 2H), 7.60 (d, J = 8.2 Hz, 1H), 6.83 (t, J = 53.0, 2.8 Hz, 1H), 5.35-5.22 (m, 1H), 4.56-4.43 (m, 1H), 4.10-3.95 (m, 2H), 3.55-3.41 (m, 2H), 3.21-3.05 (m, 4H), 2.67-2.43 (m, 3H), 2.07-1.96 (m, 1H), 1.52 (d, J = 6.2 Hz, 3H). |
| 837 | 457.2 | 1H NMR (400 MHz, DMSO-d6) δ 8.88 (s, 3H), 7.68 (s, 1H), 7.65-7.60 (m, 1H), 7.49 (d, J = 7.9 Hz, 1H), 5.16-5.03 (m, 3H), 4.85 (d, J = 8.0 Hz, 2H), 4.22-4.07 (m, 2H), 3.88 (s, 3H), 3.34-3.12 (m, 2H), 2.73-2.58 (m, 3H), 2.50-2.39 (m, 1H). |
| 838 | 417.3 | 1H NMR (400 MHz, DMSO-d6) δ 8.41 (s, 3H), 8.05 (d, J = 8.4 Hz, 2H), 7.80 (d, J = 8.6 Hz, 2H), 4.31-4.20 (m, 1H), 4.17-4.09 (m, 2H), 3.92-3.82 (m, 2H), 3.72-3.65 (m, 1H), 3.47-3.36 (m, 2H), 3.19-3.07 (m, 2H), 2.68-2.53 (m, 2H), 2.47 (s, 2H), 2.16-2.03 (m, 2H), 1.50 (d, J = 5.8 Hz, 3H). |
| 839 | 449.1 | 1H NMR (400 MHz, DMSO-d6) δ 8.57-8.51 (m, 1H), 8.30-8.23 (m, 1H), 7.81-7.72 (m, 2H), 7.59-7.52 (m, 3H), 7.47-7.40 (m, 2H), 5.59-5.35 (m, 2H), 4.53-4.26 (m, 1H), 3.99-3.86 (m, 2H), 3.55 (s, 3H), 3.20-2.93 (m, 3H), 2.88-2.78 (m, 2H), 2.40-2.35 (m, 1H), 2.11-1.90 (m, 2H), 1.60-1.42 (m, 3H). |
| 840 | 443.1 | 1H NMR (400 MHz, DMSO-d6) δ 8.46 (d, J = 2.3 Hz, 1H), 8.33-8.16 (m, 1H), 7.44 (d, J = 8.8 Hz, 1H), 4.48-4.32 (m, 1H), 4.01 (s, 3H), 3.98-3.88 (m, 6H), 3.41-3.27 (m, 2H), 3.13-2.93 (m, 1H), 2.93-2.79 (m, 2H), 2.46-2.34 (m, 3H), 2.05-1.93 (m, 3H), 1.84-1.54 (m, 3H), 1.54-1.45 (m, 3H). |
| 841 | 399.1 | 1H NMR (400 MHz, DMSO-d6) δ 7.89 (s, 1H), 7.76-7.69 (m, 1H), 7.67-7.62 (m, 1H), 7.55-7.46 (m, 2H), 7.34-7.14 (m, 5H), 4.44-4.28 (m, 1H), 4.21 (s, 2H), 3.98-3.88 (m, 1H), 3.90-3.83 (m, 1H), 3.00-2.69 (m, 4H), 2.42-2.29 (m, 1H), 2.12-1.71 (m, 3H), 1.44 (d, J = 6.2 Hz, 3H). |
| 842 | 431.1 | 1H NMR (400 MHz, DMSO-d6) δ 7.90-7.80 (m, 2H), 7.71-7.63 (m, 1H), 7.61-7.54 (m, 1H), 7.48 (s, 1H), 7.44-7.36 (m, 2H), 7.36-7.27 (m, 2H), 7.29-7.20 (m, 1H), 4.56-4.31 (m, 1H), 4.23 (s, 2H), 4.00-3.87 (m, 2H), 2.91-2.70 (m, 4H), 2.47-2.34 (m, 1H), 2.07-1.87 (m, 3H), 1.48 (d, J = 6.2 Hz, 3H). |
| 843 | 413.1 | 1H NMR (400 MHz, DMSO-d6) δ 9.41-9.35 (m, 1H), 7.97-7.87 (m, 1H), 7.82-7.69 (m, 2H), 7.57-7.43 (m, 2H), 7.41-7.23 (m, 3H), 4.46-4.28 (m, 1H), 3.96-3.81 (m, 2H), 3.05-2.69 (m, 4H), 2.41-2.26 (m, 1H), 2.02-1.85 (m, 3H), 1.45 (d, J = 6.2 Hz, 3H). |
| 844 | 459.1 | 1H NMR (400 MHz, DMSO-d6) δ 8.64-8.43 (m, 1H), 8.42-8.13 (m, 1H), 7.46 (d, J = 8.8 Hz, 1H), 4.82-4.63 (m, 2H), 4.48-4.38 (m, 1H), 4.03 (s, 3H), 3.99-3.86 (m, 4H), 3.72-3.49 (m, 4H), 3.23-2.89 (m, 2H), 2.86-2.79 (m, 2H), 2.44-2.32 (m, 1H), 2.28-2.15 (m, 1H), 2.09-1.82 (m, 3H), 1.57-1.33 (m, 3H). |
| 845 | 494.1 | 1H NMR (400 MHz, DMSO-d6) δ 8.76-8.65 (m, 1H), 8.30-8.11 (m, 3H), 8.05-7.89 (m, 1H), 7.28 (d, J = 8.8 Hz, 1H), 4.51-4.41 (m, 1H), 4.08-3.88 (m, 2H), 3.77 (s, 3H), 3.17-2.98 (m, 2H), 2.90-2.76 (m, 2H), 2.48-2.33 (m, 1H), 2.13-1.90 (m, 3H), 1.59-1.43 (m, 3H). |
| 846 | 474.1 | 1H NMR (400 MHz, DMSO-d6) δ 8.72 (dd, J = 4.6, 2.3 Hz, 1H), 8.31 (dd, J = 8.3, 2.5 Hz, 1H), 8.20 (dd, J = 8.6, 2.3 Hz, 1H), 7.98-7.85 (m, 2H), 7.84-7.73 (m, 1H), 7.26 (d, J = 8.8 Hz, 1H), 4.52-4.42 (m, 1H), 4.11-3.91 (m, 2H), 3.63 (s, 3H), 3.16-2.95 (m, 2H), 2.90-2.80 (m, 2H), 2.46-2.38 (m, 1H), 2.29 (s, 3H), 2.12-1.91 (m, 3H), 1.58-1.42 (m, 3H). |
| 847 | 470.1 | 1H NMR (400 MHz, DMSO-d6) δ 8.40 (d, J = 8.2 Hz, 1H), 8.35-8.28 (m, 1H), 8.12-8.07 (m, 1H), 7.97-7.93 (m, 1H), 7.89 (dd, J = 8.2, 1.6 Hz, 1H), 7.74-7.66 (m, 1H), 7.46 (d, J = 1.7 Hz, 1H), 4.44-4.21 (m, 1H), 4.02-3.79 (m, 2H), 3.04-2.67 (m, 6H), 2.43-2.30 (m, 1H), 2.05-1.89 (m, 3H), 1.41 (d, J = 6.2 Hz, 3H), 0.79-0.49 (m, 4H). |
| 848 | 460.1 | 1H NMR (400 MHz, DMSO-d6) δ 8.47-8.41 (m, 1H), 8.15-8.08 (m, 2H), 7.93 (d, J = 8.0 Hz, 1H), 7.77-7.69 (m, 2H), 7.61 (dd, J = 8.1, 1.6 Hz, 1H), 4.46-4.34 (m, 1H), 4.01 (s, 3H), 3.98-3.84 (m, 2H), 3.11-2.89 (m, 2H), 2.85-2.74 (m, 2H), 2.43-2.35 (m, 1H), 2.09-1.90 (m, 3H), 1.54-1.41 (m, 3H). |
| 849 | 494.1 | 1H NMR (400 MHz, DMSO-d6) δ 8.77-8.70 (m, 1H), 8.45 (dd, J = 8.1, 1.9 Hz, 1H), 8.20 (dd, J = 8.7, 2.3 Hz, 1H), 8.15-8.07 (m, 2H), 7.26 (d, J = 8.8 Hz, 1H), 4.51-4.35 (m, 1H), 4.09-3.79 (m, 2H), 3.62 (s, 3H), 3.16-2.95 (m, 2H), 2.92-2.74 (m, 2H), 2.46-2.35 (m, 1H), 2.13-1.90 (m, 3H), 1.55-1.35 (m, 3H). |
| 850 | 490.1 | 1H NMR (400 MHz, DMSO-d6) δ 8.70-8.64 (m, 1H), 8.23-8.14 (m, 1H), 7.90 (d, J = 8.1 Hz, 1H), 7.77-7.72 (m, 1H), 7.57-7.49 (m, |

TABLE 1-continued

| MS and NMR DATA | | |
|---|---|---|
| Example No | ES/MS m/z (M + H)+ | 1H NMR |
| | | 1H), 7.27 (d, J = 8.8 Hz, 1H), 4.54-4.42 (m, 1H), 4.00 (s, 3H), 3.99-3.90 (m, 2H), 3.80 (s, 3H), 3.20-2.97 (m, 2H), 2.96-2.81 (m, 2H), 2.49-2.37 (m, 1H), 2.15-1.87 (m, 3H), 1.56-1.42 (m, 3H). |
| 851 | 460.1 | 1H NMR (400 MHz, DMSO-d6) δ 8.72-8.65 (m, 1H), 8.22-8.13 (m, 1H), 8.12-8.04 (m, 2H), 8.06-7.98 (m, 2H), 7.25 (d, J = 8.8 Hz, 1H), 4.62-4.38 (m, 1H), 4.03-3.85 (m, 2H), 3.74 (s, 3H), 3.26-2.94 (m, 2H), 2.91-2.74 (m, 2H), 2.45-2.30 (m, 1H), 2.14-1.90 (m, 3H), 1.67-1.37 (m, 3H). |
| 852 | 306.1 | 1H NMR (400 MHz, DMSO-d6) δ 9.42 (s, 1H), 8.31 (s, 1H), 8.07 (d, J = 8.3 Hz, 1H), 7.99-7.91 (m, 1H), 4.52-4.35 (m, 1H), 4.06-3.82 (m, 2H), 3.16-3.00 (m, 2H), 2.91-2.77 (m, 2H), 2.42-2.27 (m, 1H), 2.16-1.80 (m, 3H), 1.52 (d, J = 6.2 Hz, 3H). |
| 853 | 320.2 | 1H NMR (400 MHz, DMSO-d6) δ 9.42 (s, 1H), 8.29 (s, 1H), 8.13-8.03 (m, 1H), 8.00-7.91 (m, 1H), 4.51-4.40 (m, 1H), 4.09 (s, 3H), 4.05-3.80 (m, 2H), 3.23-2.99 (m, 2H), 2.92-2.76 (m, 2H), 2.48-2.31 (m, 1H), 2.14-1.92 (m, 3H), 1.52 (d, J = 6.2 Hz, 3H). |
| 854 | 427.1 | 1H NMR (400 MHz, DMSO-d6) δ 7.73-7.61 (m, 3H), 7.52 (d, J = 8.0 Hz, 1H), 4.71-4.61 (m, 1H), 4.50-4.34 (m, 1H), 4.12-3.85 (m, 2H), 3.06-2.90 (m, 3H), 2.92-2.77 (m, 6H), 2.43-2.32 (m, 1H), 2.13-1.56 (m, 9H), 1.52-1.36 (m, 3H). |
| 855 | 350.1 | 1H NMR (400 MHz, DMSO-d6) δ 10.69 (bs, 1H), 9.69 (bs, 2H), 7.75-7.67 (m, 2H), 7.56 (d, J = 7.9 Hz, 1H), 4.49-4.36 (m, 1H), 4.28 (s, 2H), 4.01-3.85 (m, 2H), 3.74-3.68 (m, 2H), 3.07-2.92 (m, 2H), 2.86-2.78 (m, 2H), 2.43-2.35 (m, 1H), 2.08-1.90 (m, 3H), 1.50 (d, J = 6.1 Hz, 3H). |
| 856 | 364.2 | 1H NMR (400 MHz, DMSO-d6) δ 9.81 (bs, 2H), 7.88 (d, J = 1.6 Hz, 1H), 7.82 (dd, J = 7.9, 1.7 Hz, 1H), 7.61 (d, J = 8.0 Hz, 1H), 4.47-4.38 (m, 1H), 4.26 (s, 2H), 4.02-3.81 (m, 4H), 3.39 (s, 3H), 3.10-2.96 (m, 2H), 2.87-2.78 (m, 2H), 2.44-2.37 (m, 1H), 2.10-1.92 (m, 3H), 1.50 (d, J = 6.1 Hz, 3H). |
| 857 | 366.0 | 1H NMR (400 MHz, DMSO-d6) δ 8.66 (d, J = 1.7 Hz, 1H), 8.15 (d, J = 8.6 Hz, 1H), 8.12 (s, 1H), 8.04 (dd, J = 8.6, 1.8 Hz, 1H), 7.52 (s, 1H), 4.54-4.39 (m, 1H), 4.12-3.91 (m, 2H), 3.34-3.27 (m, 2H), 2.93-2.79 (m, 2H), 2.49-2.41 (m, 1H), 2.17-1.89 (m, 3H), 1.55 (d, J = 6.2 Hz, 3H). |
| 858 | 364.1 | 1H NMR (400 MHz, DMSO-d6) δ 11.61 (bs, 1H), 8.10 (d, J = 8.1 Hz, 1H), 7.80 (d, J = 1.4 Hz, 1H), 7.74 (dd, J = 8.2, 1.4 Hz, 1H), 4.49-4.36 (m, 1H), 4.06-3.89 (m, 2H), 3.49 (s, 3H), 3.18-2.98 (m, 2H), 2.93-2.78 (m, 2H), 2.43-2.35 (m, 1H), 2.07-1.89 (m, 3H), 1.51 (d, J = 6.1 Hz, 3H). |
| 859 | 389.1 | 1H NMR (400 MHz, DMSO-d6) δ 7.83-7.79 (m, 1H), 7.78-7.75 (m, 1H), 7.53-7.46 (m, 1H), 5.44 (bs, 1H), 4.45-4.34 (m, 1H), 4.01-3.84 (m, 2H), 3.39-3.26 (m, 2H), 3.11-2.94 (m, 4H), 2.90-2.74 (m, 2H), 2.44-2.36 (m, 1H), 2.14-1.96 (m, 3H), 1.49 (d, J = 6.2 Hz, 3H). |
| 860 | 344.1 | 1H NMR (400 MHz, DMSO-d6) δ 8.66-8.60 (m, 1H), 8.41-8.33 (m, 1H), 8.30-8.22 (m, 1H), 4.54-4.39 (m, 1H), 4.12-3.89 (m, 2H), 3.58 (s, 3H), 3.33-3.21 (m, 2H), 2.91-2.79 (m, 2H), 2.49-2.36 (m, 1H), 2.16-1.88 (m, 3H), 1.52 (d, J = 6.1 Hz, 3H). |
| 861 | 387.1 | 1H NMR (400 MHz, DMSO-d6) δ 8.53-8.48 (m, 1H), 8.41-8.34 (m, 1H), 7.55 (d, J = 8.9 Hz, 1H), 4.51-4.33 (m, 1H), 4.06 (s, 3H), 4.01-3.85 (m, 4H), 3.17-2.91 (m, 2H), 2.87-2.75 (m, 2H), 2.44-2.35 (m, 1H), 2.12-1.93 (m, 3H), 1.55-1.44 (m, 3H), 1.31-1.12 (m, 3H). |
| 862 | 389.1 | 1H NMR (400 MHz, DMSO-d6) δ 7.56-7.52 (m, 1H), 7.50-7.43 (m, 2H), 6.90 (bs, 2H), 4.54-4.42 (m, 1H), 4.36 (s, 2H), 4.06-3.92 (m, 2H), 3.86 (s, 3H), 3.14-2.96 (m, 2H), 2.89-2.78 (m, 2H), 2.48-2.39 (m, 1H), 2.23-1.80 (m, 3H), 1.52 (d, J = 6.2 Hz, 3H). |
| 863 | 399.1 | 1H NMR (400 MHz, DMSO-d6) δ 8.01-7.88 (m, 2H), 7.81-7.73 (m, 2H), 7.69-7.59 (m, 2H), 7.41-7.36 (m, 2H), 4.44-4.33 (m, 1H), 4.05-3.79 (m, 2H), 3.05-2.87 (m, 2H), 2.87-2.73 (m, 2H), 2.45-2.32 (m, 1H), 2.22-1.79 (m, 3H), 1.43 (d, J = 6.2 Hz, 3H). |
| 864 | 365.1 | 1H NMR (400 MHz, DMSO-d6) δ 9.00 (bs, 3H), 7.84 (d, J = 1.8 Hz, 1H), 7.76 (dd, J = 8.1, 1.8 Hz, 1H), 7.23 (d, J = 8.1 Hz, 1H), 5.20 (d, J = 7.7 Hz, 2H), 5.02-4.84 (m, 2H), 4.48-4.30 (m, 1H), 4.02-3.83 (m, 2H), 3.07-2.94 (m, 2H), 2.90-2.75 (m, 2H), 2.42-2.36 (m, 1H), 2.06-1.90 (m, 3H), 1.49 (d, J = 6.2 Hz, 3H), 1.27 (t, J = 7.4 Hz, 3H). |
| 865 | 375.1 | 1H NMR (400 MHz, DMSO-d6) δ 8.12-8.05 (m, 2H), 7.95 (d, J = 8.0 Hz, 1H), 7.86-7.81 (m, 1H), 4.51-4.37 (m, 2H), 4.04-3.89 (m, 2H), 3.45 (d, J = 2.9 Hz, 2H), 3.20-2.96 (m, 2H), 2.92-2.75 (m, 2H), 2.44-2.36 (m, 1H), 2.32-2.21 (m, 2H), 2.18-1.92 (m, 7H), 1.52 (d, J = 6.1 Hz, 3H). |
| 866 | 370.1 | 1H NMR (400 MHz, DMSO-d6) δ 7.63 (bs, 1H), 7.07 (s, 1H), 4.44-4.32 (m, 1H), 3.98-3.87 (m, 2H), 3.07-2.88 (m, 2H), 2.88-2.74 |

TABLE 1-continued

| | MS and NMR DATA | |
|---|---|---|
| Example No | ES/MS m/z (M + H)+ | 1H NMR |
| | | (m, 2H), 2.42-2.34 (m, 1H), 2.14-1.88 (m, 3H), 1.50 (d, J = 6.2 Hz, 3H), 1.41 (s, 6H). |
| 867 | 322.1 | 1H NMR (400 MHz, DMSO-d6) δ 8.96-8.79 (m, 1H), 8.77-8.59 (m, 1H), 4.62-4.49 (m, 1H), 4.06-3.97 (m, 2H), 3.31-3.18 (m, 2H), 2.96-2.83 (m, 2H), 2.41-2.30 (m, 1H), 2.13-1.99 (m, 3H), 1.65-1.41 (m, 3H). |
| 868 | 422.1 | 1H NMR (400 MHz, DMSO-d6) δ 9.28 (bs, 1H), 8.82-8.69 (m, 1H), 4.54-4.40 (m, 1H), 4.11-3.88 (m, 2H), 3.33-3.20 (m, 2H), 2.86-2.74 (m, 2H), 2.45-2.34 (m, 1H), 2.07-1.87 (m, 3H), 1.63 (s, 9H), 1.55 (d, J = 6.1 Hz, 3H). |
| 869 | 417.2 | 1H NMR (400 MHz, DMSO-d6) δ 8.50-8.45 (m, 1H), 8.38-8.28 (m, 1H), 7.50 (d, J = 8.8 Hz, 1H), 4.50-4.35 (m, 1H), 4.20-4.07 (m, 2H), 4.05 (s, 3H), 4.03-3.88 (m, 2H), 3.83-3.63 (m, 2H), 3.06 (d, J = 3.5 Hz, 3H), 3.05-2.98 (m, 2H), 2.89-2.76 (m, 2H), 2.45-2.31 (m, 1H), 2.12-1.89 (m, 3H), 1.60-1.48 (m, 3H). |
| 870 | 375.1 | 1H NMR (400 MHz, DMSO-d6) δ 11.59 (bs, 1H), 8.16 (d, J = 8.2 Hz, 1H), 7.87 (dd, J = 8.2, 1.5 Hz, 1H), 7.41 (d, J = 1.5 Hz, 1H), 4.47-4.37 (m, 1H), 4.03-3.86 (m, 2H), 3.09-2.90 (m, 2H), 2.90-2.74 (m, 2H), 2.45-2.32 (m, 1H), 2.09-1.90 (m, 5H), 1.78-1.66 (m, 2H), 1.49 (d, J = 6.2 Hz, 3H). |
| 871 | 350.1 | 1H NMR (400 MHz, DMSO-d6) δ 13.08 (bs, 1H), 8.13-8.01 (m, 2H), 7.99-7.85 (m, 2H), 4.55-4.30 (m, 1H), 4.05-3.88 (m, 2H), 3.17-2.93 (m, 2H), 2.87-2.74 (m, 2H), 2.45-2.32 (m, 1H), 2.09-1.85 (m, 3H), 1.50 (d, J = 6.1 Hz, 3H). |
| 872 | 350.1 | 1H NMR (400 MHz, DMSO-d6) δ 13.11 (bs, 1H), 8.29 (s, 1H), 8.17-8.06 (m, 1H), 7.95-7.89 (m, 1H), 7.76-7.67 (m, 1H), 4.58-4.36 (m, 1H), 4.06-3.89 (m, 2H), 3.18-2.94 (m, 2H), 2.92-2.74 (m, 2H), 2.47-2.34 (m, 1H), 2.20-1.90 (m, 3H), 1.50 (d, J = 6.1 Hz, 3H). |
| 873 | 344.1 | 1H NMR (400 MHz, DMSO-d6) δ 8.54-8.43 (m, 1H), 8.31-8.19 (m, 1H), 8.15-8.02 (m, 1H), 7.91-7.81 (m, 1H), 4.52-4.33 (m, 1H), 4.18-3.79 (m, 2H), 3.11-2.96 (m, 2H), 2.91-2.75 (m, 2H), 2.43-2.32 (m, 1H), 2.13-1.91 (m, 3H), 1.50 (d, J = 6.2 Hz, 3H). |
| 874 | 344.1 | 1H NMR (400 MHz, DMSO-d6) δ 8.22-8.03 (m, 4H), 4.56-4.34 (m, 1H), 4.03-3.87 (m, 2H), 3.12-2.94 (m, 2H), 2.89-2.77 (m, 2H), 2.43-2.34 (m, 1H), 2.22-1.90 (m, 3H), 1.49 (d, J = 6.2 Hz, 3H). |
| 875 | 375.1 | 1H NMR (400 MHz, DMSO-d6) δ 7.85-7.62 (m, 3H), 7.37 (d, J = 7.8 Hz, 1H), 4.52-4.34 (m, 1H), 4.04-3.90 (m, 2H), 3.41-3.26 (m, 2H), 3.12-2.88 (m, 4H), 2.88-2.77 (m, 2H), 2.44-1.88 (m, 8H), 1.50 (d, J = 6.2 Hz, 3H). |
| 876 | 334.1 | 1H NMR (400 MHz, DMSO-d6) δ 8.60-8.46 (m, 1H), 8.19-8.03 (m, 2H), 7.80-7.69 (m, 1H), 4.57-4.39 (m, 1H), 4.08-3.87 (m, 2H), 3.28-2.98 (m, 2H), 2.98-2.76 (m, 2H), 2.47-2.34 (m, 1H), 2.11-1.92 (m, 3H), 1.52 (d, J = 6.2 Hz, 3H). |
| 877 | 426.1 | 1H NMR (400 MHz, DMSO-d6) δ 8.44 (s, 1H), 8.22 (d, J = 7.8 Hz, 1H), 8.05 (d, J = 7.8 Hz, 1H), 7.88-7.71 (m, 1H), 4.49-4.38 (m, 1H), 4.31-4.19 (m, 2H), 4.19-4.08 (m, 2H), 4.04-3.90 (m, 2H), 3.89-3.68 (m, 2H), 3.19-2.92 (m, 2H), 2.88-2.76 (m, 2H), 2.45-2.33 (m, 1H), 2.24-1.89 (m, 5H), 1.51 (d, J = 6.2 Hz, 3H). |
| 878 | 405.1 | 1H NMR (400 MHz, DMSO-d6) δ 8.48-8.41 (m, 1H), 8.11-8.03 (m, 2H), 8.03-7.96 (m, 2H), 7.75-7.66 (m, 1H), 7.63-7.51 (m, 3H), 4.44-4.35 (m, 1H), 4.06-3.79 (m, 2H), 3.05-2.86 (m, 2H), 2.86-2.72 (m, 2H), 2.44-2.27 (m, 1H), 2.09-1.90 (m, 3H), 1.55-1.38 (m, 3H). |
| 879 | 430.0 | 1H NMR (400 MHz, DMSO-d6) δ 8.48-8.41 (m, 1H), 8.31-8.02 (m, 6H), 7.77-7.66 (m, 1H), 4.52-4.30 (m, 1H), 4.09-3.80 (m, 2H), 3.07-2.92 (m, 2H), 2.88-2.72 (m, 2H), 2.44-2.31 (m, 1H), 2.10-1.91 (m, 3H), 1.61-1.41 (m, 3H). |
| 880 | 413.1 | 1H NMR (400 MHz, DMSO-d6) δ 8.42-8.31 (m, 1H), 8.27-8.17 (m, 1H), 8.03-7.94 (m, 1H), 7.88-7.72 (m, 1H), 4.49-4.37 (m, 1H), 3.97-3.85 (m, 4H), 3.62-3.41 (m, 1H), 3.38-3.19 (m, 2H), 3.15-2.96 (m, 2H), 2.89-2.63 (m, 2H), 2.46-2.33 (m, 1H), 2.10-1.93 (m, 3H), 1.90-1.70 (m, 2H), 1.60-1.44 (m, 5H). |
| 881 | 458.1 | 1H NMR (400 MHz, DMSO-d6) δ 8.51-8.44 (m, 1H), 8.34-8.24 (m, 1H), 7.51-7.41 (m, 1H), 4.45-4.40 (m, 2H), 4.02 (s, 3H), 3.99-3.85 (m, 4H), 3.69-3.51 (m, 2H), 3.13-2.92 (m, 2H), 2.86-2.70 (m, 5H), 2.44-2.34 (m, 1H), 2.11-1.87 (m, 4H), 1.63 (d, J = 2.2 Hz, 2H), 1.54-1.48 (m, 3H). |
| 882 | 426.0 | 1H NMR (400 MHz, DMSO-d6) δ 8.50 (d, J = 2.4 Hz, 1H), 8.31 (dd, J = 8.8, 2.4 Hz, 1H), 7.48 (d, J = 8.8 Hz, 1H), 4.28-4.23 (m, 1H), 4.17-4.07 (m, 2H), 4.05 (s, 3H), 3.71-3.66 (m, 2H), 3.30 (s, 3H), 3.20-3.07 (m, 2H), 2.69-2.55 (m, 2H), 1.51 (d, J = 5.9 Hz, 3H). |
| 883 | 415.1 | 1H NMR (400 MHz, DMSO-d6) δ 8.07-7.89 (m, 1H), 7.86-7.63 (m, 2H), 6.88 (d, J = 8.6 Hz, 1H), 4.75-4.57 (m, 1H), 4.41-4.34 (m, |

TABLE 1-continued

| | MS and NMR DATA | |
|---|---|---|
| Example No | ES/MS m/z (M + H)+ | 1H NMR |
| | | 1H), 4.30-4.25 (m, 2H), 4.02-3.86 (m, 2H), 3.35-3.18 (m, 2H), 3.08 (s, 3H), 3.05-2.94 (m, 1H), 2.86-2.77 (m, 2H), 2.44-2.36 (m, 1H), 2.08-1.86 (m, 4H), 1.49 (d, J = 6.2 Hz, 3H). |
| 884 | 429.1 | 1H NMR (400 MHz, DMSO-d6) δ 7.99-7.74 (m, 1H), 7.59-7.39 (m, 2H), 7.34-7.22 (m, 1H), 5.18-4.79 (m, 1H), 4.62-4.36 (m, 2H), 4.04-3.84 (m, 2H), 3.12-3.05 (m, 3H), 3.03-2.93 (m, 2H), 2.86-2.75 (m, 2H), 2.47-2.32 (m, 1H), 2.12-1.92 (m, 3H), 1.89-1.69 (m, 2H), 1.49 (d, J = 6.2 Hz, 3H), 1.13-0.96 (m, 3H). |
| 885 | 417.1 | 1H NMR (400 MHz, DMSO-d6) δ 7.90 (d, J = 9.4 Hz, 1H), 7.81-7.70 (m, 2H), 7.46 (d, J = 7.9 Hz, 1H), 5.42 (dt, J = 54.0, 3.9 Hz, 1H), 5.05 (ddd, J = 25.6, 9.4, 4.0 Hz, 1H), 4.51-4.34 (m, 1H), 4.06-3.86 (m, 2H), 3.34-3.16 (m, 2H), 3.12 (s, 3H), 3.04-2.92 (m, 2H), 2.91-2.75 (m, 2H), 2.45-2.34 (m, 1H), 2.10-1.90 (m, 3H), 1.49 (d, J = 6.2 Hz, 3H). |
| 886 | 415.1 | 1H NMR (400 MHz, DMSO-d6) δ 7.80 (d, J = 9.2 Hz, 1H), 7.49 (d, J = 7.8 Hz, 1H), 7.44-7.36 (m, 1H), 7.27-7.13 (m, 1H), 5.16-5.01 (m, 1H), 4.94-4.75 (m, 1H), 4.45-4.31 (m, 1H), 4.00-3.86 (m, 2H), 3.08 (s, 3H), 3.04-2.91 (m, 2H), 2.84-2.74 (m, 2H), 2.03-1.90 (m, 4H), 1.48 (d, J = 6.1 Hz, 3H), 1.39 (d, J = 6.5 Hz, 3H). |
| 887 | 415.1 | 1H NMR (400 MHz, DMSO-d6) δ 7.92 (d, J = 8.0 Hz, 1H), 7.52-7.38 (m, 2H), 7.36-7.20 (m, 1H), 4.86-4.73 (m, 1H), 4.76-4.59 (m, 1H), 4.55-4.39 (m, 1H), 4.01-3.86 (m, 2H), 3.10 (s, 3H), 2.99-2.89 (m, 2H), 2.89-2.70 (m, 2H), 2.45-2.37 (m, 1H), 2.15-1.89 (m, 3H), 1.49 (d, J = 6.1 Hz, 3H), 1.44 (d, J = 6.4 Hz, 3H). |
| 888 | 415.1 | 1H NMR (400 MHz, DMSO-d6) δ 7.86 (s, 1H), 7.81 (dd, J = 7.9, 1.6 Hz, 1H), 7.63 (d, J = 8.9 Hz, 1H), 7.46 (d, J = 8.0 Hz, 1H), 5.01-4.87 (m, 1H), 4.73-4.60 (m, 1H), 4.48-4.37 (m, 1H), 4.04-3.87 (m, 2H), 3.06 (s, 3H), 3.05-2.86 (m, 4H), 2.86-2.76 (m, 2H), 2.45-2.37 (m, 1H), 2.10-1.92 (m, 3H), 1.83-1.68 (m, 1H), 1.50 (d, J = 6.2 Hz, 3H). |
| 889 | 415.1 | 1H NMR (400 MHz, DMSO-d6) δ 7.74 (d, J = 8.1 Hz, 1H), 7.21 (s, 1H), 7.12 (d, J = 1.4 Hz, 1H), 5.29-5.12 (m, 1H), 4.72-4.58 (m, 1H), 4.53-4.28 (m, 2H), 4.10-3.84 (m, 2H), 3.04 (s, 3H), 3.00-2.92 (m, 2H), 2.85-2.71 (m, 2H), 2.44-2.30 (m, 4H), 2.06-1.87 (m, 3H), 1.48 (d, J = 6.2 Hz, 3H). |
| 890 | 413.1 | 1H NMR (400 MHz, DMSO-d6) δ 7.69 (dd, J = 8.1, 1.9 Hz, 1H), 7.60-7.44 (m, 3H), 4.61-4.34 (m, 2H), 4.04-3.85 (m, 2H), 3.06 (s, 3H), 3.03-2.94 (m, 2H), 2.89-2.66 (m, 4H), 2.47-2.38 (m, 1H), 2.13-1.88 (m, 5H), 1.84-1.65 (m, 2H), 1.49 (d, J = 6.2 Hz, 3H). |
| 891 | 413.1 | 1H NMR (400 MHz, DMSO-d6) δ 7.78-7.61 (m, 3H), 7.50-7.39 (m, 1H), 4.47-4.33 (m, 2H), 4.03-3.89 (m, 2H), 3.09 (s, 3H), 3.05-2.95 (m, 4H), 2.87-2.76 (m, 2H), 2.45-2.35 (m, 1H), 2.06-1.89 (m, 4H), 1.49 (d, J = 6.2 Hz, 3H), 1.25 (d, J = 6.7 Hz, 3H). |
| 892 | 429.1 | 1H NMR (400 MHz, DMSO-d6) δ 7.76-7.64 (m, 2H), 7.47-7.34 (m, 2H), 5.04-4.81 (m, 1H), 4.50-4.32 (m, 1H), 4.24-4.14 (m, 1H), 4.03-3.87 (m, 2H), 3.34 (s, 3H), 3.05 (s, 3H), 3.03-2.94 (m, 4H), 2.84-2.77 (m, 2H), 2.45-2.38 (m, 1H), 2.03-1.94 (m, 3H), 1.49 (d, J = 6.2 Hz, 3H). |
| 893 | 467.1 | 1H NMR (400 MHz, DMSO-d6) δ 8.05 (dd, J = 8.7, 1.2 Hz, 1H), 7.81 (d, J = 8.0 Hz, 1H), 7.76 (s, 1H), 7.53 (d, J = 8.0 Hz, 1H), 5.20-4.97 (m, 1H), 4.53-4.36 (m, 1H), 4.03-3.87 (m, 2H), 3.43-3.21 (m, 2H), 3.07 (s, 3H), 3.05-2.95 (m, 3H), 2.90-2.75 (m, 2H), 2.44-2.31 (m, 1H), 2.10-1.93 (m, 3H), 1.49 (d, J = 6.2 Hz, 3H). |
| 894 | 413.1 | 1H NMR (400 MHz, DMSO-d6) δ 7.82-7.69 (m, 2H), 7.58 (d, J = 8.8 Hz, 1H), 7.45 (d, J = 7.9 Hz, 1H), 4.84-4.73 (m, 1H), 4.51-4.40 (m, 1H), 4.02-3.95 (m, 2H), 3.14-3.00 (m, 6H), 2.88-2.78 (m, 3H), 2.45-2.36 (m, 1H), 2.08-1.95 (m, 3H), 1.75-1.44 (m, 4H), 1.40-1.27 (m, 3H). |
| 895 | 413.1 | 1H NMR (400 MHz, DMSO-d6) δ 7.55 (s, 1H), 7.50 (s, 1H), 7.36 (d, J = 8.7 Hz, 1H), 5.03-4.89 (m, 1H), 4.60-4.37 (m, 1H), 4.04-3.95 (m, 2H), 3.20-3.07 (m, 1H), 3.06-2.91 (m, 5H), 2.87-2.78 (m, 3H), 2.45-2.33 (m, 5H), 2.15-1.90 (m, 4H), 1.50 (d, J = 6.1 Hz, 3H). |
| 896 | 433.2 | 1H NMR (400 MHz, DMSO-d6) δ 9.13 (s, 3H), 7.81 (d, J = 4.1 Hz, 1H), 7.48 (d, J = 4.0 Hz, 1H), 5.07-4.94 (m, 3H), 4.88 (d, J = 7.7 Hz, 2H), 4.18-4.04 (m, 2H), 3.27-3.13 (m, 2H), 2.77-2.61 (m, 3H), 2.46-2.39 (m, 1H). |

Pka Assay pk$_a$ Analysis:

The 10 mM DMSO stock solutions of test articles (TAs) were diluted 100-fold with either 2 mM HCl or 2 mM NaOH and methanol. The final concentration of methanol was 60%, TA concentration was 100 µM, and DMSO concentration was 1%. The TAs were transferred into 24 consecutive wells of a 96-well plate for analysis using the co-solvent method. The average pH spacing between buffer points was 0.4 pH units covering a pH range of 1.7-11.2. All data was obtained using a pK$_a$. PRO Analyzer (AATI, Ankey, IA) by performing four consecutive CE runs from 60% to 30% co-solvent buffers. Norfloxacin was used as a daily performance-indicating standard. The pK$_a$ values were predicted by using pK$_a$. Estimator® software (AATI, Ankey, IA) by relating molecular weight of the TA to its mobility.

TABLE 2

| | pKa | |
|---|---|---|
| Example No | 1st pKa | 2nd pKa |
| 8 | 4.38 | |
| 13 | 3.77 | |
| 14 | 4.28 | |
| 15 | 3.57 | 5.44 |
| 16 | 3.77 | |
| 17 | 4.69 | |
| 18 | 4.52 | |
| 19 | 4.88 | |
| 20 | 4 | |
| 21 | 1.73 | 4.48 |
| 22 | 2.86 | 4.74 |
| 23 | 4.97 | |
| 50 | 4.8 | 8.71 |
| 118 | 2.87 | 4.22 |
| 121 | 3.68 | 5.35 |
| 131 | 4.25 | 6.48 |
| 147 | 3.59 | 6.43 |
| 188 | 4.27 | 9.27 |
| 192 | 4.17 | 9.3 |
| 209 | 3.54 | 9.45 |
| 295 | 4.25 | 8.01 |
| 305 | 4.15 | |
| 329 | 4.12 | 9.27 |
| 331 | 4.14 | |
| 347 | 3.69 | 9.16 |
| 364 | 4.32 | |
| 378 | 3.29 | 6.64 |
| 379 | 4.31 | 9.19 |
| 380 | 4.21 | 9.04 |
| 381 | 4.12 | 8.07 |
| 459 | 4.27 | 8.65 |
| 460 | 4.66 | 11.2 |
| 461 | 3.9 | |
| 466 | 10.3 | |
| 471 | 6.1 | |
| 489 | 5.3 | |
| 490 | 5.5 | |
| 491 | 4.5 | |
| 492 | 2.1 | |
| 495 | 2.5 | |
| 512 | 7.8 | |
| 516 | 7.2 | |
| 646 | 6.6 | |
| 647 | 8.2 | |
| 658 | 5.6 | |
| 663 | 5.4 | |
| 687 | 6.0 | |
| 696 | 6.3 | |
| 711 | 6.3 | |
| 754 | 4.2 | |
| 755 | 7.1 | |
| 763 | 1.7 | |
| 768 | 4.2 | |
| 771 | 6.2 | |
| 773 | 6.3 | |

TABLE 2-continued

| | pKa | |
|---|---|---|
| Example No | 1st pKa | 2nd pKa |
| 777 | 6.7 | |
| 778 | 6.2 | |
| 789 | 6.4 | |
| 794 | 4.9 | |
| 795 | 4.9 | |
| 796 | 4.8 | |
| 797 | 4.7 | |
| 802 | 4.6 | |
| 835 | 6.0 | |
| Reference Compound 1 | 3.7 | 4.34 |

Reference Compound 1: 2-41R,5S,6R)-3-(2-((S)-2-methylazetidin-1-yl)-6-(trifluoromethyl)pyrimidin-4-yl)-3-azabicyclo[3.1.0]hexan-6-yl)acetic acid

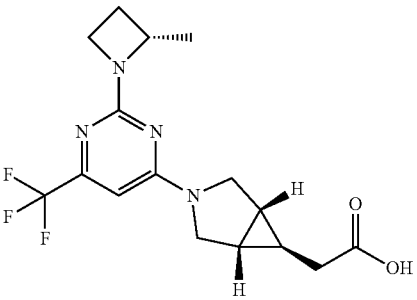 [SMILES: C[C@H]1CCN1c1nc(N2C[C@@H]3[C@@H](CC(=O)O)[C@@H]3C2)cc(C(F)(F)F)n1]

Biological Data

KHK Enzymes Preparation

The nucleotide sequences for human KHK-C and KHK-A from amino acid M1 to V298 were codon-optimized and synthesized based on public amino acid sequences (NCBI ref seq NP_006479.1 and NP_000212.1 respectively), and cloned into pLPT7 vector with N-terminal 6×His-tag followed by thrombin cleavage site. The His-tagged fusion protein was expressed using BL21 (DE3) with IPTG induction and purified using Ni-NTA column followed by dialysis into final buffer containing 25 mM Tris-HCl pH 8.0, 250 mM NaCl. The protein purified was determined to be ~95% purity on SDS-PAGE and molecular weight was confirmed by mass spectrometry.

KHK Biochemical Assay (IC$_{50}$)

Compounds were tested for KHK enzyme inhibition in a high-throughput 384-well assay format using the ADP-Glo assay (Promega) in buffer consisting of 50 mM Hepes (pH 7.4), 140 mM KCl, 5 mM MgCl$_2$ and 0.01% Triton-X. 0.2 nM. KHK-C or KHK-A enzyme was used in this assay with 0.5 mM (2×K$_m$) ATP and 1.5 mM or 10 mM fructose (5×K$_m$) for KHK-C and KHK-A, respectively. Compounds were serially diluted (1:3) in DMSO. The LabCyte ECHO Acoustic dispenser system was used to pre-spot the assay plates (384-well Non-Binding Surface plates, Corning, Catalog #3824) with 50 nL (200-fold final dilution) of compound.

The compounds were pre-incubated with 5 µL of 2× final enzyme concentration for 30 minutes before adding 5 µL of 2× final concentration of ATP and fructose. The plates were incubated at room temperature for 4 hours before adding ADP-Glo reagent to quench the enzyme reaction, followed by incubation at room temperature for 1 hour. The ADP-Glo detection reagent was then added to the plates and luminescence was measured on the Envision plate reader after 1 hour. The addition of enzyme, substrates and ADP-Glo reagents to the plates was performed using the BioTEK EL406 liquid dispenser using the 5 µL dispensing cassette (BioTek 7170011). $IC_{50}$ values were defined as the compound concentration that causes a 50% decrease in luminescence signal and were calculated using a sigmoidal dose-response model to generate curve fits.

KHK-C Cell-based Assay ($EC_{50}$)

Compounds were tested in a high-throughput 384-well assay format for their ability to attenuate fructose-mediated ATP-depletion in Normal Rat Kidney epithelial cells (NRK-52E) using the Cell-Titer Glo (CTG) assay, which measures cellular ATP levels based on luminescence signal by using the luciferase-luciferin system. Compounds were serially diluted (1:3) in DMSO.

On day 1, 1000 cells/well of NRK-52E cells (in DMEM medium containing 1 g/L Glucose (Corning, Catalog #10-014-CM), 5% FBS and Penicillin-Streptomycin) were plated in sterile 384 well plates (Greiner, Catalog #781076) on the BioTEK EL406 liquid dispenser with a 5 µL dispensing cassette (BioTek 7170011). The plates were incubated at 37° C., 5% $CO_2$ for one day. Cells were then transduced on day 2 with 200 MOI of Adenovirus (VQAd KHKC C-(K)-DYK ViraQuest Inc.) using the same medium and method as day-1 to induce KHK-C expression in the cells. Cells were incubated at 37° C., 5% $CO_2$ for one day. On day-3, the medium was changed to DMEM medium (Corning, Catalog #10-014-CM) with 0.5% FBS and Penicillin-Streptomycin after washing the cells twice with sterile PBS on the BioTEK EL406 washer and dispenser. Test compounds were then diluted 200-fold into the assay plates using the BioMek FX and were incubated for 1 hour at 37° C., 5% $CO_2$. 25 mM (final concentration) of fructose was then dispensed into the plates using the BioTEK EL406 dispenser and the plates were incubated at 37° C., 5% $CO_2$ for 48 hours before addition of CTG reagent and measurement of luminescence signal. $EC_{50}$ values were defined as the compound concentration that causes a 50% decrease in luminescence signal and were calculated using a sigmoidal dose-response model to generate curve fits.

F1P Cell-Based Assay ($EC_{50}$)

Compounds were serially diluted (1:3) in DMSO. The LabCyte ECHO Acoustic dispenser system was used to pre-spot the assay plates (Greiner, Catalog #781091) with 400 nL (200-fold final dilution in 80 µL assay volume) of compound. 25,000 cells/well HepG2 cells (ATCC Catalog #HB-8065) were plated in a 40 µL volume/well in DMEM medium with 4.5 g/L glucose, 1× Penicillin-Streptomycin-Glutamine, and 10% FBS, using a BioTEK dispenser in a biological hood and incubated overnight at 37° C., 5% $CO_2$, 90% humidity. 40 µL/well serum free assay medium (for F1P assay in cell culture medium), or 40 µL/well 100% human plasma (for F1P assay in 50% human plasma) were then added to the plates on the following day, and incubated for 1 hour at 37° C., 5% $CO_2$, 90% humidity. $^{13}C_6$-labelled fructose (Sigma, Catalog #587621) in sterile PBS was added to the plates at a final concentration of 5 mM. The plates were incubated for 2 hours at 37° C., 5% $CO_2$, 90% humidity. The assay was quenched by washing the cells with sterile PBS and adding 60 µL/well of 80% (v/v) methanol, 2 mM ammonium acetate and 2.5 µM Crotonyl-CoA, using a BioTEK washer-dispenser system. The plates were then sealed and stored in the −80° C. freezer until ready for RapidFire readout. $^{13}C_6$-fructose-1-phosphate in individual wells was quantified using the Agilent RapidFire High-Throughput MS system in negative mode using a C13 cartridge. Mobile Phase 1 consisted of 20 mM ammonium acetate with 0.05% acetic acid in 100% methanol. Mobile phase 2 consisted of 5 mM octylamine in water (pH adjusted to 5 using acetic acid). F1P signals in individual wells were normalized by crotonyl CoA internal control.

For each compound tested, the $IC_{50}$ and the $EC_{50}$ provided are the average values based on at least two separate assays conducted on separate days.

TABLE 3

KHK-C/KHK-A $IC_{50}$, NRK CTG $EC_{50}$ and F1P 10% FBS/50% HP $EC_{50}$

| Example No | KHK-C IC50 (nM) | KHK-A IC50 (nM) | NRK CTG EC50 (nM) | F1P 10% FBS EC50 (nM) | F1P 50% HP EC50 (nM) |
|---|---|---|---|---|---|
| 1 | 688.8 | 952.0 | | | |
| 2 | 30841.0 | 30991.0 | | | |
| 3 | 121.5 | 121.4 | | | |
| 4 | 46.1 | 41.4 | 309.8 | | |
| 5 | 7903.3 | 5918.6 | | | |
| 6 | 243.2 | 285.1 | | | |
| 7 | 373.4 | 438.7 | | | |
| 8 | 48.1 | 38.8 | 128.3 | | |
| 9 | 68.6 | 48.9 | 611.3 | | |
| 10 | 1145.0 | 1146.3 | | | |
| 11 | 408.4 | 453.2 | | | |
| 12 | 2603.2 | 2619.8 | | | |
| 13 | 40.8 | 34.0 | 89.4 | | |
| 14 | 104.5 | 121.2 | | | |
| 15 | 164.7 | 148.5 | | | |
| 16 | 667.2 | 782.8 | | | |
| 17 | 193.1 | 252.1 | | | |
| 18 | 73.1 | 55.1 | 143.8 | | |
| 19 | 33.2 | 38.6 | | | |
| 20 | 155.8 | 146.3 | | | |
| 21 | 292.2 | 367.0 | | | |
| 22 | 99.1 | 146.9 | 287.8 | | |
| 23 | 66.5 | 68.9 | 197.4 | | |
| 24 | 419.5 | 614.9 | | | |
| 25 | 104.1 | 142.4 | | | |
| 26 | 1538.0 | 1862.1 | | | |
| 27 | 59.7 | 58.9 | 229.3 | | |
| 28 | 50.3 | 55.2 | 137.4 | | |
| 29 | 33.0 | 55.3 | 119.6 | | |
| 30 | >50000 | >50000 | | | |
| 31 | 1479.5 | 934.6 | | | |
| 32 | 125.0 | 86.8 | | | |
| 33 | 240.2 | 271.6 | | | |
| 34 | 64.5 | 52.7 | 141.9 | | |
| 35 | 219.8 | 188.7 | | | |
| 36 | 146.5 | 146.7 | 433.6 | | |
| 37 | 212.8 | 223.5 | | | |
| 38 | 836.1 | 812.2 | 12164.0 | | |
| 39 | 112.8 | 86.2 | 210.7 | | |
| 40 | 57.0 | 54.3 | | | |
| 41 | 125.3 | 102.0 | 602.0 | | |
| 42 | 22.7 | 31.8 | | | |
| 43 | 48.1 | 66.8 | 225.3 | | |
| 44 | 259.3 | 285.5 | 328.7 | | |
| 45 | 108.0 | 117.7 | | | |
| 46 | 7.6 | 10.0 | | | |
| 47 | 15.2 | 29.4 | 2371.7 | | |
| 48 | 5.3 | 7.1 | 77.1 | | |
| 49 | 222.3 | 124.8 | | | |
| 50 | 27.5 | 18.2 | | | |
| 51 | 308.6 | 143.8 | | | |
| 52 | 42.7 | 22.2 | | | |
| 53 | 194.3 | 129.5 | | | |
| 54 | 40.4 | 42.0 | | | |
| 55 | 801.0 | 1079.3 | | | |
| 56 | 7.7 | 3.8 | | | |
| 57 | 17.8 | 12.9 | | 65.8 | |
| 58 | 7.9 | 5.8 | | | 9.5 |
| 59 | 171.4 | 42.9 | | | |
| 60 | 119.1 | 61.6 | | | |
| 61 | 90.3 | 56.8 | | | |
| 62 | 2932.3 | 1917.0 | | | |

TABLE 3-continued

KHK-C/KHK-A IC$_{50}$, NRK CTG EC$_{50}$ and F1P 10% FBS/50% HP EC$_{50}$

| Example No | KHK-C IC50 (nM) | KHK-A IC50 (nM) | NRK CTG EC50 (nM) | F1P 10% FBS EC50 (nM) | F1P 50% HP EC50 (nM) |
|---|---|---|---|---|---|
| 63 | 95.3 | 112.3 | 137.5 | | |
| 64 | 106.9 | 52.7 | | | |
| 65 | 245.0 | 150.0 | | | |
| 66 | 54.5 | 64.8 | 35462.0 | | |
| 67 | 139.9 | 127.9 | | | |
| 68 | 45.1 | 94.3 | | | |
| 69 | 145.4 | 286.2 | | | |
| 70 | 51.7 | 29.4 | >5000 | | |
| 71 | 104.5 | 107.4 | | | |
| 72 | 15.0 | 18.0 | 29.8 | | |
| 73 | 156.0 | 175.3 | | | |
| 74 | 26.3 | 22.9 | 858.5 | | |
| 75 | 18.9 | | 54.7 | | |
| 76 | 875.8 | 1147.0 | | | |
| 77 | 315.1 | 284.6 | | | |
| 78 | 238.9 | 193.4 | | | |
| 78 | 129.4 | 133.7 | | | |
| 79 | 4990.7 | 6957.4 | | | |
| 80 | 957.1 | 864.7 | | | |
| 81 | 7.6 | 9.5 | >5000 | | |
| 82 | 14.9 | 14.9 | >5000 | | |
| 83 | 10.3 | 32.5 | >5000 | | |
| 84 | 279.0 | 296.4 | | | |
| 85 | 1368.2 | 1124.2 | | | |
| 86 | 38.6 | 50.2 | >5000 | | |
| 87 | 3.4 | | 46.0 | | |
| 88 | 62.8 | 75.3 | 214.0 | | |
| 89 | 3.3 | 6.0 | 37.0 | 35.7 | 310.6 |
| 90 | 11.2 | 8.9 | 120.7 | | |
| 91 | 55.6 | 45.2 | 120.2 | | |
| 92 | 93.0 | 82.3 | 367.8 | | |
| 93 | >5000 | >5000 | | | |
| 94 | 8.4 | | 84.1 | | |
| 95 | 43.1 | 60.3 | 221.4 | | |
| 96 | >5000 | 4659.0 | | | |
| 97 | 2228.0 | 936.6 | | | |
| 98 | >5000 | >5000 | | | |
| 99 | >5000 | >5000 | | | |
| 100 | 161.1 | 161.4 | | | |
| 101 | 119.3 | 69.1 | | | |
| 102 | 420.3 | 278.6 | | | |
| 103 | 1283.0 | 706.7 | | | |
| 104 | 46.2 | 118.6 | >5000 | | |
| 105 | 204.9 | 253.1 | | | |
| 106 | 125.5 | 147.6 | 209.1 | | |
| 107 | 1059.7 | 1553.8 | 2915.4 | | |
| 108 | 465.8 | 594.1 | | | |
| 109 | 2538.1 | 3201.6 | | | |
| 110 | 135.7 | 321.9 | | | |
| 111 | 151.8 | 185.8 | | | |
| 112 | 68.8 | 102.7 | | | |
| 113 | 13.2 | 18.2 | | | |
| 114 | 46.2 | 51.0 | | | |
| 115 | 108.6 | 94.1 | | | |
| 116 | 39.8 | 54.6 | | | |
| 117 | 3780.2 | 4779.2 | | | |
| 118 | 19.7 | 28.8 | | | |
| 119 | 2.4 | 13.4 | 6.6 | | |
| 120 | 42.7 | 46.1 | | | |
| 121 | 24.1 | 29.3 | 87.3 | | |
| 122 | 41.8 | 44.5 | 51.8 | | |
| 123 | 30.5 | 40.2 | 62.4 | | |
| 124 | 328.3 | 535.2 | 972.7 | | |
| 125 | 572.3 | 931.7 | 3562.6 | | |
| 126 | 400.4 | 405.8 | 252.9 | | |
| 127 | 65.5 | 99.6 | 223.1 | | |
| 128 | 2.3 | 2.3 | 6.3 | | |
| 129 | 6.4 | 14.0 | 80.8 | 18.8 | 36.7 |
| 130 | >5000 | >5000 | >5000 | | |
| 131 | 2.6 | 6.0 | 10.9 | | |
| 132 | 71.8 | 97.6 | 130.8 | | |
| 133 | 141.3 | 236.2 | >5000 | | |
| 134 | 89.9 | 157.5 | 1034.8 | | |
| 135 | 111.2 | 126.2 | 277.4 | | |
| 136 | 62.0 | 114.2 | 2461.6 | | |
| 137 | 90.3 | 215.8 | 100.4 | | |
| 138 | 219.7 | 293.7 | 1804.0 | | |
| 139 | 55.3 | 85.8 | 2491.3 | | |
| 140 | 52.8 | 28.1 | 163.4 | | |
| 141 | 290.4 | 334.5 | 1261.6 | | |
| 142 | 2430.3 | 2111.8 | 2037.9 | | |
| 143 | 30.6 | 21.4 | 43.3 | | |
| 144 | 2402.8 | 1686.6 | 2444.9 | | |
| 145 | 125.1 | 83.7 | >5000 | | |
| 146 | 115.8 | 118.0 | 423.2 | | |
| 147 | 18.7 | 12.3 | 35.3 | | |
| 148 | 59.9 | 84.0 | 652.8 | | |
| 149 | 6.7 | 33.2 | 18.8 | | |
| 150 | 33.1 | 32.2 | 73.2 | | |
| 151 | 3893.9 | 4975.4 | 1360.8 | | |
| 152 | 94.0 | 63.6 | 199.8 | | |
| 153 | 66.6 | 185.8 | 3999.5 | | |
| 154 | 90.4 | 45.8 | 34.0 | | |
| 155 | 99.5 | 231.5 | 4793.1 | | |
| 156 | 82.0 | 99.9 | 145.1 | | |
| 157 | 211.4 | 125.4 | 291.4 | | |
| 158 | 314.3 | 217.4 | 1116.7 | | |
| 159 | 10.1 | 25.6 | 36.9 | | |
| 160 | 0.9 | 4.6 | 2.0 | 4.8 | 13.4 |
| 161 | 3.8 | 5.9 | 12.1 | 22.8 | 24.2 |
| 162 | 93.1 | | >5000 | | |
| 163 | 49.0 | | 251.0 | | |
| 164 | 16.4 | | 94.5 | | |
| 165 | 0.8 | | 2.3 | 9.7 | 49.0 |
| 166 | 5.0 | | 39.7 | 36.7 | 47.3 |
| 167 | >5000 | | >5000 | | |
| 168 | 23.3 | | 143.8 | | |
| 169 | 4433.6 | | >5000 | | |
| 170 | 11.2 | | 46.1 | 30.2 | 80.3 |
| 171 | 23.5 | | 164.5 | | |
| 172 | >5000 | | >5000 | | |
| 173 | >5000 | | >5000 | | |
| 174 | >5000 | | >5000 | | |
| 175 | 49.8 | 66.5 | 249.1 | | |
| 176 | 898.6 | | 2808.5 | | |
| 177 | 14.3 | | 88.6 | 28.4 | 66.6 |
| 178 | 5.4 | | 27.4 | 22.1 | 41.0 |
| 179 | 34.8 | | 385.8 | | |
| 180 | 27.4 | | 177.3 | | |
| 181 | 11.0 | | 579.2 | | |
| 182 | 10.2 | | 155.8 | | |
| 183 | 21.3 | | 89.1 | | |
| 184 | 210.4 | 152.4 | 275.2 | | |
| 185 | 48.8 | 60.6 | 83.9 | | |
| 186 | 66.9 | 78.2 | 143.1 | | |
| 187 | 22.4 | 33.3 | 91.6 | | |
| 188 | 2.1 | 4.2 | 177.4 | | |
| 189 | 61.7 | 81.6 | 111.7 | | |
| 190 | 40.8 | 48.7 | 28.1 | | |
| 191 | 9.5 | 8.0 | 26.4 | | |
| 192 | 15.4 | 19.3 | 14.9 | 14.2 | 89.6 |
| 193 | 97.8 | 73.4 | 412.5 | | |
| 194 | 218.9 | 308.3 | | | |
| 195 | 58.6 | | 430.9 | | |
| 196 | 86.7 | 135.5 | 366.6 | | |
| 197 | 51.6 | 65.5 | 379.2 | 120.0 | 191.0 |
| 198 | 98.3 | 123.9 | | | |
| 199 | 148.6 | 281.6 | | | |
| 200 | 10.9 | 14.9 | 49.3 | | |
| 201 | 1.7 | 2.9 | 130.1 | | |
| 202 | 7.7 | 9.8 | 110.9 | | |
| 203 | 29.8 | 66.5 | 59.5 | | |
| 204 | 37.2 | 117.8 | 109.0 | | |
| 205 | 107.6 | 79.9 | | | |
| 206 | 16.0 | 24.4 | 26.6 | | |
| 207 | 28.2 | 23.2 | 55.8 | | |

TABLE 3-continued

KHK-C/KHK-A IC$_{50}$, NRK CTG EC$_{50}$ and F1P 10% FBS/50% HP EC$_{50}$

| Example No | KHK-C IC50 (nM) | KHK-A IC50 (nM) | NRK CTG EC50 (nM) | F1P 10% FBS EC50 (nM) | F1P 50% HP EC50 (nM) |
|---|---|---|---|---|---|
| 208 | 46.6 | 36.7 | 36.4 | | |
| 209 | 55.3 | 35.4 | 249.4 | | |
| 210 | 19.7 | 17.6 | 38.2 | | |
| 211 | 4759.6 | 7308.9 | >50000 | | |
| 212 | 5594.0 | 10485.0 | | | |
| 213 | 33.3 | 52.6 | 52.5 | | |
| 214 | 37.7 | 37.5 | | | |
| 215 | 105.8 | 78.9 | | | |
| 216 | 38.4 | 37.8 | 390.3 | | |
| 217 | 90.3 | 130.4 | >5000 | | |
| 218 | 485.2 | 417.8 | | | |
| 219 | 13.1 | 17.2 | 283.5 | | |
| 220 | 57.3 | 58.6 | 190.3 | | |
| 221 | 17.2 | 17.8 | 94.4 | | |
| 222 | 79.2 | 75.1 | | | |
| 223 | 26.9 | 33.7 | 74.1 | | |
| 224 | 114.4 | 154.7 | | | |
| 225 | 343.2 | 294.5 | | | |
| 226 | 17.2 | 25.5 | 26.9 | | |
| 227 | 70.3 | 75.6 | 265.0 | | |
| 228 | 143.4 | 159.2 | | | |
| 229 | 95.7 | 107.9 | | | |
| 230 | 107.0 | 96.7 | | | |
| 231 | 50.6 | 56.7 | 198.7 | | |
| 232 | 44.8 | 46.1 | 1632.5 | | |
| 233 | 9.7 | 55.7 | | | |
| 234 | 18.9 | 39.1 | 56.4 | | |
| 235 | >5000 | >5000 | >5000 | | |
| 236 | 5.4 | | 31.3 | | |
| 237 | 26.7 | | | | |
| 238 | 68.3 | | | | |
| 239 | 70.6 | 117.4 | | | |
| 240 | 173.0 | 182.8 | 4984.0 | | |
| 241 | 1070.3 | 803.1 | | | |
| 242 | 135.2 | 98.6 | | | |
| 243 | >5000 | >5000 | | | |
| 244 | 67.8 | 149.1 | 102.2 | | |
| 245 | 80.3 | 73.6 | 374.3 | | |
| 246 | 163.0 | 359.8 | 422.0 | | |
| 247 | 49.6 | 50.0 | 106.7 | | |
| 248 | >100 | 79.6 | 154.0 | | |
| 249 | 96.3 | 104.6 | 517.2 | | |
| 250 | 129.0 | 196.5 | 852.0 | | |
| 251 | 134.7 | 126.1 | 242.8 | | |
| 252 | 946.2 | 782.6 | 1668.2 | | |
| 253 | 238.6 | 203.7 | 2766.5 | | |
| 254 | 516.9 | 600.2 | 606.7 | | |
| 255 | 65.9 | 49.8 | 70.7 | | |
| 256 | 262.3 | 519.4 | 160.8 | | |
| 257 | 128.5 | 200.7 | 185.2 | | |
| 258 | 2849.6 | 1995.6 | 525.5 | | |
| 259 | 311.8 | 380.1 | | | |
| 260 | 633.2 | 745.9 | | | |
| 261 | 152.7 | 133.4 | | | |
| 262 | 140.6 | 180.4 | | | |
| 263 | 50.0 | 96.2 | 154.9 | | |
| 264 | 645.7 | 758.2 | | | |
| 265 | 1625.3 | 2103.7 | 700.1 | | |
| 266 | >5000 | >5000 | >5000 | | |
| 267 | >5000 | >5000 | | | |
| 268 | >5000 | >5000 | >5000 | | |
| 269 | >5000 | >5000 | >5000 | | |
| 270 | 44.7 | 62.3 | 2135.5 | | |
| 271 | 532.1 | 517.9 | 2323.5 | | |
| 272 | 318.7 | 267.4 | 634.8 | | |
| 273 | 531.8 | 432.9 | | | |
| 274 | 142.3 | 203.7 | 205.1 | | |
| 275 | 617.7 | 1038.5 | 291.4 | | |
| 276 | 69.5 | 66.6 | 109.8 | | |
| 277 | 15.3 | 11.9 | 26.7 | | |
| 279 | 200.7 | 159.2 | | | |
| 280 | 187.7 | 122.5 | | | |
| 281 | 331.3 | 340.5 | | | |
| 282 | 48.2 | 42.6 | | | |
| 283 | 15.8 | 28.6 | | | |
| 284 | 16.4 | 21.8 | 55.7 | | |
| 285 | 47.8 | 57.2 | 82.4 | | |
| 286 | 753.1 | 718.3 | | | |
| 287 | 1274.5 | 695.9 | | | |
| 288 | 44.3 | 103.4 | 108.1 | | |
| 289 | 17.5 | 57.9 | 34.5 | | |
| 290 | 30.9 | 50.5 | 71.3 | | |
| 291 | 98.0 | 140.9 | | | |
| 292 | 89.1 | 65.7 | | | |
| 293 | 199.9 | 152.7 | | | |
| 294 | 3405.0 | 3891.4 | | | |
| 295 | 1.4 | 2.6 | 6.2 | | |
| 296 | 2995.9 | 2088.3 | | | |
| 297 | 2840.3 | 846.6 | | | |
| 298 | 246.9 | 373.8 | | | |
| 299 | 45.6 | 47.3 | | | |
| 300 | 33.6 | 42.8 | | | |
| 301 | 3.7 | 9.9 | | | |
| 302 | 849.0 | 635.8 | | | |
| 303 | 49.7 | 29.7 | 91.5 | | |
| 304 | 786.3 | 982.6 | | | |
| 305 | 38.9 | 61.3 | | | |
| 306 | 277.0 | 279.2 | 450.0 | | |
| 307 | 69.9 | 86.5 | 166.0 | | |
| 308 | 97.5 | 130.2 | 294.3 | | |
| 309 | 17.4 | 19.0 | 15.8 | | |
| 310 | 555.4 | 449.0 | 1808.5 | | |
| 311 | >5000 | >5000 | 915.1 | | |
| 312 | 0.9 | 1.2 | 2.1 | 3.9 | 9.3 |
| 313 | 1152.0 | 1025.4 | 2077.4 | | |
| 314 | 1939.6 | 2017.5 | 4487.8 | | |
| 315 | 34.0 | 31.5 | 57.3 | | |
| 316 | 42.9 | 19.0 | 35.0 | | |
| 317 | 1.7 | 4.9 | 3.5 | | |
| 318 | 1.6 | 6.0 | 9.1 | 9.3 | 16.1 |
| 319 | 20.9 | 25.0 | 37.3 | | |
| 320 | 244.2 | 209.9 | 637.7 | | |
| 321 | 4.4 | 4.8 | 7.3 | | |
| 322 | 7.4 | 5.1 | 76.4 | | |
| 323 | 4.2 | 4.7 | 16.1 | | |
| 324 | 8.3 | 6.6 | 72.3 | 19.0 | 59.9 |
| 325 | 451.8 | 440.5 | | | |
| 326 | 228.2 | 230.9 | | | |
| 327 | 38.2 | 96.8 | | | |
| 328 | 502.3 | 608.7 | | | |
| 329 | 18.5 | 24.5 | 339.0 | | |
| 330 | 19.2 | 22.4 | 13.1 | | |
| 331 | 242.2 | 255.3 | 384.5 | 253.3 | 4611.9 |
| 332 | 2168.6 | 1908.1 | | | |
| 333 | 1312.5 | 1314.1 | 1129.5 | | |
| 334 | 9695.2 | 9272.4 | | | |
| 335 | >50000 | >50000 | | | |
| 336 | 20146.0 | 13159.0 | | | |
| 337 | 5098.5 | 2952.4 | | | |
| 338 | >50000 | >50000 | | | |
| 339 | 2225.0 | 1899.1 | | | |
| 340 | >50000 | >50000 | | | |
| 341 | 110.6 | 132.7 | | | |
| 342 | 107.1 | 106.9 | | | |
| 343 | 408.2 | 357.4 | | | |
| 344 | 223.8 | 174.7 | | | |
| 345 | 45.1 | 12.6 | 53.7 | | |
| 346 | 14.7 | 16.7 | 27.5 | | |
| 347 | 23.8 | 22.7 | 17.1 | | |
| 348 | 22.7 | 24.2 | 35.1 | | |
| 349 | 90.6 | 79.3 | 304.6 | | |
| 350 | 19.3 | 16.8 | 14.0 | | |
| 351 | 4.1 | 6.4 | 97.2 | 27.4 | 42.9 |
| 352 | 29.8 | 35.6 | 200.8 | | |
| 353 | 59.8 | 78.9 | 599.6 | | |
| 354 | 138.4 | 177.4 | | | |

TABLE 3-continued

KHK-C/KHK-A IC$_{50}$, NRK CTG EC$_{50}$ and F1P 10% FBS/50% HP EC$_{50}$

| Example No | KHK-C IC50 (nM) | KHK-A IC50 (nM) | NRK CTG EC50 (nM) | F1P 10% FBS EC50 (nM) | F1P 50% HP EC50 (nM) |
|---|---|---|---|---|---|
| 355 | 72.7 | 33.3 | 92.4 | | |
| 356 | 79.9 | 70.6 | | | |
| 357 | 162.0 | 121.7 | | | |
| 358 | 292.7 | 435.1 | | | |
| 359 | 89.7 | 72.4 | 495.2 | | |
| 360 | 252.6 | 169.1 | | | |
| 361 | 30.3 | 68.4 | 65.7 | | |
| 362 | 44.0 | 40.8 | | | |
| 363 | 29.1 | 25.8 | | | |
| 364 | 3.3 | 10.0 | 13.1 | | |
| 365 | 19.0 | 27.2 | 29.3 | | |
| 366 | 86.5 | 54.0 | 75.4 | | |
| 367 | 175.6 | 223.8 | | | |
| 368 | 20.0 | 38.3 | | | |
| 369 | 87.1 | 186.0 | | | |
| 370 | 81.7 | 76.3 | 116.8 | | |
| 371 | 186.9 | 441.7 | | | |
| 372 | 155.9 | 166.6 | | | |
| 373 | 20.4 | 54.0 | 53.8 | | |
| 374 | 40.4 | 47.8 | 73.5 | | |
| 375 | 18.2 | 30.3 | 84.0 | | |
| 376 | 27.9 | 52.3 | 37.3 | | |
| 377 | 21.1 | 26.9 | 92.9 | | |
| 378 | 1.0 | 3.4 | 7.7 | | |
| 379 | 4.6 | 4.1 | 2.6 | 1.3 | 3.1 |
| 380 | 7.9 | 13.0 | 75.7 | | |
| 381 | 89.7 | 18.9 | >5000 | | |
| 382 | 6.3 | 16.1 | 13.8 | | |
| 383 | 4.4 | 10.8 | 7.3 | | |
| 384 | 14.7 | 2.9 | 19.7 | | |
| 385 | 1.8 | 4.2 | 4.2 | 6.5 | 11.1 |
| 386 | 18.4 | 25.6 | 33.7 | | |
| 387 | 9.9 | 5.6 | 19.6 | | |
| 388 | 81.3 | 87.7 | 402.7 | | |
| 389 | 382.2 | 295.6 | 217.3 | | |
| 390 | 2476.7 | 4224.4 | 3330.1 | | |
| 391 | 915.4 | 2191.8 | 1811.7 | | |
| 392 | 1.5 | | 3.0 | 10.9 | 85.1 |
| 393 | 219.1 | | 403.2 | | |
| 394 | 171.5 | | 785.1 | | |
| 395 | 329.4 | | >5000 | | |
| 396 | 80.0 | 129.5 | 2514.5 | | |
| 397 | 32.8 | | 166.5 | | |
| 398 | >5000 | | >5000 | | |
| 399 | 74.3 | | 138.5 | | |
| 400 | 156.2 | | 320.3 | | |
| 401 | 4626.8 | | >5000 | | |
| 402 | 3757.4 | | 1586.3 | | |
| 403 | 217.5 | | 242.0 | | |
| 404 | >5000 | | >5000 | | |
| 405 | 2468.6 | | 4771.4 | | |
| 406 | 1039.0 | 840.8 | 396.8 | | |
| 407 | 228.7 | 234.8 | 506.4 | | |
| 408 | 100.2 | 157.6 | >5000 | | |
| 409 | 34.3 | 41.0 | >5000 | | |
| 410 | 40.8 | 37.6 | 47.5 | | |
| 411 | 116.9 | 66.3 | 473.3 | | |
| 412 | 29.2 | 57.3 | 406.4 | | |
| 413 | 74.4 | 65.4 | 750.0 | | |
| 414 | 138.1 | 396.6 | >5000 | | |
| 415 | >5000 | | >5000 | | |
| 416 | >5000 | | | | |
| 417 | >5000 | | | | |
| 418 | >5000 | | >5000 | | |
| 419 | >5000 | | | | |
| 420 | 61.8 | | 382.1 | | |
| 421 | 67.0 | | 297.1 | | |
| 422 | 95.0 | | 239.9 | | |
| 423 | 81.4 | 66.1 | 239.0 | | |
| 424 | 136.5 | 168.7 | 3513.5 | | |
| 425 | 31.4 | 21.7 | 121.7 | | |
| 426 | 40.1 | 17.9 | 92.8 | | |
| 427 | 30.2 | 17.8 | 40.2 | | |
| 428 | 41.3 | 38.4 | 386.8 | | |
| 429 | 41.6 | 48.6 | 1730.4 | | |
| 430 | 2120.5 | 3162.7 | 3216.8 | | |
| 431 | 512.7 | 807.6 | 710.9 | | |
| 432 | 359.9 | 322.7 | 2626.5 | | |
| 433 | 6.3 | 27.2 | 483.9 | | |
| 434 | 1617.1 | 2925.7 | 3312.8 | | |
| 435 | 5.4 | | 78.4 | | |
| 436 | 2725.2 | | 2936.6 | | |
| 437 | >5000 | | >5000 | | |
| 438 | >5000 | | >5000 | | |
| 439 | 13.1 | 15.4 | 123.5 | | |
| 440 | 6.2 | | 81.6 | | |
| 441 | 7.0 | | 210.8 | | |
| 442 | 1580.7 | | 2725.9 | | |
| 443 | 4.2 | | 53.8 | | |
| 444 | >5000 | | >5000 | | |
| 445 | 305.5 | 130.5 | | | |
| 446 | 3.4 | | 5.0 | | |
| 447 | 67.5 | | | | |
| 448 | 121.4 | | | | |
| 449 | 99.1 | | 542.0 | | |
| 450 | 9.3 | | 297.7 | | |
| 451 | 14.1 | | 8.7 | 77.6 | 333.0 |
| 452 | 68.3 | 102.8 | | | |
| 453 | 775.8 | 1008.6 | 1041.3 | | |
| 454 | 489.1 | 459.4 | 546.2 | | |
| 455 | 248.0 | 497.2 | >5000 | | |
| 456 | 21.8 | 44.8 | 51.8 | | |
| 457 | 953.9 | | >5000 | | |
| 458 | 57.2 | | | | |
| 459 | 6.6 | 11.1 | 42.1 | | |
| 460 | 5.2 | 10.9 | 23.6 | | |
| 461 | 17.2 | | 116.1 | | |
| 462 | 3.2 | | 9.2 | 9.6 | 33.7 |
| 463 | 3.9 | | 150.4 | 7.3 | 46.3 |
| 464 | 15.7 | | 55.0 | 45.8 | 55.1 |
| 465 | 1.4 | | 14.9 | 15.4 | 33.5 |
| 466 | 0.5 | 4.0 | 11.4 | 7.3 | 20.5 |
| 467 | 1.4 | | 16.6 | | 20.6 |
| 468 | 1.8 | 5.3 | 4.3 | 7.6 | 23.8 |
| 469 | 2.5 | 6.7 | | 10.7 | 22.5 |
| 470 | 1.9 | 6.3 | 5.0 | 13.4 | 51.0 |
| 471 | 2.0 | 7.0 | 6.4 | 8.4 | 13.2 |
| 472 | 0.9 | 12.7 | | 13.3 | 39.4 |
| 473 | 7.5 | | | 63.5 | 111.4 |
| 474 | 1.0 | | | 22.5 | 45.1 |
| 475 | 15.0 | | | 104.3 | 207.2 |
| 476 | 0.2 | 10.9 | 9.5 | 23.5 | 37.5 |
| 477 | 0.4 | | | 6.0 | 25.9 |
| 478 | 2.9 | | | 28.5 | 55.5 |
| 479 | 0.7 | 7.3 | | 11.0 | 28.3 |
| 480 | 0.6 | | | 9.4 | 23.7 |
| 481 | 0.3 | | | 6.6 | 43.0 |
| 482 | 12.0 | 26.4 | | | |
| 483 | 0.2 | 4.6 | 5.4 | 5.3 | 18.4 |
| 484 | 1.2 | | | | |
| 485 | 22.6 | | | | |
| 486 | 0.2 | 1.7 | | 6.0 | 8.3 |
| 487 | 1.6 | 14.0 | | 11.9 | 72.4 |
| 488 | 0.1 | 10.6 | 4.1 | 28.7 | 44.4 |
| 489 | 3.5 | 5.2 | | 16.5 | 20.2 |
| 490 | 1.2 | 4.6 | | 9.3 | 19.3 |
| 491 | 2.0 | 24.2 | 35.8 | 31.9 | 26.2 |
| 492 | 9.0 | 12.2 | 41.8 | 20.7 | 22.2 |
| 493 | 11.7 | | 52.7 | 32.4 | 41.9 |
| 494 | 2.7 | | | 5.9 | 7.4 |
| 495 | 1.5 | 0.7 | 16.0 | 1.1 | 2.3 |
| 496 | 7.6 | 14.4 | 65.4 | 9.0 | 23.9 |
| 497 | 0.1 | 2.2 | | | |
| 498 | 1.2 | 18.9 | | | |
| 499 | 0.2 | 2.4 | 1.6 | 3.0 | 6.4 |
| 500 | 48.6 | | 237.9 | | |

TABLE 3-continued

KHK-C/KHK-A IC$_{50}$, NRK CTG EC$_{50}$ and F1P 10% FBS/50% HP EC$_{50}$

| Example No | KHK-C IC50 (nM) | KHK-A IC50 (nM) | NRK CTG EC50 (nM) | F1P 10% FBS EC50 (nM) | F1P 50% HP EC50 (nM) |
|---|---|---|---|---|---|
| 501 | 211.7 | | 596.5 | | |
| 502 | 768.2 | | 2000.0 | | |
| 503 | 5.0 | | 26.7 | | |
| 504 | 2.3 | 10.1 | 11.5 | 9.9 | 34.7 |
| 505 | 2.4 | | 11.9 | | |
| 506 | >5000 | | >5000 | | |
| 507 | 73.6 | | | 138.4 | 247.0 |
| 508 | 61.2 | | | 126.3 | 254.5 |
| 509 | 19.9 | | | 25.1 | 58.1 |
| 510 | 11.8 | | | 35.8 | 78.3 |
| 511 | 20.9 | | | 34.6 | 46.1 |
| 512 | 12.3 | | | 5.4 | 6.8 |
| 513 | 1.4 | | | 6.1 | 10.6 |
| 514 | 10.6 | | | 41.6 | 72.3 |
| 515 | 29.7 | | | 59.1 | 126.1 |
| 516 | 1.5 | | | 4.4 | 5.1 |
| 517 | 1.0 | | | 4.8 | 6.3 |
| 518 | 1.1 | 2.3 | | 3.7 | 3.0 |
| 519 | 2.2 | | | 10.1 | 23.0 |
| 520 | 11.1 | | | 49.8 | 109.4 |
| 521 | 9.8 | | | 68.4 | >100 |
| 522 | 44.5 | | | 53.3 | 454.5 |
| 523 | 0.7 | | | 5.1 | 51.3 |
| 524 | 1.0 | | | 8.2 | 60.1 |
| 525 | 1.8 | 29.8 | | 32.5 | 86.6 |
| 526 | 4.9 | | | 30.8 | 113.7 |
| 527 | 8.0 | | | 81.2 | 122.6 |
| 528 | 0.2 | | 3.4 | 2.5 | 50.2 |
| 529 | 2.7 | | | 26.2 | 65.3 |
| 530 | 1.5 | | | 29.7 | 141.5 |
| 531 | 9.0 | | | 55.1 | 438.7 |
| 532 | 2.8 | | | 5.1 | 55.1 |
| 533 | 3.8 | 4.4 | 18.2 | 7.3 | 8.9 |
| 534 | 32.0 | | | | |
| 535 | 15.8 | | | | |
| 536 | 6.1 | | | | |
| 537 | 21.4 | | | | |
| 538 | 2.3 | | | | |
| 539 | 1.0 | 0.4 | | 2.0 | 8.9 |
| 540 | 13.5 | | | | |
| 541 | 1.3 | 0.9 | | | |
| 542 | 0.6 | 0.5 | 5.7 | | |
| 543 | 10.6 | 6.2 | | | |
| 544 | 1.1 | | | | |
| 545 | 1.0 | 4.0 | | 2.4 | 24.7 |
| 546 | 23.9 | | | | |
| 547 | 33.6 | | | 313.5 | >500 |
| 548 | 0.1 | 7.3 | | | |
| 549 | 0.1 | 5.4 | 3.8 | 5.4 | 17.4 |
| 550 | 5.0 | | | | |
| 551 | 0.9 | 5.1 | | | |
| 552 | 39.2 | | | | |
| 553 | 1.6 | 15.3 | | | |
| 554 | 2.8 | 29.2 | | | |
| 555 | 1.2 | 30.5 | 29.0 | 59.7 | 117.0 |
| 556 | 26.6 | 42.1 | 201.0 | 209.9 | >500 |
| 557 | 8.6 | 10.8 | | | |
| 558 | 0.2 | 8.2 | | | |
| 559 | 0.2 | 7.8 | 3.2 | 5.6 | 16.3 |
| 560 | 16.2 | 75.2 | | | |
| 561 | 1.1 | 0.2 | 8.0 | 3.5 | 24.6 |
| 562 | 1.4 | 0.3 | 5.8 | 1.1 | 3.6 |
| 563 | 1.7 | 0.2 | 5.1 | 0.6 | 6.7 |
| 564 | 24.4 | 11.6 | 98.1 | 38.5 | 142.4 |
| 565 | 2.6 | 32.8 | 19.3 | 50.3 | 203.8 |
| 566 | 0.8 | 16.3 | 6.7 | | |
| 567 | 44.3 | 65.0 | | | |
| 568 | 4.0 | 8.0 | | | |
| 569 | 15.2 | 43.0 | | | |
| 570 | 10.9 | 25.0 | | | |
| 571 | 49.7 | 43.5 | | | |
| 572 | 56.3 | >100 | | | |
| 573 | >100 | >100 | | | |
| 574 | 9.4 | 11.1 | | | |
| 575 | 5.9 | 52.4 | | | |
| 576 | 6.8 | >100 | | | |
| 577 | 0.6 | 2.1 | | | |
| 578 | 6.1 | 22.5 | | | |
| 579 | 2.7 | 25.0 | | | |
| 580 | 3.7 | 13.0 | | | |
| 581 | 0.8 | 3.1 | | | |
| 582 | 0.8 | 7.0 | | | |
| 583 | 1.3 | 8.7 | | | |
| 584 | 2.6 | 19.8 | | | |
| 585 | 21.2 | 41.6 | | | |
| 586 | 0.7 | 1.3 | | | |
| 587 | 0.4 | 0.5 | | | |
| 588 | 3.7 | 9.3 | | | |
| 589 | 1.4 | 2.7 | | | |
| 590 | 1.8 | | | 9.1 | 23.2 |
| 591 | 5.5 | | | 13.5 | 36.0 |
| 592 | 7.3 | | | 15.3 | 56.9 |
| 593 | 7.5 | | | 22.8 | 58.7 |
| 594 | 3.3 | | | 12.6 | 21.0 |
| 595 | 4.4 | | | 34.9 | 51.0 |
| 596 | 2.0 | | | 12.2 | 13.6 |
| 597 | 5.6 | | | 16.0 | 34.4 |
| 598 | 2.4 | | 15.7 | | |
| 599 | 20.3 | | 4902.6 | | |
| 600 | 13.6 | | 125.0 | | |
| 601 | 95.1 | | >5000 | | |
| 602 | 59.7 | | | 92.9 | >500 |
| 603 | 25.5 | | | 77.2 | 102.7 |
| 604 | 238.7 | | 164.2 | | |
| 605 | 96.8 | | 150.2 | | |
| 606 | 15.3 | | 37.5 | | |
| 607 | 0.9 | | | | |
| 608 | 0.7 | | | 6.8 | 23.2 |
| 609 | 1.0 | | | 10.7 | 54.7 |
| 610 | 80.7 | | 610.1 | | |
| 611 | 32.0 | | 92.0 | | |
| 612 | 32.6 | | 32.5 | | |
| 613 | 4.3 | | | 14.5 | 26.0 |
| 614 | 1.5 | | | 9.9 | 16.0 |
| 615 | 3.5 | | | 16.1 | 30.7 |
| 616 | | | | | |
| 617 | 3.5 | | | 10.2 | 30.7 |
| 618 | 11.2 | | | 18.1 | 24.0 |
| 619 | 14.3 | | | 77.3 | >500 |
| 620 | 9.7 | | | 19.1 | 113.2 |
| 621 | 1.3 | | | 6.9 | 44.6 |
| 622 | 1.5 | | | 8.8 | 46.1 |
| 623 | 1.3 | | | 6.8 | 34.8 |
| 624 | 7.3 | | | 129.2 | 281.5 |
| 625 | 1.5 | | | 17.6 | 72.2 |
| 626 | 26.8 | | | 35.6 | 122.6 |
| 627 | 6.0 | | | 4.5 | 4.1 |
| 628 | 8.8 | 10.3 | | | |
| 629 | 4.1 | | | 106.9 | >500 |
| 630 | 2.4 | | | 68.8 | >500 |
| 631 | 10.7 | | | 78.9 | >500 |
| 632 | 0.5 | | 10.3 | 10.2 | >500 |
| 633 | 2.0 | | | | |
| 634 | 0.9 | 10.8 | | | |
| 635 | 2.9 | | | | |
| 636 | 0.5 | 11.4 | 13.0 | | |
| 637 | 22.1 | 35.1 | 160.9 | | |
| 638 | 0.3 | 8.5 | 6.1 | | |
| 639 | 1.2 | 15.9 | 35.0 | 66.3 | 190.3 |
| 640 | 29.2 | 38.8 | 280.0 | | |
| 641 | 0.9 | 14.5 | 20.3 | | |
| 642 | 0.9 | | 4.1 | 1.1 | 2.4 |
| 643 | 2.6 | | 70.8 | | |
| 644 | 220.0 | | 709.3 | | |
| 645 | 157.5 | | 398.7 | | |
| 646 | 2.7 | | 7.4 | 14.3 | 22.4 |

TABLE 3-continued

KHK-C/KHK-A IC$_{50}$, NRK CTG EC$_{50}$ and F1P 10% FBS/50% HP EC$_{50}$

| Example No | KHK-C IC50 (nM) | KHK-A IC50 (nM) | NRK CTG EC50 (nM) | F1P 10% FBS EC50 (nM) | F1P 50% HP EC50 (nM) |
|---|---|---|---|---|---|
| 647 | 15.5 | | 225.4 | | |
| 648 | 1.2 | | 7.1 | 3.9 | 27.6 |
| 649 | 2.4 | | 8.6 | 12.9 | 57.0 |
| 650 | 6.6 | | 39.1 | | |
| 651 | 11.3 | | 34.8 | | |
| 652 | 23.6 | | 192.8 | | |
| 653 | 8.2 | | | 11.0 | 10.3 |
| 654 | 16.4 | | | 128.7 | 214.4 |
| 655 | 25.1 | | | 46.2 | 236.4 |
| 656 | 1.7 | | | 4.5 | 11.8 |
| 657 | 2.7 | | | 4.1 | 4.2 |
| 658 | 4.8 | | | 20.2 | 20.8 |
| 659 | 8.0 | | | 42.5 | 54.0 |
| 660 | 5.7 | | | 19.8 | 26.7 |
| 661 | 7.3 | | | 21.6 | 59.4 |
| 662 | 3.1 | | | 22.6 | 17.2 |
| 663 | 2.7 | | | 14.0 | 16.4 |
| 664 | 17.3 | | | 80.2 | 78.6 |
| 665 | 0.9 | | | 52.7 | 88.4 |
| 666 | 3.0 | | | 16.7 | 14.8 |
| 667 | 42.3 | | | 61.3 | 305.4 |
| 668 | 32.1 | | | 46.7 | >500 |
| 669 | 16.2 | | | 28.6 | 428.7 |
| 670 | 24.3 | | | 25.3 | 31.4 |
| 671 | 32.9 | | | 35.1 | 269.1 |
| 672 | 33.2 | | | 56.2 | 104.6 |
| 673 | 9.2 | | | 20.3 | 75.8 |
| 674 | 0.2 | | | 3.0 | 231.9 |
| 675 | 0.3 | | 23.7 | 7.0 | 253.7 |
| 676 | 0.2 | | 1.2 | | |
| 677 | 4.8 | | | | |
| 678 | 1.8 | 4.6 | | | |
| 679 | 0.1 | 2.3 | | | |
| 680 | 1.4 | | | | |
| 681 | 0.5 | | | | |
| 682 | 4.0 | | | | |
| 683 | 0.9 | 2.4 | | | |
| 684 | 3.8 | | | | |
| 685 | 0.2 | | 2.1 | | |
| 686 | 0.1 | 16.7 | 6.4 | 67.8 | 71.0 |
| 687 | 1.2 | 2.8 | 6.2 | 7.6 | 14.6 |
| 688 | 59.6 | 96.5 | | | |
| 689 | 0.2 | 14.2 | | | |
| 690 | 0.3 | 45.4 | | | |
| 691 | 7.4 | 7.5 | 50.4 | | |
| 692 | 8.3 | 6.9 | 44.9 | | |
| 693 | 0.2 | 47.2 | 6.4 | 22.4 | 141.3 |
| 694 | 0.4 | 24.5 | 17.2 | 54.3 | 109.0 |
| 695 | 0.5 | 16.2 | 10.3 | 27.1 | 213.3 |
| 696 | 0.5 | 1.0 | 5.7 | 1.7 | 6.8 |
| 697 | 0.1 | 8.6 | 3.7 | 20.1 | 23.7 |
| 698 | 5.6 | 47.4 | 71.5 | 152.2 | 267.4 |
| 699 | 0.3 | 88.7 | 32.8 | 85.2 | 491.8 |
| 700 | 0.2 | 16.1 | 37.3 | 163.0 | 249.5 |
| 701 | 20.5 | 31.8 | 108.3 | | |
| 702 | 0.2 | 11.7 | 3.9 | | |
| 703 | 0.4 | 1.0 | | | |
| 704 | 253.9 | | 1330.2 | | |
| 705 | 3.2 | | 629.6 | 52.4 | 55.2 |
| 706 | 67.2 | | 365.9 | | |
| 707 | 43.4 | | 330.2 | | |
| 708 | >5000 | | >5000 | | |
| 709 | 41.7 | | | 75.2 | 100.8 |
| 710 | 7.2 | | | 12.9 | 42.6 |
| 711 | 6.1 | | 35.2 | 28.2 | 33.7 |
| 712 | >5000 | | >5000 | | |
| 713 | 2342.7 | | 4898.7 | | |
| 714 | >5000 | | >5000 | | |
| 715 | 35.2 | | 258.4 | | |
| 716 | 3.8 | | | | |
| 717 | >100 | >100 | >500 | >500 | >500 |
| 718 | 4.2 | 5.1 | 17.6 | 11.5 | 23.7 |
| 719 | 21.7 | 32.1 | | | |
| 720 | 8.8 | 11.6 | | | |
| 721 | 23.2 | 28.3 | | | |
| 722 | 5.0 | 8.0 | 25.7 | | |
| 723 | 19.0 | | | 44.3 | 41.3 |
| 724 | 25.4 | | | 165.9 | 233.6 |
| 725 | 0.9 | 2.2 | | 37.7 | 23.5 |
| 726 | 16.7 | | | 62.1 | 306.5 |
| 727 | >500 | | | | |
| 728 | 22.2 | | 52.1 | | |
| 729 | 33.5 | 29.1 | 273.0 | | |
| 730 | 2390.2 | | 4997.5 | | |
| 731 | 5.2 | | 250.1 | | |
| 732 | 87.9 | | 360.9 | | |
| 733 | 49.8 | | 124.0 | | |
| 734 | 72.3 | | 91.1 | | |
| 735 | 6.5 | | 52.1 | | |
| 736 | 21.0 | | 34.9 | | |
| 737 | 9.7 | | 241.7 | | |
| 738 | 2.0 | 2.0 | | | |
| 739 | 38.4 | | 215.0 | | |
| 740 | 40.3 | | 323.0 | | |
| 741 | 24.9 | | 223.5 | | |
| 742 | 1.3 | | 4.1 | | |
| 743 | 1020.2 | | 1683.5 | | |
| 744 | 17.2 | | 142.1 | | |
| 745 | 25.4 | | 161.7 | | |
| 746 | 7.4 | 46.7 | 108.0 | 49.2 | 76.8 |
| 747 | 6.1 | | 15.1 | | |
| 748 | 23.2 | | 85.9 | | |
| 749 | 18.8 | | 69.7 | | |
| 750 | 9.0 | | 14.8 | | |
| 751 | 10.8 | | 17.9 | | |
| 752 | 79.2 | | 223.2 | | |
| 753 | 10.7 | | 33.1 | | |
| 754 | 1.9 | | 14.6 | | 11.7 |
| 755 | 30.1 | | 37.0 | | |
| 756 | 7.0 | | 52.2 | | |
| 757 | 2.6 | | 32.4 | 20.6 | 59.7 |
| 758 | 0.5 | | 2.2 | 6.5 | 41.0 |
| 759 | 2.3 | | 6.9 | | |
| 760 | 1.7 | 6.0 | 1.4 | 1.1 | 1.4 |
| 761 | 3.3 | | 27.4 | 28.1 | 129.1 |
| 762 | 2.0 | | | 11.4 | 159.4 |
| 763 | 3.0 | 3.6 | | 6.9 | 8.0 |
| 764 | 5.5 | | | 8.9 | 22.1 |
| 765 | 7.7 | | | 15.5 | 53.2 |
| 766 | 11.8 | | | 38.4 | 149.6 |
| 767 | 4.8 | | | 20.9 | 97.9 |
| 768 | 18.7 | | 32.1 | | |
| 769 | 0.8 | | 3.1 | 6.7 | 18.4 |
| 770 | 5.7 | | | 44.3 | 155.5 |
| 771 | 3.3 | | | 13.0 | 11.2 |
| 772 | 1.0 | | | 10.5 | 33.8 |
| 773 | 2.3 | 8.6 | | 12.7 | 24.6 |
| 774 | 2.1 | | | 11.8 | |
| 775 | 4.3 | | | | |
| 776 | 2.8 | | | | |
| 777 | 1.8 | | | 15.7 | 19.0 |
| 778 | 3.1 | | | 19.0 | 17.2 |
| 779 | 7.1 | | | 47.5 | 37.7 |
| 780 | 4.8 | | | 22.8 | 35.0 |
| 781 | 2.9 | | | 7.1 | 20.1 |
| 782 | 6.3 | | | 134.9 | 129.5 |
| 783 | 98.7 | | | >500 | >500 |
| 784 | 7.9 | | | 118.7 | 91.9 |
| 785 | 0.7 | | | 15.2 | 23.7 |
| 786 | 6.1 | | | 58.0 | 97.6 |
| 787 | 1.1 | 7.0 | | 14.9 | 27.5 |
| 788 | 2.5 | 6.0 | | 18.6 | 76.5 |
| 789 | 3.9 | 12.5 | | 22.7 | 30.6 |
| 790 | 14.2 | | | 29.0 | 103.9 |
| 791 | 80.5 | | | 316.4 | >500 |
| 792 | 2.2 | | | 57.7 | 140.2 |

TABLE 3-continued

KHK-C/KHK-A IC$_{50}$, NRK CTG EC$_{50}$ and F1P 10% FBS/50% HP EC$_{50}$

| Example No | KHK-C IC50 (nM) | KHK-A IC50 (nM) | NRK CTG EC50 (nM) | F1P 10% FBS EC50 (nM) | F1P 50% HP EC50 (nM) |
|---|---|---|---|---|---|
| 793 | 4.8 | | | 55.6 | 75.5 |
| 794 | 4.4 | | | | |
| 795 | 4.6 | 24.1 | 54.5 | 52.7 | 88.8 |
| 796 | 1.8 | | | | |
| 797 | 0.2 | 7.3 | 16.4 | | |
| 798 | 51.9 | 70.1 | >500 | 120.5 | 93.5 |
| 799 | 1.9 | 16.2 | 21.5 | | |
| 800 | 1.3 | 7.8 | | | |
| 801 | 52.2 | >100 | | | |
| 802 | 0.4 | 2.4 | 2.5 | | |
| 803 | 0.5 | 0.8 | 11.3 | | |
| 804 | 3.5 | | | 22.5 | 41.8 |
| 805 | 18.0 | | | 67.9 | 74.1 |
| 806 | 1.6 | | | 61.6 | 112.6 |
| 807 | 15.7 | | | 35.2 | 99.4 |
| 808 | 6.3 | | 695.5 | 38.6 | 41.8 |
| 809 | 24.8 | | | 109.5 | 179.3 |
| 810 | 34.9 | | | 206.3 | >500 |
| 811 | 5.2 | | | 126.9 | 342.9 |
| 812 | 0.7 | | | 11.2 | 40.3 |
| 813 | 2.5 | 34.7 | | 25.2 | 78.4 |
| 814 | 1.8 | 71.3 | | 91.6 | 154.8 |
| 815 | 9.2 | | | 64.3 | 138.0 |
| 816 | 23.4 | | | | |
| 817 | 5.9 | | | 39.7 | 67.1 |
| 818 | 2.5 | | | | |
| 819 | 0.2 | 14.6 | 2.0 | 2.9 | 10.4 |
| 820 | 6.2 | 14.3 | 26.5 | 20.3 | 67.8 |
| 821 | 5.0 | | 42.2 | 20.0 | 75.4 |
| 822 | 24.2 | >100 | | | |
| 823 | 6.4 | 48.2 | 56.3 | 90.6 | 216.3 |
| 824 | 8.6 | 91.6 | | | |
| 825 | 0.9 | 0.5 | 5.6 | 0.9 | 2.3 |
| 826 | 0.3 | 12.3 | 4.2 | 15.7 | 16.8 |
| 827 | 11.8 | >100 | | | |
| 828 | 9.5 | 2.0 | 43.1 | 6.4 | 12.7 |
| 829 | 1.0 | 25.8 | 10.4 | | |
| 830 | 0.2 | 2.0 | 3.2 | | |
| 831 | 0.6 | 6.3 | 8.7 | | |
| 832 | 5.7 | 2.5 | 20.5 | | |
| 833 | 4.0 | 99.8 | | | |
| 834 | 17.8 | 56.8 | | | |
| 835 | 7.5 | | | 25.2 | 65.2 |
| 836 | 5.8 | | | 16.9 | 158.5 |
| 837 | 0.7 | 1.0 | | | |
| 838 | 4.1 | 4.8 | | | |
| 839 | 15.9 | 15.8 | | | |
| 840 | 26.3 | 7.7 | | | |
| 841 | 40.5 | 28.1 | | | |
| 842 | 575.9 | 304.0 | | | |
| 843 | 80.8 | 129.5 | | | |
| 844 | 8.5 | 2.5 | | | |
| 845 | 181.6 | 47.0 | | | |
| 846 | 46.1 | 33.6 | | | |
| 847 | 117.6 | 199.7 | | | |
| 848 | 185.9 | 249.4 | | | |
| 849 | 25.4 | 16.3 | | | |
| 850 | 140.6 | 59.6 | | | |
| 851 | 17.8 | 10.1 | | | |
| 852 | 18.9 | 21.8 | | | |
| 853 | 35.3 | 73.2 | | | |
| 854 | 441.8 | 543.1 | | | |
| 855 | 80.5 | 84.9 | | | |
| 856 | 174.7 | 143.3 | | | |
| 857 | 149.3 | 140.7 | | | |
| 858 | 43.6 | 18.0 | | | |
| 859 | 301.3 | 433.6 | | | |
| 860 | 224.3 | 191.1 | | | |
| 861 | 15.2 | 4.9 | | | |
| 862 | 76.4 | 48.1 | | | |
| 863 | >1000 | >1000 | | | |
| 864 | 6.3 | 10.0 | | | |
| 865 | 17.3 | 25.4 | | | |
| 866 | 27.7 | 18.9 | | | |
| 867 | >1000 | >1000 | | | |
| 868 | 229.6 | 157.7 | | | |
| 869 | 21.6 | 5.9 | | | |
| 870 | 69.5 | 10.9 | | | |
| 871 | 23.4 | 50.4 | | | |
| 872 | 28.9 | 27.0 | | | |
| 873 | 23.6 | 24.1 | | | |
| 874 | 72.3 | 88.4 | | | |
| 875 | 58.0 | 67.0 | | | |
| 876 | 99.4 | 70.4 | | | |
| 877 | 207.9 | 186.4 | | | |
| 878 | 86.9 | 37.8 | | | |
| 879 | 46.7 | 41.6 | | | |
| 880 | 31.6 | 22.5 | >100 | | |
| 881 | 70.5 | 46.0 | | | |
| 882 | 5.1 | 4.5 | 34.6 | | |
| 883 | 14.6 | 21.0 | | | |
| 884 | 46.1 | 96.2 | | | |
| 885 | 26.1 | 149.9 | | | |
| 886 | 13.2 | 27.1 | | | |
| 887 | 10.5 | 44.4 | | | |
| 888 | 4.1 | 51.3 | | | |
| 889 | 17.1 | 98.8 | | | |
| 890 | 60.8 | 141.1 | | | |
| 891 | 59.5 | 166.8 | | | |
| 892 | 99.5 | 329.7 | | | |
| 893 | 733.1 | 1781.9 | | | |
| 894 | 20.5 | 105.6 | | | |
| 895 | 38.1 | 174.7 | | | |
| 896 | 1.7 | 2.1 | | | |

In Vitro Inhibition Assessment with Human OATP1B1 and OATP1B3 Transporters

Assay Protocol

The purpose of this assay was to assess the inhibition potential of test article (TA) toward human OATP1B1 and OATP1B3 transporters in vitro using cell lines transfected with the individual transporters. The assays used clinically relevant probe substrate pravastatin and a known positive control inhibitor rifampicin. HEK293 mock, HEK293-OATP1B1, and HEK293-OATP1B3 transfected cells were seeded onto CellCoat Poly-D-Lysine coated 96 well black cell culture plates with clear bottoms (Greiner bio-one, Cat. #655946) at a density of 70,000 cells/well and cultured to confluency overnight. Seeding media used was Dulbecco's Modification of Eagle's Medium (DMEM—with Gluta-MAX high glucose; Gibco, Cat #: 10569-010) supplemented with 10% fetal bovine serum, 0.1 mM non-essential amino acids, 100 U/mL penicillin, and 100 μg/mL streptomycin. On assay day, media were removed from the assay plates and cells were washed with Hanks' Balanced Salt Solution (HBSS Buffer) (Corning, Cat. #21-023-CV). All TAs and reference inhibitor were serially diluted in DMSO to create spiking solutions at concentrations of 250-fold of final assay concentrations (final DMSO content 0.4%). Cells were preincubated with HBSS buffer containing test compounds for 15 minutes. After the removal of HBSS buffer, dose solution containing TA or reference inhibitor and probe substrate were added to the HEK293-OATP1B1, HEK-293-OATP1B3 and its associated mock cell plate, respectively. The co-incubation period of TAs with the corresponding probe substrate for all plates was 5 minutes. An aliquot of the dose solution was removed from the HEK293 mock cell plates and analysed for dose recovery. Cells were then washed three times with ice cold HBSS buffer and then immediately extracted with methanol:water (70:30 v:v) containing internal standard labetolol (30 nM). The supernatants were evaporated to dryness on injection plates and reconstituted in 80% water containing 20% acetonitrile and 0.1% formic acid for analysis by liquid chromatography with tandem mass spectrometry (LC-MS-MS).

Data Analysis

Fractional transport activities were calculated from the equation:

Activity % = $(A-B)/(C-D) \times 100$

Legend

A: translocated amount of substrate in the presence of TA on transfected cells
B: translocated amount of substrate in the presence of TA on Mock cells
C: translocated amount of substrate in the presence of solvent on transfected cells
D: translocated amount of substrate in the presence of solvent on Mock cells GraphPad Prism 7.0 (GraphPad Software Inc., San Diego, CA) was used for curve fitting and determination of reaction parameters. In uptake transporter inhibition assays, the $IC_{50}$ (µM) was calculated, where applicable. $IC_{50}$ was defined as the concentration of TA required to inhibit maximal activity by 50%.

In Vitro Substrate Assessment with Human OATP1B1 and OATP1B3 Transporters

Assay Protocol

The purpose of this assay was to assess whether test articles (TAs), were substrates for the hepatic uptake transporters organic anion transporting polypeptide (OATP) 1B1 (SLCO1B1) and 1B3 (SLCO1B3) using non-transfected (Mock) and transfected human embryonic kidney (HEK293) cells. HEK293 mock, HEK293-OATP1B1, and HEK293-OATP1B3 transfected cells were seeded directly onto Cell-Coat Poly-D-Lysine coated 96 well black cell culture plates with clear bottoms (Greiner bio-one, Cat. #655946) at a density of 70,000 cells/well and cultured to confluency overnight. Media used for seeding were Dulbecco's Modification of Eagle's Medium (DMEM—with GlutaMAX high glucose; Gibco, Cat #: 10569-010) supplemented with 10% fetal bovine serum, 0.1 mM non-essential amino acids, 100 U/mL penicillin, and 100 µg/mL streptomycin. On assay day, media were removed from the assay plates and cells were washed with Hanks' Balanced Salt Solution (HBSS Buffer) (Corning, Cat. #21-023-CV). Cells were preincubated with HBSS buffer with or without known OATP inhibitors for 30 minutes. After the removal of HBSS buffer, dose solution containing test article with or without a reference inhibitor were added to the HEK293-OATP1B1, HEK-293-OATP1B3 and its associated mock cells, respectively. The incubation period was 2 minutes. Cells were then washed three times with ice cold HBSS buffer and then were immediately extracted with methanol:water (70:30 v:v) containing internal standard labetolol (30 nM). The supernatants were evaporated to dryness on injection plates and reconstituted in 80% water containing 20% acetonitrile and 0.1% formic acid for analysis by liquid chromatography with tandem mass spectrometry (LC-MS-MS).

Data Analysis

The rate of uptake into cells was determined by the following formula:

Rate of uptake = $(A*B)/(C*D)$

Legend

A: concentration of compound in cell lysate
B: volume of sample
C: Incubation time
D: millions of cells in sample A TA was considered a substrate for OATP transporter if: (1) the rate of uptake in the transporter transfected cells was ≥2-fold of the rate of uptake in the mock cells; and (2) the rate of uptake in the transporter transfected cells was decreased by ≥30% in the presence of a known OATP inhibitor.

TABLE 4

| | OATP 1B1 $IC_{50}$/Substrate | |
| --- | --- | --- |
| Example No | OATP1B1 $IC_{50}$ (nM) | OATP1B1 Substrate |
| 4 | 928 | |
| 8 | 1316 | |
| 9 | 448 | |
| 89 | 160.3 | |
| 129 | 13214 | NO |
| 159 | 7400 | |
| 161 | 9120 | NO |
| 166 | 1740 | YES |
| 170 | 892 | |
| 177 | 3712 | |
| 178 | 1350 | |
| 182 | 2843 | |
| 188 | 10200 | |
| 197 | 5920 | |
| 209 | 5570 | YES |
| 236 | 1390 | |
| 285 | 1260 | |
| 317 | 284 | |
| 318 | 350 | |
| 322 | 13300 | NO |
| 324 | 5800 | NO |
| 364 | 38.9 | |
| 373 | 379 | |
| 378 | 1693 | |
| 382 | 149 | |
| 383 | 194 | |
| 385 | 687 | NO |
| 386 | 18 | |
| 392 | 100 | |
| 427 | 210 | |
| 433 | 967 | |
| 446 | 1810 | |
| 447 | 529 | |
| 450 | 991.8 | |
| 459 | 13200 | |
| 462 | 2760.0 | |
| 463 | 1363.0 | |
| 464 | >40000 | |
| 465 | 4581.0 | |
| 466 | 3010.0 | NO |
| 467 | 3120.0 | |
| 471 | 23260.0 | NO |
| 472 | 6223.0 | |
| 476 | 5976.0 | |
| 479 | 993.9 | |
| 483 | 17440.0 | |
| 487 | 9767.0 | |
| 489 | 2670.0 | |
| 490 | 939.0 | |
| 491 | 36030.0 | NO |
| 492 | 31670.0 | NO |
| 494 | 24300.0 | |
| 495 | >40000 | NO |
| 499 | 24300.0 | |
| 510 | 8708.0 | |
| 513 | 5897.0 | |
| 518 | 27110.0 | |
| 598 | 3143.0 | |
| 599 | 4382.0 | |

TABLE 4-continued

OATP 1B1 IC$_{50}$/Substrate

| Example No | OATP1B1 IC$_{50}$ (nM) | OATP1B1 Substrate |
|---|---|---|
| 614 | 7351.0 | |
| 621 | 1639.0 | |
| 642 | 22470.0 | NO |
| 643 | 797.8 | |
| 646 | 5009.0 | |
| 666 | 23400.0 | |
| 687 | 6551.0 | |
| 696 | 5415.0 | |
| 705 | 8908.0 | |
| 711 | 12840.0 | NO |
| 715 | 30470.0 | |
| 725 | >40000 | |
| 735 | 2870.0 | |
| 746 | 1073.0 | |
| 756 | 1749.0 | |
| 763 | 2569.0 | NO |
| 769 | 19080.0 | |
| 781 | 325.8 | |
| 789 | 19670.0 | |
| 802 | 10560.0 | |
| 804 | 1195.0 | |
| 806 | 660.0 | |
| Reference Compound 1 | 1190 | YES |
| Reference Compound 2 | 267 | YES |
| Reference Compound 3 | 1460 | NO |
| Reference Compound 4 | 100 | NO |
| Reference Compound 5 | 720 | YES |
| Reference Compound 6 | 960 | YES |

Reference Compound 1: 2-41R,5 S,6R)-3-(2-((S)-2-methylazetidin-1-yl)-6-(trifluoromethyl)pyrimidin-4-yl)-3-azabicyclo[3.1.0]hexan-6-yl)acetic acid; KHK-C IC$_{50}$=14 nM

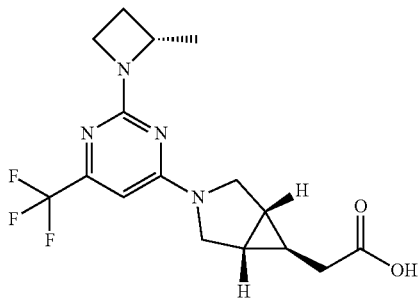 [SMILES: C[C@H]1CCN1c1nc(N2C[C@@H]3[C@@H](CC(=O)O)[C@@H]3C2)cc(C(F)(F)F)n1]

Reference Compound 1b: 3-(2-((S)-2-methylazetidin-1-yl)-6-(trifluoromethyl)pyrimidin-4-yl)-3-azabicyclo[3.1.0]hexane; KHK-C IC$_{50}$=13,132 nM

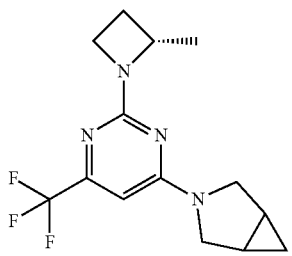 [SMILES: C[C@H]1CCN1c1nc(N2CC3CC3C2)cc(C(F)(F)F)n1]

Reference Compound 2: 2-((R)-1-(5-cyano-6-((S)-2-methylazetidin-1-yl)-4-(trifluoromethyl)pyridin-2-yl)pyrrolidin-3-yl)acetic acid

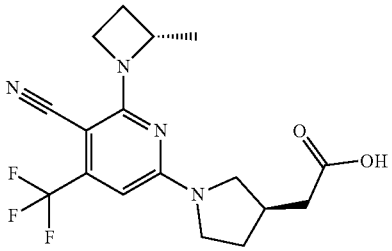 [SMILES: C[C@H]1CCN1c1nc(N2CC[C@H](CC(=O)O)C2)cc(C(F)(F)F)c1C#N]

Reference Compound 3: 2-41R,5 S,6S)-3-(2-((S)-2-methylazetidin-1-yl)-6-(trifluoromethyl)pyrimidin-4-yl)-3-azabicyclo[3.1.1]heptan-6-yl)acetic acid

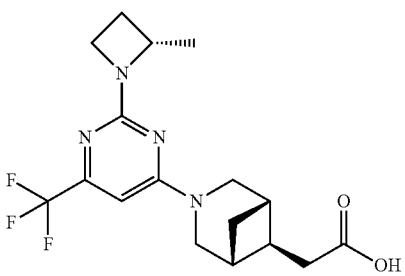 [SMILES: C[C@H]1CCN1c1nc(N2C[C@H]3C[C@@H](C2)[C@@H]3CC(=O)O)cc(C(F)(F)F)n1]

Reference Compound 4: 2-41R,5S,6S)-3-(5-cyano-6-((S)-2-methylazetidin-1-yl)-4-(trifluoromethyl)pyridin-2-yl)-3-azabicyclo[3.1.1]heptan-6-yl)acetic acid

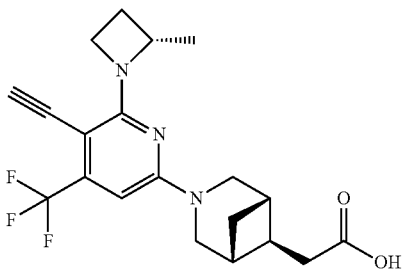 [SMILES: C#Cc1c(C(F)(F)F)cc(N2C[C@H]3C[C@@H](C2)[C@@H]3CC(=O)O)nc1N1CC[C@@H]1C]

Reference Compound 5: 2-41R,5 S,6R)-3-(7,7-difluoro-2-((S)-2-methylazetidin-1-yl)-6,7-dihydro-5H-cyclopenta[d]pyrimidin-4-yl)-3-azabicyclo[3.1.0]hexan-6-yl)acetic acid

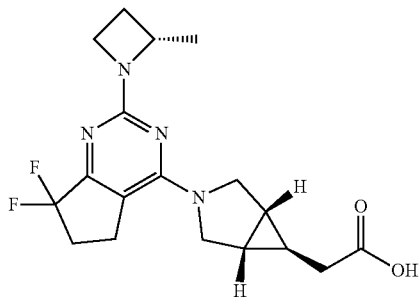 [SMILES: C[C@H]1CCN1c1nc(N2C[C@@H]3[C@@H](CC(=O)O)[C@@H]3C2)c2c(n1)C(F)(F)CC2]

Reference Compound 6: 2-41R,5 S,6R)-3-(8,8-difluoro-2-((S)-2-methylazetidin-1-yl)-5,6,7,8-tetrahydroquinazolin-4-yl)-3-azabicyclo[3.1.0]hexan-6-yl)acetic acid

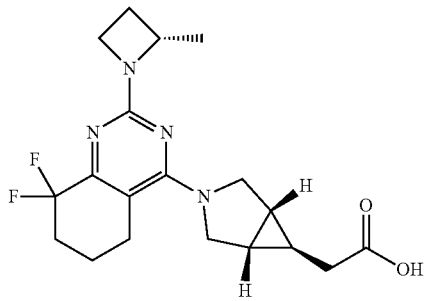 [SMILES: C[C@H]1CCN1c1nc(N2C[C@@H]3[C@@H](CC(=O)O)[C@@H]3C2)c2c(n1)C(F)(F)CCC2]

What is claimed is:

1. A compound of Formula II, or a pharmaceutically acceptable salt or stereoisomer thereof, Formula II

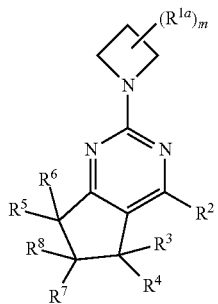

wherein m is 0-4;

each $R^{1a}$ is independently $C_{1-6}$ alkyl, $C_{2-6}$ alkenyl, $C_{2-6}$ alkynyl, OH, $OR^{1b}$, $CH_2OH$, $CO_2R^{12}$, halogen, oxo, $CONH_2$, CN, $NH_2$, $NHR^{11}$, $C_{1-6}$ alkyl-$NHSO_2R^{13}$, $C_{1-6}$ alkyl-$NHCOR^{13}$, $C_{1-6}$ alkoxy or $C_{1-6}$ haloalkyl, wherein the alkyl, alkenyl, or alkynyl are optionally substituted with up to three $R^{1c}$, alternatively two $R^{1a}$ can be combined with the atoms to which they are attached to form a 3-6 membered spiro, fused or bridged ring;

$R^{1b}$ is H, or $C_{1-6}$ alkyl, wherein the alkyl is optionally substituted with up to three halogens, CN, or OH;

each $R^{1c}$ is independently OH, $OR^{11}$, halogen, oxo, $SOR^{13}$, $SO_2R^{13}$, $SR^{13}$, $SO_2NH_2$, $CONH_2$, $C_{1-6}$ alkoxy, $C_{6-10}$ aryl, $C_{6-10}$ aryloxy, 5-11 membered heteroaryl, or $C_{3-7}$ cycloalkyl;

$R^2$ is $C_{6-10}$ aryl, or a 6-14 membered heteroaryl, wherein the aryl, or heteroaryl are optionally substituted with up to eight $R^{2a}$, and wherein $R^2$ is attached to the core through a carbon atom of $R^2$;

each $R^{2a}$ is independently $C_{1-6}$ alkyl, $C_{2-6}$ alkenyl, $C_{2-6}$ alkynyl, $C_{1-6}$ alkoxy, $C_{1-6}$ haloalkyl, $SO_2R^{2c}$, $SOR^{2c}$, $SO_2NH_2$, $CONH_2$, $COR^{2c}$, $CONHR^{2e}$, $CON(R^{2c})_2$, halogen, oxo, OH, CN, $NH_2$, $NHR^{2c}$, $N(R^{2c})_2$, $NHCOR^{2c}$, $N(R^{2c})$ $COR^{2c}$, $NO_2$, $SO_2NHR^{2c}$, $SO_2N(R^{2c})_2$, $NHSO_2R^{2c}$, $N(R^{2c})$ $SO_2R^{2c}$, S(O)(NH) $R^{2c}$, S(O)(NH) $NH_2$, NHS(O)(NH) $R^{2c}$, NS(O) $(NH_2)$ $R^{2c}$, NS(O) $(R^{2c})_2$, $S(O)(NR^{2c})$ $R^{2c}$, $S(O)(NR^{2c})$ $NH_2$, S(O) (NH) $NHR^{2c}$, $S(O)(NR^{2c})$ $NH(R^{2c})$, $OR^{2c}$, $C_{3-7}$ cycloalkyl, 4-7 membered heterocyclyl, $C_{6-10}$ aryl, or 5-11 membered heteroaryl, wherein the alkyl, alkenyl, alkynyl, cycloalkyl, heterocyclyl, aryl or heteroaryl are substituted with up to seven $R^{2b}$, and wherein the cycloalkyl can be fused or spiro to the heteroaryl, or the cycloalkyl can be fused to the aryl; alternatively two $R^{2a}$ can be combined with the atoms to which they are attached to form a 3-7 membered spiro, fused or bridged ring;

each $R^{2b}$ is independently $C_{1-6}$ alkyl, $C_{1-6}$ haloalkyl, $C_{1-6}$ alkoxy, OH, halogen, oxo, $CONH_2$, $NHCOR^{2c}$, $N(R^{2c})$ $COR^{2c}$, $NHCO_2R^{2c}$, $NH_2$, $N(R^{2c})_2$, $NHR^{2c}$, S(O)(NH) $R^{2c}$, S(O)(NH) $NH_2$, NHS(O)(NH) $R^{2c}$, NS(O) $(NH_2)$ $R^{2c}$, NS(O) $(R^{2c})_2$, $S(O)(NR^{2c})$ $R^{2c}$, $S(O)(NR^{2c})$ $NH_2$, S(O)(NH) $NHR^{2c}$, $S(O)(NR^{2c})$ $NH(R^{2c})$, $OR^{2c}$, $NHSO_2R^{2c}$, $N(R^{2c})$ $SO_2R^{2c}$, $C_{1-6}$ alkyl-$CO_2R^{12}$, $C_{1-6}$ alkyl-$CONH_2$, $C_{1-6}$ alkyl-$NHSO_2R^{2c}$, CN, $COR^{2c}$, $NHCO_2R^{2c}$, $SO_2NH_2$, $SO_2NHR^{2c}$, $SO_2R^{2c}$, $C_{3-7}$ cycloalkyl, 4-7 membered heterocyclyl, $C_{6-10}$ aryl or 5-11 membered heteroaryl, wherein the alkyl, alkoxy, haloalkyl, cycloalkyl, heterocyclyl, aryl or heteroaryl can be optionally substituted with up to four $R^{2d}$; alternatively two $R^{2b}$ can be combined with the atoms to which they are attached to form a 3-7 membered spiro, fused or bridged ring;

each $R^{2c}$ is independently $C_{1-6}$ alkyl, $C_{1-6}$ haloalkyl, $C_{1-6}$ alkoxy, $C_{6-10}$ aryl, 5-11 membered heteroaryl, or 4-7 membered heterocyclyl, wherein the alkyl, haloalkyl, alkoxy, aryl, heteroaryl or heterocyclyl are optionally substituted with up to four $R^{2d}$;

each $R^{2d}$ is independently OH, halogen, $NH_2$, $C_{1-6}$ alkoxy, $CONH_2$, $SO_2NH_2$, $NHCOR^{13}$, $C_{1-6}$ alkyl, $C_{1-6}$ haloalkyl, $C_{1-6}$ alkyl-$NH_2$, $C_{1-6}$ alkyl-$CO_2R^{12}$, oxo, or CN;

$R^{2e}$ is $C_{1-6}$ alkyl, $C_{3-7}$ cycloalkyl, $C_{6-10}$ aryl, $C_{1-6}$ alkyl-$C_{6-10}$ aryl, 4-7 membered heterocyclyl, or 5-11 membered heteroaryl, wherein the alkyl, cycloalkyl, aryl, alkyl-aryl, heterocyclyl or heteroaryl are optionally substituted with up to three $R^{10}$;

$R^3$, $R^4$, $R^5$, $R^6$, $R^7$, $R^8$ are independently H, $C_{1-6}$ alkyl, halogen, or $C_{3-7}$ cycloalkyl;

alternatively $R^3$, $R^4$, $R^5$, $R^6$, $R^7$ or $R^8$ can be combined with the atoms to which they are attached to form a 3-6 membered spiro, bridged or fused ring;

each $R^{10}$ is independently $C_{1-6}$ alkoxy, CN, halogen, OH, $NH_2$, $NHR^{11}$, $CONH_2$, $SO_2NH_2$, or $NHCO_2$—$C_{1-6}$ alkyl;

$R^{11}$ is H, $C_{1-6}$ alkyl, or $C_{1-6}$ haloalkyl;

$R^{12}$ is $C_{1-6}$ alkyl, $C_{1-6}$ haloalkyl, 3-7 cycloalkyl, 4-7 heterocyclyl, $C_{6-10}$ aryl, or 5-11 heteroaryl; and $R^{13}$ is $C_{1-6}$ alkyl, or $C_{1-6}$ haloalkyl.

2. The compound of claim 1, or a pharmaceutically acceptable salt or stereoisomer thereof, wherein each $R^{1a}$ is independently $C_{1-6}$ alkyl, $C_{1-6}$ alkynyl, OH, $OR^{1b}$, $CH_2OH$, halogen, oxo, $CONH_2$, CN, $C_{1-6}$ alkyl-$NHSO_2R^{13}$, $C_{1-6}$ alkoxy or $C_{1-6}$ haloalkyl, wherein the alkyl, or alkynyl are optionally substituted with up to three $R^{1c}$; alternatively two $R^{1a}$ can be combined with the atoms to which they are attached to form a 3-6 membered spiro, fused or bridged ring;

$R^{1b}$ is H, or $C_{1-6}$ alkyl;

each $R^{1c}$ is independently OH, $SR^{13}$, or $C_{6-10}$ aryl;

$R^2$ is $C_{6-10}$ aryl, or a 6-11 membered heteroaryl, wherein the aryl, or heteroaryl are optionally substituted with up to three $R^{2a}$, and wherein $R^2$ is attached to the core through a carbon atom of $R^2$;

each $R^{2a}$ is independently $C_{1-6}$ alkyl, $C_{1-6}$ alkoxy, $C_{1-6}$ haloalkyl, $SO_2R^{2c}$, $SO_2NH_2$, $CONH_2$, $COR^{2c}$, $CONHR^{2e}$, $CON(R^{2c})_2$, halogen, oxo, OH, CN, $NH_2$, $NHR^{2c}$, $NHCOR^{2c}$, $NO_2$, $SO_2NHR^{2c}$, $NHSO_2R^{2c}$, SO(NH) $R^{2c}$, $OR^{2c}$, $C_{3-7}$ cycloalkyl, 4-7 membered heterocyclyl, or 5-11 membered heteroaryl, wherein the alkyl, cycloalkyl, heterocyclyl, or heteroaryl are substituted with up to four $R^{2b}$, and wherein the cycloalkyl can be fused or spiro to the heteroaryl, or the cycloalkyl can be fused to the aryl; alternatively two $R^{2a}$ can be combined with the atoms to which they are attached to form a 3-7 membered spiro, fused or bridged ring;

each $R^{2b}$ is independently $C_{1-6}$ alkyl, $C_{1-6}$ haloalkyl, OH, halogen, oxo, $CONH_2$, $NHCOR^{2c}$, $NHCO_2R^{2c}$, $NH_2$, $N(R^{2c})_2$, $NHR^{2c}$, $NHSO_2R^{2c}$, $N(R^{2c})$ $SO_2R^{2c}$, CN, $COR^{2c}$, $SO_2NH_2$, $SO_2R^{2c}$, $C_{3-7}$ cycloalkyl, 4-7 membered heterocyclyl, or 5-11 membered heteroaryl, wherein the alkyl, haloalkyl, cycloalkyl, heterocyclyl, or heteroaryl can be optionally substituted with up to four $R^{2d}$;

each $R^{2c}$ is independently $C_{1-6}$ alkyl, $C_{1-6}$ haloalkyl, $C_{6-10}$ aryl, 5-11 membered heteroaryl, or 4-7 membered heterocyclyl, wherein the alkyl, haloalkyl, aryl, heteroaryl or heterocyclyl are optionally substituted with up to four $R^{2d}$;

each $R^{2d}$ is independently OH, $NHCOR^{13}$, $C_{1-6}$ alkyl, oxo, or CN;

$R^{2e}$ is $C_{1-6}$ alkyl, $C_{3-7}$ cycloalkyl, $C_{6-10}$ aryl, $C_{1-6}$ alkyl-$C_{6-10}$ aryl, or 5-11 membered heteroaryl, wherein the alkyl, cycloalkyl, aryl, alkyl-aryl, or heteroaryl are optionally substituted with up to three $R^{10}$;

$R^3$, $R^4$, $R^5$, $R^6$, $R^7$, $R^8$ are independently absent, H, $C_{1-6}$ alkyl, halogen, or $C_{3-7}$ cycloalkyl;

alternatively $R^3$, $R^4$, $R^5$, $R^6$, $R^7$ or $R^8$ can be combined with the atoms to which they are attached to form a 3-6 membered spiro, bridged or fused ring;

each $R^{10}$ is independently $C_{1-6}$ alkoxy, CN, halogen, OH, $NH_2$, $NHR^{11}$, $CONH_2$, $SO_2NH_2$, or $NHCO_2$-$C_{1-6}$ alkyl;

$R^{11}$ is H, or $C_{1-6}$ alkyl;

$R^{12}$ is $C_{1-6}$ alkyl; and $R^{13}$ is $C_{1-6}$ alkyl, or $C_{1-6}$ haloalkyl.

3. The compound of claim 1, or a pharmaceutically acceptable salt or stereoisomer thereof, having the structure of Formula III:

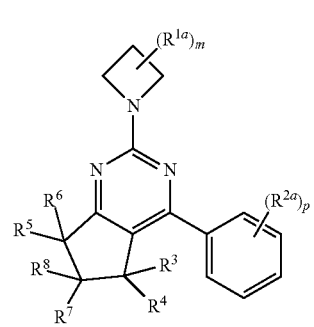

Formula III wherein p is 0, 1, 2, 3, or 4;

m is 0, 1, 2, 3, or 4;

each $R^{1a}$ is independently $C_{1-6}$ alkyl, $C_{2-6}$ alkenyl, $C_{2-6}$ alkynyl, OH, $OR^{1b}$, $CH_2OH$, $CO_2R^{12}$, halogen, oxo, $CONH_2$, CN, $NH_2$, $NHR^{11}$, $C_{1-6}$ alkyl-$NHSO_2R^{13}$, $C_{1-6}$ alkyl-$NHCOR^{13}$, $C_{1-6}$ alkoxy or $C_{1-6}$ haloalkyl, wherein the alkyl, alkenyl, or alkynyl are optionally substituted with up to three $R^{1c}$; alternatively two $R^{1a}$ can be combined with the atoms to which they are attached to form a 3-6 membered spiro, fused or bridged ring;

$R^{1b}$ is H, or $C_{1-6}$ alkyl, wherein the alkyl is optionally substituted with up to three halogens, CN, or OH;

each $R^{1c}$ is independently OH, $OR^{11}$, halogen, oxo, $SOR^{13}$, $SO_2R^{13}$, $SR^{13}$, $SO_2NH_2$, $CONH_2$, $C_{1-6}$ alkoxy, $C_{6-10}$ aryl, $C_{6-10}$ aryloxy, 5-11 membered heteroaryl, or $C_{3-7}$ cycloalkyl;

each $R^{2a}$ is independently $C_{1-6}$ alkyl, $C_{2-6}$ alkenyl, $C_{2-6}$ alkynyl, $C_{1-6}$ alkoxy, $C_{1-6}$ haloalkyl, $SO_2R^{2c}$, $SOR^{2c}$, $SO_2NH_2$, $CONH_2$, $COR^{2c}$, $CONHR^{2e}$, $CON(R^{2c})_2$, halogen, oxo, OH, CN, $NH_2$, $NHR^{2c}$, $N(R^{2c})_2$, $NHCOR^{2c}$, $N(R^{2c})$ $COR^{2c}$, $NO_2$, $SO_2NHR^{2c}$, $SO_2N(R^{2c})_2$, $NHSO_2R^{2c}$, $N(R^{2c})$ $SO_2R^{2e}$, S(O)(NH) $R^{2c}$, S(O)(NH) $NH_2$, NHS(O)(NH) $R^{2c}$, NS(O) $(NH_2)$ $R^{2c}$, NS(O) $(R^{2c})_2$, $S(O)(NR^{2c})$ $R^{2c}$, $S(O)(NR^{2c})$ $NH_2$, $S(O)(NH)$ $NHR^{2e}$, $S(O)(NR^{2c})$ $NH(R^{2c})$, $OR^{2c}$, $C_{3-7}$ cycloalkyl, 4-7 membered heterocyclyl, $C_{6-10}$ aryl, or 5-11 membered heteroaryl, wherein the alkyl, alkenyl, alkynyl, cycloalkyl, heterocyclyl, aryl or heteroaryl are substituted with up to seven $R^{2b}$, and wherein the cycloalkyl can be fused to the aryl; alternatively two $R^{2a}$ can be combined with the atoms to which they are attached to form a 3-7 membered spiro, fused or bridged ring;

each $R^{2b}$ is independently $C_{1-6}$ alkyl, $C_{1-6}$ haloalkyl, $C_{1-6}$ alkoxy, OH, halogen, oxo, $CONH_2$, $NHCOR^{2c}$, $N(R^{2c})$ $COR^{2c}$, $NHCO_2R^{2c}$, $NH_2$, $N(R^{2c})_2$, $NHR^{2c}$, S(O)(NH) $R^{2c}$, S(O)(NH) $NH_2$, NHS(O)(NH) $R^{2c}$, NS(O) $(NH_2)$ $R^{2c}$, NS(O) $(R^{2c})_2$, $S(O)(NR^{2c})$ $R^{2c}$, $S(O)(NR^{2c})$ $NH_2$, S(O)(NH) $NHR^{2c}$, $S(O)(NR^{2c})$ $NH(R^{2c})$, $OR^{2c}$, $NHSO_2R^{2c}$, $N(R^{2c})$ $SO_2R^{2c}$, $C_{1-6}$ alkyl-$CO_2R^{12}$, $C_{1-6}$ alkyl-$CONH_2$, $C_{1-6}$ alkyl-$NHSO_2R^{2c}$, CN, $COR^{2c}$, $NHCO_2R^{2c}$, $SO_2NH_2$, $SO_2NHR^{2c}$, $SO_2R^{2c}$, $C_{3-7}$ cycloalkyl, 4-7 membered heterocyclyl, $C_{6-10}$ aryl or 5-11 membered heteroaryl, wherein the alkyl, alkoxy, haloalkyl, cycloalkyl, heterocyclyl, aryl or heteroaryl can be optionally substituted with up to four $R^{2d}$;

alternatively two $R^{2b}$ can be combined with the atoms to which they are attached to form a 3-7 membered spiro, fused or bridged ring;

each $R^{2c}$ is independently $C_{1-6}$ alkyl, $C_{1-6}$ haloalkyl, $C_{1-6}$ alkoxy, $C_{6-10}$ aryl, 5-11 membered heteroaryl, or 4-7 membered heterocyclyl, wherein the alkyl, haloalkyl, alkoxy, aryl, heteroaryl or heterocyclyl are optionally substituted with up to four $R^{2d}$;

each $R^{2d}$ is independently OH, halogen, $NH_2$, $C_{1-6}$ alkoxy, $CONH_2$, $SO_2NH_2$, $NHCOR^{13}$, $C_{1-6}$ alkyl, $C_{1-6}$ haloalkyl, $C_{1-6}$ alkyl-$NH_2$, $C_{1-6}$ alkyl-$CO_2R^{12}$, oxo, or CN;

$R^{2e}$ is $C_{1-6}$ alkyl, $C_{3-7}$ cycloalkyl, $C_{6-10}$ aryl, $C_{1-6}$ alkyl-$C_{6-10}$ aryl, 4-7 membered heterocyclyl, or 5-11 membered heteroaryl, wherein the alkyl, cycloalkyl, aryl, alkyl-aryl, heterocyclyl or heteroaryl are optionally substituted with up to three $R^{10}$;

$R^3$, $R^4$, $R^5$, $R^6$, $R^7$, $R^8$ are independently H, $C_{1-6}$ alkyl, halogen, or $C_{3-7}$ cycloalkyl;

alternatively $R^3$, $R^4$, $R^5$, $R^6$, $R^7$ or $R^8$ can be combined with the atoms to which they are attached to form a 3-6 membered spiro, bridged or fused ring;

each $R^{10}$ is independently $C_{1-6}$ alkoxy, CN, halogen, OH, $NH_2$, $NHR^{11}$, $CONH_2$, $SO_2NH_2$, or $NHCO_2$-$C_{1-6}$ alkyl;

$R^{11}$ is H, $C_{1-6}$ alkyl, or $C_{1-6}$ haloalkyl;

$R^{12}$ is $C_{1-6}$ alkyl, $C_{1-6}$ haloalkyl, 3-7 cycloalkyl, 4-7 heterocyclyl, $C_{6-10}$ aryl, or 5-11 heteroaryl; and $R^{13}$ is $C_{1-6}$ alkyl, or $C_{1-6}$ haloalkyl.

4. The compound of claim 1, or a pharmaceutically acceptable salt or stereoisomer thereof, wherein $R^2$ is

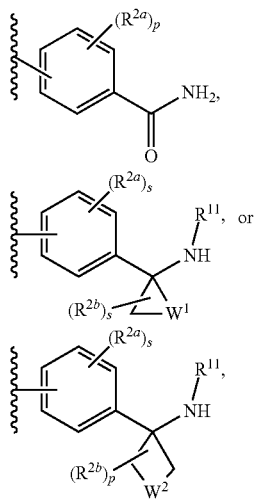

wherein
p is 0, 1, 2, or 3;
s is independently 0, 1 or 2;
$W^1$ is $CHF_2$ or $CF_2$; and
$W^2$ is O, $CF_2$, CHF, S, SO, SO(NH), SO($NR^{2c}$), $CH_2O$, $CH_2OCH_2$, $OCH_2O$, $CH_2SO_2$, $CH_2SO_2CH_2$, or $SO_2$.

5. The compound of claim 1, or a pharmaceutically acceptable salt or stereoisomer thereof, wherein $R^2$ is

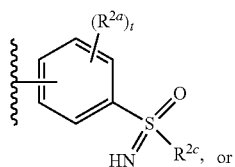

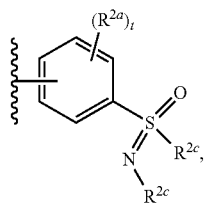

wherein t is 0, 1, 2 or 3.

6. The compound of claim 1, or a pharmaceutically acceptable salt or stereoisomer thereof, wherein $R^2$ is

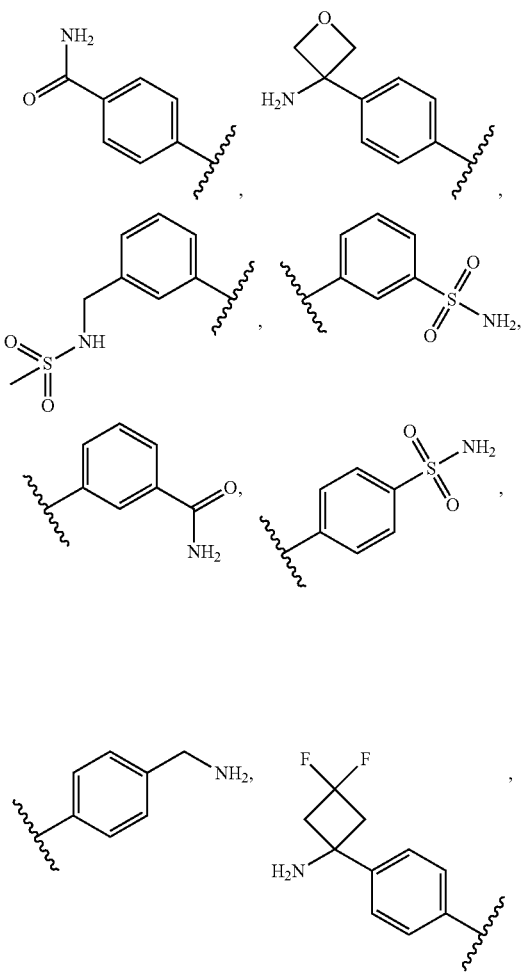

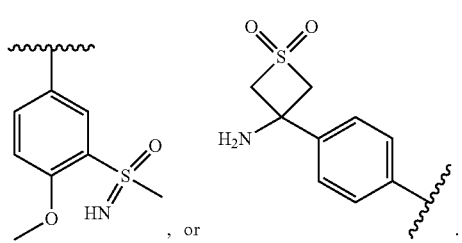

, or

7. The compound of claim 1, or a pharmaceutically acceptable salt or stereoisomer thereof, having the structure of Formula IV:

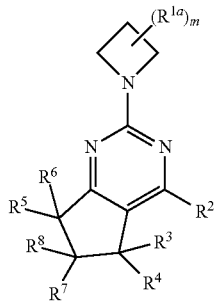

Formula IV wherein m is 0-4;
each $R^{1a}$ is independently $C_{1-6}$ alkyl, $C_{2-6}$ alkenyl, $C_{2-6}$ alkynyl, OH, $OR^{1b}$, $CH_2OH$, $CO_2R^{12}$, halogen, oxo, $CONH_2$, CN, $NH_2$, $NHR^{11}$, $C_{1-6}$ alkyl-$NHSO_2R^{13}$, $C_{1-6}$ alkyl-$NHCOR^{13}$, $C_{1-6}$ alkoxy or $C_{1-6}$ haloalkyl, wherein the alkyl, alkenyl, or alkynyl are optionally substituted with up to three $R^{1c}$; alternatively two $R^{1a}$ can be combined with the atoms to which they are attached to form a 3-6 membered spiro, fused or bridged ring;
$R^{1b}$ is H, or $C_{1-6}$ alkyl, wherein the alkyl is optionally substituted with up to three halogens, CN, or OH;
each $R^{1c}$ is independently OH, $OR^{11}$, halogen, oxo, $SOR^{13}$, $SO_2R^{13}$, $SR^{13}$, $SO_2NH_2$, $CONH_2$, $C_{1-6}$ alkoxy, $C_{6-10}$ aryl, $C_{6-10}$ aryloxy, 5-11 membered heteroaryl, or $C_{3-7}$ cycloalkyl;
$R^{2a}$ is a 6-14 membered heteroaryl, wherein the heteroaryl is optionally substituted with up to eight $R^{2a}$, and wherein $R^2$ is attached to the core through a carbon atom of $R^2$;
each $R^{2a}$ is independently $C_{1-6}$ alkyl, $C_{2-6}$ alkenyl, $C_{2-6}$ alkynyl, $C_{1-6}$ alkoxy, $C_{1-6}$ haloalkyl, $SO_2R^{2c}$, $SOR^{2c}$, $SO_2NH_2$, $CONH_2$, $COR^{2c}$, $CONHR^{2e}$, $CON(R^{2c})_2$, halogen, oxo, CN, $NH_2$, $NHR^{2c}$, $N(R^{2c})_2$, $NHCOR^{2c}$, $N(R^{2c})$ $COR^{2c}$, $NO_2$, $SO_2NHR^{2c}$, $SO_2N$ $(R^{2c})_2$, $NHSO_2R^{2c}$ $N(R^{2c})$ $SO_2R^{2c}$, $S(O)(NH)$ $R^{2c}$, $S(O)(NH)$ $NH_2$, $NHS(O)(NH)$ $R^{2c}$, $NS(O)$ $(NH_2)$ $R^{2c}$, $NS(O)$ $(R^{2c})_2$, $S(O)(NR^{2c})$ $R^{2c}$, $S(O)(NR^{2c})$ $NH_2$, $S(O)$ $(NH)$ $NHR^{2c}$, $S(O)(NR^{2c})$ $NH(R^{2c})$, $OR^{2c}$, $C_{3-7}$ cycloalkyl, 4-7 membered heterocyclyl, $C_{6-10}$ aryl, or 5-11 membered heteroaryl, wherein the alkyl, alkenyl, alkynyl, cycloalkyl, heterocyclyl, aryl or heteroaryl are substituted with up to seven $R^{2b}$, and wherein the cycloalkyl can be fused or spiro to the heteroaryl; alternatively two $R^{2a}$ can be combined with the atoms to which they are attached to form a 3-7 membered spiro, fused or bridged ring;
each $R^{2b}$ is independently $C_{1-6}$ alkyl, $C_{1-6}$ haloalkyl, $C_{1-6}$ alkoxy, OH, halogen, oxo, $CONH_2$, $NHCOR^{2c}$, $N(R^{2c})$ $COR^{2c}$, $NHCO_2R^{2c}$, $NH_2$, $N(R^{2c})_2$, $NHR^{2c}$, $S(O)(NH)$ $R^{2c}$, $S(O)(NH)$ $NH_2$, $NHS(O)(NH)$ $R^{2c}$, $NS(O)$ $(NH_2)$ $R^{2c}$, $NS(O)$ $(R^{2c})_2$, $S(O)(NR^{2c})$ $R^{2c}$, $S(O)(NR^{2c})$ $NH_2$, $S(O)(NH)$ $NHR^{2c}$, $S(O)(NR^{2c})$ $NH(R^{2c})$, $OR^{2c}$, $NHSO_2R^{2c}$, $N(R^{2c})$ $SO_2R^{2c}$, $C_{1-6}$ alkyl-$CO_2R^{12}$, $C_{1-6}$ alkyl-$CONH_2$, $C_{1-6}$ alkyl-$NHSO_2R^{2c}$, CN, $COR^{2c}$, $NHCO_2R^{2c}$, $SO_2NH_2$, $SO_2NHR^{2c}$ $SO_2R^{2c}$, $C_{3-7}$ cycloalkyl, 4-7 membered heterocyclyl, $C_{6-10}$ aryl or 5-11 membered heteroaryl, wherein the alkyl, alkoxy, haloalkyl, cycloalkyl, heterocyclyl, aryl or heteroaryl can be optionally substituted with up to four $R^{2d}$; alternatively two $R^{2b}$ can be combined with the atoms to which they are attached to form a 3-7 membered spiro, fused or bridged ring;
each $R^{2c}$ is independently $C_{1-6}$ alkyl, $C_{1-6}$ haloalkyl, $C_{1-6}$ alkoxy, $C_{6-10}$ aryl, 5-11 membered heteroaryl, or 4-7 membered heterocyclyl, wherein the alkyl, haloalkyl, alkoxy, aryl, heteroaryl or heterocyclyl are optionally substituted with up to four $R^{2d}$;
each $R^{2d}$ is independently OH, halogen, $NH_2$, $C_{1-6}$ alkoxy, $CONH_2$, $SO_2NH_2$, $NHCOR^{13}$, $C_{1-6}$ alkyl, $C_{1-6}$ haloalkyl, $C_{1-6}$ alkyl-$NH_2$, $C_{1-6}$ alkyl-$CO_2R^{12}$, oxo, or CN;
$R^{2e}$ is $C_{1-6}$ alkyl, $C_{3-7}$ cycloalkyl, $C_{6-10}$ aryl, $C_{1-6}$ alkyl-$C_{6-10}$ aryl, 4-7 membered heterocyclyl, or 5-11 membered heteroaryl, wherein the alkyl, cycloalkyl, aryl, alkyl-aryl, heterocyclyl or heteroaryl are optionally substituted with up to three $R^{10}$;
$R^3$, $R^4$, $R^5$, $R^6$, $R^7$, $R^8$ are independently H, $C_{1-6}$ alkyl, halogen, or $C_{3-7}$ cycloalkyl;
alternatively $R^3$, $R^4$, $R^5$, $R^6$, $R^7$ or $R^8$ can be combined with the atoms to which they are attached to form a 3-6 membered spiro, bridged or fused ring;
each $R^{10}$ is independently $C_{1-6}$ alkoxy, CN, halogen, OH, $NH_2$, $NHR^{11}$, $CONH_2$, $SO_2NH_2$, or $NHCO_2$-$C_{1-6}$ alkyl;
$R^{11}$ is H, $C_{1-6}$ alkyl, or $C_{1-6}$ haloalkyl;
$R^{12}$ is $C_{1-6}$ alkyl, $C_{1-6}$ haloalkyl, 3-7 cycloalkyl, 4-7 heterocyclyl, $C_{6-10}$ aryl, or 5-11 heteroaryl; and
$R^{13}$ is $C_{1-6}$ alkyl, or $C_{1-6}$ haloalkyl.

8. The compound of claim 1, or a pharmaceutically acceptable salt or stereoisomer thereof, wherein $R^2$ is attached to the core through a carbon atom of $R^2$, and wherein $R^2$ is

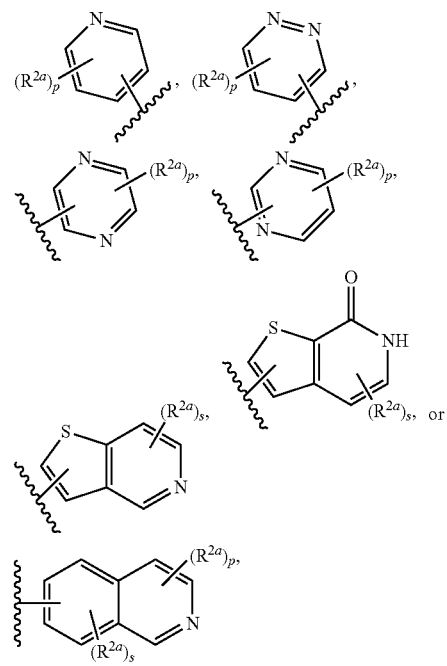

wherein p is 0, 1, 2, or 3; and
s is 0, 1 or 2.

9. The compound of claim 1, or a pharmaceutically acceptable salt or stereoisomer thereof, wherein $R^2$ is

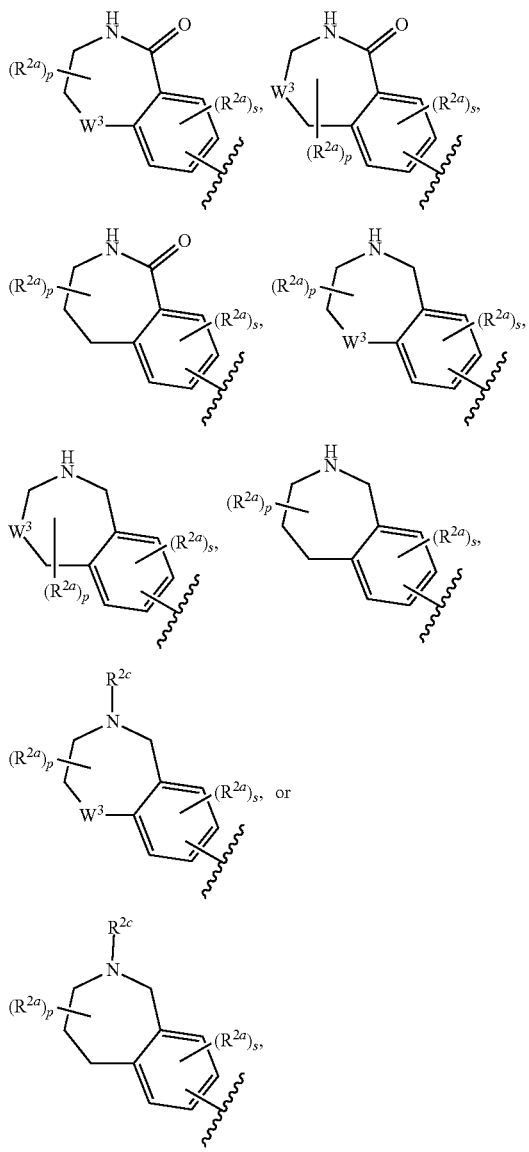

wherein p is 0, 1, 2, 3 or 4;
s is 0 or 1; and
$W^3$ is O, NH, SO(NH), SO($NR^{2c}$), $SO_2$ or $NR^{11}$.

10. The compound of claim 1, or a pharmaceutically acceptable salt or stereoisomer thereof, wherein $R^2$ is

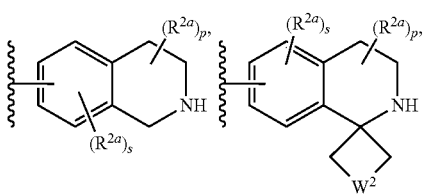

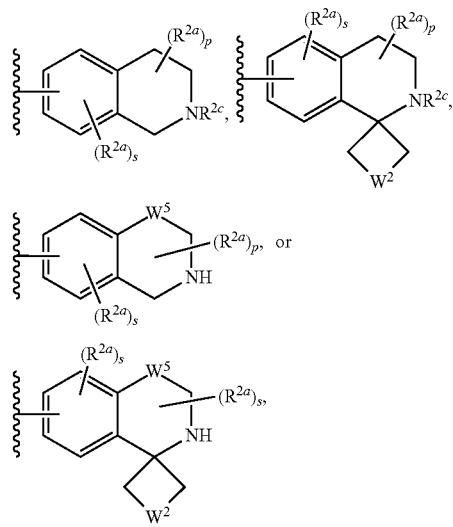

wherein
p is 0, 1, 2, 3 or 4;
s is independently 0 or 1;
$W^2$ is O, $CF_2$, CHF, S, SO, SO(NH), SO($NR^{2c}$), or $SO_2$; and
$W^5$ is SO(NH), SO($NR^{2c}$), $SO_2$ or absent.

11. The compound of claim 1, or a pharmaceutically acceptable salt or stereoisomer thereof, wherein $R^2$ is

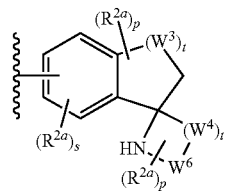

wherein
p is independently 0, 1 or 2;
s is 0 or 1;
t is independently 1, 2, or 3;
Each $W^3$ is independently O, $CH_2$, CHF, $CF_2$, S, CO, SO, $SO_2$, SO(NH), SO($NR^{11}$), or $NR^{11}$, wherein when one $W^3$ is $NR^{11}$, an adjacent $W^3$ cannot be O, S, or $NR^{11}$, wherein when one $W^3$ is O, S, CO, SO, $SO_2$, SO($NR^{11}$), or SO(NH), an adjacent $W^3$ cannot be O, S, CO, SO, $SO_2$, SO($NR^{11}$), or SO(NH);
Each $W^4$ is independently O, CO, SO($NR^{11}$), SO(NH), $CH_2$, CHF, $CF_2$, $SO_2$, or $NR^{11}$, wherein when one $W^4$ is O, $SO_2$, CO, SO($NR^{11}$), or SO(NH), an adjacent $W^4$ cannot be O, $SO_2$, CO, SO($NR^{11}$), or SO(NH);
and
$W^6$ is CO, SO, $SO_2$, SO(NH), SO($NR^{11}$), or $CH_2$, wherein when $W^6$ is CO, SO, $SO_2$, SO(NH), SO($NR^{11}$), adjacent $W^4$ cannot be CO, $SO_2$, SO(NH), SO($NR^{11}$).

12. The compound of claim 1, or a pharmaceutically acceptable salt thereof, wherein $R^2$ is

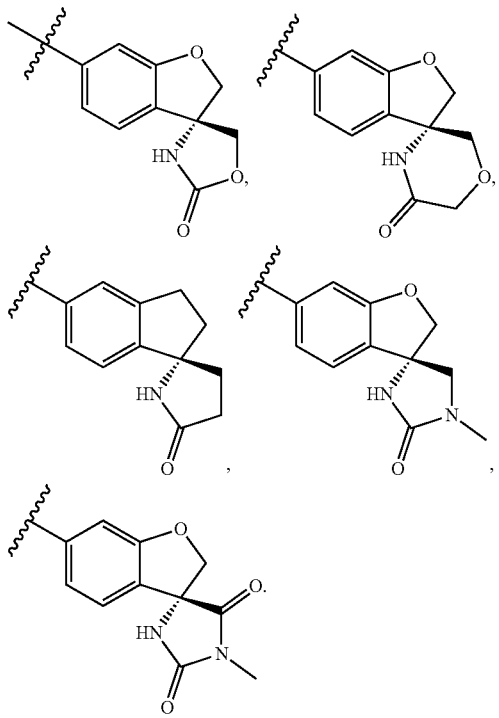

13. The compound of claim 1, or a pharmaceutically acceptable salt or stereoisomer thereof, wherein $R^2$ is

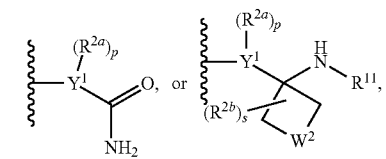

wherein
$Y^1$ is a 6-14 membered heteroaryl, wherein $Y^1$ is attached to the core through a carbon atom of $Y^1$;
p is 0, 1, 2, or 3;
s is 0, 1, or 2; and
$W^2$ is O, $CF_2$, CHF, SO, SO(NH), SO($NR^{2c}$), $CH_2O$, $CH_2OCH_2$, $OCH_2$, $CH_2SO_2$, $CH_2SO_2CH_2$, or $SO_2$.

14. The compound of claim 1, or a pharmaceutically acceptable salt or stereoisomer thereof, wherein $R^2$ is

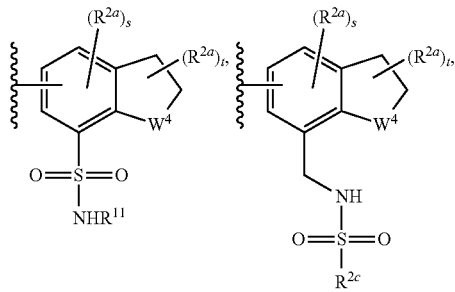

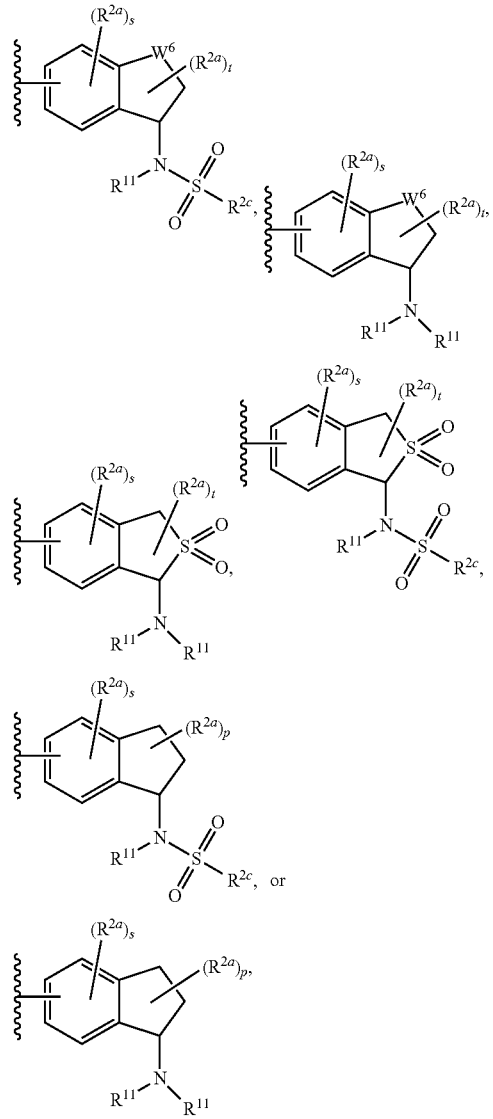

wherein s is 0 or 1;
p is 0, 1, 2, 3, or 4;
t is 0, 1, 2 or 3;
$W^4$ is absent, $CH_2$, O, $CF_2$, $CH_2NH$, $CH_2NHCH_2$, $OCH_2$, $OCH_2CH_2$, CONH, or $CONHCH_2$; and
$W^6$ is $CH_2$, O, $SO_2$ or SO(NH), SO($NR^{2c}$).

15. The compound of claim 1, or a pharmaceutically acceptable salt thereof, wherein $R^2$ is

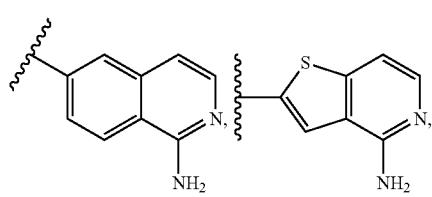

-continued

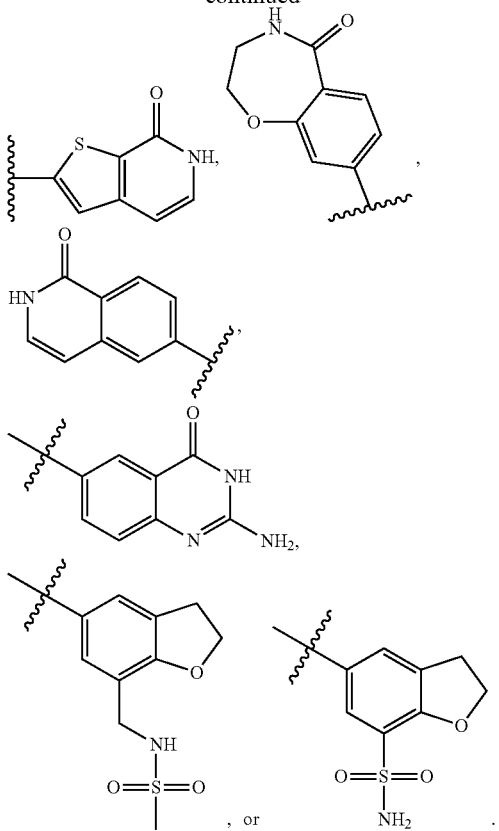

, or

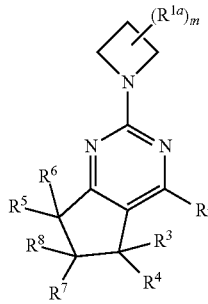

16. A compound, or a pharmaceutically acceptable salt or stereoisomer thereof, having the structure of Formula VI Formula VI

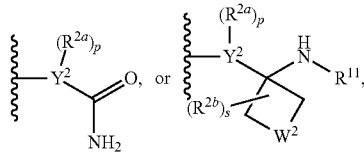

wherein m is 0-4:
each $R^{1a}$ is independently $C_{1-6}$ alkyl, $C_{2-6}$ alkenyl, $C_{2-6}$ alkynyl, OH, $OR^{1b}$, $CH_2OH$, $CO_2R^{12}$, halogen, oxo, $CONH_2$, CN, $NH_2$, $NHR^{11}$, $C_{1-6}$ alkyl-$NHSO_2R^{13}$, $C_{1-6}$ alkyl-$NHCOR^{13}$, $C_{1-6}$ alkoxy or $C_{1-6}$ haloalkyl, wherein the alkyl, alkenyl, or alkynyl are optionally substituted with up to three R1c; alternatively two R1a can be combined with the atoms to which they are attached to form a 3-6 membered spiro, fused or bridged ring;
$R^{1b}$ is H, or $C_{1-6}$ alkyl, wherein the alkyl is optionally substituted with up to three halogens, CN, or OH;
each $R^{1c}$ is independently OH, $OR^{11}$, halogen, oxo, $SOR^{13}$, $SO_2R^{13}$, $SR^{13}$, $SO_2NH_2$, $CONH_2$, $C_{1-6}$ alkoxy, $C_{6-10}$ aryl, $C_{6-10}$ aryloxy, 5-11 membered heteroaryl, or $C_{3-7}$ cycloalkyl;

wherein $R^2$ is

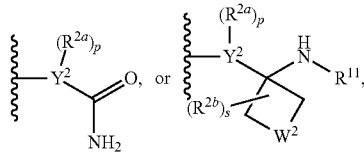

wherein
$Y^2$ is a 5 membered heteroaryl, wherein $Y^2$ is attached to the core through a carbon atom of $Y^2$;
p is 0, or 1;
s is 0, 1, or 2; and
$W^2$ is O, $CF_2$, CHF, SO, SO(NH), $SO(NR^{2c})$, $CH_2O$, $CH_2OCH_2$, $OCH_2O$, $CH_2SO_2$, $CH_2SO_2CH_2$, or $SO_2$;
each $R^{2a}$ is independently $C_{1-6}$ alkyl, $C_{2-6}$ alkenyl, $C_{2-6}$ alkynyl, $C_{1-6}$ alkoxy, $C_{1-6}$ haloalkyl $SO_2R^{2c}$, $SOR^{2c}$, $SO_2NH_2$, $CONH_2$, $COR^{2c}$, $CON(R^{2c})_2$, halogen, oxo, OH, CN, $NH_2$, $NHR^{2c}$, $N(R^{2c})_2$, $NHCOR^{2c}$, $N(R^{2c})COR^{2c}$, $NO_2$, $SO_2NHR^{2c}$, $SON(R^{2c})_2$, $NHSO_2R^{2c}$ $N(R^{2c})SO_2R^{2c}$, $S(O)(NH)R^{2c}$, $S(O)(NH)NH_2$, NHS(O)(NH)$R^{2c}$, NS(O)($NH_2$)$R^{2c}$, NS(O)($R^{2c}$)$_2$, $S(O)(NR^{2c})R^{2c}$, $S(O)(NR^{2c})NH_2$, $S(O)(NH)NHR^{2c}$ $S(O)(NR^{2c})NH$($R^{2c}$), $OR^{2c}$, $C_{3-7}$ cycloalkyl, 4-7 membered heterocyclyl, $C_{6-10}$ aryl, or 5-11 membered heteroaryl, wherein the alkyl, alkenyl, alkynyl, cycloalkyl, heterocyclyl, aryl or heteroaryl are substituted with up to seven $R^{2b}$, and wherein the cycloalkyl can be fused or spiro to the heteroaryl; alternatively two $R^{2a}$ can be combined with the atoms to which they are attached to form a 3-7 membered spiro, fused or bridged ring:
each $R^{2b}$ is independently $C_{1-6}$ alkyl, $C_{1-6}$ haloalkyl, $C_{1-6}$ alkoxy, OH, halogen, oxo, $CONH_2$, $NHCOR^{2c}$, $N(R^{2c})COR^{2c}$, $NHCO_2R^{2c}$, $NH_2$, $N(R^{2c})_2$, $NHR^{2c}$, S(O)(NH)$R^{2c}$, $S(O)(NH)NH_2$, NHS(O)(NH)$R^{2c}$, NS(O)($NH_2$)$R^{2c}$, NS(O)($R^{2c}$)$_2$, $S(O)(NR^{2c})R^{2c}$, $S(O)(NR^{2c})NH_2$, $S(O)(NH)NHR^{2c}$, $S(O)(NR^{2c})NH(R^{2c})$, $OR^{2c}$, $NHSO_2R^{2c}$, $N(R^{2c})SO_2R^{2c}$, $C_{1-6}$ alkyl-CO-$R^{12}$, $C_{1-6}$ alkyl-$CONH_2$, $C_{1-6}$ alkyl-$NHSO_2R^{2c}$, CN, $COR^{2c}$, $NHCOR^{2c}$, $SO_2NH_2$, $SO_2NHR^{2c}$, $SO_2R^{2c}$, $C_{3-7}$ cycloalkyl, 4-7 membered heterocyclyl, $C_{6-10}$ aryl or 5-11 membered heteroaryl, wherein the alkyl, alkoxy, haloalkyl, cycloalkyl, heterocyclyl, aryl or heteroaryl can be optionally substituted with up to four $R^{2d}$, alternatively two $R^{2b}$ can be combined with the atoms to which they are attached to form a 3-7 membered spiro, fused or bridged ring;
each $R^{2c}$ is independently $C_{1-6}$ alkyl, $C_{1-6}$ haloalkyl, $C_{1-6}$ alkoxy, $C_{6-10}$ aryl, 5-11 membered heteroaryl, or 4-7 membered heterocyclyl, wherein the alkyl, haloalkyl, alkoxy, aryl, heteroaryl or heterocyclyl are optionally substituted with up to four $R^{2d}$;
each $R^{2d}$ is independently OH, halogen, $NH_2$, $C_{1-6}$ alkoxy, $CONH_2$, $SO_2NH_2$, $NHCOR^{13}$, $C_{1-6}$ alkyl, $C_{1-6}$ haloalkyl, $C_{1-6}$ alkyl-$NH_2$, $C_{1-6}$ alkyl-$CO_2R^{12}$, oxo, or CN;
$R^{2e}$ is $C_{1-6}$ alkyl, $C_{3-7}$ cycloalkyl, $C_{6-10}$ aryl, $C_{1-6}$ alkyl-$C_{6-10}$ aryl, 4-7 membered heterocyclyl, or 5-11 membered heteroaryl, wherein the alkyl, cycloalkyl, aryl, alkyl-aryl, heterocyclyl or heteroaryl are optionally substituted with up to three $R^{10}$;
$R^3$, $R^4$, $R^5$, $R^6$, $R^7$, $R^8$ are independently H, $C_{1-6}$ alkyl, halogen, or $C_{3-7}$ cycloalkyl; alternatively $R^3$, $R^4$, $R^5$, R[6], R[7], R[8] can be combined with the atoms to which they are attached to form a 3-6 membered spiro, bridged or fused ring;

each R[10] is independently $C_{1-6}$ alkoxy, CN, halogen, OH, $NH_2$, NHR[11], $CONH_2$, $SO_2NH_2$, or $NHCO_2$—$C_{1-6}$ alkyl;

R[11] is H, $C_{1-6}$ alkyl, or $C_{1-6}$ haloalkyl;

R[12] is $C_{1-6}$ alkyl, $C_{1-6}$ haloalkyl, 3-7 cycloalkyl, 4-7 heterocyclyl, $C_{6-10}$ aryl, or 5-11 heteroaryl; and R[13] is $C_{1-6}$ alkyl, or $C_{1-6}$ haloalkyl.

17. A compound, or a pharmaceutically acceptable salt thereof, having the structure of Formula VI

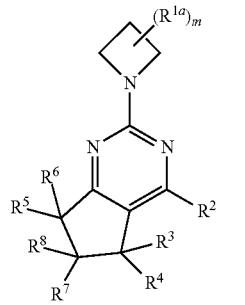

Formula VI wherein m is 0-4;

each R[1a] is independently $C_{1-6}$ alkyl, $C_{2-6}$ alkenyl, $C_{2-6}$ alkynyl, OH, OR[1b], $CH_2OH$, $CO_2R^{12}$, halogen, oxo, $CONH_2$, CN, $NH_2$, NHR[11], $C_{1-6}$ alkyl-$NHSO_2R^{13}$, $C_{1-6}$ alkyl-NHCOR[13], $C_{1-6}$ alkoxy or $C_{1-6}$ haloalkyl, wherein the alkyl, alkenyl, or alkynyl are optionally substituted with up to three R[1c]; alternatively two R[1a] can be combined with the atoms to which they are attached to form a 3-6 membered spiro, fused or bridged ring;

R[1b] is H, or $C_{1-6}$ alkyl, wherein the alkyl is optionally substituted with up to three halogens, CN, or OH;

each R[1c] is independently OH, OR[11], halogen, oxo, SOR[13], $SO_2R^{13}$, SR[13], $SO_2NH_2$, $CONH_2$, $C_{1-6}$ alkoxy, $C_{6-10}$ aryl, $C_{6-10}$ aryloxy, 5-11 membered heteroaryl, or $C_{3-7}$ cycloalkyl; wherein R[2] is

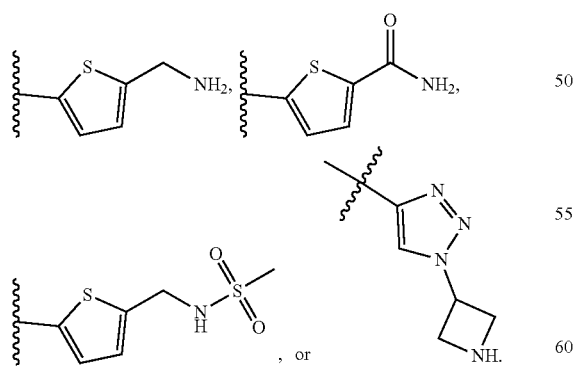

R[3], R[4], R[5], R[6], R[7], R[8] are independently H, $C_{1-6}$ alkyl, halogen, or $C_{3-7}$ cycloalkyl: alternatively R[3], R[4], R[5], R[6], R[7] or R[8] can be combined with the atoms to which they are attached to form a 3-6 membered spiro, bridged or fused ring.

18. The compound of claim 17, or a pharmaceutically acceptable salt thereof, with the structure shown below:

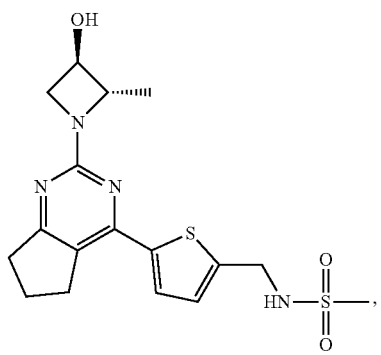

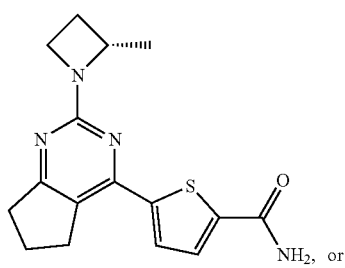

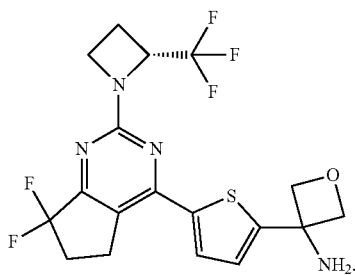

19. The compound of claim 1, or a pharmaceutically acceptable salt thereof, with the structure shown below:

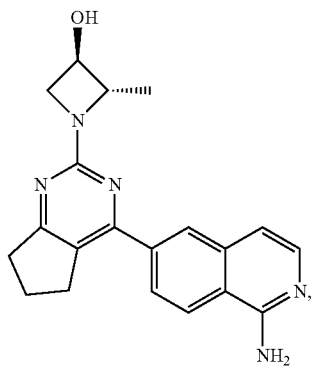

651
-continued
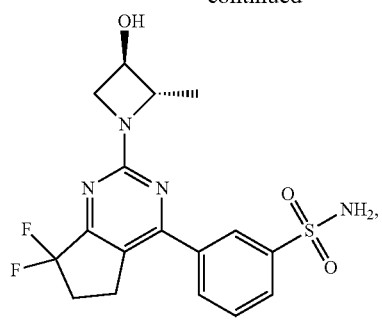
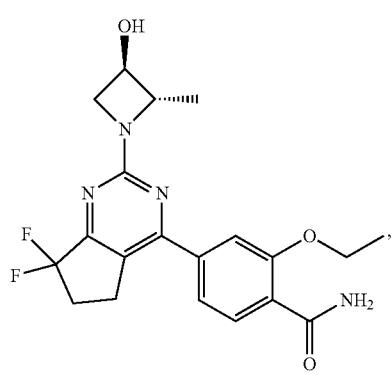
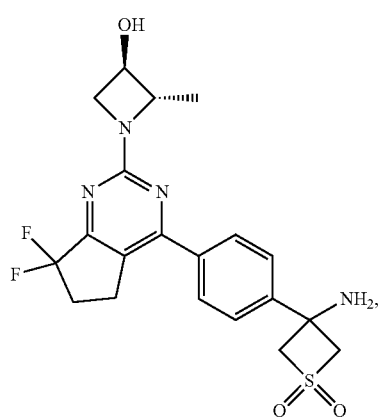
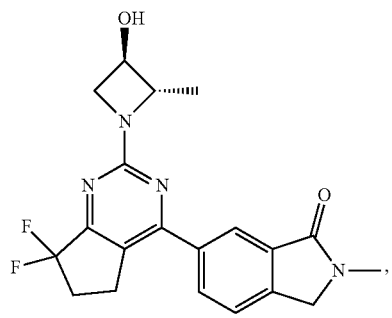
652
-continued
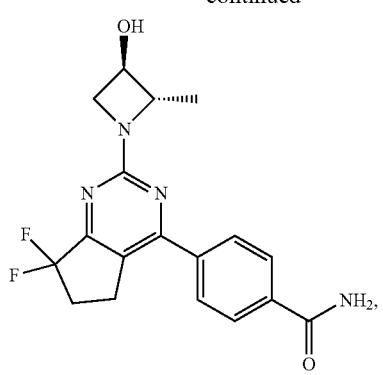
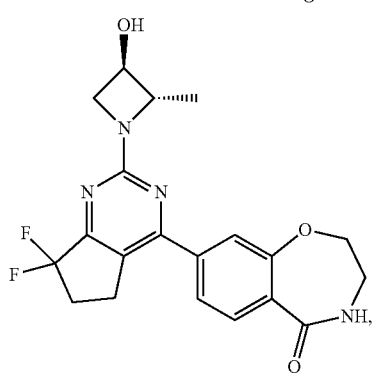
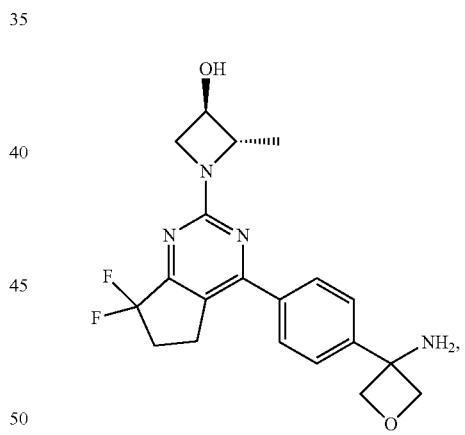
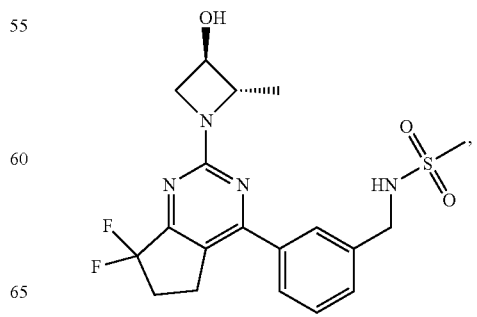

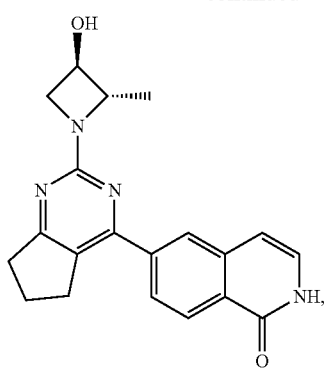
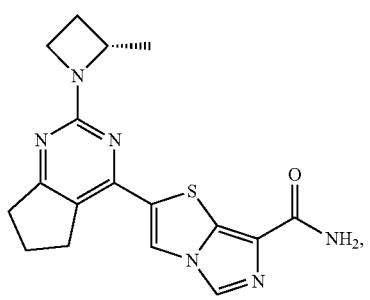
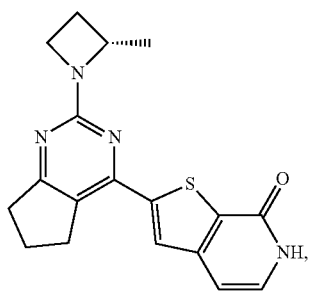
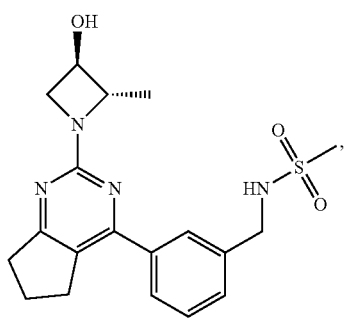
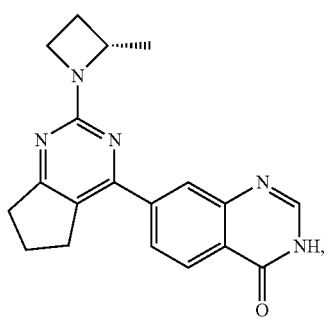
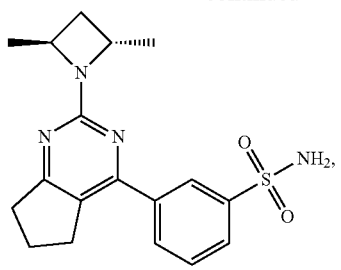
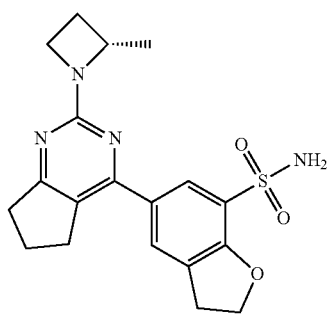
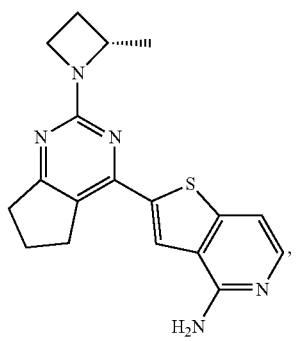
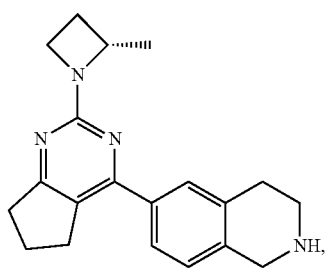
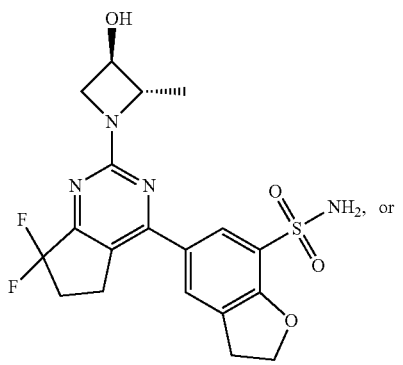

655
-continued
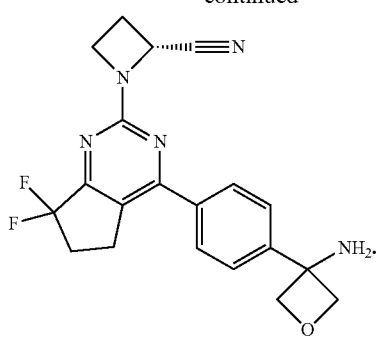
20. The compound of claim 1, or a pharmaceutically acceptable salt thereof, with the structure shown below:
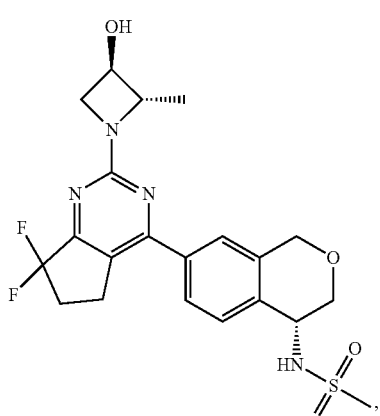
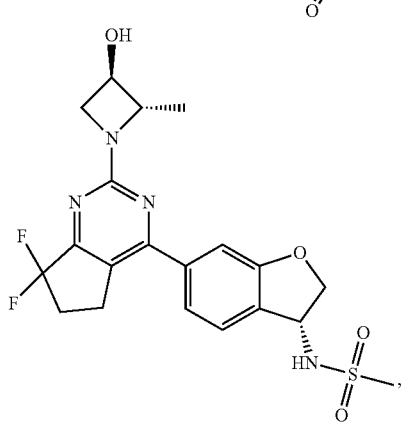
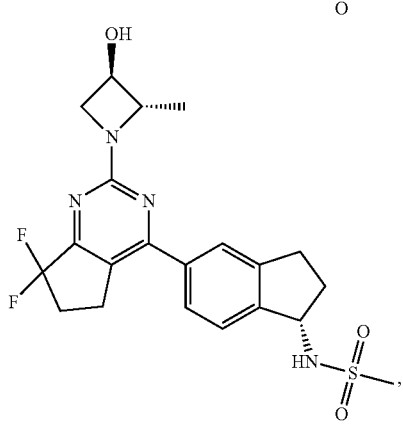
656
-continued
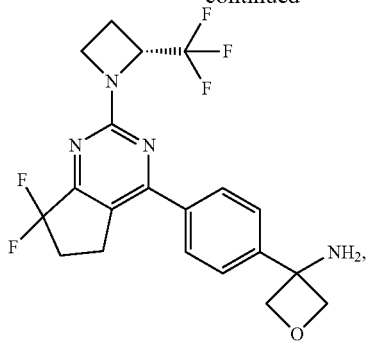
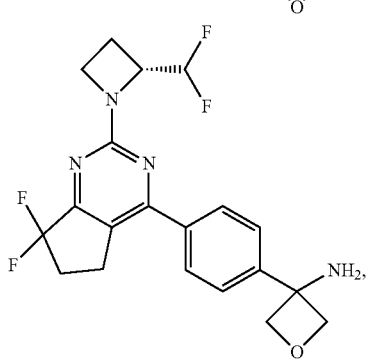
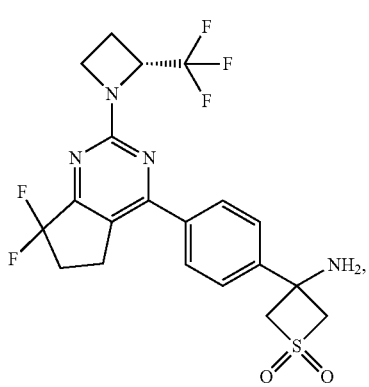
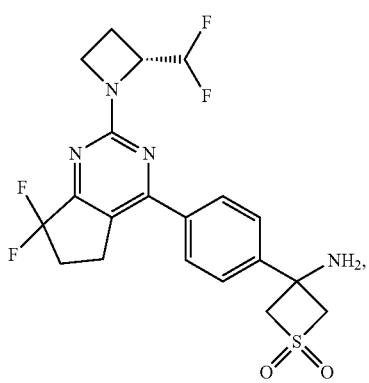

657
-continued
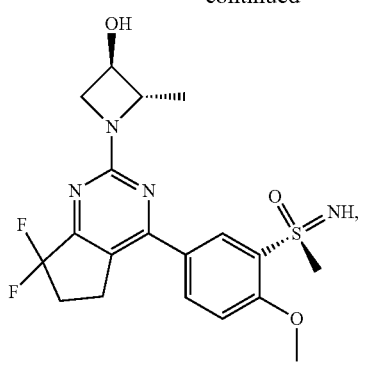
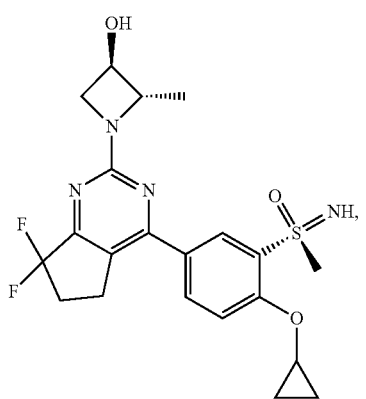
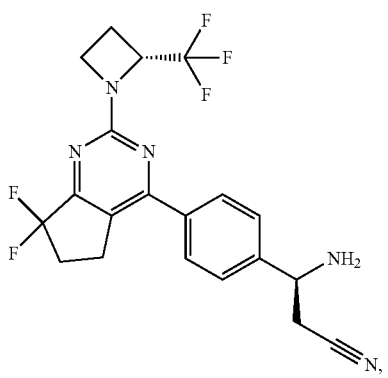
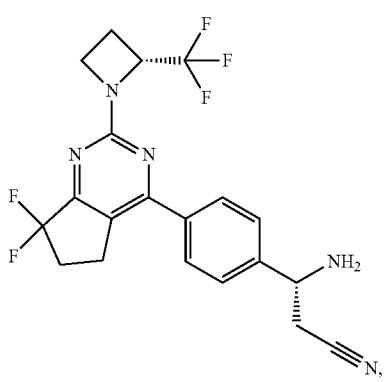
658
-continued
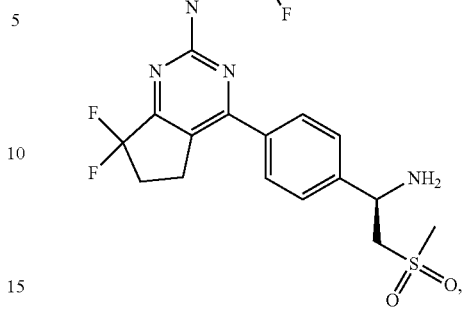
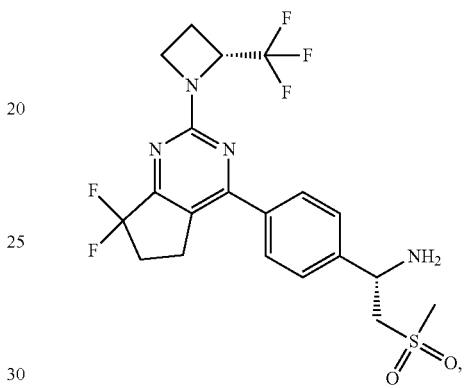
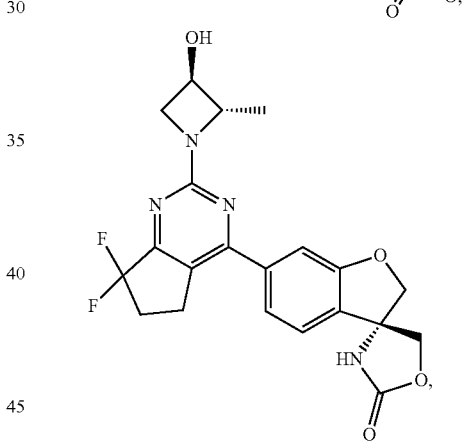
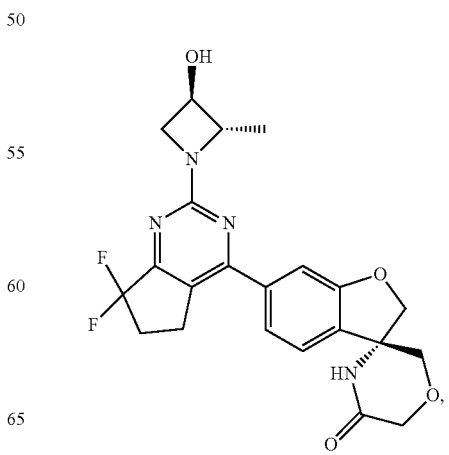

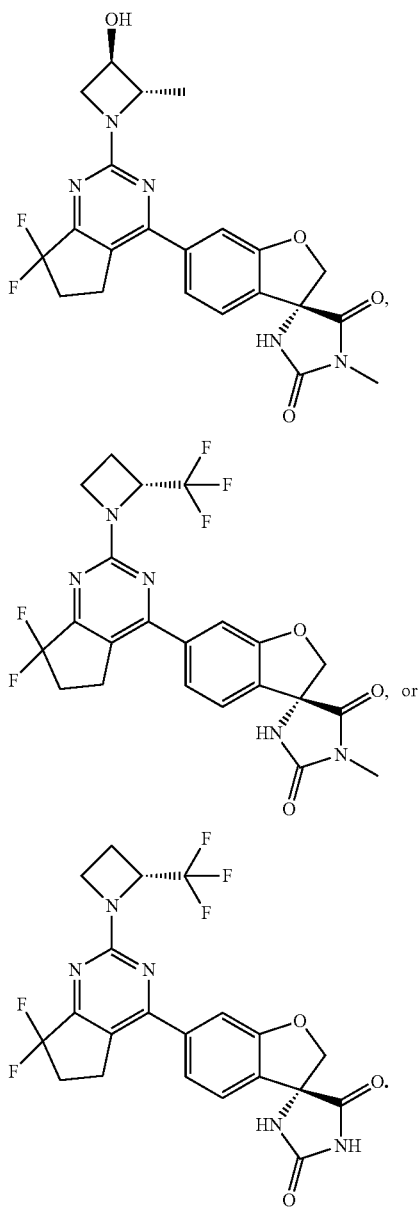
21. The compound of claim 1, or a pharmaceutically acceptable salt thereof, with the structure shown below:
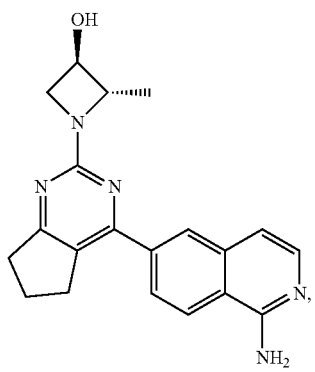
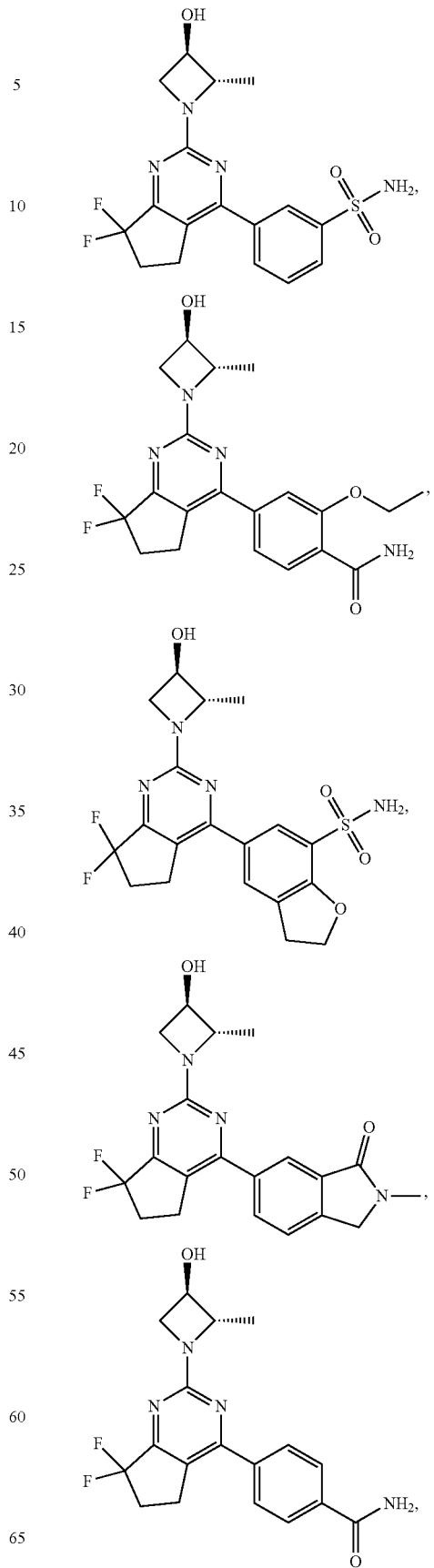

661
-continued
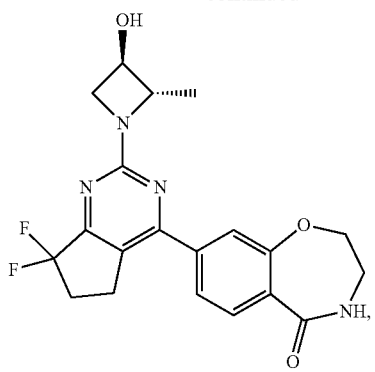
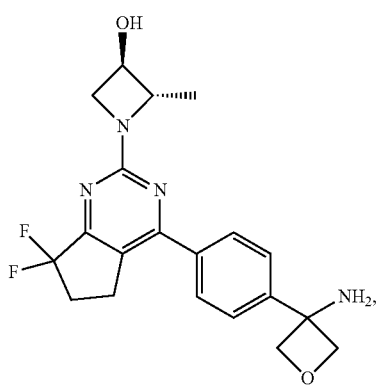
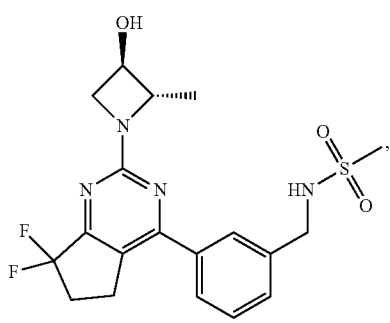
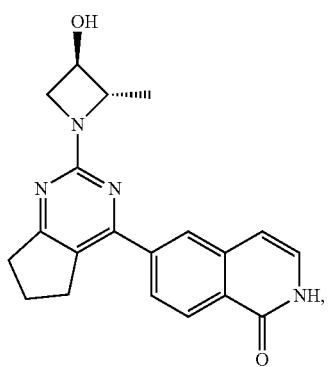
662
-continued
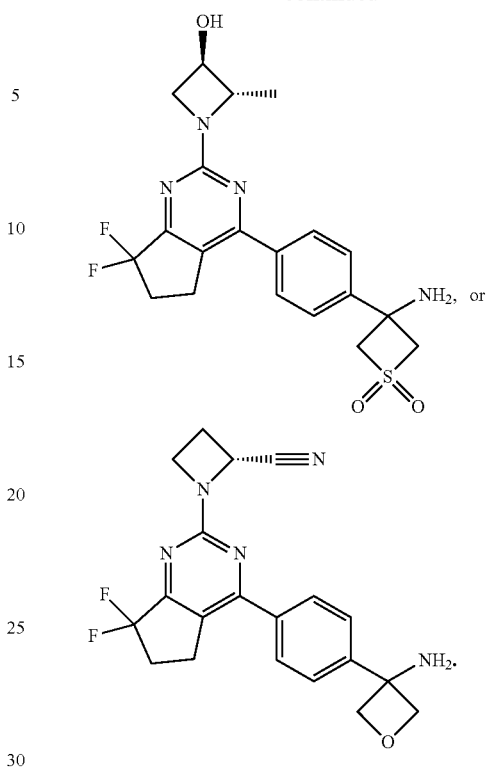
22. The compound of claim 1, or a pharmaceutically acceptable salt thereof, with the structure shown below:
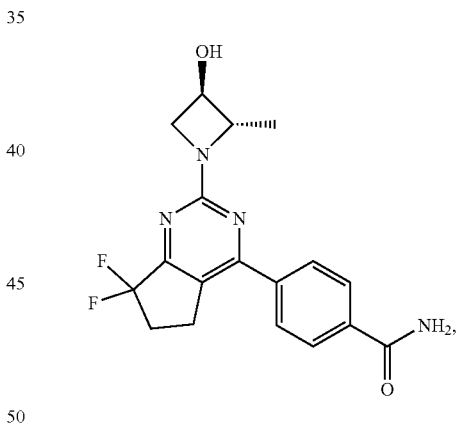
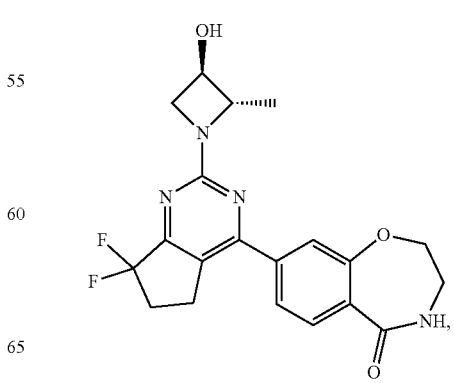

663
-continued
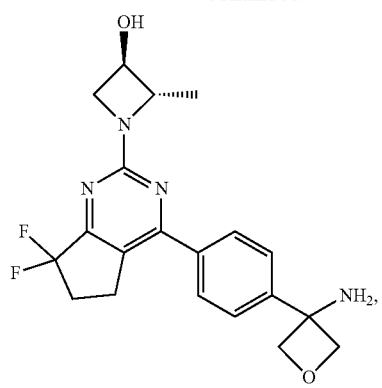
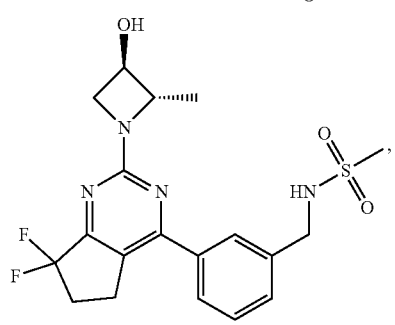
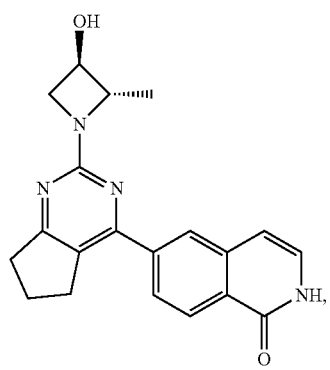
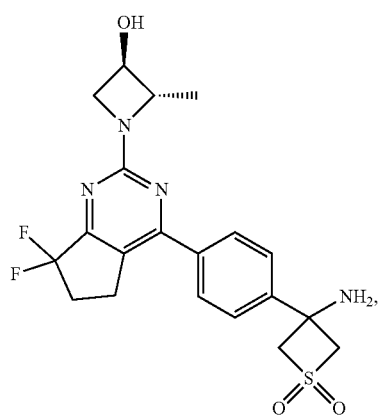
664
-continued
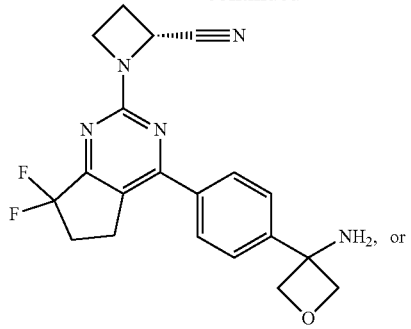
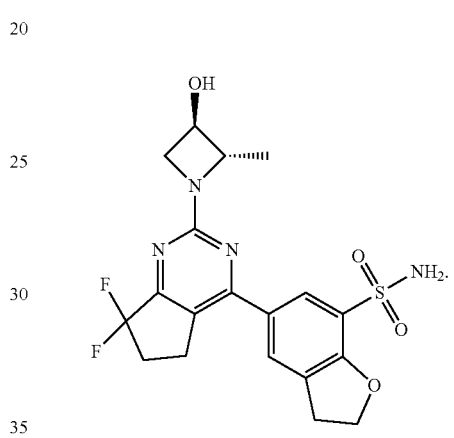
23. The compound of claim 1, or a pharmaceutically acceptable salt thereof, with the structure shown below:
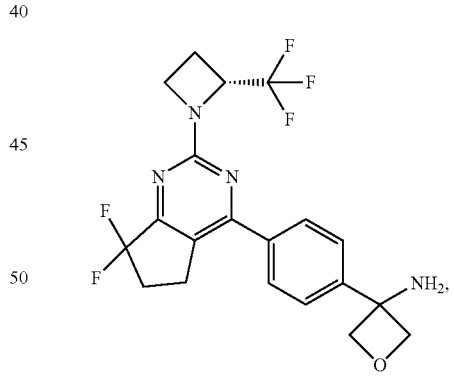
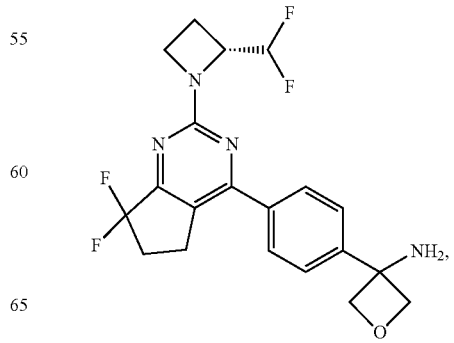

665
-continued

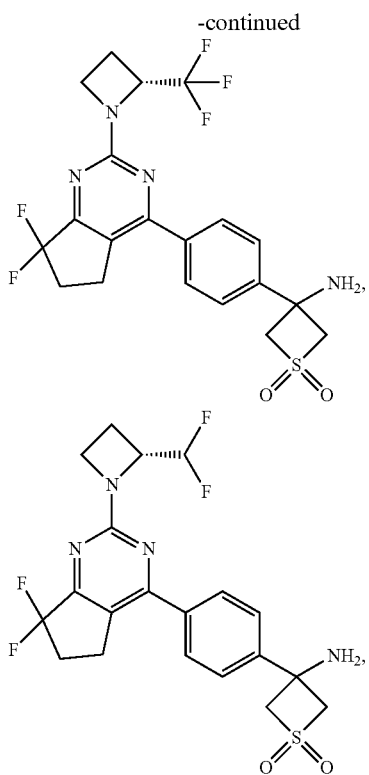

666
-continued

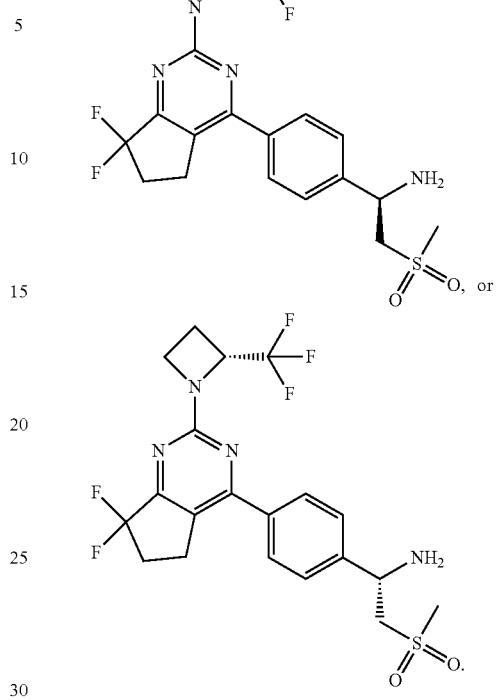

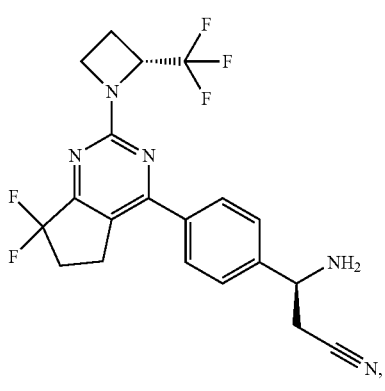

24. A pharmaceutical composition comprising a pharmaceutically effective amount of a compound of any one of claim 1, or a pharmaceutically acceptable salt thereof, and at least one pharmaceutically acceptable carrier or excipient.

25. The pharmaceutical composition of claim 24 further comprising one or more additional therapeutic agents.

26. The pharmaceutical composition of claim 25, wherein the additional therapeutic agent comprises an SGLT2 inhibitor, an ACE inhibitor and/or a pharmaceutically acceptable salt thereof.

27. The pharmaceutical composition of claim 26, wherein the additional therapeutic agent comprises empagliflozin, canagliflozin, dapagliflozin, ipragliflozin, tofogliflozin, remogliflozin, or ertugliflozin.

28. The pharmaceutical composition of claim 26, wherein the additional therapeutic agent comprises benazepril, imidapril, or enalapril and/or a pharmaceutically acceptable salt thereof.

29. A pharmaceutical composition comprising a pharmaceutically effective amount of a

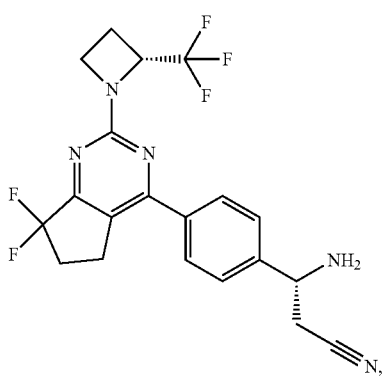

Formula VI

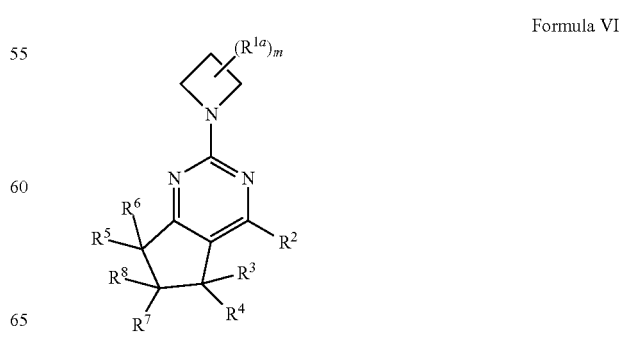

wherein m is 0-4;
each $R^{1a}$ is independently $C_{1-6}$ alkyl, $C_{2-6}$ alkenyl, $C_{2-6}$ alkynyl, OH, $OR^{1b}$, $CH_2OH$, $CO_2R^{12}$, halogen, oxo, $CONH_2$, CN, $NH_2$, $NHR^{11}$, $C_{1-6}$ alkyl-$NHSO_2R^{13}$, $C_{1-6}$ alkyl-$NHCOR^{13}$, $C_{1-6}$ alkoxy or $C_{1-6}$ haloalkyl, wherein the alkyl, alkenyl, or alkynyl are optionally substituted with up to three $R^{1c}$; alternatively two $R^{1a}$ can be combined with the atoms to which they are attached to form a 3-6 membered spiro, fused or bridged ring;
$R^{1b}$ is H, or $C_{1-6}$ alkyl, wherein the alkyl is optionally substituted with up to three halogens, CN, or OH;
each $R^{1c}$ is independently OH, $OR^{11}$, halogen, oxo, $SOR^{13}$, $SO2R^{13}$, $SR^{13}$, $SO_2NH_2$, $CONH_2$, $C_{1-6}$ alkoxy, $C_{6-10}$ aryl, $C_{6-10}$ aryloxy, 5-11 membered heteroaryl, or $C_{3-7}$ cycloalkyl;

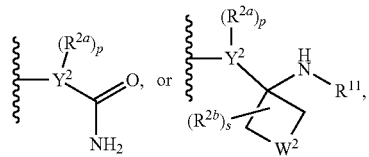

wherein
$Y^2$ is a 5 membered heteroaryl, wherein Y2 is attached to the core through a carbon atom of $Y^2$;
p is 0, or 1;
s is 0, 1, or 2; and
$W^2$ is O, $CF_2$, CHF, SO, SO(NH), $SO(NR^{2c})$, $CH_2O$, $CH_2OCH_2$, $OCH_2O$, $CH_2SO_2$, $CH_2SO_2CH_2$, or $SO_2$;
each $R^{2a}$ is independently $C_{1-6}$ alkyl, $C_{2-6}$ alkenyl, $C_{2-6}$ alkynyl, $C_{1-6}$ alkoxy, $C_{1-6}$ haloalkyl, $SO_2R^{2c}$, $SOR_2$, $SO_2NH_2$, $CONH_2$, $COR^{2c}$, $CONHR^{2e}$, $CON(R^{2c})_2$, halogen, oxo, OH, CN, $NH_2$, $NHR_2$, $N(R^{2c})_2$, $NHCOR^{2c}$, $N(R^{2c})COR^{2c}$, $NO_2$, $SO_2NHR^{2c}$, $SO_2N(R^{2c})_2$, $NHSO_2R^{2c}$, $N(R^{2c})SO_2R^{2c}$, $S(O)(NH)R^{2c}$, $S(O)(NH)NH_2$, $NHS(O)(NH)R^{2c}$, $NS(O)(NH_2)R^{2c}$, $NS(O)(R^{2c})_2$, $S(O)(NR^{2c})R^{2c}$, $S(O)(NR^{2c})NH2$, $S(O)(NH)NHR^{2c}$, $S(O)(NR^{2c})NH(R^{2c})$, $OR^{2c}$, $C_{3-7}$ cycloalkyl, 4-7 membered heterocyclyl, $C_{6-10}$ aryl, or 5-11 membered heteroaryl, wherein the alkyl, alkenyl, alkynyl, cycloalkyl, heterocyclyl, aryl or heteroaryl are substituted with up to seven $R^{2b}$, and wherein the cycloalkyl can be fused or spiro to the heteroaryl; alternatively two $R^{2a}$ can be combined with the atoms to which they are attached to form a 3-7 membered spiro, fused or bridged ring;
each $R^{2b}$ is independently $C_{1-6}$ alkyl, $C_{1-6}$ haloalkyl, $C_{1-6}$ alkoxy, OH, halogen, oxo, $CONH_2$, $NHCOR^{2c}$, $N(R^{2c})COR^{2c}$, $NHCO_2R^{2c}$, $NH_2$, $N(R^{2c})_2$, $NHR^{2c}$, $S(O)(NH)R^{2c}$, $S(O)(NH)NH_2$, $NHS(O)(NH)R^{2c}$, $NS(O)(NH_2)R^{2c}$, $NS(O)(R^{2c})_2$, $S(O)(NR^{2c})R^{2c}$, $S(O)(NR^{2c})NH_2$, $S(O)(NH)NHR^{2c}$, $S(O)(NR^{2c})NH(R^{2c})$, $OR^{2c}$, $NHSO_2R^{2c}$, $N(R^{2c})SO_2R^{2c}$, $C_{1-6}$ alkyl-$CO_2R^{12}$, $C_{1-6}$ alkyl-$CONH_2$, $C_{1-6}$ alkyl-$NHSO_2R^{2c}$, CN, $COR^{2c}$, $NHCO_2R^{2c}$, $SO_2NH_2$, $SO_2NHR^{2c}$, $SO_2R^{2c}$, $C_{3-7}$ cycloalkyl, 4-7 membered heterocyclyl, $C_{6-10}$ aryl or 5-11 membered heteroaryl, wherein the alkyl, alkoxy, haloalkyl, cycloalkyl, heterocyclyl, aryl or heteroaryl can be optionally substituted with up to four $R^{2d}$; alternatively two $R^{2b}$ can be combined with the atoms to which they are attached to form a 3-7 membered spiro, fused or bridged ring; each $R^{2c}$ is independently $C_{1-6}$ alkyl, $C_{1-6}$ haloalkyl, $C_{1-6}$ alkoxy, $C_{6-10}$ aryl, 5-11 membered heteroaryl, or 4-7 membered heterocyclyl, wherein the alkyl, haloalkyl, alkoxy, aryl, heteroaryl or heterocyclyl are optionally substituted with up to four $R^{2d}$; each $R^{2d}$ is independently OH, halogen, $NH_2$, $C_{1-6}$ alkoxy, $CONH_2$, $SO_2NH_2$, $NHCOR^{13}$, $C_{1-6}$ alkyl, $C_{1-6}$ haloalkyl, $C_{1-6}$ alkyl-$NH_2$, $C_{1-6}$ alkyl-$CO_2R^{12}$, oxo, or CN; R2e is $C_{1-6}$ alkyl, $C_{3-7}$ cycloalkyl, $C_{6-10}$ aryl, $C_{1-6}$ alkyl-$C_{6-10}$ aryl, 4-7 membered heterocyclyl, or 5-11 membered heteroaryl, wherein the alkyl, cycloalkyl, aryl, alkyl-aryl, heterocyclyl or heteroaryl are optionally substituted with up to three R10;
$R^3$, $R^4$, $R^5$, $R^6$, $R^7$, $R^8$ are independently H, $C_{1-6}$ alkyl, halogen, or $C_{3-7}$ cycloalkyl; alternatively $R^3$, $R^4$, $R^5$, $R^6$, $R^7$ or $R^8$ can be combined with the atoms to which they are attached to form a 3-6 membered spiro, bridged or fused ring;
each $R^{10}$ is independently $C_{1-6}$ alkoxy, CN, halogen, OH, $NH_2$, $NHR^{11}$, $CONH_2$, $SO_2NH_2$, or $NHCO_2$-$C_{1-6}$ alkyl;
$R^{11}$ is H, $C_{1-6}$ alkyl, or $C_{1-6}$ haloalkyl;
$R^{12}$ is $C_{1-6}$ alkyl, $C_{1-6}$ haloalkyl, 3-7 cycloalkyl, 4-7 heterocyclyl, $C_{6-10}$ aryl, or 5-11 heteroaryl; and
$R^{13}$ is $C_{1-6}$ alkyl, or $C_{1-6}$ haloalkyl; or a pharmaceutically acceptable salt thereof, and at least one pharmaceutically acceptable carrier or excipient.

30. The pharmaceutical composition of claim 29 further comprising one or more additional therapeutic agents.

31. The pharmaceutical composition of claim 30, wherein the additional therapeutic agent comprises an SGLT2 inhibitor, an ACE inhibitor and/or a pharmaceutically acceptable salt thereof.

32. The pharmaceutical composition of claim 31, wherein the additional therapeutic agent comprises empagliflozin, canagliflozin, dapagliflozin, ipragliflozin, tofogliflozin, remogliflozin, or ertugliflozin.

33. The pharmaceutical composition of claim 31, wherein the additional therapeutic agent comprises benazepril, imidapril, or enalapril and/or a pharmaceutically acceptable salt thereof.

34. A pharmaceutical composition comprising a pharmaceutically effective amount of a compound having the structure of Formula VI Formula VI

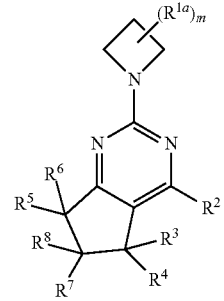

wherein m is 0-4;
each $R^{1a}$ is independently $C_{1-6}$ alkyl, $C_{2-6}$ alkenyl, $C_{2-6}$ alkynyl, OH, $OR^{1b}$, $CH_2OH$, $CO_2R^{12}$, halogen, oxo, $CONH_2$, CN, $NH_2$, $NHR^{11}$, $C_{1-6}$ alkyl-$NHSO_2R^{13}$, $C_{1-6}$ alkyl-$NHCOR^{13}$, $C_{1-6}$ alkoxy or $C_{1-6}$ haloalkyl, wherein the alkyl, alkenyl, or alkynyl are optionally substituted with up to three $R^{1c}$; alternatively two $R^{1a}$ can be combined with the atoms to which they are attached to form a 3-6 membered spiro, fused or bridged ring;

$R^{1b}$ H, or $C_{1-6}$ alkyl, wherein the alkyl is optionally substituted with up to three halogens, CN, or OH;

each $R^{1c}$ is independently OH, $OR^{11}$, halogen, oxo, $SOR^{13}$, $SO_2R^{13}$, $SR^{13}$, $SO_2NH_2$, $CONH_2$, $C_{1-6}$ alkoxy, $C_{6-10}$ aryl, $C_{6-10}$ aryloxy, 5-11 membered heteroaryl, or $C_{3-7}$ cycloalkyl; wherein $R^2$ is

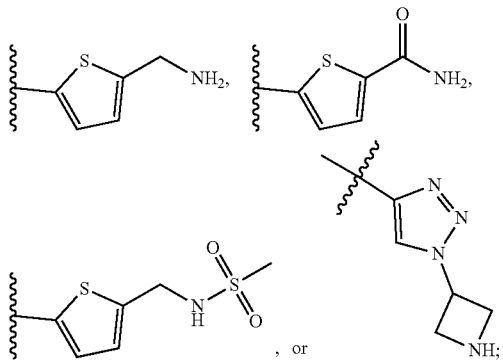

$R^3$, $R^4$, $R^5$, $R^6$, $R^7$, $R^8$ are independently H, $C_{1-6}$ alkyl, halogen, or $C_{3-7}$ cycloalkyl;

alternatively $R^3$, $R^4$, $R^5$, $R^6$, $R^7$ or $R^8$ can be combined with the atoms to which they are attached to form a 3-6 membered spiro, bridged or fused ring;

or a pharmaceutically acceptable salt thereof, and at least one pharmaceutically acceptable carrier or excipient.

35. The pharmaceutical composition of claim 34 further comprising one or more additional therapeutic agents.

36. The pharmaceutical composition of claim 34, wherein the additional therapeutic agent comprises an SGLT2 inhibitor, an ACE inhibitor and/or a pharmaceutically acceptable salt thereof.

37. The pharmaceutical composition of claim 36, wherein the additional therapeutic agent comprises empagliflozin, canagliflozin, dapagliflozin, ipragliflozin, tofogliflozin, remogliflozin, or ertugliflozin.

38. The pharmaceutical composition of claim 36, wherein the additional therapeutic agent comprises benazepril, imidapril, or enalapril and/or a pharmaceutically acceptable salt thereof.

* * * * *